(12) United States Patent
Sakai et al.

(10) Patent No.: US 7,135,466 B2
(45) Date of Patent: Nov. 14, 2006

(54) QUINOLINE AND QUINAZOLINE DERIVATIVES AND DRUGS CONTAINING THE SAME

(75) Inventors: Teruyuki Sakai, Gunma (JP); Terufumi Senga, Gunma (JP); Takayuki Furuta, Gunma (JP); Atushi Miwa, Gunma (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 2 days.

(21) Appl. No.: 10/168,392

(22) PCT Filed: Dec. 22, 2000

(86) PCT No.: PCT/JP00/09157

§ 371 (c)(1),
(2), (4) Date: Oct. 25, 2002

(87) PCT Pub. No.: WO01/47890

PCT Pub. Date: Jul. 5, 2001

(65) Prior Publication Data

US 2004/0132727 A1 Jul. 8, 2004

(30) Foreign Application Priority Data

Dec. 24, 1999 (JP) .................. 11/377486
Dec. 28, 1999 (JP) .................. 11/374494
Jun. 14, 2000 (JP) .................. 2000-177790

(51) Int. Cl.
C07D 215/233 (2006.01)
C07D 401/12 (2006.01)
A61K 31/47 (2006.01)

(52) U.S. Cl. ............. 514/217.07; 514/235.2; 514/253.07; 514/312; 540/597; 544/128; 544/363; 546/153

(58) Field of Classification Search ........... 546/153; 514/312, 235.2, 253.07, 217.07; 544/128, 544/363; 540/597

See application file for complete search history.

(56) References Cited

U.S. PATENT DOCUMENTS 4,675,047 A 6/1987 Serban et al. ........... 71/92
5,480,883 A 1/1996 Spada et al. ........... 514/249
6,143,764 A 11/2000 Kubo et al. ........... 514/312

FOREIGN PATENT DOCUMENTS

DE  3101544  * 8/1982
EP  860433    8/1998
JP  11-158149 * 6/1999
WO  00/43366  7/2000
WO  WO 01/21594  3/2001

OTHER PUBLICATIONS

CAPLUS Abstract 97:198123, 1982.*
CAPLUS Abstract 133:135235, 2000.*
CAPLUS Abstract 131:68130, 1999.*
Simone, Oncology: Introduction, Cecil Textbook of Medicine, 20th Edition, vol. 1, pp. 1004-1010, 1996.*
Traxler, Protein Tyrosine Kinase Inhibitors in Cancer Treatment, Exp. Opin. Ther. Patents 7(6):571-588, 1997.*
Yarnal, et al., Database Crossfire Beilstein Online! Beilstein Institut zur Foerderung der Chemischen Wissenschaften, pp. 1-2, Database accession No. 561265, XP-002237136, "Cinnoline Chemistry. IV. Synthesis of Substituted Phenyl Cinnolyl Esters", 1973.
Kazuo Kubo et al.: "A novel series of 4-phenoxyquinolines: potent and highly selective inhibitors of PDGF receptor autophosphorylation" Bioorg. Med. Chem. Lett., vol. 7, No. 23, pp. 2935-2940 1997.
George C. Wright et al.: "Synthesis and hypotensive properties of new 4-aminoquinolines" J. Med. Chem., vol. 14, No. 11, pp. 1060-1066 1971.
Hattab Alsaidi et al.: "Convenient synthesis of heteroaryl phenyl ethers from chloropyridines and chloroquinolines using phase-transfer catalysis" Synthesis, No. 11, pp. 921-924 1980.

(Continued)

*Primary Examiner*—Deepak Rao
(74) *Attorney, Agent, or Firm*—Oblon, Spivak, McClelland, Maier & Neustadt, P.C.

(57) ABSTRACT

There are provided compounds which can be used in the treatment of diseases mediated by the autophosphorylation of a PDGF receptor, specifically, compounds which can inhibit neointima formation hypertrophy. The compounds are those represented by formula (I) or pharmacologically acceptable salts or solvates thereof:

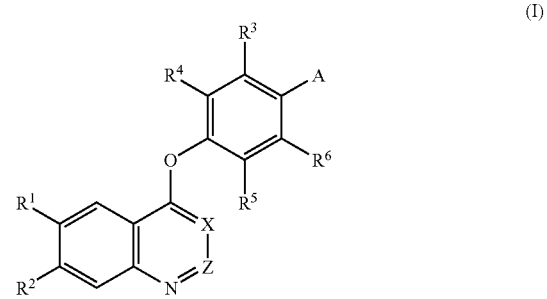

wherein $R^1$ and $R^2$ represent hydrogen, alkyl or the like; $R^3$, $R^4$, $R^5$ and $R^6$ represent hydrogen, halogen, alkyl, alkoxy or the like; $R^{11}$ and $R^{12}$ represent hydrogen, alkyl, alkylcarbonyl or the like; and A represents any one of formulae (i) to (x), provided that compounds wherein $R^3$, $R^4$, $R^5$ and $R^6$ represent hydrogen and A represents group (v) wherein u is 0 (zero) and $R^{19}$ represents phenyl optionally substituted by halogen, alkyl, or alkoxy are excluded.

30 Claims, No Drawings

OTHER PUBLICATIONS

Chemical Abstracts, vol. 58, 4563e, 1960.

Elaine F. Remmers, et al., "Cytokines and Growth Regulation of Synoviocytes from Patients with Rheumatoid Arthritis and Rats with Streptococcal Cell Wall Arthritis", The Journal of Rheumatology, vol. 2, 1990, pp. 179-189.

Madathia Sarkissian, et al., "Transforming Growth Factor-β and Platelet Derived Growth Factor Regulation of Fibrillar Fibronectin Matrix Formation by Synovial Fibroblasts", The Journal of Rheumatology, vol. 25, No. 4, 1998, pp. 613-622.

Annette B. Rice, et al., "Specific Inhibitors of Platelet-Derived Growth Factor or Epidermal Growth Factor Receptor Tyrosine Kinase Reduce Pulmonary Fibrosis in Rats", American Journal of Pathology, vol. 155, No. 1, Jul. 1999, pp. 213-221.

Theresa C. Peterson, "Pentoxifyline Prevents Fibrosis in an Animal Model and Inhibits Platelet-derived Growth Factor-driven Proliferation of Fibroblasts", Hepatology, vol. 17, No. 3, 1993, pp. 486-493.

Flemming S. Vassbotn, et al., "Activated Platelet-Derived Growth Factor Autocrine Pathway Drives the Transformed Phenotype of a Human Glioblastoma Cell Line", Journal of Cellular Physiology, vol. 158, No. 2, 1994, pp. 381-389.

* cited by examiner

QUINOLINE AND QUINAZOLINE DERIVATIVES AND DRUGS CONTAINING THE SAME

This application is a 371 of PCT/JP00/09157 filed Dec. 22, 2000.

BACKGROUND OF THE INVENTION

1. Field of the Invention

The present invention relates to quinoline derivatives and quinazoline derivatives and more particularly to quinoline derivatives and quinazoline derivatives that can be used in the treatment of diseases associated with the autophosphorylation of a PDGF receptor and particularly can inhibit angiostenosis.

2. Background Art

PTCA (percutaneous transluminal coronary angioplasty) is widely adopted as therapy useful for ischemic heart diseases resulting from coronary stenosis. Vascular restenosis, which is observed in a frequency of about 30% within 3 to 6 months after the operation of PTCA, however, has become a serious problem associated with long-term prognosis and medical economy. The restenosis is considered attributable to the fact that vascular smooth muscular cells or fibroblasts of the vascular outer membrane are activated, for example, by platelet activation caused by the tear of vascular tunica intima or media, extension stimulation, and vascular endothelial cell injury at the time of catheter therapy and consequently migrate and proliferate and excessively accumulate at injured vascular sites.

Various growth factors have hitherto been assumed as the vascular smooth muscle cells or fibroblasts activation factors. In particular, since R. Ross et al. have proposed a hypothesis of a injury reaction (N. Engl. J. Med., 295, 369 (1976)), PDGF (platelet-derived growth factor) has drawn attention as one of factors causative of arteriosclerosis and has been also considered as a major factor causative of restenosis from both fundamental and clinical aspects (G. A. A. Ferns et al., Science, 253, 1129 (1991), M. G. Sirois et al., Circulation, 95, 669 (1997), and M. Ueda et al., Am. J. Pathol., 149, 831 (1996) etc.)

PDGF-R (PDGF receptor) autophosphorylation inhibitory compounds (WO 97/17329 and The FASEB Journal, Vol. 11, pp. 1119–1126 (1997)) have been reported up to now.

For PDGF receptor autophosphorylation inhibitory compounds which have been reported, however, the selectivity for VEGF receptors (such as KDR) and c-kit (SCF receptors) belonging to the PDGF receptor family has not been discussed.

VEGF is one of major growth factors of vascular endothelial cells (EC), and VEGF receptor inhibitory compounds possibly inhibit the regeneration of EC in injured blood vessels to promote the formation of thrombus and to accelerate angiostenosis.

Further, SCF is a growth factor involved in the upstream of hematopoietic system and the movement of intestinal tracts, and substances that inhibit receptors of SCF possibly induce hematopoietic failure and intestinal tract movement failure.

For these reasons, compounds that can selectively inhibit PDGF receptors for c-kit, KDR, and the like are family are expected as anti-restenosis agents that have no significant side effect.

Although various restenosis inhibitors have been developed up to now, any pharmaceutical compound having potent angiostenosis inhibitory activity has not yet been developed.

SUMMARY OF THE INVENTION

The present inventors have now found out compounds having PDGF receptor autophosphorylation inhibitory activity.

The present inventors have also found out compounds inhibiting angiostenosis in rat carotid balloon injury models and porcine coronary balloon injury models.

The present inventors have further found out compounds having potent PDGF receptor autophosphorylation inhibitory activity and having low VEGF receptor autophosphorylation inhibitory activity.

The present inventors have further found out compounds having PDGF receptor autophosphorylation inhibitory activity and having low c-kit autophosphorylation inhibitory activity.

An object of the present invention is to provide compounds that can be used in the treatment of diseases mediated by the autophosphorylation of PDGF receptors, particularly compounds having inhibitory activity against angiostenosis.

Another object of the present invention is to provide compounds that can be used in the treatment of diseases mediated by the autophosphorylation of PDGF receptors and have a low level of side effects attributable to c-kit autophosphorylation inhibitory activity.

According to the present invention, there is provided a compound represented by formula (I) or a pharmacologically acceptable salt or solvate thereof:

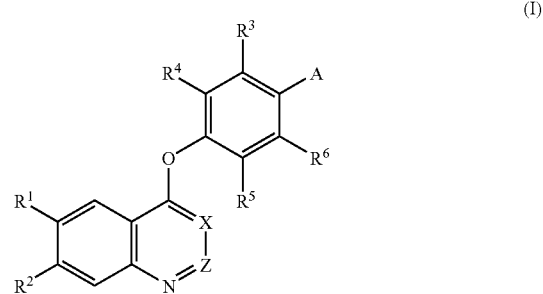

wherein

X and Z, which may be the same or different, represent CH or N;

$R^1$ and $R^2$, which may be the same or different, represent a hydrogen atom or $C_{1-4}$ alkoxy optionally substituted by a halogen atom;

$R^3$, $R^4$, $R^5$, and $R^6$, which may be the same or different, represent a hydrogen atom; a halogen atom; $C_{1-4}$ alkyl optionally substituted by a halogen atom; $C_{1-4}$ alkoxy optionally substituted by a halogen atom; nitro; amino; or morpholyl;

A represents a group selected from the group consisting of formulae (i) to (x), wherein $R^{11}$ and $R^{12}$, which may be the same or different, represent a hydrogen atom, $C_{1-4}$ alkyl optionally substituted by a halogen atom, or $C_{1-4}$ alkylcarbonyl optionally substituted by a halogen atom;

provided that compounds wherein $R^3$, $R^4$, $R^5$ and $R^6$ represent a hydrogen atom and A represents group (v) wherein u is 0 (zero) and $R^{19}$ represents phenyl optionally substituted by a halogen atom, $C_{1-4}$ alkyl, or $C_{1-4}$ alkoxy are excluded:

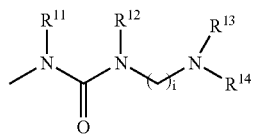
(i)

wherein i is an integer of 0 to 10, $R^{13}$ and $R^{14}$, which may be the same or different, represent a hydrogen atom; $C_{1-6}$ alkyl optionally substituted by a halogen atom; or phenyl optionally substituted by a halogen atom or $C_{1-4}$ alkyl optionally substituted by a halogen atom, $R^{13}$ and $R^{14}$ may form a five- to seven-membered saturated or unsaturated heterocyclic ring optionally containing one or more additional hetero-atoms together with the nitrogen atom to which they are attached, and this heterocyclic ring is optionally substituted by a halogen atom or $C_{1-4}$ alkyl optionally substituted by a halogen atom, or, $R^{13}$ or $R^{14}$ may form $C_{1-4}$ alkylene optionally substituted by a halogen atom together with $R^{12}$;

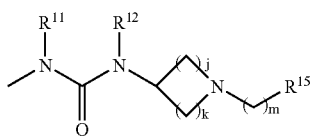
(ii)

wherein j is an integer of 0 to 3, k is an integer of 0 to 3, provided that both j and k are not 0 (zero), m is an integer of 0 to 2, carbon atoms in the following

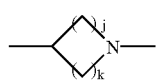

are optionally substituted by one or more $C_{1-4}$ alkyl groups, which may be the same or different, optionally substituted by a halogen atom, and $R^{15}$ represents a hydrogen atom; cyclic $C_{3-7}$ alkyl optionally substituted by a halogen atom; phenyl optionally substituted by $C_{1-6}$ alkyl or a halogen atom; or $C_{1-4}$ alkoxycarbonyl;

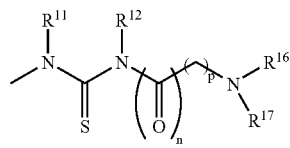
(iii)

wherein n is 0 (zero) or 1, p is an integer of 0 to 10, and $R^{16}$ and $R^{17}$, which may be the same or different, represent a hydrogen atom; $C_{1-6}$ alkyl optionally substituted by a halogen atom; $C_{1-4}$ alkylcarbonyl optionally substituted by a halogen atom; cyclic $C_{3-7}$ alkyl optionally substituted by $C_{1-4}$ alkyl optionally substituted by a halogen atom; or phenyl optionally substituted by a halogen atom or $C_{1-4}$ alkyl optionally substituted by a halogen atom, or $R^{16}$ and $R^{17}$ may form a five- to seven-membered saturated or unsaturated heterocyclic ring optionally containing one or more additional hetero-atoms together with the nitrogen atom to which they are attached, this heterocyclic ring is optionally condensed with another one or two carbocyclic or heterocyclic ring to form a ten- to twelve-membered saturated or unsaturated bicyclic carbocyclic ring or heterocyclic ring or a ten- to fifteen-membered saturated or unsaturated tricyclic carbocyclic ring or heterocyclic ring, and these heterocyclic rings are optionally substituted by an oxygen atom or $C_{1-4}$ alkyl optionally substituted by a halogen atom;

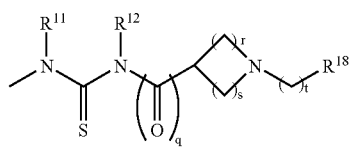
(iv)

wherein q is 0 (zero) or 1, r is an integer of 0 to 3, s is an integer of 0 to 3, provided that both r and s are not 0 (zero), t is an integer of 0 to 2, carbon atoms in the following

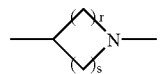

are optionally substituted by one or more $C_{1-4}$ alkyl groups, which may be the same or different, and $R^{18}$ represents a hydrogen atom; phenyl optionally substituted by a halogen atom or $C_{1-6}$ alkyl optionally substituted by a halogen atom; or $C_{1-4}$ alkoxycarbonyl optionally substituted by a halogen atom;

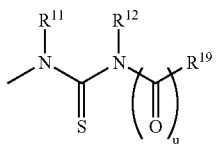

wherein
u is 0 (zero) or 1,
$R^{19}$ represents (1) phenyl which is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$, which may be the same or different, represent a hydrogen atom or $C_{1-4}$ alkyl optionally substituted by a halogen atom; phenyl optionally substituted by a halogen atom; a halogen atom; or cyano, (2) phenoxy of which the phenyl portion is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$ are as defined above; phenyl optionally substituted by a halogen atom; a halogen atom; or cyano, (3) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom; phenyl optionally substituted by a halogen atom; cyclic $C_{3-7}$ alkyl optionally substituted by a halogen atom; or a halogen atom, (4) a five- to seven-membered saturated or unsaturated heterocyclic ring which is optionally condensed with another carbocyclic or heterocyclic ring to form a ten- to twelve-membered bicyclic saturated or unsaturated heterocyclic ring optionally substituted by $C_{1-4}$ alkyl optionally substituted by a halogen atom, or a halogen atom, (5) $C_{1-16}$ alkyl,
(6) $C_{2-6}$ alkenyl, or
(7) $C_{2-6}$ alkynyl, wherein (5) $C_{1-16}$ alkyl, (6) $C_{2-6}$ alkenyl, and (7) $C_{2-6}$ alkynyl are optionally substituted by one or more of the following groups:

(a) phenyl optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$ are as defined above; phenyl optionally substituted by a halogen atom; a halogen atom; or cyano, (b) phenoxy of which the phenyl portion is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$ are as defined above; phenyl optionally substituted by a halogen atom; a halogen atom; or cyano, (c) phenylthio of which the phenyl portion is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$ are as defined above; phenyl optionally substituted by a halogen atom; a halogen atom; or cyano, (d) —$NR^{33}R^{34}$ wherein $R^{33}$ and $R^{34}$ are as defined in $R^{13}$ and $R_{14}$, (e) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom; phenyl optionally substituted by a halogen atom; or a halogen atom, (f) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom, (g) naphthyl,
(h) cyano,
(i) $C_{1-4}$ alkylthio optionally substituted by a halogen atom,
(j) a halogen atom, or
(k) alkoxycarbonyl optionally substituted by a halogen atom;

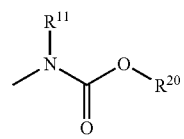

wherein
$R^{20}$ represents (1) phenyl optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$, which may be the same or different, represent a hydrogen atom or $C_{1-4}$ alkyl optionally substituted by a halogen atom; phenyl optionally substituted by a halogen atom; a halogen atom; or cyano, (2) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom, (3) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom, (4) $C_{1-20}$ alkyl,
(5) $C_{2-6}$ alkenyl, or
(6) $C_{2-6}$ alkynyl, and wherein (4) $C_{1-20}$ alkyl, (5) $C_{2-6}$ alkenyl, and (6) $C_{2-6}$ alkynyl are optionally substituted by one or more of the following groups:

(a) phenyl optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$ are as defined above; phenyl optionally substituted by a halogen atom; a halogen atom; or cyano, (b) phenoxy of which the phenyl portion is optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$ are as defined above; phenyl optionally substituted by a halogen atom; a halogen atom; or cyano, (c) phenylthio of which the phenyl portion is optionally substituted by $C_{1-6}$ alkyl optionally substituted by a halogen atom; $C_{1-6}$ alkoxy optionally substituted by a halogen atom; —NR$^{35}$R$^{36}$ wherein R$^{35}$ and R$^{36}$ are as defined above; phenyl optionally substituted by a halogen atom; a halogen atom; or cyano, (d) —NR$^{37}$R$^{38}$ wherein R$^{37}$ and R$^{38}$ are as defined in R$^{13}$ and R$^{14}$, (e) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom, (f) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom, (g) naphthyl, or (h) cyano;

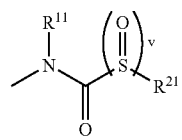

(vii)

wherein v is an integer of 0 to 2,

R$^{21}$ represents (1) phenyl optionally substituted by $C_{1-6}$ alkyl optionally substituted by a halogen atom; $C_{1-6}$ alkoxy optionally substituted by a halogen atom; —NR$^{39}$R$^{40}$ wherein R$^{39}$ and R$^{40}$, which may be the same or different, represent a hydrogen atom or $C_{1-4}$ alkyl optionally substituted by a halogen atom; phenyl optionally substituted by a halogen atom; a halogen atom; or cyano, (2) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom, (3) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom, (4) $C_{1-20}$ alkyl, (5) $C_{2-6}$ alkenyl, or (6) $C_{2-6}$ alkynyl, and wherein (4) $C_{1-20}$ alkyl, (5) $C_{2-6}$ alkenyl, and (6) $C_{2-6}$ alkynyl are optionally substituted by one or more of the following groups:

(a) phenyl optionally substituted by $C_{1-6}$ alkyl optionally substituted by a halogen atom; $C_{1-6}$ alkoxy optionally substituted by a halogen atom; —NR$^{39}$R$^{40}$ wherein R$^{39}$ and R$^{40}$ are as defined above; phenyl optionally substituted by a halogen atom; a halogen atom; or cyano, (b) phenoxy of which the phenyl portion is optionally substituted by $C_{1-6}$ alkyl optionally substituted by a halogen atom; $C_{1-6}$ alkoxy optionally substituted by a halogen atom; —NR$^{39}$R$^{40}$ wherein R$^{39}$ and R$^{40}$ are as defined above; phenyl optionally substituted by a halogen atom; a halogen atom; or cyano, (c) phenylthio of which the phenyl portion is optionally substituted by $C_{1-6}$ alkyl optionally substituted by a halogen atom; $C_{1-6}$ alkoxy optionally substituted by a halogen atom; —NR$^{39}$R$^{40}$ wherein R$^{39}$ and R$^{40}$ are as defined above; phenyl optionally substituted by a halogen atom; a halogen atom; or cyano, (d) —NR$^{41}$R$^{42}$ wherein R$^{41}$ and R$^{42}$ are as defined in R$^{13}$ and R$^{14}$, (e) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom, (f) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom, (g) naphthyl, or (h) cyano;

(viii)

wherein w is an integer of 1 to 4,

L represents —O—, —S(=O)y—, wherein y is an integer of 0 to 2, or —N(—R$^{11}$)—, M represents —O—, —C(=O)—O—, —S(=O)z—, wherein z is an integer of 0 to 2, —N(—R$^{12}$)—, —C(=O)—N(—R$^{12}$)—, or —C(=O)—, R$^{22}$ represents a hydrogen atom; $C_{1-4}$ alkyl optionally substituted by a halogen atom; or phenyl optionally substituted by $C_{1-4}$ alkyl optionally substituted by a halogen atom, $C_{1-4}$ alkoxy optionally substituted by a halogen atom, nitro, amino, or a halogen atom, when M represents —N(—R$^{12}$)— or —C(=O)—N(—R$^{12}$)—, R$^{22}$ and R$^{12}$ may form a five- to seven-membered saturated or unsaturated heterocyclic ring optionally containing one or more additional hetero-atoms together with the nitrogen atom to which they are attached, this heterocyclic ring is optionally condensed with another carbocyclic ring or heterocyclic ring to form a ten- to twelve-membered bicyclic saturated or unsaturated heterocyclic ring, and these heterocyclic rings are optionally substituted by $C_{1-4}$ alkyl optionally substituted by a halogen atom; phenyl; benzyl; or piperidine;

 (ix)

wherein R$^{23}$ represents a hydrogen atom or $C_{1-4}$ alkyl optionally substituted by a halogen atom; and

 (X)

wherein $R^{24}$ and $R^{25}$, which may be the same or different, represent a hydrogen atom or $C_{1-4}$ alkyl optionally substituted by a halogen atom.

The compounds according to the present invention are useful for the treatment of diseases mediated by the autophosphorylation of PDGF receptors.

DETAILED DESCRIPTION OF THE INVENTION

Compound

The terms "alkyl," "alkoxy," "alkenyl," and "alkynyl" as used herein as a group or a part of a group respectively mean straight chain or branched chain alkyl, alkoxy, alkenyl, and alkynyl.

$C_{1-6}$ alkyl is preferably $C_{1-4}$ alkyl.
$C_{1-10}$ alkyl is preferably $C_{1-8}$ alkyl.
$C_{1-16}$ alkyl is preferably $C_{1-13}$ alkyl.
$C_{1-20}$ alkyl is preferably $C_{1-18}$ alkyl.
$C_{1-6}$ alkoxy is preferably $C_{1-4}$ alkoxy.
$C_{1-10}$ alkoxy is preferably $C_{1-8}$ alkoxy.
$C_{2-6}$ alkenyl is preferably $C_{2-4}$ alkenyl.
$C_{2-6}$ alkynyl is preferably $C_{2-4}$ alkynyl.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The expression "alkyl optionally substituted by" as used herein means alkyl, of which one or more hydrogen atoms are substituted by one or more substituents which may be the same or different, or unsubstituted alkyl. It will be understood by a person skilled in the art that the maximum number of the substituents can be determined depending upon the number of substitutable hydrogen atoms on the alkyl group. This will apply to groups having substituents other than alkyl.

The term "halogen atom" as used herein means a fluorine, chlorine, bromine, or iodine atom.

The saturated or unsaturated five- to seven-membered heterocyclic ring contains one or more hetero-atoms selected from oxygen, nitrogen, and sulfur atoms. Examples of the saturated or unsaturated five- to seven-membered heterocyclic group include pyridyl, piperidino, piperazino, morpholino, imidazolyl, triazolyl, tetrazolyl, oxazolyl, thiazolyl, pyrrolidinyl, and pyrazolyl.

The five- to seven-membered saturated or unsaturated heterocyclic group may be condensed with another saturated or unsaturated carbocyclic ring or heterocyclic ring to form a ten- to twelve-membered bicyclic ring or a ten- to fifteen-membered tricyclic ring. Condensed bicyclic groups include indanyl, quinolyl, and quinazolinyl. Condensed tricyclic groups include phenythiazyl, phenoxazyl, and dihydrodibenzoazepinyl.

Cyclic $C_{3-7}$ alkyl may be condensed with another saturated or unsaturated carbocyclic ring or heterocyclic ring to form an eight- to twelve-membered bicyclic saturated or unsaturated carbocyclic ring or heterocyclic ring. Condensed bicyclic groups include indanyl, quinolyl, and quinazolinyl.

In group (i), i is preferably an integer of 0 to 4, more preferably 1 to 3.

An example of preferred group (i) is a group wherein i is an integer of 1 to 3, $R^{13}$ and $R^{14}$, which may be the same or different, represent $C_{1-4}$ alkyl or may form a five- to seven-membered saturated heterocyclic ring optionally substituted by $C_{1-4}$ alkyl together with the nitrogen atom, to which they are attached.

In group (ii), j is preferably an integer of 1 or 2. k is preferably an integer of 1 or 2. m is preferably an integer of 1 or 2.

An example of preferred group (ii) is a group wherein j is 1 or 2, k is 1 or 2, m is 1 or 2, and $R^{15}$ represents optionally substituted phenyl.

In group (iii), p is preferably an integer of 0 to 3.

An example of preferred group (iii) is a group wherein n is 0 (zero), p is an integer of 1 to 3, and $R^{16}$ and $R^{17}$, which may be the same or different, represent $C_{1-4}$ alkyl or may form a five- to seven-membered saturated heterocyclic ring optionally substituted by $C_{1-4}$ alkyl or an oxygen atom together with the nitrogen atom, to which they are attached.

Another example of preferred group (iii) is a group wherein n is 1 and p is 0 (zero).

In group (iv), r is preferably an integer of 1 or 2. s is preferably an integer of 1 or 2. t is preferably an integer of 0 or 1.

An example of preferred group (iv) is a group wherein q is 0 (zero), r is 1 or 2, s is 1 or 2, t is 1 or 2, and $R^{18}$ represents optionally substituted phenyl.

In group (v), the phenyl and phenoxy groups presented by $R^{19}$ are optionally substituted by $C_{6-10}$ alkyl or $C_{6-10}$ alkoxy, preferably $C_{6-8}$ alkyl or $C_{6-8}$ alkoxy.

In group (v), the alkyl, alkenyl, and alkynyl groups presented by $R^{19}$ are optionally substituted by phenyl, phenoxy, or phenylthio, and this phenyl, phenoxy, or phenylthio group is optionally substituted by $C_{6-10}$ alkyl or $C_{6-10}$ alkoxy, preferably $C_{6-8}$ alkyl or $C_{6-8}$ alkoxy.

An example of preferred group (v) is a group wherein u is 1 and $R^{19}$ represents $C_{1-4}$ alkyl substituted by optionally substituted phenyl.

An example of preferred group (vi) is a group wherein $R^{20}$ represents optionally substituted phenyl or $C_{1-6}$ alkyl optionally substituted by optionally substituted phenyl.

In group (viii), w is preferably an integer of 1 to 3.

When L represents —O—, preferably, M represents —O—, —C(=O)—O—, —N(—$R^{12}$)—, —C(=O)—N(—$R^{12}$)—, or —C(=O)—. When L represents —S(=O)y—, preferably, M represents —O—. When L represents —N(—$R^{11}$)—, preferably, M represents —O—.

An example of prefer red group (viii) is a group wherein w is an integer of 1 to 3, L represents —O—, M represents —O— or —C(=O)—O—, and $R^{22}$ represents optionally substituted phenyl.

Examples of preferred compounds represented by formula (I) according to the present invention include the following compounds:

compounds wherein X represents CH or N and Z represents CH;

compounds wherein $R^1$ and $R^2$ represent $C_{1-4}$ alkoxy and at least one of $R^3$, $R^4$, $R^5$ and $R^6$ represents a group other than a hydrogen atom;

compounds wherein $R^1$ and $R^2$ represent $C_{1-4}$ alkoxy, $R^3$ represents a group other than a hydrogen atom, and $R^4$, $R^5$, and $R^6$ represent a hydrogen atom;

compounds wherein $R^1$ and $R^2$ represent $C_{1-4}$ alkoxy, A represents group (i), wherein i is an integer of 1 to 3, and $R^{13}$ and $R^{14}$, which may be the same or different, represent $C_{1-4}$ alkyl or may form a five- to seven-membered saturated heterocyclic ring optionally substituted by $C_{1-4}$ alkyl together with the nitrogen atom, to which they are attached and, more preferably, X represents CH or N and Z represents CH;

compounds wherein $R^1$ and $R^2$ represent $C_{1-4}$ alkoxy, $R^3$, $R^4$, $R^5$ and $R^6$ represent a hydrogen atom, A represents group (i), wherein i is an integer of 1 to 3, and $R^{13}$ and $R^{14}$, which may be the same or different, represent $C_{1-4}$ alkyl or may form a five- to seven-membered saturated heterocyclic ring optionally substituted by $C_{1-4}$ alkyl together with the nitrogen atom to which they are attached and, more preferably, X represents CH or N and Z represents CH;

compounds wherein $R^1$ and $R^2$ represent $C_{1-4}$ alkoxy, $R^3$ represents a group other than a hydrogen atom, $R^4$, $R^5$ and $R^6$ represent a hydrogen atom, A represents group (i) wherein i is an integer of 1 to 3, and $R^{13}$ and $R^{14}$, which may be the same or different, represent $C_{1-4}$ alkyl or may form a five- to seven-membered saturated heterocyclic ring optionally substituted by $C_{1-4}$ alkyl together with the nitrogen atom, to which they are attached, and, more preferably, X represents CH or N and Z represents CH;

compounds wherein $R^1$ and $R^2$ represent $C_{1-4}$ alkoxy, $R^3$ represents nitro, $R^4$, $R^5$, and $R^6$ represent a hydrogen atom, A represents group (i) wherein i is an integer of 1 to 3, and $R^{13}$ and $R^{14}$, which may be the same or different, represent $C_{1-4}$ alkyl or may form a five- to seven-membered saturated heterocyclic ring optionally substituted by $C_{1-4}$ alkyl together with the nitrogen atom, to which they are attached, and, more preferably, X represents CH or N and Z represents CH;

compounds wherein X represents N, Z represents CH, $R^1$ and $R^2$ represent $C_{1-4}$ alkoxy, $R^3$ represents nitro, $R^4$, $R^5$, and $R^6$ represent a hydrogen atom, A represents group (i) wherein i is 2, and $R^{13}$ and $R^{14}$, which may be the same or different, represent $C_{2-3}$ alkyl or may form a six-membered saturated heterocyclic ring optionally substituted by $C_{1-4}$ alkyl together with the nitrogen atom, to which they are attached;

compounds wherein $R^1$ and $R^2$ represent $C_{1-4}$ alkoxy, A represents group (ii) wherein j is 1 or 2, k is 1 or 2, m is 1 or 2, and $R^{15}$ represents optionally substituted phenyl and, more preferably, X represents CH or N and Z represents CH;

compounds wherein $R^1$ and $R^2$ represent $C_{1-4}$ alkoxy, $R^3$, $R^4$, $R^5$, and $R^6$ represent a hydrogen atom, A represents group (ii) wherein j is 1 or 2, k is 1 or 2, m is 1 or 2, and $R^{15}$ represents optionally substituted phenyl;

compounds wherein $R^1$ and $R^2$ represent $C_{1-4}$ alkoxy, $R^3$ represents a group other than a hydrogen atom, $R^4$, $R^5$, and $R^6$ represent a hydrogen atom, A represents group (ii) wherein j is 1 or 2, k is 1 or 2, m is 1 or 2, and $R^{15}$ represents optionally substituted phenyl and, more preferably, X represents CH or N and Z represents CH;

compounds wherein $R^1$ and $R^2$ represent $C_{1-4}$ alkoxy, A represents group (iii) wherein n is 0 (zero), p is an integer of 1 to 3, and $R^{16}$ and $R^{17}$, which may be the same or different, represent $C_{1-4}$ alkyl or may form a five- to seven-membered saturated heterocyclic ring optionally substituted by $C_{1-4}$ alkyl or an oxygen atom together with the nitrogen atom, to which they are attached, and, more preferably, X represents CH or N and Z represents CH;

compounds wherein $R^1$ and $R^2$ represent $C_{1-4}$ alkoxy, $R^3$, $R^4$, $R^5$, and $R^6$ represent a hydrogen atom, A represents group (iii) wherein n is 0 (zero), p is an integer of 1 to 3, and $R^{16}$ and $R^{17}$, which may be the same or different, represent $C_{1-4}$ alkyl or may form a five- to seven-membered saturated heterocyclic ring optionally substituted by $C_{1-4}$ alkyl or an oxygen atom together with the nitrogen atom, to which they are attached, and, more preferably, X represents CH or N and Z represents CH;

compounds wherein $R^1$ and $R^2$ represent $C_{1-4}$ alkoxy, $R^3$ represents a group other than a hydrogen atom, $R^4$, $R^5$, and $R^6$ represent a hydrogen atom, A represents group (iii) wherein n is 0 (zero), p is an integer of 1 to 3, and $R^{16}$ and $R^{17}$, which may be the same or different, represent $C_{1-4}$ alkyl or may form a five- to seven-membered saturated heterocyclic ring optionally substituted by $C_{1-4}$ alkyl or an oxygen atom together with the nitrogen atom, to which they are attached, and, more preferably, X represents CH or N and Z represents CH;

compounds wherein $R^1$ and $R^2$ represent $C_{1-4}$ alkoxy, A represents group (iv) wherein q is 0 (zero), r is 1 or 2, s is 1 or 2, t is 1 or 2, and $R^{18}$ represents optionally substituted phenyl, and, more preferably, X represents CH or N and Z represents CH;

compounds wherein $R^1$ and $R^2$ represent $C_{1-4}$ alkoxy, $R^3$, $R^4$, $R^5$ and $R^6$ represent a hydrogen atom, and A represents group (iv) wherein q is 0 (zero), r is 1 or 2, s is 1 or 2, t is 1 or 2, and $R^{18}$ represents optionally substituted phenyl;

compounds wherein $R^1$ and $R^2$ represent $C_{1-4}$ alkoxy, $R^3$ represents a group other than a hydrogen atom, $R^4$, $R^5$, and $R^6$ represent a hydrogen atom, and A represents group (iv) wherein q is 0 (zero), r is 1 or 2, s is 1 or 2, t is 1 or 2, and $R^{18}$ represents optionally substituted phenyl, and, more preferably, X represents CH or N and Z represents CH;

compounds wherein $R^1$ and $R^2$ represent $C_{1-4}$ alkoxy and A represents group (v), wherein u is 1, and $R^{19}$ represents optionally substituted phenyl, or $C_{1-4}$ alkyl substituted by optionally substituted phenyl, and, more preferably, X represents CH or N and Z represents CH;

compounds wherein $R^1$ and $R^2$ represent $C_{1-4}$ alkoxy, $R^3$, $R^4$, $R^5$, and $R^6$ represent a hydrogen atom, A represents group (v) wherein u is 1, $R^{19}$ represents optionally substituted phenyl, or $C_{1-4}$ alkyl substituted by optionally substituted phenyl;

compounds wherein $R^1$ and $R^2$ represent $C_{1-4}$ alkoxy, $R^5$ represents a group other than a hydrogen atom, $R^3$, $R^4$, and $R^6$ represent a hydrogen atom, and A represents group (v) wherein u is 1, $R^{19}$ represents optionally substituted phenyl, or $C_{1-4}$ alkyl substituted by optionally substituted phenyl, and, more preferably, X represents CH or N and Z represents CH;

compounds wherein $R^1$ and $R^2$ represent $C_{1-4}$ alkoxy and A represents group (vi) wherein $R^{20}$ represents optionally substituted phenyl or $C_{1-6}$ alkyl optionally substituted by optionally substituted phenyl, and, more preferably, X represents CH or N and Z represents CH;

compounds wherein $R^1$ and $R^2$ represent $C_{1-4}$ alkoxy and A represents group (vii) wherein $R^{21}$ represents optionally substituted phenyl, or $C_{1-6}$ alkyl optionally substituted by optionally substituted phenyl, and, more preferably, X represents CH or N and Z represents CH;

compounds wherein $R^1$ and $R^2$ represent $C_{1-4}$ alkoxy and A represents group (viii) wherein w is an integer of 1 to 3, L represents —O—, M represents —O— or —C(=O)—O—, $R^{22}$ represents optionally substituted phenyl, and, more preferably, X represents CH or N and Z represents CH;

compounds wherein $R^1$ and $R^2$ represent $C_{1-4}$ alkoxy and A represents group (viii) wherein, when L represents —O—, M represents —O—, —C(=O)—O—, —N(—$R^{12}$)—, —C(=O)—N(—$R^{12}$)—, or —C(=O)—; when L represents —S(=O)y—, M represents —O—; and when L represents —N(—$R^{11}$)—, M represents —O—, and, more preferably, X represents CH or N and Z represents CH;

compounds wherein $R^1$ and $R^2$ represent $C_{1-4}$ alkoxy and A represents group (iii), wherein n is 1 and p is 0 (zero), and, more preferably, X represents CH or N and Z represents CH; and compounds wherein $R^1$ and $R^2$ represent $C_{1-4}$ alkoxy, $R^3$ represents morpholyl, $R^4$, $R^5$, and $R^6$ represent a hydrogen atom, and A represents group (x), and, more preferably, X represents CH or N and Z represents CH.

Examples of particularly preferred compounds according to the present invention include compounds described in Examples 1 to 1209.

In addition to the compounds described in Examples 1 to 1209, the following compounds may be included in examples of particularly preferred compounds according to the present invention:

N-{4-[(6,7-dimethoxy-4-quinazolinyl)oxy]-2-nitrophenyl}-N-(4-piperidinobutyl)urea;

N-{4-[(6,7-dimethoxy-4-quinazolinyl)oxy]-2-nitrophenyl}-N-(3-piperidinopropyl)urea;

N-[4-(diethylamino)butyl]-N-{4-[(6,7-dimethoxy-4-quinazolinyl)oxy]-2-nitrophenyl}urea;

N-[3-(diethylamino)propyl]-N-{4-[(6,7-dimethoxy-4-quinazolinyl)oxy]-2-nitrophenyl}urea;

N-{4-[(6,7-dimethoxy-4-quinazolinyl)oxy]phenyl}-N-(4-methylpiperazino)urea; and

N-{4-[(6,7-dimethoxy-4-quinolyl)oxy]phenyl}-N-(4-methylpiperazino)urea.

Examples of more preferred compounds according to the present invention are the following compounds:

N-{4-[(6,7-dimethoxy-4-quinazolinyl)oxy]-2-nitrophenyl}-N'-(2-piperidinoethyl)urea; and N-[2-(diethylamino)ethyl]-N'-{4-[(6,7-dimethoxy-4-quinazolinyl)oxy]-2-nitrophenyl}urea.

One or more enantiomeric carbon atoms, which form enantiomer configuration, may exist in the compounds represented by formula (I). The compounds represented by formula (I) include all enantiomers.

Pharmacologically acceptable salts of the compounds represented by formula (I) include acid addition salts. Acid addition salts include: salts with inorganic acids such as hydrochloric acid, sulfuric acid, phosphoric acid, hydrobromic acid, and nitric acid; or organic acids such as maleic acid, fumaric acid, malic acid, oxalic acid, tartaric acid, succinic acid, citric acid, acetic acid, lactic acid, methanesulfonic acid, and p-toluenesulfonic acid.

Pharmacologically acceptable solvates of the compounds represented by formula (I) include hydrates and ethanolates.

Production Process of Compounds (1) Compounds represented by formula (I), wherein A represents groups (i), (ii), (xi), and (x), may be produced, for example, according to scheme 1 and scheme 2.

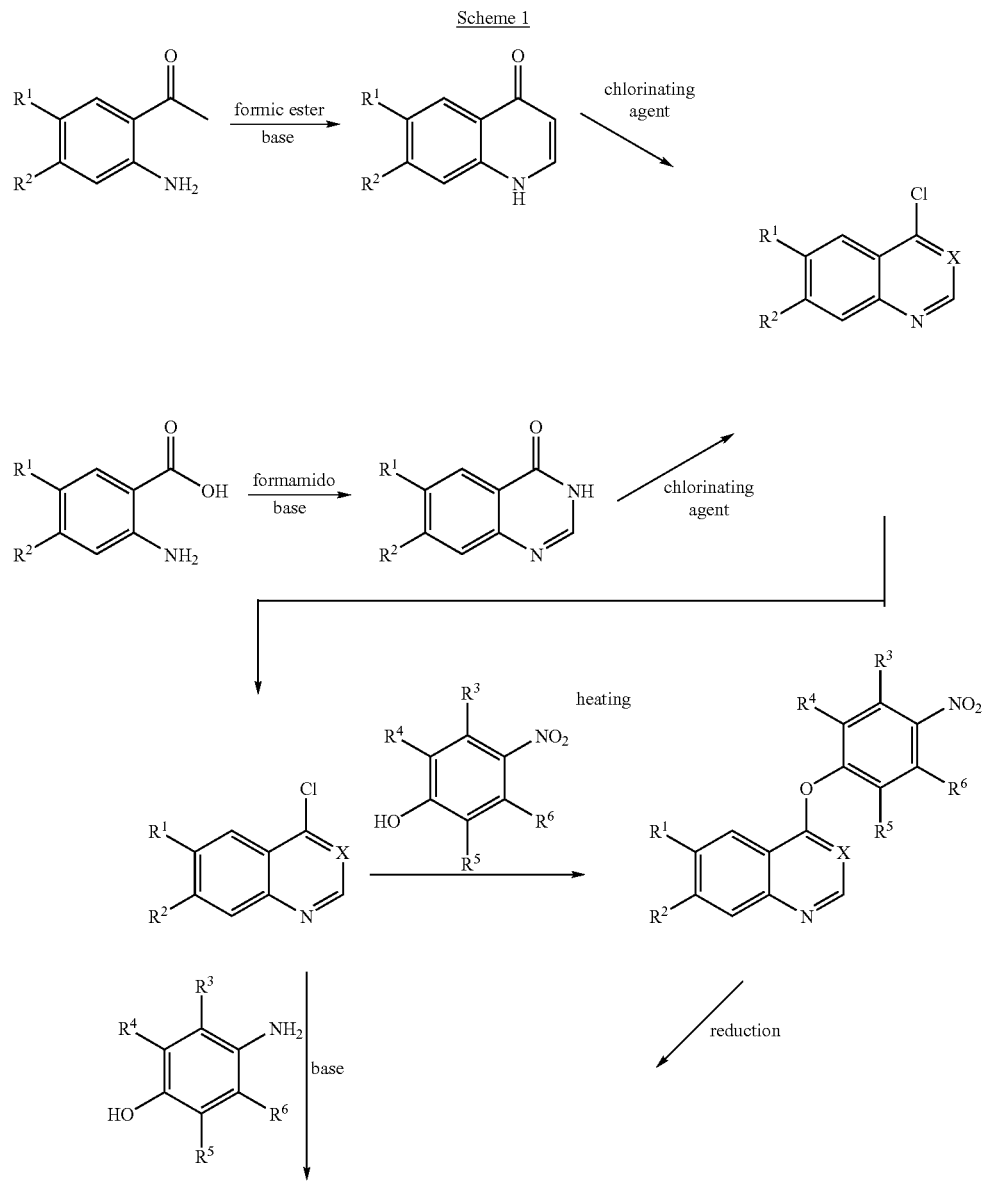

Scheme 1

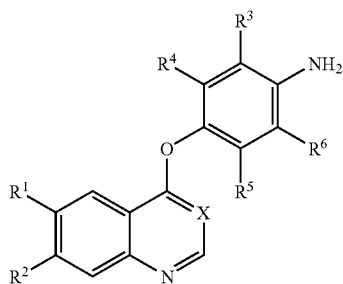

Starting compounds necessary for the synthesis of the compounds according to the present invention are commercially available or can be easily produced by a conventional method.

Quinolone derivatives as an intermediate may be synthesized according to the method described, for example, in WO 97/17329. Further, 4-chloroquinoline derivatives may be synthesized by a conventional method described, for example, in Org. Synth. Col., Vol. 3, 272 (1955), Acta Chim. Hung., 112, 241 (1983) or WO 98/47873. Further, 4-chloroquinazoline derivatives may be synthesized by a conventional method described, for example, in J. Am. Chem. Soc., 68, 1299 (1946), J. Am. Chem. Soc., 68, 1305 (1946) or Dai-Yukikagaku, supervised by Kotake, Vol. 17, p. 150, Asakura Publishing Co., Ltd., 1967.

4-(Nitrophenoxy)quinoline derivatives or corresponding quinazoline derivatives may be synthesized by reacting nitrophenol with a 4-chloroquinoline derivative or a corresponding quinazoline derivative in the presence or absence of a suitable solvent. 4-(Aminophenoxy)quinoline derivatives or corresponding quinazoline derivatives may be synthesized by stirring a 4-(nitrophenoxy)quinoline derivative or a corresponding quinazoline derivative in a suitable solvent, for example, N,N-dimethylformamide, in the presence of a catalyst, for example, palladium hydroxide-carbon or palladium-carbon) in a hydrogen atmosphere. Alternatively, 4-(aminophenoxy)quinoline derivatives or corresponding quinazoline derivatives may be sythesized by reacting an aminophenol derivative with a 4-chloroquinoline derivative or a corresponding quinazoline derivative in the presence of a base, for example, sodium hydride.

Scheme 2

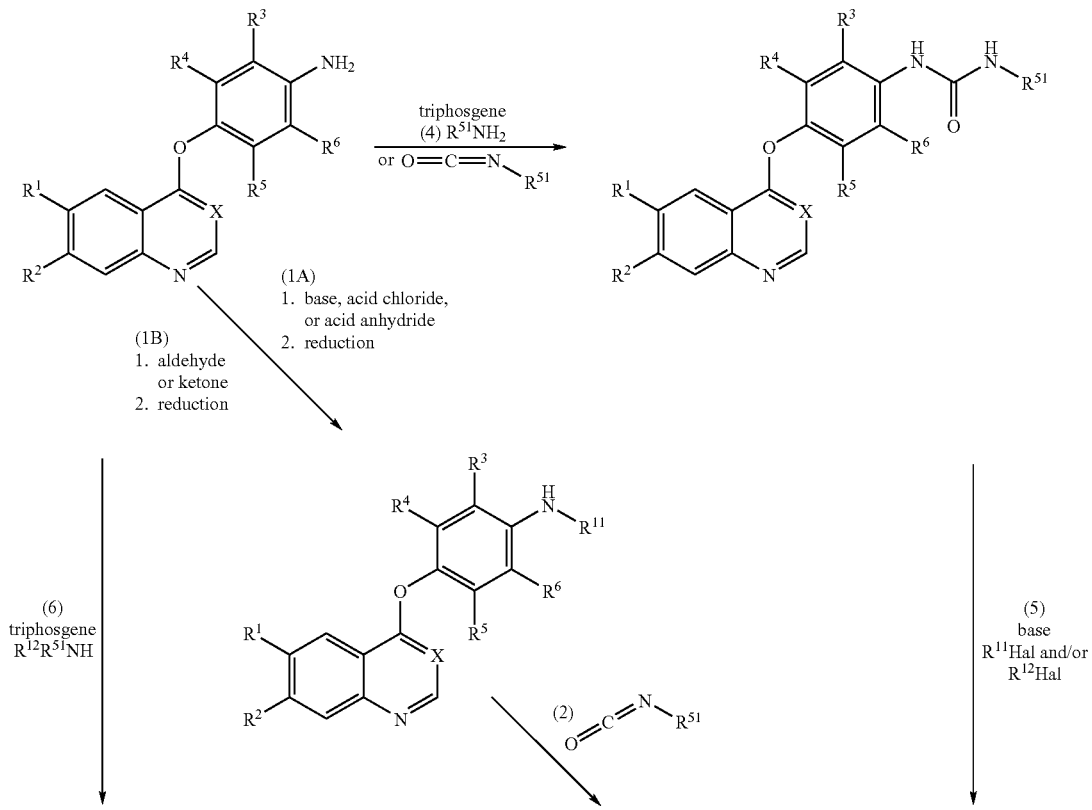

-continued

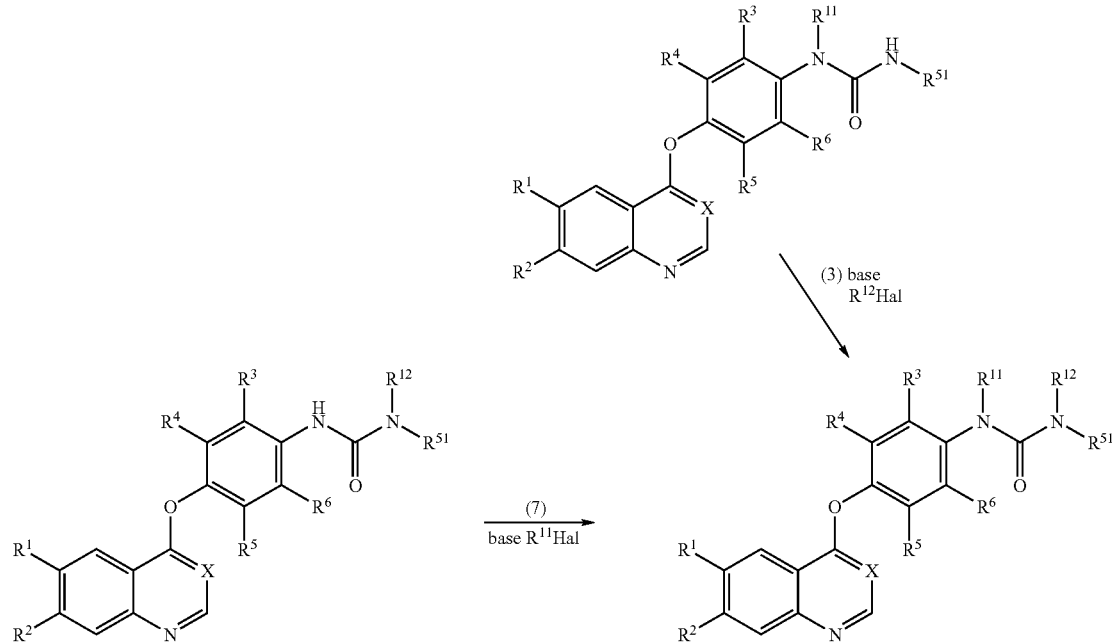

A substituent can be introduced into $R^{11}$ by reacting a 4-(aminophenoxy)quinoline derivative or a corresponding quinazoline derivative with an acid chloride or an acid anhydride in the presence of a base and then reducing the reaction product with lithium aluminum hydride or the like (step 1A).

Alternatively, a substituent can be introduced into $R^{11}$ by reacting a 4-(aminophenoxy)quinoline derivative or a corresponding quinazoline derivative with an aldehyde or a ketone to form an imine compound and then reducing the imine compound with sodium cyanoborohydride or the like (step 1B).

Compounds represented by formula (I) may be produced by reacting a derivative having a substituent at $R^{11}$ with an isocyanate derivative (O=C=N—$R^{51}$ wherein $R^{51}$ represents a portion of groups (i) and (ii) not having a urea portion according to a conventional method (step 2) and, if necessary, reacting the reaction product with a suitable alkylating agent ($R^{12}$Hal) in the presence of a base, for example, sodium hydride (step 3).

$R^{11}$ and $R^{12}$ may also be introduced by reacting a urea derivative, wherein $R^{10}$ and/or $R^{11}$ represent a hydrogen atom, with a suitable alkylating agent ($R^{11}$Hal or $R^{12}$Hal) in the presence of a base, for example, sodium hydride (steps 5 and 7).

Urea derivatives, wherein $R^{11}$ and/or $R^{12}$ represent a hydrogen atom, may be produced by reacting a 4-(aminophenoxy)quinoline derivative or a corresponding quinazoline derivative produced in scheme 1 with an isocyanate derivative according to a conventional method, or by adding triphosgene in the presence of a base, for example, triethylamine and then reacting the mixture with a suitable alkylamine ($R^{51}NH_2$ or $R^{11}R^{51}NH$) (steps 4 and 6).

(2) Compounds represented by formula (I), wherein A represents groups (iii), (iv), and (v), may be produced, for example, according to scheme 3.

Scheme 3

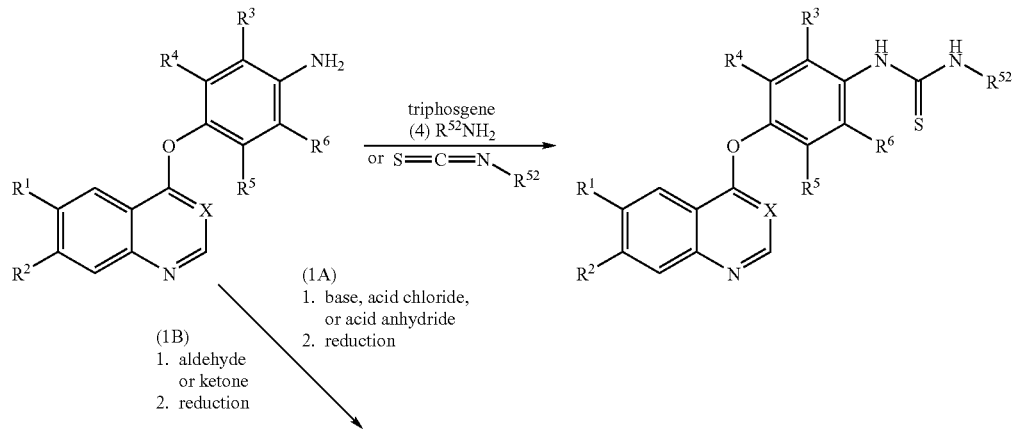

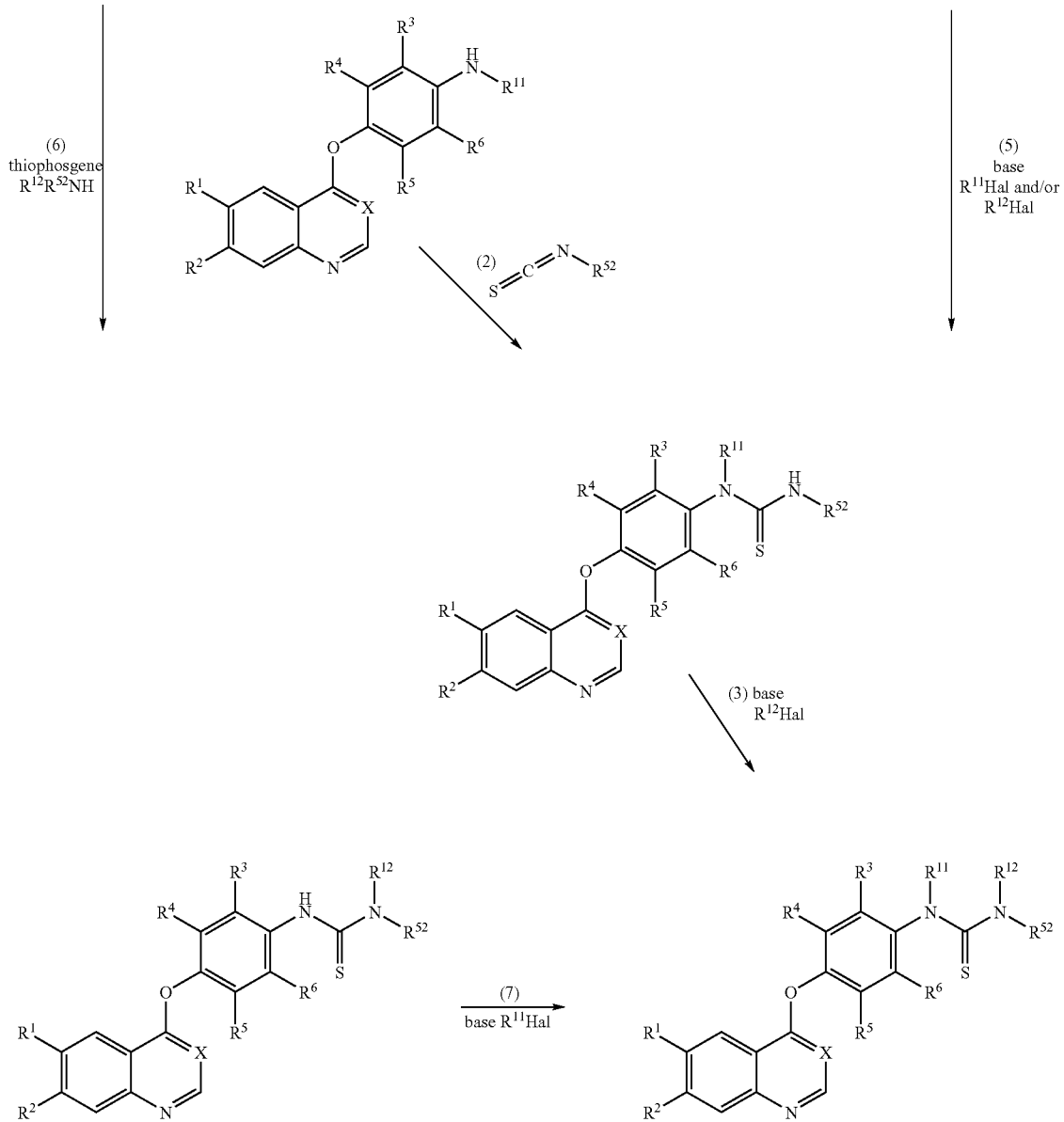

A substituent can be introduced into $R^{11}$ by reacting a 4-(aminophenoxy)quinoline derivative or a corresponding quinazoline derivative with an acid chloride or an acid anhydride in the presence of a base and then reducing the reaction product with lithium aluminum hydride or the like (step 1A).

Alternatively, a substituent can be introduced into $R^{11}$ by reacting a 4-(aminophenoxy)quinoline derivative or a corresponding quinazoline derivative with an aldehyde or a ketone to form an imine derivative and then reducing the imine derivative with sodium cyanoborohydride or the like (step 1B).

Compounds represented by formula (I) may be produced by reacting a derivative having a substituent at $R^{11}$ with an isothiocyanate derivative, (S=C=N—$R^{52}$ wherein $R^{52}$ represents a portion of groups (iii), (iv), and (v), not having a thiourea portion according to a conventional method (step 2) and, if necessary, reacting the reaction product with a suitable alkylating agent ($R^{12}$Hal) in the presence of a base, for example, sodium hydride (step 3).

$R^{11}$ and $R^{12}$ may also be introduced by reacting a thiourea derivative, wherein $R^{11}$ and/or $R^{12}$ represent a hydrogen atom, with a suitable alkylating agent ($R^{11}$Hal or $R^{12}$Hal) in the presence of a base, for example, sodium hydride (steps 5 and 7).

Thiourea derivatives, wherein $R^{11}$ and/or $R^{12}$ represent a hydrogen atom, may be produced by reacting a 4-(aminophenoxy)quinoline derivative or a corresponding quinazoline derivative produced in scheme 1 with an isothiocyanate derivative (S=C=N—$R^{52}$) according to a conventional method, or by adding thiophosgene in the presence of a base, for example, triethylamine and then reacting the mixture with a suitable alkylamine ($R^{52}NH_2$ or $R^{11}R^{52}NH$) (steps 4 and 6).

(3) Compounds represented by formula (I), wherein A represents group (vi), may be produced, for example, according to scheme 4.

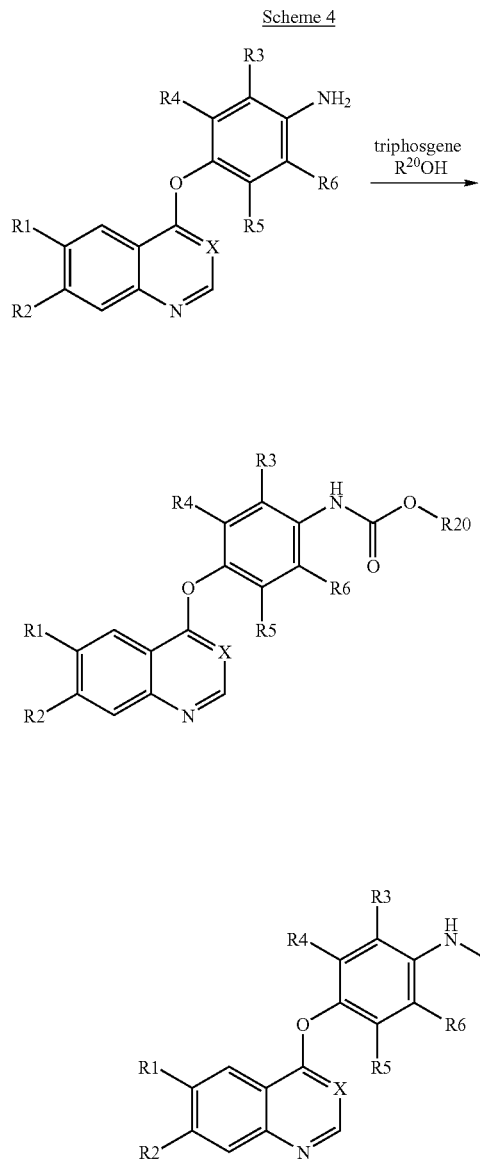

Urethane derivatives, wherein $R^{11}$ and/or $R^{12}$ represent a hydrogen atom, may be produced according to a conventional method by adding triphosgene to a 4-(aminophenoxy)quinoline derivative or a corresponding quinazoline derivative produced according to scheme 1 in the presence of a base, for example, triethylamine and then reacting the mixture with a suitable alcohol ($R^{20}$OH). $R^{11}$ may be introduced by reacting a urethane derivative, wherein $R^{11}$ represents a hydrogen atom, with a suitable alkylating agent ($R^{11}$Hal) in the presence of a base, for example, sodium hydride.

(4) Compounds represented by formula (I), wherein A represents group (vii), may be produced, for example, according to scheme 5.

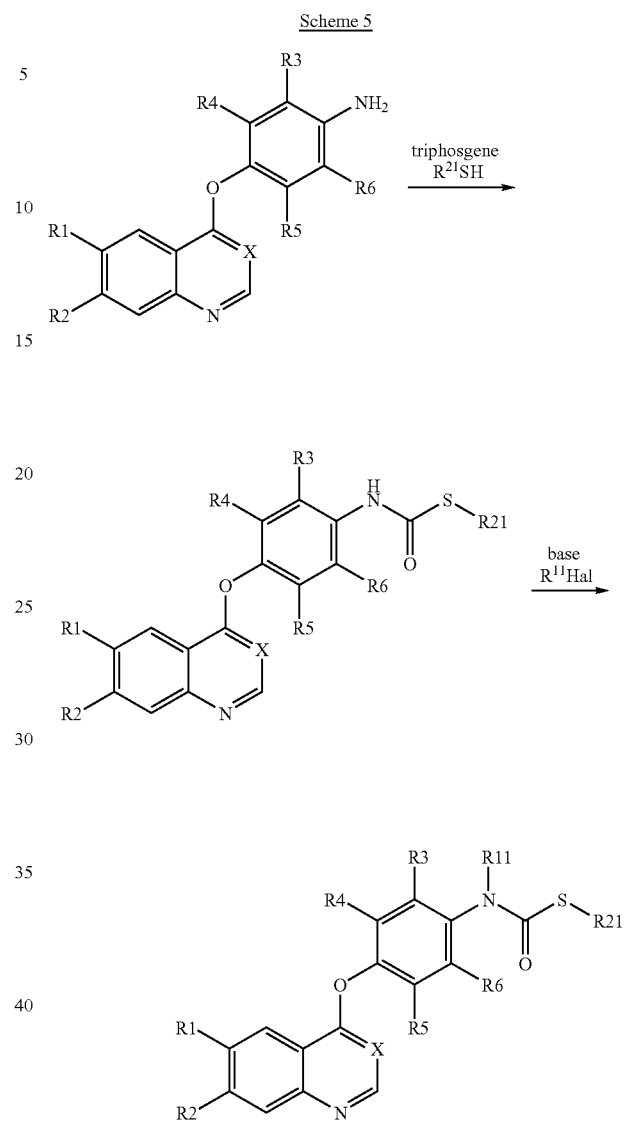

Thiocarbamate derivatives, wherein $R^{11}$ and/or $R^{12}$ represent a hydrogen atom (v=0), may be produced by adding triphosgene to a 4-(aminophenoxy)quinoline derivative or a corresponding quinazoline derivative produced in scheme 1 in the presence of a base, for example, triethylamine according to a conventional method and then reacting the mixture with a suitable thiol ($R^{21}$SH). $R^{11}$ may be introduced by reacting a thiocarbamate derivative, wherein $R^{11}$ represents a hydrogen atom, with a suitable alkylating agent ($R^{11}$Hal) in the presence of a base, for example, sodium hydride.

Oxidation derivatives (v=1) may be produced by oxidizing the thiocarbamate derivative with an oxidizing agent such as m-chloroperbenzoic acid. Further, oxidation derivatives (v=2) may be produced by oxidizing a thiocarbamate derivative with an oxidizing agent such as potassium permanganate or oxone.

(5) Compounds represented by formula (I), wherein A represents groups (viii) and (ix), may be produced, for example, according to schemes 6, 7, and 8.

Where L = O (schemes 6-1 and 6-2):
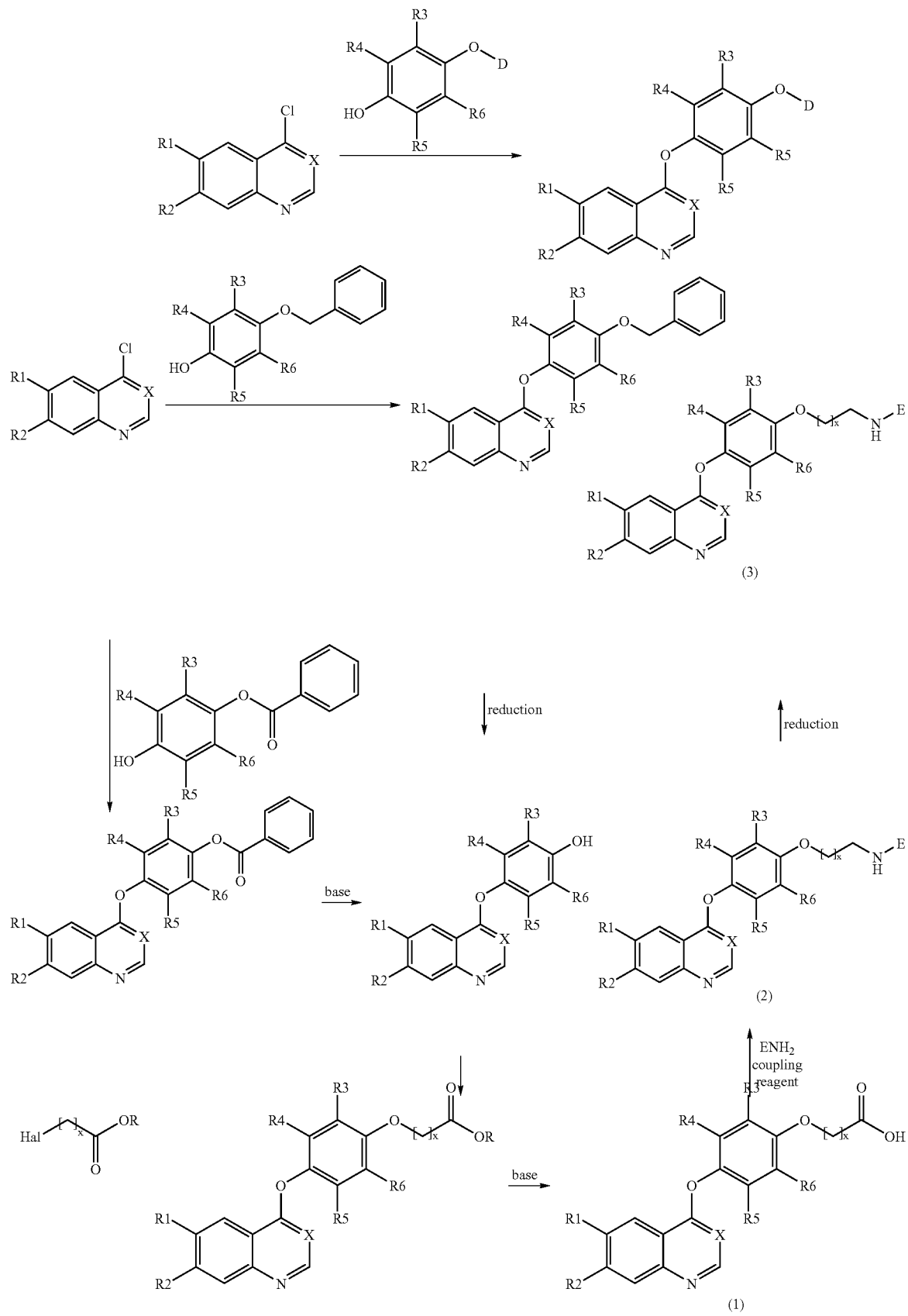
x = w-1

4-(Alkyloxyphenoxy) quinoline derivatives or corresponding quinazoline derivatives, or 4-(acyloxyphenoxy) quinoline derivatives or corresponding quinazoline derivatives may be synthesized by reacting a 4-alkyloxyphenol derivative or a 4-acyloxyphenol derivative with a 4-chloroquinoline derivative or a corresponding quinazoline derivative in the presence or absence of a suitable solvent (scheme 6-1). In the scheme, D represents —$(CH_2)w$—M—$R^{20}$.

4-(Benzyloxyphenoxy)quinoline derivatives or corresponding quinazoline derivatives, or 4-(benzoyloxyphenoxy)quinoline derivatives or corresponding quinazoline derivatives may be synthesized by reacting a 4-benzyloxyphenol derivative or a 4-benzoyloxyphenol derivative with a 4-chloroquinoline derivative or a corresponding quinazoline derivative in the presence or absence of a suitable solvent (scheme 6-1).

4-(Hydroxyphenoxy)quinoline derivatives or corresponding quinazoline derivatives may be synthesized by deprotecting a 4-(benzyloxyphenoxy)quinoline derivative or a corresponding quinazoline derivative in a suitable solvent, for example, N,N-dimethylformamide, in the presence of a catalyst, for example, palladium hydroxide-carbon or palladium-carbon in a hydrogen atmosphere. 4-(Hydroxyphenoxy)quinoline derivatives or corresponding quinazoline derivatives may also be synthesized by deprotecting the benzoyl group in the 4-(benzoyloxyphenoxy)quinoline derivative or corresponding quinazoline derivative under basic conditions, for example, using sodium hydroxide.

Carboxylic acid compound (1) is produced by reacting a 4-(hydroxyphenoxy)quinoline derivative or a corresponding quinazoline derivative with a ω-halogenated alkyl carboxylic acid ester under basic conditions, for example, using sodium hydride and then deprotecting the ester under basic conditions, for example, using sodium hydroxide. Amide derivative (2) may be produced by reacting carboxylic acid compound (1) with an amine in the presence of a coupling reagent, for example, N,N'-dicyclohexylcarbodiimide. Subsequently, reduced derivative (3) may be produced by reducing amide derivative (2) with diborane, lithium aluminum hydride or the like (scheme 6-2).

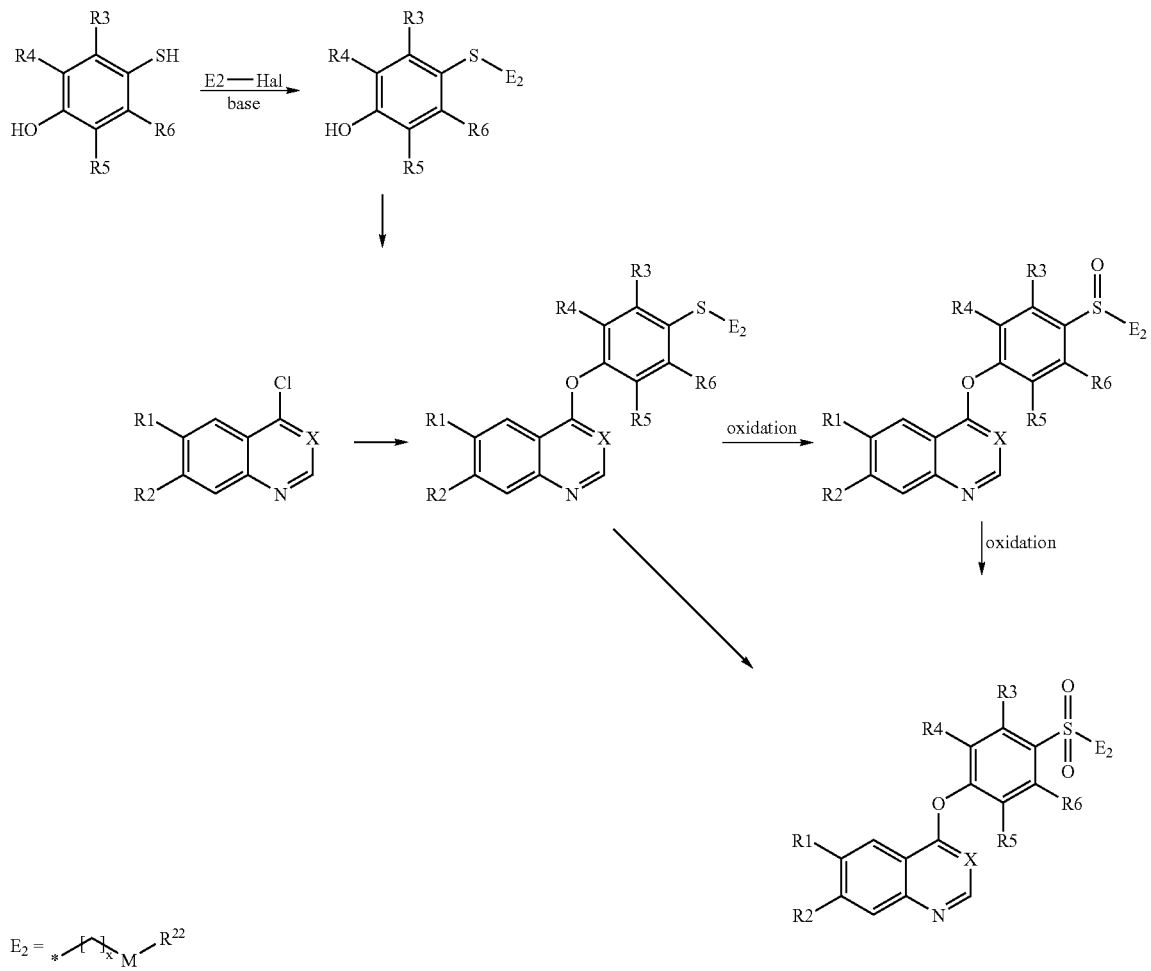

Where L = S (scheme 7):

$E_2 = $ *\_(\_)_x\_M\_$R^{22}$

S-Alkyl-substituted phenols may be produced by reacting a 4-hydroxythiophenol derivative with a suitable alkyl halide derivative in the presence or absence of a suitable solvent under basic conditions, for example, using potassium carbonate. Thio derivatives may be synthesized by reacting the S-alkyl-substituted phenol with a 4-chloroquinoline derivative or a corresponding quinazoline derivative.

Sulfoxide derivatives may be produced by oxidizing the thio derivative with an oxidizing agent such as m-chloroperbenzoic acid. Sulfone derivatives may be produced by oxidizing the thio derivative with an oxidizing agent such as potassium permanganate or oxone, or by oxidizing the sulfoxide derivative with an oxidizing agent such as potassium permanganate or oxone.

proliferation and organ fibrosis induced by PDGF, for example, chronic rheumatism, PDGF-dependent tumors such as glioma, cirrhosis, pulmonary fibrosis, and occlusion of arteriovenous shunt resulting, for example, from dialysis of patients suffering from renal failure (Gordon A. A. Ferns et al., Science, Vol. 253, pp 1129–1132 (1991), Martin G Sirois et al., Circulation, Vol. 95, No. 3, pp 669–675 (1997),

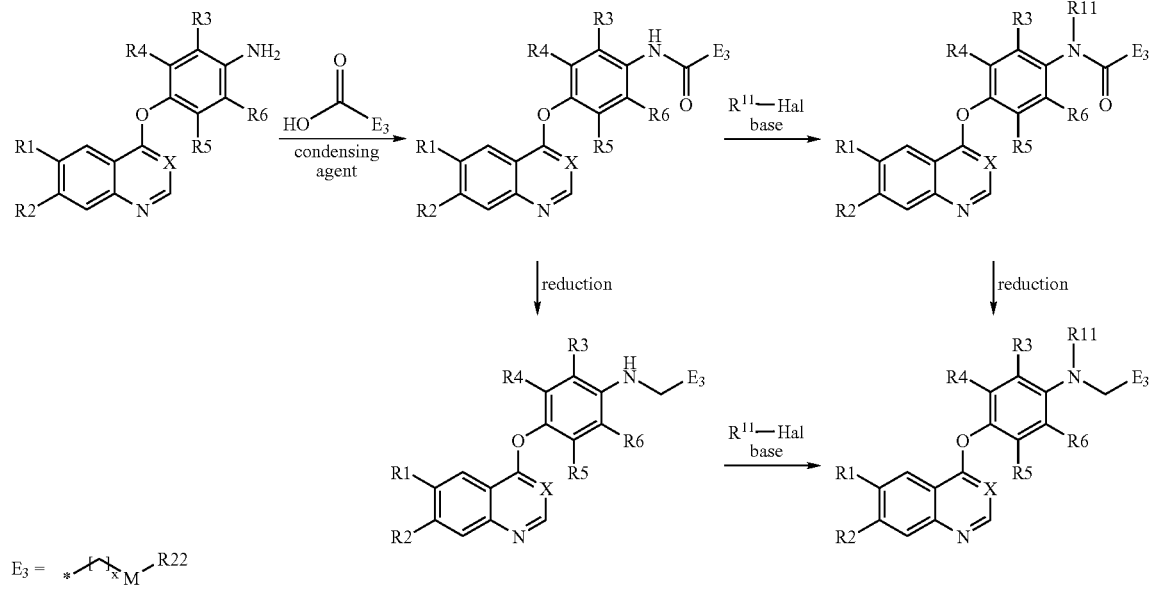

A reduced derivative may be produced by reacting a fatty acid with a 4-(aminophenoxy)quinoline derivative or a corresponding quinazoline derivative produced by a conventional method in the presence of a coupling reagent to give an amide derivative and reducing the amide derivative with diborane, lithium aluminum hydride or the like. $R^{11}$ may be introduced by reacting a reduced derivative, wherein $R^{11}$ represents a hydrogen atom, with a suitable alkylating agent ($R^{11}$Hal) in the presence of a base, for example, sodium hydride. Alternatively, $R^{11}$ may be introduced by reacting an amide derivative, wherein $R^{11}$ represents a hydrogen atom, with a suitable alkylating agent ($R^{11}$Hal) in the presence of a base, for example, sodium hydride. Further, a reduced derivative having a substituent at $R^{11}$ may be produced by reducing the derivative with diborane, lithium aluminum hydride or the like.

Use of Compounds

The compounds according to the present invention inhibit, in vitro, PDGF-R autophosphorylation and the growth and migration of vascular smooth muscle cells induced by PDGF stimulation (see Pharmacological Test Examples 1 and 2). The autophosphorylation of PDGF receptors mediates diseases, for example, ischemic diseases involving blood vessel occlusion or angiostenosis induced by angiopathy, ischemic diseases involving blood vessel occlusion or angiostenosis induced by vascular autotransplantation or allotransplantation, and diseases involving cell proliferation and organ fibrosis induced by PDGF, for example, chronic rheumatism, PDGF-dependent tumors such as glioma, cirrhosis, pulmonary fibrosis, and occlusion of arteriovenous shunt resulting, for example, from dialysis of patients suffering from renal failure (Gordon A. A. Ferns et al., Science, Vol. 253, pp 1129–1132 (1991), Martin G Sirois et al., Circulation, Vol. 95, No. 3, pp 669–675 (1997), Marukka Myllarniemi et al., The FASEB Journal, Vol. 11, pp 1119–1126 (1997), H. Ohnishi et al., Life Science, Vol. 28, pp 1641–1646 (1981), J. Gastroenterol. Vol. 32, pp 496–501 (1997), Toxicol. Appl. Pharmacol. Vol. 149, pp 120–126 (1998), and Am. J. Pathol. Vol. 148, pp 785–800 (1996)). Further, the compounds according to the present invention have low VEGF-R inhibitory activity (Pharmacological Test Example 5). Compounds, which do not inhibit VEGF-R, are expected not to accelerate angiostenosis. Furthermore, the compounds according to the present invention inhibit, in vivo, neointima formation hypertrophy of injured blood vessels (Pharmacological Test Examples 4 and 6). Therefore, the compounds according to the present invention can be used in the treatment of diseases mediated by the autophosphorylation of PDGF receptors, particularly ischemic diseases involving blood vessel occlusion/angiostenosis induced by blood vessel injury or vascular autotransplantation or allotransplantation.

The compounds according to the present invention have low c-kit autophosphorylation inhibitory activity. The c-kit autophosphorylation inhibitory activity crucially affects hematopoiesis and intestinal tract movements (Experimental Medicine, Vol. 11, No. 13, pp 42–53). Therefore, the present invention can provide compounds which do not cause any significant side effect attributable to c-kit autophosphorylation inhibitory activity.

Pharmaceutical compositions comprising compounds of the present invention as an active ingredient can be administered to human and non-human animals orally or parenterally by administration routes, for example, intravenous administration, intramuscular administration, subcutaneous administration, rectal administration, or percutaneous administration. Therefore, the pharmaceutical composition comprising the compound according to the present invention as active ingredient may be formulated into suitable dosage forms according to the administration routes.

Specifically, oral preparations include tablets, capsules, powders, granules, and syrups, and parental preparations include injections, suppositories, tapes, and ointments.

These various preparations may be prepared by conventional methods, for example, with commonly used component, such as excipients, disintegrants, binders, lubricants, colorants, and diluents.

Excipients include, for example, lactose, glucose, corn starch, sorbit, and crystalline cellulose; disintegrants include, for example, starch, sodium alginate, gelatin powder, calcium carbonate, calcium citrate, and dextrin; binders include, for example, dimethylcellulose, polyvinyl alcohol, polyvinyl ether, methylcellulose, ethylcellulose, gum arabic, gelatin, hydroxypropylcellulose, polyvinyl pyrrolidone, carboxymethylcellulose sodium salt, and chremophore; lubricants include, for example, talc, magnesium stearate, polyethylene glycol, and hydrogenated vegetable oils.

In preparing injections, if necessary, for example, buffers, pH adjustors, stabilizers, tonicity agents, and preservatives may be added.

The dose of the compound according to the present invention in the pharmaceutical composition may vary depending upon the dosage form. In general, however, the dose is about 0.5 to 50% by weight, preferably about 1 to 20% by weight, based on the whole composition.

The dose may be appropriately determined depending upon, for example, the age, weight, sex, difference in diseases, and severity of condition of patients, and the active ingredient may be administered, for example, in an amount of 0.1 to 100 mg/kg, preferably 0.1 to 30 mg/kg. This dose can be administered at a time daily or divided doses of several times daily.

EXAMPLES

The present invention will be described in more detail with reference to the following examples, though it is not limited to these examples only.

Production Example 1

4-[(6,7-Dimethoxy-4-quinazolinyl)oxy]-2-nitroaniline

Sodium hydride (60 wt%, 0.20 g) was added to dimethyl sulfoxide (15 ml), and the mixture was stirred at room temperature for 10 min. 4-Amino-3-nitrophenol (0.77 g) was added thereto, and the mixture was stirred at room temperature for 10 min. Next, 4-chloro-6,7-dimethoxyquinazoline (1.12 g) was added thereto, and the mixture was stirred at 100° C. for 3 hr. Water was added to the reaction solution, followed by extraction with chloroform. The chloroform layer was then washed with a 1 N aqueous sodium hydroxide solution and was dried over anhydrous sodium sulfate. The solvent was removed by distillation under the reduced pressure, and methanol was added to the residue to prepare a suspension. The precipitated crystal was collected by suction filtration to give the title compound (1.10 g, yield 64%).

$^1$H-NMR (CDCl$_3$-d$_1$, 400 MHz): δ 4.07 (s, 3H), 4.08 (s, 3H), 6.10–6.15 (m, 2H), 6.92 (d, J=9.0 Hz, 1H), 7.34 (s, 1H), 7.35 (dd, J=9.0 Hz, J=2.7 Hz, 1H), 7.52 (s, 1H), 8.06 (d, J=2.9 Hz, 1H), 8.62 (s, 1H) Mass spectrometry value (ESI-MS, m/z): 343 (M$^+$+1)

Production Example 2

4-[(6,7-Dimethoxy-4-quinolyl)oxy]-3-fluoroaniline

4-Chloro-6,7-dimethoxyquinazoline (10.23 g) and 2-fluoro-4-nitrophenol (14.37 g) were suspended in monochlorobenzene (100 ml), and the suspension was heated under reflux overnight. The solvent was removed by distillation under the reduced pressure, and the residue was washed with toluene, was filtered, and was dried. The crystal thus obtained was then suspended in an aqueous sodium hydroxide solution, and the suspension was filtered, followed by drying to give 4-(3-fluoro-4-nitrophenoxy)-6,7-dimethoxyquinoline (14.2 g, yield 90%). 4-(2-Fluoro-4-nitrophenoxy)-6,7-dimethoxy-quinoline (4.57 g) was dissolved in ethyl acetate/N,N-dimethylformamide/triethylamine (100 ml/100 ml/20 ml) to prepare a solution. Palladium hydroxide (1.2 g) was added to the solution, and the mixture was stirred in a hydrogen atmosphere at room temperature overnight. After filtration through Celite, the solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure to quantitatively give 4.27 g of the title compound.

$^1$H-NMR (CDCl$_3$-d$_1$, 400 MHz): δ 3.85 (m, 2H), 4.07 (s, 3H), 4.08 (s, 3H), 6.50–6.60 (m, 3H), 7.02–7.07 (m, 1H), 7.55–7.65 (m, 2H), 8.48 (d, J=5.6 Hz, 1H) Mass spectrometry value (ESI-MS, m/z): 315 (M$^+$+1)

Production Example 3

3-Chloro-4-[(6,7-dimethoxy-4-quinolyl)oxy]aniline

Sodium hydride (60 wt %, 0.72 g) was added to dimethyl sulfoxide (10 ml), and the mixture was stirred at 50° C. for 20 min. 4-Amino-3-chlorophenol hydrochloride (1.61 g) was added thereto, and the mixture was stirred at room temperature for 10 min. Next, 4-chloro-6,7-dimethoxyquinoline (1.00 g) was added thereto, and the mixture was stirred at 100° C. overnight. Water was added to the reaction solution, and the mixture was extracted with chloroform. The chloroform layer was then washed with a saturated aqueous sodium hydrogencarbonate solution and was dried over anhydrous sodium sulfate. The solvent was removed by distillation under the reduced pressure. Methanol was added to the residue, and the precipitated crystal was collected by suction filtration to give the title compound (0.80 g, yield 60%).

$^1$H-NMR (CDCl$_3$-d$_1$, 400 MHz): δ 4.06 (3H), 4.07 (s, 3H), 6.36 (d, J=5.4 Hz, 1H), 6.65 (dd, J=8.5 Hz, J=2.9 Hz, 1H), 6.76 (d, J=8.8 Hz, 1H), 7.34 (d, J=8.5 Hz, 1H), 7.51 (s, 1H), 8.46 (d, J=6.0 Hz, 1H) Mass spectrometry value (ESI-MS, m/z): 332 (M$^+$+1)

Production Example 4

4-[(6,7-Dimethoxy-4-quinolyl)oxy]-3-methylaniline

4-Chloro-6,7-dimethoxyquinazoline (5.00 g) and 4-nitro-2-methylphenol (6.85 g) were suspended in monochlorobenzene (25 ml) to prepare a suspension which was then heated under reflux overnight. The solvent was removed by distillation under the reduced pressure. The residue was washed with ethyl acetate, was filtered, and was dried. Next, the resultant crystal was suspended in an aqueous sodium hydroxide solution to prepare a suspension. The suspension was then filtered, followed by drying to give 6.89 g of 4-(2-methyl-4-nitrophenoxy)-6,7-dimethoxyquinoline. 4-(2-Methyl-4-nitrophenoxy)-6,7-dimethoxyquinoline (1.36 g) was dissolved in ethyl acetate/N,N-dimethylformamide/triethylamine (25 ml/25 ml/5 ml). Palladium hydroxide (0.4 g) was added to the solution, and the mixture was stirred in a hydrogen atmosphere at room temperature overnight. After filtration through Celite, the solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure to give the title compound (1.31 g, yield 91%).

Mass spectrometry value (ESI-MS, m/z): 311 ($M^+$+1)

Production Example 5

4-[(6,7-Dimethoxy-4-quinazolinyl)oxy]-2-methoxyaniline

Sodium hydride (60 wt %, 3.2 g) was added to dimethyl sulfoxide (50 ml), and the mixture was stirred at 50° C. for 20 min. 4-Amino-3-methoxyphenol (5.6 g) was added thereto, and the mixture was stirred at room temperature for 10 min. Next, 4-chloro-6,7-dimethoxyquinazoline (7.0 g) was added thereto, and the mixture was stirred at 100° C. overnight. Water was added to the reaction solution, and the mixture was extracted with chloroform. The chloroform layer was then washed with a saturated aqueous sodium hydrogencarbonate solution and was dried over anhydrous sodium sulfate. The solvent was removed by distillation under the reduced pressure. Methanol was added to the residue, and the precipitated crystal was collected by suction filtration to give the title compound (7.3 g, yield 72%).

Mass spectrometry value (ESI-MS, m/z): 328 ($M^+$+1)

Example 1

4-Methylbenzyl N-{4-[(6,7-dimethoxy-4-quinazolinyl)oxy]phenyl}carbamate

4-[(6,7-Dimethoxy-4-quinazolinyl)oxy]aniline (129 mg) was added to toluene/triethylamine=10/1 (10 ml), and the mixture was heated under reflux to prepare a solution. A solution of triphosgene (193 mg) in methylene chloride was then added to the solution, and the mixture was heated under reflux for 15 min. Subsequently, 4-methylbenzyl alcohol (79 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated, and the residue was purified on a column using chloroform/methanol to give the title compound (108 mg, yield 51%).

$^1$H-NMR (CDCl$_3$, 400 MHz): 8.61 (1H, s), 7.16–7.54 (10H, m), 6,70 (1H, s), 5.16 (2H, s), 4.05 (6H, s), 2.35 (3H, s) Mass spectrometry value (ESI-MS, m/z): 446 ($M^+$+1)

Example 2

4-Methylbenzyl N-{2-chloro-4-[(6,7-dimethoxy-4-quinazolinyl)oxy]phenyl}carbamate 2-Chloro-4-[(6,7-dimethoxy-4-quinazolinyl)oxy]aniline (109 mg) was added to toluene/triethylamine=10/1 (10 ml), and the mixture was heated under reflux to prepare a solution. A solution of triphosgene (146 mg) in methylene chloride was then added to the solution, and the mixture was heated under reflux for 15 min. Subsequently, 4-methylbenzyl alcohol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 28%).

$^1$H-NMR (CDCl$_3$, 400 MHz): 8.61 (1H, s), 8.29 (1H, d, J=9.0), 7.50 (1H, s), 7.15–7.35 (8H, m), 5.18 (2H, s), 4.05 (3H, s), 4.05 (3H, s), 2.36 (3H, s) Mass spectrometry value (ESI-MS, m/z): 481 ($M^+$+1)

Example 3

1-(3-Chlorophenyl)ethyl N-{4-((6,7-dimethoxy-4-quinazolinyl)oxy)phenyl}carbamate 4-[(6,7-Dimethoxy-4-quinolyl)oxy]aniline (72 mg) was added to toluene/triethylamine=10/1 (8 ml), and the mixture was heated under reflux to prepare a solution. A solution of triphosgene (109 mg) in methylene chloride was then added to the solution, and the mixture was heated under reflux for 15 min. Subsequently, 3-chloro-α-methylbenzyl alcohol (46 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 70%).

$^1$H-NMR (CDCl$_3$, 400 MHz): 8.44–8.50 (1H, m), 8.14 (1H, s), 7.58–7.64 (3H, m), 7.26–7.42 (4H, m), 7.15–7.19 (2H, m), 6.86 (1H, s), 6.67 (1H, d, J=6.6), 5.88 (1H, q, J=6.6), 4.16

Example 4

1-(3-Chlorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (75 mg) was added to toluene/triethylamine=10/1 (8 ml), and the mixture was heated under reflux to prepare a solution. A solution of triphosgene (100 mg) in methylene chloride was then added to the solution, and the mixture was heated under reflux for 15 min. Subsequently, 3-chloro-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (62 mg, yield 49%).
$^1$H-NMR (CDCl$_3$, 400 MHz): 8.41–8.47 (1H, m), 8.15 (1H, s), 7.71–7.76 (1H, m), 7.66 (1H, s), 7.25–7.45 (4H, m), 7.01 (1H, d, J=9.2 Hz), 6.50–6.55 (2H, m), 5.87 (1H, q, J=6.5 Hz), 4.17 (3H, s), 4.11 (3H, s), 2.27 (3H, s), 2.10 (3H, s), 1.62 (3H, d, J=6.5 Hz) Mass spectrometry value (ESI-MS, m/z): 508 (M$^+$+1)

Example 5

1-(3-Chlorophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (75 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-chloro-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (70 mg, yield 56%).
$^1$H-NMR (CDCl$_3$, 400 MHz): 8.37–8.44 (1H, m), 8.07 (1H, s), 7.82 (1H, bs), 7.57 (1H, s), 7.34 (1H, s), 7.20–7.26 (3H, m), 6.88 (1H, s), 6.49 (1H, d, J=6.6 Hz), 6.44 (1H, m), 5.80 (1H, q, J=6.6 Hz), 4.10 (3H, s), 4.03 (3H, s), 2.22 (3H, s), 2.04 (3H, s), 1.56 (3H, d, J=6.6 Hz) Mass spectrometry value (ESI-MS, m/z): 508 (M$^+$+1)

Example 6

1-(3-Chlorophenyl)ethyl N-{4-[(6,7-dimethoxy-4-quinazolinyl)oxy]phenyl}carbamate 4-[(6,7-Dimethoxy-4-quinazolinyl)oxy]aniline (72 mg) was added to toluene/triethylamine=10/1 (8 ml), and the mixture was heated under reflux to prepare a solution. A solution of triphosgene (100 mg) in methylene chloride was then added thereto, and the mixture was heated under reflux for 15 min. Subsequently, 3-chloro-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (71 mg, yield 57%).
$^1$H-NMR (CDCl$_3$, 400 MHz): 8.76 (1H, s), 8.07 (1H, s), 7.50–7.60 (3H, m), 7.15–7.39 (5H, m), 6.83 (1H, s), 6.75–6.78 (1H, m), 5.84 (1H, q, J=6.8 Hz), 4.16 (3H, s), 4.09 (3H, s), 1.59 (3H, d, J=6.8 Hz) Mass spectrometry value (ESI-MS, m/z): 481 (M$^+$+1)

Example 7

1-(3-Chlorophenyl)ethyl N-{2-chloro-4-[6,7-dimethoxy-4-quinazolinyl)oxy]phenyl}carbamate 2-Chloro-4-[(6,7-dimethoxy-4-quinazolinyl)oxy]-aniline (72 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 3-chloro-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (43 mg, yield 36%).
$^1$H-NMR (CDCl$_3$, 400 MHz): 8.77 (1H, s), 8.33 (1H, d, J=9.0 Hz), 8.06 (1H, s), 7.55 (1H, s), 7.39 (1H, s), 7.22–7.32 (6H, m), 5.85 (1H, q, J=6.7 Hz), 4.16 (3H, s), 4.09 (3H, s), 1.61 (3H, d, J=6.6 Hz) Mass spectrometry value (ESI-MS, m/z): 415 (M$^+$+1)

Example 8

4-Fluorobenzyl N-{4-[(6,7-dimethoxy-4-quinolyl)oxy]phenyl}carbamate

4-[(6,7-Dimethoxy-4-quinolyl)oxy]aniline (72 mg) was added to toluene/triethylamine=10/1 (8 ml), and the mixture was heated under reflux to prepare a solution. A solution of triphosgene (108 mg) in methylene chloride was then added to the solution, and the mixture was heated under reflux for 15 min. Subsequently, 4-fluorobenzyl alcohol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 58%).

$^1$H-NMR (CDCl$_3$, 400 MHz): 8.44–8.50 (1H, m), 8.14 (1H, s), 7.63 (1H, s), 7.56–7.66 (2H, m), 7.38–7.44 (2H, m), 7.16–7.20 (2H, m), 7.05–7.11 (2H, m), 6.85 (1H, s), 6.68 (1H, s), 5.20 (2H, s), 4.17 (3H, s), 4.10 (3H, s) Mass spectrometry value (ESI-MS, m/z): 429 (M$^+$+1)

Example 9

4-Fluorobenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (78 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 4-fluorobenzyl alcohol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 62%).

$^1$H-NMR (CDCl$_3$, 400 MHz): 8.42–8.47 (1H, m), 8.16 (1H, s), 7.66 (1H, s), 6.99–7.45 (6H, m), 6.50–6.56 (2H, m), 5.20 (2H, s), 4.17 (3H, s), 4.11 (3H, s), 2.25 (3H, s), 2.10 (3H, s) Mass spectrometry value (ESI-MS, m/z): 477 (M$^+$+1)

Example 10

4-Fluorobenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (82 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 4-fluorobenzyl alcohol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 68%).

$^1$H-NMR (CDCl$_3$, 400 MHz): 8.43–8.48 (1H, m), 8.15 (1H, m), 7.91 (1H, s), 7.64 (1H, s), 6.94–7.53 (6H, m), 6.57 (1H, d, J=6.6 Hz), 6.49 (1H, s), 5.20 (2H, s), 4.17 (3H, s), 4.11 (3H, s), 2.27 (3H, s), 2.13 (3H, s) Mass spectrometry value (ESI-MS, m/z): 477 (M$^+$+1)

Example 11

4-Fluorobenzyl N-{4-[(6,7-dimethoxy-4-quinazolinyl)oxy]phenyl}carbamate

4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (115 mg) in methylene chloride was then added thereto, and the mixture was heated under reflux for 15 min. Subsequently, 4-fluorobenzyl alcohol (45 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (43 mg, yield 33%).

$^1$H-NMR (CDCl$_3$, 400 MHz): 8.64 (1H, s), 7.56 (1H, s), 7.00–7.54 (9H, m), 6.72 (1H, s), 5.19 (2H, s), 4.09 (3H, s), 4.08 (3H, s) Mass spectrometry value (ESI-MS, m/z): 450 (M$^+$+1)

Example 12

4-Fuorobenzyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (72 mg) was added to toluene/triethylamine=10/1 (8 ml), and the mixture was heated under reflux to prepare a solution. A solution of triphosgene (116 mg) in methylene chloride was then added thereto, and the mixture was heated under reflux for 15 min. Subsequently, 4-fluorobenzyl alcohol (45 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (38 mg, yield 34%).

$^1$H-NMR (CDCl$_3$, 400 MHz): 8.64 (1H, s), 8.30 (1H, d, J=9.3 Hz), 7.52 (1H, s), 7.40–7.45 (3H, m), 7.32–7.34 (1H, m), 7.18–7.22 (2H, m), 7.06–7.12 (2H, m), 5.21 (2H, s), 4.08 (3H, s), 4.07 (3H, s) Mass spectrometry value (ESI-MS, m/z): 485 (M$^+$+1)

Example 13

1-(2-Chlorophenyl)ethyl N-{4-[(6,7-dimethoxy-4-quinolyl)oxy]phenyl}carbamate

4-[(6,7-Dimethoxy-4-quinolyl)oxy]aniline (69 mg) was added to toluene/triethylamine=10/1 (8 ml), and the mixture was heated under reflux to prepare a solution. A solution of triphosgene (103 mg) in methylene chloride was then added thereto, and the mixture was heated under reflux for 15 min. Subsequently, 2-chloro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 64%).

$^1$H-NMR (CDCl$_3$, 400 MHz): 8.40–8.48 (1H, m), 8.14 (1H, s), 7.15–7.64 (9H, m), 6.86 (1H, s), 6.67 (1H, d, J=6.6 Hz), 6.28 (1H, q, J=6.6 Hz), 4.16 (3H, s), 4.19 (3H, s), 1.63 (3H, d, J=6.6 Hz) Mass spectrometry value (ESI-MS, m/z): 480 (M$^+$+1)

Example 14

1-(2-Chlorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (67 mg) was added to toluene/triethylamine=10/1 (8 ml), and the mixture was heated under reflux to prepare a solution. A solution of triphosgene (92 mg) in methylene chloride was then added thereto, and the mixture was heated under reflux for 15 min. Subsequently, 2-chloro-α-methylbenzyl alcohol (48 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 79%).

$^1$H-NMR (CDCl$_3$, 400 MHz): 8.43 (1H, d, J=6.6 Hz), 8.14 (1H, s), 7.72–7.78 (1H, m), 7.66 (1H, s), 7.25–7.54 (4H, m), 7.00 (1H, d, J=8.6 Hz), 6.50–6.57 (2H, m), 6.27 (1H, q, J=6.6 Hz), 4.17 (3H, s), 4.11 (3H, s), 2.27 (3H, s), 2.09 (3H, s), 1.63 (3H, d, J=6.6 Hz) Mass spectrometry value (ESI-MS, m/z): 508 (M$^+$+1)

Example 15

1-(2-Chlorophenyl)ethyl N-{4-[(6,7-dimethoxy-4-quinazolinyl)oxy]phenyl}carbamate 4-[(6,7-Dimethoxy-4-quinazolinyl)oxy]aniline (62 mg) was added to toluene/triethylamine=10/1 (6 ml), and the mixture was heated under reflux to prepare a solution. A solution of triphosgene (93 mg) in methylene chloride was then added thereto, and the mixture was heated under reflux for 15 min. Subsequently, 2-chloro-α-methylbenzyl alcohol (49 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (52 mg, yield 48%). Mass spectrometry value (ESI-MS, m/z): 480 (M$^+$+1)

Example 16

1-(2-Chlorophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (61 mg) was added to toluene/triethylamine=10/1 (7 ml), and the mixture was heated under reflux to prepare a solution. A solution of triphosgene (91 mg) in methylene chloride was then added thereto, and the mixture was heated under reflux for 15 min. Subsequently, 2-chloro-α-methylbenzyl alcohol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 69%).

$^1$H-NMR (CDCl$_3$, 400 MHz): 8.77 (1H, s), 8.36 (1H, d, J=8.8 Hz), 8.00–8.05 (1H, m), 7.16–7.57 (8H, m), 6.28 (1H, q, J=6.8 Hz), 4.17 (3H, s), 4.10 (3H, s), 1.63 (3H, d, J=6.8 Hz) Mass spectrometry value (ESI-MS, m/z): 515 (M$^+$+1)

Example 17

3-(2-Chlorophenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (78 mg) was added to toluene/triethylamine=10/1 (8 ml), and the mixture was heated under reflux to prepare a solution. A solution of triphosgene (117 mg) in methylene chloride was then added to the solution, and the mixture was heated under reflux for 15 min. Subsequently, 3-(2-chlorophenoxy)-1-propanol (67 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 58%).

$^1$H-NMR (CDCl$_3$, 400 MHz): 8.43 (1H, d, J=5.4 Hz), 7.61 (1H, s), 7.48 (1H, s), 7.35–7.40 (1H, m), 7.18–7.25 (2H, m), 6.87–7.05 (3H, m), 6.43 (1H, bs), 6.27 (1H, d, J=4.9 Hz), 4.46 (2H, t, J=6.2 Hz), 4.05–4.22 (2H, m), 4.07 (3H, s), 4.06 (3H, s), 2.24 (3H, s), 2.11 (3H, s), 2.10–2.22 (2H, m) Mass spectrometry value (ESI-MS, m/z): 538 (M$^+$+1)

Example 18

3-(2-Chlorophenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (71 mg) was added to toluene/triethylamine=10/1 (8 ml), and the mixture was heated under reflux to prepare a solution. A solution of triphosgene (97 mg) in methylene chloride was then added to the solution, and the mixture was heated under reflux for 15 min. Subsequently, 3-(2-chlorophenoxy)-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (62 mg, yield 44%).

$^1$H-NMR (CDCl$_3$, 400 MHz): 8.44 (1H, d, J=5.4 Hz), 7.50–7.80 (2H, m), 7.19–7.40 (3H, m), 6.88–6.98 (3H, m), 6.35–6.48 (2H, m), 4.65 (2H, t, J=6.2 Hz), 4.18 (2H, t, J=6.0 Hz), 4.07 (3H, s), 4.07 (3H, s), 2.10–2.30 (8H, m) Mass spectrometry value (ESI-MS, m/z): 538 (M$^+$+1)

Example 19

3-(2-Chlorophenoxy)propyl N-{4-[(6,7-dimethoxy-4-quinazolinyl)oxy]phenyl}carbamate 4-[(6,7-Dimethoxy-4-quinazolinyl)oxy]aniline (77 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 3-(2-chlorophenoxy)-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (62 mg, yield 44%).

$^1$H-NMR (CDCl$_3$, 400 MHz): 8.62–8.64 (1H, m), 7.55–7.57 (1H, m), 7.48–7.53 (2H, m), 7.35–7.40 (2H, m), 7.19–7.28 (3H, m), 6.87–6.97 (2H, m), 6.77 (1H, bs), 4.43–4.48 (2H, m), 4.14–4.20 (2H, m), 4.08 (3H, s), 4.07 (3H, s), 2.15–2.28 (2H, m) Mass spectrometry value (ESI-MS, m/z): 511 (M$^+$+1)

Example 20

3-(2-Chlorophenoxy)propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (70 mg) was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 3-(2-chlorophenoxy)-1-propanol (59 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 50%).

$^1$H-NMR (CDCl$_3$, 400 MHz): 8.63 (1H, s), 8.25–8.35 (1H, d), 7.52 (1H, s), 7.14–7.41 (6H, m), 6.88–6.98 (2H, m), 4.48 (2H, t, J=6.2 Hz), 4.18 (2H, t, J=6.2 Hz), 4.08 (3H, s), 4.07 (3H, s), 2.10–2.50 (2H, m) Mass spectrometry value (ESI-MS, m/z): 545 (M$^+$+1)

Example 21

4-(Trifluoromethyl)benzyl N-{4-[(6,7-dimethoxy-4-quinolyl)oxy]phenyl}carbamate

4-[(6,7-Dimethoxy-4-quinolyl)oxy]aniline (75 mg) was added to toluene/triethylamine=10/1 (8 ml), and the mixture was heated under reflux to prepare a solution. A solution of triphosgene (112 mg) in methylene chloride was then added to the solution, and the mixture was heated under reflux for 15 min. Subsequently, 4-trifluoromethylbenzyl alcohol (67 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 57%).

$^1$H-NMR (CDCl$_3$, 400 MHz): 8.43–8.48 (1H, m), 8.14 (1H, s), 7.47–7.70 (7H, m), 7.15–7.22 (3H, m), 6.68 (1H, d, J=6.6 Hz), 5.29 (2H, s), 4.16 (3H, s), 4.10 (3H, s) Mass spectrometry value (ESI-MS, m/z): 499 (M$^+$+1)

Example 22

4-(Trifluoromethyl)benzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (77 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 4-trifluoromethylbenzyl alcohol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 60%).

$^1$H-NMR (CDCl$_3$, 400 MHz): 8.44 (1H, d, J=6.4 Hz), 8.00–8.15 (1H, m), 7.53–7.69 (6H, m), 7.03 (1H, d, J=9.0 Hz), 6.54–6.65 (1H, m), 6.47–6.53 (1H, m), 5.29 (3H, s), 4.15 (3H, s), 4.11 (3H, s), 2.27 (3H, s), 2.11 (3H, s) Mass spectrometry value (ESI-MS, m/z): 528 (M$^+$+1)

Example 23

4-(Trifluoromethyl)benzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (77 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 4-trifluoromethylbenzyl alcohol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 48%).
$^1$H-NMR (CDCl$_3$, 400 MHz): 8.43–8.48 (1H, m), 8.16 (1H, s), 7.50–7.95 (6H, m), 6.97 (1H, s), 6.55–6.60 (2H, m), 5.29 (2H, m), 4.17 (3H, s), 4.11 (3H, s), 2.29 (3H, s), 2.14 (3H, s) Mass spectrometry value (ESI-MS, m/z): 528 (M$^+$+1)

Example 24

4-(Trifluoromethyl)benzyl N-{4-[(6,7-dimethoxy-4-quinazolinyl)oxy]phenyl}carbamate 4-[(6,7-Dimethoxy-4-quinazolinyl)oxy]aniline (70 mg) was added to toluene/triethylamine=10/1 (7 ml), and the mixture was heated under reflux to prepare a solution. A solution of triphosgene (105 mg) in methylene chloride was then added to the solution, and the mixture was heated under reflux for 15 min. Subsequently, 4-trifluoromethylbenzyl alcohol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 48%).
$^1$H-NMR (CDCl$_3$, 400 MHz): 8.70 (1H, s), 7.48–7.78 (8H, m), 7.20–7.24 (2H, m), 6.94 (1H, bs), 5.28 (2H, s), 4.13 (3H, s), 4.10 (3H, s) Mass spectrometry value (ESI-MS, m/z): 500 (M$^+$+1)

Example 25

4-(Trifluoromethyl)benzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (74 mg) was added to toluene/triethylamine=10/1 (7 ml), and the mixture was heated under reflux to prepare a solution. A solution of triphosgene (99 mg) in methylene chloride was then added to the solution, and the mixture was heated under reflux for 15 min. Subsequently, 4-trifluoromethylbenzyl alcohol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (52 mg, yield 41%).
$^1$H-NMR (CDCl$_3$, 400 MHz): 8.62–8.65 (1H, m), 8.25–8.34 (1H, m), 7.16–7.71 (9H, m), 5.27–5.31 (2H, m), 4.05–4.08 (6H, m) Mass spectrometry value (ESI-MS, m/z): 535 (M$^+$+1)

Example 26

3-(2-Chlorophenoxy)propyl N-{4-[(6,7-dimethoxy-4-quinolyl)oxy]phenyl}carbamate

4-[(6,7-Dimethoxy-4-quinolyl)oxy]aniline (61 mg) was added to toluene/triethylamine=10/1 (6 ml), and the mixture was heated under reflux to prepare a solution. A solution of triphosgene (91 mg) in methylene chloride was then added to the solution, and the mixture was heated under reflux for 15 min. Subsequently, 3-(2-chlorophenoxy)-1-propanol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 69%).
$^1$H-NMR (CDCl$_3$, 400 MHz): 8.43–8.50 (1H, m), 8.15 (1H, s), 7.64 (1H, s), 7.56–7.65 (2H, m), 6.89–7.40 (6H, m), 6.81 (1H, s), 6.68 (1H, d, J=6.4 Hz), 4.48 (2H, t, J=6.2 Hz), 4.15–4.22 (2H, m), 4.17 (3H, s), 4.10 (3H, s), 2.20–2.30 (2H, m) Mass spectrometry value (ESI-MS, m/z): 510 (M$^+$+1)

Example 27

3-(4-Chlorophenoxy)propyl N-{4-[(6,7-dimethoxy-4-quinolyl)oxy]phenyl}carbamate

4-[(6,7-Dimethoxy-4-quinolyl)oxy]aniline (79 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-(4-chlorophenoxy)-1-propanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 55%).

$^1$H-NMR (CDCl$_3$, 400 MHz): 8.44–8.50 (1H, m), 8.15 (1H, s), 7.63 (1H, s), 7.52–7.64 (4H, m), 6.77–6.87 (3H, m), 6.68 (1H, d, J=6.3 Hz), 4.41 (2H, t, J=6.3 Hz), 4.17 (3H, s), 4.10 (3H, s), 4.05–4.10 (2H, m), 2.15–2.22 (2H, m) Mass spectrometry value (ESI-MS, m/z): 510 (M$^+$+1)

Example 28

3-(4-Chlorophenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (80 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 3-(4-chlorophenoxy)-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (84 mg, yield 60%).
$^1$H-NMR (CDCl$_3$, 400 MHz): 8.41–8.48 (1H, m), 8.16 (1H, s), 7.65–7.75 (1H, m), 6.82–7.27 (7H, m), 6.43–6.58 (1H, m), 4.41 (2H, d, J=6.3 Hz), 4.17 (3H, s), 4.11 (3H, s), 4.05–4.15 (2H, m), 2.26 (3H, s), 2.10 (3H, s), 2.00–2.08 (2H, m) Mass spectrometry value (ESI-MS, m/z): 538 (M$^+$+1)

Example 29

3-(4-Chlorophenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (78 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 3-(4-chlorophenoxy)-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (71 mg, yield 51%).
$^1$H-NMR (CDCl$_3$, 400 MHz): 8.43–8.48 (1H, m), 8.15 (1H, s), 7.88 (1H, bs), 7.64 (1H, s), 6.82–7.26 (6H, m), 6.57 (1H, d, J=6.6 Hz), 6.43 (1H, bs), 4.12 (2H, t, J=6.6 Hz), 4.17 (3H, s), 4.11 (3H, s), 4.05–4.11 (2H, m), 2.28 (3H, s), 2.15–2.23 (2H, m), 2.12 (3H, s) Mass spectrometry value (ESI-MS, m/z): 538 (M$^+$+1)

Example 30

3-(4-Chlorophenoxy)propyl N-{4-[(6,7-dimethoxy-4-quinazolinyl)oxy]phenyl}carbamate 4-[(6,7-Dimethoxy-4-quinazolinyl)oxy]aniline (78 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-(4-chlorophenoxy)-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 37%).
$^1$H-NMR (CDCl$_3$, 400 MHz): 8.79 (1H, s), 8.14 (1H, s), 7.61 (1H, s), 7.53–7.58 (2H, m), 7.16–7.26 (4H, m), 6.76–6.86 (3H, m), 4.40 (2H, t, J=6.2 Hz), 4.19 (3H, s), 4.12 (3H, s), 4.02–4.10 (2H, m), 2.15–2.21 (2H, m) Mass spectrometry value (ESI-MS, m/z): 511 (M$^+$+1)

Example 31

3-(4-Chlorophenoxy)propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (75 mg) was added to toluene/triethylamine=10/1 (8 ml), and the mixture was heated under reflux to prepare a solution. A solution of triphosgene (121 mg) in methylene chloride was then added to the solution, and the mixture was heated under reflux for 15 min. Subsequently, 3-(4-chlorophenoxy)-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 44%).
$^1$H-NMR (CDCl$_3$, 400 MHz): 8.70 (1H, s), 8.25–8.35 (1H, m), 7.65–7.70 (1H, m), 7.54 (1H, s), 7.15–7.35 (4H, m), 6.82–6.87 (3H, m), 4.42 (2H, t, J=6.4 Hz), 4.12 (3H, s), 4.09 (3H, s), 4.05–4.13 (2H, m), 2.17–2.25 (2H, m) Mass spectrometry value (ESI-MS, m/z): 545 (M$^+$+1)

Example 32

1-(4-Methoxyphenyl)ethyl N-{4-[(6,7-dimethoxy-4-quinolyl)oxy]phenyl}carbamate

4-[(6,7-Dimethoxy-4-quinolyl)oxy]aniline (73 mg) was added to toluene/triethylamine=10/1 (7 ml), and the mixture was heated under reflux to prepare a solution. A solution of triphosgene (110 mg) in methylene chloride was then added to the solution, and the mixture was heated under reflux for 15 min. Subsequently, 4-methoxy-α-methylbenzyl alcohol (56 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (74 mg, yield 59%).

$^1$H-NMR (CDCl$_3$, 400 MHz): 8.44–8.48 (1H, m), 8.14 (1H, s), 7.63 (1H, s), 7.55–7.62 (2H, m), 7.33–7.38 (2H, m), 7.14–7.18 (2H, m), 6.88–6.94 (2H, m), 6.79 (1H, s), 6.67 (1H, d, J=6.4 Hz), 5.86–5.93 (1H, m), 4.16 (3H, s), 4.10 (3H, s), 3.82 (3H, s), 1.63 (3H, d, J=6.6 Hz) Mass spectrometry value (ESI-MS, m/z): 476 (M$^+$+1)

Example 33

1-(4-Methoxyphenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (68 mg) was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 4-methoxy-α-methylbenzyl alcohol (48 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (75 mg, yield 66%).

$^1$H-NMR (CDCl$_3$, 400 MHz): 8.40–8.45 (1H, m), 8.15 (1H, s), 7.73–7.78 (1H, m), 7.66 (1H, s), 7.33–7.38 (2H, m), 6.98–7.02 (1H, m), 6.89–6.94 (2H, m), 6.53 (1H, d, J=6.6 Hz), 6.46 (1H, bs), 5.85–5.92 (1H, m), 4.20 (3H, s), 4.11 (3H, s), 3.82 (3H, s), 2.24 (3H, s), 2.09 (3H, s), 1.63 (3H, d, J=6.6 Hz) Mass spectrometry value (ESI-MS, m/z): 504 (M$^+$+1)

Example 34

1-(4-Methoxyphenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 4-methoxy-α-methylbenzyl alcohol (56 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 60%).

$^1$H-NMR (CDCl$_3$, 400 MHz): 8.41–8.47 (1H, m), 8.15 (1H, s), 7.92 (1H, s), 7.64 (1H, s), 6.80–7.40 (5H, m), 6.55 (1H, d, J=6.6 Hz), 6.44 (1H, s), 5.85–5.92 (1H, m), 4.17 (3H, s), 4.11 (3H, s), 3.82 (3H, s), 2.26 (3H, s), 2.11 (3H, s), 1.64 (3H, d, J=6.6 Hz) Mass spectrometry value (ESI-MS, m/z): 504 (M$^+$+1)

Example 35

1-(4-Methoxyphenyl)ethyl N-{4-[(6,7-dimethoxy-4-quinazolinyl)oxy]phenyl}carbamate 4-[(6,7-Dimethoxy-4-quinazolinyl)oxy]aniline (68 mg) was added to toluene/triethylamine=10/1 (7 ml), and the mixture was heated under reflux to prepare a solution. A solution of triphosgene (102 mg) in methylene chloride was then added to the solution, and the mixture was heated under reflux for 15 min. Subsequently, 4-methoxy-α-methylbenzyl alcohol (52 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 52%).

$^1$H-NMR (CDCl$_3$, 400 MHz): 8.72 (1H, s), 7.85 (1H, s like), 7.58 (1H, s), 7.48–7.55 (2H, m), 7.32–7.37 (2H, m), 7.15–7.20 (2H, m), 6.87–6.93 (2H, m), 6.72 (1H, s), 5.85–5.92 (1H, m), 4.14 (3H, s), 4.10 (3H, s), 3.81 (3H, s), 1.61 (3H, d, J=6.6 Hz) Mass spectrometry value (ESI-MS, m/z): 477 (M$^+$+1)

Example 36

1-(4-Methoxyphenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (66 mg) was added to toluene/triethylamine=10/1 (7 ml), and the mixture was heated under reflux to prepare a solution. A solution of triphosgene (88 mg) in methylene chloride was then added to the solution, and the mixture was heated under reflux for 15 min. Subsequently, 4-methoxy-α-methylbenzyl alcohol (45 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 53%).

$^1$H-NMR (CDCl$_3$, 400 MHz): 8.76 (1H, s like), 8.32–8.40 (1H, m), 6.88–8.00 (9H, m), 5.87–5.93 (1H, m), 4.16 (3H, s), 4.10 (3H, s), 3.82 (3H, s), 1.63 (3H, d, J=6.6 Hz) Mass spectrometry value (ESI-MS, m/z): 511 (M$^+$+1)

Example 37

3-[(4-Methylphenyl)sulfanyl)propyl N-{4-[(6,7-dimethoxy-4-quinolyl)oxy]phenyl}carbamate 4-[(6,7-Dimethoxy-4-quinolyl)oxy]aniline (80 mg) was added to toluene/triethylamine=10/1 (8 ml), and the mixture was heated under reflux to prepare a solution. A solution of triphosgene (121 mg) in methylene chloride was then added to the solution, and the mixture was heated under reflux for 15 min. Subsequently, 3-[(4-methylphenyl)sulfanyl]-1-propanol (74 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (98 mg, yield 67%).

$^1$H-NMR (CDCl$_3$, 400 MHz): 8.44–8.50 (H, m), 8.15 (1H, s), 7.64 (1H, s), 7.55–7.64 (2H, m), 7.10–7.31 (6H, m), 6.77 (1H, s), 6.69 (1H, d, J=6.6 Hz), 4.32 (2H, t, J=6.2 Hz), 4.17 (3H, s), 4.10 (3H, s), 2.97–3.03 (2H, m), 2.33 (3H, s), 1.95–2.05 (2H, m) Mass spectrometry value (ESI-MS, m/z): 506 (M$^+$+1)

Example 38

3-[(4-Methylphenyl)sulfanyl)propyl N-{4-(6,7-dimethoxy-4-quinolyl)oxy]-2,3-dimethylphenyl}carbamate 4-[(6,7-Dimethoxy-4-quinolyl)oxy]-2,3-dimethylaniline (85 mg) was added to toluene/triethylamine=10/1 (9 ml), and the mixture was heated under reflux to prepare a solution. A solution of triphosgene (122 mg) in methylene chloride was then added to the solution, and the mixture was heated under reflux for 15 min. Subsequently, 3-[(4-methylphenyl)sulfanyl]-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (93 mg, yield 62%).

$^1$H-NMR (CDCl$_3$, 400 MHz): 8.40–8.48 (1H, m), 8.16 (1H, s), 7.65–7.77 (2H, m), 7.00–7.31 (5H, m), 6.55 (1H, d, J=6.4 Hz), 6.40–6.50 (1H, m), 4.29–4.40 (1H, m), 4.17 (3H, s), 4.11 (3H, s), 3.74–3.80 (1H, m), 2.95–3.05 (2H, m), 2.26–2.34 (6H, m), 2.10 (3H, s), 1.84–2.04 (2H, m) Mass spectrometry value (ESI-MS, m/z): 523 (M$^+$+1)

Example 39

3-[(4-Methylphenyl)sulfanyl)propyl N-{4-[(6,7-dimethoxy-4-quinolyl)oxy]-2,5-dimethylphenyl}-carbamate 4-[(6,7-Dimethoxy-4-quinolyl)oxy]-2,5-dimethylaniline (85 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-[(4-methylphenyl)sulfanyl]-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (82 mg, yield 56%).

$^1$H-NMR (CDCl$_3$, 400 MHz): 8.40–8.49 (1H, m), 8.16 (1H, s), 7.85–7.92 (1H, m), 7.64 (1H, s), 7.08–7.32 (4H, m), 6.95 (1H, s), 6.57 (1H, d, J=6.6 Hz), 6.40 (1H, s), 4.30–4.40 (2H, m), 4.17 (3H, s), 4.11 (3H, s), 2.95–3.15 (2H, m), 2.27–2.34 (6H, m), 2.13 (3H, s), 1.98–2.06 (2H, m) Mass spectrometry value (ESI-MS, m/z): 524 (M$^+$+1)

Example 40

3-[(4-Methylphenyl)sulfanyl)propyl N-{4-[(6,7-dimethoxy-4-quinazolinyl)oxy]phenyl}carbamate 4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-[(4-methylphenyl)sulfanyl]-1-propanol (74 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (82 mg, yield 56%).

$^1$H-NMR (CDCl$_3$, 400 MHz): 8.66 (1H, s), 7.57 (1H, s), 7.48–7.55 (2H, m), 7.10–7.31 (7H, m), 6.65 (1H, bs), 4.27–4.38 (2H, m), 4.10 (3H, s), 4.09 (3H, s), 2.95–3.15 (2H, m), 2.32 (3H, s), 1.95–2.05 (2H, m) Mass spectrometry value (ESI-MS, m/z): 507 (M$^+$+1)

Example 41

3-[(4-Methylphenyl)sulfanyl)propyl N-{2-chloro-4-[(6,7-dimethoxy-4-quinazolinyl)oxy]phenyl}-carbamate 2-Chloro-4-[(6,7-dimethoxy-4-quinazolinyl)oxy]-aniline (80 mg) was added to toluene/triethylamine=10/1 (8 ml), and the mixture was heated under reflux to prepare a solution. A solution of triphosgene (125 mg) in methylene chloride was then added to the solution, and the mixture was heated under reflux for 15 min. Subsequently, 3-[(4-methylphenyl)sulfanyl]-1-propanol (66 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 49%).

$^1$H-NMR (CDCl$_3$, 400 MHz): 8.76 (1H, s), 8.31–8.38 (1H, m), 7.91 (1H, bs), 7.56 (2H, s), 7.10–7.34 (6H, m), 4.30–4.43 (2H, m), 4.16 (3H, s), 4.11 (3H, s), 3.00 (2H, t, J=7.0 Hz), 2.32 (3H, s), 1.97–2.06 (2H, m) Mass spectrometry value (ESI-MS, m/z): 541 (M$^+$+1)

Example 42

3-(4-Methoxyphenoxy)propyl N-{4-[(6,7-dimethoxy-4-quinolyl)oxy]phenyl}carbamate

4-[(6,7-Dimethoxy-4-quinolyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-(4-methoxyphenoxy)-1-propanol (73 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (118 mg, yield 80%).

$^1$H-NMR (CDCl$_3$, 400 MHz): 8.44–8.48 (1H, m), 8.14 (1H, s), 7.64 (1H, s), 7.57–7.64 (2H, m), 7.15–7.20 (2H, m), 6.83–6.87 (5H, m), 6.65–6.72 (1H, m), 4.17 (3H, s), 4.10 (3H, s), 4.42 (2H, t, J=6.2 Hz), 4.06 (2H, t, J=6.2 Hz), 3.77 (3H, s), 2.17 (2H, t, J=6.2 Hz) Mass spectrometry value (ESI-MS, m/z): 506 (M$^+$+1)

Example 43

3-(4-Methoxyphenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (88 mg) was added to toluene/triethylamine=10/1 (9 ml), and the mixture was heated under reflux to prepare a solution. A solution of triphosgene (122 mg) in methylene chloride was then added to the solution, and the mixture was heated under reflux for 15 min. Subsequently, 3-(4-methoxyphenoxy)-1-propanol (74 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (128 mg, yield 83%).

$^1$H-NMR (CDCl$_3$, 400 MHz): 8.42–8.46 (1H, m), 8.16 (1H, s), 7.66–7.75 (1H, m), 7.02 (1H, d, J=8.8 Hz), 6.80–6.87 (5H, m), 6.55 (1H, d, J=6.6 Hz), 6.46 (1H, bs), 4.41 (2H, t, J=6.4 Hz), 4.17 (3H, s), 4.11 (3H, s), 4.04–4.10 (2H, m), 3.77 (3H, s), 2.26 (3H, s), 2.10 (3H, s), 2.14–2.21 (2H, m) Mass spectrometry value (ESI-MS, m/z): 534 (M$^+$+1)

Example 44

3-(4-Methoxyphenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (98 mg) was added to toluene/triethylamine=10/1 (10 ml), and the mixture was heated under reflux to prepare a solution. A solution of triphosgene (136 mg) in methylene chloride was then added to the solution, and the mixture was heated under reflux for 15 min. Subsequently, 3-(4-methoxyphenoxy)-1-propanol (83 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (130 mg, yield 76%).

$^1$H-NMR (CDCl$_3$, 400 MHz): 8.43–8.47 (1H, m), 8.15 (1H, s), 7.89 (1H, bs), 7.64 (1H, s), 6.80–6.97 (5H, m), 6.57 (1H, d, J=6.6 Hz), 6.44 (1H, s), 4.42 (2H, t, J=6.3 Hz), 4.17 (3H, s), 4.11 (3H, s), 4.06 (2H, t, J=6.3 Hz), 3.77 (3H, s), 2.28 (3H, s), 2.14–2.24 (2H, m), 2.12 (3H, s) Mass spectrometry value (ESI-MS, m/z): 534 (M$^+$+1)

Example 45

3-(4-Methoxyphenoxy)propyl N-{4-[(6,7-dimethoxy-4-quinazolinyl)oxy]phenyl}carbamate 4-[(6,7-Dimethoxy-4-quinazolinyl)oxy]aniline (82 mg) was added to toluene/triethylamine=10/1 (8 ml), and the mixture was heated under reflux to prepare a solution. A solution of triphosgene (122 mg) in methylene chloride was then added to the solution, and the mixture was heated under reflux for 15 min. Subsequently, 3-(4-methoxyphenoxy)-1-propanol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (92 mg, yield 62%).

$^1$H-NMR (CDCl$_3$, 400 MHz): 8.66 (1H, s), 7.57 (1H, s), 7.40–7.54 (3H, m), 7.18–7.24 (2H, m), 6.65–6.85 (5H, m), 4.40 (2H, t, J=63 Hz), 4.09 (3H, s), 4.08 (3H, s), 4.05 (2H, t, J=6.1 Hz), 3.77 (3H, s), 2.10–2.20 (2H, m) Mass spectrometry value (ESI-MS, m/z): 507 (M$^+$+1)

Example 46

3-(4-Methoxyphenoxy)propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (87 mg) was added to toluene/triethylamine=10/1 (9 ml), and the mixture was heated under reflux to prepare a solution. A solution of triphosgene (117 mg) in methylene chloride was then added to the solution, and the mixture was heated under reflux for 15 min. Subsequently, 3-(4-methoxyphenoxy)-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 45%).
$^1$H-NMR (CDCl$_3$, 400 MHz): 8.68 (1H, s), 8.30 (1H, d, J=8.5 Hz), 7.53–7.60 (2H, m), 6.80–7.34 (7H, m), 4.42 (2H, t, J=6.4 Hz), 4.11 (3H, s), 4.08 (3H, s), 4.06 (2H, t, J=6.2 Hz), 3.77 (3H, s), 2.15–2.22 (2H, m) Mass spectrometry value (ESI-MS, m/z): 540 (M$^+$+1)

Example 47

3-(3-Methoxyphenoxy)propyl N-{4-[(6,7-dimethoxy-4-quinolyl)oxy]phenyl}carbamate

4-[(6,7-Dimethoxy-4-quinolyl)oxy]aniline (75 mg) was added to toluene/triethylamine=10/1 (8 ml), and the mixture was heated under reflux to prepare a solution. A solution of triphosgene (112 mg) in methylene chloride was then added to the solution, and the mixture was heated under reflux for 15 min. Subsequently, 3-(3-methoxyphenoxy)-1-propanol (69 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 69%).
$^1$H-NMR (CDCl$_3$, 400 MHz): 8.45–8.51 (1H, m), 8.14 (1H, s), 7.63 (1H, s), 7.54–7.64 (2H, m), 7.15–7.23 (3H, m), 6.82 (1H, s), 6.69 (1H, d, J=6.6 Hz), 6.45–6.55 (3H, m), 4.42 (2H, t, J=6.2 Hz), 4.17 (3H, s), 4.10 (3H, s), 4.09 (2H, t, J=6.1 Hz), 3.79 (3H, s), 2.15–2.22 (2H, m) Mass spectrometry value (ESI-MS, m/z): 506 (M$^+$+1)

Example 48

3-(3-Methoxyphenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (85 mg) was added to toluene/triethylamine=10/1 (9 ml), and the mixture was heated under reflux to prepare a solution. A solution of triphosgene (116 mg) in methylene chloride was then added to the solution, and the mixture was heated under reflux for 15 min. Subsequently, 3-(3-methoxyphenoxy)-1-propanol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (91 mg, yield 72%).
$^1$H-NMR (CDCl$_3$, 400 MHz): 8.43 (1H, d, J=5.4 Hz), 7.50–7.63 (2H, m), 6.28–7.24 (8H, m), 4.40 (2H, t, J=6.3 Hz), 4.07 (6H, s), 4.05–4.10 (2H, m), 3.79 (3H, s), 2.24 (3H, s), 2.15–2.23 (2H, m), 2.11 (3H, s) Mass spectrometry value (ESI-MS, m/z): 534 (M$^+$+1)

Example 49

3-(3-Methoxyphenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (77 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 3-(3-methoxyphenoxy)-1-propanol (65 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (91 mg, yield 72%).
$^1$H-NMR (CDCl$_3$, 400 MHz): 8.40–8.48 (1H, m), 8.15 (1H, s), 7.89 (1H, s), 8.63–8.68 (1H, m), 6.93–7.25 (2H, m), 6.40–6.59 (5H, m), 4.38–4.45 (2H, m), 4.17 (3H, s), 4.11 (3H, s), 4.05–4.14 (2H, m), 3.79 (3H, s), 2.15–2.25 (2H, m), 2.28 (3H, s), 2.12 (3H, s) Mass spectrometry value (ESI-MS, m/z): 534 (M$^+$+1)

Example 50

3-(3-Methoxyphenoxy)propyl N-{4-[(6,7-dimethoxy-4-quinazolinyl)oxy]phenyl}carbamate 4-[(6,7-Dimethoxy-4-quinazolinyl)oxy]aniline (95 mg) was added to toluene/triethylamine=10/1 (10 ml), and the mixture was then added to the solution, and the mixture was heated under reflux to prepare a solution. A solution of triphosgene (142 mg) in methylene chloride was then added to the solution, and the mixture was heated under reflux for 15 min. Subsequently, 3-(3-methoxyphenoxy)-1-propanol (87 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (105 mg, yield 65%).

$^1$H-NMR (CDCl$_3$, 400 MHz): 8.69 (1H, s), 7.45–7.97 (3H, m), 7.13–7.21 (3H, m), 6.40–6.80 (5H, m), 4.38 (2H, t, J=6.4 Hz), 4.10 (3H, s), 4.07 (3H, s), 3.98–4.08 (2H, m), 3.77 (3H, s), 2.08–2.20 (2H, m) Mass spectrometry value (ESI-MS, m/z): 507 (M$^+$+1)

Example 51

3-(3-Methoxyphenoxy)propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (80 mg) was added to toluene/triethylamine=10/1 (8 ml), and the mixture was heated under reflux to prepare a solution. A solution of triphosgene (107 mg) in methylene chloride was then added to the solution, and the mixture was heated under reflux for 15 min. Subsequently, 3-(3-methoxyphenoxy)-1-propanol (67 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (67 mg, yield 52%).

$^1$H-NMR (CDCl$_3$, 400 MHz): 8.70 (1H, s), 8.31 (1H, d, J=9.0 Hz), 7.54 (1H, s), 7.33 (1H, d, J=2.7 Hz), 7.15–7.23 (3H, m), 6.47–6.55 (4H, m), 4.43 (2H, t, J=6.2 Hz), 4.12 (3H, s), 4.09 (3H, s), 4.08–4.13 (2H, m), 3.79 (3H, s), 2.15–2.25 (2H, m) Mass spectrometry value (ESI-MS, m/z): 541 (M$^+$+1)

Example 52

1-(3-Methoxyphenyl)ethyl N-{4-[(6,7-dimethoxy-4-quinolyl)oxy]phenyl}carbamate

4-[(6,7-Dimethoxy-4-quinolyl)oxy]aniline (83 mg) was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 3-methoxy-α-methylbenzyl alcohol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 66%).

$^1$H-NMR (CDCl$_3$, 400 MHz): 8.46 (1H, dd, J=6.5 Hz), 8.14 (1H, s), 7.58–7.64 (2H, m), 7.38–7.42 (1H, m), 7.29–7.32 (1H, m), 7.14–7.18 (2H, m), 6.96–7.02 (1H, m), 6.91 (1H, d, J=8.3 Hz), 6.86 (1H, s), 6.68 (1H, d, J=6.6 Hz), 6.29 (1H, q, J=6.5 Hz), 4.16 (3H, s), 4.10 (3H, s), 3.88 (3H, s), 1.58 (3H, d, J=6.5 Hz) Mass spectrometry value (ESI-MS, m/z): 476 (M$^+$+1)

Example 53

1-(3-Methoxyphenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (90 mg) was added to toluene/triethylamine=10/1 (9 ml), and the mixture was heated under reflux to prepare a solution. A solution of triphosgene (123 mg) in methylene chloride was then added to the solution, and the mixture was heated under reflux for 15 min. Subsequently, 3-methoxy-α-methylbenzyl alcohol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (97 mg, yield 70%).

$^1$H-NMR (CDCl$_3$, 400 MHz): 8.41–8.46 (1H, m), 8.15 (1H, s), 7.77 (1H, d, J=8.6 Hz), 7.66 (1H, s), 7.40 (1H, d, J=7.8 Hz), 7.30 (1H, d, J=7.3 Hz), 6.96–7.20 (2H, m), 6.91 (1H, d, J=8.3 Hz), 6.50–6.55 (2H, m), 6.29 (1H, q, J=6.5 Hz), 4.17 (3H, s), 4.11 (3H, s), 3.87 (3H, s), 2.27 (3H, s), 2.09 (3H, s), 1.59 (3H, d, J=6.5 Hz) Mass spectrometry value (ESI-MS, m/z): 504 (M$^+$+1)

Example 54

1-(3-Methoxyphenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (123 mg) in methylene chloride was then added to the solution, and the mixture was heated under reflux for 15 min. Subsequently, 3-methoxy-α-methylbenzyl alcohol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 56%).

$^1$H-NMR (CDCl$_3$, 400 MHz): 8.41–8.48 (1H, m), 8.12 (1H, s), 7.92 (1H, s), 7.62 (1H, s), 7.26–7.42 (2H, m), 6.85–7.00 (3H, m), 6.45–6.58 (2H, m), 6.27 (1H, q, J=6.5 Hz), 4.14 (3H, s), 4.08 (3H, s), 3.86 (3H, s), 2.27 (3H, s), 2.08 (3H, s), 1.57 (3H, d, J=6.6 Hz) Mass spectrometry value (ESI-MS, m/z): 504 (M$^+$+1)

Example 55

1-(3-Methoxyphenyl)ethyl N-{4-[(6,7-dimethoxy-4-quinazolinyl)oxy]phenyl}carbamate 4-[(6,17-Dimethoxy-4-quinazolinyl)oxy]aniline (83 mg) was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 3-methoxy-α-methylbenzyl alcohol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (76 mg, yield 58%).

$^1$H-NMR (CDCl$_3$, 400 MHz): 8.75 (1H, s), 8.00 (1H, bs), 7.16–7.62 (7H, m), 6.88–7.02 (2H, m), 6.79 (1H, bs), 6.28 (1H, q, J=6.4 Hz), 4.16 (3H, s), 4.11 (3H, s), 3.87 (3H, s), 1.58 (3H, d, J=6.4 Hz) Mass spectrometry value (ESI-MS, m/z): 477 (M$^+$+1)

Example 56

1-(3-Methoxyphenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (82 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-methoxy-α-methylbenzyl alcohol (56 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (69 mg, yield 55%).

$^1$H-NMR (CDCl$_3$, 400 MHz): 8.80 (1H, s), 8.40 (1H, d, J=9.0 Hz), 8.14 (1H, s), 7.14–7.60 (5H, m), 6.97–7.03 (1H, m), 6.91 (1H, d, J=8.3 Hz), 6.30 (1H, q, J=6.5 Hz), 4.19 (3H, s), 4.12 (3H, s), 3.88 (3H, s), 1.60 (3H, d, J=6.5 Hz) Mass spectrometry value (ESI-MS, m/z): 511 (M$^+$+1)

Example 57

4-(Tert-butyl)benzyl N-{4-[(6,7-dimethoxy-4-quinolyl)oxy]phenyl}carbamate

4-[(6,7-Dimethoxy-4-quinolyl)oxy]aniline (90 mg) was added to toluene/triethylamine=10/1 (9 ml), and the mixture was heated under reflux to prepare a solution. A solution of triphosgene (137 mg) in methylene chloride was then added to the solution, and the mixture was heated under reflux for 15 min. Subsequently, 4-methoxy-tert-butylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (109 mg, yield 69%).

$^1$H-NMR (CDCl$_3$, 400 MHz): 8.46 (1H, dd, J=6.7 Hz), 8.15 (1H, s), 7.64 (1H, s), 7.59 (2H, d, J=9.0 Hz), 7.43 (2H, d, J=9.0 Hz), 7.36 (2H, d, J=8.3 Hz), 7.18 (2H, d, J=9.0 Hz), 6.82 (1H, s), 6.68 (1H, d, J=6.7 Hz), 5.21 (2H, s), 4.17 (3H, s), 4.19 (3H, s), 1.34 (9H, s) Mass spectrometry value (ESI-MS, m/z): 488 (M$^+$+1)

Example 58

4-(Tert-butyl)benzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (83 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 4-methoxy-tert-butylbenzyl alcohol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (101 mg, yield 72%).

$^1$H-NMR (CDCl$_3$, 400 MHz): 8.42–8.47 (1H, m), 8.16 (1H, s), 7.75–7.85 (1H, m), 7.67 (1H, s), 7.44 (2H, d, J=8.6 Hz), 7.38 (2H, d, J=8.3 Hz), 7.03 (1H, d, J=9.0 Hz), 6.55 (1H, d, J=6.6 Hz), 6.52 (1H, bs), 5.21 (2H, s), 4.17 (3H, s), 4.11 (3H, s), 2.25 (3H, s), 2.09 (3H, s), 1.34 (9H, s) Mass spectrometry value (ESI-MS, m/z): 516 (M$^+$+1)

Example 59

4-(Tert-butyl)benzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 4-methoxy-tert-butylbenzyl alcohol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (93 mg, yield 68%).

$^1$H-NMR (CDCl$_3$, 400 MHz): 8.40–8.47 (1H, m), 8.15 (1H, s), 7.95 (1H, bs), 7.64 (1H, s), 7.36–7.46 (4H, m), 6.95 (1H, s), 6.57 (1H, d, J=6.6 Hz), 6.50 (1H, s), 5.21 (2H, s), 4.17 (3H, s), 4.11 (3H, s), 2.26 (3H, s), 2.13 (3H, s), 1.34 (9H, s) Mass spectrometry value (ESI-MS, m/z): 516 (M$^+$+1)

Example 60

4-(Tert-butyl)benzyl N-{4-[(6,7-dimethoxy-4-quinazolinyl)oxy]phenyl}carbamate

4-[(6,7-Dimethoxy-4-quinazolinyl)oxy]aniline (95 mg) was added to toluene/triethylamine=10/1 (10 ml), and the mixture was heated under reflux to prepare a solution. A solution of triphosgene (144 mg) in methylene chloride was then added to the solution, and the mixture was heated under reflux for 15 min. Subsequently, 4-methoxy-tert-butylbenzyl alcohol (79 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (71 mg, yield 42%).

$^1$H-NMR (CDCl$_3$, 400 MHz): 8.77 (1H, s), 8.07 (1H, bs), 7.61 (1H, s), 7.51–7.58 (2H, m), 7.42 (2H, d, J=8.6 Hz), 7.36 (2H, d, J=8.3 Hz), 7.19 (2H, d, J=9.0 Hz), 6.79 (1H, s), 5.20 (2H, s), 4.18 (3H, s), 4.12 (3H, s), 1.33 (3H, s) Mass spectrometry value (ESI-MS, m/z): 489 (M$^+$+1)

Example 61

4-(Tert-butyl)benzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (90 mg) was added to toluene/triethylamine=10/1 (9 ml), and the mixture was heated under reflux to prepare a solution. A solution of triphosgene (122 mg) in methylene chloride was then added to the solution, and the mixture was heated under reflux for 15 min. Subsequently, 4-methoxy-tert-butylbenzyl alcohol (67 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (55 mg, yield 36%).

$^1$H-NMR (CDCl$_3$, 400 MHz): 8.80 (1H, s), 8.41 (1H, d, J=9.2 Hz), 8.13 (1H, s), 7.58 (1H, s), 7.36–7.46 (4H, m), 7.24–7.34 (2H, m), 7.17–7.22 (1H, m), 5.22 (2H, s), 4.19 (3H, s), 4.12 (3H, s), 1.34 (9H, s) Mass spectrometry value (ESI-MS, m/z): 523 (M$^+$+1)

Example 62

3,4-Dimethoxybenzyl N-{4-[(6,7-dimethoxy-4-quinolyl)oxy]phenyl}carbamate

4-[(6,7-Dimethoxy-4-quinolyl)oxy]aniline (65 mg) was added to toluene/triethylamine=10/1 (7 ml), and the mixture was heated under reflux to prepare a solution. A solution of triphosgene (100 mg) in methylene chloride was then added to the solution, and the mixture was heated under reflux for 15 min. Subsequently, 3,4-dimethoxybenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (70 mg, yield 60%).

$^1$H-NMR (CDCl$_3$, 400 MHz): 8.49 (1H, s), 8.14 (1H, s), 7.58–7.64 (3H, m), 7.17–7.22 (2H, m), 6.86–7.04 (4H, m), 6.69 (1H, m), 5.17 (2H, s), 4.17 (3H, s), 4.10 (3H, s), 3.92 (3H, s), 3.90 (3H, s) Mass spectrometry value (ESI-MS, m/z): 492 (M$^+$+1)

Example 63

3,4-Dimethoxybenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (65 mg) was added to toluene/triethylamine=10/1 (7 ml), and the mixture was heated under reflux to prepare a solution. A solution of triphosgene (107 mg) in methylene chloride was then added to the solution, and the mixture was heated under reflux for 15 min. Subsequently, 3,4-dimethoxybenzyl alcohol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (73 mg, yield 55%).

$^1$H-NMR (CDCl$_3$, 400 MHz): 8.46 (1H, dd, J=6.6 Hz), 8.15 (1H, s), 7.75–7.80 (1H, m), 7.66 (1H, s), 6.83–7.05 (4H, m), 6.55 (1H, d, J=6.4 Hz), 6.51 (1H, s), 5.17 (2H, s), 4.17 (3H, s), 4.12 (3H, s), 3.92 (3H, s), 3.91 (3H, s) Mass spectrometry value (ESI-MS, m/z): 520 (M$^+$+1)

Example 64

3,4-Dimethoxybenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (89 mg) was added to toluene/triethylamine=10/1 (9 ml), and the mixture was heated under reflux to prepare a solution. A solution of triphosgene (124 mg) in methylene chloride was then added to the solution, and the mixture was heated under reflux for 15 min. Subsequently, 3,4-dimethoxybenzyl alcohol (72 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (102 mg, yield 67%).

$^1$H-NMR (CDCl$_3$, 400 MHz): 8.44–8.50 (1H, m), 8.12 (1H, s), 7.91 (1H, s), 7.62 (1H, s), 6.80–7.03 (4H, m), 6.55 (1H, d, J=6.3 Hz), 6.48 (1H, s), 5.15 (2H, s), 4.15 (3H, s), 4.08 (3H, s), 3.90 (3H, s), 3.88 (3H, s), 2.24 (3H, s), 2.11 (3H, s) Mass spectrometry value (ESI-MS, m/z): 519 (M$^+$+1)

Example 65

3,4-Dimethoxybenzyl N-{4-[(6,7-dimethoxy-4-quinazolinyl)oxy]phenyl}carbamate

4-[(6,7-Dimethoxy-4-quinazolinyl)oxy]aniline (83 mg) was added to toluene/triethylamine=10/1 (9 ml), and the mixture was heated under reflux to prepare a solution. A solution of triphosgene (147 mg) in methylene chloride was then added to the solution, and the mixture was heated under reflux for 15 min. Subsequently, 3,4-dimethoxybenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (70 mg, yield 48%).

$^1$H-NMR (CDCl$_3$, 400 MHz): 8.79 (1H, s), 8.14 (1H, s), 7.54–7.64 (3H, m), 7.18–7.24 (2H, m), 6.79–7.01 (4H, m), 5.16 (2H, s), 4.19 (3H, s), 4.12 (3H, s), 3.92 (3H, s), 3.90 (3H, s) Mass spectrometry value (ESI-MS, m/z): 492 (M$^+$+1)

Example 66

3,4-Dimethoxybenzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (76 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 3,4-dimethoxybenzyl alcohol (58 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (53 mg, yield 42%).

$^1$H-NMR (CDCl$_3$, 400 MHz): 8.68 (1H, s), 8.33 (1H, d, J=8.8 Hz), 7.50–7.60 (2H, m), 6.83–7.35 (6H, m), 5.18 (2H, s), 4.11 (3H, s), 4.08 (3H, s), 3.93 (3H, s), 3.90 (3H, s) Mass spectrometry value (ESI-MS, m/z): 527 (M$^+$+1)

Example 67

2,5-Dimethoxybenzyl N-{4-[(6,7-dimethoxy-4-quinolyl)oxy]phenyl}carbamate

4-[(6,7-Dimethoxy-4-quinolyl)oxy]aniline (75 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3,5-dimethoxybenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (90 mg, yield 68%).

$^1$H-NMR (CDCl$_3$, 400 MHz): 8.47 (1H, d like, J=6.6 Hz), 8.14 (1H, s), 6.67–7.66 (10H, m), 5.27 (2H, s), 4.17 (3H, s), 4.10 (3H, s), 3.84 (3H, s), 3.79 (3H, s) Mass spectrometry value (ESI-MS, m/z): 491 (M$^+$+1)

Example 68

2,5-Dimethoxybenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (85 mg) was added to toluene/triethylamine=10/1 (9 ml), and the mixture was heated under reflux to prepare a solution. A solution of triphosgene (140 mg) in methylene chloride was then added to the solution, and the mixture was heated under reflux for 15 min. Subsequently, 3,5-dimethoxybenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (92 mg, yield 60%).

$^1$H-NMR (CDCl$_3$, 400 MHz): 8.44 (1H, d, J=6.4 Hz), 8.05 (1H, s), 7.74–7.80 (1H, m), 7.66 (1H, s), 6.78–7.40 (4H, m), 6.50–6.58 (2H, m), 5.27 (2H, s), 4.16 (3H, s), 4.11 (3H, s); 3.85 (3H, s), 3.79 (3H, s) Mass spectrometry value (ESI-MS, m/z): 520 (M$^+$+1)

Example 69

2,5-Dimethoxybenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (125 mg) in methylene chloride was then added to the solution, and the mixture was heated under reflux for 15 min. Subsequently, 3,5-dimethoxybenzyl alcohol (73 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (92 mg, yield 60%).

$^1$H-NMR (CDCl$_3$, 400 MHz): 8.46 (1H, d like, J=6.6 Hz), 8.15 (1H, s), 7.95 (1H, s), 7.65 (1H, s), 6.85–7.02 (4H, m), 6.58 (1H, d, J=6.6 Hz), 6.53 (2H, s), 5.28 (2H, s), 4.17 (3H, s), 4.11 (3H, s), 3.85 (3H, s), 3.80 (3H, s) Mass spectrometry value (ESI-MS, m/z): 519 (M$^+$+1)

Example 70

2,5-Dimethoxybenzyl N-{4-[(6,7-dimethoxy-4-quinazolinyl)oxy]phenyl}carbamate

4-[(6,7-Dimethoxy-4-quinazolinyl)oxy]aniline (72 mg) was added to toluene/triethylamine=10/1 (7 ml), and the mixture was heated under reflux to prepare a solution. A solution of triphosgene (120 mg) in methylene chloride was then added to the solution, and the mixture was heated under reflux for 15 min. Subsequently, 3,5-dimethoxybenzyl alcohol (65 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (66 mg, yield 52%).

$^1$H-NMR (CDCl$_3$, 400 MHz): 8.80 (1H, s), 8.14 (1H, s), 7.55–7.63 (3H, m), 7.16–7.22 (2H, m), 6.83–7.00 (3H, m), 5.26 (2H, s), 4.19 (3H, s), 4.12 (3H, s), 3.83 (3H, s), 3.79 (3H, s) Mass spectrometry value (ESI-MS, m/z): 492 (M$^+$+1)

Example 71

2,5-Dimethoxybenzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (76 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 3,5-dimethoxybenzyl alcohol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (59 mg, yield 46%).

$^1$H-NMR (CDCl$_3$, 400 MHz): 8.75 (1H, s), 8.39 (1H, d, J=9.3 Hz), 6.73–7.85 (8H, m), 5.28 (2H, s), 4.15 (3H, s), 4.10 (3H, s), 3.84 (3H, s), 3.80 (3H, s) Mass spectrometry value (ESI-MS, m/z): 527 (M$^+$+1)

Example 72

3-{4-(Tert-butyl)phenyl]sulfanyl]propyl N-{4-[(6,7-dimethoxy-4-quinolyl)oxy]phenyl]carbamate 4-[(6,7-Dimethoxy-4-quinolyl)oxy]aniline (72 mg) was added to toluene/triethylamine=10/1 (7 ml), and the mixture was heated under reflux to prepare a solution. A solution of triphosgene (120 mg) in methylene chloride was then added to the solution, and the mixture was heated under reflux for 15 min. Subsequently, 3-[4-(tert-butyl)phenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (81 mg, yield 57%).

$^1$H-NMR (CDCl$_3$, 400 MHz): 8.45–8.50 (1H, m), 8.14 (1H, s), 7.64 (1H, s), 7.58–7.66 (2H, m), 7.16–7.33 (6H, m), 6.80 (1H, s), 6.69 (1H, d, J=6.6 Hz), 4.33 (2H, t, J=6.2 Hz), 4.17 (3H, s), 4.10 (3H, s), 3.01 (2H, t, J=7.2 Hz), 1.99–2.07 (2H, m), 1.31 (9H, s) Mass spectrometry value (ESI-MS, m/z): 548 (M$^+$+1)

Example 73

3-{[4-(Tert-butyl)phenyl]sulfanyl}-propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (78 mg) was added to toluene/triethylamine=10/1 (8 ml), and the mixture was heated under reflux to prepare a solution. A solution of triphosgene (121 mg) in methylene chloride was then added to the solution, and the mixture was heated under reflux for 15 min. Subsequently, 3-[4-(tert-butyl)phenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (109 mg, yield 74%).

$^1$H-NMR (CDCl$_3$, 400 MHz): 8.44 (1H, d, J=5.4 Hz), 7.48–7.64 (3H, m), 7.27–7.35 (4H, m), 6.97–7.03 (1H, m), 6.38 (1H, bs), 6.28 (1H, d, J=5.4 Hz), 4.31 (2H, t, J=6.2 Hz), 4.07 (3H, s), 2.98–3.13 (2H, m), 2.25 (3H, s), 2.12 (3H, s), 1.98–2.06 (2H, m), 1.30 (9H, s) Mass spectrometry value (ESI-MS, m/z): 576 (M$^+$+1)

Example 74

3-{[4-(Tert-butyl)phenyl]sulfanyl}propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (82 mg) was added to toluene/triethylamine=10/1 (8 ml), and the mixture was heated under reflux to prepare a solution. A solution of triphosgene (122 mg) in methylene chloride was then added to the solution, and the mixture was heated under reflux for 15 min. Subsequently, 3-[4-(tert-butyl)phenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (113 mg, yield 73%).

$^1$H-NMR (CDCl$_3$, 400 MHz): 8.45–8.50 (1H, m), 8.15 (1H, s), 7.89 (1H, s), 7.65 (1H, s), 7.32 (4H, s), 6.95 (1H, s), 6.58 (1H, d, J=6.4 Hz), 6.44 (1H, s), 4.33 (2H, t, J=6.4 Hz), 4.17 (3H, s), 4.11 (3H, s), 3.02 (2H, t, J=7.1 Hz), 2.29 (3H, s), 2.13 (3H, s), 2.00–2.08 (2H, m), 1.31 (9H, s) Mass spectrometry value (ESI-MS, m/z): 576 (M$^+$+1)

Example 75

3-{[4-(Tert-butyl)phenyl]sulfanyl}propyl N-{4-[(6,7-dimethoxy-4-quinazolinyl)oxy]phenyl}carbamate 4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-[4-(tert-butyl)phenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (100 mg, yield 64%).

$^1$H-NMR (CDCl$_3$, 400 MHz): 8.73 (1H, s like), 8.52–8.60 (1H, m), 7.70–7.90 (2H, m), 6.80–7.65 (8H, m), 4.29–4.33 (2H, m), 4.10–4.16 (6H, m), 2.98–3.04 (2H, m), 1.90–2.10 (2H, m), 1.31 (9H, s) Mass spectrometry value (ESI-MS, m/z): 549 (M$^+$+1)

Example 76

3-{[4-(Tert-butyl)phenyl]sulfanyl}propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (77 mg) was added to toluene/triethylamine=10/1 (8 ml), and the mixture was heated under reflux to prepare a solution. A solution of triphosgene (125 mg) in methylene chloride was then added to the solution, and the mixture was heated under reflux for 15 min. Subsequently, 3-[4-(tert-butyl)phenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 47%).

$^1$H-NMR (CDCl$_3$, 400 MHz): 8.80 (1H, s), 8.33–8.38 (1H, m), 8.07 (1H, bs), 7.15–7.62 (8H, m), 4.35 (2H, t, J=6.2 Hz), 4.18 (3H, s), 4.12 (3H, s), 3.02 (2H, t, J=7.1 Hz), 2.00–2.08 (2H, m), 1.31 (9H, s) Mass spectrometry value (ESI-MS, m/z): 583 (M$^+$+1)

Example 77

3-[(4-Chloro-2-methylphenyl)sulfanyl]propyl N-{4-[(6,7-dimethoxy-4-quinolyl)oxy]phenyl}carbamate 4-[(6,7-Dimethoxy-4-quinolyl)oxy]aniline (73 mg) was added to toluene/triethylamine=10/1 (7 ml), and the mixture was heated under reflux to prepare a solution. A solution of triphosgene (120 mg) in methylene chloride was then added to the solution, and the mixture was heated under reflux for 15 min. Subsequently, 3-[4-chloro-2-methylphenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (98 mg, yield 69%).

$^1$H-NMR (CDCl$_3$, 400 MHz): 8.45–8.50 (1H, m), 8.15 (1H, s), 7.57–7.65 (3H, m), 7.12–7.25 (5H, m), 6.82 (1H, s), 6.69 (1H, d, J=6.6 Hz), 4.33 (2H, t, J=6.2 Hz), 4.17 (3H, s), 4.10 (3H, s), 2.99 (2H, t, J=7.2 Hz), 2.37 (3H, s), 1.95–2.08 (2H, m) Mass spectrometry value (ESI-MS, m/z): 540 (M$^+$+1)

Example 78

3-[(4-Chloro-2-methylphenyl)sulfanyl]propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (82 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-[4-chloro-2-methylphenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 58%).

$^1$H-NMR (CDCl$_3$, 400 MHz): 8.43–8.50 (1H, m), 8.16 (1H, s), 7.66–7.76 (2H, m), 7.00–7.25 (5H, m), 6.55 (1H, d, J=6.6 Hz), 6.46 (1H, s), 4.33 (2H, t, J=6.2 Hz), 4.17 (3H, s), 4.11 (3H, s), 2.96–3.03 (2H, m), 2.37 (3H, s), 2.27 (3H, s), 2.11 (3H, s), 1.98–2.10 (2H, m) Mass spectrometry value (ESI-MS, m/z): 468 (M$^+$+1)

Example 79

3-[(4-Chloro-2-methylphenyl)sulfanyl]propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (120 mg) in methylene chloride was then added to the solution, and the mixture was heated under reflux for 15 min. Subsequently, 3-[4-chloro-2-methylphenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (81 mg, yield 49%).

$^1$H-NMR (CDCl$_3$, 400 MHz): 8.42–8.48 (1H, m), 8.12 (1H, s), 7.86 (1H, s), 7.62 (1H, s), 7.08–7.23 (3H, m), 6.94 (1H, s), 6.56 (1H, d, J=6.6 Hz), 6.43 (1H, s), 4.31 (2H, t, J=6.2 Hz), 4.15 (3H, s), 4.08 (3H, s), 2.97 (2H, t, J=7.2 Hz), 2.35 (3H, s), 2.26 (3H, s), 2.11 (3H, s), 1.96–2.06 (2H, m) Mass spectrometry value (ESI-MS, m/z): 568 (M$^+$+1)

Example 80

3-[4-Chloro-2-methylphenyl)sulfanyl]propyl N-{4-[(6,7-dimethoxy-4-quinazolinyl)oxy]phenyl}carbamate 4-[(6,7-Dimethoxy-4-quinazolinyl)oxy]aniline (88 mg) was added to toluene/triethylamine=10/1 (9 ml), and the mixture was heated under reflux to prepare a solution. A solution of triphosgene (120 mg) in methylene chloride was then added to the solution, and the mixture was heated under reflux for 15 min. Subsequently, 3-[4-chloro-2-methylphenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 45%).

$^1$H-NMR (CDCl$_3$, 400 MHz): 8.73 (1H, s), 7.85 (1H, bs), 7.60 (1H, s), 7.51–7.57 (2H, m), 7.10–7.24 (5H, m), 6.74 (5H, m), 4.32 (2H, t, J=6.1 Hz), 4.15 (3H, s), 4.11 (3H, s), 2.98 (2H, t, J=7.2 Hz), 2.37 (3H, s), 1.98–2.07 (2H, m) Mass spectrometry value (ESI-MS, m/z): 541 (M$^+$+1)

Example 81

3-[(4-Chloro-2-methylphenyl)sulfanyl]propyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (75 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-[4-chloro-2-methylphenyl]sulfanyl-1-propanol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (69 mg, yield 50%).

$^1$H-NMR (CDCl$_3$, 400 MHz): 8.66 (1H, s), 8.23–8.33 (1H, m), 7.53 (1H, s), 7.46 (1H, s), 7.34 (1H, d, J=2.7 Hz), 7.12–7.25 (5H, m), 4.34 (2H, t, J=7.1 Hz), 4.09 (3H, s), 4.08 (3H, s), 3.00 (2H, t, J=7.1 Hz), 2.37 (3H, s), 2.00–2.08 (2H, m) Mass spectrometry value (ESI-MS, m/z): 575 (M$^+$+1)

Example 82

3-(Trifluoromethyl)phenethyl N-{4-[(6,7-dimethoxy-4-quinolyl)oxy]phenyl}carbamate 4-[(6,7-Dimethoxy-4-quinolyl)oxy]aniline (72 mg) was added to toluene/triethylamine=10/1 (7 ml), and the mixture was heated under reflux to prepare a solution. A solution of triphosgene (125 mg) in methylene chloride was then added to the solution, and the mixture was heated under reflux for 15 min. Subsequently, 3-trifluoromethylphenethyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (101 mg, yield 76%).

$^1$H-NMR (CDCl$_3$, 400 MHz): 8.42–8.49 (1H, m), 8.12 (1H, s), 7.61 (1H, s), 7.42–7.59 (6H, m), 7.13–7.18 (2H, m), 6.76 (1H, s), 6.66 (1H, d, J=6.6 Hz), 4.44 (2H, t, J=6.7 Hz), 4.15 (3H, s), 4.08 (3H, s), 3.07 (2H, t, J=6.7 Hz) Mass spectrometry value (ESI-MS, m/z): 513 (M$^+$+1)

Example 83

3-(Trifluoromethyl)phenethyl N-{4-[(6,7-dimethoxy-4-quinolyl)oxy]-2,3-dimethylphenyl] carbamate 4-[(6,7-Dimethoxy-4-quinolyl)oxy]-2,3-dimethylaniline (68 mg) was added to toluene/triethylamine=10/1 (7 ml), and the mixture was heated under reflux to prepare a solution. A solution of triphosgene (125 mg) in methylene chloride was then added to the solution, and the mixture was heated under reflux for 15 min. Subsequently, 3-trifluoromethylphenethyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 73%).
$^1$H-NMR (CDCl$_3$, 400 MHz): 8.4–8.49 (1H, m), 8.16 (1H, s), 7.67 (1H, s), 7.40–7.56 (5H, m), 7.02 (1H, d, J=8.8 Hz), 6.54 (1H, d, J=6.4 Hz), 6.42 (1H, bs), 4.46 (2H, t, J=6.7 Hz), 4.17 (3H, s), 4.11 (3H, s), 3.09 (2H, t, J=6.7 Hz), 2.23 (3H, s), 2.10 (3H, s) Mass spectrometry value (ESI-MS, m/z): 541 (M$^+$+1)

Example 84

3-(Trifluoromethyl)phenethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (125 mg) in methylene chloride was then added to the solution, and the mixture was heated under reflux for 15 min. Subsequently, 3-trifluoromethylphenethyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (79 mg, yield 56%).
$^1$H-NMR (CDCl$_3$, 400 MHz): 8.13–8.62 (2H, m), 7.26–8.00 (6H, m), 6.96 (1H, s), 6.64–6.28 (1H, m), 6.42 (1H, bs), 4.46 (2H, t, J=6.7 Hz), 4.03–4.18 (6H, m), 3.07–3.13 (3H, m), 2.23–2.30 (3H, m), 2.11 (3H, s) Mass spectrometry value (ESI-MS, m/z): 541 (M$^+$+1)

Example 85

3-(Trifluoromethyl)phenethyl N-{4-[(6,7-dimethoxy-4-quinazolinyl)oxy]phenyl}carbamate 4-[(6,7-Dimethoxy-4-quinazolinyl)oxy]aniline (82 mg) was added to toluene/triethylamine=10/1 (8 ml), and the mixture was heated under reflux to prepare a solution. A solution of triphosgene (125 mg) in methylene chloride was then added to the solution, and the mixture was heated under reflux for 15 min. Subsequently, 3-trifluoromethylphenethyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 45%).
$^1$H-NMR (CDCl$_3$, 400 MHz): 8.76 (1H, s), 8.01 (1H, s), 7.60 (1H, s), 7.43–7.58 (6H, m), 7.17–7.24 (2H, m), 6.79 (1H, s), 4.44 (2H, t, J=6.7 Hz), 4.17 (3H, s), 4.11 (3H, s), 3.08 (2H, t, J=6.8 Hz) Mass spectrometry value (ESI-MS, m/z): 514 (M$^+$+1)

Example 86

3-(Trifluoromethyl)phenethyl N-12-chloro-4-[(6,7-dimethoxy-4-quinazolinyl)oxy]phenyl}carbamate 2-Chloro-4-[(6,7-dimethoxy-4-quinazolinyl)oxy]-aniline (85 mg) was added to toluene/triethylamine=10/1 (9 ml), and the mixture was heated under reflux to prepare a solution. A solution of triphosgene (125 mg) in methylene chloride was then added to the solution, and the mixture was heated under reflux for 15 min. Subsequently, 3-trifluoromethylphenethyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (69 mg, yield 46%).
$^1$H-NMR (CDCl$_3$, 400 MHz): 8.79 (1H, s), 8.27–8.34 (1H, m), 8.03 (1H, s), 7.30–7.62 (6H, m), 7.24–7.23 (2H, m), 4.46 (2H, t, J=6.8 Hz), 4.18 (3H, s), 4.11 (3H, s), 3.10 (2H, t, J=6.9 Hz) Mass spectrometry value (ESI-MS, m/z): 549 (M$^+$+1)

Example 87

1-[3-(Trifluoromethyl)phenyl]ethyl N-{4-[(6,7-dimethoxy-4-quinolyl)oxy]phenyl}carbamate 4-[(6,7-Dimethoxy-4-quinolyl)oxy]aniline (74 mg) was added to toluene/triethylamine=10/1 (7 ml), and the mixture was heated under reflux to prepare a solution. A solution of triphosgene (115 mg) in methylene chloride was then added to the solution, and the mixture was heated under reflux for 15 min. Subsequently, 3-trifluoromethyl-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (81 mg, yield 59%).

$^1$H-NMR (CDCl$_3$, 400 MHz): 8.41–8.48 (1H, m), 8.11 (1H, s), 7.45–7.68 (7H, m), 7.13–7.18 (2H, m), 6.93 (1H, s), 6.65 (1H, d, J=6.6 Hz), 5.94 (1H, q, J=6.6 Hz), 4.14 (3H, s), 4.08 (3H, s), 1.63 (3H, d, J=6.6 Hz) Mass spectrometry value (ESI-MS, m/z): 513 (M$^+$+1)

Example 88

1-[3-(Trifluoromethyl)phenyl]ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (72 mg) was added to toluene/triethylamine=10/1 (7 ml), and the mixture was heated under reflux to prepare a solution. A solution of triphosgene (110 mg) in methylene chloride was then added to the solution, and the mixture was heated under reflux for 15 min. Subsequently, 3-trifluoromethyl-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (90 mg, yield 68%).

$^1$H-NMR (CDCl$_3$, 400 MHz): 8.39–8.45 (1H, m), 8.13 (1H, s), 7.40–7.72 (6H, m), 6.99 (1H, d, J=9.0 Hz), 6.48–6.55 (2H, m), 5.93 (1H, 1, J=6.6 Hz), 4.15 (3H, s), 4.09 (3H, s), 2.24 (3H, s), 2.07 (3H, s), 1.63 (3H, d, J=6.6 Hz) Mass spectrometry value (ESI-MS, m/z): 542 (M$^+$+1)

Example 89

1-[3-(Trifluoromethyl)phenyl]ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (76 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-trifluoromethyl-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 58%).

$^1$H-NMR (CDCl$_3$, 400 MHz): 8.40–8.47 (1H, m), 8.12 (1H, s), 7.84 (1H, s), 7.45–7.68 (5H, m), 6.93 (1H, s), 6.47–6.57 (2H, m), 5.93 (1H, q, J=6.8 Hz), 4.14 (3H, s), 4.08 (3H, s), 2.27 (3H, s), 2.09 (3H, s), 1.63 (3H, d, J=6.8 Hz) Mass spectrometry value (ESI-MS, m/z): 542 (M$^+$+1)

Example 90

1-[3-(Trifluoromethyl)phenyl]ethyl N-{4-[(6,7-dimethoxy-4-quinazolinyl)oxy]phenyl}carbamate 4-[(6,7-Dimethoxy-4-quinazolinyl)oxy]aniline (89 mg) was added to toluene/triethylamine=10/1 (9 ml), and the mixture was heated under reflux to prepare a solution. A solution of triphosgene (120 mg) in methylene chloride was then added to the solution, and the mixture was heated under reflux for 15 min. Subsequently, 3-trifluoromethyl-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (80 mg, yield 48%).

$^1$H-NMR (CDCl$_3$, 400 MHz): 8.75 (1H, s), 8.07 (1H, s), 7.14–7.63 (8H, m), 6.95 (1H, s), 6.79 (1H, d, J=8.8 Hz), 5.93 (1H, q, J=6.6 Hz), 4.15 (3H, s), 4.09 (3H, s), 1.61 (3H, d, J=6.6 Hz) Mass spectrometry value (ESI-MS, m/z): 514 (M$^+$+1)

Example 91

1-[3-(Trifluoromethyl)phenyl]ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (76 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-trifluoromethyl-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (53 mg, yield 39%).

$^1$H-NMR (CDCl$_3$, 400 MHz): 8.76 (1H, s), 7.86 (1H, s), 7.20–7.65 (6H, m), 6.88–6.92 (2H, m), 6.72–6.77 (1H, m), 5.87–5.95 (1H, m), 4.15 (3H, s), 4.09 (3H, s), 1.60 (3H, d, J=6.6 Hz) Mass spectrometry value (ESI-MS, m/z): 549 (M$^+$+1)

Example 92

1-(2,4,5-Trifluorophenyl)ethyl N-{4-[(6 7-dimethoxy-4-quinolyl)oxy]phenyl}carbamate 4-[(6,7-Dimethoxy-4-quinolyl)oxy]aniline (87 mg) was added to toluene/triethylamine=10/1 (9 ml), and the mixture was heated under reflux to prepare a solution. A solution of triphosgene (130 mg) in methylene chloride was then added to the solution, and the mixture was heated under reflux for 15 min. Subsequently, 2,4,5-trifluoro-α-methylbenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 49%).

$^1$H-NMR (CDCl$_3$, 400 MHz): 8.41–8.49 (1H, m), 8.11 (1H, s), 7.56–7.64 (4H, m), 7.12–7.20 (2H, m), 6.80–6.72 (2H, m), 6.65 (1H, d, J=6.4 Hz), 6.07 (1H, q, J=6.4 Hz), 4.14 (3H, s), 4.08 (3H, s), 1.59 (3H, d, J=6.6 Hz) Mass spectrometry value (ESI-MS, m/z): 499 (M$^+$+1)

Example 93

1-(2,4,5-Trifluorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (76 mg) was added to toluene/triethylamine=10/1 (8 ml), and the mixture was heated under reflux to prepare a solution. A solution of triphosgene (130 mg) in methylene chloride was then added to the solution, and the mixture was heated under reflux for 15 min. Subsequently, 2,4,5-trifluoro-α-methylbenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 46%).

$^1$H-NMR (CDCl$_3$, 400 MHz): 8.40–8.47 (1H, m), 8.13 (1H, s), 7.62–7.74 (2H, m), 6.82–6.72 (3H, m), 6.48–6.55 (2H, m), 6.07 (1H, q, J=6.6 Hz), 4.15 (3H, s), 4.09 (3H, s), 2.26 (3H, s), 2.08 (3H, s), 1.59 (3H, d, J=6.6 Hz) Mass spectrometry value (ESI-MS, m/z): 528 (M$^+$+1)

Example 94

1-(2,4,5-Trifluorophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (82 mg) was added to toluene/triethylamine=10/1 (8 ml), and the mixture was heated under reflux to prepare a solution. A solution of triphosgene (130 mg) in methylene chloride was then added to the solution, and the mixture was heated under reflux for 15 min. Subsequently, 2,4,5-trifluoro-α-methylbenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 48%).

$^1$H-NMR (CDCl$_3$, 400 MHz): 8.4–8.48 (1H, m), 8.11 (1H, s), 7.84 (1H, s), 7.61 (1H, s), 6.80–7.30 (3H, m), 6.52–6.57 (2H, m), 6.06 (1H, q, J=6.7 Hz), 4.14 (3H, s), 4.08 (3H, s), 2.28 (3H, s), 2.09 (3H, s), 1.59 (3H, d, J=6.6 Hz) Mass spectrometry value (ESI-MS, m/z): 527 (M$^+$+1)

Example 95

1-(2,4,5-Trifluorophenyl)ethyl N-{4-[(6,7-dimethoxy-4-quinazolinyl)oxy]phenyl}carbamate 4-[(6,7-Dimethoxy-4-quinazolinyl)oxy]aniline (89 mg) was added to toluene/triethylamine=10/1 (9 ml), and the mixture was heated under reflux to prepare a solution. A solution of triphosgene (130 mg) in methylene chloride was then added to the solution, and the mixture was heated under reflux for 15 min. Subsequently, 2,4,5-trifluoro-α-methylbenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 32%).

$^1$H-NMR (CDCl$_3$, 400 MHz): 8.73 (1H, s), 8.05 (1H, s), 7.58 (1H, s), 7.53–7.58 (1H, m), 6.50–7.25 (6H, m), 6.00–6.10 (1H, m), 4.15 (3H, s), 4.09 (3H, s), 1.57 (3H, d, J=6.6 Hz) Mass spectrometry value (ESI-MS, m/z): 500 (M$^+$+1)

Example 96

1-(2,4,5-Trifluorophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (80 mg) was added to toluene/triethylamine=10/1 (8 ml), and the mixture was heated under reflux to prepare a solution. A solution of triphosgene (130 mg) in methylene chloride was then added to the solution, and the mixture was heated under reflux for 15 min. Subsequently, 2,4,5-trifluoro-α-methylbenzyl alcohol (80 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 35%).

$^1$H-NMR (CDCl$_3$, 400 MHz): 8.72 (1H, s), 8.27 (1H, d, J=9.0 Hz), 7.99 (1H, s), 7.50 (1H, s), 6.80–7.28 (5H, m), 5.95–6.08 (1H, m), 4.11 (3H, s), 4.04 (3H, s), 1.56 (3H, d, J=6.6 Hz) Mass spectrometry value (ESI-MS, m/z): 535 (M$^+$+1)

Example 97

1-(3-Fluorophenyl)ethyl N-{4-[(6,7-dimethoxy-4-quinolyl)oxy]phenyl}carbamate

4-[(6,7-Dimethoxy-4-quinolyl)oxy]aniline (97 mg) was added to toluene/triethylamine=10/1 (10 ml), and the mixture was heated under reflux to prepare a solution. A solution of triphosgene (150 mg) in methylene chloride was then added to the solution, and the mixture was heated under reflux for 15 min. Subsequently, 3-fluoro-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (111 mg, yield 68%).

$^1$H-NMR (CDCl$_3$, 400 MHz): 8.41–8.47 (1H, m), 8.12 (1H, s), 7.55–7.62 (3H, m), 6.86–7.38 (7H, m), 6.65 (1H, d, J=6.6 Hz), 5.88 (1H, 1, J=6.6 Hz), 4.14 (3H, s), 4.08 (3H, s), 1.60 (3H, d, J=6.6 Hz) Mass spectrometry value (ESI-MS, m/z): 463 (M$^+$+1)

Example 98

1-(3-Fluorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (86 mg) was added to toluene/triethylamine=10/1 (9 ml), and the mixture was heated under reflux to prepare a solution. A solution of triphosgene (150 mg) in methylene chloride was then added to the solution, and the mixture was heated under reflux for 15 min. Subsequently, 3-fluoro-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (89 mg, yield 64%).

$^1$H-NMR (CDCl$_3$, 400 MHz): 8.38–8.44 (1H, m), 8.13 (1H, s), 7.66–7.75 (1H, m), 7.64 (1H, s), 6.95–7.36 (6H, m), 6.51 (1H, d, J=6.4 Hz), 5.87 (1H, q, J=6.6 Hz), 4.15 (3H, s), 4.09 (3H, s), 2.25 (3H, s), 2.07 (3H, s) Mass spectrometry value (ESI-MS, m/z): 492 (M$^+$+1)

Example 99

1-(3-Fluorophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (97 mg) was added to toluene/triethylamine=10/1 (10 ml), and the mixture was heated under reflux to prepare a solution. A solution of triphosgene (150 mg) in methylene chloride was then added to the solution, and the mixture was heated under reflux for 15 min. Subsequently, 3-fluoro-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (108 mg, yield 68%).

$^1$H-NMR (CDCl$_3$, 400 MHz): 8.40–8.45 (1H, m), 8.12 (1H, s), 7.87 (1H, s), 7.62 (1H, s), 6.90–7.38 (5H, m), 6.54 (1H, d, J=6.8 Hz), 6.49 (1H, s), 4.15 (3H, s), 4.08 (3H, s), 2.27 (3H, s), 2.09 (3H, s), 1.61 (3H, d, J=6.8 Hz) Mass spectrometry value (ESI-MS, m/z): 492 (M$^+$+1)

Example 100

1-(3-Fluorophenyl)ethyl N-{4-[(6,7-dimethoxy-4-quinazolinyl)oxy]phenyl}carbamate 4-[(6,7-Dimethoxy-4-quinazolinyl)oxy]aniline (99 mg) was added to toluene/triethylamine=10/1 (10 ml), and the mixture was heated under reflux to prepare a solution. A solution of triphosgene (150 mg) in methylene chloride was then added to the solution, and the mixture was heated under reflux for 15 min. Subsequently, 3-fluoro-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 36%).

$^1$H-NMR (CDCl$_3$, 400 MHz): 8.75 (1H, s), 7.98 (1H, bs), 8.47 (1H, bs), 6.48–7.60 (9H, m), 5.82–5.90 (1H, m), 4.13 (3H, s), 4.08 (3H, s), 1.58 (3H, d, J=6.6 Hz) Mass spectrometry value (ESI-MS, m/z): 464 (M$^+$+1)

Example 101

1-(3-Fluorophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (98 mg) was added to toluene/triethylamine=10/1 (10 ml), and the mixture was heated under reflux to prepare a solution. A solution of triphosgene (150 mg) in methylene chloride was then added to the solution, and the mixture was heated under reflux for 15 min. Subsequently, 3-fluoro-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (49 mg, yield 31%).

¹H-NMR (CDCl₃, 400 MHz): 8.78 (1H, s), 8.34 (1H, d, J=9.3 Hz), 8.13 (1H, s), 7.56 (1H, s), 6.97–7.38 (7H, m), 5.88 (1H, q, J=6.5 Hz), 4.17 (3H, s), 4.17 (3H, s), 4.10 (3H, s), 1.61 (3H, d, J=6.8 Hz) Mass spectrometry value (ESI-MS, m/z): 499 (M⁺+1)

Example 102

1-(4-Fluorophenyl)ethyl N-{4-[(6,7-dimethoxy-4-quinolyl)oxy]phenyl}carbamate

4-[(6,7-Dimethoxy-4-quinolyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 4-fluoro-α-methylbenzyl alcohol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (91 mg, yield 73%).
¹H-NMR (CDCl₃, 400 MHz): 8.43–8.48 (1H, m), 8.14 (1H, s), 7.63 (1H, s), 7.57–7.61 (2H, m), 7.37–7.42 (2H, m), 7.14–7.19 (2H, m), 7.04–7.10 (2H, m), 6.86 (1H, s), 6.66 (1H, d, J=6.6 Hz), 5.90 (1H, q, J=6.6 Hz), 4.16 (3H, s), 4.10 (3H, s), 1.62 (3H, d, J=6.6 Hz) Mass spectrometry value (ESI-MS, m/z): 461 (M⁺+1)

Example 103

1-(4-Fluorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (86 mg) was added to toluene/triethylamine=10/1 (9 ml), and the mixture was heated under reflux to prepare a solution. A solution of triphosgene (117 mg) in methylene chloride was then added to the solution, and the mixture was heated under reflux for 15 min. Subsequently, 4-fluoro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (94 mg, yield 72%).
¹H-NMR (CDCl₃, 400 MHz): 8.42–8.48 (1H, m), 8.15 (1H, s), 7.74 (1H, d, J=8.5 Hz), 7.66 (1H, s), 7.37–7.43 (2H, m), 6.98–7.10 (3H, m), 6.48–6.55 (2H, m), 5.90 (1H, q, J=6.6 Hz), 4.17 (3H, s), 4.10 (3H, s), 2.25 (3H, s), 2.09 (3H, s), 1.63 (3H, d, J=6.6 Hz) Mass spectrometry value (ESI-MS, m/z): 492 (M⁺+1)

Example 104

1-(4-Fluorophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (123 mg) in methylene chloride was then added to the solution, and the mixture was heated under reflux for 15 min. Subsequently, 4-fluoro-α-methylbenzyl alcohol (58 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (87 mg, yield 64%).
¹H-NMR (CDCl₃, 400 MHz): 8.40–8.48 (1H, m), 8.12 (1H, s), 7.88 (1H, s), 7.61 (1H, s), 7.30–7.41 (2H, m), 7.30–7.41 (2H, m), 7.00–7.10 (2H, m), 6.91 (1H, s), 6.53 (1H, d, J=6.6 Hz), 6.45 (1H, s), 5.87 (1H, q, J=6.7 Hz), 4.14 (3H, s), 4.08 (3H, s), 2.25 (3H, s), 2.09 (3H, s), 1.61 (3H, d, J=6.7 Hz) Mass spectrometry value (ESI-MS, m/z): 492 (M⁺+1)

Example 105

1-(4-Fluorophenyl)ethyl N-{4-[(6,7-dimethoxy-4-quinazolinyl)oxy]phenyl}carbamate 4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 4-fluoro-α-methylbenzyl alcohol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (59 mg, yield 47%).
¹H-NMR (CDCl₃, 400 MHz): 8.77 (1H, s), 8.08 (1H, s), 7.60 (1H, s), 7.52–7.58 (2H, m), 7.36–7.41 (2H, m), 7.16–7.20 (2H, m), 7.02–7.09 (2H, m), 6.79 (1H, s), 5.89 (1H, q.J=6.6 Hz), 4.18 (3H, s), 4.11 (3H, s), 1.61 (3H, d, J=6.6 Hz) Mass spectrometry value (ESI-MS, m/z): 464 (M⁺+1)

Example 106

1-(4-Fluorophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (85 mg) was added to toluene/triethylamine=10/1 (9 ml), and the mixture was heated under reflux to prepare a solution. A solution of triphosgene (114 mg) in methylene chloride was then added to the solution, and the mixture was heated under reflux for 15 min. Subsequently, 4-fluoro-α-methylbenzyl alcohol (54 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (45 mg, yield 35%).

$^1$H-NMR (CDCl$_3$, 400 MHz): 8.80 (1H, s), 8.35 (1H, d, J=9.0 Hz), 8.12 (1H, s), 7.57 (1H, s), 7.05–7.44 (7H, m), 5.90 (1H, q, J=6.6 Hz), 4.19 (3H, s), 4.11 (3H, s), 1.63 (3H, d, J=6.8 Hz) Mass spectrometry value (ESI-MS, m/z): 499 (M$^+$+1)

Example 107

4-Methylbenzyl {4-[(6,7-dimethoxy-4-quinolyl)oxy]anilino}methanethioate

4-[(6,7-Dimethoxy-4-quinolyl)oxy]aniline (82 mg) was added to toluene/triethylamine=10/1 (8 ml), and the mixture was heated under reflux to prepare a solution. A solution of triphosgene (140 mg) in methylene chloride was then added to the solution, and the mixture was heated under reflux for 15 min. Subsequently, 4-methylbenzylmercaptan (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (90 mg, yield 65%).

$^1$H-NMR (CDCl$_3$, 400 MHz): 8.43–8.50 (1H, m), 8.13 (1H, s), 7.55–7.72 (4H, m), 7.00–7.26 (6H, m), 6.67 (1H, d, J=6.4 Hz), 4.21 (2H, s), 4.16 (3H, s), 4.10 (3H, s), 2.33 (3H, s) Mass spectrometry value (ESI-MS, m/z): 462 (M$^+$+1)

Example 108

4-Methylbenzyl {4-[(6,7-dimethoxy-4-quinolyl)oxy]-2,3-dimethylanilino}methanethioate 4-[(6,7-Dimethoxy-4-quinolyl)oxy]-2,3-dimethylaniline (90 mg) was added to toluene/triethylamine=10/1 (9 ml), and the mixture was heated under reflux to prepare a solution. A solution of triphosgene (145 mg) in methylene chloride was then added to the solution, and the mixture was heated under reflux for 15 min. Subsequently, 4-methylbenzylmercaptan (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (87 mg, yield 60%).

$^1$H-NMR (CDCl$_3$, 400 MHz): 8.47 (1H, bs), 8.16 (1H, s), 7.58–7.70 (2H, m), 6.88–7.26 (6H, m), 6.6 (1H, bs), 4.21 (2H, s), 4.17 (3H, s), 4.11 (3H, s), 2.34 (3H, s), 2.27 (3H, s), 2.14 (3H, s) Mass spectrometry value (ESI-MS, m/z): 490 (M$^+$+1)

Example 109

4-Methylbenzyl {4-[(6,7-dimethoxy-4-quinolyl)oxy]-2,5-dimethylanilino}methanethioate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (145 mg) in methylene chloride was then added to the solution, and the mixture was heated under reflux for 15 min. Subsequently, 4-methylbenzylmercaptan (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (74 mg, yield 54%).

$^1$H-NMR (CDCl$_3$, 400 MHz): 8.45–8.52 (1H, m), 8.15 (1H, s), 7.80 (1H, s), 7.64 (1H, s), 6.89–7.28 (6H, m), 6.57 (1H, d, J=6.3 Hz), 4.22 (2H, s), 4.17 (3H, s), 4.11 (3H, s), 2.34 (3H, s), 2.28 (3H, s), 2.13 (3H, s) Mass spectrometry value (ESI-MS, m/z): 490 (M$^+$+1)

Example 110

4-Methylbenzyl {4-[(6,7-dimethoxy-4-quinazolinyl)oxy]anilino}methanethioate

4-[(6,7-Dimethoxy-4-quinazolinyl)oxy]aniline (81 mg) was added to toluene/triethylamine=10/1 (8 ml), and the mixture was heated under reflux to prepare a solution. A solution of triphosgene (140 mg) in methylene chloride was then added to the solution, and the mixture was heated under reflux for 15 min. Subsequently, 4-methylbenzylmercaptan (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (74 mg, yield 54%).

$^1$H-NMR (CDCl$_3$, 400 MHz): 8.72 (1H, s), 8.12 (1H, s), 7.50–7.67 (4H, m), 7.10–7.26 (6H, m), 4.21 (2H, s), 4.18 (3H, s), 4.12 (3H, s), 2.33 (3H, s) Mass spectrometry value (ESI-MS, m/z): 462 (M$^+$+1)

Example 111

4-Methylbenzyl {2-chloro-4-[(6,7-dimethoxy-4-quinazolinyl)oxy]anilino}methanethioate 2-Chloro-4-[(6,7-dimethoxy-4-quinazolinyl)oxy]-aniline (85 mg) was added to toluene/triethylamine=10/1 (9 ml), and the mixture was heated under reflux to prepare a solution. A solution of triphosgene (140 mg) in methylene chloride was then added to the solution, and the mixture was heated under reflux for 15 min. Subsequently, 4-methylbenzylmercaptan (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 42%).

$^1$H-NMR (CDCl$_3$, 400 MHz): 8.81 (1H, s), 8.44 (1H, d, J=9.3 Hz), 8.13 (1H, s), 7.52–7.55 (2H, m), 7.11–7.34 (6H, m), 4.24 (2H, s), 4.19 (3H, s), 4.12 (3H, s), 2.34 (3H, s) Mass spectrometry value (ESI-MS, m/z): 497 (M$^+$+1)

Example 112

1-(2-Bromophenyl)ethyl N-{4-[(6,7-dimethoxy-4-quinolyl)oxy]phenyl}carbamate

4-[(6,7-Dimethoxy-4-quinolyl)oxy]aniline (88 mg) was added to toluene/triethylamine=10/1 (9 ml), and the mixture was heated under reflux to prepare a solution. A solution of triphosgene (145 mg) in methylene chloride was then added to the solution, and the mixture was heated under reflux for 15 min. Subsequently, 2-bromo-α-methylbenzyl alcohol (90 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (89 mg, yield 54%).

$^1$H-NMR (CDCl$_3$, 400 MHz): 8.44 (1H, d, J=6.7 Hz), 8.12 (1H, s), 6.90–7.61 (10H, m), 6.65 (1H, d, J=6.7 Hz), 6.20 (1H, q, J=6.4 Hz), 4.14 (3H, s), 4.08 (3H, s), 1.59 (3H, d, J=6.4 Hz) Mass spectrometry value (ESI-MS, m/z): 524 (M$^+$+1)

Example 113

1-(2-Bromophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (78 mg) was added to toluene/triethylamine=10/1 (8 ml), and the mixture was heated under reflux to prepare a solution. A solution of triphosgene (145 mg) in methylene chloride was then added to the solution, and the mixture was heated under reflux for 15 min. Subsequently, 2-bromo-α-methylbenzyl alcohol (90 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (101 mg, yield 71%).

$^1$H-NMR (CDCl$_3$, 400 MHz): 8.43 (1H, dd, J=6.5 Hz), 8.15 (1H, s), 7.15–7.78 (6H, m), 7.00 (1H, d, J=8.8 Hz), 6.57 (1H, bs), 6.52 (1H, d, J=6.5 Hz), 6.21 (1H, 2.09 (3H, s), 1.62 (3H, d, J=6.5 Hz) Mass spectrometry value (ESI-MS, m/z): 552 (M$^+$+1)

Example 114

1-(2-Bromophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (85 mg) was added to toluene/triethylamine=10/1 (9 ml), and the mixture was heated under reflux to prepare a solution. A solution of triphosgene (148 mg) in methylene chloride was then added to the solution, and the mixture was heated under reflux for 15 min. Subsequently, 2-bromo-α-methylbenzyl alcohol (90 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (70 mg, yield 45%).

$^1$H-NMR (CDCl$_3$, 400 MHz): 8.45 (1H, dd, J=6.6 Hz), 8.14 (1H, s), 7.92 (1H, bs), 7.15–7.65 (6H, m), 6.94 (1H, s), 6.46–6.58 (2H, m), 6.22 (1H, q, J=6.6 Hz), 4.17 (3H, s), 4.10 (3H, s), 2.30 (3H, s), 2.10 (3H, s), 1.63 (3H, d, J=6.6 Hz) Mass spectrometry value (ESI-MS, m/z): 552 (M$^+$+1)

Example 115

1-(2-Bromophenyl)ethyl N-{4-[(6,7-dimethoxy-4-quinazolinyl)oxy]phenyl}carbamate 4-[(6,7-Dimethoxy-4-quinazolinyl)oxy]aniline (90 mg) was added to toluene/triethylamine=10/1 (9 ml), and the mixture was heated under reflux to prepare a solution. A solution of triphosgene (151 mg) in methylene chloride was then added to the solution, and the mixture was heated under reflux for 15 min. Subsequently, 2-bromo-α-methylbenzyl alcohol (90 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 35%).

¹H-NMR (CDCl₃, 400 MHz): 8.75 (1H, s), 8.04 (1H, s), 7.14–7.61 (9H, m), 6.94 (1H, bs), 6.20 (1H, q, J=6.5 Hz), 4.17 (3H, s), 4.11 (3H, s), 1.60 (3H, di J=6.5 Hz) Mass spectrometry value (ESI-MS, m/z): 525 (M⁺+1)

Example 116

1-(2-Bromophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (85 mg) was added to toluene/triethylamine=10/1 (9 ml), and the mixture was heated under reflux to prepare a solution. A solution of triphosgene (139 mg) in methylene chloride was then added to the solution, and the mixture was heated under reflux for 15 min. Subsequently, 2-bromo-α-methylbenzyl alcohol (90 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 33%).

¹H-NMR (CDCl₃, 400 MHz): 8.80 (1H, s), 8.38 (1H, d, J=9.3 Hz), 8.14 (1H, s), 7.16–7.60 (7H, m), 6.23 (1H, q, J=6.6 Hz), 4.19 (3H, s), 4.11 (3H, s), 1.63 (3H, d, J=6.6 Hz) Mass spectrometry value (ESI-MS, m/z): 560 (M⁺+1)

Example 117

1-(3-Bromophenyl)ethyl N-{4-[(6,7-dimethoxy-4-quinolyl)oxy]phenyl}carbamate

4-[(6,7-Dimethoxy-4-quinolyl)oxy]aniline (72 mg) was added to toluene/triethylamine=10/1 (7 ml), and the mixture was heated under reflux to prepare a solution. A solution of triphosgene (111 mg) in methylene chloride was then added to the solution, and the mixture was heated under reflux for 15 min. Subsequently, 3-bromo-α-methylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (79 mg, yield 584%).

¹H-NMR (CDCl₃, 400 MHz): 8.46 (1H, dd, J=6.4 Hz) 8.13 (1H, s), 7.16–7.64 (9H, m), 7.01 (1H, s), 6.68 (1H, d, J=6.4 Hz), 5.86 (1H, q, J=6.4 Hz), 4.16 (3H, s), 4.10 (3H, s), 1.61 (3H, d, J=6.6 Hz) Mass spectrometry value (ESI-MS, m/z): 524 (M⁺+1)

Example 118

1-(3-Bromophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (68 mg) was added to toluene/triethylamine=10/1 (7 ml), and the mixture was heated under reflux to prepare a solution. A solution of triphosgene (120 mg) in methylene chloride was then added to the solution, and the mixture was heated under reflux for 15 min. Subsequently, 3-bromo-α-methylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (83 mg, yield 67%).

¹H-NMR (CDCl₃, 400 MHz): 8.45 (1H, dd, J=6.6 Hz), 8.15 (1H, s like), 7.16–7.74 (7H, m), 7.02 (1H, d, J=9.0 Hz), 6.54 (1H, d, J=6.1 Hz), 5.86 (1H, q, J=6.6 Hz), 4.17 (3H, s), 4.11 (3H, s), 2.27 (3H, s), 2.10 (3H, s), 1.62 (3H, d, J=6.6 Hz) Mass spectrometry value (ESI-MS, m/z): 552 (M⁺+1)

Example 119

1-(3-Bromophenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (88 mg) was added to toluene/triethylamine=1.0/1 (9 ml), and the mixture was heated under reflux to prepare a solution. A solution of triphosgene (138 mg) in methylene chloride was then added to the solution, and the mixture was heated under reflux for 15 min. Subsequently, 3-bromo-α-methylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 55%).

¹H-NMR (CDCl₃, 400 MHz): 8.40–8.50 (1H, m), 8.15 (1H, s like), 7.89 (1H, bs), 7.20–7.66 (5H, m), 6.95 (1H, s), 6.56 (1H, d, J=6.4 Hz), 6.50 (1H, bs), 5.86 (1H, q, J=6.6 Hz), 4.17 (3H, s), 4.10 (3H, s), 2.30 (3H, s), 2.11 (3H s), 1.62 (3H, d, J=6.6 Hz) Mass spectrometry value (ESI-MS, m/z): 552 (M⁺+1)

Example 120

1-(3-Bromophenyl)ethyl N-{4-[(6,7-dimethoxy-4-quinazolinyl)oxy]phenyl}carbamate

4-[(6,7-Dimethoxy-4-quinazolinyl)oxy]aniline (74 mg) was added to toluene/triethylamine=10/1 (8 ml), and the mixture was heated under reflux to prepare a solution. A solution of triphosgene (125 mg) in methylene chloride was then added to the solution, and the mixture was heated under reflux for 15 min. Subsequently, 3-bromo-α-methylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 44%).

$^1$H-NMR (CDCl$_3$, 400 MHz): 8.76 (1H, s), 8.06 (1H, s), 7.16–7.62 (8H, m), 6.85 (1H, bs), 5.85 (1H, q, J=6.6 Hz), 4.18 (3H, s), 4.11 (3H, s), 1.65 (3H, d, J=6.6 Hz) Mass spectrometry value (ESI-MS, m/z): 525 (M$^+$+1)

Example 121

1-(3-Bromophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (76 mg) was added to toluene/triethylamine=10/1 (8 ml), and the mixture was heat under reflux to prepare a solution. A solution of triphosgene (119 mg) in methylene chloride was then added to the solution, and the mixture was heated under reflux for 15 min. Subsequently, 3 bromo-α-methylbenzyl alcohol (75 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 40%).

$^1$H-NMR (CDCl$_3$, 400 MHz): 8.80 (1H, s), 8.35 (1H, d, J=9.0 Hz), 8.12 (1H, s), 7.54–7.60 (2H, m), 7.44–7.58 (1H, m), 7.15–7.36 (4H, m), 5.86 (1H, q, J=6.7 Hz), 4.19 (3H, s), 4.16 (3H, s), 1.63 (3H, d, J=6.7 Hz) Mass spectrometry value (ESI-MS, m/z): 560 (M$^+$+1)

Example 122

1-(2-Fluorophenyl)ethyl N-{4-[(6,7-dimethoxy-4-quinolyl)oxy]phenyl}carbamate

4-[(6,7-Dimethoxy-4-quinolyl)oxy]aniline (77 mg) was added to toluene/triethylamine=10/1 (8 ml), and the mixture was heated under reflux to prepare a solution. A solution of triphosgene (117 mg) in methylene chloride was then added to the solution, and the mixture was heated under reflux for 15 min. Subsequently, 2-fluoro-α-methylbenzyl alcohol (55 mg) was added thereto, and the mixture was further stirred with heating under reflux for 2 hr. After the completion of the reaction, the reaction was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (101 mg, yield 78%). Mass spectrometry value (ESI-MS, m/z): 524 (M$^+$+1)

Example 123

1-(2-Fluorophenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (74 mg) was added to toluene/triethylamine=10/1 (7 ml), and the mixture was heated under reflux to prepare a solution. A solution of triphosgene (103 mg) in methylene chloride was then added to the solution, and the mixture was heated under reflux for 15 min. Subsequently, 2-fluoro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 73%).

$^1$H-NMR (CDCl$_3$, 400 MHz): 8.37 (1H, dd, J=6.6 Hz), 8.08 (1H, s like), 7.67 (1H, d, J=8.1 Hz), 7.59 (1H, s), 7.37 (1H, dd, J=7.1 Hz), 7.10 (1H, dd, J=7.4 Hz), 7.01 (1H, dd, J=9.4 Hz), 6.93 (1H, d, J=8.8 Hz), 6.50 (1H, s), 6.46 (1H, d, J=6.6 Hz), 6.10 (1H, q, J=6.6 Hz), 4.10 (3H, s), 4.04 (3H, s, 2.22 (3H, s), 2.02 (3H, s), 1.59 (3H, d, J=6.6 Hz) Mass spectrometry value (ESI-MS, m/z): 4.92 (M$^+$+1)

Example 124

1-(2-Fluorophenyl)ethyl N-{4-[(6,7-dimethoxy-4-quinolyl)oxy]-2,5-dimethylphenyl}carbamate 4-[(6,7-Dimethoxy-4-quinolyl)oxy-2,5-dimethylaniline (71 mg) was added to toluene/triethylamine=10/1 (7 ml), and the mixture was heated under reflux to prepare a solution. A solution of triphosgene (99 mg) in methylene chloride was then added to the solution, and the mixture was heated under reflux for 15 min. Subsequently, 2-fluoro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 68%)

$^1$H-NMR (CDCl$_3$, 400 MHz): 8.45 (1H, dd, J=6.5 Hz), 8.15 (1H, d, J=4.2 Hz), 7.91 (1H, s), 7.64 (1H, s), 7.42–7.45 (1H, m), 7.28–7.33 (1H, m), 7.06–7.11 (1H, m), 7.15–7.20 (1H, m), 6.94 (1H, s), 6.56, (1H, d, J=6.5 Hz), 6.52 (1H, s), 6.17 (1H, q, J=6.7 Hz), 4.17 (3H, s), 4.10 (3H, s), 2.29 (3H, s), 2.11 (3H, s), 1.66 (3H, d, J=6.7 Hz) Mass spectrometry value (ESI-MS, m/z): 492 (M$^+$+1)

Example 125

1-(2-Fluorophenyl)ethyl N-{4-(6,7-dimethoxy-4-quinazolinyl)oxy]phenyl}carbamate

4-[(6,7-Dimethoxy-4-quinazolinyl)oxy]aniline (90 mg) was added to toluene/triethylamine=10/1 (9 ml), and the mixture was heated under reflux to prepare a solution. A solution of triphosgene (136 mg) in methylene chloride was then added to the solution, and the mixture was heated under reflux for 15 min.

Subsequently, 2-fluoro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (79 mg, yield 52%).

$^1$H-NMR (CDCl$_3$, 400 MHz): 8.74 (1H, s), 8.06 (1H, s), 7.58 (1H, s), 7.54 (2H, d, J=9.0 Hz), 7.39–7.43 (1H, m), 7.23–7.32 (1H, m), 7.12.–7.17 (3H, m), 7.03–7.08 (1H, m), 6.86 (1H, s), 6.14 (1H, q, J=6.6 Hz), 4.15 (3H, s), 4.09 (3H, s), 1.62 (3H, d, J=6.6 Hz) Mass spectrometry value (ESI-MS, m/z): 464 (M$^+$+1)

Example 126

1-(2-Fluorophenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (83 mg) was added to toluene/triethylamine=10/1 (8 ml), and the mixture was heated under reflux to prepare a solution. A solution of triphosgene (134 mg) in methylene chloride was then added to the solution, and the mixture was heated under reflux for 15 min. Subsequently, 2fluoro-α-methylbenzyl alcohol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 45%).

$^1$H-NMR (CDCl$_3$, 400 MHz): 8.80 (1H, s), 8.37 (1H, d, J=9.2 Hz), 8.15 (1H, s), 7.58 (1H, s), 7.43–7.52 (1H, m), 7.32 (1H, d, J=2.7 Hz), 7.28–7.35 (1H, m), 7.15–7.20 (2H, m), 7.06–7.11 (1H, q, J=6.6 Hz), 4.19 (3H, s), 4.12 (3H, s), 1.66 (3H, d, J=6.6 Hz) Mass spectrometry value (ESI-MS, m/z): 499 (M$^+$+1)

Example 127

1-(2-Ethoxyphenyl)ethyl N-{4-[(6,7-dimethoxy-4-quinolyl)oxy]phenyl}carbamate

4-[(6,7-Dimethoxy-4-quinolyl)oxy]aniline (80 mg) was added to toluene/triethylamine=10/1 (8 ml), and the mixture was heated under reflux to prepare a solution. A solution of triphosgene (122 mg) in methylene chloride was then added to the solution, and the mixture was heated under reflux for 15 min. Subsequently, 2-ethoxy-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed, solution was dried over sodium sulfate and was concentrated. The residue was purified on a column using chloroform/methanol to give the title compound (98 mg, yield 69%).

$^1$H-NMR (CDCl$_3$, 400 MHz): 8.46 (1H, dd, J=6.5 Hz), 8.14 (1H, s like), 7.58–7.64 (3H, m), 7.38–7.42 (1H, m), 7.16–7.18 (2H, m), 6.85–7.00 (3H, m), 6.68 (1H, d, J=6.6 Hz), 6.31 (1H, q, J=6.5 Hz), 4.16 (3H, s), 4.10 (3H, s), 4.05–4.13 (2H, m), 1.59 (3H, d, J=6.5 Hz), 1.44 (3H, t, J=7.1 Hz) Mass spectrometry value (ESI-MS, m/z): 490 (M$^+$+1)

Example 128

1-(2-Ethoxyphenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (72 mg) was added to toluene/triethylamine=10/1 (7 ml) and the mixture was heated under reflux to prepare a solution. A solution of triphosgene (100 mg) in methylene chloride was then added to the solution, and the mixture was heated under reflux for 15 min. Subsequently, 2-ethoxy-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (71 mg, yield 58%).

$^1$H-NMR (CDCl$_3$, 400 MHz): 8.42 (1H, d, J=6.5 Hz), 8.13 (1H, s like), 7.73–7.80 (1H, m), 7.64 (1H, s), 7.10–7.40 (2H, m), 6.80–7.00 (3H, m), 6.48–6.53 (1H, m), 6.28 (1H, q, J=6.4 Hz), 4.15 (3H, s), 4.09 (3H, s), 4.02–4.10 (2H, m), 2.24 (3H, s), 2.07 (3H, s), 1.57 (3H, d, J=6.4 Hz), 1.42 (3H, t, J=6.9 Hz) Mass spectrometry value (ESI-MS, m/z): 518 (M$^+$+1)

Example 129

1-(2-Ethoxyphenyl)-ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (83 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 2-ethoxy-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 55%).

¹H-NMR (CDCl₃, 400 MHz): 8.42 (1H dd, J=6.3 Hz), 8.13 (1H, s like), 7.93 (1H, bs), 7.38 (1H, d, J=7.6 Hz), 6.83–6.99 (4H, m), 6.53–6.58 (1H, m), 6.49 (1H, bs), 6.29. (1H, q, J32 6.5 Hz), 4.15 (3H, s), 4.08 (3H, s), 4.04–4.11 (2H, m), 2.27 (3H, s), 2.08 (3H, s), 1.58 (3H, d, J=6.5 Hz), 1.43 (3H, t, J=6.9 Hz) Mass spectrometry value (ESI-MS, m/z): 518 (M⁺+1)

Example 130

1-(2-Ethoxyphenyl)ethyl N-{4-[(6,7-dimethoxy-4-quinazolinyl)oxy]phenyl}carbamate 4-[(6,7-Dimethoxy-4-quinazolinyl)oxy]aniline (77 mg) was added to toluene/triethylamine=10/1 (8 ml), and the mixture was heated under reflux to prepare a solution. A solution of triphosgene (117 mg) in methylene chloride was then added to the solution, and the mixture was heated under reflux for 15 min. Subsequently, 2-ethoxy-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (63 mg, yield 46%).

¹H-NMR (CDCl₃, 400 MHz): 8.74 (1H, s like), 8.05 (1H, s), 7.53–7.59 (3H, m), 7.34–7.38 (1H, m), 7.13–7.26 (3H, m), 6.82–6.98 (3H, m), 6.27 (1H, m), 6.27 (1H, q, J=6.5 Hz), 4.15 (3H, s), 4.09 (3H, s), 4.02–4.10 (2H, m), 1.56 (3H, d, J=6.5 Hz), 1.42. (3H, t, J=7.0 Hz) Mass spectrometry value (ESI-MS, m/z): 491 (M⁺+1)

Example 131

1-(2-Ethoxyphenyl)ethyl N-{-chloro-4-[(6,7-dimethoxy-4-quinazolinyl)oxy]phenyl}carbamate 2-Chloro-4-[(6,7-dimethoxy-4-quinazolinyl)oxy]-aniline (80 mg) was added to toluene/triethylamine=10/1 (9 ml) and the mixture was heated under reflux to prepare a solution. A solution of triphosgene (109 mg) in methylene chloride was then added to the solution, and the mixture was heated under reflux for 15 min. Subsequently, 2-ethoxy-α-methylbenzyl alcohol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 43%).

¹H-NMR (CDCl₃, 400 MHz): 8.80 (1H, s), 8.40 (1H, d, J=9.0 Hz), 8.13 (1H, s), 7.58 (1H, s), 7.14–7.45 (4H, m), 6.86–7.01 (3H, m), 6.32 (1H, q, J=6.3 Hz), 4.19 (3H, s), 4.12 (3H, s), 4.05–4.13 (2H, m), 1.61 (3H, d, J=6.3 Hz), 1.39–1.45 (3H, m) Mass spectrometry value (ESI-MS, m/z): 525 (M⁺+1)

Example 132

1-(4-Methylphenyl)ethyl N-{4-[(6,7-dimethoxy-4-quinolyl)oxy]phenyl}carbamate

4-[(6,7-Dimethoxy-4-quinolyl)oxy]aniline (72 mg) was added to toluene/triethylamine=10/1 (7 ml), and the mixture was heated under reflux to prepare a solution. A solution of triphosgene (109 mg) in methylene chloride was then added to the solution, and the mixture was heated under reflux for 15 min. Subsequently 4-methyl-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (98 mg, yield 81%)

¹H-NMR (CDCl₃, 400 MHz): 8.40–8.45 (1H, m), 8.11 (1H, s), 7.61 (1H, s), 7.53–7.59 (2H, m), 7.10–7.32 (6H, m), 6.78–6.85 (1H, m), 6.65 (1H, d, J=6.6 Hz), 5.87 (1H, q, J=6.6 Hz), 4.14 (3H, s), 4.08 (3H, s), 2.34 (3H, s), 1.60 (3H, d, J=6.6 Hz) Mass spectrometry value (ESI-MS, m/z): 460 (M⁺+1)

Example 133

1-(4-Methylphenyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 4-methyl-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (97 mg, yield 75%).

¹H-NMR (CDCl₃, 400 MHz): 8.40–8.45 (1H, m), 8.12 (1H, s), 7.73 (1H, d, J=8.3 Hz), 7.64 (1H, s), 7.15–7.32 (4H, m), 6.97 (1H, d, J=8.8 Hz), 6.51 (1H, d, J=6.6 Hz), 6.48 (1H, s), 5.87 (1H, q, J=6.5 Hz), 4.14 (3H, s), 4.08 (3H, s), 2.34 (3H, s), 2.22 (3H, s), 2.06 (3H, s), 1.60 (3H, d, J=6.4 Hz) Mass spectrometer value (ESI-M,S m/z): 488 (M⁺+1)

Example 134

1-(4-Methylphenyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 4-methyl-α-methylbenzyl alcohol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88mg, yield 68%).

$^1$H-NMR (CDCl$_3$, 400 MHz): 8.41–8.47 (1H, m), 8.12 (1H, s), 7.90 (1H, s), 7.62 (1H, s), 7.15–7.33 (4H, m), 6.91 (1H, s), 6.54 (1H, d, J=6.4 Hz), 6.45 (1H, s), 5.87 (1H, q, J=6.6 Hz), 4.14 (3H, s), 4.08 (3H, s), 2.34 (3H, s), 2.22 (3H, s), 2.08 (3H, s), 1.61 (3H, d, J=6.6 Hz) Mass spectrometry value (ESI-MS, m/z): 488 (M$^+$+1)

Example 135

1-(4-Methylphenyl)ethyl N{4-[(6,7-dimethoxy-4-quinazolinyl)oxy]phenyl}carbamate

4-[(6,7-Dimethoxy-4-quinazolinyl)oxy]aniline (76 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 4-methyl-α-methylbenzyl alcohol (52 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (85 mg, yield 67%).

$^1$H-NMR (CDCl$_3$, 400 MHz): 8.74 (1H, s), 8.03 (1H, s), 7.43–7.60 (3H, m), 6.74–7.30 (6H, m), 6.45 (1H, bs), 5.80–5.90 (1H, m), 4.14 (3H, s), 4.09 (3H, s), 2.33 (3H, s), 1.59 (3H, d, J=6.6 Hz) Mass spectrometry value (ESI-MS, m/z): 461 (M$^+$+1)

Example 136

1-(4-Methylphenyl)ethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (78 mg) was added to toluene/triethylamine=10/1 (8 ml), and the mixture was heated under reflux to prepare a solution. A solution of triphosgene (106 mg) in methylene chloride was then added to the solution, and the mixture was heated under reflux for 15 min. Subsequently, 4-methyl-α-methylbenzyl alcohol (48 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 49%).

$^1$H-NMR (CDCl$_3$, 400 MHz): 8.78 (1H, s), 8.35 (1H, d, J=9.0 Hz), 8.12 (1H, s), 7.55 (1H, s), 7.12–7.34 (7H, m), 5.83–5.91 (1H, m), 4.17 (3H, s), 4.09 (3H, s), 2.34 (3H, s), 1.62 (3H, d, J=6.5 Hz) Mass spectrometry value (ESI-MS, m/z): 405 (M$^+$+1)

Example 137

3-[(4-Methylphenyl)sulfanyl]ethyl N-{4-[(dimethoxy-4-quinolyl)oxy]-phenyl}carbamate 4-[(6,7-Dimethoxy-4-quinolyl)oxy]aniline (78 mg) was added to toluene/triethylamine=10/1 (8 ml), and the mixture was heated under reflux to prepare a solution. A solution of triphosgene (118 mg) in methylene chloride was then added to the solution, and the mixture was heated under reflux for 15 min. Subsequently, 2-[(4-methylphenyl)sulfanyl]-1-ethanol (66 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 35%).

$^1$H-NMR (CDCl$_3$, 400 MHz): 8.40–8.49 (1H, M), 8.13 (1H, s), 7.62 (1H, s), 7.55 (1H, d, J=9.0 Hz), 7.09–7.35 (6H, m), 6.75 (1H, s), 6.66 (1H, d, J=6.4 Hz), 4.33 (2H, t, J=6.4 Hz), 4.15 (3H, s), 4.08 (3H, s), 3.15 (2H, t, J=6.4 Hz), 2.31 (3H, s) Mass spectrometry value (ESI-MS, m/z): 492 (M$^+$+1)

Example 138

3-[(4-Methylphenyl)sulfanyl]ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (72 mg) was added to toluene/triethylamine=10/1 (7 ml), and the mixture was heated under reflux to prepare a solution. A solution of triphosgene (100 mg) in methylene chloride was then added to the solution, and the mixture was heated under reflux 15 min. Subsequently, 2-[(4-methylphenyl)sulfanyl]-1-ethanol (56 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (53 mg, yield 43%).

$^1$H-NMR (CDCl$_3$, 400 MHz.): 8.40–8.46 (1H, m), 8.13 (1H, s), 7.63–7.74 (2H, m), 6.98–7.36 (5H, m), 5.53 (1H, d, J=6.6 Hz), 6.43 (1H, s), 4.33 (2H, t, J=6.7 Hz), 4.15 (3H, s), 4.09 (3H, s), 3.16 (2H, t, J=6.7 Hz), 2.30 (6H, s), 2.23 (3H, s) Mass spectrometry value (ESI-MS, m/z): 520 (M$^+$+1)

Example 139

3-[(4-Methylphenyl)sulfanyl]ethyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (74 mg) was added to toluene/triethylamine=10/1 (7 ml), and the mixture was heated under reflux to prepare a solution. A solution of triphosgene (103 mg) in methylene chloride was then added to the solution, and the mixture was heated under reflux for 15 min. Subsequently, 2-[(4-methylphenyl)sulfanyl]-1-ethanol (58 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 40%).
$^1$H-NMR (CDCl$_3$, 400 MHz): 8.41–8.48 (1H, m), 8.13 (1H, s), 7.85 (1H, s), 7.62 (1H, s), 6.92–7.35 (5H, m), 6.55 (1H, d, J=6.1 Hz), 6.39 (1H, s), 4.33 (1H, t, J=6.7 Hz), 4.15 (3H, s), 4.08 (3H, s), 3.16 (2H, t, J=6.7 Hz), 2.31 (3H, s), 2.24 (3H, s), 2.14 (3H, s) Mass spectrometry value (ESI-MS, m/z): 520 (M$^+$+1)

Example 140

3-[(4-Methylphenyl)sulfanyl]ethyl N-{4-[(6,7-dimethoxy-4-quinazolinyl)oxy]phenyl}carbamate

4-[(6,7-Dimethoxy-4-quinazolinyl)oxy]aniline (69 mg) was added to toluene/triethylamine=10/1 (7 ml), and the mixture was heated under reflux to prepare a solution. A solution of triphosgene (105 mg) in methylene chloride was then added to the solution, and the mixture was heated under reflux for 15 min. Subsequently, 2-[(4-methylphenyl)sulfanyl]-1-ethanol (59 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (29 mg, yield 24%).
$^1$H-NMR (CDCl$_3$, 400 MHz): 8.76 (1H, s), 8.10 (1H, s), 7.59 (1H, s), 7.49–7.56 (2H, m), 6.70–7.33 (7H, m), 4.32 (2H, t, J=6.7 Hz), 4.17 (3H, s), 4.10 (3H, s), 3.14 (2H, t, J=6.7 Hz)), 2.31 (3H, s) Mass spectrometry value (ESI-MS m/z): 4.93 (M$^+$+1)

Example 141

3-[(4-Methylphenyl)sulfanyl]ethyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (75 mg) was added to toluene/triethylamine=10/1 (8 ml), and the mixture was heated under reflux to prepare a solution. A solution of triphosgene (102 mg) in methylene chloride was then added to the solution, and the mixture was heated under reflux for 15 min. Subsequently, 2-[(4-methylphenyl)sulfanyl]-1-ethanol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (57 mg, yield 30%).
$^1$H-NMR (CDCl$_3$, 400 MHz): 8.79 (1H, s), 8.32 (1H, d, J=9.3 Hz), 8.13 (1H, s), 7.56 (1H, s), 7.08–7.36 (7H, m), 4.35 (2H, t, J=6.7 Hz), 4.18 (3H, s), 4.10 (3H, s), 3.16 (2H, t, J=6.7 Hz), 2.30 (3H, s) Mass spectrometry value (ESI-MS, m/z): 527 (M$^+$+1)

Example 142

3-(2-Fluorophenoxy)propyl N-{4-[(6,7-dimethoxy-4-quinolyl)oxy]phenyl}carbamate

4-[(6,7-Dimethoxy-4-quinolyl)oxy]aniline (70 mg) was added to toluene/triethylamine=10/1 (7 ml), and the mixture was heated under reflux to prepare a solution. A solution of triphosgene (106 mg) in methylene chlorides was then added to the solution, and the mixture was heated under reflux for 15 min. Subsequently, 3-(2-fluorophenoxy)-1-propanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (60 mg, yield 55%).
$^1$H-NMR (CDCl$_3$, 400 MHz): 8.44–8.47 (1H, m), 8.11–8.13 (1H, m), 7.54–7.60 (2H, m), 7.61 (1H, s), 7.14–7.18 (2H, m), 7.01–7.08 (2H, m), 6.86–6.98 (3H, m), 4.14 (3H, s), 4.08 (3H, s), 4.11–4.20 (2H, m), 4.34–4.44 (2H, m), 2.12–2.24 (2H, m) Mass spectrometry value (ESI-MS, m/z): 494 (M$^+$+1)

Example 143

3-(2-Fluorophenoxy)propyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (72 mg) was added to toluene/triethylamine=10/1 (7 ml), and the mixture was heated under reflux to prepare a solution. A solution of triphosgene (100 mg) in methylene chloride was then added to the solution, and the mixture was heated under reflux for 15 min. Subsequently, 3-(2-fluorophenoxy)-1-propanol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 63%).

$^1$H-NMR (CDCl$_3$, 400 MHz): 8.41–8.46 (1H, m), 8.13–8.14 (1H, d, J=3.9 Hz), 7.72 (1H, s like), 7.64 (1H, s), 5.94–7.09 (3H, m), 6.87–6.93 (1H, m), 6.53 (1H, d, J=6.6 Hz), 6.47 (1H, s), 4.42 (1H, t, J=6.2 Hz), 4.35 (1H, t, J=6.2 Hz), 4.15–4.20 (2H, m), 4.15 (3H, s), 4.09 (3H, s), 2.2 (3H, s), 2.08 (3H, s), 2.14–2.25 (2H, m) Mass spectrometry value (ESI-MS, m/z): 522 (M$^+$+1)

Example-144

3-(2-Fluorophenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (71 mg) was added to toluene/triethylamine=10/1 (7 ml), and the mixture was heated under reflux to prepare a solution. A solution of triphosgene (100 mg) in methylene chloride was then added to the solution, and the mixture was heated under reflux for 15 min. Subsequently, 3-(2-fluorophenoxy)-1-propanol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (53 mg, yield 42%).

H-NMR (CDCl$_3$, 400 MHz), 8.45–8.49 (1H, m), 8.13 (1H, d like), 7.87 (1H, s), 7.62 (1H, s), 6.87–7.09 (4H, m), 6.56 (1H, d, J=6.3 Hz), 6.45 (1H, s), 4.42 (1H, d, J=6.2 Hz), 4.36 (1H, d, J=6.2 Hz), 4.13–4.20 (2H, m), 4.15 (3H, s), 4.08 (3H, s), 2.05–2.24 (2H, m), 2.26 (3H, s), 2.10 (3H, s) Mass spectrometry value (ESI-MS, m/z): 522 (M$^+$+1)

Example 145

3-(2-Fluorophenoxy) propyl N-{4-[(6,7-dimethoxy-4-quinazolinyl)oxy]phenyl}carbamate 4-[(6,7-Dimethoxy-4-quinazolinyl)oxy]aniline (65 mg) was added to toluene/triethylamine=10/1 (7 ml), and the mixture was heated under reflux to prepare a solution. A solution of triphosgene (90 mg) in methylene chloride was then added to the solution, and the mixture was heated under reflux for 15 min. Subsequently, 3-(2-fluorophenoxy)-1-propanol (51 mg) was added thereto, and the mixture was further stirred with heating under reflux for 2 hr. After the completion of the reaction, the reaction solution was allowed to cool to room temperature before distilled water was added thereto., The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (52 mg, yield 46%).

$^1$H-NMR (CDCl$_3$, 400 MHz): 8.74 (1H, s), 7.96 (1H, s), 7.58 (1H, s), 7.52–7.56 (1H, m), 7.16–7.21 (2H, m), 6.77–7.08 (5H, m), 4.40 (1H, t, J=6.2 Hz), 4.34 (1H, t, J=6.2 Hz), 4.07–4.19 (2H, m), 4.14 (3H, s), 4.09 (3H, s), 2.03.–2.27 (2H, m) Mass spectrometry value (ESI-MS, m/z): 494 (M$^+$+1)

Example 146

3-(2-Fluorophenoxy)propyl N-{4-[(6,7-dimethoxy-4-quinazolinyl)oxy]-2,3-dimethylphenyl}carbamate 4-[(6,7-Dimethoxy-4-quinazolinyl)oxy]-2,3-dimethylaniline (65 mg) was added to toluene/triethylamine=10/1 (7 ml), and the mixture was heated under reflux to prepare a solution. A solution of triphosgene (90 mg) in methylene chloride was then added to the solution, and the mixture was heated under reflux for 15 min. Subsequently, 3-(2-fluorophenoxy)-1-propanol (51 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (52 mg, yield 46%).

$^1$H-NMR (CDCl$_3$, 400 MHz), 8.69 (1H, s like), 8.07 (1H, s), 7.65 (1H, bs), 7.57 (1H, s), 6.80–6.87 (1H, m), 6.89–7.04 (4H, m), 4.35 (1H, t, J=6.2 Hz), 4.28 (1H, d, J=6.2 Hz), 4.08–4.14 (2H, m), 4.12 (3H, s), 4.06 (3H, s), 2.05–2.19 (2H, m), 2.00 (3H, s) Mass spectrometry value (ESI-MS, m/z): 523 (M$^+$+1)

Example 147

3-(3-Fluorophenoxy)propyl N-{4-[(6,7-dimethoxy-4-quinolyl)oxy]phenyl}carbamate

4-[(6,7-Dimethoxy-4-quinolyl)oxy]aniline (71 mg) was added to toluene/triethylamine=10/1 (7 ml), and the mixture was heated under reflux to prepare a solution. A solution of triphosgene (108 mg) in methylene chloride was then added to the solution, and the mixture was heated under reflux for 15 min. Subsequently, 3-(3-fluorophenoxy)-1-propanol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 69%).

$^1$H-NMR (CDCl$_3$, 400 MHz), 8.44–8.48 (1H, m), 8.12 (1H, d, J=3.7 Hz), 7.61 (1H, s), 7.57–7.61 (2H, m), 7.14–7.21 (3H, m), 66.92 (1H, d, J=9.2 Hz), 6.57–6.68 (3H, m), 4.39 (1H, t, J=6.2 Hz), 4.35 (1H, d, J=6.2 Hz), 4.12 (3H, s), 4.08 (3H, s), 4.05–4.09 (2H, m), 2.12–2.1 (2H, m) Mass spectrometry value (ESI-MS, m/z): 494 (M$^+$+1)

Example 148

3-(3-Fluorophenoxy)propyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (66 mg) was added to toluene/triethylamine=10/1 (7 ml), and the mixture was heated under reflux to prepare a solution. A solution of triphosgene (92 mg) in methylene chloride was then added to the solution, and the mixture was heated under reflux for 15 min. Subsequently, 3-(3-fluorophenoxy)-1-propanol (52 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (63 mg, yield 55%).

$^1$H-NMR (CDCl$_3$, 400 MHz), 8.41–8.45 (1H, m), 8.14 (1H, d, J=3.9 Hz), 7.72 (1H, bs), 7.64 (1H, s), 7.16–7.22 (1H, m), 7.00 (1H, dd, J=8.8 Hz, J=5.6 Hz), 6.58–6.70 (2H, m), 6.53 (1H, d, J=6.6 Hz), 6.43–6.49 (1H, m), 4.39 (1H, t, J=6.2 Hz), 4.35 (1H, t, J=6.2 Hz), 4.15 (3H, s), 4.10 (3H, s), 4.05–4.10 (2H, m), 2.25 (3H d, J=4.9 Hz), 2.08 (3H, s, J=3.2 Hz), 2.13–2.21 (2H, m) Mass spectrometry value (ESI-MS, m/z): 522 (M$^+$+1)

Example 149

3-(3-Fluorophenoxy)propyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (79 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-(3-fluorophenoxy)-1-propanol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (74 mg, yield 54%).

$^1$H-NMR (CDCl$_3$, 400 MHz), 8.45–8.50 (1H, m), 8.12 (1H, d, J=3.7 Hz), 7.86 (1H, bs), 7.62 (1H, s), 7.16–7.25 (1H, m), 6.93 (1H, d, J=3.2 Hz), 6.54–6.70 (3H, m), 6.43–6.47 (1H, m), 4.39 (1H, t, J=6.2 Hz), 4.36 (1H, t, J=6.2 Hz), 4.14 (3H, s), 4.08 (3H, s), 4.05–4.10 (2H, m), 2.26 (3H, d, J=4.6 Hz), 2.10 (3H, d, J=5.4H), 2.13–2.22 (2H, m) Mass spectrometry value (ESI-MS, m/z): 522 (M$^+$+1)

Example 150

3-(3-Fluorophenoxy)propyl N-{4-[(6,7-dimethoxy-4-quinazolinyl)oxy]phenyl}carbamate

4-[(6,7-Dimethoxy-4-quinazolinyl)oxy]aniline (82 mg) was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 3-(3-fluorophenoxy)-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (59 mg, yield 46%).

$^1$H-NMR (CDCl$_3$, 400 MHz): 8.69 (1H, s), 8.01 (1H, s), 7.54 (1H, s), 7.46–7.54 (2H, m), 7.10–7.15 (3H, m), 6.76–6.85 (1H, m), 6.51–6.64 (2H, m), 4.32 (1H, t, J=6.2 Hz), 4.29 (1H, t, J=6.2 Hz), 4.10 (3H, s), 4.04 (3H, s), 3.96–4.04 (2H, m), 2.05–2.15 (2H, m) Mass spectrometry value (ESI-MS, m/z): 494 (M$^+$+1)

Example 151

3-(3-Fluorophenoxy)propyl N-{4-[(6,7-dimethoxy-4-quinazolinyl)oxy]-2,3-dimethylphenyl}carbamate

4-[(6,7-Dimethoxy-4-quinazolinyl)oxy]-2,3-di-methylaniline (68 mg) was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 3-(3-fluorophenoxy)-1-propanol (53 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 56%).

$^1$H-NMR (CDCl$_3$, 400 MHz): 8.74 (1H, s), 8.08 (1H, s), 7.67 (1H, bs), 7.61 (1H, s), 7.14–7.23 (1H, m), 6.96–7.02 (1H, m), 6.55–6.68 (2H, m), 6.43–6.53 (1H, m), 4.30–4.38 (2H, m), 4.16 (3H, s), 4.10 (3H, s), 4.03–4.10 (2H, m), 2.22–2.25 (3H, m), 2.10–2.18 (2H, m), 2.04–2.07 (3H, m) Mass spectrometry value (ESI-MS, m/z): 523 (M$^+$+1)

Example 152

3-(4-Fluorophenoxy)propyl N-{4-[(6,7-dimethoxy-4-quinolyl)oxy]phenyl}carbamate

4-[(6,7-Dimethoxy-4-quinolyl)oxy-]aniline (71 mg) was added to toluene/triethylamine=10/1 (7 ml), and the mixture was heated under reflux to prepare a solution. A solution of triphosgene (108 mg) in methylene chloride was then added to the solution, and the mixture was heated under reflux for 15 min. Subsequently, 3-(4-fluorophenoxy)-1-propanol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (81 mg, yield 64%).

$^1$H-NMR (CDCl$_3$, 400 MHz): 8.45 (1H, d, J=4.2 Hz), 8.12 (1H, d, J=3.6 Hz), 7.62 (1H, s), 7.56–7.62 (2H, m), 7.14–7.18 (2H, m), 6.94–6.98 (1H, m), 6.80–6.89 (2H, m), 6.67 (1H, d, J=6.4 Hz), 4.39 (1H, t, J=6.2 Hz), 4.36 (1H, t, J=6.2 Hz), 4.14 (3H, s), 4.08 (3H, s), 4.04 (2H, t, J=6.0 Hz), 2.12–2.20 (2H, m) Mass spectrometry value (ESI-MS, m/z): 494 (M$^+$+1)

Example 153

3-(4-Fluorophenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (66 mg) was added to toluene/triethylamine=10/1 (7 ml), and the mixture was heated under reflux to prepare a solution. A solution of triphosgene (92 mg) in methylene chloride was then added to the solution, and the mixture was heated under reflux for 15 min. Subsequently, 3-(4-fluorophenoxy)-1-propanol (52 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (79 mg, yield 70%).

$^1$H-NMR (CDCl$_3$, 400 MHz): 8.44 (1H, dd, J=6.2 Hz), 8.13 (1H, d, J=3.9 Hz), 7.72 (1H, bs), 7.64 (1H, s), 6.92–7.02 (3H, m), 6.81–6.85 (1H, m), 6.53 (1H, d, J=6.2 Hz), 6.48 (1H, d, J=5.6 Hz), 4.39 (1H, t, J=6.3 Hz), 4.35 (1H, t, J=6.3 Hz), 4.15 (3H, s), 4.09 (3H, s), 4.04 (2H, t, J=6.1 Hz), 2.25 (3H, d, J=6.3 Hz), 2.08 (3H, d, J=3.2 Hz), 2.13–2.20 (2H, m) Mass spectrometry value (ESI-MS, m/z): 522 (M$^+$+1)

Example 154

3-(4-Fluorophenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (68 mg), was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 3-(4-fluorophenoxy)-1-propanol (54 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 58%).

$^1$H-NMR (CDCl$_3$, 400 MHz): 8.49 (1H, dd, J=6.5 Hz), 8.10 (1H, s), 7.85 (1H, bs), 7.61 (1H, s), 6.78–6.97 (4H, m), 6.56 (1H, d, J=6.3 Hz), 6.50 (1H, d, J=6.8 Hz), 4.38 (1H, t, J=6.3 Hz), 4.34 (1H, t, J=6.3 Hz), 4.13 (3H, s), 4.13 (3H, s), 4.07 (3H, s), 4.04 (2H, t, J=6.0 Hz), 2.25 (3H, d, J=5.6 Hz), 2.09 (3H, d, J=5.1 Hz) Mass spectrometry value (ESI-MS, m/z): 522 (M$^+$+1)

Example 155

3-(4-Fluorophenoxy)propyl N-{4-[(6,7-dimethoxy-4-quinazolinyl)oxy]phenyl}carbamate 4-[(6,7-Dimethoxy-4-quinazolinyl)oxy]aniline (59 mg) was added to toluene/triethylamine=10/1 (6 ml), and the mixture was heated under reflux to prepare a solution. A solution of triphosgene (89 mg) in methylene chloride was then added to the solution, and the mixture was heated under reflux for 15 min. Subsequently, 3-(4-fluorophenoxy)-1-propanol (51 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 49%).

$^1$H-NMR (CDCl$_3$, 400 MHz): 8.73 (1H, s), 7.97 (1H, s), 7.58 (1H, s), 7.53–7.57 (2H, m), 7.16–7.19 (2H, m), 6.89–6.98 (2H, m), 6.78–6.85 (2H, m), 4.37 (1H, t, J=6.3 Hz), 4.34 (1H, t, J=6.3 Hz), 4.14 (3H, s), 4.09 (3H, s), 4.03 (2H, t, J=6.3 Hz), 2.08–2.20 (2H, m) Mass spectrometry value (ESI-MS, m/z): 494 (M$^+$+1)

Example 156

3-(4-Fluorophenoxy)propyl N-{4-[(6,7-dimethoxy-4-quinazolinyl)oxy]-2,3-dimethylphenyl}-carbamate 4-[(6,7-Dimethoxy-4-quinazolinyl)oxy]-2,3-dimethylaniline (68 mg) was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 3-(4-fluorophenoxy)-1-propanol (53 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 41%).

¹H-NMR (CDCl₃, 400 MHz): 8.71 (1H, s), 7.91 (1H, s), 7.66 (1H, bs), 7.61 (1H, s), 6.91–7.02 (3H, m), 6.78–6.84 (2H, m), 6.44 (1H, bs), 4.37 (1H, t, J=6.5 Hz), 4.33 (1H, t, J=6.5 Hz), 4.14 (3H, s), 4.10 (3H, s), 4.00–4.08 (2H, m), 2.23 (3H, d, J=6.1 Hz), 2.06 (3H, d, J=3.2 Hz), 2.10–2.20 (2H, m, Mass spectrometry value (ESI-MS, m/z): 523 (M⁺+1)

Example 157

3-(2-Methoxyphenoxy)propyl N-{4-[(6,7-dimethoxy-4-quinolyl)oxy]phenyl}carbamate

4-[(6,7-Dimethoxy-4-quinolyl)oxy]aniline (72 mg) was added to toluene/triethylamine=10/1 (7 ml), and the mixture was heated under reflux to prepare a solution. A solution of triphosgene (109 mg) in methylene chloride was then added to the solution, and the mixture was heated under reflux for 15 min. Subsequently, 3-(2-methoxyphenoxy)-1-propanol (66 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (91 mg, yield 69%).

¹H-NMR (CDCl₃, 400 MHz): 8.47 (1H, bs), 8.12 (1H, s), 7.61 (1H, s), 7.55–7.60 (2H, m), 7.13–7.18 (2H, m), 6.85–6.95 (4H, m), 6.68 (1H, bs), 4.42 (2H, t, J=6.2 Hz), 4.12–4.20 (2H, m), 4.14 (3H, s), 4.08 (3H, s), 3.85 (3H, s), 2.17–2.26 (2H, m) Mass spectrometry value (ESI-MS, m/z): 506 (M⁺+1)

Example 158

3-(2-Methoxyphenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (70 mg) was added to toluene/triethylamine=10/1 (7 ml), and the mixture was heated under reflux to prepare a solution. A solution of triphosgene (97 mg) in methylene chloride was then added to the solution, and the mixture was heated under reflux for 15 min. Subsequently, 3-(2-methoxyphenoxy)-1-propanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 63%).

¹H-NMR (CDCl₃, 400 MHz): 8.43 (1H, dd, J=6.6 Hz), 8.14 (1H, d like, J=4.1 Hz), 7,72 (1H, bs), 7.64 (1H, s), 6.99 (1H, d, J=8.8 Hz), 6.86–6.96 (4H, m), 6.53 (1H, d, J=6.6 Hz), 6.47 (1H, bs), 4.41 (2H, t, J=6.3 Hz), 4.15 (3H, s), 4.15 (2H, t, J=6.2 Hz), 4.09 (3H, s), 3.85 (3H, s), 2.24 (3H, s), 2.07 (3H, s), 2.19–2.26 (2H, m) Mass spectrometry value (ESI-MS, m/z): 534 (M⁺+1)

Example 159

3-(2-Methoxyphenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (68 mg) was added to toluene/triethylamine=10/1 (7 ml), and the mixture was heated under reflux to prepare a solution. A solution of triphosgene (94 mg) in methylene chloride was then added to the solution, and the mixture was heated under reflux for 15 min. Subsequently, 3-(2-methoxyphenoxy)-1-propanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 51%).

¹H-NMR (CDCl₃, 400 MHz): 8.44 (1H, d, J=6.4 Hz), 8.14 (1H, d like, J=3.9 Hz), 7.87 (1H, bs), 6.87–6.97 (5H, m), 7.62 (1H, s), 6.56 (1H, d, J=6.4 Hz), 6.43 (1H, bs), 4.42 (2H, t, J=6.2 Hz), 4.15 (3H, s), 4.15 (2H, t, J=6.2 Hz), 4.08 (3H, s), 3.85 (3H, s), 2.23 (2H, t, J=6.2 Hz), 2.26 (3H, s), 2.10 (3H, s) Mass spectrometry value (ESI-MS, m/z): 534 (M⁺+1)

Example 160

3-(2-Methoxyphenoxy)propyl N-{4-[(6,7-dimethoxy-4-quinazolinyl)oxy]phenyl}carbamate 4-[(6,7-Dimethoxy-4-quinazolinyl)oxy]aniline (75 mg) was added to toluene/triethylamine=10/1 (8 ml), and the mixture was heated under reflux to prepare a solution. A solution of triphosgene (114 mg) in methylene chloride was then added to the solution, and the mixture was heated under reflux for 15 min. Subsequently, 3-(2-methoxyphenoxy)-1-propanol (69 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 35%).

¹H-NMR (CDCl₃, 400 MHz): 8.71 (1H, s), 8.04 (1H, s), 7.54 (1H, s), 7.46–7.53 (2H, m), 6.70–7.20 (7H, m), 4.36 (1H, t, J=6.2 Hz), 4.30 (1H, t, J=6.2 Hz), 4.12 (3H, s), 4.05 (3H, s), 4.05–4.11 (2H, m), 3.79 (3H, s), 2.10–2.20 (2H, m) Mass spectrometry value (ESI-MS, m/z): 507 (M⁺+1)

Example 161

3-(3-Methoxyphenoxy)propyl N-{4-[(6,7-dimethoxy-4-quinolyl)oxy]phenyl}carbamate

4-[(6,7-Dimethoxy-4-quinolyl)oxy]aniline (70 mg) was added to toluene/triethylamine=10/1 (7 ml), and the mixture was heated under reflux to prepare a solution. A solution of triphosgene (106 mg) in methylene chloride was then added to the solution, and the mixture was heated under reflux for 15 min. Subsequently, 3-(3-methoxyphenoxy)-1-propanol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (69 mg, yield 54%).

$^1$H-NMR (CDCl$_3$, 400 MHz): 8.45 (1H, dd, J=6.3 Hz), 8.13 (1H, d like, J=3.9 Hz), 7.62 (1H, s), 7.55–7.65 (3H, m), 7.12–7.18 (3H, m), 6.65–6.75 (1H, m), 6.43–6.52 (1H, m), 6.44–6.47 (1H, m), 4.22–4.41 (2H, m), 4.14 (3H, s), 4.08 (3H, s), 4.05–4.14 (2H, m), 3.76 (3H, s), 2.14–2.20 (2H, m) Mass spectrometry value (ESI-MS, m/z): 506 (M$^+$+1)

Example 162

3-(3-Methoxyphenoxy)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (72 mg) was added to toluene/triethylamine=10/1 (7 ml), and the mixture was heated under reflux to prepare a solution. A solution of triphosgene (100 mg) in methylene chloride was then added to the solution, and the mixture was heated under reflux for 15 min. Subsequently, 3-(3-methoxyphenoxy)-1-propanol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (83 mg, yield 66%).

$^1$H-NMR (CDCl$_3$, 400 MHz): 8.39 (1H, d like, J=6.7 Hz), 8.08 (1H, d like, J=3.4 Hz), 7.60–7.70 (1H, m), 7.59 (1H, s), 7.11 (1H, dd, J=8.2 Hz), 6.94 (1H, d, J=9.0 Hz), 6.39–6.50 (4H, m), 4.34 (2H, t, J=6.3 Hz), 4.09 (3H, s), 4.04 (3H, s), 4.01 (2H, t, J=6.2 Hz), 3.72 (3H, s), 2.19 (3H, s), 2.08–2.15 (2H, m), 2.02 (3H, s) Mass spectrometry value (ESI-MS, m/z): 534 (M$^+$+1)

Example 163

3-(3-Methoxyphenoxy)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (73 mg) was added to toluene/triethylamine=10/1 (7 ml), and the mixture was heated under reflux to prepare a solution. A solution of triphosgene (101 mg) in methylene chloride was then added to the solution, and the mixture was heated under reflux for 15 min. Subsequently, 3-(3-methoxyphenoxy)-1-propanol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (59 mg, yield 46%).

$^1$H-NMR (CDCl$_3$, 400 MHz): 8.45–8.55 (1H, m), 8.11 (1H, s), 7.86 (1H, s), 7.62 (1H, s), 7.16 (1H, dd, J=8.2 Hz), 6.92 (1H, s), 6.56 (1H, d, J=6.4 Hz), 6.40–6.52 (4H, m), 4.39 (2H, t, J=6.2 Hz), 4.14 (3H, s), 4.08 (3H, s), 4.07 (2H, t, J=6.4 Hz), 3.77 (3H, s), 2.26 (3H, s), 2.14–2.22 (2H, m), 2.10 (3H, s) Mass spectrometry value (ESI-MS, m/z): 534 (M$^+$+1)

Example 164

3-(3-Methoxyphenoxy)propyl N-{4-[(6,7-dimethoxy-4-quinazolinyl)oxy]phenyl}carbamate 4-[(6,7-Dimethoxy-4-quinazolinyl)oxy]aniline (75 mg) was added to toluene/triethylamine=10/1 (8 ml), and the mixture was heated under reflux to prepare a solution. A solution of triphosgene (114 mg) in methylene chloride was then added to the solution, and the mixture was heated under reflux for 15 min. Subsequently, 3-(3-methoxyphenoxy)-1-propanol (69 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 35%).

$^1$H-NMR (CDCl$_3$, 400 MHz): 8.71 (1H, s), 8.04 (1H, s), 7.54 (1H, s), 7.46–7.53 (2H, m), 6.70–7.20 (7H, m), 4.36 (1H, t, J=6.2 Hz), 4.30 (1H, t, J=6.2 Hz), 4.12 (3H, s), 4.05 (3H, s), 4.05–4.11 (2H, m), 3.79 (3H, s), 2.10–2.20 (2H, m) Mass spectrometry value (ESI-MS, m/z): 507 (M$^+$+1)

Example 165

2-[(2,5-dimethylphenyl)sulfanyl]ethyl N-{4-[(6,7-dimethoxy-4-quinolyl)oxy]phenyl}carbamate 4-[(6,7-Dimethoxy-4-quinolyl)oxy]aniline (77 mg) was added to toluene/triethylamine=10/1 (8 ml), and the mixture was heated under reflux to prepare a solution. A solution of triphosgene (105 mg) in methylene chloride was then added to the solution, and the mixture was heated under reflux for 15 min. Subsequently, 2-[(2,5-dimethylphenyl)sulfanyl]-1-ethanol (78 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, follow by washing with a 1 N aqueous hydrochloric acid solution and saturated brine. The washed solution was dried over sodium sulfate and was concentrated. The residue was purified on a column using chloroform/methanol to give the title compound (105 mg, yield 74%).

¹H-NMR (CDCl₃, 400 MHz): 8.43–8.48 (1H, m), 8.13 (1H, d like, J=3.9 Hz), 7.62 (1H, s), 7.56 (2H, d, J=9.0 Hz), 7.16 (2H, d, J=9.0 Hz), 7.02 (2H, d, J=9.0 Hz), 6.84 (1H, s), 6.76 (1H, s), 6.67 (1H, d, J=6.6 Hz), 4.35 (2H, t, J=6.6 Hz), 4.15 (3H, s), 4.08 (3H, s), 3.18 (2H, t, J=6.6 Hz), 2.27 (6H, s) Mass spectrometry value (ESI-MS, m/z): 506 (M⁺+1)

Example 166

2-[(2,5-Dimethylphenyl)sulfanyl]ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (62 mg) was added to toluene/triethylamine=10/1 (61 ml), and the mixture was heated under reflux to prepare a solution. A solution of triphosgene (85 mg) in methylene chloride was then added to the solution, and the mixture was heated under reflux for 15 min. Subsequently, 2-[(2,5-dimethylphenyl)sulfanyl]-1-ethanol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (88 mg, yield 81%).

¹H-NMR (CDCl₃, 400 MHz): 8.44 (1H, d, J=6.6 Hz), 8.14 (1H, s, J=4.2 Hz), 7.72 (1H, bs), 7.64 (1H, s), 7.01–7.04 (2H, m), 6.99 (1H, s), 6.84 (1H, s), 6.53 (1H, d, J=6.4 Hz), 6.43 (1H, s), 3.71 (1H, t, J=6.0 Hz), 4.15 (3H, s), 4.09 (3H, s), 3.19 (2H, t, J=6.0 Hz), 2.27 (6H, s), 2.23 (3H, s), 2.08 (3H, s) Mass spectrometry value (ESI-MS, m/z): 534 (M⁺+1)

Example 167

2-[(2,5-Dimethylphenyl)sulfanyl]ethyl N-{4-[(6,7-Dimethoxy-4-quinolyl)oxy]-2,5-dimethylphenyl}carbamate 4-[(6,7-Dimethoxy-4-quinolyl)oxy]-2,5-dimethylaniline (68 mg) was added to toluene/triethylamine=10/1 (7 ml), and the mixture was heated under reflux to prepare a solution. A solution of triphosgene (97 mg) in methylene chloride was then added to the solution, and the mixture was heated under reflux for 15 min. Subsequently, 2-[(2,5-dimethylphenyl)sulfanyl]-1-ethanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (79 mg, yield 66%).

¹H-NMR (CDCl₃, 400 MHz): 8.45 (1H, dd, J=6.6 Hz), 8.13 (1H, d, J=4.2 Hz), 7.86 (1H, s), 7.62 (1H, s), 7.02 (2H, s), 6.93 (1H, s), 6.84 (1H, s), 6.55 (1H, d, J=6.6 Hz), 6.40 (1H, s), 4.36 (1H, t, J=6.7 Hz), 4.15 (3H, s), 4.08 (3H, s), 3.20 (2H, t, J=6.7 Hz), 2.27 (6H, s), 2.24 (3H, s), 2.11 (3H, s). Mass spectrometry value (ESI-MS, m/z): 534 (M⁺+1)

Example 168

2-[(2,5-Dimethylphenyl)sulfanyl]ethyl N-{4-[(6,7-dimethoxy-4-quinazolinyl)oxy]phenyl}carbamate 4-[(6,7-Dimethoxy-4-quinazolinyl)oxy]aniline (70 mg) was added to toluene/triethylamine=10/1 (7 ml), and the mixture was heated under reflux to prepare a solution. A solution of triphosgene (108 mg) in methylene chloride was then added to the solution, and the mixture was heated under reflux for 15 min. Subsequently, 2-[(2,5-dimethylphenyl)sulfanyl]-1-ethanol (65 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (101 mg, yield 79%).

¹H-NMR (CDCl₃, 400 MHz): 8.77 (1H, s), 8.09 (1H, s), 7.59 (1H, s), 7.53 (2H, d, J=9.0 Hz), 7.17 (2H, d, J=8.8 Hz), 6.97–7.03 (2H, m), 6.72–6.85 (2H, m), 4.34 (2H, t, J=6.6 Hz), 4.16 (3H, s), 4.10 (3H, s), 3.17 (2H, t, J=6.6 Hz), 2.27 (6H, s) Mass spectrometry value (ESI-MS, m/z): 507 (M⁺+1)

Example 169

3-[(2,5-Dimethylphenyl)sulfanyl)propyl N-{4-[(6,7-dimethoxy-4-quinolyl)oxy]phenyl}carbamate 4-[(6,7-Dimethoxy-4-quinolyl)oxy]aniline (70 mg) was added to toluene/triethylamine=10/1 (7 ml), and the mixture was heated under reflux to prepare a solution. A solution of triphosgene (105 mg) in methylene chloride was then added to the solution, and the mixture was heated under reflux for 15 min. Subsequently, 2-[(2,5-dimethylphenyl)sulfanyl]-1-propanol (78 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 37%).

¹H-NMR (CDCl₃, 400 MHz): 8.45 (1H, dd, J=6.6 Hz), 8.12 (1H, s), 7.62 (1H, s), 7.56–7.61 (2H, m), 7.15–7.61 (2H, m), 7.15–7.25 (3H, m), 6.96 (1H, s), 6.80–6.85 (1H, m), 6.67 (1H, d, J=6.4 Hz), 4.36 (1H, t, J=6.4 Hz), 4.31 (1H, t, J=6.4 Hz), 4.14 (3H, s), 4.08 (3H, s), 3.00 (2H, t, J=7.1 Hz), 2.27 (6H, s), 1.97–2.25 (2H, m) Mass spectrometry value (ESI-MS, m/z): 520 (M⁺+1)

Example 170

3-[(2,5-Dimethylphenyl)sulfanyl]propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (72 mg) was added to toluene/triethylamine=10/1 (7 ml), and the mixture was heated under reflux to prepare a solution. A solution of triphosgene (100 mg) in methylene chloride was then added to the solution, and the mixture was heated under reflux for 15 min. Subsequently, 2-[(2,5-dimethylphenyl)sulfanyl]-1-propanol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (33 mg, yield 25%).

$^1$H-NMR (CDCl$_3$, 400 MHz): 8.40–8.46 (1H, m), 8.14 (1H, s), 7.73 (1H, bs), 7.65 (1H, s), 6.94–7.02 (3H, m), 6.82–7.02 (3H, m), 6.82 (1H, s), 6.53 (1H, d, J=6.6 Hz), 6.43–6.48 (1H, m), 4.28–4.37 (2H, m), 4.15 (3H, s), 4.09 (3H, s), 4.00 (2H, t, J=7.1 Hz), 2.27 (6H, s), 2.25 (3H, s), 2.08 (3H, s), 1.98–2.20 (2H, m) Mass spectrometry value (ESI-MS, m/z): 548 (M$^+$+1)

Example 171

3-[(2,5-Dimethylphenyl)sulfanyl]propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (68 mg) was added to toluene/triethylamine=10/1 (7 ml), and the mixture was heated under reflux to prepare a solution. A solution of triphosgene (97 mg) in methylene chloride was then added to the solution, and the mixture was heated under reflux for 15 min. Subsequently, 2-[(2,5-dimethylphenyl)sulfanyl]-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 42%).

$^1$H-NMR (CDCl$_3$, 400 MHz): 8.41–8.45 (1H, m), 8.14 (1H, bs), 7.68 (1H, bs), 7.62 (1H, s), 6.97 (1H, s), 6.92–6.96 (1H, m), 6.82 (1H, s), 6.56 (1H, d, J=6.6 Hz), 6.40–6.45 (1H, m), 4.36 (1H, t, J=6.0 Hz), 4.32 (1H, t, J=6.0 Hz), 3.00 (2H, t, J=7.1 Hz), 2.27 (6H, s), 2.26 (3Hz, s), 2.14–2.20 (1H, m), 2.11 (3H, s), 1.98–2.05 (1H, m) Mass spectrometry value (ESI-MS, m/z): 548 (M$^+$+1)

Example 172

3-[(2,5-Dimethylphenyl)sulfanyl]-propyl N-{4-[(6,7-dimethoxy-4-quinazolinyl)oxy]phenyl}carbamate 4-[(6,7-Dimethoxy-4-quinazolinyl)oxy]aniline (66 mg) was added to toluene/triethylamine=10/1 (7 ml), and the mixture wasp heated under reflux to prepare a solution. A solution of triphosgene (100 mg) in methylene chloride was then added to the solution, and the mixture was heated under reflux for 15 min. Subsequently, 2-[(2,5-dimethylphenyl)sulfanyl]-1-propanol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (29 mg, yield 23%).

$^1$H-NMR (CDCl$_3$, 400 MHz): 8.75 (1H, s), 8.07 (1H, s), 7.59 (1H, s), 7.52–7.58 (2H, m), 6.79–7.21 (5H, m), 4.34 (1H, d, J=6.1 Hz), 4.30 (1H, d, J=6.1 Hz), 4.16 (3H, s), 4.10 (3H, s), 2.99 (2H, t, J=7.1 Hz), 2.27 (6H, s), 2.11–2.19 (1H, m), 2.15–2.03 (1H, m) Mass spectrometry value (ESI-MS, m/z): 521 (M$^+$+1)

Example 173

3-(2-Pyridylsulfanyl)propyl N-{4-[(6,7-dimethoxy-4-quinolyl)oxy]-2,3-dimethylphenyl}-carbamate 4-[(6,7-Dimethoxy-4-quinolyl)oxy]-2,3-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 3-(2-pyridylsulfanyl)-1-propanol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (18 mg, yield 13%).

$^1$H-NMR (CDCl$_3$, 400 MHz): 8.39–8.44 (2H, m), 7.90–7.95 (1H, m), 7.64–7.70 (1H, m), 7.63 (1H, s), 7.44–7.50 (1H, m), 7.15–7.20 (1H, m), 6.95–7.02 (2H, m), 6.42–6.48 (1H, m), 4.33 (2H, t, J=6.2 Hz), 4.12 (3H, s), 4.08 (3H, s), 3.29 (2H, t, J=7.1 Hz), 2.25 (3H, s), 2.09–2.15 (2H, m), 2.09 (3H, s) Mass spectrometry value (ESI-MS, m/z): 521 (M$^+$+1)

Example 174

3-(2-Pyridylsulfanyl)propyl N-{4-[(6,7-dimethoxy-4-quinolyl)oxy]-2,5-dimethylphenyl}-carbamate 4-[(6,7-Dimethoxy-4-quinolyl)oxy]-2,5-dimethylaniline (78 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-(2-pyridylsulfanyl)-1-propanol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (13 mg, yield 10%).

¹H-NMR, (CDCl₃, 400 MHz): 8.75–8.79 (1H, m), 8.41–8.47 (1H, m), 8.12 (1H, s), 8.06–8.14 (1H, m), 7.99 (1H, bs), 7.81 (1H, s), 7.69 (1H, d, J=8.5 Hz), 7.63 (1H, s like), 7.52–7.58 (1H, m), 6.92 (1H, s), 6.58 (1H, d, J=6.3 Hz), 4.30 (2H, t, J=5.6 Hz), 4.14 (3H, s), 4.09 (3H, s), 3.99 (2H, t, J=7.3 Hz), 2.40 (3H, s), 2.08–2.22 (2H, m), 2.08 (3H, s) Mass spectrometry value (ESI-MS, m/z): 521 (M⁺+1)

Example 175

3-(2-Pyridylsulfanyl)propyl N-{4-[(6,7-dimethoxy-4-quinazolinyl)oxy]phenyl}carbamate 4-[(6,7-Dimethoxy-4-quinazolinyl)oxy]aniline (73 mg) was added to toluene/triethylamine=10/1 (7 ml), and the mixture was heated under reflux to prepare a solution. A solution of triphosgene (110 mg) in methylene chloride was then added to the solution, and the mixture was heated under reflux for 15 min. Subsequently, 3-(2-pyridylsulfanyl)-1-propanol (62 mg) was added thereto, and the mixture was further stirred with heating under reflux for 2 hr After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (5 mg, yield 4%). Mass spectrometry value (ESI-MS, m/z): 494 (M⁺+1)

Example 176

4-Chloro-2-methylphenyl{4-[(6,7-dimethoxy-4-quinolyl)oxy]anilino}methanethioate

4-[(6,7-Dimethoxy-4-quinolyl)oxy]aniline (88 mg) was added to toluene/triethylamine=10/1 (9 ml), and the mixture was heated under reflux to prepare a solution. A solution of triphosgene (70 mg) in methylene chlorides was then added to the solution, and the mixture was heated under reflux for 15 min. Subsequently, 2-methyl-4-chlorothiophenol (70 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (108 mg, yield 70%). Mass spectrometry value (ESI-MS, m/z): 482 (M⁺+1)

Example 177

4-Chloro-2-methylphenyl{4-[(6,7-dimethoxy-4-quinolyl)oxy]-2,3-dimethylanilino}methanethioate 4-[(6,7-Dimethoxy-4-quinolyl)oxy]-2,3-dimethylaniline (82 mg) was added to toluene/triethylamine=10/1 (8 ml), and the mixture was heated under reflux to prepare a solution. A solution of triphosgene (114 mg) in methylene chloride was then added to the solution, and the mixture was heated under reflux for 15 min. Subsequently, 2-methyl-4-chlorothiophenol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (91 mg, yield 66%). Mass spectrometry value (ESI-MS, m/z): 510 (M⁺+1)

Example 178

4-Chloro-2-methylphenyl{4-[(6,7-dimethoxy-4-quinolyl)oxy]-2,5-dimethylanilino}methanethioate 4-(6,7-Dimethoxy-4-quinolyl)oxy]-2,5-dimethylaniline (79 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 2-methyl-4-chlorothiophenol (58 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (71 mg, yield 53%).

Mass spectrometry value (ESI-MS, m/z): 510 (M⁺+1)

Example 179

4-Chloro-2-methylphenyl{4-[(6,7-dimethoxy-4-quinazolinyl)oxy]anilino}methanethioate 4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (121 mg) in methylene chloride was then added to the solution, and the mixture was heated under reflux for 15 min. Subsequently, 2-methyl-4-chlorothiophenol (64 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (68 mg, yield 49%).

Mass spectrometry value (ESI-MS, m/z): 493 (M⁺+1)

Example 180

1-[3-(Trifluoromethoxy)phenyl]ethyl N-{4-[(6,7-dimethoxy-4-quinolyl)oxy]phenol}carbamate 4-[(6,7-Dimethoxy-4-quinolyl)oxy]aniline (82 mg), was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 4-trifluoromethoxy-α-methylbenzyl alcohol (85 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 39%).

$^1$H-NMR (CDCl$_3$, 400 MHz): 8.39 (1H, dd, J=6.6 Hz), 8.07 (1H, s like), 7.50–7.56 (2H, m), 7.31–7.36 (3H, m), 7.23–7.28 (1H, m), 7.08–7.13 (2H, m), 6.82 (1H, s), 6.60 (1H, d, J=6.6 Hz), 5.85 (1H, q, J=6.6 Hz), 4.09 (3H, s), 4.02 (3H, s), 1.55 (3H, d, J=6.6 Hz) Mass spectrometry value (ESI-MS, m/z): 529, (M$^{+1}$+1)

Example 181

1-[3-(Trifluoromethoxy)phenyl]ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (88 mg) was added to toluene/triethylamine=10/1 (9 ml), and the mixture was heated under reflux to prepare a solution. A solution of triphosgene (122 mg) in methylene chloride was then added to the solution, and the mixture was heated under reflux for 15 min. Subsequently, 4-trifluoromethoxy-α-methylbenzyl alcohol (83 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (73 mg, yield 46%).

$^1$H-NMR (CDCl$_3$, 400 MHz): 8.42 (1H, dd, J=6.5 Hz), 8.13 (1H, s), 7.63–7.75 (2H, m), 6.96–7.42 (5H, m), 6.51 (2H, d, J=6.5 Hz), 5.89 (1H, q, J=6.6 Hz), 4.15 (3H, s), 4.09 (3H, s), 2.24 (3H, s), 2.07 (3H, s), 1.61 (3H, d, J=6.6 Hz) Mass spectrometry value (ESI-MS, m/z): 558 (M$^+$+1)

Example 182

1-[3-(Trifluoromethoxy)phenyl]ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (90 mg) was added to toluene/triethylamine=10/1 (9 ml), and the mixture was heated under reflux to prepare a solution. A solution of triphosgene (125 mg) in methylene chloride was then added to the solution, and the mixture was heated under reflux for 15 min. Subsequently, 4-trifluoromethoxy-α-methylbenzyl alcohol (85 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give $^1$H-NMR; (CDCl$_3$, 400 MHz): 8.43 (1H, dd J=6.6 Hz), 8.13 (1H, s), 7.85 (1H, s), 7.62 (1H, s), 7.40 (1H, dd, J=7.8 Hz), 7.31 (1H, d, J=7.8 Hz), 7.16 (1H, d, J=8.0 Hz), 6.93 (1H, s), 6.54 (1H, d, J=6.6 Hz), 6.48 (1H, s), 5.89 (1H, q, J=6.7Hz), 4.15 (3H, s), 4.08 (3H, s), 2.27 (3H, s), 2.09 (3H, s), 1.62 (,3H, d, J=6.7 Hz) Mass spectrometry value (ESI-MS, m/z): 558 (M$^+$+1)

Example 183

1-[3-(Trifluoromethoxy)phenyl]ethyl N-{4-[(6,7-dimethoxy-4-quinazolinyl)oxy]phenyl}carbamate 4-[(6,7-Dimethoxy-4-quinazolinyl)oxy]aniline (82 mg) was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 4-trifluoromethoxy-α-methylbenzyl alcohol (85 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (48 mg, yield 31%).

$^1$H-NMR (CDCl$_3$, 400 MHz): 8.75 (1H, s), 8.11 (1H, s), 7.53–7.59 (3H, m), 7.38 (1H, dd, J=7.9 Hz), 7.30 (1H, d, J=7.9 Hz), 7.12–7.19 (3H, m), 6.87 (1H, s), 5.89 (1H, q, J=6.6 Hz), 4.16 (3H, s), 4.10 (3H, s), 1.60 (3H, d, J=6.6 Hz) Mass spectrometry value (ESI-MS, m/z): 530 (M$^+$+1)

Example 184

1-Phenylbutyl N{4-[(6,7-dimethoxy-4-quinolyl)oxy]phenyl}carbamate

4-[(6,7-Dimethoxy-4-quinolyl)oxy]aniline (78 mg) was added to toluene/triethylamine=10/1 (8 ml), and the mixture was heated under reflux to prepared a solution. A solution of triphosgene (118 mg) in methylene chloride was then added to the solution, and the mixture was heated under reflux for 15 min. Subsequently, 1-phenyl-1-butanol (59 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 58%).

¹H-NMR (CDCl₃, 400 MHz): 8.43 (1H, dd, J=6.6 Hz), 8.12 (1H, s like), 7.60 (1H, s), 7.53–7.58 (2H, m), 7.23–7.38 (4H, m), 7.12–7.15 (2H, m), 6.80 (1H, s), 6.64 (1H, d, J=6.6 Hz), 5.72–5.78 (1H, m), 4.14 (3H, s), 4.07 (3H, s), 1.75–2.03 (2H, m), 1.35–1.45 (2H, m), 0.94 (2H, d, J=7.3 Hz) Mass spectrometry value (ESI-MS, m/z): 474 (M$^{+1}$+1)

Example 185

1-Phenylbutyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (90 mg) was added to toluene/triethylamine=10/1 (9 ml), and the mixture was heated under reflux to prepare a solution. A solution of triphosgene (125 mg) in methylene chloride was then added to the solution, and the mixture was heated under reflux form 15 min. Subsequently, 1-phenyl-1-butanol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (59 mg, yield 40%).
¹H-NMR (CDCl₃, 400 MHz): 8.36 (1H, dd, J=6.5 Hz), 8.08 (1H, s), 7.67 (1H, d, J=8.8 Hz), 7.59 (1H, s), 7.24–7.34 (5H, m), 6.92 (1H, d, J=8.8 Hz), 6.42–6.47 (2H, m), 5.69 (1H, t, J=6.9 Hz), 4.10 (3H, s), 4.04 (3H, s), 2.18 (3H, s), 2.01 (3H, s), 1.70–2.00 (2H, m), 1.2–1.42 (2H, m), 0.90 (3H, t, J=7.4 Hz) Mass spectrometry value (ESI-MS, m/z): 502 (M⁺+1)

Example 186

1-Phenylbutyl N-{4-[(6,7-dimethoxy-4-quinolyl)oxy]-2,5-dimethylphenyl}carbamate

4-[(6,7Dimethoxy-4-quinolyl)oxy]2,5-dimethylaniline (89 mg) was added to toluene/triethylamine=10/1 (9 ml ) and the mixture was heated under reflux to prepare a solution. A solution of triphosgene (126 mg), in methylene chloride was then added to the solution, and the mixture was heated under reflux for 15 min. Subsequently, 1-phenyl-1-butanol (63 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 39%).
¹H-NMR (CDCl₃, 400 MHz): 8.43 (1H, dd, J=6.5 Hz), 8.12 (1H, s, like), 7.89 (1H, s), 7.61 (1H, s), 7.26–7.40 (5H, m), 6.91 (1H, s), 6.53 (1H, d, J=6.5 Hz), 6.47 (1H,s), 5.71–5.76 (1H, m), 4.14 (3H, s), 4.08 (3H, s9, 2.25 (3H, s), 2.07 (3H, s), 1.75–2.05 (2H, m), 1.25–1.50 (2H, m), 0.95 (3H, t, J=7.3 Hz) Mass spectrometry value (ESI-MS, m/z): 502 (M⁺+1)

Example 187

1-Phenylbutyl N-{4-[(6,7-dimethoxy-4-quinazolinyl)oxy]phenyl}carbamate

4-[(6,7-Dimethoxy-4-quinazolinyl)oxy]aniline (76 mg) was added to toluene/triethylamine=10/1 (8 ml), and the mixture was heated under reflux to prepare a solution. A solution of triphosgene (115 mg) in methylene chloride was then added to the solution, and the mixture was heated under reflux for 15 min. Subsequently, 1-phenyl-1-butanol (57 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (38 mg, yield 29%).
¹H-NMR (CDCl₃, 400 MHz): 8.71 (1H, s), 8.07 (1H, s), 7.54 (1H, s), 7.44–7.52 (2H, m), 7.18–7.33 (5H, m), 7.08–7.13 (2H, m), 6.73 (1H, s), 5.65–5.72 (1H, m), 4.12 (3H, s), 4.05 (3H, s), 1.65–1.95 (2H, m), 1.30–1.40 (2H, m), 0.89 (3H, t, J=7.4 Hz) Mass spectrometry value (ESI-MS m/z): 475 (M⁺+1)

Example 188

2-(Dimethylamino)ethyl N-{4-[(6,7-dimethoxy-4-quinolyl)oxy]phenyl}carbamate

4-[(6,7-Dimethoxy-4-quinolyl)oxy]aniline (83 mg) was added to toluene/triethylamine=10/1 (8 ml), and the mixture was heated under reflux to prepare a solution. A solution of triphosgene (40 mg) in methylene chloride was then added to the solution and the mixture was heated under reflux for 15 min. Subsequently, 2-dimethylaminoethanol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (31 mg, yield 25%).
¹H-NMR (CDCl₃, 400 MHz): 8.41 (1H, d, J=5.4 Hz), 7.56–7.65 (2H, m), 7.43 (1H, s), 7.20–7.26 (2H, m), 6.97 (1H, d, J=8.8 Hz), 6.25 (1H, d, J=5.1 Hz), 4.34–4.41 (2H, m), 4.05 (2H, s), 4.04 (3H, s), 2.92 (2H, bs), 2.57 (6H, bs) Mass spectrometry value (ESI-MS, M/z): 412 (M⁺+1)

Example 189

2-(Dimethylamino)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 2-dimethylaminoethanol (31 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (41 mg, yield 35%).

$^1$H-NMR (CDCl$_3$, 400 MHz): 8.41 (1H, d, =5.3 Hz), 7.59 (2H, s), 7.42 (1H, s), 6.96 (1H, d, H=8.8 Hz), 6.24 (1H, d, J=5.3 Hz), 4.30–4.38 (2H, m), 4.04 (3H, s), 4.03 (3H, s), 2.81 (2H, bs), 2.47 (6H, bs), 2.25 (3H, s), 2.09 (3H, s) Mass spectrometry value (ESI-MS, m/z): 441 (M$^+$+1)

Example 190

2-(Dimethylamino)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (85 mg) was added to toluene/triethylamine=10/1 (9 ml), and the mixture was heated under reflux to prepare a solution. A solution of triphosgene (115 mg) in methylene chloride was then added to the solution, and the mixture was heated under reflux for 15 min. Subsequently, 2-dimethylaminoethanol (33 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (28 mg, yield 22%).

$^1$H-NMR (CDCl$_3$, 400 MHz): Mass spectrometry value (ESI-MS, m/z): 441 (M$^+$+1)

Example 191

2-(Dimethylamino)ethyl N-{4-[(6,7-dimethoxy-4-quinazolinyl)oxy]phenyl}carbamate

4-[(6,7-Dimethoxy-4-quinazolinyl)oxy]aniline (74 mg) was added to toluene/triethylamine=10/1 (8 ml), and the mixture was heated under reflux to prepare a solution. A solution of triphosgene (112 mg) in methylene chloride was then added to the solution, and the mixture was heated under reflux for 15 min. Subsequently, 2-dimethylaminoethanol (32 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (13 mg, yield 12%).

$^1$H-NMR (CDCl$_3$, 400 MHz): 8.42 (1H, m), 8.07 (1H, s), 7.10–7.70 (5H, m), 6.62–6.68 (1H, m), 4.47–4.52 (2H, m), 4.14 (3H, s), 4.08 (3H, s), 3.30–3.35 (2H, m), 2.94 (6H, s) Mass spectrometry value (ESI-MS, m/z): 413 (M$^+$+1)

Example 192

4-(Dimethylamino)butyl N-{4-[(6,7-dimethoxy-4-quinolyl)oxy]phenyl}carbamate

4-[(6,7-Dimethoxy-4-quinolyl)oxy]aniline (80 mg) was added to toluene/triethylamine=10/1 (8 ml), and the mixture was heated under reflux to prepare a solution. A solution of triphosgene (130 mg) in methylene chloride was then added to the solution, and the mixture was heated under reflux for 15 min. Subsequently, 4-dimethylaminopropanol (40 mg) was added thereto, and the mixture was further stirred with heating under reflux for 2 hr. After the completion of the reaction, the reaction solution was allowed to cool to room temperatures before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (22 mg, yield 17%). Mass spectrometry value (ESI-MS, m/z): 441 (M$^+$+1)

Example 193

4-(Dimethylamino)butyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (76 mg) was added to toluene/triethylamine=10/1 (8 ml), and the mixture was heated under reflux to prepare a solution. A solution of triphosgene (106 mg) in methylene chloride was then added to the solution, and the mixture was heated under reflux for 15 min. Subsequently, 4-dimethylaminopropanol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (29 mg, yield 25%). Mass spectrometry value (ESI-MS, m/z): 469 (M$^+$+1)

Example 194

4-(Dimethylamino)butyl N-{4-[(6,7-dimethoxy-4-quinazolinyl)oxy]phenyl}carbamate

4-[(6,7-Dimethoxy-4-quinazolinyl)oxy]aniline (75 mg) was added to toluene/triethylamine=10/1 (8 ml), and the mixture was heated under reflux to prepare a solution. A solution of triphosgene (114 mg) in methylene chloride was then added to the solution, and the mixture was heated under reflux for 15 min. Subsequently, 4-dimethylaminopropanol (43 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solutions was dried over sodium sulfate and was concentrated. The residue was purified on a column using chloroform/methanol to give the title compound (18 mg, yield 15%). Mass spectrometry value (ESI-MS, m/z): 413 (M$^+$+1)

Example 195

2-Methyl-1-phenylpropyl N-{4-[(6,7-dimethoxy-4-quinolyl)oxy]phenyl}carbamate

4-[(6,7-Dimethoxy-4-quinolyl)oxy]aniline (77 mg) was added to toluene/triethylamine=10/1 (8 ml), and the mixture was heated under reflux to prepare a solution. A solution of triphosgene (118 mg) in methylene chloride was then added to the solution, and the mixture was heated under reflux for 15 min. Subsequently, 2-methyl-1-phenyl-1-propanol (39 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 59%).

$^1$H-NMR, (CDC$_3$, 400 MHz): 8.40–8.45 (1H, m), 8.10–8.13 (1H, m), 7.10–7.61 (10H, m), 6.62–6.65 (1H, m), 5.45 (1H, d, J=7.8 Hz), 4.14 (3H, s), 4.07 (3H, s), 2.00–2.25 (1H, m), 1.04 (3H, d, J=6.6 Hz), 0.83 (3H, d, J=6.8 Hz) Mass spectrometry value (ESI-MS, m/z): 474 (M$^+$+1)

Example 196

2-Methyl-1-phenylpropyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 2-methyl-1-phenyl-1-propanol (55 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (69 mg, yield 52%).

$^1$H-NMR (CDCl$_3$, 400 MHz): 8.38–8.43 (1H, m), 8.11–8.15 (1H, m), 7.00–7.80 (8H, m), 6.95–7.00 (1H, m)), 6.47–6.52 (1H, m), 5.45 (1H, d, J=7.6 Hz), 4.14 (3H, s), 4.09 (3H, s), 2.23 (3H, s), 2.06 (3H, s), 2.00–2.25 (1H, m), 1.04 (3H, d, J=6.6 Hz), 0.83 (3H, d, J=6.6 Hz) Mass spectrometry value (ESI-MS, m/z): 502 (M$^+$+1)

Example 197

2-Methyl-1-phenylpropyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (124 mg) in methylene chloride was then added to the solution, and the mixture was heated under reflux for 15 min. Subsequently, 2-methyl-1-phenyl-1-propanol (61 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 44%).

$^1$H-NMR (CDCl$_3$, 400 MHz): 8.39–8.44 (1H, m), 8.12–8.14 (1H, m), 7.85–7.90 (1H, s like), 7.61 (1H, s), 7.24–7.36 (5H, m), 6.91 (1H, s), 6.45–6.55 (2H, m), 5.45 (1H, d, J=7.8 Hz), 4.14 (3H, s), 4.08 (3H, s), 2.26 (3H, s), 2.10–2.22 (1H, m), 2.07 (3H, s), 1.05 (3H, d, J=6.6 Hz), 0.83 (3H, d, J=6.8 Hz) Mass spectrometry value (ESI-MS, m/z): 502 (M$^+$+1)

Example 198

2-Methyl-1-phenylpropyl N-{4-[(6,7-dimethoxy-4-quinazolinyl)oxy]phenyl}carbamate 4-[(6,7-Dimethoxy-4-quinazolinyl)oxy]aniline (75 mg) was added to toluene/triethylamine=10/1 (8 ml), and the mixture was heated under reflux to prepare a solution. A solution of triphosgene (137 mg) in methylene chloride was then added to the solution, and the mixture was heated under reflux for 15 min. Subsequently, 2-methyl-1-phenyl-1-propanol (56 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (38 mg, yield 29%).

$^1$H-NMR (CDCl$_3$, 400 MHz): 8.72 (1H, s), 8.09 (1H, s), 7.58 (1H, s), 7.55 (2H, d, J=8.8 Hz), 7.20–7.36 (5H, m), 7.13–7.16 (2H, m), 6.93 (1H, bs), 5.45 (1H, d, J=7.6 Hz), 4.15 (3H, s), 4.09 (3H, s), 2.09–2.18 (1H, m), 1.02 (3H, d, J=6.6 Hz), 0.82 (3H, d, J=6.8 Hz) Mass spectrometry value (ESI-MS, m/z): 475 (M$^+$+1)

Example 199

1-[3-(Dimethylamino)phenyl]ethyl N-{4-[(6,7-dimethoxy-4-quinolyl)oxy]phenyl}carbamate 4-[(6,7-Dimethoxy-4-quinolyl)oxy]aniline (78 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-dimethylamino-α-methylbenzyl alcohol (65 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 44%).

$^1$H-NMR (CDCl$_3$, 400 MHz): 8.39 (1H, d, J=5.6 Hz), 7.42–7.57 (3H, m), 7.06–7.22 (2H, m), 6.54–6.74 (5H, m), 6.42 (1H, d, J=5.6 Hz), 5.80 (1H, q, J=6.6 Hz), 4.01 (3H, s), 3.99 (3H, s), 2.90 (3H, s), 2.89 (3H, s), 1.56 (3H, d, J=6.6 Hz) Mass spectrometry value (ESI-MS, m/z): 489 (M$^+$+1)

Example 200

1-[3-(Dimethylamino)phenyl]ethyl N-{4-[(6,7-dimethoxy-4-quinolyl)oxy]-2,3-dimethylphenyl}-carbamate 4-[(6,7-Dimethoxy-4-quinolyl)oxy]-2,3-dimethylaniline (83 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-dimethylamino-α-methylbenzyl alcohol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (77 mg, yield 55%).

$^1$H-NMR (CDCl$_3$, 400 MHz): 8.41 (1H, d, J=5.4 Hz), 7.48–7.65 (3H, m), 7.20–7.26 (1H, m), 6.96 (1H, d, J=8.8 Hz), 6.65–6.78 (3H, m), 6.42 (1H, bs), 6.25–6.30 (1H, m), 5.85 (1H, q, J=6.6 Hz), 4.04–4.06 (6H, m), 2.95 (6H, s), 2.22 (3H, s), 2.08 (3H, s), 1.61 (3H, d, J=6.6 Hz) Mass spectrometry value (ESI-MS, m/z): 517 (M$^+$+1)

Example 201

1-[3-(Dimethylamino)phenyl]ethyl N-{4-[(6,7-dimethoxy-4-quinolyl)oxy]-2,5-dimethylphenyl}-carbamate 4-[(6,7-Dimethoxy-4-quinolyl)oxy]-2,5-dimethylaniline (80 mg) was added to toluene/triethylamine=10/1 (8 ml), and the mixture was heated under reflux to prepare a solution. A solution of triphosgene (110 mg) in methylene chloride was then added to the solution, and the mixture was heated under reflux for 15 min. Subsequently, 3-dimethylamino-α-methylbenzyl alcohol (60 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (58 mg, yield 43%).

$^1$H-NMR (CDCl$_3$, 400 MHz): 8.41 (1H, d, J=5.6 Hz), 7.80 (1H, bs), 7.57 (1H, s), 7.55 (1H, bs), 7.20–7.26 (1H, m), 6.89 (1H, s), 6.72–6.79 (2H, m), 6.65–6.70 (1H, m), 6.41 (1H, bs), 6.31 (1H, q, J=5.4 Hz), 5.85 (1H, q, J=6.6 Hz), 4.05 (3H, s), 4.05 (3H, s), 2.96 (6H, s), 2.22 (3H, s), 2.10 (3H, s), 1.62 (3H, d, J=6.6 Hz) Mass spectrometry value (ESI-MS, m/z): 517 (M$^+$+1)

Example 202

1-[3-(Dimethylamino)phenyl]ethyl N-{4-[(6,7-dimethoxy-4-quinazolinyl)oxy]phenyl}carbamate 4-[(6,7-Dimethoxy-4-quinazolinyl)oxy]aniline (80 mg) was added to toluene/triethylamine=10/1 (8 ml), and the mixture was heated under reflux to prepare a solution. A solution of triphosgene (120 mg) in methylene chloride was then added to the solution, and the mixture was heated under reflux for 15 min. Subsequently, 3-dimethylamino-α-methylbenzyl alcohol (66 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (51 mg, yield 36%).

$^1$H-NMR (CDCl$_3$, 400 MHz): 8.54 (1H, s), 7.48 (1H, s), 7.42 (1H, d, J=7.8 Hz), 7.25 (1H, s), 7.10–7.20 (3H, m), 6.58–6.74 (5H, m), 5.80 (1H, q, J=6.5 Hz), 3.99 (3H, s), 3.99 (3H, s), 2.90 (6H, s), 1.55 (3H, d, J=6.5 Hz) Mass spectrometry value (ESI-MS, m/z): 490 (M$^+$+1)

Example 203

2-(2-Fluorophenoxy)ethyl N-{4-[(6,7-dimethoxy-4-quinolyl)oxy]phenyl}carbamate

4-[(6,7-Dimethoxy-4-quinolyl)oxy]aniline (60 mg) was added to toluene/triethylamine=10/1 (6 ml), and the mixture was heated under reflux to prepare a solution. A solution of triphosgene (91 mg) in methylene chloride was then added to the solution, and the mixture was heated under reflux for 15 min. Subsequently, 2-(2-fluorophenoxy)-1-ethanol (47 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (52 mg, yield 50%).

$^1$H-NMR (CDCl$_3$, 400 MHz): 8.43–8.49 (1H, m), 8.13 (1H, d, J=3.9 Hz), 7.62 (1H, s), 7.59 (2H, d, J=8.6 Hz), 7.17 (2H, d, J=9.0 Hz), 6.90–7.12 (5H, m), 6.68 (1H, d, J=6.1 Hz), 4.54–4.59 (2H, m), 4.28–4.33 (2H, m), 4.15 (3H, s), 4.08 (3H, s) Mass spectrometry value (ESI-MS, m/z): 479 (M$^+$+1)

Example 204

2-(2-Fluorophenoxy)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (62 mg) was added to toluene/triethylamine=10/1 (6 ml), and the mixture was heated under reflux to prepare a solution. A solution of triphosgene (86 mg) in methylene chloride was then added to the solution, and the mixture was heated under reflux for 15 min. Subsequently, 2-(2-fluorophenoxy)-1-ethanol (45 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (49 mg, yield 47%).
$^1$H-NMR (CDCl$_3$, 400 MHz): 8.40–8.45 (1H, t, J=6.5 Hz), 8.14 (1H, s like), 7.72 (1H, bs), 7.64 (1H, s), 6.90–7.12 (5H, m), 6.59 (1H, bs), 6.53 (1H, d, J=6.4 Hz), 4.56 (2H, t, J=4.6 Hz), 4.30 (2H, t, J=4.6 Hz), 4.15 (3H, s), 4.09 (3H, s), 2.25 (3H, s), 2.08 (3H, s) Mass spectrometry value (ESI-MS, m/z): 508 (M$^+$+1)

Example 205

2-(2-Fluorophenoxy)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (55 mg) was added to toluene/triethylamine=10/1 (6 ml), and the mixture was heated under reflux to prepare a solution. A solution of triphosgene (76 mg) in methylene chloride was then added to the solution, and the mixture was heated under reflux for 15 min. Subsequently, 2-(2-fluorophenoxy)-1-ethanol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (61 mg, yield 66%).
$^1$H-NMR (CDCl$_3$, 400 MHz): 8.46–8.53 (1H, m), 8.11 (1H, d, J=1.7 Hz), 7.85 (1H, bs), 7.62 (1H, s), 6.85–7.12 (5H, m), 6.54–6.64 (2H, m), 4.54–4.58 (2H, m), 4.29–4.32 (2H, m), 4.14 (3H, s), 4.08 (3H, s), 2.26 (3H, s), 2.10 (3H, s) Mass spectrometry value (ESI-MS, m/z): 508 (M$^+$+1)

Example 206

2-(2-Fluorophenoxy)ethyl N-{4-[(6,7-dimethoxy-4-quinazolinyl)oxy]phenyl}carbamate 4-[(6,7-Dimethoxy-4-quinazolinyl)oxy]aniline (50 mg) was added to toluene/triethylamine=10/1 (5 ml), and the mixture was heated under reflux to prepare a solution. A solution of triphosgene (76 mg) in methylene chloride was then added to the solution, and the mixture was heated under reflux for 15 min. Subsequently, 2-(2-fluorophenoxy)-1-ethanol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (38 mg, yield 44%).
$^1$H-NMR (CDCl$_3$, 400 MHz): 8.75 (1H, s), 7.99 (1H, s), 7.59 (1H, s), 7.54 (2H, d, J=8.8 Hz), 7.19 (2H, d, J=9.0 Hz), 6.85–7.12 (5H, m), 4.53–4.56 (2H, m), 4.28–4.32 (2H, m), 4.15 (3H, s), 4.09 (3H, s) Mass spectrometry value (ESI-MS, m/z): 480 (M$^+$+1)

Example 207

2-(3-Fluorophenoxy)ethyl N-{4-[(6,7-dimethoxy-4-quinolyl)oxy]phenyl}carbamate

4-[(6,7-Dimethoxy-4-quinolyl)oxy]aniline (62 mg) was added to toluene/triethylamine=10/1 (6 ml), and the mixture was heated under reflux to prepare a solution. A solution of triphosgene (92 mg) in methylene chloride was then added to the solution, and the mixture was heated under reflux for 15 min. Subsequently, 2-(3-fluorophenoxy)-1-ethanol (48 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (55 mg, yield 51%).
$^1$H-NMR (CDCl$_3$, 400 MHz): 8.43–8.49 (1H, m), 8.10–8.13 (1H, m), 7.57–7.64 (3H, m), 6.60–7.25 (7H, m), 4.52–4.57 (2H, m), 4.18–4.27 (2H, m), 4.14 (3H, s), 4.08 (3H, s) Mass spectrometry value (ESI-MS, m/z): 479 (M$^+$+1)

Example 208

2-(3-Fluorophenoxy)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (70 mg) was added to toluene/triethylamine=10/1 (7 ml), and the mixture was heated under reflux to prepare a solution. A solution of triphosgene (97 mg) in methylene chloride was then added to the solution, and the mixture was heated under reflux for 15 min. Subsequently, 2-(3-fluorophenoxy)-1-ethanol (50 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (78 mg, yield 67%).

¹H-NMR (CDCl₃, 400 MHz): 8.42–8.49 (1H, m), 8.12–8.14 (1H, m), 7.73 (1H, bs), 7.64 (1H, s), 7.21 (1H, d, J=8.0 Hz), 7.00 (1H, d, J=8.8 Hz), 6.50–6.74 (4H, m), 4.54 (2H, t, J=4.5 Hz), 4.21 (2H, t, J=4.5 Hz), 4.15 (3H, s), 4.09 (3H, s), 2.25 (3H, s), 2.08 (3H, s) Mass spectrometry value (ESI-MS, m/z): 508 (M⁺+1)

Example 209

2-(3-Fluorophenoxy)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (56 mg) was added to toluene/triethylamine=10/1 (6 ml), and the mixture was heated under reflux to prepare a solution. A solution of triphosgene (78 mg) in methylene chloride was then added to the solution, and the mixture was heated under reflux for 15 min. Subsequently, 2-(3-fluorophenoxy)-1-ethanol (40 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (54 mg, yield 57%).

¹H-NMR (CDCl₃, 400 MHz): 8.40–8.50 (1H, m), 8.11 (1H, s), 8.00 (1H, s), 7.84–7.91 (1H, m), 7.60–7.67 (2H, m), 6.40–6.99 (5H, m), 4.08–4.28 (4H, m), 4.14 (3H, s), 4.09 (3H, s), 2.26 (3H, s), 2.11 (3H, s) Mass spectrometry value (ESI-MS, m/z): 508 (M⁺+1)

Example 210

2-(3-Fluorophenoxy)ethyl N-{4-[(6,7-dimethoxy-4-quinazolinyl)oxy]phenyl}carbamate 4-[(6,7-Dimethoxy-4-quinazolinyl)oxy]aniline (55 mg) was added to toluene/triethylamine=10/1 (6 ml), and the mixture was heated under reflux to prepare a solution. A solution of triphosgene (83 mg) in methylene chloride was then added to the solution, and the mixture was heated under reflux for 15 min. Subsequently, 2-(3-fluorophenoxy)-1-ethanol (43 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (28 mg, yield 29%).

¹H-NMR (CDCl₃, 400 MHz): 8.75 (1H, m), 8.05 (1H, s like), 7.59 (1H, s), 7.50–7.58 (2H, m), 7.17–7.24 (2H, m), 6.60–6.73 (4H, m), 4.52–4.56 (2H, m), 4.19–4.23 (2H, m), 4.16 (3H, s), 4.10 (3H, s) Mass spectrometry value (ESI-MS, m/z): 480 (M⁺+1)

Example 211

3-(2-Chlorophenoxy)propyl N-{4-[(6,7-dimethoxy-4-quinazolinyl)oxy]-2,3-dimethylphenyl}-carbamate 4-[(6,7-Dimethoxy-4-quinazolinyl)oxy]-2,3-aniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 3-(2-chlorophenoxy)-1-propanol (69 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (70 mg, yield 50%).

¹H-NMR (CDCl₃, 400 MHz): 8.74 (1H, d, J=1.7 Hz), 8.08 (1H, s), 7.70 (1H, bs), 7.62 (1H, s), 7.32–7.36 (1H, m), 7.17–7.22 (1H, m), 7.00 (1H, dd, J=6.8 Hz, J=9.3 Hz), 6.85–6.95 (2H, m), 6.44 (1H, bs), 4.43 (1H, t, J=6.2 Hz), 4.34 (1H, t, J=6.2 Hz), 4.10–4.20 (1H, m), 4.18 (3H, s), 4.11 (3H, s), 3.60–3.70 (1H, m), 2.23 (1H, d, J=5.9 Hz), 2.06 (1H, d, J=4.1 Hz), 2.08–2.22 (2H, m) Mass spectrometry value (ESI-MS, m/z): 539 (M⁺+1)

Example 212

3-(3-Chlorophenoxy)propyl N-{4-[(6,7-dimethoxy-4-quinazolinyl)oxy]-2,3-dimethylphenyl}carbamate 4-[(6,7-Dimethoxy-4-quinazolinyl)oxy]-2,3-aniline (80 mg) was added to toluene/triethylamine=10/1 (8 ml), and the mixture was heated under reflux to prepare a solution. A solution of triphosgene (111 mg) in methylene chloride was then added to the solution, and the mixture was heated under reflux for 15 min. Subsequently, 3-(3-chlorophenoxy)-1-propanol (62 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (65 mg, yield 46%).

¹H-NMR (CDCl₃, 400 MHz): 8.75 (1H, d, J=2.7 Hz), 8.14 (1H, s), 7.70 (1H, bs), 7.62 (1H, s), 7.15–7.22 (1H, m), 6.97–7.03 (1H, m), 6.87–6.95 (1H, m), 6.76–6.82 (1H, m), 6.42 (1H, bs), 4.32–4.39 (2H, m), 4.18 (3H, s), 4.11 (3H, s), 4.03–4.08 (1H, m), 3.62–3.68 (1H, m), 2.23–2.26 (3H, m), 2.12–2.21 (2H, m), 2.05–2.07 (3H, m) Mass spectrometry value (ESI-MS, m/z): 539 (M⁺+1)

Example 213

3-(4-Chlorophenoxy)propyl N-{4-[(6,7-dimethoxy-4-quinazolinyl)oxy]-2,3-dimethylphenyl}-carbamate 4-[(6,7-Dimethoxy-4-quinazolinyl)oxy]-2,3-aniline (82 mg) was added to toluene/triethylamine=10/1 (8 ml), and the mixture was heated under reflux to prepare a solution. A solution of triphosgene (114 mg) in methylene chloride was then added to the solution, and the mixture was heated under reflux for 15 min. Subsequently, 3-(4-chlorophenoxy)-1-propanol (71 mg) was added thereto, and the mixture was further stirred with heating under reflux for 2 hr. After the completion of the reaction, the reaction solution was allowed to cool to room temperature before distilled water was added thereto. The mixture was subjected to separatory extraction with chloroform, followed by washing with a 1 N aqueous hydrochloric acid solution and saturated brine. The washed solution was dried over sodium sulfate and was concentrated. The residue was purified on a column using chloroform/methanol to give the title compound (85 mg, yield 59%).
$^1$H-NMR (CDCl$_3$, 400 MHz): 8.74 (1H, s like), 8.09 (1H, s), 7.69 (1H, bs), 7.62 (1H, s), 7.19–7.23 (2H, m), 7.97–7.02 (1H, m), 6.79–6.84 (2H, m), 6.42 (1H, bs), 4.32–4.39 (2H, m), 4.17 (3H, s), 4.11 (3H, s), 4.02–4.09 (2H, m), 2.23–2.26 (3H, m), 2.10–2.20 (2H, m), 2.05–2.07 (3H, m) Mass spectrometry value (ESI-MS, m/z): 539 (M$^+$+1)

Example 214

3-Methoxyphenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (150 mg) in methylene chloride was then added to the solution, and the mixture was heated under reflux for 10 min. Next, 3-methoxyphenol (55 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (108 mg, yield 68%)
$^1$H-NMR (CDCl$_3$-d$_1$, 400 MHz): δ 2.29 (s, 3H), 4.07 (s, 3H), 4.09 (s, 3H), 6.54 (brs, 1H), 7.13–7.29 (m, 8H), 7.59–7.60 (m, 3H), 8.49 (d, J=5.9 Hz, 1H) Mass spectrometry value (ESI-MS, m/z): 447 (M$^+$+1)

Example 215

Propyl N-{4-[(6,7-Dimethoxy-4-quinolin)oxy]-2,3-dimethylphenyl}carbamate

4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (138 mg) in methylene chloride was then added to the solution, and the mixture was heated under reflux for 10 min. Next, 1-propanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 87%).
$^1$H-NMR (DMSO-d$_6$, 400 MHz): δ 0.95 (t, J=7.6 Hz, 3H), 1.63–1.66 (m, 2H), 2.07 (s, 3H), 2.20 (s, 3H), 4.04 (t, J=6.8 Hz, 2H), 4.05 (s, 6H), 6.67 (d, J=6.6 Hz, 1H), 7.15 (d, J=8.3 Hz, 1H), 7.37 (d, J=9.0 Hz, 1H), 7.60 (s, 1H), 7.79 (s, 1H), 8.77 (d, J=6.6 Hz, 1H), 9.06 (s, 1H) Mass spectrometry value (ESI-MS, m/z): 411 (M$^+$+1)

Example 216

Phenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added to the solution, and the mixture was heated under reflux for 10 min. Next, phenol (48 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (97 mg, yield 63%).
$^1$H-NMR (DMSO-d$_6$, 400 MHz): δ 4.03 (s, 3H), 4.04 (s, 3H), 6.83 (d, J=6.3 Hz, 1H), 7.24–7.30 (m, 3H), 7.38–7.47 (m, 3H), 7.57 (s, 1H), 7.72–7.74 (m, 3H), 8.79 (d, J=6.6 Hz, 1H), 10.50 (s, 1H) Mass spectrometry value (ESI-MS, m/z): 417 (M$^+$+1)

Example 217

Phenyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (139 mg) in methylene chloride was then added to the solution, and the mixture was heated under reflux for 10 min. Next, phenol (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (73 mg, yield 49%).
$^1$H-NMR (DMSO-d$_6$, 400 MHz): δ 2.10 (s, 3H), 2.30 (s, 3H), 4.05 (s, 6H), 6.69 (d, J=6.6 Hz, 1H), 7.15–7.28 (m, 4H), 7.42–7.48 (m, 3H), 7.61 (s, 1H), 7.79 (s, 1H), 8.76 (d, J=6.3 Hz, 1H) Mass spectrometry value (ESI-MS, m/z): 445 (M$^+$+1)

Example 218

Benzyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, phenylmethanol (51 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (137 mg, yield 89%).

$^1$H-NMR (CDCl$_3$-d$_1$, 400 MHz): δ 2.13 (s, 3H), 2.27 (s, 3H), 4.11 (s, 3H), 4.17 (s, 3H), 5.24 (s, 2H), 6.52 (s, 1H), 6.59 (brs, 1H), 6.95 (s, 1H), 7.26–7.45 (m, 5H), 7.64 (s, 1H), 7.93 (s, 1H), 8.14 (s, 1H), 8.51 (brs, 1H) Mass spectrometry value (ESI-MS, m/z): 459 (M$^+$+1)

Example 219

Benzyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, phenylmethanol (51 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 78%).

$^1$H-NMR (CDCl$_3$-d$_1$, 400 MHz): δ 2.10 (s, 3H), 2.26 (s, 3H), 4.11 (s, 3H), 4.17 (s, 3H), 5.24 (s, 2H), 6.55 (s, 2H), 7.03 (d, J=8.8 Hz, 1H), 7.37–7.43 (m, 5H), 7.67 (s, 1H), 7.76 (brs, 1H), 8.15 (s, 1H), 8.50 (brs, 1H) Mass spectrometry value (ESI-MS, m/z): 459 (M$^+$+1)

Example 220

Benzyl N-{4-[(6,7-dimethoxy-4-quinazolinyl)oxy]phenyl}carbamate

4-[(6,7-Dimethoxy-4-quinazolinyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, phenylmethanol (55 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (100 mg, yield 58%).

$^1$H-NMR (CDCl$_3$-d$_1$, 400 MHz): δ 4.12 (s, 3H), 4.19 (s, 3H), 5.23 (s, 2H), 6.96 (s, 1H), 7.19 (d, J=9.0 Hz, 2H), 7.35–7.43 (m, 5H), 7.59 (d, J=8.8 Hz, 2H), 7.61 (s, 1H), 8.14 (s, 1H), 8.79 (s, 1H) Mass spectrometry value (ESI-MS, m/z): 432 (M$^+$+1)

Example 221

Cyclohexyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cyclohexanol (47 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (80 mg, yield 53%).

$^1$H-NMR (CDCl$_3$-d$_1$, 400 MHz): δ 1.49–1.57 (m, 10H), 1.76–1.80 (m, 2H), 1.97–2.01 (m, 2H), 2.13 (s, 3H), 2.29 (s, 3H), 4.11 (s, 3H), 4.17 (s, 3H), 6.39 (s, 1H), 6.59 (d, J=9.0 Hz, 1H), 6.94 (s, 1H), 7.65 (s, 1H), 7.95 (s, 1H), 8.15 (s, 1H), 8.49 (brs, 1H) Mass spectrometry value (ESI-MS, m/z): 451 (M$^+$+1)

Example 222

Cyclohexyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cyclohexanol (47 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (85 mg, yield 56%).

$^1$H-NMR (CDCl$_3$-d$_1$, 400 MHz): δ 1.47–2.20 (m, 13H), 2.28 (s, 3H), 4.11 (s, 3H), 4.17 (s, 3H), 4.74 (brs, 1H), 6.43 (s, 1H), 6.57 (brs, 1H), 7.02 (d, J=8.8 Hz, 1H), 7.67 (s, 1H), 7.75 (brs, 1H), 8.14 (s, 1H), 8.49 (brs, 1H) Mass spectrometry value (ESI-MS, m/z): 451 (M$^+$+1)

Example 223

2-Methylphenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, o-cresol (55 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (116 mg, yield 80%). Mass spectrometry value (ESI-MS, m/z): 432 ($M^+$+1)

Example 224

Phenyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, phenol (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (69 mg, yield 50%).

$^1$H-NMR (CDCl$_3$-d$_1$, 400 MHz): δ 2.15 (s, 3H), 2.34 (s, 3H), 4.01 (s, 3H), 4.07 (s, 3H), 6.32 (d, J=5.4 Hz, 1H), 6.77 (brs, 1H), 6.97 (s, 1H), 7.22–7.28 (m, 3H), 7.40–7.47 (m, 3H), 7.60 (s, 1H), 7.85 (brs, 1H), 8.46 (d, J=5.4 Hz, 1H) Mass spectrometry value (ESI-MS, m/z): 445 ($M^+$+1)

Example 225

Benzyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (100 mg) was added to toluene (10 ml) and triethylamine (1 ml), and the mixture was heated under reflux to prepare a solution. A solution of triphosgene (134 mg) in methylene chloride was then added thereto, and the mixture was heated under reflux for 10 min. Next, phenylmethanol (49 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (100 mg, yield 72%).

$^1$H-NMR (CDCl$_3$-d$_1$, 400 MHz): δ 4.00 (s, 6H), 5.17 (s, 2H), 7.12–7.37 (m, 9H), 7.44 (s, 1H), 8.24 (d, J=8.8 Hz, 1H), 8.56 (s, 1H) Mass spectrometry value (ESI-MS, m/z): 467 ($M^+$+1)

Example 226

3-Methoxybenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (3-methoxyphenyl)methanol (71 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (133 mg, yield 79%).

$^1$H-NMR (CDCl$_3$-d$_1$, 400 MHz): δ 3.83 (s, 3H), 4.10 (s, 3H), 4.17 (s, 3H), 5.21 (s, 2H), 6.58 (brs, 1H), 6.88–7.01 (m, 4H), 7.18 (d, J=8.8 Hz, 1H), 7.29–7.33 (m, 1H), 7.61–7.63 (m, 3H), 8.14 (s, 1H), 8.50 (brs, 1H) Mass spectrometry value (ESI-MS, m/z): 462 ($M^+$+1)

Example 227

2-Chlorobenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (2-chlorophenyl)methanol (73 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (153 mg, yield 90%).

$^1$H-NMR (CDCl$_3$-d$_1$, 400 MHz): δ 4.03 (s, 3H), 4.04 (s, 3H), 5.27 (s, 2H), 6.83 (d, J=6.6 Hz, 1H), 7.35 (d, J=9.0 Hz, 2H), 7.41–7.43 (m, 2H), 7.52–7.54 (m, 1H), 7.58–7.61 (m, 2H), 7.69 (d, J=8.8 Hz, 2H), 7.74 (s, 1H), 8.77 (d, J=6.6 Hz, 1H), 10.12 (s, 1H) Mass spectrometry value (ESI-MS, m/z): 466 ($M^+$+1)

Example 228

3-Chlorobenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (3-chlorophenyl)methanol (73 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (158 mg, yield 93%).

$^1$H-NMR (CDCl$_3$-d$_1$, 400 MHz): δ 4.03 (s, 3H), 4.04 (s, 3H), 5.20 (s, 2H), 6.82 (d, J=6.6 Hz, 1H), 7.35 (d, J=9.0 Hz, 2H), 7.42–7.47 (m, 3H), 7.52 (s, 1H), 7.63 (s, 1H), 7.69 (d, J=9.0 Hz, 2H), 7.74 (s, 1H), 8.78 (d, J=6.6 Hz, 1H), 10.09 (s, 1H) Mass spectrometry value (ESI-MS, m/z): 466 (M$^+$+1)

Example 229

4-Chlorobenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (4-chlorophenyl)methanol (73 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (147 mg, yield 86%).

$^1$H-NMR (CDCl$_3$-d$_1$, 400 MHz): δ 4.03 (s, 3H), 4.04 (s, 3H), 5.18 (s, 2H), 6.82 (d, J=6.6 Hz, 1H), 7.35 (d, J=9.0 Hz, 2H), 7.48 (s, 4H), 7.64 (s, 1H), 7.68 (d, J=8.8 Hz, 2H), 7.74 (s, 1H), 8.78 (d, J=6.6 Hz, 1H), 10.07 (s, 1H) Mass spectrometry value (ESI-MS, m/z): 466 (M$^+$+1)

Example 230

Cyclohexyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 1-cyclohexanol (51 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 77%).

$^1$H-NMR (CDCl$_3$-d$_1$, 400 MHz): δ 1.24–1.58 (m, 6H), 1.73–1.76 (m, 2H), 1.90–1.94 (m, 2H), 4.02 (s, 3H), 4.04 (s, 3H), 4.54 (brs, 1H), 6.79 (d, J=6.3 Hz, 1H), 7.32 (d, J=9.0 Hz, 2H), 7.55 (s, 1H), 7.67 (d, J=9.0 Hz, 2H), 7.72 (s, 1H), 8.76 (d, J=6.6 Hz, 1H), 9.82 (s, 1H) Mass spectrometry value (ESI-MS, m/z): 423 (M$^+$+1)

Example 231

Benzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, phenylmethanol (55 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (130 mg, yield 82%)

$^1$H-NMR (CDCl$_3$-d$_1$, 400 MHz): δ 4.03 (s, 3H), 4.04 (s, 3H), 5.19 (s, 2H), 6.82 (d, J=6.6 Hz, 1H), 7.30–7.46 (m, 7H), 7.62 (s, 1H), 7.69 (d, J=9.0 Hz, 2H), 7.74 (s, 1H), 8.78 (d, J=6.6 Hz, 1H), 10.04 (s, 1H) Mass spectrometry value (ESI-MS, m/z): 431 (M$^+$+1)

Example 232

2-Methylbenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (140 mg, yield 89%).

$^1$H-NMR (CDCl$_3$-d$_1$, 400 MHz): δ 2.07 (s, 3H), 2.20 (s, 3H), 2.36 (s, 3H), 4.05 (s, 6H), 5.17 (s, 2H), 6.67 (d, J=6.6 Hz, 1H), 7.13–7.27 (m, 4H), 7.39 (d, J=9.0 Hz, 2H), 7.62 (s, 1H), 7.79 (s, 1H), 8.76 (d, J=6.6 Hz, 1H), 9.22 (s, 1H) Mass spectrometry value (ESI-MS, m/z): 473 (M$^+$+1)

Example 233

3-Methylbenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (140 mg, yield 89%).

$^1$H-NMR (CDCl$_3$-d$_1$, 400 MHz): δ 2.07 (s, 3H), 2.20 (s, 3H), 2.33 (s, 3H), 4.05 (s, 6H), 5.12 (s, 2H), 6.65 (d, J=6.8 Hz, 1H), 7.12–7.31 (m, 5H), 7.39 (d, J=8.8 Hz, 2H), 7.60 (s, 1H), 7.78 (s, 1H), 8.75 (d, J=6.8 Hz, 1H), 9.21 (s, 1H) Mass spectrometry value (ESI-MS, m/z): 473 (M$^+$+1)

Example 234

4-Methylbenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (4-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 25%).

$^1$H-NMR (CDCl$_3$-d$_1$, 400 MHz): δ 2.07 (s, 3H), 2.19 (s, 3H), 2.32 (s, 3H), 4.04 (s, 6H), 5.11 (s, 2H), 6.65 (d, J=6.3 Hz, 1H), 7.14–7.22 (m, 3H), 7.32 (d, J=8.1 Hz, 2H), 7.38 (d, J=8.8 Hz, 1H), 7.56 (s, 1H), 7.78 (s, 1H), 8.75 (d, J=6.3 Hz, 1H), 9.19 (s, 1H) Mass spectrometry value (ESI-MS, m/z): 473 (M$^+$+1)

Example 235

2-Chlorobenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (127 mg, yield 77%).

$^1$H-NMR (CDCl$_3$-d$_1$, 400 MHz): δ 2.10 (s, 3H), 2.27 (s, 3H), 4.11 (s, 3H), 4.17 (s, 3H), 5.36 (s, 2H), 6.55–6.56 (m, 2H), 7.03 (d, J=9.0 Hz, 1H), 7.25–7.33 (m, 1H), 7.43–7.50 (m, 2H), 7.67 (s, 1H), 8.15 (s, 1H), 8.48 (s, 1H) Mass spectrometry value (ESI-MS, m/z): 494 (M$^+$+1)

Example 236

3-Chlorobenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (147 mg, yield 90%).

$^1$H-NMR (CDCl$_3$-d$_1$, 400 MHz): δ 2.10 (s, 3H), 2.27 (s, 3H), 4.11 (s, 3H), 4.17 (s, 3H), 5.21 (s, 2H), 6.56 (d, J=6.3 Hz, 2H), 7.03 (d, J=8.5 Hz, 1H), 7.25–7.35 (m, 3H), 7.43 (s, 1H), 7.67 (s, 1H), 7.75 (brs, 1H), 8.15 (s, 1H), 8.49 (brs, 1H) Mass spectrometry value (ESI-MS, m/z): 494 (M$^+$+1)

Example 237

4-Chlorobenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (4-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (103 mg, yield 63%).

$^1$H-NMR (CDCl$_3$-d$_1$, 400 MHz): δ 2.10 (s, 3H), 2.26 (s, 3H), 4.11 (s, 3H), 4.17 (s, 3H), 5.20 (s, 2H), 6.54 (brs, 2H), 7.03 (d, J=8.8 Hz, 1H), 7.38 (s, 4H), 7.66 (s, 1H), 7.71 (brs, 1H), 8.15 (s, 1H), 8.50 (brs, 1H) Mass spectrometry value (ESI-MS, m/z): 494 (M$^+$+1)

Example 238

3-Methoxybenzyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-methoxyphenyl)methanol (65 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (136 mg, yield 84%).
$^1$H-NMR (CDCl$_3$-d$_1$, 400 MHz): δ 2.10 (s, 3H), 2.26 (s, 3H), 3.84 (s, 3H), 4.11 (s, 3H), 4.18 (s, 3H), 5.21 (s, 2H), 6.55 (brs, 2H), 6.84–7.02 (m, 4H), 7.25–7.32 (m, 1H), 7.67 (s, 1H), 7.83 (brs, 1H), 8.16 (s, 1H), 8.44 (brs, 1H) Mass spectrometry value (ESI-MS, m/z): 489 (M$^+$+1)

Example 239

2-Methoxybenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methoxyphenyl)methanol (65 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (130 mg, yield 80%).
$^1$H-NMR (CDCl$_3$-d$_1$, 400 MHz): δ 2.13 (s, 3H), 2.26 (s, 3H), 3.90 (s, 3H), 4.11 (s, 3H), 4.17 (s, 3H), 5.31 (s, 2H), 6.51 (s, 1H), 6.58 (d, J=6.6 Hz, 1H), 6.88–7.01 (m, 3H), 7.34–7.42 (m, 2H), 7.64 (s, 1H), 7.96 (s, 1H), 8.15 (s, 1H), 8.47 (brs, 1H) Mass spectrometry value (ESI-MS, m/z): 489 (M$^+$+1)

Example 240

3-Methoxybenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-methoxyphenyl)methanol (65 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 74%).
$^1$H-NMR (CDCl$_3$-d$_1$, 400 MHz): δ 2.13 (s, 3H), 2.27 (s, 3H), 3.84 (s, 3H), 4.11 (s, 3H), 4.17 (s, 3H), 5.22 (s, 2H), 6.51 (s, 1H), 6.58 (d, J=6.3 Hz, 1H), 6.91–7.03 (m, 4H), 7.25–7.35 (m, 1H), 7.64 (s, 1H), 7.93 (s, 1H), 8.15 (s, 1H), 8.47 (brs, 1H) Mass spectrometry value (ESI-MS, m/z): 489 (M$^+$+1)

Example 241

2-Chlorobenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (112 mg, yield 68%).
$^1$H-NMR (CDCl$_3$-d$_1$, 400 MHz): δ 2.13 (s, 3H), 2.28 (s, 3H), 4.11 (s, 3H), 4.17 (s, 3H), 5.36 (s, 2H), 6.54 (s, 1H), 6.58 (d, J=6.3 Hz, 1H), 6.96 (s, 1H), 7.26–7.33 (m, 2H), 7.43–7.49 (m, 2H), 7.64 (s, 1H), 7.93 (s, 1H), 8.15 (s, 1H), 8.47 (brs, 1H) Mass spectrometry value (ESI-MS, m/z): 494 (M$^+$+1)

Example 242

3-Chlorobenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (117 mg, yield 71%).
$^1$H-NMR (CDCl$_3$-d$_1$, 400 MHz): δ 2.14 (s, 3H), 2.29 (s, 3H), 4.11 (s, 3H), 4.17 (s, 3H), 5.21 (s, 2H), 6.53 (s, 1H), 6.56 (s, 1H), 6.96 (s, 1H), 7.26–7.38 (m, 3H), 7.44 (s, 1H), 7.64 (s, 1H), 7.91 (s, 1H), 8.15 (s, 1H), 8.43 (brs, 1H) Mass spectrometry value (ESI-MS, m/z): 494 (M$^+$+1)

Example 243

4-Chlorobenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (4-chlorophenyl)methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (154 mg, yield 94%).

$^1$H-NMR (CDCl$_3$-d$_1$, 400 MHz): δ 2.13 (s, 3H), 2.27 (s, 3H), 4.11 (s, 3H), 4.17 (s, 3H), 5.20 (s, 2H), 6.50 (s, 1H), 6.58 (s, 1H), 6.95 (s, 1H), 7.38 (s, 4H), 7.64 (s, 1H), 7.90 (s, 1H), 8.15 (s, 1H), 8.47 (brs, 1H) Mass spectrometry value (ESI-MS, m/z): 494 (M$^+$+1)

Example 244

Propyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-propanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (115 mg, yield 83%).

$^1$H-NMR (CDCl$_3$-d$_1$, 400 MHz): δ 1.01 (t, J=7.3 Hz, 3H), 1.72–1.77 (m, 2H), 2.13 (s, 3H), 2.29 (s, 3H), 4.11 (s, 3H), 4.17 (s, 3H), 4.17 (t, J=7.8 Hz, 2H), 6.42 (s, 1H), 6.60 (brs, 1H), 6.95 (s, 1H), 7.65 (s, 1H), 7.92 (s, 1H), 8.15 (s, 1H), 8.50 (brs, 1H) Mass spectrometry value (ESI-MS, m/z): 411 (M$^+$+1)

Example 245

2-Methylbenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (140 mg, yield 89%).

$^1$H-NMR (CDCl$_3$-d$_1$, 400 MHz): δ 2.13 (s, 3H), 2.26 (s, 3H), 2.43 (s, 3H), 4.11 (s, 3H), 4.17 (s, 3H), 5.27 (s, 2H), 6.50 (s, 1H), 6.58 (brs, 1H), 6.95 (s, 1H), 7.25–7.30 (m, 3H), 7.40 (d, J=7.1 Hz, 1H), 7.64 (s, 1H), 7.94 (s, 1H), 8.15 (s, 1H), 8.50 (brs, 1H) Mass spectrometry value (ESI-MS, m/z): 473 (M$^+$+1)

Example 246

2-Naphthylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 2-naphthylmethanol (87 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (160 mg, yield 90%).

$^1$H-NMR (CDCl$_3$-d$_1$, 400 MHz): δ 2.14 (s, 3H), 2.28 (s, 3H), 4.11 (s, 3H), 4.17 (s, 3H), 5.29 (s, 2H), 6.53 (s, 1H), 6.58 (s, 1H), 6.95 (s, 1H), 7.37–7.53 (m, 4H), 7.59–7.65 (m, 4H), 7.95 (s, 1H), 8.15 (s, 1H), 8.50 (brs, 1H) Mass spectrometry value (ESI-MS, m/z): 510 (M$^+$+1)

Example 247

Propyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (104 mg, yield 73%).

$^1$H-NMR (CDCl$_3$-d$_1$, 400 MHz): δ 1.01 (t, J=7.6 Hz, 3H), 1.71–1.76 (m, 2H), 4.10 (s, 3H), 4.17 (s, 3H), 4.17 (t, J=8.1

Hz, 2H), 6.69 (brs, 1H), 6.81 (s, 1H), 7.18 (d, J=8.8 Hz, 2H), 7.61 (d, J=8.3 Hz, 2H), 7.64 (s, 1H), 8.14 (s, 1H), 8.50 (brs, 1H) Mass spectrometry value (ESI-MS, m/z): 383 (M$^+$+1)

Example 248

2-Methoxybenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (2-methoxyphenyl)methanol (71 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (123 mg, yield 73%).

$^1$H-NMR (CDCl$_3$-d$_1$, 400 MHz): δ 3.89 (s, 3H), 4.10 (s, 3H), 4.17 (s, 3H), 5.30 (s, 2H), 6.69 (d, J=6.3 Hz, 1H), 6.83 (s, 1H), 6.93–7.00 (m, 2H), 7.18–7.52 (m, 4H), 7.59–7.63 (m, 3H), 8.15 (s, 1H), 8.49 (brs, 1H) Mass spectrometry value (ESI-MS, m/z): 462 (M$^+$+1)

Example 249

4-Methoxybenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (4-methoxyphenyl)methanol (71 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (140 mg, yield 83%).

$^1$H-NMR (CDCl$_3$-d$_1$, 400 MHz): δ 3.83 (s, 3H), 4.10 (s, 3H), 4.17 (s, 3H), 5.17 (s, 2H), 6.68 (d, J=6.3 Hz, 1H), 6.83 (s, 1H), 6.92 (d, J=8.5 Hz, 2H), 7.17 (d, J=9.0 Hz, 2H), 7.37 (d, J=8.5 Hz, 2H), 7.59 (d, J=9.0 Hz, 2H), 7.63 (s, 1H), 8.14 (s, 1H), 8.49 (t, J=6.6 Hz, 1H) Mass spectrometry value (ESI-MS, m/z): 462 (M$^+$+1)

Example 250

2-Methylbenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (2-methylphenyl)methanol (62 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (143 mg, yield 88%).

$^1$H-NMR (CDCl$_3$-d$_1$, 400 MHz): δ 2.42 (s, 3H), 4.10 (s, 3H), 4.17 (s, 3H), 5.27 (s, 2H), 6.68 (d, J=6.3 Hz, 1H), 6.87 (s, 1H), 7.17–7.28 (m, 5H), 7.38 (d, J=7.1 Hz, 1H), 7.61 (d, J=9.0 Hz, 2H), 7.63 (s, 1H), 8.14 (s, 1H), 8.49 (brs, 1H) Mass spectrometry value (ESI-MS, m/z): 446 (M$^+$+1)

Example 251

3-Methylbenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (3-methylphenyl)methanol (62 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (146 mg, yield 89%).

$^1$H-NMR (CDCl$_3$-d$_1$, 400 MHz): δ 2.38 (s, 3H), 4.10 (s, 3H), 4.17 (s, 3H), 5.20 (s, 2H), 6.69 (brs, 1H), 6.92 (s, 1H), 7.17–7.31 (m, 6H), 7.61–7.63 (m, 3H), 8.14 (s, 1H), 8.51 (brs, 1H) Mass spectrometry value (ESI-MS, m/z): 446 (M$^+$+1)

Example 252

4-Methylbenzyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, (4-methylphenyl)methanol (62 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (133 mg, yield 81%).

$^1$H-NMR (CDCl$_3$-d$_1$, 400 MHz): δ 2.37 (s, 3H), 4.10 (s, 3H), 4.17 (s, 3H), 5.20 (s, 2H), 6.69 (brs, 1H), 6.92 (s, 1H), 7.16–7.33 (m, 6H), 7.60 (d, J=7.3 Hz, 2H), 7.64 (s, 1H), 8.15 (s, 1H), 8.49 (brs, 1H) Mass spectrometry value (ESI-MS, m/z): 446 (M$^+$+1)

Example 253

2-Methylbenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (122 mg, yield 77%).

$^1$H-NMR (CDCl$_3$-d$_1$, 400 MHz): δ 2.26 (s, 3H), 2.43 (s, 3H), 4.11 (s, 3H), 4.17 (s, 3H), 5.27 (s, 2H), 6.52 (s, 1H), 6.58 (d, J=6.3 Hz, 1H), 6.95 (s, 1H), 7.24–7.30 (m, 3H), 7.40 (d, J=7.1 Hz, 1H), 7.65 (s, 1H), 7.93 (s, 1H), 8.15 (s, 1H), 8.49 (brs, 1H) Mass spectrometry value (ESI-MS, m/z): 474 (M$^+$+1)

Example 254

3-Methylbenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (3-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 76%).

$^1$H-NMR (CDCl$_3$-d$_1$, 400 MHz): δ 2.13 (s, 3H), 2.27 (s, 3H), 2.39 (s, 3H), 4.11 (s, 3H), 4.17 (s, 3H), 5.21 (s, 2H), 6.53 (s, 1H), 6.58 (brs, 1H), 6.95 (s, 1H), 7.18–7.30 (m, 4H), 7.64 (s, 1H), 7.94 (s, 1H), 8.15 (s, 1H), 8.48 (brs, 1H) Mass spectrometry value (ESI-MS, m/z): 474 (M$^+$+1)

Example 255

4-Methylbenzyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (4-methylphenyl)methanol (57 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (139 mg, yield 88%).

$^1$H-NMR (CDCl$_3$-d$_1$, 400 MHz): δ 2.13 (s, 3H), 2.26 (s, 3H), 2.38 (s, 3H), 4.11 (s, 3H), 4.17 (s, 3H), 5.20 (s, 2H), 6.49 (s, 1H), 6.58 (brs, 1H), 6.94 (s, 1H), 7.22 (d, J=7.8 Hz, 2H), 7.34 (d, J=8.1 Hz, 2H), 7.64 (s, 1H), 7.94 (s, 1H), 8.15 (s, 1H), 8.50 (brs, 1H) Mass spectrometry value (ESI-MS, m/z): 474 (M$^+$+1)

Example 256

Hexyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 1-hexanol (52 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (110 mg, yield 70%).

$^1$H-NMR (CDCl$_3$-d$_1$, 400 MHz): δ 0.92 (t, J=6.8 Hz, 3H), 1.33–1.35 (m, 6H), 1.67–1.72 (m, 2H), 4.10 (s, 3H), 4.17 (s, 3H), 4.20 (t, J=6.8 Hz, 2H), 6.70 (d, J=6.3 Hz, 1H), 6.79 (s, 1H), 7.18 (d, J=9.0 Hz, 2H), 7.60 (d, J=8.8 Hz, 2H), 7.64 (s, 1H), 8.14 (s, 1H), 8.51 (brs, 1H) Mass spectrometry value (ESI-MS, m/z): 426 (M$^+$+1)

Example 257

4-Butylphenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 4-butylphenol (77 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (130 mg, yield 75%).

$^1$H-NMR (CDCl$_3$-d$_1$, 400 MHz): δ 0.94 (t, J=7.3 Hz, 3H), 1.34–1.40 (m, 2H), 1.51–1.63 (m, 2H), 2.63 (t, J=7.8 Hz, 2H), 4.11 (s, 3H), 4.17 (s, 3H), 6.71 (d, J=6.3 Hz, 1H), 7.09 (d, J=8.5 Hz, 2H), 7.20–7.23 (m, 4H), 7.64 (s, 1H), 7.69 (d,

J=8.8 Hz, 2H), 8.15 (s, 1H), 8.52 (brs, 1H) Mass spectrometry value (ESI-MS, m/z): 474 (M$^+$+1)

Example 258

1-Ethylbutyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 3-hexanol (52 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (130 mg, yield 83%).
$^1$H-NMR (CDCl$_3$-d$_1$, 400 MHz): δ 0.95–0.98 (m, 6H), 1.39–1.67 (m, 6H), 4.11 (s, 3H), 4.17 (s, 3H), 4.84–4.86 (m, 1H), 6.70 (d, J=6.1 Hz, 1H), 6.77 (s, 1H), 7.18 (d, J=9.0 Hz, 2H), 7.61 (d, J=8.8 Hz, 2H), 7.64 (s, 1H), 8.13 (s, 1H), 8.53 (brs, 1H) Mass spectrometry value (ESI-MS, m/z): 426 (M$^+$+1)

Example 259

4-(Tert-butyl)phenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 4-(tert-butyl)phenol (77 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (150 mg, yield 87%).
$^1$H-NMR (CDCl$_3$-d$_1$, 400 MHz): δ 1.34 (s, 9H), 4.11 (s, 3H), 4.17 (s, 3H), 6.71 (d, J=6.1 Hz, 1H), 7.13 (d, J=8.8 Hz, 2H), 7.21–7.27 (m, 3H), 7.43 (d, J=8.8 Hz, 2H), 7.64 (s, 1H), 7.68 (d, J=8.8 Hz, 2H), 8.15 (s, 1H), 8.51 (brs, 1H) Mass spectrometry value (ESI-MS, m/z): 474 (M$^+$+1)

Example 260

2-Methoxyphenyl N-{4-[(6,7-dimethoxy-4-quinolyl)oxy]phenyl}carbamate

4-[(6,7-Dimethoxy-4-quinolyl)oxy]aniline (100 mg) was added to toluene (10 ml) and triethylamine (1 ml), and the mixture was heated under reflux to prepare a solution. A solution of triphosgene (151 mg) in methylene chloride was then added thereto, and the mixture was heated under reflux for 10 min. Next, 2-methoxyphenol (63 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (75 mg, yield 46%).
$^1$H-NMR (CDCl$_3$-d$_1$, 400 MHz): δ 3.90 (s, 3H), 4.11 (s, 3H), 4.17 (s, 3H), 6.70 (brs, 1H), 6.85 (s, 1H), 6.92–7.02 (m, 4H), 7.15–7.25 (m, 3H), 7.64 (s, 1H), 7.70 (d, J=8.3 Hz, 1H), 8.14 (s, 1H), 8.52 (brs, 1H) Mass spectrometry value (ESI-MS, m/z): 448 (M$^+$+1)

Example 261

Hexyl N-{4-[(6,7-Dimethoxy-4-quinolyl)oxy]-2,3-dimethylphenyl}carbamate

4-[(6,7-Dimethoxy-4-quinolyl)oxy]-2,3-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-hexanol (48 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (106 mg, yield 72%).
$^1$H-NMR (CDCl$_3$-d$_1$, 400 MHz): δ 0.92 (t, J=7.1 Hz, 3H), 1.34–1.44 (m, 6H), 1.67–1.74 (m, 2H), 2.10 (s, 3H), 2.28 (s, 3H), 4.11 (s, 3H), 4.17 (s, 3H), 4.20 (t, J=6.8 Hz, 2H), 6.45 (s, 1H), 6.56 (d, J=6.6 Hz, 1H), 7.02 (d, J=9.0 Hz, 1H), 7.67 (s, 1H), 7.75 (d, J=9.3 Hz, 1H), 8.16 (s, 1H), 8.46 (t, J=6.3 Hz, 1H) Mass spectrometry value (ESI-MS, m/z): 454 (M$^+$+1)

Example 262

Hexyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-hexanol (48 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (154 mg, yield 100%).
$^1$H-NMR (CDCl$_3$-d$_1$, 400 MHz): δ 0.92 (t, J=7.1 Hz, 3H), 1.34–1.42 (m, 6H), 1.68–1.73 (m, 2H), 2.13 (s, 3H), 2.29 (s, 3H), 4.11 (s, 3H), 4.18 (s, 3H), 4.21 (t, J=6.8 Hz, 2H), 6.42

(s, 1H), 6.59 (brs, 1H), 6.95 (s, 1H), 7.65 (s, 1H), 7.92 (s, 1H), 8.15 (s, 1H), 8.47 (brs, 1H) Mass spectrometry value (ESI-MS, m/z): 454 (M$^+$+1)

Example 263

1-Phenylpropyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-phenyl-1-propanol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 92%).
$^1$H-NMR (CDCl$_3$-d$_1$, 400 MHz): δ 0.96 (t, J=7.6 Hz, 3H), 1.88–1.93 (m, 1H), 1.99–2.05 (m, 1H), 4.10 (s, 3H), 4.16 (s, 3H), 5.69 (t, J=7.3 Hz, 1H), 6.66 (d, J=5.6 Hz, 1H), 6.84 (s, 1H), 7.16 (d, J=8.8 Hz, 2H), 7.32–7.39 (m, 5H), 7.59 (d, J=8.8 Hz, 2H), 7.63 (s, 1H), 8.15 (d, J=4.1 Hz, 1H), 8.45–8.47 (m, 1H) Mass spectrometry value (ESI-MS, m/z): 460 (M$^+$+1)

Example 264

1-Phenylpropyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (76 mg, yield 97%).
$^1$H-NMR (CDCl$_3$-d$_1$, 400 MHz): δ 0.97 (t, J=7.5 Hz, 3H), 1.89–1.94 (m, 1H), 2.01–2.17 (m, 1H), 2.10 (s, 3H), 2.28 (s, 3H), 4.10 (s, 3H), 4.17 (s, 3H), 5.68 (t, J=7.3 Hz, 1H), 6.50 (s, 1H), 6.55 (d, J=6.3 Hz, 1H), 6.93 (s, 1H), 7.33–7.39 (m, 5H), 7.64 (s, 1H), 7.91 (s, 1H), 8.14 (s, 1H), 8.45 (brs, 1H) Mass spectrometry value (ESI-MS, m/z): 488 (M$^+$+1)

Example 265

1-Phenylpropyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (52 mg, yield 66%).
$^1$H-NMR (CDCl$_3$-d$_1$, 400 MHz): δ 0.96 (t, J=7.3 Hz, 3H), 1.89–1.92 (m, 1H), 1.94–2.05 (m, 1H), 2.09 (s, 3H), 2.25 (s, 3H), 4.11 (s, 3H), 4.17 (s, 3H), 5.69 (t, J=7.1 Hz, 1H), 6.52 (s, 1H), 6.54 (s, 1H), 6.99 (d, J=8.5 Hz, 1H), 7.32–7.39 (m, 5H), 7.66 (s, 1H), 7.73 (brs, 1H), 8.15 (s, 1H), 8.45 (t, J=6.6 Hz, 1H) Mass spectrometry value (ESI-MS, m/z): 488 (M$^+$+1)

Example 266

4-Pentenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-penten-1-ol (22 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 100%).
$^1$H-NMR (CDCl$_3$-d$_1$, 400 MHz): δ 1.80–1.83 (m, 2H), 2.16–2.20 (m, 2H), 4.10 (s, 3H), 4.17 (s, 3H), 4.23 (t, J=6.6 Hz, 2H), 5.02–5.10 (m, 2H), 5.83–5.85 (m, 1H), 6.69 (d, J=6.3 Hz, 1H), 6.76 (s, 1H), 7.18 (d, J=8.8 Hz, 2H), 7.60 (d, J=9.0 Hz, 2H), 7.64 (s, 1H), 8.15 (s, 1H), 8.48 (brs, 1H) Mass spectrometry value (ESI-MS, m/z): 410 (M$^+$+1)

Example 267

4-Pentenyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-penten-1-ol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (71 mg, yield 100%).

$^1$H-NMR (CDCl$_3$-d$_1$, 400 MHz): δ 1.81–1.85 (m, 2H) 2.13 (s, 3H), 2.18–2.20 (m, 2H), 2.29 (s, 3H), 4.11 (s, 3H), 4.17 (s, 3H), 4.23 (t, J=6.6 Hz, 2H), 5.02–5.11 (m, 2H), 5.81–5.88 (m, 1H), 6.42 (s, 1H), 6.58 (d, J=6.3 Hz, 1H), 6.95 (s, 1H), 7.64 (s, 1H), 7.91 (s, 1H), 8.16 (s, 1H), 8.46 (brs, 1H) Mass spectrometry value (ESI-MS, m/z): 438 (M$^+$+1)

Example 268

4-Pentenyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-penten-1-ol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (67 mg, yield 95%).

$^1$H-NMR (CDCl$_3$-d$_1$, 400 MHz): δ 1.79–1.86 (m, 2H), 2.10 (s, 3H), 2.16–2.20 (m, 2H), 2.27 (s, 3H), 4.12 (s, 3H), 4.17 (s, 3H), 4.22 (t, J=6.6 Hz, 2H), 5.02–5.10 (m, 2H), 5.81–5.88 (m, 1H), 6.44 (s, 1H), 6.56 (d, J=6.6 Hz, 1H), 7.03 (d, J=8.5 Hz, 1H), 7.67 (s, 1H), 7.76 (brs, 1H), 8.16 (d, J=4.1 Hz, 1H), 8.45 (brs, 1H) Mass spectrometry value (ESI-MS, m/z): 438 (M$^+$+1)

Example 269

2,6-Dimethylphenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2,6-dimethylphenol (32 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (82 mg, yield 100%).

$^1$H-NMR (CDCl$_3$-d$_1$, 400 MHz): δ 2.26 (s, 6H), 4.11 (s, 3H), 4.17 (s, 3H), 6.70 (d, J=7.6 Hz, 1H), 7.10 (s, 2H), 7.22–7.26 (m, 4H), 7.65 (s, 1H), 7.71 (d, J=8.5 Hz, 2H), 8.16 (d, J=4.1 Hz, 1H), 8.48 (brs, 1H) Mass spectrometry value (ESI-MS, m/z): 446 (M$^+$+1)

Example 270

2,6-Dimethylphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2,6-dimethylphenol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (76 mg, yield 100%).

$^1$H-NMR (CDCl$_3$-d$_1$, 400 MHz): δ 2.13 (s, 3H), 2.28 (s, 6H), 2.39 (s, 3H), 4.11 (s, 3H), 4.17 (s, 3H), 6.59 (d, J=5.9 Hz, 1H), 7.01 (s, 1H), 7.11 (s, 2H), 7.25–7.27 (m, 2H), 7.65 (s, 1H), 7.98 (brs, 1H), 8.16 (s, 1H), 8.47 (brs, 1H) Mass spectrometry value (ESI-MS, m/z): 474 (M$^+$+1)

Example 271

2,6-Dimethylphenyl N-(4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2,6-dimethylphenol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (68 mg, yield 89%).

$^1$H-NMR (CDCl$_3$-d$_1$, 400 MHz): δ 2.14 (s, 3H), 2.28 (s, 6H), 2.38 (s, 3H), 4.12 (s, 3H), 4.18 (s, 3H), 6.56 (d, J=6.8 Hz, 1H), 7.00–7.10 (m, 4H), 7.25–7.27 (m, 1H), 7.67 (s, 1H), 8.16 (s, 1H), 8.46 (brs, 1H) Mass spectrometry value (ESI-MS, m/z): 474 (M$^+$+1)

Example 272

4-Butylphenyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-butylphenol (35 mg) was added thereto, and the mixture was further stirred with heating under reflux for 3 hr. A saturated aqueous sodium bicarbonate solution was added to stop the reaction, and the reaction solution was then extracted with chloroform, fol-

Example 273

4-Butylphenyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-butylphenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (44 mg, yield 55%).

$^1$H-NMR (CDCl$_3$-d$_1$, 400 MHz): δ 0.94 (t, J=7.3 Hz, 3H), 1.34–1.44 (m, 2H), 1.56–1.63 (m, 2H), 2.13 (s, 3H), 2.36 (s, 3H), 2.63 (t, J=7.8 Hz, 2H), 4.12 (s, 3H), 4.17 (s, 3H), 6.57 (d, J=10.7 Hz, 1H), 7.04–7.26 (m, 6H), 7.67 (s, 1H), 7.84 (brs, 1H), 8.17 (d, J=4.4 Hz, 1H), 8.46 (brs, 1H) Mass spectrometry value (ESI-MS, m/z): 502 (M$^+$+1)

Example 274

4-(Tert-butyl)phenyl N-{4-[(6,7-dimethoxy-4-quinolyl)oxy]-2,5-dimethylphenyl}carbamate 4-[(6,7-dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-(tert-butyl)phenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (35 mg, yield 44%).

$^1$H-NMR (CDCl$_3$-d$_1$, 400 MHz): δ 1.54 (s, 9H), 2.13 (s, 3H), 2.37 (s, 3H), 4.11 (s, 3H), 4.17 (s, 3H), 6.59 (s, 1H), 6.77 (d, J=8.8 Hz, 1H), 6.95 (s, 1H), 7.00 (s, 1H), 7.14 (d, J=8.8 Hz, 2H), 7.43 (d, J=8.8 Hz, 2H), 7.65 (s, 1H), 7.99 (brs, 1H), 8.16 (s, 1H), 8.46 (brs, 1H) Mass spectrometry value (ESI-MS, m/z): 502 (M$^+$+1)

Example 275

4-(Tert-butyl)phenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-(tert-butyl)phenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (34 mg, yield 42%).

$^1$H-NMR (CDCl$_3$-d$_1$, 400 MHz): δ 1.54 (s, 9H), 2.13 (s, 3H), 2.36 (s, 3H), 4.12 (s, 3H), 4.17 (s, 3H), 6.57 (d, J=5.6 Hz, 1H), 6.77 (d, J=8.8 Hz, 1H), 7.05 (d, J=9.3 Hz, 1H), 7.14 (d, J=8.8 Hz, 2H), 7.42 (d, J=8.8 Hz, 2H), 7.67 (s, 1H), 7.84 (brs, 1H), 8.17 (d, J=3.9 Hz, 1H), 8.45 (brs, 1H) Mass spectrometry value (ESI-MS, m/z): 502 (M$^+$+1)

Example 276

1-Ethylbutyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-hexanol (24 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (20 mg, yield 27%).

$^1$H-NMR (CDCl$_3$-d$_1$, 400 MHz): δ 0.95–0.99 (m, 6H), 1.40–1.65 (m, 6H), 2.13 (s, 3H), 2.29 (s, 3H), 4.11 (s, 3H), 4.17 (s, 3H), 4.85 (brs, 1H), 6.41 (s, 1H), 6.57 (d, J=4.6 Hz, 1H), 6.94 (s, 1H), 7.65 (s, 1H), 7.96 (s, 1H), 8.15 (s, 1H), 8.45 (brs, 1H) Mass spectrometry value (ESI-MS, m/z): 454 (M$^+$+1)

Example 277

1-Ethylbutyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-hexanol (24 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (39 mg, yield 53%).

$^1$H-NMR (CDCl$_3$-d$_1$, 400 MHz): δ 0.94–0.99 (m, 6H), 1.40–1.68 (m, 6H), 2.10 (s, 3H), 2.28 (s, 3H), 4.12 (s, 3H), 4.17 (s, 3H), 4.85 (brs, 1H), 6.55 (d, J=5.9 Hz, 1H), 7.00–7.03 (m, 1H), 7.79 (s, 1H), 8.16–8.17 (m, 1H), 8.44 (brs, 1H) Mass spectrometry value (ESI-MS, m/z): 454 (M$^+$+1)

Example 278

2-Methoxyphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-methoxyphenol (29 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (39 mg, yield 51%).

$^1$H-NMR (CDCl$_3$-d$_1$, 400 MHz): δ 2.12 (s, 3H), 2.38 (s, 3H), 3.90 (s, 3H), 4.11 (s, 3H), 4.17 (s, 3H), 6.60 (d, J=5.9 Hz, 1H), 6.86–7.04 (m, 4H), 7.17–7.19 (m, 1H), 7.65 (s, 1H), 7.99 (s, 1H), 8.16 (d, J=4.1 Hz, 1H), 8.47 (brs, 1H) Mass spectrometry value (ESI-MS, m/z): 476 (M$^+$+1)

Example 279

2-Methoxyphenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-methoxyphenol (29 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (31 mg, yield 41%).

$^1$H-NMR (CDCl$_3$-d$_1$, 400 MHz): δ 2.13 (s, 3H), 2.37 (s, 3H), 3.89 (s, 3H), 4.12 (s, 3H), 4.17 (s, 3H), 6.57 (brs, 1H), 6.86–7.06 (m, 5H), 7.18 (d, J=6.3 Hz, 1H), 7.67 (d, J=2.0 Hz, 1H), 8.17 (d, J=3.9 Hz, 1H), 8.46 (brs, 1H) Mass spectrometry value (ESI-MS, m/z): 476 (M$^+$+1)

Example 280

2,6-Dimethoxyphenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2,6-dimethoxyphenol (40 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (80 mg, yield 92%).

$^1$H-NMR (CDCl$_3$-d$_1$, 400 MHz): δ 3.87 (s, 3H), 4.11 (s, 3H), 4.17 (s, 3H), 6.60–6.67 (m, 4H), 7.17–7.21 (m, 2H), 7.64 (s, 1H), 7.70 (d, J=8.8 Hz, 2H), 8.15 (s, 1H), 8.49 (s, 1H) Mass spectrometry value (ESI-MS, m/z): 478 (M$^+$+1)

Example 281

2,6-Dimethoxyphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2,6-dimethoxyphenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (75 mg, yield 93%).

$^1$H-NMR (CDCl$_3$-d$_1$, 400 MHz): δ 2.33 (s, 3H), 2.38 (s, 3H), 3.89 (s, 6H), 4.11 (s, 3H), 4.17 (s, 3H), 6.60 (brs, 1H), 6.67 (d, J=8.5 Hz, 1H), 6.98–7.19 (m, 2H), 7.65 (s, 1H), 8.04 (s, 1H), 8.15 (s, 1H), 8.48 (s, 1H) Mass spectrometry value (ESI-MS, m/z): 506 (M$^+$+1)

Example 282

2,6-Dimethoxyphenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2,6-dimethoxyphenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (74 mg, yield 91%).

$^1$H-NMR (CDCl$_3$-d$_1$, 400 MHz): δ 2.21 (s, 3H), 2.37 (s, 3H), 3.88 (s, 3H), 3.89 (s, 3H), 4.12 (s, 3H), 4.17 (s, 3H), 6.58–6.60 (m, 2H), 6.66 (d, J=8.5 Hz, 1H), 6.78–6.82 (m, 1H), 7.02–7.05 (m, 1H), 7.16–7.20 (m, 1H), 7.67 (s, 1H), 7.87 (s, 1H), 8.16 (s, 1H), 8.47 (brs, 1H) Mass spectrometry value (ESI-MS, m/z): 506 (M$^+$+1)

Example 283

Cyclohexylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclohexylmethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (49 mg, yield 61%).

$^1$H-NMR (CDCl$_3$-d$_1$, 400 MHz): δ 1.03–1.04 (m, 2H), 1.21–1.27 (m, 4H), 1.78–1.80 (m, 5H), 4.02 (d, J=6.3 Hz, 2H), 4.11 (s, 3H), 4.17 (s, 3H), 6.70 (d, J=5.9 Hz, 1H), 6.88 (s, 1H), 7.18 (d, J=8.8 Hz, 2H), 7.61 (d, J=8.5 Hz, 2H), 7.64 (s, 1H), 8.15 (d, J=4.1 Hz, 1H), 8.47 (s, 1H) Mass spectrometry value (ESI-MS, m/z): 438 (M$^+$+1)

Example 284

Cyclohexylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclohexylmethanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 83%).

$^1$H-NMR (CDCl$_3$-d$_1$, 400 MHz): δ 1.02–1.04 (m, 2H), 1.21–1.31 (m, 4H), 1.72–1.79 (m, 5H), 2.13 (s, 3H), 2.29 (s, 3H), 4.03 (d, J=6.3 Hz, 2H), 4.11 (s, 3H), 4.17 (s, 3H), 6.42 (s, 1H), 6.58 (d, J=4.9 Hz, 1H), 6.95 (s, 1H), 7.65 (s, 1H), 7.93 (s, 1H), 8.16 (d, J=4.1 Hz, 1H), 8.46 (brs, 1H) Mass spectrometry value (ESI-MS, m/z): 466 (M$^+$+1)

Example 285

Cyclohexylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclohexylmethanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 64%).

$^1$H-NMR (CDCl$_3$-d$_1$, 400 MHz): δ 0.97–1.07 (m, 2H), 1.17–1.32 (m, 4H), 1.69–1.82 (m, 5H), 2.10 (s, 3H), 2.28 (s, 3H), 4.02 (d, J=6.6 Hz, 2H), 4.11 (s, 3H), 4.17 (s, 3H), 6.44 (s, 1H), 6.55 (d, J=5.4 Hz, 1H), 7.00–7.04 (m, 2H), 7.67 (s, 1H), 7.77 (brs, 1H), 8.16 (d, J=4.1 Hz, 1H), 8.44 (brs, 1H) Mass spectrometry value (ESI-MS, m/z): 466 (M$^+$+1)

Example 286

Cycloheptyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-cycloheptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (68 mg, yield 85%).

$^1$H-NMR (CDCl$_3$-d$_1$, 400 MHz): δ 1.47–1.79 (m, 12H), 4.10 (s, 3H), 4.17 (s, 3H), 4.90–4.96 (m, 1H), 6.70 (d, J=5.9 Hz, 1H), 6.83 (s, 1H), 7.17 (d, J=9.0 Hz, 2H), 7.60 (d, J=8.5 Hz, 2H), 7.64 (s, 1H), 8.15 (s, 1H), 8.47 (brs, 1H) Mass spectrometry value (ESI-MS, m/z): 438 (M$^+$+1)

Example 287

Cycloheptyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cycloheptanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (68 mg, yield 91%).

$^1$H-NMR (CDCl$_3$-d$_1$, 400 MHz): δ 1.51–1.74 (m, 12H), 2.13 (s, 3H), 2.29 (s, 3H), 4.11 (s, 3H), 4.17 (s, 3H), 4.96 (brs, 1H), 6.40 (s, 1H), 6.58 (d, J=6.3 Hz, 1H), 6.94 (s, 1H), 7.65 (s, 1H), 7.95 (s, 1H), 8.16 (d, J=4.1 Hz, 1H), 8.46 (brs, 1H) Mass spectrometry value (ESI-MS, m/z): 466 (M$^+$+1)

Example 288

Cycloheptyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cycloheptanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (66 mg, yield 88%).

$^1$H-NMR (CDCl$_3$-d$_1$, 400 MHz): δ 1.51–1.74 (m, 12H), 2.10 (s, 3H), 2.27 (s, 3H), 4.12 (s, 3H), 4.17 (s, 3H), 4.96 (brs, 1H), 6.43 (s, 1H), 6.56 (d, J=6.6 Hz, 1H), 7.02 (d, J=9.3 Hz, 1H), 7.67 (s, 1H), 7.78 (s, 1H), 8.16 (d, J=3.9 Hz, 1H), 8.45 (brs, 1H) Mass spectrometry value (ESI-MS, m/z): 466 (M$^+$+1)

Example 289

2-Methylphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, o-cresol (25 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 84%).

$^1$H-NMR (CDCl$_3$-d$_1$, 400 MHz): δ 2.13 (s, 3H), 2.31 (s, 3H), 2.39 (s, 3H), 4.11 (s, 3H), 4.17 (s, 3H), 6.60 (d, J=6.3 Hz, 1H), 6.85 (s, 1H), 7.00 (s, 1H), 7.14–7.27 (m, 4H), 7.65 (s, 1H), 7.98 (brs, 1H), 8.15 (d, J=3.7 Hz, 1H), 8.52 (brs, 1H) Mass spectrometry value (ESI-MS, m/z): 460 (M$^+$+1)

Example 290

3-Methoxyphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-methoxyphenol (29 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (30 mg, yield 39%).

$^1$H-NMR (CDCl$_3$-d$_1$, 400 MHz): δ 2.14 (s, 3H), 2.37 (s, 3H), 3.83 (s, 3H), 4.11 (s, 3H), 4.17 (s, 3H), 6.42 (s, 1H), 6.59 (brs, 1H), 6.79–6.84 (m, 3H), 7.00 (s, 1H), 7.30–7.34 (m, 1H), 7.65 (s, 1H), 7.98 (brs, 1H), 8.16 (s, 1H), 8.49 (brs, 1H) Mass spectrometry value (ESI-MS, m/z): 476 (M$^+$+1)

Example 291

3-Methoxyphenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-methoxyphenol (29 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (23 mg, yield 30%).

$^1$H-NMR (CDCl$_3$-d$_1$, 400 MHz): δ 2.13 (s, 3H), 2.36 (s, 3H), 3.83 (s, 3H), 4.12 (s, 3H), 4.17 (s, 3H), 6.44–6.48 (m, 1H), 6.56–6.58 (m, 1H), 6.78–6.83 (m, 3H), 7.06 (d, J=8.8 Hz, 1H), 7.29–7.33 (m, 1H), 7.67 (s, 1H), 7.81 (brs, 1H), 8.16 (d, J=3.4 Hz, 1H), 8.50 (brs, 1H) Mass spectrometry value (ESI-MS, m/z): 476 (M$^+$+1)

Example 292

1,2,3,4-Tetrahydro-2-naphthalenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1,2,3,4-tetrahydro-2-naphthalenol (34 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (80 mg, yield 100%).

$^1$H-NMR (CDCl$_3$-d$_1$, 400 MHz): δ 2.08–2.13 (m, 2H), 2.12 (s, 3H), 2.27 (s, 3H), 2.80–3.24 (m, 4H), 4.11 (s, 3H), 4.17 (s, 3H), 5.30 (brs, 1H), 6.43 (s, 1H), 6.57 (d, J=6.6 Hz, 1H), 6.94 (s, 1H), 7.11–7.18 (m, 4H), 7.64 (s, 1H), 7.94 (brs, 1H), 8.15 (d, J=3.9 Hz, 1H), 8.48 (brs, 1H) Mass spectrometry value (ESI-MS, m/z): 500 (M$^+$+1)

Example 293

1,2,3,4-Tetrahydro-2-naphthalenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1,2,3,4-tetrahydro-2-naphthalenol (34 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 69%).

$^1$H-NMR (CDCl$_3$-d$_1$, 400 MHz): δ 2.08–2.13 (m, 2H), 2.09 (s, 3H), 2.25 (s, 3H), 2.92–3.23 (m, 4H), 4.11 (s, 3H), 4.17 (s, 3H), 5.29 (brs, 1H), 6.46 (s, 1H), 6.55 (d, J=6.1 Hz, 1H), 7.01 (d, J=8.8 Hz, 1H), 7.12–7.18 (m, 4H), 7.67 (s, 1H), 7.77 (brs, 1H), 8.16 (d, J=3.7 Hz, 1H), 8.48 (brs, 1H) Mass spectrometry value (ESI-MS, m/z): 500 (M$^+$+1)

Example 294

4-Phenylphenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-phenylphenol (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (29 mg, yield 32%).

$^1$H-NMR (CDCl$_3$-d$_1$, 400 MHz): δ 4.11 (s, 3H), 4.17 (s, 3H), 6.71 (s, 1H), 6.93 (d, J=8.5 Hz, 1H), 7.26–7.78 (m, 13H), 8.14 (brs, 1H), 8.53 (brs, 1H) Mass spectrometry value (ESI-MS, m/z): 494 (M$^+$+1)

Example 295

4-Phenylphenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-phenylphenol (39 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 66%).

$^1$H-NMR (CDCl$_3$-d$_1$, 400 MHz): δ 2.14 (s, 3H), 2.28 (s, 3H), 4.11 (s, 3H), 4.17 (s, 3H), 6.44 (s, 1H), 6.60 (brs, 1H), 6.95 (s, 1H), 7.01 (brs, 1H), 7.26–7.52 (m, 4H), 7.57–7.65 (m, 5H), 7.89 (s, 1H), 8.15 (brs, 1H), 8.48 (brs, 1H) Mass spectrometry value (EST-MS, m/z): 522 (M$^+$+1)

Example 296

4-Phenylphenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-phenylphenol (39 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (36 mg, yield 43%).

$^1$H-NMR (CDCl$_3$-d$_1$, 400 MHz): δ 2.14 (s, 3H), 2.38 (s, 3H), 4.12 (s, 3H), 4.17 (s, 3H), 6.57–6.59 (m, 1H), 6.92–7.08 (m, 2H), 7.25–7.79 (m, 10H), 8.16–8.17 (m, 1H), 8.47–8.52 (m, 1H) Mass spectrometry value (ESI-MS, m/z): 522 (M$^+$+1)

Example 297

Phenethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-phenyl-1-ethanol (32 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 51%).

$^1$H-NMR (CDCl$_3$-d$_1$, 400 MHz): δ 3.03 (t, J=6.8 Hz, 2H), 4.10 (s, 3H), 4.17 (s, 3H), 4.45 (t, J=7.1 Hz, 2H), 6.69 (s, 1H), 6.78 (s, 1H), 7.16–7.36 (m, 7H), 7.52–7.64 (m, 3H), 8.15 (s, 1H), 8.49 (brs, 1H) Mass spectrometry value (ESI-MS, m/z): 446 (M$^+$+1)

Example 298

Phenethyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-phenyl-1-ethanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (76 mg, yield 100%).

$^1$H-NMR (CDCl$_3$-d$_1$, 400 MHz): δ 2.12 (s, 3H), 2.26 (s, 3H), 3.04 (t, J=6.8 Hz, 2H), 4.11 (s, 3H), 4.17 (s, 3H), 4.44 (t, J=7.1 Hz, 2H), 6.40 (s, 1H), 6.59 (s, 1H), 6.95 (s, 1H), 7.26–7.36 (m, 5H), 7.64 (s, 1H), 7.86 (brs, 1H), 8.16 (s, 1H), 8.47 (brs, 1H) Mass spectrometry value (ESI-MS, m/z): 474 (M$^+$+1)

Example 299

Phenethyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-phenyl-1-ethanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (60 mg, yield 79%).

$^1$H-NMR (CDCl$_3$-d$_1$, 400 MHz): δ 2.09 (s, 3H), 2.24 (s, 3H), 3.03 (t, J=6.8 Hz, 2H), 4.11 (s, 3H), 4.17 (s, 3H), 4.44 (t, J=7.1 Hz, 2H), 6.42 (s, 1H), 6.55 (d, J=5.9 Hz, 1H), 7.01 (d, J=8.5 Hz, 1H), 7.26–7.36 (m, 5H), 7.66 (s, 1H), 8.16 (d, J=4.1 Hz, 1H), 8.46 (brs, 1H) Mass spectrometry value (ESI-MS, m/z): 474 (M$^+$+1)

Example 300

2-(Tert-butylphenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-(tert-butyl)phenol (39 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (64 mg, yield 74%).

$^1$H-NMR (CDCl$_3$-d$_1$, 400 MHz): δ 1.42 (s, 9H), 4.11 (s, 3H), 4.17 (s, 3H), 6.72 (brs, 1H), 7.11 (d, J=6.3 Hz, 1H), 7.22–7.26 (m, 6H), 7.43–7.45 (m, 1H), 7.65 (s, 1H), 7.71 (brs, 1H), 8.15 (brs, 1H), 8.51 (brs, 1H) Mass spectrometry value (ESI-MS, m/z): 474 (M$^+$+1)

Example 301

2-(Tert-butyl)phenyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(tert-butyl)phenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 96%).

$^1$H-NMR (CDCl$_3$-d$_1$, 400 MHz): δ 1.56 (s, 9H), 2.13 (s, 3H), 2.39 (s, 3H), 4.12 (s, 3H), 4.17 (s, 3H), 6.59 (brs, 1H), 7.01 (s, 1H), 7.13 (d, J=7.8 Hz, 1H), 7.21–7.26 (m, 3H), 7.43–7.45 (m, 1H), 7.65 (s, 1H), 8.15 (s, 1H), 8.49 (brs, 1H) Mass spectrometry value (ESI-MS, m/z): 502 (M$^+$+1)

Example 302

2-(Tert-butyl)phenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(tert-butyl)phenol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 60%).

$^1$H-NMR (CDCl$_3$-d$_1$, 400 MHz): δ 1.56 (s, 9H), 2.14 (s, 3H), 2.38 (s, 3H), 4.12 (s, 3H), 4.18 (s, 3H), 6.55 (brs, 1H), 7.06 (d, J=9.0 Hz, 1H), 7.14 (d, J=7.8 Hz, 1H), 7.21–7.26 (m, 4H), 7.42 (brs, 1H), 7.67 (s, 1H), 8.16 (s, 1H), 8.48 (brs, 1H) Mass spectrometry value (ESI-MS, m/z): 502 (M$^+$+1)

Example 303

2-Piperidinoethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-piperidino-1-ethanol (34 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (66 mg, yield 74%).

$^1$H-NMR (CDCl$_3$-d$_1$, 400 MHz): δ 1.89–1.93 (m, 4H), 2.29–2.45 (m, 2H), 2.74–2.86 (m, 2H), 3.36 (brs, 1H), 3.70–3.73 (m, 2H), 4.10 (s, 3H), 4.16 (s, 3H), 4.56–4.58 (m, 2H), 6.72 (d, J=6.3 Hz, 1H), 7.15 (d, J=8.8 Hz, 2H), 7.65 (s, 1H), 7.74 (d, J=8.8 Hz, 2H), 8.10 (s, 1H), 8.52 (t, J=6.3 Hz, 1H), 9.60 (brs, 1H), 11.42 (brs, 1H) Mass spectrometry value (ESI-MS, m/z): 453 (M$^+$+1)

Example 304

2-Piperidinoethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-piperidino-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (42 mg, yield 51%).

$^1$H-NMR (CDCl$_3$-d$_1$, 400 MHz): δ 1.50 (brs, 2H), 1.85 (brs, 2H), 2.11 (s, 3H), 2.43 (brs, 5H), 2.78 (brs, 2H), 3.34 (brs, 2H), 3.70 (brs, 2H), 4.11 (s, 3H), 4.17 (s, 3H), 4.56 (brs, 2H), 6.61 (brs, 1H), 6.95 (s, 1H), 7.66 (s, 1H), 7.86 (s, 1H), 8.13 (s, 1H), 8.48 (brs, 1H), 11.85 (brs, 1H) Mass spectrometry value (ESI-MS, m/z): 481 (M$^+$+1)

Example 305

2-Piperidinoethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-piperidino-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (83 mg, yield 100%).

$^1$H-NMR (CDCl$_3$-d$_1$, 400 MHz): δ 1.88 (brs, 2H), 2.09 (s, 3H), 2.31–2.39 (m, 1H), 2.39 (s, 3H), 2.47–2.51 (m, 1H), 2.71–2.80 (m, 2H), 3.12–3.14 (m, 1H), 3.33 (brs, 2H), 3.69 (brs, 2H), 4.01–4.03 (m, 1H), 4.12 (s, 3H), 4.17 (s, 3H), 4.54–4.55 (m, 2H), 6.58 (d, J=6.3 Hz, 1H), 6.98 (d, J=8.8 Hz, 1H), 7.68 (s, 1H), 7.76 (d, J=9.0 Hz, 1H), 8.14 (s, 1H), 8.48–8.49 (m, 1H), 11.83 (brs, 1H) Mass spectrometry value (ESI-MS, m/z): 481 (M$^+$+1)

Example 306

2-Morpholinoethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-morpholino-1-ethanol (34 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (43 mg, yield 48%).

$^1$H-NMR (CDCl$_3$-d$_1$, 400 MHz): δ 3.11 (brs, 2H), 3.42 (brs, 2H), 3.66 (brs, 2H), 4.01–4.19 (m, 2H), 4.10 (s, 3H), 4.16 (s, 3H), 4.46 (brs, 2H), 4.62 (brs, 2H), 6.73 (s, 1H), 7.14 (s, 1H), 7.65 (s, 1H), 7.73 (s, 2H), 8.09 (s, 1H), 8.54 (brs, 1H), 9.45 (s, 1H), 12.38 (brs, 1H) Mass spectrometry value (ESI-MS, m/z): 455 (M$^+$+1)

Example 307

2-Morpholinoethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-morpholino-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (63 mg, yield 76%).

$^1$H-NMR (CDCl$_3$-d$_1$, 400 MHz): δ 2.11 (s, 3H), 2.42 (s, 3H), 3.06 (brs, 2H), 3.41 (brs, 2H), 3.62 (brs, 2H), 4.02–4.17 (m, 2H), 4.11 (s, 3H), 4.17 (s, 3H), 4.52–4.59 (m, 4H), 6.60 (brs, 1H), 6.95 (s, 1H), 7.66 (s, 1H), 7.85 (s, 1H), 8.13 (s, 2H), 8.30 (brs, 1H), 8.50 (brs, 1H), 12.79 (brs, 1H) Mass spectrometry value (ESI-MS, m/z): 483 (M$^+$+1)

Example 308

2-Morpholinoethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-morpholino-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (74 mg, yield 89%).

$^1$H-NMR (CDCl$_3$-d$_1$, 400 MHz): δ 2.09 (s, 3H), 2.39 (s, 3H), 3.03 (brs, 2H), 3.38 (brs, 2H), 3.62 (d, J=11.7 Hz, 2H), 4.02–4.04 (m, 2H), 4.12 (s, 3H), 4.17 (s, 3H), 4.50–4.59 (m, 4H), 6.57 (d, J=6.3 Hz, 1H), 6.99 (d, J=8.8 Hz, 1H), 7.67 (s, 1H), 7.77 (d, J=9.3 Hz, 1H), 8.14 (s, 1H), 8.32 (brs, 1H), 8.48 (s, 1H), 12.87 (brs, 1H) Mass spectrometry value (ESI-MS, m/z): 483 (M$^+$+1)

Example 309

6-(Dimethylamino)hexyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 6-(dimethylamino)-1-hexanol (38 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (31 mg, yield 34%).

$^1$H-NMR (CDCl$_3$-d$_1$, 400 MHz): δ 1.43–1.87 (m, 8H), 2.82–3.08 (m, 8H), 4.11 (s, 3H), 4.16 (s, 3H), 4.11–4.22 (m, 2H), 6.72 (s, 1H), 7.14 (s, 2H), 7.65 (s, 1H), 7.87 (s, 2H), 8.11 (s, 1H), 8.50 (brs, 1H), 8.80 (brs, 1H), 12.00 (brs, 1H) Mass spectrometry value (ESI-MS, m/z): 469 (M$^+$+1)

Example 310

6-(Dimethylamino)hexyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 6-(dimethylamino)-1-hexanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (48 mg, yield 56%).

$^1$H-NMR (CDCl$_3$-d$_1$, 400 MHz): δ 1.53–1.93 (m, 8H), 2.13 (s, 3H), 2.33 (s, 3H), 2.83 (s, 6H), 3.02 (brs, 2H), 4.11 (s, 3H), 4.17 (s, 3H), 4.11–4.21 (m, 2H), 6.61 (brs, 1H), 6.95 (s, 1H), 7.65 (s, 1H), 7.85 (s, 1H), 8.14 (s, 1H), 8.49 (brs, 1H), 12.39 (brs, 1H) Mass spectrometry value (ESI-MS, m/z): 497 (M$^+$+1)

Example 311

6-(Dimethylamino)hexyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 6-(dimethylamino)-1-hexanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (66 mg, yield 77%).

$^1$H-NMR (CDCl$_3$-d$_1$, 400 MHz): δ 1.75–2.01 (m, 8H), 2.10 (s, 3H), 2.31 (s, 3H), 2.83 (s, 6H), 3.03 (s, 2H), 4.12 (s, 3H), 4.17 (s, 3H), 4.12–4.21 (m, 2H), 6.59 (s, 1H), 7.01 (d, J=8.1 Hz, 1H), 7.68 (s, 1H), 8.13 (s, 1H), 8.50 (brs, 1H), 12.02 (brs, 1H), 12.30 (brs, 1H) Mass spectrometry value (ESI-MS, m/z): 497 (M$^+$+1)

Example 312

Cyclohexyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-cyclohexanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (60 mg, yield 71%).

$^1$H-NMR (CDCl$_3$-d$_1$, 400 MHz): δ 1.21–1.57 (m, 6H), 1.76 (brs, 2H), 1.94 (brs, 2H), 4.12 (s, 3H), 4.19 (s, 3H), 4.78 (brs, 1H), 6.72 (s, 1H), 7.19 (d, J=9.0 Hz, 2H), 7.57 (d, J=8.8 Hz, 2H), 7.62 (s, 1H), 8.15 (s, 1H), 8.80 (s, 1H) Mass spectrometry value (ESI-MS, m/z): 425 (M$^+$+1)

Example 313

Cyclohexyl N-12-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclohexanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (61 mg, yield 77%).

$^1$H-NMR (CDCl$_3$-d$_1$, 400 MHz): δ 1.30–1.58 (m, 6H), 1.78 (brs, 2H), 1.95 (brs, 2H), 4.12 (s, 3H), 4.20 (s, 3H), 4.79 (brs, 1H), 7.16–7.20 (m, 2H), 7.32 (s, 1H), 7.59 (s, 1H), 8.17 (s, 1H), 8.40 (d, J=9.3 Hz, 1H), 8.82 (s, 1H) Mass spectrometry value (ESI-MS, m/z): 459 (M$^+$+1)

Example 314

Propyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-propanol (16 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 100%).

$^1$H-NMR (CDCl$_3$-d$_1$, 400 MHz): δ 1.00 (t, J=7.3 Hz, 3H), 1.68–1.75 (m, 2H), 4.12 (s, 3H), 4.16 (t, J=6.8 Hz, 2H), 4.19 (s, 3H), 6.77 (s, 1H), 7.20 (d, J=9.0 Hz, 2H), 7.58 (d, J=8.8 Hz, 2H), 7.62 (s, 1H), 8.15 (s, 1H), 8.81 (s, 1H) Mass spectrometry value (ESI-MS, m/z): 384 (M$^+$+1)

Example 315

2-Methoxybenzyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, (2-methoxyphenyl)methanol (36 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (91 mg, yield 100%).

$^1$H-NMR (CDCl$_3$-d$_1$, 400 MHz): δ 3.88 (s, 3H), 4.12 (s, 3H), 4.19 (s, 3H), 5.29 (s, 2H), 6.84 (s, 1H), 6.92–7.00 (m, 2H), 7.19 (d, J=9.0 Hz, 2H), 7.33–7.40 (m, 2H), 7.57 (d, J=9.0 Hz, 2H), 7.62 (s, 1H), 8.15 (s, 1H), 8.80 (s, 1H) Mass spectrometry value (ESI-MS, m/z): 463 (M$^+$+1)

Example 316

2-Methoxybenzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, (2-methoxyphenyl)methanol (32 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (79 mg, yield 93%).

$^1$H-NMR (CDCl$_3$-d$_1$, 400 MHz): δ 3.89 (s, 3H), 4.12 (s, 3H), 4.20 (s, 3H), 5.32 (s, 2H), 6.89 (s, 2H), 6.89–7.01 (m, 3H), 7.18–7.21 (m, 1H), 7.29–7.43 (m, 3H), 7.59 (s, 1H), 8.16 (s, 1H), 8.43 (d, J=9.0 Hz, 1H), 8.83 (s, 1H), 9.57 (brs, 1H) Mass spectrometry value (ESI-MS, m/z): 497 (M$^+$+1)

Example 317

2-Chlorobenzyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, (2-chlorophenyl)methanol (37 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (92 mg, yield 100%).

$^1$H-NMR (CDCl$_3$-d$_1$, 400 MHz): δ 4.12 (s, 3H), 4.19 (s, 3H), 5.35 (s, 2H), 7.20 (d, J=9.0 Hz, 2H), 7.29–7.32 (m, 2H), 7.42–7.44 (m, 1H), 7.48–7.52 (m, 1H), 7.59 (d, J=8.8 Hz, 2H), 7.62 (s, 1H), 8.15 (s, 1H), 8.79 (s, 1H) Mass spectrometry value (ESI-MS, m/z): 467 (M$^+$+1)

Example 318

2-Chlorobenzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, (2-chlorophenyl)methanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (80 mg, yield 93%).

$^1$H-NMR (CDCl$_3$-d$_1$, 400 MHz): δ 4.12 (s, 3H), 4.20 (s, 3H), 5.38 (s, 2H), 7.19–7.22 (m, 1H), 7.30–7.35 (m, 3H), 7.43–7.45 (m, 1H), 7.49–7.51 (m, 1H), 7.59 (s, 1H), 8.16 (s, 1H), 8.41 (d, J=9.0 Hz, 1H), 8.82 (s, 1H) Mass spectrometry value (ESI-MS, m/z): 501 (M$^+$+1)

Example 319

2-Methylbenzyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, (2-methylphenyl)methanol (32 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (79 mg, yield 90%).

$^1$H-NMR (CDCl$_3$-d$_1$, 400 MHz): δ 2.41 (s, 3H), 4.12 (s, 3H), 4.19 (s, 3H), 5.26 (s, 2H), 6.87 (s, 1H), 7.20 (d, J=9.0 Hz, 2H), 7.22–7.30 (m, 3H), 7.37–7.39 (m, 1H), 7.58 (d, J=8.8 Hz, 2H), 7.61 (s, 1H), 8.15 (s, 1H), 8.79 (s, 1H) Mass spectrometry value (ESI-MS, m/z): 447 (M$^+$+1)

Example 320

2-Methylbenzyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, (2-methylphenyl)methanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 75%).

$^1$H-NMR (CDCl$_3$-d$_1$, 400 MHz): δ 2.43 (s, 3H), 4.12 (s, 3H), 4.20 (s, 3H), 5.28 (s, 2H), 7.18–7.33 (m, 5H), 7.40 (d, J=6.8 Hz, 1H), 7.59 (s, 1H), 8.16 (s, 1H), 8.41 (d, J=9.0 Hz, 1H), 8.82 (s, 1H) Mass spectrometry value (ESI-MS, m/z): 481 (M$^+$+1)

Example 321

Butyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-butanol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (34 mg, yield 46%).

$^1$H-NMR (CDCl$_3$-d$_1$, 400 MHz): δ 0.97 (t, J=7.3 Hz, 3H), 1.41–1.49 (m, 2H), 1.62–1.72 (m, 2H), 4.10 (s, 3H), 4.17 (s, 3H), 4.21 (t, J=6.8 Hz, 2H), 6.70 (d, J=6.3 Hz, 1H), 6.85 (s, 1H), 7.18 (d, J=8.8 Hz, 2H), 7.61 (d, J=8.8 Hz, 2H), 7.64 (s, 1H), 8.15 (s, 1H), 8.47 (brs, 1H) Mass spectrometry value (ESI-MS, m/z): 397 (M$^+$+1)

Example 322

Butyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-butanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (65 mg, yield 94%).

$^1$H-NMR (CDCl$_3$-d$_1$, 400 MHz): δ 0.99 (t, J=7.3 Hz, 3H), 1.41–1.50 (m, 2H), 1.67–1.74 (m, 2H), 2.13 (s, 3H), 2.29 (s, 3H), 4.11 (s, 3H), 4.17 (s, 3H), 4.22 (t, J=6.8 Hz, 2H), 6.42 (s, 1H), 6.59 (brs, 1H), 6.95 (s, 1H), 7.65 (s, 1H), 7.92 (s, 1H), 8.16 (s, 1H), 8.46 (brs, 1H) Mass spectrometry value (ESI-MS, m/z): 426 (M$^+$+1)

Example 323

Butyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-butanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (60 mg, yield 87%).

$^1$H-NMR (CDCl$_3$-d$_1$, 400 MHz): δ 0.98 (t, J=7.3 Hz, 3H), 1.40–1.49 (m, 2H), 1.67–1.73 (m, 2H), 2.10 (s, 3H), 2.28 (s, 3H), 4.12 (s, 3H), 4.17 (s, 3H), 4.21 (t, J=6.8 Hz, 2H), 6.46 (s, 1H), 6.56 (d, J=6.3 Hz, 1H), 7.02 (d, J=8.8 Hz, 1H), 7.67 (s, 1H), 7.76 (d, J=8.5 Hz, 1H), 8.15 (s, 1H), 8.47 (t, J=6.3 Hz, 1H) Mass spectrometry value (ESI-MS, m/z): 426 (M$^+$+1)

Example 324

Isopropyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-propanol (16 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 59%).

$^1$H-NMR (CDCl$_3$-d$_1$, 400 MHz): δ 1.33 (d, J=6.3 Hz, 6H), 4.11 (s, 3H), 4.17 (s, 3H), 5.02–5.09 (m, 1H), 6.70 (d, J=6.1 Hz, 1H), 6.74 (s, 1H), 7.18 (d, J=9.0 Hz, 1H), 7.60 (d, J=8.8 Hz, 2H), 7.64 (s, 1H), 8.15 (s, 1H), 8.47 (brs, 1H) Mass spectrometry value (ESI-MS, m/z): 383 (M$^+$+1)

Example 325

Isopropyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-propanol (14 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (50 mg, yield 75%).

$^1$H-NMR (CDCl$_3$-d$_1$, 400 MHz): δ 1.34 (d, J=6.3 Hz, 6H), 2.13 (s, 3H), 2.29 (s, 3H), 4.11 (s, 3H), 4.17 (s, 3H), 5.04–5.07 (m, 1H), 6.38 (s, 1H), 6.58 (brs, 1H), 6.95 (s, 1H), 7.65 (s, 1H), 7.95 (s, 1H), 8.15 (s, 1H), 8.46 (brs, 1H) Mass spectrometry value (ESI-MS, m/z): 412 (M$^+$+1)

Example 326

Octadecyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-octadecanol (70 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (54 mg, yield 51%).

$^1$H-NMR (CDCl$_3$-d$_1$, 400 MHz): δ 0.88 (t, J=7.1 Hz, 3H), 1.20–1.45 (m, 30H), 1.68–1.72 (m, 2H), 4.10 (s, 3H), 4.17 (s, 3H), 4.20 (t, J=6.6 Hz, 2H), 6.69 (d, J=6.3 Hz, 1H), 6.77 (s, 1H), 7.18 (d, J=8.8 Hz, 2H), 7.60 (d, J=8.8 Hz, 2H), 7.64 (s, 1H), 8.15 (s, 1H), 8.47 (brs, 1H) Mass spectrometry value (ESI-MS, m/z): 594 (M$^+$+1)

Example 327

Octadecyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-octadecanol (62 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (83 mg, yield 84%).

$^1$H-NMR (CDCl$_3$-d$_1$, 400 MHz): δ 0.88 (t, J=7.1 Hz, 3H), 1.26–1.42 (m, 30H), 1.67–1.73 (m, 2H), 2.13 (s, 3H), 2.29 (s, 3H), 4.11 (s, 3H), 4.17 (s, 3H), 4.20 (t, J=6.6 Hz, 2H), 6.42 (s, 1H), 6.59 (brs, 1H), 6.95 (s, 1H), 7.65 (s, 1H), 7.92 (s, 1H), 8.15 (s, 1H), 8.47 (brs, 1H) Mass spectrometry value (ESI-MS, m/z): 622 (M$^+$+1)

Example 328

Octadecyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-octadecanol (62 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (96 mg, yield 97%).

$^1$H-NMR (CDCl$_3$-d$_1$, 400 MHz): δ 0.88 (t, J=6.8 Hz, 3H), 1.21–1.42 (m, 30H), 1.67–1.72 (m, 2H), 2.10 (s, 3H), 2.27 (s, 3H), 4.11 (s, 3H), 4.17 (s, 3H), 4.20 (t, J=6.8 Hz, 2H), 6.44 (s, 1H), 6.56 (d, J=6.6 Hz, 1H), 7.02 (d, J=8.5 Hz, 1H), 7.67 (s, 1H), 7.75 (brs, 1H), 8.15 (s, 1H), 8.47 (brs, 1H) Mass spectrometry value (ESI-MS, m/z): 622 (M$^+$+1)

Example 329

1-Ethylpentyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-heptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (46 mg, yield 57%).

$^1$H-NMR (CDCl$_3$-d$_1$, 400 MHz): δ 0.90–0.98 (m, 6H), 1.35–1.36 (m, 4H), 1.62–1.69 (m, 4H), 4.11 (s, 3H), 4.17 (s, 3H), 4.80–4.86 (m, 1H), 6.69 (d, J=6.3 Hz, 1H), 6.79 (s, 1H), 7.18 (d, J=8.8 Hz, 2H), 7.62 (d, J=9.0 Hz, 2H), 7.64 (s, 1H), 8.15 (s, 1H), 8.47 (t, J=6.6 Hz, 1H) Mass spectrometry value (ESI-MS, m/z): 440 (M$^+$+1)

Example 330

1-Ethylpentyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (59 mg, yield 78%).

$^1$H-NMR (CDCl$_3$-d$_1$, 400 MHz): δ 0.93–0.99 (m, 6H), 1.30–1.45 (m, 4H), 1.57–1.68 (m, 4H), 2.13 (s, 3H), 2.30 (s, 3H), 4.11 (s, 3H), 4.17 (s, 3H), 4.82–4.85 (m, 1H), 6.42 (s, 1H), 6.58 (d, J=6.3 Hz, 1H), 6.95 (s, 1H), 7.65 (s, 1H), 7.96 (s, 1H), 8.15 (s, 1H), 8.46 (brs, 1H) Mass spectrometry value (ESI-MS, m/z): 468 (M$^+$+1)

Example 331

1-Ethylpentyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (46 mg, yield 61%).

$^1$H-NMR (CDCl$_3$-d$_1$, 400 MHz): δ 0.91–0.99 (m, 6H), 1.30–1.45 (m, 4H), 1.59–1.68 (m, 4H), 2.10 (s, 3H), 2.28 (s, 3H), 4.12 (s, 3H), 4.17 (s, 3H), 4.82–4.84 (m, 1H), 6.43 (s, 1H), 6.55 (d, J=6.6 Hz, 1H), 7.02 (d, J=8.8 Hz, 1H), 7.67 (s, 1H), 7.78 (brs, 1H), 8.15 (s, 1H), 8.47 (t, J=6.6 Hz, 1H) Mass spectrometry value (ESI-MS, m/z): 468 (M$^+$+1)

Example 332

1-Propylbutyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-heptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 60%).

$^1$H-NMR (CDCl$_3$-d$_1$, 400 MHz): δ 0.95 (t, J=7.3 Hz, 6H), 1.37–1.45 (m, 4H), 1.53–1.63 (m, 4H), 4.11 (s, 3H), 4.17 (s, 3H), 4.89–4.94 (m, 1H), 6.69 (d, J=6.6 Hz, 1H), 6.76 (s, 1H), 7.18 (d, J=8.8 Hz, 2H), 7.61 (d, J=8.8 Hz, 2H), 7.64 (s, 1H), 8.15 (s, 1H), 8.47 (t, J=6.1 Hz, 1H) Mass spectrometry value (ESI-MS, m/z): 440 (M$^+$+1)

Example 333

1-Propylbutyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (57 mg, yield 76%).

$^1$H-NMR (CDCl$_3$-d$_1$, 400 MHz): δ 0.96 (t, J=7.3 Hz, 6H), 1.38–1.46 (m, 4H), 1.54–1.64 (m, 4H), 2.13 (s, 3H), 2.29 (s, 3H), 4.11 (s, 3H), 4.17 (s, 3H), 4.91–4.94 (m, 1H), 6.41 (s, 1H), 6.57 (d, J=6.3 Hz, 1H), 6.95 (s, 1H), 7.65 (s, 1H), 7.96 (s, 1H), 8.15 (s, 1H), 8.46 (t, J=6.3 Hz, 1H) Mass spectrometry value (ESI-MS, m/z): 468 (M$^+$+1)

Example 334

1-Propylbutyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 4-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (44 mg, yield 58%).

$^1$H-NMR (CDCl$_3$-d$_1$, 400 MHz): δ 0.96 (t, J=7.1 Hz, 6H), 1.37–1.45 (m, 4H), 1.57–1.64 (m, 4H), 2.10 (s, 3H), 2.27 (s, 3H), 4.12 (s, 3H), 4.17 (s, 3H), 4.90–4.93 (m, 1H), 6.42 (s, 1H), 6.55 (d, J=6.3 Hz, 1H), 7.02 (d, J=8.8 Hz, 1H), 7.67 (s, 1H), 7.78 (brs, 1H), 8.15 (s, 1H), 8.45 (t, J=6.3 Hz, 1H) Mass spectrometry value (ESI-MS, m/z): 468 (M$^+$+1)

Example 335

Hexyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-hexanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (69 mg, yield 82%).

$^1$H-NMR (CDCl$_3$-d$_1$, 400 MHz): δ 0.91 (t, J=7.1 Hz, 3H), 1.31–1.49 (m, 6H), 1.66–1.73 (m, 2H), 4.12 (s, 3H), 4.19 (s, 3H), 4.19 (t, J=7.1 Hz, 2H), 6.79 (s, 1H), 7.20 (d, J=8.8 Hz, 2H), 7.58 (d, J=8.8 Hz, 2H), 7.62 (s, 1H), 8.15 (s, 1H), 8.79 (s, 1H) Mass spectrometry value (ESI-MS, m/z): 427 (M$^+$+1)

Example 336

Hexyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-hexanol (24 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (54 mg, yield 68%).

$^1$H-NMR (CDCl$_3$-d$_1$, 400 MHz): δ 0.92 (t, J=7.1 Hz, 3H), 1.32–1.49 (m, 6H), 1.68–1.75 (m, 2H), 4.12 (s, 3H), 4.20 (s, 3H), 4.22 (t, J=6.8 Hz, 2H), 7.18 (d, J=2.4 Hz, 1H), 7.21 (d, J=2.7 Hz, 1H), 7.33 (d, J=2.7 Hz, 1H), 7.59 (s, 1H), 8.16 (s, 1H), 8.39 (d, J=9.0 Hz, 1H), 8.82 (s, 1H) Mass spectrometry value (ESI-MS, m/z): 461 (M$^+$+1)

Example 337

1-Ethylbutyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-hexanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 73%).

$^1$H-NMR (CDCl$_3$-d$_1$, 400 MHz): δ 0.93–0.97 (m, 6H), 1.36–1.68 (m, 6H), 4.13 (s, 3H), 4.19 (s, 3H), 4.82–4.87 (m, 1H), 6.75 (s, 1H), 7.20 (d, J=9.0 Hz, 2H), 7.59 (d, J=8.8 Hz, 2H), 7.62 (s, 1H), 8.15 (s, 1H), 8.80 (s, 1H) Mass spectrometry value (ESI-MS, m/z): 427 (M$^+$+1)

Example 338

1-Ethylbutyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-hexanol (24 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 69%).

$^1$H-NMR (CDCl$_3$-d$_1$, 400 MHz): δ 0.94–0.99 (m, 6H), 1.37–1.70 (m, 6H), 4.12 (s, 3H), 4.20 (s, 3H), 4.83–4.87 (m, 1H), 7.18 (d, J=2.7 Hz, 1H), 7.20 (d, J=2.7 Hz, 1H), 7.33 (d, J=2.7 Hz, 1H), 7.59 (s, 1H), 8.16 (s, 1H), 8.42 (d, J=9.3 Hz, 1H), 8.82 (s, 1H) Mass spectrometry value (ESI-MS, m/z): 461 (M$^+$+1)

Example 339

Phenethyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-phenyl-1-ethanol (28 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (18 mg, yield 22%).

$^1$H-NMR (CDCl$_3$-d$_1$, 400 MHz): δ 3.03 (t, J=7.1 Hz, 2H), 4.12 (s, 3H), 4.20 (s, 3H), 4.45 (t, J=7.1 Hz, 2H), 7.17 (d, J=2.4 Hz, 1H), 7.20 (d, J=2.7 Hz, 1H), 7.29–7.34 (m, 6H), 7.58 (s, 1H), 8.16 (s, 1H), 8.33 (brs, 1H), 8.82 (s, 1H) Mass spectrometry value (ESI-MS, m/z): 481 (M$^+$+1)

Example 340

Cyclohexylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclohexylmethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (61 mg, yield 70%).

$^1$H-NMR (CDCl$_3$-d$_1$, 400 MHz): δ 1.00–1.06 (m, 2H), 1.17–1.29 (m, 3H), 1.69–1.79 (m, 6H), 4.01 (d, J=6.3 Hz, 2H), 4.12 (s, 3H), 4.19 (s, 3H), 6.80 (s, 1H), 7.19 (d, J=9.0 Hz, 2H), 7.58 (d, J=8.8 Hz, 2H), 7.62 (s, 1H), 8.15 (s, 1H), 8.79 (s, 1H) Mass spectrometry value (ESI-MS, m/z): 439 (M$^+$+1)

Example 341

Cyclohexylmethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclohexylmethanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (54 mg, yield 66%).

$^1$H-NMR (CDCl$_3$-d$_1$, 400 MHz): δ 1.01–1.07 (m, 2H), 1.18–1.31 (m, 3H), 1.70–1.82 (m, 6H), 4.04 (d, J=6.3 Hz, 2H), 4.12 (s, 3H), 4.20 (s, 3H), 7.18 (d, J=2.7 Hz, 1H), 7.21 (d, J=2.7 Hz, 1H), 7.33 (d, J=2.7 Hz, 1H), 7.59 (s, 1H), 8.16 (s, 1H), 8.39 (d, J=9.0 Hz, 1H), 8.82 (s, 1H) Mass spectrometry value (ESI-MS, m/z): 473 (M$^+$+1)

Example 342

Cycloheptyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-cycloheptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 72%).

$^1$H-NMR (CDCl$_3$-d$_1$, 400 MHz): δ 1.49–1.77 (m, 10H), 1.97–2.04 (m, 2H), 4.12 (s, 3H), 4.19 (s, 3H), 4.92–4.99 (m, 1H), 6.74 (s, 1H), 7.19 (d, J=9.0 Hz, 2H), 7.57 (d, J=9.0 Hz, 2H), 7.62 (s, 1H), 8.15 (s, 1H), 8.79 (s, 1H) Mass spectrometry value (ESI-MS, m/z): 439 (M$^+$+1)

Example 343

Cycloheptyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cycloheptanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (60 mg, yield 73%).

$^1$H-NMR (CDCl$_3$-d$_1$, 400 MHz): δ 1.42–1.79 (m, 10H), 1.80–2.04 (m, 2H), 4.12 (s, 3H), 4.20 (s, 3H), 4.95–4.99 (m, 1H), 7.14–7.20 (m, 2H), 7.32 (d, J=2.7 Hz, 1H), 7.59 (s, 1H), 8.16 (s, 1H), 8.40 (d, J=8.8 Hz, 1H), 8.82 (s, 1H) Mass spectrometry value (ESI-MS, m/z): 473 (M$^+$+1)

Example 344

Butyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-butanol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (46 mg, yield 58%).

$^1$H-NMR (CDCl$_3$-d$_1$, 400 MHz): δ 0.97 (t, J=7.3 Hz, 3H), 1.40–1.51 (m, 2H), 1.60–1.72 (m, 2H), 4.12 (s, 3H), 4.19 (s, 3H), 4.19 (t, J=6.6 Hz, 2H), 6.77 (s, 1H), 7.20 (d, J=9.0 Hz, 2H), 7.58 (d, J=8.8 Hz, 2H), 7.62 (s, 1H), 8.14 (s, 1H), 8.80 (s, 1H) Mass spectrometry value (ESI-MS, m/z): 398 (M$^+$+1)

Example 345

Butyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-butanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (50 mg, yield 66%).

$^1$H-NMR (CDCl$_3$-d$_1$, 400 MHz): δ 0.98 (t, J=7.3 Hz, 3H), 1.40–1.51 (m, 2H), 1.58–1.74 (m, 2H), 4.12 (s, 3H), 4.20 (s, 3H), 4.23 (t, J=6.6 Hz, 2H), 7.19–7.25 (m, 2H), 7.33 (d, J=2.7 Hz, 1H), 7.59 (s, 1H), 8.15 (s, 1H), 8.39 (d, J=8.8 Hz, 1H), 8.82 (s, 1H) Mass spectrometry value (ESI-MS, m/z): 433 (M$^+$+1)

Example 346

1-Phenylpropyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (43 mg, yield 51%).

$^1$H-NMR (CDCl$_3$-d$_1$, 400 MHz): δ 0.96 (t, J=7.3 Hz, 3H), 1.86–1.95 (m, 1H), 2.00–2.08 (m, 1H), 4.11 (s, 3H), 4.19 (s, 3H), 5.68 (t, J=7.3 Hz, 1H), 7.15–7.17 (m, 1H), 7.25–7.38 (m, 5H), 7.39 (d, J=4.6 Hz, 2H), 7.57 (s, 1H), 8.15 (s, 1H), 8.37 (d, J=9.3 Hz, 1H), 8.81 (s, 1H) Mass spectrometry value (ESI-MS, m/z): 495 (M$^+$+1)

Example 347

Isopropyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-propanol (14 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (50 mg, yield 75%).

$^1$H-NMR (CDCl$_3$-d$_1$, 400 MHz): δ 1.34 (d, J=6.3 Hz, 6H), 2.13 (s, 3H), 2.29 (s, 3H), 4.11 (s, 3H), 4.17 (s, 3H), 5.04–5.07 (m, 1H), 6.38 (s, 1H), 6.58 (brs, 1H), 6.95 (s, 1H), 7.65 (s, 1H), 7.95 (s, 1H), 8.15 (s, 1H), 8.46 (brs, 1H) Mass spectrometry value (ESI-MS, m/z): 412 (M$^+$+1)

Example 348

Cycloheptylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cycloheptylmethanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (64 mg, yield 77%).

$^1$H-NMR (CDCl$_3$-d$_1$, 400 MHz): δ 1.23–1.31 (m, 2H), 1.45–1.60 (m, 6H), 1.70–1.89 (m, 5H), 4.01 (d, J=6.8 Hz, 2H), 4.10 (s, 3H), 4.17 (s, 3H), 6.70 (d, J=6.3 Hz, 1H), 6.80 (s, 1H), 7.18 (d, J=9.0 Hz, 2H), 7.61 (d, J=8.8 Hz, 2H), 7.64 (s, 1H), 8.15 (s, 1H), 8.48 (t, J=6.6 Hz, 1H) Mass spectrometry value (ESI-MS, m/z): 452 (M$^+$+1)

Example 349

Cycloheptylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cycloheptylmethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (64 mg, yield 83%).

$^1$H-NMR (CDCl$_3$-d$_1$, 400 MHz): δ 1.23–1.31 (m, 2H), 1.47–1.59 (m, 6H), 1.70–1.90 (m, 5H), 2.13 (s, 3H), 2.29 (s, 3H), 4.01 (d, J=6.8 Hz, 2H), 4.11 (s, 3H), 4.17 (s, 3H), 6.43 (s, 1H), 6.58 (d, J=6.3 Hz, 1H), 6.95 (s, 1H), 7.65 (s, 1H), 7.92 (brs, 1H), 8.15 (s, 1H), 8.48 (t, J=6.6 Hz, 1H) Mass spectrometry value (ESI-MS, m/z): 480 (M$^+$+1)

Example 350

Cycloheptylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cycloheptylmethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 100%).

$^1$H-NMR (CDCl$_3$-d$_1$, 400 MHz): δ 1.19–1.31 (m, 2H), 1.40–1.90 (m, 11H), 2.10 (s, 3H), 2.28 (s, 3H), 4.01 (d, J=6.8 Hz, 2H), 4.12 (s, 3H), 4.17 (s, 3H), 6.47 (s, 1H), 6.57 (d, J=6.1 Hz, 1H), 7.02 (d, J=9.0 Hz, 1H), 7.67 (s, 1H), 7.74 (brs, 1H), 8.14 (s, 1H), 8.50 (brs, 1H) Mass spectrometry value (ESI-MS, m/z): 480 (M$^+$+1)

Example 351

Cycloheptylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cycloheptylmethanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (41 mg, yield 46%).

$^1$H-NMR (CDCl$_3$-d$_1$, 400 MHz): δ 1.22–1.30 (m, 2H), 1.46–1.88 (m, 11H), 4.00 (d, J=6.8 Hz, 2H), 4.12 (s, 3H), 4.19 (s, 3H), 6.78 (s, 1H), 7.20 (d, J=8.8 Hz, 2H), 7.58 (d, J=9.0 Hz, 2H), 7.62 (s, 1H), 8.15 (s, 1H), 8.79 (s, 1H) Mass spectrometry value (ESI-MS, m/z): 453 (M$^+$+1)

Example 352

Cycloheptylmethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cycloheptylmethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (53 mg, yield 63%).

1H-NMR (CDCl$_3$-d$_1$, 400 MHz): δ 1.23–1.31 (m, 2H), 1.47–1.91 (m, 11H), 4.02 (d, J=6.8 Hz, 2H), 4.12 (s, 3H), 4.20 (s, 3H), 7.19 (s, 1H), 7.21 (d, J=2.7 Hz, 1H), 7.33 (d, J=2.7 Hz, 1H), 7.59 (s, 1H), 8.15 (s, 1H), 8.39 (d, J=9.0 Hz, 1H), 8.82 (s, 1H) Mass spectrometry value (ESI-MS, m/z): 487 (M$^+$+1)

Example 353

2-Cyclohexylethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-cyclohexyl-1-ethanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (63 mg, yield 76%).

$^1$H-NMR (CDCl$_3$-d$_1$, 400 MHz): δ 0.95–1.01 (m, 2H), 1.15–1.27 (m, 3H), 1.40–1.43 (m, 1H), 1.57–1.77 (m, 7H), 4.10 (s, 3H), 4.17 (s, 3H), 4.24 (t, J=6.8 Hz, 2H), 6.70 (d, J=6.3 Hz, 1H), 6.82 (s, 1H), 7.18 (d, J=8.8 Hz, 2H), 7.61 (d, J=8.8 Hz, 2H), 7.64 (s, 1H), 8.15 (s, 1H), 8.48 (t, J=6.6 Hz, 1H) Mass spectrometry value (ESI-MS, m/z): 452 (M$^+$+1)

Example 354

2-Cyclohexylethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-cyclohexyl-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (68 mg, yield 88%).

$^1$H-NMR (CDCl$_3$-d$_1$, 400 MHz): δ 0.94–1.02 (m, 2H), 1.16–1.28 (m, 3H), 1.40–1.44 (m, 1H), 1.58–1.78 (m, 7H), 2.13 (s, 3H), 2.29 (s, 3H), 4.11 (s, 3H), 4.17 (s, 3H), 4.25 (t, J=6.8 Hz, 2H), 6.42 (s, 1H), 6.59 (d, J=6.6 Hz, 1H), 6.95 (s, 1H), 7.65 (s, 1H), 7.91 (s, 1H), 8.15 (s, 1H), 8.49 (t, J=6.3 Hz, 1H) Mass spectrometry value (ESI-MS, m/z): 480 (M$^+$+1)

Example 355

2-Cyclohexylethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-cyclohexyl-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (65 mg, yield 84%).

$^1$H-NMR (CDCl$_3$-d$_1$, 400 MHz): δ 0.93–1.01 (m, 2H), 1.16–1.24 (m, 3H), 1.27–1.42 (m, 1H), 1.51–1.77 (m, 7H), 2.10 (s, 3H), 2.28 (s, 3H), 4.11 (s, 3H), 4.17 (s, 3H), 4.24 (t, J=6.8 Hz, 2H), 6.45 (s, 1H), 6.56 (d, J=6.6 Hz, 1H), 7.02 (d, J=8.8 Hz, 1H), 7.67 (s, 1H), 7.74 (brs, 1H), 8.15 (s, 1H), 8.49 (t, J=6.6 Hz, 1H) Mass spectrometry value (ESI-MS, m/z): 480 (M$^+$+1)

Example 356

2-Cyclohexylethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-cyclohexyl-1-ethanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 54%).

$^1$H-NMR (CDCl$_3$-d$_1$, 400 MHz): δ 0.95–1.01 (m, 2H), 1.15–1.27 (m, 3H), 1.41–1.77 (m, 8H), 4.12 (s, 3H), 4.19 (s, 3H), 4.23 (t, J=6.8 Hz, 2H), 6.76 (s, 1H), 7.20 (d, J=9.0 Hz, 1H), 7.58 (d, J=8.5 Hz, 1H), 7.62 (s, 1H), 8.15 (s, 1H), 8.80 (s, 1H) Mass spectrometry value (ESI-MS, m/z): 453 (M$^+$+1)

Example 357

2-Cyclohexylethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-cyclohexyl-1-ethanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (56 mg, yield 67%).

$^1$H-NMR (CDCl$_3$-d$_1$, 400 MHz): δ 0.96–1.02 (m, 2H), 1.16–1.28 (m, 3H), 1.42–1.78 (m, 8H), 4.12 (s, 3H), 4.20 (s, 3H), 4.26 (t, J=6.8 Hz, 2H), 7.18 (s, 1H), 7.20 (d, J=2.7 Hz, 1H), 7.33 (d, J=2.7 Hz, 1H), 7.59 (s, 1H), 8.16 (s, 1H), 8.39 (d, J=9.0 Hz, 1H), 8.83 (s, 1H) Mass spectrometry value (ESI-MS, m/z): 487 (M$^+$+1)

Example 358

1-Ethylpropyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-pentanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).

$^1$H-NMR (CDCl$_3$-d$_1$, 400 MHz): δ 0.96 (t, J=7.6 Hz, 6H), 1.62–1.71 (m, 4H), 4.10 (s, 3H), 4.17 (s, 3H), 4.75–4.79 (m, 1H), 6.70 (d, J=6.6 Hz, 1H), 6.80 (s, 1H), 7.18 (d, J=8.8 Hz, 2H), 7.62 (d, J=9.0 Hz, 2H), 7.64 (s, 1H), 8.14 (s, 1H), 8.49 (t, J=6.6 Hz, 1H) Mass spectrometry value (ESI-MS, m/z): 412 (M$^+$+1)

Example 359

1-Ethylpropyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-pentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (53 mg, yield 74%).

$^1$H-NMR (CDCl$_3$-d$_1$, 400 MHz): δ 0.97 (t, J=7.6 Hz, 6H), 1.59–1.70 (m, 4H), 2.13 (s, 3H), 2.30 (s, 3H), 4.11 (s, 3H), 4.17 (s, 3H), 4.76–4.79 (m, 1H), 6.43 (s, 1H), 6.58 (d, J=6.3 Hz, 1H), 6.95 (s, 1H), 7.65 (s, 1H), 7.96 (s, 1H), 8.14 (s, 1H), 8.46 (t, J=6.6 Hz, 1H) Mass spectrometry value (ESI-MS, m/z): 440 (M$^+$+1)

Example 360

1-Ethylpropyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-pentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 87%).

$^1$H-NMR (CDCl$_3$-d$_1$, 400 MHz): δ 0.97 (t, J=7.6 Hz, 6H), 1.59–1.70 (m, 4H), 2.10 (s, 3H), 2.28 (s, 3H), 4.12 (s, 3H), 4.17 (s, 3H), 4.76–4.79 (m, 1H), 6.44 (s, 1H), 6.56 (d, J=6.3 Hz, 1H), 7.02 (d, J=8.8 Hz, 1H), 7.67 (s, 1H), 7.78 (brs, 1H), 8.15 (s, 1H), 8.46 (t, J=6.6 Hz, 1H) Mass spectrometry value (ESI-MS, m/z): 440 (M$^+$+1)

Example 361

1-Ethylpropyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-pentanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 67%).

$^1$H-NMR (CDCl$_3$-d$_1$, 400 MHz): δ 0.95 (t, J=7.6 Hz, 6H), 1.59–1.69 (m, 4H), 4.13 (s, 3H), 4.19 (s, 3H), 4.75–4.78 (m, 1H), 6.75 (s, 1H), 7.19 (d, J=9.0 Hz, 2H), 7.59 (d, J=9.0 Hz, 2H), 7.62 (s, 1H), 8.15 (s, 1H), 8.80 (s, 1H) Mass spectrometry value (ESI-MS, m/z): 413 (M$^+$+1)

Example 362

1-Ethylpropyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-pentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (49 mg, yield 63%).

$^1$H-NMR (CDCl$_3$-d$_1$, 400 MHz): δ 0.97 (t, J=7.6 Hz, 6H), 1.58–1.69 (m, 4H), 4.12 (s, 3H), 4.20 (s, 3H), 4.77–4.80 (m, 1H), 7.18 (s, 1H), 7.33 (d, J=2.4 Hz, 1H), 7.59 (s, 1H), 8.16 (s, 1H), 8.42 (d, J=9.0 Hz, 1H), 8.82 (s, 1H) Mass spectrometry value (ESI-MS, m/z): 447 (M$^+$+1)

Example 363

Cyclopentyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-cyclopentanol (22 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).

$^1$H-NMR (CDCl$_3$-d$_1$, 400 MHz): δ 1.60–1.94 (m, 8H), 4.10 (s, 3H), 4.17 (s, 3H), 5.23–5.24 (m, 1H), 6.69 (d, J=6.3 Hz, 1H), 6.74 (s, 1H), 7.17 (d, J=9.0 Hz, 2H), 7.60 (d, J=9.0 Hz, 2H), 7.64 (s, 1H), 8.15 (s, 1H), 8.48 (t, J=6.3 Hz, 1H) Mass spectrometry value (ESI-MS, m/z): 410 (M$^+$+1)

Example 364

Cyclopentyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclopentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (70 mg, yield 99%).

$^1$H-NMR (CDCl$_3$-d$_1$, 400 MHz): δ 1.58–1.96 (m, 8H), 2.13 (s, 3H), 2.29 (s, 3H), 4.11 (s, 3H), 4.17 (s, 3H), 5.22–5.23 (m, 1H), 6.38 (s, 1H), 6.58 (d, J=6.6 Hz, 1H), 6.94 (s, 1H), 7.65 (s, 1H), 7.95 (s, 1H), 8.15 (s, 1H), 8.47 (brs, 1H) Mass spectrometry value (ESI-MS, m/z): 438 (M$^+$+1)

Example 365

Cyclopentyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclopentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 84%).

$^1$H-NMR (CDCl$_3$-d$_1$, 400 MHz): δ 1.66–1.95 (m, 8H), 2.10 (s, 3H), 2.27 (s, 3H), 4.11 (s, 3H), 4.17 (s, 3H), 5.21–5.25 (m, 1H), 6.41 (s, 1H), 6.56 (d, J=6.3 Hz, 1H), 7.01 (d, J=8.8 Hz, 1H), 7.67 (s, 1H), 7.78 (d, J=8.8 Hz, 1H), 8.15 (s, 1H), 8.47 (t, J=6.6 Hz, 1H) Mass spectrometry value (ESI-MS, m/z): 438 (M$^+$+1)

Example 366

Cyclopentyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-cyclopentanol (22 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 76%).

$^1$H-NMR (CDCl$_3$-d$_1$, 400 MHz): δ 1.49–1.93 (m, 8H), 4.12 (s, 3H), 4.19 (s, 3H), 5.22–5.23 (m, 1H), 6.71 (s, 1H), 7.19 (d, J=9.0 Hz, 2H), 7.57 (d, J=8.8 Hz, 2H), 7.62 (s, 1H), 8.15 (s, 1H), 8.80 (s, 1H) Mass spectrometry value (ESI-MS, m/z): 410 (M$^+$+1)

Example 367

Cyclopentyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then dded thereto, and the mixture was heated under reflux for 10 min. Next, 1-cyclopentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 80%).

$^1$H-NMR (CDCl$_3$-d$_1$, 400 MHz): δ 1.49–1.99 (m, 8H), 4.12 (s, 3H), 4.20 (s, 3H), 5.23–5.27 (m, 1H), 7.13 (s, 1H), 7.19 (dd, J=2.9, 9.0 Hz, 1H), 7.32 (d, J=2.7 Hz, 1H), 7.59 (s, 1H), 8.16 (s, 1H), 8.40 (d, J=9.0 Hz, 1H), 8.82 (s, 1H) Mass spectrometry value (ESI-MS, m/z): 445 (M$^+$+1)

Example 368

1-Butylpentyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 5-nonanol (38 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (2 mg, yield 2%).

$^1$H-NMR (CDCl$_3$-d$_1$, 400 MHz): δ 0.92 (t, J=7.1 Hz, 6H), 1.31–1.39 (m, 8H), 1.57–1.64 (m, 4H), 4.11 (s, 3H), 4.17 (s, 3H), 4.85–4.91 (m, 1H), 6.69 (d, J=6.8 Hz, 1H), 7.18 (d, J=9.0 Hz, 2H), 7.61 (d, J=8.8 Hz, 2H), 7.64 (s, 1H), 8.15 (d, J=3.9 Hz, 1H), 8.46 (brs, 1H) Mass spectrometry value (ESI-MS, m/z): 468 (M$^+$+1)

Example 369

1-Butylpentyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 5-nonanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (56 mg, yield 70%).

$^1$H-NMR (CDCl$_3$-d$_1$, 400 MHz): δ 0.93 (t, J=7.1 Hz, 6H), 1.37–1.39 (m, 8H), 1.61 (brs, 1H), 2.13 (s, 3H), 2.29 (s, 3H), 4.11 (s, 3H), 4.17 (s, 3H), 4.87–4.90 (m, 1H), 6.41 (s, 1H), 6.58 (d, J=6.6 Hz, 1H), 6.95 (s, 1H), 7.65 (s, 1H), 7.97 (s, 1H), 8.15 (d, J=3.9 Hz, 1H), 8.46 (t, J=6.3 Hz, 1H) Mass spectrometry value (ESI-MS, m/z): 496 (M$^+$+1)

Example 370

1-Butylpentyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 5-nonanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (57 mg, yield 72%).

$^1$H-NMR (CDCl$_3$-d$_1$, 400 MHz): δ 0.92 (t, J=7.1 Hz, 6H), 1.36 (brs, 8H), 1.56–1.60 (m, 4H), 2.10 (s, 3H), 2.28 (s, 3H), 4.12 (s, 3H), 4.17 (s, 3H), 4.87–4.90 (m, 1H), 6.42 (s, 1H), 6.55 (d, J=6.1 Hz, 1H), 7.02 (d, J=8.8 Hz, 1H), 7.67 (s, 1H), 7.80 (brs, 1H), 8.16 (d, J=3.9 Hz, 1H), 8.45 (brs, 1H) Mass spectrometry value (ESI-MS, m/z): 496 (M$^+$+1)

Example 371

1-Butylpentyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 5-nonanol (38 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 44%).

$^1$H-NMR (CDCl$_3$-d$_1$, 400 MHz): δ 0.90–0.93 (m, 6H), 1.34–1.35 (m, 8H), 1.59 (brs, 4H), 4.13 (s, 3H), 4.19 (s, 3H), 4.86–4.89 (m, 1H), 6.71 (s, 1H), 7.19 (d, J=9.0 Hz, 2H), 7.59 (d, J=8.8 Hz, 2H), 7.62 (s, 1H), 8.15 (s, 1H), 8.80 (s, 1H) Mass spectrometry value (ESI-MS, m/z): 469 (M$^+$+1)

Example 372

1-Butylpentyl N-{2-chloro-4-[(6,7-dimethoxy-4-quinazolinyl)oxy]phenyl}carbamate

2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 5-nonanol (33 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 49%).

$^1$H-NMR (CDCl$_3$-d$_1$, 400 MHz): δ 0.92 (t, J=7.1 Hz, 6H), 1.36 (brs, 8H), 1.61 (brs, 4H), 4.13 (s, 3H), 4.20 (s, 3H), 4.88–4.91 (m, 1H), 7.17 (s, 1H), 7.20 (s, 1H), 7.33 (s, 1H), 7.59 (s, 1H), 8.17 (s, 1H), 8.43 (d, J=9.0 Hz, 1H), 8.82 (s, 1H) Mass spectrometry value (ESI-MS, m/z): 503 (M$^+$+1)

Example 373

Allyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-propen-1-ol (13 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (56 mg, yield 84%).

$^1$H-NMR (CDCl$_3$-d$_1$, 400 MHz): δ 2.13 (s, 3H), 2.29 (s, 3H), 4.11 (s, 3H), 4.17 (s, 3H), 4.71 (d, J=5.9 Hz, 2H), 5.32 (dd, J=1.2, 10.5 Hz, 1H), 5.40 (dd, J=1.5, 17.3 Hz, 1H), 5.96–6.06 (m, 1H), 6.49 (s, 1H), 6.59 (d, J=6.6 Hz, 1H), 6.96 (s, 1H), 7.65 (s, 1H), 7.91 (s, 1H), 8.16 (d, J=3.9 Hz, 1H), 8.49 (t, J=7.3 Hz, 1H) Mass spectrometry value (ESI-MS, m/z): 410 (M$^+$+1)

Example 374

Allyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-propen-1-ol (13 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (50 mg, yield 75%).

$^1$H-NMR (CDCl$_3$-d$_1$, 400 MHz): δ 2.10 (s, 3H), 2.28 (s, 3H), 4.12 (s, 3H), 4.17 (s, 3H), 4.71 (d, J=5.9 Hz, 2H), 5.31 (d, J=10.2 Hz, 1H), 5.40 (d, J=17.3 Hz, 1H), 5.96–6.04 (m, 1H), 6.50 (s, 1H), 6.56 (d, J=6.1 Hz, 1H), 7.03 (d, J=8.8 Hz, 1H), 7.67 (s, 1H), 7.76 (s, 1H), 8.16 (d, J=3.9 Hz, 1H), 8.48 (t, J=6.6 Hz, 1H) Mass spectrometry value (ESI-MS, m/z): 410 (M$^+$+1)

Example 375

Allyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-propen-1-ol (15 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 54%).

$^1$H-NMR (CDCl$_3$-d$_1$, 400 MHz): δ 4.13 (s, 3H), 4.19 (s, 3H), 4.70 (d, J=5.9 Hz, 2H), 5.29 (dd, J=1.2, 10.5 Hz, 1H), 5.39 (dd, J=1.5, 17.3 Hz, 1H), 5.93–6.03 (m, 1H), 6.81–6.87 (m, 1H), 7.20 (d, J=9.0 Hz, 2H), 7.59 (d, J=8.8 Hz, 2H), 7.62 (s, 1H), 8.15 (s, 1H), 8.80 (s, 1H) Mass spectrometry value (ESI-MS, m/z): 382 (M$^+$+1)

Example 376

3-Phenylpropyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-phenyl-1-propanol (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric-acid solution, water, and saturated brine in that order. The extract was dried over sodium sulfate and was then concentrated. The residue was purified on a column using chloroform/methanol to give the title compound (54 mg, yield 64%).

$^1$H-NMR (CDCl$_3$-d$_1$, 400 MHz): δ 2.01–2.08 (m, 2H), 2.75 (t, J=8.1 Hz, 2H), 4.11 (s, 3H), 4.17 (s, 3H), 4.24 (t, J=6.6 Hz, 2H), 6.70 (d, J=6.3 Hz, 1H), 6.80 (s, 1H), 7.17–7.33 (m, 7H), 7.61 (d, J=8.8 Hz, 2H), 7.64 (s, 1H), 8.15 (d, J=3.7 Hz, 1H), 8.50 (t, J=6.8 Hz, 1H) Mass spectrometry value (ESI-MS, m/z): 460 (M$^+$+1)

Example 377

3-Phenylpropyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (77 mg, yield 98%).

$^1$H-NMR (CDCl$_3$-d$_1$, 400 MHz): δ 2.02–2.09 (m, 2H), 2.13 (s, 3H), 2.29 (s, 3H), 2.76 (t, J=7.8 Hz, 2H), 4.11 (s, 3H), 4.17 (s, 3H), 4.25 (t, J=6.6 Hz, 2H), 6.41 (s, 1H), 6.59 (d, J=6.3 Hz, 1H), 6.95 (s, 1H), 7.22–7.33 (m, 5H), 7.65 (s, 1H), 7.91 (s, 1H), 8.15 (d, J=3.7 Hz, 1H), 8.49 (t, J=6.8 Hz, 1H) Mass spectrometry value (ESI-MS, m/z): 488 (M$^+$+1)

Example 378

3-Phenylpropyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (56 mg, yield 71%).

$^1$H-NMR (CDCl$_3$-d$_1$, 400 MHz): δ 2.01–2.09 (m, 2H), 2.11 (s, 3H), 2.28 (s, 3H), 2.75 (t, J=8.1 Hz, 2H), 4.11 (s, 3H), 4.17 (s, 3H), 4.24 (t, J=6.6 Hz, 2H), 6.43 (s, 1H), 6.56 (d, J=6.6 Hz, 1H), 7.03 (d, J=8.8 Hz, 1H), 7.21–7.33 (m, 5H), 7.67 (s, 1H), 7.75 (brs, 1H), 8.16 (d, J=3.9 Hz, 1H), 8.49 (brs, 1H) Mass spectrometry value (ESI-MS, m/z): 488 (M$^+$+1)

Example 379

3-Phenylpropyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-phenyl-1-propanol (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 49%).

$^1$H-NMR (CDCl$_3$-d$_1$, 400 MHz): δ 2.04–2.08 (m, 2H), 2.76 (t, J=8.3 Hz, 2H), 4.12 (s, 3H), 4.20 (s, 3H), 4.26 (t, J=6.6 Hz, 2H), 7.18–7.34 (m, 8H), 7.59 (s, 1H), 8.17 (s, 1H), 8.38 (d, J=8.8 Hz, 1H), 8.83 (s, 1H) Mass spectrometry value (ESI-MS, m/z): 495 (M$^+$+1)

Example 380

Cyclopropylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclopropylmethanol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (25 mg, yield 34%).

$^1$H-NMR (CDCl$_3$-d$_1$, 400 MHz): δ 0.33–0.37 (m, 2H), 0.60–0.65 (m, 2H), 1.18–1.22 (m, 1H), 4.04 (d, J=7.3 Hz, 2H), 4.11 (s, 3H), 4.17 (s, 3H), 6.71 (s, 1H), 6.85 (s, 1H), 7.18 (d, J=8.5 Hz, 2H), 7.61 (d, J=8.3 Hz, 2H), 7.65 (s, 1H), 8.14 (s, 3H), 8.51 (brs, 1H) Mass spectrometry value (ESI-MS, m/z): 395 (M$^+$+1)

Example 381

Cyclopropylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopropylmethanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (51 mg, yield 74%).

$^1$H-NMR (CDCl$_3$-d$_1$, 400 MHz): δ 0.34–0.38 (m, 2H), 0.61–0.66 (m, 2H), 1.18–1.24 (m, 1H), 2.13 (s, 3H), 2.30 (s, 3H), 4.04 (d, J=7.3 Hz, 2H), 4.11 (s, 3H), 4.17 (s, 3H), 6.47 (s, 1H), 6.59 (s, 1H), 6.95 (s, 1H), 7.65 (s, 1H), 7.92 (s, 1H), 8.15 (s, 1H), 8.48 (brs, 1H) Mass spectrometry value (ESI-MS, m/z): 424 (M$^+$+1)

Example 382

Cyclopropylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopropylmethanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 80%).

$^1$H-NMR (CDCl$_3$-d$_1$, 400 MHz): δ 0.34–0.38 (m, 2H), 0.61–0.66 (m, 2H), 1.19–1.23 (m, 1H), 2.11 (s, 3H), 2.28 (s, 3H), 4.04 (d, J=7.3 Hz, 2H), 4.12 (s, 3H), 4.17 (s, 3H), 6.50 (s, 1H), 6.56 (s, 1H), 7.03 (d, J=8.8 Hz, 1H), 7.67 (s, 1H), 7.78 (s, 1H), 8.15 (s, 1H), 8.48 (brs, 1H) Mass spectrometry value (ESI-MS, m/z): 424 (M$^+$+1)

Example 383

Cyclopropylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclopropylmethanol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (60 mg, yield 75%).

$^1$H-NMR (CDCl$_3$-d$_1$, 400 MHz): δ 0.33–0.36 (m, 2H), 0.59–0.64 (m, 2H), 1.16–1.23 (m, 1H), 4.03 (d, J=7.6 Hz, 2H), 4.12 (s, 3H), 4.17 (s, 3H), 6.81 (s, 1H), 7.20 (d, J=9.0 Hz, 2H), 7.57 (d, J=8.5 Hz, 2H), 7.61 (s, 1H), 7.99 (s, 1H), 8.77 (s, 1H) Mass spectrometry value (ESI-MS, m/z): 396 (M$^+$+1)

Example 384

Cyclopropylmethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopropylmethanol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (49 mg, yield 65%).

$^1$H-NMR (CDCl$_3$-d$_1$, 400 MHz): δ 0.34–0.38 (m, 2H), 0.62–0.66 (m, 2H), 1.20–1.24 (m, 1H), 4.06 (d, J=7.3 Hz, 2H), 4.12 (s, 3H), 4.20 (s, 3H), 7.19–7.21 (m, 2H), 7.33 (s, 1H), 7.59 (s, 1H), 8.17 (s, 1H), 8.40 (d, J=8.8 Hz, 1H), 8.83 (s, 1H) Mass spectrometry value (ESI-MS, m/z): 431 (M$^+$+1)

Example 385

Cyclobutylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclobutylmethanol (22 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 64%).

$^1$H-NMR (CDCl$_3$-d$_1$, 400 MHz): δ 1.80–2.13 (m, 6H), 2.65–2.71 (m, 1H), 4.10 (s, 3H), 4.17 (s, 3H), 4.18 (d, J=6.8 Hz, 2H), 6.70 (s, 1H), 6.80 (s, 1H), 7.18 (d, J=8.8 Hz, 2H), 7.60 (d, J=8.5 Hz, 2H), 7.64 (s, 1H), 8.14 (s, 1H), 8.50 (brs, 1H) Mass spectrometry value (ESI-MS, m/z): 410 (M$^+$+1)

Example 386

Cyclobutylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclobutylmethanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (61 mg, yield 86%).

$^1$H-NMR (CDCl$_3$-d$_1$, 400 MHz): δ 1.81–1.99 (m, 4H), 2.05–2.20 (m, 2H), 2.13 (s, 3H), 2.29 (s, 3H), 2.66–2.73 (m, 1H), 4.11 (s, 3H), 4.17 (s, 3H), 4.19 (d, J=7.1 Hz, 2H), 6.43 (s, 1H), 6.60 (s, 1H), 7.95 (s, 1H), 7.65 (s, 1H), 7.91 (s, 1H), 8.15 (s, 1H), 8.49 (brs, 1H) Mass spectrometry value (ESI-MS, m/z): 438 (M$^+$+1)

Example 387

Cyclobutylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclobutylmethanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (59 mg, yield 83%).

$^1$H-NMR (CDCl$_3$-d$_1$, 400 MHz): δ 1.78–2.08 (m, 6H), 2.08 (s, 3H), 2.26 (s, 3H), 2.60–2.70 (m, 1H), 4.09 (s, 3H), 4.15 (s, 3H), 4.16 (d, J=6.8 Hz, 2H), 6.43 (s, 1H), 6.55 (s, 1H), 7.00 (d, J=8.5 Hz, 1H), 7.65 (s, 1H), 7.74 (brs, 1H), 8.13 (s, 1H), 8.47 (brs, 1H) Mass spectrometry value (ESI-MS, m/z): 438 (M$^+$+1)

Example 388

Cyclobutylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclobutylmethanol (22 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (55 mg, yield 67%).

$^1$H-NMR (CDCl$_3$-d$_1$, 400 MHz): δ 1.80–1.99 (m, 4H), 2.07–2.14 (m, 2H), 2.64–2.71 (m, 1H), 4.12 (s, 3H), 4.17 (d, J=6.8 Hz, 2H), 4.19 (s, 3H), 6.79 (s, 1H), 7.20 (d, J=8.8 Hz, 2H), 7.58 (d, J=8.3 Hz, 2H), 7.62 (s, 1H), 8.11 (s, 1H), 8.80 (s, 1H) Mass spectrometry value (ESI-MS, m/z): 410 (M$^+$+1)

Example 389

Cyclobutylmethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclobutylmethanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (46 mg, yield 59%).

$^1$H-NMR (CDCl$_3$-d$_1$, 400 MHz): δ 1.81–2.01 (m, 4H), 2.09–2.17 (m, 2H), 2.66–2.74 (m, 1H), 4.12 (s, 3H), 4.20 (d, J=6.8 Hz, 2H), 4.20 (s, 3H), 7.19 (s, 1H), 7.21 (d, J=2.7 Hz, 1H), 7.33 (d, J=2.4 Hz, 1H), 7.59 (s, 1H), 8.17 (s, 1H), 8.39 (d, J=9.3 Hz, 1H), 8.83 (s, 1H) Mass spectrometry value (ESI-MS, m/z): 445 (M$^+$+1)

Example 390

Cyclohexyl N-{4-[(6,7-dimethoxy-4-quinazolinyl)oxy]-2,5-dimethylphenyl}carbamate 4-[(6,7-Dimethoxy-4-quinazolinyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclohexanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (58 mg, yield 74%).

$^1$H-NMR (CDCl$_3$-d$_1$, 400 MHz): δ 1.29–1.58 (m, 6H), 1.74–1.81 (m, 2H), 1.95–2.00 (m, 2H), 2.12 (s, 3H), 2.29 (s, 3H), 4.13 (s, 3H), 4.20 (s, 3H), 4.76–4.77 (m, 1H), 6.38 (s, 1H), 6.95 (s, 1H), 7.62 (s, 1H), 7.93 (s, 1H), 8.16 (s, 1H), 8.79 (s, 1H) Mass spectrometry value (ESI-MS, m/z): 453 (M$^+$+1)

Example 391

Cyclohexyl N-{4-[(6,7-dimethoxy-4-quinazolinyl)oxy]-2,3-dimethylphenyl}carbamate 4-[(6,7-Dimethoxy-4-quinazolinyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclohexanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (50 mg, yield 64%).

$^1$H-NMR (CDCl$_3$-d$_1$, 400 MHz): δ 1.21–1.57 (m, 6H), 1.73–1.79 (m, 2H), 1.94–2.00 (m, 2H), 2.08 (s, 3H), 2.27 (s, 3H), 4.14 (s, 3H), 4.20 (s, 3H), 4.70–4.80 (m, 1H), 6.40 (s, 1H), 7.01 (d, J=8.8 Hz, 1H), 7.65 (s, 1H), 7.78 (brs, 1H), 8.16 (s, 1H), 8.78 (s, 1H) Mass spectrometry value (ESI-MS, m/z): 453 (M$^+$+1)

Example 392

Cyclopentyl N-{4-[(6,7-dimethoxy-4-quinazolinyl)oxy]-2,5-dimethylphenyl}carbamate 4-[(6,7-Dimethoxy-4-quinazolinyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclopentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (47 mg, yield 61%).

$^1$H-NMR (CDCl$_3$-d$_1$, 400 MHz): δ 1.49–1.84 (m, 6H), 1.89–1.98 (m, 2H), 2.12 (s, 3H), 2.28 (s, 3H), 4.13 (s, 3H), 4.20 (s, 3H), 5.21–5.22 (m, 1H), 6.36 (s, 1H), 6.95 (s, 1H), 7.62 (s, 1H), 7.93 (s, 1H), 8.16 (s, 1H), 8.79 (s, 1H) Mass spectrometry value (ESI-MS, m/z): 439 (M$^+$+1)

Example 393

Cyclopentyl N-{4-[(6,7-dimethoxy-4-quinazolinyl)oxy]-2,3-dimethylphenyl}carbamate 4-[(6,7-Dimethoxy-4-quinazolinyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-cyclopentanol (20 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (43 mg, yield 56%).

$^1$H-NMR (CDCl$_3$-d$_1$, 400 MHz): δ 1.49–1.83 (m, 6H), 1.88–1.97 (m, 2H), 2.08 (s, 3H), 2.26 (s, 3H), 4.14 (s, 3H), 4.20 (s, 3H), 5.20–5.25 (m, 1H), 6.39 (s, 1H), 7.01 (d, J=8.8 Hz, 1H), 7.65 (s, 1H), 7.77 (brs, 1H), 8.16 (s, 1H), 8.78 (s, 1H) Mass spectrometry value (ESI-MS, m/z): 439 (M$^+$+1)

Example 394

Cyclopentylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclopentylmethanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (42 mg, yield 54%).

$^1$H-NMR (CDCl$_3$-d$_1$, 400 MHz): δ 1.22–1.84 (m, 8H), 2.25–2.29 (m, 1H), 4.10–4.17 (m, 8H), 6.69 (d, J=6.1 Hz, 1H), 6.80 (s, 1H), 7.18 (d, J=9.0 Hz, 2H), 7.61 (d, J=8.5 Hz, 2H), 7.64 (s, 1H), 8.15 (s, 1H), 8.47 (s, 1H) Mass spectrometry value (ESI-MS, m/z): 424 (M$^+$+1)

Example 395

Cyclopentylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopentylmethanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (62 mg, yield 85%).

$^1$H-NMR (CDCl$_3$-d$_1$, 400 MHz): δ 1.31–1.68 (m, 6H), 1.78–1.86 (m, 2H), 2.13 (s, 3H), 2.20–2.30 (m, 1H), 2.29 (s, 3H), 4.10 (d, J=6.3 Hz, 2H), 4.11 (s, 3H), 4.17 (s, 3H), 6.42 (s, 1H), 6.58 (d, J=6.3 Hz, 1H), 6.95 (s, 1H), 7.65 (s, 1H), 7.91 (s, 1H), 8.16 (s, 1H), 8.46 (s, 1H) Mass spectrometry value (ESI-MS, m/z): 452 (M$^+$+1)

Example 396

Cyclopentylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopentylmethanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 66%).

$^1$H-NMR (CDCl$_3$-d$_1$, 400 MHz): δ 1.27–1.35 (m, 2H), 1.55–1.67 (m, 4H), 1.76–1.84 (m, 2H), 2.10 (s, 3H), 2.26–2.30 (m, 1H), 2.28 (s, 3H), 4.09 (d, J=7.1 Hz, 2H), 4.12 (s, 3H), 4.18 (s, 3H), 6.44 (s, 1H), 6.56 (s, 1H), 7.03 (d, J=8.5 Hz, 1H), 7.67 (s, 1H), 7.76 (brs, 1H), 8.16 (s, 1H), 8.45 (brs, 1H) Mass spectrometry value (ESI-MS, m/z): 452 (M$^+$+1)

Example 397

Cyclopentylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, cyclopentylmethanol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (64 mg, yield 75%).

$^1$H-NMR (CDCl$_3$-d$_1$, 400 MHz): δ 1.30–1.33 (m, 2H), 1.59–1.65 (m, 4H), 1.76–1.83 (m, 2H), 4.09 (d, J=7.3 Hz, 2H), 4.12 (s, 3H), 4.19 (s, 3H), 6.76 (s, 1H), 7.20 (d, J=9.0 Hz, 2H), 7.58 (d, J=8.8 Hz, 2H), 7.62 (s, 1H), 8.15 (s, 1H), 8.80 (s, 1H) Mass spectrometry value (ESI-MS, m/z): 425 (M$^+$+1)

Example 398

Cyclopentylmethyl N-{2-chloro-4-[(6,7-dimethoxy-4-quinazolinyl)oxy]phenyl}carbamate 2-Chloro-4-[(6,7-dimethoxy-4-quinazolinyl)oxy]-aniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, cyclopentylmethanol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (47 mg, yield 59%).

$^1$H-NMR (CDCl$_3$-d$_1$, 400 MHz): δ 1.29–1.34 (m, 2H), 1.57–1.66 (m, 4H), 1.77–1.85 (m, 2H), 4.11 (d, J=7.1 Hz, 2H), 4.12 (s, 3H), 4.20 (s, 3H), 7.19 (s, 1H), 7.33 (d, J=2.7 Hz, 1H), 7.59 (s, 1H), 8.17 (s, 1H), 8.39 (d, J=9.0 Hz, 1H), 8.82 (s, 1H) Mass spectrometry value (ESI-MS, m/z): 459 (M$^+$+1)

Example 399

2-Morpholinoethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-morpholino-1-ethanol (34 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (54 mg, yield 60%).

$^1$H-NMR (CDCl$_3$-d$_1$, 400 MHz): δ 2.94–3.04 (m, 2H), 3.30–3.36 (m, 2H), 3.58–3.63 (m, 2H), 4.01–4.07 (m, 2H), 4.12 (s, 3H), 4.19 (s, 3H), 4.53–4.59 (m, 4H), 7.19 (d, J=9.0 Hz, 2H), 7.62 (s, 1H), 7.67 (d, J=9.0 Hz, 2H), 8.14 (s, 1H), 8.80 (s, 1H) Mass spectrometry value (ESI-MS, m/z): 456 (M$^+$+1)

Example 400

1-Propylbutyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-heptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (53 mg, yield 61%).

$^1$H-NMR (CDCl$_3$-d$_1$, 400 MHz): δ 0.95 (t, J=7.3 Hz, 6H), 1.19–1.62 (m, 8H), 4.13 (s, 3H), 4.19 (s, 3H), 4.90–4.93 (m, 1H), 6.72 (s, 1H), 7.19 (d, J=9.0 Hz, 2H), 7.58 (d, J=8.8 Hz, 2H), 7.62 (s, 1H), 8.15 (s, 1H), 8.80 (s, 1H) Mass spectrometry value (ESI-MS, m/z): 441 (M$^+$+1)

Example 401

1-Ethylpentyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-heptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (63 mg, yield 72%).

$^1$H-NMR (CDCl$_3$-d$_1$, 400 MHz): δ 0.92–0.97 (m, 6H), 1.34–1.67 (m, 8H), 4.13 (s, 3H), 4.19 (s, 3H), 4.81–4.84 (m, 1H), 6.72 (s, 1H), 7.19 (d, J=9.0 Hz, 2H), 7.58 (d, J=9.0 Hz, 2H), 7.62 (s, 1H), 8.15 (s, 1H), 8.80 (s, 1H) Mass spectrometry value (ESI-MS, m/z): 441 (M$^+$+1)

Example 402

2-(Tert-butyl)phenyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-(tert-butyl)phenol (39 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (74 mg, yield 80%).

$^1$H-NMR (CDCl$_3$-d$_1$, 400 MHz): δ 1.41 (s, 9H), 4.13 (s, 3H), 4.19 (s, 3H), 7.08–7.11 (m, 1H), 7.19–7.29 (m, 5H), 7.41–7.44 (m, 1H), 7.63 (s, 1H), 7.70 (d, J=8.5 Hz, 2H), 8.15 (s, 1H), 8.79 (s, 1H) Mass spectrometry value (ESI-MS, m/z): 475 (M$^+$+1)

Example 403

2-Methoxyphenyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-methoxyphenol (32 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (16 mg, yield 18%).

$^1$H-NMR (CDCl$_3$-d$_1$, 400 MHz): δ 3.87 (s, 3H), 4.13 (s, 3H), 4.19 (s, 3H), 6.97–7.02 (m, 2H), 7.15–7.26 (m, 5H), 7.62 (s, 1H), 7.66 (d, J=8.8 Hz, 2H), 8.16 (s, 1H), 8.80 (s, 1H) Mass spectrometry value (ESI-MS, m/z): 448 (M$^+$+1)

Example 404

2-Methylallyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-methyl-2-propen-1-ol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (38 mg, yield 52%).

$^1$H-NMR (CDCl$_3$-d$_1$, 400 MHz): δ 1.82 (s, 3H), 4.11 (s, 3H), 4.17 (s, 3H), 4.63 (s, 2H), 4.99 (s, 1H), 5.06 (s, 1H), 6.70 (d, J=6.3 Hz, 1H), 6.87 (s, 1H), 7.19 (d, J=9.0 Hz, 2H), 7.62 (d, J=9.0 Hz, 2H), 7.64 (s, 1H), 8.15 (s, 1H), 8.48 (t, J=6.6 Hz, 1H) Mass spectrometry value (ESI-MS, m/z): 395 (M$^+$+1)

Example 405

2-Methylallyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-methyl-2-propen-1-ol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (31 mg, yield 45%).

$^1$H-NMR (CDCl$_3$-d$_1$, 400 MHz): δ 1.83 (s, 3H), 2.13 (s, 3H), 2.30 (s, 3H), 4.11 (s, 3H), 4.17 (s, 3H), 4.64 (s, 2H), 5.00 (s, 1H), 5.06 (s, 1H), 6.59 (s, 1H), 6.96 (s, 1H), 7.65 (s, 1H), 8.16 (s, 1H), 8.46 (s, 1H) Mass spectrometry value (ESI-MS, m/z): 424 (M$^+$+1)

Example 406

2-Methylallyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-methyl-2-propen-1-ol (17 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 58%).

$^1$H-NMR (CDCl$_3$-d$_1$, 400 MHz): δ 1.83 (s, 3H), 2.11 (s, 3H), 2.29 (s, 3H), 4.12 (s, 3H), 4.17 (s, 3H), 4.63 (s, 2H), 5.00 (s, 1H), 5.06 (s, 1H), 6.56 (d, J=5.9 Hz, 1H), 7.03 (d, J=8.8 Hz, 1H), 7.67 (s, 1H), 8.16 (s, 1H), 8.46 (s, 1H) Mass spectrometry value (ESI-MS, m/z): 424 (M$^+$+1)

Example 407

2-Methylallyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-methyl-2-propen-1-ol (19 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (37 mg, yield 47%).

$^1$H-NMR (CDCl$_3$-d$_1$, 400 MHz): δ 4.13 (s, 3H), 4.19 (s, 3H), 4.62 (s, 2H), 4.98 (s, 1H), 5.05 (s, 1H), 6.87 (s, 1H), 7.21 (d, J=9.0 Hz, 2H), 7.59 (d, J=9.0 Hz, 2H), 7.62 (s, 1H), 8.15 (s, 1H), 8.80 (s, 1H) Mass spectrometry value (ESI-MS, m/z): 396 (M$^+$+1)

Example 408

1-Ethyl-3-butynyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 5-hexyn-3-ol (26 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (30 mg, yield 39%).

$^1$H-NMR (CDCl$_3$-d$_1$, 400 MHz): δ 1.01 (t, J=7.6 Hz, 3H), 1.79–1.83 (m, 2H), 2.04–2.05 (m, 1H), 2.57–2.61 (m, 2H), 4.11 (s, 3H), 4.17 (s, 3H), 4.90–4.93 (m, 1H), 6.69 (d, J=6.1 Hz, 1H), 6.83 (s, 1H), 7.19 (d, J=9.0 Hz, 2H), 7.61 (d, J=8.8 Hz, 2H), 7.64 (s, 1H), 8.15 (s, 1H), 8.47 (s, 1H) Mass spectrometry value (ESI-MS, m/z): 422 (M$^+$+1)

Example 409

1-Ethyl-3-butynyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 5-hexyn-3-ol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (52 mg, yield 72%).

$^1$H-NMR (CDCl$_3$-d$_1$, 400 MHz): δ 1.01 (t, J=7.6 Hz, 3H), 1.79–1.83 (m, 2H), 2.05 (s, 1H), 2.13 (s, 3H), 2.30 (s, 3H), 2.55–2.60 (m, 2H), 4.11 (s, 3H), 4.17 (s, 3H), 4.92–4.93 (m, 1H), 6.48 (s, 1H), 6.59 (s, 1H), 6.96 (s, 1H), 7.65 (s, 1H), 7.93 (s, 1H), 8.15 (s, 1H), 8.47 (s, 1H) Mass spectrometry value (ESI-MS, m/z): 450 (M$^+$+1)

Example 410

1-Ethyl-3-butynyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 5-hexyn-3-ol (23 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (43 mg, yield 59%).

$^1$H-NMR (CDCl$_3$-d$_1$, 400 MHz): δ 1.01 (t, J=7.6 Hz, 3H), 1.79–1.81 (m, 2H), 2.04–2.05 (m, 1H), 2.11 (s, 3H), 2.29 (s, 3H), 2.57–2.61 (m, 2H), 4.12 (s, 3H), 4.17 (s, 3H), 4.90–4.93 (m, 1H), 6.50 (s, 1H), 6.56 (d, J=6.3 Hz, 1H), 7.03 (d, J=9.0 Hz, 1H), 7.67 (s, 1H), 7.75 (s, 1H), 8.16 (s, 1H), 8.45 (s, 1H) Mass spectrometry value (ESI-MS, m/z): 450 (M$^+$+1)

Example 411

1-Methylhexyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-heptanol (30 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was, then concentrated. The residue was purified on a column using chloroform/methanol to give the title compound (25 mg, yield 31%).

$^1$H-NMR (CDCl$_3$-d$_1$, 400 MHz): δ 0.91 (t, J=7.1 Hz, 3H), 1.26–1.32 (m, 11H), 4.11 (s, 3H), 4.17 (s, 3H), 4.92–4.96 (m, 1H), 6.70 (s, 1H), 6.72 (s, 1H), 7.18 (d, J=8.5 Hz, 2H), 7.61 (d, J=8.3 Hz, 2H), 7.64 (s, 1H), 8.15 (s, 1H), 8.46 (s, 1H) Mass spectrometry value (ESI-MS, m/z): 440 (M$^+$+1)

Example 412

1-Methylhexyl N-{4-[(6,7-dimethoxy-4-quinolyl oxy]-2,5-dimethylphenyl}carbamate

4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (54 mg, yield 72%).

$^{1}$H-NMR (CDCl$_3$-d$_1$, 400 MHz): δ 0.91 (t, J=7.1 Hz, 3H), 1.31–1.32 (m, 11H), 2.13 (s, 3H), 2.29 (s, 3H), 4.11 (s, 3H), 4.17 (s, 3H), 4.93–4.95 (m, 1H), 6.39 (s, 1H), 6.58 (d, J=5.6 Hz, 1H), 6.95 (s, 1H), 7.65 (s, 1H), 7.96 (s, 1H), 8.15 (s, 1H), 8.45 (s, 1H) Mass spectrometry value (ESI-MS, m/z): 468 (M$^+$+1)

Example 413

1-Methylhexyl N-{4-[(6,7-dimethoxy-4-quinolyl) oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-heptanol (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (49 mg, yield 65%).

$^{1}$H-NMR (CDCl$_3$-d$_1$, 400 MHz): δ 0.91 (t, J=6.6 Hz, 3H), 1.30–1.32 (m, 11H), 2.12 (s, 3H), 2.29 (s, 3H), 4.12 (s, 3H), 4.18 (s, 3H), 4.93–4.94 (m, 1H), 6.41 (s, 1H), 7.03 (s, 1H), 7.67 (s, 1H), 7.79 (s, 1H), 8.15 (s, 1H) Mass spectrometry value (ESI-MS, m/z): 468 (M$^+$+1)

Example 414

3-Piperidinopropyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-piperidino-1-propanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (90 mg, yield 100%).

$^{1}$H-NMR (CDCl$_3$-d$_1$, 400 MHz): δ 1.26 (s, 4H), 1.87–1.96 (m, 2H), 2.13 (s, 3H), 2.29–2.42 (m, 2H), 2.33 (s, 3H), 2.64–2.73 (m, 2H), 3.11–3.16 (m, 2H), 3.61–3.63 (m, 2H), 4.11 (s, 3H), 4.17 (s, 3H), 4.31 (t, J=5.6 Hz, 2H), 6.59 (d, J=6.6 Hz, 1H), 6.96 (s, 1H), 7.65 (s, 1H), 7.84 (s, 1H), 8.15 (s, 1H), 8.47 (s, 1H) Mass spectrometry value (ESI-MS, m/z): 495 (M$^+$+1)

Example 415

3-Piperidinopropyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-piperidino-1-propanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (62 mg, yield 73%).

$^{1}$H-NMR (CDCl$_3$-d$_1$, 400 MHz): δ 1.62 (brs, 8H), 2.01 (brs, 2H), 2.13 (s, 3H), 2.27 (s, 3H), 3.00 (brs, 2H), 4.06 (s, 3H), 4.07 (s, 3H), 4.29 (t, J=5.9 Hz, 2H), 6.27 (d, J=5.1 Hz, 1H), 6.99 (d, J=8.8 Hz, 1H), 7.44 (s, 1H), 7.57 (s, 1H), 7.61 (s, 1H), 8.44 (d, J=5.4 Hz, 1H) Mass spectrometry value (ESI-MS, m/z): 495 (M$^+$+1)

Example 416

1,3-Dioxo-2,3-dihydro-1H-2-isoindolyl N-{4-[(6,7-dimethoxy-4-quinolyl)oxy]phenyl}carbamate 4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-hydroxy-1,3-isoindolinedione (42 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (11 mg, yield 12%).

$^{1}$H-NMR (CDCl$_3$-d$_1$, 400 MHz): δ 4.12 (s, 3H), 4.18 (s, 3H), 6.83 (d, J=6.1 Hz, 1H), 7.39 (d, J=9.0 Hz, 2H), 7.66 (s, 1H), 7.72 (d, J=9.0 Hz, 2H), 7.85–7.87 (m, 2H), 8.00–8.02 (m, 3H), 8.19 (s, 1H), 8.52–8.53 (m, 1H) Mass spectrometry value (ESI-MS, m/z): 486 (M$^+$+1)

Example 417

(1,3-Dioxo-2,3-dihydro-1H-2-isoindolyl)methyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(hydroxymethyl)-1,3-isoindolinedione (41 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (48 mg, yield 57%).

$^1$H-NMR (CDCl$_3$-d$_1$, 400 MHz): δ 2.13 (s, 3H), 2.25 (s, 3H), 3.10–3.11 (m, 1H), 4.10 (s, 3H), 4.17 (s, 3H), 5.87 (s, 1H), 6.50 (s, 1H), 6.55 (s, 1H), 6.94 (s, 1H), 7.64 (s, 1H), 7.81–7.83 (m, 2H), 7.96–7.98 (m, 2H), 8.15 (s, 1H), 8.46 (brs, 1H) Mass spectrometry value (ESI-MS, m/z): 529 (M$^+$+1)

Example 418

(1,3-Dioxo-2,3-dihydro-1H-2-isoindolyl)methyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(hydroxymethyl)-1,3-isoindolinedione (41 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (14 mg, yield 17%).

$^1$H-NMR (CDCl$_3$-d$_1$, 400 MHz): δ 2.09 (s, 3H), 2.24 (s, 3H), 3.10–3.11 (m, 1H), 4.11 (s, 3H), 4.17 (s, 3H), 5.27 (s, 1H), 5.87 (s, 1H), 6.53 (s, 1H), 7.01–7.04 (m, 1H), 7.66–7.96 (m, 7H) Mass spectrometry value (ESI-MS, m/z): 529 (M$^+$+1)

Example 419

2-(1,3-Dioxo-2,3-dihydro-1H-2-isoindolyl)ethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(2-hydroxyethyl)-1,3-isoindolinedione (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (57 mg, yield 66%).

$^1$H-NMR (CDCl$_3$-d$_1$, 400 MHz): δ 2.10 (s, 3H), 2.26 (s, 3H), 4.05 (t, J=5.1 Hz, 2H), 4.11 (s, 3H), 4.17 (s, 3H), 4.46 (t, J=5.4 Hz, 2H), 6.42 (s, 1H), 6.59 (d, J=6.3 Hz, 1H), 6.94 (s, 1H), 7.64 (s, 1H), 7.75–7.77 (m, 3H), 7.87–7.89 (m, 2H), 8.15 (s, 1H), 8.47 (t, J=6.3 Hz, 1H) Mass spectrometry value (ESI-MS, m/z): 543 (M$^+$+1)

Example 420

2-(1,3-Dioxo-2,3-dihydro-1H-2-isoindolyl)ethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-(2-hydroxyethyl)-1,3-isoindolinedione (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (21 mg, yield 24%).

$^1$H-NMR (CDCl$_3$-d$_1$, 400 MHz): δ 2.08 (s, 3H), 2.24 (s, 3H), 4.05 (t, J=5.1 Hz, 2H), 4.11 (s, 3H), 4.17 (s, 3H), 4.46 (t, J=5.4 Hz, 2H), 6.45 (s, 1H), 6.55 (s, 1H), 6.99 (d, J=8.5 Hz, 1H), 7.66 (s, 2H), 7.74–7.76 (m, 2H), 7.86–7.88 (m, 2H), 8.16 (s, 1H), 8.46 (s, 1H) Mass spectrometry value (ESI-MS, m/z): 543 (M$^+$+1)

Example 421

3-Morpholinopropyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-morpholino-1-propanol (38 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (38 mg, yield 41%).

$^1$H-NMR (CDCl$_3$-d$_1$, 400 MHz): δ 1.89–1.96 (m, 2H), 2.51–2.53 (m, 6H), 3.76 (t, J=4.9 Hz, 4H), 4.05 (s, 3H), 4.06 (s, 3H), 4.27 (t, J=6.6 Hz, 2H), 6.45 (d, J=5.4 Hz, 1H), 6.74 (s, 1H), 7.15 (d, J=9.0 Hz, 2H), 7.45 (s, 1H), 7.49 (d, J=8.8 Hz, 2H), 7.56 (s, 1H), 8.48 (d, J=5.4 Hz, 1H) Mass spectrometry value (ESI-MS, m/z): 469 (M$^+$+1)

Example 422

3-Morpholinopropyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-morpholino-1-propanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (56 mg, yield 66%).

$^1$H-NMR (CDCl$_3$-d$_1$, 400 MHz): δ 1.89–1.96 (m, 2H), 2.15 (s, 3H), 2.25 (s, 3H), 2.50 (brs, 6H), 3.75 (t, J=4.6 Hz, 4H), 4.057 (s, 3H), 4.063 (s, 3H), 4.27 (t, J=6.6 Hz, 2H), 6.30 (d, J=5.1 Hz, 1H), 6.38 (s, 1H), 6.93 (s, 1H), 7.45 (s, 1H), 7.59 (s, 1H), 7.77 (s, 1H), 8.45 (d, J=5.1 Hz, 1H) Mass spectrometry value (ESI-MS, m/z): 497 (M$^+$+1)

Example 423

3-Morpholinopropyl N-{4-[(6,7-dimethoxy-4-quinolyl)oxy]-2,5-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-morpholino-1-propanol (33 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (66 mg, yield 77%).

$^1$H-NMR (CDCl$_3$-d$_1$, 400 MHz): δ 2.10 (s, 3H), 2.31 (s, 3H), 2.39 (brs, 2H), 2.93 (brs, 2H), 3.22 (brs, 2H), 3.53 (brs, 2H), 4.00–4.03 (m, 2H), 4.12 (s, 3H), 4.17 (s, 3H), 4.32 (brs, 4H), 6.57 (s, 1H), 7.01 (brs, 1H), 7.67 (s, 2H), 8.14 (s, 1H), 8.50 (s, 1H) Mass spectrometry value (ESI-MS, m/z): 497 (M$^+$+1)

Example 424

3-(4-Methylpiperazino)propyl N-{4-[(6,7-dimethoxy-4-quinolyl)oxy]phenyl}carbamate 4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-(4-methylpiperazino)-1-propanol (41 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (9 mg, yield 9%).

$^1$H-NMR (CDCl$_3$-d$_1$, 400 MHz): δ 1.89–1.93 (m, 2H), 2.39 (s, 3H), 2.49–2.62 (m, 10H)), 4.05 (s, 6H), 4.25 (t, J=6.3 Hz, 2H), 6.44 (d, J=5.4 Hz, 1H), 6.79 (s, 1H), 7.15 (d, J=8.8 Hz, 2H), 7.42 (s, 1H), 7.49 (d, J=8.5 Hz, 2H), 7.56 (s, 1H), 8.48 (d, J=5.4 Hz, 1H) Mass spectrometry value (ESI-MS, m/z): 482 (M$^+$+1)

Example 425

3-(4-Methylpiperazino)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-(4-methylpiperazino)-1-propanol (36 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (33 mg, yield 36%).

$^1$H-NMR (CDCl$_3$-d$_1$, 400 MHz): δ 1.90–1.95 (m, 2H), 2.15 (s, 3H), 2.25 (s, 3H), 2.35 (s, 3H), 2.42–2.53 (m, 10H), 4.05 (s, 3H), 4.06 (s, 3H), 4.25 (t, J=6.3 Hz, 2H), 6.29 (d, J=5.4 Hz, 1H), 6.38 (s, 1H), 6.92 (s, 1H), 7.42 (s, 1H), 7.59 (s, 1H), 7.75 (s, 1H), 8.45 (d, J=5.4 Hz, 1H) Mass spectrometry value (ESI-MS, m/z): 509 (M$^+$+1)

Example 426

3-(Diethylamino)propyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-(diethylamino)-1-propanol (34 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (32 mg, yield 36%).

$^1$H-NMR (CDCl$_3$-d$_1$, 400 MHz): δ 1.39 (t, J=7.1 Hz, 6H), 2.20–2.22 (m, 2H), 3.14–3.16 (m, 6H), 4.04 (s, 6H), 4.30 (t, J=5.6 Hz, 2H), 6.44 (d, J=5.1 Hz, 1H), 7.12 (d, J=8.8 Hz, 2H), 7.42 (s, 1H), 7.56 (s, 1H), 7.64 (d, J=8.1 Hz, 2H), 7.47 (d, J=5.1 Hz, 1H), 8.77 (brs, 1H) Mass spectrometry value (ESI-MS, m/z): 455 (M$^+$+1)

Example 427

3-(Diethylamino)propyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-(diethylamino)-1-propanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (50 mg, yield 61%).

$^1$H-NMR (CDCl$_3$-d$_1$, 400 MHz): δ 1.32 (t, J=7.1 Hz, 6H), 2.14 (s, 3H), 2.17–2.19 (m, 2H), 2.28 (s, 3H), 2.94–3.01 (m, 6H), 4.05 (s, 3H), 4.06 (s, 3H), 4.30 (t, J=5.9 Hz, 2H), 6.30 (d, J=5.4 Hz, 1H), 6.93 (s, 1H), 7.11 (s, 1H), 7.42 (s, 1H), 7.59 (s, 1H), 7.68 (s, 1H), 8.44 (d, J=5.1 Hz, 1H) Mass spectrometry value (ESI-MS, m/z): 483 (M$^+$+1)

Example 428

3-(Diethylamino)propyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-(diethylamino)-1-propanol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (65 mg, yield 78%).

$^1$H-NMR (CDCl$_3$-d$_1$, 400 MHz): δ 1.47 (t, J=7.1 Hz, 6H), 2.09 (s, 3H), 2.30 (s, 2H), 2.33 (s, 3H), 3.24 (brs, 6H), 4.12 (s, 3H), 4.17 (s, 3H), 4.33 (s, 2H), 6.57 (s, 1H), 7.01 (d, J=8.5 Hz, 1H), 7.67 (s, 2H), 8.15 (s, 1H), 8.46 (s, 1H) Mass spectrometry value (ESI-MS, m/z): 483 (M$^+$+1)

Example 429

3-(Diethylamino)propyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-(diethylamino)-1-propanol (34 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (25 mg, yield 27%).

$^1$H-NMR (CDCl$_3$-d$_1$, 400 MHz): δ 1.24–1.35 (m, 6H), 2.16–2.17 (m, 2H), 3.05 (brs, 6H), 4.07 (s, 6H), 4.28 (s, 2H), 7.19 (d, J=8.5 Hz, 2H), 7.31 (s, 1H), 7.55 (s, 1H), 7.60 (d, J=8.5 Hz, 2H), 8.22 (s, 1H), 8.60 (s, 1H) Mass spectrometry value (ESI-MS, m/z): 456 (M$^+$+1)

Example 430

2-Pyridylmethyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-pyridylmethanol (25 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (75 mg, yield 94%).

$^1$H-NMR (CDCl$_3$-d$_1$, 400 MHz): δ 2.12 (s, 3H), 2.50 (s, 3H), 4.11 (s, 3H), 4.17 (s, 3H), 5.70 (s, 2H), 6.60 (s, 1H), 6.97 (s, 1H), 7.66 (s, 1H), 7.84–7.96 (m, 4H), 8.15 (s, 1H), 8.48 (s, 2H), 9.02 (s, 1H) Mass spectrometry value (ESI-MS, m/z): 461 (M$^+$+1)

Example 431

2-Pyridylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-pyridylmethanol (25 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (50 mg, yield 63%).

$^1$H-NMR (CDCl$_3$-d$_1$, 400 MHz): δ 2.10 (s, 3H), 2.47 (s, 3H), 4.12 (s, 3H), 4.17 (s, 3H), 5.70 (s, 2H), 6.59 (d, J=5.9 Hz, 1H), 7.00 (d, J=9.5 Hz, 1H), 7.68 (s, 2H), 7.75–7.97 (m, 3H), 8.15 (s, 1H), 8.48 (t, J=7.1 Hz, 2H), 9.02 (d, J=4.6 Hz, 1H) Mass spectrometry value (ESI-MS, m/z): 461 (M$^+$+1)

Example 432

3-Pyridylmethyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 3-pyridylmethanol (25 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (80 mg, yield 100%).

$^1$H-NMR (CDCl$_3$-d$_1$, 400 MHz): δ 2.12 (s, 3H), 2.33 (s, 3H), 4.12 (s, 3H), 4.17 (s, 3H), 5.47 (s, 2H), 6.58 (d, J=6.8 Hz, 1H), 7.04 (d, J=8.8 Hz, 1H), 7.67 (s, 2H), 7.98–8.01 (m, 1H), 8.14 (s, 1H), 8.46 (d, J=8.1 Hz, 1H), 8.53 (s, 1H), 8.79 (d, J=5.4 Hz, 1H), 9.22 (s, 1H) Mass spectrometry value (ESI-MS, m/z): 461 (M$^+$+1)

Example 433

4-Pyridylmethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-pyridylmethanol (28 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (10 mg, yield 12%).

$^1$H-NMR (CDCl$_3$-d$_1$, 400 MHz): δ 4.046 (s, 3H), 4.049 (s, 3H), 5.24 (s, 2H), 6.45 (d, J=5.4 Hz, 1H), 7.17 (d, J=8.8 Hz, 2H), 7.23 (s, 1H), 7.30 (d, J=5.4 Hz, 2H), 7.45 (s, 1H), 7.53 (d, J=8.3 Hz, 2H), 7.56 (s, 1H), 8.48 (d, J=5.4 Hz, 1H), 8.62 (d, J=5.4 Hz, 2H) Mass spectrometry value (ESI-MS, m/z): 433 (M$^+$+1)

Example 434

4-Pyridylmethyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 4-pyridylmethanol (28 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (21 mg, yield 23%).

$^1$H-NMR (CDCl$_3$-d$_1$, 400 MHz): δ 4.069 (s, 3H), 4.073 (s, 3H), 5.25 (s, 2H), 7.22–7.27 (m, 2H), 7.32 (d, J=5.9 Hz, 2H), 7.34 (s, 1H), 7.53 (d, J=8.8 Hz, 2H), 7.55 (s, 1H), 8.63 (d, J=6.3 Hz, 3H) Mass spectrometry value (ESI-MS, m/z): 433 (M$^+$+1)

Example 435

2-(Diethylamino)ethyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-(diethylamino)-1-ethanol (31 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (53 mg, yield 61%).

$^1$H-NMR (CDCl$_3$-d$_1$, 400 MHz): δ 1.08 (t, J=7.1 Hz, 6H), 2.65 (q, J=7.1 Hz, 4H), 2.79 (t, J=5.9 Hz, 2H), 4.04 (s, 3H), 4.05 (s, 3H), 4.28 (t, J=5.9 Hz, 2H), 6.44 (d, J=5.4 Hz, 1H), 7.13–7.15 (m, 2H), 7.25–7.28 (m, 1H), 7.42 (s, 1H), 7.50 (d, J=8.8 Hz, 2H), 7.56 (s, 1H), 8.48 (d, J=5.4 Hz, 1H) Mass spectrometry value (ESI-MS, m/z): 441 (M$^+$+1)

Example 436

2-(Diethylamino)ethyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-(diethylamino)-1-ethanol (31 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (66 mg, yield 71%).

$^1$H-NMR (CDCl$_3$-d$_1$, 400 MHz): δ 1.10 (t, J=7.1 Hz, 6H), 2.67 (q, J=7.1 Hz, 4H), 2.80 (t, J=5.9 Hz, 2H), 4.06 (s, 3H), 4.07 (s, 3H), 4.28 (t, J=5.9 Hz, 2H), 7.10 (s, 1H), 7.19–7.21 (m, 2H), 7.32 (s, 1H), 7.51 (d, J=8.8 Hz, 2H), 7.55 (s, 1H), 8.62 (s, 1H) Mass spectrometry value (ESI-MS, m/z): 442 (M$^+$+1)

Example 437

1-(2-Morpholinoethyl)butyl N-{4-[(6,7-dimethoxy-4-quinolyl)oxy]phenyl}carbamate

4-[(6,7-Dimethoxy-4-quinolyl)oxy]aniline (50 mg) was added to toluene. (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-morpholino-3-hexanol (49 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (80 mg, yield 81%).
$^1$H-NMR (CDCl$_3$-d$_1$, 400 MHz): δ 0.91–0.96 (m, 3H), 1.36–1.82 (m, 6H), 2.41–2.45 (m, 6H), 3.70–3.72 (m, 4H), 4.04 (s, 3H), 4.05 (s, 3H), 4.95–4.97 (m, 1H), 6.44 (d, J=5.1 Hz, 1H), 7.14 (d, J=8.8 Hz, 2H), 7.30 (s, 1H), 7.42 (s, 1H), 7.53 (d, J=8.5 Hz, 2H), 7.57 (s, 1H), 8.47 (d, J=5.4 Hz, 1H) Mass spectrometry value (ESI-MS, m/z): 511 (M$^+$+1)

Example 438

1-(2-Morpholinoethyl)butyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-morpholino-3-hexanol (43 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (74 mg, yield 81%).
$^1$H-NMR (CDCl$_3$-d$_1$, 400 MHz): δ 0.96 (t, J=7.3 Hz, 3H), 1.39–1.48 (m, 2H), 1.55–1.67 (m, 2H), 1.79–1.88 (m, 2H), 2.15 (s, 3H), 2.26 (s, 3H), 2.44–2.47 (m, 6H), 3.69–3.74 (m, 4H), 4.05 (s, 3H), 4.06 (s, 3H), 4.93–5.00 (m, 1H), 6.29 (d, J=5.1 Hz, 1H), 6.51 (s, 1H), 6.93 (s, 1H), 7.29 (s, 1H), 7.42 (s, 1H), 7.60 (s, 1H), 7.79 (s, 1H), 8.44 (d, J=5.1 Hz, 1H) Mass spectrometry value (ESI-MS, m/z): 539 (M$^+$+1)

Example 439

1-(2-Morpholinoethyl)butyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-morpholino-3-hexanol (43 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (82 mg, yield 90%).
$^1$H-NMR (CDCl$_3$-d$_1$, 400 MHz): δ 0.96 (t, J=7.3 Hz, 3H), 1.39–1.46 (m, 2H), 1.57–1.64 (m, 2H), 1.78–1.86 (m, 2H), 2.13 (s, 3H), 2.26 (s, 3H), 2.46 (s, 6H), 3.69–3.73 (m, 4H), 4.04 (s, 3H), 4.07 (s, 3H), 4.95–4.97 (m, 1H), 6.27 (d, J=5.4 Hz, 1H), 6.75 (s, 1H), 7.00 (d, J=8.5 Hz, 1H), 7.31 (s, 1H), 7.42 (s, 1H), 7.59 (s, 1H), 7.62 (s, 1H), 8.43 (d, J=5.1 Hz, 1H) Mass spectrometry value (ESI-MS, m/z): 539 (M$^+$+1)

Example 440

1-(2-Morpholinoethylbutyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-morpholino-3-hexanol (49 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (77 mg, yield 73%).
$^1$H-NMR (CDCl$_3$-d$_1$, 400 MHz): δ 0.84–0.88 (m, 3H), 1.28–1.75 (m, 6H), 2.34–2.37 (m, 6H), 3.63–3.65 (m, 4H), 3.98 (s, 3H), 3.99 (s, 3H), 4.86–4.87 (m, 1H), 7.00 (s, 1H), 7.12 (d, J=8.8 Hz, 2H), 7.24 (s, 1H), 7.43 (d, J=8.5 Hz, 2H), 7.48 (s, 1H), 8.54 (s, 1H) Mass spectrometry value (ESI-MS, m/z): 512 (M$^+$+1)

Example 441

1-[2-(Diethylamino)ethyl]butyl N-{4-[(6,7-dimethoxy-4-quinolyl)oxy]phenyl}carbamate 4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-(diethylamino)-3-hexanol (45 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (10 mg, yield 10%).

¹H-NMR (CDCl₃-d₁, 400 MHz): δ 0.96 (t, J=7.6 Hz, 3H), 1.28 (t, J=7.6 Hz, 6H), 1.38–1.46 (m, 2H), 1.55–1.73 (m, 4H), 2.93–2.95 (m, 6H), 4.05 (s, 6H), 4.90–4.93 (m, 1H), 6.44 (d, J=5.4 Hz, 1H), 7.14 (d, J=9.0 Hz, 2H), 7.42 (s, 1H), 7.54 (d, J=9.0 Hz, 2H), 7.56 (s, 1H), 8.47 (d, J=5.1 Hz, 1H) Mass spectrometry value (ESI-MS, m/z): 497 (M⁺+1)

Example 442

1-[2-(Diethylamino)ethyl]butyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-(diethylamino)-3-hexanol (40 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (29 mg, yield 32%).

¹H-NMR (CDCl₃-d₁, 400 MHz): δ 0.96 (t, J=7.3 Hz, 3H), 1.20 (t, J=7.3 Hz, 6H), 1.37–1.49 (m, 2H), 1.55–1.71 (m, 2H), 1.93–1.98 (m, 2H), 2.15 (s, 3H), 2.26 (s, 3H), 2.76–2.80 (m, 6H), 4.05 (s, 3H), 4.06 (s, 3H), 4.89–4.96 (m, 1H), 6.29 (d, J=5.4 Hz, 1H), 6.59 (s, 1H), 6.93 (s, 1H), 7.42 (s, 1H), 7.59 (s, 1H), 7.76 (s, 1H), 8.44 (d, J=5.4 Hz, 1H) Mass spectrometry value (ESI-MS, m/z): 525 (M⁺+1)

Example 443

1-[2-(Diethylamino)ethyl]butyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-(diethylamino)-3-hexanol (40 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (30 mg, yield 34%).

¹H-NMR (CDCl₃-d₁, 400 MHz): δ 0.96 (t, J=7.3 Hz, 3H), 1.19 (t, J=6.6 Hz, 6H), 1.41–1.45 (m, 2H), 1.60–1.68 (m, 2H), 1.95 (brs, 2H), 2.12 (s, 3H), 2.26 (s, 3H), 2.78–2.80 (m, 6H), 4.05 (s, 3H), 4.07 (s, 3H), 4.92 (brs, 1H), 6.26 (d, J=5.1 Hz, 1H), 6.65 (s, 1H), 6.99 (d, J=8.5 Hz, 1H), 7.27 (s, 1H), 7.43 (s, 1H), 7.61 (s, 1H), 8.43 (d, J=4.9 Hz, 1H) Mass spectrometry value (ESI-MS, m/z): 525 (M⁺+1)

Example 444

1-[2-(Diethylamino)ethyl]butyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-(diethylamino)-3-hexanol (45 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (5 mg, yield 5%).

¹H-NMR (CDCl₃-d₁, 400 MHz): δ 0.93–1.02 (m, 3H), 1.26 (t, J=6.8 Hz, 6H), 1.37–1.45 (m, 2H), 1.54–2.03 (m, 4H), 2.90 (brs, 6H), 4.067 (s, 3H), 4.072 (s, 3H), 4.90–4.93 (m, 1H), 7.21 (d, J=8.8 Hz, 2H), 7.32 (s, 1H), 7.49–7.56 (m, 3H), 8.61 (s, 1H) Mass spectrometry value (ESI-MS, m/z): 498 (M⁺+1)

Example 445

1-(2-Piperidinoethyl)butyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-piperidino-3-hexanol (48 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (57 mg, yield 58%).

¹H-NMR (CDCl₃-d₁, 400 MHz): δ 0.94 (t, J=7.3 Hz, 3H), 1.35–1.46 (m, 4H), 1.52–1.67 (m, 6H), 1.85–1.90 (m, 2H), 2.40–2.56 (m, 6H), 4.04 (s, 3H), 4.05 (s, 3H), 4.90–4.93 (m, 1H), 6.44 (d, J=5.4 Hz, 1H), 7.14 (d, J=8.8 Hz, 2H), 7.28 (s, 3H), 7.42 (s, 1H), 7.52 (d, J=8.8 Hz, 2H), 7.56 (s, 1H), 8.47 (d, J=5.4 Hz, 1H) Mass spectrometry value (ESI-MS, m/z): 509 (M⁺+1)

Example 446

1-(2-Piperidinoethyl)butyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-piperidino-3-hexanol (43 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (75 mg, yield 82%).

$^1$H-NMR (CDCl$_3$-d$_1$, 400 MHz): δ 0.96 (t, J=7.3 Hz, 3H), 1.38–1.46 (m, 4H), 1.57–1.67 (m, 6H), 1.84–1.89 (m, 2H), 2.15 (s, 3H), 2.25 (s, 3H), 2.43–2.47 (m, 6H), 4.05 (s, 3H), 4.06 (s, 3H), 4.89–4.95 (m, 1H), 6.29 (d, J=5.1 Hz, 1H), 6.49 (s, 1H), 6.92 (s, 1H), 7.42 (s, 1H), 7.60 (s, 1H), 7.78 (s, 1H), 8.44 (d, J=5.1 Hz, 1H) Mass spectrometry value (ESI-MS, m/z): 537 (M$^+$+1)

Example 447

1-(2-Piperidinoethylbutyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-piperidino-3-hexanol (43 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (76 mg, yield 83%).

$^1$H-NMR (CDCl$_3$-d$_1$, 400 MHz): δ 0.95 (t, J=7.1 Hz, 3H), 1.46 (brs, 4H), 1.64 (brs, 6H), 1.87–1.88 (m, 2H), 2.04 (s, 3H), 2.12 (s, 3H), 2.26 (brs, 6H), 4.05 (s, 3H), 4.07 (s, 3H), 4.92 (brs, 1H), 6.26 (d, J=4.9 Hz, 1H), 6.68 (s, 1H), 6.99 (d, J=8.8 Hz, 1H), 7.42 (s, 1H), 7.62 (s, 2H), 8.43 (d, J=4.9 Hz, 1H) Mass spectrometry value (ESI-MS, m/z): 537 (M$^+$+1)

Example 448

1-(2-Piperidinoethyl)butyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-piperidino-3-hexanol (48 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (75 mg, yield 71%).

$^1$H-NMR (CDCl$_3$-d$_1$, 400 MHz): δ 0.86 (t, J=7.1 Hz, 3H), 1.30–1.33 (m, 4H), 1.39–1.57 (m, 6H), 1.77–1.80 (m, 2H), 2.34–2.41 (m, 6H), 3.99 (s, 3H), 4.00 (s, 3H), 4.82–4.83 (m, 1H), 7.12 (d, J=8.5 Hz, 2H), 7.21 (s, 1H), 7.25 (s, 1H), 7.44 (d, J=8.3 Hz, 2H), 7.48 (s, 1H), 8.54 (s, 1H) Mass spectrometry value (ESI-MS, m/z): 510 (M$^+$+1)

Example 449

1-[2-(4-Methylpiperazino)ethyl]butyl N-{4-[(6,7-dimethoxy-4-quinolyl)oxy]phenyl}carbamate 4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-(4-methylpiperazino)-3-hexanol (52 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (37 mg, yield 35%).

$^1$H-NMR (CDCl$_3$-d$_1$, 400 MHz): δ 0.95 (t, J=7.1 Hz, 3H), 1.37–1.44 (m, 2H), 1.56–1.65 (m, 2H), 1.78–1.83 (m, 2H), 2.30 (s, 3H), 2.44–2.48 (m, 10H), 4.047 (s, 3H), 4.050 (s, 3H), 4.93–4.94 (m, 1H), 6.43 (d, J=5.4 Hz, 1H), 6.97 (s, 1H), 7.14 (d, J=9.0 Hz, 2H), 7.42 (s, 1H), 7.50 (d, J=8.5 Hz, 2H), 7.56 (s, 1H), 8.47 (d, J=5.4 Hz, 1H) Mass spectrometry value (ESI-MS, m/z): 524 (M$^+$+1)

Example 450

1-[2-(4-Methylpiperazino)ethyl]butyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-(4-methylpiperazino)-3-hexanol (46 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (48 mg, yield 49%).

$^1$H-NMR (CDCl$_3$-d$_1$, 400 MHz): δ 0.96 (t, J=7.3 Hz, 3H), 1.39–1.46 (m, 2H), 1.58–1.64 (m, 2H), 1.82–1.85 (m, 2H), 2.15 (s, 3H), 2.25 (s, 3H), 2.31 (s, 3H), 2.48–2.50 (m, 10H), 4.05 (s, 3H), 4.07 (s, 3H), 6.29 (d, J=5.1 Hz, 1H), 6.41 (s, 1H), 6.93 (s, 1H), 7.43 (s, 1H), 7.60 (s, 1H), 7.79 (s, 1H), 8.44 (d, J=5.1 Hz, 1H) Mass spectrometry value (ESI-MS, m/z): 552 (M$^+$+1)

Example 451

1-[2-(4-Methylpiperazino)ethyl]butyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 1-(4-methylpiperazino)-3-hexanol (46 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (25 mg, yield 25%).
$^1$H-NMR (CDCl$_3$-d$_1$, 400 MHz): δ 0.96 (t, J=7.3 Hz, 3H), 1.40–1.45 (m, 2H), 1.57–1.63 (m, 2H), 1.82–1.84 (m, 2H), 2.12 (s, 3H), 2.25 (s, 3H), 2.31 (s, 3H), 2.46–2.49 (m, 10H), 4.05 (s, 3H), 4.07 (s, 3H), 4.94 (brs, 1H), 6.25 (d, J=5.1 Hz, 1H), 6.45 (s, 1H), 6.99 (d, J=8.8 Hz, 1H), 7.43 (s, 1H), 7.62 (s, 2H), 8.43 (d, J=5.1 Hz, 1H) Mass spectrometry value (ESI-MS, m/z): 552 (M$^+$+1)

Example 452

1-[2-(4-Methylpiperazino)ethyl]butyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 1-(4-methylpiperazino)-3-hexanol (52 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (12 mg, yield 11%).
$^1$H-NMR (CDCl$_3$-d$_1$, 400 MHz): δ 1.11 (t, J=7.1 Hz, 3H), 1.37–1.42 (m, 2H), 1.53–1.60 (m, 2H), 1.70–1.80 (m, 2H), 2.21 (s, 3H), 2.31–2.50 (m, 10H), 4.07 (s, 6H), 4.94 (brs, 1H), 6.78 (s, 1H), 7.20 (d, J=8.5 Hz, 1H), 7.32 (s, 1H), 7.50 (d, J=8.5 Hz, 2H), 7.56 (s, 1H), 8.61 (s, 2H) Mass spectrometry value (ESI-MS, m/z): 525 (M$^+$+1)

Example 453

Cyano(phenyl)methyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-hydroxy-2-phenylacetonitrile (35 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (20 mg, yield 24%).
$^1$H-NMR (CDCl$_3$-d$_1$, 400 MHz): δ 4.04 (s, 3H), 4.06 (s, 3H), 5.95 (s, 1H), 6.58 (d, J=5.1 Hz, 1H), 7.27 (s, 1H), 7.30 (d, J=9.0 Hz, 2H), 7.46–7.58 (m, 8H), 8.54 (d, J=5.4 Hz, 1H) Mass spectrometry value (ESI-MS, m/z): 457 (M$^+$+1)

Example 454

Cyano(phenyl)methyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-hydroxy-2-phenylacetonitrile (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (30 mg, yield 39%).
$^1$H-NMR (CDCl$_3$-d$_1$, 400 MHz): δ 2.11–2.27 (m, 6H), 4.05 (s, 3H), 4.06 (s, 3H), 5.96–6.01 (m, 1H), 6.41–6.43 (m, 1H), 7.05–7.12 (m, 1H), 7.24–7.27 (m, 1H), 7.46–7.54 (m, 7H), 8.49–8.51 (m, 1H) Mass spectrometry value (ESI-MS, m/z): 485 (M$^+$+1)

Example 455

Cyano(phenyl)methyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (68 mg) in methylene chloride was then added thereto, and the mixture was heated under reflux for 10 min. Next, 2-hydroxy-2-phenylacetonitrile (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (30 mg, yield 39%).
$^1$H-NMR (CDCl$_3$-d$_1$, 400 MHz): δ 2.10–2.26 (m, 6H), 4.06 (s, 6H), 5.98–6.02 (m, 1H), 6.36–6.38 (m, 1H), 7.08–7.12 (m, 1H), 7.20–7.27 (m, 1H), 7.46–7.57 (m, 7H), 8.47–8.49 (m, 1H) Mass spectrometry value (ESI-MS, m/z): 485 (M$^+$+1)

Example 456

2-Cyanophenyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 2-hydroxyphenyl cyanide (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (5 mg, yield 6%).

$^1$H-NMR (CDCl$_3$-d$_1$, 400 MHz): δ 4.01 (s, 3H), 4.02 (s, 3H), 6.78–6.85 (m, 2H), 6.96–7.01 (m, 3H), 7.13–7.15 (m, 1H), 7.31–7.35 (m, 1H), 7.43–7.51 (m, 3H), 7.61 (s, 1H), 7.95 (s, 1H) Mass spectrometry value (ESI-MS, m/z): 443 (M$^+$+1)

Example 457

3-Cyanophenyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (77 mg) in methylene chloride was then added thereto, and the mixture was heated under reflux for 10 min. Next, 3-hydroxybenzonitrile (31 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (5 mg, yield 6%).

$^1$H-NMR (CDCl$_3$-d$_1$, 400 MHz): δ 4.11 (s, 3H), 4.19 (s, 3H), 6.78 (d, J=5.6 Hz, 1H), 7.52–7.54 (m, 1H), 7.60 (s, 1H), 7.73–7.76 (m, 2H), 8.20 (s, 1H), 8.55 (s, 1H) Mass spectrometry value (ESI-MS, m/z): 442 (M$^+$+1)

Example 458

3-Cyanophenyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 3-hydroxybenzonitrile (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).

$^1$H-NMR (CDCl$_3$-d$_1$, 400 MHz): δ 2.13–2.16 (m, 3H), 2.28–2.39 (m, 3H), 4.11 (s, 3H), 4.17 (s, 3H), 6.59 (d, J=6.8 Hz, 1H), 7.03 (s, 1H), 7.15–7.19 (m, 2H), 7.52–7.57 (m, 3H), 7.65 (s, 1H), 8.12–8.13 (m, 1H), 8.45–8.47 (m, 1H) Mass spectrometry value (ESI-MS, m/z): 471 (M$^+$+1)

Example 459

3-Cyanophenyl N-{4-[(6,7-dimethoxy-4-quinolyl)oxy]-2,3-dimethylphenyl}carbamate

4-[(6,7-Dimethoxy-4-quinolyl)oxy]-2,3-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 3-hydroxybenzonitrile (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).

$^1$H-NMR (CDCl$_3$-d$_1$, 400 MHz): δ 2.10–2.15 (m, 3H), 2.27–2.37 (m, 3H), 4.11 (s, 3H), 4.16 (s, 3H), 6.56 (d, J=6.6 Hz, 1H), 7.02–7.20 (m, 3H), 7.52–7.56 (m, 3H), 7.67 (s, 1H), 8.13–8.14 (m, 1H), 8.44–8.46 (m, 1H) Mass spectrometry value (ESI-MS, m/z): 471 (M$^+$+1)

Example 460

4-Cyanophenyl N-{4-[(6,7-dimethoxy-4-quinolyl)oxy]-2,5-dimethylphenyl}carbamate

4-[(6,7-Dimethoxy-4-quinolyl)oxy]-2,5-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 4-hydroxybenzonitrile (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).

$^1$H-NMR (CDCl$_3$-d$_1$, 400 MHz): δ 2.16 (s, 3H), 2.39 (s, 3H), 4.11 (s, 3H), 4.17 (s, 3H), 6.97 (d, J=8.3 Hz, 1H), 7.03 (s, 1H), 7.38 (d, J=8.1 Hz, 2H), 7.65 (s, 1H), 7.74 (d, J=8.3 Hz, 2H), 7.91 (brs, 1H), 8.15 (s, 1H), 8.49 (brs, 1H) Mass spectrometry value (ESI-MS, m/z): 471 (M$^+$+1)

Example 461

4-Cyanophenyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 4-hydroxybenzonitrile (27 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (40 mg, yield 53%).
$^1$H-NMR (CDCl$_3$-d$_1$, 400 MHz): δ 2.10–2.14 (m, 3H), 2.27–2.37 (m, 3H), 4.11–4.17 (m, 6H), 6.56 (d, J=6.1 Hz, 1H), 7.00 (d, J=8.8 Hz, 2H), 7.38 (d, J=8.8 Hz, 1H), 7.49 (d, J=9.0 Hz, 2H), 7.67 (s, 1H), 7.73 (d, J=8.8 Hz, 1H), 8.10–8.11 (m, 1H), 8.45–8.47 (m, 1H) Mass spectrometry value (ESI-MS, m/z): 471 (M$^+$+1)

Example 462

1-Methyl-3-piperidyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, 1-methyl-3-piperidinol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (23 mg, yield 27%).
$^1$H-NMR (CDCl$_3$-d$_1$, 400 MHz): δ 1.69–1.88 (m, 6H), 2.37 (s, 3H), 2.54–2.57 (m, 1H), 2.72 (brs, 1H), 4.05 (s, 6H), 5.02 (s, 1H), 6.44 (d, J=5.1 Hz, 1H), 7.14 (d, J=8.8 Hz, 2H), 7.42 (s, 1H), 7.50 (d, J=8.8 Hz, 2H), 7.56 (s, 1H), 8.47 (d, J=5.1 Hz, 1H) Mass spectrometry value (ESI-MS, m/z): 439 (M$^+$+1)

Example 463

1-Methyl-3-piperidyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 1-methyl-3-piperidinol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (29 mg, yield 36%).
$^1$H-NMR (CDCl$_3$-d$_1$, 400 MHz): δ 1.77 (brs, 2H), 1.97 (brs, 2H), 2.14 (s, 3H), 2.25 (s, 3H), 2.35 (s, 3H), 2.60–2.67 (m, 4H), 4.05 (s, 3H), 4.06 (s, 3H), 5.01 (d, J=4.1 Hz, 1H), 6.29 (d, J=5.1 Hz, 1H), 6.69 (s, 1H), 6.91 (s, 1H), 7.42 (s, 1H), 7.59 (s, 1H), 7.82 (s, 1H), 8.44 (d, J=5.1 Hz, 1H) Mass spectrometry value (ESI-MS, m/z): 467 (M$^+$+1)

Example 464

1-Methyl-3-piperidyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 1-methyl-3-piperidinol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (22 mg, yield 27%).
$^1$H-NMR (CDCl$_3$-d$_1$, 400 MHz): δ 1.69–1.90 (m, 6H), 2.11 (s, 3H), 2.26 (s, 3H), 2.37 (s, 3H), 2.62 (brs, 2H), 4.05 (s, 3H), 4.07 (s, 3H), 5.01 (s, 1H), 6.26 (d, J=5.4 Hz, 1H), 6.99 (d, J=8.8 Hz, 1H), 7.43 (s, 1H), 7.62 (s, 2H), 8.43 (d, J=5.4 Hz, 1H) Mass spectrometry value (ESI-MS, m/z): 467 (M$^+$+1)

Example 465

1-Methyl-3-piperidyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, 1-methyl-3-piperidinol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (26 mg, yield 28%).
$^1$H-NMR (CDCl$_3$-d$_1$, 400 MHz): δ 1.69–1.96 (m, 6H), 2.37 (s, 3H), 2.57–2.70 (m, 2H), 4.066 (s, 3H), 4.071 (s, 3H), 5.01 (s, 1H), 7.20 (d, J=8.8 Hz, 2H), 7.32 (s, 1H), 7.51 (d, J=9.0 Hz, 2H), 7.56 (s, 1H), 8.62 (s, 1H) Mass spectrometry value (ESI-MS, m/z): 440 (M$^+$+1)

Example 466

1-Methyl-4-piperidyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, 1-methyl-4-piperidinol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (41 mg, yield 47%).

$^1$H-NMR (CDCl$_3$-d$_1$, 400 MHz): δ 1.76–1.85 (m, 2H), 2.01–2.09 (m, 4H), 2.31 (s, 3H), 2.71 (brs, 2H), 4.05 (s, 6H), 4.82 (brs, 1H), 6.44 (d, J=5.1 Hz, 1H), 6.89 (s, 1H), 7.15 (d, J=8.8 Hz, 2H), 7.42 (s, 1H), 7.49 (d, J=8.8 Hz, 2H), 7.56 (s, 1H), 8.48 (d, J=5.1 Hz, 2H) Mass spectrometry value (ESI-MS, m/z): 439 (M$^+$+1)

Example 467

1-Methyl-4-piperidyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 1-methyl-4-piperidinol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (41 mg, yield 51%).

$^1$H-NMR (CDCl$_3$-d$_1$, 400 MHz): δ 1.77–1.86 (m, 2H), 1.92 (brs, 2H), 2.03–2.05 (m, 2H), 2.16 (d, J=9.0 Hz, 3H), 2.26 (s, 3H), 2.32 (s, 3H), 4.05 (s, 3H), 4.06 (s, 3H), 4.80–4.82 (m, 1H), 6.29 (d, J=5.4 Hz, 1H), 6.40 (s, 1H), 6.92 (s, 1H), 7.42 (s, 1H), 7.59 (s, 1H), 7.77 (brs, 1H), 8.44 (d, J=5.4 Hz, 1H) Mass spectrometry value (ESI-MS, m/z): 467 (M$^+$+1)

Example 468

1-Methyl-4-piperidyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, 1-methyl-4-piperidinol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (33 mg, yield 41%).

$^1$H-NMR (CDCl$_3$-d$_1$, 400 MHz): δ 1.76–1.85 (m, 2H), 2.01 (brs, 4H), 2.12 (s, 3H), 2.26 (s, 3H), 2.31 (s, 3H), 2.72 (brs, 2H), 4.05 (s, 3H), 4.07 (s, 3H), 4.78–4.82 (m, 1H), 6.26 (d, J=5.4 Hz, 1H), 6.47 (s, 1H), 7.00 (d, J=8.8 Hz, 1H), 7.43 (s, 1H), 7.62 (s, 2H), 8.44 (d, J=5.4 Hz, 1H) Mass spectrometry value (ESI-MS, m/z): 467 (M$^+$+1)

Example 469

1-Methyl-4-piperidyl N-{4-[(6,7-dimethoxy-4-quinazolinyl)oxy]phenyl}carbamate

4-[(6,7-Dimethoxy-4-quinazolinyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, 1-methyl-4-piperidinol (30 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (33 mg, yield 37%).

$^1$H-NMR (CDCl$_3$-d$_1$, 400 MHz): δ 1.78–1.85 (m, 4H), 2.01 (brs, 2H), 2.32 (s, 3H), 2.71 (brs, 2H), 4.067 (s, 3H), 4.071 (s, 3H), 4.81 (s, 1H), 6.74 (s, 1H), 7.21 (d, J=9.0 Hz, 2H), 7.32 (s, 1H), 7.49 (d, J=8.5 Hz, 2H), 7.55 (s, 1H), 8.62 (s, 1H) Mass spectrometry value (ESI-MS, m/z): 440 (M$^+$+1)

Example 470

Tetrahydro-2H-4-pyranyl N-{4-[(6,7-dimethoxy-4-quinolyl)oxy]phenyl}carbamate

4-[(6,7-Dimethoxy-4-quinolyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, tetrahydro-2H-4-pyranol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (60 mg, yield 83%).

$^1$H-NMR (CDCl$_3$-d$_1$, 400 MHz): δ 1.73–1.78 (m, 2H), 2.01–2.03 (m, 2H), 3.55–3.61 (m, 2H), 3.94–3.98 (m, 2H), 4.055 (s, 3H), 4.060 (s, 3H), 4.90–5.05 (m, 1H), 6.46 (d, J=5.4 Hz, 1H), 6.67 (s, 1H), 7.16 (d, J=8.8 Hz, 2H), 7.50 (d,

J=8.5 Hz, 2H), 7.56 (s, 1H), 8.48 (d, J=5.4 Hz, 1H) Mass spectrometry value (ESI-MS, m/z): 426 (M$^+$+1)

Example 471

Tetrahydro-2H-4-pyranyl N-{4-[(6,7-dimethoxy-4-quinolyl)oxy]-2,5-dimethylphenyl}carbamate 4-[(6,7-Dimethoxy-4-quinolyl)oxy]-2,5-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, tetrahydro-2H-4-pyranol (24 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (57 mg, yield 84%).

$^1$H-NMR (CDCl$_3$-d$_1$, 400 MHz): δ 1.75–1.79 (m, 2H), 1.98–2.10 (m, 2H), 2.15 (s, 3H), 2.27 (s, 3H), 3.55–3.61 (m, 2H), 3.96–3.99 (m, 2H), 4.07 (s, 6H), 4.90–5.00 (m, 1H), 6.31 (d, J=4.9 Hz, 1H), 6.37 (s, 1H), 6.93 (s, 1H), 7.49 (s, 1H), 7.60 (s, 1H), 7.78 (s, 1H), 8.45 (d, J=5.4 Hz, 1H) Mass spectrometry value (ESI-MS, m/z): 454 (M$^+$+1)

Example 472

Tetrahydro-2H-4-pyranyl N-{4-[(6,7-dimethoxy-4-quinolyl)oxy]-2,3-dimethylphenyl}carbamate 4-[(6,7-Dimethoxy-4-quinolyl)oxy]-2,3-dimethylaniline (50 mg) was added to toluene (5 ml) and triethylamine (0.5 ml), and the mixture was heated under reflux to prepare a solution. A solution of triphosgene (68 mg) in methylene chloride was then added thereto, and the mixture was heated under reflux for 10 min. Next, tetrahydro-2H-4-pyranol (24 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (23 mg, yield 34%).

$^1$H-NMR (CDCl$_3$-d$_1$, 400 MHz): δ 1.72–1.81 (m, 2H), 2.01–2.06 (m, 2H), 2.13 (s, 3H), 2.26 (s, 3H), 3.55–3.60 (m, 2H), 3.94–3.99 (m, 2H), 4.071 (s, 3H), 4.073 (s, 3H), 4.95–5.00 (m, 1H), 6.30 (d, J=5.4 Hz, 1H), 6.40 (s, 1H), 7.01 (d, J=8.8 Hz, 1H), 7.52 (s, 1H), 7.62 (s, 1H), 8.44 (d, J=5.4 Hz, 1H) Mass spectrometry value (ESI-MS, m/z): 454 (M$^+$+1)

Example 473

Tetrahydro-2H-4-pyranyl N-{4-[(6,7-dimethoxy-4-quinazolinyl)oxy]phenyl}carbamate 4-[(6,7-Dimethoxy-4-quinazolinyl)oxy]aniline (50 mg) was added to toluene (5 ml) and triethylamine (0.5 ml), and the mixture was heated under reflux to prepare a solution. A solution of triphosgene (77 mg) in methylene chloride was then added thereto, and the mixture was heated under reflux for 10 min. Next, tetrahydro-2H-4-pyranol (27 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (38 mg, yield 53%).

$^1$H-NMR (CDCl$_3$-d$_1$, 400 MHz): δ 1.70–1.80 (m, 2H), 2.00–2.05 (m, 2H), 3.55–3.60 (m, 2H), 3.94–3.98 (m, 2H), 4.07 (s, 6H), 4.93–5.01 (m, 1H), 6.65 (s, 1H), 7.22 (d, J=8.8 Hz, 2H), 7.35 (s, 1H), 7.51 (d, J=10.5 Hz, 2H), 7.56 (s, 1H), 8.63 (s, 1H) Mass spectrometry value (ESI-MS, m/z): 426 (M$^+$+1)

Example 474

Cyclohexyl N-{2-chloro-4-[(6,7-dimethoxy-4-quinazolinyl)oxy]phenyl}-N-methylcarbamate Dimethylformamide (5 ml) was added to sodium hydride (12 mg), and cyclohexyl N-{2-chloro-4-[(6,7-dimethoxy-4-quinazolinyl)oxy]phenyl}carbamate (70 mg) was added to the mixture. Subsequently, a dimethylformamide solution (2 ml) of methyl iodide (43 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (70 mg, yield 99%).

$^1$H-NMR (CDCl$_3$-d$_1$, 400 MHz): δ 1.23–1.92 (m, 10H), 3.26 (s, 3H), 4.07 (s, 3H), 4.08 (s, 3H), 4.73 (s, 1H), 7.21–7.23 (m, 1H), 7.27 (s, 1H), 7.34 (s, 1H), 7.41 (d, J=2.7 Hz, 1H), 7.52 (s, 1H), 8.65 (s, 1H) Mass spectrometry value (ESI-MS, m/z): 473 (M$^+$+1)

Example 475

Cyclohexyl N-{2-chloro-4-[(6,7-dimethoxy-4-quinazolinyl)oxy]phenyl}-N-ethylcarbamate Dimethylformamide (5 ml) was added to sodium hydride (11 mg), and cyclohexyl N-{2-chloro-4-[(6,7-dimethoxy-4-quinazolinyl)oxy]phenyl}carbamate (65 mg) was added to the mixture. Subsequently, a dimethylformamide solution (2 ml) of ethyl iodide (87 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (60 mg, yield 88%).

$^1$H-NMR (CDCl$_3$-d$_1$, 400 MHz): δ 1.20 (t, J=6.8 Hz, 3H), 1.24–1.91 (m, 1OH), 3.54–3.59 (m, 1H), 3.83–3.89 (m, 1H), 4.07 (s, 3H), 4.08 (s, 3H), 4.73 (brs, 1H), 7.21–7.24 (m, 2H), 7.34 (s, 1H), 7.43 (d, J=2.7 Hz, 1H), 7.52 (s, 1H), 8.65 (s, 1H) Mass spectrometry value (ESI-MS, m/z): 487 (M$^+$+1)

Example 476

Cyclohexyl N-{4-[(6,7-dimethoxy-4-quinazolinyl)oxy]phenyl}-N-methylcarbamate

Dimethylformamide (5 ml) was added to sodium hydride (7 mg), and cyclohexyl N-{4-[(6,7-dimethoxy-4-quinazolinyl)oxy]phenyl}carbamate (35 mg) was added to the mixture. Subsequently, a dimethylformamide solution (2 ml) of methyl iodide (47 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (30 mg, yield 83%).

$^1$H-NMR (CDCl$_3$-d$_1$, 400 MHz): δ 1.26–1.83 (m, 10H), 3.35 (s, 3H), 4.07 (s, 6H), 4.75–4.79 (m, 1H), 7.24 (d, J=8.8 Hz, 2H), 7.34–7.35 (m, 3H), 7.56 (s, 1H), 8.65 (s, 1H) Mass spectrometry value (ESI-MS, m/z): 439 (M$^+$+1)

Example 477

Cyclohexyl N-{4-[(6,7-dimethoxy-4-quinazolinyl)oxy]phenyl}-N-ethylcarbamate

Dimethylformamide (5 ml) was added to sodium hydride (7 mg), and cyclohexyl N-{4-[(6,7-dimethoxy-4-quinazolinyl)oxy]phenyl}carbamate (35 mg) was added to the mixture. Subsequently, a dimethylformamide solution (2 ml) of ethyl iodide (52 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (35 mg, yield 93%).

$^1$H-NMR (CDCl$_3$-d$_1$, 400 MHz): δ 1.23 (t, J=7.1 Hz, 3H), 1.36–1.93 (m, 10H), 3.73–3.78 (m, 1H), 3.91–3.98 (m, 1H), 4.07 (s, 6H), 4.76 (s, 1H), 7.19–7.34 (m, 4H), 7.51 (d, J=11.0 Hz, 1H), 7.56 (s, 1H), 8.64 (s, 1H) Mass spectrometry value (ESI-MS, m/z): 453 (M$^+$+1)

Example 478

2-Methoxybenzyl N-{2-chloro-4-[(6,7-dimethoxy-4-quinazolinyl)oxy]phenyl}-N-methylcarbamate Dimethylformamide (5 ml) was added to sodium hydride (11 mg), and 2-methoxybenzyl N-{2-chloro-4-[(6,7-dimethoxy-4-quinazolinyl)oxy]phenyl}carbamate (66 mg) was added to the mixture. Subsequently, a dimethylformamide solution (2 ml) of methyl iodide (77 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (50 mg, yield 75%).

$^1$H-NMR (CDCl$_3$-d$_1$, 400 MHz): δ 3.29 (s, 3H), 3.87 (s, 3H), 4.065 (s, 3H), 4.07 (s, 3H), 4.69 (s, 2H), 6.83–6.96 (m, 4H), 7.20–7.50 (m, 5H), 8.64 (s, 1H) Mass spectrometry value (ESI-MS, m/z): 511 (M$^+$+1)

Example 479

2-Methylbenzyl N-{2-chloro-4-[(6,7-dimethoxy-4-quinazolinyl)oxy]phenyl}-N-methylcarbamate Dimethylformamide (5 ml) was added to sodium hydride (11 mg), and 2-methylbenzyl N-{2-chloro-4-[(6,7-dimethoxy-4-quinazolinyl)oxy]phenyl}carbamate (62 mg) was added to the mixture. Subsequently, a dimethylformamide solution (2 ml) of methyl iodide (77 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (57 mg, yield 89%).

$^1$H-NMR (CDCl$_3$-d$_1$, 400 MHz): δ 2.21 (s, 3H), 3.28 (s, 3H), 4.069 (s, 3H), 4.074 (s, 3H), 5.10–5.19 (m, 2H), 7.12–7.23 (m, 5H), 7.33–7.35 (m, 2H), 7.41 (d, J=2.4 Hz, 1H), 7.51 (s, 1H), 8.64 (s, 1H) Mass spectrometry value (ESI-MS, m/z): 495 (M$^+$+1)

Example 480

2-Chlorobenzyl N-{2-chloro-4-[(6,7-dimethoxy-4-quinazolinyl)oxy]phenyl}-N-methylcarbamate Dimethylformamide (5 ml) was added to sodium hydride (11 mg), and 2-chlorobenzyl N-{2-chloro-4-[(6,7-dimethoxy-4-quinazolinyl)oxy]phenyl}carbamate (65 mg) was added to the mixture. Subsequently, a dimethylformamide solution (2 ml) of methyl iodide (77 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (57 mg, yield 85%).

$^1$H-NMR (CDCl$_3$-d$_1$, 400 MHz): δ 3.30 (s, 3H), 4.07 (s, 3H), 4.08 (s, 3H), 5.20–5.27 (m, 2H), 7.20–7.27 (m, 4H), 7.34–7.44 (m, 4H), 7.51 (s, 1H), 8.65 (s, 1H) Mass spectrometry value (ESI-MS, m/z): 515 (M$^+$+1)

Example 481

1-Propylbutyl N-{2-chloro-4-[(6,7-dimethoxy-4-quinazolinyl)oxy]phenyl}-N-methylcarbamate Dimethylformamide (5 ml) was added to sodium hydride (11 mg), and 1-propylbutyl N-{2-chloro-4-[(6,7-dimethoxy-4-quinazolinyl)oxy]phenyl}carbamate (62 mg) was added to the mixture. Subsequently, a dimethylformamide solution (2 ml) of methyl iodide (77 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (43 mg, yield 68%).

$^1$H-NMR (CDCl$_3$-d$_1$, 400 MHz): δ 0.87 (t, J=7.1 Hz, 6H), 1.24–1.82 (s, 8H), 3.26 (s, 3H), 4.07 (s, 3H), 4.08 (s, 3H), 4.80–4.83 (m, 1H), 7.21–7.24 (m, 1H), 7.31 (s, 1H), 7.34 (s,

1H), 7.42 (s, 1H), 7.52 (s, 1H), 8.66 (s, 1H) Mass spectrometry value (ESI-MS, m/z): 489 (M$^+$+1)

Example 482

Cycloheptyl N-{2-chloro-4-[(6,7-dimethoxy-4-quinazolinyl)oxy]phenyl}-N-methylcarbamate Dimethylformamide (5 ml) was added to sodium hydride (11 mg), and cycloheptyl N-2-chloro-4-[(6,7-dimethoxy-4-quinazolinyl)oxy]phenylcarbamate (61 mg) was added to the mixture. Subsequently, a dimethylformamide solution (2 ml) of methyl iodide (77 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (60 mg, yield 95%).
$^1$H-NMR (CDCl$_3$-d$_1$, 400 MHz): δ 1.44–1.93 (m, 12H), 3.25 (s, 3H), 4.07 (s, 3H), 4.08 (s, 3H), 4.90 (brs, 1H), 7.20–7.23 (m, 1H), 7.33–7.34 (m, 2H), 7.41 (d, J=2.7 Hz, 1H), 7.52 (s, 1H), 8.65 (s, 1H) Mass spectrometry value (ESI-MS, m/z): 487 (M$^+$+1)

Example 483

Cycloheptylmethyl N-{4-[(6,7-dimethoxy-4-quinolyl)oxy]phenyl}-N-methylcarbamate

Dimethylformamide (5 ml) was added to sodium hydride (27 mg), and cycloheptylmethyl N-4-[(6,7-dimethoxy-4-quinolyl)oxy]phenylcarbamate (153 mg) was added to the mixture. Subsequently, a dimethylformamide solution (2 ml) of methyl iodide (193 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (100 mg, yield 63%).
$^1$H-NMR (CDCl$_3$-d$_1$, 400 MHz): δ 1.15–1.81 (m, 13H), 3.42 (d, J=6.6 Hz, 3H), 3.99 (d, J=6.6 Hz, 2H), 4.05 (s, 6H), 6.44 (d, J=5.4 Hz, 1H), 7.14 (d, J=9.0 Hz, 2H), 7.43 (s, 1H), 7.49 (d, J=8.5 Hz, 2H), 7.56 (s, 1H), 8.48 (d, J=5.1 Hz, 1H) Mass spectrometry value (ESI-MS, m/z): 466 (M$^+$+1)

Example 484

Cycloheptylmethyl N-{4-[(6,7-dimethoxy-4-quinazolinyl oxy]phenyl}-N-methylcarbamate Dimethylformamide (5 ml) was added to sodium hydride (27 mg), and cycloheptylmethyl N-4-[(6,7-dimethoxy-4-quinazolinyl)oxy]phenylcarbamate (154 mg) was added to the mixture. Subsequently, a dimethylformamide solution (2 ml) of methyl iodide (193 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (90 mg, yield 57%).
$^1$H-NMR (CDCl$_3$-d$_1$, 400 MHz): δ 1.10–1.81 (m, 13H), 3.35 (s, 3H), 3.94 (d, J=6.6 Hz, 2H), 4.07 (s, 6H), 7.23–7.26 (m, 3H), 7.34–7.35 (m, 2H), 7.56 (s, 1H), 8.64 (s, 1H) Mass spectrometry value (ESI-MS, m/z): 467 (M$^+$+1)

Example 485

2-Methoxybenzyl N-{2-chloro-4-[(6,7-dimethoxy-4-quinazolinyl)oxy]phenyl}-N-ethylcarbamate Dimethylformamide (5 ml) was added to sodium hydride (11 mg), and 2-methoxybenzyl N-{2-chloro-4-[(6,7-dimethoxy-4-quinazolinyl)oxy]phenyl}carbamate (66 mg) was added to the mixture. Subsequently, a dimethylformamide solution (2 ml) of ethyl iodide (84 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (63 mg, yield 93%).
$^1$H-NMR (CDCl$_3$-d$_1$, 400 MHz): δ 1.22 (t, J=7.1 Hz, 3H), 3.55–3.60 (m, 1H), 3.76–3.94 (m, 1H), 3.87 (s, 3H), 4.067 (s, 3H), 4.074 (s, 3H), 5.19 (d, J=3.4 Hz, 2H), 6.81–7.09 (m, 4H), 7.21–7.40 (m, 3H), 7.43 (d, J=2.7 Hz, 1H), 7.51 (s, 1H), 8.65 (s, 1H) Mass spectrometry value (ESI-MS, m/z): 525 (M$^+$+1)

Example 486

2-Methylbenzyl N-{2-chloro-4-[(6,7-dimethoxy-4-quinazolinyl)oxy]phenyl}-N-ethylcarbamate Dimethylformamide (5 ml) was added to sodium hydride (11 mg), and 2-methylbenzyl N-{2-chloro-4-[(6,7-dimethoxy-4-quinazolinyl)oxy]phenyl}carbamate (62 mg) was added to the mixture. Subsequently, a dimethylformamide solution (2 ml) of ethyl iodide (84 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (53 mg, yield 79%).
$^1$H-NMR (CDCl$_3$-d$_1$, 400 MHz): δ 1.20–1.23 (m, 3H), 2.21 (s, 3H), 3.56–3.59 (m, 1H), 3.90–3.92 (m, 1H), 4.069 (s, 3H), 4.073 (s, 3H), 5.13–5.18 (m, 1H), 7.12–7.36 (m, 7H), 7.43 (s, 1H), 7.51 (s, 1H), 8.64 (s, 1H) Mass spectrometry value (ESI-MS, m/z): 509 (M$^+$+1)

Example 487

2-Chlorobenzyl N-{2-chloro-4-[(6,7-dimethoxy-4-quinazolinyl)oxy]phenyl}-N-ethylcarbamate Dimethylformamide (5 ml) was added to sodium hydride (11 mg), and 2-chlorobenzyl N-{2-chloro-4-[(6,7-dimethoxy-4-quinazolinyl)oxy]phenyl}carbamate (65 mg) was added to the mixture. Subsequently, a dimethylformamide solution (2 ml) of ethyl iodide (84 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (68 mg, yield 100%).

$^1$H-NMR (CDCl$_3$-d$_1$, 400 MHz): δ 1.23 (t, J=7.1 Hz, 3H), 3.54–3.63 (m, 1H), 3.88–3.97 (m, 1H), 4.07 (s, 3H), 4.08 (s, 3H), 5.23 (s, 2H), 7.19–7.36 (m, 7H), 7.45 (d, J=2.4 Hz, 1H), 7.51 (s, 1H), 8.65 (s, 1H) Mass spectrometry value (ESI-MS, m/z): 529 (M$^+$+1)

Example 488

1-Propylbutyl N-{2-chloro-4-[(6,7-dimethoxy-4-quinazolinyl)oxy]phenyl}-N-ethylcarbamate Dimethylformamide (5 ml) was added to sodium hydride (11 mg), and 1-propylbutyl N-{2-chloro-4-[(6,7-dimethoxy-4-quinazolinyl)oxy]phenyl}carbamate (62 mg) was added to the mixture. Subsequently, a dimethylformamide solution (2 ml) of ethyl iodide (84 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (49 mg, yield 75%)

$^1$H-NMR (CDCl$_3$-d$_1$, 400 MHz): δ 0.85–0.88 (m, 3H), 0.93–0.97 (s, 3H), 1.18–1.70 (m, 11H), 3.47–3.53 (m, 1H), 3.88–3.91 (m, 1H), 4.07 (s, 3H), 4.08 (s, 3H), 4.78–4.95 (m, 1H), 7.21–7.23 (m, 1H), 7.32–7.34 (m, 2H), 7.43 (s, 1H), 7.52 (s, 1H), 8.62 (s, 1H) Mass spectrometry value (ESI-MS, m/z): 503 (M$^+$+1)

Example 489

Cycloheptyl N-{2-chloro-4-[(6,7-dimethoxy-4-quinazolinyl)oxy]phenyl}-N-ethylcarbamate Dimethylformamide (5 ml) was added to sodium hydride (11 mg), and cycloheptyl N-2-chloro-4-[(6,7-dimethoxy-4-quinazolinyl)oxy]phenylcarbamate (61 mg) was added to the mixture. Subsequently, a dimethylformamide solution (2 ml) of ethyl iodide (84 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (51 mg, yield 78%).

$^1$H-NMR (CDCl$_3$-d$_1$, 400 MHz): δ 1.20 (t, J=7.1 Hz, 3H), 1.29–2.03 (m, 12H), 3.53–3.58 (m, 1H), 3.83–3.88 (m, 1H), 4.07 (s, 3H), 4.08 (s, 3H), 4.89–4.98 (m, 1H), 7.21–7.23 (m, 1H), 7.27–7.34 (m, 2H), 7.43 (d, J=2.7 Hz, 1H), 7.52 (s, 1H), 8.65 (s, 1H) Mass spectrometry value (ESI-MS, m/z): 501 (M$^+$+1)

Example 490

2-Methoxybenzyl N-{4-[(6,7-dimethoxy-4-quinazolinyl)oxy]phenyl}-N-methylcarbamate Dimethylformamide (5 ml) was added to sodium hydride (24 mg), and 2-methoxybenzyl N-4-[(6,7-dimethoxy-4-quinazolinyl)oxy]phenylcarbamate (145 mg) was added to the mixture. Subsequently, a dimethylformamide solution (2 ml) of methyl iodide (170 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (115 mg, yield 81%).

$^1$H-NMR (CDCl$_3$-d$_1$, 400 MHz): δ 3.38 (s, 3H), 3.84 (s, 3H), 4.06 (s, 6H), 5.24 (s, 2H), 6.86–6.93 (m, 3H), 7.23–7.28 (m, 3H), 7.33 (s, 1H), 7.38 (d, J=8.8 Hz, 2H), 7.54 (s, 1H), 8.63 (s, 1H) Mass spectrometry value (ESI-MS, m/z): 477 (M$^+$+1)

Example 491

2-Methylbenzyl N-{4-[(6,7-dimethoxy-4-quinazolinyl)oxy]phenyl}-N-methylcarbamate Dimethylformamide (5 ml) was added to sodium hydride (24 mg), and 2-methylbenzyl N-4-[(6,7-dimethoxy-4-quinazolinyl)oxy]phenylcarbamate (148 mg) was added to the mixture. Subsequently, a dimethylformamide solution (2 ml) of methyl iodide (170 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (115 mg, yield 83%).

$^1$H-NMR (CDCl$_3$-d$_1$, 400 MHz): δ 2.32 (s, 3H), 3.37 (s, 3H), 4.07 (s, 6H), 5.20 (s, 2H), 7.16–7.27 (m, 6H), 7.33 (s, 1H), 7.36 (d, J=6.6 Hz, 2H), 7.55 (s, 1H), 8.63 (s, 1H) Mass spectrometry value (ESI-MS, m/z): 461 (M$^+$+1)

Example 492

2-Chlorobenzyl N-{4-[(6,7-dimethoxy-4-quinazolinyl)oxy]phenyl}-N-methylcarbamate Dimethylformamide (5 ml) was added to sodium hydride (16 mg), and 2-chlorobenzyl N-4-[(6,7-dimethoxy-4-quinazolinyl)oxy]phenylcarbamate (107 mg) was added to the mixture. Subsequently, a dimethylformamide solution (2 ml) of methyl iodide (114 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (75 mg, yield 78%).

$^1$H-NMR (CDCl$_3$-d$_1$, 400 MHz): δ 3.39 (s, 3H), 4.07 (s, 6H), 5.29 (s, 2H), 7.24–7.41 (m, 9H), 7.55 (s, 1H), 8.64 (s, 1H) Mass spectrometry value (ESI-MS, m/z): 481 (M$^+$+1)

Example 493

1-Propylbutyl N-{4-[(6,7-dimethoxy-4-quinazolinyl)oxy]phenyl}-N-methylcarbamate

Dimethylformamide (5 ml) was added to sodium hydride (16 mg), and 1-propylbutyl N-4-[(6,7-dimethoxy-4-quinazolinyl)oxy]phenylcarbamate (99 mg) was added to the mixture. Subsequently, a dimethylformamide solution (2 ml) of methyl iodide (114 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (84 mg, yield 93%).

$^1$H-NMR (CDCl$_3$-d$_1$, 400 MHz): δ 0.92 (t, J=7.3 Hz, 6H), 1.18–1.42 (m, 4H), 1.45–1.55 (m, 4H), 3.35 (s, 3H), 4.07 (s, 6H), 4.83–4.89 (m, 1H), 7.25 (d, J=8.8 Hz, 2H), 7.33 (s, 1H), 7.36 (d, J=8.5 Hz, 2H), 7.55 (s, 1H), 8.64 (s, 1H) Mass spectrometry value (ESI-MS, m/z): 455 (M$^+$+1)

Example 494

Cycloheptyl N-{4-[(6,7-dimethoxy-4-quinazolinyl)oxy]phenyl}-N-methylcarbamate

Dimethylformamide (5 ml) was added to sodium hydride (24 mg), and cycloheptyl N-4-[(6,7-dimethoxy-4-quinazolinyl)oxy]phenylcarbamate (144 mg) was added to the mixture. Subsequently, a dimethylformamide solution (2 ml) of methyl iodide (170 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (117 mg, yield 86%).

$^1$H-NMR (CDCl$_3$-d$_1$, 400 MHz): δ 1.26–1.93 (m, 12H), 3.34 (s, 3H), 4.07 (s, 6H), 4.91–4.95 (m, 1H), 7.24 (d, J=8.8 Hz, 2H), 7.33 (s, 1H), 7.36 (d, J=8.8 Hz, 2H), 7.55 (s, 1H), 8.64 (s, 1H) Mass spectrometry value (ESI-MS, m/z): 453 (M$^+$+1)

Example 495

1-Ethyl-3-butynyl N-{4-[(6,7-dimethoxy-4-quinazolinyl)oxy]phenyl}-N-methylcarbamate Dimethylformamide (5 ml) was added to sodium hydride (27 mg), and 1-ethyl-3-butynyl N-4-[(6,7-dimethoxy-4-quinazolinyl)oxy]phenylcarbamate (143 mg) was added to the mixture. Subsequently, a dimethylformamide solution (2 ml) of methyl iodide (193 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (83 mg, yield 56%).

$^1$H-NMR (CDCl$_3$-d$_1$, 400 MHz): δ 0.84 (t, J=7.6 Hz, 3H), 1.64–1.65 (m, 2H), 1.93 (t, J=2.7 Hz, 2H), 2.44 (brs, 2H), 3.28 (s, 3H), 3.99 (s, 3H), 4.75–4.78 (m, 1H), 7.17 (d, J=8.8 Hz, 2H), 7.21 (s, 1H), 7.31 (d, J=8.8 Hz, 2H), 7.47 (s, 1H), 8.56 (s, 1H) Mass spectrometry value (ESI-MS, m/z): 437 (M$^+$+1)

Example 496

1-Ethyl-3-butynyl N-{4-[(6,7-dimethoxy-4-quinolyl)oxy]phenyl}-N-methylcarbamate

Dimethylformamide (5 ml) was added to sodium hydride (27 mg), and 1-ethyl-3-butynyl N-4-[(6,7-dimethoxy-4-quinolyl)oxy]phenylcarbamate (143 mg) was added to the mixture. Subsequently, a dimethylformamide solution (2 ml) of methyl iodide (193 mg) was added thereto, and the mixture was stirred at room temperature for 10 min. Water was added to stop the reaction, and the reaction solution was then extracted with ethyl acetate, followed by washing with water and saturated brine in that order. The extract was dried over sodium sulfate and was then concentrated. The residue was purified on a column using chloroform/methanol to give the title compound (24 mg, yield 16%).

$^1$H-NMR (CDCl$_3$-d$_1$, 400 MHz): δ 0.85–0.87 (m, 3H), 1.67–1.75 (m, 2H), 1.918–1.924 (m, 1H), 2.46 (s, 2H), 3.29 (s, 3H), 3.97 (s, 3H), 3.98 (s, 3H), 4.76–4.79 (m, 1H), 6.44 (d, J=5.4 Hz, 1H), 7.09 (d, J=9.0 Hz, 2H), 7.30 (d, J=8.5 Hz, 2H), 7.36 (s, 1H), 7.47 (s, 1H), 8.43 (d, J=5.4 Hz, 1H) Mass spectrometry value (ESI-MS, m/z): 436 (M$^+$+1)

Example 497

Cyclohexyl N-{4-[(6,7-dimethoxy-4-quinazolinyl)oxy]-2-methoxyphenyl}carbamate

4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cyclohexanol (47 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 85%).

$^1$H-NMR (CDCl$_3$-d$_1$, 400 MHz): δ 1.26–1.95 (m, 10H), 3.88 (s, 3H), 4.07 (s, 6H), 4.68–4.77 (m, 1H), 6.79–6.80 (m, 1H), 6.84–6.87 (m, 1H), 7.17 (s, 1H), 7.32 (s, 1H), 7.55 (s, 1H), 8.19 (s, 1H), 8.63 (s, 1H) Mass spectrometry value (ESI-MS, m/z): 455 (M$^+$+1)

Example 498

Cycloheptyl N-{4-[(6,7-dimethoxy-4-quinazolinyl)oxy]-2-methoxyphenyl}carbamate

4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cycloheptanol (54 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (89 mg, yield 61%).

$^1$H-NMR (CDCl$_3$-d$_1$, 400 MHz): δ 1.49–2.03 (m, 13H), 3.88 (s, 3H), 4.07 (s, 6H), 4.84–4.97 (m, 1H), 6,788–6.794 (m, 1H), 6.84–6.87 (m, 1H), 7.15 (s, 1H), 7.36 (s, 1H), 7.55 (s, 1H), 8.19 (s, 1H), 8.64 (s, 1H) Mass spectrometry value (ESI-MS, m/z): 469 (M$^+$+i)

Example 499

2-Chlorobenzyl N-{4-[(6,7-dimethoxy-4-quinazolinyl)oxy]-2-methoxyphenyl}carbamate 4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-chlorophenyl) methanol (67 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (147 mg, yield 96%).

$^1$H-NMR (CDCl$_3$-d$_1$, 400 MHz): δ 3.86 (s, 3H), 4.06 (s, 3H), 4.07 (s, 3H), 5.34 (s, 2H), 6.80–6.81 (m, 1H), 6.85–6.88 (m, 1H), 7.27–7.35 (m, 4H), 7.40–7.42 (m, 1H), 7.48–7.51 (m, 1H), 7.55 (s, 1H), 8.21 (s, 1H), 8.63 (s, 1H) Mass spectrometry value (ESI-MS, m/z): 497 (M$^+$+1)

Example 500

2-Methoxybenzyl N-{4-[(6,7-dimethoxy-4-quinazolinyl)oxy]-2-methoxyphenyl}carbamate 4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methoxyphenyl)methanol (58 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (148 mg, yield 100%).

$^1$H-NMR (CDCl$_3$-d$_1$, 400 MHz): δ 3.86–3.91 (m, 8H), 4.06 (s, 3H), 4.07 (s, 3H), 6.84–7.32 (m, 6H), 7.33 (s, 1H), 7.55 (s, 1H), 8.23–8.30 (m, 1H), 8.65 (s, 1H) Mass spectrometry value (ESI-MS, m/z): 493 (M$^+$+1)

Example 501

2-(2-Pyridyl)ethyl N-{4-[(6,7-dimethoxy-4-quinazolinyl)oxy]-2-methoxyphenyl}carbamate 4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 2-(2-pyridyl)-1-ethanol (58 mg) was added thereto, and the mixture was further stirred with heating under reflux for 3 hr. A saturated aqueous sodium bicarbonate solution was added to stop the reaction, and the reaction solution was then extracted with chloroform, and the extract was washed with water and saturated brine in that order. The extract was dried over sodium sulfate and was then concentrated. The residue was purified on a column using chloroform/methanol to give the title compound (110 mg, yield 75%).

$^1$H-NMR (CDCl$_3$-d$_1$, 400 MHz): δ 3.20 (t, J=6.8 Hz, 2H), 3.85 (d, J=1.5 Hz, 3H), 4.07 (d, J=1.5 Hz, 6H), 4.60 (t, J=6.6 Hz, 2H), 6.78–6.89 (m, 1H), 6.84 (d, J=8.8 Hz, 1H), 7.16–7.27 (m, 3H), 7.32 (d, J=1.5 Hz, 1H), 7.54 (d, J=1.5 Hz, 1H), 7.62–7.66 (m, 1H), 8.18 (brs, 1H), 8.58 (d, J=4.9 Hz, 1H), 8.63 (d, J=1.7 Hz, 1H) Mass spectrometry value (ESI-MS, m/z): 478 (M$^+$+1)

Example 502

1-Ethyl-3-butynyl N-{4-[(6,7-dimethoxy-4-quinazolinyl)oxy]-2-methoxyphenyl}carbamate 4-[(6,7-Dimethoxy-4-quinazolinyl)oxy]-2-methoxyaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 5-hexyn-3-ol (46 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (73 mg, yield 52%).

$^1$H-NMR (CDCl$_3$-d$_1$, 400 MHz): δ 1.00 (t, J=7.3 Hz, 3H), 1.74–1.85 (m, 2H), 2.56–2.59 (m, 1H), 3.31–3.49 (m, 2H), 3.89 (s, 3H), 4.07 (s, 6H), 4.89–4.92 (m, 1H), 6.80 (d, J=2.4 Hz, 1H), 6.85–6.87 (m, 1H), 7.27 (s, 1H), 7.33 (s, 1H), 7.55 (s, 1H), 8.20 (brs, 1H), 8.63 (s, 1H) Mass spectrometry value (ESI-MS, m/z): 453 (M$^+$+1)

Example 503

Cyclohexyl N-{4-[(6,7-dimethoxy-4-quinazolinyl) oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cyclohexanol (44 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (120 mg, yield 88%).

$^1$H-NMR (CDCl$_3$-d$_1$, 400 MHz): δ 1.24–1.57 (m, 6H), 1.78–1.81 (m, 2H), 1.96–2.04 (m, 2H), 4.07 (s, 6H), 4.78–4.82 (m, 1H), 7.34 (s, 1H), 7.52 (s, 1H), 7.58–7.61 (m, 1H), 8.17 (d, J=2.9 Hz, 1H), 8.61 (s, 1H), 8.73 (d, J=9.3 Hz, 1H), 9.80 (s, 1H) Mass spectrometry value (ESI-MS, m/z): 470 (M$^+$+1)

Example 504

2-Chlorobenzyl N-{4-[(6,7-dimethoxy-4-quinazolinyl)oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-chlorophenyl)methanol (63 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (74 mg, yield 50%).

$^1$H-NMR (CDCl$_3$-d$_1$, 400 MHz): δ 4.08 (s, 6H), 5.39 (s, 2H), 7.26–7.33 (m, 2H), 7.37 (s, 1H), 7.43–7.45 (m, 1H), 7.49–7.52 (m, 2H), 7.59–7.62 (m, 1H), 8.18 (d, J=2.7 Hz, 1H), 8.61 (s, 1H), 8.74 (d, J=9.3 Hz, 1H), 9.97 (s, 1H) Mass spectrometry value (ESI-MS, m/z): 512 (M$^+$+1)

Example 505

2-Methylbenzyl N-{4-[(6,7-dimethoxy-4-quinazolinyl)oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, (2-methylphenyl)methanol (54 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (130 mg, yield 91%).

$^1$H-NMR (CDCl$_3$-d$_1$, 400 MHz): δ 2.42 (s, 3H), 4.06 (s, 3H), 4.07 (s, 3H), 5.29 (s, 2H), 7.17–7.41 (m, 5H), 7.51 (s, 1H), 7.58–7.61 (m, 1H), 8.16 (d, J=2.9 Hz, 1H), 8.59 (s, 1H), 8.73 (d, J=9.3 Hz, 1H), 9.90 (s, 1H) Mass spectrometry value (ESI-MS, m/z): 492 (M$^+$+1)

Example 506

Cycloheptylmethyl N-{4-[(6,7-dimethoxy-4-quinazolinyl)oxy]-2-nitrophenyl}carbamate 4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, cycloheptylmethanol (56 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (115 mg, yield 80%).

$^1$H-NMR (CDCl$_3$-d$_1$, 400 MHz): δ 1.23–1.93 (m, 13H), 4.03 (d, J=6.8 Hz, 2H), 4.077 (s, 3H), 4.081 (s, 3H), 7.27 (s, 1H), 7.34 (s, 1H), 7.52 (s, 1H), 7.58–7.61 (m, 1H), 8.17 (d, J=2.7 Hz, 1H), 8.61 (s, 1H), 8.73 (d, J=9.3 Hz, 1H), 9.85 (s, 1H) Mass spectrometry value (ESI-MS, m/z): 498 (M$^+$+1)

Example 507

Cycloheptyl N-{4-[(6,7-dimethoxy-4-quinazolinyl)oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-cycloheptanol (50 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (140 mg, yield 100%).

$^1$H-NMR (CDCl$_3$-d$_1$, 400 MHz): δ 1.40–1.82 (m, 8H), 1.88–1.94 (m, 2H), 1.98–2.04 (m, 2H), 4.077 (s, 3H), 4.080 (s, 3H), 4.95–5.00 (m, 1H), 7.35 (s, 1H), 7.52 (s, 1H), 7.57–7.60 (m, 1H), 8.16 (d, J=2.7 Hz, 1H), 8.61 (s, 1H), 8.74 (d, J=9.3 Hz, 1H), 9.79 (s, 1H) Mass spectrometry value (ESI-MS, m/z): 484 (M$^+$+1)

Example 508

1-Butylpentyl N-{4-[(6,7-dimethoxy-4-quinazolinyl)oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 5-nonanol (64 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (143 mg, yield 96%).

$^1$H-NMR (CDCl$_3$-d$_1$, 400 MHz): δ 0.89–0.94 (m, 6H), 1.33–1.65 (m, 12H), 4.077 (s, 3H), 4.083 (s, 3H), 4.89–4.92 (m, 1H), 7.35 (s, 1H), 7.52 (s, 1H), 7.57–7.60 (m, 1H), 8.17 (d, J=2.7 Hz, 1H), 8.60 (s, 1H), 8.76 (d, J=9.3 Hz, 1H), 9.83 (s, 1H) Mass spectrometry value (ESI-MS, m/z): 514 (M$^+$+1)

Example 509

Hexyl N-{4-[(6,7-dimethoxy-4-quinazolinyl)oxy]-2-nitrophenyl}carbamate

4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 1-hexanol (45 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (109 mg, yield 80%).

$^1$H-NMR (CDCl$_3$-d$_1$, 400 MHz): δ 0.92 (t, J=7.1 Hz, 3H), 1.34–1.42 (m, 6H), 1.69–1.76 (m, 2H), 4.079 (s, 3H), 4.082 (s, 3H), 4.23 (t, J=6.8 Hz, 2H), 7.35 (s, 1H), 7.52 (s, 1H), 7.58–7.61 (m, 1H), 8.17 (d, J=2.9 Hz, 1H), 8.61 (s, 1H), 8.73 (d, J=9.3 Hz, 1H), 9.85 (s, 1H) Mass spectrometry value (ESI-MS, m/z): 472 (M$^+$+1)

Example 510

1-Ethyl-3-butynyl N-{4-[(6,7-dimethoxy-4-quinazolinyl)oxy]-2-nitrophenyl}carbamate 4-[(6,7-Dimethoxy-4-quinazolinyl)oxy]-2-nitroaniline (100 mg) was added to toluene (10 ml) and triethylamine (1 ml), and the mixture was heated under reflux to prepare a solution. A solution of triphosgene (140 mg) in methylene chloride was then added thereto, and the mixture was heated under reflux for 10 min. Next, 5-hexyn-3-ol (43 mg) was added thereto, and the mixture was further stirred with heating under reflux for 3 hr. A saturated aqueous sodium bicarbonate solution was added to stop the reaction, and the reaction solution was then extracted with chloroform, followed by washing with a 1 N aqueous hydrochloric acid solution, water, and saturated brine in that order. The extract was dried over sodium sulfate and was then concentrated. The residue was purified on a column using chloroform/methanol to give the title compound (115 mg, yield 85%).

$^1$H-NMR (CDCl$_3$-d$_1$, 400 MHz): δ 1.01 (t, J=7.3 Hz, 3H), 1.77–1.87 (m, 2H), 2.04–2.05 (m, 1H), 2.58–2.60 (m, 2H), 4.079 (s, 3H), 4.083 (s, 3H), 4.91–4.96 (m, 1H), 7.35 (s, 1H), 7.52 (s, 1H), 7.59–7.62 (m, 1H), 8.18 (d, J=2.7 Hz, 1H), 8.61 (s, 1H), 8.73 (d, J=9.3 Hz, 1H), 9.87 (s, 1H) Mass spectrometry value (ESI-MS, m/z): 467 (M$^+$+1)

Example 511

N-{4-[(6,7-Dimethoxy-4-quinolyl)oxy]-2,3-dimethylphenyl}-N'-(2-diethylaminoethyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diethylphenylenediamine (50 mg) was added to thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (5 mg, yield 5%).

$^1$H-NMR (CDCl$_3$, 400 MHz): 0.89 (m, 6H), 2.15 (s, 3H), 2.28 (s, 3H), 2.46 (m, 4H), 2.62 (m, 2H), 3.67 (m, 2H), 4.06 (s, 3H), 4.07 (s, 3H), 6.25 (m, 1H), 6.76 (br, 1H), 7.04 (d, J=8.5 Hz, 1H), 7.18 (d, J=8.6 Hz, 1H), 7.44 (s, 1H), 7.46 (br, 1H), 7.59 (s, 1H), 8.44 (d, J=5.4 Hz, 1H) Mass spectrometry value (ESI-MS, m/z): 483 (M$^+$+1)

Example 512

N-{4-[(6,7-Dimethoxy-4-quinolyl)oxy]-2,3-dimethylphenyl}-N'-(2-piperidinylethyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 3 hr. Next, 2-piperidinylethylamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (25 mg, yield 33%)

$^1$H-NMR (CDCl$_3$, 400 MHz): 1.35–1.46 (m, 6H), 2.17 (s, 3H), 2.29 (s, 3H), 2.32–2.56 (m, 6H), 3.69 (m, 2H), 4.06 (s, 6H), 6.29 (m, 1H), 6.78 (br, 1H), 7.05 (d, J=8.3 Hz, 1H), 7.19 (d, J=8.6 Hz, 1H), 7.48 (s, 1H), 7.50 (br, 1H), 7.59 (s, 1H), 8.45 (d, J=5.1 Hz, 1H) Mass spectrometry value (ESI-MS, m/z): 494 (M$^+$+1)

Example 513

N-{4-[(6,7-Dimethoxy-4-quinolyl)oxy]-2,3-dimethylphenyl}-N'-[4-(N-benzyl)piperidinyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 3 hr. Next, 4-amino-1-benzylpiperidine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (27 mg, yield 31%).

$^1$H-NMR (CDCl$_3$, 400 MHz): 1.38–2.26 (m, 10H), 2.80–2.88 (m, 4H), 3.53 (m, 2H), 4.06 (s, 3H), 4.07 (s, 3H), 5.46 (br, 1H), 6.28 (d, J=5.4 Hz, 1H), 7.03 (d, J=8.3 Hz, 1H), 7.14 (d, J=8.5 Hz, 1H), 7.28–7.33 (m, 5H), 7.45 (s, 1H), 7.47 (br, 1H), 7.58 (s, 1H), 8.49 (d, J=5.4 Hz, 1H) Mass spectrometry value (ESI-MS, m/z): 556 (M$^+$+1)

Example 514

N-{4-[(6,7-Dimethoxy-4-quinolyloxy]-2,5-dimethylphenyl}-N'-(2-piperidinylethyl)thiourea 4-[(6,7-Dimethoxy-4-quinolyl)oxy]-2,5-dimethylaniline (52 mg) was dissolved in N,N-dimethylformamide (2 ml) and triethylamine (1 ml) to prepare a solution. Thiophosgene (51 mg) was then added to the solution, and the mixture was stirred at room temperature for 5 hr. Next, 2-piperidinylethylamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (32 mg, yield 40%).

$^1$H-NMR (CDCl$_3$, 400 MHz): 1.35–1.46 (m, 6H), 2.17 (s, 3H), 2.29 (s, 3H), 2.32–2.56 (m, 6H), 3.69 (m, 2H), 4.06 (s, 6H), 6.29 (m, 1H), 6.78 (br, 1H), 7.05 (d, J=8.3 Hz, 1H), 7.19 (d, J=8.6 Hz, 1H), 7.48 (s, 1H), 7.50 (br, 1H), 7.59 (s, 1H), 8.45 (d, J=5.1 Hz, 1H) Mass spectrometry value (ESI-MS, m/z): 494 (M$^+$+1)

Example 515

N-{4-[(6,7-Dimethoxy-4-quinolyl)oxy]-2,5-dimethylphenyl}-N'-(2-acetamidoethyl)thiourea 4-[(6,7-Dimethoxy-4-quinolyl)oxy]-2,5-dimethylaniline (52 mg) was dissolved in N,N-dimethylformamide (2 ml) and triethylamine (1 ml) to prepare a solution. Thiophosgene (51 mg) was then added to the solution, and the mixture was stirred at room temperature for 5 hr. Next, 2-acetamidoethylamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (6 mg, yield 8%).

$^1$H-NMR (CDCl$_3$, 400 MHz): 1.94 (s, 3H), 2.17 (s, 3H), 2.25 (s, 3H), 3.44 (m, 2H), 3.78 (m, 2H), 4.07 (s, 6H), 6.20 (m, 1H), 6.67 (br, 1H), 6.78 (br, 1H), 7.07 (s, 1H), 7.18 (s, 1H), 7.41 (br, 1H), 7.54 (s, 1H), 7.59 (s, 1H), 8.47 (d, J=5.4 Hz, 1H) Mass spectrometry value (ESI-MS, m/z): 468 (M$^+$+1)

Example 516

N-{4-[(6,7-Dimethoxy-4-quinazolinyl)oxy]phenyl}-N'-(2-diethylaminoethyl)thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 5 hr. Next, N,N-diethylethylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (62 mg, yield 81%).

$^1$H-NMR (CDCl$_3$, 400 MHz): 0.96 (br, 6H), 2.52 (br, 4H), 2.67 (br, 2H), 3.68 (br, 2H), 4.07 (s, 6H), 7.26–7.54 (m, 7H), 7.83 (br, 1H), 8.59 (s, 1H) Mass spectrometry value (ESI-MS, m/z): 456 (M$^+$+1)

Example 517

N-{4-[(6,7-Dimethoxy-4-quinazolinyl)oxy]phenyl}-N'-[2-(1-piperidinyl)ethyl]thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 2-(1-piperidinyl)ethylamine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (35 mg, yield 45%).

$^1$H-NMR (CDCl$_3$, 400 MHz): 1.40–1.55 (m, 6H), 2.40–2.60 (m, 6H), 3.72 (m, 2H), 4.07 (s, 6H), 7.30–7.38 (m, 7H), 7.54 (s, 1H), 8.60 (s, 1H) Mass spectrometry value (ESI-MS, m/z): 468 (M$^+$+1)

Example 518

N-{4-[(6,7-Dimethoxy-4-quinazolinyl)oxy]phenyl}-N'-[4-(1-benzylpiperidinyl)]thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 4-amino-1-benzylpiperidine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (40 mg, yield 44%).

¹H-NMR (CDCl₃, 400 MHz): 1.52 (m, 2H), 2.09 (m, 2H), 2.19 (m, 2H), 2.83 (m, 2H), 3.52 (s, 2H), 4.08 (s, 6H), 4.37 (m, 1H), 6.06 (d, J=7.8 Hz, 1H), 7.28–7.35 (m, 10H), 7.53 (s, 1H), 7.80 (br, 1H), 8.63 (s, 1H) Mass spectrometry value (ESI-MS, m/z): 530 (M⁺+1)

Example 519

N-{4-[(6,7-Dimethoxy-4-quinazolinyl)oxy]phenyl}-N'-(2-acetamidomethyl)thiourea

4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N-acetylethylenediamine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (13 mg, yield 17%).
¹H-NMR (CDCl₃, 400 MHz): 2.00 (s, 3H), 3.47 (m, 2H), 3.84 (m, 2H), 4.08 (s, 6H), 6.36 (br, 1H), 6.89 (br, 1H), 7.32–7.40 (m, 5H), 7.55 (s, 1H), 7.86 (br, 1H), 8.61 (s, 1H) Mass spectrometry value (ESI-MS, m/z): 442 (M⁺+1)

Example 520

N-{4-[(6,7-Dimethoxy-4-quinolyl)oxy]-2,3-dimethylphenyl}-N'-(N-cyclohexylamino)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 7 hr. Next, cyclohexylhydrazine (50 mg) was added thereto, and the mixture was further stirred at room temperature for 12 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (8 mg, yield 10%).
¹H-NMR (CDCl₃, 400 MHz): 1.20–2.27 (m, 16H), 3.83 (m, 1H), 4.06 (s, 6H), 5.51 (m, 1H), 6.34 (m, 1H), 7.00 (m, 1H), 7.18 (m, 1H), 7.36 (m, 1H), 7.43 (s, 1H), 7.61 (s, 1H), 8.46 (d, J=5.1 Hz, 1H) Mass spectrometry value (ESI-MS, m/z): 481 (M⁺+1)

Example 521

N-{4-[(6,7-Dimethoxy-4-quinolyl)oxy]-2,3-dimethylphenyl}-N'-(1-piperidinyl)thiourea 4-[(6,7-Dimethoxy-4-quinolyl)oxy]-2,3-dimethylaniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-aminopiperidine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (20 mg, yield 27%).
¹H-NMR (CDCl₃, 400 MHz): 1.20–1.88 (m, 6H), 2.15 (s, 3H), 2.26 (s, 3H), 2.51 (m, 2H), 3.23 (m, 2H), 4.06 (s, 3H), 4.07 (s, 3H), 6.33 (d, J=5.4 Hz, 1H), 6.93 (br, 1H), 7.03 (d, J=8.5 Hz, 1H), 7.47 (s, 1H), 7.57 (d, J=8.6 Hz, 1H), 7.62 (s, 1H), 8.46 (d, J=5.4 Hz, 1H), 9.00 (br, 1H) Mass spectrometry value (ESI-MS, m/z): 467 (M⁺+1)

Example 522

N-{4-[(6,7-Dimethoxy-4-quinolyl)oxy]-2,5-dimethylphenyl}-N'-(1-piperidinyl)thiourea 4-[(6,7-Dimethoxy-4-quinolyl)oxy]-2,5-dimethylaniline (50 mg) was dissolved in N,N-dimethylformamide (2 ml) and triethylamine (1 ml) to prepare a solution. Thiophosgene (51 mg) was then added to the solution, and the mixture was stirred at room temperature for 7 hr. Next, 1-aminopiperidine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (9 mg, yield 12%).
¹H-NMR (CDCl₃, 400 MHz): 1.20–1.90 (m, 6H), 2.18 (s, 3H), 2.27 (s, 3H), 2.50 (m, 2H), 3.21 (m, 2H), 4.07 (s, 6H), 6.38 (d, J=5.4 Hz, 1H), 6.86 (br, 1H), 6.98 (s, 1H), 7.49 (s, 1H), 7.59 (s, 1H), 7.79 (s, 1H), 8.47 (d, J=5.4 Hz, 1H), 9.05 (br, 1H) Mass spectrometry value (ESI-MS, m/z): 467 (M⁺+1)

Example 523

N-{4-[(6,7-Dimethoxy-4-quinolyl)oxy]-2,5-dimethylphenyl}-N'-(N-cyclohexylamino)thiourea 4-[(6,7-Dimethoxy-4-quinolyl)oxy]-2,5-dimethylaniline (52 mg) was dissolved in N,N-dimethylformamide (2 ml) and triethylamine (1 ml) to prepare a solution. Thiophosgene (51 mg) was then added to the solution, and the mixture was stirred at room temperature for 1.5 hr. Next, cyclohexylhydrazine (50 mg) was added thereto, and the mixture was further stirred at room temperature for 7 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (10 mg, yield 13%).
¹H-NMR (CDCl₃, 400 MHz): 1.12–1.95 (m, 10H), 2.16 (s, 3H), 2.25 (s, 3H), 3.69 (m, 1H), 4.06 (s, 6H), 5.52 (m, 1H), 6.40 (d, J=5.4 Hz, 1H), 6.97 (m, 1H), 7.46 (s, 1H), 7.52 (s, 1H), 7.59 (s, 1H), 8.47 (d, J=5.4 Hz, 1H), 9.41 (br, 1H) Mass spectrometry value (ESI-MS, m/z): 436 (?)

Example 524

N-{4-[(6,7-Dimethoxy-4-quinazolinyl)oxy]phenyl}-
N'-(1-piperidinyl)thiourea

4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 2 hr. Next, 1-aminopiperidine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (49 mg, yield 66%).

$^1$H-NMR (CDCl$_3$, 400 MHz): 1.18–1.83 (m, 6H), 2.48 (m, 2H), 3.18 (m, 2H), 4.07 (s, 3H), 4.08 (s, 3H), 6.99 (s, 1H), 7.26 (d, J=8.1 Hz, 2H), 7.34 (s, 1H), 7.56 (s, 1H), 7.76 (d, J=8.5 Hz, 2H), 7.53 (s, 1H), 8.61 (s, 1H), 9.27 (br, 1H) Mass spectrometry value (ESI-MS, m/z): 440 (M$^+$+1)

Example 525

N-{4-[(6,7-Dimethoxy-4-quinazolinyl)oxy]phenyl}-
N'-[3-(2-oxotetrahydro-1H-1-pyrrolyl)-propyl]thiourea 4-[(6,7-Dimethoxy-4-quinazolinyl)oxy]aniline (56 mg) was dissolved in N,N-dimethylformamide (2 ml) and triethylamine (1 ml) to prepare a solution. Thiophosgene (50 mg) was then added to the solution, and the mixture was stirred at room temperature for 7 hr. Next, 1-(3-aminopropyl)pyrrolidone (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (15 mg, yield 17%).

$^1$H-NMR (CDCl$_3$, 400 MHz): 1.87 (m, 2H), 2.04 (m, 2H), 2.37 (t, J=8.2 Hz, 2H), 3.30 (t, J=6.2 Hz, 2H), 3.41 (t, J=7.2 Hz, 2H), 3.64 (m, 2H), 4.07 (s, 6H), 7.31–7.42 (m, 6H), 7.55 (s, 1H), 7.79 (br, 1H), 8.62 (s, 1H) Mass spectrometry value (ESI-MS, m/z): 482 (M$^+$+1)

Example 526

N-{4-[(6,7-Dimethoxy-4-quinazolinyl)oxy]phenyl}-
N'-[3-(1-imidazoyl)propyl]thiourea 4-[(6,7-Dimethoxy-4-quinazolinyl)oxy]aniline (56 mg) was dissolved in N,N-dimethylformamide (2 ml) and triethylamine (1 ml) to prepare a solution. Thiophosgene (50 mg) was then added to the solution, and the mixture was stirred at room temperature for 7 hr. Next, 3-(1-imidazoyl)propylamine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (16 mg, yield 18%).

$^1$H-NMR (CDCl$_3$, 400 MHz): 2.29 (m, 2H), 3.69 (m, 2H), 4.06 (s, 3H), 4.07 (s, 3H), 4.38 (m, 2H), 7.20–7.57 (m, 11H), 8.58 (s, 1H) Mass spectrometry value (ESI-MS, m/z): 465 (M$^+$+1)

Example 527

N-{4-[(6,7-Dimethoxy-4-quinazolinyl)oxy]phenyl}-
N'-[2-(1-morpholinyl)ethyl]thiourea 4-[(6,7-Dimethoxy-4-quinazolinyl)oxy]aniline (56 mg) was dissolved in N,N-dimethylformamide (2 ml) and triethylamine (1 ml) to prepare a solution. Thiophosgene (50 mg) was then added to the solution, and the mixture was stirred at room temperature for 7 hr. Next, 2-(1-morpholinyl)ethylamine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (9 mg, yield 10%).

$^1$H-NMR (CDCl$_3$, 400 MHz): 2.50 (m, 4H), 2.64 (m, 2H), 3.65 (m, 4H), 3.75 (m, 2H), 4.08 (s, 3H), 4.08 (s, 3H), 7.14 (br, 1H), 7.34 (m, 4H), 7.35 (s, 1H), 7.54 (s, 1H), 7.73 (br, 1H), 8.61 (s, 1H) Mass spectrometry value (ESI-MS, m/z): 470 (M$^+$+1)

Example 528

N-{4-[(6,7-Dimethoxy-4-quinazolinyl)oxy]-N'-{2-[N-ethyl-N-(o-tolyl)aminoethyl]thiourea 4-[(6,7-Dimethoxy-4-quinazolinyl)oxy]aniline (56 mg) was dissolved in N,N-dimethylformamide (2 ml) and triethylamine (1 ml) to prepare a solution. Thiophosgene (50 mg) was then added to the solution, and the mixture was stirred at room temperature for 7 hr. Next, N-ethyl-N-(o-tolyl)ethylenediamine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (22 mg, yield 22%).

$^1$H-NMR (CDCl$_3$, 400 MHz): 1.11 (t, J=7.1 Hz, 3H), 2.29 (s, 2H), 3.34 (q, J=7.1H, 2H), 3.55 (t, J=6.3 Hz, 2H), 3.84 (m, 2H), 4.08 (s, 6H), 6.43 (br, 1H), 6.54–6.61 (m, 3H), 7.10 (m, 1H), 7.19 (d, J=8.8 Hz, 2H), 7.24 (d, J=8.8 Hz, 2H), 7.35 (s, 1H), 7.53 (s, 1H), 7.77 (br, 1H), 8.60 (s, 1H) Mass spectrometry value (ESI-MS, m/z): 518 (M$^+$+1)

Example 529

N-{4-[(6,7-Dimethoxy-4-quinazolinyl)oxy]phenyl}-
N'-(2-dimethylaminoethyl) thiourea 4-[(6,7-Dimethoxy-4-quinazolinyl)oxy]aniline (51 mg) was dissolved in N,N-dimethylformamide (2 ml) and triethylamine (1 ml) to prepare a solution. Thiophosgene (50 mg) was then added to the solution, and the mixture was stirred at room temperature for 5 hr. Next, N,N-dimethylethylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (18 mg, yield 24%).

$^1$H-NMR (CDCl$_3$, 400 MHz): 1.83 (br, 2H), 2.26 (br, 6H), 2.55 (br, 2H), 4.07 (s, 6H), 7.29–7.30 (m, 5H), 7.34 (s, 1H), 7.54 (s, 1H), 8.62 (s, 1H) Mass spectrometry value (ESI-MS, m/z): 428 (M$^+$+1)

Example 530

N-{4-[(6,7-Dimethoxy-4-quinazolinyl)oxy]phenyl}-N'-[2-(1-pyrrolidyl)ethyl]thiourea 4-[(6,7-Dimethoxy-4-quinazolinyl)oxy]aniline (51 mg) was dissolved in N,N-dimethylformamide (2 ml) and triethylamine (1 ml) to prepare a solution. Thiophosgene (50 mg) was then added to the solution, and the mixture was stirred at room temperature for 5 hr. Next, 2-(1-pyrrolidyl)ethylamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (16 mg, yield 21%).

$^1$H-NMR (CDCl$_3$, 400 MHz): 1.77 (br, 4H), 1.86 (br, 2H), 2.58 (br, 2H), 2.75 (br, 2H), 4.07 (s, 6H), 7.29–7.30 (m, 5H), 7.34 (s, 1H), 7.54 (s, 1H), 8.60 (s, 1H) Mass spectrometry value (ESI-MS, m/z): 454 (M$^+$+1)

Example 531

N-{4-[(6,7-Dimethoxy-4-quinazolinyl)oxy]phenyl}-N'-(3-diethylaminopropyl)thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 6 hr. Next, N,N-diethylpropylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (10 mg, yield 12%).

$^1$H-NMR (CDCl$_3$, 400 MHz): 0.86 (br, 6H), 1.74 (br, 2H), 2.42 (br, 4H), 2.55 (br, 2H), 3.81 (br, 2H), 4.07 (s, 3H), 4.08 (s, 3H), 7.29 (s, 1H), 7.34 (m, 4H), 7.53 (s, 1H), 7.57 (br, 1H), 8.56 (s, 1H), 8.69 (br, 1H) Mass spectrometry value (ESI-MS, m/z): 470 (M$^+$+1)

Example 532

N-{4-[(6,7-Dimethoxy-4-quinazolinyl)oxy]phenyl}-N'-(2-dibutylaminopropyl)thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 6 hr. Next, N,N-diethylpropylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (41 mg, yield 46%).

$^1$H-NMR (CDCl$_3$, 400 MHz): 0.87 (t, J=7.1 Hz, 6H), 1.19 (m, 8H), 1.71 (m, 2H), 2.28 (m, 4H), 2.52 (m, 2H), 3.79 (m, 2H), 4.07 (s, 3H), 4.08 (s, 3H), 7.27–7.32 (m, 4H), 7.34 (s, 1H), 7.52 (s, 1H), 7.75 (br, 1H), 8.44 (br, 1H), 8.57 (s, 1H) Mass spectrometry value (ESI-MS, m/z): 526 (M$^+$+1)

Example 533

N-{4-[(6,7-Dimethoxy-4-quinazolinyl)oxy]phenyl}-N'-[3-(1-morpholino)propyl]thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 6 hr. Next, 3-(1-morpholino)propylamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (16 mg, yield 20%).

$^1$H-NMR (CDCl$_3$, 400 MHz): 1.81 (m, 2H), 2.39 (m, 4H), 2.46 (m, 2H), 3.50 (m, 4H), 3.79 (m, 2H), 4.07 (s, 6H), 7.31–7.37 (m, 5H), 7.53 (s, 1H), 7.69 (br, 1H), 8.61 (s, 1H) Mass spectrometry value (ESI-MS, m/z): 484 (M$^+$+1)

Example 534

N-{4-[(6,7-Dimethoxy-4-quinazolinyl)oxy]phenyl}-N'-{3-[1-(2-methylpiperidinyl)]propyl}thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 6 hr. Next, 3-[1-(2-methylpiperidinyl)]propylamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (30 mg, yield 36%).

¹H-NMR (CDCl₃, 400 MHz): 0.99 (d, J=6.4 Hz, 3H), 1.24–2.53 (m, 11H), 2.81 (m, 2H), 3.71 (m, 1H), 3.81 (m, 1H), 4.07 (s, 3H), 4.07 (s, 3H), 7.29–7.37 (m, 5H), 7.52 (s, 1H), 7.74 (br, 1H), 7.83 (br, 1H), 8.59 (s, 1H) Mass spectrometry value (ESI-MS, m/z): 496 (M⁺+1)

Example 535

N-{4-[(6,7-Dimethoxy-4-quinazolinyl)oxy]phenyl}-N'-(2-diisopropylaminoethyl)thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (50 mg) was then added to the solution, and the mixture was stirred at room temperature for 6 hr. Next, N,N-diisopropylethylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 58%).

¹H-NMR (CDCl₃, 400 MHz): 0.91 (br, 12H), 2.67 (br, 2H), 2.96 (br, 2H), 3.64 (br, 2H), 4.07 (s, 3H), 4.08 (s, 3H), 7.17 (br, 1H), 7.28–7.34 (m, 4H), 7.34 (s, 1H), 7.54 (s, 1H), 7.85 (br, 1H), 8.58 (s, 1H) Mass spectrometry value (ESI-MS, m/z): 484 (M⁺+1)

Example 536

N-{4-[(6,7-Dimethoxy-4-quinazolinyl)oxy]phenyl}-N'-{3-[1-(4-methylpiperazinyl)]propylthiourea 4-[(6,7-Dimethoxy-4-quinazolinyl)oxy]aniline (51 mg) was dissolved in N,N-dimethylformamide (2 ml) and triethylamine (1 ml) to prepare a solution. Thiophosgene (50 mg) was then added to the solution, and the mixture was stirred at room temperature for 1 hr. Next, 1-(3-aminopropyl)-4-methylpiperazine (50 mg) was added thereto, and the mixture was further stirred at room temperature for 6 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (6 mg, yield 7%).

¹H-NMR (CDCl₃, 400 MHz): 1.75–1.83 (m, 6H), 2.23 (s, 3H), 2.23 (m, 2H), 2.44 (m, 4H), 3.78 (br, 2H), 4.06 (s, 3H), 4.08 (s, 3H), 7.31–7.34 (m, 5H), 7.51 (s, 1H), 7.59 (br, 1H), 8.61 (s, 1H) Mass spectrometry value (ESI-MS, m/z): 497 (M⁺+1)

Example 537

N-{4-[(6,7-Dimethoxy-4-quinazolinyl)oxy]phenyl}-N'-[3-(1-pyrrolidinyl)propyl]thiourea 4-[(6,7-Dimethoxy-4-quinazolinyl)oxy]aniline (51 mg) was dissolved in N,N-dimethylformamide (2 ml) and triethylamine (1 ml) to prepare a solution. Thiophosgene (50 mg) was then added to the solution, and the mixture was stirred at room temperature for 1 hr. Next, N,N-diethylpropylenediamine (50 mg) was added thereto, and the mixture was further stirred at room temperature for 6 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (19 mg, yield 24%).

¹H-NMR (CDCl₃, 400 MHz): 1.55 (br, 2H), 1.79 (m, 2H), 2.42 (br, 4H), 2.58 (br, 2H), 3.81 (br, 2H), 4.07 (s, 3H), 4.07 (s, 3H), 7.27–7.34 (m, 4H), 7.34 (s, 1H), 7.52 (s, 1H), 7.73 (br, 1H), 8.19 (br, 1H), 8.59 (s, 1H) Mass spectrometry value (ESI-MS, m/z): 467 (M⁺+1)

Example 538

N-{4-[(6,7-Dimethoxy-4-quinolyl)oxy]-2,5-dimethylphenyl}-N'-(2-dimethylaminoethyl)thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-dimethylethylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (24 mg, yield 34%).

¹H-NMR (CDCl₃, 400 MHz): 2.16 (s, 3H), 2.22 (br, 6H), 2.28 (s, 3H), 2.51 (br, 2H), 3.68 (br, 2H), 4.06 (s, 3H), 4.06 (s, 3H), 6.27 (m, 1H), 6.68 (br, 1H), 7.05 (s, 1H), 7.21 (s, 1H), 7.44 (s, 1H), 7.49 (br, 1H), 7.57 (s, 1H), 8.46 (d, J=5.2 Hz, 1H) Mass spectrometry value (ESI-MS, m/z): 455 (M⁺+1)

Example 539

N-{4-[(6,7-Dimethoxy-4-quinolyl)oxy]-2,5-dimethylphenyl}-N'-[3-(1-imidazoyl)propyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)imidazole (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (20 mg, yield 25%).

¹H-NMR (CDCl₃, 400 MHz): 2.00 (m, 2H), 2.15 (m, 2H), 2.18 (s, 3H), 2.25 (s, 3H), 3.67 (m, 2H), 4.05 (s, 3H), 4.06 (s, 3H), 5.98 (br, 1H), 6.33 (d, J=5.4 Hz, 1H), 6.93 (s, 1H), 7.04 (s, 1H), 7.05 (s, 1H), 7.17 (s, 1H), 7.43 (s, 1H), 7.50 (br, 1H), 7.54 (s, 1H), 7.74 (s, 1H), 8.47 (d, J=5.1 Hz, 1H) Mass spectrometry value (ESI-MS, m/z): 492 (M⁺+1)

Example 540

N-{4-[(6,7-Dimethoxy-4-quinolyl)oxy]-2,5-dimethylphenyl}-N'-{2-[N-ethyl-N-(o-tolyl)amino]-ethyl}thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-dimethylethylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (28 mg, yield 32%).

$^1$H-NMR (CDCl$_3$, 400 MHz): 1.07 (t, J=7.1 Hz, 3H), 2.07 (s, 3H), 2.22 (s, 3H), 2.29 (s, 3H), 3.30 (q, J=7.1 Hz, 2H), 3.51 (t, J=6.0 Hz, 2H), 3.84 (m, 2H), 4.06 (s, 3H), 4.06 (s, 3H), 6.06 (br, 1H), 6.22 (d, J=5.4 Hz, 1H), 6.53–6.68 (m, 3H), 6.99 (s, 1H), 7.02 (s, 1H), 7.09 (m, 1H), 7.45 (s, 1H), 7.52 (br, 1H), 7.54 (s, 1H), 8.43 (d, J=5.2 Hz, 1H) Mass spectrometry value (ESI-MS, m/z): 545 (M$^+$+1)

Example 541

N-{4-[(6,7-Dimethoxy-4-quinolyl)oxy]-2,5-dimethylphenyl}-N'-[2-(1-pyrrolidinyl)ethyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(2-aminoethyl)pyrrolidine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (8 mg, yield 10%).

$^1$H-NMR (CDCl$_3$, 400 MHz): 1.72 (br, 4H), 2.16 (s, 3H), 2.27 (s, 3H), 2.54 (br, 4H), 2.73 (br, 2H), 3.72 (br, 2H), 4.06 (s, 6H), 6.28 (m, 1H), 6.77 (br, 1H), 7.04 (s, 1H), 7.19 (s, 1H), 7.43 (s, 1H), 7.56 (s, 1H), 8.46 (d, J=5.1 Hz, 1H) Mass spectrometry value (ESI-MS, m/z): 481 (M$^+$+1)

Example 542

N-{4-[(6,7-Dimethoxy-4-quinolyl)oxy]-2,3-dimethylphenyl}-N'-(2-dimethylaminoethyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 7 hr. Next, N,N-dimethylethylenediamine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (12 mg, yield 17%).

$^1$H-NMR (CDCl$_3$, 400 MHz): 2.16 (s, 3H), 2.19 (br, 6H), 2.28 (s, 3H), 2.48 (br, 2H), 3.66 (br, 2H), 4.06 (s, 3H), 4.07 (s, 3H), 6.22 (m, 1H), 6.56 (br, 1H), 7.04 (d, J=8.3 Hz, 1H), 7.19 (d, J=8.5 Hz, 1H), 7.44 (s, 1H), 7.60 (s, 1H), 8.45 (d, J=5.1 Hz, 1H) Mass spectrometry value (ESI-MS, m/z): 455 (M$^+$+1)

Example 543

N-{4-[(6,7-Dimethoxy-4-quinolyl)oxy]-2,3-dimethylphenyl}-N'-[3-(1-imidazoyl)propyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 7 hr. Next, 1-(3-aminopropyl)imidazole (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (13 mg, yield 17%).

$^1$H-NMR (CDCl$_3$, 400 MHz): 2.14 (m, 2H), 2.18 (s, 3H), 2.26 (s, 3H), 3.66 (m, 2H), 4.04 (m, 2H), 4.05 (s, 3H), 4.06 (s, 3H), 5.79 (br, 1H), 6.30 (d, J=5.4 Hz, 1H), 6.92 (s, 1H), 7.04 (s, 1H), 7.05 (d, J=8.6 Hz, 1H), 7.14 (d, J=8.6 Hz, 1H), 7.44 (s, 1H), 7.51 (br, 1H), 7.56 (s, 1H), 7.62 (s, 1H), 8.47 (d, J=5.4 Hz, 1H) Mass spectrometry value (ESI-MS, m/z): 492 (M$^+$+1)

Example 544

N-{4-[(6,7-Dimethoxy-4-quinolyl)oxy]-2,3-dimethylphenyl}-N'-{2-[N-ethyl-N-(o-tolyl)amino]-ethyl}thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 7 hr. Next, N,N-dimethylethylenediamine (50 mg) was added thereto, and the mixture was further stirred at room temperature for 13 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (4 mg, yield 4%).

$^1$H-NMR (CDCl$_3$, 400 MHz): 1.06 (t, J=7.1 Hz, 3H), 2.10 (s, 3H), 2.21 (s, 3H), 2.28 (s, 3H), 3.28 (q, J=7.1 Hz, 2H), 3.49 (t, J=6.1 Hz, 2H), 3.83 (m, 2H), 4.07 (s, 6H), 5.94 (br,

Example 545

N-{4-[(6,7-Dimethoxy-4-quinolyl)oxy]-2,5-dimethylphenyl}-N'-[2-(1-morpholino)ethyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(2-aminoethyl)morpholine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (23 mg, yield 29%).

$^1$H-NMR (CDCl$_3$, 400 MHz): 2.19 (s, 3H), 2.28 (s, 3H), 2.43 (br, 4H), 2.58 (m, 2H), 3.56 (m, 4H), 3.71 (m, 2H), 4.06 (s, 3H), 4.07 (s, 3H), 6.30 (d, J=5.1 Hz, 1H), 6.60 (br, 1H), 7.07 (s, 1H), 7.21 (s, 1H), 7.45 (s, 1H), 7.46 (br, 1H), 7.56 (s, 1H), 8.48 (d, J=5.1 Hz, 1H) Mass spectrometry value (ESI-MS, m/z): 497 (M$^+$+1)

Example 546

N-{4-[(6,7-Dimethoxy-4-quinolyl)oxy]-2,3-dimethylphenyl}-N'-(3-diethylaminopropyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diethylpropylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (36 mg, yield 45%).

$^1$H-NMR (CDCl$_3$, 400 MHz): 0.83 (t, J=7.1 Hz, 6H), 1.70 (m, 2H), 2.16 (s, 3H), 2.29 (s, 3H), 2.32 (m, 4H), 2.49 (m, 2H), 3.78 (m, 2H), 4.06 (s, 3H), 4.06 (s, 3H), 6.30 (d, J=5.4 Hz, 1H), 7.00 (d, J=8.5 Hz, 1H), 7.19 (d, J=8.5 Hz, 1H), 7.44 (s, 1H), 7.56 (br, 1H), 7.57 (s, 1H), 7.80 (br, 1H), 8.46 (d, J=5.4 Hz, 1H) Mass spectrometry value (ESI-MS, m/z): 497 (M$^+$+1)

Example 547

N-{4-[(6,7-Dimethoxy-4-quinolyl)oxy]-2,3-dimethylphenyl}-N'-(3-dibutylaminopropyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-dibutylpropylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (33 mg, yield 37%).

$^1$H-NMR (CDCl$_3$, 400 MHz): 0.89 (t, J=6.8 Hz, 6H), 1.19 (m, 8H), 1.69 (m, 2H), 2.15 (s, 3H), 2.20 (m, 4H), 2.29 (s, 3H), 2.49 (m, 2H), 3.78 (m, 2H), 4.05 (s, 3H), 4.06 (s, 3H), 6.30 (d, J=5.1 Hz, 1H), 7.01 (d, J=8.6 Hz, 1H), 7.19 (d, J=8.5 Hz, 1H), 7.44 (s, 1H), 7.48 (br, 1H), 7.56 (s, 1H), 7.79 (br, 1H), 8.46 (d, J=5.1 Hz, 1H) Mass spectrometry value (ESI-MS, m/z): 552 (M$^+$+1)

Example 548

N-{4-[(6,7-Dimethoxy-4-quinolyl)oxy]-2,3-dimethylphenyl}-N'-[3-(1-morpholino)propyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)morpholine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (16 mg, yield 19%).

$^1$H-NMR (CDCl$_3$, 400 MHz): 1.78 (m, 4H), 2.19 (s, 3H), 2.29 (s, 3H), 2.36 (m, 4H), 3.45 (m, 4H), 3.78 (m, 2H), 4.06 (s, 3H), 4.06 (s, 3H), 6.33 (d, J=5.1 Hz, 1H), 6.70 (br, 1H), 7.03 (d, J=8.6 Hz, 1H), 7.19 (d, J=8.5 Hz, 1H), 7.44 (s, 1H), 7.56 (s, 1H), 8.48 (d, J=5.1 Hz, 1H) Mass spectrometry value (ESI-MS, m/z): 511 (M$^+$+1)

Example 549

N-{4-[(6,7-Dimethoxy-4-quinolyl)oxy]-2,3-dimethylphenyl}-N'-[3-(2-methylpiperidinyl)propyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)-2-methylpiperidine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (39 mg, yield 47%).

$^1$H-NMR (CDCl$_3$, 400 MHz): 0.94–2.20 (m, 14H), 2.17 (s, 3H), 2.29 (s, 3H), 2.76 (m, 2H), 3.68 (m, 1H), 3.85 (m, 1H), 4.05 (s, 3H), 4.06 (s, 3H), 6.34 (d, J=5.1 Hz, 1H), 7.02 (d, J=8.6 Hz, 1H), 7.20 (d, J=8.3 Hz, 1H), 7.44 (s, 1H), 7.50

Example 550

N-{4-[(6,7-Dimethoxy-4-quinolyl)oxy]-2,3-dimethylphenyl}-N'-(2-diisopropylaminoethyl)thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diisopropylethylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (52 mg, yield 64%).

$^1$H-NMR (CDCl$_3$, 400 MHz): 0.84 (br, 12H), 2.13 (s, 3H), 2.27 (s, 3H), 2.62 (m, 2H), 2.89 (m, 2H), 3.61 (m, 2H), 4.06 (s, 3H), 4.07 (s, 3H), 6.24 (m, 1H), 7.02 (d, J=8.5 Hz, 1H), 7.18 (d, J=8.3 Hz, 1H), 7.44 (s, 1H), 7.52 (br, 1H), 7.58 (s, 1H), 8.44 (d, J=5.4 Hz, 1H) Mass spectrometry value (ESI-MS, m/z): 511 (M$^+$+1)

Example 551

N-{4-[(6,7-Dimethoxy-4-quinolyl)oxy]-2,5-dimethylphenyl}-N'-(3-diethylaminopropyl)thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diethylpropylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (38 mg, yield 49%).

$^1$H-NMR (CDCl$_3$, 400 MHz): 0.86 (t, J=7.2 Hz, 6H), 1.72 (m, 2H), 2.16 (s, 3H), 2.27 (s, 3H), 2.34 (m, 4H), 2.51 (m, 2H), 3.79 (m, 2H), 4.06 (s, 6H), 6.34 (d, J=5.1 Hz, 1H), 7.01 (s, 1H), 7.21 (s, 1H), 7.38 (br, 1H), 7.44 (s, 1H), 7.54 (s, 1H), 7.93 (br, 1H), 8.48 (d, J=5.1 Hz, 1H) Mass spectrometry value (ESI-MS, m/z): 497 (M$^+$+1)

Example 552

N-{4-[(6,7-Dimethoxy-4-quinolyl)oxy]-2,5-dimethylphenyl}-N'-(3-dibutylaminopropyl)thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-dibutylpropylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (34 mg, yield 40%).

$^1$H-NMR (CDCl$_3$, 400 MHz): 0.90 (t, J=7.0 Hz, 6H), 1.20 (m, 8H), 1.70 (m, 2H), 2.16 (s, 3H), 2.23 (m, 4H), 2.27 (s, 3H), 2.51 (m, 2H), 3.79 (m, 2H), 4.05 (s, 3H), 4.06 (s, 3H), 6.34 (d, J=5.2 Hz, 1H), 7.02 (s, 1H), 7.20 (s, 1H), 7.30 (br, 1H), 7.44 (s, 1H), 7.54 (s, 1H), 7.88 (br, 1H), 8.48 (d, J=5.1 Hz, 1H) Mass spectrometry value (ESI-MS, m/z): 553 (M$^+$+1)

Example 553

N-{4-[(6,7-Dimethoxy-4-quinolyl)oxy]-2,5-dimethylphenyl}-N'-[3-(1-morpholino)propyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)morpholine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (18 mg, yield 23%).

$^1$H-NMR (CDCl$_3$, 400 MHz): 1.78 (m, 4H), 2.19 (s, 3H), 2.27 (s, 3H), 2.36 (m, 4H), 3.45 (m, 4H), 3.79 (m, 2H), 4.05 (s, 3H), 4.06 (s, 3H), 6.37 (d, J=5.4 Hz, 1H), 6.83 (br, 1H), 7.03 (s, 1H), 7.22 (s, 1H), 7.44 (s, 1H), 7.54 (s, 1H), 8.50 (d, J=5.1 Hz, 1H) Mass spectrometry value (ESI-MS, m/z): 511 (M$^+$+1)

Example 554

N-{4-[(6,7-Dimethoxy-4-quinolyl)oxy]-2,5-dimethylphenyl}-N'-[3-(2-methylpiperidinyl)propyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)-2-methylpiperidine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (46 mg, yield 56%).

$^1$H-NMR (CDCl$_3$, 400 MHz): 0.90–2.20 (m, 14H), 2.17 (s, 3H), 2.27 (s, 3H), 2.79 (m, 2H), 3.68 (m, 1H), 3.88 (m, 1H), 4.04 (s, 3H), 4.06 (s, 3H), 6.39 (d, J=5.2 Hz, 1H), 7.02 (s, 1H), 7.22 (s, 1H), 7.38 (br, 1H), 7.44 (s, 1H), 7.53 (s, 1H), 8.49 (d, J=5.1 Hz, 1H) Mass spectrometry value (ESI-MS, m/z): 523 (M$^+$)

Example 555

N-{4-[(6,7-Dimethoxy-4-quinolyl)oxy]-2,5-dimethylphenyl}-N'-(2-diisopropylaminoethyl)thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diisopropylethylenediamine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (13 mg, yield 17%).

$^1$H-NMR (CDCl$_3$, 400 MHz): 0.86 (br, 12H), 2.14 (s, 3H), 2.26 (s, 3H), 2.62 (m, 2H), 2.91 (m, 2H), 3.61 (m, 2H), 4.06 (s, 3H), 4.07 (s, 3H), 6.27 (m, 1H), 6.68 (br, 1H), 7.03 (s, 1H), 7.19 (s, 1H), 7.36 (br, 1H), 7.44 (s, 1H), 7.56 (s, 1H), 8.46 (d, J=5.1 Hz, 1H) Mass spectrometry value (ESI-MS, m/z): 511 (M$^+$+1)

Example 556

N-{4-[(6,7-Dimethoxy-4-quinolyl)oxy]-2,5-dimethylphenyl}-N'-[3-(4-methylpiperazinyl)propyl]thiourea 4-[(6,7-Dimethoxy-4-quinolyl)oxy]-2,5-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)-4-methylpiperazine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (20 mg, yield 24%).

$^1$H-NMR (CDCl$_3$, 400 MHz): 1.76 (m, 6H), 2.17 (s, 3H), 2.26 (m, 2H), 2.28 (s, 3H), 2.41 (m, 4H), 3.77 (m, 2H), 4.03 (s, 3H), 4.06 (s, 3H), 6.34 (d, J=5.1 Hz, 1H), 6.83 (br, 1H), 7.05 (s, 1H), 7.22 (s, 1H), 7.37 (br, 1H), 7.44 (s, 1H), 7.52 (s, 1H), 8.48 (d, J=5.1 Hz, 1H) Mass spectrometry value (ESI-MS, m/z): 524 (M$^+$+1)

Example 557

N-{4-[(6,7-Dimethoxy-4-quinolyl)oxy]-2,3-dimethylphenyl}-N'-[3-(4-methylpiperazinyl)propyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)-4-methylpiperazine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (10 mg, yield 11%).

$^1$H-NMR (CDCl$_3$, 400 MHz): 1.73 (m, 6H), 2.17 (s, 3H), 2.25 (m, 2H), 2.29 (s, 3H), 2.39 (m, 4H), 3.77 (m, 2H), 4.04 (s, 3H), 4.06 (s, 3H), 6.30 (d, J=5.1 Hz, 1H), 6.76 (br, 1H), 7.05 (d, J=8.6 Hz, 1H), 7.20 (d, J=8.6 Hz, 1H), 7.38 (br, 1H), 7.44 (s, 1H), 7.55 (s, 1H), 8.47 (d, J=5.4 Hz, 1H) Mass spectrometry value (ESI-MS, m/z): 524 (M$^+$+1)

Example 558

N-{4-[(6,7-Dimethoxy-4-quinolyl)oxy]-2,3-dimethylphenyl}-N'-[3-(1-piperidinyl)propyl]thiourea 4-[(6,7-Dimethoxy-4-quinolyl)oxy]-2,3-dimethylaniline (51 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, 1-(3-aminopropyl)pyrrolidine (50 mg) was added thereto, and the mixture was further stirred at room temperature for 16 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (18 mg, yield 22%).

$^1$H-NMR (CDCl$_3$, 400 MHz): 1.55 (br, 4H), 1.77 (br, 2H), 2.17 (s, 3H), 2.28 (s, 3H), 2.39 (br, 4H), 2.55 (br, 2H), 3.78 (br, 2H), 4.05 (s, 3H), 4.06 (s, 3H), 6.32 (d, J=5.4 Hz, 1H), 7.00 (d, J=8.6 Hz, 1H), 7.18 (m, 1H), 7.44 (s, 1H), 7.46 (br, 1H), 7.56 (s, 1H), 8.47 (d, J=5.4 Hz, 1H) Mass spectrometry value (ESI-MS, m/z): 475

Example 559

N-{4-[(6,7-Dimethoxy-4-quinazolinyl)oxy]phenyl}-N'-(2-dimethylaminoethyl)thiourea 4-[(6,7-Dimethoxy-4-quinazolinyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 5 hr. Next, N,N-dimethylethylenediamine (50 mg) was added thereto, and the mixture was further stirred at room temperature for 15 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (62 mg, yield 83%).

$^1$H-NMR (CDCl$_3$, 400 MHz): 2.52 (s, 6H), 2.67 (br, 2H), 3.68 (br, 2H), 4.07 (s, 6H), 7.26–7.54 (m, 7H), 7.83 (br, 1H), 8.59 (s, 1H) Mass spectrometry value (ESI-MS, m/z): 428 (M$^+$+1)

Example 560

N-(1-Benzyltetrahydro-1H-3-pyrrolyl)-N'-{4-[(6,7-dimethoxy-4-quinolyl)oxy]phenyl}urea Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. 1-Benzyl-3-aminopyrrolidine (89 mg) was then added thereto, and the mixture was stirred at room temperature for 3 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (76 mg, yield 45%).

$^1$H-NMR (chloroform-d, 400 MHz): δ 1.97–2.08 (m, 1H), 2.38–2.49 (m, 1H), 2.55–2.64 (m, 1H), 2.78–2.85 (m, 1H), 3.13–3.19 (m, 1H), 3.34–3.41 (m, 1H), 3.91 (s, 1H), 3.92 (s, 1H), 4.04 (s, 6H), 4.45–4.53 (m, 1H), 6.23 (br, 1H), 6.44 (d, J=5.4 Hz, 1H), 7.07–7.11 (m, 2H), 7.35–7.47 (m, 8H), 7.56 (s, 1H), 8.46 (d, J=5.4 Hz, 1H) Mass spectrometry value (ESI-MS, m/z): 499 (M$^+$+1)

Example 561

Ethyl 4-[({4-[(6,7-dimethoxy-4-quinolyl)oxy]anilino}carbonyl)amino]-1-piperidine-carboxylate Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. Ethyl 4-amino-1-piperidine (87 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (108 mg, yield 65%).

$^1$H-NMR (chloroform-d, 400 MHz): δ 1.25 (t, J=7.1 Hz, 3H), 1.32–1.45 (m, 2H), 1.93–2.02 (m, 2H), 2.92–3.05 (m, 2H), 3.83–3.94 (m, 1H), 3.98–4.06 (m, 2H), 4.07 (s, 3H), 4.08 (s, 3H), 4.09–4.16 (m, 2H), 5.57 (d, J=7.8 Hz, 1H), 6.48 (d, J=5.9 Hz, 1H), 7.05–7.10 (m, 2H), 7.50–7.55 (m, 2H), 7.58 (s, 1H), 7.59 (s, 1H), 7.74 (s, 1H), 8.36 (d, J=5.9 Hz, 1H) Mass spectrometry value (ESI-MS, m/z): 495 (M$^+$+1)

Example 562

N-{4-[(6,7-Dimethoxy-4-quinolyl)oxy]-phenyl}-N'-(2,2,6,6-tetramethyl-4-piperidyl)urea Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. 4-Amino-2,2,6,6-tetramethylpiperidine (79 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (27 mg, yield 17%).

$^1$H-NMR (chloroform-d, 400 MHz): δ 1.53–2.09 (m, 16H), 4.02 (s, 3H), 4.06 (s, 3H), 4.22–4.37 (m, 1H), 6.51 (d, J=5.6 Hz, 1H), 7.05 (d, J=8.8 Hz, 2H), 7.42 (s, 1H), 7.54–7.64 (m, 3H), 8.42 (d, J=5.9 Hz, 1H), 8.65 (br, 1H) Mass spectrometry value (ESI-MS, m/z): 479 (M$^+$+1)

Example 563

N-{4-[(6,7-Dimethoxy-4-quinazolinyl)oxy]phenyl}-N'-(2,2,6,6-tetramethyl-4-piperidyl)urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. 4-Amino-2,2,6,6-tetramethylpiperidine (79 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (66 mg, yield 41%).

$^1$H-NMR (chloroform-d, 400 MHz): δ 1.28–2.09 (m, 16H), 4.05 (s, 3H), 4.06 (s, 3H), 4.11–4.28 (m, 1H), 7.13 (d, J=8.8 Hz, 2H), 7.29 (s, 1H), 7.46–7.55 (m, 3H), 8.57 (s, 1H) Mass spectrometry value (ESI-MS, m/z): 480 (M$^+$+1)

Example 564

N-[(3R)-1-Benzyltetrahydro-1H-3-pyrrolyl]-N'-{4-[(6,7-dimethoxy-4-quinolyl)oxy]phenyl}urea Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. (3R)-(−)-1-Benzyl-3-aminopyrrolidine (89 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (54 mg, yield 32%).

$^1$H-NMR (chloroform-d, 400 MHz): δ 2.00–2.16 (m, 2H), 2.41–2.52 (m, 1H), 2.63–2.72 (m, 1H), 2.84–2.92 (m, 1H), 3.21–3.29 (m, 1H), 3.99 (s, 1H), 4.01 (s, 1H), 4.04 (s, 3H), 4.05 (s, 3H), 4.50–4.61 (m, 1H), 6.44 (d, J=5.1 Hz, 1H), 7.06–7.12 (m, 2H), 7.37–7.48 (m, 8H), 7.56 (s, 1H), 8.46 (d, J=5.4 Hz, 1H) Mass spectrometry value (ESI-MS, m/z): 499 (M$^+$+1)

Example 565

N-[(3S)-1-Benzyltetrahydro-1H-3-pyrrolyl]-N'-{4-[(6,7-dimethoxy-4-quinolyl)oxy]phenyl}urea Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. (3S)-(+)-1-Benzyl-3-aminopyrrolidine (89 mg) was then added thereto, and the mixture was stirred at room temperature for 5 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (48 mg, yield 29%).

$^1$H-NMR (chloroform-d, 400 MHz): δ 1.92–2.17 (m, 2H), 2.40–2.51 (m, 1H), 2.60–2.71 (m, 1H), 2.81–2.90 (m, 1H), 3.18–3.25 (m, 1H), 3.96 (s, 1H), 3.98 (s, 1H), 4.05 (s, 6H), 4.49–4.58 (m, 1H), 6.44 (d, J=5.1 Hz, 1H), 7.06–7.12 (m, 2H), 7.37–7.49 (m, 7H), 7.56 (s, 1H), 7.61 (s, 1H), 8.46 (d, J=5.4 Hz, 1H) Mass spectrometry value (ESI-MS, m/z): 499 (M$^+$+1)

Example 566

N-[(3R)-1-Benzyltetrahydro-1H-3-pyrrolyl]-N'-{4-[(6,7-dimethoxy-4-quinazolinyl)oxy]phenyl}urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. (3R)-(−)-1-Benzyl-3-aminopyrrolidine (89 mg) was then added thereto, and the mixture was stirred at room temperature for 5 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (114 mg, yield 68%).

$^1$H-NMR (chloroform-d, 400 MHz): δ 2.07–2.20 (m, 1H), 2.40–2.52 (m, 1H), 2.76–2.87 (m, 1H), 2.99–3.07 (m, 1H), 3.29–3.38 (m, 1H), 3.51–3.60 (m, 1H), 4.06 (s, 6H), 4.08 (s, 1H), 4.10 (s, 1H), 4.57–4.66 (m, 1H), 6.75–6.85 (m, 1H), 7.11–7.17 (m, 2H), 7.29–7.57 (m, 9H), 8.59 (s, 1H) Mass spectrometry value (ESI-MS, m/z): 500 (M$^+$+1)

Example 567

N-[(3S)-1-Benzyltetrahydro-1H-3-pyrrolyl]-N'-{4-[(6,7-dimethoxy-4-quinazolinyl)oxy]phenyl}urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. (3S)-(+)-1-Benzyl-3-aminopyrrolidine (89 mg) was then added thereto, and the mixture was stirred at room temperature for 5 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (100 mg, yield 60%).

$^1$H-NMR (chloroform-d, 400 MHz): δ 1.97–2.08 (m, 1H), 2.33–2.48 (m, 1H), 2.60–2.69 (m, 1H), 2.82–2.91 (m, 1H), 3.11–3.20 (m, 1H), 3.32–3.42 (m, 1H), 3.94 (s, 1H), 3.96 (s, 1H), 4.06 (s, 6H), 4.46–4.57 (m, 1H), 6.37 (br, 1H), 7.12–7.18 (m, 2H), 7.29–7.50 (m, 8H), 7.54 (s, 1H), 8.62 (s, 1H) Mass spectrometry value (ESI-MS, m/z): 500 (M$^+$+1)

Example 568

N-{4-[(6,7-Dimethoxy-4-quinolyl)oxy]phenyl}-N'-[1-(2-methylbenzyl)-4-piperidyl]urea N-(1-Benzyl-4-piperidyl)-N'-{4-[(6,7-dimethoxy-4-quinolyl)oxy]phenyl}urea (100 mg) was dissolved in 1,2-dichloroethane (25 ml) to prepare a solution. 1-Chloroethyl chloroformate (0.10 ml) was then added to the solution, and the mixture was heated under reflux overnight. The solvent was removed by distillation under the reduced pressure. Methanol (20 ml) was added to the residue, followed by heating under reflux for 2 hr. The solvent was removed by distillation under the reduced pressure to give 139 mg of N-{4-[(6,7-dimethoxy-4-quinolyl)oxy]phenyl}-N'-(4-piperidyl)urea (1).

Acetonitrile (10 ml) was added to the compound (1) (139 mg), 2-methylbenzyl bromide (0.03 ml), and potassium carbonate (81 mg), and the mixture was stirred at room temperature overnight. Water was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (46 mg, yield 45%).

$^1$H-NMR (chloroform-d, 400 MHz): δ 1.88–2.01 (m, 2H), 2.09–2.19 (m, 2H), 2.42 (s, 3H), 2.53–2.67 (m, 2H), 3.19–3.29 (m, 2H), 3.30–3.39 (m, 1H), 3.90 (s, 2H), 4.04 (s, 3H), 4.04 (s, 3H), 6.42 (d, J=5.4 Hz, 1H), 7.05–7.12 (m, 2H), 7.17–7.27 (m, 4H), 7.42 (s, 1H), 7.47–7.53 (m, 2H), 7.55 (s, 1H), 7.56 (s, 1H), 8.45 (d, J=5.4 Hz, 1H) Mass spectrometry value (ESI-MS, m/z): 527 (M$^+$+1)

Example 569

N-{4-[(6,7-Dimethoxy-4-quinazolinyl)oxy]phenyl}-N'-[1-(2-methylbenzyl)tetrahydro-1H-3-pyrrolyl]urea 3-Aminopyrrolidine (500 mg) was dissolved in acetonitrile (10 ml) to prepare a solution. 2-Methylbenzyl bromide (0.78 ml) and potassium carbonate (2.40 g) were added to the solution, and the mixture was stirred at room temperature for 3 hr. Water was added to the reaction solution, and the mixture was extracted with chloroform. The extract was washed with saturated brine and was then dried over anhydrous sodium sulfate. The solvent was removed by distillation under the reduced pressure. The residue was purified by chromatography on silica gel using chloroform/methanol for development to give 1-(2-methylbenzyl)-3-pyrrolidinamine (1) (604 mg, yield 55%).

Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. The compund (1) (96 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (64 mg, yield 37%).

$^1$H-NMR (chloroform-d, 400 MHz): δ 1.95–2.05 (m, 1H), 2.41 (s, 3H), 2.40–2.48 (m, 1H), 2.55–2.63 (m, 1H), 2.79–2.87 (m, 1H), 3.08–3.14 (m, 1H), 3.30–3.38 (m, 1H), 3.90 (s, 2H), 4.06 (s, 3H), 4.07 (s, 3H), 4.44–4.55 (m, 1H), 7.13–7.18 (m, 2H), 7.18–7.40 (m, 5H), 7.40–7.47 (m, 2H), 7.55 (s, 1H), 8.60 (s, 1H) Mass spectrometry value (ESI-MS, m/z): 514 (M$^+$+1)

Example 570

N-{4-[(6,7-Dimethoxy-4-quinazolinyl)oxy]-2-nitrophenyl}-N'-[1-(2-methylbenzyl)tetrahydro-1H-3-pyrrolyl]urea Chloroform (13 ml) and triethylamine (2 ml) were added to 4-[(6,7-dimethoxy-4-quinazolinyl)oxy]-2-nitroaniline (100 mg) to prepare a solution. Triphosgene (96 mg) was added to the solution, and the mixture was stirred at room temperature for 30 min. 1-(2-Methylbenzyl)-3-pyrrolidinamine (83 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (38 mg, yield 23%).

$^1$H-NMR (chloroform-d, 400 MHz): δ 1.94–2.04 (m, 1H), 2.44 (s, 3H), 2.42–2.50 (m, 1H), 2.55–2.65 (m, 1H), 2.81–2.90 (m, 1H), 3.02–3.10 (m, 1H), 3.27–3.34 (m, 1H), 3.88–3.92 (m, 2H), 4.07 (s, 3H), 4.09 (s, 3H), 4.50–4.59 (m, 1H), 7.18–7.26 (m, 2H), 7.32–7.43 (3m, 2H), 7.49–7.55 (m, 2H), 8.12 (d, J=2.7 Hz, 1H), 8.60 (s, 1H), 8.71–8.77 (m, 1H), 9.78 (s, 1H) Mass spectrometry value (ESI-MS, m/z): 559 (M$^+$+1)

Example 571

N-{4-[(6,7-Dimethoxy-4-quinazolinyl)oxy]-2-methoxyphenyl}-N'-[1-(2-methylbenzyl)tetrahydro-1H-3-pyrrolyl]urea Chloroform (10 ml) and triethylamine (2 ml) were added to 4-[(6,7-dimethoxy-4-quinazolinyl)oxy]-2-methoxyaniline (100 mg) to prepare a solution. Triphosgene (99 mg) was added to the solution, and the mixture was stirred at room temperature for 30 min. 1-(2-Methylbenzyl)-3-pyrrolidinamine (87 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (58 mg, yield 35%).

$^1$H-NMR (chloroform-d, 400 MHz): δ 2.01–2.11 (m, 1H), 2.21–2.33 (m, 1H), 2.50 (s, 3H), 2.48–2.58 (m, 1H), 2.86–2.98 (m, 1H), 3.43–3.52 (m, 1H), 3.68–3.78 (m, 1H), 3.84 (s, 3H), 4.07 (s, 6H), 4.21 (s, 1H), 4.23 (s, 1H), 4.71–4.82 (m, 1H), 6.75 (d, J=2.4 Hz, 1H), 6.79 (dd, J=2.4 Hz, 8.8 Hz, 1H), 7.17–7.22 (m, 1H), 7.27–7.36 (m, 3H), 7.54 (s, 1H), 7.54–7.59 (m, 1H), 8.13 (d, J=8.8 Hz, 1H), 8.62 (s, 1H) Mass spectrometry value (ESI-MS, m/z): 544 (M$^+$+1)

Example 572

N-{4-[(6,7-Dimethoxy-4-quinolyl)oxy]-2,3-dimethylphenyl}-N'-[1-(2-methylbenzyl)tetrahydro-1H-3-pyrrolyl]urea Chloroform (10 ml) and triethylamine (2 ml) were added to 4-[(6,7-dimethoxy-4-quinolyl)oxy]-2,3-dimethylaniline (100 mg) to prepare a solution. Triphosgene (101 mg) was added to the solution, and the mixture was stirred at room temperature for 30 min. 1-(2-Methylbenzyl)-3-pyrrolidinamine (88 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (68 mg, yield 41%).

$^1$H-NMR (chloroform-d, 400 MHz): δ 2.01–2.10 (m, 1H), 2.11 (s, 3H), 2.22 (s, 3H), 2.36 (s, 3H), 2.38–2.47 (m, 1H), 2.50–2.59 (m, 1H), 2.73–2.81 (m, 1H), 3.01–3.09 (m, 1H), 3.23–3.33 (m, 1H), 3.86 (s, 2H), 4.06 (s, 3H), 4.07 (s, 3H), 4.48–4.58 (m, 1H), 6.30 (d, J=5.4 Hz, 1H), 6.97 (d, J=8.8

Hz, 1H), 7.14–7.36 (m, 4H), 7.44 (s, 1H), 7.62 (s, 1H), 8.44 (d, J=5.4 Hz, 1H) Mass spectrometry value (ESI-MS, m/z): 541 (M$^+$+1)

Example 573

N-{2-Chloro-4-[(6,7-dimethoxy-4-quinazolinyl)oxy]phenyl}-N'-[1-(2-methylbenzyl)tetrahydro-1H-3-pyrrolyl]urea Chloroform (10 ml) and triethylamine (2 ml) were added to 2-chloro-4-[(6,7-dimethoxy-4-quinazolinyl)oxy]aniline (100 mg) to prepare a solution. Triphosgene (99 mg) was added to the solution, and the mixture was stirred at room temperature for 30 min. 1-(2-Methylbenzyl)-3-pyrrolidinamine (86 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (82 mg, yield 50%).

$^1$H-NMR (chloroform-d, 400 MHz): δ 1.92–2.01 (m, 1H), 2.39–2.47 (m, 1H), 2.41 (s, 3H), 2.51–2.60 (m, 1H), 2.77–2.84 (m, 1H), 3.01–3.08 (m, 1H), 3.23–3.33 (m, 1H), 3.86 (s, 1H), 3.87 (s, 1H), 4.07 (s, 6H), 4.27–4.38 (m, 1H), 7.12–7.40 (m, 7H), 7.51 (s, 1H), 8.19 (d, J=9.0 Hz, 1H), 8.61 (s, 1H) Mass spectrometry value (ESI-MS, m/z): 548 (M$^+$+1)

Example 574

N-{4-[(6,7-Dimethoxy-4-quinolyl)oxy]phenyl}-N'-[1-(2-methylbenzyl)tetrahydro-1H-3-pyrrolyl]urea Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. 1-(2-Methylbenzyl)-3-pyrrolidinamine (96 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (101 mg, yield 59%).

$^1$H-NMR (chloroform-d, 400 MHz): δ 1.98–2.10 (m, 1H), 2.38–2.50 (m, 1H), 2.41 (s, 3H), 2.58–2.68 (m, 1H), 2.83–2.93 (m, 1H), 3.15–3.22 (m, 1H), 3.37–3.44 (m, 1H), 3.95 (s, 2H), 4.04 (s, 6H), 4.46–4.58 (m, 1H), 6.43 (d, J=5.4 Hz, 1H), 7.05–7.12 (m, 2H), 7.18–7.47 (m, 7H), 7.56 (s, 1H), 8.46 (d, J=5.4 Hz, 1H) Mass spectrometry value (ESI-MS, m/z): 513 (M$^+$+1)

Example 575

N-[(3R)-1-Benzyltetrahydro-1H-3-pyrrolyl]-N'-{2-chloro-4-[(6,7-dimethoxy-4-quinazolinyl)oxy]phenyl}urea Chloroform (15 ml) and triethylamine (3 ml) were added to 2-chloro-4-[(6,7-dimethoxy-4-quinazolinyl)oxy]aniline (200 mg) to prepare a solution. Triphosgene (198 mg) was added to the solution, and the mixture was stirred at room temperature for 30 min. (3R)-(−)-1-Benzyl-3-aminopyrrolidine (80 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (189 mg, yield 59%).

$^1$H-NMR (chloroform-d, 400 MHz): δ 1.90–2.02 (m, 1H), 2.37–2.47 (m, 1H), 2.48–2.58 (m, 1H), 2.72–2.80 (m, 1H), 2.98–3.06 (m, 1H), 3.21–3.29 (m, 1H), 3.83 (s, 1H), 3.85 (s, 1H), 4.07 (s, 6H), 4.45–4.56 (m, 1H), 7.14 (dd, J=2.7 Hz, 9.0 Hz, 1H), 7.28–7.43 (m, 7H), 7.51 (s, 1H), 8.20 (d, J=9.0 Hz, 1H), 8.61 (s, 1H) Mass spectrometry value (ESI-MS, m/z): 534 (M$^+$+1)

Example 576

N-[(3S)-1-Benzyltetrahydro-1H-3-pyrrolyl]-N'-{2-chloro-4-[(6,7-dimethoxy-4-quinazolinyl)oxy]phenyl}urea Chloroform (15 ml) and triethylamine (3 ml) were added to 2-chloro-4-[ (6,7-dimethoxy-4-quinazolinyl)oxy]aniline (200 mg) to prepare a solution. Triphosgene (198 mg) was added to the solution, and the mixture was stirred at room temperature for 30 min. (3S)-(+)-1-Benzyl-3-aminopyrrolidine (80 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (204 mg, yield 63%).

$^1$H-NMR (chloroform-d, 400 MHz): δ 1.90–2.00 (m, 1H), 2.35–2.48 (m, 1H), 2.50–2.58 (m, 1H), 2.73–2.80 (m, 1H), 2.98–3.05 (m, 1H), 3.20–3.29 (m, 1H), 3.83 (s, 1H), 3.85 (s, 1H), 4.07 (s, 6H), 4.45–4.54 (m, 1H), 7.15 (dd, J=2.7 Hz, 9.0 Hz, 1H), 7.28–7.43 (m, 7H), 7.51 (s, 1H), 8.20 (d, J=9.0 Hz, 1H), 8.62 (s, 1H) Mass spectrometry value (ESI-MS, m/z): 534 (M$^+$+1)

Example 577

N-[(3R)-1-Benzyltetrahydro-1H-3-pyrrolyl]-N'-{4-[(6,7-dimethoxy-4-quinazolinyl)oxy]-2-nitrophenyl}urea Chloroform (27 ml) and triethylamine (4 ml) were added to 4-[(6,7-dimethoxy-4-quinazolinyl)oxy]-2-nitroaniline (200 mg) to prepare a solution. Triphosgene (192 mg) was added to the solution, and the mixture was stirred at room temperature for 30 min. (3R)-(−)-1-Benzyl-3-aminopyrrolidine (77 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (184 mg, yield 58%).

$^1$H-NMR (chloroform-d, 400 MHz): δ 1.96–2.05 (m, 1H), 2.39–2.49 (m, 1H), 2.56–2.66 (m, 1H), 2.81–2.89 (m, 1H), 3.04–3.12 (m, 1H), 3.26–3.36 (m, 1H), 3.91 (s, 2H), 4.07 (s, 6H), 4.50–4.59 (m, 1H), 7.30–7.55 (m, 7H), 8.12 (d, J=2.9 Hz, 1H), 8.60 (s, 1H), 8.73 (d, J=9.3 Hz, 1H), 9.80 (s, 1H) Mass spectrometry value (ESI-MS, m/z): 545 (M$^+$+1)

Example 578

N-[(3S)-1-Benzyltetrahydro-1H-3-pyrrolyl]-N'-{4-[(6,7-dimethoxy-4-quinazolinyl)oxy]-2-nitrophenyl}urea Chloroform (27 ml) and triethylamine (4 ml) were added to 4-[(6,7-dimethoxy-4-quinazolinyl)oxy]-2-nitroaniline (200 mg) to prepare a solution. Triphosgene (192 mg) was added to the solution, and the mixture was stirred at room temperature for 30 min. (3S)-(+)-1-Benzyl-3-aminopyrrolidine (77 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (153 mg, yield 48%).

$^1$H-NMR (chloroform-d, 400 MHz): δ 1.95–2.07 (m, 1H), 2.39–2.49 (m, 1H), 2.57–2.67 (m, 1H), 2.82–2.90 (m, 1H), 3.04–3.12 (m, 1H), 3.27–3.36 (m, 1H), 3.92 (s, 2H), 4.07 (s, 6H), 4.50–4.60 (m, 1H), 7.29–7.55 (m, 7H), 8.12 (d, J=2.9 Hz, 1H), 8.60 (s, 1H), 8.73 (d, J=9.5 Hz, 1H), 9.80 (s, 1H) Mass spectrometry value (ESI-MS, m/z): 545 (M$^+$+1)

Example 579

N-[1-(2-Chlorobenzyl)tetrahydro-1H-3-pyrrolyl]-N'-{4-[(6,7-dimethoxy-4-quinolyl)oxy]phenyl}urea 3-Aminopyrrolidine (500 mg) was dissolved in acetonitrile (10 ml) to prepare a solution. 2-Chlorobenzyl bromide (0.75 ml), potassium carbonate (2.40 g) were added to the solution, and the mixture was stirred at room temperature for one hr. Water was added to the reaction solution, and the mixture was extracted with chloroform. The extract was washed with saturated brine and was then dried over anhydrous sodium sulfate. The solvent was removed by distillation under the reduced pressure. The residue was purified by chromatography on silica gel using chloroform/methanol for development to give 1-(2-chlorobenzyl)-3-pyrrolidinamine (1) (453 mg, yield 37%).

Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. The compound (1) (106 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (76 mg, yield 42%).

$^1$H-NMR (chloroform-d, 400 MHz): δ 1.93–2.03 (m, 1H), 2.39–2.49 (m, 1H), 2.58–2.69 (m, 1H), 2.84–2.92 (m, 1H), 3.11–3.18 (m, 1H), 3.32–3.40 (m, 1H), 4.05 (s, 6H), 4.45–4.53 (m, 1H), 6.44 (d, J=5.4 Hz, 1H), 7.05–7.12 (m, 2H), 7.27–7.34 (m, 2H), 7.38–7.47 (m, 4H), 7.54–7.64 (m, 2H), 8.46 (d, J=5.4 Hz, 1H) Mass spectrometry value (ESI-MS, m/z): 533 (M$^+$+1)

Example 580

N-[1-(2-Chlorobenzyl)tetrahydro-1H-3-pyrrolyl]-N'-{4-[(6,7-dimethoxy-4-quinazolinyl)oxy]phenyl}urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. 1-(2-Chlorobenzyl)-3-pyrrolidinamine (106 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (109 mg, yield 61%).

$^1$H-NMR (chloroform-d, 400 MHz): δ 1.86–1.97 (m, 1H), 2.34–2.47 (m, 1H), 2.51–2.61 (m, 1H), 2.78–2.85 (m, 1H), 3.00–3.07 (m, 1H), 3.21–3.29 (m, 1H), 3.98 (s, 2H), 4.07 (s, 6H), 4.40–4.50 (m, 1H), 5.80–5.90 (m, 1H), 7.13–7.18 (m, 2H), 7.25–7.46 (m, 6H), 7.53–7.57 (m, 2H), 8.60 (s, 1H) Mass spectrometry value (ESI-MS, m/z): 534 (M$^+$+1)

Example 581

N-[1-(2-Chlorobenzyl)tetrahydro-1H-3-pyrrolyl]-N'-{4-[(6,7-dimethoxy-4-quinazolinyl)oxy]-2-nitrophenyl}urea Chloroform (13 ml) and triethylamine (2 ml) were added to 4-[(6,7-dimethoxy-4-quinazolinyl)oxy]-2-nitroaniline (100 mg) to prepare a solution. Triphosgene (96 mg) was added to the solution, and the mixture was stirred at room temperature for 30 min. 1-(2-Chlorobenzyl)-3-pyrrolidinamine (92 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (66 mg, yield 39%).

$^1$H-NMR (chloroform-d, 400 MHz): δ 2.05–2.16 (m, 1H), 2.40–2.50 (m, 1H), 2.60–2.69 (m, 1H), 2.87–2.93 (m, 1H), 3.03–3.10 (m, 1H), 3.25–3.33 (m, 1H), 4.04 (s, 2H), 4.07 (s, 6H), 4.51–4.60 (m, 1H), 7.26–7.56 (m, 5H), 7.62–7.68 (m, 1H), 8.12 (d, J=2.7 Hz, 1H), 8.60 (s, 1H), 8.74 (d, J=9.3 Hz, 1H), 9.79 (s, 1H) Mass spectrometry value (ESI-MS, m/z): 579 (M$^+$+1)

Example 582

N-{1-[4-(Tert-butyl)benzyl]tetrahydro-1H-3-pyrrolyl}-N'-{4-[(6,7-dimethoxy-4-quinolyl)oxy]phenyl}urea 3-Aminopyrrolidine (500 mg) was dissolved in acetonitrile (10 ml) to prepare a solution. 4-(Tert-butyl)benzyl bromide (1.07 ml) and potassium carbonate (2.40 g) were added to the solution, and the mixture was stirred at room temperature for one hr. Water was added to the reaction solution, and the mixture was extracted with chloroform. The extract was washed with saturated brine and was then dried over anhydrous sodium sulfate. The solvent was removed by distillation under the reduced pressure. The residue was purified by chromatography on silica gel using chloroform/methanol for development to give 1-[4-(tert-butyl)benzyl]-3-pyrrolidinamine (1) (589 mg, yield 44%).

Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. (1) (117 mg) was then added thereto, and the mixture was stirred at room temperature for 5 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (71 mg, yield 38%).

$^1$H-NMR (chloroform-d, 400 MHz): δ 1.32 (s, 9H), 2.12–2.28 (m, 1H), 2.43–2.55 (m, 1H), 2.83–2.93 (m, 1H), 3.01–3.09 (m, 1H), 3.38–3.45 (m, 1H), 3.62–3.72 (m, 1H), 4.04 (s, 3H), 4.04 (s, 3H), 4.11 (s, 1H), 4.13 (s, 1H), 4.61–4.70 (m, 1H), 6.43 (d, J=5.4 Hz, 1H), 7.04–7.10 (m, 2H), 7.38–7.58 (m, 8H), 8.45 (d, J=5.4 Hz, 1H) Mass spectrometry value (ESI-MS, m/z): 555 (M$^+$+1)

Example 583

N-{1-[4-(Tert-butyl)benzyl]tetrahydro-1H-3-pyrrolyl}-N'-{4-[(6,7-dimethoxy-4-quinazolinyl)oxy]phenyl}urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. 1-[4-(Tert-butyl)benzyl]-3-pyrrolidinamine (117 mg) was then added thereto, and the mixture was stirred at room temperature for 5 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (76 mg, yield 41%).

$^1$H-NMR (chloroform-d, 400 MHz): δ 1.31 (s, 9H), 2.07–2.12 (m, 1H), 2.37–2.48 (m, 1H), 2.57–2.66 (m, 1H), 2.78–2.88 (m, 1H), 3.11–3.19 (m, 1H), 3.32–3.42 (m, 1H), 3.89 (s, 1H), 3.91 (s, 1H), 4.06 (s, 6H), 4.44–4.55 (m, 1H), 7.12–7.17 (m, 2H), 7.28–7.57 (m, 8H), 8.60 (s, 1H) Mass spectrometry value (ESI-MS, m/z): 556 (M$^+$+1)

Example 584

N-{1-[4-(Tert-butyl)benzyl]tetrahydro-1H-3-pyrrolyl}-N'-{4-[(6,7-dimethoxy-4-quinazolinyl)oxy]-2-nitrophenyl}urea Chloroform (13 ml) and triethylamine (2 ml) were added to 4-[(6,7-dimethoxy-4-quinazolinyl)oxy]-2-nitroaniline (100 mg) to prepare a solution. Triphosgene (96 mg) was added to the solution, and the mixture was stirred at room temperature for 30 min. 1-[4-(Tert-butyl)benzyl]-3-pyrrolidinamine (102 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (38 mg, yield 22%).

$^1$H-NMR (chloroform-d, 400 MHz): δ 1.32 (s, 9H), 1.92–2.04 (m, 1H), 2.38–2.48 (m, 1H), 2.53–2.64 (m, 1H), 2.78–2.86 (m, 1H), 3.03–3.11 (m, 1H), 3.27–3.35 (m, 1H), 3.86 (s, 1H), 3.87 (s, 1H), 4.07 (s, 6H), 4.50–4.58 (m, 1H), 7.32–7.54 (m, 6H), 8.12 (d, J=2.9 Hz, 1H), 8.60 (s, 1H), 8.71–8.75 (m, 1H), 9.80 (s, 1H) Mass spectrometry value (ESI-MS, m/z): 601 (M$^+$+1)

Example 585

N-[1-(Cyclohexylmethyl)tetrahydro-1H-3-pyrrolyl]-
N'-{4-[(6,7-dimethoxy-4-quinolyl)oxy]phenyl}urea 3-Aminopyrrolidine (500 mg) was dissolved in acetonitrile (10 ml) to prepare a solution. Cyclohexylmethyl bromide (0.81 ml), potassium carbonate (2.40 g), and tetra-n-butylammonium iodide (100 mg) were added to the solution, and the mixture was stirred at room temperature for 7 hr. Water was added to the reaction solution, and the mixture was extracted with chloroform. The extract was washed with saturated brine and was then dried over anhydrous sodium sulfate. The solvent was removed by distillation under the reduced pressure. The residue was purified by chromatography on silica gel using chloroform/methanol for development to give 1-(cyclohexylmethyl)-3-pyrrolidinamine (1) (271 mg, yield 26%).

Chloroform (10 ml) and triethylamine (2 ml) were added to 4-[(6,7-dimethoxy-4-quinolyl)oxy]aniline (100 mg) to prepare a solution. Triphosgene (110 mg) was added to the solution, and the mixture was stirred at room temperature for 30 min. The compound (1) (74 mg) was then added thereto, and the mixture was stirred at room temperature for 3 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (85 mg, yield 50%).

$^1$H-NMR (chloroform-d, 400 MHz): δ 1.00–1.32 (m, 6H), 1.64–1.85 (m, 4H), 1.91–2.03 (m, 2H), 2.27–2.38 (m, 1H), 2.48–2.60 (m, 1H), 2.88–2.98 (m, 2H), 3.65–3.73 (m, 1H), 4.04 (s, 6H), 4.05 (s, 2H), 4.68–4.78 (m, 1H), 6.44 (d, J=5.4 Hz, 1H), 7.06–7.11 (m, 2H), 7.42 (s, 1H), 7.47–7.55 (m, 2H), 7.56 (s, 1H), 8.46 (d, J=5.4 Hz, 1H) Mass spectrometry value (ESI-MS, m/z): 505 (M$^+$+1)

Example 586

N-[1-(Cyclohexylmethyl)tetrahydro-1H-3-pyrrolyl]-
N'-{4-[(6,7-dimethoxy-4-quinazolinyl)oxy]phenyl}urea Chloroform (10 ml) and triethylamine (2 ml) were added to 4-[(6,7-dimethoxy-4-quinazolinyl)oxy]aniline (100 mg) to prepare a solution. Triphosgene (110 mg) was added to the solution, and the mixture was stirred at room temperature for 30 min. 1-(Cyclohexylmethyl)-3-pyrrolidinamine (74 mg) was then added thereto, and the mixture was stirred at room temperature for 3 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (94 mg, yield 55%).

$^1$H-NMR (chloroform-d, 400 MHz): δ 1.00–1.37 (m, 6H), 1.63–1.88 (m, 4H), 1.90–1.98 (m, 1H), 2.27–2.39 (m, 1H), 2.47–2.60 (m, 1H), 2.84–3.01 (m, 2H), 3.07–3.18 (m, 1H), 3.68–3.78 (m, 1H), 3.95–4.06 (m, 2H), 4.07 (s, 3H), 4.08 (s, 3H), 4.70–4.79 (m, 1H), 7.10–7.17 (m, 2H), 7.41 (s, 1H), 7.52 (s, 1H), 7.52–7.58 (m, 2H), 7.88 (s, 1H), 8.64 (s, 1H) Mass spectrometry value (ESI-MS, m/z): 506 (M$^+$+1)

Example 587

N-[1-(Cyclohexylmethyl)tetrahydro-1H-3-pyrrolyl]-
N'-{4-[(6,7-dimethoxy-4-quinazolinyl)oxy]-2-nitrophenyl}urea Chloroform (13 ml) and triethylamine (2 ml) were added to 4-[(6,7-dimethoxy-4-quinazolinyl)oxy]-2-nitroaniline (100 mg) to prepare a solution. Triphosgene (96 mg) was added to the solution, and the mixture was stirred at room temperature for 30 min. 1-(Cyclohexylmethyl)-3-pyrrolidinamine (64 mg) was then added thereto, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/acetone for development. Diethyl ether was added to the purification product, and the precipitated crystal was collected by filtration and was washed to give the title compound (34 mg, yield 21%).

$^1$H-NMR (chloroform-d, 400 MHz): δ 0.94–1.34 (m, 6H), 1.61–1.81 (m, 4H), 1.87–1.99 (m, 2H), 2.06–2.20 (m, 1H), 2.40–2.52 (m, 1H), 2.61–2.73 (m, 2H), 2.83–2.93 (m, 1H), 3.28–3.40 (m, 1H), 3.52–3.63 (m, 1H), 4.07 (s, 6H), 4.57–4.68 (m, 1H), 7.33 (s, 1H), 7.51 (s, 2H), 8.12 (d, J=2.9 Hz, 1H), 8.60 (s, 1H), 8.72 (d, J=9.3 HZ, 1H), 9.82 (s, 1H) Mass spectrometry value (ESI-MS, m/z): 551 (M$^+$+1)

Example 588

N-{4-[(6,7-Dimethoxy-4-quinolyl)oxy]phenyl}-N'-(2-diethylaminopropyl)thiourea

4-[(6,7-Dimethoxy-4-quinolyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diethylpropylenediamine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (25 mg, yield %).

$^1$H-NMR (CDCl$_3$, 400 MHz): 1.00–1.10 (m, 6H), 1.85–2.00 (m, 2H), 2.55–2.80 (m, 6H), 3.80–3.90 (m, 2H), 4.04 (s, 3H), 4.06 (s, 3H), 6.54 (d, J=5.4 Hz, 1H), 7.19 (d, J=6.8 Hz, 1H), 7.24–7.28 (m, 2H), 7.36–7.44 (m, 2H), 7.44 (s, 1H), 7.516 (s, 1H), 8.51 (d, J=5.1 Hz, 1H) Mass spectrometry value (ESI-MS, m/z): 469 (M$^+$+1)

Example 589

N-{4-[(6,7-Dimethoxy-4-quinolyl)oxy]phenyl}-N'-(2-diethylaminoethyl)thiourea

4-[(6,7-Dimethoxy-4-quinolyl)oxy]aniline (50 mg) was dissolved in N,N-dimethylformamide (2 ml) and triethylamine (1 ml) to prepare a solution. Thiophosgene (51 mg) was then added to the solution, and the mixture was stirred at room temperature for 6 hr. Next, N,N-diethylethylenediamine (50 mg) was added thereto, and the mixture was further stirred at room temperature for 14 hr. Ethyl acetate was added to the reaction solution, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (25 mg, yield 33%).
$^1$H-NMR (CDCl$_3$, 400 MHz): 0.90–1.10 (m, 6H), 2.45–2.75 (m, 2H), 3.60–3.75 (m, 2H), 4.05 (s, 3H), 4.06 (s, 3H), 6.49 (s, 1H), 7.20–7.38 (m, 4H), 7.43 (s, 1H), 7.53 (s, 1H), 8.50 (d, J=5.1 Hz, 1H) Mass spectrometry value (ESI-MS, m/z): 455 (M$^+$+1)

Example 590

N-{4-[(6,7-Dimethoxy-4-quinolyl)oxy]phenyl}-N'-[4-(N-benzyl)piperidinyl]urea

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (27 mg, yield 32%).
$^1$H-NMR (CDCl$_3$, 400 MHz): 1.45–1.55 (m, 2H), 1.95–2.05 (m, 2H), 2.13–2.23 (m, 2H), 2.80–2.90 (m, 2H), 3.52 (s, 2H), 3.70–3.80 (m, 1H), 4.04 (s, 6H), 4.85–4.95 (m, 1H), 6.44 (d, J=5.4 Hz, 1H), 6.80–6.82 (m, 2H), 7.10–7.14 (m, 2H), 7.26–7.34 (m, 5H), 7.40–7.44 (m, 2H), 7.55 (s, 1H), 8.46 (d, J=5.1 Hz, 1H) Mass spectrometry value (ESI-MS, m/z): 513 (M$^+$+1)

Example 591

N-{4-[(6,7-Dimethoxy-4-quinazolinyl)oxy]phenyl}-N'-[4-(N-benzyl)piperidinyl]urea 4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (30 mg, yield 35%).
$^1$H-NMR (CDCl$_3$, 400 MHz): 1.45–1.60 (m, 2H), 1.95–2.05 (m, 2H), 2.15–2.25 (m, 2H), 2.80–2.90 (m, 2H), 3.55 (s, 2H), 3.70–3.80 (m, 1H), 4.07 (s, 6H), 4.70–4.80 (m, 1H), 4.47 (s, 1H), 7.19 (d, J=9.2 Hz, 1H), 7.30–7.34 (m, 5H), 7.40 (d, J=8.8 Hz, 2H), 7.55 (s, 1H), 8.62 (s, 1H) Mass spectrometry value (ESI-MS, m/z): 514 (M$^+$+1)

Example 592

N-{4-[(6,7-Dimethoxy-4-quinolyl)oxy]phenyl}-N'-(1-piperidinyl)urea

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (40 mg, yield 56%).
$^1$H-NMR (CDCl$_3$, 400 MHz): 1.60–1.85 (m, 6H), 2.33–2.46 (m, 2H), 3.15–3.25 (m, 2H), 4.057 (s, 3H), 4.059 (s, 3H), 5.33 (s, 1H), 6.45 (d, J=5.4 Hz, 1H), 7.14 (d, J=9.0 Hz, 2H), 7.45 (s, 1H), 7.57–7.62 (m, 3H), 8.23 (s, 1H), 8.47 (d, J=5.4 Hz, 1H) Mass spectrometry value (ESI-MS, m/z): 423 (M$^+$+1)

Example 593

N-{4-[(6,7-Dimethoxy-4-quinolyl)oxy]-2,3-dimethylphenyl}-N'-(1-piperidinyl)urea

4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (40 mg, yield 58%).

¹H-NMR (CDCl₃, 400 MHz): 1.50–1.90 (m, 6H), 2.12 (s, 3H), 2.25 (s, 3H), 2.35–2.50 (m, 2H), 3.15–3.25 (m, 2H), 4.07 (s, 3H), 4.08 (s, 3H), 5.41 (s, 1H), 6.30 (d, J=5.6 Hz, 1H), 7.00 (d, J=8.8 Hz, 1H), 7.53 (s, 1H), 7.64 (s, 1H), 7.84 (d, J=8.8 Hz, 1H), 8.25 (s, 1H), 8.43 (d, J=5.4 Hz, 1H) Mass spectrometry value (ESI-MS, m/z): 451 (M⁺+1)

Example 594

N-{4-[(6,7-Dimethoxy-4-quinolyl)oxy]-2-nitrophenyl}-N'-(1-piperidinyl)urea

4-[(6,7-Dimethoxy-4-quinolyl)oxy]-2-nitroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (35 mg, yield 51%).
¹H-NMR (CDCl₃, 400 MHz): 1.60–1.85 (m, 6H), 2.43–2.48 (m, 2H), 3.15–3.25 (m, 2H), 4.09 (s, 3H), 4.12 (s, 3H), 5.63 (s, 1H), 6.59 (d, J=5.6 Hz, 1H), 7.47–7.52 (m, 1H), 7.57 (s, 1H), 7.82 (m, 1H), 8.12 (d, J=2.9 Hz, 1H), 9.00 (d, J=9.3 Hz, 1H), 11.42 (s, 1H) Mass spectrometry value (ESI-MS, m/z): 468 (M⁺+1)

Example 595

N-{4-[(6,7-Dimethoxy-4-quinolyl)oxy]-2-chlorophenyl}-N'-(1-piperidinyl)urea

4-[(6,7-Dimethoxy-4-quinolyl)oxy]-2-chloroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (38 mg, yield 55%).
¹H-NMR (CDCl₃, 400 MHz): 1.60–1.85 (m, 6H), 2.35–2.50 (m, 2H), 3.15–3.25 (m, 2H), 4.07 (s, 6H), 5.45–5.50 (m, 1H), 7.15–7.19 (m, 1H), 7.34–7.36 (m, 2H), 7.53 (s, 1H), 8.44–8.47 (m, 1H), 8.63 (d, J=1.2 Hz, 1H), 9.04 (s, 1H) Mass spectrometry value (ESI-MS, m/z): 468 (M⁺+1)

Example 596

N-{4-[(6,7-Dimethoxy-4-quinazolinyl)oxy]-2-methoxyphenyl}-N'-(1-piperidinyl)urea 4-[(6,7-Dimethoxy-4-quinazolinyl)oxy]-2-methoxyaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (45 mg, yield 65%).
¹H-NMR (CDCl₃, 400 MHz): 1.60–1.85 (m, 6H), 2.30–2.45 (m, 2H), 3.10–3.20 (m, 2H), 3.91 (s, 3H), 4.07 (s, 6H), 5.30–5.40 (m, 1H), 6.79 (d, J=2.4 Hz, 1H), 6.82–6.86 (m, 1H), 7.33 (d, J=2.2 Hz, 1H), 7.57 (d, J=1.0 Hz, 1H), 8.33 (dd, J=1.2 Hz, J=8.5 Hz, 1H), 8.63 (d, J=1.5 Hz, 1H), 8.80 (s, 1H) Mass spectrometry value (ESI-MS, m/z): 454 (M⁺+1)

Example 597

N-{4-[(6,7-Dimethoxy-4-quinazolinyl)oxy]-2-nitrophenyl}-N'-(1-piperidinyl)urea

4-[(6,7-Dimethoxy-4-quinazolinyl)oxy]-2-nitroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (50 mg, yield 73%).
¹H-NMR (CDCl₃, 400 MHz): 1.50–2.00 (m, 6H), 2.38–2.48 (m, 2H), 3.15–3.20 (m, 2H), 4.08 (s, 3H), 4.09 (s, 3H), 5.57 (s, 1H), 7.36 (s, 1H), 7.53–7.57 (m, 2H), 8.17 (d, J=2.9 Hz, 1H), 8.61 (s, 1H), 8.93 (d, J=9.3 Hz, 1H), 11.41 (s, 1H) Mass spectrometry value (ESI-MS, m/z): 469 (M⁺+1)

Example 598

N-{4-[(6,7-Dimethoxy-4-quinolyl)oxy]-2-methoxyphenyl}-N'-(1-piperidinyl)urea

4-[(6,7-Dimethoxy-4-quinolyl)oxy]-2-methoxyaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (43 mg, yield 62%).

$^1$H-NMR (CDCl$_3$, 400 MHz): 1.50–1.80 (m, 6H), 2.30–2.45 (m, 2H), 3.15–3.25 (m, 2H), 3.89 (s, 3H), 4.07 (s, 6H), 5.33 (s, 1H), 6.50 (d, J=5.6 Hz, 1H), 6.72 (d, J=2.4 Hz, 1H), 6.80 (dd, J=2.4 Hz, J=8.8 Hz, 1H), 7.52 (s, 1H), 7.59 (s, 1H), 8.32 (d, J=8.8 Hz, 1H), 8.47 (d, J=5.4 Hz, 1H), 8.80 (s, 1H) Mass spectrometry value (ESI-MS, m/z): 453 (M$^+$+1)

Example 599

N-{4-[(6,7-Dimethoxy-4-quinazolinyl)oxy]-2-methoxyphenyl}-N'-(1-morphonyl)urea

4-[(6,7-Dimethoxy-4-quinazolinyl)oxy]-2-methoxyaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminomorpholine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (26 mg, yield 37%).

$^1$H-NMR (CDCl$_3$, 400 MHz): 2.60–2.75 (m, 2H), 2.90–3.10 (m, 2H), 3.40–3.55 (m, 2H), 3.65–3.80 (m, 2H), 3.91 (s, 3H), 4.07 (s, 3H), 4.08 (s, 3H), 5.45 (s, 1H), 6.80 (d, J=2.7 Hz, 1H), 6.85 (dd, J=2.4 Hz, J=8.8 Hz, 1H), 7.34 (s, 1H), 7.56 (s, 1H), 8.33 (d, J=8.8 Hz, 1H), 8.63 (s, 1H), 8.73 (s, 1H) Mass spectrometry value (ESI-MS, m/z): 456 (M$^+$+1)

Example 600

N-{4-[(6,7-Dimethoxy-4-quinolyl)oxy]-2-methoxyphenyl}-N'-(1-homopiperidinyl)urea 4-[(6,7-Dimethoxy-4-quinolyl)oxy]-2-methoxyaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminohomopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (35 mg, yield 49%).

$^1$H-NMR (CDCl$_3$, 400 MHz): 1.50–1.90 (m, 8H), 2.85–3.00 (m, 2H), 3.05–3.20 (m, 2H), 3.90 (s, 3H), 4.07 (s, 3H), 4.08 (s, 3H), 5.66 (s, 1H), 6.75–6.90 (m, 2H), 7.32 (s, 1H), 7.57 (s, 1H), 8.35 (d, J=8.5 Hz, 1H), 8.63 (s, 1H), 8.95 (s, 1H) Mass spectrometry value (ESI-MS, m/z): 468 (M$^+$+1)

Example 601

N-{4-[(6,7-Dimethoxy-4-quinazolinyl)oxy]phenyl}-N'-(1-morphonyl)urea

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminomorpholine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 66%).

$^1$H-NMR (CDCl$_3$, 400 MHz): 2.50–2.70 (m, 2H), 2.90–3.10 (m, 2H), 3.65–3.85 (m, 2H), 3.85–4.00 (m, 2H), 4.07 (s, 3H), 4.08 (s, 3H), 5.45 (s, 1H), 7.21 (d, J=9.0 Hz, 2H), 7.33 (s, 1H), 7.56 (s, 1H), 7.60 (d, J=9.0 Hz, 2H), 8.12 (s, 1H), 8.61 (s, 1H) Mass spectrometry value (ESI-MS, m/z): 426 (M$^+$+1)

Example 602

N-{4-[(6,7-Dimethoxy-4-quinazolinyl)oxy]phenyl}-N'-(1-homopiperidinyl)urea

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminohomopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (48 mg, yield 65%).

$^1$H-NMR (CDCl$_3$, 400 MHz): 1.55–1.85 (m, 8H), 2.85–3.00 (m, 2H), 3.05–3.20 (m, 2H), 4.07 (s, 3H), 4.08 (s, 3H), 5.67 (s, 1H), 7.19 (d, J=9.0 Hz, 2H), 7.33 (s, 1H), 7.57

(s, 1H), 7.60 (d, J=8.8 Hz, 2H), 8.33 (s, 1H), 8.62 (s, 1H) Mass spectrometry value (ESI-MS, m/z): 438 (M$^+$+1)

Example 603

N-{4-[(6,7-Dimethoxy-4-quinazolinyl)oxy]phenyl}-N'-(1-piperidinyl)urea

4-[(6,7-Dimethoxy-4-quinazolinyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 66%).

$^1$H-NMR (CDCl$_3$, 400 MHz): 1.50–1.80 (m, 6H), 2.30–2.45 (m, 2H), 3.10–3.20 (m, 2H), 4.07 (s, 3H), 4.08 (s, 3H), 5.40–5.50 (m, 1H), 7.19 (d, J=8.8 Hz, 2H), 7.35 (s, 1H), 7.57 (s, 1H), 7.59 (d, J=8.8 Hz, 2H), 8.25 (s, 1H), 8.62 (s, 1H) Mass spectrometry value (ESI-MS, m/z): 424 (M$^+$+1)

Example 604

N-{4-[(6,7-Dimethoxy-4-quinolyl)oxy]-2,3-dimethylphenyl}-N'-[4-(N-benzyl)piperidinyl]urea 4-[(6,7-Dimethoxy-4-quinolyl)oxy]-2,3-dimethylaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (45 mg, yield 55%).

$^1$H-NMR (CDCl$_3$, 400 MHz): 2.07–2.18 (m, 4H), 2.24 (s, 3H), 2.40–2.54 (m, 1H), 2.80–2.95 (m, 1H), 3.25–3.30 (m, 1H), 3.45–3.60 (m, 2H), 4.05 (s, 3H), 4.06 (s, 3H), 4.09 (d, J=12.7 Hz, 1H), 4.14 (d, J=12.7 Hz, 1H), 4.60 (s, 1H), 6.30 (d, J=5.4 Hz, 1H), 6.90–7.00 (m, 2H), 7.10–7.54 (m, 7H), 7.61 (s, 1H), 8.63 (d, J=5.4 Hz, 1H) Mass spectrometry value (ESI-MS, m/z): 527 (M$^+$+1)

Example 605

N-{4-[(6,7-Dimethoxy-4-quinolyl)oxy]-2-chlorophenyl}-N'-[4-(N-benzyl)piperidinyl]urea 4-[(6,7-Dimethoxy-4-quinolyl)oxy]-2-chloroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (35 mg, yield 43%).

$^1$H-NMR (CDCl$_3$, 400 MHz): 1.73–1.80 (m, 2H), 2.25–2.40 (m, 2H), 2.56–2.63 (m, 1H), 2.71–2.76 (m, 1H), 2.98–3.00 (m, 1H), 3.62 (d, J=12.7 Hz, 1H), 3.66 (d, J=12.9 Hz, 1H), 4.07 (s, 6H), 4.30–4.40 (m, 1H), 5.30 (br, 1H), 7.14–7.18 (m, 1H), 7.30–7.33 (m, 7H), 7.52 (s, 1H), 8.17–8.22 (m, 1H), 8.63 (s, 1H) Mass spectrometry value (ESI-MS, m/z): 534 (M$^+$+1)

Example 606

N-{4-[(6,7-Dimethoxy-4-quinazolinyl)oxy]-2-nitrophenyl}-N'-[4-(N-benzyl)piperidinyl]urea 4-[(6,7-Dimethoxy-4-quinazolinyl)oxy]-2-nitroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (45 mg, yield 57%).

$^1$H-NMR (CDCl$_3$, 400 MHz): 1.75–1.80 (m, 2H), 2.32–2.43 (m, 2H), 2.62–2.68 (m, 1H), 2.73–2.78 (m, 1H), 2.95–3.01 (m, 1H), 3.68 (s, 2H), 4.07 (s, 3H), 4.08 (s, 3H), 4.41 (s, 1H), 5.48 (s, 1H), 7.27–7.36 (m, 6H), 7.50–7.55 (m, 2H), 8.13 (d, J=2.7 Hz, 1H), 8.60 (s, 1H), 8.77 (d, J=9.3 Hz, 1H) Mass spectrometry value (ESI-MS, m/z): 545 (M$^+$+1)

Example 607

N-{4-[(6,7-Dimethoxy-4-quinolyl)oxy]-2-methoxyphenyl}-N'-[4-(N-benzyl)piperidinyl]urea 4-[(6,7-Dimethoxy-4-quinolyl)oxy]-2-methoxyaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 4-amino-1-benzylpiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (55 mg, yield 68%).

$^1$H-NMR (CDCl$_3$, 400 MHz): 1.80–1.90 (m, 1H), 2.35–2.50 (m, 2H), 2.70–2.75 (m, 1H), 2.88–2.93 (m, 1H), 3.09–3.16 (m, 1H), 3.23–3.31 (m, 1H), 3.75 (d, J=12.9 Hz, 1H), 3.79 (d, J=12.9 Hz, 1H), 3.84 (s, 3H), 4.07 (s, 6H), 4.45–4.55 (m, 1H), 5.67 (d, J=7.6 Hz, 1H), 6.77 (d, J=2.4 Hz, 1H), 6.82 (dd, J=2.4 Hz, J=8.8 Hz, 1H), 6.92 (s, 1H), 7.30–7.40 (m, 5H), 7.55 (s, 1H), 8.63 (s, 1H) Mass spectrometry value (ESI-MS, m/z): 530 (M$^+$+1)

Example 608

N-{4-[(6,7-Dimethoxy-4-quinolyl)oxy]phenyl}-N'-(1-homopiperidinyl)urea

4-[(6,7-Dimethoxy-4-quinolyl)oxy]aniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminohomopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (35 mg, yield 47%).

$^1$H-NMR (CDCl$_3$, 400 MHz): $^1$H-NMR (CDCl$_3$, 400 MHz): 1.50–1.80 (m, 8H), 2.85–3.00 (m, 2H), 3.10–3.20 (m, 2H), 4.055 (s, 3H), 4.059 (s, 3H), 5.66 (s, 1H), 6.45 (d, J=5.4 Hz, 1H), 7.14 (d, J=6.8 Hz, 2H), 7.44 (s, 1H), 7.58 (s, 1H), 7.59 (d, J=6.8 Hz, 2H), 8.32 (s, 1H), 8.47 (d, J=5.1 Hz, 1H) Mass spectrometry value (ESI-MS, m/z): 437 (M$^+$+1)

Example 609

N-{4-[(6,7-Dimethoxy-4-quinolyl)oxy]-2-fluorophenyl}-N'-(1-homopiperidinyl)urea

4-[(6,7-Dimethoxy-4-quinolyl)oxy]-2-fluoroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminohomopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (43 mg, yield 55%).

$^1$H-NMR (CDCl$_3$, 400 MHz): 1.55–1.85 (m, 8H), 2.85–3.00 (m, 2H), 3.10–3.20 (m, 2H), 4.07 (s, 3H), 4.09 (s, 3H), 5.80 (s, 1H), 6.55 (d, J=5.6 Hz, 1H), 6.98–7.03 (m, 2H), 7.55 (s, 1H), 7.65 (s, 1H), 8.37–8.43 (m, 1H), 8.50 (d, J=5.9 Hz, 1H), 8.65–8.70 (m, 1H) Mass spectrometry value (ESI-MS, m/z): 491 (M$^+$+1)

Example 610

N-{4-[(6,7-Dimethoxy-4-quinolyl)oxy]-2-fluorophenyl}-N'-(1-pyrrolidinyl)urea

4-[(6,7-Dimethoxy-4-quinolyl)oxy]-2-fluoroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopyrrolidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 69%).

$^1$H-NMR (CDCl$_3$, 400 MHz): 1.86–2.00 (m, 4H), 2.50–2.70 (m, 2H), 2.85–3.05 (m, 2H), 4.05 (s, 3H), 4.06 (s, 3H), 6.05 (s, 1H), 6.50 (d, J=5.4 Hz, 1H), 6.95–7.05 (m, 2H), 7.45 (s, 1H), 7.53 (s, 1H), 8.30–8.35 (m, 1H), 8.45–8.55 (m, 2H) Mass spectrometry value (ESI-MS, m/z): 463 (M$^+$+1)

Example 611

N-{4-[(6,7-Dimethoxy-4-quinolyl)oxy]-2-fluorophenyl}-N'-(methylamino)urea

4-[(6,7-Dimethoxy-4-quinolyl)oxy]-2-fluoroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, methylhydrazine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 76%).

$^1$H-NMR (CDCl$_3$, 400 MHz): 3.18 (s, 3H), 4.06 (s, 3H), 4.08 (s, 3H), 6.55 (d, J=8.5 Hz, 1H), 7.53 (s, 1H), 7.60 (s, 1H), 8.05 (s, 1H), 8.37 (t, J=9.3 Hz, 1H), 8.49 (d, J=5.6 Hz, 1H) Mass spectrometry value (ESI-MS, m/z): 423 (M$^+$+1)

Example 612

N-{4-[(6,7-Dimethoxy-4-quinolyl)oxy]-2-fluorophenyl}-N'-(phenylamino)urea

4-[(6,7-Dimethoxy-4-quinolyl)oxy]-2-fluoroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, phenylhydrazine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (47 mg, yield 66%).
$^1$H-NMR (CDCl$_3$, 400 MHz): 4.06 (s, 3H), 4.08 (s, 3H), 5.95 (s, 1H), 6.36 (s, 1H), 6.55 (d, J=5.6 Hz, 1H), 6.94–7.07 (m, 5H), 7.30–7.36 (m, 2H), 7.53 (s, 1H), 7.62 (s, 1H), 8.15–8.20 (m, 1H), 8.38 (d, J=9.0 Hz, 1H), 8.49 (d, J=5.6 Hz, 1H) Mass spectrometry value (ESI-MS, m/z): 485 (M$^+$+1)

Example 613

N-{4-[(6,7-Dimethoxy-4-quinolyl)oxy]-2-fluorophenyl}-N'-(1-piperidinyl)urea

4-[(6,7-Dimethoxy-4-quinolyl)oxy]-2-fluoroaniline (50 mg) was added to toluene (5 ml), and triethylamine (0.5 ml), and the mixture was heated under reflux to prepare a solution. A solution of triphosgene (50 mg) in methylene chloride was then added thereto, and the mixture was heated under reflux for 10 min. Next, 1-aminopiperidine (50 mg) was added thereto, and the mixture was further stirred with heating under reflux for 3 hr. A saturated aqueous sodium bicarbonate solution was added to the reaction solution to stop the reaction, and the reaction solution was then extracted with chloroform, followed by washing with water and saturated brine in that order. The organic layer was then dried over anhydrous sodium sulfate. The solvent was removed by distillation under the reduced pressure, and the residue was purified by HPLC using chloroform/methanol for development to give the title compound (43 mg, yield 61%)
$^1$H-NMR (CDCl$_3$, 400 MHz): 1.60–1.90 (m, 6H), 2.35–2.50 (m, 2H), 3.15–3.25 (m, 2H), 4.06 (s, 3H), 4.08 (s, 3H), 5.49 (s, 1H), 6.54 (d, J=5.6 Hz, 1H), 6.96–7.03 (m, 2H), 7.55 (s, 1H), 7.61 (s, 1H), 8.35–8.40 (m, 1H), 8.50 (d, J=5.6 Hz, 1H), 8.53–8.56 (m, 1H) Mass spectrometry value (ESI-MS, m/z): 477 (M$^+$+1)

Example 614

N-{4-[(6,7-Dimethoxy-4-quinolyl)oxy]-phenyl}-N'-(2-methylbenzoyl)thiourea

4-[(6,7-Dimethoxy-4-quinolyl)oxy]aniline (50 mg) was dissolved in toluene (5 ml), and ethanol (1 ml) to prepare a solution. Commercially available 2-methyl-1-benzenecarbonyl isothiocyanate (50 μl) was then added thereto, and the mixture was stirred at room temperature for 2 hr. The reaction solution was concentrated, and the residue was purified by chromatography on silica gel using chloroform/acetone for development to give the title compound (78 mg, yield 97%).
$^1$H-NMR (CDCl$_3$, 400 MHz): δ 2.17 (s, 3H), 4.09 (s, 3H), 4.13 (s, 3H), 6.69 (d, J=5.86 Hz, 1H), 7.26–7.36 (m, 5H), 7.47–7.49 (m, 1H), 7.58 (d, J=8.05 Hz, 1H), 7.61 (s, 1H), 7.88 (bs, 1H), 7.94 (d, J=9.03 Hz, 2H), 8.52 (d, J=5.86 Hz, 1H), 8.89 (s, 1H) Mass spectrometry value (ESI-MS, m/z): 474 (M$^+$+1)

Example 615

N-{4-[(6,7-Dimethoxy-4-quinolyl)oxy]-3-fluorophenyl}-N'-(2-phenylacetyl)thiourea According to the description of technical literature, commercially available 2-phenylethanoyl chloride (80 mg) was dissolved in acetonitrile (20 ml). Potassium thiocyanate (300 mg) was added to the solution, and the mixture was heated at 80° C. for 2 hr. Water was added to the reaction solution, and the organic layer was extracted and was concentrated to give 2-phenylethanoyl isothiocyanate. 2-Phenylethanoyl isothiocyanate thus obtained was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (66 mg, yield 85%) (Referenc: Elmore, D. T. et al., Journal of chemical Society 1956, 4458).
$^1$H-NMR (DMSO-d$_6$, 400 MHz): δ 3.84 (s, 2H), 3.94 (s, 3H), 3.95 (s, 3H), 6.50 (d, J=5.37 Hz, 1H), 7.27–7.55 (m, 9H), 8.01 (dd, J=2.07 Hz, J=12.32 Hz, 1H), 8.51 (d, J=5.37 Hz, 1H), 11.82 (s, 1H), 2.49 (s, 1H) Mass spectrometry value (ESI-MS, m/z): 492 (M$^+$+1)

In the following examples, when carbonyl isothiocyanate is used, except for the case where the carbonyl isothiocyanate is purchasable, this compound was prepared from a fatty acid or an acid chloride by the method described in Example 615 according to the method of the literature and was used in the reaction without isolation and purification

Example 616

N-{4-[(6,7-Dimethoxy-4-quinolyl)oxy]-2,5-dimethylphenyl}-N'-(2-morpholinoethyl)urea 4-[(6,7-Dimethoxy-4-quinolyl)oxy]-2,5-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, 2-morpholino-1-ethanamine (30 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (70 mg, yield 84%).
$^1$H-NMR (CDCl$_3$-d$_1$, 400 MHz): δ 2.15 (s, 3H), 2.26 (s, 3H), 2.47 (s, 4H), 2.52–2.55 (m, 2H), 3.38–3.42 (m, 2H), 3.63–3.66 (m, 4H), 4.05 (s, 3H), 4.07 (s, 3H), 5.43–5.45 (m, 1H), 6.30 (d, J=5.4 Hz, 1H), 6.49 (s, 1H), 6.97 (s, 1H), 7.43 (s, 1H), 7.47 (s, 1H), 7.59 (s, 1H), 8.45 (d, J=5.1 Hz, 1H)

Example 617

N-{4-[(6,7-Dimethoxy-4-quinolyl)oxy]-2,3-dimethylphenyl}-N'-(2-morpholinoethyl)urea 4-[(6,7-Dimethyl-4-quinolyl)oxy]-2,3-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, 2-morpholino-1-ethanamine (30 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (90 mg, yield 100%).

$^1$H-NMR (CDCl$_3$-d$_1$, 400 MHz): δ 2.14 (s, 3H), 2.28 (s, 3H), 2.48–2.53 (m, 6H), 3.24–3.41 (m, 2H), 3.62–3.64 (m, 4H), 4.06 (s, 3H), 4.07 (s, 3H), 5.31–5.32 (m, 1H), 6.26 (d, J=5.4 Hz, 1H), 6.49 (s, 1H), 7.01 (d, J=8.5 Hz, 1H), 7.32 (d, J=8.5 Hz, 1H), 7.44 (s, 1H), 7.61 (s, 1H), 8.45 (d, J=5.1 Hz, 1H) Mass spectrometry value (ESI-MS, m/z): 481 (M$^+$+1)

Example 618

N-{4-[(6,7-Dimethoxy-4-quinolyl)oxy]phenyl}-N'-(2-tetrahydro-1H-1-pyrrolylethyl)urea 4-[(6,7-Dimethoxy-4-quinolyl)oxy]aniline (50 mg) was dissolved in chloroform (5 ml), and triethylamine (0.5 ml) to prepare a solution. A solution of triphosgene (77 mg) in chloroform was then added to the solution, and the mixture was stirred at room temperature for 10 min. Next, 2-tetrahydro-1H-1-pyrrolyl-1-ethanamine (30 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (40 mg, yield 46%).

$^1$H-NMR (CDCl$_3$-d$_1$, 400 MHz): δ 1.82–1.90 (m, 4H), 2.68–2.85 (m, 6H), 3.38–3.46 (m, 2H), 4.05 (s, 6H), 5.35 (s, 1H), 5.97 (s, 1H), 6.44 (d, J=5.4 Hz, 1H), 7.09 (d, J=8.8 Hz, 2H), 7.41 (s, 1H), 7.48 (d, J=8.8 Hz, 2H), 7.57 (s, 1H), 8.46 (d, J=5.4 Hz, 1H)

Example 619

N-{4-[(6,7-Dimethoxy-4-quinolyl)oxy]-2,5-dimethylphenyl}-N'-(2-tetrahydro-1H-1-pyrrolylethyl)urea 4-[(6,7-Dimethoxy-4-quinolyl)oxy]-2,5-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, 2-tetrahydro-1H-1-pyrrolyl-1-ethanamine (26 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (26 mg, yield 32%).

$^1$H-NMR (CDCl$_3$-d$_1$, 400 MHz): δ 1.86 (s, 4H), 2.13 (s, 3H), 2.26 (s, 3H), 2.70–2.77 (m, 4H), 2.81 (t, J=5.6 Hz, 2H), 3.45–3.49 (m, 2H), 4.05 (s, 3H), 4.06 (s, 3H), 5.89 (s, 1H), 6.30 (d, J=5.1 Hz, 1H), 6.93 (s, 1H), 7.42 (s, 1H), 7.55 (s, 1H), 7.59 (s, 1H), 8.44 (d, J=5.1 Hz, 1H)

Example 620

N-{4-[(6,7-Dimethoxy-4-quinolyl)oxy]-2,3-dimethylphenyl}-N'-(2-tetrahydro-1H-1-pyrrolylethyl)urea 4-[(6,7-Dimethyl-4-quinolyl)oxy]-2,3-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, 2-tetrahydro-1H-1-pyrrolyl-1-ethanamine (26 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (21 mg, yield 26%).

$^1$H-NMR (CDCl$_3$-d$_1$, 400 MHz): δ 1.86 (s, 4H), 2.11 (s, 3H), 2.27 (s, 3H), 2.76 (s, 4H), 2.82 (t, J=5.6 Hz, 2H), 3.42–3.49 (m, 2H), 4.05 (s, 3H), 4.06 (s, 3H), 5.86 (s, 1H), 6.27 (d, J=5.1 Hz, 1H), 6.97 (d, J=8.8 Hz, 1H), 7.39 (d, J=8.8 Hz, 1H), 7.43 (s, 1H), 7.61 (s, 1H), 8.43 (d, J=5.1 Hz, 1H)

Example 621

N-{4-[(6,7-Dimethoxy-4-quinazolinyl)oxy]phenyl}-N'-(2-tetrahydro-1H-1-pyrrolylethyl)urea 4-[(6,7-Dimethoxy-4-quinazolinyl)oxy]aniline (50 mg) was dissolved in chloroform (5 ml), and triethylamine (0.5 ml) to prepare a solution. A solution of triphosgene (77 mg) in chloroform was then added to the solution, and the mixture was stirred at room temperature for 10 min. Next, 2-tetrahydro-1H-1-pyrrolyl-1-ethanamine (30 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (8 mg, yield 9%).

$^1$H-NMR (CDCl$_3$-d$_1$, 400 MHz): δ 1.86 (s, 4H), 2.72–2.92 (m, 6H), 3.39–3.45 (m, 2H), 4.06 (s, 3H), 4.07 (s, 3H), 5.42 (s, 1H), 7.16 (d, J=9.0 Hz, 2H), 7.31 (s, 1H), 7.48 (d, J=8.8 Hz, 2H), 7.56 (s, 1H), 8.61 (s, 1H)

Example 622

N-[2-(Diethylamino)ethyl]-N'-{4-[(6,7-dimethoxy-4-quinolyl)oxy]phenyl}urea

4-[(6,7-Dimethoxy-4-quinolyl)oxy]aniline (50 mg) was dissolved in chloroform (5 ml), and triethylamine (0.5 ml) to prepare a solution. A solution of triphosgene (77 mg) in chloroform was then added to the solution, and the mixture was stirred at room temperature for 10 min. Next, N1,N1-diethyl-1,2-ethanediamine (30 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (10 mg, yield 13%).

$^1$H-NMR (CDCl$_3$-d$_1$, 400 MHz): δ 1.12 (t, J=7.1 Hz, 6H), 2.66–2.71 (m, 6H), 3.35–3.36 (m, 2H), 4.05 (s, 6H), 6.46 (d, J=5.4 Hz, 1H), 7.10–7.13 (m, 2H), 7.42 (s, 1H), 7.45 (d, J=9.0 Hz, 2H), 7.57 (s, 1H), 8.47 (d, J=5.1 Hz, 1H) Mass spectrometry value (ESI-MS, m/z): 439 (M$^+$+1)

Example 623

N-[2-(Diethylamino)ethyl]-N'-{4-[(6,7-dimethoxy-4-quinolyl)oxy]-2,5-dimethylphenyl}urea 4-[(6,7-Dimethoxy-4-quinolyl)oxy]-2,5-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, N1,N1-diethyl-1,2-ethanediamine (27 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (7 mg, yield 10%).

$^1$H-NMR (CDCl$_3$-d$_1$, 400 MHz): δ 1.12 (t, J=7.1 Hz, 6H), 2.13 (s, 3H), 2.27 (s, 3H), 2.70–2.77 (m, 6H), 3.43–3.45 (m, 2H), 4.05 (s, 3H), 4.06 (s, 3H), 6.30 (d, J=5.4 Hz, 1H), 6.95 (s, 1H), 7.42 (s, 1H), 7.49 (s, 1H), 7.59 (s, 1H), 8.44 (d, J=5.4 Hz, 1H) Mass spectrometry value (ESI-MS, m/z): 467 (M$^+$+1)

Example 624

N-[2-(Diethylamino)ethyl]-N'-{4-[(6,7-dimethoxy-4-quinolyl)oxy]-2,3-dimethylphenyl}urea 4-[(6,7-Dimethyl-4-quinolyl)oxy]-2,3-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, N1,N1-diethyl-1,2-ethanediamine (27 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (8 mg, yield 11%).

$^1$H-NMR (CDCl$_3$-d$_1$, 400 MHz): δ 1.03 (t, J=7.1 Hz, 6H), 2.12 (s, 3H), 2.28 (s, 3H), 2.58–2.67 (m, 6H), 3.35–3.38 (m, 2H), 4.06 (s, 3H), 4.07 (s, 3H), 6.26 (d, J=5.4 Hz, 1H), 6.98 (d, J=8.8 Hz, 1H), 7.32 (d, J=8.8 Hz, 1H), 7.43 (s, 1H), 7.61 (s, 1H), 8.43 (d, J=5.4 Hz, 1H) Mass spectrometry value (ESI-MS, m/z): 467 (M$^+$+1)

Example 625

N-{4-[(6,7-Dimethoxy-4-quinolyl)oxy]-2,5-dimethylphenyl}-N'-[2-(dimethylamino)ethyl]urea 4-[(6,7-Dimethoxy-4-quinolyl)oxy]-2,5-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, N1,N1-dimethyl-1,2-ethanediamine (20 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (24 mg, yield 36%).

$^1$H-NMR (CDCl$_3$-d$_1$, 400 MHz): δ 2.03 (s, 3H), 2.13 (s, 3H), 2.25 (s, 3H), 2.28 (s, 3H), 2.51 (s, 2H), 3.38–3.39 (m, 2H), 4.05 (s, 3H), 4.06 (s, 3H), 5.59 (s, 1H), 6.30 (d, J=4.9 Hz, 1H), 6.94 (s, 1H), 7.42 (s, 1H), 7.55 (s, 1H), 7.59 (s, 1H), 8.44 (d, J=5.1 Hz, 1H)

Example 626

N-{4-[(6,7-Dimethoxy-4-quinolyl)oxy]-2,3-dimethylphenyl}-N'-[2-(dimethylamino)ethyl]urea 4-[(6,7-Dimethyl-4-quinolyl)oxy]-2,3-dimethylaniline (50 mg) was dissolved in chloroform (5 ml), and triethylamine (0.5 ml) to prepare a solution. A solution of triphosgene (68 mg) in chloroform was then added to the solution, and the mixture was stirred at room temperature for 10 min. Next, N1,N1-dimethyl-1,2-ethanediamine (20 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (18 mg, yield 28%).

$^1$H-NMR (CDCl$_3$-d$_1$, 400 MHz): δ 2.02 (s, 3H), 2.12 (s, 3H), 2.26 (s, 6H), 2.44–2.51 (m, 2H), 3.37–3.38 (m, 2H), 4.06 (s, 3H), 4.07 (s, 3H), 5.45 (s, 1H), 6.26 (d, J=5.1 Hz, 1H), 6.99 (d, J=8.8 Hz, 1H), 7.38 (d, J=8.3 Hz, 1H), 7.43 (s, 1H), 7.61 (s, 1H), 8.44 (d, J=5.1 Hz, 1H)

Example 627

N-{4-[(6,7-Dimethoxy-4-quinazolinyl)oxy]phenyl}-N'-[2-(dimethylamino)ethyl]urea

4-[(6,7-Dimethoxy-4-quinazolinyl)oxy]aniline (50 mg) was dissolved in chloroform (5 ml), and triethylamine (0.5 ml) to prepare a solution. A solution of triphosgene (77 mg) in chloroform was then added to the solution, and the mixture was stirred at room temperature for 10 min. Next, N1,N1-dimethyl-1,2-ethanediamine (23 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (14 mg, yield 21%).

$^1$H-NMR (CDCl$_3$-d$_1$, 400 MHz): δ 2.27 (s, 3H), 2.34 (s, 3H), 2.46–2.49 (m, 2H), 3.31–3.35 (m, 2H), 4.07 (s, 6H), 5.14 (s, 1H), 5.59 (s, 1H), 7.16 (d, J=8.3 Hz, 2H), 7.31 (s, 1H), 7.47 (d, J=8.5 Hz, 2H), 7.56 (s, 1H), 8.61 (s, 1H)

Example 628

N-{4-[(6,7-Dimethoxy-4-quinolyl)oxy]phenyl}-N'-(2-morpholinoethyl)urea

4-[(6,7-Dimethoxy-4-quinolyl)oxy]aniline (100 mg) was dissolved in chloroform (10 ml) and triethylamine (1 ml) to prepare a solution. A solution of triphosgene (100 mg) in chloroform was then added to the solution, and the mixture was stirred at room temperature for 10 min. Next, 2-morpholino-1-ethanamine (66 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (162 mg, yield 100%).

$^1$H-NMR (CDCl$_3$-d$_1$, 400 MHz): δ 2.46–2.48 (m, 4H), 2.54 (t, J=5.9 Hz, 2H), 3.40 (q, J=5.4 Hz, 2H), 3.64 (t, J=4.6 Hz, 4H), 4.03 (s, 3H), 4.05 (s, 3H), 5.59 (s, 1H), 6.45 (d, J=5.4 Hz, 1H), 7.12 (d, J=8.8 Hz, 2H), 7.41 (s, 1H), 7.47 (d, J=8.8 Hz, 2H), 7.57 (s, 1H), 8.47 (d, J=5.4 Hz, 1H) Mass spectrometry value (ESI-MS, m/z): 453 (M$^+$+1)

Example 629

N-{4-[(6,7-Dimethoxy-4-quinazolinyl)oxy]phenyl}-N'-(2-morpholinoethyl)urea

4-[(6,7-Dimethoxy-4-quinazolinyl)oxy]aniline (100 mg) was dissolved in chloroform (10 ml) and triethylamine (1 ml) to prepare a solution. A solution of triphosgene (100 mg) in chloroform was then added to the solution, and the mixture was stirred at room temperature for 10 min. Next, 2-morpholino-1-ethanamine (66 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (41 mg, yield 27%).

$^1$H-NMR (CDCl$_3$-d$_1$, 400 MHz): δ 2.45 (t, J=4.1 Hz, 4H), 2.51 (t, J=5.6 Hz, 2H), 3.38 (q, J=5.6 Hz, 2H), 3.63 (t, J=4.6 Hz, 4H), 4.06 (s, 3H), 4.07 (s, 3H), 5.66 (t, J=5.1 Hz, 1H), 7.17 (d, J=8.8 Hz, 2H), 7.31 (s, 1H), 7.44 (d, J=8.8 Hz, 2H), 7.55 (s, 1H), 7.64 (s, 1H), 8.60 (s, 1H) Mass spectrometry value (ESI-MS, m/z): 454 (M$^+$+1)

Example 630

N-[2-(Diethylamino)ethyl]-N'-{4-[(6,7-dimethoxy-4-quinazolinyl)oxy]-2-methoxyphenyl}urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (140 mg) in chloroform was then added to the solution, and the mixture was stirred at room temperature for 10 min. Next, N1,N1-diethyl-1,2-ethanediamine (55 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (83 mg, yield 57%).

$^1$H-NMR (CDCl$_3$-d$_1$, 400 MHz): δ 1.39 (t, J=7.3 Hz, 6H), 3.11–3.20 (m, 6H), 3.65–3.68 (m, 2H), 3.85 (s, 3H), 4.065 (s, 3H), 4.067 (s, 3H), 6.77–6.82 (m, 2H), 7.30 (s, 1H), 7.54 (s, 1H), 7.62 (s, 1H), 8.16 (d, J=8.8 Hz, 1H), 8.61 (s, 1H) Mass spectrometry value (ESI-MS, m/z): 470 (M$^+$+1)

Example 631

N-{4-[(6,7-Dimethoxy-4-quinazolinyl)oxy]-2-methoxyphenyl}-N'-(2-morpholinoethyl)urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (140 mg) in chloroform was then added to the solution, and the mixture was stirred at room temperature for 10 min. Next, 2-morpholino-1-ethanamine (61 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (165 mg, yield 100%).

$^1$H-NMR (CDCl$_3$-d$_1$, 400 MHz): δ 2.49–2.57 (m, 6H), 3.39–3.43 (m, 2H), 3.70–3.73 (m, 4H), 3.84 (s, 3H), 4.068 (s, 3H), 4.072 (s, 3H), 5.53 (s, 1H), 6.79–6.86 (m, 2H), 6.97–6.98 (m, 1H), 7.33 (s, 1H), 7.55 (s, 1H), 8.14 (d, J=8.8 Hz, 1H), 8.63 (s, 1H) Mass spectrometry value (ESI-MS, m/z): 484 (M$^+$+1)

Example 632

N-{4-[(6,7-Dimethoxy-4-quinazolinyl)oxy]-2-methoxyphenyl}-N'-(2-tetrahydro-1H-1-pyrrolylethyl)urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (140 mg) in chloroform was then added to the solution, and the mixture was stirred at room temperature for 10 min. Next, 2-tetrahydro-1H-1-pyrrolyl-1-ethanamine (54 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (26 mg, yield 18%).

$^1$H-NMR (CDCl$_3$-d$_1$, 400 MHz): δ 2.16–2.19 (m, 4H), 3.08–3.14 (m, 4H), 3.31–3.34 (m, 2H), 3.70–3.74 (m, 2H), 3.87 (s, 3H), 4.065 (s, 3H), 4.068 (s, 3H), 6.76–6.81 (m, 2H), 7.31 (s, 1H), 7.36 (s, 1H), 7.55 (s, 1H), 7.59 (s, 1H), 8.19 (d, J=8.5 Hz, 1H), 8.62 (s, 1H)

Example 633

N-{4-[(6,7-Dimethoxy-4-quinazolinyl)oxy]-2-methoxyphenyl}-N'-[3-(4-methylpiperazino)-propyl]urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (140 mg) in chloroform was then added to the solution, and the mixture was stirred at room temperature for 10 min. Next, 3-(4-methylpiperazino)-1-propaneamine (74 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (62 mg, yield 39%).

$^1$H-NMR (CDCl$_3$-d$_1$, 400 MHz): δ 1.70–1.75 (m, 2H), 2.29 (d, J=7.6 Hz, 3H), 2.41–2.52 (m, 10H), 3.24–3.46 (m,

2H), 3.84 (d, J=4.4 Hz, 3H), 4.07 (s, 6H), 6.77–6.85 (m, 3H), 7.32 (d, J=1.7 Hz, 1H), 7.55 (s, 1H), 8.18 (d, J=8.8 Hz, 1H), 8.63 (s, 1H)

Example 634

N-(1-Benzyl-4-piperidyl)-N'-{4-[(6,7-dimethoxy-4-quinolyl)oxy]-2,5-dimethylphenyl}urea 4-[(6,7-Dimethoxy-4-quinolyl)oxy]-2,5-dimethylaniline (100 mg) was dissolved in chloroform (10 ml) and triethylamine (1 ml) to prepare a solution. A solution of triphosgene (140 mg) in chloroform was then added to the solution, and the mixture was stirred at room temperature for 10 min. Next, 1-benzyl-4-piperidineamine (89 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (124 mg, yield 74%).
$^1$H-NMR (CDCl$_3$-d$_1$, 400 MHz): δ 1.43–1.51 (m, 2H), 1.97–1.99 (m, 4H), 2.14 (s, 3H), 2.21 (s, 3H), 2.82–2.84 (m, 2H), 3.50 (s, 2H), 4.047 (s, 3H), 4.053 (s, 3H), 4.95 (d, J=7.8 Hz, 1H), 6.30 (d, J=5.4 Hz, 1H), 6.35 (s, 1H), 6.94 (s, 1H), 7.27–7.31 (m, 5H), 7.43 (s, 1H), 7.51 (s, 1H), 7.59 (s, 1H), 8.45 (d, J=5.1 Hz, 1H) Mass spectrometry value (ESI-MS, m/z): 541 (M$^+$+1)

Example 635

N-(1-Benzyl-4-piperidyl)-N'-{4-[(6,7-dimethoxy-4-quinolyl)oxy]-2,3-dimethylphenyl}urea 4-[(6,7-Dimethyl-4-quinolyl)oxy]-2,3-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 1-benzyl-4-piperidineamine (89 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (101 mg, yield 60%).
$^1$H-NMR (CDCl$_3$-d$_1$, 400 MHz): δ 1.41–1.44 (m, 2H), 1.95–1.97 (m, 4H), 2.13 (s, 3H), 2.25 (s, 3H), 2.81 (d, J=11.7 Hz, 2H), 3.49 (s, 2H), 3.71–3.75 (m, 1H), 4.05 (s, 3H), 4.06 (s, 3H), 6.26 (d, J=5.4 Hz, 1H), 6.99 (d, J=8.5 Hz, 1H), 7.26–7.32 (m, 7H), 7.44 (s, 1H), 7.61 (s, 1H), 8.45 (d, J=5.1 Hz, 1H) Mass spectrometry value (ESI-MS, m/z): 541 (M$^+$+1)

Example 636

N-(1-Benzyl-4-piperidyl)-N'-{4-[(6,7-dimethoxy-4-quinazolinyl)oxy]phenyl}urea

4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, 1-benzyl-4-piperidineamine (97 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (142 mg, yield 81%).
$^1$H-NMR (CDCl$_3$-d$_1$, 400 MHz): δ 1.41–1.51 (m, 2H), 1.94–1.96 (m, 2H), 2.07–2.16 (m, 2H), 2.79–2.82 (m, 2H), 3.48 (s, 2H), 3.68–3.75 (m, 1H), 4.05 (s, 6H), 5.09 (d, J=7.8 Hz, 1H), 7.07 (s, 1H), 7.16 (d, J=9.0 Hz, 2H), 7.26–7.31 (m, 5H), 7.40 (d, J=9.0 Hz, 2H), 7.54 (s, 1H), 8.59 (s, 1H) Mass spectrometry value (ESI-MS, m/z): 514 (M$^+$+1)

Example 637

N-(1-Benzyl-4-piperidyl)-N'-{2-chloro-4-[(6,7-dimethoxy-4-quinazolinyl)oxy]phenyl}urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, 1-benzyl-4-piperidineamine (85 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (185 mg, yield 100%).
$^1$H-NMR (CDCl$_3$-d$_1$, 400 MHz): δ 1.40–1.55 (m, 2H), 1.93–1.99 (m, 2H), 2.12–2.17 (m, 2H), 2.81–2.83 (m, 2H), 3.49 (s, 2H), 3.70–3.74 (m, 1H), 4.05 (s, 3H), 4.06 (s, 3H), 5.74 (d, J=7.8 Hz, 1H), 7.13–7.16 (m, 1H), 7.23–7.32 (m, 7H), 7.51 (s, 1H), 8.29 (d, J=9.0 Hz, 1H), 8.61 (s, 1H) Mass spectrometry value (ESI-MS, m/z): 548 (M$^+$+1)

Example 638

N-(1-Benzyl-4-piperidyl)-N'-{4-[(6,7-dimethoxy-4-quinolyl)oxy]-2-nitrophenyl}urea 4-[(6,7-Dimethoxy-4-quinolyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 1-benzyl-4-piperidineamine (84 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (141 mg, yield 86%).
$^1$H-NMR (CDCl$_3$-d$_1$, 400 MHz): δ 1.55–1.63 (m, 2H), 1.97–2.03 (m, 4H), 2.81–2.90 (m, 2H), 3.53 (s, 2H), 3.72–3.73 (m, 1H), 4.04 (s, 3H), 4.05 (s, 3H), 5.35–5.36 (m, 1H), 6.47 (d, J=5.1 Hz, 1H), 7.26–7.50 (m, 7H), 8.01 (d, J=2.9 Hz, 1H), 8.52 (d, J=5.4 Hz, 1H), 8.77 (d, J=9.3 Hz, 1H), 9.72 (s, 1H) Mass spectrometry value (ESI-MS, m/z): 558 (M$^+$+1)

Example 639

N-(1-Benzyl-4-piperidyl)-N'-{4-[(6,7-dimethoxy-4-quinolyl)oxy]-3-fluorophenyl}urea 4-[(6,7-Dimethoxy-4-quinolyl)oxy]-3-fluoroaniline (100 mg) was dissolved in chloroform (10 ml) and triethylamine (1 ml) to prepare a solution. A solution of triphosgene (142 mg) in chloroform was then added to the solution, and the mixture was stirred at room temperature for 10 min. Next, 1-benzyl-4-piperidineamine (91 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (47 mg, yield 28%).

$^1$H-NMR (CDCl$_3$-d$_1$, 400 MHz): δ 1.47–1.55 (m, 2H), 1.98–2.00 (m, 2H), 2.15–2.20 (m, 2H), 2.84–2.87 (m, 2H), 3.53 (s, 2H), 3.70–3.80 (m, 1H), 4.04 (s, 3H), 4.05 (s, 3H), 4.89 (d, J=7.3 Hz, 1H), 6.40 (d, J=5.1 Hz, 1H), 6.93 (s, 1H), 7.06–7.17 (m, 2H), 7.26–7.32 (m, 5H), 7.41 (s, 1H), 7.49–7.53 (m, 1H), 7.58 (s, 1H), 8.47 (d, J=5.1 Hz, 1H) Mass spectrometry value (ESI-MS, m/z): 531 (M$^+$+1)

Example 640

N-(1-Benzyl-4-piperidyl)-N'-{4-[(6,7-dimethoxy-4-quinazolinyl)oxy]-2-nitrophenyl}urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 1-benzyl-4-piperidineamine (89 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (151 mg, yield 93%).

$^1$H-NMR (CDCl$_3$-d$_1$, 400 MHz): δ 1.54–1.63 (m, 2H), 2.01–2.03 (m, 2H), 2.16–2.21 (m, 2H), 2.87–2.90 (m, 2H), 3.54 (s, 2H), 3.72–3.73 (m, 1H), 4.07 (s, 3H), 4.08 (s, 3H), 4.97 (brs, 1H), 7.26–7.34 (m, 5H), 7.51–7.56 (m, 2H), 8.13 (d, J=2.9 Hz, 1H), 8.60 (s, 1H), 8.80 (d, J=9.5 Hz, 1H), 9.77 (s, 1H) Mass spectrometry value (ESI-MS, m/z): 559 (M$^+$+1)

Example 641

N-(1-Benzyl-4-piperidyl)-N'-{4-[(6,7-dimethoxy-4-quinazolinyl)oxy]-2-methoxyphenyl}urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 1-benzyl-4-piperidineamine (89 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (118 mg, yield 71%).

$^1$H-NMR (CDCl$_3$-d$_1$, 400 MHz): δ 1.47–1.54 (m, 2H), 1.98–2.01 (m, 2H), 2.13–2.19 (m, 2H), 2.83–2.86 (m, 2H), 3.52 (s, 2H), 3.70–3.73 (m, 1H), 3.85 (s, 3H), 4.07 (s, 6H), 4.66 (d, J=8.1 Hz, 1H), 6.71 (s, 1H), 6.78 (d, J=2.4 Hz, 1H), 6.82–6.85 (m, 1H), 7.26–7.52 (m, 5H), 7.55 (s, 1H), 8.10 (d, J=8.8 Hz, 1H), 8.63 (s, 1H) Mass spectrometry value (ESI-MS, m/z): 544 (M$^+$+1)

Example 642

N-(1-Benzyl-4-piperidyl)-N'-{4-[(6,7-dimethoxy-4-quinolyl)oxy]-3-methylphenyl}urea 4-[(6,7-Dimethoxy-4-quinolyl)oxy]-3-methylaniline (100 mg) was dissolved in chloroform (10 ml) and triethylamine (1 ml) to prepare a solution. A solution of triphosgene (142 mg) in chloroform was then added to the solution, and the mixture was stirred at room temperature for 10 min. Next, 1-benzyl-4-piperidineamine (91 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (84 mg, yield 50%).

$^1$H-NMR (CDCl$_3$-d$_1$, 400 MHz): δ 1.46–1.54 (m, 2H), 1.97–2.00 (m, 2H), 2.13 (s, 3H), 2.13–2.23 (m, 2H), 2.82–2.85 (m, 2H), 3.51 (s, 2H), 3.73–3.75 (m, 1H), 4.04 (s, 3H), 4.05 (s, 3H), 4.98 (d, J=7.8 Hz, 1H), 6.27 (d, J=5.4 Hz, 1H), 6.90 (s, 1H), 7.02 (d, J=8.5 Hz, 1H), 7.18–7.21 (m, 1H), 7.25–7.31 (m, 4H), 7.36 (d, J=2.4 Hz, 1H), 7.42 (s, 1H), 7.60 (s, 1H), 8.43 (d, J=5.4 Hz, 1H) Mass spectrometry value (ESI-MS, m/z): 527 (M$^+$+1)

Example 643

N-(1-Benzyl-4-piperidyl)-N'-{4-[(6,7-dimethoxy-4-quinolyl)oxy]-2-methylphenyl}urea 4-[(6,7-Dimethoxy-4-quinolyl)oxy]-2-methylaniline (100 mg) was dissolved in chloroform (10 ml) and triethylamine (1 ml) to prepare a solution. A solution of triphosgene (142 mg) in chloroform was then added to the solution, and the mixture was stirred at room temperature for 10 min. Next, 1-benzyl-4-piperidineamine (91 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (88 mg, yield 52%).

$^1$H-NMR (CDCl$_3$-d$_1$, 400 MHz): δ 1.42–1.50 (m, 2H) 1.96–1.98 (m, 2H), 2.12–2.18 (m, 2H), 2.28 (s, 3H), 2.81–2.84 (m, 2H), 3.50 (s, 2H), 3.73–3.75 (m, 1H), 4.04 (s, 3H), 4.05 (s, 3H), 4.68 (d, J=7.6 Hz, 1H), 6.15 (s, 1H), 6.49 (d, J=5.4 Hz, 1H), 7.02–7.05 (m, 2H), 7.23–7.33 (m, 4H), 7.43 (s, 1H), 7.53–7.55 (m, 2H), 8.50 (d, J=5.4 Hz, 1H) Mass spectrometry value (ESI-MS, m/z): 527 (M$^+$+1)

Example 644

N-(1-Benzyl-4-piperidyl)-N'-{3-chloro-4-[(6,7-dimethoxy-4-quinolyl)oxy]phenyl}urea 3-Chloro-4-[(6,7-dimethoxy-4-quinolyl)oxy]aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, 1-benzyl-4-piperidineamine (86 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (112 mg, yield 68%).

¹H-NMR (CDCl₃-d₁, 400 MHz): δ 1.44–1.53 (m, 2H), 1.96–1.98 (m, 2H), 2.12–2.17 (m, 2H), 2.80–2.83 (m, 2H), 3.49 (s, 2H), 3.72–3.74 (m, 1H), 4.03 (s, 3H), 4.04 (s, 3H), 5.18 (d, J=7.8 Hz, 1H), 6.29 (d, J=5.4 Hz, 1H), 7.12 (d, J=8.8 Hz, 1H), 7.23–7.32 (m, 5H), 7.39–7.40 (m, 2H), 7.60 (s, 1H), 7.64 (d, J=2.4 Hz, 1H), 8.44 (d, J=5.4 Hz, 1H) Mass spectrometry value (ESI-MS, m/z): 547 (M⁺+1)

Example 645

N-{2-Chloro-4-[(6,7-dimethoxy-4-quinazolinyl)oxy]phenyl}-N'-[2-(diethylamino)ethyl]urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diethyl-1,2-ethanediamine (52 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (64 mg, yield 45%).
¹H-NMR (CDCl₃-d₁, 400 MHz): δ 1.16 (t, J=7.3 Hz, 6H), 2.75–2.83 (m, 6H), 3.45–3.49 (m, 2H), 4.07 (s, 6H), 6.41 (brs, 1H), 7.14–7.17 (m, 1H), 7.28–7.32 (m, 2H), 7.51 (s, 1H), 8.20 (d, J=9.0 Hz, 1H), 8.62 (s, 1H) Mass spectrometry value (ESI-MS, m/z): 474 (M⁺+1)

Example 646

N-[2-(Diethylamino)ethyl]-N'-{4-[(6,7-dimethoxy-4-quinolyl)oxy]-2-nitrophenyl}urea 4-[(6,7-Dimethoxy-4-quinolyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1,N1-diethyl-1,2-ethanediamine (51 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (65 mg, yield 46%).
¹H-NMR (CDCl₃-d₁, 400 MHz): δ 1.16–1.20 (m, 6H), 2.77–2.86 (m, 6H), 3.48–3.52 (m, 2H), 4.05 (s, 3H), 4.06 (s, 3H), 6.48 (d, J=5.4 Hz, 1H), 7.44–7.50 (m, 3H), 8.01 (d, J=2.9 Hz, 1H), 8.53 (d, J=5.1 Hz, 1H), 8.70 (d, J=9.5 Hz, 1H), 9.79 (s, 1H) Mass spectrometry value (ESI-MS, m/z): 484 (M⁺+1)

Example 647

N-[2-(Diethylamino)ethyl]-N'-{4-[(6,7-dimethoxy-4-quinazolinyl)oxy]-2-nitrophenyl}urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1,N1-diethyl-1,2-ethanediamine (51 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (107 mg, yield 76%).
¹H-NMR (CDCl₃-d₁, 400 MHz): δ 1.10 (t, J=7.1 Hz, 6H), 2.67 (q, J=7.1 Hz, 4H), 2.72 (t, J=5.9 Hz, 2H), 3.40–3.44 (m, 2H), 4.075 (s, 3H), 4.079 (s, 3H), 6.07 (brs, 1H), 7.34 (s, 1H), 7.52 (s, 1H), 7.54 (dd, J=2.7, J=9.3 Hz, 1H), 8.13 (d, J=2.9 Hz, 1H), 8.61 (s, 1H), 8.78 (d, J=9.3 Hz, 1H), 9.82 (s, 1H) Mass spectrometry value (ESI-MS, m/z): 485 (M⁺+1)

Example 648

N-[2-(Diethylamino)ethyl]-N'-{4-[(6,7-dimethoxy-4-quinolyl)oxy]-3-methylphenyl}urea 4-[(6,7-Dimethoxy-4-quinolyl)oxy]-3-methylaniline (100 mg) was dissolved in chloroform (10 ml) and triethylamine (1 ml) to prepare a solution. A solution of triphosgene (142 mg) in chloroform was then added to the solution, and the mixture was stirred at room temperature for 10 min. Next, N1,N1-diethyl-1,2-ethanediamine (56 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (48 mg, yield 33%).
¹H-NMR (CDCl₃-d₁, 400 MHz): δ 1.39 (t, J=7.3 Hz, 6H), 2.12 (s, 3H), 3.12–3.20 (m, 6H), 3.67–3.68 (m, 2H), 4.046 (s, 3H), 4.052 (s, 3H), 6.27 (d, J=5.4 Hz, 1H), 7.00 (d, J=8.5 Hz, 1H), 7.28 (s, 1H), 7.36–7.44 (m, 3H), 7.60 (s, 1H), 8.42 (d, J=5.4 Hz, 1H)

Example 649

N-[2-(Diethylamino)ethyl]-N'-{4-[(6,7-dimethoxy-4-quinolyl)oxy]-2-methylphenyl}urea 4-[(6,7-Dimethoxy-4-quinolyl)oxy]-2-methylaniline (100 mg) was dissolved in chloroform (10 ml) and triethylamine (1 ml) to prepare a solution. A solution of triphosgene (142 mg) in chloroform was then added to the solution, and the mixture was stirred at room temperature for 10 min. Next, N1,N1-diethyl-1,2-ethanediamine (56 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (49 mg, yield 34%).
¹H-NMR (CDCl₃-d₁, 400 MHz): δ 1.32–1.36 (m, 6H), 2.35 (s, 3H), 2.99–3.14 (m, 6H), 3.62–3.66 (m, 2H), 4.04 (s, 3H), 4.05 (s, 3H), 6.49 (d, J=5.4 Hz, 1H), 6.97–7.00 (m, 2H), 7.28 (s, 1H), 7.41 (s, 1H), 7.55 (s, 1H), 7.72 (d, J=9.3 Hz, 1H), 8.47 (d, J=5.1 Hz, 1H)

Example 650

N-{2-Chloro-4-[(6,7-dimethoxy-4-quinolyl)oxy]phenyl}-N'-[2-(diethylamino)ethyl]urea 2-Chloro-4-[(6,7-dimethoxy-4-quinolyl)oxy]aniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diethyl-1,2-ethanediamine (52 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (32 mg, yield 22%).

$^1$H-NMR (CDCl$_3$-d$_1$, 400 MHz): δ 1.26 (t, J=7.1 Hz, 6H), 2.91–2.99 (m, 6H), 3.55–3.59 (m, 2H), 4.04 (s, 3H), 4.05 (s, 3H), 6.49 (d, J=5.1 Hz, 1H), 7.07–7.10 (m, 2H), 7.21 (d, J=2.7 Hz, 1H), 7.28 (s, 1H), 7.42 (s, 1H), 7.51 (s, 1H), 8.16 (d, J=9.0 Hz, 1H), 8.50 (d, J=5.1 Hz, 1H) Mass spectrometry value (ESI-MS, m/z): 473 (M$^+$+1)

Example 651

N-{3-Chloro-4-[(6,7-dimethoxy-4-quinolyl)oxy]phenyl}-N'-[2-(diethylamino)ethyl]urea 3-Chloro-4-[(6,7-dimethoxy-4-quinolyl)oxy]aniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diethyl-1,2-ethanediamine (52 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (59 mg, yield 41%).

$^1$H-NMR (CDCl$_3$-d$_1$, 400 MHz): δ 1.41 (brs, 6H), 3.18–3.19 (m, 6H), 3.64–3.73 (m, 2H), 4.05 (s, 6H), 6.31 (s, 1H), 7.12 (d, J=8.3 Hz, 1H), 7.42 (s, 2H), 7.60 (s, 1H), 7.81 (s, 1H), 8.46 (s, 1H), 8.88 (brs, 1H) Mass spectrometry value (ESI-MS, m/z): 473 (M$^+$+1)

Example 652

N-{4-[(6,7-Dimethoxy-4-quinazolinyl)oxy]-2-nitrophenyl}-N'-(2-morpholinoethyl)urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 2-morpholino-1-ethanamine (57 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (30 mg, yield 21%).

$^1$H-NMR (CDCl$_3$-d$_1$, 400 MHz): δ 2.60–2.73 (m, 4H), 3.46–3.50 (m, 2H), 3.79–3.84 (m, 4H), 4.08 (s, 6H), 7.34 (s, 1H), 7.52–7.56 (m, 2H), 8.13 (d, J=2.7 Hz, 1H), 8.61 (s, 1H), 8.78 (d, J=9.5 Hz, 1H), 9.81 (s, 1H)

Example 653

N-{4-[(6,7-Dimethoxy-4-quinazolinyl)oxy]-2-nitrophenyl}-N'-(2-tetrahydro-1H-1-pyrrolylethyl)urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 2-tetrahydro-1H-1-pyrrolyl-1-ethanamine (50 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound 42 mg, yield 30%).

$^1$H-NMR (CDCl$_3$-d$_1$, 400 MHz): δ 1.90 (s, 4H), 2.74 (s, 4H), 2.82 (t, J=5.6 Hz, 2H), 3.50 (q, J=5.4 Hz, 2H), 4.075 (s, 3H), 4.078 (s, 3H), 7.34 (s, 1H), 7.52–7.55 (m, 2H), 8.12 (d, J=2.9 Hz, 1H), 8.61 (s, 1H), 8.78 (d, J=9.3 Hz, 1H), 9.82 (s, 1H) Mass spectrometry value (ESI-MS, m/z): 483 (M$^+$+1)

Example 654

N-[2-(Diisopropylamino)ethyl]-N'-{4-[(6,7-dimethoxy-4-quinolyl)oxy]phenyl}urea

4-[(6,7-Dimethoxy-4-quinolyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1,N1-diisopropyl-1,2-ethanediamine (74 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (52 mg, yield 33%).

$^1$H-NMR (CDCl$_3$-d$_1$, 400 MHz): δ 1.06 (d, J=6.3 Hz, 12H), 2.67 (t, J=4.9 Hz, 2H), 3.07–3.11 (m, 2H), 3.24–3.31 (m, 2H), 4.05 (s, 6H), 6.45 (d, J=5.4 Hz, 1H), 7.13 (d, J=8.8 Hz, 2H), 7.42–7.44 (m, 3H), 7.56 (s, 1H), 8.47 (d, J=5.1 Hz, 1H) Mass spectrometry value (ESI-MS, m/z): 467 (M$^+$+1)

Example 655

N-[2-(Diisopropylamino)ethyl]-N'-{4-[(6,7-dimethoxy-4-quinolyl)oxy]-2,3-dimethylphenyl}urea 4-[(6,7-Dimethoxy-4-quinolyl)oxy]-2,3-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diisopropyl-1,2-ethanediamine (68 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (46 mg, yield 30%).

$^1$H-NMR (CDCl$_3$-d$_1$, 400 MHz): δ 1.01–1.15 (m, 12H), 2.12 (s, 3H), 2.28 (s, 3H), 2.62 (brs, 2H), 3.00 (brs, 2H), 3.28 (brs, 2H), 4.06 (s, 3H), 4.07 (s, 3H), 6.25 (s, 1H), 6.99 (d, J=8.8 Hz, 1H), 7.43 (s, 1H), 7.61 (s, 1H), 8.43 (d, J=5.1 Hz, 1H) Mass spectrometry value (ESI-MS, m/z): 495 (M$^+$+1)

Example 656

N-[2-(Diisopropylamino)ethyl]-N'-{4-[(6,7-dimethoxy-4-quinazolinyl)oxy]phenyl}urea 4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1,N1-diisopropyl-1,2-ethanediamine (74 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (58 mg, yield 37%).

$^1$H-NMR (CDCl$_3$-d$_1$, 400 MHz): δ 1.12–1.15 (m, 12H), 2.74 (brs, 2H), 3.16 (brs, 2H), 3.34 (brs, 2H), 4.067 (s, 3H), 4.073 (s, 3H), 7.19 (d, J=9.0 Hz, 1H), 7.32 (s, 1H), 7.46 (d, J=9.0 Hz, 1H), 7.56 (s, 1H), 8.62 (s, 1H) Mass spectrometry value (ESI-MS, m/z): 468 (M$^+$+1)

Example 657

N-{2-Chloro-4-[(6,7-dimethoxy-4-quinazolinyl)oxy]phenyl}-N'-[2-(diisopropylamino)ethyl]urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, N1,N1-diisopropyl-1,2-ethanediamine (65 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (64 mg, yield 43%).

$^1$H-NMR (CDCl$_3$-d$_1$, 400 MHz): δ 1.45–1.48 (m, 12H), 3.19–3.22 (m, 2H), 3.60–3.65 (m, 2H), 3.73–3.74 (m, 2H), 4.07 (s, 6H), 7.12–7.15 (m, 2H), 7.51 (s, 1H), 7.70 (s, 1H), 7.97 (s, 1H), 8.16 (d, J=9.0 Hz, 1H), 8.62 (s, 1H) Mass spectrometry value (ESI-MS, m/z): 502 (M$^+$+1)

Example 658

N-[2-(Diisopropylamino)ethyl]-N'-{4-[(6,7-dimethoxy-4-quinolyl)oxy]-2-nitrophenyl}urea 4-[(6,7-Dimethoxy-4-quinolyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1,N1-diisopropyl-1,2-ethanediamine (63 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (103 mg, yield 70%).

$^1$H-NMR (CDCl$_3$-d$_1$, 400 MHz): δ 1.33–1.37 (m, 12H), 3.04–3.07 (m, 2H), 3.45–3.51 (m, 2H), 3.61 (s, 3H), 4.05 (s, 3H), 4.06 (s, 3H), 6.49 (d, J=5.1 Hz, 1H), 7.42–7.45 (m, 2H), 7.50 (s, 1H), 8.00 (d, J=2.9 Hz, 1H), 8.52 (d, J=5.4 Hz, 1H), 8.58–8.62 (m, 1H), 9.76 (s, 1H) Mass spectrometry value (ESI-MS, m/z): 512 (M$^+$+1)

Example 659

N-[2-(Diisopropylamino)ethyl]-N'-{4-[(6,7-dimethoxy-4-quinazolinyl)oxy]-2-nitrophenyl}urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1,N1-diisopropyl-1,2-ethanediamine (63 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (71 mg, yield 48%).

$^1$H-NMR (CDCl$_3$-d$_1$, 400 MHz): δ 1.20–1.23 (m, 12H), 2.87 (s, 2H), 3.27–3.28 (m, 2H), 3.45–3.49 (m, 2H), 4.075 (s, 3H), 4.080 (s, 3H), 7.34 (s, 1H), 7.52 (s, 1H), 7.54 (d, J=2.9 Hz, 1H), 8.12 (d, J=2.7 Hz, 1H), 8.61 (s, 1H), 8.74 (d, J=9.3 Hz, 1H), 9.84 (s, 1H) Mass spectrometry value (ESI-MS, m/z): 513 (M$^+$+1)

Example 660

N-[2-(Diisopropylamino)ethyl]-N'-{4-[(6,7-dimethoxy-4-quinazolinyl)oxy]-2-methoxyphenyl}urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diisopropyl-1,2-ethanediamine (68 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (50 mg, yield 32%).

$^1$H-NMR (CDCl$_3$-d$_1$, 400 MHz): δ 1.07 (brs, 12H), 2.69 (brs, 2H), 3.10 (brs, 2H), 3.27 (brs, 2H), 3.84 (s, 3H), 4.05 (s, 3H), 4.06 (s, 3H), 6.48 (d, J=5.1 Hz, 1H), 7.72 (d, J=2.4 Hz, 1H), 6.78 (dd, J=2.7, 8.8 Hz, 1H), 7.42 (s, 1H), 7.56 (s, 1H), 8.05 (d, J=9.0 Hz, 1H), 8.48 (d, J=5.4 Hz, 1H) Mass spectrometry value (ESI-MS, m/z): 497 (M$^+$+1)

Example 661

N-{4-[(6,7-Dimethoxy-4-quinolyl)oxy]phenyl}-N'-[2-(ethyl-3-methylanilino)ethyl]urea 4-[(6,7-Dimethoxy-4-quinolyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1-ethyl-N1-(3-methylphenyl)-1,2-ethanediamine (91 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (139 mg, yield 82%).
$^1$H-NMR (CDCl$_3$-d$_1$, 400 MHz): δ 1.15 (t, J=7.1 Hz, 3H), 2.30 (s, 3H), 3.39 (q, J=7.1 Hz, 2H), 3.48 (s, 4H), 4.05 (s, 3H), 4.06 (s, 3H), 6.44 (d, J=5.4 Hz, 1H), 6.56 (d, J=7.1 Hz, 1H), 6.61 (s, 2H), 7.09–7.15 (m, 3H), 7.35 (d, J=8.8 Hz, 2H), 7.46 (s, 1H), 7.55 (s, 1H), 8.46 (d, J=5.4 Hz, 1H)

Example 662

N-{4-[(6,7-Dimethoxy-4-quinolyl)oxy]-2,5-dimethylphenyl}-N'-[2-(ethyl-3-methylanilino)ethyl]urea 4-[(6,7-Dimethoxy-4-quinolyl)oxy]-2,5-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1-ethyl-N1-(3-methylphenyl)-1,2-ethanediamine (84 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (137 mg, yield 84%).
$^1$H-NMR (CDCl$_3$-d$_1$, 400 MHz): δ 1.13 (t, J=7.1 Hz, 3H), 2.09 (s, 3H), 2.21 (s, 3H), 2.30 (s, 3H), 3.37 (q, J=6.8 Hz, 2H), 3.46 (s, 4H), 4.06 (s, 6H), 4.84 (s, 1H), 5.92 (s, 1H), 6.27 (d, J=5.1 Hz, 1H), 6.53–6.57 (m, 3H), 6.95 (s, 1H), 7.09–7.13 (m, 1H), 7.31 (s, 1H), 7.45 (s, 1H), 7.57 (s, 1H), 8.44 (d, J=5.4 Hz, 1H) Mass spectrometry value (ESI-MS, m/z): 529 (M$^+$+1)

Example 663

N-{4-[(6,7-Dimethoxy-4-quinolyl)oxy]-2,3-dimethylphenyl}-N'-[2-(ethyl-3-methylanilino)ethyl]urea 4-[(6,7-Dimethoxy-4-quinolyl)oxy]-2,3-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1-ethyl-N1-(3-methylphenyl)-1,2-ethanediamine (84 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (112 mg, yield 68%).
$^1$H-NMR (CDCl$_3$-d$_1$, 400 MHz): δ 1.12 (t, J=7.1 Hz, 3H), 2.10 (s, 3H), 2.24 (s, 3H), 2.30 (s, 3H), 3.35 (q, J=6.8 Hz, 2H), 3.45 (s, 4H), 4.07 (s, 6H), 6.57 (s, 1H), 6.95 (d, J=8.5 Hz, 1H), 7.60 (s, 1H), 8.43 (d, J=5.4 Hz, 1H) Mass spectrometry value (ESI-MS, m/z): 529 (M$^+$+1)

Example 664

N-{4-[(6,7-Dimethoxy-4-quinazolinyl)oxy]phenyl}-N'-[2-(ethyl-3-methylanilino)ethyl]urea 4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1-ethyl-N1-(3-methylphenyl)-1,2-ethanediamine (91 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (177 mg, yield 100%).
$^1$H-NMR (CDCl$_3$-d$_1$, 400 MHz): δ 1.07–1.16 (m, 3H), 2.31 (s, 3H), 3.39–3.48 (m, 6H), 4.07 (s, 6H), 7.16–7.19 (m, 3H), 7.32–7.35 (m, 2H), 7.55 (s, 1H), 8.62 (s, 1H) Mass spectrometry value (ESI-MS, m/z): 502 (M$^+$+1)

Example 665

N-{2-Chloro-4-[(6,7-dimethoxy-4-quinazolinyl)oxy]phenyl}-N'-[2-(ethyl-3-methylanilino)ethyl]urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, N1-ethyl-N1-(3-methylphenyl)-1,2-ethanediamine (80 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (146 mg, yield 91%).
$^1$H-NMR (CDCl$_3$-d$_1$, 400 MHz): δ 1.09–1.17 (m, 3H), 2.31 (s, 3H), 3.41–3.50 (m, 6H), 4.07 (s, 6H), 6.60 (s, 1H), 7.31–7.33 (m, 2H), 7.52 (s, 1H), 8.18 (d, J=9.0 Hz, 1H), 8.63 (s, 1H)

Example 666

N-{4-[(6,7-Dimethoxy-4-quinolyl)oxy]-2-nitrophenyl}-N'-[2-(ethyl-3-methylanilino)ethyl]urea 4-[(6,7-Dimethoxy-4-quinolyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1-ethyl-N1-(3-methylphenyl)-1,2-ethanediamine (78 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (101 mg, yield 64%).
$^1$H-NMR (CDCl$_3$-d$_1$, 400 MHz): δ 1.17 (t, J=7.1 Hz, 3H), 2.31 (s, 3H), 3.39–3.44 (q, J=7.1 Hz, 2H), 3.52 (s, 4H), 4.05 (s, 3H), 4.07 (s, 3H), 6.49 (d, J=5.4 Hz, 1H), 6.58–6.62 (m, 2H), 7.12–7.14 (m, 1H), 7.47–7.51 (m, 3H), 8.04 (d, J=2.9 Hz, 1H), 8.53 (d, J=5.4 Hz, 1H), 8.78 (d, J=9.5 Hz, 1H), 9.68 (s, 1H) Mass spectrometry value (ESI-MS, m/z): 546 (M$^+$+1)

Example 667

N-{4-[(6,7-Dimethoxy-4-quinazolinyl)oxy]-2-nitrophenyl}-N'-[2-(ethyl-3-methylanilino)ethyl]urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1-ethyl-N1-(3-methylphenyl)-1,2-ethanediamine (78 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (110 mg, yield 69%).

$^1$H-NMR (CDCl$_3$-d$_1$, 400 MHz): δ 1.07–1.19 (m, 3H), 2.30–2.31 (m, 3H), 3.36–3.42 (m, 2H), 3.52 (s, 4H), 4.078 (s, 3H), 4.083 (s, 3H), 6.57–6.61 (m, 4H), 7.35 (s, 1H), 7.52–7.57 (m, 2H), 8.14 (d, J=2.9 Hz, 1H), 8.61 (s, 1H), 8.80 (d, J=9.8 Hz, 1H), 9.74 (s, 1H)

Example 668

N-{4-[(6,7-Dimethoxy-4-quinazolinyl)oxy]-2-methoxyphenyl}-N'-[2-(ethyl-3-methylanilino)ethyl]urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1-ethyl-N1-(3-methylphenyl)-1,2-ethanediamine (84 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (140 mg, yield 85%).

$^1$H-NMR (CDCl$_3$-d$_1$, 400 MHz): δ 1.16 (t, J=7.1 Hz, 3H), 2.31 (s, 3H), 3.40 (q, J=7.1 Hz, 2H), 3.48 (s, 4H), 3.83 (s, 3H), 4.07 (s, 6H), 6.55–6.65 (m, 2H), 6.78 (d, J=2.4 Hz, 1H), 6.83 (dd, J=2.4, 8.8 Hz, 1H), 7.13 (s, 1H), 7.33 (s, 1H), 7.55 (s, 1H), 8.07 (d, J=8.5 Hz, 1H), 8.64 (s, 1H) Mass spectrometry value (ESI-MS, m/z): 532 (M$^+$+1)

Example 669

N-{2-Chloro-4-[(6,7-dimethoxy-4-quinolyl)oxy]phenyl}-N'-[2-(ethyl-3-methylanilino)ethyl]urea 2-Chloro-4-[(6,7-dimethoxy-4-quinolyl)oxy]aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, N1-ethyl-N1-(3-methylphenyl)-1,2-ethanediamine (80 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (100 mg, yield 62%).

$^1$H-NMR (CDCl$_3$-d$_1$, 400 MHz): δ 1.16 (t, J=7.1 Hz, 3H), 2.30 (s, 3H), 3.40 (q, J=7.1 Hz, 2H), 3.50 (s, 4H), 4.045 (s, 3H), 4.054 (s, 3H), 6.49 (d, J=5.1 Hz, 1H), 6.56 (d, J=7.6 Hz, 1H), 6.60 (s, 1H), 7.04 (d, J=5.1 Hz, 1H), 7.09–7.13 (m, 1H), 7.21 (d, J=2.7 Hz, 1H), 7.43 (d, J=11.5 Hz, 2H), 7.51 (s, 1H), 8.19–8.22 (m, 1H), 8.50 (d, J=5.1 Hz, 1H), 8.57 (d, J=4.9 Hz, 1H) Mass spectrometry value (ESI-MS, m/z): 535 (M$^+$+1)

Example 670

N-{4-[(6,7-Dimethoxy-4-quinolyl)oxy]-2-methoxyphenyl}-N'-[2-(ethyl-3-methylanilino)ethyl]urea 4-[(6,7-Dimethoxy-4-quinolyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1-ethyl-N1-(3-methylphenyl)-1,2-ethanediamine (84 mg) was added. thereto, and the mixture was further stirred at room temperature for one hr. Water was added to stop the reaction, and the reaction solution was then extracted with chloroform, followed by concentration. The residue was purified on a column using chloroform/methanol to give the title compound (130 mg, yield 79%).

$^1$H-NMR (CDCl$_3$-d$_1$, 400 MHz): δ 1.16 (t, J=7.1 Hz, 3H), 2.30 (s, 3H), 3.40 (q, J=7.1 Hz, 2H), 3.49 (s, 4H), 3.81 (s, 3H), 4.06 (s, 6H), 6.48 (d, J=5.4 Hz, 1H), 6.55 (d, J=7.3 Hz, 1H), 6.60 (s, 1H), 6.70 (d, J=2.4 Hz, 1H), 6.79 (dd, J=2.4, 8.8 Hz, 1H), 7.11–7.15 (m, 1H), 7.45 (s, 1H), 7.56 (s, 1H), 8.10 (d, J=8.3 Hz, 1H), 8.48 (d, J=5.4 Hz, 1H) Mass spectrometry value (ESI-MS, m/z): 531 (M$^+$+1)

Example 671

N-[2-(Diisopropylamino)ethyl]-N'-{4-[(6,7-dimethoxy-4-quinolyl)oxy]-2,5-dimethylphenyl}urea 4-[(6,7-Dimethoxy-4-quinolyl)oxy]-2,5-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diisopropyl-1,2-ethanediamine (68 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (63 mg, yield 41%).

$^1$H-NMR (CDCl$_3$-d$_1$, 400 MHz): δ 1.00 (brs, 12H), 2.13 (s, 3H), 2.27 (s, 3H), 2.63 (brs, 2H), 3.02 (brs, 2H), 3.27 (brs, 2H), 4.06 (s, 3H), 4.07 (s, 3H), 6.29 (d, J=5.1 Hz, 1H), 6.98 (s, 1H), 7.43 (s, 1H), 7.59 (s, 1H), 8.44 (d, J=5.1 Hz, 1H) Mass spectrometry value (ESI-MS, m/z): 495 (M$^+$+1)

Example 672

N-[2-(Diisopropylamino)ethyl]-N'-{4-[(6,7-dimethoxy-4-quinolyl)oxy]-2-methoxyphenyl}urea 4-[(6,7-Dimethoxy-4-quinolyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-diisopropyl-1,2-ethanediamine (68 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (80 mg, yield 52%).

$^1$H-NMR (CDCl$_3$-d$_1$, 400 MHz): δ 1.02–1.15 (m, 12H), 3.03 (brs, 2H), 3.26 (brs, 2H), 3.48–3.50 (m, 2H), 3.86 (s, 3H), 4.07 (s, 3H), 6.79–6.84 (m, 3H), 7.32 (s, 1H), 7.55 (s, 1H), 8.07 (s, 1H), 8.63 (s, 1H) Mass spectrometry value (ESI-MS, m/z): 498 (M$^+$+1)

Example 673

N-{4-[(6,7-Dimethoxy-4-quinolyl)oxy]phenyl}-N'-(2-piperidinoethyl)urea

4-[(6,7-Dimethoxy-4-quinolyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, 2-piperidino-1-ethanamine (65 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (119 mg, yield 78%).
$^1$H-NMR (CDCl$_3$-d$_1$, 400 MHz): δ 1.51–1.70 (m, 6H), 2.44–2.65 (m, 6H), 3.41–3.45 (m, 2H), 4.04 (s, 6H), 6.45 (d, J=5.4 Hz, 1H), 7.11 (d, J=8.8 Hz, 2H), 7.27 (s, 1H), 7.41 (s, 1H), 7.49 (d, J=8.8 Hz, 2H), 7.56 (s, 1H), 8.46 (d, J=5.4 Hz, 1H) Mass spectrometry value (ESI-MS, m/z): 451 (M$^+$+1)

Example 674

N-{4-[(6,7-Dimethoxy-4-quinolyl)oxy]-2,5-dimethylphenyl}-N'-(2-piperidinoethyl)urea 4-[(6,7-Dimethoxy-4-quinolyl)oxy]-2,5-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 2-piperidino-1-ethanamine (60 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (123 mg, yield 83%).
$^1$H-NMR (CDCl$_3$-d$_1$, 400 MHz): δ 1.57–1.63 (m, 6H), 2.14 (s, 3H), 2.27 (s, 3H), 2.50–2.59 (m, 6H), 3.40–3.44 (m, 2H), 4.05 (s, 3H), 4.06 (s, 3H), 5.80 (s, 1H), 6.31 (d, J=5.1 Hz, 1H), 6.96 (s, 1H), 7.27 (s, 1H), 7.42 (s, 1H), 7.49 (s, 1H), 7.59 (s, 1H), 8.44 (d, J=5.4 Hz, 1H) Mass spectrometry value (ESI-MS, m/z): 479 (M$^+$+1)

Example 675

N-{4-[(6,7-Dimethoxy-4-quinolyl)oxy]-2,3-dimethylphenyl}-N'-(2-piperidinoethyl)urea 4-[(6,7-Dimethoxy-4-quinolyl)oxy]-2,3-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 2-piperidino-1-ethanamine (60 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (48 mg, yield 32%).
$^1$H-NMR (CDCl$_3$-d$_1$, 400 MHz): δ 2.00 (brs, 6H), 2.09 (s, 3H), 2.30 (s, 3H), 3.08–3.18 (m, 6H), 3.70–3.74 (m, 2H), 4.05 (s, 3H), 4.06 (s, 3H), 6.29 (d, J=5.1 Hz, 1H), 6.94 (d, J=8.8 Hz, 1H), 7.28 (s, 1H), 7.43 (s, 1H), 7.52 (d, J=8.8 Hz, 1H), 7.62 (s, 1H), 8.42 (d, J=5.4 Hz, 1H) Mass spectrometry value (ESI-MS, m/z): 479 (M$^+$+1)

Example 676

N-{4-[(6,7-Dimethoxy-4-quinazolinyl)oxy]phenyl}-N'-(2-piperidinoethyl)urea

4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, 2-piperidino-1-ethanamine (65 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (84 mg, yield 55%).
$^1$H-NMR (CDCl$_3$-d$_1$, 400 MHz): δ 2.03 (brs, 6H), 3.09–3.18 (m, 6H), 3.66–3.76 (m, 2H), 4.060 (s, 3H), 4.063 (s, 3H), 6.73 (brs, 1H), 7.13 (d, J=8.8 Hz, 2H), 7.30 (s, 1H), 7.35 (brs, 1H), 7.54 (s, 1H), 7.59 (d, J=8.8 Hz, 2H), 8.58 (s, 1H) Mass spectrometry value (ESI-MS, m/z): 452 (M$^+$+1)

Example 677

N-{2-Chloro-4-[(6,7-dimethoxy-4-quinazolinyl)oxy]phenyl}-N'-(2-piperidinoethyl)urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, 2-piperidino-1-ethanamine (58 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (118 mg, yield 81%).
$^1$H-NMR (CDCl$_3$-d$_1$, 400 MHz): δ 1.84–1.88 (m, 6H), 2.86–2.92 (m, 6H), 3.52–3.62 (m, 2H), 4.06 (s, 6H), 6.16 (brs, 1H), 6.98 (brs, 1H), 7.14 (dd, J=2.7, 9.0 Hz, 1H), 7.30 (d, J=2.7 Hz, 1H), 7.32 (s, 1H), 7.52 (s, 1H), 8.23 (d, J=9.0 Hz, 1H), 8.61 (s, 1H) Mass spectrometry value (ESI-MS, m/z): 486 (M$^+$+1)

Example 678

N-{4-[(6,7-Dimethoxy-4-quinolyl)oxy]-2-nitrophenyl}-N'-(2-piperidinoethyl)urea

4-[(6,7-Dimethoxy-4-quinolyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 2-piperidino-1-ethanamine (56 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (58 mg, yield 40%).

¹H-NMR (CDCl₃-d₁, 400 MHz): δ 1.69–1.82 (m, 6H), 2.59–2.81 (m, 6H), 3.49–3.50 (m, 2H), 4.05 (s, 3H), 4.06 (s, 3H), 5.95 (brs, 1H), 6.48 (d, J=5.4 Hz, 1H), 7.44 (s, 1H), 7.47 (d, J=2.9 Hz, 1H), 7.50 (s, 1H), 8.01 (d, J=2.9 Hz, 1H), 8.53 (d, J=5.1 Hz, 1H), 8.73 (d, J=9.3 Hz, 1H), 9.78 (s, 1H)

Example 679

N-{4-[(6,7-Dimethoxy-4-quinazolinyl)oxy]-2-nitrophenyl}-N'-(2-piperidinoethyl)urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, 2-piperidino-1-ethanamine (56 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (79 mg, yield 55%).

¹H-NMR (CDCl₃-d₁, 400 MHz): δ 1.49–1.66 (m, 6H), 2.48 (brs, 4H), 2.57 (t, J=5.9 Hz, 2H), 3.43–3.45 (m, 2H), 4.077 (s, 3H), 4.082 (s, 3H), 5.82 (s, 1H), 7.34 (s, 1H), 7.52 (s, 1H) 7.54 (dd, J=2.9, 9.5 Hz, 1H), 8.14 (d, J=2.7 Hz, 1H), 8.61 (s, 1H), 8.81 (d, J=9.5 Hz, 1H), 9.81 (s, 1H) Mass spectrometry value (ESI-MS, m/z): 497 (M⁺+1)

Example 680

N-{4-[(6,7-Dimethoxy-4-quinazolinyl)oxy]-2-methoxyphenyl}-N'-(2-piperidinoethyl)urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 2-piperidino-1-ethanamine (60 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (80 mg, yield 54%).

¹H-NMR (CDCl₃-d₁, 400 MHz): δ 1.96 (brs, 6H), 2.97–3.02 (m, 6H), 3.59–3.65 (m, 2H), 3.87 (s, 3H), 4.07 (s, 6H), 6.37 (brs, 1H), 6.77 (d, J=2.4 Hz, 1H), 6.81 (dd, J=2.4, 8.8 Hz, 1H), 7.32 (s, 1H), 7.37 (s, 1H), 7.55 (s, 1H), 8.18 (d, J=8.8 Hz, 1H), 8.63 (s, 1H) Mass spectrometry value (ESI-MS, m/z): 482 (M⁺+1)

Example 681

N-{4-[(6,7-Dimethoxy-4-quinolyl)oxy]-2-methoxyphenyl}-N'-(2-piperidinoethyl)urea 4-[(6,7-Dimethoxy-4-quinolyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, 2-piperidino-1-ethanamine (60 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (100 mg, yield 67%).

¹H-NMR (CDCl₃-d₁, 400 MHz): δ 1.97–1.98 (m, 6H), 3.00–3.09 (m, 6H), 3.60–3.68 (m, 2H), 3.85 (s, 3H), 4.050 (s, 3H), 4.054 (s, 3H), 6.42 (brs, 1H), 6.48 (d, J=5.4 Hz, 1H), 6.70 (d, J=2.4 Hz, 1H), 6.76 (dd, J=2.4, 8.8 Hz, 1H), 7.42 (s, 1H), 7.48 (s, 1H), 7.57 (s, 1H), 8.14 (d, J=8.8 Hz, 1H), 8.47 (d, J=5.4 Hz, 1H) Mass spectrometry value. (ESI-MS, m/z): 481 (M⁺+1)

Example 682

N-[2-(Dibutylamino)ethyl]-N'-{4-[(6,7-dimethoxy-4-quinolyl)oxy]phenyl}urea

4-[(6,7-Dimethoxy-4-quinolyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1,N1-dibutyl-1,2-ethanediamine (88 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (72 mg, yield 43%).

¹H-NMR (CDCl₃-d₁, 400 MHz): δ 0.96 (t, J=7.6 Hz, 6H), 1.34–1.42 (m, 4H), 1.65–1.73 (m, 4H), 2.90–2.94 (m, 4H), 3.08 (brs, 2H), 3.59–3.60 (m, 2H), 4.04 (s, 6H), 6.44 (d, J=5.4 Hz, 1H), 7.10 (d, J=9.0 Hz, 2H), 7.41 (s, 1H), 7.52 (d, J=9.0 Hz, 2H), 7.56 (s, 1H), 8.46 (d, J=5.1 Hz, 1H) Mass spectrometry value (ESI-MS, m/z): 495 (M⁺+1)

Example 683

N-[2-(Dibutylamino)ethyl]-N'-{4-[(6,7-dimethoxy-4-quinolyl)oxy]-2,5-dimethylphenyl}urea 4-[(6,7-Dimethoxy-4-quinolyl)oxy]-2,5-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-dibutyl-1,2-ethanediamine (81 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (82 mg, yield 51%).

¹H-NMR (CDCl₃-d₁, 400 MHz): δ 0.89 (t, J=7.3 Hz, 6H), 1.21–1.28 (m, 4H), 1.35–1.41 (m, 4H), 2.14 (s, 3H), 2.27 (s, 3H), 2.46 (t, J=7.6 Hz, 4H), 2.61–2.64 (m, 2H), 3.34–3.38 (m, 2H), 4.055 (s, 3H), 4.058 (s, 3H), 6.29 (d, J=5.1 Hz, 1H), 6.97 (s, 1H), 7.40 (s, 1H), 7.43 (s, 1H), 7.59 (s, 1H), 8.45 (d, J=5.4 Hz, 1H) Mass spectrometry value (ESI-MS, m/z): 523 (M⁺+1)

Example 684

N-[2-(Dibutylamino)ethyl]-N'-{4-[(6,7-dimethoxy-4-quinolyl)oxy]-2,3-dimethylphenyl}urea 4-[(6,7-Dimethoxy-4-quinolyl)oxy]-2,3-dimethylaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-dibutyl-1,2-ethanediamine (81 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (80 mg, yield 49%).

$^1$H-NMR (CDCl$_3$-d$_1$, 400 MHz): δ 0.86–0.93 (m, 6H), 1.12–1.47 (m, 8H), 2.13 (s, 3H), 2.29 (s, 3H), 2.40–2.49 (m, 4H), 2.57–2.62 (m, 2H), 3.24–3.36 (m, 2H), 4.055 (s, 3H), 4.063 (s, 3H), 6.26 (d, J=5.1 Hz, 1H), 6.98 (d, J=8.5 Hz, 1H), 7.30 (d, J=8.5 Hz, 1H), 7.43 (s, 1H), 7.61 (s, 1H), 8.43 (d, J=5.4 Hz, 1H) Mass spectrometry value (ESI-MS, m/z): 523 (M$^+$+1)

Example 685

N-[2-(Dibutylamino)ethyl]-N'-{4-[(6,7-dimethoxy-4-quinazolinyl)oxy]phenyl}urea

4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, N1,N1-dibutyl-1,2-ethanediamine (88 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (110 mg, yield 65%).

$^1$H-NMR (CDCl$_3$-d$_1$, 400 MHz): δ 0.92 (t, J=7.3 Hz, 6H), 1.25–1.32 (m, 4H), 1.45–1.52 (m, 4H), 2.54–2.58 (m, 4H), 2.68–2.71 (m, 2H), 3.36–3.37 (m, 2H), 4.06 (s, 6H), 7.18 (d, J=8.5 Hz, 2H), 7.32 (s, 1H), 7.47 (d, J=8.5 Hz, 2H), 7.55 (s, 1H), 8.61 (s, 1H) Mass spectrometry value (ESI-MS, m/z): 496 (M$^+$+1)

Example 686

N-{2-Chloro-4-[(6,7-dimethoxy-4-quinazolinyl)oxy]phenyl}-N'-[2-(dibutylamino)ethyl]urea 2-Chloro-4-[(6,7-dimethoxy-4-quinazolinyl)oxy]-aniline (100 mg) was dissolved in chloroform (10 ml) and triethylamine (1 ml) to prepare a solution. A solution of triphosgene (134 mg) in chloroform was then added to the solution, and the mixture was stirred at room temperature for 10 min. Next, N1,N1-dibutyl-1,2-ethanediamine (78 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (69 mg, yield 43%).

$^1$H-NMR (CDCl$_3$-d$_1$, 400 MHz): δ 0.93 (t, J=7.3 Hz, 6H), 1.28–1.33 (m, 4H), 1.40–1.46 (m, 4H), 2.47 (t, J=7.6 Hz, 4H), 2.60–2.63 (m, 2H), 3.32–3.35 (m, 2H), 4.07 (s, 6H), 7.17 (dd, J=2.7, 9.0 Hz, 1H), 7.32 (d, J=2.7 Hz, 1H), 7.33 (s, 1H), 7.52 (s, 1H), 8.19 (d, J=9.0 Hz, 1H), 8.63 (s, 1H) Mass spectrometry value (ESI-MS, m/z): 530 (M$^+$+1)

Example 687

N-[2-(Dibutylamino)ethyl]-N'-{4-[(6,7-dimethoxy-4-quinazolinyl)oxy]-2-nitrophenyl}urea 4-[(6,7-Dimethoxy-4-quinazolinyl)oxy]-2-nitroaniline (100 mg) was dissolved in chloroform (10 ml) and triethylamine (1 ml) to prepare a solution. A solution of triphosgene (131 mg) in chloroform was then added to the solution, and the mixture was stirred at room temperature for 10 min. Next, N1,N1-dibutyl-1,2-ethanediamine (76 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (66 mg, yield 42%).

$^1$H-NMR (CDCl$_3$-d$_1$, 400 MHz): δ 0.89–0.96 (m, 6H), 1.27–1.38 (m, 4H), 1.42–1.49 (m, 4H), 2.48 (t, J=7.3 Hz, 4H), 2.62–2.65 (m, 2H), 3.35–3.37 (m, 2H), 4.076 (s, 3H), 4.080 (s, 3H), 7.34 (s, 1H), 7.52–7.56 (m, 2H), 8.14 (d, J=2.9 Hz, 1H), 8.61 (s, 1H), 8.81 (d, J=9.3 Hz, 1H), 9.81 (s, 1H) Mass spectrometry value (ESI-MS, m/z): 541 (M$^+$+1)

Example 688

N-[2-(Dibutylamino)ethyl]-N'-{4-[(6,7-dimethoxy-4-quinazolinyl)oxy]-2-methoxyphenyl}urea 4-[(6,7-Dimethoxy-4-quinazolinyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min. Next, N1,N1-dibutyl-1,2-ethanediamine (81 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (79 mg, yield 49%).

$^1$H-NMR (CDCl$_3$-d$_1$, 400 MHz): δ 0.90–0.95 (m, 6H), 1.29–1.36 (m, 4H), 1.44–1.51 (m, 4H), 2.53 (t, J=7.6 Hz, 4H), 2.66–2.69 (m, 2H), 3.35–3.38 (m, 2H), 3.86 (s, 3H), 4.07 (s, 3H), 4.09 (s, 3H), 6.78 (d, J=2.4 Hz, 1H), 6.83 (dd, J=2.4, 8.8 Hz, 1H), 6.96 (brs, 1H), 7.32 (s, 1H), 7.55 (s, 1H), 8.10 (d, J=8.8 Hz, 1H), 8.63 (s, 1H) Mass spectrometry value (ESI-MS, m/z): 526 (M$^+$+1)

Example 689

N-[2-(Dibutylamino)ethyl]-N'-{4-[(6,7-dimethoxy-4-quinolyl)oxy]-2-methoxyphenyl}urea 4-[(6,7-Dimethoxy-4-quinolyl)oxy]-2-methoxyaniline (100 mg) was dissolved in chloroform (10 ml) and triethylamine (1 ml) to prepare a solution. A solution of triphosgene (139 mg) in chloroform was then added to the solution, and the mixture was stirred at room temperature for 10 min.

Next, N1,N1-dibutyl-1,2-ethanediamine (81 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (56 mg, yield 34%).

$^1$H-NMR (CDCl$_3$-d$_1$, 400 MHz): δ 0.90–0.95 (m, 6H), 1.28–1.37 (m, 4H), 1.46–1.54 (m, 4H), 2.56–2.60 (m, 4H), 2.72–2.74 (m, 2H), 3.35–3.43 (m, 2H), 3.84 (s, 3H), 4.05 (s, 6H), 6.48 (d, J=5.1 Hz, 1H), 6.71 (d, J=2.4 Hz, 1H), 6.78 (dd, J=2.4, 8.8 Hz, 1H), 7.42 (s, 1H), 7.57 (s, 1H), 8.09 (d, J=8.5 Hz, 1H), 8.48 (d, J=5.4 Hz, 1H) Mass spectrometry value (ESI-MS, m/z): 525 (M$^+$+1)

Example 690

N1-{4-[(6,7-Dimethoxy-4-quinazolinyl)oxy]phenyl}-4-benzyl-1-piperazinecarboxamide 4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, 1-benzylpiperazine (90 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (93 mg, yield 55%).

$^1$H-NMR (CDCl$_3$-d$_1$, 400 MHz): δ 2.51 (t, J=4.9 Hz, 4H), 3.52 (t, J=5.1 Hz, 4H), 3.56 (s, 2H), 4.06 (s, 3H), 4.07 (s, 3H), 6.44 (s, 1H), 7.18 (d, J=8.8 Hz, 2H), 7.26–7.35 (m, 5H), 7.47 (d, J=9.0 Hz, 2H), 7.55 (s, 1H), 8.61 (s, 1H)

Example 691

N1-{4-[(6,7-Dimethoxy-4-quinazolinyl)oxy]phenyl}-4-phenyl-1-piperazinecarboxamide 4-[(6,7-Dimethoxy-4-quinazolinyl)oxy]aniline (100 mg) was dissolved in chloroform (10 ml) and triethylamine (1 ml) to prepare a solution. A solution of triphosgene (151 mg) in chloroform was then added to the solution, and the mixture was stirred at room temperature for 10 min. Next, 1-phenylpiperazine (83 mg) was added thereto, and the mixture was further stirred at room temperature for one hr. Water was added to stop the reaction, and the reaction solution was then extracted with chloroform, followed by concentration. The residue was purified on a column using chloroform/methanol to give the title compound (130 mg, yield 79%)

$^1$H-NMR (CDCl$_3$-d$_1$, 400 MHz): δ 3.27 (t, J=5.1 Hz, 4H), 3.69 (t, J=5.1 Hz, 4H), 4.066 (s, 3H), 4.072 (s, 3H), 6.50 (s, 1H), 6.90–6.97 (m, 3H), 7.20 (d, J=8.8 Hz, 2H), 7.28–7.32 (m, 2H), 7.49 (d, J=8.8 Hz, 2H), 7.56 (s, 1H), 8.62 (s, 1H)

Example 692

N-[(5-Bromo-2-thienyl)carbonyl]-N'-{4-[(6,7-dimethoxy-4-quinolyl)oxy]-2-methylphenyl}thiourea Toluene (20 ml) and thionyl chloride (1 ml) were added to commercially available 5-bromo-2-thiophenecarboxylic acid (80 mg), and the mixture was heated at 100° C. for one hr. The solvent was removed by distillation, and 5-bromo-2-thiophene isothiocyanate was prepared using the resultant 5-bromo-2-thiophenecarbonyl chloride as a starting compound according to the description of the literature. 5-Bromo-2-thiophenecarbonyl isothiocyanate was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 18 hr. The reaction solution was concentrated, and the residue was purified by chromatography on silica gel using chloroform/acetone for development to give the title compound (58 mg, yield 65%).

$^1$H-NMR (DMSO-d$_6$, 400 MHz): δ 2.26 (s, 3H), 3.94 (s, 3H), 3.96 (s, 3H), 6.53 (d, J=5.4 Hz, 1H), 7.11–7.16 (m, 1H), 7.21–7.24 (m, 1H), 7.37–7.45 (m, 2H), 7.49–7.54 (m, 1H), 7.82–7.85 (m, 1H), 8.51 (d, J=5.1 Hz, 1H), 10.04 (s, 1H) Mass spectrometry value (ESI-MS, m/z): 559 (M$^+$+1)

Example 693

N-[(5-Bromo-2-thienyl)carbonyl]-N'-{3-chloro-4-[(6,7-dimethoxy-4-quinolyl)oxy]phenyl}thiourea Toluene (20 ml) and thionyl chloride (1 ml) were added to commercially available 5-bromo-2-thiophenecarboxylic acid (80 mg), and the mixture was heated at 100° C. for one hr. The solvent was removed by distillation, and 5-bromo-2-thiophene isothiocyanate was prepared using the resultant 5-bromo-2-thiophenecarbonyl chloride as a starting compound according to the description of the literature. 5-Bromo-2-thiophenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 18 hr. The reaction solution was concentrated, and the residue was purified by chromatography on silica gel using chloroform/acetone for development to give the title compound (65 mg, yield 75%).

$^1$H-NMR (DMSO-d$_6$, 400 MHz): δ 3.95 (s, 3H), 3.96 (s, 3H), 6.39 (d, J=5.4 Hz, 1H), 7.39–7.43 (m, 2H), 7.45–7.55 (m, 2H), 7.77–7.81 (m, 1H), 7.88 (d, J=4.1 Hz, 1H), 8.12 (d, J=2.4 Hz, 1H), 8.49 (d, J=5.1 Hz, 1H), 10.55 (s, 1H) Mass spectrometry value (ESI-MS, m/z): 579 (M$^+$+1)

Example 694

N-[(5-Chloro-2-thienyl)carbonyl]-N'-{4[(6,7-dimethoxy-4-quinolyl)oxy]-2-methylphenyl}thiourea Toluene (20 ml) and thionyl chloride (1 ml) were added to commercially available 5-chloro-2-thiophenecarboxylic acid (80 mg), and the mixture was heated at 100° C. for one hr. The solvent was removed by distillation, and 5-chloro-2-thiophene isothiocyanate was prepared using the resultant 5-chloro-2-thiophenecarbonyl chloride as a starting compound according to the description of the literature. 5-Chloro-2-thiophenecarbonyl isothiocyanate thus obtained was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (43 mg, yield 52%).

$^1$H-NMR (DMSO-d$_6$, 400 MHz): δ 2.26 (s, 3H), 3.93 (s, 3H), 3.95 (s, 3H), 6.52 (d, J=5.1 Hz, 1H), 7.11–7.15 (m, 1H), 7.21–7.23 (m, 1H), 7.27–7.29 (m, 1H), 7.38–7.46 (m, 3H), 7.86–7.88 (m, 1H), 8.51 (d, J=5.1 Hz, 1H), 10.05–10.08 (bs, 1H) Mass spectrometry value (ESI-MS, m/z): 514 (M$^+$+1)

Example 695

N-{3-Chloro-4-[(6,7-dimethoxy-4-quinolyl)oxy]phenyl}-N'-[(5-chloro-2-thienyl)carbonyl]thiourea Toluene (20 ml) and thionyl chloride (1 ml) were added to commercially available 5-chloro-2-thiophenecarboxylic acid (80 mg), and the mixture was heated at 100° C. for one hr. The solvent was removed by distillation, and 5-chloro-2-thiophene isothiocyanate was prepared using the resultant 5-chloro-2-thiophenecarbonyl chloride as a starting compound according to the description of the literature. 5-Chloro-2-thiophenecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (46 mg, yield 58%).

$^1$H-NMR (DMSO-d$_6$, 400 MHz): δ 3.95 (s, 3H), 3.96 (s, 3H), 6.38 (d, J=5.4 Hz, 1H), 7.31 (d, J=4.1 Hz, 1H), 7.41 (s, 1H), 7.46 (s, 1H), 7.49 (s, 1H), 7.77–7.82 (m, 1H), 7.92–7.95 (m, 1H), 8.10–8.12 (m, 1H), 8.48 (d, J=5.1 Hz, 1H), 10.57 (s, 1H) Mass spectrometry value (ESI-MS, m/z): 535 (M$^+$+1)

Example 696

N-{4-[(6,7-Dimethoxy-4-quinolyl)oxy]-2-methylphenyl}-N'-[3-(methylthio)propanoyl]-thiourea 3-(Methylthio)propanoyl isothiocyanate was prepared using commercially available 3-(methylthio)propanoyl chloride (80 mg) as a starting compound according to the description of the literature. 3-(Methylthio)propanoyl isothiocyanate thus obtained was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 19 hr. The reaction solution was concentrated, and the residue was purified by chromatography on silica gel using chloroform/acetone for development to give the title compound (27 mg, yield 35%).

$^1$H-NMR (DMSO-d$_6$, 400 MHz): δ 2.10 (s, 3H), 2.24 (s, 3H), 2.74–2.84 (m, 4H), 3.93 (s, 3H), 3.95 (s, 3H), 6.55 (d, J=5.4 Hz, 1H), 7.11–7.72 (m, 5H), 8.52 (d, J=5.4 Hz, 1H), 11.57–11.60 (bs, 1H), 12.10–12.13 (bs, 1H) Mass spectrometry value (ESI-MS, m/z): 472 (M$^+$+1)

Example 697

N-{3-Chloro-4-[(6,7-dimethoxy-4-quinolyl)oxy]phenyl}-N'-[3-(methylthio)propanoyl]thiourea 3-(Methylthio)propanoyl isothiocyanate was prepared using commercially available 3-(methylthio)propanoyl chloride (80 mg) as a starting compound according to the description of the literature. 3-(Methylthio)propanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (14 mg, yield 18%).

$^1$H-NMR (DMSO-d$_6$, 400 MHz): δ 2.10 (s, 3H), 2.71–2.84 (m, 4H), 3.94 (s, 3H), 3.96 (s, 3H), 6.41 (d, J=5.4 Hz, 1H), 7.31–7.72 (m, 5H), 8.50 (d, J=5.1 Hz, 1H), 11.63–11.66 (bs, 1H), 12.49–12.52 (bs, 1H) Mass spectrometry value (ESI-MS, m/z): 492 (M$^+$+1)

Example 698

N-{4-[(6,7-Dimethoxy-4-quinolyl)oxy]-2-methylphenyl}-N'-[(2,5-dimethyl-3-furyl)carbonyl]thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate thus obtained was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 15 hr. The reaction solution was concentrated, and the residue was purified by chromatography on silica gel using chloroform/acetone for development to give the title compound (41 mg, yield 52%).

$^1$H-NMR (DMSO-d$_6$, 400 MHz): δ 2.26 (s, 3H), 2.28 (s, 3H), 2.55 (s, 3H), 3.93 (s, 3H), 3.96 (s, 3H), 6.56 (d, J=5.1 Hz, 1H), 6.90 (s, 1H), 7.14 (dd, J=2.7, 8.8 Hz, 1H), 7.23 (d, J=2.7 Hz, 1H), 7.41 (s, 1H), 7.50 (s, 1H), 7.67 (t, J=8.7 Hz, 1H), 8.53 (d, J=5.1 Hz, 1H), 10.97–11.00 (bs, 1H), 12.33–12.36 (bs, 1H) Mass spectrometry value (ESI-MS, m/z): 492 (M$^+$+1)

Example 699

N-{3-Chloro-4-[(6,7-dimethoxy-4-quinolyl)oxy]phenyl}-N'-[(2,5-dimethyl-3-furyl)carbonyl]thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 15 hr. The reaction solution was concentrated, and the residue was purified by chromatography on silica gel using chloroform/acetone for development to give the title compound (38 mg, yield 50%).

¹H-NMR (DMSO-d₆, 400 MHz): δ 2.26 (s, 3H), 2.55 (s, 3H), 3.95 (s, 3H), 3.96 (s, 3H), 6.42 (d, J=5.1 Hz, 1H), 6.89 (s, 1H), 7.43 (s, 1H), 7.49 (d, J=8.8 Hz, 1H), 7.53 (s, 1H), 7.70–7.76 (m, 1H), 8.16–8.21 (m, 1H), 8.51 (d, J=5.1 Hz, 1H), 11.03–11.05 (bs, 1H), 12.71–12.74 (bs, 1H) Mass spectrometry value (ESI-MS, m/z): 512 (M$^+$+1)

Example 700

N-{4-[(6,7-Dimethoxy-4-quinolyl)oxy]-2-methylphenyl}-N'-[2-(2-thienyl)acetyl]thiourea Toluene (20 ml) and thionyl chloride (1 ml) were added to commercially available 2-(2-thienyl)acetic acid (80 mg), and the mixture was heated at 100° C. for one hr. The solvent was removed by distillation, and 2-(2-thienyl)ethanoyl isothiocyanate was prepared using the resultant 2-(2-thienyl) ethanoyl chloride as a starting compound according to the description of the literature. 2-(2-Thienyl)ethanoyl isothiocyanate thus obtained was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 15 hr. The reaction solution was concentrated, and the residue was purified by chromatography on silica gel using chloroform/acetone for development to give the title compound (18 mg, yield 23%).
¹H-NMR (DMSO-d₆, 400 MHz): δ 2.23 (s, 3H), 3.81 (s, 1H), 3.95 (s, 3H), 3.98 (s, 3H), 4.08 (s, 1H), 6.63 (d, J =5.4 Hz, 1H), 6.93–7.05 (m, 3H), 7.16–7.19 (m, 1H), 7.24–7.27 (m, 1H), 7.36–7.46 (m, 3H), 7.55 (s, 1H), 7.70 (d, J=8.8 Hz, 1H), 8.60 (d, J=5.6 Hz, 1H) Mass spectrometry value (ESI-MS, m/z): 494 (M$^+$+1)

Example 701

N-{3-Chloro-4-[(6,7-dimethoxy-4-quinolyl)oxy]phenyl}-N'-[2-(2-thienyl)acetyl]thiourea Toluene (20 ml) and thionyl chloride (1 ml) were added to commercially available 2-(2-thienyl)acetic acid (80 mg), and the mixture was heated at 100° C. for one hr. The solvent was removed by distillation, and 2-(2-thienyl)ethanoyl isothiocyanate was prepared using the resultant 2-(2-thienyl) ethanoyl chloride as a starting compound according to the description of the literature. 2-(2-Thienyl)ethanoyl isothiocyanate thus obtained was dissolved in ethanol (1 ml) to prepare a solution. 3-Chloro-4-[(6,7-dimethoxy-4-quinolyl) oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (15 mg, yield 20%).
¹H-NMR (DMSO-d₆, 400 MHz): δ 3.81 (s, 1H), 4.00 (s, 3H), 4.02 (s, 3H), 4.08 (s, 1H), 6.68 (d, J=5.6 Hz, 1H), 6.93–7.05 (m, 3H), 7.37–7.40 (m, 1H), 7.44–7.47 (m, 1H), 7.49 (s, 1H), 7.58 (d, J=8.8 Hz, 1H), 7.67 (s, 1H), 7.74–7.79 (m, 1H), 8.16–8.20 (m, 1H), 8.71 (d, J=5.6 Hz, 1H) Mass spectrometry value (ESI-MS, m/z): 514 (M$^+$+1)

Example 702

N-{3-Chloro-4-[(6,7-dimethoxy-4-quinolyl) oxy]phenyl}-N'-[2-(2-methylphenyl)acetyl]thiourea Toluene (20 ml) and thionyl chloride (1 ml) were added to commercially available 2-(2-methylphenyl)acetic acid (80 mg), and the mixture was heated at 100° C. for one hr. The solvent was removed by distillation, and 2-(2-methylphenyl)ethanoyl isothiocyanate was prepared using the resultant 2-(2-methylphenyl)ethanoyl chloride as a starting compound according to the description of the literature. 2-(2-Methylphenyl)ethanoyl isothiocyanate thus obtained was dissolved in ethanol (1 ml) to prepare a solution. 3-Chloro-4-[(6,7-dimethoxy-4-quinolyl)oxy]-aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (45 mg, yield 57%).
¹H-NMR (DMSO-d₆, 400 MHz): δ 2.30 (s, 3H), 3.89 (s, 2H), 3.96 (s, 3H), 3.98 (s, 3H), 6.51 (d, J=5.6 Hz, 1H), 7.12–7.28 (m, 5H), 7.45 (s, 1H), 7.50 (d, J=9.0 Hz, 1H), 7.58 (s, 1H), 7.70–7.75 (m, 1H), 8.58 (d, J=5.6 Hz, 1H), 11.80–11.83 (bs, 1H), 12.44–12.48 (bs, 1H) Mass spectrometry value (ESI-MS, m/z): 522 (M$^+$+1)

Example 703

N-{4-[(6,7-Dimethoxy-4-quinazolinyl)oxy]phenyl}-N'-[2-(2-methylphenyl)acetyl]thiourea Toluene (20 ml) and thionyl chloride (1 ml) were added to commercially available 2-(2-methylphenyl)acetic acid (80 mg), and the mixture was heated 100° C. for one hr. The solvent was removed by distillation, and 2-(2-methylphenyl) ethanoyl isothiocyanate was prepared using the resultant 2-(2-methylphenyl)ethanoyl chloride as a starting compound according to the description of the literature. 2-(2-Methylphenyl)ethanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (36 mg, yield 43%).
¹H-NMR (DMSO-d₆, 400 MHz): δ 2.30 (s, 3H), 3.88 (s, 2H), 3.97 (s, 3H), 3.99 (s, 3H), 7.14–7.36 (m, 7H), 7.39 (s, 1H), 7.56 (s, 1H), 7.70–7.75 (m, 1H), 8.55–8.57 (bs, 1H), 11.70–11.73 (bs, 1H), 12.39–12.42 (bs, 1H) Mass spectrometry value (ESI-MS, m/z): 489 (M$^+$+1)

Example 704

N-{3-Chloro-4-[(6,7-dimethoxy-4-quinolyl)oxy]phenyl}-N'-(2-cyclohexylacetyl)thiourea Toluene (20 ml) and thionyl chloride (1 ml) were added to commercially available 2-cyclohexylacetic acid (80 mg), and the mixture was heated at 100° C. for one hr. The solvent was removed by distillation, and 2-cyclohexyletanoyl isothiocyanate was prepared using the resultant 2-cyclohexylethanoyl chloride as a starting compound according to the description of the literature. 2-Cyclohexylethanoyl isothiocyanate thus obtained was dissolved in ethanol (1 ml) to prepare a solution. 3-Chloro-4-[(6,7-dimethoxy-4-quinolyl)oxy]-aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (36 mg, yield 46%).

$^1$H-NMR (DMSO-$d_6$, 400 MHz): δ 0.88–1.30 (m, 5H), 1.58–1.80 (m, 6H), 2.07 (d, J=6.6 Hz, 1H), 2.37 (d, J=7.1 Hz, 1H), 3.94 (s, 3H), 3.96 (s, 3H), 6.41 (d, J=5.4 Hz, 1H), 7.42 (s, 1H), 7.47 (d, J=8.8 Hz, 1H), 7.53 (s, 1H), 7.67–7.72 (m, 1H), 8.14–8.18 (m, 1H), 8.51 (d, J=5.1 Hz, 1H), 11.53–11.56 (bs, 1H), 12.59–12.63 (bs, 1H) Mass spectrometry value (ESI-MS, m/z): 514 (M$^+$+1)

Example 705

N-(2-Cyclohexylacetyl)-N'-{4-[(6,7-dimethoxy-4-quinazolinyl)oxy]phenyl}thiourea

Toluene (20 ml) and thionyl chloride (1 ml) were added to commercially available 2-cyclohexylacetic acid (80 mg), and the mixture was heated at 100° C. for one hr. The solvent was removed by distillation, and 2-cyclohexylethanoyl isothiocyanate was prepared using the resultant 2-cyclohexylethanoyl chloride as a starting compound according to the description of the literature. 2-Cyclohexylethanoyl isothiocyanate thus obtained was dissolved in ethanol (1 ml) to prepare a solution. 4-[(6,7-Dimethoxy-4-quinazolinyl) oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (30 mg, yield 44%)

$^1$H-NMR (DMSO-$d_6$, 400 MHz): δ 0.93–1.30 (m, 5H), 1.58–1.81 (m, 6H), 2.37 (d, J=7.1 Hz, 2H), 3.98 (s, 3H), 3.99 (s, 3H), 7.35 (d, J=8.8 Hz, 2H), 7.40 (s, 1H), 7.57 (s, 1H), 7.73 (d, J=9.0 Hz, 2H), 8.57 (s, 1H), 11.44–11.47 (bs, 1H), 12.58 (d, J=4.4 Hz, 1H) Mass spectrometry value (ESI-MS, m/z): 481 (M$^+$+1)

Example 706

N-Benzyl-N'-{3-chloro-4-[(6,7-dimethoxy-4-quinolyl)oxy]phenyl}thiourea

3-Chloro-4-[(6,7-dimethoxy-4-quinolyl)oxy]aniline (50 mg) was added to toluene (2 ml) and ethanol (2 ml) to prepare a solution. Benzyl isothiocyanate (48 µl) was then added to the solution, and the mixture was stirred at 80° C. for 6 hr. The reaction solution was concentrated, and ether and hexane were added to the residue. The resultant crystal was collected by filtration to give the title compound (46 mg, yield 65%).

$^1$H-NMR (DMSO-$d_6$, 400 MHz): δ 3.95 (s, 3H), 3.96 (s, 3H), 4.77 (d, J=5.1 Hz, 1H), 6.42 (d, J=5.4 Hz, 1H), 7.25–7.55 (m, 9H), 7.95–8.01 (bs, 1H), 8.37–8.43 (bs, 1H), 8.51 (d, J=5.1 Hz, 1H), 9.80–9.86 (bs, 1H) Mass spectrometry value (ESI-MS, m/z): 480 (M$^+$+1)

Example 707

N-Benzyl-N'-{4-[(6,7-dimethoxy-4-quinazolinyl) oxy]phenyl}thiourea

4□[(6,7-Dimethoxy-4-quinazolinyl)oxy]aniline (50 mg) was dissolved in toluene (4 ml) and ethanol (6 ml) to prepare a solution. Benzyl isothiocyanate (81 µl) was added to the solution, and the mixture was stirred at 80° C. for 6 hr. The reaction solution was concentrated, and ether and hexane were added to the residue. The resultant crystal was collected by filtration to give the title compound (74 mg, yield 98%).

$^1$H-NMR (DMSO-$d_6$, 400 MHz): δ 3.97 (s, 3H), 3.99 (s, 3H), 4.73–4.79 (bs, 2H), 7.24–7.56 (m, 11H), 8.18–8.25 (bs, 1H), 8.55 (s, 1H), 9.63–9.67 (bs, 1H) Mass spectrometry value (ESI-MS, m/z): 447 (M$^+$+1)

Example 708

N-{3-Chloro-4-[(6,7-dimethoxy-4-quinolyl)oxy] phenyl}-N'-[2-(1-naphthyl)acetyl]thiourea Toluene (20 ml) and thionyl chloride (1 ml) were added to commercially available 2-(1-naphthyl)acetic acid (80 mg), and the mixture was heated at 100° C. for one hr. The solvent was removed by distillation, and 2-(1-naphthyl) ethanoyl isothiocyanate was prepared using the resultant 2-(1-naphthyl)ethanoyl chloride as a starting compound according to the description of the literature. 2-(1-Naphthyl) ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (67 mg, yield 78%).

$^1$H-NMR (DMSO-$d_6$, 400 MHz): δ 3.94 (s, 3H), 3.96 (s, 3H), 4.36 (s, 2H), 6.45 (d, J=5.4 Hz, 1H), 7.41–8.15 (m, 12H), 8.53 (d, J=5.4 Hz, 1H), 11.97–12.00 (bs, 1H), 12.39–12.42 (bs, 1H) Mass spectrometry value (ESI-MS, m/z): 558 (M$^+$+1)

Example 709

N-{4-[(6,7-Dimethoxy-4-quinazolinyl)oxy]phenyl}-N'-[2-(1-naphthyl) acetyl]thiourea Toluene (20 ml) and thionyl chloride (1 ml) were added to commercially available 2-(1-naphthyl)acetic acid (80 mg), and the mixture was heated at 100° C. for one hr. The solvent was removed by distillation, and 2-(1-naphthyl) ethanoyl isothiocyanate was prepared using the resultant 2-(1-naphthyl)ethanoyl chloride as a starting compound according to the description of the literature. 2-(1-Naphthyl) ethanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (24 mg, yield 27%).

$^1$H-NMR (DMSO-d$_6$, 400 MHz): δ 3.92 (s, 3H), 3.95 (s, 3H), 4.08 (s, 2H), 6.68 (d, J=8.8 Hz, 1H), 7.29–8.16 (m, 13H), 8.63 (s, 1H), 10.03 (s, 1H) Mass spectrometry value (ESI-MS, m/z): 525 (M$^+$+1)

Example 710

N-{3-Chloro-4-[(6,7-dimethoxy-4-quinolyl)oxy]phenyl}-N'-[2-(2-naphthyl)acetyl]thiourea Toluene (20 ml) and thionyl chloride (1 ml) were added to commercially available 2-(2-naphthyl)acetic acid (80 mg), and the mixture was heated at 100° C. for one hr. The solvent was removed by distillation, and 2-(2-naphthyl)ethanoyl isothiocyanate was prepared using the resultant 2-(2-naphthyl)ethanoyl chloride as a starting compound according to the description of the literature. 2-(2-naphthyl)ethanoyl isothiocyanate thus obtained was dissolved in ethanol (1 ml) to prepare a solution. 3-Chloro-4-[(6,7-dimethoxy-4-quinolyl)oxy]-aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (25 mg, yield 29%).

$^1$H-NMR (DMSO-d$_6$, 400 MHz): δ 3.74 (s, 2H), 3.98 (s, 3H), 4.00 (s, 3H), 6.62 (d, J=6.4 Hz, 1H), 7.40–7.93 (m, 11H), 8.15–8.20 (m, 1H), 8.66 (d, J=5.4 Hz, 1H) Mass spectrometry value (ESI-MS, m/z): 558 (M$^+$+1)

Example 711

N-{4-[(6,7-Dimethoxy-4-quinazolinyl)oxy]phenyl}-N'-[2-(2-naphthyl)acetyl]thiourea Toluene (20 ml) and thionyl chloride (1 ml) were added to commercially available 2-(2-naphthyl)acetic acid (80 mg), and the mixture was heated at 100° C. for one hr. The solvent was removed by distillation, and 2-(2-naphthyl)ethanoyl isothiocyanate was prepared using the resultant 2-(2-naphthyl)ethanoyl chloride as a starting compound according to the description of the literature. 2-(2-Naphthyl)ethanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (33 mg, yield 38%).

$^1$H-NMR (DMSO-d$_6$, 400 MHz): δ 3.74 (s, 2H), 3.91 (s, 3H), 3.92 (s, 3H), 6.68 (d, J=8.8 Hz, 1H), 7.29–7.52 (m, 6H), 7.77–7.90 (m, 6H), 8.31 (s, 1H), 8.64–8.68 (bs, 1H), 9.96 (s, 1H) Mass spectrometry value (ESI-MS, m/z): 525 (M$^+$+1)

Example 712

N-{3-Chloro-4-[(6,7-dimethoxy-4-quinolyl)oxy]phenyl}-N'-[3-(3,4-dimethoxyphenyl)propanoyl]thiourea Toluene (20 ml) and thionyl chloride (1 ml) were added to commercially available 3-(3,4-dimethoxyphenyl)propanoic acid (80 mg), and the mixture was heated at 100° C. for one hr. The solvent was removed by distillation, and 3-(3,4-dimethoxyphenyl)propanoyl isothiocyanate was prepared using the resultant 3-(3,4-dimethoxyphenyl)propanoyl chloride as a starting compound according to the description of the literature. 3-(3,4-Dimethoxyphenyl)propanoyl isothiocyanate thus obtained was dissolved in ethanol (1 ml) to prepare a solution. 3-Chloro-4-[(6,7-dimethoxy-4-quinolyl)oxy]-aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (32 mg, yield 36%)

$^1$H-NMR (DMSO-d$_6$, 400 MHz): δ 0.94 (t, J=7.3 Hz, 2H), 2.72–2.89 (m, 2H), 3.69–3.76 (m, 6H), 3.99 (d, J=5.6 Hz, 3H), 6.57 (d, J=5.6 Hz, 1H), 6.70–6.89 (m, 3H), 7.47 (s, 1H), 7.54 (d, J=8.8 Hz, 1H), 7.62 (s, 1H), 7.70–7.76 (m, 1H), 8.16–8.20 (m, 1H), 8.63 (d, J=5.6 Hz, 1H), 11.63–11.64 (bs, 1H), 12.55–12.58 (bs, 1H) Mass spectrometry value (ESI-MS, m/z): 582 (M$^+$+1)

Example 713

N-[3-(3,4-Dimethoxyphenyl)propanoyl]-N'-{4-[(6,7-dimethoxy-4-quinazolinyl)oxy]phenyl}thiourea Toluene (20 ml) and thionyl chloride (1 ml) were added to commercially available 3-(3,4-dimethoxyphenyl)propanoic acid (80 mg), and the mixtue was heated at 100° C. for one hr. The solvent was removed by distillation, and 3-(3,4-dimethoxyphenyl)propanoyl isothiocyanate was prepared using the resultant 3-(3,4-dimethoxyphenyl)propanoyl chloride as a starting compound according to the description of the literature. 3-(3,4-Dimethoxyphenyl)propanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (37 mg, yield 40%).

$^1$H-NMR (DMSO-d$_6$, 400 MHz): δ 0.94 (t, J=7.3 Hz, 2H), 2.59–2.65 (m, 1H), 2.84–2.89 (m, 1H), 3.71 (s, 3H), 3.73 (s, 3H), 3.98 (d, J=5.9 Hz, 3H), 6.68–6.88 (m, 4H), 7.23 (d, J=8.5 Hz, 2H), 7.38 (s, 1H), 7.55 (s, 1H), 7.67 (d, J=8.8 Hz, 2H), 8.53 (s, 1H), 10.00 (s, 1H) Mass spectrometry value (ESI-MS, m/z): 549 (M$^+$+1)

Example 714

N-{3-Chloro-4-[(6,7-dimethoxy-4-quinolyl)oxy]phenyl}-N'-[2-(2-chlorophenoxy)acetyl]thiourea Toluene (20 ml) and thionyl chloride (1 ml) were added to commercially available 2-(2-chlorophenoxy)acetic acid (80 mg), and the mixture was heated at 100° C. for one hr. The solvent was removed by distillation, and 2-(2-chlorophenoxy)ethanoyl isothiocyanate was prepared using the resultant 2-(2-chlorophenoxy)ethanoyl chloride as a starting compound according to the description of the literature. 2-(2-Chlorophenoxy)ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (29 mg, yield 37%).

¹H-NMR (DMSO-d₆, 400 MHz): δ 3.95 (s, 3H), 3.95 (s, 3H), 4.88 (s, 2H), 6.35 (d, J=5.1 Hz, 1H), 6.95–7.13 (m, 3H), 7.26–7.67 (m, 6H), 8.05–8.07 (bs, 1H), 8.30–8.32 (bs, 1H), 8.47 (d, J=5.1 Hz, 1H) Mass spectrometry value (ESI-MS, m/z): 523 (M⁺+1)

Example 715

N-[2-(2-Chlorophenoxy)acetyl]-N'-{4-[(6,7-dimethoxy-4-quinazolinyl)oxy]phenyl}thiourea Toluene (20 ml) and thionyl chloride (1 ml) were added to commercially available 2-(2-chlorophenoxy)acetic acid (80 mg), and the mixture was heated at 100° C. for one hr. The solvent was removed by distillation, and 2-(2-chlorophenoxy)ethanoyl isothiocyanate was prepared using the resultant 2-(2-chlorophenoxy)ethanoyl chloride as a starting compound according to the description of the literature. 2-(2-Chlorophenoxy)ethanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (21 mg, yield 21%).
¹H-NMR (DMSO-d₆, 400 MHz): δ 4.55 (s, 6H), 4.76 (s, 2H), 6.71 (d, J=8.5 Hz, 1H), 6.95–7.47 (m, 10H), 9.24 (s, 1H), 9.84 (s, 1H) Mass spectrometry value (ESI-MS, m/z): 525 (M⁺+1)

Example 716

N-{4-[(6,7-Dimethoxy-4-quinazolinyl)oxy]phenyl}-N'-(4-ethoxybenzoyl)thiourea

4-Ethoxy-1-benzenecarbonyl isothiocyanate was prepared using 4-ethoxy-1-benzenecarbonyl chloride as a starting compound according to the description of the literature. 4-Ethoxy-1-benzenecarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (72 mg, yield 89%).
¹H-NMR (DMSO-d₆, 400 MHz): δ 1.37 (t, J=7.1 Hz, 3H), 3.99 (s, 3H), 4.00 (s, 3H), 4.15 (q, J=7.1 Hz, 2H), 7.06 (d, J=8.8 Hz, 2H), 7.35–7.41 (m, 3H), 7.58 (s, 1H), 7.75–7.82 (m, 2H), 8.03 (d, J=8.8 Hz, 2H), 8.58 (s, 1H), 11.40 (d, J=2.9 Hz, 1H), 12.74–12.75 (bs, 1H) Mass spectrometry value (ESI-MS, m/z): 505 (M⁺+1)

Example 717

N-{4-[(6,7-Dimethoxy-4-quinolyl)oxy]-2,5-dimethylphenyl}-N'-[(2 5-dimethyl-3-furyl)carbonyl]thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate thus obtained was dissolved in ethanol (1 ml) to prepare a solution. 4-[(6,7-Dimethoxy-4-quinolyl)oxy]-2,5-dimethylaniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (69 mg, yield 96%).
¹H-NMR (DMSO-d₆, 400 MHz): δ 2.11 (s, 3H), 2.23 (s, 3H), 2.26 (s, 3H), 2.55 (s, 3H), 3.95 (s, 6H), 6.35 (d, J=5.4 Hz, 1H), 6.91 (s, 1H), 7.16 (s, 1H), 7.41 (s, 1H), 7.55–7.61 (m, 2H), 8.49 (d, J=5.1 Hz, 1H), 10.98–11.10 (bs, 1H), 11.31–11.34 (bs, 1H) Mass spectrometry value (ESI-MS, m/z): 506 (M⁺+1)

Example 718

N-{4-[(6,7-Dimethoxy-4-quinazolinyl)oxy]phenyl}-N'-[(2,5-dimethyl-3-furyl)carbonyl]thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (77 mg, yield 95%).
¹H-NMR (DMSO-d₆, 400 MHz): δ 2.26 (s, 3H), 2.55 (s, 3H), 3.98 (s, 3H), 4.00 (s, 3H), 6.89 (s, 1H), 7.34–7.41 (m, 3H), 7.58 (s, 1H), 7.73–7.81 (m, 2H), 8.58 (s, 1H), 10.93 (d, J=3.9 Hz, 1H), 12.67–12.70 (bs, 1H) Mass spectrometry value (ESI-MS, m/z): 479 (M⁺+1)

Example 719

N-{3-Chloro-4-[(6,7-dimethoxy-4-quinolyl)oxy]phenyl}-N'-pentanoylthiourea

Toluene (20 ml) and thionyl chloride (1 ml) were added to commercially available pentanoic acid (80 mg), and the mixture was heated at 100° C. for one hr. The solvent was removed by distillation, and pentanoyl isothiocyanate was prepared using the resultant pentanoyl chloride as a starting compound according to the description of the literature. Pentanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (29 mg, yield 41%).
¹H-NMR (DMSO-d₆, 400 MHz): δ 0.90 (t, J=7.6 Hz, 3H), 1.28–1.39 (m, 2H), 1.52–1.63 (m, 2H), 3.95 (s, 3H), 3.97 (s, 3H), 6.45 (d, J=5.1 Hz, 1H), 7.43 (s, 1H), 7.49 (d, J=8.8 Hz, 1H), 7.55 (s, 1H), 7.67–7.73 (m, 1H), 8.14–8.18 (m, 1H), 8.53 (d, J=5.4 Hz, 1H), 11.57 (d, J=2.7 Hz, 1H), 12.58 (d, J=4.6 Hz, 1H) Mass spectrometry value (ESI-MS, m/z): 474 ($M^+$+1)

Example 720

N-{4-[(6,7-Dimethoxy-4-quinazolinyl)oxy]phenyl}-N'-pentanoylthiourea

Toluene (20 ml) and thionyl chloride (1 ml) were added to commercially available pentanoic acid (80 mg) at 100° C. for one hr. The solvent was removed by distillation, and pentanoyl isothiocyanate was prepared using the resultant pentanoyl chloride as a starting compound according to the description of the literature. Pentanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (17 mg, yield 23%).
$^1$H-NMR (DMSO-$d_6$, 400 MHz): δ 0.86 (t, J=7.3 Hz, 3H), 1.23–1.40 (m, 2H), 1.50–1.64 (m, 2H), 3.12–3.19 (m, 2H), 3.97 (s, 3H), 3.99 (s, 3H), 7.21–7.25 (m, 2H), 7.38 (s, 1H), 7.55 (s, 1H), 7.66–7.70 (m, 2H), 8.53 (s, 1H), 9.97 (s, 1H) Mass spectrometry value (ESI-MS, m/z): 441 ($M^+$+1)

Example 721

N-{4-[(6,7-Dimethoxy-4-quinolyl)oxy]phenyl}-N'-[3-(4-methylphenyl)propanoyl]thiourea Toluene (20 ml) and thionyl chloride (1 ml) were added to commercially available 3-(4-methylphenyl)propanoic acid (80 mg), and the mixture was heated at 100° C. for one hr. The solvent was removed by distillation, and 3-(4-methylphenyl)propanoyl isothiocyanate was prepared using the resultant 3-(4-methylphenyl)propanoyl chloride as a starting compound according to the description of the literature. 3-(4-Methylphenyl)propanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (90 mg, yield 99%).
$^1$H-NMR (DMSO-$d_6$, 400 MHz): δ 2.25 (s, 3H), 2.47 (s, 2H), 2.76 (t, J=7.6 Hz, 2H), 3.93 (s, 3H), 3.95 (s, 3H), 6.54 (d, J=5.1 Hz, 1H), 7.04–7.16 (m, 4H), 7.30 (d, J=8.8 Hz, 2H), 7.41 (s, 1H), 7.50 (s, 1H), 7.73–7.79 (m, 2H), 8.51 (d, J=5.1 Hz, 1H), 11.51–11.54 (bs, 1H), 12.04–12.10 (bs, 1H) Mass spectrometry value (ESI-MS, m/z): 502 ($M^+$+1)

Example 722

N-{4-[(6,7-Dimethoxy-4-quinazolinyl)oxy]phenyl}-N'-[3-(4-methylphenyl)propanoyl]thiourea Toluene (20 ml) and thionyl chloride (1 ml) were added to commercially available 3-(4-methylphenyl)propanoic acid (80 mg), and the mixture was heated at 100° C. for one hr. The solvent was removed by distillation, and 3-(4-methylphenyl)propanoyl isothiocyanate was prepared using the resultant 3-(4-methylphenyl)propanoyl chloride as a starting compound according to the description of the literature. 3-(4-Methylphenyl)propanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (54 mg, yield 63%).
$^1$H-NMR (DMSO-$d_6$, 400 MHz): δ 2.25 (s, 3H), 2.47 (s, 2H), 2.62 (t, J=7.3 Hz, 2H), 3.97 (s, 3H), 3.99 (s, 3H), 6.67 (d, J=9.0 Hz, 1H), 7.04–7.39 (m, 7H), 7.55 (s, 3H), 7.64–7.68 (m, 2H), 8.53 (s, 1H), 10.00 (s, 1H) Mass spectrometry value (ESI-MS, m/z): 503 ($M^+$+1)

Example 723

N-[2-(2-Chlorophenyl)acetyl]-N'-{4-[(6,7-dimethoxy-4-quinolyl)oxy]phenyl}thiourea Toluene (20 ml) and thionyl chloride (1 ml) were added to commercially available 2-(2-chlorophenyl)acetic acid (80 mg), and the mixture was heated at 100° C. for one hr. The solvent was removed by distillation, and 2-(2-chlorophenyl)ethanoyl isothiocyanate was prepared using the resultant 2-(2-chlorophenyl)ethanoyl chloride as a starting compound according to the description of the literature. 2-(2-Chlorophenyl)ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (77 mg, yield 89%).
$^1$H-NMR (DMSO-$d_6$, 400 MHz): δ 3.92 (s, 3H), 3.95 (s, 3H), 4.04 (s, 2H), 6.54 (d, J=5.1 Hz, 1H), 7.27–7.50 (m, 7H), 7.74–7.79 (m, 2H), 8.31 (s, 1H), 8.51 (d, J=5.1 Hz, 1H), 11.80–11.83 (bs, 1H) Mass spectrometry value (ESI-MS, m/z): 508 ($M^+$+1)

Example 724

N-[2-(2-Chlorophenyl)acetyl]-N'-{4-[(6,7-dimethoxy-4-quinazolinyl)oxy]phenyl}thiourea Toluene (20 ml) and thionyl chloride (1 ml) were added to commercially available 2-(2-chlorophenyl)acetic acid (80 mg), and the mixture was heated at 100° C. for one hr. The solvent was removed by distillation, and 2-(2-chlorophenyl)ethanoyl isothiocyanate was prepared using the resultant 2-(2-chlorophenyl)ethanoyl chloride as a starting compound according to the description of the literature. 2-(2-Chlorophenyl)ethanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (43 mg, yield 49%).

$^1$H-NMR (DMSO-d$_6$, 400 MHz): δ 3.86 (s, 2H), 3.97 (s, 3H), 3.99 (s, 3H), 7.22–7.48 (m, 8H), 7.56 (s, 1H), 7.66–7.71 (m, 2H), 8.53 (s, 1H), 10.33 (s, 1H) Mass spectrometry value (ESI-MS, m/z): 509 (M$^+$+1)

Example 725

N-{4-[(6,7-Dimethoxy-4-quinolyl)oxy]phenyl}-N'-(4-phenylbutanoyl)thiourea

Toluene (20 ml) and thionyl chloride (1 ml) were added to commercially available 4-phenylbutanoic acid (80 mg), and the mixture was heated at 100° C. for one hr. The solvent was removed by distillation, and 4-phenylbutanoyl isothiocyanate was prepared using the resultant 4-phenylbutanoyl chloride as a starting compound according to the description of the literature. 4-Phenylbutanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (50 mg, yield 59%).
$^1$H-NMR (DMSO-d$_6$, 400 MHz): δ 1.07–1.12 (m, 4H), 2.72–2.88 (m, 2H), 3.93 (s, 3H), 3.96 (s, 3H), 6.55 (d, J=5.4 Hz, 1H), 7.19–7.35 (m, 7H), 7.41 (s, 1H), 7.51 (s, 1H), 7.72–7.78 (m, 2H), 8.52 (d, J=5.1 Hz, 1H), 11.50–11.53 (bs, 1H), 12.48 (d, J=4.9 Hz, 1H) Mass spectrometry value (ESI-MS, m/z): 502 (M$^+$+1)

Example 726

N-{3-Chloro-4-[(6,7-dimethoxy-4-quinolyl)oxy]phenyl}-N'-(4-phenylbutanoyl)thiourea Toluene (20 ml) and thionyl chloride (1 ml) were added to commercially available 4-phenylbutanoic acid (80 mg), and the mixture was heated at 100° C. for one hr. The solvent was removed by distillation, and 4-phenylbutanoyl isothiocyanate was prepared using the resultant 4-phenylbutanoyl chloride as a starting compound according to the description of the literature. 4-Phenylbutanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (56 mg, yield 70%).
$^1$H-NMR (DMSO-d$_6$, 400 MHz): δ 1.23–1.28 (m, 4H) 2.72–2.88 (m, 2H), 3.94 (s, 3H), 3.96 (s, 3H), 6.42 (d, J=5.4 Hz, 1H), 7.18–7.35 (m, 5H), 7.43 (s, 1H), 7.47 (d, J=8.8 Hz, 1H), 7.53 (s, 1H), 7.64–7.70 (m, 1H), 8.11–8.15 (m, 1H), 8.51 (d, J=8.4 Hz, 1H), 11.58–11.61 (bs, 1H), 12.50 (d, J=4.9 Hz, 1H) Mass spectrometry value (ESI-MS, m/z): 536 (M$^+$+1)

Example 727

N-{4-[(6,7-Dimethoxy-4-quinolyl)oxy]phenyl}-N'-(5-phenylpentanoyl)thiourea

Toluene (20 ml) and thionyl chloride (1 ml) were added to commercially available 5-phenylpentanoic acid (80 mg), and the mixture was heated at 100° C. for one hr. The solvent was removed by distillation, and 4-phenylpentanoyl isothiocyanate was prepared using the resultant 4-phenylpentanoyl chloride as a starting compound according to the description of the literature. 4-Phenylpentanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (41 mg, yield 47%).
$^1$H-NMR (DMSO-d$_6$, 400 MHz): δ 1.56–1.64 (m, 4H), 2.57–2.63 (m, 2H), 3.94 (s, 3H), 3.96 (s, 3H), 6.58 (d, J=5.4 Hz, 1H), 7.15–7.34 (m, 7H), 7.42 (s, 1H), 7.53 (s, 1H), 7.75–7.81 (m, 2H), 8.55 (d, J=5.4 Hz, 1H), 11.48 (d, J=2.9 Hz, 1H), 12.53 (d, J=4.4 Hz, 1H) Mass spectrometry value (ESI-MS, m/z): 516 (M$^+$+1)

Example 728

N-{3-Chloro-4-[(6,7-dimethoxy-4-quinolyl)oxy]phenyl}-N'-(5-phenylpentanoyl)thiourea Toluene (20 ml) and thionyl chloride (1 ml) were added to commercially available 5-phenylpentanoic acid (80 mg), and the mixture was heated at 100° C. for one hr. The solvent was removed by distillation, and 4-phenylpentanoyl isothiocyanate was prepared using the resultant 4-phenylpentanoyl chloride as a starting compound according to the description of the literature. 4-Phenylpentanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (47 mg, yield 57%).
$^1$H-NMR (DMSO-d$_6$, 400 MHz): δ 1.56–1.64 (m, 4H), 2.56–2.63 (m, 2H), 3.95 (s, 3H), 3.96 (s, 3H), 6.44 (d, J=5.4 Hz, 1H), 7.15–7.32 (m, 5H), 7.43 (s, 1H), 7.48 (d, J=8.8 Hz, 1H), 7.54 (s, 1H), 7.67–7.72 (m, 1H), 8.13–8.18 (m, 1H), 8.53 (d, J=5.4 Hz, 1H), 11.55–11.59 (bs, 1H), 12.55 (d, J=4.4 Hz, 1H) Mass spectrometry value (ESI-MS, m/z): 550 (M$^+$+1)

Example 729

N-{4-[(6,7-Dimethoxy-4-quinolyl)oxy]phenyl}-N'-[2-(2-fluorophenyl)acetyl]thiourea Toluene (20 ml) and thionyl chloride (1 ml) were added to commercially available 2-(2-fluorophenyl)acetic acid (80 mg), and the mixture was heated at 100° C. for one hr. The solvent was removed by distillation, and 2-(2-fluorophenyl)ethanoyl isothiocyanate was prepared using the resultant 2-(2-fluorophenyl)ethanoyl chloride as a starting compound according to the description of the literature. 2-(2-Fluorophenyl)ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (55 mg, yield 66%).

$^1$H-NMR (DMSO-$d_6$, 400 MHz): δ 3.76 (s, 2H), 3.93 (s, 3H), 3.95 (s, 3H), 6.46 (d, J=5.4 Hz, 1H), 7.10–7.52 (m, 8H), 7.71–7.76 (m, 2H), 8.31 (s, 1H), 8.47 (d, J=5.1 Hz, 1H), 10.36 (s, 1H) Mass spectrometry value (ESI-MS, m/z): 492 (M$^+$+1)

Example 730

N-{3-Chloro-4-[(6,7-dimethoxy-4-quinolyl)oxy]phenyl}-N'-[2-(2-fluorophenyl)acetyl]thiourea Toluene (20 ml) and thionyl chloride (1 ml) were added to commercially available 2-(2-fluorophenyl)acetic acid (80 mg), and the mixture was heated at 100° C. for one hr. The solvent was removed by distillation, and 2-(2-fluorophenyl)ethanoyl isothiocyanate was prepared using the resultant 2-(2-fluorophenyl)ethanoyl chloride as a starting compound according to the description of the literature. 2-(2-Fluorophenyl)ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (51 mg, yield 65%).

$^1$H-NMR (DMSO-$d_6$, 400 MHz): δ 3.78 (s, 2H), 3.96 (s, 3H), 3.97 (s, 3H), 6.44 (d, J=5.6 Hz, 1H), 7.10–7.64 (m, 8H), 8.06 (d, J=2.2 Hz, 1H), 8.31 (s, 1H), 8.53 (d, J=5.6 Hz, 1H), 10.56 (s, 1H) Mass spectrometry value (ESI-MS, m/z): 526 (M$^+$+1)

Example 731

N-{4-[(6,7-Dimethoxy-4-quinolyl)oxy]phenyl}-N'-[3-(2-methylphenyl)propanoyl]thiourea Toluene (20 ml) and thionyl chloride (1 ml) were added to commercially available 3-(2-methylphenyl)propanoic acid (80 mg), and the mixture was heated at 100° C. for one hr. The solvent was removed by distillation, and 3-(2-methylphenyl)propanoyl isothiocyanate was prepared using the resultant 3-(2-methylphenyl)propanoyl chloride as a starting compound according to the description of the literature. 3-(2-Methylphenyl)propanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (14 mg, yield 16%).

$^1$H-NMR (DMSO-$d_6$, 400 MHz): δ 2.31 (s, 3H), 2.73–2.93 (m, 4H), 3.94 (s, 3H), 3.96 (s, 3H), 6.57 (d, J=5.1 Hz, 1H), 7.08–7.19 (m, 4H), 7.32 (d, J=8.8 Hz, 2H), 7.42 (s, 1H), 7.52 (s, 1H), 7.74–7.81 (m, 2H), 8.53 (d, J=5.4 Hz, 1H), 11.54–11.57 (bs, 1H), 12.53 (d, J=2.4 Hz, 1H) Mass spectrometry value (ESI-MS, m/z): 502 (M$^+$+1)

Example 732

N-{3-Chloro-4-[(6,7-dimethoxy-4-quinolyl)oxy]phenyl}-N'-[3-(2-methylphenyl)propanoyl]thiourea Toluene (20 ml) and thionyl chloride (1 ml) were added to commercially available 3-(2-methylphenyl)propanoic acid (80 mg), and the mixture was heated at 100° C. for one hr. The solvent was removed by distillation, and 3-(2-methylphenyl)propanoyl isothiocyanate was prepared using the resultant 3-(2-methylphenyl)propanoyl chloride as a starting compound according to the description of the literature. 3-(2-Methylphenyl)propanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (45 mg, yield 56%).

$^1$H-NMR (DMSO-$d_6$, 400 MHz): δ 2.31 (s, 3H), 2.74–2.92 (m, 4H), 3.97 (s, 3H), 3.98 (s, 3H), 6.51 (d, J=5.6 Hz, 1H), 7.08–7.20 (m, 4H), 7.45 (s, 1H), 7.52 (d, J=8.8 Hz, 1H), 7.58 (s, 1H), 7.69–7.75 (m, 1H), 8.15–8.19 (m, 1H), 8.58 (d, J=5.4 Hz, 1H), 11.65 (d, J=2.4 Hz, 1H), 12.56 (d, J=4.6 Hz, 1H) Mass spectrometry value (ESI-MS, m/z): 536 (M$^+$+1)

Example 733

N-{4-[(6,7-Dimethoxy-4-quinolyl)oxy]phenyl}-N'-[2-(2-methoxyphenyl)acetyl]thiourea Toluene (20 ml) and thionyl chloride (1 ml) were added to commercially available 2-(2-methoxyphenyl)acetic acid (80 mg), and the mixture was heated at 100° C. for one hr. The solvent was removed by distillation, and 2-(2-methoxyphenyl)ethanoyl isothiocyanate was prepared using the resultant 2-(2-methoxyphenyl)ethanoyl chloride as a starting compound according to the description of the literature. 2-(2-Methoxyphenyl)ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (25 mg, yield 30%).

$^1$H-NMR (DMSO-$d_6$, 400 MHz): δ 3.79 (s, 3H), 3.82 (s, 2H), 3.96 (s, 3H), 3.99 (s, 3H), 6.66 (d, J=5.9 Hz, 1H), 6.85–7.03 (m, 2H), 7.21–7.37 (m, 4H), 7.44 (s, 1H), 7.58 (s, 1H), 7.78–7.84 (m, 2H), 8.62 (d, J=5.9 Hz, 1H), 11.64–11.66 (bs, 1H), 12.47 (d, J=4.6 Hz, 1H) Mass spectrometry value (ESI-MS, m/z): 504 (M$^+$+1)

Example 734

N-{3-Chloro-4-[(6,7-dimethoxy-4-quinolyl)oxy]phenyl}-N'-[2-(2-methoxyphenyl)acetyl]thiourea Toluene (20 ml) and thionyl chloride (1 ml) were added to commercially available 2-(2-methoxyphenyl)acetic acid (80 mg), and the mixture was heated at 100° C. for one hr. The solvent was removed by distillation, and 2-(2-methoxyphenyl)ethanoyl isothiocyanate was prepared using the resultant 2-(2-methoxyphenyl)ethanoyl chloride as a starting compound according to the description of the literature. 2-(2-Methoxyphenyl)ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (45 mg, yield 55%).

$^1$H-NMR (DMSO-$d_6$, 400 MHz): δ 3.79 (s, 3H), 3.82 (s, 2H), 3.99 (s, 3H), 4.01 (s, 3H), 6.66 (d, J=5.9 Hz, 1H), 6.85–7.03 (m, 2H), 7.22–7.32 (m, 2H), 7.49 (s, 1H), 7.56 (d, J=9.0 Hz, 1H), 7.66 (s, 1H), 7.74–7.80 (m, 1H), 8.20–8.24 (m, 1H), 8.69 (d, J=5.9 Hz, 1H), 11.75 (d, J=2.4 Hz, 1H), 12.52 (d, J=4.6 Hz, 1H) Mass spectrometry value (ESI-MS, m/z): 538 (M$^+$+1)

Example 735

N-{4-[(6,7-Dimethoxy-4-quinolyl)oxy]phenyl}-N'-[2-(2-nitrophenyl)acetyl]thiourea Toluene (20 ml) and thionyl chloride (1 ml) were added to commercially available 2-(2-nitrophenyl)acetic acid (80 mg), and the mixture was heated at 100° C. for one hr. The solvent was removed by distillation, and 2-(2-nitrophenyl) ethanoyl isothiocyanate was prepared using the resultant 2-(2-nitrophenyl)ethanoyl chloride as a starting compound according to the description of the literature. 2-(2-Nitrophenyl)ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/methanol for development to give the title compound (7 mg, yield 8%).

$^1$H-NMR (DMSO-$d_6$, 400 MHz): δ 4.00 (s, 3H), 4.00 (s, 3H), 4.30 (s, 2H), 6.71 (d, J=5.9 Hz, 1H), 7.33–7.84 (m, 8H), 8.08 (d, J=7.8 Hz, 1H), 8.67 (d, J=5.9 Hz, 1H), 11.84–11.88 (bs, 1H), 12.25–12.28 (bs, 1H) Mass spectrometry value (ESI-MS, m/z): 519 (M$^+$+1)

Example 736

N-{3-Chloro-4-[(6,7-dimethoxy-4-quinolyl)oxy] phenyl}-N'-[2-(2-nitrophenyl)acetyl]thiourea Toluene (20 ml) and thionyl chloride (1 ml) were added to commercially available 2-(2-nitrophenyl)acetic acid (80 mg), and the mixture was heated at 100° C. for one hr. The solvent was removed by distillation, and 2-(2-nitrophenyl) ethanoyl isothiocyanate was prepared using the resultant 2-(2-nitrophenyl)ethanoyl chloride as a starting compound according to the description of the literature. 2-(2-Nitrophenyl)ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/methanol for development to give the title compound (8 mg, yield 10%).

$^1$H-NMR (DMSO-$d_6$, 400 MHz): δ 3.94 (s, 3H), 3.96 (s, 3H), 4.30 (s, 2H), 6.41 (d, J=5.1 Hz, 1H), 7.40–7.80 (m, 7H), 8.10–8.17 (m, 2H), 8.50 (d, J=5.1 Hz, 1H), 11.91–11.94 (bs, 1H), 12.26 (d, J=4.1 Hz, 1H) Mass spectrometry value (ESI-MS, m/z): 553 (M$^+$+1)

Example 737

N-{4-[(6,7-Dimethoxy-4-quinolyl)oxy]phenyl}-N'-(2-phenoxyacetyl)thiourea

Toluene (20 ml) and thionyl chloride (1 ml) were added to commercially available 2-phenoxyacetic acid (80 mg), and the mixture was heated at 100° C. for one hr. The solvent was removed by distillation, and 2-phenoxyethanoyl isothiocyanate was prepared using the resultant 2-phenoxyethanoyl chloride as a starting compound according to the description of the literature. 2-Phenoxyethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (40 mg, yield 48%).

$^1$H-NMR (DMSO-$d_6$, 400 MHz): δ 3.94 (s, 3H), 3.96 (s, 3H), 4.73 (s, 2H), 6.49 (d, J=5.1 Hz, 1H), 6.88–7.05 (m, 3H), 7.24–7.36 (m, 4H), 7.40 (s, 1H), 7.53 (s, 1H), 7.80 (d, J=9.0 Hz, 2H), 8.50 (d, J=5.4 Hz, 1H), 10.25 (s, 1H) Mass spectrometry value (ESI-MS, m/z): 490 (M$^+$+1)

Example 738

N-{3-Chloro-4-[(6,7-dimethoxy-4-quinolyl)oxy] phenyl}-N'-(2-phenoxyacetyl)thiourea Toluene (20 ml) and thionyl chloride (1 ml) were added to commercially available 2-phenoxyacetic acid (80 mg), and the mixture was heated at 100° C. for one hr. The solvent was removed by distillation, and 2-phenoxyethanoyl isothiocyanate was prepared using the resultant 2-phenoxyethanoyl chloride as a starting compound according to the description of the literature. 2-Phenoxyethanoyl isothiocyanate thus obtained was dissolved in ethanol (1 ml) to prepare a solution. 3-Chloro-4-[(6,7-dimethoxy-4-quinolyl)oxy] aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (50 mg, yield 64%).

$^1$H-NMR (DMSO-$d_6$, 400 MHz): δ 3.99 (s, 3H), 4.00 (s, 3H), 4.76 (s, 2H), 6.57 (d, J=5.6 Hz, 1H), 6.88–7.05 (m, 3H), 7.26–7.37 (m, 3H), 7.46 (s, 1H), 7.51 (d, J=9.0 Hz, 1H), 7.63 (s, 1H), 7.73–7.78 (m, 1H), 8.12 (d, J=2.2 Hz, 1H), 8.61 (d, J=5.9 Hz, 1H), 10.44 (s, 1H) Mass spectrometry value (ESI-MS, m/z): 524 (M$^+$+1)

Example 739

N-{4-[(6,7-Dimethoxy-4-quinolyl)oxy]phenyl}-N'-[2-(2-methylphenoxy)acetyl]thiourea Toluene (20 ml) and thionyl chloride (1 ml) were added to commercially available 2-(2-methylphenoxy)acetic acid (80 mg), and the mixture was heated at 100° C. for one hr.

The solvent was removed by distillation, and 2-(2-methylphenoxy)ethanoyl isothiocyanate was prepared using the resultant 2-(2-methylphenoxy)ethanoyl chloride as a starting compound according to the description of the literature. 2-(2-Methylphenoxy)ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (25 mg, yield 29%).

$^1$H-NMR (DMSO-$d_6$, 400 MHz): δ 2.27 (s, 3H), 3.94 (s, 3H), 3.95 (s, 3H), 4.74 (s, 2H), 6.46 (d, J=5.1 Hz, 1H), 6.78–6.92 (m, 3H), 7.09–7.28 (m, 4H), 7.40 (s, 1H), 7.51 (s, 1H), 7.78 (d, J=8.8 Hz, 2H), 8.47 (d, J=5.1 Hz, 1H), 10.20 (s, 1H) Mass spectrometry value (ESI-MS, m/z): 504 (M$^+$+1)

Example 740

N-{3-Chloro-4-[(6,7-dimethoxy-4-quinolyl)oxy]phenyl}-N'-[2-(2-methylphenoxy)acetyl]thiourea Toluene (20 ml) and thionyl chloride (1 ml) were added to commercially available 2-(2-methylphenoxy)acetic acid (80 mg), and the mixture was heated at 100° C. for one hr. The solvent was removed by distillation, and 2-(2-methylphenoxy)ethanoyl isothiocyanate was prepared using the resultant 2-(2-methylphenoxy)ethanoyl chloride as a starting compound according to the description of the literature. 2-Phenoxyethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (26 mg, yield 32%).

$^1$H-NMR (DMSO-$d_6$, 400 MHz): δ 2.27 (s, 3H), 3.96 (s, 3H), 3.96 (s, 3H), 4.77 (s, 2H), 6.42 (d, J=5.4 Hz, 1H), 6.78–7.71 (m, 9H), 8.09 (d, J=2.4 Hz, 1H), 8.51 (d, J=5.4 Hz, 1H), 10.39 (s, 1H) Mass spectrometry value (ESI-MS, m/z): 538 (M$^+$+1)

Example 741

N-{4-[(6,7-Dimethoxy-4-quinolyl)oxy]phenyl}-N'-(2-phenoxybutanoyl)thiourea

Toluene (20 ml) and thionyl chloride (1 ml) were added to commercially available 2-phenoxybutanoic acid (80 mg), and the mixture was heated at 100° C. for one hr. The solvent was removed by distillation, and 2-phenoxybutanoyl isothiocyanate was prepared using the resultant 2-phenoxybutanoyl chloride as a starting compound according to the description of the literature. 2-Phenoxybutanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (35 mg, yield 40%).

$^1$H-NMR (DMSO-$d_6$, 400 MHz): δ 1.05 (t, J=7.3 Hz, 3H), 1.87–2.01 (m, 2H), 3.92 (s, 3H), 3.95 (s, 3H), 4.95–5.00 (m, 1H), 6.54 (d, J=5.4 Hz, 1H), 6.88–7.02 (m, 3H), 7.25–7.37 (m, 4H), 7.41 (s, 1H), 7.49 (s, 1H), 7.73–7.80 (m, 2H), 8.52 (d, J=5.4 Hz, 1H), 11.73–11.76 (bs, 1H), 12.16 (d, J=4.9 Hz, 1H) Mass spectrometry value (ESI-MS, m/z): 518 (M$^+$+1)

Example 742

N-{3-Chloro-4-[(6,7-dimethoxy-4-quinolyl)oxy]phenyl}-N'-(2-phenoxybutanoyl)thiourea Toluene (20 ml) and thionyl chloride (1 ml) were added to commercially available 2-phenoxybutanoic acid (80 mg), and the mixture was heated at 100° C. for one hr. The solvent was removed by distillation, and 2-phenoxybutanoyl isothiocyanate was prepared using the resultant 2-phenoxybutanoyl chloride as a starting compound according to the description of the literature. 2-Phenoxybutanoyl isothiocyanate thus obatined was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (25 mg, yield 27%).

$^1$H-NMR (DMSO-$d_6$, 400 MHz): δ 1.06 (t, J=7.6 Hz, 3H), 1.86–2.02 (m, 2H), 3.94 (s, 3H), 3.96 (s, 3H), 4.95–5.01 (m, 1H), 6.40 (d, J=5.4 Hz, 1H), 6.90–7.02 (m, 3H), 7.30–7.37 (m, 2H), 7.42 (s, 1H), 7.46 (d, J=8.8 Hz, 1H), 7.52 (s, 1H), 7.67–7.73 (m, 1H), 8.10–8.15 (m, 1H), 8.51 (d, J=5.4 Hz, 1H), 11.82–11.86 (bs, 1H), 12.17 (d, J=5.1 Hz, 1H) Mass spectrometry value (ESI-MS, m/z): 552 (M$^+$+1)

Example 743

N-{4-[(6,7-Dimethoxy-4-quinolyl)oxy]phenyl}-N'-[(2R)-2-phenylpropanoyl]thiourea

Toluene (20 ml) and thionyl chloride (1 ml) were added to commercially available (2R)-2-phenylpropanoic acid (80 mg), and the mixture was heated at 100° C. for one hr. The solvent was removed by distillation, and (2R)-2-phenylpropanoyl isothiocyanate was prepared using the resultant (2R)-2-phenylpropanoyl chloride as a starting compound according to the description of the literature. (2R)-2-Phenylpropanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (31 mg, yield 38%).

$^1$H-NMR (DMSO-$d_6$, 400 MHz): δ 1.44 (d, J=7.1 Hz, 3H), 3.92 (s, 3H), 3.95 (s, 3H), 4.08–4.16 (m, 1H), 6.55 (d, J=5.4 Hz, 1H), 7.24–7.45 (m, 8H), 7.50 (s, 1H), 7.72–7.78 (m, 2H), 8.52 (d, J=5.1 Hz, 1H), 11.66–11.69 (bs, 1H), 12.41–12.44 (bs, 1H) Mass spectrometry value (ESI-MS, m/z): 488 (M$^+$+1)

Example 744

N-{3-Chloro-4-[(6,7-dimethoxy-4-quinolyl)oxy]phenyl}-N'-[(2R)-2-phenylpropanoyl]thiourea Toluene (20 ml) and thionyl chloride (1 ml) were added to commercially available (2R)-2-phenylpropanoic acid (80 mg), and the mixture was heated at 100° C. for one hr. The solvent was removed by distillation, and (2R)-2-phenylpropanoyl isothiocyanate was prepared using the resultant (2R)-2-phenylpropanoyl chloride as a starting compound according to the description of the literature. (2R)-2-Phenylpropanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (56 mg, yield 71%).

$^1$H-NMR (DMSO-$d_6$, 400 MHz): δ 1.44 (d, J=6.8 Hz, 3H), 3.94 (s, 3H), 3.96 (s, 3H), 4.08–4.16 (m, 1H), 6.42 (d, J=5.4 Hz, 1H), 7.27–7.49 (m, 7H), 7.53 (s, 1H), 7.66–7.72 (m, 1H), 8.10–8.14 (m, 1H), 8.52 (d, J=5.1 Hz, 1H), 11.75–11.78 (bs, 1H), 12.44–12.47 (bs, 1H) Mass spectrometry value (ESI-MS, m/z): 522 (M$^+$+1)

Example 745

N-{4-[(6,7-Dimethoxy-4-quinolyl)oxy]phenyl}-N'-(2-phenoxypropanoyl)thiourea

Toluene (20 ml) and thionyl chloride (1 ml) were added to commercially available 2-phenoxypropanoic acid (80 mg), and the mixture was heated at 100° C. for one hr. The solvent was removed by distillation, and 2-phenoxypropanoyl isothiocyanate was prepared using the resultant 2-phenoxypropanoyl chloride as a starting compound according to the description of the literature. 2-Phenoxypropanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (14 mg, yield 16%).

$^1$H-NMR (DMSO-$d_6$, 400 MHz): δ 1.58 (d, J=6.6 Hz, 3H), 3.93 (s, 3H), 3.95 (s, 3H), 4.86–4.93 (m, 1H), 6.44 (d, J=5.1 Hz, 1H), 6.96–7.01 (m, 3H), 7.21–7.35 (m, 4H), 7.39 (s, 1H), 7.50 (s, 1H), 7.75–7.80 (m, 2H), 8.46 (d, J=5.4 Hz, 1H), 10.27 (s, 1H) Mass spectrometry value (ESI-MS, m/z): 504 (M$^+$+1)

Example 746

N-{3-Chloro-4-[(6,7-dimethoxy-4-quinolyl)oxy]phenyl}-N'-(2-phenoxypropanoyl)thiourea Toluene (20 ml) and thionyl chloride (1 ml) were added to commercially available 2-phenoxypropanoic acid (80 mg), and the mixture was heated at 100° C. for one hr. The solvent was removed by distillation, and 2-phenoxypropanoyl isothiocyanate was prepared using the resultant 2-phenoxypropanoyl chloride as a starting compound according to the description of the literature. 2-Phenoxypropanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (33 mg, yield 41%).

$^1$H-NMR (DMSO-$d_6$, 400 MHz): δ 1.58 (d, J=6.6 Hz, 3H), 3.94 (s, 3H), 3.95 (s, 3H), 4.87–4.94 (m, 1H), 6.35 (d, J=5.1 Hz, 1H), 6.88–7.53 (m, 8H), 7.69–7.74 (m, 1H), 8.07 (d, J=2.4 Hz, 1H), 8.45 (d, J=5.4 Hz, 1H), 10.43 (s, 1H) Mass spectrometry value (ESI-MS, m/z): 538 (M$^+$+1)

Example 747

N-{4-[(6,7-Dimethoxy-4-quinolyl)oxy]phenyl}-N'-(2-phenylbutanoyl)thiourea

Toluene (20 ml) and thionyl chloride (1 ml) were added to commercially available 2-phenylbutanoic acid (80 mg), and the mixture was heated at 100° C. for one hr. The solvent was removed by distillation, and 2-phenylbutanoyl isothiocyanate was prepared using the resultant 2-phenylbutanoyl chloride as a starting compound according to the description of the literature. 2-Phenylbutanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (41 mg, yield 48%).

$^1$H-NMR (DMSO-$d_6$, 400 MHz): δ 0.86 (t, J=7.3 Hz, 3H), 1.22–1.28 (bs, 1H), 1.69–1.81 (m, 1H), 2.01–2.14 (m, 1H), 3.93 (s, 3H), 3.95 (s, 3H), 6.55 (d, J=5.4 Hz, 1H), 7.26–7.44 (m, 8H), 7.50 (s, 1H), 7.72–7.79 (m, 2H), 8.53 (d, J=5.1 Hz, 1H), 11.69–11.72 (bs, 1H), 12.44–12.48 (bs, 1H) Mass spectrometry value (ESI-MS, m/z): 502 (M$^+$+1)

Example 748

N-{3-Chloro-4-[(6,7-dimethoxy-4-quinolyl)oxy]phenyl}-N'-(2-phenylbutanoyl)thiourea Toluene (20 ml) and thionyl chloride (1 ml) were added to commercially available 2-phenylbutanoic acid (80 mg), and the mixture was heated at 100° C. for one hr. The solvent was removed by distillation, and 2-phenylbutanoyl isothiocyanate was prepared using the resultant 2-phenylbutanoyl chloride as a starting compound according to the description of the literature. 2-Phenylbutanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (37 mg, yield 46%).

$^1$H-NMR (DMSO-$d_6$, 400 MHz): δ 0.83–0.90 (m, 3H), 1.22–1.29 (bs, 1H), 1.69–1.81 (m, 1H), 2.01–2.14 (m, 1H), 3.94 (s, 3H), 3.95 (s, 3H), 6.40 (d, J=5.1 Hz, 1H), 7.28–7.47 (m, 7H), 7.52 (s, 1H), 7.66–7.72 (m, 1H), 8.10–8.14 (m,

1H), 8.50 (d, J=5.1 Hz, 1H), 11.77–11.80 (bs, 1H), 12.45–12.48 (bs, 1H) Mass spectrometry value (ESI-MS, m/z): 536 (M$^+$+1)

Example 749

N-[(2,2-Dichloro-1-methylcyclopropyl)carbonyl]-N'-{4-[(6,7-dimethoxy-4-quinolyl)oxy]phenyl}thiourea Toluene (20 ml) and thionyl chloride (1 ml) were added to commercially available 2,2-dichloro-1-methyl-1-cyclopropanecarboxylic acid (80 mg), and the mixture was heated at 100° C. for one hr. The solvent was removed by distillation, and 2,2-dichloro-1-methyl-1-cyclopropanecarbonyl isothiocyanate was prepared using the resultant 2,2-dichloro-1-methyl-1-cyclopropanecarbonyl chloride as a starting compound according to the description of the literature. 2,2-Dichloro-1-methyl-1-cyclopropanecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (63 mg, yield 73%).

$^1$H-NMR (DMSO-d$_6$, 400 MHz): δ 1.67 (s, 3H), 1.71 (d, J=8.1 Hz, 1H), 2.13 (d, J=7.8 Hz, 1H), 3.93 (s, 3H), 3.95 (s, 3H), 6.55 (d, J=5.1 Hz, 1H), 7.28–7.34 (m, 2H), 7.41 (s, 1H), 7.50 (s, 1H), 7.75–7.81 (bs, 2H), 8.52 (d, J=5.1 Hz, 1H), 12.11–12.20 (m, 1H) Mass spectrometry value (ESI-MS, m/z): 506 (M$^+$+1)

Example 750

N-{3-Chloro-4-[(6,7-dimethoxy-4-quinolyl)oxy]phenyl}-N'-[(2,2-dichloro-1-methylcyclopropyl)carbonyl]thiourea Toluene (20 ml) and thionyl chloride (1 ml) were added to commercially available 2,2-dichloro-1-methyl-1-cyclopropanecarboxylic acid (80 mg), and the mixture was heated at 100° C. for one hr. The solvent was removed by distillation, and 2,2-dichloro-1-methyl-1-cyclopropanecarbonyl isothiocyanate was prepared using the resultant 2,2-dichloro-1-methyl-1-cyclopropanecarbonyl chloride as a starting compound according to the description of the literature. 2,2-Dichloro-1-methyl-1-cyclopropanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography oh silica gel using chloroform/acetone for development to give the title compound (27 mg, yield 34%).

$^1$H-NMR (DMSO-d$_6$, 400 MHz): δ 1.67 (s, 3H), 1.72 (d, J=7.8 Hz, 1H), 2.13 (d, J=7.8 Hz, 1H), 3.95 (s, 3H), 3.96 (s, 3H), 6.42 (d, J=4.4 Hz, 1H), 7.43 (s, 1H), 7.48 (d, J=8.8 Hz, 1H), 7.53 (s, 1H), 7.67–7.74 (bs, 1H), 8.13–8.18 (bs, 1H), 8.51 (d, J=5.1 Hz, 1H), 12.19–12.23 (bs, 1H) Mass spectrometry value (ESI-MS, m/z): 540 (M$^+$+1)

Example 751

N-(4-Butoxybenzoyl)-N'-{4-[(6,7-dimethoxy-4-quinolyl)oxy]phenyl}thiourea

Toluene (20 ml) and thionyl chloride (1 ml) were added to commercially available 4-butoxybenzoic acid (80 mg), and the mixture was heated at 100° C. for one hr. The solvent was removed by distillation, and 4-butoxy-1-benzenecarbonyl isothiocyanate was prepared using the resultant 4-butoxy-1-benzenecarbonyl chloride as a starting compound according to the description of the literature. 4-Butoxy-1-benzenecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (59 mg, yield 65%).

$^1$H-NMR (DMSO-d$_6$, 400 MHz): δ 0.95 (t, J=7.6 Hz, 3H), 1.40–1.52 (m, 2H), 1.69–1.78 (m, 2H), 3.94 (s, 3H), 3.96 (s, 3H), 4.06–4.12 (m, 2H), 6.56 (d, J=5.1 Hz, 1H), 7.05–7.11 (m, 2H), 7.30–7.36 (m, 2H), 7.42 (s, 1H), 7.51 (s, 1H), 7.80–7.87 (m, 2H), 8.00–8.05 (m, 2H), 8.52 (d, J=5.1 Hz, 1H), 11.40–11.43 (bs, 1H), 12.72–12.76 (bs, 1H) Mass spectrometry value (ESI-MS, m/z): 532 (M$^+$+1)

Example 752

N-(4-Butoxybenzoyl)-N'-{3-chloro-4-[(6,7-dimethoxy-4-quinolyl)oxy]phenyl}thiourea Toluene (20 ml) and thionyl chloride (1 ml) were added to commercially available 4-butoxybenzoic acid (80 mg), and the mixture was heated at 100° C. for one hr. The solvent was removed by distillation, and 4-butoxy-1-benzenecarbonyl isothiocyanate was prepared using the resultant 4-butoxy-1-benzenecarbonyl chloride as a starting compound according to the description of the literature. 4-Butoxy-1-benzenecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (55 mg, yield 65%).

$^1$H-NMR (DMSO-d$_6$, 400 MHz): δ 0.92–0.99 (m, 3H), 1.40–1.52 (m, 2H), 1.69–1.79 (m, 2H), 3.95 (s, 3H), 3.96 (s, 3H), 4.06–4.12 (m, 2H), 6.43 (d, J=5.1 Hz, 1H), 7.05–7.11 (m, 2H), 7.42–7.56 (m, 3H), 7.73–7.79 (m, 1H), 8.00–8.06 (m, 2H), 8.18–8.24 (m, 1H), 8.52 (d, J=5.4 Hz, 1H), 11.50–11.54 (bs, 1H), 12.74–12.79 (bs, 1H) Mass spectrometry value (ESI-MS, m/z): 566 (M$^+$+1)

Example 753

N-{4-[(6,7-Dimethoxy-4-quinolyl)oxy]phenyl}-N'-[4-(pentyloxy)benzoyl]thiourea

Toluene (20 ml) and thionyl chloride (1 ml) were added to commercially available 4-(pentyloxy)benzoic acid (80 mg), and the mixture was heated at 100° C. for one hr. The solvent was removed by distillation, and 4-(pentyloxy)-1-benzenecarbonyl isothiocyanate was prepared using the resultant 4-(pentyloxy)-1-benzenecarbonyl chloride as a starting compound according to the description of the literature. 4-(Pentyloxy)-1-benzenecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (61 mg, yield 65%).

$^1$H-NMR (DMSO-$d_6$, 400 MHz): δ 0.88–0.94 (m, 3H), 1.31–1.46 (m, 4H), 1.71–1.80 (m, 2H), 3.94 (s, 3H), 3.96 (s, 3H), 4.08 (t, J=6.3 Hz, 2H), 6.56 (d, J=5.1 Hz, 1H), 7.04–7.10 (m, 2H), 7.30–7.36 (m, 2H), 7.42 (s, 1H), 7.51 (s, 1H), 7.80–7.87 (m, 2H), 8.00–8.05 (m, 2H), 8.52 (d, J=5.4 Hz, 1H), 11.40–11.43 (bs, 1H), 12.73–12.76 (bs, 1H) Mass spectrometry value (ESI-MS, m/z): 546 ($M^+$+1)

Example 754

N-{3-Chloro-4-[(6,7-dimethoxy-4-quinolyl)oxy]phenyl}-N'-[4-(pentyloxy)benzoyl]thiourea Toluene (20 ml) and thionyl chloride (1 ml) were added to commercially available 4-(pentyloxy)benzoic acid (80 mg), and the mixture was heated at 100° C. for one hr. The solvent was removed by distillation, and 4-(pentyloxy)-1-benzenecarbonyl isothiocyanate was prepared using the resultant 4-(pentyloxy)-1-benzenecarbonyl chloride as a starting compound according to the description of the literature. 4-(Pentyloxy)-1-benzenecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (63 mg, yield 72%).

$^1$H-NMR (DMSO-$d_6$, 400 MHz): δ 0.88–0.94 (m, 3H), 1.31–1.47 (m, 4H), 1.71–1.80 (m, 2H), 3.95 (s, 3H), 3.96 (s, 3H), 4.08 (t, J=6.6 Hz, 2H), 6.43 (d, J=5.1 Hz, 1H), 7.05–7.10 (m, 2H), 7.43 (s, 1H), 7.50 (d, J=8.8 Hz, 1H), 7.54 (s, 1H), 7.72–7.79 (m, 1H), 8.00–8.05 (m, 2H), 8.18–8.24 (m, 1H), 8.51 (d, J=5.1 Hz, 1H), 11.49–11.53 (bs, 1H), 12.74–12.78 (bs, 1H) Mass spectrometry value (ESI-MS, m/z): 580 ($M^+$+1)

Example 755

N-{4-[(6,7-Dimethoxy-4-quinolyl)oxy]phenyl}-N'-[4-(hexyloxy)benzoyl]thiourea

Toluene (20 ml) and thionyl chloride (1 ml) were added to commercially available 4-(hexyloxy)benzoic acid (80 mg), and the mixture was heated at 100° C. for one hr. The solvent was removed by distillation, and 4-(hexyloxy)-1-benzenecarbonyl isothiocyanate was prepared using the resultant 4-(hexyloxy)-1-benzenecarbonyl chloride as a starting compound according to the description of the literature. 4-(Hexyloxy)-1-benzenecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (58 mg, yield 61%).

$^1$H-NMR (DMSO-$d_6$, 400 MHz): δ 0.86–0.92 (m, 3H), 1.29–1.35 (m, 4H), 1.39–1.48 (m, 2H), 1.70–1.79 (m, 2H), 3.94 (s, 3H), 3.96 (s, 3H), 4.05–4.11 (m, 2H), 6.56 (d, J=5.1 Hz, 1H), 7.04–7.10 (m, 2H), 7.30–7.36 (m, 2H), 7.42 (s, 1H), 7.51 (s, 1H), 7.80–7.87 (m, 2H), 8.00–8.05 (m, 2H), 8.52 (d, J=5.4 Hz, 1H), 11.39–11.43 (bs, 1H), 12.72–12.76 (bs, 1H) Mass spectrometry value (ESI-MS, m/z): 560 ($M^+$+1)

Example 756

N-{3-Chloro-4-[(6,7-dimethoxy-4-quinolyl)oxy]phenyl}-N'-[4-(hexyloxy)benzoyl]thiourea Toluene (20 ml) and thionyl chloride (1 ml) were added to commercially available 4-(hexyloxy)benzoic acid (80 mg), and the mixture was heated at 100° C. for one hr. The solvent was removed by distillation, and 4-(hexyloxy)-1-benzenecarbonyl isothiocyanate was prepared using the resultant 4-(hexyloxy)-1-benzenecarbonyl chloride as a starting compound according to the description of the literature. 4-(Hexyloxy)-1-benzenecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (56 mg, yield 63%).

$^1$H-NMR (DMSO-$d_6$, 400 MHz): δ 0.86–0.91 (m, 3H), 1.28–1.35 (m, 4H), 1.39–1.47 (m, 2H), 1.70–1.79 (m, 2H), 3.95 (s, 3H), 3.96 (s, 3H), 4.08 (t, J=6.3 Hz, 2H), 6.43 (d, J=5.1 Hz, 1H), 7.05–7.10 (m, 2H), 7.43 (s, 1H), 7.50 (d, J=9.0 Hz, 1H), 7.54 (s, 1H), 7.72–7.78 (m, 1H), 8.00–8.05 (m, 2H), 8.18–8.25 (m, 1H), 8.51 (d, J=5.1 Hz, 1H), 11.49–11.52 (bs, 1H), 12.73–12.77 (bs, 1H) Mass spectrometry value (ESI-MS, m/z): 595 ($M^+$+1)

Example 757

N-[2-(4-Chlorophenoxy)-2-methylpropanoyl]-N'-{4-[(6,7-dimethoxy-4-quinolyl)oxy]phenyl}thiourea Toluene (20 ml) and thionyl chloride (1 ml) were added to commercially available 2-(4-chlorophenoxy)-2-methylpropanoic acid (80 mg), and the mixture was heated at 100° C. for one hr. The solvent was removed by distillation, and 2-(4-chlorophenoxy)-2-methylpropanoyl isothiocyanate was prepared using the resultant 2-(4-chlorophenoxy)-2-methylpropanoyl chloride as a starting compound according to the description of the literature. 2-(4-Chlorophenoxy)-2-methylpropanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (39 mg, yield 41%).

$^1$H-NMR (DMSO-$d_6$, 400 MHz): δ 1.56 (s, 6H), 3.93 (s, 3H), 3.96 (s, 3H), 6.56 (d, J=5.1 Hz, 1H), 7.07–7.13 (m, 2H), 7.31–7.53 (m, 6H), 7.78–7.85 (m, 2H), 8.53 (d, J=5.1 Hz,

1H), 10.54–10.57 (bs, 1H), 12.10–12.15 (bs, 1H) Mass spectrometry value (ESI-MS, m/z): 552 (M$^+$+1)

Example 758

N-{3-Chloro-4-[(6,7-dimethoxy-4-quinolyl)oxy]phenyl}-N'-[2-(4-chlorophenoxy)-2-methylpropanoyl]thiourea Toluene (20 ml) and thionyl chloride (1 ml) were added to commercially available 2-(4-chlorophenoxy)-2-methylpropanoic acid (80 mg), and the mixture was heated at 100° C. for one hr. The solvent was removed by distillation, and 2-(4-chlorophenoxy)-2-methylpropanoyl isothiocyanate was prepared using the resultant 2-(4-chlorophenoxy)-2-methylpropanoyl chloride as a starting compound according to the description of the literature. 2-(4-Chlorophenoxy)-2-methylpropanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (17 mg, yield 19%).

$^1$H-NMR (DMSO-d$_6$, 400 MHz): δ 1.56 (s, 6H), 3.95 (s, 3H), 3.96 (s, 3H), 6.42 (d, J=5.1 Hz, 1H), 7.07–7.12 (m, 2H), 7.38–7.55 (m, 5H), 7.71–7.78 (m, 1H), 8.13–8.19 (m, 1H), 8.52 (d, J=5.1 Hz, 1H), 10.67–10.71 (bs, 1H), 12.13–12.17 (bs, 1H) Mass spectrometry value (ESI-MS, m/z): 587 (M$^+$+1)

Example 759

N-{4-[(6,7-Dimethoxy-4-quinolyl)oxy]phenyl}-N'-(2,2,3,3-tetramethylcyclopropyl)carbonyl]-thiourea Toluene (20 ml) and thionyl chloride (1 ml) were added to commercially available 2,2,3,3-tetramethylcyclopropanecarboxylic acid (80 mg), and the mixture was heated at 100° C. for one hr. The solvent was removed by distillation, and 2,2,3,3-tetramethyl-1-cyclopropanecarbonyl isothiocyanate was prepared using the resultant 2,2,3,3-tetramethyl-1-cyclopropanecarbonyl chloride as a starting compound according to the description of the literature. 2,2,3,3-Tetramethyl-1-cyclopropanecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (11 mg, yield 14%).

$^1$H-NMR (DMSO-d$_6$, 400 MHz): δ 1.20 (s, 6H), 1.27 (s, 6H), 1.73 (s, 1H), 3.93 (s, 3H), 3.95 (s, 3H), 6.54 (d, J=5.4 Hz, 1H), 7.26–7.32 (m, 2H), 7.41 (s, 1H), 7.50 (s, 1H), 7.73–7.80 (m, 2H), 8.51 (d, J=5.1 Hz, 1H), 11.41–11.45 (bs, 1H), 12.55–12.59 (bs, 1H) Mass spectrometry value (ESI-MS, m/z): 480 (M$^+$+1)

Example 760

N-{3-Chloro-4-[(6,7-dimethoxy-4-quinolyl)oxy]phenyl}-N'-[(2,2,3,3-tetramethylcyclopropyl)carbonyl]thiourea Toluene (20 ml) and thionyl chloride (1 ml) were added to commercially available 2,2,3,3-tetramethylcyclopropanecarboxylic acid (80 mg), and the mixture was heated at 100° C. for one hr. The solvent was removed by distillation, and 2,2,3,3-tetramethyl-1-cyclopropanecarbonyl isothiocyanate was prepared using the resultant 2,2,3,3-tetramethyl-1-cyclopropanecarbonyl chloride as a starting compound according to the description of the literature. 2,2,3,3-Tetramethyl-1-cyclopropanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (17 mg, yield 21%).

$^1$H-NMR (DMSO-d$_6$, 400 MHz): δ 1.21 (s, 6H), 1.27 (s, 6H), 1.71–1.75 (m, 1H), 3.95 (s, 3H), 3.96 (s, 3H), 6.41 (d, J=5.1 Hz, 1H), 7.43 (s, 1H), 7.46 (d, J=8.5 Hz, 1H), 7.53 (s, 1H), 7.66–7.72 (m, 1H), 8.12–8.18 (m, 1H), 8.51 (d, J=5.1 Hz, 1H), 11.50–11.53 (bs, 1H), 12.59 (d, J=4.1 Hz, 1H) Mass spectrometry value (ESI-MS, m/z): 514 (M$^+$+1)

Example 761

N-{4-[(6,7-Dimethoxy-4-quinolyl)oxy]phenyl}-N'-(2-methoxy-2-phenylacetyl)thiourea Toluene (20 ml) and thionyl chloride (1 ml) were added to commercially available 2-methoxy-2-phenylacetic acid (80 mg), and the mixture was heated at 100° C. for one hr. The solvent was removed by distillation, and 2-methoxy-2-phenylethanoyl isothiocyanate was prepared using the resultant 2-methoxy-2-phenylethanoyl chloride as a starting compound according to the description of the literature. 2-Methoxy-2-phenylethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (25 mg, yield 30%).

$^1$H-NMR (DMSO-d$_6$, 400 MHz): δ 3.40 (s, 3H), 3.93 (s, 3H), 3.94 (s, 3H), 4.54 (s, 1H), 4.87 (s, 1H), 6.43 (d, J=5.1 Hz, 1H), 7.20–7.54 (m, 9H), 7.80–7.86 (m, 2H), 8.45 (d, J=5.1 Hz, 1H), 10.20 (s, 1H) Mass spectrometry value (ESI-MS, m/z): 503 (M$^+$+1)

Example 762

N-{3-Chloro-4-[(6,7-dimethoxy-4-quinolyl)oxy]phenyl}-N'-(2-methoxy-2-phenylacetyl)thiourea Toluene (20 ml) and thionyl chloride (1 ml) were added to commercially available 2-methoxy-2-phenylacetic acid (80 mg), and the mixture was heated at 100° C. for one hr. The solvent was removed by distillation, and 2-methoxy-2-phenylethanoyl isothiocyanate was prepared using the resultant 2-methoxy-2-phenylethanoyl chloride as a starting compound according to the description of the literature. 2-Methoxy-2-phenylethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (28 mg, yield 35%).

$^1$H-NMR (DMSO-$d_6$, 400 MHz): δ 3.40 (s, 3H), 3.94 (s, 3H), 3.95 (s, 3H), 4.54 (s, 1H), 4.88 (s, 1H), 6.33 (d, J=5.1 Hz, 1H), 7.28–7.55 (m, 8H), 7.77–7.83 (m, 1H), 8.11–8.16 (m, 1H), 8.44 (d, J=5.1 Hz, 1H), 10.37 (s, 1H) Mass spectrometry value (ESI-MS, m/z): 537 (M$^+$+1)

Example 763

N-[2-(2-Chlorophenoxy)propanoyl]-N'-{4-[(6,7-dimethoxy-4-quinolyl)oxy]phenyl}thiourea Toluene (20 ml) and thionyl chloride (1 ml) were added to commercially available 2-(2-chlorophenoxy)propanoic acid (80 mg), and the mixture was heated at 100° C. for one hr. The solvent was removed by distillation, and 2-(2-chlorophenoxy)propanoyl isothiocyanate was prepared using the resultant 2-(2-chlorophenoxy)propanoyl chloride as a starting compound according to the description of the literature. 2-(2-Chlorophenoxy)propanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (4 mg, yield 5%).

$^1$H-NMR (DMSO-$d_6$, 400 MHz): δ 1.62 (d, J=6.6 Hz, 3H), 3.93 (s, 3H), 3.95 (s, 3H), 4.96 (q, J=6.6 Hz, 1H), 6.46 (d, J=5.1 Hz, 1H), 6.98–7.52 (m, 8H), 7.74–7.79 (m, 2H), 8.47 (d, J=5.1 Hz, 1H), 10.31 (s, 1H) Mass spectrometry value (ESI-MS, m/z): 537 (M$^+$+1)

Example 764

N-{3-Chloro-4-[(6,7-dimethoxy-4-quinolyl)oxy]phenyl}-N'-[2-(2-chlorophenoxy)propanoyl]thiourea Toluene (20 ml) and thionyl chloride (1 ml) were added to commercially available 2-(2-chlorophenoxy)propanoic acid (80 mg), and the mixture was heated at 100° C. for one hr. The solvent was removed by distillation, and 2-(2-chlorophenoxy)propanoyl isothiocyanate was prepared using the resultant 2-(2-chlorophenoxy)propanoyl chloride as a starting compound according to the description of the literature. 2-(2-Chlorophenoxy)propanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (53 mg, yield 62%). 1H-NMR (DMSO-$d_6$, 400 MHz): δ 1.62 (d, J=6.8 Hz, 3H), 3.95 (s, 3H), 3.95 (s, 3H), 4.93–5.01 (m, 1H), 6.37 (d, J=5.4 Hz, 1H), 6.95–7.55 (m, 8H), 7.67–7.71 (m, 1H), 8.07 (s, 1H), 8.47 (d, J=5.4 Hz, 1H), 10.50 (s, 1H) Mass spectrometry value (ESI-MS, m/z): 572 (M$^+$+1)

Example 765

N-{4-[(6,7-Dimethoxy-4-quinolyl)oxy]phenyl}-N'-tetrahydro-2-furanylcarbonylthiourea Toluene (20 ml) and thionyl chloride (1 ml) were added to commercially available tetrahydro-2-furancarboxylic acid (80 mg), and the mixture was heated at 100° C. for one hr. The solvent was removed by distillation, and tetrahydro-2-furancarbonyl isothiocyanate was prepared using the resultant tetrahydro-2-furancarbonyl chloride as a starting compound according to the description of the literature. Tetrahydro-2-furancarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (5 mg, yield 6%).

$^1$H-NMR (DMSO-$d_6$, 400 MHz): δ 1.84–1.92 (m, 2H), 1.97–2.06 (m, 1H), 2.17–2.27 (m, 1H), 3.82–3.88 (m, 1H), 3.94 (s, 3H), 3.95 (s, 3H), 3.97–4.04 (m, 1H), 4.39–4.44 (m, 1H), 6.45 (d, J=5.1 Hz, 1H), 7.21–7.26 (m, 2H), 7.40 (s, 1H), 7.52 (s, 1H), 7.84 (d, J=9.0 Hz, 2H), 8.48 (d, J=5.4 Hz, 1H), 9.83 (s, 1H) Mass spectrometry value (ESI-MS, m/z): 454 (M$^+$+1)

Example 766

N-{3-Chloro-4-[(6,7-dimethoxy-4-quinolyl)oxy]phenyl}-N'-tetrahydro-2-furanylcarbonylthiourea Toluene (20 ml) and thionyl chloride (1 ml) were added to commercially available tetrahydro-2-furancarboxylic acid (80 mg), and the mixture was heated at 100° C. for one hr. The solvent was removed by distillation, and tetrahydro-2-furancarbonyl isothiocyanate was prepared using the resultant tetrahydro-2-furancarbonyl chloride as a starting compound according to the description of the literature. Tetrahydro-2-furancarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (5 mg, yield 7%).

$^1$H-NMR (DMSO-$d_6$, 400 MHz): δ 1.84–1.92 (m, 2H), 1.97–2.06 (m, 1H), 2.17–2.27 (m, 1H), 3.83–3.89 (m, 1H), 3.95 (s, 3H), 3.96 (s, 3H), 3.97–4.03 (m, 1H), 4.41–4.46 (m, 1H), 6.38 (d, J=5.4 Hz, 1H), 7.42 (s, 1H), 7.44 (s, 1H), 7.55 (s, 1H), 7.79–7.84 (m, 1H), 8.15 (d, J=2.4 Hz, 1H), 8.49 (d, J=5.4 Hz, 1H), 10.01 (s, 1H) Mass spectrometry value (ESI-MS, m/z): 488 (M$^+$+1)

Example 767

N-{4-[(6,7-Dimethoxy-4-quinolyl)oxy]phenyl}-N'-[(3-methoxycyclohexyl)carbonyl]thiourea Toluene (20 ml) and thionyl chloride (1 ml) were added to commercially available 3-methoxy-1-cyclohexanecarboxylic acid (80 mg), and the mixture was heated at 100° C. for one hr. The solvent was removed by distillation, and 3-methoxy-1-cyclohexanecarbonyl isothiocyanate was prepared using the resultant 3-methoxy-1-cyclohexanecarbonyl chloride as a starting compound according to the description of the literature. 3-Methoxy-1-cyclohexanecarbonyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (38 mg, yield 45%).
$^1$H-NMR (DMSO-$d_6$, 400 MHz): δ 1.32–1.61 (m, 5H), 1.73–1.85 (m, 2H), 1.90–1.97 (m, 1H), 2.85–2.94 (m, 1H), 3.25 (s, 3H), 3.53–3.58 (bs, 1H), 3.93 (s, 3H), 3.96 (s, 3H), 6.56 (d, J=5.1 Hz, 1H), 7.30 (d, J=8.8 Hz, 2H), 7.41 (s, 1H), 7.51 (s, 1H), 7.74–7.80 (m, 2H), 8.53 (d, J=5.4 Hz, 1H), 11.48–11.51 (bs, 1H), 12.57 (d, J=4.6 Hz, 1H) Mass spectrometry value (ESI-MS, m/z): 496 (M$^+$+1)

Example 768

N-{3-Chloro-4-[(6,7-dimethoxy-4-quinolyl)oxy]phenyl}-N'-[(3-methoxycyclohexyl)carbonyl]thiourea Toluene (20 ml) and thionyl chloride (1 ml) were added to commercially available 3-methoxy-1-cyclohexanecarboxylic acid (80 mg), and the mixture was heated at 100° C. for one hr. The solvent was removed by distillation, and 3-methoxy-1-cyclohexanecarbonyl isothiocyanate was prepared using the resultant 3-methoxy-1-cyclohexanecarbonyl chloride as a starting compound according to the description of the literature. 3-Methoxy-1-cyclohexanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (31 mg, yield 39%).
$^1$H-NMR (DMSO-$d_6$, 400 MHz): δ 1.33–1.61 (m, 5H), 1.73–1.85 (m, 2H), 1.90–1.97 (m, 1H), 2.85–2.94 (m, 1H), 3.25 (s, 3H), 3.53–3.57 (bs, 1H), 3.95 (s, 3H), 3.96 (s, 3H), 6.43 (d, J=5.1 Hz, 1H), 7.43 (s, 1H), 7.48 (d, J=8.8 Hz, 1H), 7.54 (s, 1H), 7.67–7.72 (m, 1H), 8.14–8.18 (m, 1H), 8.53 (d, J=5.4 Hz, 1H), 11.59 (d, J=2.9 Hz, 1H), 12.59 (d, J=5.1 Hz, 1H) Mass spectrometry value (ESI-MS, m/z): 530 (M$^+$+1)

Example 769

N-{4-[(6,7-Dimethoxy-4-quinolyl)oxy]phenyl}-N'-(2-ethoxyacetyl)thiourea

Toluene (20 ml) and thionyl chloride (1 ml) were added to commercially available 2-ethoxyacetic acid (80 mg), and the mixture was heated at 100° C. for one hr. The solvent was removed by distillation, and 2-ethoxyethanoyl isothiocyanate was prepared using the resultant 2-ethoxyethanoyl chloride as a starting compound according to the description of the literature. 2-Ethoxyethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (9 mg, yield 13%).
$^1$H-NMR (DMSO-$d_6$, 400 MHz): δ 1.21 (t, J=7.1 Hz, 3H), 3.55–3.62 (m, 2H), 3.96 (s, 3H), 3.97 (s, 3H), 4.06 (s, 2H), 6.54 (d, J=5.4 Hz, 1H), 7.26 (d, J=8.8 Hz, 2H), 7.42 (s, 1H), 7.56 (s, 1H), 7.82 (d, J=9.0 Hz, 2H), 8.54 (d, J=5.6 Hz, 1H), 9.87 (s, 1H) Mass spectrometry value (ESI-MS, m/z): (M$^+$+1)

Example 770

N-{4-[(6,7-Dimethoxy-4-quinolyl)oxy]phenyl}-N'-(2-{[(1R,2S,5R)-2-isopropyl-5-methylcyclohexyl]oxy}acetyl)thiourea Toluene (20 ml) and thionyl chloride (1 ml) were added to commercially available 2-{[(1R,2S,5R)-2-isopropyl-5-methylcyclohexyl]oxy}acetic acid (80 mg), and the mixture was heated at 100° C. for one hr. The solvent was removed by distillation, and 2-{[(1R,2S,5R)-2-isopropyl-5-methylcyclohexyl]oxy}ethanoyl isothiocyanate was prepared using the resultant 2-{[(1R,2S,5R)-2-isopropyl-5-methylcyclohexyl]oxy}ethanoyl chloride as a starting compound according to the description of the literature. 2-{[(1R,2S,5R)-2-Isopropyl-5-methylcyclohexyl]oxy}ethanoyl isothiocyanate thus obtained was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (27 mg, yield 29%).
$^1$H-NMR (DMSO-$d_6$, 400 MHz): δ 0.77 (d, J=6.8 Hz, 3H), 0.81–1.00 (m, 9H), 1.23–1.40 (m, 1H), 1.56–1.67 (m, 2H), 2.09–2.15 (m, 1H), 2.24–2.34 (m, 1H), 3.94 (s, 3H), 3.95 (s, 3H), 4.02–4.16 (m, 2H), 6.47 (d, J=5.4 Hz, 1H), 7.22–7.27 (m, 2H), 7.40 (s, 1H), 7.52 (s, 1H), 7.76–7.81 (m, 2H), 8.48 (d, J=5.4 Hz, 1H), 9.72 (s, 1H) Mass spectrometry value (ESI-MS, m/z): 551 (M$^+$+1)

Example 771

N-{3-Chloro-4-[(6,7-dimethoxy-4-quinazolinyl)oxy]phenyl}-N'-(2-{[(1R,2S,5R)-2-isopropyl-5-methylcyclohexyl]oxy}acetyl)thiourea Toluene (20 ml) and thionyl chloride (1 ml) were added to commercially available 2-{[(1R,2S,5R)-2-isopropyl-5-methylcyclohexyl]oxy}acetic acid (80 mg), and the mixture was heated at 100° C. for one hr. The solvent was removed by distillation, and 2-{[(1R,2S,5R)-2-isopropyl-5-methylcyclohexyl]oxy}ethanoyl isothiocyanate was prepared using the resultant 2-{[(1R,2S,5R)-2-isopropyl-5-methylcyclohexyl]oxy}ethanoyl chloride as a starting compound according to the description of the literature. 2-{[(1R,2S,5R)-2-Isopropyl-5-methylcyclohexyl]oxy}ethanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (17 mg, yield 19%).

$^1$H-NMR (DMSO-$d_6$, 400 MHz): δ 0.77 (d, J=6.8 Hz, 3H), 0.80–1.02 (m, 9H), 1.23–1.40 (m, 1H), 1.56–1.67 (m, 2H), 2.08–2.14 (m, 1H), 2.23–2.34 (m, 1H), 3.95 (s, 3H), 3.96 (s, 3H), 4.04–4.18 (m, 2H), 6.36 (d, J=5.1 Hz, 1H), 7.41 (s, 1H), 7.43 (d, J=8.8 Hz, 1H), 7.54 (s, 1H), 7.70–7.74 (m, 1H), 8.09 (d, J=2.4 Hz, 1H), 8.48 (d, J=5.1 Hz, 1H), 9.93 (s, 1H) Mass spectrometry value (ESI-MS, m/z): 585 (M$^+$+1)

Example 772

4-[(6,7-Dimethoxy-4-quinazolinyl)oxy]phenyl benzoate

Chlorobenzene (7 ml) was added to 4-chloro-6,7-dimethoxyquinazoline (2.5 g) and 4-hydroxyphenyl benzoate (4.78 g), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. Methanol was added to the residue, and the precipitated crystal was collected by filtration and was washed to give the title compound (3.49 g, yield 78%).

$^1$H-NMR (chloroform-d, 400 MHz): δ 4.10 (s, 3H), 4.10 (s, 3H), 7.31–7.38 (m, 4H), 7.49 (s, 1H), 7.51–7.59 (m, 3H), 7.64–7.69 (m, 1H), 8.20–8.25 (m, 2H), 8.68 (s, 1H) Mass spectrometry value (ESI-MS, m/z): 403 (M$^+$+1)

Example 773

4-[(6,7-Dimethoxy-4-quinazolinyl)oxy]phenol

Methanol (5 ml) and sodium hydroxide (0.2 g) were added to 4-[(6,7-dimethoxy-4-quinazolinyl)oxy]phenyl benzoate (500 mg), and the mixture was stirred at 0° C. for 30 min. A saturated aqueous ammonium chloride solution was added to the reaction solution, and the mixture was extracted with chloroform, followed by washing with saturated brine. The extract was then dried over anhydrous sodium sulfate. The solvent was removed by distillation under the reduced pressure. Methanol was added to the residue, and the precipitated crystal was collected by filtration and was washed to give the title compound (350 mg, yield 95%).

$^1$H-NMR (chloroform-d, 400 MHz): δ 4.08 (s, 3H), 4.11 (s, 3H), 6.91–6.95 (m, 2H), 7.05–7.10 (m, 2H), 7.57 (s, 1H), 7.59 (s, 1H), 8.66 (s, 1H) Mass spectrometry value (FD-MS, m/z): 298 (M$^+$)

Example 774

Methyl 2-{4-[(6,7-dimethoxy-4-quinazolinyl)oxy]phenoxy}acetate

4-[(6,7-Dimethoxy-4-quinazolinyl)oxy]phenol (100 mg) was dissolved in dimethylformamide (2 ml) to prepare a solution. Sodium hydride (15 mg) was added to the solution, and the mixture was stirred at 0° C. for 10 min. Methylbromoacetate (0.037 ml) was added thereto, and the mixture was further stirred at 0° C. for 30 min. A saturated aqueous sodium hydrogencarbonate solution was added to the reaction solution, and the mixture was extracted with ethyl acetate, followed by washing with saturated brine. The extract was then dried over anhydrous sodium sulfate. The solvent was removed by distillation under the reduced pressure. Diethyl ether was added to the residue, and the precipitated crystal was collected by filtration and was washed to give the title compound (88 mg, yield 71%).

$^1$H-NMR (chloroform-d, 400 MHz): δ 3.84 (s, 3H), 4.07 (s, 6H), 4.67 (s, 2H), 6.99–7.04 (m, 2H), 7.17–7.21 (m, 2H), 7.33 (s, 1H), 7.55 (s, 1H), 8.63 (s, 1H) Mass spectrometry value (ESI-MS, m/z): 371 (M$^+$+1)

Example 775

2-{4-[(6,7-Dimethoxy-4-quinazolinyl)oxy]phenoxy}acetic acid

Methyl 2-{4-[(6,7-dimethoxy-4-quinazolinyloxy)phenol (70 mg) was dissolved in methanol (1 ml) to prepare a solution. A solution of sodium hydroxide (70 mg) in water was added to the solution, and the mixture was stirred at 0° C. for 2 hr. Concentrated hydrochloric acid was added to the reaction solution, and the precipitated crystal was collected by filtration and was washed with methanol, diethyl ether, and hexane to give the title compound (65 mg, yield 97%).

$^1$H-NMR (DMSO-$d_6$, 400 MHz): δ 3.98 (s, 3H), 3.99 (s, 3H), 4.73 (s, 2H), 6.97–7.02 (m, 2H), 7.20–7.25 (m, 2H), 7.39 (s, 1H), 7.56 (s, 1H), 8.56 (s, 1H) Mass spectrometry value (ESI-MS, m/z): 357 (M$^+$+1)

Example 776

N1-(2-Methoxyphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), 1-ethyl-3-(3-dimethylaminopropyl)carbodiimide hydrochloride (WSC.HCl) (122 mg), and 1-hydroxybenzotriazole hydrate (HOBT.H$_2$O) (86 mg) were dissolved in chloroform (5 ml) to prepare a solution. o-Anisidine (63 mg) was then added to the solution, and the mixture was heated under reflux for 3 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (155 mg, yield 80%).

The compound (50 mg) thus obtained was dissolved in 10% hydrochloric acid-methanol solution (6 ml), and the solution was allowed to stand at room temperature for 15 min. The solvent was removed by distillation under the reduced pressure. Ethyl acetate was then added to the residue, and the precipitated crystal was collected by filtration and was washed to give 49 mg of a hydrochloride.

$^1$H-NMR (DMSO-$d_6$, 400 MHz): δ 3.88 (s, 3H), 4.04 (s, 3H), 4.05 (s, 3H), 4.77 (s, 1H), 4.86 (s, 1H), 6.80–6.83 (m, 1H), 6.93–6.97 (m, 1H), 7.09–7.42 (m, 6H), 7.64 (s, 1H), 7.75 (d, J=2.7 Hz, 1H), 8.05–8.09 (m, 1H), 8.79–8.82 (m, 1H), 9.29 (s, 1H) Mass spectrometry value (ESI-MS, m/z): 461 (M$^+$+1)

Example 777

N-(2-{4-[(6,7-Dimethoxy-4-quinolyl)oxy]phenoxy}ethyl)-N-(2-methoxyphenyl)amine N1-(2-Methoxyphenyl)-2-{4-[(6,7-dimethoxy-4-quinolyl)oxy]phenoxy}acetamide (100 mg) was dissolved in tetrahydrofuran (10 ml) to prepare a solution. A borane-tetrahydrofuran complex (1.0 M solution: 1.08 ml) was then added to the solution, and the mixture was heated under reflux for 5 hr. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (58 mg, yield 60%).

The resultant compound (55 mg) was dissolved in 10% hydrochloric acid-methanol solution (4 ml) to prepare a solution which was then allowed to stand at room temperature for 20 min. The solvent was removed by distillation under the reduced pressure. Diethyl ether was then added to the residue, and the precipitated crystal was collected by filtration and was washed to give 55 mg of a hydrochloride.

$^1$H-NMR (DMSO-$d_6$, 400 MHz): δ 3.53 (t, J=5.4 Hz, 2H), 3.80 (s, 3H), 4.04 (s, 3H), 4.05 (s, 3H), 4.23 (t, J=5.6 Hz, 2H), 6.66–6.72 (m, 1H), 6.75–6.91 (m, 4H), 7.18 (d, J=9.0 Hz, 2H), 7.36 (d, J=9.0 Hz, 2H), 7.63 (s, 1H), 7.76 (s, 1H), 8.80 (d, J=6.6 Hz, 1H) Mass spectrometry value (ESI-MS, m/z): 447 (M$^+$+1)

Example 778

N1-(3-Methoxyphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.H$_2$O (86 mg) were dissolved in chloroform (5 ml) to prepare a solution. m-Anisidine (63 mg) was then added to the solution, and the mixture was heated under reflux for 3 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (173 mg, yield 89%).

The resultant compound (45 mg) was dissolved in 10% hydrochloric acid-methanol solution (4 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 42 mg of a hydrochloride.

$^1$H-NMR (DMSO-$d_6$, 400 MHz): δ 3.74 (s, 3H), 4.04 (s, 3H), 4.05 (s, 3H), 4.77 (s, 1H), 4.80 (s, 1H), 6.67–6.70 (m, 1H), 6.80–6.83 (m, 1H), 7.13–7.40 (m, 7H), 7.62 (s, 1H), 7.75 (s, 1H), 8.80 (d, J=6.8 Hz, 1H), 10.20 (s, 1H) Mass spectrometry value (ESI-MS, m/z): 461 (M$^+$+1)

Example 779

N-(2-{4-[(6,7-Dimethoxy-4-quinolyl)oxy]phenoxy}ethyl)-N-(3-methoxyphenyl)amine N1-(3-Methoxyphenyl)-2-{4-[(6,7-dimethoxy-4-quinolyl)oxy]phenoxy}acetamide (112 mg) was dissolved in tetrahydrofuran (10 ml) to prepare a solution. A borane-tetrahydrofuran complex (1.0 M solution: 1.22 ml) was then added to the solution, and the mixture was heated under reflux for 5 hr. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (64 mg, yield 59%).

The resultant compound (60 mg) was dissolved in a 10% hydrochloric acid-methanol solution (4 ml) to prepare a solution which was then allowed to stand at room temperature for 20 min. The solvent was removed by distillation under the reduced pressure. Diethyl ether was then added to the residue, and the precipitated crystal was collected by filtration and was washed to give 58 mg of a hydrochloride.

$^1$H-NMR (DMSO-$d_6$, 400 MHz): δ 3.59 (t, J=5.1 Hz, 2H), 3.73 (s, 3H), 4.04 (s, 6H), 4.26 (t, J=5.1 Hz, 2H), 6.53–6.70 (m, 3H), 6.80 (d, J=6.8 Hz, 1H), 7.15–7.22 (m, 3H), 7.35–7.40 (m, 2H), 7.76 (d, J=5.1 Hz, 2H), 8.81 (d, J=6.8 Hz, 1H) Mass spectrometry value (ESI-MS, m/z): 447 (M$^+$+1)

Example 780

N1-(4-Methoxyphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.H$_2$O (86 mg) were dissolved in chloroform (5 ml) to prepare a solution. p-Anisidine (63 mg) was then added to the solution, and the mixture was heated under reflux for 4 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (147 mg, yield 76%).

The resultant compound (47 mg) was dissolved in a 10% hydrochloric acid-methanol solution (6 ml) which was then allowed to stand at room temperature for 15 min. The solvent was removed by distillation under the reduced pressure. Ethyl acetate was then added to the residue, and the precipitated crystal was collected by filtration and was washed to give 49 mg of a hydrochloride.

$^1$H-NMR (DMSO-$d_6$, 400 MHz): δ 3.73 (s, 3H), 4.03 (s, 3H), 4.04 (s, 3H), 4.76 (s, 2H), 6.80 (d, J=6.8 Hz, 1H), 6.90–6.92 (m, 2H), 7.12–7.40 (m, 4H), 7.55–7.63 (m, 3H), 7.74 (s, 1H), 8.79 (d, J=6.6 Hz, 1H), 10.05 (s, 1H) Mass spectrometry value (ESI-MS, m/z): 461 (M$^+$+1)

Example 781

N-(2-{4-[(6,7-Dimethoxy-4-quinolyl)oxy]
phenoxy}ethyl)-N-(4-methoxyphenyl)amine

N1-(4-Methoxyphenyl)-2-{4-[(6,7-dimethoxy-4-quinolyl)oxy]phenoxy}acetamide (90 mg) was dissolved in tetrahydrofuran (10 ml) to prepare a solution. A borane-tetrahydrofuran complex (1.0 M solution: 0.98 ml) was then added to the solution, and the mixture was heated under reflux for 3 hr. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (52 mg, yield 60%).

The resultant compound (52 mg) was dissolved in a 10% hydrochloric acid-methanol solution (4 ml) to prepare a solution which was then allowed to stand at room temperature for 20 min. The solvent was removed by distillation under the reduced pressure. Diethyl ether was then added to the residue, and the precipitated crystal was collected by filtration and was washed to give 42 mg of a hydrochloride.

$^1$H-NMR (DMSO-$d_6$, 400 MHz): δ 3.54–3.62 (m, 2H), 3.70–3.74 (m, 3H), 4.04 (s, 3H), 4.04 (s, 3H), 4.21–4.26 (m, 2H), 6.81 (d, J=6.6 Hz, 1H), 6.87–6.97 (m, 2H), 7.12–7.21 (m, 2H), 7.35–7.39 (m, 2H), 7.57–7.63 (m, 2H), 7.75 (s, 2H), 8.80 (d, J=6.8 Hz, 1H) Mass spectrometry value (ESI-MS, m/z): 447 ($M^+$+1)

Example 782

N1-(2-Methylphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.$H_2O$ (86 mg) were dissolved in chloroform (5 ml) to prepare a solution. o-Toluidine (0.055 ml) was then added to the solution, and the mixture was heated under reflux for 6 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development to give the title compound (103 mg, yield 55%).

The resultant compound (101 mg) was dissolved in a 10% hydrochloric acid-methanol solution (4 ml) to prepare a solution which was then allowed to stand at room temperature for 15 min. The solvent was removed by distillation under the reduced pressure. Diethyl ether was then added to the residue, and the precipitated crystal was collected by filtration and was washed to give 100 mg of a hydrochloride.

$^1$H-NMR (DMSO-$d_6$, 400 MHz): δ 2.20 (s, 3H), 4.04 (s, 3H), 4.05 (s, 3H), 4.77 (s, 1H), 4.83 (s, 1H), 6,79–6.83 (m, 1H), 7.11–7.46 (m, 8H), 7.63–7.69 (m, 1H), 7.76 (s, 1H), 7.76 (s, 1H), 8.82 (d, J=6.6 Hz, 1H), 9.60 (s, 1H) Mass spectrometry value (ESI-MS, m/z): 445 ($M^+$+1)

Example 783

N-(2-{4-[(6,7-Dimethoxy-4-quinolyl)oxy]
phenoxy}ethyl)-N-(2-methylphenyl)amine

N1-(2-Methylphenyl)-2-{4-[(6,7-dimethoxy-4-quinolyl)oxy]phenoxy}acetamide (65 mg) was dissolved in tetrahydrofuran (10 ml) to prepare a solution. A borane-tetrahydrofuran complex (1.0 M solution: 0.74 ml) was then added to the solution, and the mixture was heated under reflux overnight. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (29 mg, yield 46%).

The resultant compound (29 mg) was dissolved in a 10% hydrochloric acid-methanol solution (3 ml) to prepare a solution which was then allowed to stand at room temperature for 20 min. The solvent was removed by distillation under the reduced pressure. Diethyl ether was then added to the residue, and the precipitated crystal was collected by filtration and was washed to give 30 mg of a hydrochloride.

$^1$H-NMR (DMSO-$d_6$, 400 MHz): δ 2.16 (s, 3H), 3.57 (t, J=5.9 Hz, 2H), 4.04 (s, 3H), 4.05 (s, 3H), 4.25 (t, J=5.6 Hz, 2H), 6.63–6.70 (m, 1H), 6.77–6.84 (m, 2H), 7.02–7.12 (m, 2H), 7.16–7.21 (m, 2H), 7.34–7.39 (m, 2H), 7.66 (s, 1H), 7.76 (s, 1H), 8.80 (d, J=6.8 Hz, 1H) Mass spectrometry value (ESI-MS, m/z): 431 ($M^+$+1)

Example 784

N1-(3-Methylphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.$H_2O$ (86 mg) were dissolved in chloroform (5 ml) to prepare a solution. m-Toluidine (0.055 ml) was then added to the solution, and the mixture was heated under reflux for 4 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (102 mg, yield 55%).

The resultant compound (30 mg) was dissolved in a 10% hydrochloric acid-methanol solution (3 ml) to prepare a solution which was then allowed to stand at room temperature for 20 min. The solvent was removed by distillation under the reduced pressure. Diethyl ether was then added to the residue, and the precipitated crystal was collected by filtration and was washed to give 27 mg of a hydrochloride.

$^1$H-NMR (DMSO-$d_6$, 400 MHz): δ 2.29 (s, 3H), 4.03 (s, 3H), 4.05 (s, 3H), 4.76 (s, 1H), 4.79 (s, 1H), 6.78–6.83 (m, 1H), 6.89–6.93 (m, 1H), 7.01–7.51 (m, 7H), 7.61 (s, 1H), 7.75 (s, 1H), 8.79 (d, J=6.6 Hz, 1H), 10.12 (s, 1H) Mass spectrometry value (ESI-MS, m/z): 445 ($M^+$+1)

Example 785

N-(2-{4-[(6,7-Dimethoxy-4-quinolyl)oxy]phenoxy}ethyl)-N-(3-methylphenyl)amine N1-(3-Methylphenyl)-2-{4-[(6,7-dimethoxy-4-quinolyl)oxy]phenoxy}acetamide (70 mg) was dissolved in tetrahydrofuran (10 ml) to prepare a solution. A borane-tetrahydrofuran complex (1.0 M solution: 0.78 ml) was then added to the solution, and the mixture was heated under reflux overnight. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (31 mg, yield 46%).

The resultant compound (31 mg) was dissolved in a 10% hydrochloric acid-methanol solution (3 ml) to prepare a solution which was then allowed to stand at room temperature for 20 min. The solvent was removed by distillation under the reduced pressure. Diethyl ether was then added to the residue, and the precipitated crystal was collected by filtration and was washed to give 31 mg of a hydrochloride.

$^1$H-NMR (DMSO-$d_6$, 400 MHz): δ 2.23 (s, 3H), 3.49–3.53 (m, 2H), 4.04 (s, 3H), 4.05 (s, 3H), 4.20 (t, J=5.1 Hz, 2H), 6.53–6.60 (m, 1H), 6.60–6.70 (m, 1H), 6.81 (s, 1H), 6.82 (s, 1H), 7.03–7.10 (m, 1H), 7.15–7.20 (m, 2H), 7.34–7.39 (m, 2H), 7.64 (s, 1H), 7.76 (s, 1H), 8.81 (d, J=6.8 Hz, 1H) Mass spectrometry value (ESI-MS, m/z): 431 (M$^+$+1)

Example 786

N1-(4-Methylphenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.H$_2$O (86 mg) were dissolved in chloroform (5 ml) to prepare a solution. p-Toluidine (0.055 ml) was then added to the solution, and the mixture was heated under reflux for 3 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (76 mg, yield 41%).

The resultant compound (20 mg) was dissolved in a 10% hydrochloric acid-methanol solution (3 ml) to prepare a solution which was then allowed to stand at room temperature for 15 min. The solvent was removed by distillation under the reduced pressure. Diethyl ether was then added to the residue, and the precipitated crystal was collected by filtration and was washed to give 16 mg of a hydrochloride.

$^1$H-NMR (DMSO-$d_6$, 400 MHz): δ 2.27 (s, 3H), 4.03 (s, 3H), 4.04 (s, 3H), 4.76 (s, 1H), 4.78 (s, 1H), 6.78–6.82 (m, 1H), 7.12–7.16 (m, 2H), 7.19–7.25 (m, 2H), 7.36–7.40 (m, 2H), 7.52–7.57 (m, 2H), 7.63 (s, 1H), 7.74 (s, 1H), 8.79 (d, J=6.6 Hz, 1H), 10.13 (s, 1H) Mass spectrometry value (ESI-MS, m/z): 445 (M$^+$+1)

Example 787

N-(2-{4-[(6,7-Dimethoxy-4-quinolyl)oxy]phenoxy}ethyl)-N-(4-methylphenyl)amine N1-(4-Methylphenyl)-2-{4-[(6,7-dimethoxy-4-quinolyl)oxy]phenoxy}acetamide (54 mg) was dissolved in tetrahydrofuran (10 ml) to prepare a solution. A borane-tetrahydrofuran complex (1.0 M solution: 0.60 ml) was then added to the solution, and the mixture was heated under reflux for 3 hr. 1 N Hydrochloric acid was added thereto, and the mixture was further heated under reflux for 30 min. A 5% aqueous sodium hydroxide solution was added to the reaction solution, the mixture was extracted with chloroform, and the extract was dried over anhydrous sodium sulfate. The solvent was removed by distillation under the reduced pressure. The residue was purified by thin-layer chromatography using chloroform/methanol for development to give the title compound (11 mg, yield 20%).

The resultant compound (11 mg) was dissolved in a 10% hydrochloric acid-methanol solution (3 ml) to prepare a solution which was then allowed to stand at room temperature for 20 min. The solvent was removed by distillation under the reduced pressure. Diethyl ether was then added to the residue, and the precipitated crystal was collected by filtration and was washed to give 11 mg of a hydrochloride.

$^1$H-NMR (DMSO-$d_6$, 400 MHz): δ 2.24 (s, 3H), 3.54–3.60 (m, 2H), 4.04 (s, 3H), 4.05 (s, 3H), 4.16–4.27 (m, 2H), 6.81 (d, J=6.6 Hz, 1H), 6.74–7.28 (m, 4H), 7.32–7.42 (m, 2H), 7.68–7.79 (m, 2H), 7.67 (s, 1H), 7.76 (s, 1H), 8.80 (d, J=6.6 Hz, 1H) Mass spectrometry value (ESI-MS, m/z): 431 (M$^+$+1)

Example 788

N1-(3-Chlorophenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.H$_2$O (86 mg) were dissolved in chloroform (5 ml) to prepare a solution. m-Chloroaniline (65 mg) was then added to the solution, and the mixture was heated under reflux for 3 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (141 mg, yield 72%).

The resultant compound (50 mg) was dissolved in a 10% hydrochloric acid-methanol solution (3 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 40 mg of a hydrochloride. Mass spectrometry value (ESI-MS, m/z): 465 (M$^+$+1)

Example 789

N1-(4-Chlorophenyl)-2-{4-[(6,7-dimethoxy-4-quinolyl)oxy]phenoxy}acetamide

2-{4-[(6,7-Dimethoxy-4-quinolyl)oxy]phenoxy}acetic acid (150 mg), WSC.HCl (122 mg), and HOBT.H$_2$O (86 mg) were dissolved in chloroform (5 ml) to prepare a solution. 4-Chloroaniline (65 mg) was then added to the solution, and the mixture was heated under reflux for 5 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development to give the title compound (156 mg, yield 79%).

The resultant compound (49 mg) was dissolved in a 10% hydrochloric acid-methanol solution (3 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 39 mg of a hydrochloride. Mass spectrometry value (ESI-MS, m/z): 465 (M$^+$+1)

Example 790

6,7-Dimethoxy-4-{4-[3-(4-methylphenoxy)propoxy]phenoxy}quinoline p-Cresol (300 mg) was dissolved in acetone (5 ml) to prepare a solution. 1,3-Dibromopropane (0.85 ml), potassium carbonate (765 mg), and tetra-n-butylammonium iodide (102 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-4-methylbenzene (1) (466 mg, yield 74%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (85 mg) in dimethylformamide was added thereto, and the mixture was further stirred at room temperature for 4 hr. A saturated aqueous sodium hydrogencarbonate solution was added to the reaction solution, and the mixture was extracted with ethyl acetate, followed by washing three times with saturated brine. The extract was dried over anhydrous sodium sulfate. The solvent was removed by distillation under the reduced pressure. The residue was purified by thin-layer chromatography using chloroform/methanol for development to give the title compound (142 mg, yield 95%).

The resultant compound (138 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 117 mg of a hydrochloride. $^1$H-NMR (DMSO-d$_6$, 400 MHz): δ 2.16–2.22 (m, 2H), 2.23 (s, 3H), 4.03 (s, 3H), 4.04 (s, 3H), 4.12 (t, J=6.1 Hz, 2H), 4.20 (t, J=6.1 Hz, 2H), 6.80 (d, J=6.3 Hz, 1H), 6.83–6.88 (m, 2H), 7.09 (d, J=8.5 Hz, 2H), 7.14–7.20 (m, 2H), 7.31–7.36 (m, 2H), 7.59 (s, 1H), 7.74 (s, 1H), 8.77 (d, J=6.6 Hz, 1H) Mass spectrometry value (ESI-MS, m/z): 446 (M$^+$+1)

Example 791

6,7-Dimethoxy-4-{4-[3-(3-methylphenoxy)propoxy]phenoxy}quinoline m-Cresol (300 mg) was dissolved in acetone (5 ml) to prepare a solution. 1,3-Dibromopropane (0.85 ml), potassium carbonate (765 mg), and tetra-n-butylammonium iodide (102 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-3-methylbenzene (1) (490 mg, yield 78%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (85 mg) in dimethylformamide was added thereto, and the mixture was further stirred at room temperature for 4 hr. A saturated aqueous sodium hydrogencarbonate solution was added to the reaction solution, and the mixture was extracted with ethyl acetate, followed by washing three times with saturated brine. The extract was dried over anhydrous sodium sulfate. The solvent was removed by distillation under the reduced pressure. The residue was purified by thin-layer chromatography using chloroform/methanol for development to give the title compound (145 mg, yield 97%).

The resultant compound (139 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 103 mg of a hydrochloride. $^1$H-NMR (DMSO-d$_6$, 400 MHz): δ 2.16–2.24 (m, 2H), 2.28 (s, 3H), 4.03 (s, 3H), 4.04 (s, 3H), 4.14 (t, J=6.3 Hz, 2H), 4.20 (t, J=6.1 Hz, 2H), 6,74–6.81 (m, 4H), 7.14–7.20 (m, 3H), 7.32–7.37 (m, 2H), 7.58 (s, 1H), 7.74 (s, 1H), 8.77 (d, J=6.6 Hz, 1H) Mass spectrometry value (ESI-MS, m/z): 446 (M$^+$+1)

Example 792

6,7-Dimethoxy-4-{4-[3-(2-methylphenoxy)propoxy]phenoxy}quinoline o-Cresol (300 mg) was dissolved in acetone (5 ml) to prepare a solution. 1,3-Dibromopropane (0.85 ml), potassium carbonate (765 mg), and tetra-n-butylammonium iodide (102 mg) were added to the solution, and the mixture was heated under reflux for 4 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-2-methylbenzene (1) (363 mg, yield 57%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (85 mg) in dimethylformamide was added thereto, and the mixture was further stirred at room temperature for 2 hr. A saturated aqueous sodium hydrogencarbonate solution was added to the reaction solution, and the mixture was extracted with ethyl acetate, followed by washing three times with saturated brine. The extract was dried over anhydrous sodium sulfate. The solvent was removed by distillation under the reduced pressure. The residue was purified by thin-layer chromatography using chloroform/methanol for development to give the title compound (148 mg, yield 98%).

The resultant compound (145 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 106 mg of a hydrochloride.

$^1$H-NMR (DMSO-$d_6$, 400 MHz): δ 2.17 (s, 3H), 2.20–2.26 (m, 2H), 4.04 (s, 3H), 4.05 (s, 3H), 4.16 (t, J=6.1 Hz, 2H), 4.24 (t, J=6.1 Hz, 2H), 6.80–6.87 (m, 2H), 6.96 (d, J=7.8 Hz, 1H), 7.12–7.21 (m, 4H), 7.33–7.38 (m, 2H), 7.69 (s, 1H), 7.75 (s, 1H), 8.81 (d, J=6.6 Hz, 1H) Mass spectrometry value (ESI-MS, m/z): 446 ($M^+$+1)

Example 793

6,7-Dimethoxy-4-{4-[3-(3-methoxyphenoxy)propoxy]phenoxy}quinoline

3-Methoxyphenol (300 mg) was dissolved in acetone (5 ml) to prepare a solution. 1,3-Dibromopropane (0.74 ml), potassium carbonate (668 mg), and tetra-n-butylammonium iodide (89 mg) were then added to the solution, and the mixture was heated under reflux for 4 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-3-methoxybenzene (1) (440 mg, yield 74%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (91 mg) in dimethylformamide was added thereto, and the mixture was further stirred at room temperature for 2 hr. A saturated aqueous sodium hydrogencarbonate solution was added to the reaction solution, and the mixture was extracted with ethyl acetate, followed by washing three times with saturated brine. The extract was dried over anhydrous sodium sulfate. The solvent was removed by distillation under the reduced pressure. The residue was purified by thin-layer chromatography using chloroform/methanol for development to give the title compound (147 mg, yield 95%).

The resultant compound (143 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 109 mg of a hydrochloride.

$^1$H-NMR (DMSO-$d_6$, 400 MHz): δ 2.17–2.24 (m, 2H), 3.73 (s, 3H), 4.03 (s, 3H), 4.04 (s, 3H), 4.15 (t, J=6.1 Hz, 2H), 4.20 (t, J=6.1 Hz, 2H), 6.51–6.57 (m, 3H), 6.80 (d, J=6.8 Hz, 1H), 7.15–7.21 (m, 3H), 7.32–7.37 (m, 2H), 7.64 (s, 1H), 7.74 (s, 1H), 8.77 (d, J=6.6 Hz, 1H) Mass spectrometry value (ESI-MS, m/z): 462 ($M^+$+1)

Example 794

6,7-Dimethoxy-4-{4-[3-(4-methoxy-phenoxy)propoxy]phenoxy}quinoline

4-Methoxyphenol (300 mg) was dissolved in acetone (5 ml) to prepare a solution. 1,3-Dibromopropane (0.74 ml), potassium carbonate (668 mg), and tetra-n-butylammonium iodide (89 mg) were then added to the solution, and the mixture was heated under reflux for 7 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-4-methoxybenzene (1) (399 mg, yield 67%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (91 mg) in dimethylformamide was added thereto, and the mixture was further stirred at room temperature for 6 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by thin-layer chromatography using chloroform/methanol for development to give the title compound (150 mg, yield 97%).

The resultant compound (141 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 135 mg of a hydrochloride.

$^1$H-NMR (DMSO-$d_6$, 400 MHz): δ 2.15–2.23 (m, 2H), 3.70 (s, 3H), 4.03 (s, 3H), 4.04 (s, 3H), 4.10 (t, J=6.3 Hz, 2H), 4.20 (t, J=6.1 Hz, 2H), 6.80 (d, J=6.6 Hz, 1H), 6.84–6.93 (m, 4H), 7.15–7.20 (m, 2H), 7.32–7.37 (m, 2H), 7.64 (s, 1H), 7.74 (s, 1H), 8.77 (d, J=6.6 Hz, 1H) Mass spectrometry value (ESI-MS, m/z): 462 ($M^+$+1)

Example 795

6,7-Dimethoxy-4-{4-[3-(2-methoxy-phenoxy)propoxy]phenoxy}quinoline

Guaiacol (300 mg) was dissolved in acetone (5 ml) to prepare a solution. 1,3-Dibromopropane (0.74 ml), potassium carbonate (668 mg), and tetra-n-butylammonium iodide (89 mg) were then added to the solution, and the mixture was heated under reflux for 7 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-2-methoxybenzene (1) (449 mg, yield 76%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (91 mg) in dimethylformamide was added thereto, and the mixture was further stirred at room temperature for 6 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by thin-layer chromatography using chloroform/methanol for development to give the title compound (116 mg, yield 75%).

The resultant compound (103 mg) was dissolved in a 10% hydrochloric acid-methanol solution (5 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 86 mg of a hydrochloride.

$^1$H-NMR (DMSO-$d_6$, 400 MHz): δ 2.17–2.24 (m, 2H), 3.76 (s, 3H), 4.03 (s, 3H), 4.04 (s, 3H), 4.14 (t, J=6.1 Hz, 2H), 4.21 (t, J=6.1 Hz, 2H), 6.79 (d, J=6.6 Hz, 1H), 6.86–7.03 (m, 4H), 7.15–7.20 (m, 2H), 7.32–7.37 (m, 2H), 7.66 (s, 1H), 7.74 (s, 1H), 8.76 (d, J=6.6 Hz, 1H) Mass spectrometry value (ESI-MS, m/z): 462 (M$^+$+1)

Example 796

4-{4-[3-(2-Fluorophenoxy)propoxy]phenoxy}-6,7-dimethoxyquinoline o-Fluorophenol (400 mg) was dissolved in acetone (5 ml) to prepare a solution. 1,3-Dibromopropane (1.09 ml), potassium carbonate (985 mg), and tetra-n-butylammonium iodide (132 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-2-fluorobenzene (1) (750 mg, yield 91%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (86 mg) in dimethylformamide was added thereto, and the mixture was further stirred at room temperature for 5 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by thin-layer chromatography using chloroform/methanol for development to give the title compound (131 mg, yield 78%).

The resultant compound (128 mg) was dissolved in a 10% hydrochloric acid-methanol solution (5 ml) to prepare a solution which was then allowed to stand at room temperature for 15 min. The solvent was removed by distillation under the reduced pressure. Diethyl ether was then added to the residue, and the precipitated crystal was collected by filtration and was washed to give 116 mg of a hydrochloride.

$^1$H-NMR (DMSO-$d_6$, 400 MHz): δ 2.21–2.27 (m, 2H), 4.03 (s, 3H), 4.04 (s, 3H), 4.19–4.27 (m, 4H), 6.81 (d, J=6.6 Hz, 1H), 6.92–6.98 (m, 1H), 7.11–7.25 (m, 5H), 7.33–7.37 (m, 2H), 7.63–7.69 (m, 1H), 7.75 (s, 1H), 8.78 (d, J=6.6 Hz, 1H) Mass spectrometry value (ESI-MS, m/z): 450 (M$^+$+1)

Example 797

4-{4-[3-(3-Fluorophenoxy)propoxy]phenoxy}-6,7-dimethoxyquinoline

3-Fluorophenol (400 mg) was dissolved in acetone (5 ml) to prepare a solution. 1,3-Dibromopropane (1.09 ml), potassium carbonate (985 mg), and tetra-n-butylammonium iodide (132 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-3-fluorobenzene (1) (808 mg, yield 97%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (86 mg) in dimethylformamide was added thereto, and the mixture was further stirred at room temperature for 5 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by thin-layer chromatography using chloroform/methanol for development to give the title compound (128 mg, yield 84%).

The resultant compound (123 mg) was dissolved in a 10% hydrochloric acid-methanol solution (5 ml) to prepare a solution which was then allowed to stand at room temperature for 15 min. The solvent was removed by distillation under the reduced pressure. Diethyl ether was then added to the residue, and the precipitated crystal was collected by filtration and was washed to give 109 mg of a hydrochloride.

$^1$H-NMR (DMSO-$d_6$, 400 MHz): δ 2.18–2.25 (m, 2H), 4.04 (s, 3H), 4.05 (s, 3H), 4.17–4.22 (m, 4H), 6.74–6.88 (m, 4H), 7.15–7.20 (m, 2H), 7.29–7.38 (m, 3H), 7.61–7.73 (m, 1H), 7.76 (s, 1H), 8.79 (d, J=6.8 Hz, 1H) Mass spectrometry value (ESI-MS, m/z): 450 (M$^+$+1)

Example 798

4-{4-[3-(4-Fluorophenoxy)propoxy]phenoxy}-6,7-dimethoxyquinoline

4-Fluorophenol (400 mg) was dissolved in acetone (5 ml) to prepare a solution. 1,3-Dibromopropane (1.09 ml), potassium carbonate (985 mg), and tetra-n-butylammonium iodide (132 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-4-fluorobenzene (1) (713 mg, yield 86%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (86 mg) in dimethylformamide was added thereto, and the mixture was further stirred at room temperature for 4 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by thin-layer chromatography using chloroform/methanol for development to give the title compound (91 mg, yield 60%).

The resultant compound (85 mg) was dissolved in a 10% hydrochloric acid-methanol solution (5 ml) to prepare a solution which was then allowed to stand at room temperature for 15 min. The solvent was removed by distillation under the reduced pressure. Diethyl ether was then added to the residue, and the precipitated crystal was collected by filtration and was washed to give 90 mg of a hydrochloride.

$^1$H-NMR (DMSO-d$_6$, 400 MHz): δ 2.16–2.24 (m, 2H), 4.04 (s, 3H), 4.05 (s, 3H), 4.14 (t, J=6.1 Hz, 2H), 4.20 (t, J=6.1 Hz, 2H), 6.82 (d, J=6.6 Hz, 1H), 6.95–7.01 (m, 2H), 7.09–7.20 (m, 4H), 7.33–7.37 (m, 2H), 7.67 (s, 1H), 7.75 (s, 1H), 8.79 (d, J=6.8 Hz, 1H) Mass spectrometry value (ESI-MS, m/z): 450 (M$^+$+1)

Example 799

4-{4-[3-(2,6-Dimethylphenoxy)propoxy]phenoxy}-6,7-dimethoxyquinoline 2,6-Dimethylphenol (400 mg) was dissolved in acetone (5 ml) to prepare a solution. 1,3-Dibromopropane (1.00 ml), potassium carbonate (903 mg), and tetra-n-butylammonium iodide (121 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-2,6-dimethylbenzene (1) (637 mg, yield 81%).

4-[(6,7-Dimethoxy-4-quinolyl)oxy]phenol (100 mg) was dissolved in dimethylformamide (2 ml) to prepare a solution. Sodium hydride (16 mg) was then added to the solution, and the mixture was stirred at room temperature for 10 min. A solution of the compound (1) (90 mg) in dimethylformamide was added thereto, and the mixture was further stirred at room temperature for 4 hr. A saturated aqueous sodium hydrogencarbonate solution was added to the reaction solution, and the mixture was extracted with ethyl acetate, followed by washing three times with saturated brine. The extract was then dried over anhydrous sodium sulfate. The solvent was removed by distillation under the reduced pressure, and the residue was purified by thin-layer chromatography using chloroform/methanol for development to give the title compound (137 mg, yield 88%).

The resultant compound (116 mg) was dissolved in a 10% hydrochloric acid-methanol solution (5 ml) to prepare a solution which was then allowed to stand at room temperature for 15 min. The solvent was removed by distillation under the reduced pressure. Diethyl ether was then added to the residue, and the precipitated crystal was collected by filtration and was washed to give 75 mg of a hydrochloride.

$^1$H-NMR (DMSO-d$_6$, 400 MHz): δ 2.21 (s, 6H), 2.22 (t, J=6.1 Hz, 2H), 3.92 (t, J=6.1 Hz, 2H), 4.04 (s, 3H), 4.04 (s, 3H), 4.29 (t, J=6.1 Hz, 2H), 6.80 (d, J=6.6 Hz, 1H), 6.89–6.94 (m, 1H), 7.01 (s, 1H), 7.03 (s, 1H), 7.17–7.22 (m, 2H), 7.34–7.39 (m, 2H), 7.70 (s, 1H), 7.75 (s, 1H), 8.80 (d, J=6.6 Hz, 1H) Mass spectrometry value (ESI-MS, m/z): 460 (M$^+$+1)

Example 800

N1-(3-Methoxyphenyl)-2-{4-[(6,7-dimethoxy-4-quinazolinyl)oxy]phenoxy}acetamide

2-{4-[(6,7-Dimethoxy-4-quinazolinyl)oxy]phenoxy}-acetic acid (150 mg), WSC.HCl (122 mg), and HOBT.H$_2$O (86 mg) were dissolved in chloroform (5 ml) to prepare a solution. m-Anisidine (63 mg) was then added to the solution, and the mixture was stirred at room temperature for 4 hr. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (29 mg, yield 15%).

$^1$H-NMR (chloroform-d, 400 MHz): δ 3.84 (s, 3H), 4.08 (s, 3H), 4.08 (s, 3H), 4.65 (s, 2H), 6.71–6.75 (m, 1H), 7.07–7.13 (m, 3H), 7.24–7.28 (m, 2H), 7.35 (t, J=2.2 Hz, 1H), 7.40 (s, 1H), 7.56 (s, 1H), 8.25 (s, 1H), 8.64 (s, 1H) Mass spectrometry value (ESI-MS, m/z): 462 (M$^+$+1)

Example 801

N1-(3-Methoxybenzyl)-2-{4-[(6,7-dimethoxy-4-quinazolinyl)oxy]phenoxy}acetamide

2-{4-[(6,7-Dimethoxy-4-quinazolinyl)oxy]phenoxy}-acetic acid (150 mg), WSC.HCl (122 mg), and HOBT.H$_2$O (86 mg) were dissolved in chloroform (5 ml) to prepare a solution. 3-Methoxybenzylamine (70 mg) was then added to the solution, and the mixture was stirred at room temperature overnight. A saturated aqueous sodium hydrogencarbonate solution was added to the reaction solution, and the mixture was extracted with chloroform. The chloroform layer was washed with 1 N hydrochloric acid, water, and saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (31 mg, yield 16%).

$^1$H-NMR (chloroform-d, 400 MHz): δ 3.81 (s, 3H), 4.07 (s, 6H), 4.54 (s, 1H), 4.56 (s, 1H), 4.60 (s, 2H), 6.82–6.93 (m, 3H), 6.99–7.05 (m, 2H), 7.19–7.23 (m, 2H), 7.27–7.31 (m, 1H), 7.35 (s, 1H), 7.55 (s, 1H), 8.62 (s, 1H) Mass spectrometry value (ESI-MS, m/z): 476 (M$^+$+1)

Example 802

2-{4-[(6,7-Dimethoxy-4-quinazolinyl)oxy]phenoxy}-1-(1,2,3,4-tetrahydro-2-isoquinolyl)-1-ethanone 2-{4-[(6,7-Dimethoxy-4-quinazolinyl)oxy]phenoxy}acetic acid (100 mg), WSC.HCl (81 mg), and HOBT.H$_2$O (57 mg) were dissolved in chloroform (3 ml) to prepare a solution. 1,2,3,4-Tetrahydro-isoquinoline (45 mg) was then added to the solution, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (39 mg, yield 30%).

$^1$H-NMR (chloroform-d, 400 MHz): δ 2.88–2.98 (m, 2H), 3.80–3.90 (m, 2H), 4.07 (s, 3H), 4.07 (s, 3H), 4.76 (s, 1H), 4.78 (s, 1H), 4.80 (s, 2H), 7.04–7.24 (m, 8H), 7.35 (s, 1H), 7.55 (s, 1H), 8.63 (d, J=3.7 Hz, 1H) Mass spectrometry value (ESI-MS, m/z): 472 (M$^+$+1)

Example 803

2-{4-[(6,7-Dimethoxy-4-quinazolinyl)oxy]phenoxy}-1-(4-phenylpiperidino)-1-ethanone 2-{4-[(6,7-Dimethoxy-4-quinazolinyl)oxy]phenoxy}acetic acid (100 mg), WSC.HCl (81 mg), and HOBT.H$_2$O (57 mg) were dissolved in chloroform (3 ml) to prepare a solution. 4-Phenylpiperidine (54 mg) was then added to the solution, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (42 mg, yield 30%).

$^1$H-NMR (chloroform-d, 400 MHz): δ 1.61–1.73 (m, 2H), 1.90–2.00 (m, 2H), 2.68–2.83 (m, 2H), 3.16–3.26 (m, 1H), 4.08 (s, 3H), 4.14 (s, 3H), 4.08–4.20 (m, 2H), 4.76 (s, 1H), 4.77 (s, 1H), 7.06–7.12 (m, 2H), 7.17–7.34 (m, 7H), 7.39 (s, 1H), 7.56 (s, 1H), 8.63 (s, 1H) Mass spectrometry value (ESI-MS, m/z): 500 (M$^+$+1)

Example 804

1-(4-Benzylpiperidino)-2-{4-[(6,7-dimethoxy-4-quinazolinyl)oxy]phenoxy}-1-ethanone 2-{4-[(6,7-Dimethoxy-4-quinazolinyl)oxy]phenoxy}acetic acid (100 mg), WSC.HCl (81 mg), and HOBT.H$_2$O (57 mg) were dissolved in chloroform (3 ml) to prepare a solution. 4-Benzylpiperidine (59 mg) was then added to the solution, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (36 mg, yield 25%).

$^1$H-NMR (chloroform-d, 400 MHz): δ 1.15–1.30 (m, 2H), 1.73 (d, J=13.7 Hz, 2H), 1.76–1.88 (m, 1H), 2.53–2.66 (m, 3H), 2.98–3.09 (m, 1H), 3.94–4.02 (m, 1H), 4.09 (s, 3H), 4.12 (s, 3H), 4.54–4.62 (m, 1H), 4.71 (s, 2H), 7.03–7.10 (m, 2H), 7.12–7.24 (m, 5H), 7.25–7.33 (m, 2H), 7.58 (s, 1H), 7.63 (s, 1H), 8.69 (s, 1H) Mass spectrometry value (ESI-MS, m/z): 514 (M$^+$+1)

Example 805

2-{4-[(6,7-Dimethoxy-4-quinazolinyl)oxy]phenoxy}-1-(4-piperidinopiperidino)-1-ethanone 2-{4-[(6,7-Dimethoxy-4-quinazolinyl)oxy]phenoxy}acetic acid (100 mg), WSC.HCl (81 mg), and HOBT.H$_2$O (57 mg) were dissolved in chloroform (3 ml) to prepare a solution. 4-Piperidinopiperidine (57 mg) was then added to the solution, and the mixture was stirred at room temperature overnight. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (34 mg, yield 24%).

$^1$H-NMR (chloroform-d, 400 MHz): δ 1.42–2.08 (m, 10H), 2.58–2.90 (m, 5H), 3.05–3.15 (m, 1H), 4.07 (s, 6H), 4.12–4.20 (m, 1H), 4.65–4.72 (m, 1H), 4.71 (s, 1H), 4.73 (s, 1H), 7.02–7.08 (m, 2H), 7.16–7.22 (m, 2H), 7.32 (s, 1H), 7.55 (s, 1H), 8.61 (s, 1H) Mass spectrometry value (ESI-MS, m/z): 507 (M$^+$+1)

Example 806

2-{4-[(6,7-Dimethoxy-4-quinazolinyl)oxy]phenoxy}-1-piperidino-1-ethanone

2-{4-[(6,7-Dimethoxy-4-quinazolinyl)oxy]phenoxy}-acetic acid (100 mg), WSC.HCl (81 mg), and HOBT.H$_2$O (57 mg) were dissolved in chloroform (3 ml) to prepare a solution. Piperidine (29 mg) was then added to the solution, and the mixture was stirred at room temperature for 3 hr. A saturated aqueous sodium hydrogencarbonate solution was added to the reaction solution, and the mixture was extracted with chloroform. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (31 mg, yield 26%).

$^1$H-NMR (chloroform-d, 400 MHz): δ 1.54–1.90 (m, 6H), 3.49–3.61 (m, 4H), 4.07 (s, 3H), 4.08 (s, 3H), 4.71 (s, 2H), 7.04–7.09 (m, 2H), 7.16–7.20 (m, 2H), 7.40 (s, 1H), 7.56 (s, 1H), 8.64 (s, 1H) Mass spectrometry value (ESI-MS, m/z): 424 (M$^+$+1)

Example 807

N-(2-{4-[(6,7-Dimethoxy-4-quinazolinyl)oxy]phenoxy}ethyl)-N,N-diethylamine

4-[(6,7-Dimethoxy-4-quinazolinyl)oxy]phenol (100 mg) was dissolved in dimethylformamide (2 ml) to prepare a solution. Sodium hydride (27 mg) was then added to the solution, and the mixture was stirred at room temperature for 10 min. 2-(Diethylamino)ethyl bromide hydrobromide (88 mg) was added to the solution, and the mixture was stirred at room temperature for 2 hr. A saturated aqueous sodium hydrogencarbonate solution was added to the reaction solution, and the mixture was extracted with ethyl acetate. The extract was washed with saturated brine and was then dried over anhydrous sodium sulfate. The solvent was removed by distillation under the reduced pressure. The residue was purified by thin-layer chromatography using chloroform/methanol for development. Diethyl ether was added to the purification product, and the precipitated crystal was collected by filtration and was washed to give the title compound (30 mg, yield 23%).

$^1$H-NMR (chloroform-d, 400 MHz): δ 1.20–1.44 (m, 6H), 2.80–3.15 (m, 4H), 3.15–3.30 (m, 2H), 4.07 (s, 3H), 4.07 (s, 3H), 4.27–4.45 (m, 2H), 6.98–7.03 (m, 2H), 7.16–7.20 (m, 2H), 7.32 (s, 1H), 7.56 (s, 1H), 8.62 (s, 1H) Mass spectrometry value (ESI-MS, m/z): 398 (M$^+$+1)

Example 808

4-{4-[3-(4-Fluorophenoxy)propoxy]phenoxy}-6,7-dimethoxyquinazoline

4-Fluorophenol (1 g) was dissolved in acetone (10 ml) to prepare a solution. 1,3-Dibromopropane (2.72 ml), potassium carbonate (2,46 g), and tetra-n-butylammonium iodide (329 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-4-fluorobenzene (1) (1.89 g, yield 91%).

4-Hydroxyphenyl benzoate (300 mg) was dissolved in dimethylformamide (2 ml) to prepare a solution. Sodium hydride (84 mg) was then added to the solution, and the mixture was stirred at room temperature for 10 min. A solution of the compound (1) (650 mg) in dimethylformamide was added thereto, and the mixture was further stirred at room temperature for one hr. A saturated aqueous ammonium chloride solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by chromatography on silica gel using hexane/acetone for development to give 4-[3-(4-fluorophenoxy)propoxy]phenyl benzoate (2) (412 mg, yield 81%).

The compound (2) (412 mg) was dissolved in methanol (3 ml) to prepare a solution. Sodium hydroxide (60 mg) was added to the solution, and the mixture was stirred at room temperature for 3 hr. A saturated aqueous ammonium chloride solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give 4-[3-(4-fluorophenoxy)propoxy]phenol (3) (229 mg, yield 78%).

Chlorobenzene (0.4 ml) was added to the compound (3) (225 mg) and 4-chloro-6,7-dimethoxyquinazoline (275 mg), and the mixture was stirred at 140° C. overnigh. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (117 mg, yield 31%).

$^1$H-NMR (chloroform-d, 400 MHz): δ 2.24–2.31 (m, 2H), 4.07 (s, 6H), 4.14 (t, J=6.1 Hz, 2H), 4.19 (t, J=6.1 Hz, 2H), 6.83–6.88 (m, 2H), 6.94–7.03 (m, 4H), 7.14–7.19 (m, 2H), 7.33 (s, 1H), 7.56 (s, 1H), 8.63 (s, 1H) Mass spectrometry value (FD-MS, m/z): 450 (M$^+$)

Example 809

6,7-Dimethoxy-4-{4-[3-(3-methoxyphenoxy)propoxy]phenoxy}quinazoline

3-Methoxyphenol (1 g) was dissolved in acetone (10 ml) to prepare a solution. 1,3-Dibromopropane (2.45 ml), potassium carbonate (2.22 g), and tetra-n-butylammonium iodide (297 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-3-methoxybenzene (1) (1.79 g, yield 91%).

4-Hydroxyphenyl benzoate (300 mg) was dissolved in dimethylformamide (2 ml) to prepare a solution. Sodium hydride (84 mg) was then added to the solution, and the mixture was stirred at room temperature for 10 min. A solution of the compound (1) (686 mg) in dimethylformamide was added thereto, and the mixture was further stirred at room temperature for one hr. A saturated aqueous ammonium chloride solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by chromatography on silica gel using hexane/acetone for development to give 4-[3-(3-methoxyphenoxy)propoxy]-phenyl benzoate (2) (252 mg, yield 48%).

The compound (2) (252 mg) was dissolved in methanol (2 ml) to prepare a solution. Sodium hydroxide (60 mg) was then added to the solution, and the mixture was stirred at room temperature for 3 hr. A saturated aqueous ammonium chloride solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give 4-[3-(3-methoxyphenoxy)propoxy]phenol (3) (146 mg, yield 80%).

Chlorobenzene (0.4 ml) was added to the compound (3) (143 mg) and 4-chloro-6,7-dimethoxyquinazoline (167 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (118 mg, yield 50%).

$^1$H-NMR (chloroform-d, 400 MHz): δ 2.24–2.32 (m, 2H), 3.80 (s, 3H), 4.07 (s, 6H), 4.15–4.22 (m, 4H), 6.48–6.55 (m, 3H), 6.98–7.03 (m, 2H), 7.14–7.21 (m, 3H), 7.35 (s, 1H), 7.56 (s, 1H), 8.63 (s, 1H) Mass spectrometry value (FD-MS, m/z): 462 (M$^+$)

Example 810

6,7-Dimethoxy-4-{4-[3-(2-methoxyphenoxy)propoxy]phenoxy}quinazoline

2-Methoxyphenol (750 mg) was dissolved in acetonitrile (8 ml) to prepare a solution. 1,3-Dibromopropane (0.92 ml) and potassium carbonate (1.25 g) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropyl)-2-methoxybenzene (1).

4-Hydroxyphenyl benzoate (650 mg) was dissolved in dimethylformamide (6 ml) to prepare a solution. Sodium hydride (97 mg) was then added to the solution, and the mixture was stirred at room temperature for 10 min. A solution of the compound (1) (1.12 g) in dimethylformamide was added thereto, and the mixture was further stirred at room temperature for one hr. A saturated aqueous ammonium chloride solution was added to the reaction solution, and the mixture was extracted with ethyl acetate, followed by washing three times with saturated brine. The extract was then dried over anhydrous sodium sulfate. The solvent was removed by distillation under the reduced pressure. The residue was purified by chromatography on silica gel using hexane/acetone for development to give 4-[3-(2-methoxyphenoxy)propoxy]-phenyl benzoate (2) (1.15 g, yield 50%).

The compound (2) (1.15 g) was dissolved in methanol (10 ml) to prepare a solution. Sodium hydroxide (20 mg) was added to the solution, and the mixture was stirred at room temperature for 3 hr. A saturated aqueous ammonium chloride solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give 4-[3-(2-methoxyphenoxy)propoxy]phenol (3) (0.55 g, yield 66%).

Chlorobenzene (0.4 ml) was added to the compound (3) (205 mg) and 4-chloro-6,7-dimethoxyquinazoline (252 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (128 mg, yield 37%).

$^1$H-NMR (chloroform-d, 400 MHz): δ 2.30–2.38 (m, 2H), 3.87 (s, 3H), 4.08 (s, 3H), 4.09 (s, 3H), 4.21–4.26 (m, 4H), 6.88–6.96 (m, 4H), 6.99–7.03 (m, 2H), 7.13–7.17 (m, 2H), 7.47 (s, 1H), 7.57 (s, 1H), 8.66 (s, 1H) Mass spectrometry value (ESI-MS, m/z): 463 (M$^+$+1)

The resultant compound (125 mg) was dissolved in a 10% hydrochloric acid-methanol solution (6 ml) to prepare a solution which was then allowed to stand at room temperature for 15 min. The solvent was removed by distillation under the reduced pressure. Ethyl acetate was then added to the residue, and the precipitated crystal was collected by filtration and was washed to give 61 mg of a hydrochloride.

Example 811

4-{4-[3-(1H-1-Indolyl)propoxy]phenoxy}-6,7-dimethoxyquinazoline

Dimethyl sulfoxide (25 ml) was added to potassium hydroxide (2.18 g), and the mixture was stirred. A solution of indole (3 g) in dimethyl sulfoxide was added drowise thereto, and the mixture was stirred at room temperature for 10 min. 3-Bromo-1-propanol (2.31 ml) was added thereto, and the mixture was stirred at room temperature for 5 hr. Water was added to the reaction solution, and the mixture was extrated with ethyl acetate, followed by washing three times with saturated brine. The extract was then dried over anhydrous sodium sulfate. The solvent was removed by distillation under the reduced pressure. The residue was purified by chromatography on silica gel using hexane/acetone for development to give 1-(3-bromopropyl)-1H-indole (1) (3.78 g, yield 84%).

4-[(6,7-Dimethoxy-4-quinazolinyl)oxy]phenol (100 mg), the compound (1) (59 mg), and triphenylphosphine (106 mg) were dissolved in tetrahydrofuran (3 ml) to prepare a solution. Diethyl azodicarboxylate (0.063 ml) was then added to the solution, and the mixture was stirred at room temperature for 3 hr. The solvent was removed by distillation under the reduced pressure. Water was added to the residue, and the mixture was extracted with ethyl acetate, followed by washing with saturated brine. The extract was then dried over anhydrous sodium sulfate. The solvent was removed by distillation under the reduced pressure. The residue was purified by thin-layer chromatography using hexane/acetone for development. Diethyl ether was added to the purification product, and the precipitated crystal was collected by filtration and was washed to give the title compound (3 mg, yield 2%). Mass spectrometry value (FD-MS, m/z): 455 (M+)

Example 812

6,7-Dimethoxy-4-(4-{[2-(3-methoxyphenoxy)ethyl]sulfanyl}phenoxy)quinoline

3-Methoxyphenol (0.6 g) was dissolved in acetone (2 ml) to prepare a solution. 1-Bromo-2-chloroethane (0.60 ml), potassium carbonate (1.00 g), and tetra-n-butylammonium iodide (180 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure, and the residue was purified by chromatography on silica gel using hexane/ethyl acetate for development to give 1-(2-chloroethoxy)-3-methoxybenzene (1) (348 mg, yield 39%).

The compound (1) (206 mg) was dissolved in acetone (1 ml) to prepare a solution. 4-Hydroxythiophenol (160 mg) and potassium carbonate (168 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(3-methoxyphenoxy)ethyl]sulfanyl}phenol (2) (116 mg, yield 38%).

Chlorobenzene (0.2 ml) was added to the compound (2) (105 mg) and 4-chloro-6,7-dimethoxyquinoline (170 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (26 mg, yield 15%).

The resultant compound (20 mg) was dissolved in a 10% hydrochloric acid-methanol solution (3 ml) to prepare a solution which was then allowed to stand at room temperature for 15 min. The solvent was removed by distillation under the reduced pressure. Diethyl ether was then added to the residue, and the precipitated crystal was collected by filtration and was washed to give 17 mg of a hydrochloride.

$^1$H-NMR (DMSO-$d_6$, 400 MHz): δ 3.41 (t, J=6.3 Hz, 2H), 3.72 (s, 3H), 4.01 (s, 3H), 4.03 (s, 3,H), 4.19 (t, J=6.3 Hz, 2H), 6.44–6.55 (m, 3H), 6.85 (d, J=6.6 Hz, 1H), 7.18 (t, J=8.1 Hz, 1H), 7.36–7.41 (m, 2H), 7.60 (s, 1H), 7.61–7.65 (m, 2H), 7.72 (s, 1H), 8.77 (d, J=6.6 Hz, 1H) Mass spectrometry value (ESI-MS, m/z): 464 (M++1)

Example 813

6,7-Dimethoxy-4-(4-{[2-(4-methoxyphenoxy)ethyl]sulfanyl}phenoxy)quinoline

4-Methoxyphenol (0.6 g) was dissolved in acetone (2 ml) to prepare a solution. 1-Bromo-2-chloroethane (0.60 ml), potassium carbonate (1.00 g), and tetra-n-butylammonium iodide (180 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-4-methoxybenzene (1) (246 mg, yield 27%).

The compound (1) (226 mg) was dissolved in acetone (2 ml) to prepare a solution. 4-Hydroxythiophenol (170 mg) and potassium carbonate (184 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(4-methoxyphenoxy)ethyl]sulfanyl}phenol (2) (114 mg, yield 34%).

Chlorobenzene (0.3 ml) was added to the compound (2) (102 mg) and 4-chloro-6,7-dimethoxyquinoline (165 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (80 mg, yield 47%).

The resultant compound (66 mg) was dissolved in a 10% hydrochloric acid-methanol solution (6 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 51 mg of a hydrochloride.

$^1$H-NMR (DMSO-$d_6$, 400 MHz): δ 3.39–3.42 (m, 2H), 3.68 (s, 3H), 4.00 (s, 3H), 4.03 (s, 3H), 4.13 (t, J=6.1 Hz, 2H), 6.81–6.84 (m, 1H), 6.85 (s, 2H), 6.85 (s, 2H), 7.33–7.39 (m, 2H), 7.53 (s, 1H), 7.57–7.63 (m, 2H), 7.70 (s, 1H), 8.75 (d, J=6.6 Hz, 1H) Mass spectrometry value (ESI-MS, m/z): 464 (M++1)

Example 814

6,7-Dimethoxy-4-(4-{[2-(4-methylphenoxy)ethyl]sulfanyl}phenoxy)quinoline p-Cresol (0.6 g) was dissolved in acetone (2 ml) to prepare a solution. 1-Bromo-2-chloroethane (0.69 ml), potassium carbonate (1.15 g), and tetra-n-butylammonium iodide (205 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-4-methylbenzene (1) (348 mg, yield 37%).

The compound (1) (326 mg) was dissolved in acetone (2 ml) to prepare a solution. 4-Hydroxythiophenol (265 mg) and potassium carbonate (290 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(4-methylphenoxy)ethyl]sulfanyl}phenol (2) (185 mg, yield 37%).

Chlorobenzene (0.5 ml) was added to the compound (2) (170 mg) and 4-chloro-6,7-dimethoxyquinoline (292 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (124 mg, yield 42%).

The resultant compound (124 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 105 mg of a hydrochloride.

$^1$H-NMR (DMSO-$d_6$, 400 MHz): δ 2.21 (s, 3H), 3.39–3.42 (m, 2H), 4.01 (s, 3H), 4.03 (s, 3H), 4.15 (t, J=6.1 Hz, 2H), 6.77–6.83 (m, 2H), 6.86 (d, J=6.6 Hz, 1H), 7.04–7.10 (m, 2H), 7.34–7.40 (m, 2H), 7.56 (s, 1H), 7.57–7.64 (m, 2H), 7.72 (s, 1H), 8.77 (d, J=6.6 Hz, 1H) Mass spectrometry value (ESI-MS, m/z): 448 (M$^+$+1)

Example 815

4-(4-{[2-(2-Isopropylphenoxy)ethyl]sulfanyl}phenoxy)-6,7-dimethoxyquinoline

2-Isopropylphenol (1 g) was dissolved in acetone (3 ml) to prepare a solution. 1-Bromo-2-chloroethane (0.92 ml), potassium carbonate (1.52 g), and tetra-n-butylammonium iodide (271 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2-isopropylbenzene (1) (480 mg, yield 33%).

The compound (1) (438 mg) was dissolved in acetone (3 ml) to prepare a solution. 4-Hydroxythiophenol (306 mg) and potassium carbonate (335 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2-isopropylphenoxy)ethyl]sulfanyl}phenol (2) (288 mg, yield 46%).

Chlorobenzene (0.5 ml) was added to the compound (2) (252 mg) and 4-chloro-6,7-dimethoxyquinoline (390 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (183 mg, yield 44%).

The resultant compound (123 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 91 mg of a hydrochloride.

$^1$H-NMR (DMSO-$d_6$, 400 MHz): δ 1.16 (s, 3H), 1.18 (s, 3H), 3.19–3.26 (m, 1H), 3.48 (t, J=6.1 Hz, 2H), 4.02 (s, 3H), 4.04 (s, 3H), 4.22 (t, J=6.1 Hz, 2H), 6.85 (d, J=6.4 Hz, 1H), 6.89–6.95 (m, 2H), 7.10–7.22 (m, 2H), 7.35–7.41 (m, 2H), 7.59–7.65 (m, 3H), 7.72 (s, 1H), 8.78 (d, J=6.6 Hz, 1H) Mass spectrometry value (ESI-MS, m/z): 476 (M$^+$+1)

Example 816

4-(4-{[2-(4-Isopropylphenoxy)ethyl]sulfanyl}phenoxy)-6,7-dimethoxyquinoline

4-Isopropylphenol (1 g) was dissolved in acetone (3 ml) to prepare a solution. 1-Bromo-2-chloroethane (0.92 ml), potassium carbonate (1.52 g), and tetra-n-butylammonium iodide (271 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-4-isopropylbenzene (1) (616 mg, yield 42%).

The compound (1) (590 mg) was dissolved in acetone (4 ml) to prepare a solution. 4-Hydroxythiophenol (412 mg) and potassium carbonate (452 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(4-isopropylphenoxy)-ethyl]sulfanyl}phenol (2) (441 mg, yield 52%).

Chlorobenzene (0.8 ml) was added to the compound (2) (394 mg) and 4-chloro-6,7-dimethoxyquinoline (610 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (289 mg, yield 44%).

The resultant compound (217 mg) was dissolved in a 10% hydrochloric acid-methanol solution (4 ml) to prepare a solution which was then allowed to stand at room tempera ture for 10 min. The solvent was removed by distillation under the reduced pressure. Ethyl acetate was then added to the residue, and the precipitated crystal was collected by filtration and was washed to give 195 mg of a hydrochloride.

$^1$H-NMR (DMSO-d$_6$, 400 MHz): δ 1.16 (s, 3H), 1.17 (s, 3H), 2.78–2.87 (m, 1H), 3.43 (t, J=6.3 Hz, 2H), 4.03 (s, 3H), 4.05 (s, 3H), 4.18 (t, J=6.3 Hz, 2H), 6.82–6.87 (m, 2H), 6.89 (d, J=6.6 Hz, 1H), 7.12–7.17 (m, 2H), 7.38–7.43 (m, 2H), 7.61–7.66 (m, 2H), 7.69 (s, 1H), 7.74 (s, 1H), 8.80 (d, J=6.6 Hz, 1H) Mass spectrometry value (ESI-MS, m/z): 476 (M$^+$+1)

Example 817

6,7-Dimethoxy-4-(4-{[2-(2-methylphenoxy)ethyl]sulfanyl}phenoxy)quinoline o-Cresol (0.6 g) was dissolved in acetone (2 ml) to prepare a solution. 1-Bromo-2-chloroethane (0.69 ml), potassium carbonate (1.15 g), and tetra-n-butylammonium iodide (205 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2-methylbenzene (1) (345 mg, yield 36%).

The compound (1) (322 mg) was dissolved in acetone (2 ml) to prepare a solution. 4-Hydroxythiophenol (262 mg) and potassium carbonate (286 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2-methylphenoxy)ethyl]-sulfanyl}phenol (2) (231 mg, yield 47%).

Chlorobenzene (0.3 ml) was added to the compound (2) (204 mg) and 4-chloro-6,7-dimethoxyquinoline (350 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (139 mg, yield 40%).

The resultant compound (103 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 26 mg of a hydrochloride.

$^1$H-NMR (DMSO-d$_6$, 400 MHz): δ 2.13 (s, 3H), 3.47 (t, J=6.1 Hz, 2H), 4.02 (s, 3H), 4.04 (s, 3H), 4.22 (t, J=5.9 Hz, 2H), 6.81–6.94 (m, 3H), 7.11–7.17 (m, 2H), 7.35–7.40 (m, 2H), 7.59 (s, 1H), 7.60–7.66 (m, 2H), 7.72 (s, 1H), 8.78 (d, J=6.6 Hz, 1H) Mass spectrometry value (ESI-MS, m/z): 448 (M$^+$+1)

Example 818

4-(4-{[2-(4-Chlorophenoxy)ethyl]sulfanyl}phenoxy)-6,7-dimethoxyquinoline p-Chlorophenol (0.6 g) was dissolved in acetone (2 ml) to prepare a solution. 1-Bromo-2-chloroethane (0.58 ml), potassium carbonate (967 mg), and tetra-n-butylammonium iodide (173 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-chloro-4-(2-chloroethoxy)-benzene (1) (338 mg, yield 38%).

The compound (1) (338 mg) was dissolved in acetone (3 ml) to prepare a solution. 4-Hydroxythiophenol (246 mg) and potassium carbonate (270 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(4-chlorophenoxy)ethyl]sulfanyl}phenol (2) (265 mg, yield 53%).

Chlorobenzene (0.4 ml) was added to the compound (2) (215 mg) and 4-chloro-6,7-dimethoxyquinoline (343 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (5 mg, yield 1%).

The resultant compound (5 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 6 mg of a hydrochloride.

$^1$H-NMR (DMSO-d$_6$, 400 MHz): δ 3.44 (t, J=6.3 Hz, 2H), 4.02 (s, 3H), 4.04 (s, 3H), 4.21 (t, J=6.1 Hz, 2H), 6.85 (d, J=6.3 Hz, 1H), 6.93–6.99 (m, 2H), 7.30–7.35 (m, 2H), 7.38 (s, 1H), 7.40 (s, 1H), 7.60–7.65 (m, 3H), 7.72 (s, 1H), 8.78 (d, J=6.6 Hz, 1H)

Example 819

4-(4-{[2-(2-Chlorophenoxy)ethyl]sulfanyl}phenoxy)-6,7-dimethoxyquinoline

2-Chlorophenol (0.6 g) was dissolved in acetone (2 ml) to prepare a solution. 1-Bromo-2-chloroethane (0.58 ml), potassium carbonate (967 mg), and tetra-n-butylammonium iodide (173 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure, and the residue was purified by chromatography on silica gel using hexane/ethyl acetate for development to give 1-chloro-2-(2-chloroethoxy)-benzene (1) (429 mg, yield 48%).

The compound (1) (412 mg) was dissolved in acetone (4 ml) to prepare a solution. 4-Hydroxythiophenol (300 mg) and potassium carbonate (328 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2-chlorophenoxy)ethyl] sulfanyl}phenol (2) (449 mg, yield 74%).

Chlorobenzene (0.4 ml) was added to the compound (2) (320 mg) and 4-chloro-6,7-dimethoxyquinoline (510 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (2 mg, yield 0.3%).

The resultant compound (2 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 2 mg of a hydrochloride. Mass spectrometry value (ESI-MS, m/z): 468 ($M^++1$)

Example 820

4-(4-{[2-(3-Chlorophenoxy)ethyl]sufanyl}phenoxy)-6,7-dimethoxyquinoline

3-Chlorophenol (0.6 g) was dissolved in acetone (2 ml) to prepare a solution. 1-Bromo-2-chloroethane (0.58 ml), potassium carbonate (967 mg), and tetra-n-butylammonium iodide (173 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-chloro-3-(2-chloroethoxy)-benzene (1) (400 mg, yield 45%).

The compound (1) (387 mg) was dissolved in acetone (4 ml) to prepare a solution. 4-Hydroxythiophenol (281 mg) and potassium carbonate (308 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using chloroform for development to give 4-{[2-(3-chlorophenoxy)ethyl] sulfanyl}phenol (2) (322 mg, yield 57%).

Chlorobenzene (0.4 ml) was added to the compound (2) (206 mg) and 4-chloro-6,7-dimethoxyquinoline (328 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (105 mg, yield 31%).

The resultant compound (93 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 81 mg of a hydrochloride.

$^1$H-NMR (DMSO-$d_6$, 400 MHz): δ 3.43 (t, J=6.3 Hz, 2H), 4.02 (s, 3H), 4.04 (s, 3H), 4.24 (t, J=6.1 Hz, 2H), 6.83–7.03 (m, 4H), 7.28–7.41 (m, 3H), 7.60–7.65 (m, 3H), 7.72 (s, 1H), 8.78 (d, J=6.3 Hz, 1H) Mass spectrometry value (ESI-MS, m/z): 468 ($M^++1$)

Example 821

4-(4-{[2-(3-Fluorophenoxy)ethyl] sulfanyl}phenoxy)-6,7-dimethoxyquinoline

3-Fluorophenol (0.6 g) was dissolved in acetone (2 ml) to prepare a solution. 1-Bromo-2-chloroethane (0.67 ml), potassium carbonate (1.11 g), and tetra-n-butylammonium iodide (198 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-3-fluorobenzene (1) (407 mg, yield 44%).

The compound (1) (395 mg) was dissolved in acetone (4 ml) to prepare a solution. 4-Hydroxythiophenol (314 mg) and potassium carbonate (344 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using chloroform for development to give 4-{[2-(3-fluorophenoxy)ethyl] sulfanyl}phenol (2) (323 mg, yield 54%).

Chlorobenzene (0.4 ml) was added to the compound (2) (230 mg) and 4-chloro-6,7-dimethoxyquinoline (390 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (137 mg, yield 35%).

The resultant compound (110 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 93 mg of a hydrochloride.

$^1$H-NMR (DMSO-$d_6$, 400 MHz): δ 3.44 (t, J=6.3 Hz, 2H), 4.03 (s, 3H), 4.04 (s, 3H), 4.23 (t, J=6.1 Hz, 2H), 6.74–6.84 (m, 3H), 6.86 (d, J=6.6 Hz, 1H), 7.27–7.41 (m, 3H), 7.61–7.66 (m, 3H), 7.73 (s, 1H), 8.78 (d, J=6.6 Hz, 1H) Mass spectrometry value (ESI-MS, m/z): 452 (M$^+$+1)

Example 822

4-(4-{[2-(2-Fluorophenoxyethyl]sulfanyl}phenoxy)-6,7-dimethoxyquinoline o-Fluorophenol (0.6 g) was dissolved in acetone (2 ml) to prepare a solution. 1-Bromo-2-chloroethane (0.67 ml), potassium carbonate (1.11 g), and tetra-n-butylammonium iodide (198 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2-fluorobenzene (1) (406 mg, yield 44%).

The compound (1) (387 mg) was dissolved in acetone (2 ml) to prepare a solution. 4-Hydroxythiophenol (308 mg) and potassium carbonate (338 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2-fluorophenoxy)ethyl]sulfanyl}phenol (2) (244 mg, yield 42%).

Chlorobenzene (0.4 ml) was added to the compound (2) (191 mg) and 4-chloro-6,7-dimethoxyquinoline (324 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (132 mg, yield 40%).

The resultant compound (106 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 105 mg of a hydrochloride.

$^1$H-NMR (DMSO-$d_6$, 400 MHz): δ 3.48 (t, J=6.6 Hz, 2H), 4.04 (s, 3H), 4.05 (s, 3H), 4.29 (t, J=6.3 Hz, 2H), 6.89 (d, J=6.6 Hz, 1H), 6.93–7.00 (m, 1H), 7.09–7.25 (m, 3H), 7.37–7.43 (m, 2H), 7.62–7.69 (m, 3H), 7.75 (s, 1H), 8.82 (d, J=6.8 Hz, 1H) Mass spectrometry value (ESI-MS, m/z): 452 (M$^+$+1)

Example 823

6,7-Dimethoxy-4-(4-{[2-(3-methylphenoxy)ethyl]sulfanyl}phenoxy)quinoline m-Cresol (0.6 g) was dissolved in acetone (3 ml) to prepare a solution. 1-Bromo-2-chloroethane (0.69 ml), potassium carbonate (1.15 g), and tetra-n-butylammonium iodide (205 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-3-methylbenzene (1) (349 mg, yield 37%).

The compound (1) (337 mg) was dissolved in acetone (3 ml) to prepare a solution. 4-Hydroxythiophenol (275 mg) and potassium carbonate (301 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(3-methylphenoxy)ethyl]sulfanyl}phenol (2) (188 mg, yield 36%).

Chlorobenzene (0.3 ml) was added to the compound (2) (160 mg) and 4-chloro-6,7-dimethoxyquinoline (276 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate, and the solvent was removed by distillation under the reduced pressure. The residue was purified by chromatography on silica gel using hexane/acetone for development to give the title compound (129 mg, yield 47%).

The resultant compound (102 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 68 mg of a hydrochloride.

$^1$H-NMR (DMSO-$d_6$, 400 MHz): δ 2.27 (s, 3H), 3.43 (t, J=6.3 Hz, 2H), 4.02 (s, 3H), 4.04 (s, 3H), 4.19 (t, J=6.3 Hz, 2H), 6.69–6.78 (m, 3H), 6.84–6.88 (m, 1H), 7.16 (t, J=7.8 Hz, 1H), 7.36–7.41 (m, 2H), 7.59–7.65 (m, 3H), 7.72 (s, 1H), 8.78 (d, J=6.3 Hz, 1H) Mass spectrometry value (ESI-MS, m/z): 448 (M$^+$+1)

Example 824

4-(4-{[2-(4-Fluorophenoxy)ethyl]sulfanyl}phenoxy)-6,7-dimethoxyquinoline

4-Fluorophenol (0.6 g) was dissolved in acetone (3 ml) to prepare a solution. 1-Bromo-2-chloroethane (0.69 ml), potassium carbonate (1.11 g), and tetra-n-butylammonium iodide (198 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-4-fluorobenzene (1) (352 mg, yield 38%).

The compound (1) (342 mg) was dissolved in acetone (4 ml) to prepare a solution. 4-Hydroxythiophenol (273 mg) and potassium carbonate (299 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(4-fluorophenoxy)ethyl]sulfanyl}phenol (2) (233 mg, yield 45%).

Chlorobenzene (0.4 ml) was added to the compound (2) (211 mg) and 4-chloro-6,7-dimethoxyquinoline (357 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (181 mg, yield 50%).

The resultant compound (106 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 101 mg of a hydrochloride.

$^1$H-NMR (DMSO-$d_6$, 400 MHz): δ 3.43 (t, J=6.6 Hz, 2H), 4.03 (s, 3H), 4.05 (s, 3H), 4.19 (t, J=6.1 Hz, 2H), 6.88 (d, J=6.8 Hz, 1H), 6.92–6.97 (m, 2H), 7.08–7.14 (m, 2H), 7.37–7.42 (m, 2H), 7.60–7.68 (m, 3H), 7.74 (s, 1H), 8.81 (d, J=6.6 Hz, 1H) Mass spectrometry value (ESI-MS, m/z): 452 (M$^+$+1)

Example 825

4-(4-{[2-(2,4-Dichlorophenoxy)ethyl]sulfanyl}phenoxy)-6,7-dimethoxyquinoline 2,4-Dichlorophenol (0.6 g) was dissolved in acetone (3 ml) to prepare a solution. 1-Bromo-2-chloroethane (0.46 ml), potassium carbonate (763 mg), and tetra-n-butylammonium iodide (136 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 2,4-dichloro-1-(2-chloroethoxy)benzene (1) (475 mg, yield 57%).

The compound (1) (462 mg) was dissolved in acetone (4 ml) to prepare a solution. 4-Hydroxythiophenol (285 mg) and potassium carbonate (312 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2,4-dichlorophenoxy)ethyl]sulfanyl}phenol (2) (342 mg, yield 53%).

Chlorobenzene (0.3 ml) was added to the compound (2) (230 mg) and 4-chloro-6,7-dimethoxyquinoline (326 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (185 mg, yield 51%).

The resultant compound (103 mg) was dissolved in a 10% hydrochloric acid-methanol solution (10 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 83 mg of a hydrochloride.

$^1$H-NMR (DMSO-$d_6$, 400 MHz): δ 3.48 (t, J=6.8 Hz, 2H), 4.03 (s, 3H), 4.05 (s, 3H), 4.31 (t, J=6.1 Hz, 2H), 6.85–6.90 (m, 1H), 7.17–7.22 (m, 1H), 7.34–7.42 (m, 3H), 7.56–7.67 (m, 4H), 7.74 (s, 1H), 8.78–8.83 (m, 1H) Mass spectrometry value (ESI-MS, m/z): 502 (M$^+$+1)

Example 826

4-(4-{[2-(2,4-Dimethylphenoxy)ethyl]sulfanyl}phenoxy)-6,7-dimethoxyquinoline 2,4-Dimethylphenol (0.6 g) was dissolved in acetone (3 ml) to prepare a solution. 1-Bromo-2-chloroethane (0.61 ml), potassium carbonate (1.02 g), and tetra-n-butylammonium iodide (183 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2,4-dimethylbenzene (1) (231 mg, yield 26%).

The compound (1) (224 mg) was dissolved in acetone (2 ml) to prepare a solution. 4-Hydroxythiophenol (168 mg) and potassium carbonate (184 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2,4-dimethylphenoxy)ethyl]sulfanyl}phenol (2) (124 mg, yield 38%).

Chlorobenzene (0.3 ml) was added to the compound (2) (112 mg) and 4-chloro-6,7-dimethoxyquinoline (182 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (68 mg, yield 36%).

The resultant compound (51 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 35 mg of a hydrochloride.

$^1$H-NMR (DMSO-$d_6$, 400 MHz): δ 2.08 (s, 3H), 2.18 (s, 3H), 3.40–3.45 (m, 2H), 4.01 (s, 3H), 4.03 (s, 3H), 4.16 (t, J=6.1 Hz, 2H), 6.75–6.95 (m, 4H), 7.33–7.40 (m, 2H), 7.56 (s, 1H), 7.57–7.64 (m, 2H), 7.71 (s, 1H), 8.77 (d, J=6.6 Hz, 1H) Mass spectrometry value (ESI-MS, m/z): 462 (M$^+$+1)

Example 827

4-(4-{[2-(3,4-Dimethylphenoxy)ethyl]sulfanyl}phenoxy)-6,7-dimethoxyquinoline 3,4-Dimethylphenol (0.6 g) was dissolved in acetone (3 ml) to prepare a solution. 1-Bromo-2-chloroethane (0.61 ml), potassium carbonate (1.02 g), and tetra-n-butylammonium iodide (183 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-3,4-dimethylbenzene (1) (286 mg, yield 32%).

The compound (1) (279 mg) was dissolved in acetone (2 ml) to prepare a solution. 4-Hydroxythiophenol (210 mg) and potassium carbonate (230 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(3,4-dimethylphenoxy)ethyl]sulfanyl}phenol (2) (190 mg, yield 46%).

Chlorobenzene (0.3 ml) was added to the compound (2) (138 mg) and 4-chloro-6,7-dimethoxyquinoline (226 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (122 mg, yield 52%).

The resultant compound (68 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 34 mg of a hydrochloride.

$^1$H-NMR (DMSO-$d_6$, 400 MHz): δ 2.13 (s, 3H), 2.18 (s, 3H), 3.40 (t, J=6.3 Hz, 2H), 4.02 (s, 3H), 4.04 (s, 3H), 4.15 (t, J=6.3 Hz, 2H), 6.61–6.74 (m, 2H), 6.87 (d, J=6.6 Hz, 1H), 7.02 (d, J=8.1 Hz, 1H), 7.38 (d, J=8.8 Hz, 2H), 7.54–7.66 (m, 3H), 7.72 (s, 1H), 8.78 (d, J=6.3 Hz, 1H) Mass spectrometry value (ESI-MS, m/z): 462 (M$^+$+1)

Example 828

4-(4-{[2-(2,6-Dimethylphenoxy)ethyl]sulfanyl}phenoxy)-6,7-dimethoxyquinoline 2,6-Dimethylphenol (1 g) was dissolved in acetone (4 ml) to prepare a solution. 1-Bromo-2-chloroethane (1.02 ml), potassium carbonate (1.70 g), and tetra-n-butylammonium iodide (303 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2,6-dimethylbenzene (1) (513 mg, yield 34%).

The compound (1) (513 mg) was dissolved in acetone (4 ml) to prepare a solution. 4-Hydroxythiophenol (386 mg) and potassium carbonate (423 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2,6-dimethylphenoxy)ethyl]sulfanyl}phenol (2) (319 mg, yield 42%).

Chlorobenzene (0.5 ml) was added to the compound (2) (281 mg) and 4-chloro-6,7-dimethoxyquinoline (456 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (29 mg, yield 6%).

The resultant compound (29 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 25 mg of a hydrochloride.

$^1$H-NMR (chloroform-d, 400 MHz): δ 2.29 (s, 3H), 2.34 (s, 3H), 3.41 (s, 1H), 3.95–4.30 (m, 9H), 6.85–8.30 (m, 11H) Mass spectrometry value (ESI-MS, m/z): 462 (M$^+$+1)

Example 829

4-[(6,7-Dimethoxy-4-quinolyl)oxy]phenyl [2-(4-fluorophenoxy)ethyl]sulfone 4-(4-{[2-(4-Fluorophenoxy)ethyl]sulfanyl}phenoxy)-6,7-dimethoxyquinoline (20 mg) was dissolved in acetic acid (0.5 ml) to prepare a solution. Potassium permanganate (35 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (16 mg, yield 76%).

The resultant compound (16 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 17 mg of a hydrochloride.

$^1$H-NMR (DMSO-$d_6$, 400 MHz): δ 3.91 (t, J=5.6 Hz, 2H), 3.99 (s, 3H), 4.03 (s, 3H), 4.30 (t, J=5.4 Hz, 2H), 6.74–6.81 (m, 2H), 6.92 (d, J=6.3 Hz, 1H), 7.04–7.13 (m, 2H), 7.57 (s, 1H), 7.59–7.66 (m, 2H), 7.68 (s, 1H), 8.06–8.13 (m, 2H), 8.81 (d, J=6.3 Hz, 1H) Mass spectrometry value (ESI-MS, m/z): 484 (M$^+$+1)

Example 830

4-[(6,7-Dimethoxy-4-quinolyl)oxy]phenyl [2-(3-methoxyphenoxy)ethyl]sulfone 6,7-Dimethoxy-4-(4-{[2–3-methoxyphenoxy)ethyl]-sulfanyl}phenoxy)quinoline (20 mg) was dissolved in acetic acid (0.5 ml) to prepare a solution. Potassium permanganate (34 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (9 mg, yield 40%).

The resultant compound (9 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 9 mg of a hydrochloride.

$^1$H-NMR (DMSO-d6, 400 MHz): δ 3.70 (s, 3H), 3.91 (t, J=5.6 Hz, 2H), 4.01 (s, 3H), 4.04 (s, 3H), 4.31 (t, J=5.6 Hz, 2H), 6.23 (t, J=2.4 Hz, 1H), 6.32–6.37 (m, 1H), 6.50–6.55 (m, 1H), 6.93 (d, J=6.1 Hz, 1H), 7.16 (t, J=8.3 Hz, 1H), 7.57–7.69 (m, 4H), 8.07–8.13 (m, 2H), 8.80 (d, J=6.1 Hz, 1H) Mass spectrometry value (ESI-MS, m/z): 496 (M$^+$+1)

Example 831

2-(2,4-Dichlorophenoxy)ethyl{4-[(6,7-dimethoxy-4-quinolyl)oxy]phenyl}sulfone 4-(4-{[2-(2,4-Dichlorophenoxy)ethyl]sulfanyl}phenoxy)-6,7-dimethoxyquinoline (20 mg) was dissolved in acetic acid (0.5 ml) to prepare a solution. Potassium permanganate (32 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (15 mg, yield 69%).

The resultant compound (15 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 15 mg of a hydrochloride.

$^1$H-NMR (DMSO-$d_6$, 400 MHz): δ 3.94–4.07 (m, 8H), 4.42 (t, J=5.4 Hz, 2H), 6.91 (d, J=6.3 Hz, 1H), 7.19 (d, J=9.0 Hz, 1H), 7.33–7.37 (m, 1H), 7.52–7.67 (m, 5H), 7.97–8.03 (m, 2H), 8.80 (d, J=6.3 Hz, 1H) Mass spectrometry value (ESI-MS, m/z): 533 (M$^+$+1)

Example 832

2-(3-Chlorophenoxy)ethyl{4-[(6.7-dimethoxy-4-quinolyl)oxy]phenyl}sulfone 4-(4-{[2-(3-Chlorophenoxy)ethyl]sulfanyl}phenoxy)-6,7-dimethoxyquinoline (20 mg) was dissolved in acetic acid (0.5 ml) to prepare a solution. Potassium permanganate (31 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (10 mg, yield 50%).

The resultant compound (10 mg) was dissolved in a 10% hydrochloric acid-methanol solution (4 ml) to prepare a solution which was then allowed to stand at room temperature for 10 min. The solvent was removed by distillation under the reduced pressure. Diethyl ether was then added to the residue, and the precipitated crystal was collected by filtration and was washed to give 10 mg of a hydrochloride.

$^1$H-NMR (DMSO-$d_6$, 400 MHz): δ 3.92 (t, J=5.4 Hz, 2H), 3.99 (s, 3H), 4.03 (s, 3H), 4.35 (t, J=5.6 Hz, 2H), 6.70–6.76 (m, 1H), 6.78 (t, J=2.0 Hz, 1H), 6.94 (d, J=6.3 Hz, 1H), 6.97–7.03 (m, 1H), 7.28 (t, J=8.3 Hz, 1H), 7.58 (s, 1H), 7.60–7.67 (m, 2H), 7.68 (s, 1H), 8.06–8.13 (m, 2H), 8.81 (d, J=6.3 Hz, 1H) Mass spectrometry value (ESI-MS, m/z): 500 (M$^+$+1)

Example 833

4-[(6,7-Dimethoxy-4-quinolyl)oxy]phenyl [2-(3,4-dimethylphenoxy)ethyl]sulfone 4-(4-{[2-(3,4-Dimethylphenoxy)ethyl]sulfanyl}phenoxy)-6,7-dimethoxyquinoline (19 mg) was dissolved in acetic acid (0.5 ml) to prepare a solution. Potassium permanganate (33 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (4 mg, yield 17%).

The resultant compound (4 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 4 mg of a hydrochloride. Mass spectrometry value (ESI-MS, m/z): 494 ($M^+$+1)

Example 834

4-[(6,7-Dimethoxy-4-quinolyl)oxy]phenyl [2-(4-methylphenoxy)ethyl]sulfone 6,7-Dimethoxy-4-(4-{[2-(4-methylphenoxy)ethyl] sulfanyl}phenoxy)quinoline (20 mg) was dissolved in acetic acid (0.5 ml) to prepare a solution. Potassium permanganate (32 mg) was added to the solution, and the mixture was stirred at room temperature for 3 hr. Thereafter, water was further added thereto, and the mixture was stirred at room temperature for 5 min. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (1 mg, yield 4%).

The resultant compound (1 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 1 mg of a hydrochloride. Mass spectrometry value (ESI-MS, m/z): 480 ($M^+$+1)

Example 835

4-[(6,7-Dimethoxy-4-quinolyl)oxy]phenyl [2-(4-isopropylphenoxy)ethyl]sulfone 4-(4-{[2-(4-Isopropylphenoxy)ethyl]sulfanyl}phenoxy)-6,7-dimethoxyquinoline (22 mg) was dissolved in acetic acid (0.5 ml) to prepare a solution. Potassium permanganate (34 mg) was added to the solution, and the mixture was stirred at room temperature for 3 hr. Thereafter, water was further added thereto, and the mixture was stirred at room temperature for 10 min. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (2 mg, yield 8%).

The resultant compound (2 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 2 mg of a hydrochloride. Mass spectrometry value (ESI-MS, m/z): 508 ($M^+$+1)

Example 836

4-[(6,7-Dimethoxy-4-quinolyl)oxy]phenyl [2-(2-isopropylphenoxy)ethyl]sulfone 4-(4-{[2-(2-Isopropylphenoxy)ethyl]sulfanyl}phenoxy)-6,7-dimethoxyquinoline (12 mg) was dissolved in acetic acid (0.5 ml) to prepare a solution. Potassium permanganate (19 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (7 mg, yield 57%).

The resultant compound (7 mg) was dissolved in a 10% hydrochloric acid-methanol solution (4 ml) to prepare a solution which was then allowed to stand at room temperature for 10 min. The solvent was removed by distillation under the reduced pressure. Diethyl ether was then added to the residue, and the precipitated crystal was collected by filtration and was washed to give 7 mg of a hydrochloride.

$^1$H-NMR (DMSO-$d_6$, 400 MHz): δ 1.04 (s, 3H), 1.06 (s, 3H), 2.70–2.80 (m, 1H), 3.91–4.06 (m, 8H), 4.32 (t, J=5.4 Hz, 2H), 6.87–6.98 (m, 3H), 7.09–7.18 (m, 2H), 7.54–7.66 (m, 4H), 8.09–8.17 (m, 2H), 8.78 (d, J=6.1 Hz, 1H) Mass spectrometry value (ESI-MS, m/z): 508 ($M^+$+1)

Example 837

4-[(6,7-Dimethoxy-4-quinolyl)oxy]phenyl [2-(2-fluorophenoxy)ethyl]sulfone 4-(4-{[2-(2-Fluorophenoxy)ethyl]sulfanyl}-phenoxy)-6,7-dimethoxyquinoline (20 mg) was dissolved in acetic acid (0.5 ml) to prepare a solution. Potassium permanganate (33 mg) was added to the solution, and the mixture was stirred at room temperature for 2 hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/acetone for development to give the title compound (7 mg, yield 37%).

The resultant compound (7 mg) was dissolved in a 10% hydrochloric acid-methanol solution (4 ml) to prepare a solution which was then allowed to stand at room temperature for 10 min. The solvent was removed by distillation under the reduced pressure. Diethyl ether was then added to the residue, and the precipitated crystal was collected by filtration and was washed to give 7 mg of a hydrochloride.

$^1$H-NMR (DMSO-$d_6$, 400 MHz): δ 3.93–4.04 (m, 8H), 4.41 (t, J=5.4 Hz, 2H), 6.87–7.23 (m, 5H), 7.56–7.64 (m, 3H), 7.67 (s, 1H), 8.11 (d, J=8.5 Hz, 2H), 8.84 (d, J=6.1 Hz, 1H) Mass spectrometry value (ESI-MS, m/z): 484 ($M^+$+1)

Example 838

{4-[(6,7-Dimethoxy-4-quinolyl)oxy]phenyl}[2-(3-methoxy-4-nitrophenoxy)ethyl] sulfoxide Nitric acid (0.5 ml) was added to 6,7-dimethoxy-4-(4-{[2-(3-methoxyphenoxy)ethyl]sulfanyl}phenoxy)quinoline (20 mg), and the mixture was stirred at 0° C. for 30 min. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/methanol for development to give the title compound (14 mg, yield 60%).

The resultant compound (14 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 15 mg of a hydrochloride. Mass spectrometry value (ESI-MS, m/z): 541 ($M^++1$)

Example 839

{4-[(6,7-Dimethoxy-4-quinolyl)oxy]phenyl}[2-(4-fluoro-2-nitrophenoxy)ethyl] sulfoxide Nitric acid (0.5 ml) was added to 4-(4-{[2-(4-Fluorophenoxy)ethyl]sulfanyl}phenoxy)-6,7-dimethoxyquinoline (20 mg), and the mixture was stirred at 0° C. for 30 min. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/methanol for development to give the title compound (13 mg, yield 58%).

The resultant compound (13 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 14 mg of a hydrochloride.

$^1$H-NMR (DMSO-$d_6$, 400 MHz): δ 3.50–3.58 (m, 2H), 4.03 (s, 3H), 4.05 (s, 3H), 4.53 (t, J=4.9 Hz, 2H), 6.93–6.97 (m, 1H), 7.47–7.65 (m, 5H), 7.73 (s, 1H), 7.87–7.94 (m, 3H), 8.80 (d, J=6.3 Hz, 1H) Mass spectrometry value (ESI-MS, m/z): 513 ($M^++1$)

Example 840

[2-(2,4-Dichlorophenoxy)ethyl]{4-[(6,7-dimethoxy-4-quinolyl)oxy]phenyl} sulfoxide Nitric acid (0.5 ml) was added to 4-(4-{[2-(2,4-dichlorophenoxy)ethyl]sulfanyl}phenoxy)-6,7-dimethoxyquinoline (20 mg), and the mixture was stirred at 0° C. for one hr. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by thin-layer chromatography using chloroform/methanol for development to give the title compound (19 mg, yield 92%).

The resultant compound (19 mg) was dissolved in a 10% hydrochloric acid-methanol solution (2 ml) to prepare a solution which was then allowed to stand at room temperature for 10 min. The solvent was removed by distillation under the reduced pressure. Diethyl ether was then added to the residue, and the precipitated crystal was collected by filtration and was washed to give 19 mg of a hydrochloride.

$^1$H-NMR (DMSO-$d_6$, 400 MHz): δ 3.50–3.62 (m, 2H), 4.02 (s, 3H), 4.05 (s, 3H), 4.39–4.49 (m, 2H), 6.91 (d, J=6.3 Hz, 1H), 7.26 (d, J=9.0 Hz, 1H), 7.37–7.43 (m, 1H), 7.57–7.64 (m, 4H), 7.72 (s, 1H), 7.90–7.97 (m, 2H), 8.81 (d, J=6.3 Hz, 1H) Mass spectrometry value (ESI-MS, m/z): 518 ($M^++1$)

Example 841

6,7-Dimethoxy-4-(4-{[3-(3-methylphenoxy)propyl]sulfanyl}phenoxy)quinoline m-Cresol (0.6 g) was dissolved in acetonitrile (2 ml) to prepare a solution. 1,3-Dibromopropane (1.13 ml), potassium carbonate (2.30 g), and tetra-n-butylammonium iodide (205 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropoxy)-3-methylbenzene (1) (831 mg, yield 65%).

The compound (1) (1.07 g) was dissolved in acetone (5 ml) to prepare a solution. 4-Hydroxythiophenol (647 mg) and potassium carbonate (709 mg) were then added to the solution, and the mixture was stirred at room temperature for 2 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[3-(3-methylphenoxy)propyl]sulfanyl}phenol (2) (1.00 g, yield 78%).

Chlorobenzene (0.4 ml) was added to the compound (2) (200 mg) and 4-chloro-6,7-dimethoxyquinoline (326 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (134 mg, yield 37%).

The resultant compound (110 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 103 mg of a hydrochloride.

$^1$H-NMR (DMSO-$d_6$, 400 MHz): δ 2.05 (t, J=6.8 Hz, 2H), 2.27 (s, 3H), 3.19 (t, J=7.3 Hz, 2H), 4.04 (s, 3H), 4.05 (s, 3H), 4.08 (t, J=6.1 Hz, 2H), 6.70–6.77 (m, 3H), 6.88 (d,

J=6.6 Hz, 1H), 7.16 (t, J=8.3 Hz, 1H), 7.37–7.42 (m, 2H), 7.55–7.61 (m, 2H), 7.69 (s, 1H), 7.75 (s, 1H), 8.80 (d, J=6.6 Hz, 1H)

Example 842

4-(4-{[3-(2-Fluorophenoxy)propyl]sulfanyl}phenoxy)-6,7-dimethoxyquinoline o-Fluorophenol (0.6 g) was dissolved in acetonitrile (2 ml) to prepare a solution. 1,3-Dibromopropane (1.09 ml), potassium carbonate (2.22 g), and tetra-n-butylammonium iodide (198 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropoxy)-3-methylbenzene (1) (930 mg, yield 75%).

The compound (1) (1.10 g) was dissolved in acetone (5 ml) to prepare a solution. 4-Hydroxythiophenol (657 mg) and potassium carbonate (720 mg) were then added to the solution, and the mixture was stirred at room temperature for 2 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[3-(2-fluorophenoxy)propyl]sulfanyl}phenol (2) (853 mg, yield 65%).

Chlorobenzene (0.4 ml) was added to the compound (2) (200 mg) and 4-chloro-6,7-dimethoxyquinoline (322 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (167 mg, yield 50%).

The resultant compound (139 mg) was dissolved in a 10% hydrochloric acid-methanol solution (8 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 132 mg of a hydrochloride.

$^1$H-NMR (DMSO-$d_6$, 400 MHz): δ 2.04–2.13 (m, 2H), 3.20 (t, J=7.1 Hz, 2H), 4.04 (s, 3H), 4.05 (s, 3H), 4.18 (t, J=6.1 Hz, 2H), 6.87 (d, J=6.6 Hz, 1H), 6.91–6.98 (m, 1H), 7.10–7.24 (m, 3H), 7.36–7.42 (m, 2H), 7.59–7.63 (m, 2H), 7.69 (s, 1H), 7.74 (s, 1H), 8.80 (d, J=6.6 Hz, 1H)

Example 843

4-(4-{[4-(2-Fluorophenoxy)butyl]sulfanyl}phenoxy)-6,7-dimethoxyquinoline o-Fluorophenol (1.0 g) was dissolved in acetonitrile (3 ml) to prepare a solution. 1,4-Dibromobutane (2.13 ml), potassium carbonate (3.70 g), and tetra-n-butylammonium iodide (330 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(4-bromobutoxy)-2-fluorobenzene (1) (1.57 g, yield 71%).

The compound (1) (1.55 g) was dissolved in acetone (4 ml) to prepare a solution. 4-Hydroxythiophenol (873 mg) and potassium carbonate (956 mg) were then added to the solution, and the mixture was stirred at room temperature for 2 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[4-(2-fluorophenoxy)butyl]sulfanyl}phenol (2) (1.66 g, yield 90%).

Chlorobenzene (0.4 ml) was added to the compound (2) (200 mg) and 4-chloro-6,7-dimethoxyquinoline (306 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (156 mg, yield 47%).

The resultant compound (99 mg) was dissolved in a 10% hydrochloric acid-methanol solution (4 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 69 mg of a hydrochloride.

$^1$H-NMR (DMSO-$d_6$, 400 MHz): δ 1.73–1.95 (m, 4H), 3.12 (t, J=7.3 Hz, 2H), 4.03 (s, 3H), 4.04 (s, 3H), 4.09 (t, J=6.1 Hz, 2H), 6.86 (d, J=6.6 Hz, 1H), 6.88–6.97 (m, 1H), 7.08–7.23 (m, 3H), 7.34–7.39 (m, 2H), 7.52–7.57 (m, 2H), 7.61 (s, 1H), 7.73 (s, 1H), 8.78 (d, J=6.3 Hz, 1H)

Example 844

6,7-Dimethoxy-4-(4-{[4-(3-methylphenoxy)butyl]sulfanyl}phenoxy)quinoline m-Cresol (1 g) was dissolved in acetonitrile (3 ml) to prepare a solution. 1,4-Dibromobutane (2.21 ml), potassium carbonate (3.84 g), and tetra-n-butylammonium iodide (342 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(4-bromobutoxy)-3-methylbenzene (1).

The compound (1) was dissolved in acetone (4 ml) to prepare a solution. 4-Hydroxythiophenol (2.07 g) and potassium carbonate (2.27 g) were then added to the solution, and the mixture was stirred at room temperature for 6 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[4-(3-methylphenoxy)butyl]sulfanyl}phenol (2) (1.04 g, yield 39%).

Chlorobenzene (0.4 ml) was added to the compound (2) (200 mg) and 4-chloro-6,7-dimethoxyquinoline (309 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (139 mg, yield 42%).

The resultant compound (115 mg) was dissolved in a 10% hydrochloric acid-methanol solution (6 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 85 mg of a hydrochloride.

$^1$H-NMR (DMSO-d$_6$, 400 MHz): δ 1.72–1.91 (m, 4H), 2.26 (s, 3H), 3.11 (t, J=7.1 Hz, 2H), 3.98 (t, J=6.3 Hz, 2H), 4.03 (s, 3H), 4.04 (s, 3H), 6.68–6.76 (m, 3H), 6.86 (d, J=6.6 Hz, 1H), 7.11–7.17 (m, 1H), 7.33–7.39 (m, 2H), 7.52–7.57 (m, 2H), 7.60 (s, 1H), 7.73 (s, 1H), 8.78 (d, J=6.6 Hz, 1H)

Example 845

4-(4-{[3-(2-Fluorophenoxy)propyl]sulfanyl}phenoxy)-6,7-dimethoxyquinazoline o-Fluorophenol (0.6 g) was dissolved in acetonitrile (2 ml) to prepare a solution. 1,3-Dibromopropane (1.09 ml), potassium carbonate (2.22 g), and tetra-n-butylammonium iodide (198 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropoxy)-2-fluorobenzene (1) (930 mg, yield 75%).

The compound (1) (1.10 g) was dissolved in acetone (5 ml) to prepare a solution. 4-Hydroxythiophenol (657 mg) and potassium carbonate (720 mg) were then added to the solution, and the mixture was stirred at room temperature for 2 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[3-(2-fluorophenoxy)propyl]sulfanyl}phenol (2) (0.85 g, yield 65%).

Chlorobenzene (0.3 ml) was added to the compound (2) (100 mg) and 4-chloro-6,7-dimethoxyquinazoline (163 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (65 mg, yield 39%).

The resultant compound (60 mg) was dissolved in a 10% hydrochloric acid-methanol solution (8 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 36 mg of a hydrochloride.

$^1$H-NMR (DMSO-d$_6$, 400 MHz): δ 2.01–2.10 (m, 2H), 3.16 (t, J=7.3 Hz, 2H), 3.99 (s, 3H), 4.00 (s, 3H), 4.13–4.23 (m, 2H), 6.90–6.93 (m, 1H), 7.09–7.51 (m, 8H), 7.58 (s, 1H), 8.65 (s, 1H)

Example 846

6,7-Dimethoxy-4-(4-{[3-(3-methylphenoxy)propyl]sulfanyl}phenoxy)quinazoline m-Cresol (0.6 g) was dissolved in acetonitrile (2 ml) to prepare a solution. 1,3-Dibromopropane (1.13 ml), potassium carbonate (2.30 g), and tetra-n-butylammonium iodide (205 mg) were then added to the solution, and the mixture was heated under reflux for 3 hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(3-bromopropoxy)-3-methylbenzene (1) (831 mg, yield 65%).

The compound (1) (1.07 g) was dissolved in acetone (5 ml) to prepare a solution. 4-Hydroxythiophenol (647 mg), potassium carbonate (709 mg) were then added to the solution, and the mixture was stirred at room temperature for 2 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[3-(3-methylphenoxy)propyl]sulfanyl}phenol (2) (1.00 g, yield 78%).

Chlorobenzene (0.3 ml) was added to the compound (2) (100 mg) and 4-chloro-6,7-dimethoxyquinazoline (165 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (82 mg, yield 49%).

The resultant compound (70 mg) was dissolved in a 10% hydrochloric acid-methanol solution (3 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 12 mg of a hydrochloride.

Mass spectrometry value (ESI-MS, m/z): 463 (M$^+$+1)

Example 847

6,7-Dimethoxy-4-(4-{[4-(3-methylphenoxy)butyl] sulfanyl}phenoxy)quinazoline m-Cresol (1 g) was dissolved in acetonitrile (3 ml) to prepare a solution. 1,4-Dibromobutane (2.21 ml), potassium carbonate (3.84 g), and tetra-n-butylammonium iodide (342 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(4-bromobutoxy)-3-methylbenzene (1).

The compound (1) was dissolved in acetone (4 ml) to prepare a solution. 4-Hydroxythiophenol (2.07 g) and potassium carbonate (2.27 g) were then added to the solution, and the mixture was stirred at room temperature for 6 hr. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[4-(3-methylphenoxy)butyl]-sulfanyl}phenol (2) (1.04 g, yield 39%).

Chlorobenzene (0.4 ml) was added to the compound (2) (100 mg) and 4-chloro-6,7-dimethoxyquinazoline (156 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (110 mg, yield 66%).

The resultant compound (95 mg) was dissolved in a 10% hydrochloric acid-methanol solution (8 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 60 mg of a hydrochloride.

$^1$H-NMR (DMSO-$d_6$, 400 MHz): δ 1.71–1.91 (m, 4H), 2.26 (s, 3H), 3.07 (t, J=7.1 Hz, 2H), 3.93–4.04 (m, 8H), 6.68–6.76 (m, 3H), 7.14 (t, J=8.1 Hz, 1H), 7.25–7.31 (m, 2H), 7.38–7.48 (m, 3H), 7.59 (s, 1H), 8.64 (s, 1H)

Example 848

4-(4-{[4-(2-Fluorophenoxy)butyl] sulfanyl}phenoxy)-6,7-dimethoxyquinazoline o-Fluorophenol (1.0 g) was dissolved in acetonitrile (3 ml) to prepare a solution. 1,4-Dibromobutane (2.13 ml), potassium carbonate (3.70 g), and tetra-n-butylammonium iodide (330 mg) were then added to the solution, and the mixture was heated under reflux for one hr. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(4-bromobutoxy)-2-fluorobenzene (1) (1.57 g, yield 71%).

The compound (1) (1.55 g) was dissolved in acetone (4 ml) to prepare a solution. 4-Hydroxythiophenol (873 mg) and potassium carbonate (956 mg) were then added to the solution, and the mixture was stirred at room temperature for 2 hr. 1 N HCl was added to reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[3-(2-fluorophenoxy)butyl] sulfanyl}phenol (2) (1.66 g, yield 90%).

Chlorobenzene (0.4 ml) was added to the compound (2) (100 mg) and 4-chloro-6,7-dimethoxyquinazoline (154 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure, and the residue was purified by chromatography on silica gel using hexane/acetone for development to give the title compound (117 mg, yield 73%).

The resultant compound (96 mg) was dissolved in a 10% hydrochloric acid-methanol solution (6 ml) to prepare a solution which was then allowed to stand at room temperature for 10 min. The solvent was removed by distillation under the reduced pressure. Ethyl acetate was then added to the residue, and the precipitated crystal was collected by filtration and was washed to give 81 mg of a hydrochloride.

$^1$H-NMR (DMSO-$d_6$, 400 MHz): δ 1.73–1.94 (m, 4H), 3.09 (t, J=7.3 Hz, 2H), 3.99 (s, 3H), 4.01 (s, 3H), 4.08 (t, J=6.3 Hz, 2H), 6.87–6.96 (m, 1H), 7.07–7.22 (m, 3H), 7.27–7.32 (m, 2H), 7.43–7.48 (m, 3H), 7.61 (s, 1H), 8.71 (s, 1H)

Example 849

4-(4-{[2-(2-Fluorophenoxy)ethyl] sulfanyl}phenoxy)-6,7-dimethoxyquinazoline o-Fluorophenol (0.6 g) was dissolved in acetone (2 ml) to prepare a solution. 1-Bromo-2-chloroethane (0.69 ml), potassium carbonate (1.11 g), and tetra-n-butylammonium iodide (198 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure. The residue was purified by chromatography on silica gel using hexane/ethyl acetate for development to give 1-(2-chloroethoxy)-2-fluorobenzene (1) (438 mg, yield 47%).

The compound (1) (432 mg) was dissolved in acetone (3 ml) to prepare a solution. 4-Hydroxythiophenol (343 mg) and potassium carbonate (376 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(2-fluorophenoxy)ethyl] sulfanyl}phenol (2) (345 mg, yield 53%).

Chlorobenzene (0.4 ml) was added to the compound (2) (100 mg) and 4-chloro-6,7-dimethoxyquinazoline (171 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (110 mg, yield 64%).

The resultant compound (90 mg) was dissolved in a 10% hydrochloric acid-methanol solution (6 ml) to prepare a solution which was then allowed to stand at room temperature for 10 min. The solvent was removed by distillation under the reduced pressure. Diethyl ether was then added to the residue, and the precipitated crystal was collected by filtration and was washed to give 60 mg of a hydrochloride.

$^1$H-NMR (DMSO-$d_6$, 400 MHz): δ 3.42 (t, J=6.6 Hz, 2H), 3.98 (s, 3H), 4.00 (s, 3H), 4.26 (t, J=6.3 Hz, 2H), 6.92–6.99 (m, 1H), 7.08–7.62 (m, 9H), 8.65 (s, 1H)

Example 850

6,7-Dimethoxy-4-(4-{[2-(3-methylphenoxy)ethyl]sulfanyl}phenoxy)quinazoline m-Cresol (0.6 g) was dissolved in acetone (2 ml) to prepare a solution. 1-Bromo-2-chloroethane (0.69 ml), potassium carbonate (1.15 g), and tetra-n-butylammonium iodide (205 mg) were then added to the solution, and the mixture was heated under reflux overnight. Water was added to the reaction solution, and the mixture was extracted with chloroform. The extract was washed with saturated brine and was dried over anhydrous sodium sulfate. The solvent was removed by distillation under the reduced pressure, and the residue was purified by chromatography on silica gel using hexane/ethyl acetate for development to give 1-(2-chloroethoxy)-3-methylbenzene (1) (347 mg, yield 37%).

The compound (1) (341 mg) was dissolved in acetone (3 ml) to prepare a solution. 4-Hydroxythiophenol (278 mg) and potassium carbonate (304 mg) were then added to the solution, and the mixture was stirred at room temperature overnight. 1 N HCl was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using chloroform for development to give 4-{[2-(3-methylphenoxy)ethyl]sulfanyl}phenol (2) (243 mg, yield 47%).

Chlorobenzene (0.4 ml) was added to the compound (2) (100 mg) and 4-chloro-6,7-dimethoxyquinazoline (174 mg), and the mixture was stirred at 140° C. overnight. A saturated aqueous sodium hydrogencarbonate solution was added to the reaction solution, and the mixture was extracted with chloroform, followed by washing with saturated brine. The extract was then dried over anhydrous sodium sulfate. The solvent was removed by distillation under the reduced pressure. The residue was purified by chromatography on silica gel using hexane/acetone for development to give the title compound (86 mg, yield 50%).

The resultant compound (72 mg) was dissolved in a 10% hydrochloric acid-methanol solution (6 ml) to prepare a solution which was then allowed to stand at room temperature for 10 min. The solvent was removed by distillation under the reduced pressure. Diethyl ether was then added to the residue, and the precipitated crystal was collected by filtration and was washed to give 52 mg of a hydrochloride.

$^1$H-NMR (DMSO-$d_6$, 400 MHz): δ 2.27 (s, 3H), 3.38 (t, J=6.3 Hz, 2H), 3.98 (s, 3H), 4.00 (s, 3H), 4.17 (t, J=6.3 Hz, 2H), 6.68–6.78 (m, 3H), 7.12–7.18 (m, 1H), 7.27–7.34 (m, 2H), 7.41 (s, 1H), 7.50–7.56 (m, 2H), 7.58 (s, 1H), 8.62 (s, 1H)

Example 851

N-[2-(2,4-Dichlorophenoxy)ethyl]-N-{4-[(6,7-dimethoxy-4-quinolyl)oxy]phenyl}amine Sodium hydride (60 mg) was dissolved in dimethylformamide (3 ml) to prepare a solution. A dimethylformamide solution (5 ml) of 2,4-dichlorophenol (245 mg) was then added to the solution, and the mixture was stirred at room temperature for 10 min. Subsequently, a dimethylformamide solution (5 ml) of bromomethylacetate (344 mg) was added thereto, and the mixture was further stirred at room temperature for 90 min. Water was added to stop the reaction, and the reaction solution was extracted with ethyl acetate, followed by washing with water and saturated brine. The extract was then dried over sodium sulfate. After the concentration of the extract, a 5% aqueous sodium hydroxide solution (10 ml) was added thereto, and the mixture was stirred at 80° C. for 10 hr. Subsequently, the solution was acidified by the addition of 1 N hydrochloric acid. The resultant white precipitate was collected by filtration and was dried to give 2-(2,4-dichlorophenoxy)acetic acid (310 mg, yield 94%).

2-(2,4-Dichlorophenoxy)acetic acid (310 mg) was added to chloroform (5 ml), and 1-ethyl-3-(3-dimethylaminopropyl)carbodiimide hydrochloride (403 mg), 1-hydroxybenzotriazole monohydrate (284 mg), and 4-[(6,7-dimethoxy-4-quinolyl)oxy]aniline (498 mg) were added thereto. The mixture was then stirred with heating under reflux for 2 hr. A saturated aqueous sodium hydrogencarbonate solution was added to stop the reaction, and the reaction solution was extracted with chloroform, followed by washing with a saturated aqueous sodium hydrogencarbonate solution, 1 N hydrochloric acid, water, and saturated brine. The extract was then dried over sodium sulfate. After the concentration of the extract, the residue was purified on a column using chloroform/methanol to give N1-{4-[(6,7-dimethoxy-4-quinolyl)oxy]phenyl}-2-(2,4-dichlorophenoxy)acetamide (500 mg, yield 72%).

N1-{4-[(6,7-Dimethoxy-4-quinolyl)oxy]phenyl}-2-(2,4-dichlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%).

$^1$H-NMR (CDCl$_3$-$d_1$, 400 MHz): δ 3.76 (t, J=5.4 Hz, 2H), 4.11 (s, 3H), 4.14 (s, 3H), 4.47 (t, J=5.4 Hz, 2H), 6.81 (d, J=6.6 Hz, 1H), 7.08 (d, J=8.8 Hz, 1H), 7.23–7.27 (m, 3H), 7.38 (d, J=2.7 Hz, 1H), 7.54 (d, J=8.8 Hz, 2H), 7.69–7.70

(m, 1H), 8.01 (s, 1H), 8.65 (d, J=6.6 Hz, 1H) Mass spectrometry value (ESI-MS, m/z): 486 (M$^+$+1)

Example 852

N-{4-[(6,7-Dimethoxy-4-quinolyl)oxy]phenyl}-N-[2-(2-methylphenoxy)ethyl]amine

N1-{4-[(6,7-Dimethoxy-4-quinolyl)oxy]phenyl}-2-(2-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-d$_1$, 400 MHz): δ 2.11 (s, 3H), 3.88 (brs, 2H), 4.06 (s, 3H), 4.10 (s, 3H), 4.40 (brs, 2H), 6.72–6.76 (m, 3H), 6.96–7.01 (m, 2H), 7.28–7.32 (m, 2H), 7.53 (s, 1H), 7.88 (s, 1H), 7.96 (brs, 2H), 8.72 (brs, 1H) Mass spectrometry value (ESI-MS, m/z): 431 (M$^+$+1)

Example 853

N-{4-[(6,7-Dimethoxy-4-quinolyl)oxy]phenyl}-N-[2-(2-methoxyphenoxy)ethyl]amine

N1-{4-[(6,7-Dimethoxy-4-quinolyl)oxy]phenyl}-2-(2-methoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 447 (M$^+$+1)

Example 854

N-[2-(2,6-Dichlorophenoxy)ethyl]-N-{4-[(6,7-dimethoxy-4-quinolyl)oxy]phenyl}amine N1-{4-[(6,7-Dimethoxy-4-quinolyl)oxy]phenyl}-2-(2,6-dichlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%).
$^1$H-NMR (CDCl$_3$-d$_1$, 400 MHz): δ 3.59 (brs, 2H), 4.04 (s, 3H), 4.05 (s, 3H), 4.29 (t, J=5.4 Hz, 2H), 4.54 (brs, 1H), 6.43 (d, J=5.4 Hz, 1H), 6.76 (d, J=9.0 Hz, 2H), 6.98–7.05 (m, 3H), 7.27–7.31 (m, 3H), 7.41 (s, 1H), 7.59 (s, 1H), 8.46 (d, J=5.4 Hz, 1H) Mass spectrometry value (ESI-MS, m/z): 486 (M$^+$+1)

Example 855

N-{4-[(6,7-Dimethoxy-4-quinolyl)oxy]phenyl}-N-[2-(2,6-dimethylphenoxy)ethyl]amine N1-{4-[(6,7-Dimethoxy-4-quinolyl)oxy]phenyl}-2-(2,6-dimethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-d$_1$, 400 MHz): δ 2.29 (s, 6H), 3.55–3.56 (m, 2H), 3.99–4.02 (m, 2H), 4.03 (s, 3H), 4.04 (s, 3H), 4.38 (brs, 1H), 6.42 (d, J=5.4 Hz, 1H), 6.76 (d, J=8.8 Hz, 2H), 6.92–7.05 (m, 5H), 7.42 (s, 1H), 7.60 (s, 1H), 8.46 (d, J=5.4 Hz, 1H) Mass spectrometry value (ESI-MS, m/z): 445 (M$^+$+1)

Example 856

N-[2-(2,6-Dimethoxyphenoxy)ethyl]-N-{4-[(6,7-dimethoxy-4-quinolyl)oxy]phenyl}amine N1-{4-[(6,7-Dimethoxy-4-quinolyl)oxy]phenyl}-2-(2,6-dimethoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-d$_1$, 400 MHz): δ 3.37–3.39 (m, 2H), 3.85 (s, 3H), 3.88 (s, 3H), 4.039 (s, 3H), 4.044 (s, 3H), 4.28 (t, J=5.1 Hz, 2H), 5.01 (brs, 1H), 6.43 (d, J=5.4 Hz, 1H), 6.57–6.61 (m, 2H), 6.72 (d, J=8.8 Hz, 1H), 7.00–7.04 (m, 3H), 7.41 (s, 1H), 7.60 (s, 1H), 8.45 (d, J=5.1 Hz, 1H) Mass spectrometry value (ESI-MS, m/z): 477 (M$^+$+1)

Example 857

N-[2-(2,6-Difluorophenoxy)ethyl]-N-{4-[(6,7-dimethoxy-4-quinolyl)oxy]phenyl}amine N1-{4-[(6,7-Dimethoxy-4-quinolyl)oxy]phenyl}-2-(2,6-difluorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 453 ($M^+$+1)

Example 858

N-{4-[(6,7-Dimethoxy-4-quinolyl)oxy]-phenyl}-N-[2-(3,5-dimethylphenoxy)ethyl]amine N1-{4-[(6,7-Dimethoxy-4-quinolyl)oxy]phenyl}-2-(3,5-dimethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 445 ($M^+$+1)

Example 859

N-[2-(4-Chlorophenoxy)ethyl]-N-{4-[(6,7-dimethoxy-4-quinolyl)oxy]phenyl}amine

N1-{4-[(6,7-Dimethoxy-4-quinolyl)oxy]phenyl}-2-(4-chlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 452 ($M^+$+1)

Example 860

N-[2-(3-Chlorophenoxy)ethyl]-N-{4-[(6,7-dimethoxy-4-quinolyl)oxy]phenyl}amine

N1-{4-[(6,7-Dimethoxy-4-quinolyl)oxy]phenyl}-2-(3-chlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 452 ($M^+$+1)

Example 861

N-{4-[(6,7-Dimethoxy-4-quinolyl)oxy]phenyl}-N-[2-(2-ethylphenoxy)ethyl]amine

N1-{4-[(6,7-Dimethoxy-4-quinolyl)oxy]phenyl}-2-(2-ethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 445 ($M^+$+1)

Example 862

N-{4-[(6,7-Dimethoxy-4-quinazolinyl)oxy]phenyl}-N-[2-(2-methylphenoxy)ethyl]amine N1-{4-[(6,7-Dimethoxy-4-quinazolinyl)oxy]phenyl}-2-(2-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-d$_1$, 400 MHz): δ 2.26 (s, 3H), 3.58 (t, J=5.1 Hz, 2H), 4.06 (s, 3H), 4.07 (s, 3H), 4.21 (t, J=5.4 Hz, 3H), 6.75–6.91 (m, 4H), 7.08–7.18 (m, 4H), 7.31 (s, 1H), 7.57 (s, 1H), 8.63 (s, 1H) Mass spectrometry value (ESI-MS, m/z): 432 ($M^+$+1)

Example 863

N-{4-[(6,7-Dimethoxy-4-quinolyl)oxy]phenyl}-N-[2-(4-methoxyphenoxy)ethyl]amine

N1-{4-[(6,7-Dimethoxy-4-quinolyl)oxy]phenyl}-2-(4-methoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-d$_1$, 400 MHz): δ 3.52 (t, J=4.9 Hz, 2H), 3.77 (s, 3H), 4.04 (s, 3H), 4.05 (s, 3H), 4.15 (t, J=5.1 Hz, 2H), 6.74 (d, J=8.8 Hz, 2H), 6.83–6.89 (m, 4H), 7.03 (d, J=8.8 Hz, 2H), 7.41 (s, 1H), 7.59 (s, 1H), 8.45 (d, J=5.4 Hz, 1H) Mass spectrometry value (ESI-MS, m/z): 447 (M$^+$+1)

Example 864

N-{4-[(6,7-Dimethoxy-4-quinolyl)oxy]phenyl}-N-[2-(4-ethylphenoxy)ethyl]amine

N1-{4-[(6,7-Dimethoxy-4-quinolyl)oxy]phenyl}-2-(4-ethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 445 (M$^+$+1)

Example 865

N-[2-(2,5-Dichlorophenoxy)ethyl]-N-{4-[(6,7-dimethoxy-4-quinolyl)oxy]phenyl}amine

N1-{4-[(6,7-Dimethoxy-4-quinolyl)oxy]phenyl}-2-(2,5-dichlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 486 (M$^+$+1)

Example 866

N-{4-[(6,7-Dimethoxy-4-quinolyl)oxy]phenyl}-N-[2-(4-fluorophenoxy)ethyl]amine

N1-{4-[(6,7-Dimethoxy-4-quinolyl)oxy]phenyl}-2-(4-fluorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (DMSO-d$_6$, 400 MHz): δ 4.03 (s, 3H), 4.04 (s, 3H), 4.14 (t, J=5.4 Hz, 2H), 6.82–6.84 (m, 3H), 6.97–7.01 (m, 2H), 7.11–7.16 (m, 4H), 7.62 (s, 1H), 7.74 (s, 1H), 8.78 (d, J=6.6 Hz, 1H) Mass spectrometry value (ESI-MS, m/z): 435 (M$^+$+1)

Example 867

N-{4-[(6,7-Dimethoxy-4-quinolyl)oxy]phenyl}-N-[2-(4-fluorophenoxy)ethyl]-N-methylamine

Dimethylformamide (240 ml) was added to sodium hydride (1.96 g), and N1–4-[(6,7-dimethoxy-4-quinolyl)oxy]phenyl-2-(4-fluorophenoxy)acetamide (11 g) was added thereto. Subsequently, a dimethylformamide solution (10 ml) of methyl iodide (7 g) was added thereto, and the mixture was stirred at room temperature for 2 hr. Water was added to stop the reaction, and the reaction solution was then extracted with ethyl acetate, followed by washing with water and saturated brine in that order. The extract was then dried over sodium sulfate and was then concentrated, and the residue was purified on a column using hexane/acetone to give N1–4-[(6,7-dimethoxy-4-quinolyl)oxy]phenyl-N1-methyl-2-(4-fluorophenoxy)acetamide (7.1 g, yield 63%).

N1–4-[(6,7-Dimethoxy-4-quinolyl)oxy]phenyl-N1-methyl-2-(4-fluorophenoxy)acetamide (7.1 g) was dissolved in tetrahydrofuran (250 ml) to prepare a solution. A 1 M solution (46 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (3.2 g, yield 40%).
$^1$H-NMR (CDCl$_3$-d$_1$, 400 MHz): δ 3.10 (s, 3H), 3.78 (t, J=5.9 Hz, 2H), 4.07 (s, 3H), 4.08 (s, 3H), 4.14 (t, J=5.9 Hz, 2H), 6.51 (d, J=5.6 Hz, 1H), 6.82–6.85 (m, 4H), 6.94–7.00 (m, 2H), 7.06–7.08 (m, 2H), 7.61 (s, 1H), 7.64 (s, 1H), 8.45 (d, J=5.6 Hz, 1H) Mass spectrometry value (ESI-MS, m/z): 449 (M$^+$+1)

Example 868

N-[2-(2-Chlorophenoxy)ethyl]-N-{4-[(6,7-dimethoxy-4-quinolyl)oxy]phenyl}amine

N1-{4-[(6,7-Dimethoxy-4-quinolyl)oxy]phenyl}-2-(2-chlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 452 ($M^++1$)

Example 869

N-{4-[(6,7-Dimethoxy-4-quinolyl)oxy]phenyl}-N-(2-phenoxyethyl)amine

N1-{4-[(6,7-Dimethoxy-4-quinolyl)oxy]phenyl}-2-phenoxyacetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 417 ($M^++1$)

Example 870

N-{4-[(6,7-Dimethoxy-4-quinolyl)oxy]phenyl}-N-[2-(4-methylphenoxy)ethyl]amine

N1-{4-[(6,7-Dimethoxy-4-quinolyl)oxy]phenyl}-2-(4-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 431 ($M^++1$)

Example 871

N-{4-[(6,7-Dimethoxy-4-quinolyl)oxy]phenyl}-N-[2-(3-methylphenoxy)ethyl]amine

N1-{4-[(6,7-Dimethoxy-4-quinolyl)oxy]phenyl}-2-(3-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 431 ($M^++1$)

Example 872

2-(2-{4-[(6,7-Dimethoxy-4-quinolyl)oxy]anilino}ethoxy)phenol

N1-{4-[(6,7-Dimethoxy-4-quinolyl)oxy]phenyl}-2-(2-hydroxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (DMSO-$d_6$, 400 MHz): δ 4.02 (s, 3H), 4.03 (s, 3H), 4.12 (t, J=5.4 Hz, 2H), 6.71–6.95 (m, 7H), 7.15–7.17 (m, 2H), 7.62 (s, 1H), 7.73 (s, 1H), 8.77 (d, J=6.6 Hz, 1H) Mass spectrometry value (ESI-MS, m/z): 433 ($M^++1$)

Example 873

N-{4-[(6,7-Dimethoxy-4-quinazolinyl)oxy]phenyl}-N-(2-phenoxyethyl)amine

N1-{4-[(6,7-Dimethoxy-4-quinazolinyl)oxy]phenyl}-2-phenoxyacetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).
$^1$H-NMR (CDCl$_3$-$d_1$, 400 MHz): δ 3.56 (t, J=5.1 Hz, 2H), 4.07 (s, 6H), 4.21 (t, J=4.9 Hz, 2H), 6.76 (d, J=8.8 Hz, 2H), 6.93–7.00 (m, 3H), 7.09 (d, J=8.8 Hz, 2H), 7.28–7.33 (m, 2H), 7.39 (s, 1H), 7.57 (s, 1H), 8.65 (s, 1H) Mass spectrometry value (ESI-MS, m/z): 418 (M$^+$+1)

Example 874

2-(2-{4-[(6,7-Dimethoxy-4-quinazolinyl)oxy]anilino}ethoxy)phenol

N1-{4-[(6,7-Dimethoxy-4-quinazolinyl)oxy]phenyl}-2-(2-hydroxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 3.60 (t, J=5.4 Hz, 2H), 4.06 (s, 3H), 4.07 (s, 3H), 4.28 (t, J=5.4 Hz, 2H), 6.78 (d, J=8.8 Hz, 2H), 6.87–6.94 (m, 4H), 7.10 (d, J=9.0 Hz, 2H), 7.32 (s, 1H), 7.57 (s, 1H), 8.63 (s, 1H) Mass spectrometry value (ESI-MS, m/z): 434 (M$^+$+1)

Example 875

N-{4-[(6,7-Dimethoxy-4-quinolyl)oxy]-3-methylphenyl}-N-(2-phenoxyethyl)amine

N1-{4-[(6,7-Dimethoxy-4-quinolyl)oxy]-3-methylphenyl}-2-phenoxyacetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 434 (M$^+$+1)

Example 876

N-{4-[(6,7-Dimethoxy-4-quinolyl)oxy]-3-methylphenyl}-N-[2-(2-methylphenoxy)ethyl]amine N1-{4-[(6,7-Dimethoxy-4-quinolyl)oxy]-3-methylphenyl}-2-(2-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.02 (s, 3H), 2.19 (s, 3H), 3.50 (t, J=4.9 Hz, 2H), 3.96 (s, 3H), 3.98 (s, 3H), 4.12 (t, J=4.9 Hz, 2H), 6.23 (d, J=5.1 Hz, 1H), 6.50–6.54 (m, 2H), 6.76–6.89 (m, 3H), 7.07–7.10 (m, 2H), 7.34 (s, 1H), 7.55 (s, 1H), 8.35–8.36 (m, 1H) Mass spectrometry value (ESI-MS, m/z): 445 (M$^+$+1)

Example 877

N-[2-(2-Chlorophenoxy)ethyl]-N-{4-[(6,7-dimethoxy-4-quinolyl)oxy]-3-methylphenyl}amine N1-{4-[(6,7-Dimethoxy-4-quinolyl)oxy]-3-methylphenyl}-2-(2-chlorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.10 (s, 3H), 3.60 (t, J=4.9 Hz, 2H), 4.04 (s, 3H), 4.06 (s, 3H), 4.26 (t, J=5.1 Hz, 2H), 6.31 (d, J=5.4 Hz, 1H), 6.59–6.65 (m, 2H), 6.91–6.97 (m, 3H), 7.20–7.22 (m, 1H), 7.38–7.40 (m, 1H), 7.42 (s, 1H), 7.63 (s, 1H), 8.43 (d, J=5.1 Hz, 1H) Mass spectrometry value (ESI-MS, m/z): 466 (M$^+$+1)

Example 878

N-{4-[(6,7-Dimethoxy-4-quinolyl)oxy]-3-methylphenyl}-N-[2-(3-methylphenoxy)ethyl]amine N1-{4-[(6,7-Dimethoxy-4-quinolyl)oxy]-3-methylphenyl}-2-(3-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.10 (s, 3H), 2.34 (s, 3H), 3.54 (t, J=4.9 Hz, 2H), 4.04 (s, 3H), 4.06 (s, 3H), 4.18 (t, J=5.1 Hz, 2H), 6.30 (d, J=5.4 Hz, 1H), 6.56–6.61 (m, 2H), 6.74–6.81 (m, 3H), 6.95 (d, J=8.3 Hz, 1H), 7.18 (t, J=7.6 Hz, 1H), 7.42 (s, 1H), 7.63 (s, 1H), 8.43 (d, J=5.4 Hz, 1H) Mass spectrometry value (ESI-MS, m/z): 445 (M$^+$+1)

Example 879

N-{4-[(6,7-Dimethoxy-4-quinolyl)oxy]-3-methylphenyl}-N-[2-(4-methylphenoxy)ethyl]amine N1-{4-[(6,7-Dimethoxy-4-quinolyl)oxy]-3-methylphenyl}-2-(4-methylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.10 (s, 3H), 2.30 (s, 3H), 3.53 (t, J=4.9 Hz, 2H), 4.04 (s, 3H), 4.06 (s, 3H), 4.17 (t, J=5.1 Hz, 2H), 6.30 (d, J=5.1 Hz, 1H), 6.56–6.61 (m, 2H), 6.83–6.96 (m, 3H), 7.10 (d, J=8.5 Hz, 2H), 7.42 (s, 1H), 7.63 (s, 1H), 8.43 (d, J=5.4 Hz, 1H) Mass spectrometry value (ESI-MS, m/z): 445 (M$^+$+1)

Example 880

N-{4-[(6,7-Dimethoxy-4-quinolyl)oxy]-3-methylphenyl}-N-[2-(2-methoxyphenoxy)ethyl]amine N1-{4-[(6,7-Dimethoxy-4-quinolyl)oxy]-3-methylphenyl}-2-(2-methoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.10 (s, 3H), 3.55 (t, J=4.9 Hz, 2H), 3.89 (s, 3H), 4.04 (s, 3H), 4.06 (s, 3H), 4.25 (t, J=4.9 Hz, 2H), 6.29–6.31 (m, 1H), 6.57–6.61 (m, 1H), 6.89–7.11 (m, 6H), 7.43–7.44 (m, 1H), 7.61–7.65 (m, 1H), 8.44 (t, J=5.4 Hz, 1H) Mass spectrometry value (ESI-MS, m/z): 460 (M$^+$+1)

Example 881

N-{4-[(6,7-Dimethoxy-4-quinolyl)oxy]-3-methylphenyl}-N-[2-(2,6dimethylphenoxy)ethyl]amine N1-{4-[(6,7-Dimethoxy-4-quinolyl)oxy]-3-methylphenyl}-2-(2,6-dimethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.11 (s, 3H), 2.30 (s, 6H), 3.55 (t, J=5.1 Hz, 2H), 4.02 (t, J=4.9 Hz, 2H), 4.05 (s, 3H), 4.07 (s, 3H), 6.30 (d, J=5.4 Hz, 1H), 6.60–6.64 (m, 2H), 6.94–6.98 (m, 2H), 7.02–7.04 (m, 2H), 7.43 (s, 1H), 7.63 (s, 1H), 8.44 (t, J=5.1 Hz, 1H) Mass spectrometry value (ESI-MS, m/z): 459 (M$^+$+1)

Example 882

N-[2-(2 6-Dimethoxyphenoxy)ethyl]-N-{4-[(6,7-dimethoxy-4-quinolyl)oxy]-3-methylphenyl}amine N1-{4-[(6,7-Dimethoxy-4-quinolyl)oxy]-3-methylphenyl}-2-(2,6-dimethoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%).

$^1$H-NMR (CDCl$_3$-d$_1$, 400 MHz): δ 2.10 (s, 3H), 3.38 (brs, 2H), 3.89 (s, 6H), 4.05 (s, 3H), 4.06 (s, 3H), 4.27 (t, J=5.1 Hz, 2H), 4.94 (brs, 1H), 6.31 (d, J=5.1 Hz, 1H), 6.56–6.61 (m, 4H), 6.94 (d, J=8.5 Hz, 1H), 7.02 (t, J=8.3 Hz, 1H), 7.43 (s, 1H), 7.64 (s, 1H), 8.44 (t, J=5.4 Hz, 1H) Mass spectrometry value (ESI-MS, m/z): 491 (M$^+$+1)

Example 883

N-[2-(2,6-Difluorophenoxy)ethyl]-N-{4-[(6,7-dimethoxy-4-quinolyl)oxy]-3-methylphenyl}amine N1-{4-[(6,7-Dimethoxy-4-quinolyl)oxy]-3-methylphenyl}-2-(2,6-difluorophenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.10 (s, 3H), 3.50 (brs, 2H), 4.05 (s, 3H), 4.06 (s, 3H), 4.37 (t, J=5.1 Hz, 2H), 6.31 (d, J=5.4 Hz, 1H), 6.57–6.63 (m, 2H), 6.89–6.99 (m, 4H), 7.43 (s, 1H), 7.63 (s, 1H), 8.44 (d, J=5.4 Hz, 1H) Mass spectrometry value (ESI-MS, m/z): 467 (M$^+$+1)

Example 884

N-[2-(2,6-Dimethoxyphenoxy)ethyl]-N-{4-[(6,7-dimethoxy-4-quinolyl)oxy]-2,3-dimethylphenyl}amine N1-{4-[(6,7-Dimethoxy-4-quinolyl)oxy]-2,3-dimethylphenyl}-2-(2,6-dimethoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%).

$^1$H-NMR (CDCl$_3$-d$_1$, 400 MHz): δ 2.10 (s, 3H), 2.24 (s, 3H), 3.44 (t, J=4.4 Hz, 2H), 3.87 (s, 6H), 4.05 (s, 3H), 4.07 (s, 3H), 4.32 (t, J=4.6 Hz, 2H), 4.72 (brs, 1H), 6.27 (d, J=5.4 Hz, 1H), 6.58–6.62 (m, 3H), 6.91 (d, J=8.8 Hz, 1H), 7.03 (t, J=8.5 Hz, 1H), 7.43 (s, 1H), 7.66 (s, 1H), 8.42 (d, J=5.4 Hz, 1H) Mass spectrometry value (ESI-MS, m/z): 505 (M$^+$+1)

Example 885

N-{4-[(6,7-Dimethoxy-4-quinolyl)oxy]phenyl}-N-(3-phenoxypropyl)amine

N1-{4-[(6,7-Dimethoxy-4-quinolyl)oxy]phenyl}-3-phenoxypropaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.30–2.33 (m, 2H), 3.91 (s, 3H), 3.98 (s, 3H), 4.00 (t, J=5.6 Hz, 2H), 4.34 (t, J=7.1 Hz, 2H), 6.21 (d, J=7.6 Hz, 1H), 6.86–7.01 (m, 7H), 7.27–7.32 (m, 3H), 7.47 (d, J=7.6 Hz, 1H), 7.83 (s, 1H) Mass spectrometry value (ESI-MS, m/z): 431 (M$^+$+1)

Example 886

N-{4-[(6,7-Dimethoxy-4-quinolyl)oxy]-2 5-dimethylphenyl}-N-(3-phenoxypropyl)amine N1-{4-[(6,7-Dimethoxy-4-quinolyl)oxy]-2,5-dimethylphenyl}-3-phenoxypropaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.08 (s, 3H), 2.14 (s, 3H), 2.17–2.23 (m, 2H), 3.43 (t, J=6.3 Hz, 2H), 4.04 (s, 3H), 4.06 (s, 3H), 4.16 (t, J=5.9 Hz, 2H), 6.29 (d, J=5.4 Hz, 1H), 6.54 (s, 1H), 6.82 (s, 1H), 6.93–6.97 (m, 3H), 7.28–7.32 (m, 2H), 7.43 (s, 1H), 7.62 (s, 1H), 8.42 (d, J=5.4 Hz, 1H) Mass spectrometry value (ESI-MS, m/z): 459 (M$^+$+1)

Example 887

N-{4-[(6,7-Dimethoxy-4-quinolyl)oxy]-2,3-dimethylphenyl}-N-(3-phenoxypropyl)amine N1-{4-[(6,7-Dimethoxy-4-quinolyl)oxy]-2,3-dimethylphenyl}-3-phenoxypropaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mxitue was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%).

$^1$H-NMR (CDCl$_3$-d$_1$, 400 MHz): δ 2.07 (s, 3H), 2.14 (s, 3H), 2.17–2.30 (m, 2H), 3.42 (t, J=6.3 Hz, 2H), 4.05 (s, 3H), 4.06 (s, 3H), 4.17 (t, J=5.9 Hz, 2H), 6.26 (d, J=5.4 Hz, 1H), 6.59 (d, J=8.5 Hz, 1H), 6.90–6.97 (m, 3H), 7.28–7.43 (m, 3H), 7.65 (s, 1H), 8.41 (d, J=5.4 Hz, 1H), 8.58 (d, J=4.9 Hz, 1H) Mass spectrometry value (ESI-MS, m/z): 459 (M$^+$+1)

Example 888

N-{4-[(6,7-Dimethoxy-4-quinolyl)oxy]phenyl}-N-[3-(2-methylphenoxy)propyl]amine

N1-{4-[(6,7-Dimethoxy-4-quinolyl)oxy]phenyl}-3-(2-methylphenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 445 (M$^+$+1)

Example 889

N-{4-[(6,7-Dimethoxy-4-quinolyl)oxy]-2,5-dimethylphenyl}-N-[3-(2-methylphenoxy)propyl]amine N1-{4-[(6,7-Dimethoxy-4-quinolyl)oxy]-2,5-dimethylphenyl}-3-(2-methylphenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 473 (M$^+$+1)

Example 890

N-{4-[(6,7-Dimethoxy-4-quinolyl)oxy]-2,3-dimethylphenyl}-N-[3-(2-methylphenoxy)propyl]amine N1-{4-[(6,7-Dimethoxy-4-quinolyl)oxy]-2,3-dimethylphenyl}-3-(2-methylphenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH 1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 473 (M$^+$+1)

Example 891

N-[3-(2-Chlorophenoxy)propyl]-N-{4-[(6,7-dimethoxy-4-quinolyl)oxy]phenyl}amine

N1-{4-[(6,7-Dimethoxy-4-quinolyl)oxy]phenyl}-3-(2-chlorophenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 466 (M$^+$+1)

Example 892

N-[3-(2-Chlorophenoxy)propyl]-N-{4-[(6,7-dimethoxy-4-quinolyl)oxy]-2,5-dimethylphenyl}amine N1-{4-[(6,7-Dimethoxy-4-quinolyl)oxy]-2,5-dimethylphenyl}-3-(2-chlorophenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%). Mass spectrometry value (ESI-MS, m/z): 494 (M$^+$+1)

Example 893

N-[3-(2-Chlorophenoxy)propyl]-N-{4-(6,7-dimethoxy-4-quinolyl)oxy]-2,3-dimethylphenyl}amine N1-{4-[(6,7-Dimethoxy-4-quinolyl)oxy]-2,3-dimethylphenyl}-3-(2-chlorophenoxy)propaneamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%). Mass spectrometry value (ESI-MS, m/z): 494 (M$^+$+1)

Example 894

N-{4-[(6,7-Dimethoxy-4-quinolyl)oxy]-2,3-dimethylphenyl}-N-[2-(2,6-dimethylphenoxy)ethyl]amine N1-{4-[(6,7-Dimethoxy-4-quinolyl)oxy]-2,3-dimethylphenyl}-2-(2,6-dimethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 473 (M$^+$+1)

Example 895

N-{4-[(6,7-Dimethoxy-4-quinolyl)oxy]-2,5-dimethylphenyl}-N-[2-(2,6-dimethylphenoxy)ethyl]amine N1-{4-[(6,7-Dimethoxy-4-quinolyl)oxy]-2,5-dimethylphenyl}-2-(2,6-dimethylphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (155 mg, yield 80%). Mass spectrometry value (ESI-MS, m/z): 473 (M$^+$+1)

Example 896

N-[2-(2,6-Dimethoxyphenoxy)ethyl]-N-{4-[(6,7-dimethoxy-4-quinolyl)oxy]-2,5-dimethylphenyl}amine N1-{4-[(6,7-Dimethoxy-4-quinolyl)oxy]-2,5-dimethylphenyl}-2-(2,6-dimethoxyphenoxy)acetamide (200 mg) was dissolved in tetrahydrofuran (10 ml) to prepare a solution. A 1 M solution (1.3 ml) of a borane-tetrahydrofuran complex in tetrahydrofuran was then added to the solution, and the mixture was stirred with heating under reflux for 2 hr. The reaction solution was cooled to 0° C. and was adjusted to pH=1 by the addition of 1 N hydrochloric acid, followed by stirring with heating under reflux for 30 min. The reaction solution was cooled to 0° C., was adjusted to pH=12 by the addition of a 1 N aqueous sodium hydroxide solution, and was extracted with chloroform. After the concentration of the extract, the residue was purified on a column using chloroform/methanol to give the title compound (156 mg, yield 80%). Mass spectrometry value (ESI-MS, m/z): 505 (M$^+$+1)

Example 897

N-Benzoyl-N'-{4-[(6,7-dimethoxy-4-quinolyl)oxy]phenyl}thiourea

4-[(6,7-Dimethoxy-4-quinolyl)oxy]aniline (50 mg) was dissolveed in toluene (5 ml) and ethanol (1 ml) to prepare a solution. Commercially available 1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (78 mg, yield 94%).

$^1$H-NMR (CDCl$_3$, 400 MHz): δ 4.02 (s, 6H), 6.54 (d, J=5.12 Hz, 1H), 7.22 (d, J=8.78 Hz, 2H), 7.33–7.77 (m, 5H), 7.81 (t, J=3.42 Hz, 1H), 7.83–7.95 (m, 3H), 8.02 (d, J=8.76 Hz, 1H), 8.49 (d, J=5.12 Hz, 1H), 9.42 (bs, 1H) Mass spectrometry value (ESI-MS, m/z): 460 (M$^+$+1)

Example 898

N-(2-Chlorobenzoyl)-N'-{4-[(6,7-dimethoxy-4-quinolyl)oxy]phenyl}thiourea

4-[(6,7-Dimethoxy-4-quinolyl)oxy]aniline (50 mg) was dissolved in toluene (5 ml) and ethanol (1 ml) to prepare a solution. Commercially available 2-chloro-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (83 mg, yield 100%).

$^1$H-NMR (CDCl$_3$, 400 MHz): δ 4.07 (s, 6H), 6.57 (d, J=5.37 Hz, 1H), 7.23–7.29 (m, 3H), 7.44–7.47 (m, 2H), 7.53–7.54 (m, 3H), 7.79–7.86 (m, 3H), 8.53 (d, J=5.37 Hz, 1H), 9.23 (s, 1H) Mass spectrometry value (ESI-MS, m/z): 494 (M$^+$+1)

Example 899

N-{4-[(6,7-Dimethoxy-4-quinolyl)oxy]phenyl}-N'-(2-fluorobenzoyl)thiourea

2-Fluoro-1-benzenecarbonyl isothiocyanate was prepared using commercially available 2-fluoro-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (75 mg, yield 93%).

$^1$H-NMR (CDCl$_3$, 400 MHz): δ 4.06 (s, 6H), 6.57 (d, J=5.37 Hz, 1H), 7.23–7.29 (m, 5H), 7.39 (m, 1H), 7.44 (s, 1H), 7.54 (s, 1H), 7.64–7.67 (m, 1H), 7.83 (d, J=9.03 Hz, 2H), 8.13 (m, 1H), 8.53 (d, J=5.37 Hz, 1H) Mass spectrometry value (ESI-MS, m/z): 478 (M$^+$+1)

Example 900

N-(2-Bromobenzoyl)-N'-{4-[(6,7-dimethoxy-4-quinolyl)oxy]phenyl}thiourea

2-Bromo-1-benzenecarbonyl isothiocyanate was prepared using commercially available 2-bromo-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml). A solution of 2-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (85 mg, yield 93%).

$^1$H-NMR (DMSO-d$_6$, 400 MHz): δ 3.93 (s, 3H), δ 3.95 (s, 3H), 6.56 (d, J=5.12 Hz, 1H), 7.32 (d, J=8.30 Hz, 2H), 7.41 (d, J=5.61 Hz, 1H), 7.44–7.52 (m, 3H), 7.62 (t, J=7.19 Hz, 1H), 7.72 (d, J=7.81 Hz, 1H), 7.84 (d, J=8.78 Hz, 2H), 8.31 (s, 1H), 8.52 (s, 1H) Mass spectrometry value (ESI-MS, m/z): 539 (M$^+$+1)

Example 901

N-{4-[(6,7-Dimethoxy-4-quinolyl)oxy]phenyl}-N'-(2-methoxybenzoyl)thiourea

2-Methoxy-1-benzenecarbonyl isothiocyanate was prepared using commercially available 2-methoxy-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (83 mg, yield 96%).

$^1$H-NMR (CDCl$_3$, 400 MHz): δ 4.11 (s, 3H), 4.13 (s, 3H), 4.17 (s, 3H), 6.77 (d, J=6.01 Hz, 1H), 7.19 (t, J=7.69 Hz, 1H), 7.26–7.29 (m, 6H), 7.61–7.65 (m, 2H), 7.99 (d, J=8.78 Hz, 1H), 8.13 (s, 1H), 8.24 (dd, J=1.83 Hz, J=7.93 Hz, 1H), 8.51 (m, 1H) Mass spectrometry value (ESI-MS, m/z): 490 (M$^+$+1)

Example 902

N-{4-[(6,7-Dimethoxy-4-quinolyl)oxy]phenyl}-N'-[2-(trifluoromethyl)benzoyl]thiourea 2-(Trifluoromethyl)-1-benzenecarbonyl isothiocyanate was prepared using commercially available 2-(trifluoromethyl)-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (83 mg, yield 95%).

$^1$H-NMR (DMSO-d$_6$, 400 MHz): δ 3.93 (s, 3H), 3.95 (s, 3H), 6.56 (d, J=5.12 Hz, 1H), 7.32 (d, J=8.78 Hz, 2H), 7.40 (s, 1H), 7.49 (s, 1H), 7.75–7.86 (m, 6H), 8.51 (d, J=5.12 Hz, 1H), 12.13 (s, 1H), 12.33 (s, 1H) Mass spectrometry value (ESI-MS, m/z): 528 (M$^+$+1)

Example 903

N-Benzoyl-N'-{4-[(6,7-dimethoxy-4-quinolyl)oxy]-2-fluorophenyl}thiourea

4-[(6,7-Dimethoxy-4-quinolyl)oxy]-2-fluoroaniline (50 mg) was dissolved in toluene (5 ml) and ethanol (1 ml) to prepare a solution. Commercially available 1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (76 mg, yield 80%).

$^1$H-NMR (CDCl$_3$, 400 MHz): δ 4.04 (s, 3H), 4.06 (s, 3H), 6.64 (d, J=5.12 Hz, 1H), 7.04–7.07 (m, 2H), 7.26 (s, 2H), 7.45 (s, 1H), 7.48 (s, 1H), 7.57 (t, J=7.69 Hz, 1H), 7.68 (t, J=7.44 Hz, 1H), 7.93 (d, J=7.39 Hz, 2H), 8.46 (t, J=8.79 Hz, 1H), 8.57 (d, J=5.12 Hz, 1H), 9.22 (s, 1H) Mass spectrometry value (ESI-MS, m/z): 478 (M$^+$+1)

Example 904

N-{4-[(6,7-Dimethoxy-4-quinolyl)oxy]-2-fluorophenyl}-N'-(2-methylbenzoyl)thiourea 4-[(6,7-Dimethoxy-4-quinolyl)oxy]-2-fluoroaniline (50 mg) was dissolved in toluene (5 ml) and ethanol (1 ml) to prepare a solution. Commercially available 2-methyl-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (66 mg, yield 85%).

$^1$H-NMR (CDCl$_3$, 400 MHz): δ 2.58 (s, 3H), 4.08 (s, 3H), 4.12 (s, 3H), 6.72 (d, J=5.61 Hz, 1H), 7.08–7.12 (m, 2H), 7.26–7.36 (m, 3H), 7.47–7.59 (m, 3H), 7.82 (bs, 1H), 8.56 (d, J=5.85 Hz, 1H), 8.60 (m, 1H), 8.93 (s, 1H) Mass spectrometry value (ESI-MS, m/z): 492 (M$^+$+1)

Example 905

N-(2-Chlorobenzoyl)-N'-{4-[(6,7-dimethoxy-4-quinolyl)oxy]-2-fluorophenyl}thiourea 4-[(6,7-Dimethoxy-4-quinolyl)oxy]-2-fluoroaniline (50 mg) was dissolved in toluene (5 ml) and ethanol (1 ml) to prepare a solution. Commercially available 2-chloro-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (63 mg, yield 80%).

$^1$H-NMR (CDCl$_3$, 400 MHz): δ 4.04 (s, 3H), 4.06 (s, 3H), 6.64 (d, J=5.37 Hz, 1H), 7.04–7.08 (m, 2H), 7.27 (s, 1H), 7.43–7.47 (m, 3H), 7.53–7.55 (m, 2H), 7.83 (d, J=7.32 Hz, 1H), 8.48 (t, J=8.90 Hz, 1H), 8.57 (d, J=5.37 Hz, 1H), 9.39 (s, 1H) Mass spectrometry value (ESI-MS, m/z): 512 (M$^+$+1)

Example 906

N-{4-[(6,7-Dimethoxy-4-quinolyl)oxy]-2-fluorophenyl}-N'-(2-fluorobenzoyl)thiourea 2-Fluoro-1-benzenecarbonyl isothiocyanate was prepared using commercially available 2-fluoro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (63 mg, yield 80%).

$^1$H-NMR (CDCl$_3$, 400 MHz): δ 4.11 (s, 3H), 4.17 (s, 3H), 6.84 (d, J=6.59 Hz, 1H), 7.06–7.15 (m, 3H), 7.33–7.40 (m, 3H), 7.58–7.68 (m, 1H), 8.13 (bs, 2H), 8.58 (d, J=6.59 Hz, 1H), 8.73 (bs, 1H), 10.00 (bs, 1H) Mass spectrometry value (ESI-MS, m/z): 496 (M$^+$+1)

Example 907

N-(2-Bromobenzoyl)-N'-{4-[(6,7-dimethoxy-4-quinolyl)oxy]-2-fluorophenyl}thiourea 2-Bromo-1-benzenecarbonyl isothiocyanate was prepared using commercially available 2-bromo-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (73 mg, yield 83%).

$^1$H-NMR (DMSO-$d_6$, 400 MHz): δ 3.92 (s, 3H), 3.96 (s, 3H), 6.67 (d, J=5.12 Hz, 1H), 7.16 (d, J=8.78 Hz, 1H), 7.37–7.52 (m, 5H), 7.62 (d, J=7.07 Hz, 1H), 7.72 (d, J=7.56 Hz, 1H), 8.11 (t, J=8.53 Hz, 1H), 8.55 (d, J=5.12 Hz, 1H), 12.20 (s, 1H), 12.26 (s, 1H) Mass spectrometry value (ESI-MS, m/z): 557 (M$^+$+1)

Example 908

N-{4-[(6,7-Dimethoxy-4-quinolyl)oxy]-2-fluorophenyl}-N'-(2-iodobenzoyl)thiourea

2-Iodo-1-benzenecarbonyl isothiocyanate was prepared using commercially available 2-iodo-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-iodo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (86 mg, yield 90%).

$^1$H-NMR (DMSO-$d_6$, 400 MHz): δ 3.93 (s, 3H), 3.96 (s, 3H), 6.66 (d, J=5.21 Hz, 1H), 7.14 (d, J=7.56 Hz, 1H), 7.26 (t, J=5.61 Hz, 1H), 7.34–7.53 (m, 5H), 7.93 (d, J=8.35 Hz, 1H), 8.16 (m, 1H), 8.54 (d, J=5.21 Hz, 1H), 12.14 (bs, 1H), 12.32 (bs, 1H) Mass spectrometry value (ESI-MS, m/z): 604 (M$^+$+1)

Example 909

N-{4-[(6,7-Dimethoxy-4-quinolyl)oxy]-2-fluorophenyl}-N'-(2-methoxybenzoyl)thiourea 2-Methoxy-1-benzenecarbonyl isothiocyanate was prepared using commercially available 2-methoxy-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (56 mg, yield 70%).

$^1$H-NMR (DMSO-$d_6$, 400 MHz): δ 3.93 (s, 3H), 3.96 (s, 3H), 4.03 (s, 3H), 6.67 (d, J=5.37 Hz, 1H), 7.11–7.47 (m, 4H), 7.58 (m, 1H), 7.68 (m, 1H), 7.78 (m, 1H), 7.93 (d, J=6.34 Hz, 1H), 8.14 (m, 1H), 8.56 (d, J=5.37 Hz, 1H), 11.39 (s, 1H), 12.44 (s, 1H) Mass spectrometry value (ESI-MS, m/z): 508 (M$^+$+1)

Example 910

N-{4-[(6,7-Dimethoxy-4-quinolyl)oxy]-2-fluorophenyl}-N'-[2-(trifluoromethyl)benzoyl]thiourea 2-(Trifluoromethyl)-1-benzenecarbonyl isothiocyanate was prepared using commercially available 2-(trifluoromethyl)-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (69 mg, yield 80%).

$^1$H-NMR (DMSO-$d_6$, 400 MHz): δ 3.93 (s, 3H), 3.96 (s, 3H), 6.67 (d, J=5.12 Hz, 1H), 7.13 (m, 1H), 7.42–7.47 (m, 3H), 7.69–7.85 (m, 4H), 8.12 (m, 1H), 8.56 (d, J=5.12 Hz, 1H), 12.17 (s, 1H), 12.31 (s, 1H) Mass spectrometry value (ESI-MS, m/z): 546 (M$^+$+1)

Example 911

N-Benzoyl-N'-{4-[(6,7-dimethoxy-4-quinolyl)oxy]-3-fluorophenyl}thiourea

4-[(6,7-Dimethoxy-4-quinolyl)oxy]-3-fluoroaniline (50 mg) was dissolved in toluene (5 ml) and ethanol (1 ml) to prepare a solution. Commercially available 1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (64 mg, yield 85%).

$^1$H-NMR (CDCl$_3$, 400 MHz): δ 4.09 (s, 3H), 4.10 (s, 3H), 6.59 (d, J=5.85 Hz, 1H), 7.27 (s, 1H), 7.34 (t, J=8.54 Hz, 1H), 7.54–7.61 (m, 4H), 7.68–7.72 (m, 2H), 7.92 (d, J=7.80 Hz, 2H), 8.01 (d, J=11.47 Hz, 1H), 8.53 (d, J=5.85 Hz, 1H), 9.13 (bs, 1H) Mass spectrometry value (ESI-MS, m/z): 478 (M$^+$+1)

Example 912

N-{4-[(6,7-Dimethoxy-4-quinolyl)oxy]-3-fluorophenyl}-N'-(2-methylbenzoyl)thiourea 4-[(6,7-Dimethoxy-4-quinolyl)oxy]-3-fluoroaniline (50 mg) was dissolved in toluene (5 ml) and ethanol (1 ml) to prepare a solution. Commercially available 2-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (55 mg, yield 70%).

¹H-NMR (CDCl₃, 400 MHz): δ 2.58 (s, 3H), 4.11 (s, 3H), 4.16 (s, 3H), 6.71 (d, J=6.34 Hz, 1H), 7.36 (s, 1H), 7.37–7.40 (m, 3H), 7.50 (t, J=7.81 Hz, 1H), 7.57–7.64 (m, 3H), 8.06 (bs, 1H), 8.17 (d, J=9.50 Hz, 1H), 8.54 (d, J=6.34 Hz, 1H), 8.88 (s, 1H) Mass spectrometry value (ESI-MS, m/z): 492 (M⁺+1)

Example 913

N-(2-Chlorobenzoyl)-N'-{4-[(6,7-dimethoxy-4-quinolyl)oxy]-3-fluorophenyl}thiourea 4-[(6,7-Dimethoxy-4-quinolyl)oxy]-3-fluoroaniline (50 mg) was dissolved in toluene (5 ml) and ethanol (1 ml) to prepare a solution. Commercially available 2-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (61 mg, yield 75%).
¹H-NMR (CDCl₃, 400 MHz): δ 4.06 (s, 3H), 4.07 (s, 3H), 6.48 (d, J=5.12 Hz, 1H), 7.26 (s, 1H), 7.31 (t, J=8.42 Hz, 1H), 7.44–7.58 (m, 6H), 7.79 (d, J=7.56 Hz, 1H), 8.03 (d, J=11.47 Hz, 1H), 8.53 (d, J=5.12 Hz, 1H), 9.33 (bs, 1H) Mass spectrometry value (ESI-MS, m/z): 512 (M⁺+1)

Example 914

N-(2-Bromobenzoyl)-N'-{4-[(6,7-dimethoxy-4-quinolyl)oxy]-3-fluorophenyl}thiourea 2-Bromo-1-benzenecarbonyl isothiocyanate was prepared using commercially available 2-bromo-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (73 mg, yield 83%).
¹H-NMR (DMSO-d₆, 400 MHz): δ 3.96 (s, 6H), 6.51 (d, J=5.12 Hz, 1H), 7.42–7.53 (m, 7H), 7.59–7.63 (m, 2H), 7.72 (d, J=7.80 Hz, 1H), 8.10 (d, J=8.10 Hz, 1H), 8.51 (d, J=8.51 Hz, 1H) Mass spectrometry value (ESI-MS, m/z): 557 (M⁺+1)

Example 915

N-{4-[(6,7-Dimethoxy-4-quinolyl)oxy]-3-fluorophenyl}-N'-(2-iodobenzoyl)thiourea

2-Iodo-1-benzenecarbonyl isothiocyanate was prepared using commercially available 2-iodo-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2-iodo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (86 mg, yield 90%).
¹H-NMR (DMSO-d₆, 400 MHz): δ 3.25 (s, 6H), 6.50 (d, J=4.64 Hz, 1H), 7.11 (t, J=1.71 Hz, 1H), 7.24–7.52 (m, 6H), 7.61 (d, J=9.03 Hz, 1H), 7.84 (d, J=8.05 Hz, 1H), 7.93 (d, J=8.05 Hz, 1H), 8.14 (d, J=12.2 Hz, 1H), 8.49 (d, J=5.12 Hz, 1H) Mass spectrometry value (ESI-MS, m/z): 604 (M⁺+1)

Example 916

N-{4-[(6,7-Dimethoxy-4-quinolyl)oxy]-3-fluorophenyl}-N'-(2-methoxybenzoyl)thiourea 2-Methoxy-1-benzenecarbonyl isothiocyanate was prepared using commercially available 2-methoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (65 mg, yield 80%).
¹H-NMR (DMSO-d₆, 400 MHz): δ 4.03 (s, 9H), 6.95 (d, J=6.01 Hz, 1H), 7.18 (t, J=7.56 Hz, 1H), 7.31 (d, J=8.54 Hz, 1H), 7.53 (s, 1H), 7.63–7.75 (m, 4H), 7.93 (d, J=6.34 Hz, 1H), 8.21 (d, J=12.4 Hz, 1H), 8.83 (d, J=6.59 Hz, 1H), 11.35 (s, 1H), 12.72 (s, 1H) Mass spectrometry value (ESI-MS, m/z): 508 (M⁺+1)

Example 917

N-{4-[(6,7-Dimethoxy-4-quinolyl)oxy]-3-fluorophenyl}-N'-[2-(trifluoromethyl)benzoyl]thiourea 2-(Trifluoromethyl)-1-benzenecarbonyl isothiocyanate was prepared using commercially available 2-(trifluoromethyl)-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (63 mg, yield 73%).
¹H-NMR (DMSO-d₆, 400 MHz): δ 3.96 (s, 3H), 3.97 (s, 3H), 6.53 (d, J=6.34 Hz, 1H), 7.43 (s, 1H), 7.52 (t, J=9.15 Hz, 2H), 7.62–7.64 (m, 1H), 7.75–7.84 (m, 3H), 7.87–7.88 (m, 1H), 8.09 (d, J=14.6 Hz, 1H), 8.52 (d, J=5.37 Hz, 1H), 12.23 (bs, 1H), 12.37 (bs, 1H) Mass spectrometry value (ESI-MS, m/z): 546 (M⁺+1)

Example 918

N-Benzoyl-N'-{3-chloro-4-[(6,7-dimethoxy-4-quinolyl)oxy]phenyl}thiourea

3-Chloro-4-[(6,7-dimethoxy-4-quinolyl)oxy]aniline (50 mg) was dissolved in toluene (5 ml) and ethanol (1 ml) to prepare a solution. Commercially available 1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (63 mg, yield 85%).

$^1$H-NMR (CDCl$_3$, 400 MHz): δ 4.03 (s, 3H), 4.07 (s, 3H), 6.45 (d, J=5.37 Hz, 1H), 7.26 (s, 2H), 7.29 (d, J=8.78 Hz, 1H), 7.56–7.60 (m, 3H), 7.69 (t, J=7.44 Hz, 1H), 7.74 (dd, J=2.68 Hz, J=8.78 Hz, 1H), 7.92 (d, J=7.08 Hz, 2H), 8.11 (s, 1H), 8.57 (bs, 1H), 9.17 (s, 1H) Mass spectrometry value (ESI-MS, m/z): 494 (M$^+$+1)

Example 919

N-{3-Chloro-4-[(6,7-dimethoxy-4-quinolyl)oxy]phenyl}-N'-(2-methylbenzoyl)thiourea 3-Chloro-4-[(6,7-dimethoxy-4-quinolyl)oxy]aniline (50 mg) was dissolved in toluene (5 ml) and ethanol (1 ml) to prepare a solution. Commercially available 2-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (69 mg, yield 90%).

$^1$H-NMR (CDCl$_3$, 400 MHz): δ 3.51 (s, 3H) 4.06 (s, 3H), 4.07 (s, 3H), 6.42 (d, J=5.37 Hz, 1H), 7.28–7.36 (m, 4H), 7.47–7.59 (m, 4H), 7.75 (dd, J=2.44 Hz, 8.78 Hz, 1H), 8.11 (d, J=2.44 Hz, 1H), 8.50 (d, J=5.37 Hz, 1H), 8.92 (s, 1H) Mass spectrometry value (ESI-MS, m/z): 509 (M$^+$+1)

Example 920

N-(2-Chlorobenzoyl)-N'-{3-chloro-4-[(6,7-dimethoxy-4-quinazolinyl)oxy]phenyl}thiourea 3-Chloro-4-[(6,7-dimethoxy-4-quinazolinyl)oxy]aniline (50 mg) was dissolved in toluene (5 ml) and ethanol (1 ml) to prepare a solution. Commercially available 2-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (79 mg, yield 90%).

$^1$H-NMR (CDCl$_3$, 400 MHz): δ 3.95 (s, 3H), 3.96 (s, 3H), 6.43 (d, J=5.12 Hz, 1H), 7.43–7.59 (m, 5H), 7.64 (d, J=7.81 Hz, 1H), 7.76 (d, J=11.22 Hz, 1H), 8.19 (bs, 1H), 8.52 (d, 1H, J=5.37 Hz), 12.12 (bs, 1H), 12.38 (bs, 1H) Mass spectrometry value (ESI-MS, m/z): 530 (M$^+$+1)

Example 921

N-{3-Chloro-4-[(6,7-dimethoxy-4-quinolyl)oxy]phenyl}-N'-(2-fluorobenzoyl)thiourea 2-Fluoro-1-benzenecarbonyl isothiocyanate was prepared using commercially available 2-fluoro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (66 mg, yield 86%).

$^1$H-NMR (CDCl$_3$, 400 MHz): δ 3.95 (s, 3H), 3.96 (s, 3H), 6.43 (d, J=5.12 Hz, 1H), 7.34–7.39 (m, 2H), 7.43 (s, 1H), 7.51 (t, J=9.15 Hz, 2H), 7.56–7.69 (m, 3H), 8.17 (bs, 1H), 8.52 (d, J=5.37 Hz, 1H), 11.79 (bs, 1H), 12.43 (bs, 1H) Mass spectrometry value (ESI-MS, m/z): 512 (M$^+$+1)

Example 922

N-(2-Bromobenzoyl)-N'-{3-chloro-4-[(6,7-dimethoxy-4-quinolyl)oxy]phenyl}thiourea 2-Bromo-1-benzenecarbonyl isothiocyanate was prepared using commercially available 2-bromo-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (61 mg, yield 70%).

$^1$H-NMR (DMSO-d$_6$, 400 MHz): δ 3.95 (s, 3H) 3.96 (s, 3H), 6.43 (d, J=5.12 Hz, 1H), 7.32–7.53 (m, 5H), 7.60 (d, J=5.86 Hz, 1H), 7.72–7.76 (m, 2H), 8.20 (bs, 1H), 8.51 (d, J=5.12 Hz, 1H), 12.12 (s, 1H), 12.39 (s, 1H) Mass spectrometry value (ESI-MS, m/z): 573 (M$^+$+1)

Example 923

N-{3-Chloro-4-[(6,7-dimethoxy-4-quinolyl)oxy]phenyl}-N'-(2-methoxybenzoyl)thiourea 2-Methoxy-1-benzenecarbonyl isothiocyanate was prepared using commercially available 2-methoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 85%).

$^1$H-NMR (DMSO-d$_6$, 400 MHz): δ 3.95 (s, 3H), 3.96 (s, 3H), 4.03 (s, 3H), 6.43 (d, J=5.37 Hz, 1H), 7.19 (t, J=7.32 Hz, 1H), 7.31 (d, J=8.05 Hz, 1H), 7.43 (s, 1H), 7.49–7.54 (m, 3H), 7.68 (t, J=8.78 Hz, 1H), 7.78 (dd, J=2.68 Hz, J=9.03 Hz, 1H), 7.93 (d, J=9.76 Hz, 1H), 8.52 (d, J=5.13 Hz, 1H), 11.33 (bs, 1H), 2.59 (bs, 1H) Mass spectrometry value (ESI-MS, m/z): 525 (M$^+$+1)

Example 924

N-{3-Chloro-4-[(6,7-dimethoxy-4-quinolyl)oxy]phenyl}-N'-[2-(trifluoromethyl)benzoyl]thiourea 2-(Trifluoromethyl)-1-benzenecarbonyl isothiocyanate was prepared using commercially available 2-(trifluoromethyl)-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (61 mg, yield 85%).

$^1$H-NMR (DMSO-$d_6$, 400 MHz): δ 3.95 (s, 3H), 3.96 (s, 3H), 6.42 (d, J=5.02 Hz, 1H), 7.42 (s, 1H), 7.48 (d, J=8.78 Hz, 1H), 7.53 (s, 1H), 7.75–7.87 (m, 6H), 8.19 (bs, 1H), 8.50 (d, J=5.12 Hz, 1H), 12.21 (s, 1H) Mass spectrometry value (ESI-MS, m/z): 562 (M$^+$+1)

Example 925

N-{4-[(6,7-Dimethoxy-4-quinolyl)oxy]-2-nitrophenyl}-N'-(2-methylbenzoyl)thiourea 4-[(6,7-Dimethoxy-4-quinolyl)oxy]-2-nitroaniline (50 mg) was dissolved in toluene (5 ml) and ethanol (1 ml) to prepare a solution. Commercially available 2-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (66 mg, yield 80%).

$^1$H-NMR (DMSO-$d_6$, 400 MHz): δ 2.36 (s, 3H), 3.93 (s, 3H), 3.94 (s, 3H), 6.52 (d, J=5.37 Hz, 1H), 7.15–7.22 (m, 3H), 7.28–7.39 (m, 3H), 7.42 (dd, J=2.81 Hz, 9.15 Hz, 1H), 7.50 (s, 1H), 7.54 (s, 1H), 7.66 (bs, 1H), 7.81 (s, 1H), 8.46 (d, J=5.12 Hz, 1H) Mass spectrometry value (ESI-MS, m/z): 519 (M$^+$+1)

Example 926

N-Benzoyl-N'-{4-[(6,7-dimethoxy-4-quinazolinyl)oxy]phenyl}thiourea

4-[(6,7-Dimethoxy-4-quinazolinyl)oxy]aniline (50 mg) was dissolved in toluene (5 ml) and ethanol (1 ml) to prepare a solution. Commercially available 1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (69 mg, yield 89%).

$^1$H-NMR (CDCl$_3$, 400 MHz): δ 4.09 (s, 3H), 4.11 (s, 3H), 7.23–7.34 (m, 4H), 7.55–7.59 (m, 4H), 7.68 (t, J=7.56 Hz, 1H), 7.88–7.93 (m, 3H), 8.69 (s, 1H), 9.12 (s, 1H) Mass spectrometry value (ESI-MS, m/z): 461 (M$^+$+1)

Example 927

N-{4-[(6,7-Dimethoxy-4-quinazolinyl)oxy]phenyl}-N'-(2-methylbenzoyl)thiourea

4-[(6,7-Dimethoxy-4-quinazolinyl)oxy]aniline (50 mg) was dissolved in toluene (5 ml) and ethanol (1 ml) to prepare a solution. Commercially available 2-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (72 mg, yield 90%).

$^1$H-NMR (DMSO-$d_6$, 400 MHz): δ 2.50 (s, 3H), 3.98 (s, 3H), 3.99 (s, 3H), 7.29–7.38 (m, 7H), 7.42–7.46 (m, 1H), 7.52 (d, J=7.81 Hz, 1H), 7.57 (s, 1H), 7.80–7.82 (m, J=8.78 Hz, 2H), 8.56 (s, 1H) Mass spectrometry value (ESI-MS, m/z): 475 (M$^+$+1)

Example 928

N-(2-Chlorobenzoyl)-N'-{4-[(6,7-dimethoxy-4-quinazolinyl)oxy]phenyl}thiourea

4-[(6,7-Dimethoxy-4-quinazolinyl)oxy]aniline (50 mg) was dissolved in toluene (5 ml) and ethanol (1 ml) to prepare a solution. Commercially available 2-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (79 mg, yield 95%).

$^1$H-NMR (CDCl$_3$, 400 MHz): δ 3.98 (s, 3H), 3.99 (s, 3H), 7.37–7.40 (m, 3H), 7.45–7.49 (m, 1H), 7.53–7.58 (m, 3H), 7.65 (d, J=7.81 Hz, 1H), 7.79 (d, J=8.54 Hz, 2H), 8.58 (s, 1H), 12.04 (bs, 1H), 12.35 (bs, 1H) Mass spectrometry value (ESI-MS, m/z): 495 (M$^+$+1)

Example 929

N-{4-[(6,7-Dimethoxy-4-quinazolinyl)oxy]phenyl}-N'-(2-methoxybenzoyl)thiourea

2-Methoxy-1-benzenecarbonyl isothiocyanate was prepared using commercially available 2-methoxy-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (74 mg, yield 90%).

$^1$H-NMR (DMSO-$d_6$, 400 MHz): δ 3.97 (s, 3H), 4.03 (s, 3H), 4.05 (s, 3H), 6.81 (d, J=6.34 Hz, 1H), 7.11–7.12 (m, 1H), 7.17–7.23 (m, 2H), 7.31 (d, J=8.54 Hz, 1H), 7.53–7.80 (m, 3H), 7.88 (dd, J=2.56 Hz, 8.91 Hz, 1H), 7.81 (d, J=7.81 Hz, 1H), 8.30 (s, 1H), 8.81 (d, J=6.34 Hz, 1H), 11.4 (s, 1H) Mass spectrometry value (ESI-MS, m/z): 491 (M$^+$+1)

Example 930

N-{4-[(6,7-Dimethoxy-4-quinolyl)oxy]phenyl}-N'-(3-methylbenzoyl)thiourea

4-[(6,7-Dimethoxy-4-quinolyl)oxy]aniline (50 mg) was dissolved in toluene (5 ml) and ethanol (1 ml) to prepare a solution. Commercially available 3-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 96%).

$^1$H-NMR (CDCl$_3$, 400 MHz): δ 2.48 (s, 3H), 4.08 (s, 3H), 4.11 (s, 3H), 6.65 (d, J=5.85 Hz, 1H), 7.23–7.29 (m, 2H), 7.43–7.58 (m, 3H), 7.61 (s, 1H), 7.72 (t, J=8.66 Hz, 3H), 7.89 (d, J=8.78 Hz, 2H), 8.51 (d, J=5.85 Hz, 1H), 9.13 (s, 1H) Mass spectrometry value (ESI-MS, m/z): 474 (M$^+$+1)

Example 931

N-{4-[(6,7-Dimethoxy-4-quinolyl)oxy]phenyl}-N'-(3-fluorobenzoyl)thiourea

3-Fluoro-1-benzenecarbonyl isothiocyanate was prepared using commercially available 3-fluoro-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (70 mg, yield 87%).
$^1$H-NMR (CDCl$_3$, 400 MHz): δ 4.05 (s, 3H), 4.06 (s, 3H), 6.57 (d, J=5.12 Hz, 1H), 7.24–7.26 (m, 3H), 7.35–7.40 (m, 1H), 7.44 (s, 1H), 7.54–7.59 (m, 2H), 7.64–7.68 (m, 2H), 7.80–7.84 (m, 2H), 8.53 (d, J=5.12 Hz, 1H), 9.09 (bs, 1H) Mass spectrometry value (ESI-MS, m/z): 478 (M$^+$+1)

Example 932

N-(3-Chlorobenzoyl)-N'-{4-[(6,7-dimethoxy-4-quinolyl)oxy]phenyl}thiourea

4-[(6,7-Dimethoxy-4-quinolyl)oxy]aniline (50 mg) was dissolved in toluene (5 ml) and ethanol (1 ml) to prepare a solution. Commercially available 3-chloro-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (77 mg, yield 93%).
$^1$H-NMR (CDCl$_3$, 400 MHz): δ 4.05 (s, 3H), 4.06 (s, 3H), 6.58 (d, J=5.37 Hz, 1H), 7.24–7.92 (m, 11H), 8.52 (d, J=5.37 Hz, 1H), 9.13 (bs, 1H) Mass spectrometry value (ESI-MS, m/z): 494 (M$^+$+1)

Example 933

N-{4-[(6,7-Dimethoxy-4-quinolyl)oxy]phenyl}-N'-(3-methoxybenzoyl)thiourea

3-Methoxy-1-benzenecarbonyl isothiocyanate was prepared using commercially available 3-methoxy-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (70 mg, yield 80%).
$^1$H-NMR (CDCl$_3$, 400 MHz): δ 3.90 (s, 3H), 4.05 (s, 3H), 4.06 (s, 3H), 6.57 (d, J=5.37 Hz, 1H), 7.13–7.16 (m, 2H), 7.23–7.26 (m, 2H), 7.37–7.49 (m, 4H), 7.54 (s, 1H), 7.81–7.84 (m, 2H), 8.53 (d, J=5.37 Hz, 1H), 9.13 (s, 1H) Mass spectrometry value (ESI-MS, m/z): 490 (M$^+$+1)

Example 934

N-{4-[(6,7-Dimethoxy-4-quinolyl)oxy]phenyl}-N'-[3-(trifluoromethyl)benzoyl]thiourea 3-(Trifluoromethyl)-1-benzenecarbonyl isothiocyanate was prepared using commercially available 3-(trifluoromethyl)-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 75%).
$^1$H-NMR (CDCl$_3$, 400 MHz): δ 3.94 (s, 3H), 3.96 (s, 3H), 6.59 (d, J=5.37 Hz, 1H), 7.35 (d, J=8.78 Hz, 2H), 7.43 (s, 1H), 7.53 (s, 1H), 7.78–7.85 (m, 3H), 8.04 (d, J=8.05 Hz, 1H), 8.26 (d, J=8.05 Hz, 1H), 8.35 (s, 1H), 8.55 (d, J=5.37 Hz, 1H), 11.79 (s, 1H), 12.49 (s, 1H) Mass spectrometry value (ESI-MS, m/z): 528 (M$^+$+1)

Example 935

N-(3-Bromobenzoyl)-N'-{4-[(6,7-dimethoxy-4-quinolyl)oxy]phenyl}thiourea

3-Bromo-1-benzenecarbonyl isothiocyanate was prepared using commercially available 3-bromo-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 74%).
$^1$H-NMR (CDCl$_3$, 400 MHz): δ 4.05 (s, 3H), 4.06 (s, 3H), 6.66 (d, J=5.12 Hz, 1H), 7.24–7.26 (m, 3H), 7.44–7.47 (m, 2H), 7.53 (s, 1H), 7.80–7.84 (m, 4H), 8.07 (bs, 1H), 8.53 (d, J=5.12 Hz, 1H), 9.03 (bs, 1H) Mass spectrometry value (ESI-MS, m/z): 539 (M$^+$+1)

Example 936

N-{4-[(6,7-Dimethoxy-4-quinolyl)oxy]-2-fluorophenyl}-N'-(3-methylbenzoyl)thiourea 4-[(6,7-Dimethoxy-4-quinolyl)oxy]-2-fluoroaniline (50 mg) was dissolved in toluene (5 ml) and ethanol (1 ml) to prepare a solution. Commercially available 3-methyl-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (68 mg, yield 87%).
$^1$H-NMR (CDCl$_3$, 400 MHz): δ 2.47 (s, 3H), 4.04 (s, 3H), 4.06 (s, 3H), 6.64 (d, J=5.12 Hz, 1H), 7.03–7.07 (m, 2H), 7.26 (s, 2H), 7.42–7.49 (m, 3H), 7.07–7.73 (m, 2H), 8.46 (t, J=8.90 Hz, 1H), 8.57 (d, J=5.12 Hz, 1H), 9.18 (bs, 1H) Mass spectrometry value (ESI-MS, m/z): 492 (M$^+$+1)

Example 937

N-{4-[(6,7-Dimethoxy-4-quinolyl)oxy]-2-fluorophenyl}-N'-(3-fluorobenzoyl)thiourea 3-Fluoro-1-benzenecarbonyl isothiocyanate was prepared using commercially available 3-fluoro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (71 mg, yield 90%).
$^1$H-NMR (DMSO-$d_6$, 400 MHz): δ 3.93 (s, 3H), 3.96 (s, 3H), 6.67 (d, J=5.37 Hz, 1H), 7.38–7.73 (m, 6H), 7.84–7.86 (m, 1H), 8.05 (m, 2H), 8.29 (s, 1H), 8.56 (d, J=5.12 Hz, 1H), 11.9 (s, 1H) Mass spectrometry value (ESI-MS, m/z): 496 ($M^+$+1)

Example 938

N-(3-Chlorobenzoyl)-N'-{4-[(6,7-dimethoxy-4-quinolyl)oxy]-2-fluorophenyl}thiourea 4-[(6,7-Dimethoxy-4-quinolyl)oxy]-2-fluoroaniline (50 mg) was dissolved in toluene (5 ml) and ethanol (1 ml) to prepare a solution. Commercially available 3-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (76 mg, yield 93%).
$^1$H-NMR (CDCl$_3$, 400 MHz): δ 4.04 (s, 3H), 4.06 (s, 3H), 6.63 (d, J=5.13 Hz, 1H), 6.65–7.07 (m, 2H), 7.26–7.27 (m, 1H), 7.45–7.53 (m, 3H), 7.65 (d, J=8.05 Hz, 1H), 7.80 (d, J=8.78 Hz, 1H), 7.94 (s, 1H), 8.44 (t, J=7.93 Hz, 1H), 8.57 (d, J=5.13 Hz, 1H), 9.17 (bs, 1H) Mass spectrometry value (ESI-MS, m/z): 512 ($M^+$+1)

Example 939

N-{4-[(6,7-Dimethoxy-4-quinolyl)oxy]-2-fluorophenyl}-N'-(3-methoxybenzoyl)thiourea 3-Methoxy-1-benzenecarbonyl isothiocyanate was prepared using commercially available 3-methoxy-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 3-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (73 mg, yield 90%).
$^1$H-NMR (DMSO-$d_6$, 400 MHz): δ 3.86 (s, 3H), 3.93 (s, 3H), 3.96 (s, 3H), 6.66 (d, J=5.12 Hz, 1H), 7.16 (d, J=7.32 Hz, 1H), 7.22–7.24 (m, 1H), 7.38–7.48 (m, 4H), 7.57–7.60 (ma, 2H), 8.08 (t, J=8.91 Hz, 1H), 8.56 (d, J=5.12 Hz, 1H), 11.82 (bs, 1H), 12.55 (bs, 1H) Mass spectrometry value (ESI-MS, m/z): 508 ($M^+$+1)

Example 940

N-(3-Bromobenzoyl)-N'-{4-[(6,7-dimethoxy-4-quinolyl)oxy]-2-fluorophenyl}thiourea 3-Bromo-1-benzenecarbonyl isothiocyanate was prepared using commercially available 3-bromo-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (85 mg, yield 96%).
$^1$H-NMR (DMSO-$d_6$, 400 MHz): δ 3.93 (s, 3H), 3.96 (s, 3H), 6.66 (d, J=4.88 Hz, 1H), 7.15 (d, J=9.51 Hz, 1H), 7.36–7.39 (m, 2H), 7.41 (s, 1H), 7.46 (s, 1H), 7.51 (t, J=7.81 Hz, 1H), 7.86 (d, J=7.81 Hz, 1H), 7.98 (d, J=7.56 Hz, 1H), 8.07 (m, 1H), 8.19 (s, 1H), 8.70 (d, J=5.12 Hz, 1H), 11.98 (s, 1H) Mass spectrometry value (ESI-MS, m/z): 557 ($M^+$+1)

Example 941

N-{4-[(6,7-Dimethoxy-4-quinolyl)oxy]-3-fluorophenyl}-N'-(3-methylbenzoyl)thiourea 4-[(6,7-Dimethoxy-4-quinolyl)oxy]-3-fluoroaniline (50 mg) was dissolved in toluene (5 ml) and ethanol (1 ml) to prepare a solution. Commercially available 3-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (64 mg, yield 82%).
$^1$H-NMR (CDCl$_3$, 400 MHz): δ 2.48 (s, 3H), 4.06 (s, 3H), 4.07 (s, 3H), 6.49 (d, J=4.39 Hz, 1H), 7.26 (s, 1H), 7.30 (t, J=8.54 Hz, 1H), 7.44–7.52 (m, 4H), 7.58 (s, 1H), 7.69–7.12 (m, 2H), 8.03 (dd, J=2.44 Hz, 11.71 Hz, 1H), 8.53 (d, J=5.37 Hz, 1H), 9.13 (s, 1H) Mass spectrometry value (ESI-MS, m/z): 492 ($M^+$+1)

Example 942

N-{4-[(6,7-Dimethoxy-4-quinolyl)oxy]-3-fluorophenyl}-N'-(3-fluorobenzoyl)thiourea 3-Fluoro-1-benzenecarbonyl isothiocyanate was prepared using commercially available 3-fluoro-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (65 mg, yield 83%).
$^1$H-NMR (CDCl$_3$, 400 MHz): δ 4.10 (s, 3H), 4.15 (s, 3H), 6.68 (d, J=6.01 Hz, 1H), 7.27 (m, 2H), 7.35–7.42 (m, 2H), 7.57–7.69 (m, 4H), 7.98 (bs, 1H), 8.12 (m, 1H), 8.54 (d, J=6.34 Hz, 1H), 9.11 (s, 1H) Mass spectrometry value (ESI-MS, m/z): 496 ($M^+$+1)

Example 943

N-(3-Chlorobenzoyl)-N'-{4-[(6,7-dimethoxy-4-quinolyl)oxy]-3-fluorophenyl}thiourea 4-[(6,7-Dimethoxy-4-quinolyl)oxy]-3-fluoroaniline (50 mg) was dissolved in toluene (5 ml) and ethanol (1 ml) to prepare a solution. Commercially available 3-chloro-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (73 mg, yield 90%).

$^1$H-NMR (CDCl$_3$, 400 MHz): δ 4.09 (s, 3H), 4.11 (s, 3H), 6.60 (d, J=5.61 Hz, 1H), 7.26 (s, 1H), 7.35 (t, J=8.54 Hz, 1H), 7.51–7.56 (m, 2H), 7.61 (s, 1H), 7.65–7.68 (m, 1H), 7.77–7.79 (m, 2H), 7.91–7.92 (m, 1H), 8.08 (dd, J=2.68 Hz, 11.47 Hz, 1H), 8.53 (d, J=5.61 Hz, 1H), 9.08 (bs, 1H) Mass spectrometry value (ESI-MS, m/z): 512 (M$^+$+1)

Example 944

N-{4-[(6,7-Dimethoxy-4-quinolyl)oxy]3-fluorophenyl}-N'-(3-methoxybenzoyl)thiourea 3-Methoxy-1-benzenecarbonyl isothiocyanate was prepared using commercially available 3-methoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (73 mg, yield 90%).

$^1$H-NMR (CDCl$_3$, 400 MHz): δ 3.99 (s, 3H), 4.13 (s, 3H), 4.17 (s, 3H), 6.87 (d, J=5.61 Hz, 1H), 7.18 (dd, J=2.44 Hz, 8.29 Hz, 1H), 7.31–7.46 (m, 2H), 7.55–7.62 (m, 4H), 7.71 (s, 1H), 7.84 (s, 1H), 8.23 (dd, J=2.44 Hz, 11.95 Hz, 1H), 8.67 (d, J=6.59 Hz, 1H), 11.00 (s, 1H) Mass spectrometry value (ESI-MS, m/z): 508 (M$^+$+1)

Example 945

N-{4-[(6,7-Dimethoxy-4-quinolyl)oxy]-3-fluorophenyl}-N'-[3-(trifluoromethyl)benzoyl]thiourea 3-(Trifluoromethyl)-1-benzenecarbonyl isothiocyanate was prepared using commercially available 3-(trifluoromethyl)-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (77 mg, yield 89%).

$^1$H-NMR (DMSO-d$_6$, 400 MHz): δ 3.96 (s, 6H), 6.54 (d, J=5.37 Hz, 1H), 7.43 (s, 1H), 7.53–7.60 (m, 4H), 7.80 (t, J=8.05 Hz, 1H), 8.02–8.10 (m, 2H), 8.26 (d, J=7.81 Hz, 1H), 8.35 (s, 1H), 8.53 (d, J=4.88 Hz, 1H), 12.03 (s, 1H) Mass spectrometry value (ESI-MS, m/z): 546 (M$^+$+1)

Example 946

N-(3-Bromobenzoyl)-N'-{4-[(6,7-dimethoxy-4-quinolyl)oxy]-3-fluorophenyl}thiourea 3-Bromo-1-benzenecarbonyl isothiocyanate was prepared using commercially available 3-bromo-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (79 mg, yield 90%).

$^1$H-NMR (DMSO-d$_6$, 400 MHz): δ 3.96 (s, 6H), 6.51 (d, J=5.37 Hz, 1H), 7.41 (s, 1H), 7.48–7.60 (m, 5H), 7.86 (d, J=7.56 Hz, 1H), 7.97 (d, J=8.05 Hz, 1H), 8.08 (d, J=12.44 Hz, 1H), 8.18 (s, 1H), 8.50 (d, J=5.37 Hz, 1H), 11.84 (s, 1H) Mass spectrometry value (ESI-MS, m/z): 557 (M$^+$+1)

Example 947

N-{3-Chloro-4-[(67-dimethoxy-4-quinolyl)oxy]phenyl}-N'-(3-methylbenzoyl)thiourea 3-Chloro-4-[(6,7-dimethoxy-4-quinolyl)oxy]aniline (50 mg) was dissolved in toluene (5 ml) and ethanol (1 ml) to prepare a solution. Commercially available 3-methyl-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (71 mg, yield 92%)

$^1$H-NMR (CDCl$_3$, 400 MHz): δ 2.48 (s, 3H), 4.07 (s, 6H), 6.44 (d, J=5.61 Hz, 1H), 7.26 (s, 3H), 7.29 (d, J=8.78 Hz, 1H), 7.43–7.50 (m, 2H), 7.59 (s, 1H), 7.69–7.74 (m, 3H), 8.11 (d, J=2.44 Hz, 1H), 9.14 (s, 1H) Mass spectrometry value (ESI-MS, m/z): 509 (M$^+$+1)

Example 948

N-{3-Chloro-4-[(67-dimethoxy-4-quinolyl)oxy]phenyl}-N'-(3-fluorobenzoyl)thiourea 3-Fluoro-1-benzenecarbonyl isothiocyanate was prepared using commercially available 3-fluoro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (64 mg, yield 83%).

$^1$H-NMR (CDCl$_3$, 400 MHz): δ 3.95 (s, 3H), 3.96 (s, 3H), 6.43 (d, J=5.12 Hz, 1H), 7.43 (s, 3H), 7.49–7.54 (m, 2H), 7.59–7.62 (m, 1H), 7.75 (d, J=8.78 Hz, 1H), 7.82–7.86 (m,

1H), 8.18 (bs, 1H), 8.51 (d, J=5.12 Hz, 1H), 11.79 (bs, 1H), 12.43 (bs, 1H) Mass spectrometry value (ESI-MS, m/z): 512 (M$^+$+1)

Example 949

N-(3-Chlorobenzoyl)-N'-[3-chloro-4-(6,7-dimethoxy-4-quinolyl)oxy]phenyl}thiourea 3-Chloro-4-[(6,7-dimethoxy-4-quinolyl)oxy]aniline (50 mg) was dissolved in toluene (5 ml) and ethanol (1 ml) to prepare a solution. Commercially available 3-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 97%).
$^1$H-NMR (CDCl$_3$, 400 MHz): δ 4.06 (s, 3H), 4.07 (s, 3H), 6.46 (d, J=5.37 Hz, 1H), 7.29–7.32 (m, 4H), 7.52 (t, J=7.93 Hz, 1H), 7.61 (s, 1H), 7.64–7.66 (m, 1H), 7.71 (dd, J=2.68 Hz, 8.78 Hz, 1H), 7.87 (d, J=7.81 Hz, 1H), 8.00 (s, 1H), 8.07 (d, J=2.44 Hz, 1H), 8.51 (d, J=5.37 Hz, 1H) Mass spectrometry value (ESI-MS, m/z): 529 (M$^+$+1)

Example 950

N-{3-Chloro-4-[(6,7-dimethoxy-4-quinolyl)oxy]phenyl}-N'-(3-methoxybenzoyl)thiourea 3-Methoxy-1-benzenecarbonyl isothiocyanate was prepared using commercially available 3-methoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (65 mg, yield 82%).
$^1$H-NMR (DMSO-d$_6$, 400 MHz): δ 3.86 (s, 3H), 3.95 (s, 3H), 3.96 (s, 3H), 6.41 (d, J=5.12 Hz, 1H), 7.22 (d, J=8.54 Hz, 1H), 7.41–7.60 (m, 8H), 7.74 (d, J=8.78 Hz, 1H), 8.12 (bs, 1H), 8.50 (d, J=5.37 Hz, 1H) Mass spectrometry value (ESI-MS, m/z): 525 (M$^+$+1)

Example 951

N-{3-Chloro-4-[(6,7-dimethoxy-4-quinolyl)oxy]phenyl}-N'-[3-(trifluoromethyl)benzoyl]-thiourea 3-(Trifluoromethyl)-1-benzenecarbonyl isothiocyanate was prepared using commercially available 3-(trifluoromethyl)-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (75 mg, yield 88%).
$^1$H-NMR (DMSO-d$_6$, 400 MHz): δ 3.95 (s, 3H), 3.96 (s, 3H), 6.43 (d, J=5.37 Hz, 1H), 7.42 (s, 1H), 7.49–7.53 (m, 2H), 7.74 (d, J=9.27 Hz, 1H), 7.80 (t, J=8.05 Hz, 1H), 8.03 (d, J=7.56 Hz, 1H), 8.18 (s, 1H), 8.26 (d, J=5.37 Hz, 1H), 8.35 (s, 1H), 8.51 (d, J=5.37 Hz, 1H), 12.04 (s, 1H), 12.52 (s, 1H) Mass spectrometry value (ESI-MS, m/z): 562 (M$^+$+1)

Example 952

N-(3-Bromobenzoyl)-N'-{3-chloro-4-[(6,7-dimethoxy-4-quinolyl)oxy]phenyl}thiourea 3-Bromo-1-benzenecarbonyl isothiocyanate was prepared using commercially available 3-bromo-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (81 mg, yield 93%).
$^1$H-NMR (DMSO-d$_6$, 400 MHz): δ 4.05 (s, 3H), 4.06 (s, 3H), 6.85 (d, J=6.34 Hz, 1H), 7.50–7.54 (m, 2H), 7.66 (d, J=8.78 Hz, 1H), 7.76 (s, 1H), 7.85–7.89 (m, 2H), 7.98 (d, J=7.80 Hz, 1H), 8.19 (s, 1H), 8.28 (s, 1H), 8.84 (d, J=6.34 Hz, 1H), 11.8 (s, 1H), 12.56 (s, 1H) Mass spectrometry value (ESI-MS, m/z): 573 (M$^+$+1)

Example 953

N-{4-[(6,7-Dimethoxy-4-quinolyl)oxy]-2-nitrophenyl}-N'-(3-methylbenzoyl)thiourea 4-[(6,7-Dimethoxy-4-quinolyl)oxy]-2-nitroaniline (50 mg) was dissolved in toluene (5 ml) and ethanol (1 ml) to prepare a solution. Commercially available 3-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (69 mg, yield 91%).
$^1$H-NMR (CDCl$_3$, 400 MHz): δ 2.47 (s, 3H), 4.04 (s, 3H), 4.07 (s, 3H), 6.67 (d, J=5.37 Hz, 1H), 7.26 (s, 2H), 7.43–7.51 (m, 4H), 7.73 (d, J=7.32 Hz, 1H), 7.77 (s, 1H), 7.94 (d, J=2.68 Hz, 1H), 8.52 (d, J=9.03 Hz, 1H), 8.61 (d, J=5.12 Hz, 1H), 9.24 (s, 1H) Mass spectrometry value (ESI-MS, m/z): 519 (M$^+$+1)

Example 954

N-{4-[(6,7-Dimethoxy-4-quinazolinyl)-oxy]phenyl}-N'-(3-methylbenzoyl)thiourea

4-[(6,7-Dimethoxy-4-quinazolinyl)oxy]aniline (50 mg) was dissolved in toluene (5 ml) and ethanol (1 ml) to prepare a solution. Commercially available 3-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (76 mg, yield 95%).

$^1$H-NMR (CDCl$_3$, 400 MHz): δ 2.47 (s, 3H), 4.12 (s, 3H), 4.17 (s, 3H), 7.26–7.34 (m, 5H), 7.45–7.47 (m, 1H), 7.61 (s, 1H), 7.71 (m, 2H), 7.93 (d, J=9.03 Hz, 2H), 8.77 (s, 1H), 9.10 (s, 1H) Mass spectrometry value (ESI-MS, m/z): 475 (M$^+$+1)

Example 955

N-(3-Chlorobenzoyl)-N'-{4-[(6,7-dimethoxy-4-quinazolinyl)oxy]phenyl}thiourea

4-[(6,7-Dimethoxy-4-quinazolinyl)oxy]aniline (50 mg) was dissolved in toluene (5 ml) and ethanol (1 ml) to prepare a solution. Commercially available 3-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (80 mg, yield 96%).
$^1$H-NMR (CDCl$_3$, 400 MHz): δ 4.08 (s, 6H), 7.29 (s, 2H), 7.33 (d, J=8.78 Hz, 1H), 7.41 (s, 1H), 7.50 (t, J=7.81 Hz, 1H), 7.57 (s, 1H), 7.63 (d, J=7.32 Hz, 1H), 7.83–7.86 (m, 3H), 7.98 (s, 1H), 8.65 (s, 1H), 9.71 (s, 1H) Mass spectrometry value (ESI-MS, m/z): 495 (M$^+$+1)

Example 956

N-{4-[(6,7-Dimethoxy-4-quinazolinyl)oxy]phenyl}-N'-(3-methoxybenzoyl)thiourea

3-Methoxy-1-benzenecarbonyl isothiocyanate was prepared using commercially available 3-methoxy-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 81%).
$^1$H-NMR (DMSO-d$_6$, 400 MHz): δ 3.87 (s, 3H), 3.98 (s, 3H), 3.99 (s, 3H), 7.21–7.23 (m, 1H), 7.28–7.39 (m, 3H), 7.46 (t, J=7.93 Hz, 1H), 7.56–7.60 (m, 3H), 7.79 (d, J=8.78 Hz, 2H), 8.56 (s, 1H), 11.59 (s, 1H), 12.66 (s, 1H) Mass spectrometry value (ESI-MS, m/z): 491 (M$^+$+1)

Example 957

N-{4-[(6,7-Dimethoxy-4-quinazolinyl)oxy]phenyl}-N'-[3-(trifluoromethyl)benzoyl]thiourea 3-(Trifluoromethyl)-1-benzenecarbonyl isothiocyanate was prepared using commercially available 3-(trifluoromethyl)-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (75 mg, yield 85%).
$^1$H-NMR (DMSO-d$_6$, 400 MHz): δ 3.97 (s, 3H), 3.99 (s, 3H), 7.38–7.44 (m, 3H), 7.58 (s, 1H), 7.78–7.82 (m, 3H), 8.04 (d, J=8.05 Hz, 1H), 8.26 (d, J=7.81 Hz, 1H), 8.36 (s, 1H), 8.56 (s, 1H), 11.97 (s, 1H), 12.95 (s, 1H) Mass spectrometry value (ESI-MS, m/z): 529 (M$^+$+1)

Example 958

N-(3-Bromobenzoyl)-N'-{4-[(6,7-dimethoxy-4-quinazolinyl)oxy]phenyl}thiourea

3-Bromo-1-benzenecarbonyl isothiocyanate was prepared using commercially available 3-bromo-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (61 mg, yield 70%).
$^1$H-NMR (DMSO-d$_6$, 400 MHz): δ 3.98 (s, 3H), 3.99 (s, 3H), 7.37–7.40 (m, 3H), 7.52 (t, J=7.93 Hz, 1H), 7.58 (s, 1H), 7.78 (d, J=8.78 Hz, 2H), 7.87 (d, J=7.08 Hz, 1H), 7.97 (d, J=7.81 Hz, 1H), 8.18 (s, 1H), 8.58 (s, 1H), 11.89 (bs, 1H), 12.48 (bs, 1H) Mass spectrometry value (ESI-MS, m/z): 540 (M$^+$+1)

Example 959

N-{4-[(6,7-Dimethoxy-4-quinolyl)oxy]phenyl}-N'-(4-methylbenzoyl)thiourea

4-[(6,7-Dimethoxy-4-quinolyl)oxy]aniline (50 mg) was dissolved in toluene (5 ml) and ethanol (1 ml) to prepare a solution. Commercially available 4-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (70 mg, yield 89%).
$^1$H-NMR (CDCl$_3$, 400 MHz): δ 2.48 (s, 3H), 4.09 (s, 3H), 4.15 (s, 3H), 6.72 (d, J=6.34 Hz, 1H), 7.23–7.29 (m, 3H), 7.37 (d, J=7.81 Hz, 2H), 7.62 (s, 1H), 7.82 (d, J=8.05 Hz, 2H), 7.94 (d, J=9.03 Hz, 2H), 7.98 (s, 1H), 8.51 (d, J=5.12 Hz, 1H), 9.12 (s, 1H) Mass spectrometry value (ESI-MS, m/z): 474 (M$^+$+1)

Example 960

N-(4-Chlorobenzoyl)-N'-{4-[(6,7-dimethoxy-4-quinolyl)oxy]phenyl}thiourea

4-[(6,7-Dimethoxy-4-quinolyl)oxy]aniline (50 mg) was dissolved in toluene (5 ml) and ethanol (1 ml) to prepare a solution. Commercially available 4-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 92%).
$^1$H-NMR (CDCl$_3$, 400 MHz): δ 4.06 (s, 3H), 4.07 (s, 3H), 6.59 (d, J=5.37 Hz, 1H), 7.24–7.30 (m, 3H), 7.46–7.56 (m, 4H), 7.76–7.88 (m, 4H), 8.53 (d, J=5.37 Hz, 1H), 9.08 (bs, 1H) Mass spectrometry value (ESI-MS, m/z): 494 (M$^+$+1)

Example 961

N-{4-[(6,7-Dimethoxy-4-quinolyl)oxy]phenyl}-N'-(4-fluorobenzoyl)thiourea

4-Fluoro-1-benzenecarbonyl isothiocyanate was prepared using commercially available 4-fluoro-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (69 mg, yield 85%).
$^1$H-NMR (CDCl$_3$, 400 MHz): δ 4.05 (s, 3H), 4.06 (s, 3H), 6.57 (d, J=5.12 Hz, 1H), 7.24–7.26 (m, 5H), 7.44 (s, 1H), 7.54 (s, 1H), 7.80–7.83 (m, 2H), 7.95 (m, 2H), 8.53 (d, J=5.37 Hz, 1H), 9.09 (bs, 1H) Mass spectrometry value (ESI-MS, m/z): 478 (M$^+$+1)

Example 962

N-{4-[(6,7-Dimethoxy-4-quinolyl)oxy]phenyl}-N'-(4-nitrobenzoyl)thiourea

4-[(6,7-Dimethoxy-4-quinolyl)oxy]aniline (50 mg) was dissolved in toluene (5 ml) and ethanol (1 ml) to prepare a solution. Commercially available 4-nitro-1-benzenecarbonyl isothiocyanate (30 mg) was then added to the solution, and the mixture was stirred at room temperature for 2 hr. The reaction solution was concentrated, and the residue was purified by chromatography on silica gel using chloroform/acetone for development to give the title compound (80 mg, yield 94%).
$^1$H-NMR (CDCl$_3$, 400 MHz): δ 4.06 (s, 3H), 4.08 (s, 3H), 6.59 (d, J=5.37 Hz, 1H), 7.24–7.30 (m, 5H), 7.50 (s, 1H), 7.54 (s, 1H), 7.82–7.85 (m, 2H), 8.01–8.12 (m, 2H), 8.41–8.43 (m, 2H), 8.53 (d, J=5.37 Hz, 1H), 9.16 (bs, 1H) Mass spectrometry value (ESI-MS, m/z): 507 (M$^+$+1)

Example 963

N-{4-[(6,7-Dimethoxy-4-quinolyl)oxy]phenyl}-N'-(4-methoxybenzoyl)thiourea

4-Methoxy-1-benzenecarbonyl isothiocyanate was prepared using commercially available 4-methoxy-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 81%).
$^1$H-NMR (CDCl$_3$, 400 MHz): δ 3.92 (s, 3H), 4.05 (s, 3H), 4.06 (s, 3H), 6.57 (d, J=5.37 Hz, 1H), 7.02–7.04 (m, 2H), 7.23–7.26 (m, 3H), 7.44 (s, 1H), 7.54 (s, 1H), 7.77–7.85 (m, 2H), 7.88–7.90 (m, 2H), 8.53 (d, J=5.37 Hz, 1H), 9.07 (bs, 1H) Mass spectrometry value (ESI-MS, m/z): 490 (M$^+$+1)

Example 964

N-{4-[(6,7-Dimethoxy-4-quinolyl)oxy]-2-fluorophenyl}-N'-(4-methylbenzoyl)thiourea 4-[(6,7-Dimethoxy-4-quinolyl)oxy]-2-fluoroaniline (50 mg) was dissolved in toluene (5 ml) and ethanol (1 ml) to prepare a solution. Commercially available 4-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 98%).
$^1$H-NMR (CDCl$_3$, 400 MHz): δ 2.47 (s, 3H), 4.04 (s, 3H), 4.06 (s, 3H), 6.64 (d, J=5.37 Hz, 1H), 7.04–7.07 (m, 2H), 7.26 (s, 1H), 7.36 (d, J=8.54 Hz, 2H), 7.46 (d, J=11.95 Hz, 2H), 7.83 (d, J=8.29 Hz, 2H), 8.46 (t, J=8.90 Hz, 1H), 8.56 (d, J=5.12 Hz, 1H), 9.18 (bs, 1H) Mass spectrometry value (ESI-MS, m/z): 492 (M$^+$+1)

Example 965

N-(4-Chlorobenzoyl)-N'-{4-[(6,7-dimethoxy-4-quinolyl)oxy]-2-fluorophenyl}thiourea 4-[(6,7-Dimethoxy-4-quinolyl)oxy]-2-fluoroaniline (50 mg) was dissolved in toluene (5 ml) and ethanol (1 ml) to prepare a solution. Commercially available 4-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 94%).
$^1$H-NMR (CDCl$_3$, 400 MHz): δ 4.04 (s, 3H), 4.06 (s, 3H), 6.64 (d, J=5.12 Hz, 1H), 7.04–7.07 (m, 2H), 7.26 (s, 1H), 7.45–7.46 (m, 2H), 7.54–7.56 (m, 2H), 7.87–7.89 (m, 2H), 8.39 (t, J=8.78 Hz, 1H), 8.57 (d, J=5.37 Hz, 1H), 9.17 (s, 1H) Mass spectrometry value (ESI-MS, m/z): 512 (M$^+$+1)

Example 966

N-{4-[(6,7-Dimethoxy-4-quinolyl)oxy]-2-fluorophenyl}-N'-(4-fluorobenzoyl)thiourea 4-Fluoro-1-benzenecarbonyl isothiocyanate was prepared using commercially available 4-fluoro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (65 mg, yield 83%).
$^1$H-NMR (DMSO-d$_6$, 400 MHz): δ 3.93 (s, 3H), 3.96 (s, 3H), 6.62 (d, J=5.37 Hz, 1H), 7.17 (d, J=11.2 Hz, 1H), 7.36–7.47 (m, 5H), 8.05–8.11 (m, 3H), 8.56 (d, J=5.12 Hz, 1H), 11.88 (s, 1H), 12.48 (s, 1H) Mass spectrometry value (ESI-MS, m/z): 496 (M$^+$+1)

Example 967

N-{4-[(6,7-Dimethoxy-4-quinolyl)oxy]-2-fluorophenyl}-N'-(4-iodobenzoyl)thiourea

4-Iodo-1-benzenecarbonyl isothiocyanate was prepared using commercially available 4-iodo-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-iodo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (92 mg, yield 96%).

$^1$H-NMR (DMSO-$d_6$, 400 MHz): δ 3.96 (s, 3H), 4.03 (s, 3H), 6.67 (d, J=4.88 Hz, 1H), 7.17 (d, J=8.29 Hz, 2H), 7.39–7.47 (m, 2H), 7.77 (d, J=8.05 Hz, 2H), 7.94 (d, J=8.29 Hz, 2H), 8.06 (t, J=8.54 Hz, 1H), 8.56 (d, J=5.12 Hz, 1H), 11.90 (s, 1H), 12.44 (s, 1H) Mass spectrometry value (ESI-MS, m/z): 604 (M$^+$+1)

Example 968

N-{4-[(6,7-Dimethoxy-4-quinolyl)oxy]-2-fluorophenyl}-N'-(4-nitrobenzoyl)thiourea 4-[(6,7-Dimethoxy-4-quinolyl)oxy]-2-fluoroaniline (50 mg) was dissolved in toluene (5 ml) and ethanol (1 ml) to prepare a solution. Commercially available 4-nitro-1-benzenecarbonyl isothiocyanate (30 mg) was then added to the solution, and the mixture was stirred at room temperature for 2 hr. The reaction solution was concentrated, and the residue was purified by chromatography on silica gel using chloroform/acetone for development to give the title compound (75 mg, yield 90%).

$^1$H-NMR (CDCl$_3$, 400 MHz): δ 4.04 (s, 3H), 4.06 (s, 3H), 6.64 (dd, J=3.42 Hz, J=5.12 Hz, 1H), 7.05–7.08 (m, 2H), 7.25–7.26 (m, 2H), 7.45 (dd, J=3.17 Hz, 6.59 Hz, 2H), 8.12 (dd, J=2.93 Hz, 8.66 Hz, 2H), 8.39–8.45 (m, 3H), 8.57 (dd, J=3.42 Hz, J=5.12 Hz, 1H) Mass spectrometry value (ESI-MS, m/z): 523 (M$^+$+1)

Example 969

N-{4-[(6,7-Dimethoxy-4-quinolyl)oxy]-2-fluorophenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (71 mg, yield 88%).

$^1$H-NMR (CDCl$_3$, 400 MHz): δ 3.92 (s, 3H), 4.04 (s, 3H), 4.02 (s, 3H), 6.64 (d, J=5.12 Hz, 1H), 7.02–7.06 (m, 4H), 7.26 (s, 1H), 7.46 (d, J=12.06 Hz, 2H), 7.90 (d, J=9.03 Hz, 2H), 8.46 (t, J=9.03 Hz, 1H), 8.56 (d, J=5.12 Hz, 1H), 9.14 (s, 1H) Mass spectrometry value (ESI-MS, m/z): 508 (M$^+$+1)

Example 970

N-{4-[(6,7-Dimethoxy-4-quinolyl)oxy]-3-fluorophenyl}-N'-(4-methylbenzoyl)thiourea 4-[(6,7-Dimethoxy-4-quinolyl)oxy]-3-fluoroaniline (50 mg) was dissolved in toluene (5 ml) and ethanol (1 ml) to prepare a solution. Commercially available 4-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (77 mg, yield 98%).

$^1$H-NMR (CDCl$_3$, 400 MHz): δ 2.46 (s, 3H), 4.09 (s, 3H), 4.10 (s, 3H), 6.57 (d, J=5.37 Hz, 1H), 7.26–7.38 (m, 4H), 7.54 (d, J=8.54 Hz, 1H), 7.59 (s, 1H), 7.68 (s, 1H), 7.81 (d, J=8.29 Hz, 2H), 8.08 (dd, J=2.47 Hz, J=11.47 Hz, 1H), 8.53 (d, J=5.61 Hz, 1H), 9.09 (s, 1H) Mass spectrometry value (ESI-MS, m/z): 492 (M$^+$+1)

Example 971

N-(4-Chlorobenzoyl)-N'-{4-[(6,7-dimethoxy-4-quinolyl)oxy]-3-fluorophenyl}thiourea 4-[(6,7-Dimethoxy-4-quinolyl)oxy]-3-fluoroaniline (50 mg) was dissolved in toluene (5 ml) and ethanol (1 ml) to prepare a solution. Commercially available 4-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (78 mg, yield 96%).

$^1$H-NMR (CDCl$_3$, 400 MHz): δ 4.06 (s, 3H), 4.07 (s, 3H), 6.49 (d, J=5.12 Hz, 1H), 7.26 (s, 1H), 7.31 (t, J=8.66 Hz, 1H), 7.44 (s, 1H), 7.50 (d, J=8.78 Hz, 1H), 7.55–7.57 (m, 3H), 7.86–7.88 (m, 2H), 8.00 (dd, J=2.44 Hz, J=11.47 Hz, 1H), 8.52 (d, J=5.12 Hz, 1H)), 9.11 (s, 1H) Mass spectrometry value (ESI-MS, m/z): 512 (M$^+$+1)

Example 972

N-{4-[(6,7-Dimethoxy-4-quinolyl)oxy]-3-fluorophenyl}-N'-(4-fluorobenzoyl)thiourea 4-Fluoro-1-benzenecarbonyl isothiocyanate was prepared using commercially available 4-fluoro-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 86%).

$^1$H-NMR (CDCl$_3$, 400 MHz): δ 4.11 (s, 3H), 4.15 (s, 3H), 6.68 (d, J=6.34 Hz, 1H), 7.25–7.29 (m, 3H), 7.37 (t, J=8.54 Hz, 1H), 7.58 (d, J=9.76 Hz, 1H), 7.63 (s, 1H), 7.95–7.98

(m, 3H), 8.12 (dd, J=2.56 Hz, J=11.59 Hz, 1H), 8.54 (d, J=6.01 Hz, 1H), 9.09 (s, 1H) Mass spectrometry value (ESI-MS, m/z): 496 (M⁺+1)

Example 973

N-(4-Bromobenzoyl)-N'-{4-[(6,7-dimethoxy-4-quinolyl)oxy]-3-fluorophenyl}thiourea 4-Bromo-1-benzenecarbonyl isothiocyanate was prepared using commercially available 4-bromo-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (81 mg, yield 91%).
¹H-NMR (DMSO-d₆, 400 MHz): δ 3.96 (s, 6H), 6.52 (d, J=5.37 Hz, 1H), 7.42 (s, 1H), 7.49–7.59 (m, 3H), 7.76 (d, J=8.54 Hz, 2H), 7.94 (d, J=8.54 Hz, 2H), 8.08 (d, J=11.95 Hz, 1H), 8.51 (d, J=5.12 Hz, 1H), 11.79 (s, 1H), 12.61 (s, 1H) Mass spectrometry value (ESI-MS, m/z): 557 (M⁺+1)

Example 974

N-{4-[(6,7-Dimethoxy-4-quinolyl)oxy]-3-fluorophenyl}-N'-(4-iodobenzoyl)thiourea

4-Iodo-1-benzenecarbonyl isothiocyanate was prepared using commercially available 4-iodo-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-iodo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (84 mg, yield 88%).
¹H-NMR (DMSO-d₆, 400 MHz): δ 3.96 (s, 5H), 6.52 (d, J=5.37 Hz, 1H), 7.42–7.61 (m, 5H), 7.77 (d, J=7.07 Hz, 2H), 7.85 (d, J=8.29 Hz, 2H), 8.11 (d, J=8.54 Hz, 3H), 8.51 (d, J=5.37 Hz, 1H) Mass spectrometry value (ESI-MS, m/z): 604 (M⁺+1)

Example 975

N-{4-[(6,7-Dimethoxy-4-quinolyl)oxy]-3-fluorophenyl}-N'-(4-nitrobenzoyl)thiourea 4-[(6,7-Dimethoxy-4-quinolyl)oxy]-3-fluoroaniline (50 mg) was dissolved in toluene (5 ml) and ethanol (1 ml) to prepare a solution. Commercially available 4-nitro-1-benzenecarbonyl isothiocyanate (30 mg) was then added to the solution, and the mixture was stirred at room temperature for 2 hr. The reaction solution was concentrated, and the residue was purified by chromatography on silica gel using chloroform/acetone for development to give the title compound (79 mg, yield 96%).
¹H-NMR (CDCl₃, 400 MHz): δ 4.11 (s, 3H), 4.17 (s, 3H), 6.75 (m, 1H), 7.29 (s, 2H), 7.40 (t, J=8.54 Hz, 1H), 7.57 (m, 1H), 7.65 (s, 1H), 7.94 (s, 1H), 8.10 (d, J=11.47 Hz, 1H), 8.18–8.21 (m, 2H), 8.40–8.43 (m, 2H), 8.62 (d, J=6.34 Hz, 1H) Mass spectrometry value (ESI-MS, m/z): 523 (M⁺+1)

Example 976

N-{4-[(6,7-Dimethoxy-4-quinolyl)oxy]-3-fluorophenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (70 mg, yield 87%).
¹H-NMR (CDCl₃, 400 MHz): δ 3.87 (s, 3H), 3.96 (s, 6H), 6.52 (d, J=5.12 Hz, 1H), 7.09 (d, J=8.78 Hz, 2H), 7.43 (s, 1H), 7.49–7.54 (m, 2H), 7.61 (d, J=8.78 Hz, 1H), 8.03–8.11 (m, 3H), 8.52 (d, J=5.37 Hz, 1H), 11.52 (bs, 1H), 12.82 (bs, 1H) Mass spectrometry value (ESI-MS, m/z): 523 (M⁺+1) Mass spectrometry value (ESI-MS, m/z): 508 (M⁺+1)

Example 977

N-{3-Chloro-4-[(6,7-dimethoxy-4-quinolyl)oxy]phenyl}-N'-(4-methylbenzoyl)thiourea 3-Chloro-4-[(6,7-dimethoxy-4-quinolyl)oxy]aniline (50 mg) was dissolved in toluene (5 ml) and ethanol (1 ml) to prepare a solution. Commercially available 4-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (76 mg, yield 99%).
¹H-NMR (CDCl₃, 400 MHz): δ 2.47 (s, 3H), 4.07 (s, 6H), 6.43 (d, J=5.37 Hz, 1H), 7.26 (s, 2H), 7.29 (d, J=8.78 Hz, 2H), 7.37 (d, J=8.05 Hz, 2H), 7.59 (s, 1H), 7.73 (dd, J=2.44 Hz, J=8.78 Hz, 1H), 7.81 (d, J=8.29 Hz, 2H), 8.10 (d, J=2.44 Hz, 1H), 9.13 (s, 1H) Mass spectrometry value (ESI-MS, m/z): 509 (M⁺+1)

Example 978

N-(4-Chlorobenzoyl)-N'-[3-chloro-4-(6,7-dimethoxy-4-quinolyl)oxy]phenyl}thiourea 3-Chloro-4-[(6,7-dimethoxy-4-quinolyl)oxy]aniline (50 mg) was dissolved in toluene (5 ml) and ethanol (1 ml) to prepare a solution. Commercially available 4-chloro-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (74 mg, yield 93%).
¹H-NMR (CDCl₃, 400 MHz): δ 4.04 (s, 3H), 4.07 (s, 3H), 6.44 (d, J=5.37 Hz, 1H), 7.29–7.32 (m, 3H), 7.54–7.60 (m, 4H), 7.71 (dd, J=2.68 Hz, J=8.78 Hz, 1H), 7.93–7.95 (m, 2H), 8.07 (d, J=2.44 Hz, 1H), 8.53 (d, J=5.34 Hz, 1H) Mass spectrometry value (ESI-MS, m/z): 529 (M$^+$+1)

Example 979

N-{3-Chloro-4-[(6,7-dimethoxy-4-quinolyl)oxy]phenyl}-N'-(4-fluorobenzoyl)thiourea 4-Fluoro-1-benzenecarbonyl isothiocyanate was prepared using commercially available 4-fluoro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (67 mg, yield 87%).

$^1$H-NMR (CDCl$_3$, 400 MHz): δ 4.06 (s, 3H), 4.07 (s, 3H), 6.42 (d, J=5.37 Hz, 1H), 7.05–7.29 (m, 4H), 7.45 (s, 1H), 7.58 (s, 1H), 7.71 (dd, J=2.44 Hz, J=8.78 Hz, 1H), 7.94–7.98 (m, 2H), 8.08 (d, J=2.44 Hz, 1H), 8.52 (d, J=5.37 Hz, 1H), 9.12 (s, 1H) Mass spectrometry value (ESI-MS, m/z): 512 (M$^+$+1)

Example 980

N-(4-Bromobenzoyl)-N'-{3-chloro-4-[(6,7-dimethoxy-4-quinolyl)oxy]phenyl}thiourea 4-Bromo-1-benzenecarbonyl isothiocyanate was prepared using commercially available 4-bromo-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (80 mg, yield 83%).

$^1$H-NMR (CDCd$_3$, 400 MHz): δ 3.95 (s, 3H), 3.96 (s, 3H), 6.43 (d, J=5.12 Hz, 1H), 7.43 (s, 1H), 7.51 (d, J=8.54 Hz, 1H), 7.54 (s, 1H), 7.65–7.85 (m, 3H), 7.93 (d, J=8.54 Hz, 2H), 8.31 (bs, 1H), 8.51 (d, J=5.12 Hz, 1H), 11.81 (bs, 1H), 12.53 (bs, 1H) Mass spectrometry value (ESI-MS, m/z): 573 (M$^+$+1)

Example 981

N-{3-Chloro-4-[(6,7-dimethoxy-4-quinolyl)oxy]phenyl}-N'-(4-iodobenzoyl)thiourea

4-Iodo-1-benzenecarbonyl isothiocyanate was prepared using commercially available 4-iodo-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-iodo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (94 mg, yield 90%).

$^1$H-NMR (DMSO-d$_6$, 400 MHz): δ 3.95 (s, 3H), 3.96 (s, 3H), 6.43 (d, J=5.12 Hz, 1H), 7.43 (s, 1H), 7.49–7.54 (m, 2H), 7.66 (d, J=8.05 Hz, 1H), 7.75–7.77 (m, 2H), 7.89–7.96 (m, 2H), 8.18 (s, 1H), 8.51 (d, J=5.37 Hz, 1H), 11.77 (s, 1H), 12.54 (s, 1H) Mass spectrometry value (ESI-MS, m/z): 620 (M$^+$+1)

Example 982

N-{3-Chloro-4-[(6,7-dimethoxy-4-quinolyl)oxy]phenyl}-N'-(4-nitrobenzoyl)thiourea 3-Chloro-4-[(6,7-dimethoxy-4-quinolyl)oxy]aniline (50 mg) was dissolved in toluene (5 ml) and ethanol (1 ml) to prepare a solution. Commercially available 4-nitro-1-benzenecarbonyl isothiocyanate (30 mg) was then added to the solution, and the mixture was stirred at room temperature for 2 hr. The reaction solution was concentrated, and the residue was purified by chromatography on silica gel using chloroform/acetone for development to give the title compound (78 mg, yield 95%).

$^1$H-NMR (CDCl$_3$, 400 MHz): δ 4.08 (s, 6H), 6.45 (d, J=5.37 Hz, 1H), 7.31–7.33 (m, 3H), 7.46 (s, 1H), 7.61 (s, 1H)7.69–7.72 (m, 1H), 8.07 (d, J=2.44 Hz, 1H), 8.19–8.21 (m, 2H), 8.39–8.42 (m, 2H), 8.48 (d, J=5.37 Hz, 1H) Mass spectrometry value (ESI-MS, m/z): 539 (M$^+$+1)

Example 983

N-{3-Chloro-4-[(6,7-dimethoxy-4-quinolyl)oxy]phenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 86%).

$^1$H-NMR (CDCl$_3$, 400 MHz): δ 3.92 (s, 3H), 4.08 (s, 6H), 6.47 (d, J=5.61 Hz, 1H), 7.04–7.05 (m, 2H), 7.31–7.34 (m, 3H), 7.52 (bs, 1H), 7.62 (s, 1H), 7.73 (dd, J=2.44 Hz, 8.78 Hz, 1H), 7.97 (d, J=9.03 Hz, 2H), 8.09 (d, J=2.68 Hz, 1H), 8.50 (d, J=5.38 Hz, 1H) Mass spectrometry value (ESI-MS, m/z): 524 (M$^+$+1)

Example 984

N-{4-[(6,7-Dimethoxy-4-quinazolinyl)oxy]phenyl}-N'-(4-methylbenzoyl)thiourea

4-[(6,7-Dimethoxy-4-quinazolinyl)oxy]aniline (50 mg) was dissolved in toluene (5 ml) and ethanol (1 ml) to prepare a solution. Commercially available 4-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (73 mg, yield 92%).

¹H-NMR (CDCl₃, 400 MHz): δ 2.47 (s, 3H), 4.09 (s, 3H), 4.12 (s, 3H), 7.26–7.37 (m, 5H), 7.58–7.62 (m, 2H), 7.81 (d, J=8.29 Hz, 2H), 7.89 (d, J=8.93 Hz, 2H), 8.69 (s, 1H), 9.09 (s, 1H) Mass spectrometry value (ESI-MS, m/z): 475 (M$^+$+1)

Example 985

N-(4-Chlorobenzoyl)-N'-{4-[(6,7-dimethoxy-4-quinazolinyl)oxy]phenyl}thiourea

4-[(6,7-Dimethoxy-4-quinazolinyl)oxy]aniline (50 mg) was dissolved in toluene (5 ml) and ethanol (1 ml) to prepare a solution. Commercially available 4-chloro-1-benzenecarbonyl isothiocyanate (50 µl) was then added to the solution, and the mixture was stirred at room temperature for 2 hr. The reaction solution was concentrated, and the residue was purified by chromatography on silica gel using chloroform/acetone for development to give the title compound (82 mg, yield 98%).

¹H-NMR (CDCl₃, 400 MHz): δ 3.98 (s, 3H), 3.99 (s, 3H), 7.36–7.40 (m, 3H), 7.58–7.63 (m, 3H), 7.78 (d, J=8.54 Hz, 2H), 8.01 (d, J=8.29 Hz, 2H), 8.58 (s, 1H), 11.71 (bs, 1H), 12.50 (bs, 1H) Mass spectrometry value (ESI-MS, m/z): 495 (M$^+$+1)

Example 986

N-{4-[(6,7-Dimethoxy-4-quinazolinyl)oxy]phenyl}-N'-(4-fluorobenzoyl)thiourea

4-Fluoro-1-benzenecarbonyl isothiocyanate was prepared using commercially available 4-fluoro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (64 mg, yield 80%).

¹H-NMR (DMSO-d₆, 400 MHz): δ 3.98 (s, 3H), 3.99 (s, 3H), 7.36–7.40 (m, 5H), 7.57 (s, 1H), 7.79 (d, J=8.78 Hz, 2H), 8.07–8.11 (m, 2H), 8.57 (s, 1H), 11.65 (s, 1H), 12.58 (s, 1H) Mass spectrometry value (ESI-MS, m/z): 479 (M$^+$+1)

Example 987

N-{4-[(6,7-Dimethoxy-4-quinazolinyl)oxy]phenyl}-N'-(4-nitrobenzoyl)thiourea

4-Nitro-1-benzenecarbonyl isothiocyanate (30 mg) was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (74 mg, yield 87%).

¹H-NMR (CDCl₃, 400 MHz): δ 4.11 (s, 3H), 4.14 (s, 3H), 7.26 (s, 1H), 7.34 (d, J=8.78 Hz, 2H), 7.59 (s, 1H), 7.72 (bs, 1H), 7.89 (d, J=8.78 Hz, 2H), 8.12 (d, J=8.78 Hz, 2H), 8.42 (d, J=8.41 Hz, 2H), 8.72 (s, 1H), 9.19 (s, 1H) Mass spectrometry value (ESI-MS, m/z): 506 (M$^+$+1)

Example 988

N-{4-[(6,7-Dimethoxy-4-quinazolinyl)oxy]phenyl}-N'-(4-methoxybenzoyl)thiourea

4-Methoxy-1-benzenecarbonyl isothiocyanate was prepared using commercially available 4-methoxy-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (71 mg, yield 86%).

¹H-NMR (CDCl₃, 400 MHz): δ 3.95 (s, 3H), 4.09 (s, 3H), 4.12 (s, 3H), 7.03 (d, J=9.03 Hz, 2H), 7.26–7.33 (m, 3H), 7.58–7.63 (m, 2H), 7.89 (d, J=9.03 Hz, 4H), 8.69 (s, 1H), 9.05 (bs, 1H) Mass spectrometry value (ESI-MS, m/z): 491 (M$^+$+1)

Example 989

N-(1,3-Benzodioxol-5-ylcarbonyl)-N'-{4-[(6,7-dimethoxy-4-quinolyl)oxy]phenyl}thiourea 1,3-Benzodioxole-5-carbonyl isothiocyanate was prepared using commercially available 1,3-benzodioxole-5-carbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 1,3-benzodioxole-5-carbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 86%).

¹H-NMR (CDCl₃, 400 MHz): δ 3.93 (s, 3H), 3.95 (s, 3H), 6.15 (s, 2H), 6.56 (d, J=5.37 Hz, 1H), 7.08 (d, J=8.29 Hz, 1H), 7.32 (d, J=8.78 Hz, 2H), 7.41 (s, 1H), 7.51 (s, 1H), 7.52 (s, 1H), 7.67 (d, J=8.30 Hz, 1H), 7.82 (d, J=8.54 Hz, 2H), 8.52 (d, J=5.37 Hz, 1H), 11.39 (bs, 1H), 12.65 (bs, 1H) Mass spectrometry value (ESI-MS, m/z): 504 (M$^+$+1)

Example 990

N-{4-[(6,7-Dimethoxy-4-quinolyl)oxy]-3-fluorophenyl}-N'-(4-ethoxybenzoyl)thiourea 4-Ethoxy-1-benzenecarbonyl isothiocyanate was prepared using commercially available 4-ethoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-ethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/ acetone for development to give the title compound (76 mg, yield 92%). Mass spectrometry value (ESI-MS, m/z): 554 (M$^+$+1)

Example 991

N-{4-[(6,7-Dimethoxy-4-quinolyl)oxy]-3-fluorophenyl}-N'-(4-phenylbenzoyl)thiourea Toluene (20 ml) and thionyl chloride (1 ml) were added to commercially available 4-phenylbenzoic acid (80 mg), and the mixture was heated at 100° C. for one hr. The solvent was removed by distillation, and 4-phenyl-1-benzenecarbonyl isothiocyanate was prepared using the resultant 4-phenyl-1-benzenecarbonyl chloride as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-phenyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (76 mg, yield 92%). Mass spectrometry value (ESI-MS, m/z): 554 (M$^+$+1)

Example 992

N-{3-Chloro-4-[(6,7-dimethoxy-4-quinolyl)oxy]phenyl}-N'-(4-ethoxybenzoyl)thiourea 4-Ethoxy-1-benzenecarbonyl isothiocyanate was prepared using commercially available 4-ethoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-ethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (72 mg, yield 89%).

$^1$H-NMR (DMSO-d$_6$, 400 MHz): δ 1.38 (t, J=6.95 Hz, 3H), 3.95 (s, 3H), 3.96 (s, 3H), 4.14 (dd, J=7.08 Hz, 13.93 Hz, 2H), 6.41 (d, J=5.12 Hz, 1H), 7.05 (d, J=8.78 Hz, 2H), 7.42 (s, 1H), 7.47 (d, J=8.78 Hz, 1H), 7.53 (s, 2H), 7.26–7.75 (m, 1H), 8.02 (d, J=8.78 Hz, 2H), 8.19 (bs, 1H), 8.50 (d, J=5.37 Hz, 1H), 11.51 (s, 1H) Mass spectrometry value (ESI-MS, m/z): 539 (M$^+$+1)

Example 993

N-{4-[(6,7-Dimethoxy-4-quinolyl)oxy]-2-fluorophenyl}-N'-(4-ethylbenzoyl)thiourea 4-Ethyl-1-benzenecarbonyl isothiocyanate was prepared using commercially available 4-ethyl-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-ethyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (69 mg, yield 87%).

$^1$H-NMR (DMSO-d$_6$, 400 MHz): δ 1.21–1.24 (m, 3H), 2.69–2.72 (m, 2H), 3.93 (s, 3H), 3.96 (s, 3H), 6.65 (m, 1H), 7.14 (m, 1H), 7.38–7.47 (m, 7H), 7.95–7.97 (m, 2H), 8.11 (m, 1H), 8.55–8.56 (m, 1H) Mass spectrometry value (ESI-MS, m/z): 506 (M$^+$+1)

Example 994

N-{4-[(6,7-Dimethoxy-4-quinolyl)oxy]-2-fluorophenyl}-N'-(4-propylbenzoyl)thiourea 4-Propyl-1-benzenecarbonyl isothiocyanate was prepared using commercially available 4-propyl-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-propyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (74 mg, yield 90%).

$^1$H-NMR (DMSO-d$_6$, 400 MHz): δ 0.92 (t, J=7.08 Hz, 3H), 1.63–1.65 (m, 2H), 2.66 (m, 2H), 3.93 (s, 3H), 3.96 (s, 3H), 6.67 (m, 1H), 7.17 (m, 1H), 7.36–7.47 (m, 5H), 7.95 (d, J=8.05 Hz, 2H), 8.09 (m, 1H), 8.31 (s, 1H), 8.55 (d, J=5.37 Hz, 1H), 11.71 (s, 1H), 12.59 (s, 1H) Mass spectrometry value (ESI-MS, m/z): 520 (M$^+$+1)

Example 995

N-(4-Butylbenzoyl)-N'-{4-[(6,7-dimethoxy-4-quinolyl)oxy]-2-fluorophenyl}thiourea 4-Butyl-1-benzenecarbonyl isothiocyanate was prepared using commercially available 4-butyl-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-butyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 80%).

$^1$H-NMR (DMSO-d$_6$, 400 MHz): δ 0.92 (t, J=7.44 Hz, 3H), 1.30–1.36 (m, 2H), 1.58–1.62 (m, 2H), 2.68 (t, J=7.69 Hz, 3H), 3.93 (s, 3H), 3.96 (s, 3H), 6.57 (d, J=5.12 Hz, 1H), 7.16 (d, J=9.27 Hz, 1H), 7.36–7.47 (m, 5H), 7.95 (d, J=8.29 Hz, 2H), 8.11 (t, J=9.03 Hz, 1H), 8.29 (s, 1H), 8.55 (d, J=5.37 Hz, 1H) Mass spectrometry value (ESI-MS, m/z): 534 (M$^+$+1)

Example 996

N-[4-(Chloromethyl)benzoyl]-N'-{4-[(6,7-dimethoxy-4-quinolyl)oxy]-2-fluorophenyl}thiourea 4-(Chloromethyl)-1-benzenecarbonyl isothiocyanate was prepared using commercially available 4-(chloromethyl)-1-benzenecarbonyl chloride (80 mg) as a starting compound according to the description of the literature. 4-[(6,7-

Dimethoxy-4-quinolyl)oxy]-2-fluoroaniline (50 mg) was dissolved in toluene (5 ml) and ethanol (1 ml) to prepare a solution. A solution of 4-(chloromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 80%).

$^1$H-NMR (DMSO-d$_6$, 400 MHz): δ 3.96 (s, 3H), 3.99 (s, 3H), 4.44–4.45 (m, 2H), 6.76 (d, J=5.61 Hz, 1H), 7.22 (d, J=5.61 Hz, 1H), 7.46–7.60 (m, 4H), 7.93–7.95 (m, 1H), 8.03–8.05 (m, 1H), 8.14 (m, 1H), 8.34 (s, 1H), 8.65 (d, J=5.61 Hz, 1H), 11.88 (s, 1H), 12.55 (s, 1H) Mass spectrometry value (ESI-MS, m/z): 526 (M$^+$+1)

Example 997

N-{4-[(6,7-Dimethoxy-4-quinolyl)oxy]-3-fluorophenyl}-N'-(4-ethylbenzoyl)thiourea 4-Ethyl-1-benzenecarbonyl isothiocyanate was prepared using commercially available 4-ethyl-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-ethyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 84%).

$^1$H-NMR (DMSO-d$_6$, 400 MHz): δ 1.23 (t, J=7.50 Hz, 3H), 2.71 (dd, J=7.56 Hz, J=15.13 Hz, 2H), 3.96 (s, 6H), 6.51 (d, J=4.88 Hz, 1H), 7.39 (d, J=8.29 Hz, 2H), 7.42 (s, 1H), 7.50 (t, J=8.90 Hz, 1H), 7.54 (s, 1H), 7.61 (d, J=9.27 Hz, 1H), 7.95 (d, J=8.05 Hz, 2H), 8.10 (d, J=10.25 Hz, 1H), 8.51 (d, J=5.37 Hz, 1H), 11.40 (s, 1H), 12.50 (s, 1H) Mass spectrometry value (ESI-MS, m/z): 506 (M$^+$+1)

Example 998

N-{4-[(6,7-Dimethoxy-4-quinolyl)oxy]-3-fluorophenyl}-N'-(4-propylbenzoyl)thiourea 4-Propyl-1-benzenecarbonyl isothiocyanate was prepared using commercially available 4-propyl-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-propyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (71 mg, yield 86%).

$^1$H-NMR (DMSO-d$_6$, 400 MHz): δ 0.89–0.93 (m, 3H), 1.63–1.65 (m, 2H), 2.66 (m, 2H), 3.96 (s, 6H), 6.52 (m, 1H), 7.37–7.61 (m, 6H), 7.95 (d, J=6.83 Hz, 2H), 8.11 (m, 1H), 8.51 (d, J=5.12 Hz, 1H), 11.59 (s, 1H), 12.76 (s, 1H) Mass spectrometry value (ESI-MS, m/z): 520 (M$^+$+1)

Example 999

N-(4-Butylbenzoyl)-N'-{4-[(6,7-dimethoxy-4-quinolyl)oxy]-3-fluorophenyl}thiourea 4-Butyl-1-benzenecarbonyl isothiocyanate was prepared using commercially available 4-butyl-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-butyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (66 mg, yield 78%).

$^1$H-NMR (DMSO-d$_6$, 400 MHz): δ 0.92 (t, J=7.20 Hz, 3H), 1.32–1.36 (m, 2H), 1.58–1.62 (m, 2H), 2.68 (t, J=7.32 Hz, 2H), 3.96 (s, 6H), 6.51 (d, J=5.37 Hz, 1H), 7.36–7.59 (m, 7H), 7.94 (d, J=8.05 Hz, 2H), 8.10 (d, J=12.9 Hz, 1H), 8.30 (s, 1H), 8.51 (d, J=5.37 Hz, 1H) Mass spectrometry value (ESI-MS, m/z): 534 (M$^+$+1)

Example 1000

N-[4-(Chloromethyl)benzoyl]-N'-{4-[(6,7-dimethoxy-4-quinolyl)oxy]-3-fluorophenyl}thiourea 4-(Chloromethyl)-1-benzenecarbonyl isothiocyanate was prepared using commercially available 4-(chloromethyl)-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 4-(chloromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 81%).

$^1$H-NMR (DMSO-d$_6$, 400 MHz): δ 4.02 (s, 6H), 4.45 (s, 2H), 6.84 (m, 1H), 7.54–7.70 (m, 6H), 8.03 (d, J=6.83 Hz, 2H), 8.19 (m, 2H), 8.74 (m, 1H), 11.75 (s, 1H) Mass spectrometry value (ESI-MS, m/z): 526 (M$^+$+1)

Example 1001

N-{3-Chloro-4-[(6,7-dimethoxy-4-quinolyl)oxy]phenyl}-N'-(4-propylbenzoyl)thiourea 4-Propyl-1-benzenecarbonyl isothiocyanate was prepared using commercially available 4-propyl-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-propyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (47 mg, yield 58%).

$^1$H-NMR (DMSO-d$_6$, 400 MHz): δ 0.92–0.96 (m, 3H), 1.64–1.69 (m, 2H), 2.65–2.69 (m, 2H), 4.03 (s, 3H), 4.05 (s, 3H), 6.76 (bs, 1H), 7.34–7.36 (m, 3H), 7.70–7.72 (m, 1H), 7.81–7.83 (m, 1H), 7.96–8.01 (m, 3H), 8.23 (s, 1H), 8.28 (s, 1H), 11.08 (s, 1H), 11.57 (s, 1H) Mass spectrometry value (ESI-MS, m/z): 537 (M$^+$+1)

Example 1002

N-[4-(Chloromethyl)benzoyl]-N'-{4-[(6,7-dimethoxy-4-quinazolinyl)oxy]phenyl}thiourea 4-(Chloromethyl)-1-benzenecarbonyl isothiocyanate was prepared using commercially available 4-(chloromethyl)-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-(chloromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (77 mg, yield 90%).

$^1$H-NMR (DMSO-d$_6$, 400 MHz): δ 3.98 (s, 3H), 3.99 (s, 3H), 4.44 (d, J=5.86 Hz, 2H), 7.36–7.39 (m, 2H), 7.54–7.59 (m, 4H), 7.78–7.81 (m, 2H), 7.94 (d, J=8.29 Hz, 2H), 8.03 (d, J=8.29 Hz, 2H), 8.57 (s, 1H) Mass spectrometry value (ESI-MS, m/z): 509 (M$^+$+1)

Example 1003

N-{4-[(6,7-Dimethoxy-4-quinolyl)oxy]phenyl}-N'-(2,4-dimethylbenzoyl)thiourea

Toluene (20 ml) and thionyl chloride (1 ml) were added to commercially available 2,4-dimethylbenzoic acid (80 mg), and the mixture was heated at 100° C. for one hr. The solvent was removed by distillation, and 2,4-dimethyl-1-benzenecarbonyl isothiocyanate was prepared using the resultant 2,4-dimethyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2,4-dimethyl-1-benzenecarbonyl isothiocyanate in ethanol (1 ml) was added to the solution, and the mixture was stirred at room temperature for 2 hr. The reaction solution was concentrated, and the residue was purified by chromatography on silica gel using chloroform/acetone for development to give the title compound (77 mg, yield 93%).

$^1$H-NMR (DMSO-d$_6$, 400 MHz): δ 2.45 (s, 3H), 2.49 (s, 3H), 3.94 (s, 3H), 3.96 (s, 3H), 6.51–6.57 (m, 1H), 7.08–7.11 (m, 1H), 7.25–7.50 (m, 7H), 7.83–7.84 (m, 2H), 8.46–8.51 (m, 1H), 11.59 (s, 1H) Mass spectrometry value (ESI-MS, m/z): 488 (M$^+$+1)

Example 1004

N-{4-[(6,7-Dimethoxy-4-quinolyl)oxy]phenyl}-N'-(2,5-dimethylbenzoyl)thiourea

Toluene (20 ml) and thionyl chloride (1 ml) were added to commercially available 2,5-dimethylbenzoic acid (80 mg), and the mixture was heated at 100° C. for one hr. The solvent was removed by distillation, and 2,5-dimethyl-1-benzenecarbonyl isothiocyanate was prepared using the resultant 2,5-dimethyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2,5-dimethyl-1-benzenecarbonyl isothiocyanate in ethanol (1 ml) was added to the solution, and the mixture was stirred at room temperature for 2 hr. The reaction solution was concentrated, and the residue was purified by chromatography on silica gel using chloroform/acetone for development to give the title compound (75 mg, yield 91%).

$^1$H-NMR (DMSO-d$_6$, 400 MHz): δ 2.33 (s, 3H), 2.39 (s, 3H), 3.93 (s, 3H), 3.96 (s, 3H), 6.56 (d, J=5.37 Hz, 1H), 7.18–7.36 (m, 7H), 7.39 (s, 1H), 7.50 (s, 1H), 7.83–7.86 (m, 2H), 8.51 (d, J=5.12 Hz, 1H) Mass spectrometry value (ESI-MS, m/z): 488 (M$^+$+1)

Example 1005

N-{4-[(6,7-Dimethoxy-4-quinolyl)oxy]phenyl}-N'-(2,3-dimethylbenzoyl)thiourea

Toluene (20 ml) and thionyl chloride (1 ml) were added to commercially available 2,3-dimethylbenzoic acid (80 mg), and the mixture was heated at 100° C. for one hr. The solvent was removed by distillation, and 2,3-dimethyl-1-benzenecarbonyl isothiocyanate was prepared using the resultant 2,3-dimethyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml), and a solution of 2,3-dimethyl-1-benzenecarbonyl isothiocyanate in ethanol (1 ml) was added to the solution, and the mixture was stirred at room temperature for 2 hr. The reaction solution was concentrated, and the residue was purified by chromatography on silica gel using chloroform/acetone for development to give the title compound (81 mg, yield 98%).

$^1$H-NMR (DMSO-d$_6$, 400 MHz): δ 2.31 (s, 6H), 3.95 (s, 3H), 3.96 (s, 3H), 6.42 (d, J=5.36 Hz, 1H), 7.19 (t, J=7.40 Hz, 1H), 7.29–7.34 (m, 4H), 7.41 (s, 1H), 7.48 (d, J=8.78 Hz, 1H), 7.53 (s, 1H), 7.44–7.78 (m, 1H), 8.22–8.24 (m, 1H), 11.82 (s, 1H), 12.63 (s, 1H) Mass spectrometry value (ESI-MS, m/z): 488 (M$^+$+1)

Example 1006

N-(2,4-Difluorobenzoyl)-N'-{4-[(6,7-dimethoxy-4-quinolyl)oxy]phenyl}thiourea 2,4-Difluoro-1-benzenecarbonyl isothiocyanate was prepared using commercially available 2,4-difluoro-1-benzenecarbonyl chloride (80 mg) as a starting compound according to the description of the literature. 2,4-Difluoro-1-benzenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (69 mg, yield 82%).

$^1$H-NMR (CDCl$_3$, 400 MHz): δ 3.92 (s, 3H), 3.94 (s, 3H), 6.55 (d, J=5.12 Hz, 1H), 7.22–7.27 (m, 2H), 7.32 (d, J=9.08 Hz, 2H), 7.40–7.47 (m, 2H), 7.49 (s, 1H), 7.79–7.83 (m, 1H), 8.51 (d, J=5.12 Hz, 1H), 11.76 (s, 1H), 12.30 (s, 1H) Mass spectrometry value (ESI-MS, m/z): 496 (M$^+$+1)

Example 1007

N-(2,6-Difluorobenzoyl)-N'-{4-[(6,7-dimethoxy-4-quinolyl)oxy]phenyl}thiourea 2,6-Difluoro-1-benzenecarbonyl isothiocyanate was prepared using commercially available 2,6-difluoro-1-benzenecarbonyl chloride (80 mg) as a starting compound according to the description of the literature. 2,6-Difluoro-1-benzenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (62 mg, yield 74%).

$^1$H-NMR (DMSO-$d_6$, 400 MHz): δ 3.93 (s, 3H), 3.94 (s, 3H), 6.44 (d, J=5.12 Hz, 1H), 6.84–6.87 (m, 1H), 7.02–7.25 (m, 4H), 7.37–7.49 (m, 2H), 7.59–7.63 (m, 2H), 7.80 (bs, 1H), 8.09 (bs, 1H), 8.45 (d, J=5.37 Hz, 1H) Mass spectrometry value (ESI-MS, m/z): 496 ($M^+$+1)

Example 1008

N-(2,4-Dichlorobenzoyl)-N'-{4-[(6,7-dimethoxy-4-quinolyl)oxy]phenyl}thiourea 2,4-Dichloro-1-benzenecarbonyl isothiocyanate was prepared using commercially available 2,4-dichloro-1-benzenecarbonyl chloride (80 mg) as a starting compound according to the description of the literature. 2,4-Dichloro-1-benzenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (70 mg, yield 78%).

$^1$H-NMR (CDCl$_3$, 400 MHz): δ 4.05 (s, 3H), 4.06 (s, 3H), 6.57 (d, J=5.37 Hz, 1H), 7.26 (s, 1H), 7.35 (dd, J=2.19 Hz, J=8.42 Hz, 1H), 7.44–7.46 (m, 2H), 7.54–7.56 (m, 2H), 7.76–7.84 (m, 4H), 8.53 (d, J=5.37 Hz, 1H), 9.29 (s, 1H) Mass spectrometry value (ESI-MS, m/z): 529 ($M^+$+1)

Example 1009

N-(3,5-Dichlorobenzoyl)-N'-{4-[(6,7-dimethoxy-4-quinolyl)oxy]phenyl}thiourea 3,5-Dichloro-1-benzenecarbonyl isothiocyanate was prepared using commercially available 3,5-dichloro-1-benzenecarbonyl chloride (80 mg) as a starting compound according to the description of the literature. 3,5-Dichloro-1-benzenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (73 mg, yield 79%). Mass spectrometry value (ESI-MS, m/z): 529 ($M^+$+1)

Example 1010

N-(3,4-Dimethoxybenzoyl)-N'-{4-[(6,7-dimethoxy-4-quinolyl)oxy]phenyl}thiourea 3,5-Dimethoxy-1-benzenecarbonyl isothiocyanate was prepared using commercially available 3,5-dimethoxy-1-benzenecarbonyl chloride (80 mg) as a starting compound according to the description of the literature. 3,4-Dimethoxy-1-benzenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (70 mg, yield 80%).

$^1$H-NMR (DMSO-$d_6$, 400 MHz): δ 3.79 (s, 3H), 3.82 (s, 3H), 3.93 (s, 6H), 5.11 (bs, 1H), 6.37 (d, J=5.12 Hz, 1H), 6.66 (d, J=8.54 Hz, 2H), 6.91 (d, J=8.54 Hz, 2H), 7.03 (d, J=8.05 Hz, 1H), 7.35 (s, 1H), 7.43 (s, 1H), 7.49 (s, 1H), 7.55 (d, J=8.78 Hz, 1H), 8.29 (s, 1H), 8.41 (d, J=5.37 Hz, 1H) Mass spectrometry value (ESI-MS, m/z): 520 ($M^+$+1)

Example 1011

N-(2,4-Dichlorobenzoyl)-N'-{4-[(6,7-dimethoxy-4-quinolyl)oxy]-2-fluorophenyl}thiourea 2,4-Dichloro-1-benzenecarbonyl isothiocyanate was prepared using commercially available 2,4-dichloro-1-benzenecarbonyl chloride (80 mg) as a starting compound according to the description of the literature. 2,4-Dichloro-1-benzenecarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (78 mg, yield 90%).

$^1$H-NMR (CDCl$_3$, 400 MHz): δ 4.11 (s, 3H), 4.17 (s, 3H), 6.79 (d, J=6.34 Hz, 1H), 7.21–7.17 (m, 1H), 7.26 (s, 1H), 7.34 (d, J=10.25 Hz, 1H), 7.45–7.47 (m, 2H), 7.57 (d, J=1.95 Hz, 1H), 7.60 (s, 1H), 7.79 (d, J=8.29 Hz, 1H), 7.83 (d, J=8.29 Hz, 1H), 8.54 (d, J=6.34 Hz, 1H), 9.44 (bs, 1H) Mass spectrometry value (ESI-MS, m/z): 547 ($M^+$+1)

Example 1012

N-(2,6-Dichlorobenzoyl)-N'-{4-[(6,7-dimethoxy-4-quinolyl)oxy]-2-fluorophenyl}thiourea 2,6-Dichloro-1-benzenecarbonyl isothiocyanate was prepared using commercially available 2,6-dichloro-1-benzenecarbonyl chloride (80 mg) as a starting compound according to the description of the literature. 2,6-Dichloro-1-benzenecarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (71 mg, yield 82%).

$^1$H-NMR (CDCl$_3$, 400 MHz): δ 4.07 (s, 3H), 4.10 (s, 3H), 6.69 (d, J=5.86 Hz, 1H), 7.08–7.12 (m, 2H), 7.26–7.44 (m, 5H), 7.53 (s, 1H), 7.72 (bs, 1H), 8.55 (d, J=5.85 Hz, 1H), 8.89 (bs, 1H) Mass spectrometry value (ESI-MS, m/z): 547 (M$^+$+1)

Example 1013

N-(2,4-Difluorobenzoyl)-N'-{4-[(6,7-dimethoxy-4-quinolyl)oxy]-3-fluorophenyl}thiourea 2,4-Difluoro-1-benzenecarbonyl isothiocyanate was prepared using commercially available 2,4-difluoro-1-benzenecarbonyl chloride (80 mg) as a starting compound according to the description of the literature. 2,4-Difluoro-1-benzenecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (66 mg, yield 81%).

$^1$H-NMR (CDCl$_3$, 400 MHz): δ 4.11 (s, 3H), 4.14 (s, 3H), 6.74 (d, J=5.86 Hz, 1H), 6.89–6.99 (m, 1H), 7.00–7.09 (m, 1H), 7.12–7.16 (m, 1H), 7.37–7.42 (m, 2H), 7.58 (d, J=7.56 Hz, 1H), 7.67 (s, 1H), 7.72 (s, 1H), 8.05–8.14 (m, 2H), 8.58 (d, J=6.10 Hz, 1H) Mass spectrometry value (ESI-MS, m/z): 514 (M$^+$+1)

Example 1014

N-(2,4-Dichlorobenzoyl)-N'-{4-[(6,7-dimethoxy-4-quinolyl)oxy]-3-fluorophenyl}thiourea 2,4-Dichloro-1-benzenecarbonyl isothiocyanate was prepared using commercially available 2,4-dichloro-1-benzenecarbonyl chloride (80 mg) as a starting compound according to the description of the literature. 2,4-Dichloro-1-benzenecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (64 mg, yield 74%).

$^1$H-NMR (CDCl$_3$, 400 MHz): δ 4.14 (s, 3H), 4.18 (s, 3H), 6.91 (d, J=6.83 Hz, 1H), 7.36 (dd, J=2.07 Hz, 8.42 Hz, 1H), 7.42–7.46 (m, 4H), 7.56–7.65 (m, 2H), 7.72 (s, 1H), 7.86 (s, 1H), 8.21 (dd, J=2.44 Hz, J=11.71 Hz, 1H), 8.66 (d, J=6.59 Hz, 1H) Mass spectrometry value (ESI-MS, m/z): 547 (M$^+$+1)

Example 1015

N-(3,5-Dichlorobenzoyl)-N'-{4-[(6,7-dimethoxy-4-quinolyl)oxy]-3-fluorophenyl}thiourea 3,5-Dichloro-1-benzenecarbonyl isothiocyanate was prepared using commercially available 3,5-dichloro-1-benzenecarbonyl chloride (80 mg) as a starting compound according to the description of the literature. 3,5-Dichloro-1-benzenecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (73 mg, yield 84%).

$^1$H-NMR (CDCl$_3$, 400 MHz): δ 3.96 (s, 3H), 3.97 (s, 3H), 6.52 (d, J=5.12 Hz, 1H), 7.43 (s, 2H), 7.51–7.55 (m, 2H), 7.59 (m, 1H), 7.95 (s, 1H), 8.00 (s, 1H), 8.05–8.78 (m, 1H), 8.53 (d, J=5.37 Hz, 1H), 11.93 (bs, 1H), 12.42 (bs, 1H) Mass spectrometry value (ESI-MS, m/z): 547 (M$^+$+1)

Example 1016

N-{3-Chloro-4-[(6,7-dimethoxy-4-quinolyl)oxy]phenyl}-N'-(2,4-dimethylbenzoyl)thiourea Toluene (20 ml) and thionyl chloride (1 ml) were added to commercially available 2,4-dimethylbenzoic acid (80 mg), and the mixture was heated at 100° C. for one hr. The solvent was removed by distillation, and 2,4-dimethyl-1-benzenecarbonyl isothiocyanate was prepared using the resultant 2,4-dimethyl-1-benzenecarbonyl chloride as a starting compound according to the description of the literature. 2,4-Dimethyl-1-benzenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (75 mg, yield 97%).

$^1$H-NMR (DMSO-d$_6$, 400 MHz): δ 2.34 (s, 3H), 2.42 (s, 3H), 3.95 (s, 3H), 3.96 (s, 3H), 6.42–6.44 (m, 1H), 7.10–7.13 (m, 2H), 7.41–7.53 (m, 5H), 7.73 (m, 1H), 8.22 (m, 1H), 8.50 (m, 1H), 11.96 (s, 1H) Mass spectrometry value (ESI-MS, m/z): 523 (M$^+$+1)

Example 1017

N-{3-Chloro-4-[(6,7-dimethoxy-4-quinolyl)oxy]phenyl}-N'-(2,5-dimethylbenzoyl)thiourea Toluene (20 ml) and thionyl chloride (1 ml) were added to commercially available 2,5-dimethylbenzoic acid (80 mg), and the mixture was heated at 100° C. for one hr. The solvent was removed by distillation, and 2,4-dimethyl-1-benzenecarbonyl isothiocyanate was prepared using the resultant 2,5-dimethyl-1-benzenecarbonyl chloride as a starting compound according to the description of the literature. 2,5-Dimethyl-1-benzenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (74 mg, yield 94%).

$^1$H-NMR (DMSO-d$_6$, 400 MHz): δ 2.33 (s, 3H), 2.39 (s, 3H), 3.97 (s, 3H), 3.98 (s, 3H), 6.48 (d, J=5.37 Hz, 1H), 7.14–7.27 (m, 2H), 7.35 (s, 1H), 7.43 (s, 1H), 7.50 (d, J=8.78 Hz, 1H), 7.56 (s, 1H), 7.76 (m, 1H), 8.22–8.24 (m, 1H), 8.55 (d, J=5.37 Hz, 1H), 11.77 (s, 1H), 12.64 (s, 1H) Mass spectrometry value (ESI-MS, m/z): 523 (M$^+$+1)

Example 1018

N-{3-Chloro-4-[(6,7-dimethoxy-4-quinolyl)oxy]phenyl}-N'-(2,3-dimethylbenzoyl)thiourea Toluene (20 ml) and thionyl chloride (1 ml) were added to commercially available 2,3-dimethylbenzoic acid (80 mg), and the mixture was heated at 100° C. for one hr. The solvent was removed by distillation, and 2,3-dimethyl-1-benzenecarbonyl isothiocyanate was prepared using the resultant 2,3-dimethyl-1-benzenecarbonyl chloride as a starting compound according to the description of the literature. 2,3-Dimethyl-1-benzenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (76 mg, yield 96%).

$^1$H-NMR (DMSO-$d_6$, 400 MHz): δ 2.29 (s, 6H), 3.94 (s, 3H), 3.96 (s, 3H), 6.57 (d, J=5.12 Hz, 1H), 7.20 (t, J=7.45 Hz, 1H), 7.30–7.34 (m, 4H), 7.41 (s, 1H), 7.51 (s, 1H), 7.85–7.87 (m, 3H), 8.53 (d, J=5.12 Hz, 1H) Mass spectrometry value (ESI-MS, m/z): 523 (M$^+$+1)

Example 1019

N-{3-Chloro-4-[(6,7-dimethoxy-4-quinolyl)oxy]phenyl}-N'-(3,5-dimethylbenzoyl)thiourea Toluene (20 ml) and thionyl chloride (1 ml) were added to commercially available 3,5-dimethylbenzoic acid (80 mg), and the mixture was heated at 100° C. for one hr. The solvent was removed by distillation, and 3,5-dimethyl-1-benzenecarbonyl isothiocyanate was prepared using the resultant 3,5-dimethyl-1-benzenecarbonyl chloride as a starting compound according to the description of the literature. 3,5-Dimethyl-1-benzenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (77 mg, yield 97%).

$^1$H-NMR (DMSO-$d_6$, 400 MHz): δ 2.36 (s, 6H), 3.94 (s, 3H), 3.96 (s, 3H), 6.62 (d, J=5.12 Hz, 1H), 7.31–7.32 (m, 2H), 7.41 (s, 1H), 7.52 (s, 1H), 7.64 (s, 2H), 7.84 (m, 2H), 8.53 (d, J=5.37 Hz, 1H), 11.47 (s, 1H), 12.67 (s, 1H) Mass spectrometry value (ESI-MS, m/z): 523 (M$^+$+1)

Example 1020

N-{3-Chloro-4-[(6,7-dimethoxy-4-quinolyl)oxy]phenyl}-N'-(2,6-difluorobenzoyl)thiourea 2,6-Difluoro-1-benzenecarbonyl isothiocyanate was prepared using commercially available 2,6-difluoro-1-benzenecarbonyl chloride (80 mg) as a starting compound according to the description of the literature. 2,6-Difluoro-1-benzenecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (59 mg, yield 74%). $^1$H-NMR (DMSO-$d_6$, 400 MHz): δ 3.94 (s, 3H), 3.96 (s, 3H), 6.57 (d, J=4.64 Hz, 1H), 7.11–7.51 (m, 4H), 7.62–7.64 (m, 1H), 7.80–7.83 (m, 2H), 8.08 (m, 1H), 8.52 (d, J=5.12 Hz, 1H), 12.16 (s, 1H), 12.28 (s, 1H) Mass spectrometry value (ESI-MS, m/z): 530 (M$^+$+1)

Example 1021

N-(2,4-Difluorobenzoyl)-N'-{4-[(6,7-dimethoxy-4-quinazolinyl)oxy]phenyl}thiourea 2,4-Difluoro-1-benzenecarbonyl isothiocyanate was prepared using commercially available 2,4-difluoro-1-benzenecarbonyl chloride (80 mg) as a starting compound according to the description of the literature. 2,4-Difluoro-1-benzenecarbonyl isothiocyanate was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (77 mg, yield 92%).

$^1$H-NMR (CDCl$_3$, 400 MHz): δ 4.06 (s, 3H), 4.09 (s, 3H), 6.62 (d, J=5.61 Hz, 1H), 6.99–7.05 (m, 1H), 7.10–7.14 (m, 1H), 7.25–7.27 (m, 2H), 7.56 (s, 1H), 7.63 (s, 1H), 7.86 (d, J=8.78 Hz, 2H), 8.15–8.21 (m, 1H), 8.52 (d, J=5.61 Hz, 1H), 9.61 (d, J=14.64 Hz, 1H) Mass spectrometry value (ESI-MS, m/z): 497 (M$^+$+1)

Example 1022

N-{4-[(6,7-Dimethoxy-4-quinolyl)oxy]phenyl}-N'-(2-phenylacetyl)thiourea

2-Phenylethanoyl isothiocyanate was prepared using commercially available 2-phenylethanoyl chloride (80 mg) as a starting compound according to the description of the literature. 2-Phenylethanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (64 mg, yield 80%).

$^1$H-NMR (DMSO-$d_6$, 400 MHz): δ 3.82 (s, 2H), 3.96 (s, 3H), 3.98 (s, 3H), 6.51 (d, J=6.01 Hz, 1H), 7.25–7.35 (m, 7H), 7.44 (s, 1H), 7.48 (d, J=8.78 Hz, 1H), 7.51 (s, 1H), 7.69 (m, 1H), 8.14–8.16 (m, 1H), 8.57 (bs, 1H), 11.81 (s, 1H) Mass spectrometry value (ESI-MS, m/z): 474 (M$^+$+1)

Example 1023

N-(2-Cyclohexylacetyl)-N'-{4-[(6,7-dimethoxy-4-quinolyl)oxy]phenyl}thiourea

2-Cyclohexylethanoyl isothiocyanate was prepared using commercially available 2-cyclohexylethanoyl chloride (80 mg) as a starting compound according to the description of the literature. 2-Cyclohexylethanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (73 mg, yield 90%).

$^1$H-NMR (DMSO-$d_6$, 400 MHz): δ 0.86–1.00 (m, 2H), 1.19–1.25 (m, 6H), 1.69 (m, 3H), 2.37 (d, J=6.83 Hz, 2H), 3.96 (s, 3H), 3.99 (s, 3H), 6.67 (m, 1H), 7.34–7.36 (m, 2H), 7.44 (s, 1H), 7.59 (s, 1H), 7.81–7.84 (m, 2H), 8.63 (m, 1H), 11.48 (s, 1H), 12.41 (s, 1H) Mass spectrometry value (ESI-MS, m/z): 480 (M$^+$+1)

Example 1024

N-{4-[(6,7-Dimethoxy-4-quinolyl)oxy]-2-fluorophenyl}-N'-(2-phenylacetyl)thiourea 2-Phenylethanoyl isothiocyanate was prepared using commercially available 2-phenylethanoyl chloride (80 mg) as a starting compound according to the description of the literature. 2-Phenylethanoyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (65 mg, yield 83%).

$^1$H-NMR (DMSO-$d_6$, 400 MHz): δ 3.83 (s, 2H), 3.92 (s, 3H), 3.95 (s, 3H), 6.64 (d, J=5.12 Hz, 1H), 7.13 (d, J=9.51 Hz, 1H), 7.29–7.36 (m, 6H), 7.41 (s, 1H), 7.46 (s, 1H), 8.05 (t, J=8.66 Hz, 1H), 8.55 (d, J=5.12 Hz, 1H), 11.89 (s, 1H), 12.26 (s, 1H) Mass spectrometry value (ESI-MS, m/z): 492 (M$^+$+1)

Example 1025

N-{4-[(6,7-Dimethoxy-4-quinolyl)oxy]phenyl}-N'-[3-(2-methoxyphenyl)propanoyl]thiourea Toluene (20 ml) and thionyl chloride (1 ml) were added to commercially available 3-(2-methoxyphenyl)propanoic acid (80 mg), and the mixture was heated at 100° C. for one hr. The solvent was removed by distillation, and 3-(2-methoxyphenyl)propanoyl isothiocyanate was prepared using the resultant 3-(2-methoxyphenyl)propanoyl chloride as a starting compound according to the description of the literature. 3-(2-Methoxyphenyl)propanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 74%).

$^1$H-NMR (DMSO-$d_6$, 400 MHz): δ 2.71–2.75 (m, 2H), 2.85–2.89 (m, 2H), 3.81 (s, 3H), 3.94 (s, 3H), 3.96 (s, 3H), 6.55 (d, J=5.12 Hz, 1H), 6.87 (t, J=7.44 Hz, 1H), 6.95 (d, J=8.29 Hz, 1H), 7.16–7.22 (m, 2H), 7.28 (d, J=8.54 Hz, 2H), 7.39 (s, 1H), 7.49 (s, 1H), 7.76–7.79 (m, 2H), 8.50 (d, J=6.04 Hz, 1H), 11.49 (s, 1H), 12.59 (s, 1H) Mass spectrometry value (ESI-MS, m/z): 518 (M$^+$+1)

Example 1026

N-{4-[(6,7-Dimethoxy-4-quinolyl)oxy]-2-fluorophenyl}-N'-(3-phenylpropanoyl)thiourea Toluene (20 ml) and thionyl chloride (1 ml) were added to commercially available 3-phenylpropanoic acid (80 mg), and the mixture was heated at 100° C. for one hr. The solvent was removed by distillation, and 3-phenylpropanoyl isothiocyanate was prepared using the resultant 3-phenylpropanoyl chloride as a starting compound according to the description of the literature. 3-Phenylpropanoyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 74%).

$^1$H-NMR (CDCl$_3$, 400 MHz): δ 2.81–2.91 (m, 2H), 2.99–3.03 (m, 2H), 4.07 (s, 3H), 4.09 (s, 3H), 6.76 (d, J=6.01 Hz, 1H), 7.06–7.11 (m, 2H), 7.21–7.32 (m, 3H), 7.56 (s, 3H), 7.73 (bs, 1H), 8.48 (m, 1H), 8.59 (d, J=5.86 Hz, 1H), 11.49 (s, 1H), 12.74 (s, 1H) Mass spectrometry value (ESI-MS, m/z): 506 (M$^+$+1)

Example 1027

N-(3-Cyclopentylpropanoyl)-N'-{4-[(6,7-dimethoxy-4-quinolyl)oxy]-2-fluorophenyl}thiourea 3-Cyclopentylpropanoyl isothiocyanate was prepared using commercially available 3-cyclopentylpropanoyl chloride (80 mg) as a starting compound according to the description of the literature. 3-Cyclopentylpropanoyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (63 mg, yield 80%).

$^1$H-NMR (DMSO-$d_6$, 400 MHz): δ 1.13–1.25 (m, 4H), 1.50–1.61 (m, 7H), 1.75 (m, 2H), 3.92 (s, 3H), 3.95 (s, 3H), 6.60 (d, J=5.12 Hz, 1H), 7.34 (d, J=11.22 Hz, 1H), 7.28 (m, 1H), 7.32–7.35 (m, 1H), 7.41 (s, 1H), 7.45 (s, 1H), 8.11 (m, 1H), 8.53 (d, J=5.12 Hz, 1H), 11.63 (s, 1H) Mass spectrometry value (ESI-MS, m/z): 498 (M$^+$+1)

Example 1028

N-{4-[(6,7-Dimethoxy-4-quinolyl)oxy]-3-fluorophenyl}-N'-(3-phenylpropanoyl)thiourea Toluene (20 ml) and thionyl chloride (1 ml) were added to commercially available 3-phenylpropanoic acid (80 mg), and the mixture was heated at 100° C. for one hr. The solvent was removed by distillation, and 3-phenylpropanoyl isothiocyanate was prepared using the resultant 3-phenylpropanoyl chloride as a starting compound according to the description of the literature. 3-Phenylpropanoyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (57 mg, yield 71%).

$^1$H-NMR (DMSO-$d_6$, 400 MHz): δ 2.79–2.84 (m, 2H), 2.89–2.94 (m, 2H), 4.02 (s, 3H), 4.03 (s, 3H), 6.88 (bs, 1H), 7.21–7.33 (m, 6H), 7.59–7.61 (m, 3H), 7.72 (s, 1H), 8.13 (d, J=13.17 Hz, 1H), 11.65 (s, 1H), 12.67 (s, 1H) Mass spectrometry value (ESI-MS, m/z): 506 (M$^+$+1)

Example 1029

N-(3-Cyclopentylpropanoyl)-N'-{4-[(6,7-dimethoxy-4-quinolyl)oxy]-3-fluorophenyl}thiourea 3-Cyclopentylpropanoyl isothiocyanate was prepared using commercially available 3-cyclopentylpropanoyl chloride (80 mg) as a starting compound according to the description of the literature. 3-Cyclopentylpropanoyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (69 mg, yield 88%).

$^1$H-NMR (DMSO-$d_6$, 400 MHz): δ 1.11 (m, 2H), 1.49–1.62 (m, 7H), 1.75–1.91 (m, 4H), 3.95 (s, 3H), 3.96 (s, 3H), 6.52 (d, J=5.37 Hz, 1H), 7.43 (s, 1H), 7.47–7.56 (m, 3H), 8.05 (d, J=4.39 Hz, 1H), 8.52 (d, J=5.12 Hz, 1H), 11.58 (s, 1H), 12.66 (s, 1H) Mass spectrometry value (ESI-MS, m/z): 498 (M$^+$+1)

Example 1030

N-{3-Chloro-4-[(6,7-dimethoxy-4-quinolyl)oxy]phenyl}-N'-(3-cyclopentylpropanoyl)thiourea 3-Cyclopentylpropanoyl isothiocyanate was prepared using commercially available 3-cyclopentylpropanoyl chloride (80 mg) as a starting compound according to the description of the literature. 3-Cyclopentylpropanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (68 mg, yield 88%).

$^1$H-NMR (DMSO-$d_6$, 400 MHz): δ 1.07 (m, 4H), 1.48–1.71 (m, 9H), 4.05 (s, 3H), 4.07 (s, 3H), 6.88 (d, J=6.83 Hz, 1H), 7.55 (s, 1H), 7.65 (d, J=9.03 Hz, 1H), 7.78–7.81 (m, 2H), 8.26–8.28 (m, 1H), 8.87 (d, J=6.59 Hz, 1H), 11.61 (s, 1H), 12.66 (s, 1H) Mass spectrometry value (ESI-MS, m/z): 515 (M$^+$+1)

Example 1031

N-[2-(Benzyloxy)acetyl]-N'-{4-[(6,7-dimethoxy-4-quinolyl)oxy]-2-fluorophenyl}thiourea 2-(Benzyloxy)ethanoyl isothiocyanate was prepared using commercially available 2-(benzyloxy)ethanoyl chloride (80 mg) as a starting compound according to the description of the literature. 2-(Benzyloxy)ethanoyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (38 mg, yield 43%). Mass spectrometry value (ESI-MS, m/z): 522 (M$^+$+1)

Example 1032

N-[2-(Benzyloxy)acetyl]-N'-{4-[(6,7-dimethoxy-4-quinolyl)oxy]-3-fluorophenyl}thiourea 2-(Benzyloxy)ethanoyl isothiocyanate was prepared using commercially available 2-(benzyloxy)ethanoyl chloride (80 mg) as a starting compound according to the description of the literature. 2-(Benzyloxy)ethanoyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (33 mg, yield 40%).

$^1$H-NMR (DMSO-$d_6$, 400 MHz): δ 3.96 (s, 6H), 4.13 (s, 2H), 4.64 (s, 2H), 6.48 (d, J=5.37 Hz, 2H), 7.32–7.45 (m, 6H), 7.54 (m, 2H), 7.90–7.94 (m, 2H), 8.50 (d, J=5.12 Hz, 1H), 10.15 (s, 1H) Mass spectrometry value (ESI-MS, m/z): 522 (M$^+$+1)

Example 1033

N-{4-[(6,7-Dimethoxy-4-quinolyl)oxy]phenyl}-N'-(2-furylcarbonyl)thiourea

2-Furancarbonyl isothiocyanate was prepared using commercially available 2-furancarbonyl chloride (80 mg) as a starting compound according to the description of the literature. 2-Furancarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (40 mg, yield 53%).

$^1$H-NMR (DMSO-$d_6$, 400 MHz): δ 3.94 (s, 3H), 3.96 (s, 3H), 6.56 (d, J=5.12 Hz, 1H), 6.73–6.77 (m, 2H), 7.32 (d, J=8.78 Hz, 1H), 7.41 (s, 1H), 7.51–7.52 (m, 2H), 7.79 (d, J=8.78 Hz, 1H), 7.86 (m, 1H), 8.01 (s, 2H), 8.08 (s, 1H), 8.51 (d, J=4.88, 1H) Mass spectrometry value (ESI-MS, m/z): 450 (M$^+$+1)

Example 1034

N-{4-[(6,7-Dimethoxy-4-quinolyl)oxy]phenyl}-N'-(3-thienylcarbonyl)thiourea

3-Thiophenecarbonyl isothiocyanate was prepared using commercially available 3-thiophenecarbonyl chloride (80 mg) as a starting compound according to the description of the literature. 3-Thiophenecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (45 mg, yield 68%).

$^1$H-NMR (DMSO-$d_6$, 400 MHz): δ 3.93 (s, 3H), 3.95 (s, 3H), 6.55 (d, J=5.37 Hz, 1H), 7.26 (t, J=4.27 Hz, 1H), 7.31 (d, J=9.03 Hz, 2H), 7.41 (s, 1H), 7.50 (s, 1H), 7.81 (d, J=9.03 Hz, 2H), 8.05 (d, J=4.88 Hz, 1H), 8.41 (d, J=3.90 Hz, 1H), 8.51 (d, J=5.12 Hz, 1H), 11.65 (s, 1H), 12.49 (s, 1H) Mass spectrometry value (ESI-MS, m/z): 466 (M$^+$+1)

Example 1035

N-{4-[(6,7-Dimethoxy-4-quinolyl)oxy]-2-fluorophenyl}-N'-(2-furylcarbonyl)thiourea 2-Furancarbonyl isothiocyanate was prepared using commercially available 2-furancarbonyl chloride (80 mg) as a starting compound according to the description of the literature. 2-Furancarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (47 mg, yield 68%). Mass spectrometry value (ESI-MS, m/z): 468 (M$^+$+1)

Example 1036

N-{4-[(6,7-Dimethoxy-4-quinolyl)oxy]-2-fluorophenyl}-N'-(3-thienylcarbonyl)thiourea 3-Thiophenecarbonyl isothiocyanate was prepared using commercially available 3-thiophenecarbonyl chloride (80 mg) as a starting compound according to the description of the literature. 3-Thiophenecarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (45 mg, yield 58%).

$^1$H-NMR (DMSO-$d_6$, 400 MHz): δ 3.93 (s, 3H), 3.96 (s, 3H), 6.67 (d, J=5.12 Hz, 1H), 7.15–7.18 (m, 1H), 7.26–7.28 (m, 2H), 7.39–7.43 (m, 2H), 7.48 (s, 1H), 7.99–8.08 (m, 2H), 8.42 (d, J=3.42 Hz, 1H), 8.57 (d, J=5.12 Hz, 1H), 10.01 (s, 1H) Mass spectrometry value (ESI-MS, m/z): 484 (M$^+$+1)

Example 1037

N-{4-[(6,7-Dimethoxy-4-quinolyl)oxy]-2-fluorophenyl}-N'-[(2,5-dimethyl-3-furyl)carbonyl]-thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (38 mg, yield 48%).

$^1$H-NMR (DMSO-$d_6$, 400 MHz): δ 2.26 (s, 3H), 2.55 (s, 3H), 3.92 (s, 3H), 3.95 (s, 3H), 6.65 (d, J=5.37 Hz, 1H), 6.89 (s, 1H), 7.13–7.14 (m, 1H), 7.34–7.37 (m, 1H), 7.41 (s, 1H), 7.46 (s, 1H), 8.05–8.07 (m, 1H), 8.54 (d, J=5.15 Hz, 1H), 11.13 (s, 1H), 12.61 (s, 1H) Mass spectrometry value (ESI-MS, m/z): 496 (M$^+$+1)

Example 1038

N-{4-[(6,7-Dimethoxy-4-quinolyl)oxy]-2-fluorophenyl}-N'-[(3-methyl-2-thienyl)carbonyl]thiourea Toluene (20 ml) and thionyl chloride (1 ml) were added to commercially available 3-methyl-2-thiophenecarboxylic acid (80 mg), and the mixture was heated at 100° C. for one hr. The solvent was removed by distillation, and 3-methyl-2-thiophenecarbonyl isothiocyanate was prepared using the resultant 3-methyl-2-thiophenecarbonyl chloride as a starting compound according to the description of the literature. 3-Methyl-2-thiophenecarbonyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (42 mg, yield 53%).

$^1$H-NMR (DMSO-$d_6$, 400 MHz): δ 2.51 (s, 3H), 3.92 (s, 3H), 3.96 (s, 3H), 6.66 (d, J=5.12 Hz, 1H), 7.09 (d, J=4.88 Hz, 1H), 7.14–7.16 (m, 1H), 7.38 (dd, J=2.56 Hz, 11.01 Hz, 1H), 7.42 (s, 1H), 7.46 (s, 1H), 7.86 (d, J=4.88 Hz, 1H), 8.07 (t, J=8.54 Hz, 1H), 8.55 (d, J=5.37 Hz, 1H), 11.25 (s, 1H), 12.22 (s, 1H) Mass spectrometry value (ESI-MS, m/z): 498 (M$^+$+1)

Example 1039

N-{4-[(6,7-Dimethoxy-4-quinolyl)oxy]-3-fluorophenyl}-N'-[(2,5-dimethyl-3-furyl)carbonyl]thiourea Toluene (20 ml) and thionyl chloride (1 ml) were added to commercially available 2,5-dimethyl-3-furoic acid (80 mg), and the mixture was heated at 100° C. for one hr. The solvent was removed by distillation, and 2,5-dimethyl-3-furancarbonyl isothiocyanate was prepared using the resultant 2,5-dimethyl-3-furancarbonyl chloride as a starting compound according to the description of the literature. 2,5-Dimethyl-3-furancarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (51 mg, yield 64%).

$^1$H-NMR (DMSO-$d_6$, 400 MHz): δ 2.26 (s, 3H), 2.55 (s, 3H), 3.96 (s, 6H), 6.51 (d, J=5.37 Hz, 1H), 6.87 (s, 1H), 7.42 (s, 1H), 7.47–7.59 (m, 3H), 8.07 (d, J=10.25 Hz, 1H), 8.51

(d, J=5.12 Hz, 1H), 11.02 (s, 1H), 12.81 (s, 1H) Mass spectrometry value (ESI-MS, m/z): 496 (M$^+$+1)

Example 1040

N-{4-[(6,7-Dimethoxy-4-quinolyl)oxy]-3-fluorophenyl}-N'-[(5-methyl-2-thienyl)carbonyl]thiourea Toluene (20 ml) and thionyl chloride (1 ml) were added to commercially available 5-methyl-2-thiophenecarboxylic acid (80 mg), and the mixture was heated at 100° C. for one hr. The solvent was removed by distillation, and 5-methyl-2-thiophenecarbonyl isothiocyanate was prepared using the resultant 5-methyl-2-thiophenecarbonyl chloride as a starting compound according to the description of the literature. 5-Methyl-2-thiophenecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (49 mg, yield 62%).

$^1$H-NMR (CDCl$_3$, 400 MHz): δ 2.58 (s, 3H), 4.07 (s, 3H), 4.09 (s, 3H), 6.62 (d, J=5.61 Hz, 1H), 7.25–7.27 (m, 1H), 7.32–7.35 (m, 1H), 7.46–7.50 (m, 1H), 7.57–7.58 (m, 2H), 7.63 (s, 1H), 7.88–7.90 (m, 2H), 8.53 (d, J=5.61 Hz, 1H), 8.86 (bs, 1H) Mass spectrometry value (ESI-MS, m/z): 498 (M$^+$+1)

Example 1041

N-{4-[(6,7-Dimethoxy-4-quinolyl)oxy]phenyl}-{[(diethylamino)carbonyl]amino}methanethioamide (Diethylamino)methanoyl isothiocyanate was prepared using commercially available N,N-diethylcarbamic chloride (80 mg) as a starting compound according to the description of the literature. (Diethylamino)methanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (42 mg, yield 55%).

$^1$H-NMR (DMSO-d$_6$, 400 MHz): δ 1.26–1.29 (m, 6H), 3.93 (s, 3H), 3.95 (s, 3H), 4.22–4.24 (m, 4H), 6.54 (d, J=5.12 Hz, 1H), 7.11 (m, 2H), 7.29–7.31 (m, 2H), 7.41 (s, 1H), 7.50 (s, 1H), 7.73 (m, 2H), 8.52 (d, J=5.12 Hz, 1H) Mass spectrometry value (ESI-MS, m/z): 455 (M$^+$+1)

Example 1042

N-{4-[(6,7-Dimethoxy-4-quinolyl)oxy]phenyl}-[{[di(2-chloroethyl)amino]carbonyl}amino]methanethioamide

[Di(2-chloroethyl)amino]methanoyl isothiocyanate was prepared using commercially available N,N-di(2-chloroethyl)carbamic chloride (80 mg) as a starting compound according to the description of the literature. [Di(2-chloroethyl)amino]methanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (48 mg, yield 55%).

$^1$H-NMR (DMSO-d$_6$, 400 MHz): δ 3.57–3.62 (m, 4H), 3.80–3.82 (m, 2H), 3.95 (s, 3H), 3.97 (s, 3H), 4.11–4.13 (m, 2H), 7.55 (m, 1H), 7.29–7.31 (m, 2H), 7.42 (s, 1H), 7.55 (s, 1H), 7.73–7.75 (m, 3H), 8.57 (d, J=5.37 Hz, 1H), 12.25 (s, 1H) Mass spectrometry value (ESI-MS, m/z): 524 (M$^+$+1)

Example 1043

N-{4-[(6,7-Dimethoxy-4-quinolyl)oxy]phenyl}-{[(diisopropylamino)carbonyl]amino}methanethioamide (Diisopropylamino)methanoyl isothiocyanate was prepared using commercially available N,N-diisopropylcarbamic chloride (80 mg) as a starting compound according to the description of the literature. (Diisopropylamino)methanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (50 mg, yield 62%).

$^1$H-NMR (DMSO-d$_6$, 400 MHz): δ 1.19 (d, J=6.10 Hz, 2H), 1.27 (d, J=6.83 Hz, 12H), 3.94 (s, 3H), 3.96 (s, 3H), 6.39 (d, J=5.12 Hz, 1H), 7.42–7.46 (m, 4H), 7.53 (s, 2H), 7.64 (m, 1H), 8.13 (m, 1H), 8.49 (d, J=4.88 Hz, 1H) Mass spectrometry value (ESI-MS, m/z): 483 (M$^+$+1)

Example 1044

N-{4-[(6,7-Dimethoxy-4-quinolyl)oxy]phenyl}-N'-tetrahydro-1H-1-pyrrolylcarbonylthiourea 1-Pyrrolidinecarbonyl isothiocyanate was prepared using commercially available 1-pyrrolidinecarbonyl chloride (80 mg) as a starting compound according to the description of the literature. 1-Pyrrolidinecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (48 mg, yield 63%).

$^1$H-NMR (DMSO-d$_6$, 400 MHz): δ 1.85 (m, 8H), 3.92 (s, 3H), 3.94 (s, 3H), 6.52 (d, J=4.88 Hz, 1H), 7.27 (d, J=7.81 Hz, 2H), 7.39 (s, 1H), 7.49 (s, 1H), 7.75 (m, 2H), 8.49 (d, J=5.13 Hz, 1H), 9.59 (s, 1H), 12.80 (s, 1H) Mass spectrometry value (ESI-MS, m/z): 453 (M$^+$+1)

Example 1045

N-{4-[(6,7-Dimethoxy-4-quinolyl)oxy]phenyl}-N'-morpholinocarbonylthiourea

4-Morpholinecarbonyl isothiocyanate was prepared using commercially available 4-morpholinecarbonyl chloride (80 mg) as a starting compound according to the description of the literature. 4-Morpholinecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (49 mg, yield 62%).

$^1$H-NMR (CDCl$_3$, 400 MHz): δ 3.53–3.55 (m, 4H), 3.74–3.78 (m, 4H), 4.05 (s, 3H), 4.07 (s, 3H), 6.58 (d, J=5.61 Hz, 1H), 7.21 (d, J=8.78 Hz, 2H), 7.26 (s, 1H), 7.54 (d, J=4.88 Hz, 2H), 7.76 (d, J=9.03 Hz, 2H), 7.98 (bs, 1H), 8.51 (d, J=5.37 Hz, 1H) Mass spectrometry value (ESI-MS, m/z): 469 (M$^+$+1)

Example 1046

N-{4-[(6,7-Dimethoxy-4-quinolyl)oxy]phenyl}-{[(methylanilino)carbonyl]amino}methanethioamide (Methylanilino)methanoyl isothiocyanate was prepared using commercially available N-methyl-N-phenylcarbamic chloride (80 mg) as a starting compound according to the description of the literature. (Methylanilino)methanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (52 mg, yield 63%).

$^1$H-NMR (DMSO-d$_6$, 400 MHz): δ 1.57 (bs, 3H), 3.93 (s, 3H), 3.94 (s, 3H), 6.43 (d, J=5.37 Hz, 1H), 7.13–7.16 (m, 2H), 7.26–7.28 (m, 1H), 7.34–7.45 (m, 6H), 7.51 (s, 1H), 7.57 (d, J=9.03 Hz, 2H), 8.31 (s, 1H), 8.46 (d, J=5.37 Hz, 1H) Mass spectrometry value (ESI-MS, m/z): 489 (M$^+$+1)

Example 1047

N-[10,11-Dihydro-5H-dibenzo(b,f)azepin-5-ylcarbonyl]-N'-{4-[(6,7-dimethoxy-4-quinolyl)oxy]phenyl}thiourea 10,11-Dihydro-5H-dibenzo(b,f)azepine-5-carbonyl isothiocyanate was prepared using commercially available 10,11-dihydro-5H-dibenzo(b,f)azepine-5-carbonyl chloride (80 mg) as a starting compound according to the description of the literature. 10,11-Dihydro-5H-dibenzo(b,f)azepine-5-carbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (61 mg, yield 65%).

$^1$H-NMR (DMSO-d$_6$, 400 MHz): δ 0.86 (m, 2H), 1.25 (m, 2H), 3.94 (s, 3H), 3.95 (s, 3H), 6.49 (d, J=5.37 Hz, 1H), 7.35–7.56 (m, 12H), 8.02 (m, 1H), 8.49–8.51 (m, 2H), 12.36 (s, 1H) Mass spectrometry value (ESI-MS, m/z): 595 (M$^+$+1)

Example 1048

N-{3-Chloro-4-[(6,7-dimethoxy-4-quinolyl)oxy]phenyl}-{[(diethylamino)carbonyl]amino}methanethioamide (Diethylamino)methanoyl isothiocyanate was prepared using commercially available N,N-diethylcarbamic chloride (80 mg) as a starting compound according to the description of the literature. (Diethylamino)methanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (52 mg, yield 38%).

$^1$H-NMR (DMSO-d$_6$, 400 MHz): δ 1.29 (t, J=7.19 Hz, 6H), 3.95 (s, 6H), 4.23–4.25 (m, 4H), 6.39 (d, J=5.12 Hz, 1H), 7.41 (s, 1H), 7.45 (d, J=8.78 Hz, 1H), 7.52 (s, 1H), 7.65 (m, 2H), 8.09 (m, 1H), 8.49 (d, J=5.61 Hz, 1H), 11.37 (s, 1H) Mass spectrometry value (ESI-MS, m/z): 489 (M$^+$+1)

Example 1049

N-{3-Chloro-4-[(6,7-dimethoxy-4-quinolyl)oxy]phenyl}-[{[di(2-chloroethyl)amino]carbonyl}amino]methanethioamide

[Di(2-chloroethyl)amino]methanoyl isothiocyanate was prepared using commercially available N,N-di(2-chloroethyl)carbamic chloride (80 mg) as a starting compound according to the description of the literature. [Di(2-chloroethyl)amino]methanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (51 mg, yield 60%).

$^1$H-NMR (DMSO-d$_6$, 400 MHz): δ 3.55–3.63 (m, 4H), 3.81–3.84 (m, 2H), 3.95 (s, 6H), 4.11–4.15 (m, 2H), 6.41 (d, J=5.12 Hz, 1H), 7.40–7.44 (m, 3H), 7.52 (s, 1H), 7.61–7.63 (m, 1H), 8.09–8.12 (m, 1H), 8.49 (d, J=5.12 Hz, 1H), 12.29 (s, 1H) Mass spectrometry value (ESI-MS, m/z): 558 (M$^+$+1)

Example 1050

N-{3-Chloro-4-[(6,7-dimethoxy-4-quinolyl)oxy]phenyl}-{[(diisopropylamino)carbonyl]amino}methanethioamide (Diisopropylamino)methanoyl isothiocyanate was prepared using commercially available N,N-diisopropylcarbamic chloride (80 mg) as a starting compound according to the description of the literature. (Diisopropylamino)methanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (49 mg, yield 63%).

$^1$H-NMR (DMSO-d$_6$, 400 MHz): δ 1.18 (d, J=6.01 Hz, 2H), 1.27 (d, J=6.83 Hz, 12H), 3.93 (s, 3H), 3.95 (s, 3H), 6.53 (d, J=5.12 Hz, 1H), 7.28 (d, J=8.78 Hz, 2H), 7.41 (s, 1H), 7.50 (s, 1H), 7.73–7.75 (m, 3H), 8.51 (d, J=5.12 Hz, 1H) Mass spectrometry value (ESI-MS, m/z): 518 (M$^+$+1)

Example 1051

N-{3-Chloro-4-[(6,7-dimethoxy-4-quinolyl)oxy]phenyl}-N'-tetrahydro-1H-1-pyrrolylcarbonylthiourea 1-Pyrrolidinecarbonyl isothiocyanate was prepared using commercially available 1-pyrrolidinecarbonyl chloride (80 mg) as a starting compound according to the description of the literature. 1-Pyrrolidinecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (52 mg, yield 70%).

$^1$H-NMR (DMSO-d$_6$, 400 MHz): δ 1.85–1.99 (m, 8H), 3.95 (s, 6H), 6.41 (d, J=5.37 Hz, 1H), 7.42 (s, 1H), 7.46 (d, J=8.54 Hz, 1H), 7.53 (s, 1H), 7.64–7.66 (m, 2H), 8.17–8.19 (m, 2H), 8.50 (d, J=5.37 Hz, 1H) Mass spectrometry value (ESI-MS, m/z): 487 (M$^+$+1)

Example 1052

N-{3-Chloro-4-[(6,7-dimethoxy-4-quinolyl)oxy]phenyl}-N'-morpholinocarbonylthiourea 4-Morpholinecarbonyl isothiocyanate was prepared using commercially available 4-morpholinecarbonyl chloride (80 mg) as a starting compound according to the description of the literature. 4-Morpholinecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (40 mg, yield 52%).

$^1$H-NMR (CDCl$_3$, 400 MHz): δ 3.53–3.56 (m, 4H), 3.75–3.77 (m, 4H), 4.08 (s, 3H), 4.10 (s, 3H), 5.77 (bs, 1H), 6.49 (d, J=5.61 Hz, 1H), 7.26–7.29 (m, 1H), 7.63 (s, 1H), 7.68–7.70 (m, 2H), 8.01 (s, 1H), 8.04 (d, J=2.44 Hz, 1H), 8.52 (d, J=5.85 Hz, 1H) Mass spectrometry value (ESI-MS, m/z): 503 (M$^+$+1)

Example 1053

N-{3-Chloro-4-[(6,7-dimethoxy-4-quinolyl)oxy]phenyl}-{[(methylanilino)carbonyl]amino}methanethioamide (Methylanilino)methanoyl isothiocyanate was prepared using commercially available N-methyl-N-phenylcarbamic chloride (80 mg) as a starting compound according to the description of the literature. (Methylanilino)methanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (56 mg, yield 71%).

$^1$H-NMR (DMSO-d$_6$, 400 MHz): δ 1.57 (bs, 3H), 3.94 (s, 6H), 6.32 (d, J=5.12 Hz, 1H), 7.28–7.44 (m, 8H), 7.52–7.58 (m, 2H), 7.56 (s, 1H), 8.46–8.48 (m, 2H) Mass spectrometry value (ESI-MS, m/z): 524 (M$^+$+1)

Example 1054

N-{3-Chloro-4-[(6,7-dimethoxy-4-quinolyl)oxy]phenyl}-N'-[10,11-dihydro-5H-dibenzo(b,f)azepin-5-ylcarbonyl]thiourea 10,11-Dihydro-5H-dibenzo(b,f)azepine-5-carbonyl isothiocyanate was prepared using commercially available 10,11-dihydro-5H-dibenzo(b,f)azepin-5-carbonyl chloride (80 mg) as a starting compound according to the description of the literature. 10,11-Dihydro-5H-dibenzo(b,f)azepine-5-carbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (46 mg, yield 50%).

$^1$H-NMR (DMSO-d$_6$, 400 MHz): δ 0.86 (m, 2H), 1.25 (m, 2H), 3.94 (s, 3H), 3.95 (s, 3H), 6.39 (d, J=5.12 Hz, 1H), 7.35 (m, 6H), 7.41 (s, 1H), 7.45 (d, J=8.78 Hz, 1H), 7.51 (s, 1H), 7.56–7.57 (m, 2H), 7.68 (dd, J=2.44 Hz, 9.03 Hz, 1H), 8.14 (s, 1H), 8.49 (d, J=5.12 Hz, 1H), 8.53 (s, 1H), 12.29 (s, 1H) Mass spectrometry value (ESI-MS, m/z): 612 (M$^+$+1)

Example 1055

N-{4-[(6,7-Dimethoxy-4-quinolyl)oxy]phenyl}-N'-[(2-phenylcyclopropyl)carbonyl]thiourea 2-Phenyl-1-cyclopropanecarbonyl isothiocyanate was prepared using commercially available 2-phenyl-1-cyclopropanecarbonyl chloride (80 mg) as a starting compound according to the description of the literature. 2-Phenyl-1-cyclopropanecarbonyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (53 mg, yield 63%).

$^1$H-NMR (DMSO-d$_6$, 400 MHz): δ 1.09 (m, 1H), 1.52 (m, 2H), 1.59 (m, 2H), 3.94 (s, 3H), 3.96 (s, 3H), 6.59 (d, J=5.37 Hz, 1H), 7.19–7.32 (m, 5H), 7.41 (m, 2H), 7.52 (m, 2H), 7.78–7.80 (m, 3H), 8.54 (m, 1H) Mass spectrometry value (ESI-MS, m/z): 500 (M$^+$+1)

Example 1056

N-Cyclopropylcarbonyl-N'-{4-[(6,7-dimethoxy-4-quinolyl)oxy]-3-fluorophenyl}thiourea 1-Cyclopropanecarbonyl isothiocyanate was prepared using commercially available 1-cyclopropanecarbonyl chloride (80 mg) as a starting compound according to the description of the literature. 1-Cyclopropanecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (46 mg, yield 66%).

$^1$H-NMR (DMSO-$d_6$, 400 MHz): δ 0.96–0.99 (m, 4H), 2.08–2.13 (m, 2H), 3.95 (s, 6H), 6.72 (d, J=5.12 Hz, 1H), 7.41 (s, 1H), 7.45–7.52 (m, 2H), 8.04 (d, J=11.95 Hz, 1H), 8.50 (d, J=5.12 Hz, 1H), 11.89 (s, 1H), 12.64 (s, 1H) Mass spectrometry value (ESI-MS, m/z): 442 ($M^+$+1)

Example 1057

N-{4-[(6,7-Dimethoxy-4-quinolyl)oxy]-3-fluorophenyl}-N'-[(2-phenylcyclopropyl)carbonyl]thiourea 2-Phenyl-1-cyclopropanecarbonyl isothiocyanate was prepared using commercially available 2-phenyl-1-cyclopropanecarbonyl chloride (80 mg) as a starting compound according to the description of the literature. 2-Phenyl-1-cyclopropanecarbonyl isothiocyanate was dissolved in ethanol (1 ml) to prepare a solution. 4-[(6,7-Dimethoxy-4-quinolyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (51 mg, yield 62%).

$^1$H-NMR (DMSO-$d_6$, 400 MHz): δ 1.08–1.25 (m, 1H), 1.53 (m, 2H), 1.59–1.62 (m, 2H), 3.95 (s, 6H), 6.49 (d, J=5.12 Hz, 1H), 7.19–7.55 (m, 8H), 8.05 (d, J=10.00 Hz, 1H), 8.50 (d, J=5.37 Hz, 1H), 11.88 (s, 1H), 12.62 (s, 1H) Mass spectrometry value (ESI-MS, m/z): 518 ($M^+$+1)

Example 1058

N-{3-Chloro-4-[(6,7-dimethoxy-4-quinolyl)oxy]phenyl}-N'-cyclopropylcarbonylthiourea 1-Cyclopropanecarbonyl isothiocyanate was prepared using commercially available 1-cyclopropanecarbonyl chloride (80 mg) as a starting compound according to the description of the literature. 1-Cyclopropanecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (36 mg, yield 52%).

$^1$H-NMR (DMSO-$d_6$, 400 MHz): δ 0.93–0.99 (m, 4H), 2.12 (m, 2H), 3.94 (s, 3H), 3.96 (s, 3H), 6.41 (d, J=5.37 Hz, 1H), 7.33 (d, J=11.95 Hz, 1H), 7.41 (s, 1H), 7.45 (d, J=8.78 Hz, 1H), 7.52 (s, 1H), 7.64–7.67 (m, 1H), 8.14 (s, 1H), 8.49 (d, J=5.37 Hz, 1H) Mass spectrometry value (ESI-MS, m/z): 458 ($M^+$+1)

Example 1059

N-{3-Chloro-4-[(6,7-dimethoxy-4-quinolyl)oxy]phenyl}-N'-[(2-phenylcyclopropyl)carbonyl]thiourea 2-Phenyl-1-cyclopropanecarbonyl isothiocyanate was prepared using commercially available 2-phenyl-1-cyclopropanecarbonyl chloride (80 mg) as a starting compound according to the description of the literature. 2-Phenyl-1-cyclopropanecarbonyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (48 mg, yield 60%).

$^1$H-NMR (DMSO-$d_6$, 400 MHz): δ 1.09–1.11 (m, 1H), 1.53 (m, 2H), 1.60 (m, 2H), 3.94 (s, 3H), 3.96 (s, 3H), 6.40 (d, J=5.37 Hz, 1H), 7.16–7.34 (m, 5H), 7.41 (s, 1H), 7.45 (d, J=8.78 Hz, 1H), 7.52 (s, 1H), 7.67 (dd, J=2.32 Hz, 8.91 Hz, 1H), 8.14 (d, J=2.44 Hz, 1H), 8.49 (d, J=5.12 Hz, 1H), 11.88 (s, 1H) Mass spectrometry value (ESI-MS, m/z): 535 ($M^+$+1)

Example 1060

N-{4-[(6,7-Dimethoxy-4-quinazolinyl)oxy]phenyl}-N'-[(2-phenylcyclopropyl)carbonyl]thiourea 2-Phenyl-1-cyclopropanecarbonyl isothiocyanate was prepared using commercially available 2-phenyl-1-cyclopropanecarbonyl chloride (80 mg) as a starting compound according to the description of the literature. 2-Phenyl-1-cyclopropanecarbonyl isothiocyanate was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (50 mg, yield 60%).

$^1$H-NMR (DMSO-$d_6$, 400 MHz): δ 0.93–0.97 (m, 1H), 1.31 (m, 1H), 1.52–1.60 (m, 2H), 3.98 (s, 6H), 6.55 (d, J=5.61 Hz, 1H), 7.18–7.33 (m, 5H), 7.45 (s, 1H), 7.56 (d, J=8.54 Hz, 1H), 7.59 (s, 1H), 7.69 (m, 1H), 8.17–8.19 (m, 1H), 8.60 (d, J=5.91 Hz, 1H), 11.88 (s, 1H), 12.59 (s, 1H) Mass spectrometry value (ESI-MS, m/z): 501 ($M^+$+1)

Example 1061

N-Cyclopentylcarbonyl-N'-{4-[(6,7-dimethoxy-4-quinolyl)oxy]phenyl}thiourea

1-Cyclopentanecarbonyl isothiocyanate was prepared using commercially available 1-cyclopentanecarbonyl chloride (80 mg) as a starting compound according to the description of the literature. 1-Cyclopentanecarbonyl isothiocyanate was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (43 mg, yield 57%).

$^1$H-NMR (DMSO-$d_6$, 400 MHz): δ 0.85–0.88 (m, 1H), 1.08–1.11 (m, 1H), 1.24 (bs, 1H), 1.57–1.91 (m, 6H), 3.93 (s, 3H), 3.95 (s, 3H), 6.54 (d, J=5.37 Hz, 1H), 7.19 (d, J=8.78 Hz, 1H), 7.29 (d, J=8.78 Hz, 2H), 7.39 (d, J=7.81 Hz, 1H), 7.50 (d, J=5.61 Hz, 1H), 7.73–7.78 (m, 3H), 8.51 (d, J=5.37 Hz, 1H) Mass spectrometry value (ESI-MS, m/z): 452 (M$^+$+1)

Example 1062

N-Cyclohexylcarbonyl-N'-{4-[(6,7-dimethoxy-4-quinolyl)oxy]phenyl}thiourea

1-Cyclohexanecarbonyl isothiocyanate was prepared using commercially available 1-cyclohexanecarbonyl chloride (80 mg) as a starting compound according to the description of the literature. 1-Cyclohexanecarbonyl isothiocyanate was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 47%).

$^1$H-NMR (DMSO-$d_6$, 400 MHz): δ 1.21–1.38 (m, 6H), 1.66–1.85 (m, 5H), 3.92 (s, 3H), 3.95 (s, 3H), 6.54 (d, J=5.12 Hz, 1H), 7.28 (d, J=9.03 Hz, 3H), 7.39 (s, 1H), 7.49 (s, 1H), 7.76 (d, J=8.78 Hz, 1H), 8.50 (d, J=5.12 Hz, 1H), 11.41 (bs, 1H), 12.56 (bs, 1H) Mass spectrometry value (ESI-MS, m/z): 466 (M$^+$+1)

Example 1063

N-Cyclopentylcarbonyl-N'-{4-[(6,7-dimethoxy-4-quinolyl)oxy]-2-fluorophenyl}thiourea 1-Cyclopentanecarbonyl isothiocyanate was prepared using commercially available 1-cyclopentanecarbonyl chloride (80 mg) as a starting compound according to the description of the literature. 1-Cyclopentanecarbonyl isothiocyanate was dissolved in ethanol (1 ml) to prepare a solution. 4-[(6,7-Dimethoxy-4-quinazolinyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (35 mg, yield 47%).

$^1$H-NMR (CDCl$_3$, 400 MHz): δ 0.879 (m, 1H), 1.08 (m, 1H), 1.17 (m, 1H), 1.63–1.97 (m, 6H), 4.07 (s, 3H), 4.09 (s, 3H), 6.86 (d, J=6.01 Hz, 1H), 7.16 (dd, J=9.52 Hz, 22.93 Hz, 1H), 7.63 (s, 1H), 7.69 (s, 2H), 8.56 (m, 1H), 8.68 (d, J=6.34 Hz, 1H), 11.47 (bs, 1H), 12.88 (bs, 1H) Mass spectrometry value (ESI-MS, m/z): 470 (M$^+$+1)

Example 1064

N-Cyclohexylcarbonyl-N'-{4-[(6,7-dimethoxy-4-quinolyl)oxy]-2-fluorophenyl}thiourea 1-Cyclohexanecarbonyl isothiocyanate was prepared using commercially available 1-cyclohexanecarbonyl chloride (80 mg) as a starting compound according to the description of the literature. 1-Cyclohexanecarbonyl isothiocyanate was dissolved in ethanol (1 ml) to prepare a solution. 4-[(6,7-Dimethoxy-4-quinazolinyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (47 mg, yield 61%).

$^1$H-NMR (DMSO-$d_6$, 400 MHz): δ 1.21–1.39 (m, 6H), 1.66–1.90 (m, 5H), 3.92 (s, 3H), 3.95 (s, 3H), 6.64 (d, J=5.12 Hz, 1H), 7.12 (d, J=8.78 Hz, 1H), 7.35 (dd, J=2.55 Hz, 11.10 Hz, 1H), 7.41 (s, 1H), 7.45 (s, 1H), 8.09 (t, J=8.79 Hz, 1H), 8.53 (d, J=5.37 Hz, 1H), 11.57 (s, 1H), 12.42 (s, 1H) Mass spectrometry value (ESI-MS, m/z): 484 (M$^+$+1)

Example 1065

N-{4-[(6,7-Dimethoxy-4-quinolyl)oxy]phenyl}-N'-(3-ethoxypropanoyl)thiourea

Toluene (20 ml) and thionyl chloride (1 ml) were added to commercially available 3-ethoxypropanoic acid (80 mg), and the mixture was heated at 100° C. for one hr. The solvent was removed by distillation, and 3-ethoxypropanoyl isothiocyanate was prepared using the resultant 3-ethoxypropanoyl chloride as a starting compound according to the description of the literature. 3-Ethoxypropanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (55 mg, yield 72%).

$^1$H-NMR (DMSO-$d_6$, 400 MHz): δ 0.92–0.95 (m, 3H), 2.74 (m, 2H), 3.44–3.46 (m, 2H), 3.64–3.65 (m, 2H), 3.95 (s, 3H), 3.96 (s, 3H), 6.44 (d, J=5.37 Hz, 1H), 7.43 (s, 1H), 7.49 (d, J=8.78 Hz, 2H), 7.54 (s, 1H), 7.70 (m, 1H), 8.16 (m, 1H), 8.53 (d, J=5.12 Hz, 1H), 11.71 (s, 1H), 12.32 (s, 1H) Mass spectrometry value (ESI-MS, m/z): 456 (M$^+$+1)

Example 1066

N-(4-Chlorobutanoyl)-N'-{4-[(6,7-dimethoxy-4-quinolyl)oxy]-2-fluorophenyl}thiourea 4-Chlorobutanoyl isothiocyanate was prepared using commercially available 4-chlorobutanoyl chloride (80 mg) as a starting compound according to the description of the literature. 4-Chlorobutanoyl isothiocyanate was dissolved in ethanol (1 ml) to prepare a solution. 4-[(6,7-Dimethoxy-4-quinazolinyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (51 mg, yield 67%).

$^1$H-NMR (DMSO-$d_6$, 400 MHz): δ 2.02–2.05 (m, 2H), 2.63–2.67 (m, 2H), 3.67–3.70 (m, 2H), 3.93 (s, 3H), 3.96 (s, 3H), 6.66 (d, J=5.37 Hz, 1H), 7.14 (d, J=6.59 Hz, 1H), 7.36–7.38 (m, 1H), 7.42 (s, 1H), 7.47 (s, 1H), 8.08 (t, J=8.78 Hz, 1H), 8.56 (d, J=5.37 Hz, 1H), 11.71 (s, 1H), 12.32 (s, 1H) Mass spectrometry value (ESI-MS, m/z): 479 (M$^+$+1)

Example 1067

N-{4-[(6,7-Dimethoxy-4-quinolyl)oxy]-2-fluorophenyl}-N'-[3-(methylsulfanyl)propanoyl]thiourea 3-(Methylsulfanyl)propanoyl isothiocyanate was prepared using commercially available 3-(methylsulfanyl)propanoyl chloride (80 mg) as a starting compound according to the description of the literature. 3-(Methylsulfanyl)propanoyl isothiocyanate was dissolved in ethanol (1 ml) to prepare a solution. 4-[(6,7-Dimethoxy-4-quinazolinyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (43 mg, yield 57%).

$^1$H-NMR (DMSO-d$_6$, 400 MHz): δ 2.74–2.76 (m, 2H), 2.79–2.81 (m, 2H), 3.17 (s, 3H), 3.92 (s, 3H), 3.96 (s, 3H), 6.65 (d, J=5.12 Hz, 1H), 7.14 (d, J=9.27 Hz, 1H), 7.35–7.38 (m, 1H), 7.42 (s, 1H), 7.46 (s, 1H), 8.08 (t, J=8.90 Hz, 1H), 8.55 (d, J=5.12 Hz, 1H), 11.71 (s, 1H), 12.34 (s, 1H) Mass spectrometry value (ESI-MS, m/z): 476 (M$^+$+1)

Example 1068

N-(4-Chlorobutanoyl)-N'-{4-[(6,7-dimethoxy-4-quinolyl)oxy]-3-fluorophenyl}thiourea 4-Chlorobutanoyl isothiocyanate was prepared using commercially available 4-chlorobutanoyl chloride (80 mg) as a starting compound according to the description of the literature. 4-Chlorobutanoyl isothiocyanate was dissolved in ethanol (1 ml) to prepare a solution. 4-[(6,7-Dimethoxy-4-quinazolinyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (41 mg, yield 54%).

$^1$H-NMR (DMSO-d$_6$, 400 MHz): δ 2.02–2.06 (m, 2H), 2.63–2.67 (m, 2H), 3.68–3.71 (m, 2H), 3.97 (s, 3H), 3.98 (s, 3H), 6.63 (d, J=5.61 Hz, 1H), 7.44–7.59 (m, 6H), 8.07 (d, J=11.95 Hz, 1H), 8.59 (d, J=5.61 Hz, 1H) Mass spectrometry value (ESI-MS, m/z): 478 (M$^+$+1)

Example 1069

N-{4-[(6,7-Dimethoxy-4-quinolyl)oxy]-3-fluorophenyl}-N'-[3-(methylsulfanyl)propanoyl]thiourea 3-(Methylsulfanyl)propanoyl isothiocyanate was prepared using commercially available 3-(methylsulfanyl)propanoyl chloride (80 mg) as a starting compound according to the description of the literature. 3-(Methylsulfanyl)propanoyl isothiocyanate was dissolved in ethanol (1 ml) to prepare a solution. 4-[(6,7-Dimethoxy-4-quinazolinyl)oxy]-3-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (38 mg, yield 50%).

$^1$H-NMR (DMSO-d$_6$, 400 MHz): δ 2.54 (s, 3H), 2.74–2.81 (m, 4H), 3.95 (s, 6H), 6.51 (d, J=5.12 Hz, 1H), 7.41 (s, 1H), 7.48–7.53 (m, 3H), 8.04 (d, J=10.49 Hz, aH), 8.50 (d, J=5.12 Hz, 1H), 11.64 (s, 1H), 12.59 (s, 1H) Mass spectrometry value (ESI-MS, m/z): 476 (M$^+$+1)

Example 1070

N-(3,4-Dimethoxybenzoyl)-N'-{4-[(6,7-dimethoxy-4-quinolyl)oxy]-3-fluorophenyl}thiourea 3,4-Dimethoxy-1-benzenecarbonyl isothiocyanate was prepared using commercially available 3,4-dimethoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (54 mg, yield 63%).

$^1$H-NMR (DMSO-d$_6$, 400 MHz): δ 3.79 (s, 3H), 3.81 (s, 3H), 3.96 (s, 3H), 5.47 (bs, 1H), 6.38 (bs, 1H), 6.44–6.47 (m, 1H), 6.54 (dd, J=2.52 Hz, J=14.79 Hz, 1H), 7.02–7.08 (m, 3H), 7.37 (s, 1H), 7.43 (s, 2H), 7.49 (s, 1H), 7.53–7.57 (m, 2H), 8.46 (d, J=5.12 Hz, 1H), 12.64 (bs, 1H) Mass spectrometry value (ESI-MS, m/z): 538 (M$^+$+1)

Example 1071

N-{3-Chloro-4-[(6,7-dimethoxy-4-quinolyl)oxy]phenyl}-N'-(3-ethoxypropanoyl)thiourea Toluene (20 ml) and thionyl chloride (1 ml) were added to commercially available 3-ethoxypropanoic acid (80 mg), and the mixture was heated at 100° C. for one hr. The solvent was removed by distillation, and 3-ethoxypropanoyl isothiocyanate was prepared using the resultant 3-ethoxypropanoyl chloride as a starting compound according to the description of the literature. 3-Ethoxypropanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (46 mg, yield 62%).

$^1$H-NMR (DMSO-d$_6$, 400 MHz): δ 1.06–1.13 (m, 3H), 2.72–2.75 (m, 2H), 3.44–3.47 (m, 2H), 3.64–3.67 (m, 2H), 3.95 (s, 3H), 3.97 (s, 3H), 6.63 (d, J=5.37 Hz, 1H), 7.29 (d, J=8.54 Hz, 2H), 7.44 (s, 1H), 7.56 (s, 1H), 7.78–7.82 (m, 2H), 8.59 (d, J=5.61 Hz, 1H), 11.51 (s, 1H) Mass spectrometry value (ESI-MS, m/z): 490 (M$^+$+1)

Example 1072

N-{4-[(6,7-Dimethoxy-4-quinolyl)oxy]phenyl}-N'-dodecanoylthiourea

Toluene (20 ml) and thionyl chloride (1 ml) were added to commercially available dodecanoic acid (80 mg), and the mixture was heated at 100° C. for one hr. The solvent was removed by distillation, and dodecanoyl isothiocyanate was prepared using the resultant dodecanoyl chloride as a starting compound according to the description of the literature.

Dodecanoyl isothiocyanate was dissolved in ethanol (1 ml) to prepare a solution. 4-[(6,7-Dimethoxy-4-quinolyl)oxy] aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (58 mg, yield 60%).

$^1$H-NMR (CDCl$_3$, 400 MHz): δ 0.87–0.89 (m, 3H), 1.27 (m, 14H), 1.71–1.72 (m, 2H), 2.39–2.43 (m, 2H), 3.49 (s, 2H), 4.06 (s, 3H), 4.08 (s, 3H), 6.59 (d, J=5.61 Hz, 1H), 7.21–7.26 (m, 4H), 7.55 (s, 1H), 7.59 (s, 1H), 7.79 (d, J=8.98 Hz, 1H), 8.52 (d, J=5.61 Hz, 1H), 8.66 (bs, 1H) Mass spectrometry value (ESI-MS, m/z): 538 (M$^+$+1)

Example 1073

N-{4-[(6,7-Dimethoxy-4-quinolyl)oxy]phenyl}-N'-tetradecanoylthiourea

Toluene (20 ml) and thionyl chloride (1 ml) were added to commercially available tetradecanoic acid (80 mg), and the mixture was heated at 100° C. for one hr. The solvent was removed by distillation, and tetradecanoyl isothiocyanate was prepared using the resultant tetradecanoyl chloride as a starting compound according to the description of the literature. Tetradecanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (58 mg, yield 60%).

$^1$H-NMR (CDCl$_3$, 400 MHz): δ 0.87–0.90 (m, 3H), 1.27 (m, 20H), 1.73 (m, 2H), 2.40–2.44 (m, 2H), 4.08 (s, 3H), 4.12 (s, 3H), 5.29 (s, 1H), 6.65 (d, J=6.09 Hz, 1H), 7.23–7.26 (m, 2H), 7.58 (s, 1H), 7.83–7.85 (m, 3H), 8.52 (d, J=6.09 Hz, 1H), 8.63 (bs, 1H) Mass spectrometry value (ESI-MS, m/z): 566 (M$^+$+1)

Example 1074

N-{4-[(6,7-Dimethoxy-4-quinolyl)oxy]phenyl}-N'-(2-methylhexanoyl)thiourea

Toluene (20 ml) and thionyl chloride (1 ml) were added to commercially available 2-methylhexanoic acid (80 mg), and the mixture was heated at 100° C. for one hr. The solvent was removed by distillation, and 2-methylhexanoyl isothiocyanate was prepared using the resultant 2-methylhexanoyl chloride as a starting compound according to the description of the literature. 2-Methylhexanoyl isothiocyanate was dissolved in ethanol (1 ml) to prepare a solution. 4-[(6,7-Dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (54 mg, yield 68%).

$^1$H-NMR (DMSO-d$_6$, 400 MHz): δ 0.86–0.89 (m, 4H), 1.10 (d, J=6.83 Hz, 3H), 1.27–1.32 (m, 5H), 2.74–2.76 (m, 1H), 3.94 (s, 3H), 3.96 (s, 3H), 6.58 (d, J=5.97 Hz, 1H), 7.31 (d, J=8.78 Hz, 2H), 7.42 (s, 1H), 7.52 (s, 1H), 7.78–7.82 (m, 3H), 8.55 (d, J=5.37 Hz, 1H), 11.50 (s, 1H) Mass spectrometry value (ESI-MS, m/z): 468 (M$^+$+1)

Example 1075

N-{4-[(6,7-Dimethoxy-4-quinolyl)oxy]-2-fluorophenyl}-N'-dodecanoylthiourea

Toluene (20 ml) and thionyl chloride (1 ml) were added to commercially available dodecanoic acid (80 mg), and the mixture was heated at 100° C. for one hr. The solvent was removed by distillation, and dodecanoyl isothiocyanate was prepared using the resultant dodecanoyl chloride as a starting compound according to the description of the literature. Dodecanoyl isothiocyanate was dissolved in ethanol (1 ml) to prepare a solution. 4-[(6,7-Dimethoxy-4-quinolyl)oxy]-2-fluoroaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 68%).

$^1$H-NMR (CDCl$_3$, 400 MHz): δ 0.86–0.89 (m, 6H), 1.26–1.27 (m, 6H), 1.56–1.64 (m, 11H), 4.09 (s, 3H), 4.17 (s, 3H), 6.78 (d, J=6.34 Hz, 1H), 7.08–7.13 (m, 2H), 7.26 (s, 1H), 7.59 (s, 1H), 8.12 (bs, 1H), 8.56 (d, J=6.34 Hz, 1H), 8.62 (m, 1H), 8.79 (bs, 1H) Mass spectrometry value (ESI-MS, m/z): 556 (M$^+$+1)

Example 1076

N-{4-[(6,7-Dimethoxy-4-quinolyl)oxy]-2-fluorophenyl}-N'-tetradecanoylthiourea

Toluene (20 ml) and thionyl chloride (1 ml) were added to commercially available tetradecanoic acid (80 mg), and the mixture was heated at 100° C. for one hr. The solvent was removed by distillation, and tetradecanoyl isothiocyanate was prepared using the resultant tetradecanoyl chloride as a starting compound according to the description of the literature. Tetradecanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (58 mg, yield 63%).

$^1$H-NMR (CDCl$_3$, 400 MHz): δ 0.86–0.89 (m, 3H), 1.27 (m, 18H), 2.49 (m, 2H), 2.58–2.59 (m, 4H), 4.11 (s, 3H), 4.17 (s, 3H), 6.38 (m, 1H), 7.08–7.11 (m, 2H), 7.35 (s, 3H), 7.61–7.63 (m, 2H), 8.17 (m, 1H) Mass spectrometry value (ESI-MS, m/z): 584 (M$^+$+1)

Example 1077

N-{3-Chloro-4-[(6,7-dimethoxy-4-quinolyl)oxy]phenyl}-N'-(2-methylhexanoyl)thiourea Toluene (20 ml) and thionyl chloride (1 ml) were added to commercially available 2-methylhexanoic acid (80 mg), and the mixture was heated at 100° C. for one hr. The solvent was removed by distillation, and 2-methylhexanoyl isothiocyanate was prepared using the resultant 2-methylhexanoyl chloride as a starting compound according to the description of the literature. 2-Methylhexanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (44 mg, yield 58%).

$^1$H-NMR (DMSO-d$_6$, 400 MHz): δ 0.84–0.94 (m, 5H), 1.03–1.11 (m, 4H), 1.25–1.59 (m, 4H), 3.94 (s, 3H), 3.96 (s, 3H), 6.42 (d, J=5.37 Hz, 1H), 7.42 (s, 1H), 7.47 (d, J=8.78 Hz, 1H), 7.53 (s, 1H), 7.70–7.73 (m, 1H), 8.17–8.19 (m, 1H), 8.51 (d, J=5.12 Hz, 1H), 11.58 (s, 1H), 12.62 (s, 1H) Mass spectrometry value (ESI-MS, m/z): 503 (M$^+$+1)

Example 1078

N-(2-Chlorobenzoyl)-N'-{4-[(6,7-dimethoxy-4-quinolyl)oxy]-2,3-dimethylphenyl}thiourea Commercially available 2-chloro-1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (68 mg, yield 85%).

$^1$H-NMR (CDCl$_3$, 400 MHz): δ 2.18 (s, 3H), 2.35 (s, 3H), 4.07 (s, 6H), 6.35 (d, J=5.37 Hz, 1H), 7.07 (d, J=8.54 Hz, 1H), 7.26 (s, 1H), 7.44–7.49 (m, 2H), 7.52–7.57 (m, 3H), 7.61 (s, 1H), 7.68 (d, J=7.32 Hz, 1H), 8.48 (d, J=5.37 Hz, 1H), 9.41 (bs, 1H) Mass spectrometry value (ESI-MS, m/z): 523 (M$^+$+1)

Example 1079

N-{4-[(6,7-Dimethoxy-4-quinolyl)oxy]-2,3-dimethylphenyl}-N'-(3-methylbenzoyl)thiourea Commercially available 3-methyl-1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (64 mg, yield 83%).

$^1$H-NMR (CDCl$_3$, 400 MHz): δ 2.24 (s, 3H), 2.34 (s, 3H), 2.47 (s, 3H), 4.07 (s, 6H), 6.35 (d, J=5.37 Hz, 1H), 7.06 (d, J=8.54 Hz, 1H), 7.26 (s, 1H), 7.43–7.49 (m, 3H), 7.55 (d, J=8.78 Hz, 1H), 7.61 (s, 1H), 7.71–7.74 (m, 2H), 8.48 (d, J=5.12 Hz, 1H), 9.23 (s, 1H) Mass spectrometry value (ESI-MS, m/z): 502 (M$^+$+1)

Example 1080

N-{4-[(6,7-Dimethoxy-4-quinolyl)oxy]-2,3-dimethylphenyl}-N'-(4-methylbenzoyl)thiourea Commercially available 4-methyl-1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 78%).

$^1$H-NMR (CDCl$_3$, 400 MHz): δ 2.18 (s, 3H), 2.33 (s, 3H), 2.47 (s, 3H), 4.07 (s, 6H), 6.35 (d, J=5.37 Hz, 1H), 7.26 (s, 2H), 7.37 (d, J=7.81 Hz, 2H), 7.44 (s, 1H), 7.54 (d, J=8.78 Hz, 1H), 7.61 (s, 1H), 7.83 (d, J=8.29 Hz, 2H), 8.48 (d, J=5.37 Hz, 1H), 9.22 (bs, 1H) Mass spectrometry value (ESI-MS, m/z): 502 (M$^+$+1)

Example 1081

N-{4-[(6,7-Dimethoxy-4-quinolyl)oxy]-2,3-dimethylphenyl}-N'-(4-nitrobenzoyl)thiourea Commercially available 4-nitro-1-benzenecarbonyl isothiocyanate (30 mg) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (62 mg, yield 75%).

$^1$H-NMR (CDCl$_3$, 400 MHz): δ 2.42 (s, 3H), 2.34 (s, 3H), 4.07 (s, 6H), 6.35 (d, J=5.12 Hz, 1H), 7.07 (d, J=8.54 Hz, 1H), 7.27 (s, 2H), 7.44 (s, 1H), 7.52 (d, J=8.54 Hz, 1H), 7.61 (s, 1H), 8.17 (d, J=9.03 Hz, 2H), 8.42 (d, J=9.03 Hz, 2H), 8.48 (d, J=5.12 Hz, 1H) Mass spectrometry value (ESI-MS, m/z): 533 (M$^+$+1)

Example 1082

N-(4-Chlorobenzoyl)-N'-{4-[(6,7dimethoxy-4-quinolyl)oxy]-2,3-dimethylphenyl}thiourea Commercially available 4-chloro-1-benzenecarbonyl isothiocyanate (50 μl) was dissolved in ethanol (1 ml) to prepare a solution. 4-[(6,7-Dimethoxy-4quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (55 mg, yield 68%).

$^1$H-NMR (CDCl$_3$, 400 MHz): δ 2.19 (s, 3H), 2.33 (s, 3H), 4.06 (s, 6H), 6.35 (d, J=5.12 Hz, 1H), 7.06 (d, J=8.54 Hz, 1H), 7.26 (s, 1H), 7.44 (s, 1H), 7.51–7.56 (m, 3H), 7.61 (s, 1H), 7.89 (d, J=11.22 Hz, 2H), 8.48 (d, J=5.37 Hz, 1H), 9.22 (bs, 1H) Mass spectrometry value (ESI-MS, m/z): 523 (M$^+$+1)

Example 1083

N-(3-Chlorobenzoyl)-N'-{4-[(6,7-dimethoxy-4-quinolyl)oxy]-2,3-dimethylphenyl}thiourea Commercially available 3-chloro-1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (70 mg, yield 87%).

$^1$H-NMR (CDCl$_3$, 400 MHz): δ 2.19 (s, 3H), 2.33 (s, 3H), 4.07 (s, 6H), 6.35 (d, J=5.37 Hz, 1H), 7.06 (d, J=8.54 Hz,

1H), 7.26 (s, 1H), 7.44 (s, 1H), 7.49–7.54 (m, 2H), 7.61 (s, 1H), 7.65 (d, J=9.03 Hz, 1H), 7.80 (d, J=10.49 Hz, 1H), 7.95 (s, 1H), 8.48 (d, J=5.12 Hz, 1H), 9.24 (bs, 1H) Mass spectrometry value (ESI-MS, m/z): 523 ($M^+$+1)

Example 1084

N-Benzoyl-N'-{4-[(6,7-dimethoxy-4-quinolyl)oxy]-2,3-dimethylphenyl}thiourea

Comercially available 1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (50 mg, yield 67%).

$^1$H-NMR (CDCl$_3$, 400 MHz): δ 2.19 (s, 3H), 2.34 (s, 3H), 4.07 (s, 6H), 6.35 (d, J=5.37 Hz, 1H), 7.06 (d, J=8.54 Hz, 1H), 7.26 (s, 1H), 7.44 (s, 1H), 7.49–7.61 (m, 4H), 7.67–7.70 (m, 1H), 7.94 (d, J=8.54 Hz, 2H), 8.48 (d, J=5.37 Hz, 1H), 9.27 (bs, 1H) Mass spectrometry value (ESI-MS, m/z): 488 ($M^+$+1)

Example 1085

N-{4-[(6,7-Dimethoxy-4-quinolyl)oxy]-2,3-dimethylphenyl}-N'-(2-methylbenzoyl)thiourea Commercially available 2-methyl-1-benzenecarbonyl isothiocyanate (50 μl) was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (61 mg, yield 79%).

$^1$H-NMR (CDCl$_3$, 400 MHz): δ 2.19 (s, 3H), 2.35 (s, 3H), 2.59 (s, 3H), 4.07 (s, 6H), 6.35 (d, J=5.37 Hz, 1H), 7.07 (d, J=8.78 Hz, 1H), 7.26 (s, 1H), 7.33–7.36 (m, 2H), 7.45–7.49 (m, 2H), 7.55–7.61 (m, 3H), 8.48 (d, J=5.12 Hz, 1H), 8.96 (bs, 1H) Mass spectrometry value (ESI-MS, m/z): 502 ($M^+$+1)

Example 1086

N-(2,4-Dichlorobenzoyl)-N'-{4-[(6,7-dimethoxy-4-quinolyl)oxy]-2,3-dimethylphenyl}thiourea 2,4-Dichloro-1-benzenecarbonyl isothiocyanate was prepared using commercially available 2,4-dichloro-1-benzenecarbonyl chloride (80 mg) as a starting compound according to the description of the literature. 2,4-Dichloro-1-benzenecarbonyl isothiocyanate was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 69%).

$^1$H-NMR (CDCl$_3$, 400 MHz): δ 2.19 (s, 3H), 2.37 (s, 3H), 3.35 (s, 6H), 6.70 (d, J=6.59 Hz, 1H), 7.11 (d, J=8.54 Hz, 1H), 7.34 (dd, J=1.95, 8.29 Hz, 1H), 7.45–7.48 (m, 2H), 7.56–7.72 (m, 5H), 8.54 (d, J=6.31 Hz, 1H) Mass spectrometry value (ESI-MS, m/z): 557 ($M^+$+1)

Example 1087

N-{4-[(6,7-Dimethoxy-4-quinolyl)oxy]-2,3-dimethylphenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 4-Methoxy-1-benzenecarbonyl isothiocyanate was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (55 mg, yield 69%).

$^1$H-NMR (DMSO-d$_6$, 400 MHz): δ 2.09 (s, 3H), 2.22 (s, 3H), 3.86 (s, 3H), 3.95 (s, 6H), 6.29 (d, J=5.37 Hz, 1H), 7.06–7.12 (m, 3H), 7.40–7.46 (m, 2H), 7.57 (s, 1H), 8.05 (d, J=9.03 Hz, 2H), 8.47 (d, J=5.37 Hz, 1H), 11.47 (bs, 1H), 3.95 (bs, 1H) Mass spectrometry value (ESI-MS, m/z): 518 ($M^+$+1)

Example 1088

N-(2,4-Difluorobenzoyl)-N'-{4-[(6,7-dimethoxy-4-quinolyl)oxy]-2,3-dimethylphenyl}thiourea 2,4-Difluoro-1-benzenecarbonyl isothiocyanate was prepared using commercially available 2,4-difluoro-1-benzenecarbonyl chloride (80 mg) as a starting compound according to the description of the literature. 2,4-Difluoro-1-benzenecarbonyl isothiocyanate was dissolved in ethanol (1 ml) to prepare a solution. 4-[(6,7-Dimethoxy-4-quinolyl)oxy]-2,3-dimethylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (60 mg, yield 74%).

$^1$H-NMR (CDCl$_3$, 400 MHz): δ 2.17 (s, 3H), 2.34 (s, 3H), 4.09 (s, 3H), 4.11 (s, 3H), 6.49 (d, J=6.59 Hz, 1H), 6.87–6.93 (m, 2H), 6.99–7.15 (m, 2H), 7.26–7.30 (m, 1H), 7.57–7.64 (m, 2H), 8.09–8.17 (m, 2H), 8.49 (d, J=6.58 Hz, 1H) Mass spectrometry value (ESI-MS, m/z): 524 ($M^+$+1)

Example 1089

N-(4-Chlorobenzoyl)-N'-{4-[(6,7-dimethoxy-4-quinolyl)oxy]-2-methylphenyl}thiourea Commercially available 4-chloro-1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (46 mg, yield 56%).

$^1$H-NMR (CDCl$_3$, 400 MHz): δ 2.29 (s, 3H), 4.04 (s, 3H), 4.06 (s, 3H), 6.59 (d, J=5.37 Hz, 1H), 7.09–7.12 (m, 2H), 7.26 (s, 1H), 7.44 (s, 1H), 7.53–7.58 (m, 3H), 7.83–7.89 (m,

3H), 8.53 (d, J=5.37 Hz, 1H), 9.19 (bs, 1H) Mass spectrometry value (ESI-MS, m/z): 509 (M$^+$+1)

Example 1090

N-{4-[(6,7-Dimethoxy-4-quinolyl)oxy]-2-methylphenyl}-N'-(2-methylbenzoyl)thiourea Commercially available 2-methyl-1-benzenecarbonyl isothiocyanate (50 µl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (46 mg, yield 59%).

$^1$H-NMR (CDCl$_3$, 400 MHz): δ 2.41 (s, 3H), 2.58 (s, 3H), 4.05 (s, 3H), 4.06 (s, 3H), 6.59 (d, J=5.37 Hz, 1H), 7.09–7.12 (m, 3H), 7.26 (s, 1H), 7.34–7.35 (m, 1H), 7.44 (s, 1H), 7.48 (t, J=7.56 Hz, 1H), 7.53 (s, 1H), 7.59 (d, J=7.81 Hz, 1H), 7.84 (d, J=8.54 Hz, 1H), 8.53 (d, J=5.12 Hz, 1H), 8.95 (bs, 1H) Mass spectrometry value (ESI-MS, m/z): 488 (M$^+$+1)

Example 1091

N-{4-[(6,7-Dimethoxy-4-quinolyl)oxy]-2-methylphenyl}-N'-(3-fluorobenzoyl)thiourea 3-Fluoro-1-benzenecarbonyl isothiocyanate was prepared using commercially available 3-fluoro-1-benzenecarbonyl chloride (80 mg) as a starting compound according to the description of the literature. 3-Fluoro-1-benzenecarbonyl isothiocyanate was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (64 mg, yield 81%).

$^1$H-NMR (CDCl$_3$, 400 MHz): δ 2.39 (s, 3H), 4.05 (s, 3H), 4.06 (s, 3H), 6.59 (d, J=5.37 Hz, 1H), 7.09–7.12 (m, 2H), 7.26 (s, 1H), 7.36–7.41 (m, 1H), 7.44 (s, 1H), 7.53–7.59 (m, 2H), 7.66–7.71 (m, 2H), 7.84 (d, J=8.29 Hz, 1H), 8.54 (d, J=5.12 Hz, 1H), 9.19 (bs, 1H) Mass spectrometry value (ESI-MS, m/z): 492 (M$^+$+1)

Example 1092

N-{4-[(6,7-Dimethoxy-4-quinolyl)oxy]-2-methylphenyl}-N'-(4-nitrobenzoyl)thiourea Commercially available 4-nitro-1-benzenecarbonyl isothiocyanate (30 mg) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (41 mg, yield 49%).

$^1$H-NMR (CDCl$_3$, 400 MHz): δ 2.39 (s, 3H), 4.05 (s, 3H), 4.06 (s, 3H), 6.59 (d, J=5.37 Hz, 1H), 7.11–7.13 (m, 2H), 7.26 (s, 2H), 7.44 (s, 1H), 7.52 (s, 1H), 7.83 (d, J=8.54 Hz, 1H), 8.13 (d, J=9.03 Hz, 2H), 8.42 (d, J=8.78 Hz, 2H), 8.54 (d, J=5.37 Hz, 1H) Mass spectrometry value (ESI-MS, m/z): 519 (M$^+$+1)

Example 1093

N-{4-[(6,7-Dimethoxy-4-quinolyl)oxy]-2-methylphenyl}-N'-(4-fluorobenzoyl)thiourea 4-Fluoro-1-benzenecarbonyl isothiocyanate was prepared using commercially available 4-fluoro-1-benzenecarbonyl chloride (80 mg) as a starting compound according to the description of the literature. 4-Fluoro-1-benzenecarbonyl isothiocyanate was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (35 mg, yield 44%).

$^1$H-NMR (CDCl$_3$, 400 MHz): δ 2.39 (s, 3H), 4.05 (s, 3H), 4.06 (s, 3H), 6.59 (d, J=5.37 Hz, 1H), 7.09–7.12 (m, 2H), 7.23–7.28 (m, 3H), 7.44 (s, 1H), 7.53 (s, 1H), 7.84 (d, J=8.29 Hz, 1H), 7.96–7.99 (m, 2H), 8.53 (d, J=5.37 Hz, 1H), 9.19 (bs, 1H) Mass spectrometry value (ESI-MS, m/z): 492 (M$^+$+1)

Example 1094

N-{4-[(6,7-Dimethoxy-4-quinolyl)oxy]-2-methylphenyl}-N'-(2-fluorobenzoyl)thiourea 2-Fluoro-1-benzenecarbonyl isothiocyanate was prepared using commercially available 2-fluoro-1-benzenecarbonyl chloride (80 mg) as a starting compound according to the description of the literature. 2-Fluoro-1-benzenecarbonyl isothiocyanate was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (41 mg, yield 52%).

$^1$H-NMR (CDCl$_3$, 400 MHz): δ 2.39 (s, 3H), 4.05 (s, 3H), 4.06 (s, 3H), 6.59 (d, J=5.37 Hz, 1H), 7.09–7.12 (m, 2H), 7.24–7.29 (m, 3H), 7.39 (t, J=7.68 Hz, 1H), 7.44 (s, 1H), 7.53 (s, 1H), 7.64–7.69 (m, 1H), 7.86 (d, J=8.29 Hz, 1H), 8.12–8.16 (m, 1H), 8.53 (d, J=5.12 Hz, 1H) Mass spectrometry value (ESI-MS, m/z): 492 (M$^+$+1)

Example 1095

N-{4-[(6,7-Dimethoxy-4-quinolyl)oxy]-2-methylphenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 4-Methoxy-1-benzenecarbonyl isothiocyanate was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (37 mg, yield 45%).

$^1$H-NMR (CDCl$_3$, 400 MHz): δ 2.40 (s, 3H), 3.92 (s, 6H), 4.05 (s, 3H), 7.03–7.11 (m, 4H), 7.26 (s, 5H), 7.56 (s, 1H), 7.90–7.92 (m, 3H) Mass spectrometry value (ESI-MS, m/z): 504 (M$^+$+1)

Example 1096

N-{4-[(6,7-Dimethoxy-4-quinolyl)oxy]-2-methylphenyl}-N'-(4-methylbenzoyl)thiourea Commercially available 4-methyl-1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (44 mg, yield 56%).

$^1$H-NMR (CDCl$_3$, 400 MHz): δ 2.39 (s, 3H), 2.47 (s, 3H), 4.05 (s, 3H), 4.06 (s, 3H), 6.59 (d, J=5.37 Hz, 1H), 7.08–7.12 (m, 2H), 7.26 (s, 1H), 7.36 (d, J=7.81 Hz, 2H), 7.44 (s, 1H), 7.53 (s, 1H), 7.81–7.86 (m, 3H), 8.53 (d, J=5.12 Hz, 1H), 9.19 (s, 1H) Mass spectrometry value (ESI-MS, m/z): 488 (M$^+$+1)

Example 1097

N-(2-Chlorobenzoyl)-N'-{4-[(6,7-dimethoxy-4-quinolyl)oxy]-2-methylphenyl}thiourea Commercially available 2-chloro-1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (47 mg, yield 57%).

$^1$H-NMR (CDCl$_3$, 400 MHz): δ 2.41 (s, 3H), 4.05 (s, 3H), 4.06 (s, 3H), 6.59 (d, J=5.12 Hz, 1H), 7.09–7.12 (m, 2H), 7.26 (s, 2H), 7.44–7.48 (m, 2H), 7.53–7.54 (m, 2H), 7.82 (d, J=7.08 Hz, 1H), 7.88 (d, J=8.54 Hz, 1H), 8.54 (d, J=5.12 Hz, 1H), 9.38 (bs, 1H) Mass spectrometry value (ESI-MS, m/z): 508 (M$^+$+1)

Example 1098

N-{4-[(6,7-Dimethoxy-4-quinolyl)oxy]-2-methylphenyl}-N'-(3-methylbenzoyl)thiourea Commercially available 3-methyl-1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (32 mg, yield 40%).

$^1$H-NMR (CDCl$_3$, 400 MHz): δ 2.39 (s, 3H), 2.47 (s, 3H), 4.05 (s, 3H), 4.06 (s, 3H), 6.59 (d, J=5.37 Hz, 1H), 7.09–7.12 (m, 2H), 7.26 (s, 1H), 7.44–7.49 (m, 3H), 7.53 (s, 1H), 7.71–7.74 (m, 2H), 7.87 (d, J=8.29 Hz, 1H), 8.53 (d, J=5.37 Hz, 1H), 9.21 (bs, 1H) Mass spectrometry value (ESI-MS, m/z): 488 (M$^+$+1)

Example 1099

N-Benzoyl-N'-{4-[(6,7-dimethoxy-4-quinolyl)oxy]-2-methylphenyl}thiourea

Commercially available 1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (44 mg, yield 58%).

$^1$H-NMR (CDCl$_3$, 400 MHz): δ 2.39 (s, 3H), 4.05 (s, 3H), 4.06 (s, 3H), 6.59 (d, J=5.37 Hz, 1H), 7.09–7.12 (m, 3H), 7.25 (s, 1H), 7.44 (s, 1H), 7.53 (s, 1H), 7.58 (t, J=7.08 Hz, 2H), 7.68 (t, J=7.32 Hz, 1H), 7.86 (d, J=8.29 Hz, 2H), 7.94 (d, J=8.54 Hz, 1H), 9.23 (bs, 1H) Mass spectrometry value (ESI-MS, m/z): 474 (M$^+$+1)

Example 1100

N-(3-Chlorobenzoyl)-N'-{4-[(6,7-dimethoxy-4-quinolyl)oxy]-2-methylphenyl}thiourea Commercially available 3-chloro-1-benzenecarbonyl isothiocyanate (50 μl) was dissolved in ethanol (1 ml) to prepare a solution. 4-[(6,7-Dimethoxy-4-quinolyl)oxy]-2-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (41 mg, yield 50%).

$^1$H-NMR (CDCl$_3$, 400 MHz): δ 2.39 (s, 3H), 4.05 (s, 3H), 4.06 (s, 3H), 6.59 (d, J=5.12 Hz, 1H), 7.09–7.12 (m, 2H), 7.27 (s, 1H), 7.44 (s, 1H), 7.49–7.54 (m, 2H), 7.65 (d, J=8.05 Hz, 1H), 7.79 (d, J=8.29 Hz, 1H), 7.85 (d, J=8.54 Hz, 1H), 7.95 (s, 1H), 8.53 (d, J=5.37 Hz, 1H), 9.19 (bs, 1H) Mass spectrometry value (ESI-MS, m/z): 508 (M$^+$+1)

Example 1101

N-{2-Chloro-4-[(6,7-dimethoxy-4-quinolyl)oxy]phenyl}-N'-(2-methylbenzoyl)thiourea Commercially available 2-methyl-1-benzenecarbonyl isothiocyanate (50 μl) was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (40 mg, yield 52%).

$^1$H-NMR (DMSO-d$_6$, 400 MHz): δ 2.64 (s, 3H), 3.92 (s, 3H), 3.93 (s, 3H), 6.60 (d, J=5.12 Hz, 1H), 7.19–7.21 (m, 2H), 7.34 (m, 2H), 7.41–7.47 (m, 3H), 7.52 (m, 2H), 8.16–8.20 (m, 1H), 8.52–8.53 (m, 2H) Mass spectrometry value (ESI-MS, m/z): 508 (M$^+$+1)

Example 1102

N-{2-Chloro-4-[(6,7-dimethoxy-4-quinolyl)oxy]phenyl}-N'-(4-methylbenzoyl)thiourea

Commercially available 4-methyl-1-benzenecarbonyl isothiocyanate (50 μl) was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (38 mg, yield 49%).

$^1$H-NMR (DMSO-$d_6$, 400 MHz): δ 2.41 (s, 3H), 3.94 (s, 3H), 3.97 (s, 3H), 6.69 (d, J=5.37 Hz, 1H), 7.33–7.37 (m, 4H), 7.44 (s, 1H), 7.54 (s, 1H), 7.60 (d, J=2.68 Hz, 1H), 7.94 (d, J=8.29 Hz, 1H), 8.14 (d, J=9.03 Hz, 1H), 8.59 (d, J=5.37 Hz, 1H), 11.74 (s, 1H), 12.75 (s, 1H) Mass spectrometry value (ESI-MS, m/z): 509 (M$^+$+1)

Example 1103

N-{2-Chloro-4-[(6,7-dimethoxy-4-quinolyl)oxy]phenyl}-N'-(2-methoxybenzoyl)thiourea

2-Methoxy-1-benzenecarbonyl isothiocyanate was prepared using commercially available 2-methoxy-1-benzenecarbonyl chloride (80 mg) as a starting compound according to the description of the literature. 2-Methoxy-1-benzenecarbonyl isothiocyanate was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (36 mg, yield 45%).

$^1$H-NMR (DMSO-$d_6$, 400 MHz): δ 3.95 (s, 3H), 3.96 (s, 3H), 4.04 (s, 3H), 6.42 (d, J=5.12 Hz, 1H), 7.18 (t, J=7.69 Hz, 1H), 7.30 (d, J=8.54 Hz, 1H), 7.41 (s, 1H), 7.48 (d, J=8.76 Hz, 1H), 7.52 (s, 1H), 7.68 (t, J=6.96 Hz, 1H), 7.76 (dd, J=2.56, 8.90 Hz, 1H), 7.94 (d, J=7.81 Hz, 1H), 8.20 (d, J=2.44 Hz, 1H), 8.49 (d, J=5.12 Hz, 1H), 11.29 (s, 1H), 12.62 (s, 1H) Mass spectrometry value (ESI-MS, m/z): 525 (M$^+$+1)

Example 1104

N-(2-Chlorobenzoyl)-N'-{2-chloro-4-[(6,7-dimethoxy-4-quinolyl)oxy]phenyl}thiourea

Commercially available 2-chloro-1-benzenecarbonyl isothiocyanate (50 μl) was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (38 mg, yield 48%).

$^1$H-NMR (DMSO-$d_6$, 400 MHz): δ 3.93 (s, 3H), 4.05 (s, 3H), 6.67 (d, J=5.12 Hz, 1H), 7.20 (d, J=7.81 Hz, 1H), 7.32–7.36 (m, 2H), 7.43 (s, 1H), 7.47 (s, 1H), 7.54–7.66 (m, 2H), 7.67 (d, J=6.59 Hz, 1H), 8.13 (d, J=8.78 Hz, 1H), 8.58 (d, J=5.12 Hz, 1H), 12.23 (s, 1H), 12.36 (s, 1H) Mass spectrometry value (ESI-MS, m/z): 529 (M$^+$+1)

Example 1105

N-{4-[(6,7-Dimethoxy-4-quinolyl)oxy]-2,3-dimethylphenyl}-N'-(2-phenylacetyl)thiourea

2-Phenylethanoyl isothiocyanate was prepared using commercially available 2-phenylethanoyl chloride (80 mg) as a starting compound according to the description of the literature. 4-[(6,7-Dimethoxy-4-quinolyl)oxy]-2,3-dimethylaniline (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (44 mg, yield 58%).

$^1$H-NMR (DMSO-$d_6$, 400 MHz): δ 2.08 (s, 3H), 2.15 (s, 3H), 3.85 (s, 2H), 3.94 (s, 3H), 3.95 (s, 3H), 6.28 (d, J=5.12 Hz, 1H), 7.08 (d, J=8.54 Hz, 1H), 7.27–7.41 (m, 7H), 7.57 (s, 1H), 8.47 (d, J=5.37 Hz, 1H), 11.75 (bs, 1H), 12.01 (bs, 1H) Mass spectrometry value (ESI-MS, m/z): 502 (M$^+$+1)

Example 1106

N-{2-Chloro-4-[(6,7-dimethoxy-4-quinolyl)oxy]phenyl}-N'-(3-cyclopentylpropanoyl)thiourea

3-Cyclopentylpropanoyl isothiocyanate was prepared using commercially available 3-cyclopentylpropanoyl chloride (80 mg) as a starting compound according to the description of the literature. 3-Cyclopentylpropanoyl isothiocyanate was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (32 mg, yield 41%).

$^1$H-NMR (DMSO-$d_6$, 400 MHz): δ 1.11 (m, 2H), 1.49 1.61 (m, 7H), 1.63–1.79 (m, 4H), 3.92 (s, 3H), 3.93 (s, 3H), 6.65 (d, J=5.37 Hz, 1H), 7.31 (d, J=11.71 Hz, 1H), 7.47 (s, 1H), 7.48 (s, 1H), 7.58 (d, J=2.68 Hz, 1H), 8.12 (d, J=8.78 Hz, 1H), 8.56 (d, J=6.83 Hz, 1H), 11.67 (s, 1H), 12.53 (s, 1H) Mass spectrometry value (ESI-MS, m/z): 515 (M$^+$+1)

Example 1107

N-Benzoyl-N'-{2-chloro-4-[(6,7-dimethoxy-4-quinolyl)oxy]phenyl}thiourea

Commercially available 1-benzenecarbonyl isothiocyanate (50 μl) was dissolved in ethanol (1 ml) to prepare a solution. 2-Chloro-4-[(6,7-dimethoxy-4-quinolyl)oxy]aniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (36 mg, yield 48%).

$^1$H-NMR (DMSO-$d_6$, 400 MHz): δ 3.92 (s, 3H), 3.96 (s, 3H), 6.66 (d, J=5.37 Hz, 1H), 7.32 (d, J=8.78 Hz, 1H), 7.42 (s, 1H), 7.48 (s, 1H), 7.53–7.57 (m, 3H), 7.66–7.68 (m, 1H), 8.02 (d, J=8.54 Hz, 2H), 8.13 (d, J=9.03 Hz, 1H), 8.56 (d, J=5.37 Hz, 1H), 11.38 (s, 1H), 12.70 (s, 1H) Mass spectrometry value (ESI-MS, m/z): 495 (M$^+$+1)

Example 1108

N-{4-[(6,7-Dimethoxy-4-quinolyl)oxy]-3-methylphenyl}-N'-(4-nitrobenzoyl)thiourea

Commercially available 4-nitro-1-benzenecarbonyl isothiocyanate (30 mg) was dissolved in ethanol (1 ml) to prepare a solution. 4-[(6,7-Dimethoxy-4-quinolyl)oxy]-3-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (79 mg, yield 94%).

$^1$H-NMR (DMSO-$d_6$, 400 MHz): δ 2.17 (s, 3H), 3.96 (s, 6H), 6.36 (d, J=5.12 Hz, 1H), 7.41 (s, 1H), 7.57 (s, 2H), 7.72 (bs, 2H), 8.19 (d, J=8.78 Hz, 2H), 8.29 (s, 1H), 8.36 (d, J=8.54 Hz, 2H), 8.48 (d, J=5.12 Hz, 2H) Mass spectrometry value (ESI-MS, m/z): 519 (M$^+$+1)

Example 1109

N-Benzoyl-N'-{4-[(6,7-dimethoxy-4-quinolyl)oxy]-3-methylphenyl}thiourea

Commercially available 1-benzenecarbonyl isothiocyanate (50 μl) was dissolved in ethanol (1 ml) to prepare a solution. 4-[(6,7-Dimethoxy-4-quinolyl)oxy]-3-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (61 mg, yield 80%).

$^1$H-NMR (CDCl$_3$, 400 MHz): δ 2.24 (s, 3H), 4.09 (s, 3H), 4.12 (s, 3H), 6.58 (d, J=6.09 Hz, 1H), 7.26 (s, 1H), 7.56–7.81 (m, 8H), 7.93 (d, J=7.32 Hz, 2H), 8.49 (d, J=5.86 Hz, 1H), 9.14 (bs, 1H) Mass spectrometry value (ESI-MS, m/z): 474 (M$^+$+1)

Example 1110

N-{4-[(6,7-Dimethoxy-4-quinolyl)oxy]-3-methylphenyl}-N'-(3-methylbenzoyl)thiourea

Commercially available 3-methyl-1-benzenecarbonyl isothiocyanate (50 μl) was dissolved in ethanol (1 ml) to prepare a solution. 4-[(6,7-Dimethoxy-4-quinolyl)oxy]-3-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (65 mg, yield 83%).

$^1$H-NMR (DMSO-$d_6$, 400 MHz): δ 2.17 (s, 3H), 2.41 (s, 3H), 3.96 (s, 6H), 6.37 (d, J=4.88 Hz, 1H), 7.33 (d, J=9.02 Hz, 1H), 7.41–7.48 (m, 4H), 7.56 (s, 1H), 7.72–7.85 (m, 3H), 8.48 (d, J=5.37 Hz, 1H), 11.53 (s, 1H), 12.67 (s, 1H) Mass spectrometry value (ESI-MS, m/z): 488 (M$^+$+1)

Example 1111

N-(4-Chlorobenzoyl)-N'-{4-[(6,7-dimethoxy-4-quinolyl)oxy]-3-methylphenyl}thiourea

Commercially available 4-chloro-1-benzenecarbonyl isothiocyanate (50 μl) was dissolved in ethanol (1 ml) to prepare a solution. 4-[(6,7-Dimethoxy-4-quinolyl)oxy]-3-methylaniline (50 mg), toluene (5 ml), and ethanol (1 ml) were added to the solution, and the mixture was stirred at room temperature for 2 hr. The reaction solution was concentrated, and the residue was purified by chromatography on silica gel using chloroform/acetone for development to give the title compound (52 mg, yield 64%).

$^1$H-NMR (CDCl$_3$, 400 MHz): δ 2.24 (s, 3H), 4.08 (s, 3H), 4.09 (s, 3H), 6.44 (d, J=5.37 Hz, 1H), 7.17 (d, J=8.54 Hz, 1H), 7.26 (s, 1H), 7.55 (d, J=8.29 Hz, 3H), 7.62 (d, J=7.81 Hz, 3H), 7.71 (d, J=7.81 Hz, 1H), 7.87 (d, J=8.54 Hz, 1H), 8.49 (d, J=5.61 Hz, 1H), 9.11 (bs, 1H) Mass spectrometry value (ESI-MS, m/z): 508 (M$^+$+1)

Example 1112

N-(2,6-Dichlorobenzoyl)-N'-{4-[(6,7-dimethoxy-4-quinolyl)oxy]-3-fluorophenyl}thiourea

2,6-Dichloro-1-benzenecarbonyl isothiocyanate was prepared using commercially available 2,6-dichloro-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2,6-dichloro-1-benzenecarbonyl in ethanol (1 ml) was then added to the solution, and the mixture was stirred at room temperature for 2 hr. The reaction solution was concentrated, and the residue was purified by chromatography on silica gel using chloroform/acetone for development to give the title compound (55 mg, yield 63%).

$^1$H-NMR (DMSO-$d_6$, 400 MHz): δ 3.95 (s, 3H), 3.96 (s, 3H), 6.52 (d, J=5.12 Hz, 1H), 7.38–7.79 (m, 7H), 8.07–8.10 (m, 1H), 8.52 (d, J=5.12 Hz, 1H), 12.30 (bs, 1H), 12.43 (bs, 1H) Mass spectrometry value (ESI-MS, m/z): 547 (M$^+$+1)

Example 1113

N-(2,4-Dimethoxybenzoyl)-N'-{4-[(6,7-dimethoxy-4-quinolyl)oxy]-3-fluorophenyl}thiourea

2,4-Dimethoxy-1-benzenecarbonyl isothiocyanate was prepared using commercially available 2,4-dimethoxy-1-benzenecarbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (45 mg, yield 53%).

$^1$H-NMR (DMSO-$d_6$, 400 MHz): δ 3.87 (s, 3H), 3.90 (s, 3H), 3.96 (s, 3H), 4.06 (s, 3H), 6.52 (d, J=6.34 Hz, 1H), 6.79–6.81 (m, 2H), 7.43 (s, 2H), 7.50–7.55 (m, 1H), 7.64 (d, J=11.22 Hz, 1H), 7.99 (d, J=9.03 Hz, 1H), 8.11 (d, J=14.64 Hz, 1H), 8.52 (d, J=5.12 Hz, 1H), 11.09 (bs, 1H), 12.76 (bs, 1H) Mass spectrometry value (ESI-MS, m/z): 538 (M$^+$+1)

Example 1114

N-{3-Chloro-4-[(6,7-dimethoxy-4-quinolyl)oxy]phenyl}-N'-(2,4-dichlorobenzoyl)thiourea 2,4-Dichloro-1-benzenecarbonyl isothiocyanate was prepared using commercially available 2,4-dichloro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2,4-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (53 mg, yield 62%).

$^1$H-NMR (DMSO-$d_6$, 400 MHz): δ 3.95 (s, 3H), 3.96 (s, 3H), 6.43 (d, J=5.12 Hz, 1H), 7.43–8.17 (m, 7H), 8.17 (bs, 1H), 8.52 (d, J=5.12 Hz, 1H), 12.13 (bs, 1H), 12.28 (bs, 1H) Mass spectrometry value (ESI-MS, m/z): 563 (M$^+$+1)

Example 1115

N-{3-Chloro-4-[(6,7-dimethoxy-4-quinolyl)oxy]phenyl}-N'-(2,6-dichlorobenzoyl)thiourea 2,6-Dichloro-1-benzenecarbonyl isothiocyanate was prepared using commercially available 2,6-dichloro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2,6-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (40 mg, yield 47%).

$^1$H-NMR (DMSO-$d_6$, 400 MHz): δ 3.95 (s, 3H), 3.96 (s, 3H), 6.43 (d, J=5.37 Hz, 1H), 7.43 (s, 1H), 7.47–7.61 (m, 5H), 7.77–7.98 (m, 1H), 8.18–8.20 (m, 1H), 8.52 (d, J=5.12 Hz, 1H), 12.24 (bs, 1H), 12.43 (bs, 1H) Mass spectrometry value (ESI-MS, m/z): 563 (M$^+$+1)

Example 1116

N-{3-Chloro-4-[(6,7-dimethoxy-4-quinolyl)oxy]phenyl}-N'-(3,5-dichlorobenzoyl)thiourea 3,5-Dichloro-1-benzenecarbonyl isothiocyanate was prepared using commercially available 3,5-dichloro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3,5-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (55 mg, yield 63%).

$^1$H-NMR (DMSO-$d_6$, 400 MHz): δ 3.95 (s, 3H), 3.96 (s, 3H), 6.42 (d, J=4.64 Hz, 1H), 7.42 (s, 1H), 7.49 (d, J=8.78 Hz, 1H), 7.53 (s, 1H), 7.72–8.00 (m, 6H), 8.16 (bs, 1H), 8.50 (d, J=5.12 Hz, 1H) Mass spectrometry value (ESI-MS, m/z): 563 (M$^+$+1)

Example 1117

N-{3-Chloro-4-[(6,7-dimethoxy-4-quinolyl)oxy]phenyl}-N'-(2,4-dimethoxybenzoyl)thiourea 2,4-Dimethoxy-1-benzenecarbonyl isothiocyanate was prepared using commercially available 2,4-dimethoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (53 mg, yield 63%).

$^1$H-NMR (DMSO-$d_6$, 400 MHz): δ 3.90 (s, 3H), 3.95 (s, 3H), 3.96 (s, 3H), 4.06 (s, 3H), 6.43 (d, J=5.12 Hz, 1H), 6.73–6.81 (m, 2H), 7.43 (s, 1H), 7.49–7.53 (m, 3H), 7.78 (dd, J=2.44 Hz, J=8.78 Hz, 1H), 8.12 (bs, 1H), 8.51 (d, J=5.12 Hz, 1H), 11.09 (bs, 1H), 12.69 (bs, 1H) Mass spectrometry value (EST-MS, m/z): 555 (M$^+$+1)

Example 1118

N-(2,6-Dichlorobenzoyl)-N'-{4-[(6,7-dimethoxy-4-quinolyl)oxy]phenyl}thiourea 2,6-Dichloro-1-benzenecarbonyl isothiocyanate was prepared using commercially available 2,6-dichloro-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2,6-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (57 mg, yield 64%).

$^1$H-NMR (DMSO-$d_6$, 400 MHz): δ 4.09 (s, 3H), 4.13 (s, 3H), 6.69 (d, J=6.09 Hz, 1H), 7.11–7.44 (m, 6H), 7.62 (s, 1H), 7.79–7.98 (m, 3H), 8.52 (d, J=6.34 Hz, 1H), 8.81 (bs, 1H) Mass spectrometry value (ESI-MS, m/z): 529 (M$^+$+1)

Example 1119

N-(2,4-Dimethoxybenzoyl)-N'-{4-[(6,7-dimethoxy-4-quinolyl)oxy]phenyl}thiourea 2,4-Dimethoxy-1-benzenecarbonyl isothiocyanate was prepared using commercially available 2,4-dimethoxy-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (42 mg, yield 48%).

$^1$H-NMR (DMSO-$d_6$, 400 MHz): δ 3.90 (s, 3H), 3.93 (s, 3H), 3.95 (s, 3H), 4.06 (s, 3H), 6.56 (d, J=5.37 Hz, 1H), 6.79–6.81 (m, 2H), 7.33 (d, J=9.03 Hz, 2H), 7.41 (s, 1H), 7.50 (s, 1H), 7.84 (d, J=8.78 Hz, 2H), 8.01 (d, J=9.03 Hz, 1H), 8.52 (d, J=5.12 Hz, 1H), 11.05 (bs, 1H), 12.67 (bs, 1H) Mass spectrometry value (ESI-MS, m/z): 520 (M$^+$+1)

Example 1120

N-(3,4-Dichlorobenzoyl)-N'-{4-[(6,7-dimethoxy-4-quinolyl oxy]phenyl}thiourea 3,4-Dichloro-1-benzenecarbonyl isothiocyanate was prepared using commercially available 3,4-dichloro-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3,4-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (56 mg, yield 63%).

1H-NMR (CDCl$_3$, 400 MHz): δ 4.05 (s, 3H), 4.06 (s, 3H), 6.62 (d, J=5.37 Hz, 1H), 7.24 (s, 1H), 7.26 (s, 1H), 7.61–7.68 (m, 6H), 7.73 (m, 1H), 7.81 (d, J=9.03 Hz, 1H), 8.04 (d, J=1.95 Hz, 1H), 8.54 (d, J=5.12 Hz, 1H) Mass spectrometry value (ESI-MS, m/z): 529 (M$^+$+1)

Example 1121

N-(2,4-Difluorobenzoyl)-N'-{4-[(6,7-dimethoxy-4-quinolyl)oxy]-2-fluorophenyl}thiourea 2,4-Difluoro-1-benzenecarbonyl isothiocyanate was prepared using commercially available 2,4-difluoro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2,4-difluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (56 mg, yield 68%).

$^1$H-NMR (DMSO-$d_6$, 400 MHz): δ 3.93 (s, 3H), 3.96 (s, 3H), 6.66 (d, J=5.12 Hz, 1H), 7.13–7.84 (m, 7H), 8.04 (m, 1H), 8.56 (d, J=5.12 Hz, 1H), 11.95 (s, 1H), 12.18 (bs, 1H) Mass spectrometry value (ESI-MS, m/z): 514 (M$^+$+1)

Example 1122

N-(3,5-Dichlorobenzoyl)-N'-{4-[(6,7-dimethoxy-4-quinolyl)oxy]-2-fluorophenyl}thiourea 3,5-Dichloro-1-benzenecarbonyl isothiocyanate was prepared using commercially available 3,5-dichloro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 3,5-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (51 mg, yield 64%). Mass spectrometry value (ESI-MS, m/z): 547 (M$^+$+1)

Example 1123

N-(2,4-Dimethoxybenzoyl)-N'-{4-[(6,7-dimethoxy-4-quinolyl)oxy]-2-fluorophenyl}thiourea 2,4-Dimethoxy-1-benzenecarbonyl isothiocyanate was prepared using commercially available 2,4-dimethoxy-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (54 mg, yield 67%). Mass spectrometry value (ESI-MS, m/z): 538 (M$^+$+1)

Example 1124

N-(4-Cyclohexylbenzoyl)-N'-{4-[(6,7-dimethoxy-4-quinolyl)oxy]phenyl}thiourea

Toluene (20 ml) and thionyl chloride (1 ml) were added to commercially available 4-cyclohexylbenzoic acid (80 mg), and the mixture was heated at 100° C. for one hr. The solvent was removed by distillation, and 4-cyclohexyl-1-benzenecarbonyl isothiocyanate was prepared using the resultant 4-cyclohexyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-cyclohexyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (44 mg, yield 48%).

$^1$H-NMR (DMSO-$d_6$, 400 MHz): δ 1.31–1.83 (m, 11H), 3.93 (s, 3H), 3.95 (s, 3H), 6.56 (d, J=5.12 Hz, 1H), 7.31 (d, J=8.54 Hz, 3H), 7.39 (d, J=6.83 Hz, 4H), 7.49 (s, 1H), 7.83 (m, 3H), 7.95 (d, J=8.05 Hz, 3H), 8.50 (d, J=5.12 Hz, 1H) Mass spectrometry value (ESI-MS, m/z): 542 (M$^+$+1)

Example 1125

N-(4-Phenylbenzoyl)-N'-{4-[(6,7-dimethoxy-4-quinolyl)oxy]-2-fluorophenyl}thiourea 4-Phenyl-1-benzenecarbonyl isothiocyanate was prepared using commercially available 4-phenyl-1benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 4-phenyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (41 mg, yield 47%).

$^1$H-NMR (DMSO-d$_6$, 400 MHz): δ 3.93 (s, 3H), 3.96 (s, 3H), 6.67 (d, J=5.12 Hz, 1H), 7.19 (m, 1H), 7.43–7.53 (m, 7H), 7.78 (d, J=7.81 Hz, 2H), 7.86 (d, J=8.19 Hz, 2H), 8.11–8.13 (m, 2H), 8.56 (d, J=5.37 Hz, 1H), 11.87 (s, 1H), 12.57 (s, 1H) Mass spectrometry value (ESI-MS, m/z): 554 (M$^+$+1)

Example 1126

N-(1,3-Benzodioxol-5-ylcarbonyl)-N'-{3-chloro-4-[(6,7-dimethoxy-4-quinolyl)oxy]phenyl}thiourea 1,3-Benzodioxole-5-carbonyl isothiocyanate was prepared using commercially available 1,3-benzodioxole-5-carbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 1,3-benzodioxole-5-carbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (47 mg, yield 58%).

$^1$H-NMR (DMSO-d$_6$, 400 MHz): δ 3.95 (s, 3H), 3.96 (s, 3H), 6.18 (s, 2H), 6.42 (d, J=5.12 Hz, 1H), 7.08 (d, J=8.48 Hz, 1H), 7.43 (s, 1H), 7.50 (d, J=8.78 Hz, 1H), 7.54 (s, 1H), 7.57 (s, 1H), 7.67 (d, J=8.29 Hz, 1H), 7.74 (d, J=9.03 Hz, 1H), 8.19 (bs, 1H), 8.51 (d, J=5.12 Hz, 1H), 11.49 (bs, 1H), 12.67 (bs, 1H) Mass spectrometry value (ESI-MS, m/z): 538 (M$^+$+1)

Example 1127

N-{3-Chloro-4-[(6,7-dimethoxy-4-quinolyl)oxy]phenyl}-N'-(4-cyclohexylbenzoyl)thiourea Toluene (20 ml) and thionyl chloride (1 ml) were added to commercially available 4-cyclohexylbenzoic acid (80 mg), and the mixture was heated at 100° C. for one hr. The solvent was removed by distillation, and 4-cyclohexyl-1-benzenecarbonyl isothiocyanate was prepared using the resultant 4-cyclohexyl-1-benzenecarbonyl chloride as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-cyclohexyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (47 mg, yield 54%).

$^1$H-NMR (DMSO-d$_6$, 400 MHz): δ 1.31–1.83 (m, 11 H), 3.95 (s, 6H), 6.41 (d, J=4.88 Hz, 1H), 7.39 (d, J=9.27 Hz, 4H), 7.47 (d, J=8.54 Hz, 1H), 7.73 (m, 1H), 7.95 (d, J=7.56 Hz, 2H), 8.21 (m, 1H), 8.49 (d, J=5.61 Hz, 1H), 11.54 (s, 1H), 12.74 (bs, 1H) Mass spectrometry value (ESI-MS, m/z): 577 (M$^+$+1)

Example 1128

N-{4-[(6,7-Dimethoxy-4-quinolyl)oxy]phenyl}-N'-(4-octylbenzoyl)thiourea

Toluene (20 ml) and thionyl chloride (1 ml) were added to commercially available 4-octylbenzoic acid (80 mg), and the mixture was heated at 100° C. for one hr. The solvent was removed by distillation, and 4-octyl-1-benzenecarbonyl isothiocyanate was prepared using the resultant 4-octyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-octyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (47 mg, yield 54%).

$^1$H-NMR (DMSO-d$_6$, 400 MHz): δ 0.83–0.88 (m, 4H), 1.25–1.28 (m, 7H), 1.58–1.60 (m, 3H), 2.60–2.69 (m, 3H), 3.91 (s, 3H), 3.96 (s, 3H), 6.57 (d, J=5.12 Hz, 1H), 7.25 (d, J=8.05 Hz, 1H), 7.32–7.42 (m, 4H), 7.51 (s, 1H), 7.58 (s, 1H), 7.78 (d, J=8.05 Hz, 1H), 7.84–7.86 (m, 2H), 7.94 (d, J=8.05 Hz, 2H), 8.53 (d, J=5.37 Hz, 1H) Mass spectrometry value (ESI-MS, m/z): 572 (M$^+$+1)

Example 1129

N-{4-[(6,7-Dimethoxy-4-quinolyl)oxy]phenyl}-N'-(3 5-dimethylbenzoyl)thiourea

Toluene (20 ml) and thionyl chloride (1 ml) was added to commercially available 3,5-dimethylbenzoic acid (80 mg), and the mixture was heated at 100° C. for one hr. The solvent was removed by distillation, and 3,5-dimethyl-1-benzenecarbonyl isothiocyanate was prepared using the resultant 3,5-dimethyl-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3,5-dimethyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (39 mg, yield 47%).

$^1$H-NMR (DMSO-d$_6$, 400 MHz): δ 2.37 (s, 6H), 3.95 (s, 3H), 3.96 (s, 3H), 6.41 (d, J=5.37 Hz, 1H), 7.29 (s, 1H), 7.41 (s, 1H), 7.47 (d, J=8.78 Hz, 1H), 7.53 (s, 1H), 7.63 (s, 2H), 7.71–7.74 (m, 2H), 8.19–8.20 (m, 1H), 8.50 (d, J=5.37 Hz, 1H), 11.54 (s, 1H), 12.72 (s, 1H) Mass spectrometry value (ESI-MS, m/z): 488 (M$^+$+1)

Example 1130

N-{4-[(6,7-Dimethoxy-4-quinolyl)oxy]phenyl}-N'-(1,2,3,4-tetrahydro-2-isoquinolylcarbonyl)thiourea Commercially available 1,2,3,4-tetrahydroisoquinoline (50 mg) was dissolved in chloroform (10 ml), and triphosgene (111 mg) was added to the solution. The mixture was stirred at room temperature for 2 hr. The solvent was removed by distillation to give 1,2,3,4-tetrahydro-2-isoquinolinecarbonyl chloride. 1,2,3,4-Tetrahydro-2-isoquinolinecarbonyl isothiocyanate was prepared using this compound as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 1,2,3,4-tetrahydro-2-isoquinolinecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (78 mg, yield 94%).

$^1$H-NMR (DMSO-$d_6$, 400 MHz): δ 2.81–2.89 (m, 4H), 3.92 (s, 3H), 3.94 (s, 3H), 4.87 (m, 2H), 6.52 (d, J=5.12 Hz, 1H), 7.13–7.28 (m, 4H), 7.39–7.49 (m, 4H), 7.73 (d, J=8.29 Hz, 2H), 8.49 (d, J=5.12 Hz, 1H), 10.18 (bs, 1H), 12.51 (bs, 1H)

Mass spectrometry value (ESI-MS, m/z): 515 ($M^+$+1)

Example 1131

N-(3-Cyclopentylpropanoyl)-N'-{4-[(6,7-dimethoxy-4-quinolyl)oxy]phenyl}thiourea

3-Cyclopentylpropanoyl isothiocyanate was prepared using commercially available 3-cyclopentylpropanoyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-cyclopentylpropanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (46 mg, yield 57%).

$^1$H-NMR (DMSO-$d_6$, 400 MHz): δ1.11 (m, 1H), 1.50–1.76 (m, 8H), 2.32–2.33 (m, 2H), 2.67–2.68 (m, 2H), 3.95 (s, 3H), 3.98 (s, 3H), 6.51 (d, J=4.39 Hz, 1H), 6.79 (d, J=2.68 Hz, 1H), 7.39–7.52 (m, 4H), 8.04 (d, J=12.20 Hz, 1H), 8.52 (d, J=5.37 Hz, 1H), 11.58 (bs, 1H), 12.65 (bs, 1H)

Mass spectrometry value (ESI-MS, m/z): 480 ($M^+$+1)

Example 1132

N-(3-Cyclopentylpropanoyl)-N'-{4-[(6,7-dimethoxy-4-quinazolinyl)oxy]phenyl}thiourea 3-Cyclopentylpropanoyl isothiocyanate was prepared using commercially available 3-cyclopentylpropanoyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-cyclopentylpropanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (37 mg, yield 46%).

$^1$H-NMR (DMSO-$d_6$, 400 MHz): δ 1.28–1.32 (m, 1H), 1.48–1.63 (m, 5H), 1.73–1.79 (m, 3H), 2.32–2.33 (m, 2H), 2.67–2.68 (m, 2H), 3.98 (s, 3H), 3.99 (s, 3H), 7.34–7.39 (m, 3H), 7.58 (s, 2H), 7.71–7.75 (m, 2H), 8.57 (s, 2H), 11.48 (bs, 1H), 12.54 (bs, 1H) Mass spectrometry value (ESI-MS, m/z): 481 ($M^+$+1)

Example 1133

N-{4-[(6,7-Dimethoxy-4-quinazolinyl)oxy]phenyl}-N'-[3-(2-methylphenyl)propanoyl]thiourea Toluene (20 ml) and thionyl chloride (1 ml) were added to commercially available 3-(2-methylphenyl)propanoic acid (80 mg), and the mixture was heated at 100° C. for one hr. The solvent was removed by distillation, and 3-(2-methylphenyl)propanoyl isothiocyanate was prepared using the resultant 3-(2-methylphenyl)propanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-(2-methylphenyl)propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (48 mg, yield 57%).

$^1$H-NMR (DMSO-$d_6$, 400 MHz): δ 2.32 (s, 3H), 2.59–2.63 (m, 2H), 2.89–2.94 (m, 2H), 3.93 (s, 3H), 3.99 (s, 3H), 7.09–7.24 (m, 7H), 7.38 (s, 1H), 7.55 (s, 1H), 7.67 (d, J=8.78 Hz, 2H), 8.53 (s, 1H), 10.03 (bs, 1H) Mass spectrometry value (ESI-MS, m/z): 503 ($M^+$+1)

Example 1134

N-{4-[(6,7-Dimethoxy-4-quinolyl)oxy]-3-fluorophenyl}-N'-[3-(2-methylphenyl)propanoyl]thiourea Toluene (20 ml) and thionyl chloride (1 ml) were added to commercially available 3-(2-methylphenyl)propanoic acid (80 mg), and the mixture was heated at 100° C. for one hr. The solvent was removed by distillation, and 3-(2-methylphenyl)propanoyl isothiocyanate was prepared using the resultant 3-(2-methylphenyl)propanoyl chloride as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 3-(2-methylphenyl) propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (45 mg, yield 54%).

$^1$H-NMR (DMSO-$d_6$, 400 MHz): δ 2.33 (s, 3H), 2.75–2.79 (m, 2H), 2.87–2.91 (m, 2H), 3.95 (s, 3H), 3.96 (s, 3H), 6.51 (d, J=5.12 Hz, 1H), 7.11–7.16 (m, 5H), 7.42 (s, 1H), 7.48–7.57 (m, 2H), 8.04 (d, J=14.63 Hz, 1H), 8.51 (d, J=5.37 Hz, 1H), 11.64 (s, 1H), 12.62 (bs, 1H) Mass spectrometry value (ESI-MS, m/z): 520 ($M^+$+1)

Example 1135

N-{4-[(6,7-Dimethoxy-4-quinolyl)oxy]phenyl}-N'-[3-(methylsulphenyl)propanoyl]thiourea 3-(Methylsulphenyl)propanoyl isothiocyanate was prepared using commercially available 3-(methylsulphenyl) propanoyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-(methylsulphenyl)propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (41 mg, yield 56%).

$^1$H-NMR (DMSO-d$_6$, 400 MHz): δ 2.05 (s, 3H), 2.73–2.82 (m, 4H), 4.02 (s, 3H), 4.04 (s, 3H), 6.84 (m, 1H), 7.35 (d, J=7.32 Hz, 1H), 7.45 (d, J=7.32 Hz, 1H), 7.53 (s, 1H), 7.73 (s, 1H), 7.86–7.90 (m, 4H), 8.79 (d, J=5.13 Hz, 1H) Mass spectrometry value (ESI-MS, m/z): 458 (M$^+$+1)

Example 1136

N-[4-(Chloromethyl)benzoyl]-N'-{4-[(6,7-dimethoxy-4-quinolyl)oxy]phenyl}thiourea 4-(Chloromethyl)-1-benzenecarbonyl isothiocyanate was prepared using commercially available 4-(chloromethyl)-1-benzenecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-(chloromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (54 mg, yield 63%).

$^1$H-NMR (DMSO-d$_6$, 400 MHz): δ 3.98 (s, 3H), 4.00 (s, 3H), 4.44 (s, 2H), 6.72 (d, J=5.86 Hz, 1H), 7.40 (d, J=8.54 Hz, 2H), 7.47 (s, 1H), 7.58–7.63 (m, 3H), 7.88–7.89 (m, 2H), 8.03 (d, J=8.29 Hz, 2H), 8.67 (d, J=5.61 Hz, 1H), 11.68 (bs, 1H), 12.62 (bs, 1H) Mass spectrometry value (ESI-MS, m/z): 508 (M$^+$+1)

Example 1137

N-{3-Chloro-4-[(6,7-dimethoxy-4-quinolyl)oxy]phenyl}-N'-[4-(chloromethyl)benzoyl]thiourea 4-(Chloromethyl)-1-benzenecarbonyl isothiocyanate was prepared using commercially available 4-(chloromethyl)-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-(chloromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (52 mg, yield 63%).

$^1$H-NMR (DMSO-d$_6$, 400 MHz): δ 3.99 (s, 3H), 4.00 (s, 3H), 4.45 (s, 2H), 6.62 (d, J=5.85 Hz, 1H), 7.48 (s, 1H), 7.57–7.65 (m, 4H), 7.82 (m, 1H), 8.03 (d, J=7.47 Hz, 2H), 8.25 (m, 1H), 8.66 (d, J=5.86 Hz, 1H), 11.77 (bs, 1H), 12.62 (bs, 1H) Mass spectrometry value (ESI-MS, m/z): 543 (M$^+$+1)

Example 1138

N-{4-[(6,7-Dimethoxy-4-quinazolinyl)oxy]phenyl}-N'-[2-(2-methylphenoxy)acetyl]thiourea Toluene (20 ml) and thionyl chloride (1 ml) were added to commercially available 2-(2-methylphenoxy)acetic acid (80 mg), and the mixture was heated at 100° C. for one hr. The solvent was removed by distillation, and 2-(2-methylphenoxy)ethanoyl isothiocyanate was prepared using the resultant 2-(2-methylphenoxy)ethanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-(2-methylphenoxy)ethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (37 mg, yield 44%).

$^1$H-NMR (DMSO-d$_6$, 400 MHz): δ 2.22 (s, 3H), 3.96 (s, 3H), 3.98 (s, 3H), 4.44 (s, 2H), 6.62 (d, J=8.78 Hz, 2H), 6.80–6.93 (m, 5H), 7.11–7.16 (m, 2H), 7.35 (s, 1H), 7.39 (bs, 1H), 7.52 (s, 1H), 8.51 (s, 1H) Mass spectrometry value (ESI-MS, m/z): 505 (M$^+$+1)

Example 1139

N-{4-[(6,7-Dimethoxy-4-quinazolinyl)oxy]phenyl}-N'-(4-phenylbutanoyl)thiourea

Toluene (20 ml) and thionyl chloride (1 ml) were added to commercially available 4-phenylbutanoic acid (80 mg), and the mixture was heated at 100° C. for one hr. The solvent was removed by distillation, and 4-phenylbutanoyl isothiocyanate was prepared using the resultant 4-phenylbutanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-phenylbutanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (37 mg, yield 45%).

$^1$H-NMR (DMSO-d$_6$, 400 MHz): δ 1.85–1.93 (m, 3H), 2.59–2.68 (m, 3H), 3.98 (s, 3H), 3.99 (s, 3H), 6.76 (d, J=8.78 Hz, 1H), 7.19–7.36 (m, 6H), 7.39 (s, 1H), 7.57 (s, 1H), 7.73 (d, J=8.78 Hz, 2H), 8.57 (s, 1H), 11.49 (s, 1H), 12.51 (s, 1H) Mass spectrometry value (ESI-MS, m/z): 503 (M$^+$+1)

Example 1140

N-{4-[(6,7-Dimethoxy-4-quinazolinyl)oxy]phenyl}-N-ethyl-N'-(4-phenylbutanoyl)thiourea Toluene (20 ml) and thionyl chloride (1 ml) were added to commercially available 4-phenylbutanoic acid (80 mg), and the mixture was heated at 100° C. for one hr. The solvent was removed by distillation, and 4-phenylbutanoyl isothiocyanate was prepared using the resultant 4-phenylbutanoyl chloride as a starting compound according to the description of the literature. N-{4-[(6,7-Dimethoxy-4-quinolyl)oxy]phenyl}-N-ethylamine (50 mg) was dissolved in toluene (5 ml) and ethanol (1 ml) to prepare a solution. A solution of 4-phenylbutanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (45 mg, yield 56%).

$^1$H-NMR (DMSO-d$_6$, 400 MHz): δ 1.15–1.19 (m, 3H), 1.52 (m, 2H), 2.04–2.09 (m, 2H), 2.21–2.33 (m, 2H), 3.85 (s, 3H), 3.94 (s, 3H), 4.21 (bs, 1H), 6.40 (d, J=5.12 Hz, 1H), 7.08–7.40 (m, 12H), 8.33 (d, J=4.88 Hz, 1H), 10.48 (bs, 1H) Mass spectrometry value (ESI-MS, m/z): 530 (M$^+$+1)

Example 1141

N-{4-[(6,7-Dimethoxy-4-quinazolinyl)oxy]phenyl}-N'-[3-(2-methoxyphenyl)propanoyl]thiourea Toluene (20 ml) and thionyl chloride (1 ml) were added to commercially available 3-(2-methoxyphenyl)propanoic acid (80 mg), and the mixture was heated at 100° C. for one hr. The solvent was removed by distillation, and 3-(2-methoxyphenyl)propanoyl isothiocyanate was prepared using the resultant 4-phenylbutanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-(2-methoxyphenyl)propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (37 mg, yield 43%).

$^1$H-NMR (DMSO-d$_6$, 400 MHz): δ 2.73–2.77 (m, 2H), 2.85–2.89 (m, 2H), 3.92 (s, 3H), 3.98 (s, 3H), 3.99 (s, 3H), 6.87–6.91 (m, 2H), 6.97 (d, J=8.29 Hz, 1H), 7.17–7.23 (m, 1H), 7.36 (d, J=8.78 Hz, 2H), 7.39 (s, 1H), 7.57 (s, 1H), 7.73 (d, J=8.78 Hz, 2H), 8.57 (s, 1H), 11.51 (bs, 1H), 12.52 (bs, 1H) Mass spectrometry value (ESI-MS, m/z): 519 (M$^+$+1)

Example 1142

N-{4-[(6,7-Dimethoxy-4-quinolyl)oxy]phenyl}-N-ethyl-N'-[3-(2-methoxyphenyl)propanoyl]thiourea Toluene (20 ml) and thionyl chloride (1 ml) were added to commercially available 3-(2-methoxyphenyl)propanoic acid (80 mg), and the mixture was heated at 100° C. for one hr. The solvent was removed by distillation, and 3-(2-methoxyphenyl)propanoyl isothiocyanate was prepared using the resultant 4-phenylbutanoyl chloride as a starting compound according to the description of the literature. N-{4-[(6,7-Dimethoxy-4-quinolyl)oxy]phenyl}-N-ethylamine (50 mg) was dissolved in toluene (5 ml) and ethanol (1 ml) to prepare a solution. A solution of 3-(2-methoxyphenyl)propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (44 mg, yield 52%).

$^1$H-NMR (DMSO-d$_6$, 400 MHz): δ 1.19–1.18 (m, 3H), 2.32 (m, 2H), 2.52–2.54 (m, 2H), 3.72 (s, 3H), 3.93 (s, 3H), 3.97 (s, 3H), 6.51 (d, J=5.37 Hz, 1H), 6.82–6.85 (m, 1H), 6.91 (d, J=7.56 Hz, 1H), 6.95–6.99 (m, 1H), 7.00–7.19 (m, 7H), 7.42 (s, 1H), 7.53 (s, 1H), 8.42 (bs, 1H), 10.49 (s, 1H) Mass spectrometry value (ESI-MS, m/z): 546 (M$^+$+1)

Example 1143

N-{4-[(6,7-Dimethoxy-4-quinolyl)oxy]phenyl}-N-ethyl-N'-[(2-phenylcyclopropyl)carbonyl]thiourea 2-Phenyl-1-cyclopropanecarbonyl isothiocyanate was prepared using commercially available 2-phenyl-1-cyclopropanecarbonyl chloride (80 mg) as a starting compound according to the description of the literature. N-{4-[(6,7-Dimethoxy-4-quinolyl)oxy]phenyl}-N-ethylamine (50 mg) was dissolved in toluene (5 ml) and ethanol (1 ml) to prepare a solution. A solution of 2-phenyl-1-cyclopropanecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (43 mg, yield 53%).

$^1$H-NMR (DMSO-d$_6$, 400 MHz): δ 1.60–1.19 (m, 3H), 1.23 (m, 2H), 1.91 (m, 2H), 1.91 (bs, 2H), 3.91 (s, 3H), 3.95 (s, 3H), 4.21 (m, 2H), 6.46 (d, J=5.12 Hz, 1H), 7.03 (d, J=7.56 Hz, 2H), 7.15–7.33 (m, 5H), 7.42 (s, 1H), 7.50 (s, 1H), 8.45 (d, J=5.37 Hz, 1H), 10.78 (s, 1H) Mass spectrometry value (ESI-MS, m/z): 528 (M$^+$+1)

Example 1144

N-[2-(2-Chlorophenoxy)propanoyl]-N'-{4-[(6,7-dimethoxy-4-quinazolinyl)oxy]phenyl}thiourea Toluene (20 ml) and thionyl chloride (1 ml) were added to commercially available 2-(2-chlorophenoxy)propanoic acid (80 mg), and the mixture was heated at 100° C. for one hr. The solvent was removed by distillation, and 2-(2-chlorophenoxy)propanoyl isothiocyanate was prepared using the resultant 2-(2-chlorophenoxy)propanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-(2-chlorophenoxy)propanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (45 mg, yield 50%).

$^1$H-NMR (DMSO-d$_6$, 400 MHz): δ 1.61 (d, J=6.59 Hz, 3H), 3.93 (s, 3H), 3.98 (s, 3H), 5.21–5.22 (m, 1H), 6.99–7.05 (m, 2H), 7.32–7.35 (m, 3H), 7.38 (s, 1H), 7.47 (d, J=8.05 Hz, 1H), 7.70–7.74 (m, 3H), 8.55 (s, 1H), 11.65 (bs, 1H), 12.09 (bs, 1H) Mass spectrometry value (ESI-MS, m/z): 540 (M$^+$+1)

Example 1145

N-(1,3-Benzodioxol-5-ylcarbonyl)-N'-{4-[(6,7-dimethoxy-4-quinolyl)oxy]-3-fluorophenyl}thiourea 1,3-Benzodioxole-5-carbonyl isothiocyanate was prepared using commercially available 1,3-benzodioxole-5-carbonyl chloride (80 mg) as a starting compound according to the description of the literature. 4-[(6,7-Dimethoxy-4-quinolyl)oxy]-3-fluoroaniline (50 mg) was dissolved in toluene (5 ml) and ethanol (1 ml) to prepare a solution. A solution of 1,3-benzodioxole-5-carbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (62 mg, yield 75%).

$^1$H-NMR (DMSO-d$_6$, 400 MHz): δ 3.95 (s, 3H), 3.96 (s, 3H), 6.18 (s, 2H), 6.52 (d, J=4.88 Hz, 1H), 7.09 (d, J=8.30 Hz, 1H), 7.43 (s, 1H), 7.49–7.61 (m, 4H), 7.67 (d, J=1.87 Hz, J=7.29 Hz, 1H), 8.08 (d, J=11.22 Hz, 1H), 8.52 (d, J=5.16 Hz, 1H), 11.49 (bs, 1H), 12.72 (bs, 1H) Mass spectrometry value (ESI-MS, m/z): 522 (M$^+$+1)

Example 1146

N-{4-[(6,7-Dimethoxy-4-quinolyl)oxy]phenyl}-N'-[(5-methyl-2-thienyl)carbonyl]thiourea Toluene (20 ml) and thionyl chloride (1 ml) were added to commercially available 5-methyl-2-thiophenecarboxylic acid (80 mg), and the mixture was heated at 100° C. for one hr. The solvent was removed by distillation, and 5-methyl-2-thiophenecarbonyl isothiocyanate was prepared using the resultant 5-methyl-2-thiophenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 5-methyl-2-thiophenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (42 mg, yield 52%).

$^1$H-NMR (DMSO-d$_6$, 400 MHz): δ 2.51 (s, 3H), 4.01 (s, 6H), 6.78–6.82 (m, 1H), 6.96 (s, 1H), 6.99 (s, 1H), 7.53–7.65 (m, 3H), 7.91 (d, J=3.42 Hz, 1H), 8.14 (d, J=10.98 Hz, 1H), 8.24 (d, J=3.42 Hz, 1H), 8.71 (d, J=5.86 Hz, 1H), 11.66 (bs, 1H), 12.62 (bs, 1H) Mass spectrometry value (ESI-MS, m/z): 480 (M$^+$+1)

Example 1147

N-{3-Chloro-4-[(6,7-dimethoxy-4-quinolyl)oxy]phenyl}-N'-(2-phenylacetyl)thiourea 2-Phenylethanoyl isothiocyanate was prepared using commercially available 2-phenylethanoyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (41 mg, yield 53%).

$^1$H-NMR (DMSO-d$_6$, 400 MHz): δ 3.88 (s, 2H), 3.94 (s, 3H), 3.96 (s, 3H), 6.41 (d, J=5.12 Hz, 1H), 7.29–7.36 (m, 5H), 7.42 (s, 1H), 7.46 (d, J=8.78 Hz, 1H), 7.52 (s, 1H), 7.66–7.69 (m, 1H), 8.11–8.14 (m, 1H), 8.51 (d, J=5.12 Hz, 1H), 11.82 (s, 1H), 12.44 (s, 1H) Mass spectrometry value (ESI-MS, m/z): 508 (M$^+$+1)

Example 1148

N-{4-[(6,7-Dimethoxy-4-quinazolinyl)oxy]phenyl}-N'-(2-phenylacetyl)thiourea

2-Phenylethanoyl isothiocyanate was prepared using commercially available 2-phenylethanoyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (38 mg, yield 48%).

$^1$H-NMR (DMSO-d$_6$, 400 MHz): δ 3.66 (s, 2H), 3.97 (s, 3H), 3.99 (s, 3H), 7.23–7.34 (m, 10H), 7.55 (s, 1H), 7.69 (d, J=9.03 Hz, 1H), 8.53 (s, 1H), 10.28 (s, 1H) Mass spectrometry value (ESI-MS, m/z): 475 (M$^+$+1)

Example 1149

N-{4-[(6,7-Dimethoxy-4-quinolyl)oxy]phenyl}-N-ethyl-N'-(2-phenylacetyl)thiourea

2-Phenylethanoyl isothiocyanate was prepared using commercially available 2-phenylethanoyl chloride (80 mg) as a starting compound according to the description of the literature. N-{4-[(6,7-Dimethoxy-4-quinolyl)oxy]phenyl}-N-ethylamine (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (38 mg, yield 48%).

$^1$H-NMR (DMSO-d$_6$, 400 MHz): δ 1.13–1.19 (m, 3H), 3.44 (bs, 2H), 3.94 (s, 3H), 3.96 (s, 3H), 4.19 (bs, 2H), 6.55 (d, J=5.37 Hz, 1H), 7.06–7.11 (m, 3H), 7.19–7.34 (m, 6H), 7.42 (s, 1H), 7.47 (s, 1H), 8.53 (d, J=5.12 Hz, 1H), 10.74 (s, 1H) Mass spectrometry value (ESI-MS, m/z): 502 (M$^+$+1)

Example 1150

N-{4-[(6,7-Dimethoxy-4-quinazolinyl)oxy]phenyl}-2-morpholinoaniline

3-Fluoro4-nitrophenol (300 mg), morpholine (800 μl), and calcium carbonate (50 mg) were added to dimethylformamide (3 ml), and the mixture was heated at 130° C. for 12 hr. The reaction solution was concentrated, and the residue was purified by chromatography on silica gel using chloroform/acetone for development to give 3-morpholino-4-nitrophenol (400 mg, yield 94%). The resultant 3-morpholino-4-nitrophenol (400 mg) was added to dimethylformamide (3 ml). Palladium hydroxid-carbon (110 mg) and hydrogen were added thereto, and the mixture was stirred at room temperature for 4 hr. The reaction solution was filtered through Celite, and the filtrate was concentrated. The residue was then purified by chromatography on silica gel using chloroform/acetone for development to give 4-amino-3-morpholinophenol (296 mg, yield 85%). The resultant 4-amino-3-morpholinophenol (296 mg), 4-chloro-6,7-dimethoxyquinazoline (479 mg), and n-tetraethylammonium bromide (244 mg) were dissolved in ethyl methyl ketone (10 ml) to prepare a solution. A solution (10 ml) of sodium hydroxide (479 mg) in water was added to the solution, and the mixture was sitrred at 80° C. for 4 hr. Water was added to the reaction solution, and the organic layer was extracted and was concentrated. The residue was purified by chromatography on silica gel using chloroform/acetone for development to give the title compound (396 mg, yield 68%).

$^1$H-NMR (DMSO-$d_6$, 400 MHz): δ 3.59–3.61 (m, 4H), 3.76–3.81 (m, 4H), 3.92 (s, 3H), 3.93 (s, 3H), 7.16 (s, 2H), 7.23 (s, 2H), 8.52 (s, 2H) Mass spectrometry value (ESI-MS, m/z): 383 ($M^+$+1)

Example 1151

N-{4-[(6,7-Dimethoxy-4-quinazolinyl)oxy]-2-morpholinophenyl}-N'-(2-methylbenzoyl)thiourea N-{4-[(6,7-Dimethoxy-4-quinazolinyl)oxy]phenyl}-2-morpholinoaniline (50 mg) was dissolved in toluene (5 ml) and ethanol (1 ml) to prepare a solution. Commercially available 2-methyl-1-benzenecarbonyl isothiocyanate (50 μl) was then added to the solution, and the mixture was stirred at room temperature for 2 hr. The reaction solution was concentrated, and the residue was purified by chromatography on silica gel using chloroform/acetone for development to give the title compound (65 mg, yield 89%).

$^1$H-NMR (DMSO-$d_6$, 400 MHz): δ 2.50 (s, 3H), 2.88–2.91 (m, 4H), 3.79–3.81 (m, 4H), 3.98 (s, 3H), 3.99 (s, 3H), 7.14 (d, J=11.22 Hz, 1H), 7.18 (s, 1H), 7.33 (d, J=9.76 Hz, 2H), 7.40 (s, 1H), 7.45 (t, J=7.40 Hz, 1H), 7.54 (d, J=7.56 Hz, 1H), 7.57 (s, 1H), 7.59 (s, 1H), 8.67 (d, J=12.93 Hz, 1H), 11.76 (s, 1H), 13.09 (s, 1H) Mass spectrometry value (ESI-MS, m/z): 560 ($M^+$+1)

Example 1152

N-{4-[(6,7-Dimethoxy-4-quinolyl)oxy]phenyl}-N'-(3-pyridylcarbonyl)thiourea

3-Pyridinecarbonyl isothiocyanate was prepared using commercially available 3-pyridinecarbonyl chloride (80 mg) as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 3-pyridinecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (83 mg, yield 64%).

$^1$H-NMR (CDCl$_3$, 400 MHz): δ 3.95 (s, 3H), 4.06 (s, 3H), 6.57 (d, J=5.12 Hz, 1H), 7.24–7.27 (m, 3H), 7.45 (s, 1H), 7.51–7.54 (m, 2H), 7.82 (d, J=6.83 Hz, 2H), 8.21–8.24 (m, 1H), 8.53 (d, J=5.12 Hz, 1H), 8.89–8.91 (m, 1H), 9.18 (d, J=2.44 Hz, 1H), 9.22 (bs, 1H) Mass spectrometry value (ESI-MS, m/z): 461 ($M^+$+1)

Example 1153

N-{4-[(6,7-Dimethoxy-4-quinolyl)oxy]phenyl}-N'-[4-(morpholinomethyl)benzoyl]thiourea Commercially available 4-bromomethylbenzoic acid (300 mg) was dissolved in acetonitrile (10 ml). Potassium carbonate (30 mg) and morpholine (130 μl) were added to the solution, and the mixture was stirred at room temperature for one hr. The reaction layer was subjected to separation with chloroform and a saturated aqueous sodium hydrogencarbonate solution. The organic layer was then concentrated to give methyl 4-(morpholinomethyl)benzoate. Methanol (1 ml), water (150 μl), and potassium hydroxide (15 mg) were added to the residue, and the mixture was heated at 60° C. for one hr. After the completion of the reaction, the solvent was removed by distillation to give 4-(morpholinomethyl) benzoic acid. Toluene (20 ml) and thionyl chloride (1 ml) were added to the residule, and the mixture was heated at 100° C. for one hr. The solvent was removed by distillation, and 4-(morpholinomethyl)-1-benzenecarbonyl isothiocyanate was prepared using the resultant 4-(morpholinomethyl)-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 4-(morpholinomethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (74 mg, yield 78%).

$^1$H-NMR (CDCl$_3$, 400 MHz): δ 2.47 (s, 4H), 3.59 (s, 2H), 3.72–3.75 (m, 4H), 4.07 (s, 3H), 4.08 (s, 3H), 7.27 (s, 2H), 7.32–7.34 (m, 3H), 7.53–7.56 (m, 3H), 7.85–7.88 (m, 4H), 8.64 (s, 1H), 9.12 (s, 1H) Mass spectrometry value (ESI-MS, m/z): 559 ($M^+$+1)

Example 1154

N-{4-[(6,7-Dimethoxy-4-quinazolinyl)oxy]phenyl}-N'-[(6-methyl-3-pyridyl)carbonyl]thiourea Toluene (20 ml) and thionyl chloride (1 ml) were added to commercially available 6-methylnicotinic acid (80 mg), and the mixture was heated at 100° C. for one hr. The solvent was removed by distillation, and 6-methyl-3-pyridinecarbonyl isothiocyanate was prepared using the resultant 6-methyl-3-pyridinecarbonyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 6-methyl-3-pyridinecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (71 mg, yield 89%).

$^1$H-NMR (CDCl$_3$, 400 MHz): δ 2.58 (s, 3H), 3.97 (s, 3H), 3.99 (s, 3H), 7.37–7.40 (m, 3H), 7.46 (d, J=8.29 Hz, 1H), 7.58 (s, 1H), 7.79 (d, J=8.78 Hz, 2H), 8.26 (dd, J=2.44 Hz, J=8.05 Hz, 1H), 8.59 (s, 1H), 9.00 (d, J=2.19 Hz, 1H), 11.82 (bs, 1H), 12.52 (bs, 1H) Mass spectrometry value (ESI-MS, m/z): 476 ($M^+$+1)

Example 1155

N-{4-[(6,7-Dimethoxy-4-quinazolinyl)oxy]phenyl}-N'-(4-pyridylcarbonyl)thiourea

4-Pyridinecarbonyl isothiocyanate was prepared using commercially available 4-pyridinecarbonyl chloride (80 mg)

as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-pyridinecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (73 mg, yield 94%).

$^1$H-NMR (DMSO-d$_6$, 400 MHz): δ 3.98 (s, 3H), 3.99 (s, 3H), 7.37–7.40 (m, 3H), 7.58 (s, 1H), 7.79 (d, J=8.78 Hz, 2H), 7.87 (d, J=6.09 Hz, 2H), 8.58 (s, 1H), 8.79 (d, J=6.09 Hz, 2H), 11.89 (bs, 1H), 12.34 (bs, 1H) Mass spectrometry value (ESI-MS, m/z): 462 (M$^+$+1)

Example 1156

N-{4-[(6,7-Dimethoxy-4-quinazolinyl)oxy]phenyl}-N'-(2-pyridylcarbonyl)thiourea

2-Pyridinecarbonyl isothiocyanate was prepared using commercially available 2-pyridinecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-pyridinecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (69 mg, yield 90%).

$^1$H-NMR (DMSO-d$_6$, 400 MHz): δ 3.98 (s, 3H), 3.99 (s, 3H), 7.39–7.42 (m, 3H), 7.58 (s, 1H), 7.81–7.84 (m, 3H), 8.16–8.20 (m, 1H), 8.28 (d, J=7.56 Hz, 1H), 8.58 (s, 1H), 8.82 (d, J=4.64 Hz, 1H), 10.85 (bs, 1H), 12.18 (bs, 1H) Mass spectrometry value (ESI-MS, m/z): 462 (M$^+$+1)

Example 1157

N-{4-[(6,7-Dimethoxy-4-quinazolinyl)oxy]phenyl}-N'-[2-(trifluoromethyl)benzoyl]thiourea 2-(Trifluoromethyl)-1-benzenecarbonyl isothiocyanate was prepared using commercially available 2-(trifluoromethyl)-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-(trifluoromethyl)-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (49 mg, yield 56%).

$^1$H-NMR (DMSO-d$_6$, 400 MHz): δ 3.99 (s, 3H), 4.02 (s, 3H), 7.38–7.40 (m, 2H), 7.59 (s, 1H), 7.76–7.88 (m, 7H), 8.58 (s, 1H), 12.14 (bs, 1H), 12.29 (bs, 1H) Mass spectrometry value (ESI-MS, m/z): 529 (M$^+$+1)

Example 1158

N-(3,5-Dichlorobenzoyl)-N'-{4-[(6,7-dimethoxy-4-quinazolinyl)oxy]phenyl}thiourea 3,5-Dichloro-1-benzenecarbonyl isothiocyanate was prepared using commercially available 3,5-dichloro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3,5-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (40 mg, yield 45%).

$^1$H-NMR (DMSO-d$_6$, 400 MHz): δ 3.98 (s, 3H), 3.99 (s, 3H), 7.37–7.40 (m, 4H), 7.58 (s, 1H), 7.67 (bs, 1H), 7.76–7.81 (m, 1H), 7.88 (s, 1H), 7.94 (s, 1H), 8.00 (s, 1H), 8.17 (bs, 1H), 8.58 (bs, 1H) Mass spectrometry value (ESI-MS, m/z): 530 (M$^+$+1)

Example 1159

N-{2-Chloro-4-[(6,7-dimethoxy-4-quinolyl)oxy]phenyl}-N'-(3,5-dichlorobenzoyl)thiourea 3,5-Dichloro-1-benzenecarbonyl isothiocyanate was prepared using commercially available 3,5-dichloro-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 3,5-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (40 mg, yield 47%).

$^1$H-NMR (DMSO-d$_6$, 400 MHz): δ 3.93 (s, 3H), 3.96 (s, 3H), 6.66 (d, J=4.88 Hz, 1H), 7.43 (s, 1H), 7.48 (s, 1H), 7.61 (s, 1H), 7.67 (s, 1H), 7.79 (s, 1H), 7.94–8.17 (m, 3H), 8.57 (d, J=5.12 Hz, 1H), 12.09 (bs, 1H), 12.42 (bs, 1H) Mass spectrometry value (ESI-MS, m/z): 563 (M$^+$+1)

Example 1160

N-{4-[(6,7-Dimethoxy-4-quinolyl)oxy]-3-fluorophenyl}-N'-(2-fluorobenzoyl)thiourea 2-Fluoro-1-benzenecarbonyl isothiocyanate was prepared using commercially available 2-fluoro-1-benzenecarbonyl chloride (80 mg) as a starting compound according to the description of the literature. 4-[(6,7-Dimethoxy-4-quinolyl)oxy]-2-fluoroaniline (50 mg) was dissolved in toluene (5 ml) and ethanol (1 ml) to prepare a solution. A solution of 2-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (68 mg, yield 86%).

$^1$H-NMR (DMSO-d$_6$, 400 MHz): δ 3.95 (s, 3H), 3.96 (s, 3H), 6.52 (d, J=4.88 Hz, 1H), 7.35–7.40 (m, 2H), 7.43 (s, 1H), 7.50–7.55 (m, 2H), 7.61–7.73 (m, 2H), 7.75 (t, J=5.85

Hz, 1H), 8.07 (d, J=11.95 Hz, 1H), 8.52 (d, J=5.37 Hz, 1H), 11.85 (s, 1H), 12.43 (s, 1H) Mass spectrometry value (ESI-MS, m/z): 496 (M$^+$+1)

Example 1161

N-{4-[(6,7-Dimethoxy-4-quinazolinyl)oxy]phenyl}-N'-(2-fluorobenzoyl)thiourea

2-Fluoro-1-benzenecarbonyl isothiocyanate was prepared using commercially available 2-fluoro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-fluoro-1-benzenecarbonyl isothiocyanate (50 μl) in ethanol (1 ml) was then added to the solution, and the mixture was stirred at room temperature for 2 hr. The reaction solution was concentrated, and the residue was purified by chromatography on silica gel using chloroform/acetone for development to give the title compound (43 mg, yield 53%).
$^1$H-NMR (DMSO-d$_6$, 400 MHz): δ 3.98 (s, 3H), 3.99 (s, 3H), 7.34–7.40 (m, 5H), 7.58 (s, 1H), 7.60–7.79 (m, 4H), 8.58 (s, 1H), 11.74 (s, 1H), 12.32 (s, 1H) Mass spectrometry value (ESI-MS, m/z): 479 (M$^+$+1)

Example 1162

N-(2,6-Dichlorobenzoyl)-N'-{4-[(6,7-dimethoxy-4-quinazolinyl)oxy]phenyl}thiourea 2,6-Dichloro-1-benzenecarbonyl isothiocyanate was prepared using commercially available 2,6-dichloro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2,6-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (56 mg, yield 63%).
$^1$H-NMR (DMSO-d$_6$, 400 MHz): δ 3.98 (s, 3H), 3.99 (s, 3H), 7.39 (d, J=10.73 Hz, 3H), 7.47–7.61 (m, 4H), 7.79 (d, J=8.78 Hz, 2H), 8.59 (s, 1H), 12.22 (bs, 1H), 12.35 (bs, 1H) Mass spectrometry value (ESI-MS, m/z): 530 (M$^+$+1)

Example 1163

N-{2-Chloro-4-[(6,7-dimethoxy-4-quinolyl)oxy]phenyl}-N'-(3-fluorobenzoyl)thiourea 3-Fluoro-1-benzenecarbonyl isothiocyanate was prepared using commercially available 3-fluoro-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (50 mg, yield 58%).
$^1$H-NMR (DMSO-d$_6$, 400 MHz): δ 3.92 (s, 3H), 3.93 (s, 3H), 6.66 (d, J=5.12 Hz, 1H), 7.20 (s, 1H), 7.32–7.36 (m, 1H), 7.43 (s, 1H), 7.48 (s, 1H), 7.60–7.62 (m, 2H), 7.86 (d, J=9.03 Hz, 1H), 8.56 (d, J=5.12 Hz, 1H), 11.95 (bs, 1H), 12.55 (bs, 1H) Mass spectrometry value (ESI-MS, m/z): 512 (M$^+$+1)

Example 1164

N-{4-[(6,7-Dimethoxy-4-quinazolinyl)oxy]phenyl}-N'-(3-fluorobenzoyl)thiourea

3-Fluoro-1-benzenecarbonyl isothiocyanate was prepared using commercially available 3-fluoro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3-fluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (60 mg, yield 75%).
$^1$H-NMR (DMSO-d$_6$, 400 MHz): δ 3.98 (s, 3H), 3.99 (s, 3H), 7.37–7.40 (m, 3H), 7.52–7.55 (m, 1H), 7.58–7.61 (m, 2H), 7.78–7.86 (m, 4H), 8.58 (s, 1H), 12.05 (bs, 1H), 12.43 (bs, 1H) Mass spectrometry value (ESI-MS, m/z): 479 (M$^+$+1)

Example 1165

N-(3-Bromobenzoyl)-N'-{2-chloro-4-[(6,7-dimethoxy-4-quinolyl)oxy]phenyl}thiourea 3-Bromo-1-benzenecarbonyl isothiocyanate was prepared using commercially available 3-bromo-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 3-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (56 mg, yield 58%).
$^1$H-NMR (DMSO-d$_6$, 400 MHz): δ 3.46 (s, 3H), 3.92 (s, 3H), 6.61 (d, J=5.37 Hz, 1H), 7.19–7.22 (m, 1H), 7.32–7.36 (m, 1H), 7.48 (s, 1H), 7.52 (t, J=7.93 Hz, 1H), 7.61 (d, J=2.68 Hz, 1H), 7.88 (d, J=8.05 Hz, 1H), 7.99 (d, J=8.05 Hz, 1H), 8.09 (d, J=9.06 Hz, 1H), 8.21 (s, 1H), 8.56 (d, J=5.12 Hz, 1H), 12.02 (bs, 1H), 12.53 (bs, 1H) Mass spectrometry value (ESI-MS, m/z): 573 (M$^+$+1)

Example 1166

N-(4-Bromobenzoyl)-N'-{4-[(6,7-dimethoxy-4-quinolyl)oxy]phenyl}thiourea

4-Bromo-1-benzenecarbonyl isothiocyanate was prepared using commercially available 4-bromo-1-benzenecarbonyl chloride (80 mg) as a starting compound according to the description of the literature. 4-[(6,7Dimethoxy-4-quinolyl)oxy]aniline (50 mg) was dissolved in toluene (5 ml) and ethanol (1 ml) to prepare a solution. A solution of 4-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (57 mg, yield 63%).

$^1$H-NMR (DMSO-$d_6$, 400 MHz): δ 3.93 (s, 3H), 3.96 (s, 3H), 6.55 (d, J=5.12 Hz, 1H), 7.33 (d, J=8.78 Hz, 2H), 7.41 (s, 1H), 7.51 (s, 1H), 7.77 (d, J=8.78 Hz, 2H), 7.82 (d, J=8.78 Hz, 2H), 7.93 (d, J=8.54 Hz, 2H), 8.52 (d, J=5.37 Hz, 1H), 11.65 (bs, 1H), 12.47 (bs, 1H) Mass spectrometry value (ESI-MS, m/z): 539 (M$^+$+1)

Example 1167

N-(4-Bromobenzoyl)-N'-{2-chloro-4-[(6,7-dimethoxy-4-quinolyl)oxy]phenyl}thiourea 4-Bromo-1-benzenecarbonyl isothiocyanate was prepared using commercially available 4-bromo-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 4-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (46 mg, yield 53%).

$^1$H-NMR (DMSO-$d_6$, 400 MHz): δ 3.92 (s, 3H), 3.93 (s, 3H), 6.66 (d, J=5.12 Hz, 1H), 7.20 (s, 1H), 7.32–7.36 (m, 1H), 7.43 (s, 1H), 7.48 (s, 1H), 7.60 (d, J=2.68 Hz, 1H), 7.78 (d, J=8.78 Hz, 1H), 7.95 (d, J=8.78 Hz, 1H), 8.56 (d, J=5.12 Hz, 1H), 11.96 (bs, 1H), 12.57 (bs, 1H) Mass spectrometry value (ESI-MS, m/z): 573 (M$^+$+1)

Example 1168

N-(4-Bromobenzoyl)-N'-{4-[(6,7-dimethoxy-4-quinazolinyl)oxy]phenyl}thiourea

4-Bromo-1-benzenecarbonyl isothiocyanate was prepared using commercially available 4-bromo-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 4-bromo-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (53 mg, yield 58%).

$^1$H-NMR (DMSO-$d_6$, 400 MHz): δ 3.98 (s, 3H), 3.99 (s, 3H), 7.37–7.40 (m, 3H), 7.58 (s, 1H), 7.76–7.92 (m, 4H), 7.94 (d, J=6.59 Hz, 2H), 8.58 (s, 1H), 11.72 (bs, 1H), 12.52 (bs, 1H) Mass spectrometry value (ESI-MS, m/z): 541 (M$^+$+1)

Example 1169

N-{2-[4-(Bromomethyl)phenyl]acetyl}-N'-{4-[(6,7-dimethoxy-4-quinolyl)oxy]phenyl}thiourea Toluene (20 ml) and thionyl chloride (1 ml) were added to commercially available 4-(bromomethyl)benzoic acid (80 mg), and the mixture was heated at 100° C. for one hr. The solvent was removed by distillation, and 2-[4-(bromomethyl)phenyl]ethanoyl isothiocyanate was prepared using the resultant 4-(bromomethyl)-1-benzenecarbonyl chloride as a starting compound according to the description of the literature. 4-[(6,7-Dimethoxy-4-quinolyl)oxy]aniline (50 mg) was dissolved in toluene (5 ml) and ethanol (1 ml) to prepare a solution. A solution of 2-[4-(bromomethyl)phenyl] ethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (50 mg, yield 52%).

$^1$H-NMR (DMSO-$d_6$, 400 MHz): δ 3.85 (s, 2H), 3.92 (s, 3H), 3.95 (s, 3H), 4.36 (s, 2H), 6.55 (d, J=5.12 Hz, 1H), 7.29 (d, J=9.03 Hz, 2H), 7.30–7.41 (m, 5H), 7.49 (s, 1H), 7.75 (d, J=8.78 Hz, 2H), 8.29 (d, J=5.37 Hz, 1H), 11.75 (bs, 1H), 12.39 (bs, 1H) Mass spectrometry value (ESI-MS, m/z): 567 (M$^+$+1)

Example 1170

N-(5-Chloropentanoyl)-N'-{4-[(6,7-dimethoxy-4-quinazolinyl)oxy]phenyl}thiourea

5-Chloropentanoyl isothiocyanate was prepared using commercially available 5-chloropentanoyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 5-chloropentanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (46 mg, yield 58%).

$^1$H-NMR (DMSO-$d_6$, 400 MHz): δ 2.49–2.55 (m, 6H), 3.36–3.69 (m, 2H), 3.93 (s, 3H), 3.96 (s, 3H), 7.34–7.39 (m, 3H), 7.58 (s, 1H), 7.73 (d, J=9.03 Hz, 2H), 8.58 (s, 1H), 11.49 (s, 1H); 12.50 (s, 1H) Mass spectrometry value (ESI-MS, m/z): 475 (M$^+$+1)

Example 1171

N-{4-[(6,7-Dimethoxy-4-quinolyl)oxy]phenyl}-N'-[2-(2-thienyl)acetyl]thiourea

Toluene (20 ml) and thionyl chloride (1 ml) were added to commercially available 2-(2-thienyl)acetic acid (40 mg), and the mixture was heated at 100° C. for one hr. The solvent was removed by distillation, and 2-(2-thienyl)ethanoyl isothiocyanate was prepared using the resultant 2-(2-thienyl) ethanoyl chloride as a starting compound according to the description of the literature. 4-[(6,7-Dimethoxy-4-quinolyl) oxy]aniline (50 mg) was dissolved in toluene (5 ml) and ethanol (1 ml) to prepare a solution. A solution of 2-(2-thienyl)ethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (44 mg, yield 54%).

$^1$H-NMR (DMSO-$d_6$, 400 MHz): δ 3.96 (s, 3H), 3.98 (s, 3H), 4.07 (s, 2H), 6.64 (d, J=5.61 Hz, 1H), 6.96–7.03 (m, 6H), 7.33–7.38 (m, 1H), 7.45 (s, 1H), 7.78 (d, J=9.03 Hz, 1H), 8.61 (d, J=5.37 Hz, 1H), 11.75 (bs, 1H), 12.34 (bs, 1H) Mass spectrometry value (ESI-MS, m/z): 480 (M$^+$+1)

Example 1172

N-{4-[(6,7-Dimethoxy-4-quinazolinyl)oxy]phenyl}-
N'-[2-(2-thienyl)acetyl]thiourea Toluene (20 ml) and thionyl chloride (1 ml) were added to commercially available 2-(2-thienyl)acetic acid (40 mg), and the mixture was heated at 100° C. for one hr. The solvent was removed by distillation, and 2-(2-thienyl)ethanoyl isothiocyanate was prepared using the resultant 2-(2-thienyl) ethanoyl chloride as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2-(2-thienyl)ethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (46 mg, yield 57%).

$^1$H-NMR (DMSO-$d_6$, 400 MHz): δ 3.79 (s, 6H), 3.98 (d, J=6.34 Hz, 2H), 6.68 (d, J=9.03 Hz, 2H), 6.96–7.00 (m, 3H), 7.34–7.39 (m, 5H), 9.19 (s, 1H), 9.92 (bs, 1H) Mass spectrometry value (ESI-MS, m/z): 481 (M$^+$+1)

Example 1173

N-{2-Chloro-4-[(6,7-dimethoxy-4-quinolyl)oxy]
phenyl}-N'-(4-methoxybenzoyl)thiourea 4-Methoxy-1-benzenecarbonyl isothiocyanate was prepared using commercially available 4-methoxy-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 4-methoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (36 mg, yield 46%).

$^1$H-NMR (DMSO-$d_6$, 400 MHz): δ 3.92 (s, 9H), 7.09 (d, J=8.78 Hz, 1H), 7.19–7.22 (m, 3H), 7.31–7.36 (m, 2H), 7.43 (s, 1H), 7.48 (s, 1H), 8.06 (d, J=8.78 Hz, 1H), 8.12 (d, J=9.03 Hz, 1H), 8.53–8.57 (m, 1H), 11.52 (bs, 1H), 12.55 (bs, 1H) Mass spectrometry value (ESI-MS, m/z): 525 (M$^+$+1)

Example 1174

N-(4-Chlorobenzoyl)-N'-{2-chloro-4-[(6,7-
dimethoxy-4-quinolyl)oxy]phenyl}thiourea 2-Chloro-4-[(6,7-dimethoxy-4-quinolyl)oxy]aniline (50 mg) was dissolved in toluene (5 ml) and ethanol (1 ml) to prepare a solution. Commercially available 4-chloro-1-benzenecarbonyl isothiocyanate was then added to the solution, and the mixture was stirred at room temperature for 2 hr. The reaction solution was concentrated, and the residue was purified by chromatography on silica gel using chloroform/acetone for development to give the title compound (49 mg, yield 61%).

$^1$H-NMR (DMSO-$d_6$, 400 MHz): δ 3.92 (s, 3H), 3.93 (s, 3H), 6.66 (d, J=5.12 Hz, 1H), 7.19–7.21 (m, 2H), 7.32–7.36 (m, 1H), 7.43 (s, 1H), 7.47 (s, 1H), 7.48 (s, 1H), 7.63 (d, J=8.78 Hz, 1H), 8.03 (d, J=8.78 Hz, 2H), 8.57 (d, J=5.12 Hz, 1H), 11.96 (bs, 1H), 12.57 (bs, 1H) Mass spectrometry value (ESI-MS, m/z): 529 (M$^+$+1)

Example 1175

N-(2,4-Dimethoxybenzoyl)-N'-{4-[(6,7-dimethoxy-
4-quinazolinyl)oxy]phenyl}thiourea 2,4-Dimethoxy-1-benzenecarbonyl isothiocyanate was prepared using commercially available 2,4-dimethoxy-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (51 mg, yield 58%).

$^1$H-NMR (DMSO-$d_6$, 400 MHz): δ 3.90 (s, 3H), 3.98 (s, 3H), 3.99 (s, 3H), 4.07 (s, 3H), 6.79–6.81 (m, 2H), 7.37–7.40 (m, 3H), 7.58 (s, 1H), 7.79–7.81 (m, 2H), 8.00 (d, J=9.03 Hz, 1H), 8.58 (s, 1H), 11.01 (bs, 1H), 12.68 (bs, 1H) Mass spectrometry value (ESI-MS, m/z): 521 (M$^+$+1)

Example 1176

N-{2-Chloro-4-[(6,7-dimethoxy-4-quinolyl)oxy]
phenyl}-N'-(2,4-dimethoxybenzoyl)thiourea 2,4-Dimethoxy-1-benzenecarbonyl isothiocyanate was prepared using commercially available 2,4-dimethoxy-1-benzenecarbonyl chloride (80 mg) as a starting compound according to the description of the literature. 2-Chloro-4-[(6,7-Dimethoxy-4-quinazolinyl)oxy]aniline (50 mg) was dissolved in toluene (5 ml) and ethanol (1 ml) to prepare a solution. A solution of 2,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (40 mg, yield 48%).

$^1$H-NMR (DMSO-$d_6$, 400 MHz): δ 3.93 (s, 3H), 3.96 (s, 3H), 4.05 (s, 3H), 4.06 (s, 3H), 6.66 (d, J=5.12 Hz, 1H), 6.78–6.81 (m, 2H), 7.36 (s, 1H), 7.43 (s, 1H), 7.48 (s, 1H), 7.61 (s, 1H), 8.01 (d, J=8.54 Hz, 1H), 8.19 (d, J=9.03 Hz, 1H), 8.56 (d, J=5.12 Hz, 1H), 11.18 (bs, 1H), 12.67 (bs, 1H) Mass spectrometry value (ESI-MS, m/z): 555 (M$^+$+1)

Example 1177

Ethyl 5-[({4-[(6,7-dimethoxy-4-quinazolinyl)oxy]
anilino}carbothioyl)amino]-5-oxopentanoate Toluene (20 ml) and thionyl chloride (1 ml) were added to commercially available 5-ethoxy-5-oxopentanoic acid (40 mg), and the mixture was heated at 100° C. for one hr. The solvent was removed by distillation, and ethyl 5-isothiocyanat-5-oxopentanoate was prepared using the resultant ethyl 5-chloro-5-oxopentanoate as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of ethyl 5-isothiocyanat-5-oxopentanoate in ethanol (1 ml) was then added to the solution, and the mixture was stirred at room temperature for 2 hr. The reaction solution was concentrated, and the residue was purified by chromatography on silica gel using chloroform/acetone for development to give the title compound (39 mg, yield 47%)

$^1$H-NMR (DMSO-$d_6$, 400 MHz): δ 1.16–1.22 (m, 3H), 1.78–1.91 (m, 2H), 2.32–2.47 (m, 2H), 2.48–2.54 (m, 2H), 3.92 (s, 3H), 3.95 (s, 3H), 4.03–4.09 (m, 2H), 6.76 (d, J=8.78 Hz, 1H), 7.29–7.39 (m, 4H), 7.52 (s, 1H), 7.73 (d, J=5.37 Hz, 1H), 11.49 (s, 1H), 12.47 (s, 1H) Mass spectrometry value (ESI-MS, m/z): 499 (M$^+$+1)

Example 1178

Ethyl 4-[({4-[(6,7-dimethoxy-4-quinazolinyl)oxy]anilino}carbothioyl)amino]-4-oxobutanoate Toluene (20 ml) and thionyl chloride (1 ml) were added to commercially available 4-ethoxy-5-oxobutanoic acid (40 mg), and the mixture was heated at 100° C. for one hr. The solvent was removed by distillation, and ethyl 4-isothiocyanat-4-oxobutanoate was prepared using the resultant ethyl 4-chloro-4-oxobutanoate as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of ethyl 4-isothiocyanat-4-oxobutanoate in ethanol (1 ml) was then added to the solution, and the mixture was stirred at room temperature for 2 hr. The reaction solution was concentrated, and the residue was purified by chromatography on silica gel using chloroform/acetone for development to give the title compound (38 mg, yield 47%).

$^1$H-NMR (DMSO-$d_6$, 400 MHz): δ 1.16–1.24 (m, 3H), 2.51–2.63 (m, 2H), 2.73–2.78 (m, 2H), 3.92 (s, 3H), 3.95 (s, 3H), 4.02–4.11 (m, 2H), 7.29–7.39 (m, 3H), 7.57 (s, 1H), 7.70–7.74 (m, 2H), 8.62 (s, 1H), 11.60 (s, 1H), 12.38 (s, 1H) Mass spectrometry value (ESI-MS, m/z): 485 (M$^+$+1)

Example 1179

N-{3-Chloro-4-[(6,7-dimethoxy-4-quinolyl)oxy]phenyl}-N'-cyclohexylcarbonylthiourea 1-Cyclohexanecarbonyl isothiocyanate was prepared using commercially available 1-cyclohexanecarbonyl chloride (80 mg) as a starting compound according to the description of the literature. 1-Cyclohexanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (44 mg, yield 58%).

$^1$H-NMR (DMSO-$d_6$, 400 MHz): δ 1.16–1.41 (m, 6H), 1.66–1.85 (m, 4H), 2.55–2.61 (m, 1H), 3.94 (s, 3H), 3.95 (s, 3H), 6.41 (d, J=5.1 Hz, 1H), 7.42 (s, 1H), 7.46 (d, J=8.8 Hz, 1H), 7.52 (s, 1H), 7.68 (dd, J=2.2 Hz, 8.5 Hz, 1H), 8.15 (d, J=2.2 Hz, 1H), 8.50 (d, J=5.1 Hz, 1H), 11.51 (s, 1H), 12.59 (s, 1H) Mass spectrometry value (ESI-MS, m/z): 500 (M$^+$+1)

Example 1180

N-Cyclohexylcarbonyl-N'-{4-[(6,7-dimethoxy-4-quinazolinyl)oxy]phenyl}thiourea

1-Cyclohexanecarbonyl isothiocyanate was prepared using commercially available 1-cyclohexanecarbonyl chloride (80 mg) as a starting compound according to the description of the literature. 1-Cyclohexanecarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (48 mg, yield 62%).

$^1$H-NMR (DMSO-$d_6$, 400 MHz): δ 1.16–1.45 (m, 6H), 1.66–1.86 (m, 4H), 2.55–2.61 (m, 1H), 3.98 (s, 3H), 3.99 (s, 3H), 7.34 (d, J=15.6 Hz, 2H), 7.39 (s, 1H), 7.56 (s, 1H), 7.73 (d, J=9.0 Hz, 2H), 8.56 (s, 1H), 11.41 (s, 1H), 12.55 (s, 1H) Mass spectrometry value (ESI-MS, m/z): 467 (M$^+$+1)

Example 1181

N-Cyclopropylcarbonyl-N'-{4-[(6,7-dimethoxy-4-quinazolinyl)oxy]phenyl}thiourea

1-Cyclopropanecarbonyl isothiocyanate was prepared using commercially available 1-cyclopropanecarbonyl chloride (80 mg) as a starting compound according to the description of the literature. 1-Cyclopropanecarbonyl isothiocyanate thus obtained was dissolved in ethanol (1 ml) to prepare a solution. 4[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (51 mg, yield 71%).

$^1$H-NMR (DMSO-$d_6$, 400 MHz): δ 0.95–0.99 (m, 4H), 2.10–2.14 (m, 1H), 3.98 (s, 3H), 3.99 (s, 3H), 7.34 (d, J=9.0 Hz, 2H), 7.39 (s, 1H), 7.56 (s, 1H), 7.71 (d, J=8.8 Hz, 2H), 8.56 (s, 1H), 11.81 (s, 1H), 12.53 (s, 1H) Mass spectrometry value (ESI-MS, m/z)

Example 1182

N-{3-Chloro-4-[(6,7-dimethoxy-4-quinolyl)oxy]phenyl}-N'-cyclopentylcarbonylthiourea 1-Cyclopentanecarbonyl isothiocyanate was prepared using commercially available 1-cyclopentanecarbonyl chloride (80 mg) as a starting compound according to the description of the literature. 1-Cyclopentanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (38 mg, yield 52%).

$^1$H-NMR (DMSO-$d_6$, 400 MHz): δ 1.56–1.76 (m, 6H), 1.88–1.90 (m, 2H), 2.97–3.03 (m, 1H), 3.94 (s, 3H), 3.96 (s, 3H), 6.40 (d, J=5.1 Hz, 1H), 7.42 (s, 1H), 7.46 (d, J=8.8 Hz, 1H), 7.52 (s, 1H), 7.68 (dd, J=2.7 Hz, 8.8 Hz, 1H), 8.15 (d,

J=2.4 Hz, 1H), 8.50 (d, J=5.4 Hz, 1H), 11.56 (s, 1H), 12.60 (s, 1H) Mass spectrometry value (ESI-MS, m/z): 486 (M$^+$+1)

Example 1183

N-Cyclopentylcarbonyl-N'-{4-[(6,7-dimethoxy-4-quinazolinyl)oxy]phenyl}thiourea

1-Cyclopentanecarbonyl isothiocyanate was prepared using commercially available 1-cyclopentanecarbonyl chloride (80 mg) as a starting compound according to the description of the literature. 1-Cyclopentanecarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (24 mg, yield 31%).

$^1$H-NMR (DMSO-d$_6$, 400 MHz): δ 1.55–1.90 (m, 8H), 2.99–3.03 (m, 1H), 3.98 (s, 3H), 3.99 (s, 3H), 7.34 (d, J=8.8 Hz, 2H), 7.39 (s, 1H), 7.57 (s, 1H), 7.73 (d, J=8.8 Hz, 2H), 8.56 (s, 1H), 11.47 (s, 1H), 12.56 (s, 1H) Mass spectrometry value (ESI-MS, m/z): 453 (M$^+$+1)

Example 1184

N-{3-Chloro-4-[(6,7-dimethoxy-4quinolyl)oxy]phenyl}-N'-[3-(3-methylphenyl)propanoyl]thiourea Toluene (20 ml) and thionyl chloride (1 ml) were added to commercially available 3-(3-methylphenyl)propanoic acid (80 mg), and the mixture was heated at 100° C. for one hr. The solvent was removed by distillation, and 3-(3-methylphenyl)propanoyl isothiocyanate was prepared using the resultant 3-(3-methylphenyl)propanoyl chloride as a starting compound according to the description of the literature. 3-(3-Methylphenyl)propanoyl isothiocyanate thus obtained was dissolved in ethanol (1 ml) to prepare a solution. 3-Chloro-4-[(6,7-dimethoxy-4-quinolyl)oxy] aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (31 mg, yield 38%).

$^1$H-NMR (DMSO-d$_6$, 400 MHz): δ 2.29 (s, 3H), 2.77–2.89 (m, 4H), 3.94 (s, 3H), 3.96 (s, 3H), 6.41 (d, J=5.4 Hz, 1H), 7.01–7.08 (m, 3H), 7.19 (t, J=7.6 Hz, 1H), 7.42 (s, 1H), 7.47 (d, J=8.8 Hz, 1H), 7.53 (s, 1H), 7.67 (dd, J=2.4 Hz, 8.5 Hz, 1H), 8.13 (d, J=2.7 Hz, 1H), 8.50 (d, J=5.1 Hz, 1H), 11.62 (s, 1H), 12.53 (s, 1H) Mass spectrometry value (ESI-MS, m/z): 537 (M$^+$+1)

Example 1185

N-{4-[(6,7-Dimethoxy-4-quinazolinyl)oxy]phenyl}-N'-[3-(3-methylphenyl)propanoyl]thiourea Toluene (20 ml) and thionyl chloride (1 ml) were added to commercially available 3-(3-methylphenyl)propanoic acid (80 mg), and the mixture was heated at 100° C. for one hr. The solvent was removed by distillation, and 3-(3-methylphenyl)propanoyl isothiocyanate was prepared using the resultant 3-(3-methylphenyl)propanoyl chloride as a starting compound according to the description of the literature. 3-(3-Methylphenyl)propanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (32 mg, yield 38%).

$^1$H-NMR (DMSO-d$_6$, 400 MHz): δ 2.29 (s, 3H), 2.77–2.87 (m, 4H), 3.98 (s, 3H), 3.99 (s, 3H), 7.01–7.08 (m, 3H), 7.19 (t, J=7.6 Hz, 1H), 7.34 (d, J=8.8 Hz, 2H), 7.39 (s, 1H), 7.57 (s, 1H), 7.72 (d, J=8.8 Hz, 2H), 8.56 (s, 1H), 11.52 (s, 1H), 12.50 (s, 1H) Mass spectrometry value (ESI-MS, m/z): 503 (M$^+$+1)

Example 1186

N-(4-Chlorobutanoyl)-N'-{4-[(6,7-dimethoxy-4-quinazolinyl)oxy]phenyl}thiourea

4-Chlorobutanoyl isothiocyanate was prepared using commercially available 4-chlorobutanoyl chloride (80 mg) as a starting compound according to the description of the literature. 4-Chlorobutanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (30 mg, yield 38%).

$^1$H-NMR (DMSO-d$_6$, 400 MHz): δ 2.04 (t, J=6.8 Hz, 2H), 2.65 (t, J=7.3 Hz, 2H), 3.70 (t, J=6.6 Hz, 2H), 3.98 (s, 3H), 3.99 (s, 3H), 7.35 (d, J=8.8 Hz, 2H), 7.39 (s, 1H), 7.57 (s, 1H), 7.72 (d, J=8.8 Hz, 2H), 8.56 (s, 1H), 11.55 (s, 1H), 12.45 (s, 1H) Mass spectrometry value (ESI-MS, m/z): 461 (M$^+$+1)

Example 1187

N-{3-Chloro-4-[(6,7-dimethoxy-4-quinolyl)oxy]phenyl}-N'-(2,2-dimethylpropanoyl)thiourea 2,2-Dimethylpropanoyl isothiocyanate was prepared using commercially available 2,2-dimethylpropanoyl chloride (80 mg) as a starting compound according to the description of the literature. 2,2-Dimethylpropanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (31 mg, yield 43%).

$^1$H-NMR (DMSO-d$_6$, 400 MHz): 1.27 (s, 9H), 3.94 (s, 3H), 3.96 (s, 3H), 6.41 (d, J=5.1 Hz, 1H), 7.42 (s, 1H), 7.47 (d, J=8.8 Hz, 1H), 7.52 (s, 1H), 7.68 (dd, J=2.4 Hz, 8.8 Hz, 1H), 8.12 (s, 1H), 8.51 (d, J=5.1 Hz, 1H), 10.78 (s, 1H), 12.50 (s, 1H) Mass spectrometry value (ESI-MS, m/z): 474 (M$^+$+1)

Example 1188

N-{4-[(6,7-Dimethoxy-4-quinazolinyl)oxy]phenyl}-
N'-(2,2-dimethylpropanoyl)thiourea 2,2-Dimethylpropanoyl isothiocyanate was prepared using commercially available 2,2-dimethylpropanoyl chloride (80 mg) as a starting compound according to the description of the literature. 2,2-Dimethylpropanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (43 mg, yield 58%).

$^1$H-NMR (DMSO-$d_6$, 400 MHz): δ 1.28 (s, 9H), 3.98 (s, 3H), 3.99 (s, 3H), 7.35 (d, J=8.8 Hz, 2H), 7.39 (s, 1H), 7.57 (s, 1H), 7.72 (d, J=8.5 Hz, 2H), 8.57 (s, 1H), 10.66 (s, 1H), 12.59 (s, 1H) Mass spectrometry value (ESI-MS, m/z): 441 (M$^+$+1)

Example 1189

N-{4-[(6,7-Dimethoxy-4-quinazolinyl)oxy]phenyl}-
N'-hexanoylthiourea

Hexanoyl isothiocyanate was prepared using commercially available hexanoyl chloride (80 mg) as a starting compound according to the description of the literature. Hexanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (10 mg, yield 13%).

$^1$H-NMR (DMSO-$d_6$, 400 MHz): δ 0.84–0.91 (m, 3H), 1.22–1.32 (m, 4H), 1.45–1.64 (m, 2H), 2.18 (t, J=7.3 Hz, 2H), 3.98 (s, 3H), 3.99 (s, 3H), 7.33–7.37 (m, 2H), 7.39 (s, 1H), 7.57 (s, 1H), 7.70–7.75 (m, 2H), 8.56 (s, 1H), 11.45 (s, 1H), 12.59 (s, 1H) Mass spectrometry value (ESI-MS, m/z): 455 (M$^+$+1)

Example 1190

N-{3-Chloro-4-[(6,7-dimethoxy-4-quinolyl)oxy]phenyl}-N'-[(2-methylcyclopropyl)carbonyl]thiourea Toluene (20 ml) and thionyl chloride (1 ml) were added to commercially available 2-methyl-1-cyclopropanecarboxylic acid (80 mg), and the mixture was heated at 100° C. for one hr. The solvent was removed by distillation, and 2-methyl-1-cyclopropanecarbonyl isothiocyanate was prepared using the resultant 2-methyl-1-cyclopropanecarbonyl chloride as a starting compound according to the description of the literature. 2-Methyl-1-cyclopropanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (40 mg, yield 56%).

$^1$H-NMR (DMSO-$d_6$, 400 MHz): δ 0.84–0.89 (m, 1H), 1.08–1.38 (m, 5H), 1.87–1.91 (m, 1H), 3.94 (s, 3H), 3.95 (s, 3H), 6.40 (d, J=5.1 Hz, 1H), 7.42 (s, 1H), 7.46 (d, J=8.8 Hz, 1H), 7.52 (s, 1H), 7.66 (dd, J=2.7 Hz, 8.8 Hz, 1H), 8.13 (d, J=2.4 Hz, 1H), 8.49 (d, J=5.4 Hz, 1H), 11.82 (s, 1H), 12.58 (s, 1H) Mass spectrometry value (ESI-MS, m/z): 472 (M$^+$+1)

Example 1191

N-{4-[(6,7-Dimethoxy-4-quinazolinyl)oxy]phenyl}-
N'-[(2-methylcyclopropyl)carbonyl]thiourea Toluene (20 ml) and thionyl chloride (1 ml) were added to commercially available 2-methyl-1-cyclopropanecarboxylic acid (80 mg), and the mixture was heated at 100° C. for one hr. The solvent was removed by distillation, and 2-methyl-1-cyclopropanecarbonyl isothiocyanate was prepared using the resultant 2-methyl-1-cyclopropanecarbonyl chloride as a starting compound according to the description of the literature. 2-Methyl-1-cyclopropanecarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (13 mg, yield 18%).

$^1$H-NMR (DMSO-$d_6$, 400 MHz): δ 0.84–0.88 (m, 1H), 1.09–1.24 (m, 5H), 1.88–1.90 (m, 1H), 3.98 (s, 3H), 3.99 (s, 3H), 7.33 (d, J=9.0 Hz, 2H), 7.39 (s, 1H), 7.56 (s, 1H), 7.71 (d, J=9.0 Hz, 2H), 8.56 (s, 1H), 11.73 (s, 1H), 12.54 (s, 1H) Mass spectrometry value (ESI-MS, m/z): 439 (M$^+$+1)

Example 1192

N-{3-Chloro-4-[(6,7-dimethoxy-4-quinolyl)oxy]phenyl}-N'-[(1-methylcyclohexyl)carbonyl]thiourea Toluene (20 ml) and thionyl chloride (1 ml) were added to commercially available 1-methyl-1-cyclohexanecarboxylic acid (80 mg), and the mixture was heated at 100° C. for one hr. The solvent was removed by distillation, and 1-methyl-1-cyclohexanecarbonyl isothiocyanate was prepared using the resultant 1-methyl-1-cyclohexanecarbonyl chloride as a starting compound according to the description of the literature. 1-Methyl-1-cyclohexanecarbonyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (38 mg, yield 49%).

$^1$H-NMR (DMSO-$d_6$, 400 MHz): δ 1.26 (s, 3H), 1.35–1.52 (m, 8H), 2.06–2.09 (m, 2H), 3.94 (s, 3H), 3.96 (s, 3H), 6.41 (d, J=5.1 Hz, 1H), 7.42 (s, 1H), 7.47 (d, J=8.8 Hz, 1H), 7.52 (s, 1H), 7.68–7.72 (m, 1H), 8.15 (s, 1H), 8.50 (d, J=5.1 Hz, 1H), 10.66 (s, 1H), 12.65 (s, 1H) Mass spectrometry value (ESI-MS, m/z): 515 (M$^+$+1)

Example 1193

N-{4-[(6,7-Dimethoxy-4-quinazolinyl)oxy]phenyl}-
N'-[(1-methylcyclohexyl)carbonyl]thiourea Toluene (20 ml) and thionyl chloride (1 ml) were added to commercially available 1-methyl-1-cyclohexanecarboxylic acid (80 mg), and the mixture was heated at 100° C. for one hr. The solvent was removed by distillation, and 1-methyl-1-cyclohexanecarbonyl isothiocyanate was prepared using the resultant 1-methyl-1-cyclohexanecarbonyl chloride as a starting compound according to the description of the literature. 1-Methyl-1-cyclohexanecarbonyl isothiocyanate thus obtained was dissolved in ethanol (1 ml) to prepare a solution. 4-[(6,7-Dimethoxy-4-quinazolinyl)oxy] aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (31 mg, yield 38%).

$^1$H-NMR (DMSO-$d_6$, 400 MHz): δ 1.26 (s, 3H), 1.38–1.52 (m, 8H), 2.05–2.11 (m, 2H), 3.98 (s, 3H), 3.99 (s, 3H), 7.35 (d, J=8.8 Hz, 2H), 7.39 (s, 1H), 7.57 (s, 1H), 7.74 (d, J=8.8 Hz, 2H), 8.57 (s, 1H), 10.54 (s, 1H), 12.62 (s, 1H) Mass spectrometry value (ESI-MS, m/z): 481 (M$^+$+1)

Example 1194

N-{3-Chloro-4-[(6,7-dimethoxy-4-quinolyl)oxy]
phenyl}-N'-[(1-phenylcyclopropyl)carbonyl]thiourea Toluene (20 ml) and thionyl chloride (1 ml) were added to commercially available 1-phenyl-1-cyclopropanecarboxylic acid (80 mg), and the mixture was heated at 100° C. for one hr. The solvent was removed by distillation, and 1-phenyl-1-cyclopropanecarbonyl isothiocyanate was prepared using the resultant 1-phenyl-1-cyclopropanecarbonyl chloride as a starting compound according to the description of the literature. 1-Phenyl-1-cyclopropanecarbonyl isothiocyanate thus obtained was dissolved in ethanol (1 ml) to prepare a solution. 3-Chloro-4-[(6,7-dimethoxy-4-quinolyl) oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (24 mg, yield 30%).

$^1$H-NMR (DMSO-$d_6$, 400 MHz): δ 1.34 (s, 2H), 1.63 (s, 2H), 3.94 (s, 3H), 3.95 (s, 3H), 6.40 (d, J=5.1 Hz, 1H), 7.42–7.55 (m, 7H), 7.66 (d, J=8.5 Hz, 1H), 8.07 (s, 1H), 8.50 (d, J=5.1 Hz, 1H), 9.22 (s, 1H), 12.28 (s, 1H) Mass spectrometry value (ESI-MS, m/z): 534 (M$^+$+1)

Example 1195

N-{4-[(6,7-Dimethoxy-4-quinazolinyl)oxy]phenyl}-
N'-[(1-phenylcyclopropyl)carbonyl]thiourea Toluene (20 ml) and thionyl chloride (1 ml) were added to commercially available 1-phenyl-1-cyclopropanecarboxylic acid (80 mg), and the mixture was heated at 100° C. for one hr. The solvent was removed by distillation, and 1-phenyl-1-cyclopropanecarbonyl isothiocyanate was prepared using the resultant 1-phenyl-1-cyclopropanecarbonyl chloride as a starting compound according to the description of the literature. 1-Phenyl-1-cyclopropanecarbonyl isothiocyanate thus obtained was dissolved in ethanol (1 ml) to prepare a solution. 4-[(6,7-Dimethoxy-4-quinazolinyl)oxy] aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (58 mg, yield 69%).

$^1$H-NMR (DMSO-$d_6$, 400 MHz): δ 1.34 (s, 2H), 1.64 (s, 2H), 3.97 (s, 3H), 3.99 (s, 3H), 7.32–7.55 (m, 8H), 7.69 (d, J=7.3 Hz, 2H), 8.55 (s, 1H), 9.00 (s, 1H), 12.25 (s, 1H) Mass spectrometry value (ESI-MS, m/z): 501 (M$^+$+1)

Example 1196

N-{3-Chloro-4-[(6,7-dimethoxy-4-quinolyl)oxy]
phenyl}-N'-[(4-propylcyclohexyl)carbonyl]thiourea Toluene (20 ml) and thionyl chloride (1 ml) were added to commercially available 4-propyl-1-cyclohexanecarboxylic acid (80 mg), and the mixture was heated at 100° C. for one hr. The solvent was removed by distillation, and 4-propyl-1-cyclohexanecarbonyl isothiocyanate was prepared using the resultant 4-propyl-1-cyclohexanecarbonyl chloride as a starting compound according to the description of the literature. 4-Propyl-1-cyclohexanecarbonyl isothiocyanate thus obtained was dissolved in ethanol (1 ml) to prepare a solution. 3-Chloro-4-[(6,7-dimethoxy-4-quinolyl)oxy] aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (51 mg, yield 63%).

$^1$H-NMR (DMSO-$d_6$, 400 MHz): δ 0.85–0.94 (m, 5H), 1.07–1.44 (m, 7H), 1.77–1.89 (m, 4H), 2.66–2.70 (m, 1H), 3.95 (s, 3H), 3.96 (s, 3H), 6.41 (d, J=5.1 Hz, 1H), 7.43 (s, 1H), 7.47 (d, J=8.8 Hz, 1H), 7.53 (s, 1H), 7.67–7.73 (m, 1H), 8.14–8.19 (m, 1H), 8.49–8.53 (m, 1H), 11.53 (s, 1H), 12.58 (s, 1H) Mass spectrometry value (ESI-MS, m/z): 542 (M$^+$+1)

Example 1197

N-{4-[(6,7-Dimethoxy-4-quinazolinyl)oxy]phenyl}-
N'-[(4-propylcyclohexyl)carbonyl]thiourea Toluene (20 ml) and thionyl chloride (1 ml) were added to commercially available 4-propyl-1-cyclohexanecarboxylic acid (80 mg), and the mixture was heated at 100° C. for one hr. The solvent was removed by distillation, and 4-propyl-1-cyclohexanecarbonyl isothiocyanate was prepared using the resultant 4-propyl-1-cyclohexanecarbonyl chloride as a starting compound according to the description of the literature. 4-Propyl-1-cyclohexanecarbonyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by thin-layer chromatography using chloroform/acetone for development to give the title compound (59 mg, yield 69%).

$^1$H-NMR (DMSO-$d_6$, 400 MHz): δ 0.85–0.91 (m, 5H), 1.15–1.41 (m, 7H), 1.78–1.89 (m, 4H), 2.66–2.69 (m, 1H), 3.98 (s, 3H), 3.99 (s, 3H), 7.35 (d, J=6.6 Hz, 2H), 7.40 (s,

1H), 7.57 (s, 1H), 7.71–7.77 (m, 2H), 8.57 (s, 1H), 11.43 (s, 1H), 12.55 (s, 1H) Mass spectrometry value (ESI-MS, m/z): 509 (M$^+$+1)

Example 1198

N-(4-Chlorobutanoyl)-N'-{3-chloro-4-[(6,7-dimethoxy-4-quinolyl)oxy]phenyl}thiourea 4-Chlorobutanoyl isothiocyanate was prepared using commercially available 4-chlorobutanoyl chloride (80 mg) as a starting compound according to the description of the literature. 4-Chlorobutanoyl isothiocyanate thus obtained was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (35 mg, yield 48%).
$^1$H-NMR (DMSO-d$_6$, 400 MHz): δ 2.00–2.08 (m, 2H), 2.66 (t, J=7.1 Hz, 2H), 3.71 (t, J=6.6 Hz, 2H), 3.99 (s, 3H), 4.00 (s, 3H), 6.60–6.65 (m, 1H), 7.51 (s, 1H), 7.56 (d, J=8.8 Hz, 1H), 7.64 (s, 1H), 7.73–7.78 (m, 1H), 8.18–8.23 (m, 1H), 8.67 (d, J=5.6 Hz, 1H), 11.67 (s, 1H), 12.50 (s, 1H) Mass spectrometry value (ESI-MS, m/z): 495 (M$^+$+1)

Example 1199

N-(3-Chloropropanoyl)-N'-{4-[(6,7-dimethoxy-4-quinazolinyl)oxy]phenyl}thiourea

3-Chloropropanoyl isothiocyanate was prepared using commercially available 3-chloropropanoyl chloride (80 mg) as a starting compound according to the description of the literature. 3-Chloropropanoyl isothiocyanate thus obtained was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (38 mg, yield 50%).
$^1$H-NMR (DMSO-d$_6$, 400 MHz): δ 3.04 (t, J=4.6 Hz, 2H), 3.88 (t, J=3.7 Hz, 2H), 3.99 (s, 3H), 4.00 (s, 3H), 7.37 (d, J=6.6 Hz, 2H), 7.40 (s, 1H), 7.58 (s, 1H), 7.73 (d, J=6.3 Hz, 2H), 8.57 (s, 1H), 11.65 (s, 1H), 12.39 (s, 1H) Mass spectrometry value (ESI-MS, m/z): 447 (M$^+$+1)

Example 1200

N-{3-Chloro-4-[(6,7-dimethoxy-4-quinolyl)oxy]phenyl}-N'-(2-methylpentanoyl)thiourea Toluene (20 ml) and thionyl chloride (1 ml) were added to commercially available 2-methylpentanoic acid (80 mg), and the mixture was heated at 100° C. for one hr. The solvent was removed by distillation, and 2-methylpentanoyl isothiocyanate was prepared using the resultant 2-methylpentanoyl chloride as a starting compound according to the description of the literature. The resultant 2-methylpentanoyl isothiocyanate was dissolved in ethanol (1 ml) to prepare a solution. 3-Chloro-4-[(6,7-dimethoxy-4-quinolyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (69 mg, yield 94%).
$^1$H-NMR (chloroform-d, 400 MHz): δ 0.85–1.80 (m, 10H), 2.37–2.53 (m, 1H), 4.09 (s, 3H), 4.11 (s, 3H), 6.49 (d, J=5.9 Hz, 1H), 7.31 (d, J=5.1 Hz, 1H), 7.61 (s, 1H), 7.72 (dd, J=2.4 Hz, 8.8 Hz, 1H), 7.76 (s, 1H), 8.08 (d, J=2.4 Hz, 1H), 8.66 (s, 1H), 12.66 (s, 1H) Mass spectrometry value (ESI-MS, m/z): 488 (M$^+$+1)

Example 1201

N-{4-[(6,7-Dimethoxy-4-quinazolinyl)oxy]phenyl}-N'-(2-methylpentanoyl)thiourea

2-Methylpentanoyl isothiocyanate prepared according to the method 2 was dissolved in ethanol (1 ml) to prepare a solution. 4-[(6,7-Dimethoxy-4-quinazolinyl)oxy]aniline (50 mg), toluene (5 ml), and ethanol (1 ml) were added to the solution, and the mixture was stirred at room temperature for 16 hr. The reaction solution was concentrated, and the residue was purified by chromatography on silica gel using chloroform/acetone for development to give the title compound (44 mg, yield 57%).
$^1$H-NMR (DMSO-d$_6$, 400 MHz): δ 0.87–0.92 (m, 3H), 1.09–1.13 (m, 3H), 1.26–1.65 (m, 4H), 2.74–2.81 (m, 1H), 3.98 (s, 3H), 4.00 (s, 3H), 7.34–7.38 (m, 2H), 7.40 (s, 1H), 7.57 (s, 1H), 7.72–7.78 (m, 2H), 8.57 (s, 1H), 11.51 (s, 1H), 12.59 (s, 1H) Mass spectrometry value (ESI-MS, m/z): 455 (M$^+$+1)

Example 1202

N-{2-Chloro-4-[(6,7-dimethoxy-4-quinolyl)oxy]phenyl}-N'-(2,4-difluorobenzoyl)thiourea 2,4-Difluoro-1-benzenecarbonyl isothiocyanate was prepared using commercially available 2,4-difluoro-1-benzenecarbonyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 2,4-difluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (42 mg, yield 53%).
$^1$H-NMR (DMSO-d$_6$, 400 MHz): δ 3.93 (s, 3H), 3.96 (s, 3H), 6.66 (d, J=5.12 Hz, 1H), 7.16–7.36 (m, 5H), 7.61 (s, 1H), 7.82–7.83 (m, 1H), 8.10 (d, J=9.03 Hz, 1H), 8.56 (d, J=5.12 Hz, 1H), 11.98 (bs, 1H), 12.33 (bs, 1H) Mass spectrometry value (ESI-MS, m/z): 530 (M$^+$+1)

Example 1203

N-(3,4-Dimethoxybenzoyl)-N'-{4-[(6,7-dimethoxy-4-quinazolinyl)oxy]phenyl}thiourea 3,4-Dimethoxy-1-benzenecarbonyl isothiocyanate was prepared using commercially available 3,4-dimethoxy-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 3,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (57 mg, yield 65%).

$^1$H-NMR (DMSO-$d_6$, 400 MHz): δ 3.79 (s, 3H), 3.83 (s, 3H), 3.96 (s, 3H), 3.99 (s, 3H), 6.62 (d, J=15.61 Hz, 2H), 6.92 (d, J=15.61 Hz, 2H), 7.04 (d, J=8.54 Hz, 1H), 7.38 (s, 1H), 7.44 (s, 1H), 7.52 (s, 1H), 7.56 (dd, J=2.19 Hz, J=8.30 Hz, 1H), 8.56 (s, 1H), 11.88 (bs, 1H), 12.50 (bs, 1H) Mass spectrometry value (ESI-MS, m/z): 521 (M$^+$+1)

Example 1204

N-{3-Chloro-4-[(6,7-dimethoxy-4-quinolyl)oxy]phenyl}-N'-(3,4-dimethoxybenzoyl)thiourea 3,4-Dimethoxy-1-benzenecarbonyl isothiocyanate was prepared using commercially available 3,4-dimethoxy-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 3,4-dimethoxy-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (49 mg, yield 58%).

$^1$H-NMR (DMSO-$d_6$, 400 MHz): δ 3.79 (s, 3H), 3.83 (s, 3H), 3.93 (s, 3H), 3.94 (s, 3H), 5.46 (bs, 1H), 6.29 (d, J=15.37 Hz, 1H), 6.62–6.43 (m, 1H), 6.79 (s, 1H), 7.03–7.10 (m, 2H), 7.38 (s, 1H), 7.52 (s, 1H), 7.55–7.58 (m, 2H), 8.44 (d, J=5.12 Hz, 1H), 12.63 (bs, 1H) Mass spectrometry value (ESI-MS, m/z): 555 (M$^+$+1)

Example 1205

N-{2-Chloro-4-[(6,7-dimethoxy-4-quinolyl)oxy]phenyl}-N'-(2-phenylacetyl)thiourea 2-Phenylethanoyl isothiocyanate was prepared using commercially available 2-phenylethanoyl chloride (80 mg) as a starting compound according to the description of the literature. 2-Chloro-4-[(6,7-dimethoxy-4-quinolyl)oxy]aniline (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (48 mg, yield 62%).

$^1$H-NMR (DMSO-$d_6$, 400 MHz): δ 3.85 (s, 3H), 3.93 (s, 3H), 3.95 (s, 3H), 6.64 (d, J=5.08 Hz, 1H), 7.27–7.39 (m, 5H), 7.42 (s, 1H), 7.49 (s, 1H), 7.57 (s, 1H), 8.10 (d, J=8.78 Hz, 1H), 8.55 (d, J=5.38 Hz, 1H), 11.91 (bs, 1H), 12.39 (bs, 1H) Mass spectrometry value (ESI-MS, m/z): 508 (M$^+$+1)

Example 1206

N-{4-[(6,7-Dimethoxy-4-quinolyl)oxy]-2,3-dimethylphenyl}-N'-(2-phenylacetyl)thiourea 2-Phenylethanoyl isothiocyanate was prepared using commercially available 2-phenylethanoyl chloride (80 mg) as a starting compound according to the description of the literature. 4-[(6,7-Dimethoxy-4-quinolyl)oxy]-2,3-dimethylaniline (50 mg) was dissolved in toluene (5 ml) and ethanol (1 ml) to prepare a solution. A solution of 2-phenylethanoyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (44 mg, yield 58%).

$^1$H-NMR (DMSO-$d_6$, 400 MHz): δ 2.08 (s, 3H), 2.15 (s, 3H), 3.85 (s, 2H), 3.94 (s, 3H), 3.95 (s, 3H), 6.28 (d, J=5.12 Hz, 1H), 7.08 (d, J=8.54 Hz, 1H), 7.27–7.41 (m, 7H), 7.57 (s, 1H), 8.47 (d, J=5.37 Hz, 1H), 11.75 (bs, 1H), 12.01 (bs, 1H) Mass spectrometry value (ESI-MS, m/z): 502 (M$^+$+1)

Example 1207

N-(2,4-Dichlorobenzoyl)-N'-{4-[(6,7-dimethoxy-4-quinazolinyl)oxy]phenyl}thiourea 2,4-Dichloro-1-benzenecarbonyl isothiocyanate was prepared using commercially available 2,4-dichloro-1-benzenecarbonyl chloride (80 mg) as a starting compound according to the description of the literature. 4-[(6,7-Dimethoxy-4-quinazolinyl)oxy]aniline (50 mg) was dissolved in toluene (5 ml) and ethanol (1 ml) to prepare a solution. A solution of 2,4-dichloro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (65 mg, yield 73%).

$^1$H-NMR (DMSO-$d_6$, 400 MHz): δ 3.97 (s, 3H), 3.99 (s, 3H), 7.38 (d, J=11.22 Hz, 3H), 7.55–7.58 (m, 2H), 7.69 (d, J=8.29 Hz, 1H), 7.76–7.78 (m, 3H), 8.57 (s, 1H), 12.04 (bs, 1H), 12.26 (bs, 1H) Mass spectrometry value (ESI-MS, m/z): 530 (M$^+$+1)

Example 1208

N-{3-Chloro-4-[(6,7-dimethoxy-4-quinolyl)oxy]phenyl}-N'-(2,4-difluorobenzoyl)thiourea 2,4-Difluoro-1-benzenecarbonyl isothiocyanate was prepared using commercially available 2,4-difluoro-1-benzenecarbonyl chloride (80 mg) as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 2,4-difluoro-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (50 mg, yield 63%).

$^1$H-NMR (DMSO-$d_6$, 400 MHz): δ 3.95 (s, 3H), 3.96 (s, 3H), 6.43 (d, J=5.37 Hz, 1H), 7.24–7.29 (m, 1H), 7.43–7.55 (m, 3H), 7.75 (dd, J=2.44 Hz, J=8.78 Hz, 1H), 7.79–7.90 (m,

2H), 8.16 (bs, 1H), 8.52 (d, J=5.12 Hz, 1H), 11.86 (bs, 1H), 12.32 (bs, 1H) Mass spectrometry value (ESI-MS, m/z): 530 (M$^+$+1)

Example 1209

N-{3-Chloro-4-[(6,7-dimethoxy-4-quinolyl)oxy]phenyl}-N'-(4-octylbenzoyl)thiourea Toluene (20 ml) and thionyl chloride (1 ml) were added to commercially available 4-octylbenzoic acid (40 mg), and the mixture was heated at 100° C. for one hr. The solvent was removed by distillation, and 4-octyl-1-benzenecarbonyl isothiocyanate was prepared using the resultant 4-octyl-1-benzenecarbonyl chloride as a starting compound according to the description of the literature. 3-Chloro-4-[(6,7-dimethoxy-4-quinolyl)oxy]aniline (50 mg) was dissolved in toluene (5 ml) and ethanol (1 ml) to prepare a solution. A solution of 4-octyl-1-benzenecarbonyl isothiocyanate in ethanol (1 ml) was then added to the solution, and the mixture was stirred at room temperature for 2 hr. The reaction solution was concentrated, and the residue was purified by chromatography on silica gel using chloroform/acetone for development to give the title compound (53 mg, yield 58%).

$^1$H-NMR (DMSO-d$_6$, 400 MHz): δ 0.84–0.87 (m, 4H) 1.60 (m, 2H), 2.09 (s, 2H), 2.50 (s, 7H), 2.65–2.69 (m, 2H), 3.94 (s, 3H), 5.46 (bs, 1H), 6.29 (d, J=15.37 Hz, 1H), 6.42 (d, J=5.12 Hz, 1H), 7.36–7.54 (m, 6H), 7.74–7.76 (m, 1H), 7.94 (d, J=8.05 Hz, 2H), 8.19 (bs, 1H), 8.51 (d, J=5.12 Hz, 1H), 11.61 (bs, 1H), 12.70 (bs, 1H) Mass spectrometry value (ESI-MS, m/z): 607 (M$^+$+1)

Example 1210

N-4-[(6,7-Dimethoxy-4-quinazolinyl)oxy]-2-nitrophenyl-N'-(4-piperidinobutyl)urea Piperidine (357 mg) was dissolved in acetonitrile (20 ml) to prepare a solution. Potassium carbonate (97 mg) was then added to the solution. 2-(4-Bromobutyl)-1,3-isoindolinedione (1 g) was further added thereto, and the mixture was stirred with heating under reflux for 10 hr. Water was added to stop the reaction, and the reaction solution was then extracted with ethyl acetate, followed by washing with water and brine. The extract was then dried over sodium sulfate, was filtered, and was concentrated to give 850 mg of a mixture containing 2-(4-piperidinobutyl)-1,3-isoindolinedione. The mixture containing 2-(4-piperidinobutyl)-1,3-isoindolinedione (850 mg) thus obtained was dissolved in ethyl alcohol (10 ml) to prepare a solution. Hydrazine monohydrate (0.75 ml) was then added to the solution, and the mixture was stirred at room temperature for one hr. This solution was concentrated to give 980 mg of a mixture containing 4-piperidinobutylamine. 4-[(6,7-Dimethoxy-4-quinazolinyl)oxy]-2-nitroaniline (100 mg) was dissolved in chloroform (10 ml) to prepare a solution. Triethylamine (1 ml) was then added to the solution, and a solution of triphosgene (131 mg) in chloroform (5 ml) was further added thereto. The mixture was stirred at room temperature for 10 min. A solution of the mixture containing 4-piperidinobutylamine (69 mg) in chloroform (5 ml) was then added thereto, and the mixture was stirred at room temperature for 30 min. Water was added to stop the reaction, the reaction solution was then extracted with chloroform, and the extract was dried over sodium sulfate. The extract was filtered and concentrated. The powder thus obtained was then filtered and washed with diethyl ether to give N-4-[(6,7-dimethoxy-4-quinazolinyl)oxy]-2-nitrophenyl-N'-(4-piperidinobutyl)-urea (104 mg, yield 68%).

$^1$H-NMR (CDCl$_3$, 400 MHz): δ 1.54 (brs, 2H), 1.65–1.79 (m, 8H), 2.52–2.61 (m, 6H), 3.35 (t, J=5.9 Hz, 2H), 4.075 (s, 3H), 4.080 (s, 3H), 7.00 (brs, 1H), 7.34 (s, 1H), 7.51–7.54 (m, 2H), 8.12 (d, J=2.7 Hz, 1H), 8.61 (s, 1H), 8.76 (d, J=9.5 Hz, 1H), 9.73 (s, 1H) Mass spectrometry value (ESI-MS, m/z): 525 (M$^+$+1)

Example 1211

N-4-[(6,7-Dimethoxy-4-quinazolinyl)oxy]-2-nitrophenyl-N'-(4-piperidinopropyl)urea Piperidine (357 mg) was dissolved in acetonitrile (20 ml) to prepare a solution. Potassium carbonate (97 mg) was then added to the solution. Further, 2-(3-bromopropyl)-1,3-isoindolinedione (1 g) was added thereto, and the mixture was stirred with heating under reflux for 10 hr. Water was added to stop the reaction, and the reaction solution was then extracted with ethyl acetate, followed by washing with water and brine. The extract was then dried over sodium sulfate, was filtered, and was concentrated to give 850 mg of a mixture containing 2-(3-piperidinopropyl)-1,3-isoindolinedione. The mixture containing 2-(3-piperidinopropyl)-1,3-isoindolinedione (850 mg) thus obtained was dissolved in ethyl alcohol (10 ml) to prepare a solution. Hydrazine monohydrate (0.75 ml) was then added to the solution, and the mixture was stirred at room temperature for one hr. This solution was concentrated to give 980 mg of a mixture containing 3-piperidinobutylamine. 4-[(6,7-Dimethoxy-4-quinazolinyl)oxy]-2-nitroaniline (100 mg) was dissolved in chloroform (10 ml) to prepare a solution. Triethylamine (1 ml) was then added to the solution. A solution of triphosgene (131 mg) in chloroform (5 ml) was further added to the solution, and the mixture was stirred at room temperature for 10 min. A solution of the mixture containing 3-piperidinopropylamine (69 mg) in chloroform (5 ml) was then added thereto, and the mixture was stirred at room temperature for 30 min. Water was added to stop the reaction, and the reaction solution was then extracted with chloroform, followed by washing with sodium sulfate. The extract was then filtered and was concentrated to give a powder. The powder was then filtered and was washed with diethyl ether to give N-4-[(6,7-dimethoxy-4-quinazolinyl)oxy]-2-nitrophenyl-N'-(3-piperidinopropyl)urea (104 mg, yield 68%).

$^1$H-NMR (CDCl$_3$, 400 MHz) δ 1.55 (brs, 2H), 1.65–1.80 (m, 6H), 2.50–2.62 (m, 6H), 3.37 (t, J=5.9 Hz, 2H), 4.075 (s, 3H), 4.080 (s, 3H), 7.05 (brs, 1H), 7.35 (s, 1H), 7.50–7.55 (m, 2H), 8.10 (d, J=2.7 Hz, 1H), 8.60 (s, 1H), 8.78 (d, J=9.5 Hz, 1H), 9.75 (s, 1H) Mass spectrometry value (ESI-MS, m/z): 511 (M$^+$+1)

Pharmacological Test Example 1

Measurement of Inhibitory Activity Against PDGF-Ra Phosphorylation by PDGF-AA Stimulation Using G292

G-292 human osteosarcoma cells (Dainippon Pharmaceutical Co. Ltd.) were cultured in a DMEM medium (Dainippon Pharmaceutical Co. Ltd.) containing 10% FBS within an incubator containing 5% carbon dioxide until 80% confluent, and the cells were planted at 3×10$^4$ cells per well in 96-well flat-bottom plates in the same medium containing 0.1% FBS. After cultivation at 37° C. overnight, a solution of a test compound in dimethyl sulfoxide was added to each well, and a reaction was allowed to proceed at 37° C. for one hr.

After the reaction of the test compound, PDGF-AA (Upstate) was added to 50 ng/ml, and the cells were stimulated at 37° C. for 5 min. Thereafter, the cells were solubilized and shaken at room temperature for 20 min.

This solubilized cell solution was transferred to a 96-well plate coated with aniti-phosphotyrosine antibody PY-20, and a reaction was allowed to proceed at 4° C. overnight. Anti-PDGF-Ra (c-20) (Santa Cruz) was added as a primary antibody, and a reaction was allowed to proceed for one hr. GAR (Anti-rabbit Ig, horseradish peroxidase, Amersham) was then added as a secondary antibody, and a reaction was allowed to proceed for one hr. Color development was carried out using a color development kit for peroxidase (Sumitomo Bakelite Co., Ltd.), and the absorbance was measured at 450 nm. The phosphorylation of PDGF-Ra in the presence of the test compound was measured by presuming a phosphorylation degree of the receptor in the presence of a ligand to be 100% and a phosphorylation degree of PDGF-Ra in the absence of a ligand to be 0%, and $IC_{50}$ was then determined.

Pharmacological Test Example 2

PDGF-R Autophosphorylation Inhibition Screening (Dot Plotting)

Vascular smooth muscle cells (passage 5 to 10) collected from rat thoracic aorta by the explant method were planted at $8 \times 10^3$ cells per well in 96-well plates, subject to a serum starvation state, and 24 hr after the plantation then assayed.

A test compund was added, and the mixture was incubated at 37° C. for one hr. Thereafter, PDGF-BB was added to 50 ng/ml, and the mixture was incubated for 5 min, followed by washing with cold PBS. Lysate buffer (20 µl/well) was then added, SDS buffer (20 ml/well) was added thereto, and 2 µl of the mixture was then spotted on a PDVF membrane.

Treatment was carried out with anti-mouse IgG which had been labelled with peroxidase after treatment with an anti-phosphotyrosine antibody, followed by development in an ECL color development kit (Amersham). Thereafter, the color intensity was quantitatively determined by image analysis.

The inhibitory activity $IC_{50}$ of the test compound was calculated by presuming a color intensity with the addition of PDGF and without the addition of the test compound to be 0% inhibition and a color intensity without the test compound and PDGF to be 100% inhibition.

Pharmacological Test Example 3

Inhibitory Activity Against c-kit Autophosphorylation

MO7e (human megakaryocytic leukemia cell line) which had been arrested for 20 hr was seeded into 96 well plates at an amount of $2 \times 10^5$ per well. A solution of a test compound in DMSO was added, and a reaction was then allowed to proceed for one hr. Thereafter, the cells were stimulated by 50 ng/ml of h-SCF for 5 min, followed by replacement with lysate buffer to solubilize the cells.

Next, the solubilized cell sap was transferred to a 96-well plate with an anti-phosphotyrosine antibody (PY-20) previously immobilized thereon, and a reaction was allowed to proceed. Thereafter, the cells were reacted with an anti-c-kit antibody (c-19, Santa Cruz) as a primary antibody and were labelled with GAR (anti-rabbit IgG, horseradish peroxidase, Amersham) as a secondary antibody. Color development was then carried out in a peroxidase color development kit (Sumitomo Bakelite Co., Ltd.), and the absorbance was measured at a wavelength of 450 nm.

The c-kit autophosphorylation inhibitory activity of the test compound was measured by presuming c-kit autophosphorylation activity with the addition of DMSO in the absence of h-SCF to be 100% inhibition and c-kit autophosphorylation activity with the addition of DMSO in the presence of h-SCF to be 0% inhibition, and $IC_{50}$ was then determined.

The results of Pharmacological Test Examples 1 to 3 were as follows. Values within parentheses indicates $IC_{50}$ (nM). Figures within parenthesess in >100 ( ) in PDGF(E) indicate inhibition (%) at 100 nM. Figures within parentheses in >1000 ( ) and −( ) indicate inhibition (%) at 1000 nM. Figures within parentheses in −( ) of c-kit indicate inhibition (%) at 1000 nM. The symbol > indicates that the inhibition at an indicated concentration is not more than 50%. The symbols < and << indicate that the inhibition at an indicated concentration is not less than 50%.

| Example No. | PDGF (E) | PDGF (D) | c-kit |
|---|---|---|---|
| 1 | <10 | | 52 |
| 2 | 17 | | 422 |
| 3 | <10 | | 173 |
| 4 | <10 | | 133 |
| 5 | 24 | | 336 |
| 6 | <10 | | 175 |
| 7 | 12 | | 616 |
| 8 | <<10 | | 62 |
| 9 | <10 | | 45 |
| 10 | 11 | | 106 |
| 11 | <<10 | | 36 |
| 12 | 11 | | 389 |
| 13 | <10 | | 135 |
| 14 | 12 | | 209 |
| 15 | 21 | | −(48) |
| 16 | <10 | | 495 |
| 17 | <10 | | 57 |
| 18 | 22 | | 93 |
| 19 | <<10 | | 41 |
| 20 | <<10 | | 109 |
| 21 | <10 | | 135 |
| 22 | <10 | | 186 |
| 23 | <10 | | 475 |
| 24 | <<10 | | 129 |
| 25 | <10 | | 566 |
| 26 | <<10 | | 44 |
| 27 | <<10 | | 76 |
| 28 | <10 | | 118 |
| 29 | 27 | | 121 |
| 30 | <10 | | <30 |
| 31 | <10 | | 221 |
| 32 | 16 | | 227 |
| 33 | 23 | | 362 |
| 34 | >100(45) | | 800 |
| 35 | <10 | | 342 |
| 36 | >100(34) | | −(19) |
| 37 | <<10 | | <30 |
| 38 | <10 | | 33 |
| 39 | <10 | | 56 |
| 40 | <<10 | | 55 |
| 41 | <10 | | 185 |
| 42 | <10 | | 73 |
| 43 | <10 | | 158 |
| 44 | 19 | | 328 |
| 45 | <10 | | 91 |
| 46 | 22 | | 388 |
| 47 | <10 | | 178 |
| 48 | <10 | | 162 |

| Example No. | PDGF (E) | PDGF (D) | c-kit |
|---|---|---|---|
| 49 | <10 | | 185 |
| 50 | <10 | | 50 |
| 51 | 14 | | 270 |
| 52 | <10 | | 273 |
| 53 | <10 | | 480 |
| 54 | 15 | | 473 |
| 55 | <10 | | 288 |
| 56 | 11 | | 774 |
| 57 | 11 | | 393 |
| 58 | 12 | | 499 |
| 59 | 57 | | −(33) |
| 60 | <10 | | 261 |
| 61 | 10 | | −(32) |
| 62 | 13 | | 70 |
| 63 | 16 | | 211 |
| 64 | 90 | | 429 |
| 65 | <10 | | 103 |
| 66 | 50 | | 353 |
| 67 | <10 | | 342 |
| 68 | 13 | | 294 |
| 69 | 53 | | 755 |
| 70 | <10 | | 451 |
| 71 | 38 | | −(34) |
| 72 | 36 | | 387 |
| 73 | 28 | | 235 |
| 74 | 100 | | 1000 |
| 75 | 25 | | 1000 |
| 76 | >100(37) | | −(14) |
| 77 | <10 | | 99 |
| 78 | 16 | | 129 |
| 79 | 18 | | 123 |
| 80 | 12 | | 137 |
| 81 | 12 | | 408 |
| 82 | 10 | | 176 |
| 83 | 16 | | 253 |
| 84 | 27 | | 399 |
| 85 | <10 | | 163 |
| 86 | 13 | | 842 |
| 87 | <10 | | 607 |
| 88 | 19 | | −(45) |
| 89 | 14 | | −(35) |
| 90 | <10 | | 621 |
| 91 | 14 | | −(20) |
| 92 | <10 | | 677 |
| 93 | 17 | | 601 |
| 94 | 31 | | −(31) |
| 95 | 16 | | 962 |
| 96 | 38 | | −(13) |
| 97 | <10 | | 254 |
| 98 | <10 | | 152 |
| 99 | 21 | | 394 |
| 100 | 14 | | 815 |
| 101 | 12 | | −(27) |
| 102 | <10 | | 217 |
| 103 | 15 | | 200 |
| 104 | 25 | | 590 |
| 105 | <10 | | 252 |
| 106 | 12 | | 1000 |
| 107 | | | 372 |
| 108 | | | 180 |
| 109 | | | 412 |
| 110 | | | 110 |
| 111 | | | 750 |
| 112 | 16 | | 214 |
| 113 | 18 | | 402 |
| 114 | 65 | | 602 |
| 115 | <10 | | 387 |
| 116 | 31 | | 1000 |
| 117 | 26 | | 759 |
| 118 | 33 | | 746 |
| 119 | >100 | | −(31) |
| 120 | 13 | | 505 |
| 121 | 48 | | −(17) |
| 122 | 11 | | 821 |
| 123 | <10 | | 207 |
| 124 | 42 | | −(39) |
| 125 | <10 | | 671 |
| 126 | 19 | | −(10) |
| 127 | 16 | | 283 |
| 128 | 26 | | 375 |
| 129 | 64 | | 732 |
| 130 | <10 | | 714 |
| 131 | 38 | | −(40) |
| 132 | 26 | | 301 |
| 133 | 26 | | 206 |
| 134 | >100(49) | | 944 |
| 135 | 18 | | 475 |
| 136 | 43 | | −(7) |
| 137 | <10 | | 233 |
| 138 | 17 | | 74 |
| 139 | 57 | | 80 |
| 140 | <10 | | 234 |
| 141 | 36 | | −(26) |
| 142 | <10 | | <30 |
| 143 | <10 | | <30 |
| 144 | 18 | | 49 |
| 145 | <10 | | <30 |
| 146 | 11 | | 32 |
| 147 | 11 | | <30 |
| 148 | <10 | | <30 |
| 149 | 19 | | 49 |
| 150 | <10 | | 38 |
| 151 | 12 | | 32 |
| 152 | <10 | | <30 |
| 153 | <10 | | <30 |
| 154 | 40 | | 61 |
| 155 | 14 | | 41 |
| 156 | >100(48) | | 33 |
| 157 | <10 | | 35 |
| 158 | 12 | | 107 |
| 159 | 52 | | 147 |
| 160 | 16 | | 52 |
| 161 | <10 | | 178 |
| 162 | 16 | | 162 |
| 163 | <10 | | 185 |
| 164 | 12 | | 50 |
| 165 | 49 | | 149 |
| 166 | 34 | | 145 |
| 167 | 45 | | 370 |
| 168 | 15 | | 52 |
| 169 | <10 | | 31 |
| 170 | <10 | | 34 |
| 171 | 22 | | 83 |
| 172 | 17 | | 74 |
| 173 | <<10 | | 37 |
| 174 | <10 | | 70 |
| 175 | <<10 | | 45 |
| 176 | 20 | | <30 |
| 177 | 19 | | <30 |
| 178 | >100 | | |
| 179 | 70 | | |
| 180 | 63 | | |
| 181 | >100 | | |
| 182 | >100 | | |
| 183 | 35 | | 706 |
| 184 | 38 | | 369 |
| 185 | 46 | | |
| 186 | 63 | | |
| 187 | <10 | | 561 |
| 188 | 100 | | |
| 189 | 57 | | |
| 190 | >100 | | |
| 191 | 84 | | 503 |
| 192 | 56 | | |
| 193 | 57 | | |
| 194 | 91 | | 715 |
| 195 | 66 | | |
| 196 | 49 | | |
| 197 | 93 | | |
| 198 | 21 | | 1000 |
| 199 | 35 | | 807 |
| 200 | 31 | | 329 |
| 201 | >100 | | |
| 202 | 10 | | 610 |

| Example No. | PDGF (E) | PDGF (D) | c-kit | Example No. | PDGF (E) | PDGF (D) | c-kit |
|---|---|---|---|---|---|---|---|
| 203 | 25 | | 169 | 280 | <10 | | 370 |
| 204 | 28 | | 79 | 281 | >100(49) | | 268 |
| 205 | 78 | | | 282 | 34 | | 48 |
| 206 | 13 | | 80 | 283 | <10 | | 121 |
| 207 | 31 | | 55 | 284 | <10 | | 269 |
| 208 | 18 | | 53 | 285 | <10 | | 85 |
| 209 | >100 | | | 286 | <10 | | 54 |
| 210 | 16 | | 95 | 287 | 13 | | 228 |
| 211 | 17 | | 43 | 288 | <10 | | 162 |
| 212 | 28 | | 70 | 289 | <10 | | 328 |
| 213 | 21 | | 61 | 290 | 47 | | 281 |
| 214 | >30(6) | | 47 | 291 | 26 | | 124 |
| 215 | 8 | | <30 | 292 | 14 | | 262 |
| 216 | | <3 | 19 | 293 | <10 | | 145 |
| 217 | | 29 | 39 | 294 | 15 | | 109 |
| 218 | | 88 | 123 | 295 | >100(45) | | 178 |
| 219 | | 27 | <30 | 296 | 61 | | 109 |
| 220 | | 47 | 77 | 297 | <<10 | | 41 |
| 221 | | 84 | 109 | 298 | <10 | | 119 |
| 222 | | 45 | 101 | 299 | <<10 | | 53 |
| 223 | | 7 | 101 | 300 | <10 | | −(43) |
| 224 | | >100 | 147 | 301 | 43 | | −(39) |
| 225 | | 86 | 453 | 302 | 12 | | 202 |
| 226 | | 11 | 72 | 303 | 11 | | 188 |
| 227 | | 7 | 194 | 304 | 63 | | 401 |
| 228 | | 10 | 71 | 305 | 11 | | 221 |
| 229 | | 18 | 47 | 306 | 11 | | 72 |
| 230 | 8 | | 111 | 307 | >100(49) | | 165 |
| 231 | 1 | | 86 | 308 | 20 | | 101 |
| 232 | 11 | | 42 | 309 | 10 | | 285 |
| 233 | 8 | | 52 | 310 | 67 | | 607 |
| 234 | 10 | | 46 | 311 | <10 | | 329 |
| 235 | <3 | | 57 | 312 | <<10 | | 29 |
| 236 | 4 | | 47 | 313 | <10 | | 330 |
| 237 | 6 | | 42 | 314 | 44 | | 32 |
| 238 | 10 | | 36 | 315 | <10 | | 82 |
| 239 | 9 | | 183 | 316 | 10 | | −(40) |
| 240 | 17 | | 248 | 317 | <<10 | | 136 |
| 241 | 12 | | 232 | 318 | 10 | | 418 |
| 242 | 21 | | 192 | 319 | <<10 | | 98 |
| 243 | 20 | | 190 | 320 | <10 | | 596 |
| 244 | 27 | | 69 | 321 | <<10 | | 37 |
| 245 | 16 | | 408 | 322 | <10 | | 60 |
| 246 | 58 | | 243 | 323 | <<10 | | <30 |
| 247 | 3 | | 40 | 324 | 12 | | 64 |
| 248 | 11 | | 147 | 325 | <10 | | 46 |
| 249 | 4 | | 57 | 326 | >100(31) | | −(18) |
| 250 | 4 | | 184 | 327 | >100(30) | | −(6) |
| 251 | 6 | | 185 | 328 | >100(22) | | −(10) |
| 252 | 6 | | 111 | 329 | <10 | | 253 |
| 253 | 17 | | 514 | 330 | 12 | | 467 |
| 254 | >100(27) | | 396 | 331 | <10 | | 377 |
| 255 | >100(36) | | 309 | 332 | <<10 | | 259 |
| 256 | <3 | | 15 | 333 | 12 | | 712 |
| 257 | 6 | | 22 | 334 | <10 | | 484 |
| 258 | 3 | | 178 | 335 | <<10 | | <30 |
| 259 | 34 | | 184 | 336 | 14 | | 109 |
| 260 | 6 | | 180 | 337 | <10 | | 198 |
| 261 | 4 | | 44 | 338 | 25 | | 956 |
| 262 | 7 | | 83 | 339 | 38 | | 197 |
| 263 | 10 | | 329 | 340 | <10 | | 107 |
| 264 | 42 | | 486 | 341 | 32 | | 519 |
| 265 | 35 | | 122 | 342 | <<10 | | <30 |
| 266 | | 6 | 34 | 343 | <10 | | 232 |
| 267 | | 23 | 35 | 344 | <10 | | <30 |
| 268 | | 6 | 34 | 345 | 30 | | 123 |
| 269 | 17 | | −(48) | 346 | 41 | | −(37) |
| 270 | 65 | | 471 | 347 | 77 | | 228 |
| 271 | 22 | | 130 | 348 | <10 | | 90 |
| 272 | 61 | | 297 | 349 | 12 | | 309 |
| 273 | 23 | | 107 | 350 | <10 | | 238 |
| 274 | 25 | | 399 | 351 | <10 | | 64 |
| 275 | 16 | | 103 | 352 | <10 | | 195 |
| 276 | 16 | | 413 | 353 | <10 | | 80 |
| 277 | 10 | | 53 | 354 | 15 | | 384 |
| 278 | 53 | | 289 | 355 | 24 | | 252 |
| 279 | <10 | | <30 | 356 | <10 | | 66 |

-continued

| Example No. | PDGF (E) | PDGF (D) | c-kit |
|---|---|---|---|
| 357 | <10 | | 116 |
| 358 | <10 | | 366 |
| 359 | 28 | | 274 |
| 360 | 16 | | 189 |
| 361 | <10 | | 278 |
| 362 | 42 | | -(26) |
| 363 | <10 | | 72 |
| 364 | 29 | | 98 |
| 365 | <10 | | 47 |
| 366 | 27 | | 66 |
| 367 | 55 | | 207 |
| 368 | 64 | | 426 |
| 369 | >100 | | -(36) |
| 370 | 74 | | 585 |
| 371 | <10 | | 541 |
| 372 | | | -(14) |
| 373 | 43 | | 71 |
| 374 | <10 | | <30 |
| 375 | 74 | | 144 |
| 376 | <10 | | 41 |
| 377 | 21 | | 151 |
| 378 | 14 | | 92 |
| 379 | 11 | | 624 |
| 380 | <10 | | 45 |
| 381 | 66 | | |
| 382 | <10 | | 28 |
| 383 | 74 | | 90 |
| 384 | >100(37) | | |
| 385 | <10 | | 87 |
| 386 | 20 | | 105 |
| 387 | <10 | | 31 |
| 388 | 12 | | 60 |
| 389 | 51 | | |
| 390 | 33 | | 400 |
| 391 | 13 | | 129 |
| 392 | >100(38) | | 432 |
| 393 | 82 | | 90 |
| 394 | <10 | | 133 |
| 395 | 19 | | 226 |
| 396 | 19 | | 86 |
| 397 | <10 | | 77 |
| 398 | 33 | | 462 |
| 399 | 63 | | 327 |
| 400 | <10 | | 671 |
| 401 | <10 | | 586 |
| 403 | 14 | | 93 |
| 404 | <10 | | 81 |
| 405 | 46 | | 126 |
| 406 | <10 | | <30 |
| 407 | 26 | | 68 |
| 408 | <10 | | 192 |
| 409 | 26 | | 392 |
| 410 | 12 | | 79 |
| 411 | 17 | | 43 |
| 412 | 81 | | 122 |
| 413 | 39 | | 50 |
| 414 | >100(27) | | |
| 415 | 24 | | 98 |
| 416 | >100(49) | | |
| 417 | >100(42) | | |
| 418 | 26 | | 401 |
| 419 | >100(47) | | |
| 420 | 16 | | 77 |
| 421 | <10 | | 34 |
| 422 | <10 | | 119 |
| 423 | <10 | | 102 |
| 424 | 47 | | 224 |
| 425 | >100(5) | | 464 |
| 426 | 22 | | 272 |
| 427 | >100(13) | | 364 |
| 428 | 64 | | 158 |
| 429 | 54 | | 603 |
| 430 | 76 | | 182 |
| 431 | 17 | | 43 |
| 432 | 13 | | <30 |
| 433 | 11 | | <30 |
| 434 | 20 | | <30 |
| 435 | 33 | | 445 |
| 436 | >100(46) | | 878 |
| 437 | 48 | | 250 |
| 438 | >100(41) | | 414 |
| 439 | 52 | | 224 |
| 440 | 47 | | 351 |
| 441 | 70 | | 1000 |
| 442 | >100(32) | | -(28) |
| 443 | 15 | | 627 |
| 444 | 21 | | 972 |
| 445 | >100(11) | | 941 |
| 446 | >100(39) | | -(40) |
| 447 | >100(11) | | 553 |
| 448 | >100(39) | | -(25) |
| 449 | >100(26) | | 747 |
| 450 | >100(13) | | -(46) |
| 451 | >100(25) | | 613 |
| 452 | >100(31) | | -(37) |
| 453 | >100(1) | | |
| 454 | >100(23) | | |
| 455 | 77 | | |
| 456 | >100(21) | | |
| 457 | >100(29) | | |
| 458 | >100(18) | | |
| 459 | 47 | | <30 |
| 460 | >100(15) | | |
| 461 | 60 | | |
| 462 | 52 | | 575 |
| 463 | 91 | | 432 |
| 464 | 55 | | 201 |
| 465 | 56 | | 1000 |
| 466 | >100(16) | | |
| 467 | >100(8) | | |
| 468 | >100(20) | | |
| 469 | >100(0) | | -(28) |
| 470 | 26 | | 128 |
| 471 | >100(28) | | 237 |
| 472 | 31 | | 67 |
| 473 | >100(30) | | 259 |
| 474 | 46 | | -(6) |
| 475 | 15 | | -(24) |
| 476 | <10 | | 172 |
| 477 | 59 | | 248 |
| 478 | 17 | | -(28) |
| 479 | 13 | | -(17) |
| 480 | 10 | | -(22) |
| 481 | 16 | | -(3) |
| 482 | 24 | | -(5) |
| 483 | 20 | | <30 |
| 484 | 12 | | 75 |
| 485 | >100(35) | | |
| 486 | >100(36) | | |
| 487 | >100(31) | | |
| 488 | 98 | | |
| 489 | 58 | | 637 |
| 490 | 21 | | 261 |
| 491 | 24 | | 315 |
| 492 | 20 | | 321 |
| 493 | 39 | | 1000 |
| 494 | 16 | | 125 |
| 495 | 65 | | |
| 496 | 45 | | -(32) |
| 497 | <10 | | 82 |
| 498 | <10 | | 140 |
| 499 | <10 | | 98 |
| 500 | 14 | | 199 |
| 501 | 11 | | 56 |
| 502 | | | -(23) |
| 503 | 87 | | -(36) |
| 504 | 46 | | -(42) |
| 505 | 53 | | -(25) |
| 506 | 74 | | 369 |
| 507 | 44 | | 787 |
| 508 | | | -(28) |
| 509 | 26 | | 164 |
| 510 | >100(3) | | -(17) |
| 511 | 19 | | 663 |

-continued

| Example No. | PDGF (E) | PDGF (D) | c-kit |
|---|---|---|---|
| 512 | 29 | | 1000 |
| 513 | >100(28) | | 720 |
| 514 | >100(31) | | −(29) |
| 515 | >100(32) | | −(21) |
| 516 | 50 | | −(27) |
| 517 | 38 | | −(33) |
| 518 | >100(17) | | |
| 519 | >100(22) | | |
| 520 | >100(43) | | |
| 521 | >100 | | |
| 522 | >100 | | |
| 523 | >100 | | |
| 524 | >100(21) | | −(21) |
| 525 | 79 | | −(41) |
| 526 | >100(46) | | 731 |
| 527 | 65 | | 875 |
| 528 | 33 | | 343 |
| 529 | >100(38) | | −(8) |
| 530 | >100(45) | | −(34) |
| 531 | | | −(31) |
| 532 | >100(44) | | 752 |
| 533 | 64 | | 623 |
| 534 | 51 | | −(35) |
| 535 | 32 | | −(27) |
| 536 | | | −(7) |
| 537 | >100(34) | | −(34) |
| 538 | >100(22) | | 768 |
| 539 | >100(45) | | 415 |
| 540 | 48 | | 447 |
| 541 | 70 | | 794 |
| 542 | >100(45) | | 442 |
| 543 | 54 | | 328 |
| 544 | <10 | | 216 |
| 545 | 70 | | 254 |
| 546 | 54 | | −(44) |
| 547 | >100(33) | | −(41) |
| 548 | 46 | | 268 |
| 549 | 62 | | 681 |
| 550 | 77 | | 536 |
| 551 | >100(19) | | 1000 |
| 552 | >100(10) | | −(28) |
| 553 | >100(40) | | 320 |
| 554 | >100(14) | | |
| 555 | >100(29) | | −(39) |
| 556 | >100(13) | | −(28) |
| 557 | >100(33) | | 634 |
| 558 | 73 | | 724 |
| 559 | 36 | | 711 |
| 560 | 12 | | 107 |
| 561 | <10 | | 54 |
| 562 | 80 | | −(27) |
| 563 | 54 | | 406 |
| 564 | 39 | | 291 |
| 565 | 46 | | 170 |
| 566 | 17 | | 276 |
| 567 | 21 | | 118 |
| 568 | >100(28) | | −(31) |
| 569 | 12 | | 168 |
| 570 | 23 | | 173 |
| 571 | 32 | | 556 |
| 572 | 64 | | 262 |
| 573 | 39 | | 348 |
| 574 | 45 | | 147 |
| 575 | 27 | | 664 |
| 576 | 36 | | 151 |
| 577 | 14 | | 328 |
| 578 | 18 | | 104 |
| 579 | 22 | | 145 |
| 580 | 14 | | 84 |
| 581 | 14 | | 180 |
| 582 | >100(20) | | −(29) |
| 583 | >100(17) | | −(18) |
| 584 | >100(13) | | −(13) |
| 585 | >100(32) | | 1000 |
| 586 | 63 | | 734 |
| 587 | 67 | | −(16) |
| 588 | 36 | | 1000 |

-continued

| Example No. | PDGF (E) | PDGF (D) | c-kit |
|---|---|---|---|
| 589 | 28 | | 487 |
| 590 | 54 | | 296 |
| 591 | 33 | | 117 |
| 592 | 23 | | 472 |
| 593 | 51 | | 1000 |
| 594 | >100(39) | | −(10) |
| 595 | 46 | | −(0) |
| 596 | 63 | | 719 |
| 597 | >100(27) | | −(8) |
| 598 | 19 | | 423 |
| 600 | <10 | | 208 |
| 602 | 11 | | 180 |
| 603 | >100(42) | | 864 |
| 604 | 73 | | 322 |
| 605 | 31 | | 394 |
| 606 | 18 | | 263 |
| 607 | 29 | | 554 |
| 608 | <10 | | 201 |
| 609 | | 45 | |
| 610 | | 380 | |
| 611 | | 95 | 1073 |
| 612 | | 10 | 173 |
| 613 | | 56 | −(29) |
| 614 | <10 | | 434 |
| 615 | 17 | | 125 |
| 616 | 36 | | 224 |
| 617 | <10 | | 172 |
| 618 | <10 | | 948 |
| 619 | >100(49) | | −(44) |
| 620 | <10 | | 519 |
| 621 | 30 | | −(30) |
| 622 | 11 | | 355 |
| 623 | 90 | | 632 |
| 624 | 34 | | 436 |
| 625 | >100(31) | | 596 |
| 626 | 49 | | 339 |
| 627 | 65 | | 774 |
| 628 | <10 | | 81 |
| 629 | <10 | | 481 |
| 630 | 36 | | −(23) |
| 631 | 39 | | 186 |
| 632 | 36 | | 223 |
| 633 | 58 | | −(28) |
| 634 | >100(40) | | −(13) |
| 635 | >100(25) | | −(23) |
| 636 | 33 | | 106 |
| 637 | 52 | | 375 |
| 638 | >100(43) | | −(16) |
| 639 | >100(29) | | −(12) |
| 640 | 35 | | 254 |
| 641 | 28 | | 293 |
| 642 | >100(20) | | −(8) |
| 643 | >100(40) | | −(2) |
| 644 | >100(17) | | −(14) |
| 645 | 23 | | −(32) |
| 646 | 11 | | −(0) |
| 647 | 13 | | 712 |
| 648 | 16 | | 937 |
| 649 | 39 | | 1000 |
| 650 | 32 | | 420 |
| 651 | 40 | | 808 |
| 652 | 43 | | 115 |
| 653 | 23 | | 581 |
| 654 | 19 | | 698 |
| 655 | 43 | | −(43) |
| 656 | 19 | | −(32) |
| 657 | 40 | | −(27) |
| 658 | 19 | | 389 |
| 659 | 19 | | 1000 |
| 660 | 25 | | 835 |
| 661 | <10 | | 75 |
| 662 | 23 | | 296 |
| 663 | <10 | | 202 |
| 664 | <10 | | 97 |
| 665 | 11 | | 122 |
| 666 | 10 | | 134 |
| 667 | <10 | | 100 |

-continued

| Example No. | PDGF (E) | PDGF (D) | c-kit |
|---|---|---|---|
| 668 | <10 | | 144 |
| 669 | 23 | | 134 |
| 670 | 15 | | 82 |
| 671 | 64 | | −(22) |
| 672 | 53 | | −(9) |
| 673 | 15 | | 426 |
| 674 | >100(43) | | 854 |
| 675 | 46 | | 442 |
| 676 | 26 | | 632 |
| 677 | 47 | | 730 |
| 678 | <10 | | 164 |
| 679 | <10 | | 337 |
| 680 | 35 | | 570 |
| 681 | 30 | | 270 |
| 682 | >100(30) | | −(32) |
| 683 | >100(40) | | −(26) |
| 684 | 52 | | 549 |
| 685 | 22 | | −(41) |
| 686 | 38 | | −(19) |
| 687 | 26 | | −(34) |
| 688 | 34 | | −(19) |
| 689 | >100(42) | | 571 |
| 690 | >100(10) | | −(11) |
| 691 | >100(10) | | −(18) |
| 692 | >100(35) | | >1000(20) |
| 693 | 56 | | >1000(46) |
| 694 | >100(12) | | −(37) |
| 695 | >100(10) | | −(37) |
| 696 | >100(37) | | −(35) |
| 697 | <<10 | | 211 |
| 698 | >100(34) | | −(29) |
| 699 | 13 | | −(29) |
| 700 | >100(30) | | −(0) |
| 701 | <10 | | 459 |
| 702 | <10 | | 495 |
| 703 | <<10 | | 375 |
| 704 | 16 | | 177 |
| 705 | <10 | | 147 |
| 706 | <10 | | 227 |
| 707 | 17 | | 209 |
| 708 | 51 | | 348 |
| 709 | 19 | | −(19) |
| 710 | >100(33) | | −(30) |
| 711 | >100(34) | | −(17) |
| 712 | 83 | | |
| 713 | 67 | | 89 |
| 714 | 16 | | 248 |
| 716 | 11 | | −(19) |
| 717 | >100(8) | | |
| 718 | <10 | | −(19) |
| 719 | 14 | | 431 |
| 720 | 42 | | 30 |
| 721 | 36 | | −(20) |
| 722 | <10 | | 85 |
| 723 | 17 | | 380 |
| 724 | <10 | | 116 |
| 725 | <10 | | 413 |
| 726 | 37 | | 624 |
| 727 | 52 | | |
| 728 | 100 | | |
| 729 | 30 | | 302 |
| 730 | 34 | | 634 |
| 731 | 17 | | 259 |
| 732 | 48 | | |
| 733 | 29 | | 186 |
| 734 | 29 | | 216 |
| 735 | 15 | | 1000 |
| 736 | 72 | | |
| 737 | <10 | | 523 |
| 738 | 11 | | 269 |
| 739 | <10 | | 234 |
| 740 | 23 | | 335 |
| 741 | 49 | | |
| 742 | 92 | | |
| 743 | 10 | | 548 |
| 744 | 40 | | |
| 745 | 53 | | |
| 746 | >100(31) | | |
| 747 | 35 | | 759 |
| 748 | 85 | | |
| 749 | 12 | | −(41) |
| 750 | 17 | | −(43) |
| 751 | 70 | | −(23) |
| 752 | >100(37) | | |
| 753 | >100(28) | | −(9) |
| 754 | >100(7) | | |
| 755 | >100(3) | | |
| 757 | >100(45) | | |
| 758 | >100(18) | | |
| 759 | 26 | | 323 |
| 760 | 83 | | −(48) |
| 761 | >100(37) | | −(44) |
| 762 | >100 | | |
| 763 | 13 | | −(39) |
| 764 | 14 | | −(19) |
| 765 | 21 | | 937 |
| 766 | >100(45) | | |
| 772 | >100(13) | | 550 |
| 773 | >100 | | |
| 774 | >100(17) | | |
| 775 | >100(22) | | |
| 776 | | 17 | 386 |
| 777 | 11 | | 11 |
| 778 | | 6 | 84 |
| 779 | <10 | | 107 |
| 780 | | 6 | 48 |
| 781 | | 47 | 135 |
| 782 | | 14 | 365 |
| 783 | | 42 | 451 |
| 784 | | 6 | 80 |
| 785 | | 19 | 71 |
| 786 | | 5 | 46 |
| 787 | | 16 | 37 |
| 788 | | 11 | 122 |
| 789 | | 13 | 154 |
| 790 | <3 | | 107 |
| 791 | 3 | | 208 |
| 792 | 6 | | 301 |
| 793 | 6 | | 335 |
| 794 | 14 | | 192 |
| 795 | 5 | | 336 |
| 796 | 15 | | 394 |
| 797 | 27 | | 403 |
| 798 | <10 | | 439 |
| 799 | 14 | | 1000 |
| 800 | <10 | | 30 |
| 801 | 13 | | 70 |
| 802 | <10 | | −(42) |
| 803 | 13 | | −(20) |
| 804 | 37 | | −(20) |
| 805 | >100(14) | | −(35) |
| 806 | | | −(35) |
| 807 | >100(20) | | −(20) |
| 808 | <10 | | 61 |
| 809 | <10 | | 73 |
| 810 | 18 | | 269 |
| 811 | 17 | | −(20) |
| 812 | | 12 | 326 |
| 813 | | 23 | 402 |
| 814 | | 47 | 405 |
| 815 | | 74 | 180 |
| 816 | | 73 | 123 |
| 817 | | 53 | 195 |
| 818 | | 43 | 205 |
| 819 | | 48 | 212 |
| 820 | | 44 | 187 |
| 821 | | 39 | 184 |
| 822 | | 17 | 451 |
| 823 | | 11 | 236 |
| 824 | | 14 | 268 |
| 825 | | 58 | 333 |
| 826 | | 53 | 170 |
| 827 | | 38 | 175 |
| 828 | | | |

| Example No. | PDGF (E) | PDGF (D) | c-kit |
|---|---|---|---|
| 829 | | −(30) | −(10) |
| 830 | | −(23) | −(10) |
| 831 | | −(50) | −(19) |
| 832 | | −(35) | −(21) |
| 833 | | 452 | −(26) |
| 834 | | −(23) | −(1) |
| 835 | | 161 | 668 |
| 836 | | 90 | −(39) |
| 837 | | −(10) | −(19) |
| 838 | | 590 | −(23) |
| 839 | | −(24) | −(30) |
| 840 | | 812 | −(14) |
| 841 | | 28 | 118 |
| 842 | | 18 | 127 |
| 843 | | 43 | 263 |
| 844 | | 80 | 450 |
| 845 | | >100 | 453 |
| 846 | | >100 | −(33) |
| 847 | | >100 | −(9) |
| 848 | | | 943 |
| 849 | | 65 | 760 |
| 850 | | 65 | 278 |
| 851 | | 41 | 75 |
| 852 | | 20 | 179 |
| 853 | | 9 | 102 |
| 854 | | 40 | 313 |
| 855 | | 39 | 399 |
| 856 | | 25 | 255 |
| 857 | | 7 | 195 |
| 858 | | 17 | 102 |
| 859 | | 8 | 130 |
| 860 | | 11 | 75 |
| 861 | | 39 | 132 |
| 862 | | 47 | 933 |
| 863 | | 6 | 31 |
| 864 | | 23 | 32 |
| 865 | | 12 | 121 |
| 866 | | 7 | 126 |
| 867 | | 11 | 191 |
| 868 | | 26 | 70 |
| 869 | | 23 | 80 |
| 870 | | 17 | 48 |
| 871 | | 16 | 43 |
| 872 | | 7 | 32 |
| 873 | | 35 | 69 |
| 874 | | >100 | 151 |
| 875 | | 40 | 115 |
| 876 | | 40 | 242 |
| 877 | | 43 | 219 |
| 878 | 19 | | 65 |
| 879 | 20 | | 48 |
| 880 | 16 | | 149 |
| 881 | >30(29) | | 346 |
| 882 | 23 | | −(36) |
| 883 | >30(30) | | 521 |
| 884 | 44 | | −(30) |
| 885 | <3 | | 420 |
| 886 | >100(47) | | −(27) |
| 887 | 50 | | −(20) |
| 888 | 12 | | 385 |
| 889 | >100(30) | | −(28) |
| 890 | 95 | | −(39) |
| 891 | 7 | | 280 |
| 892 | >100(25) | | −(30) |
| 893 | 52 | | 640 |
| 894 | >100(49) | | −(23) |
| 895 | >100(33) | | −(20) |
| 896 | 96 | | −(31) |
| 897 | | 8 | 938 |
| 898 | | 5 | 637 |
| 899 | | 62 | 1000 |
| 900 | | 10 | 372 |
| 901 | | 65 | −(27) |
| 902 | | 15 | 299 |
| 903 | | 22 | −(34) |
| 904 | | 4 | −(46) |
| 905 | 5 | | −(40) |
| 906 | | 47 | −(29) |
| 907 | | <10 | 572 |
| 908 | 9 | | 757 |
| 909 | | 145 | −(32) |
| 910 | | 72 | −(38) |
| 911 | | 9 | 498 |
| 912 | | 8 | 497 |
| 913 | | 8 | 563 |
| 914 | | <10 | 299 |
| 915 | 9 | | 240 |
| 916 | | 42 | −(16) |
| 917 | 132 | | 546 |
| 918 | | 18 | 552 |
| 919 | | 73 | −(11) |
| 920 | | 12 | 448 |
| 921 | | 71 | −(42) |
| 922 | | 12 | 365 |
| 923 | | 50 | −(25) |
| 924 | | 23 | 440 |
| 925 | 35 | | 430 |
| 926 | | 18 | −(31) |
| 927 | 5 | | 623 |
| 928 | | 5 | 289 |
| 929 | | 94 | −(21) |
| 930 | <10 | | 184 |
| 931 | | 23 | 516 |
| 932 | | 15 | 208 |
| 933 | | 18 | 493 |
| 934 | | 55 | 143 |
| 935 | | 59 | 166 |
| 936 | | 17 | 427 |
| 937 | | 69 | 819 |
| 938 | | 31 | 532 |
| 939 | | 15 | 220 |
| 940 | | 31 | 292 |
| 941 | | 12 | 145 |
| 942 | | 11 | 335 |
| 943 | | 19 | 136 |
| 944 | | 8 | 140 |
| 945 | | 25 | 131 |
| 946 | | 13 | 142 |
| 947 | | 39 | 375 |
| 948 | | 104 | 830 |
| 949 | | 51 | 250 |
| 950 | | 17 | 224 |
| 951 | | 50 | 124 |
| 952 | | <10 | 317 |
| 953 | | 143 | −(32) |
| 954 | | 4 | 131 |
| 955 | | 12 | 251 |
| 956 | | 10 | 326 |
| 957 | | 10 | 136 |
| 958 | | 17 | 194 |
| 959 | <10 | | 300 |
| 960 | | 13 | 629 |
| 961 | | 32 | 740 |
| 962 | | 19 | −(35) |
| 963 | | 59 | 701 |
| 964 | | 35 | −(46) |
| 965 | | 51 | −(24) |
| 966 | | 25 | 233 |
| 967 | 20 | | −(15) |
| 968 | | 86 | −(27) |
| 969 | | 48 | −(19) |
| 970 | | 16 | 300 |
| 971 | | 15 | 523 |
| 972 | | 7 | 532 |
| 973 | | 30 | −(0) |
| 974 | | 49 | −(34) |
| 975 | | 26 | 290 |
| 976 | | 14 | 788 |
| 977 | | 37 | 824 |
| 978 | | 36 | −(22) |
| 979 | | 29 | −(25) |
| 980 | | 70 | 811 |
| 981 | | 100 | −(47) |
| 982 | | 96 | −(18) |

| Example No. | PDGF (E) | PDGF (D) | c-kit |
|---|---|---|---|
| 983 | | 40 | −(39) |
| 984 | | 27 | −(30) |
| 985 | | 22 | −(31) |
| 986 | | <30 | 264 |
| 987 | | 117 | −(32) |
| 988 | | 24 | −(33) |
| 989 | 14 | | 425 |
| 990 | | 20 | 481 |
| 991 | 19 | | −(20) |
| 992 | | 56 | 766 |
| 993 | | 52 | −(35) |
| 994 | 27 | | −(47) |
| 995 | 87 | | −(23) |
| 996 | 53 | | −(27) |
| 997 | 9 | | 264 |
| 998 | 25 | | 591 |
| 999 | 29 | | −(45) |
| 1000 | 3 | | 771 |
| 1001 | <10 | | −(34) |
| 1002 | <10 | | −(16) |
| 1003 | 24 | | 628 |
| 1004 | 10 | | 877 |
| 1005 | 28 | | 674 |
| 1006 | | 29 | 181 |
| 1007 | | >30 | 616 |
| 1008 | | 51 | 357 |
| 1009 | 21 | | 243 |
| 1010 | | >30 | 78 |
| 1011 | | 44 | −(20) |
| 1012 | | 58 | −(24) |
| 1013 | | 61 | −(22) |
| 1014 | | 62 | −(30) |
| 1015 | | 62 | 195 |
| 1016 | 48 | | |
| 1017 | 48 | | |
| 1018 | 10 | | 320 |
| 1019 | 22 | | 187 |
| 1020 | | 35 | −(11) |
| 1021 | | 53 | −(38) |
| 1022 | 28 | | 202 |
| 1023 | 22 | | 116 |
| 1024 | 11 | | 141 |
| 1025 | 15 | | 194 |
| 1026 | | 44 | 652 |
| 1027 | | 36 | 161 |
| 1028 | <<10 | | 545 |
| 1029 | 5 | | 126 |
| 1030 | 14 | | 337 |
| 1031 | 10 | | 254 |
| 1032 | <10 | | 321 |
| 1033 | | 67 | 177 |
| 1034 | | 27 | 378 |
| 1035 | | >30 | −(17) |
| 1036 | | 57 | −(29) |
| 1037 | | 59 | 558 |
| 1038 | | 80 | 597 |
| 1039 | | 26 | 556 |
| 1040 | <<10 | | 414 |
| 1041 | 12 | | 98 |
| 1042 | 39 | | 107 |
| 1043 | 27 | | 449 |
| 1044 | <10 | | 136 |
| 1045 | 17 | | 193 |
| 1046 | 38 | | 202 |
| 1047 | | >100 | −(7) |
| 1048 | <10 | | 250 |
| 1049 | 44 | | |
| 1050 | 23 | | 579 |
| 1051 | 14 | | 418 |
| 1052 | 21 | | 408 |
| 1053 | 30 | | 178 |
| 1054 | 27 | | −(19) |
| 1055 | 16 | | 312 |
| 1056 | | 34 | 932 |
| 1057 | | 24 | 447 |
| 1058 | 8 | | −(21) |
| 1059 | | >100 | 550 |
| 1060 | 39 | | −(30) |
| 1061 | | 20 | 136 |
| 1062 | | 15 | 233 |
| 1063 | | 27 | 491 |
| 1064 | | 12 | 279 |
| 1065 | 19 | | 566 |
| 1066 | | 32 | 279 |
| 1067 | | 70 | 449 |
| 1068 | | 14 | 124 |
| 1069 | | 13 | 189 |
| 1070 | | | 391 |
| 1071 | >100(17) | | −(0) |
| 1072 | | −(34) | −(18) |
| 1073 | | −(23) | −(20) |
| 1074 | <10 | | 289 |
| 1075 | | −(17) | −(31) |
| 1076 | | 204 | −(7) |
| 1077 | 48 | | 379 |
| 1078 | | 371 | −(32) |
| 1079 | | 196 | −(25) |
| 1080 | | 775 | −(0) |
| 1081 | | −(50) | −(47) |
| 1082 | | 573 | −(15) |
| 1083 | | 382 | −(30) |
| 1084 | | 306 | −(30) |
| 1085 | | 165 | −(25) |
| 1086 | | −(48) | −(19) |
| 1087 | | 566 | 495 |
| 1088 | | 265 | −(23) |
| 1089 | | 264 | −(28) |
| 1090 | | 562 | −(30) |
| 1091 | | 605 | −(39) |
| 1092 | | −(15) | −(10) |
| 1093 | | 621 | −(32) |
| 1094 | | 746 | −(18) |
| 1095 | | −(20) | −(25) |
| 1096 | | −(30) | −(3) |
| 1097 | | 687 | −(8) |
| 1098 | | 70 | −(41) |
| 1099 | | 18 | 552 |
| 1100 | | 553 | −(18) |
| 1101 | >100(37) | | −(26) |
| 1102 | >100(38) | | −(11) |
| 1103 | >100(25) | | −(3) |
| 1104 | 77 | | −(23) |
| 1105 | >100(31) | | −(1) |
| 1106 | >100(30) | | −(0) |
| 1107 | >100(46) | | −(24) |
| 1108 | | 135 | 962 |
| 1109 | | 12 | 353 |
| 1110 | | 16 | 113 |
| 1111 | | 46 | 405 |
| 1112 | | 124 | −(19) |
| 1113 | | 785 | 785 |
| 1114 | | 118 | 674 |
| 1115 | | 241 | −(10) |
| 1116 | | 156 | 878 |
| 1117 | | 185 | −(31) |
| 1118 | | 106 | −(0) |
| 1119 | | 334 | −(27) |
| 1120 | | 207 | 778 |
| 1121 | | 7 | <30 |
| 1122 | >100(48) | | −(26) |
| 1123 | | −(43) | 961 |
| 1124 | >100(22) | | |
| 1125 | >100(22) | | −(8) |
| 1126 | >100(70) | | −(35) |
| 1127 | >100(8) | | |
| 1128 | >100(47) | | −(17) |
| 1129 | >100(48) | | |
| 1130 | <10 | | 547 |
| 1131 | 51 | | 192 |
| 1132 | <10 | | 146 |
| 1133 | <10 | | 42 |
| 1134 | | | 169 |
| 1135 | <10 | | 239 |
| 1136 | 14 | | 639 |

-continued

| Example No. | PDGF (E) | PDGF (D) | c-kit |
|---|---|---|---|
| 1137 | 28 | | −(38) |
| 1138 | | | |
| 1139 | 12 | | 783 |
| 1140 | >100(22) | | |
| 1141 | <10 | | 416 |
| 1142 | 80 | | |
| 1143 | >100(32) | | |
| 1144 | 28 | | −(30) |
| 1145 | | | 548 |
| 1146 | 23 | | 552 |
| 1147 | 10 | | 105 |
| 1148 | <10 | | 42 |
| 1149 | 43 | | 150 |
| 1150 | 51 | | 192 |
| 1151 | <10 | | 146 |
| 1152 | <10 | | 1000 |
| 1153 | 43 | | −(13) |
| 1154 | 49 | | −(21) |
| 1155 | 17 | | −(31) |
| 1156 | >100(35) | | −(28) |
| 1157 | <10 | | |
| 1158 | 46 | | |
| 1159 | >100 | | |
| 1160 | <10 | | |
| 1161 | <10 | | |
| 1162 | 13 | | |
| 1163 | >100 | | |
| 1164 | <10 | | |
| 1165 | >100 | | |
| 1166 | <10 | | |
| 1167 | >100 | | |
| 1168 | <10 | | |
| 1169 | 37 | | |
| 1170 | <10 | | |
| 1171 | 13 | | |
| 1172 | 34 | | |
| 1173 | >100 | | |
| 1174 | >100 | | |
| 1175 | 37 | | |
| 1176 | >100 | | |
| 1177 | 17 | | |
| 1178 | 78 | | |
| 1179 | 14 | | 327 |
| 1180 | <<10 | | 480 |
| 1181 | 35 | | −(26) |
| 1182 | <10 | | 206 |
| 1183 | <10 | | 427 |
| 1184 | 55 | | |
| 1185 | 13 | | −(26) |
| 1186 | <<10 | | 405 |
| 1187 | 24 | | 1000 |
| 1188 | 76 | | |
| 1189 | 26 | | 73 |
| 1190 | 24 | | 240 |
| 1191 | 31 | | 193 |
| 1192 | 19 | | 672 |
| 1193 | <10 | | −(18) |
| 1194 | 56 | | 1000 |
| 1195 | 21 | | 530 |
| 1196 | >100 | | 700 |
| 1197 | 25 | | 219 |
| 1198 | <10 | | 247 |
| 1199 | 42 | | 1000 |
| 1200 | 25 | | 716 |
| 1201 | <10 | | 450 |
| 1202 | 50 | | −(15) |
| 1203 | <10 | | 1000 |
| 1204 | 18 | | 434 |
| 1206 | | | −(27) |
| 1207 | | | −(16) |
| 1208 | | | −(22) |

Pharmacological Test Example 4

Rat Carotid Balloon Injury Model

Wistar male rats (330 to 370 mg) were anesthetized with pentobarbital anesthesia, the right femoral region was incised from the rats, a Fogaty 2F catheter was inserted through the right femoral artery and was led to the left carotid artery, and abrasion was made three times with an expansion diameter of 2.5 mm.

The test compound was suspended in 1% cremophore, and the suspension was orally administered at 0.4 ml/100 g B.W. twice a day through an oral probe for rats for 2 weeks from the day before an operation. On the second week after the operation, the rats were sacrificed by ether. The left carotid artery was removed and was fixed in buffered formalin. Sliced preparations embedded in paraffin were stained with HE and were subjected to image analysis for the measurement of the neointima area (I) and media area (M) in the section of injured blood vessal. I/M was calculated as an index for the evaluation of drug efficacy.

The results were as follows.

| Example No | in vivo (dose: 30 mg/kg) I/M ratio, inhibition (%) |
|---|---|
| 223 | 41 |
| 287 | 37 |
| 408 | 50 |
| 421 | 42 |
| 516 | 32 |
| 567 | 24* |
| 590 | 86 |
| 614 | 92 |
| 615 | 43 |
| 622 | 38 |
| 647 | 32* |
| 679 | 54* |
| 687 | 17* |

*dose: 10 mg/kg

Pharmacological Test Example 5

Measurement of Inhibitory Activity Against KDR Phosphorylation

NIH 3T3 cells (Sawano A et al., Cell Growth & Differentiation, 7, 213–221 (1996)) prepared by transfection of human KDR were cultured in a DMEM medium containing 10% FBS (GIBCO BRL) within a 5% carbon dioxide incubator until 50 to 70% confluent. The harvested cells were inoculated into wells of a collagen-type one-coat 96-well flat-bottom plate, each containing the same medium, in an amount of $1.5 \times 10^4$ per well, followed by cultivation at 37° C. overnight. The medium was then replaced by a DMEM medium containing 0.1% FBS. A solution of a test compound in dimethyl sulfoxide was added to each well, and the cultivation was carried out at 37° C. for additional one hr. A human recombinant vascular endothelial growth factor (hereinafter abbreviated to "VEGF") was added to a concentration of 100 ng/ml, and the stimulation of cells was carried out at 37° C. for 2 min. The medium was removed, the cells were washed with phosphate buffered saline (pH 7.4), and 50 μl of a solubilization buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was then added thereto. The mixture was shaken at 4° C. for 2 hr to prepare a cell extract.

An anti-phospho-tyrosine antibody (PY20; Transduction Laboratories) was immobilized on a microplate for ELISA (Maxisorp; NUNC), and the whole quantity of the cell extract was transferred to the wells, and the immobilized antibody was reacted with the phosphorylated protein at 4° C. overnight. After washing, an anti-KDR antibody (Santa Cruz) was allowed to react at room temperature for one hr, and, further, after washing, a peroxidase-labeled anti-rabbit Ig antibody (Amersham) was allowed to react at room temperature for one hr. After washing, a chromophoric substrate for peroxidase (Sumitomo Bakelite Co., Ltd.) was added thereto and was allowed to react at room temperature. After a suitable level of color development, a reaction termination solution was added to stop the reaction, and the absorbance at 450 nm was measured with a microplate reader. The KDR phosphorylation activity for each well was determined by presuming the absorbance with the addition of VEGF and without the addition of the medicament to be 100% KDR phosphorylation activity and the absorbance without the medicament and VEGF to be 0% KDR phosphorylation activity.

The concentration of the test compound was varied on several levels, the inhibition (%) of KDR phosphorylation was determined for each case, and the concentration of the test compound necessary for inhibiting 50% of KDR phosphorylation ($IC_{50}$) was calculated.

The results were as follows.

| Example No. | $IC_{50}$ (nM) |
|---|---|
| 223 | 38 |
| 287 | >1000 |
| 408 | 108 |
| 421 | 692 |
| 516 | >1000 |
| 567 | >1000 |
| 590 | >1000 |
| 614 | 47 |
| 615 | 37 |
| 622 | >1000 |
| 647 | 599 |

-continued

| Example No. | $IC_{50}$ (nM) |
|---|---|
| 679 | 323 |
| 687 | 176 |

Pharmacological Test Example 6

Porcine Coronary Balloon Injury Model

Edible shoats (24 to 31 kg) were anesthetized with telazol and xylazine, a balloon catheter was inserted through the femoral artery, and the descending branch in front of the heart on the left and the right rotator branch were injured under vasographing.

For 28 days from the operation, the compound of Example 679 was orally administered as a gelatin capsule at a dose of 10 mg/kg twice a day. Further, only a gelatin capsule was administered as a control. In the test, each group consisted of 6 shoats.

On the 28th day from the operation, the shoats were sacrificed with pentobarbital and were perfused with buffered formalin, and the heart was then removed. Paraffin embedded preparations of the injured blood vessel portion were sliced and stained with HE, followed by image analysis to measure the intima area (IA), media area (MA), and vessel area (VA), and the fissure length (FL) and vessel perimeter (VP) of the inner elastic plate.

IA/MA and (IA/VA)/(FL/VP) were calculated as an index for the evaluation of drug efficacy.

The results were as follows.

| Dose (mg/kg) | IA/MA inhibition (%) | (IA/VA)/(FL/VP) inhibition (%) |
|---|---|---|
| Control | — | — |
| 10 | 36 ($p < 0.05$) | 47 ($p < 0.001$) |

The compounds described in the examples have the following structures.

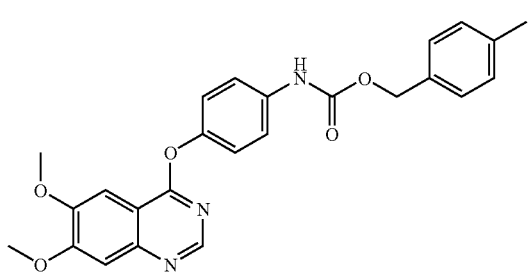

1

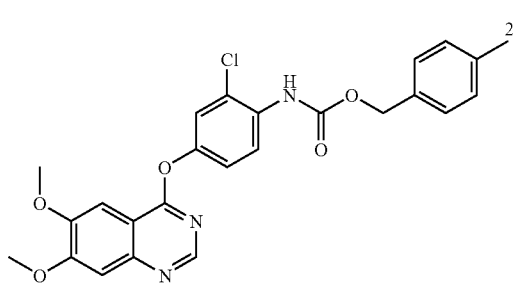

2

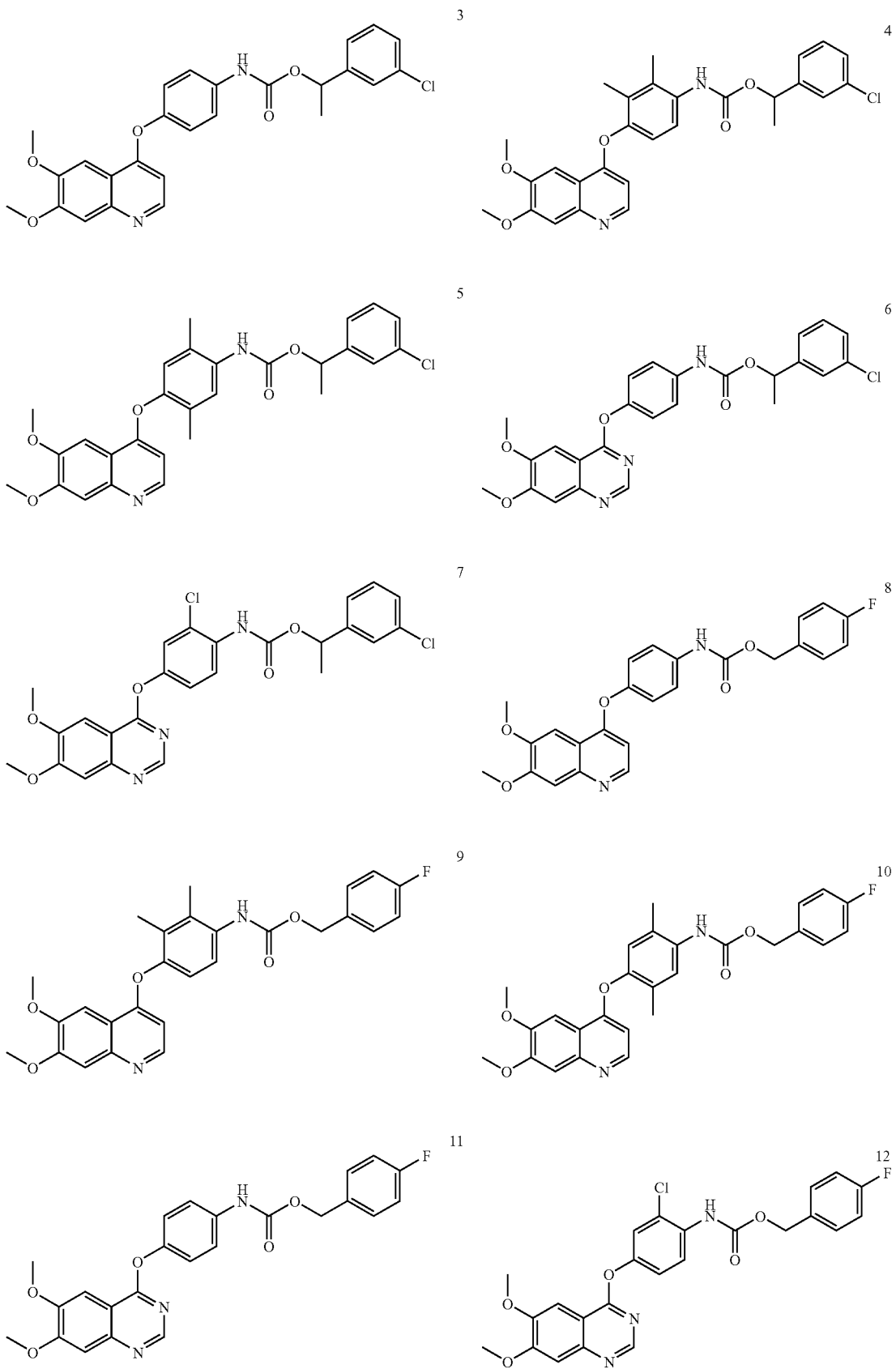

-continued
13
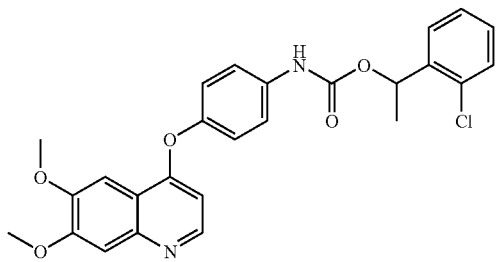
14
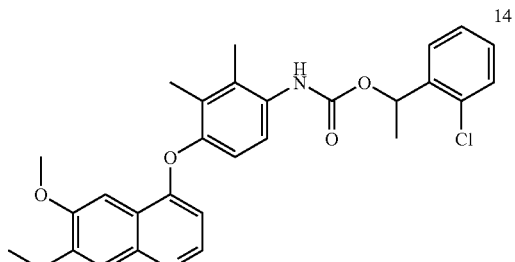
15
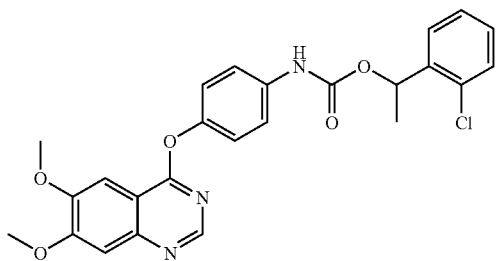
16
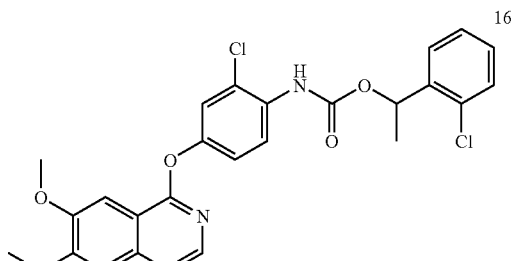
17
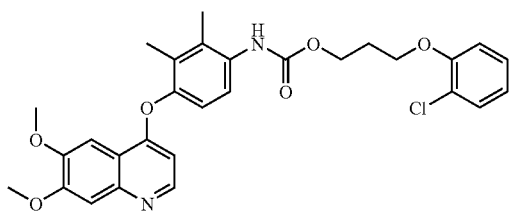
18
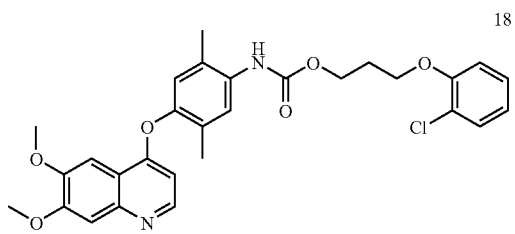
19
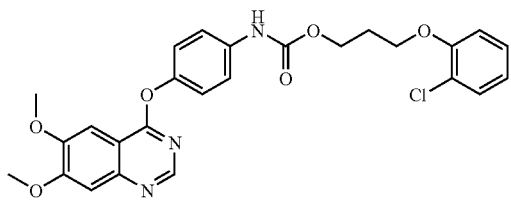
20
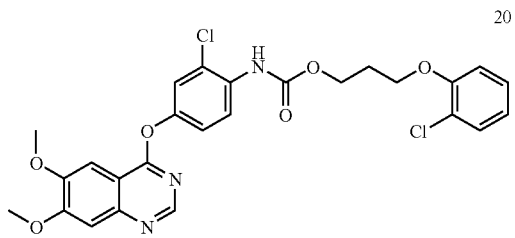
21
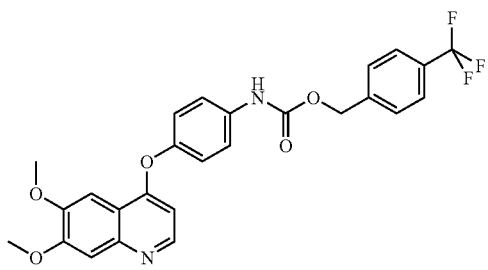
22
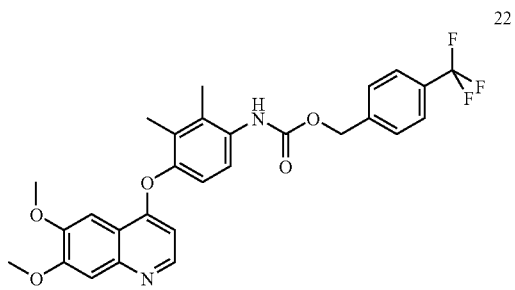
23
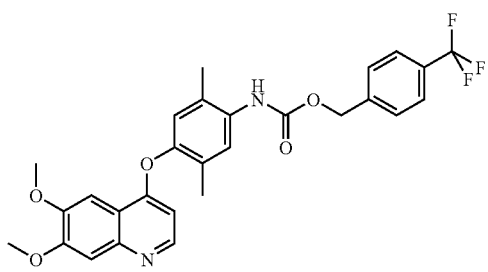
24
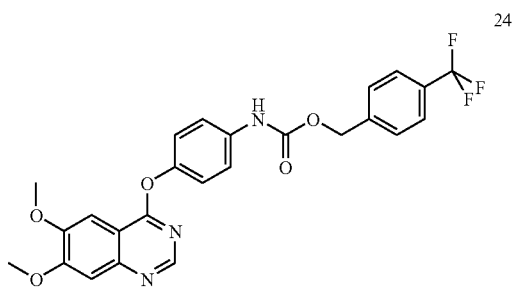

-continued
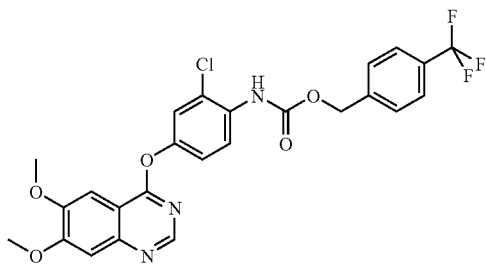
25
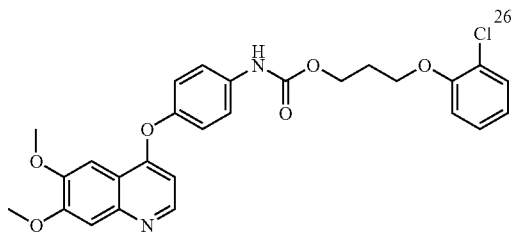
26
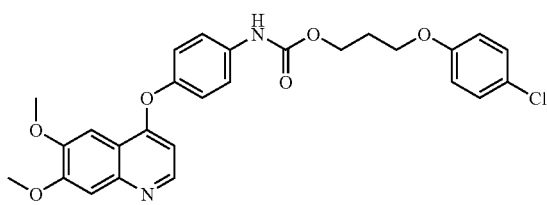
27
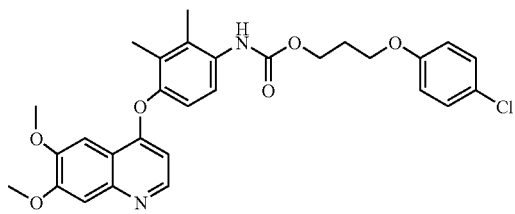
28
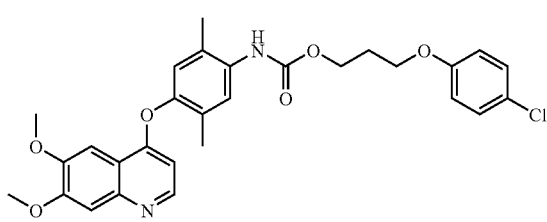
29
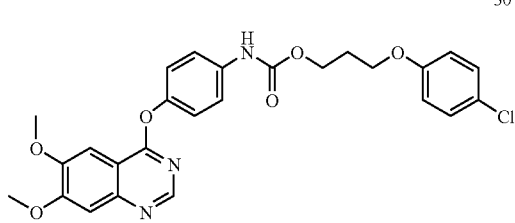
30
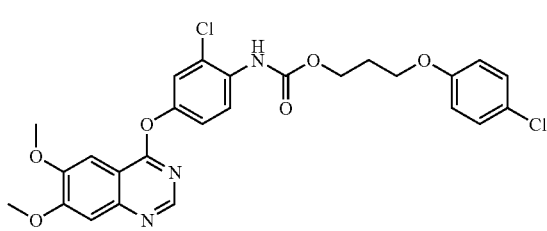
31
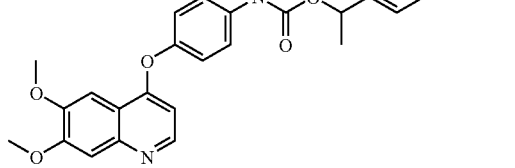
32
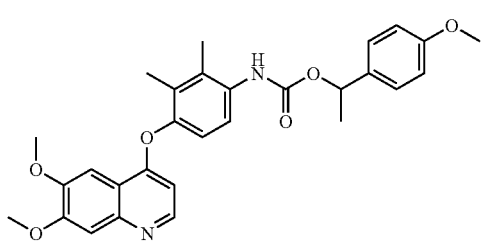
33
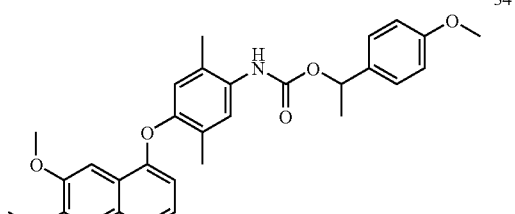
34
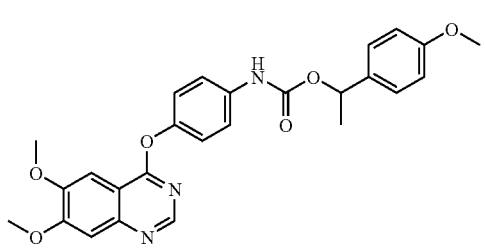
35
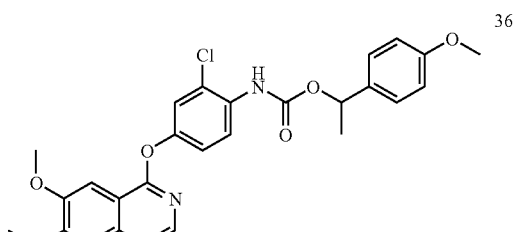
36

-continued
37
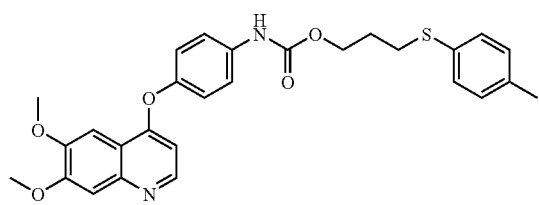
38
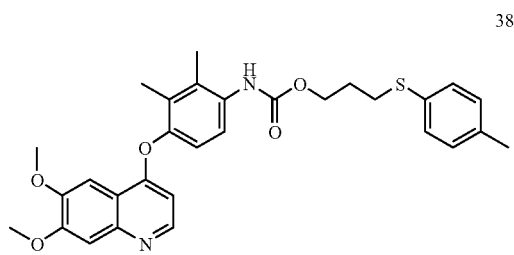
39
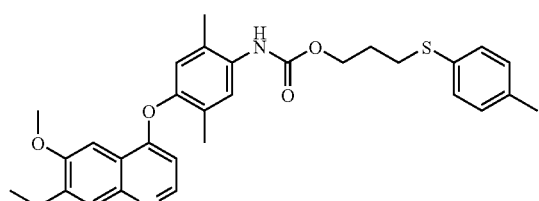
40
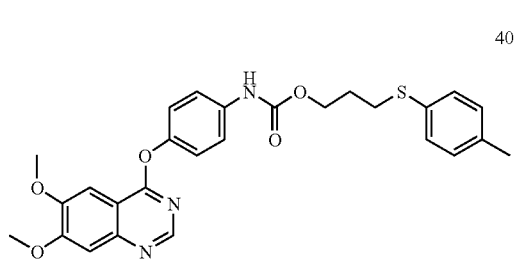
41
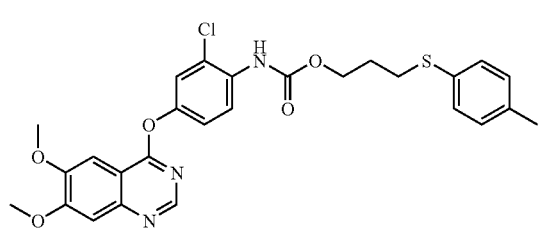
42
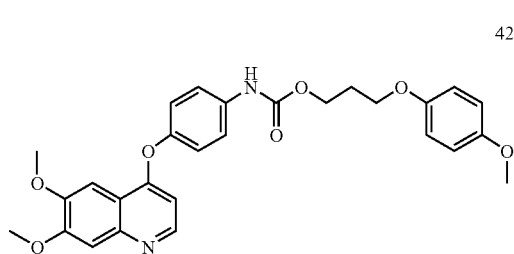
43
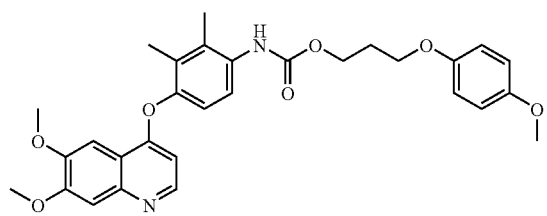
44
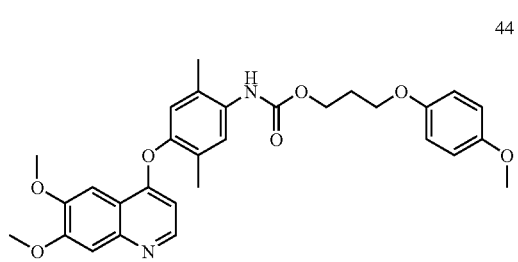
45
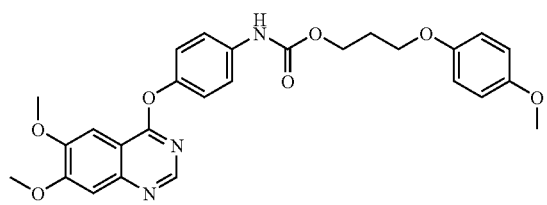
46
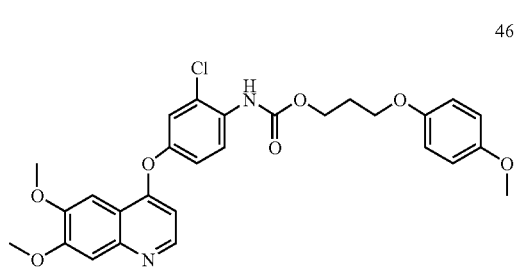
47
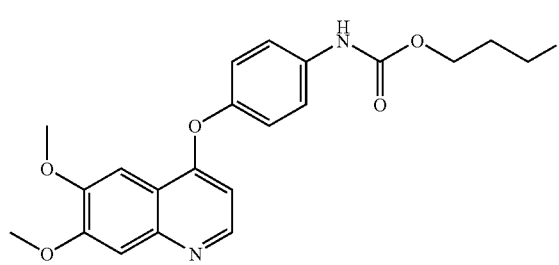

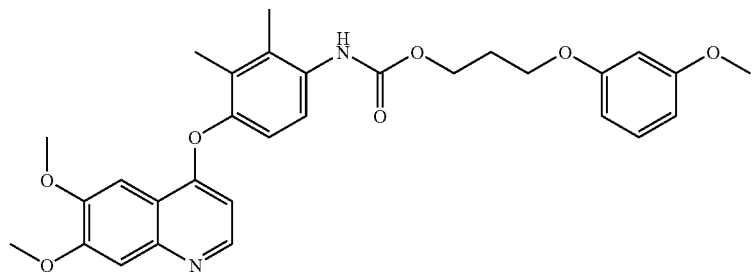
48
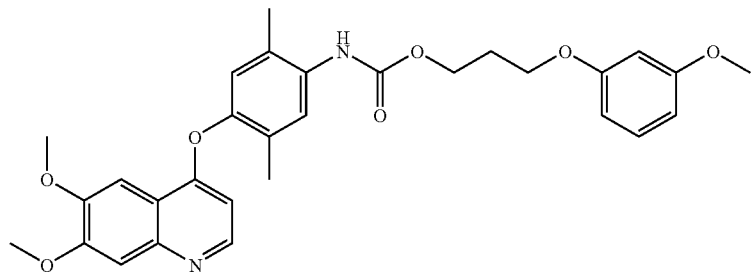
49
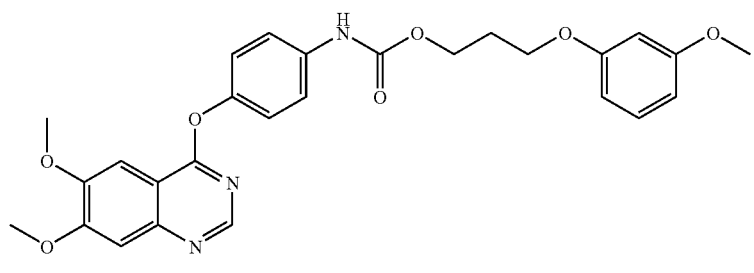
50
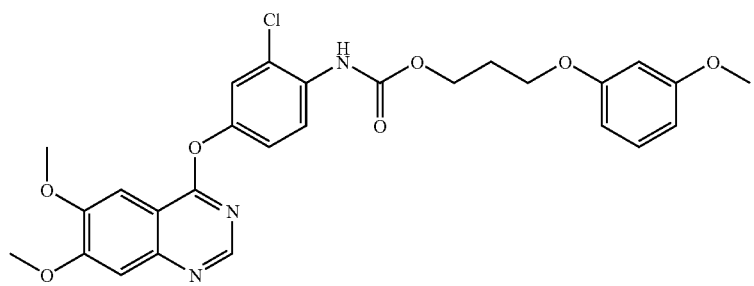
51
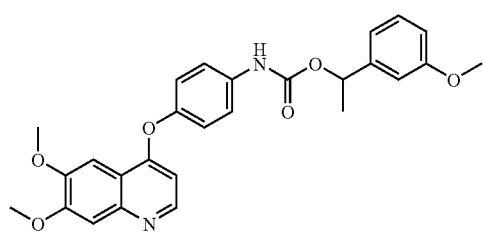
52
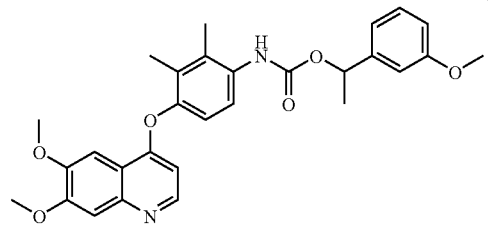
53
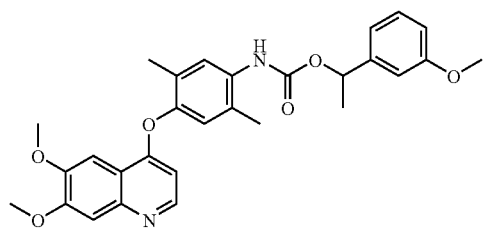
54
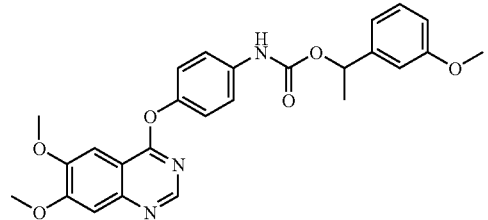
55

-continued
56
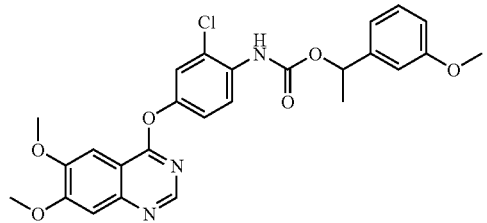
57
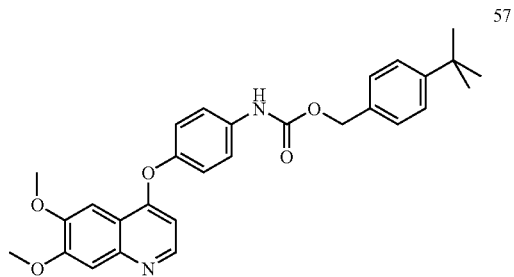
58
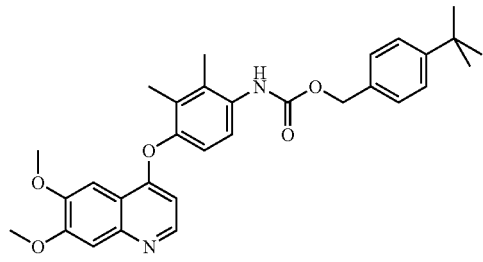
59
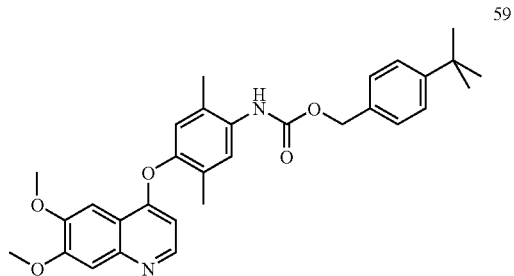
60
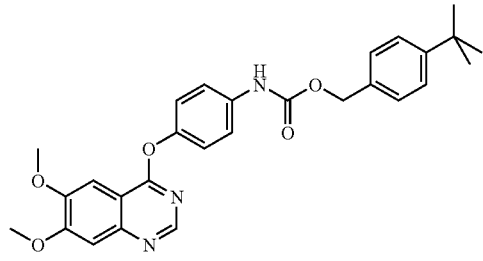
61
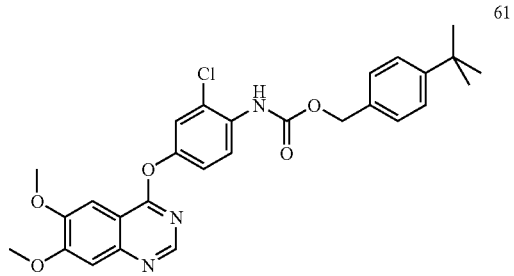
62
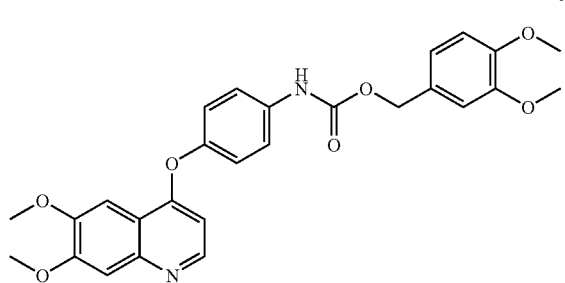
63
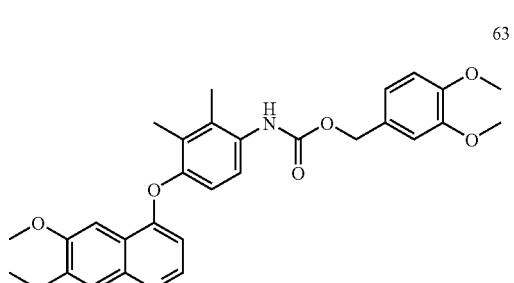
64
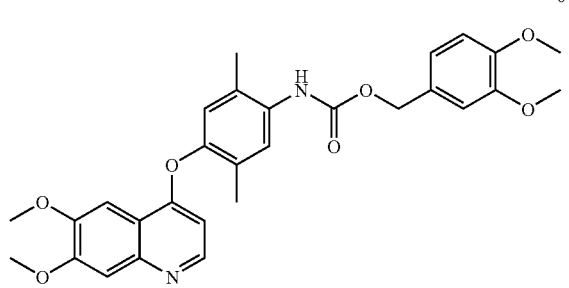
65
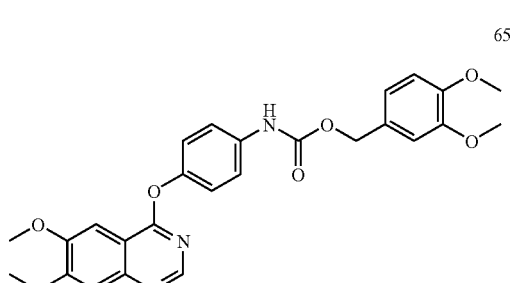

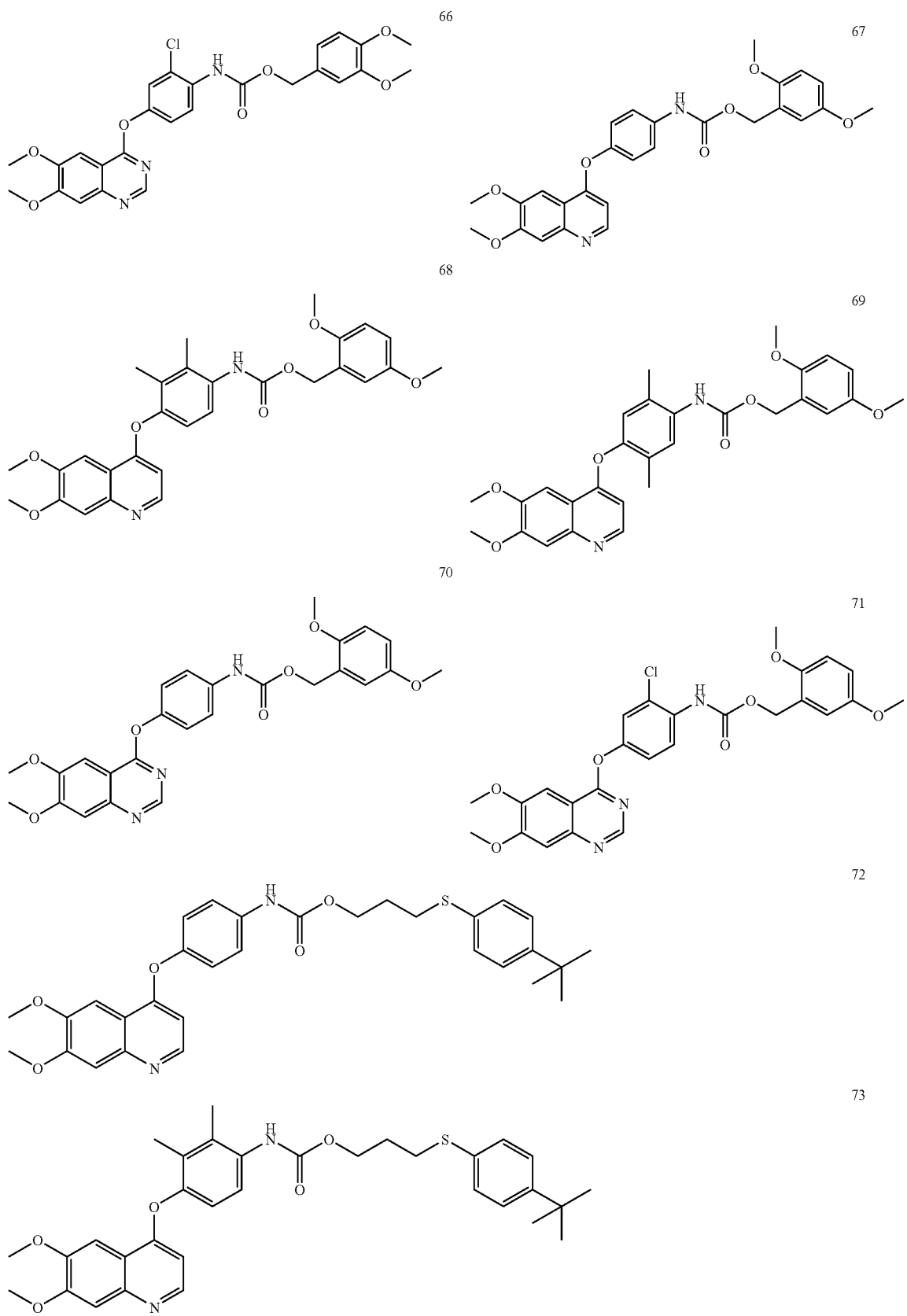

74
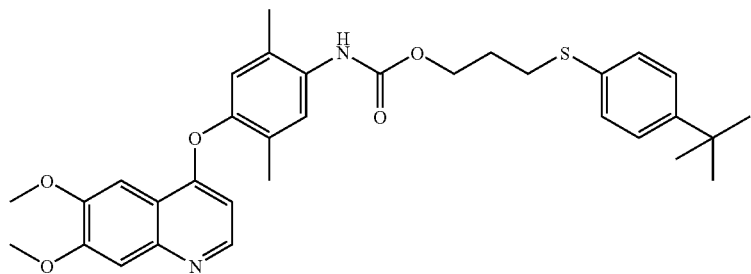
75
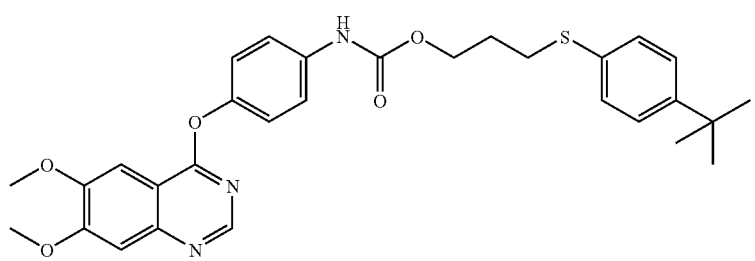
76
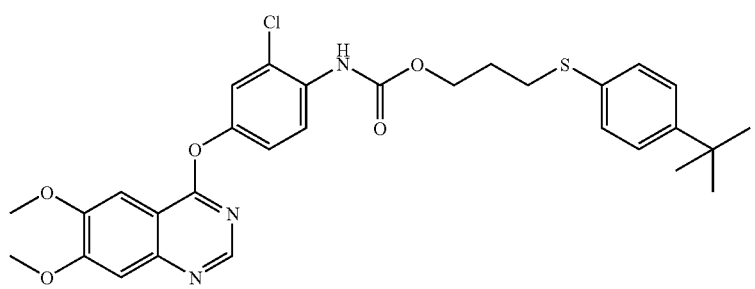
77
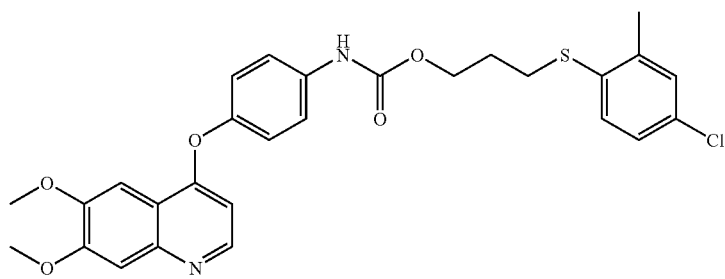
78
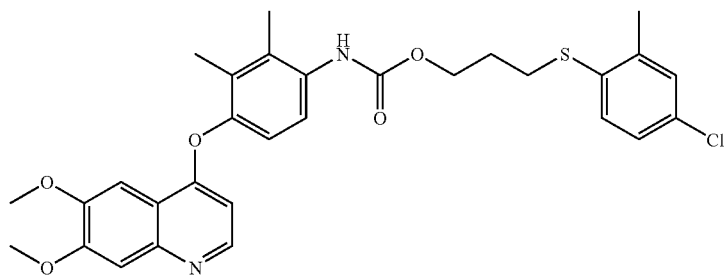

-continued
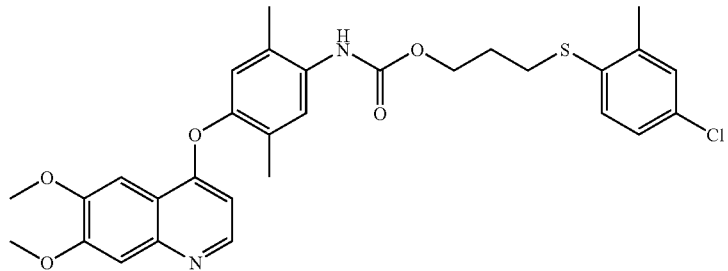
79
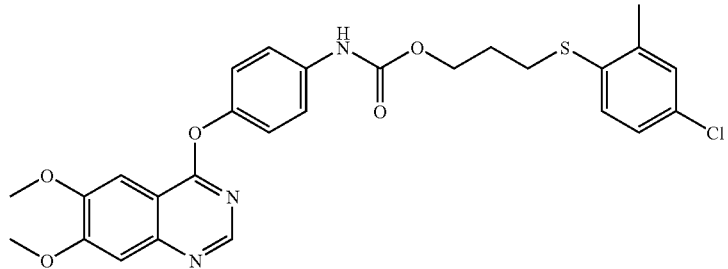
80
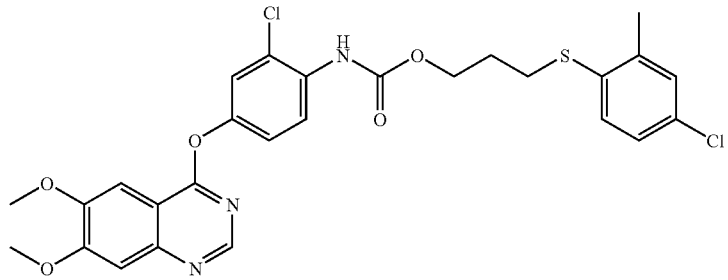
81
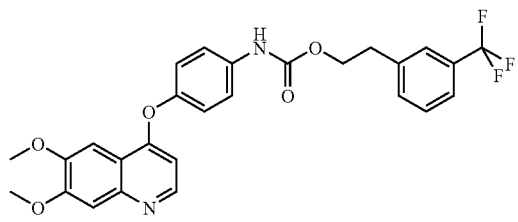
82
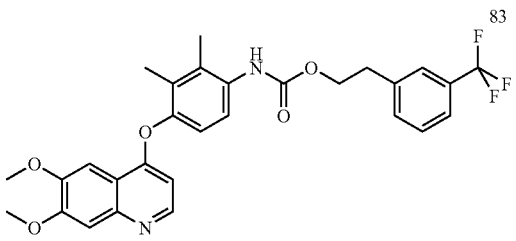
83
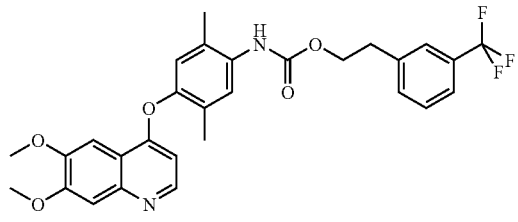
84
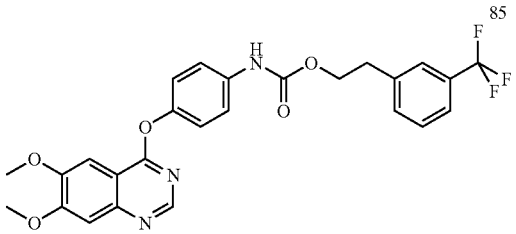
85
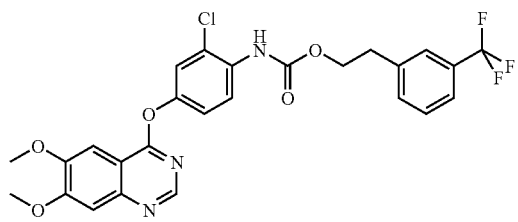
86
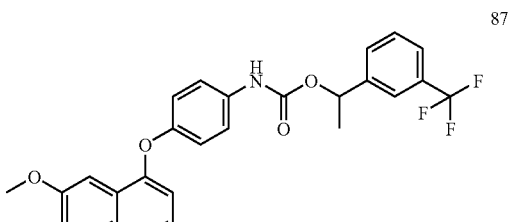
87

-continued
88
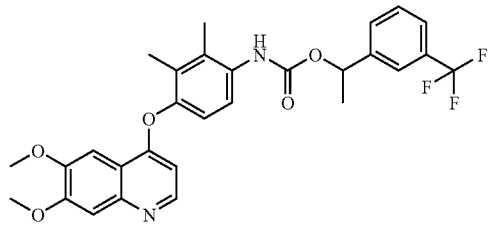
89
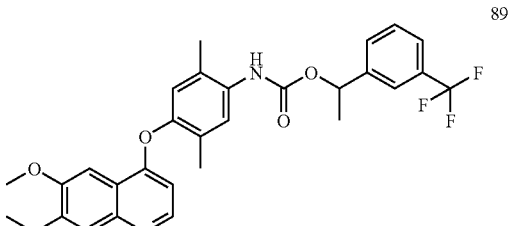
90
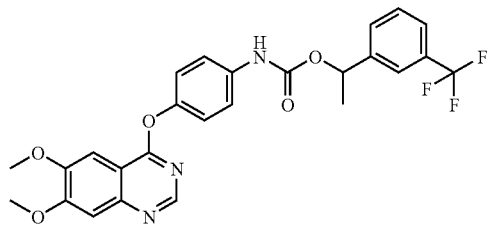
91
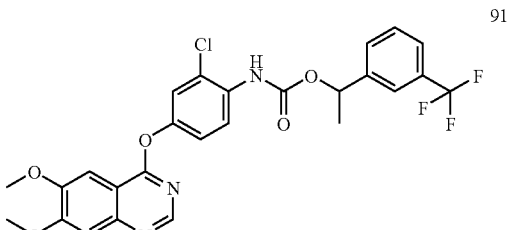
92
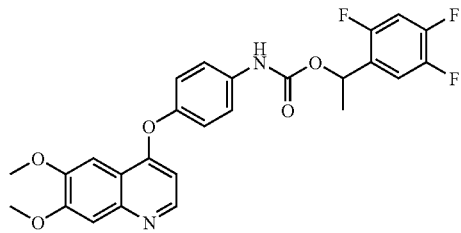
93
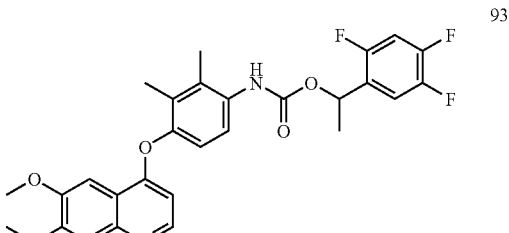
94
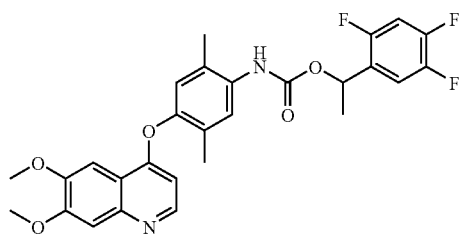
95
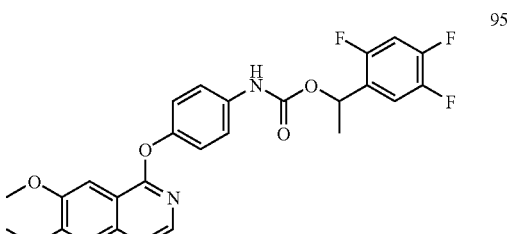
96
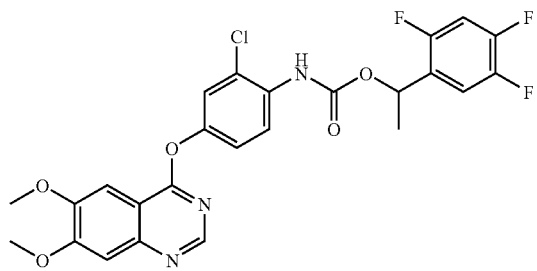
97
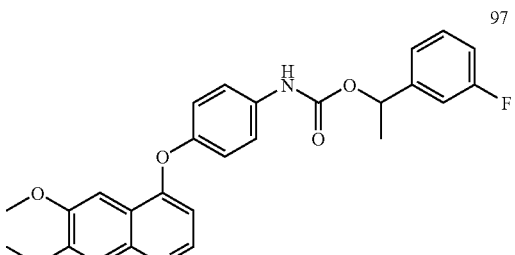
98
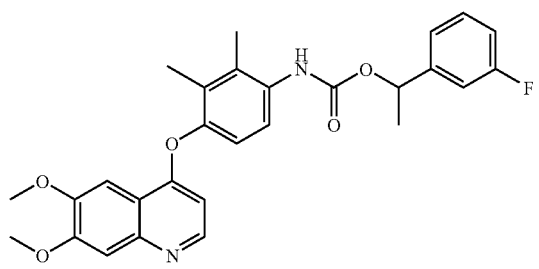
99
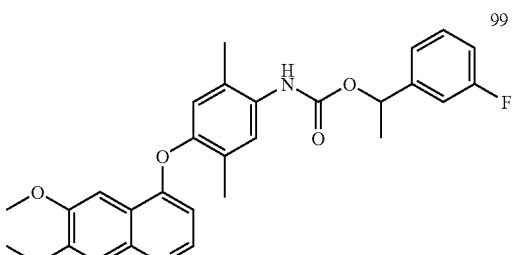

-continued
100
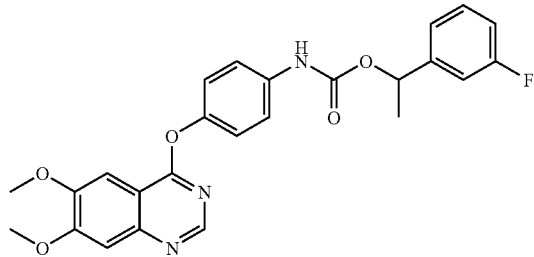
101
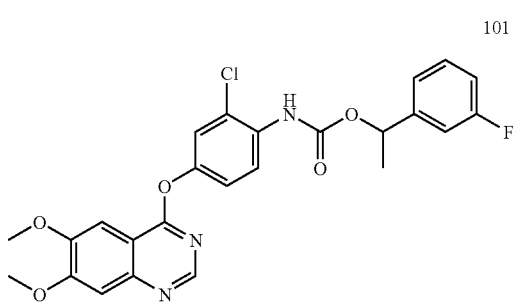
102
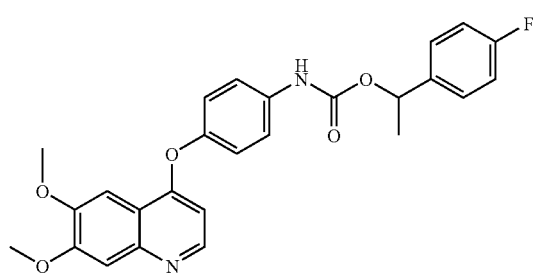
103
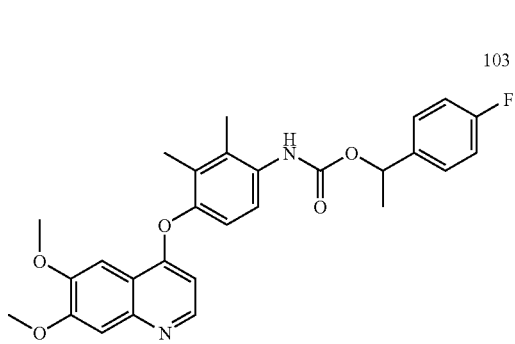
104
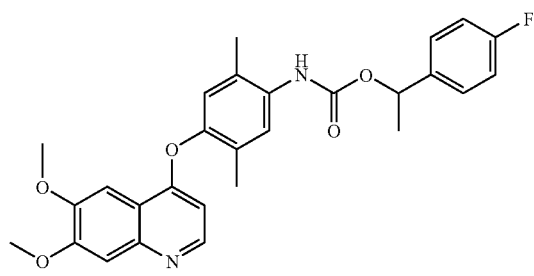
105
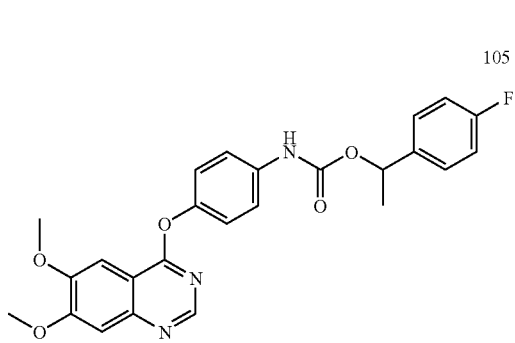
106
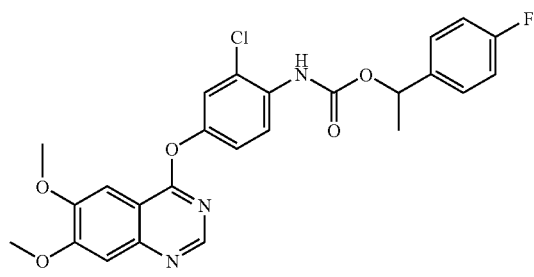
107
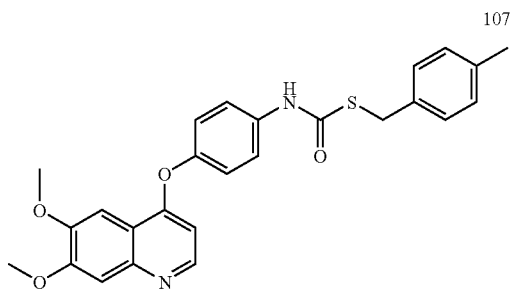
108
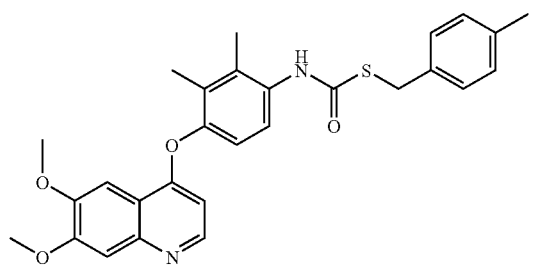
109
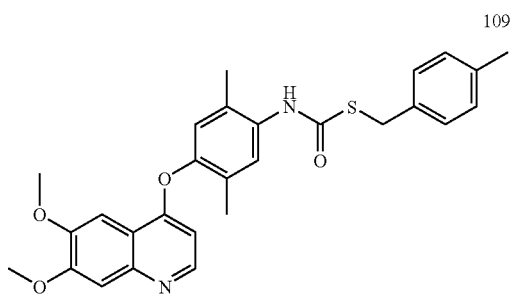

-continued
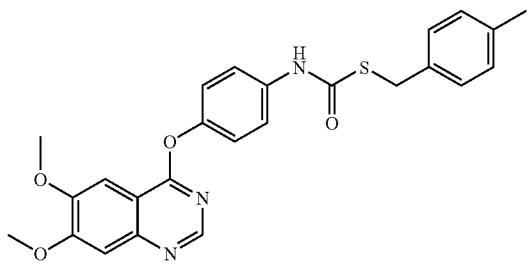
110
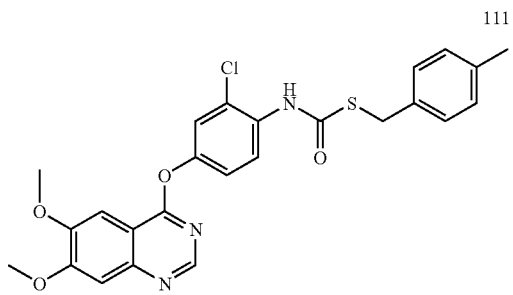
111
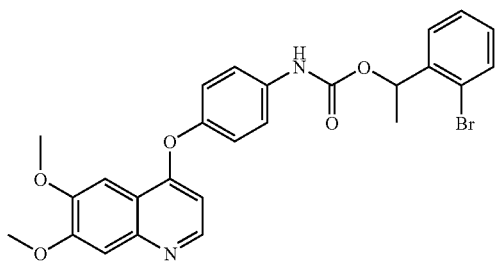
112
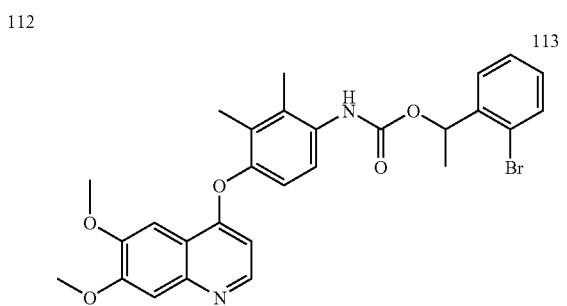
113
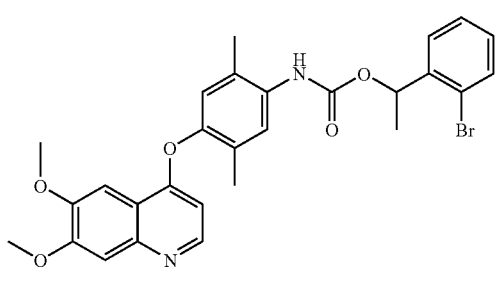
114
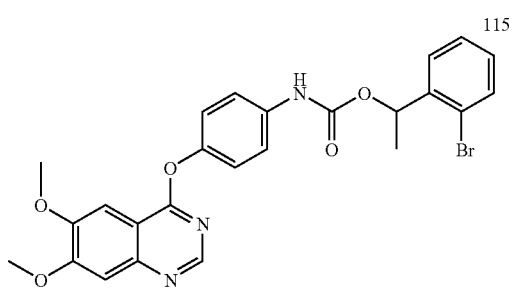
115
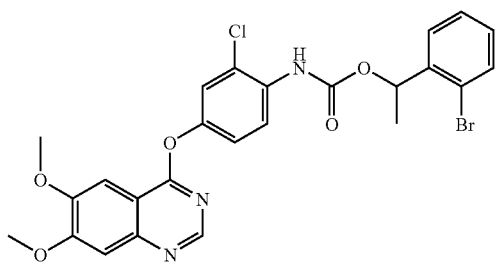
116
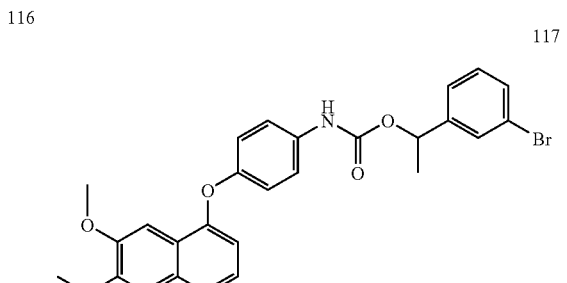
117
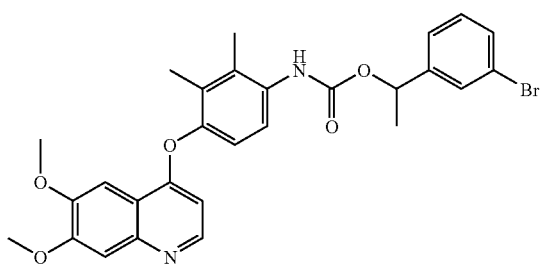
118
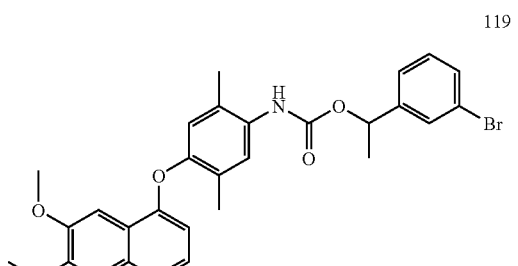
119

-continued
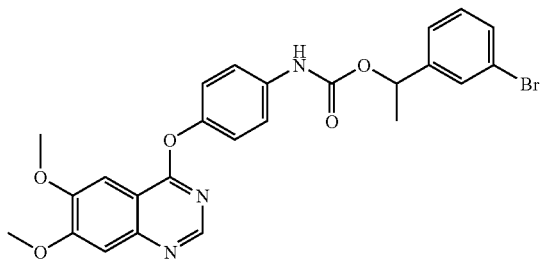
120
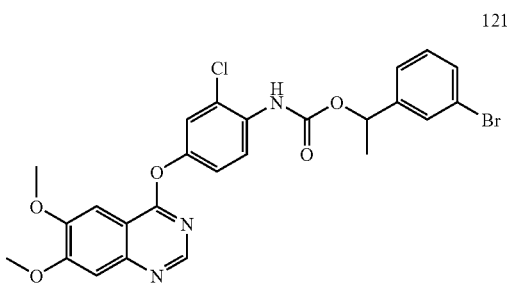
121
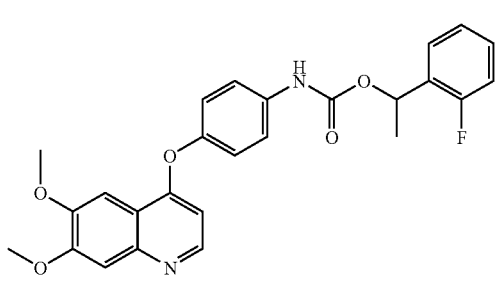
122
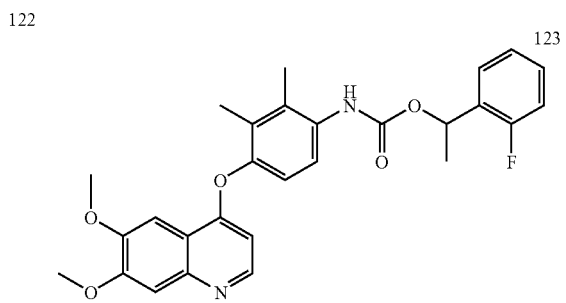
123
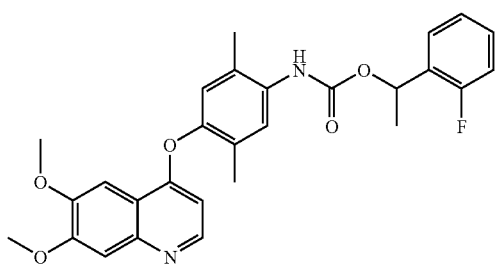
124
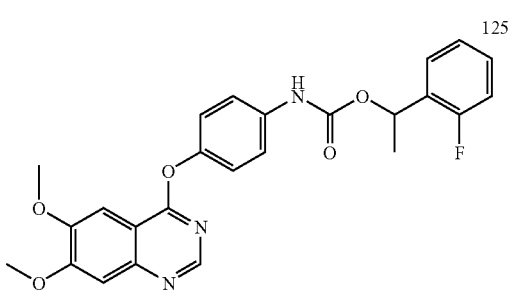
125
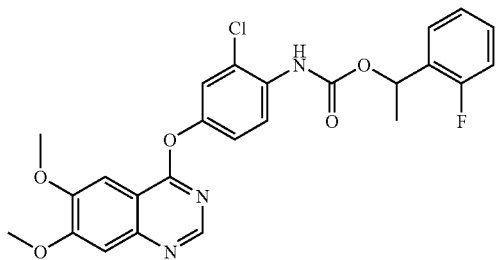
126
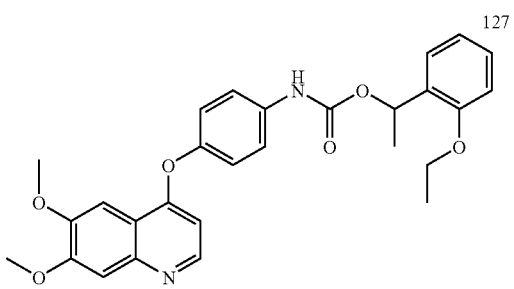
127
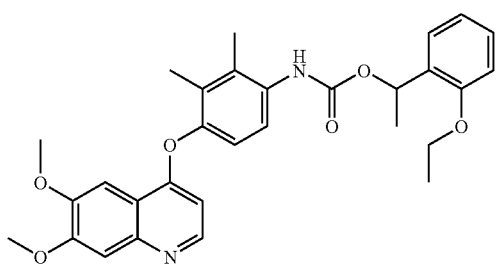
128
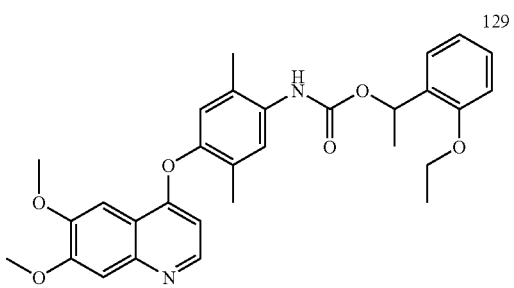
129

-continued
130
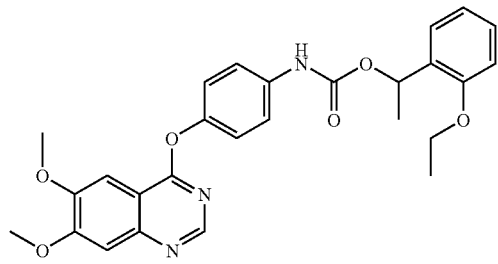
131
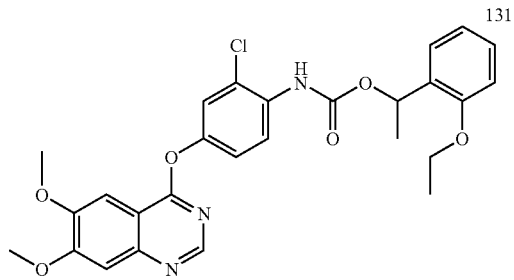
132
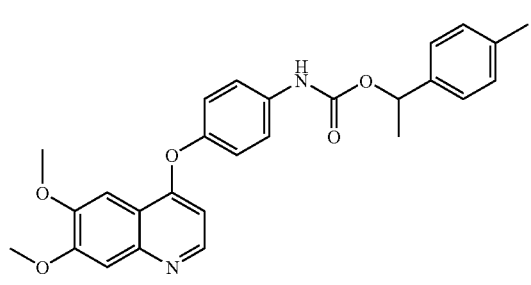
133
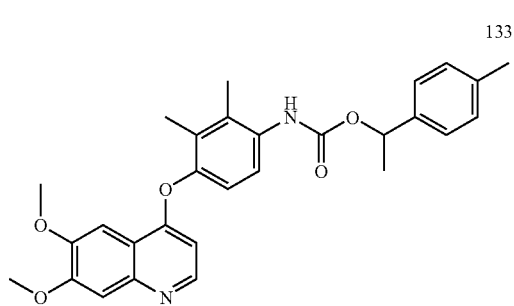
134
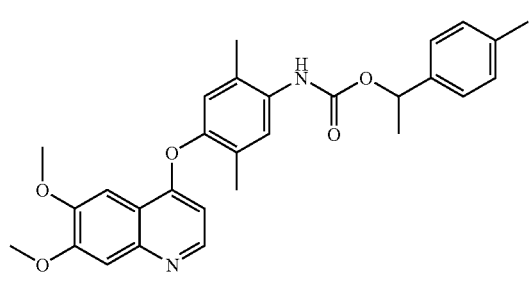
135
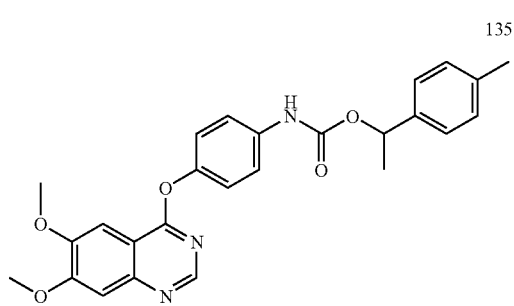
136
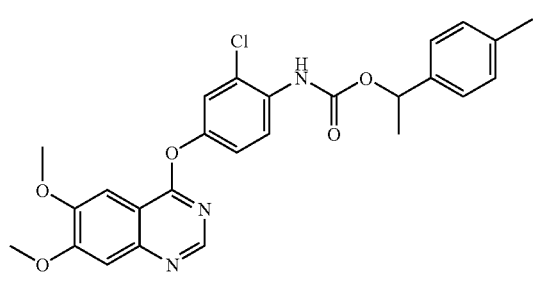
137
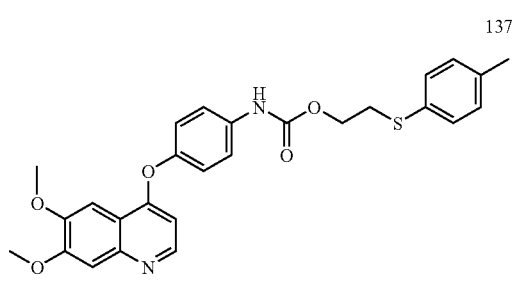
138
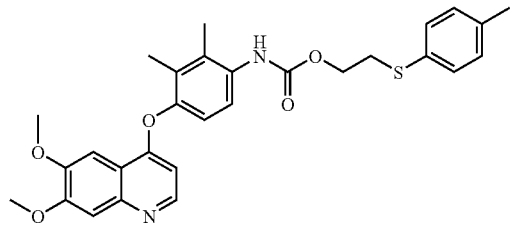
139
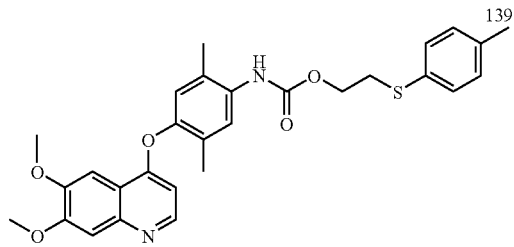

-continued
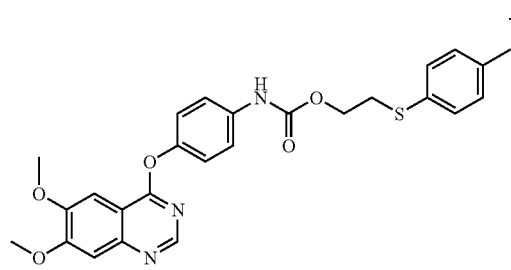
140
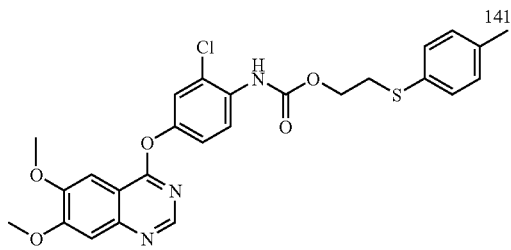
141
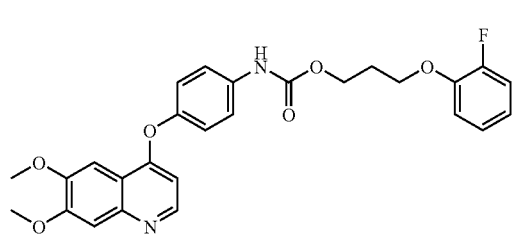
142
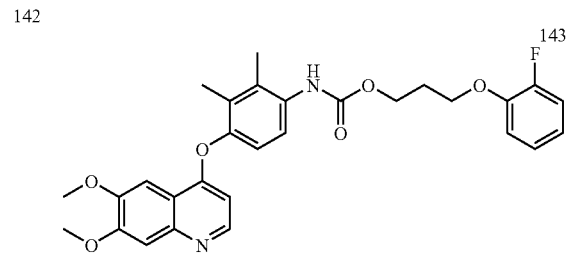
143
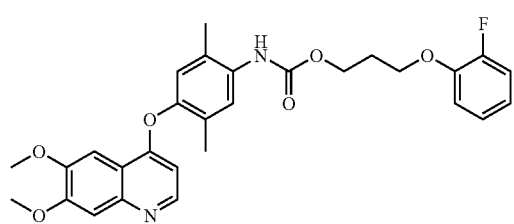
144
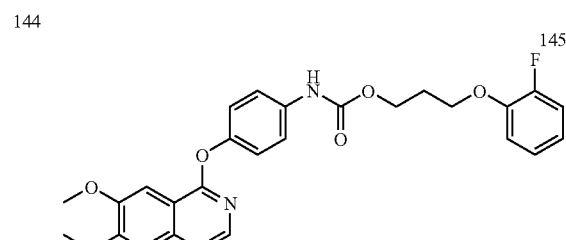
145
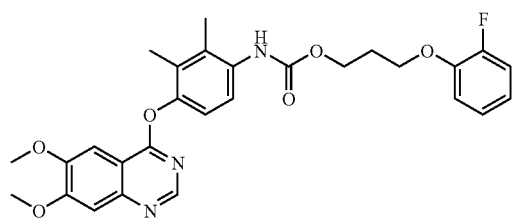
146
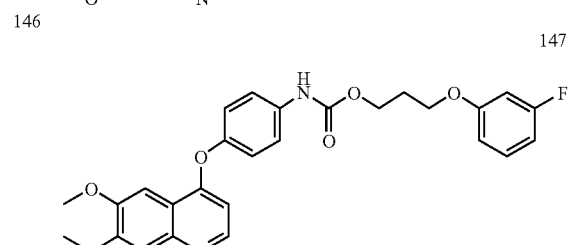
147
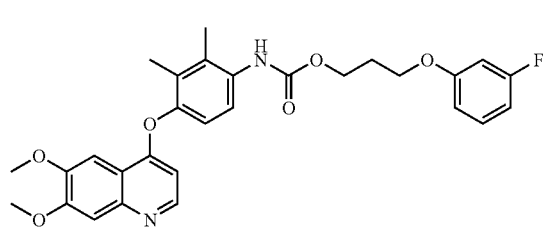
148
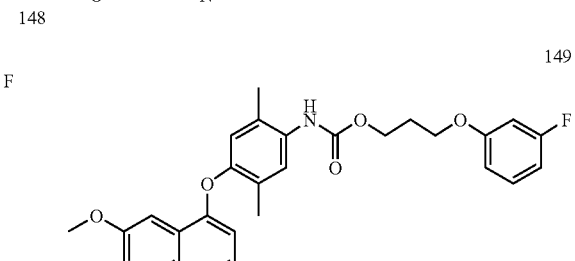
149
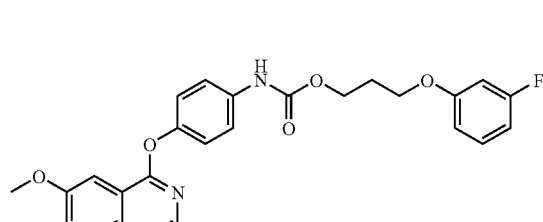
150
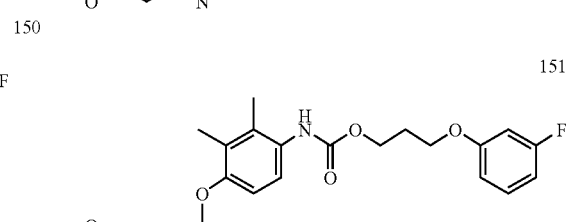
151

-continued
152
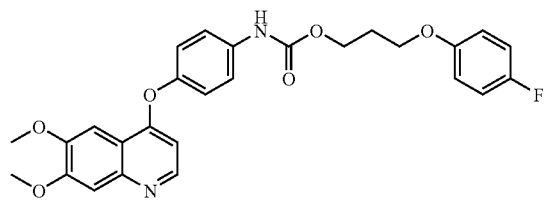
153
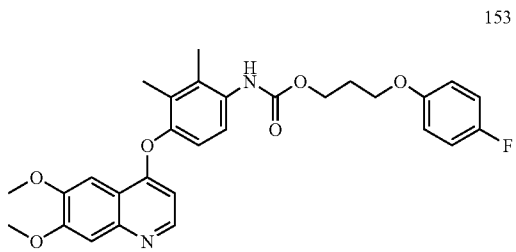
154
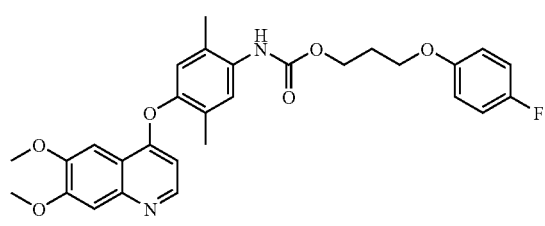
155
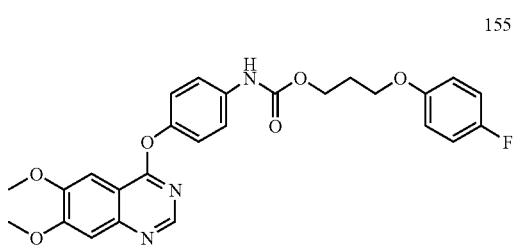
156
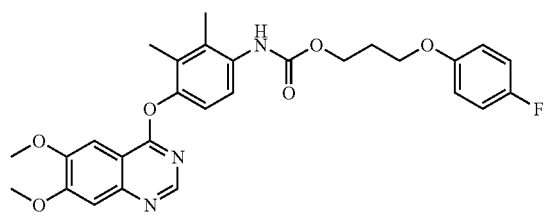
157
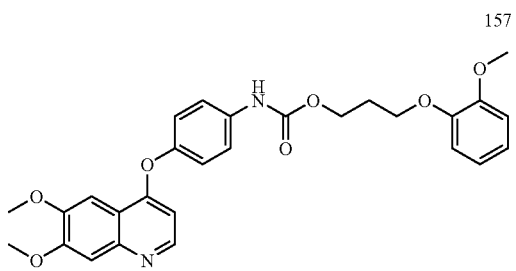
158
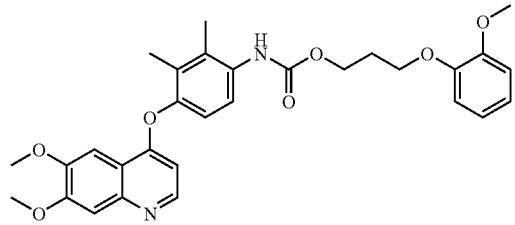
159
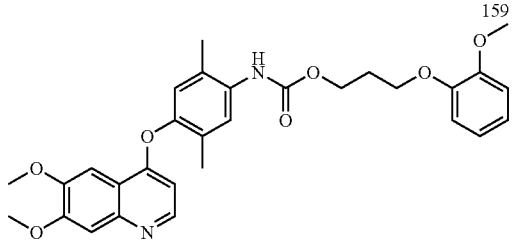
160
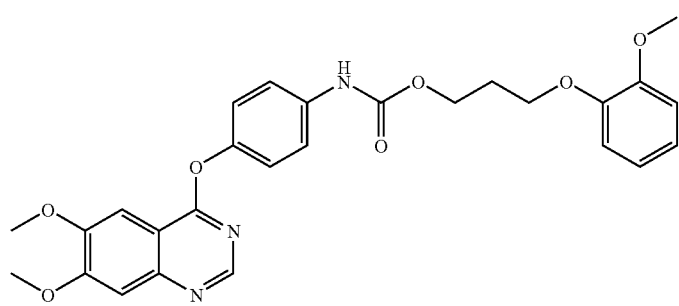

-continued
161
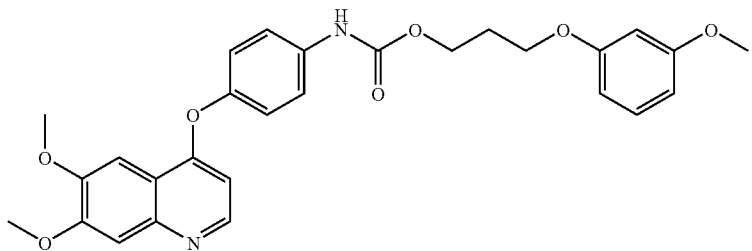
162
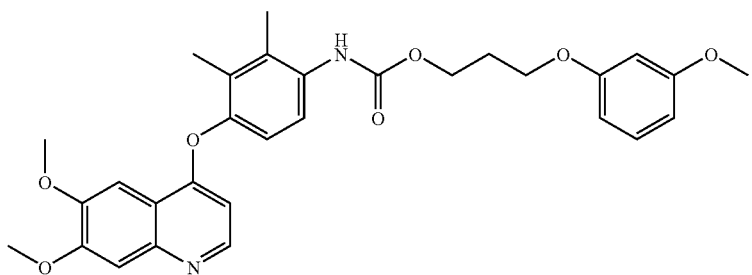
163
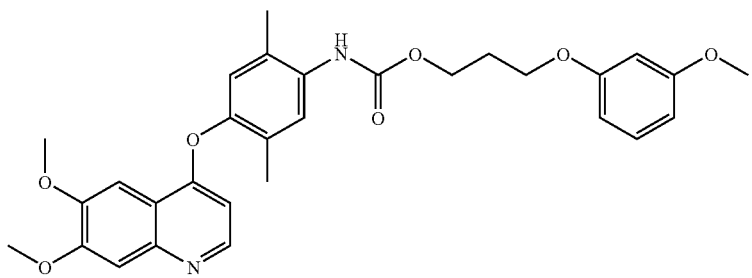
164
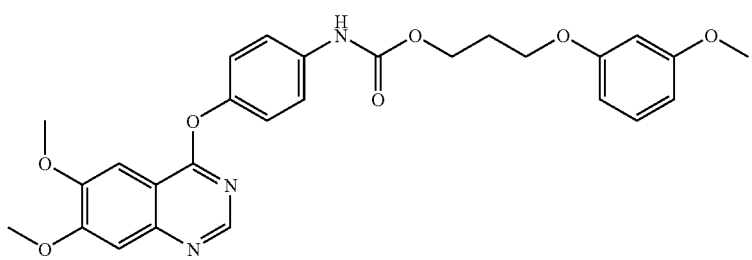
165
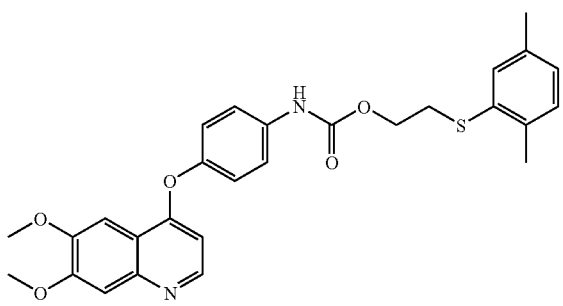
166
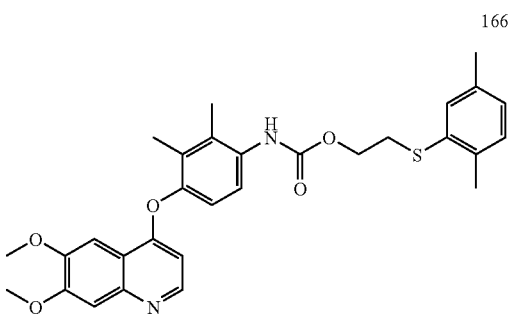

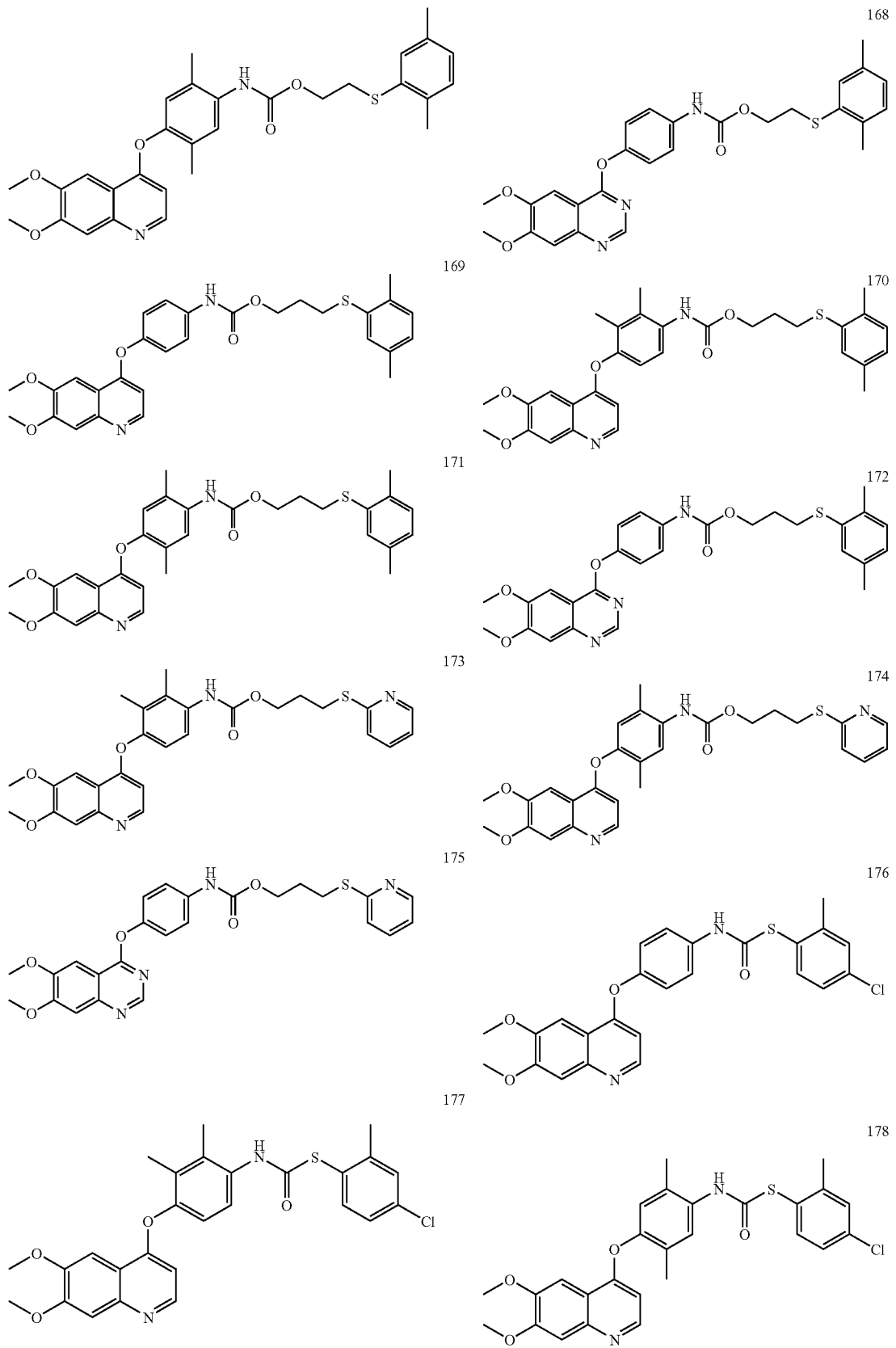

-continued
179
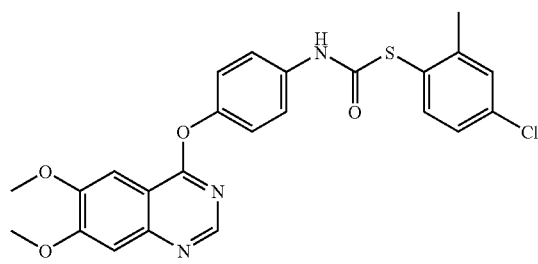
180
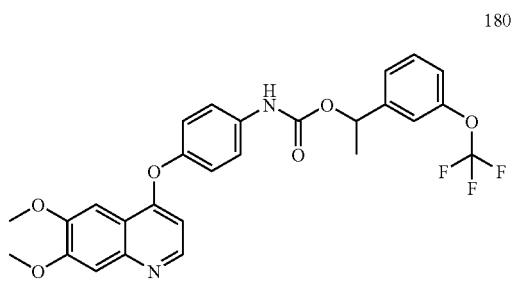
181
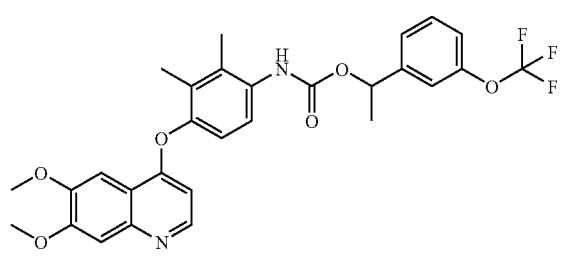
182
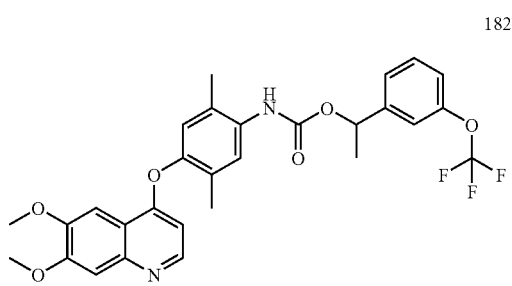
183
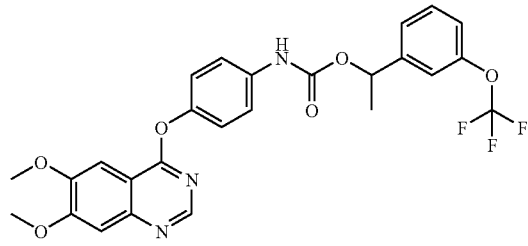
184
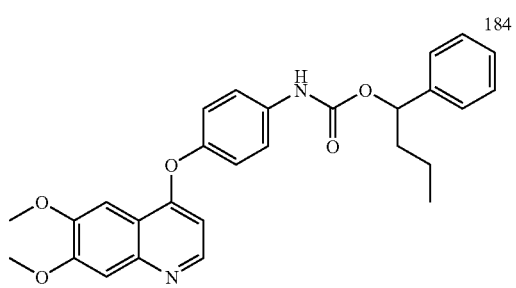
185
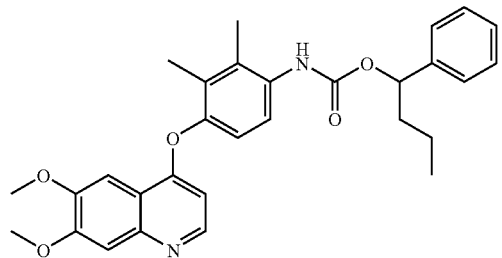
186
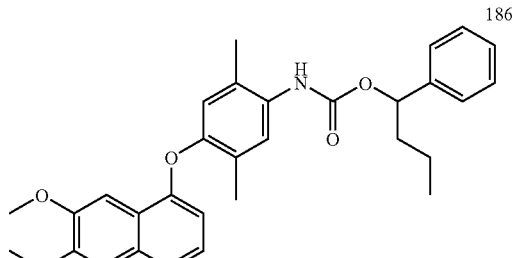
187
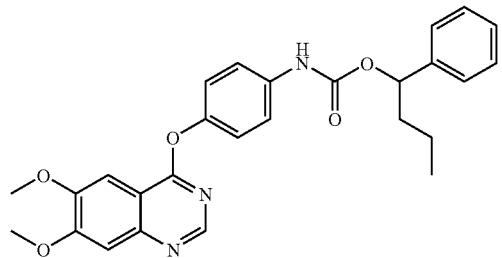
188
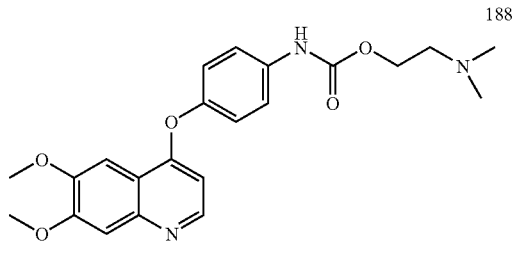

-continued
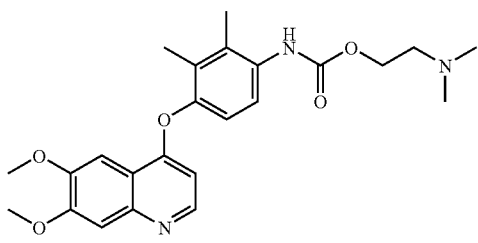
189
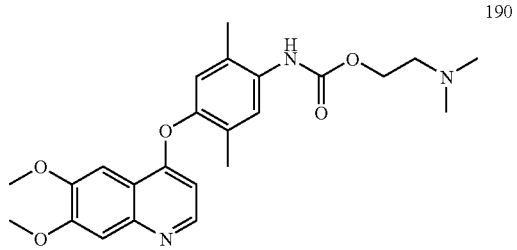
190
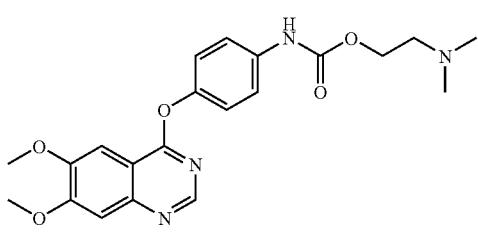
191
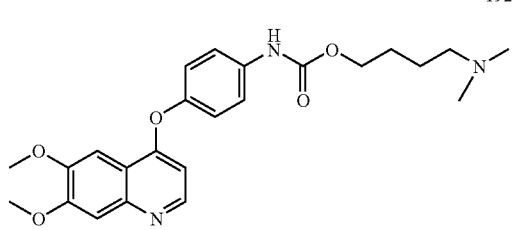
192
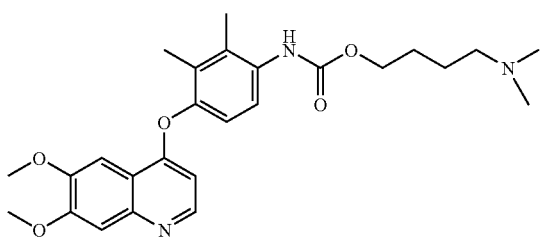
193
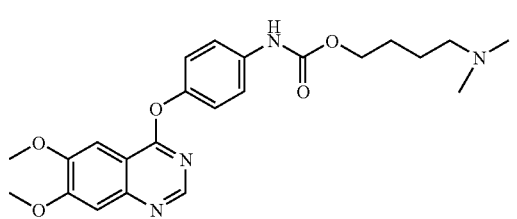
194
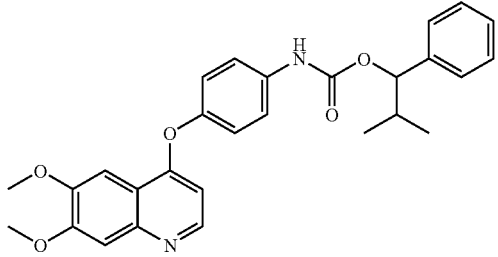
195
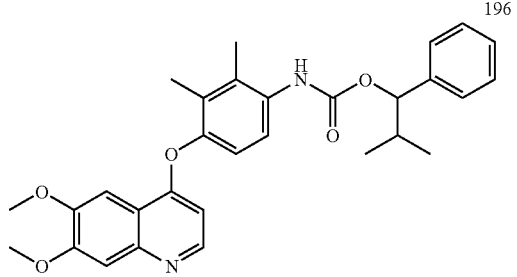
196
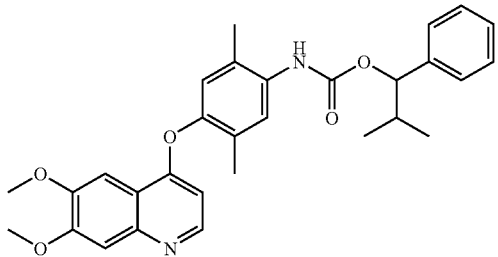
197
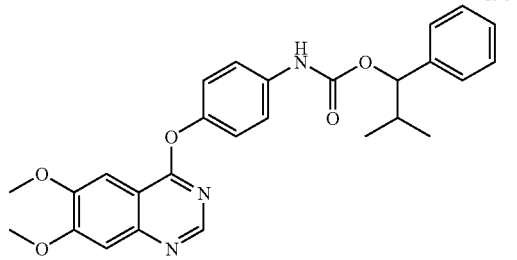
198

-continued
199
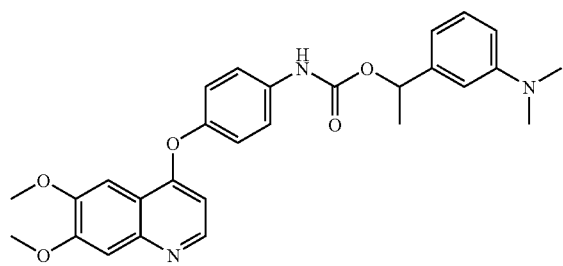
200
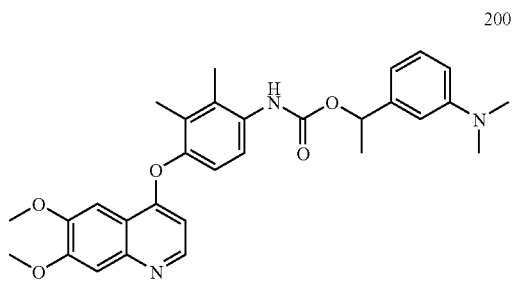
201
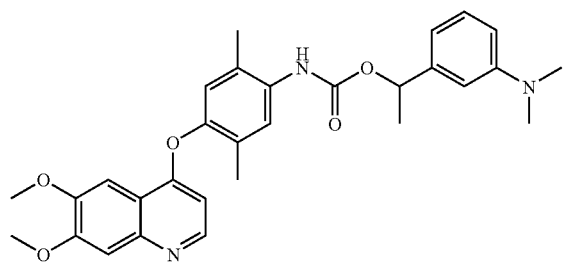
202
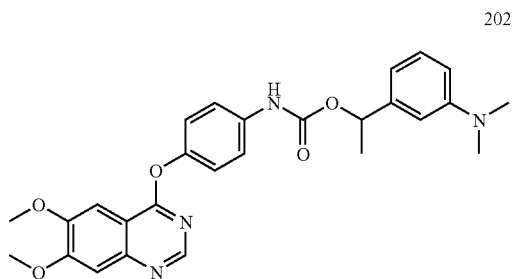
203
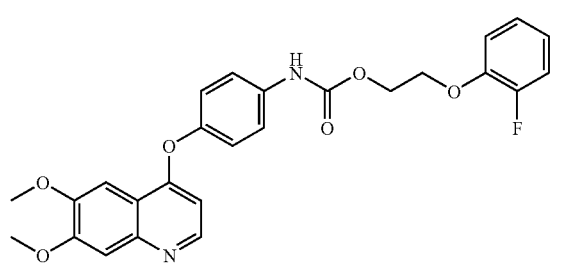
204
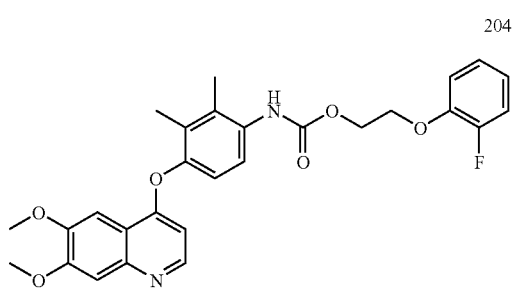
205
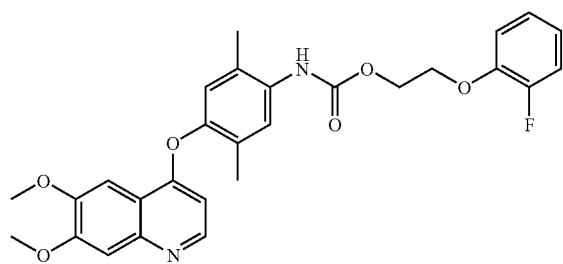
206
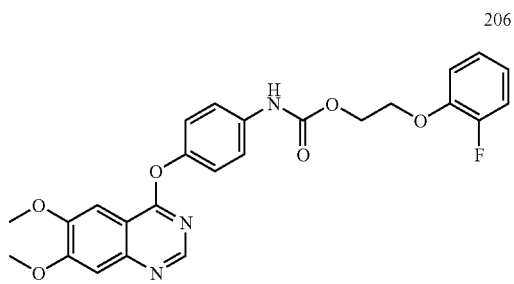
207
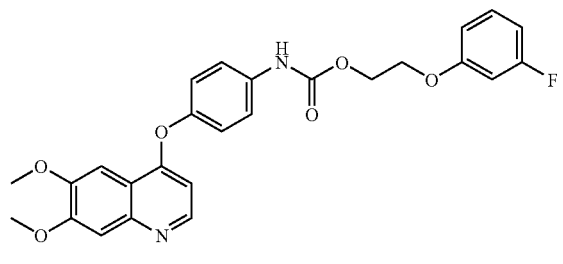
208
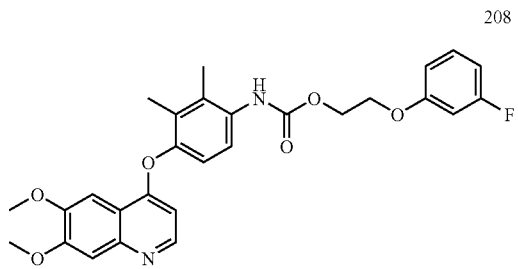

-continued
209
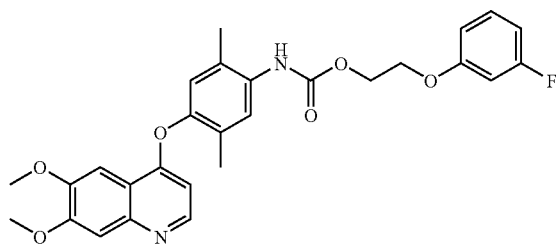
210
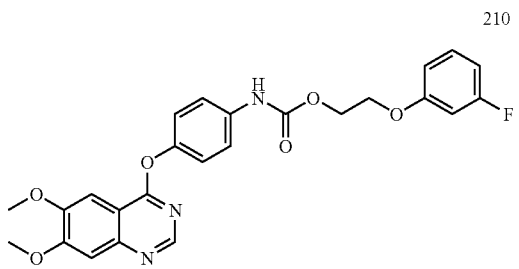
211
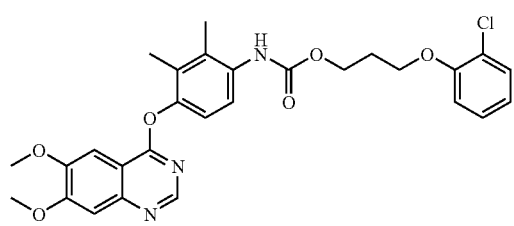
212
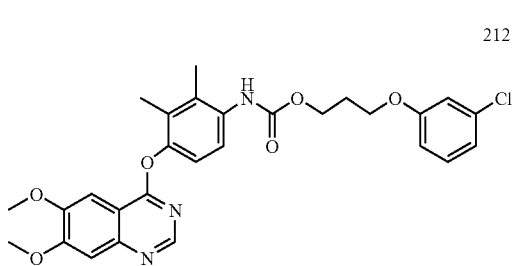
213
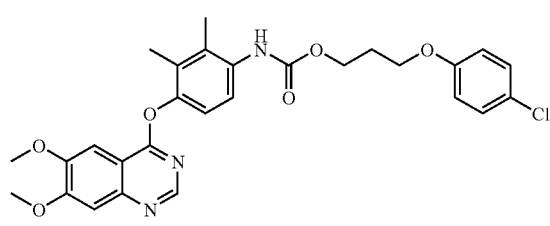
214
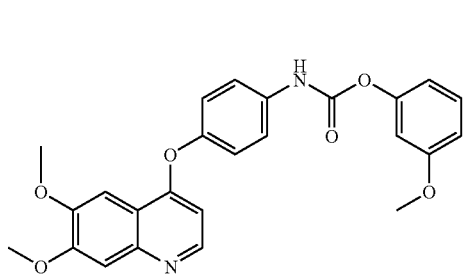
215
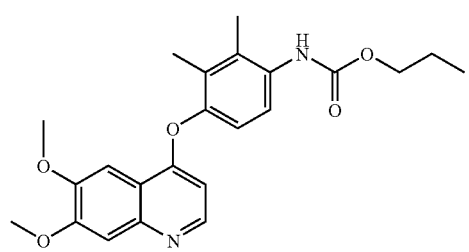
216
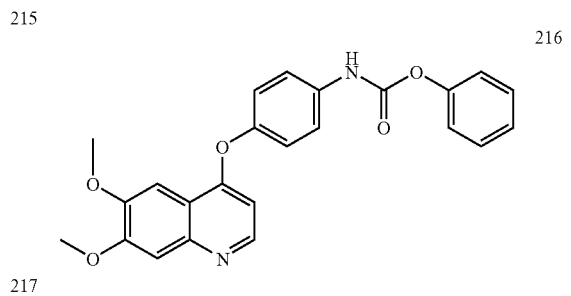
217
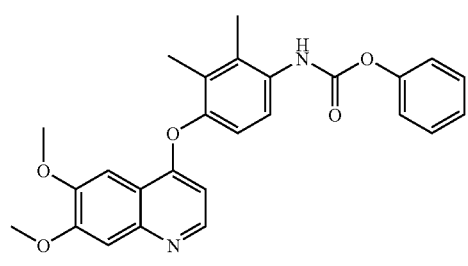
218
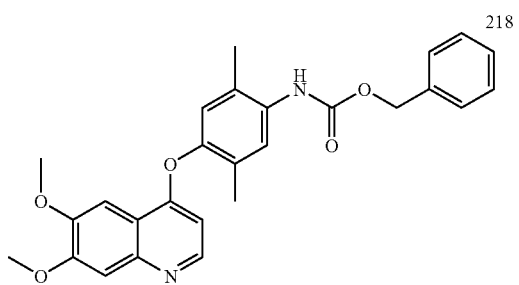

-continued
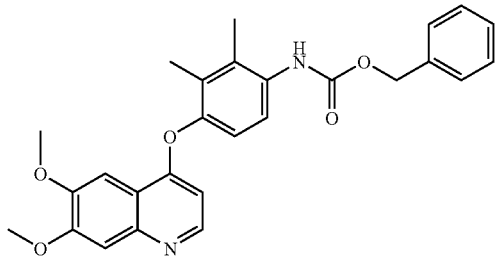
219
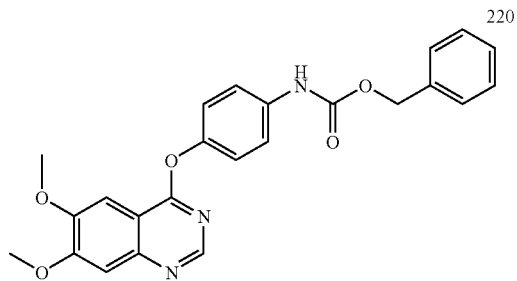
220
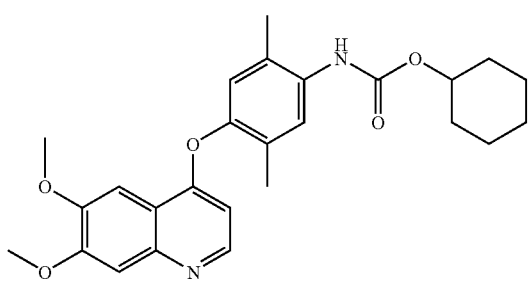
221
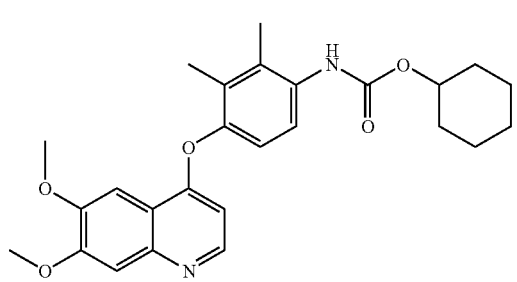
222
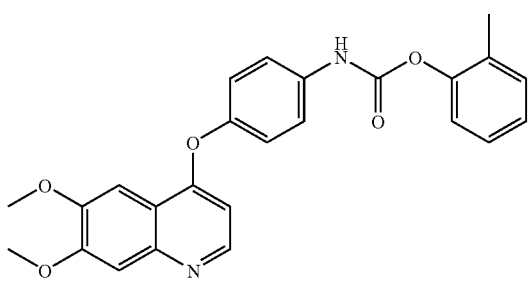
223
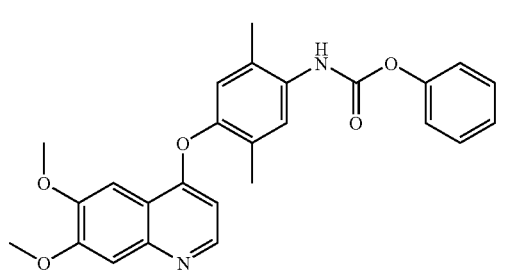
224
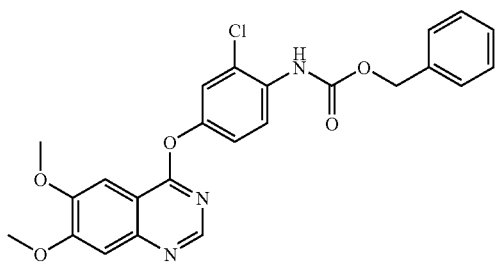
225
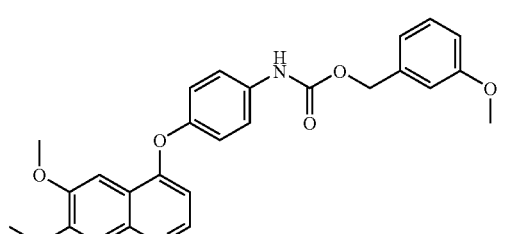
226
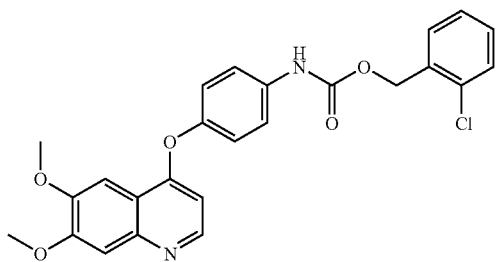
227
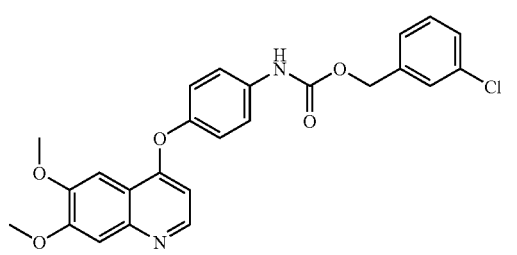
228

-continued
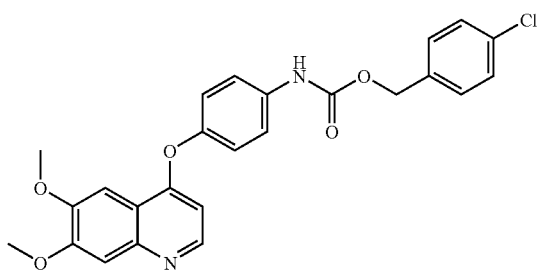
229
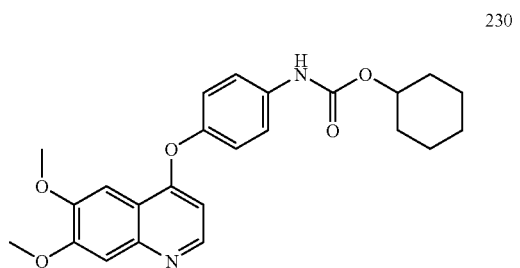
230
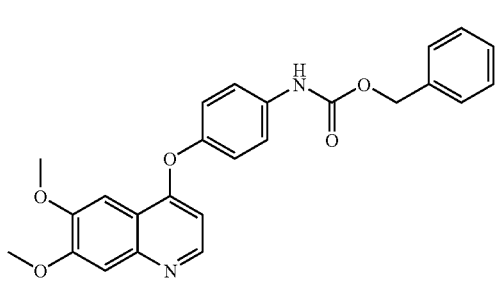
231
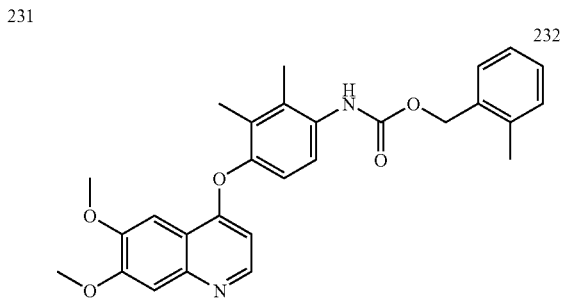
232
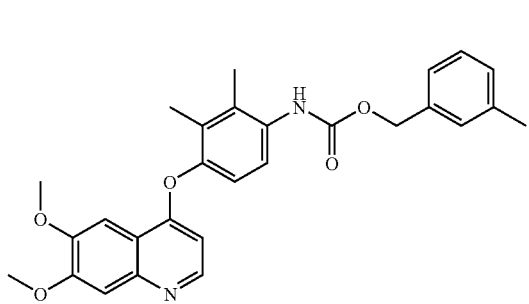
233
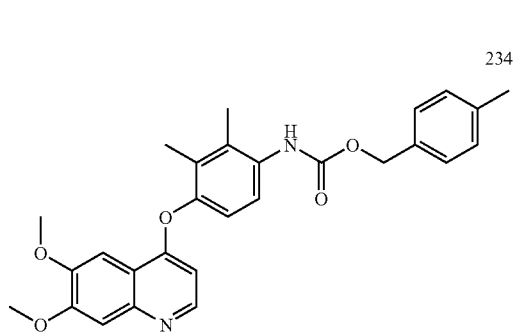
234
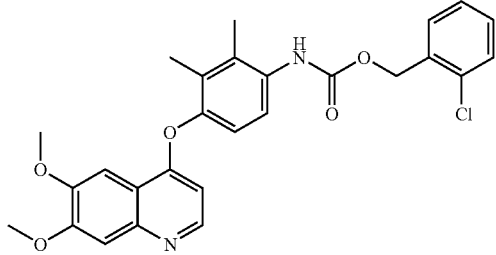
235
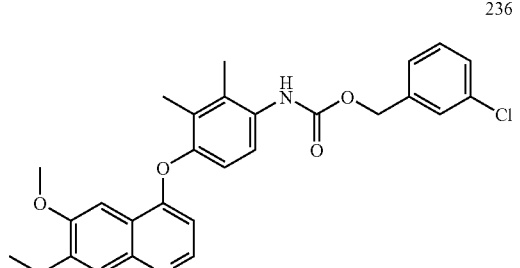
236
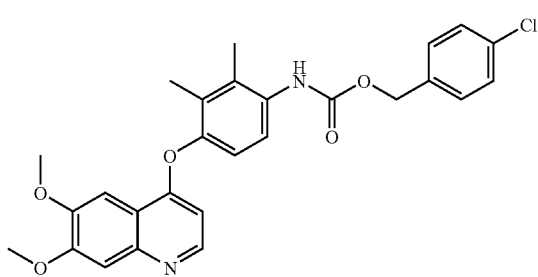
237
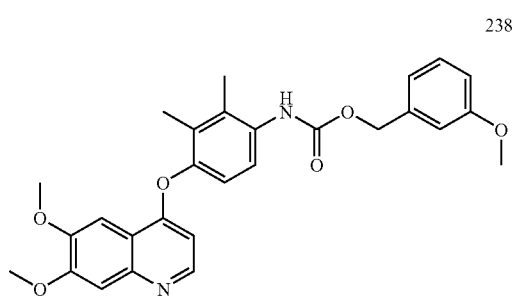
238

-continued
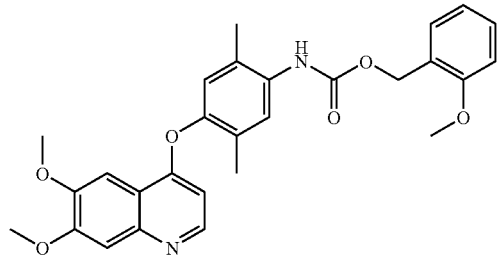
239
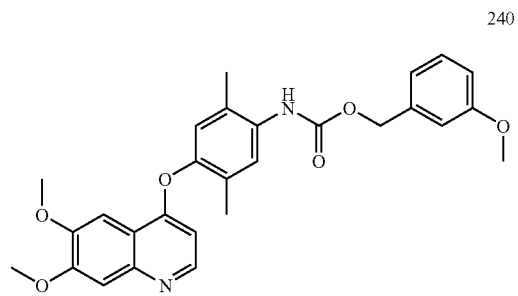
240
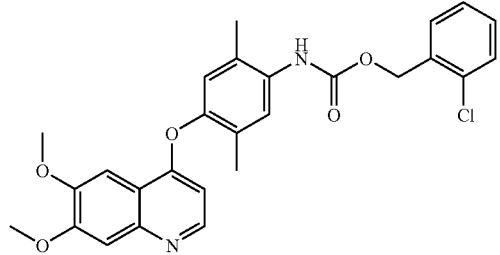
241
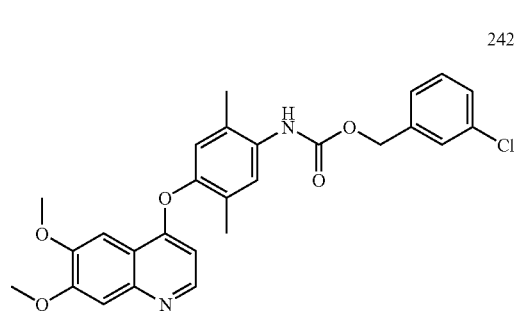
242
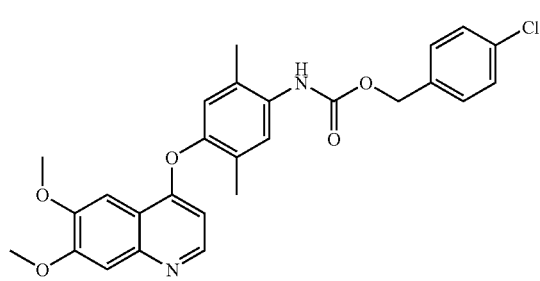
243
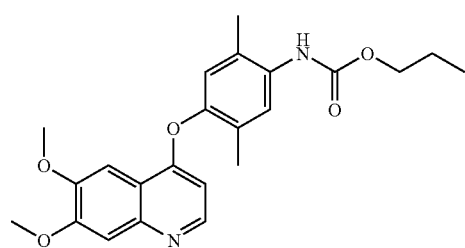
244
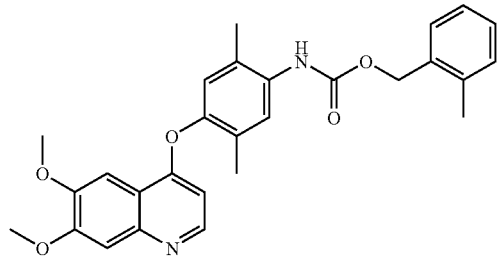
245
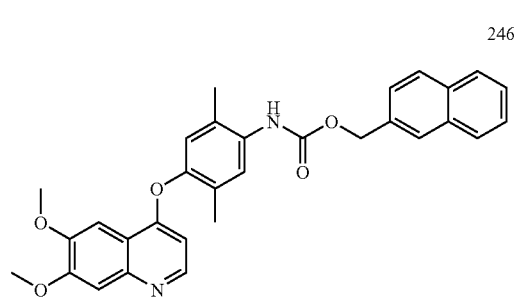
246
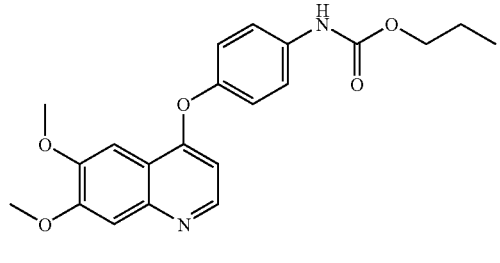
247
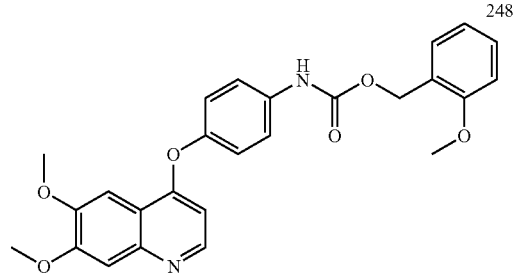
248

-continued
249
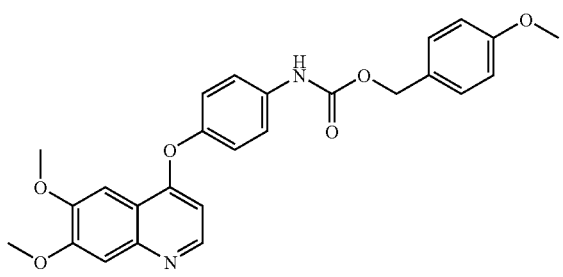
250
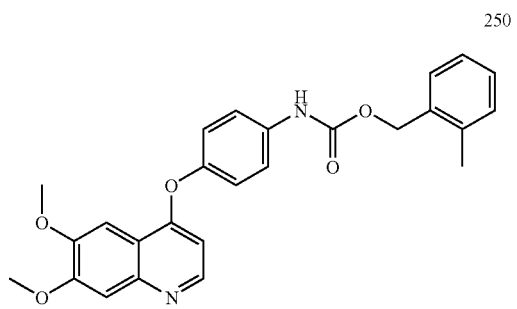
251
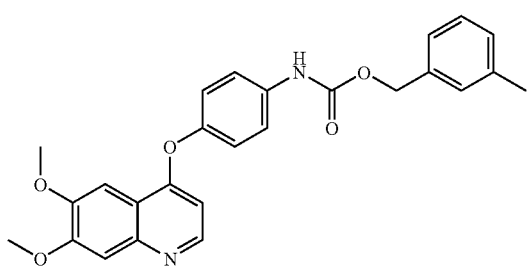
252
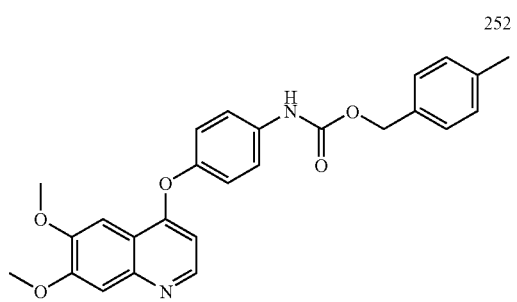
253
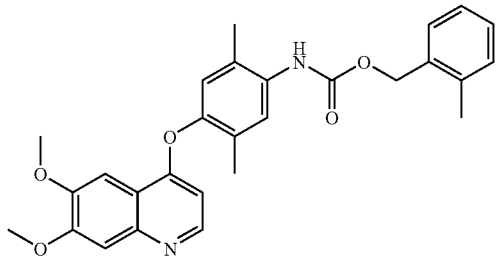
254
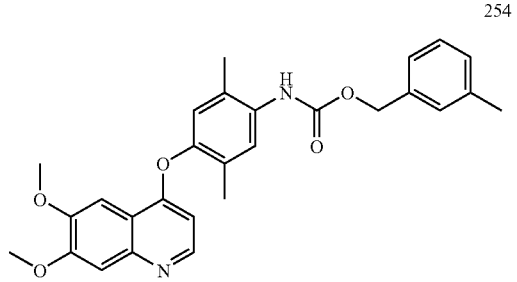
255
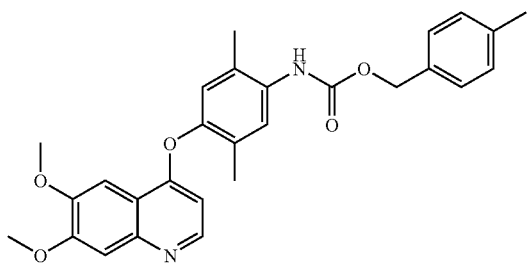
256
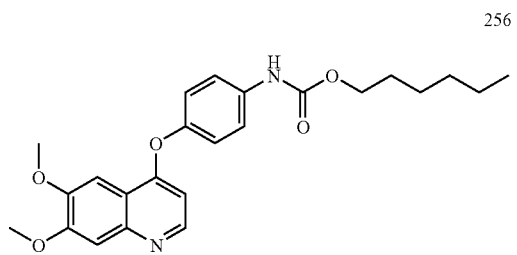
257
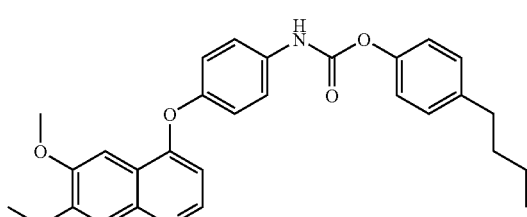
258
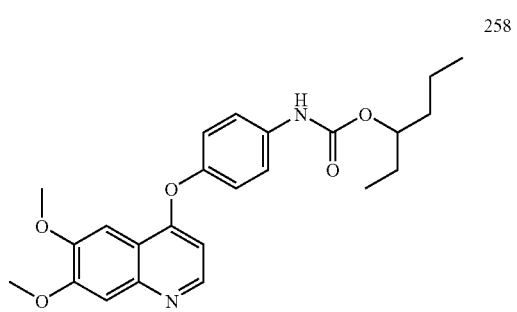

-continued
259
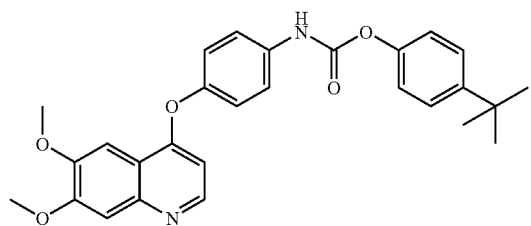
260
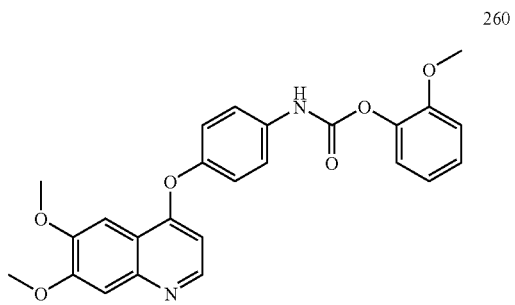
261
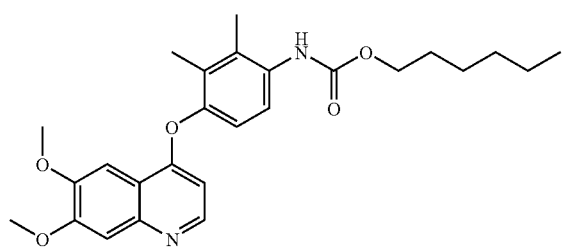
262
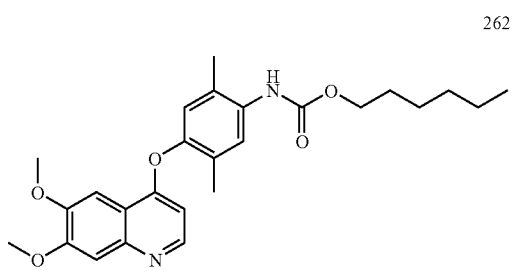
263
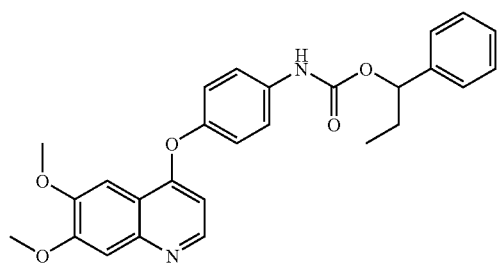
264
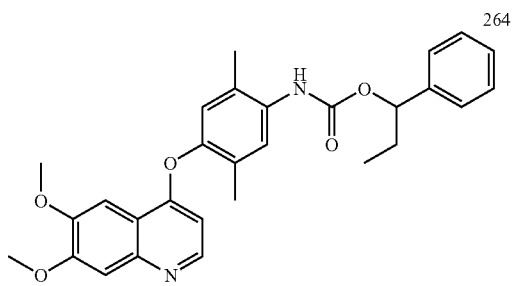
265
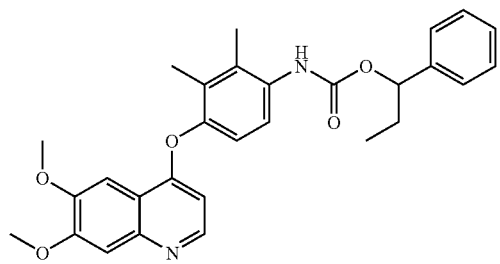
266
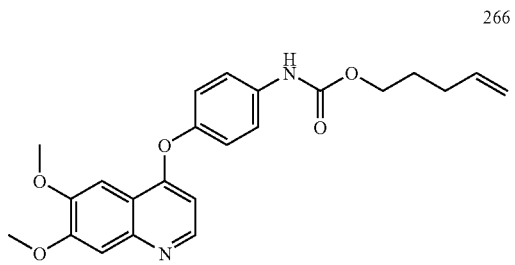
267
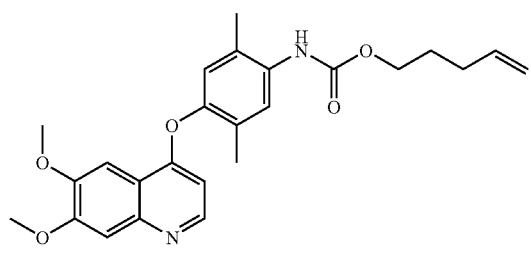
268
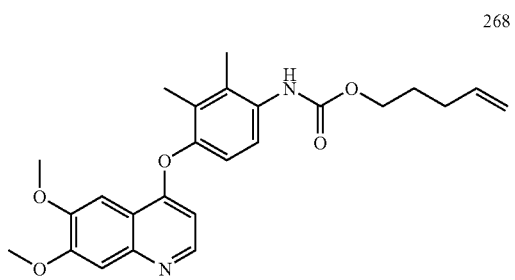

-continued
269
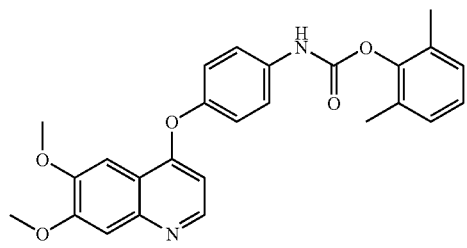
270
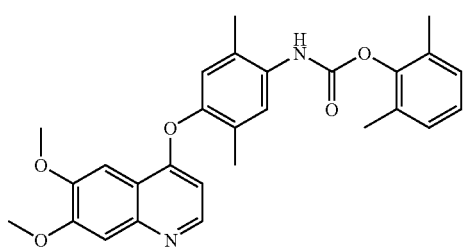
271
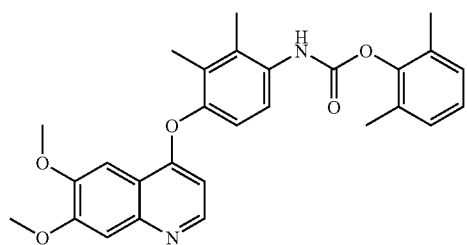
272
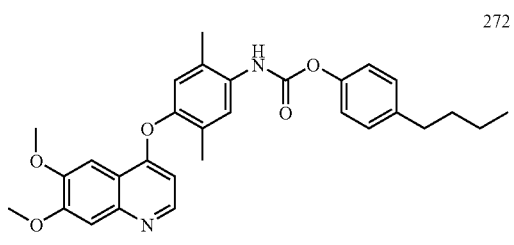
273
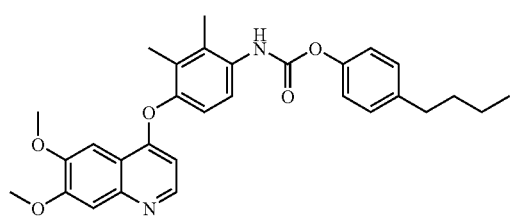
274
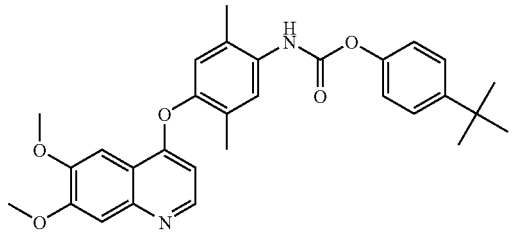
275
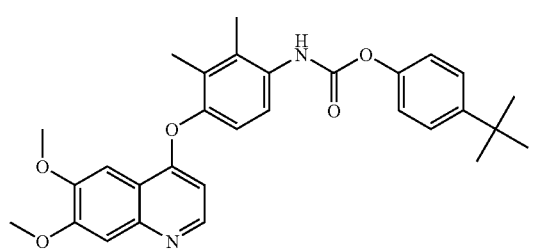
276
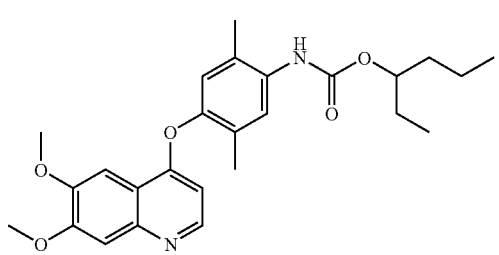
277
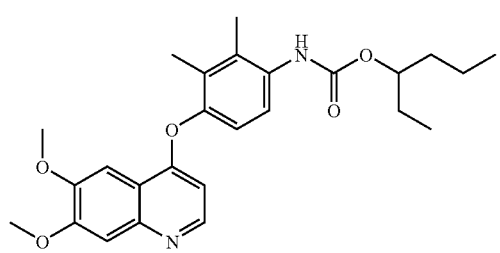
278
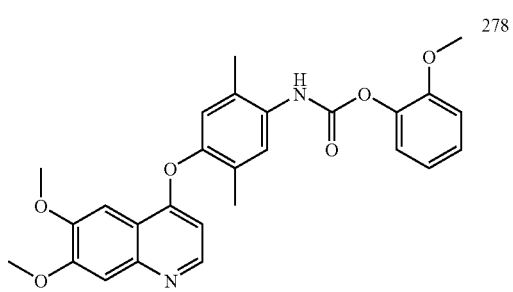

-continued
279 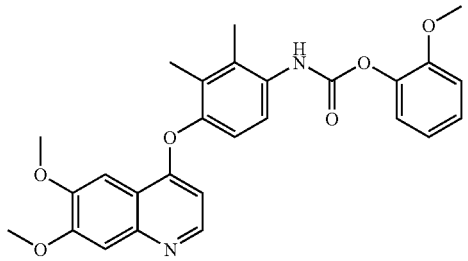
280 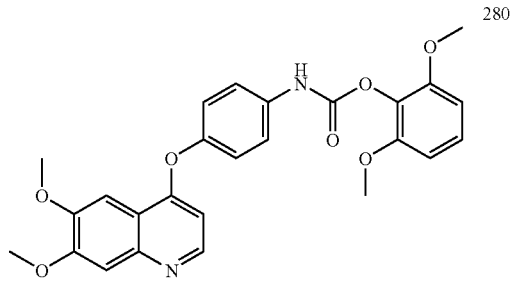
281 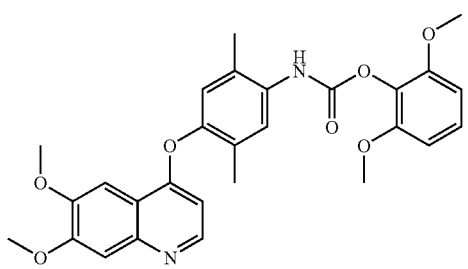
282 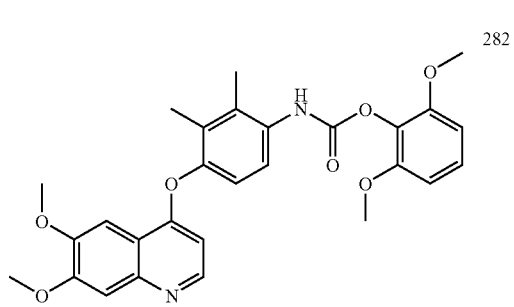
283 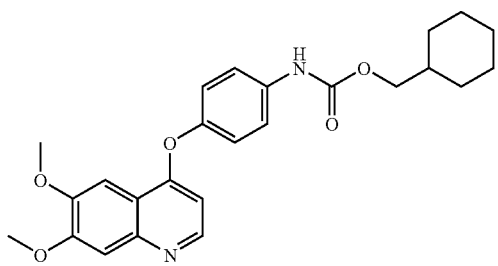
284 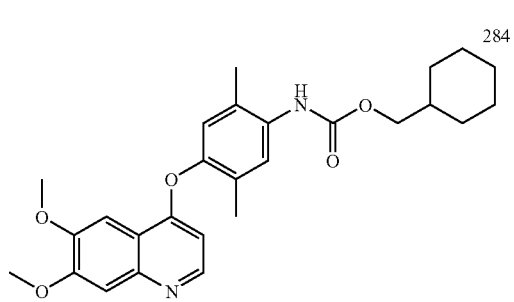
285 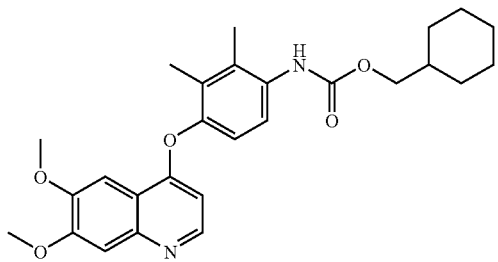
286 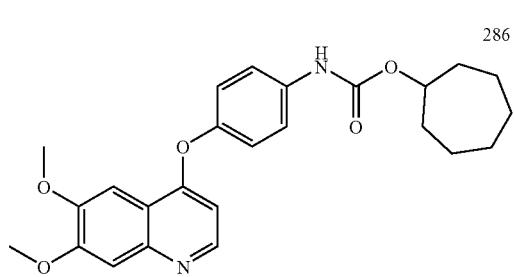
287 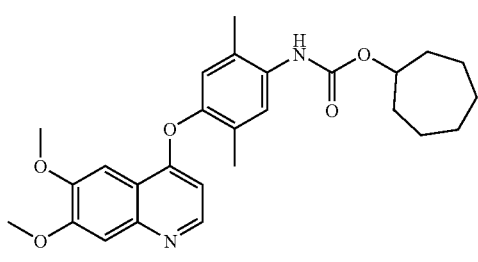
288 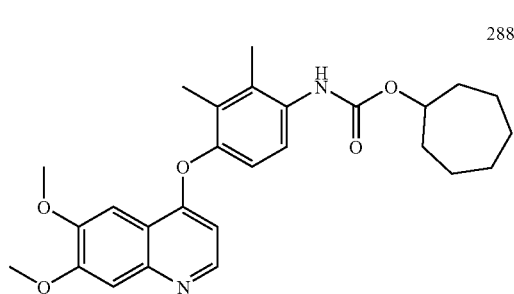

-continued
289
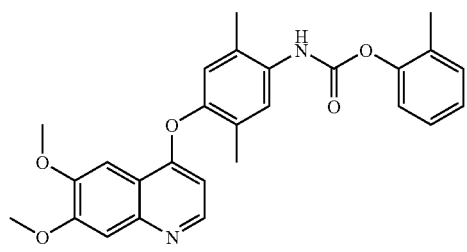
290
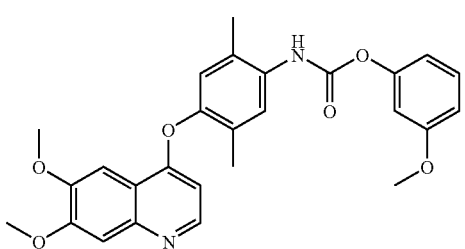
291
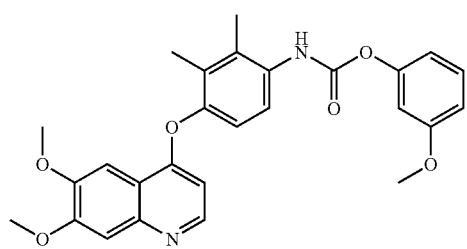
292
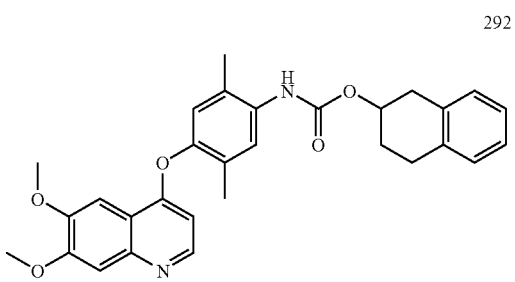
293
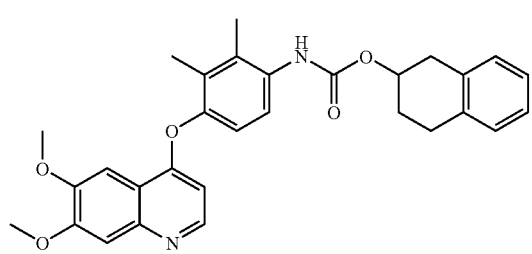
294
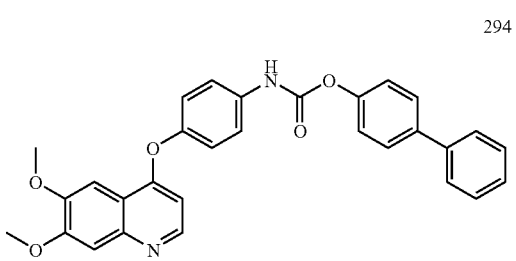
295
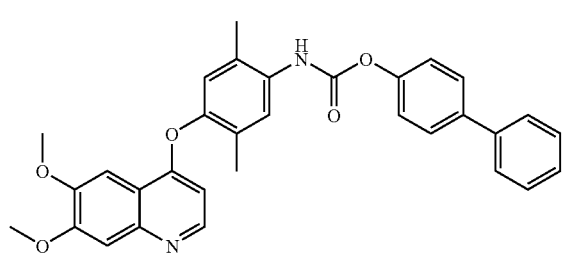
296
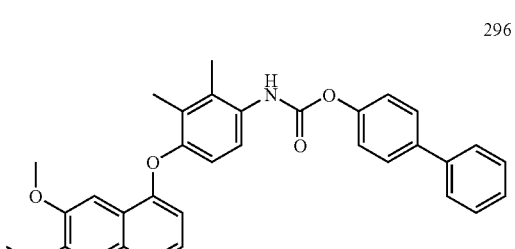
297
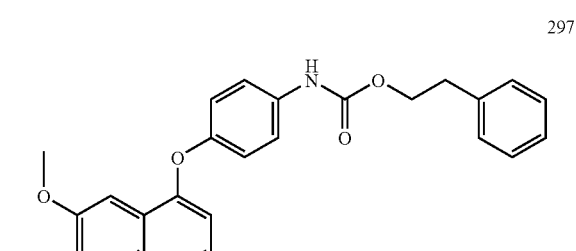
298
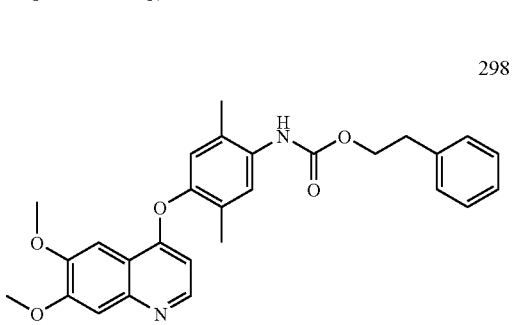

-continued
299
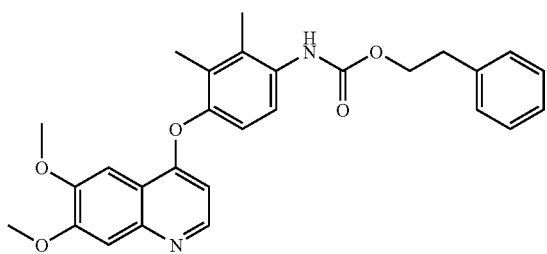
300
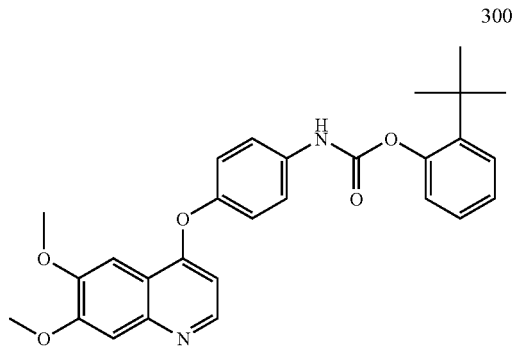
301
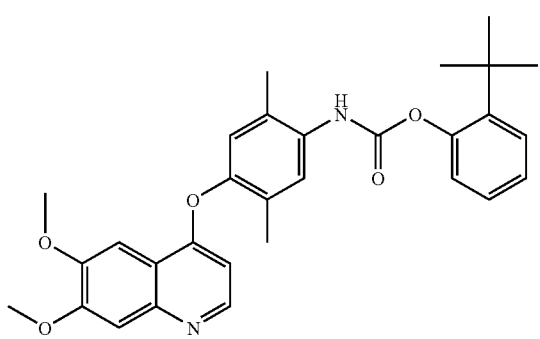
302
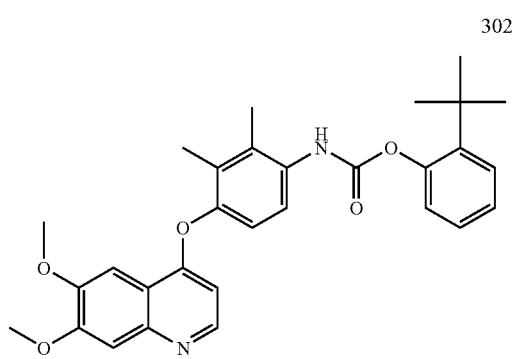
303
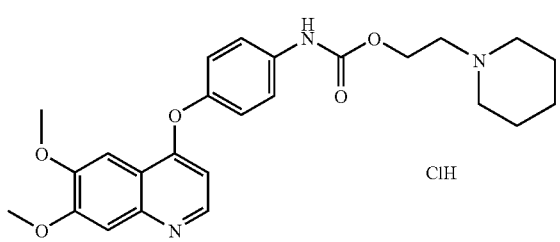
ClH
304
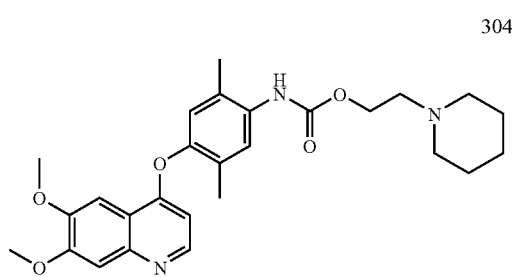
305
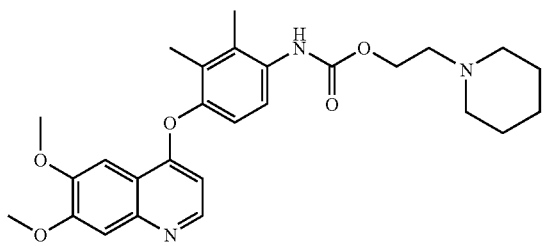
306
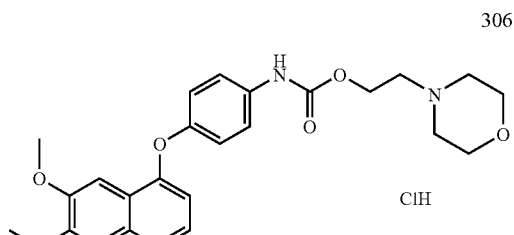
ClH
307
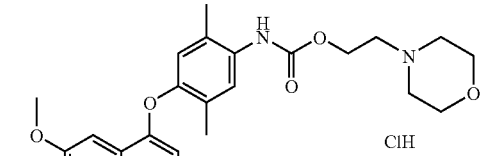
ClH
308
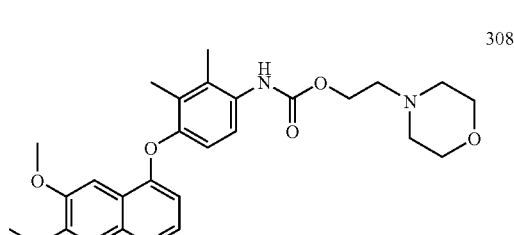

-continued
309
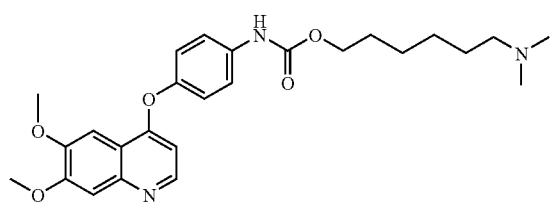
310
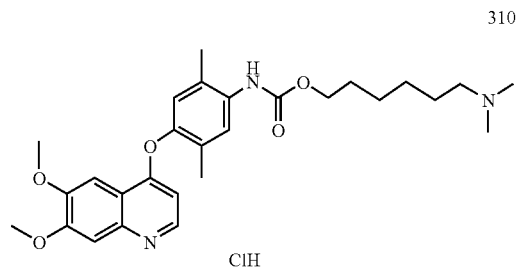
ClH
311
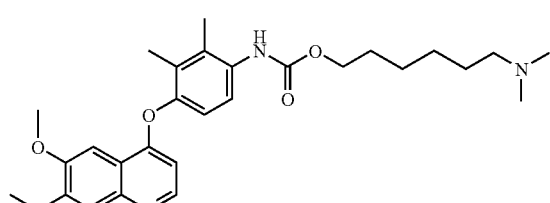
312
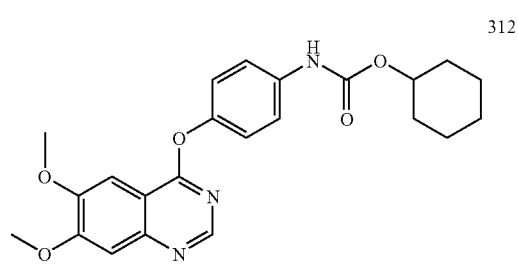
313
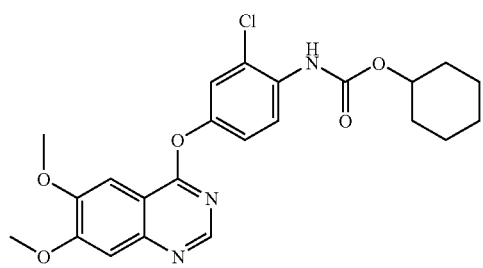
314
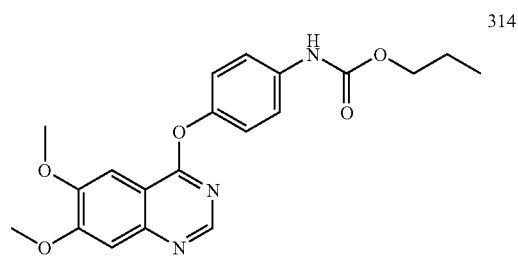
315
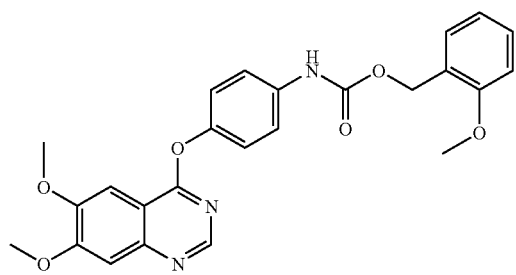
316
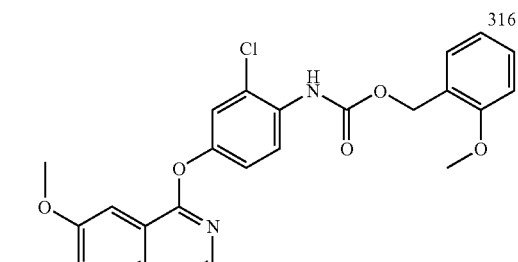
317
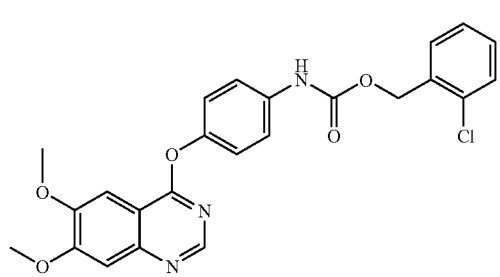
318
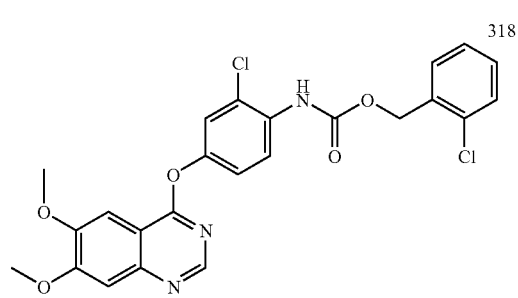

-continued
319
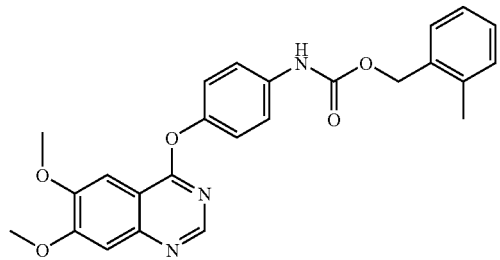
321
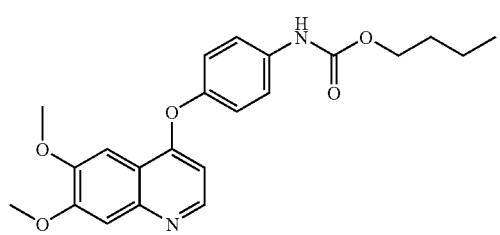
323
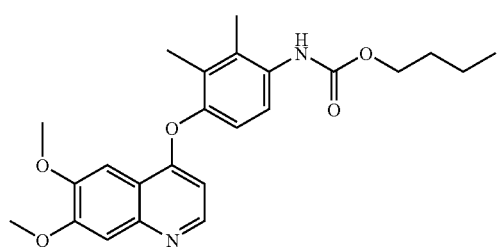
325
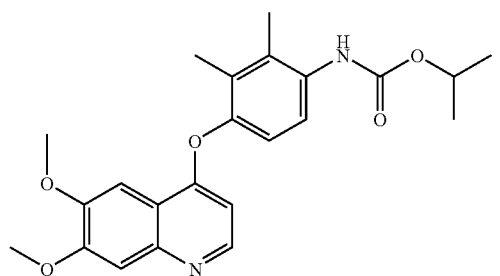
326
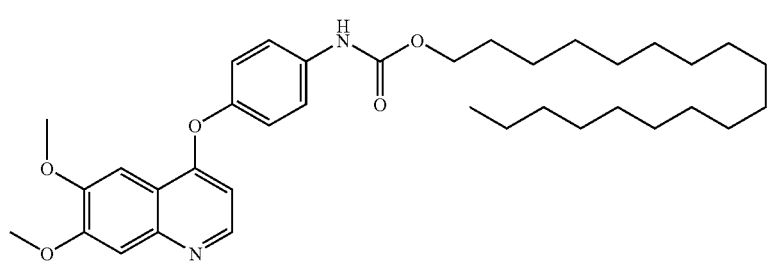
327
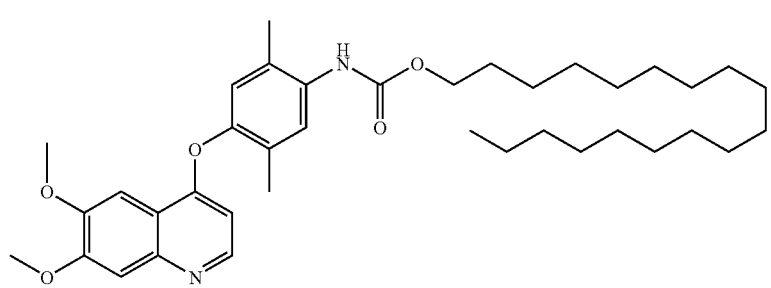
320
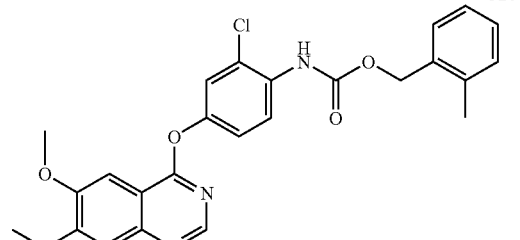
322
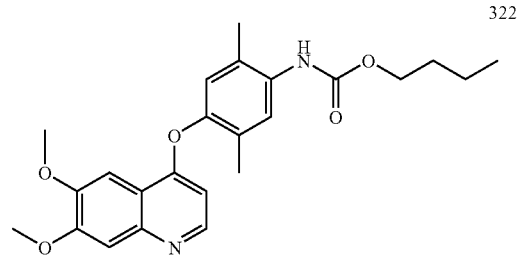
324

-continued
328
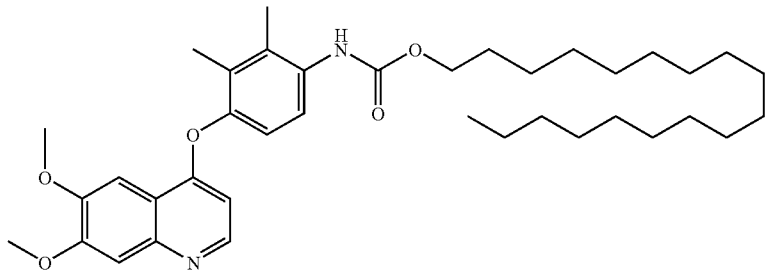
329
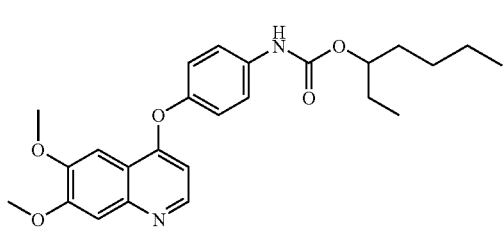
330
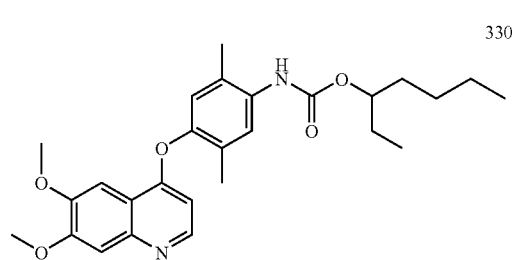
331
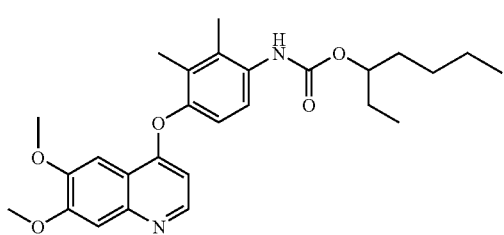
332
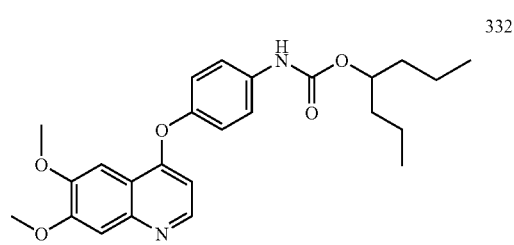
333
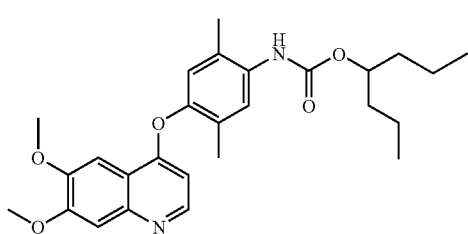
334
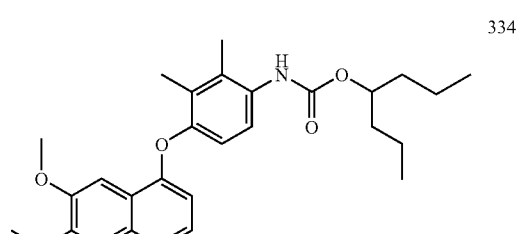
335
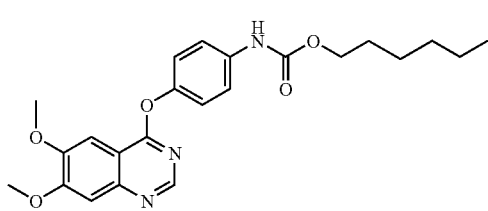
336
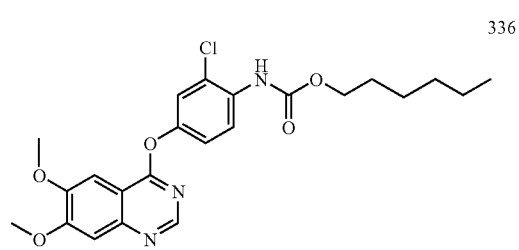
337
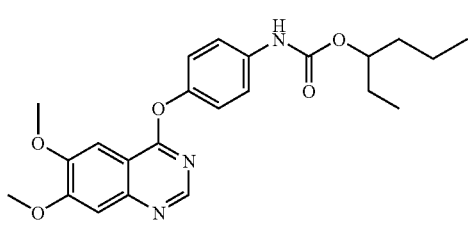
338
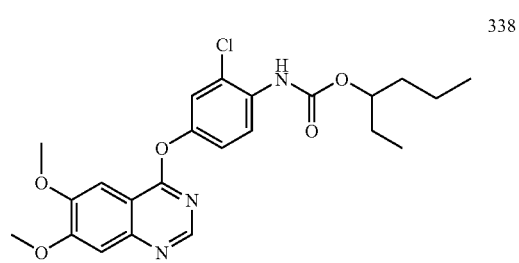

-continued
339
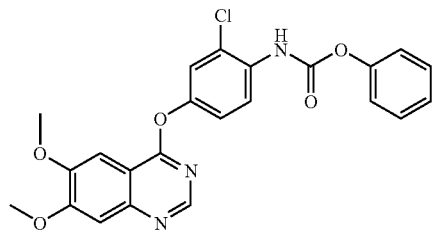
340
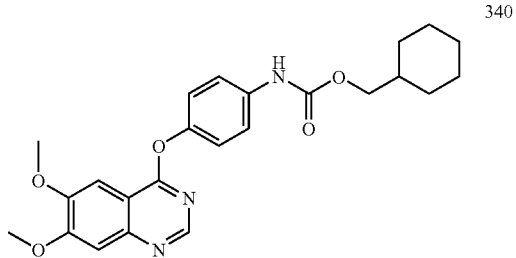
341
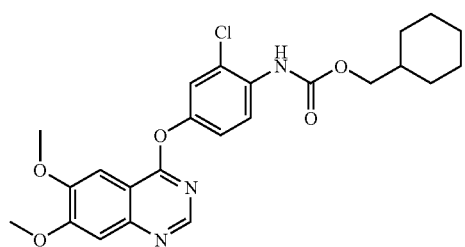
342
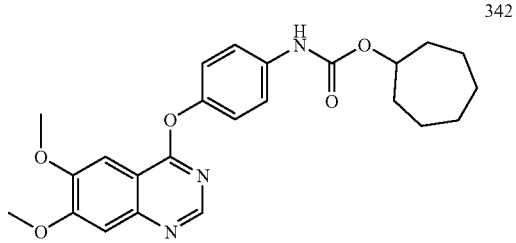
343
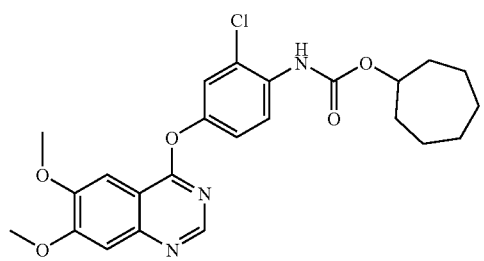
344
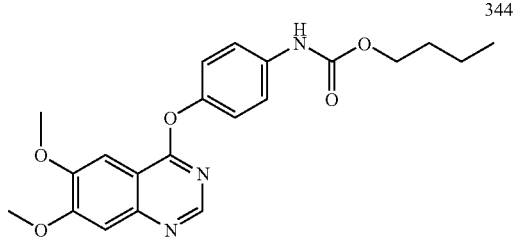
345
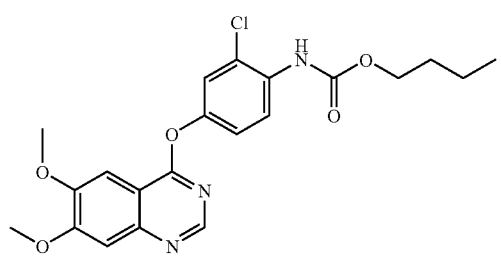
346
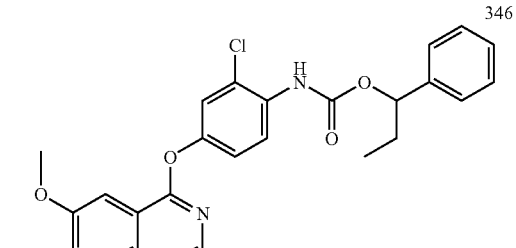
347
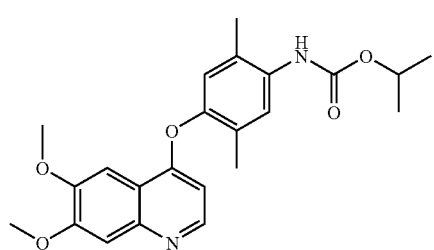
348
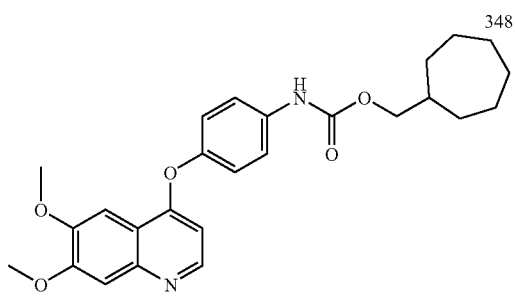

-continued
349 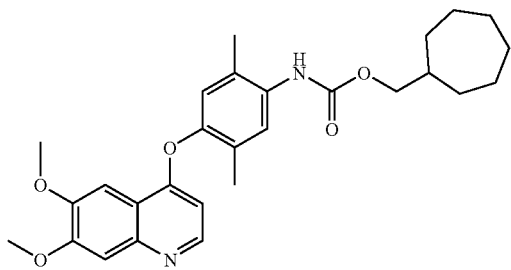
350 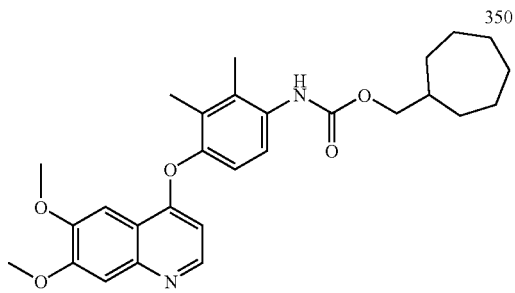
351 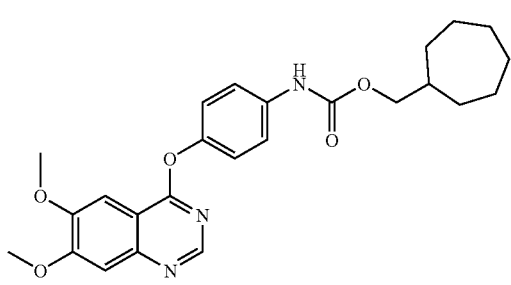
352 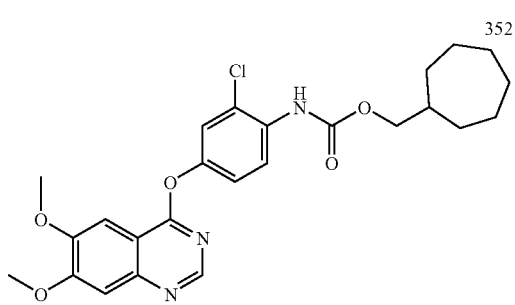
353 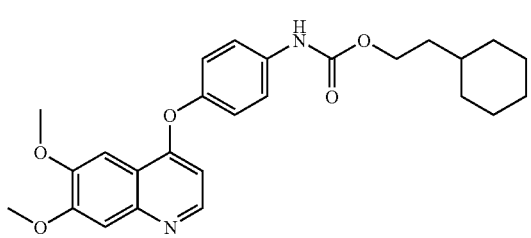
354 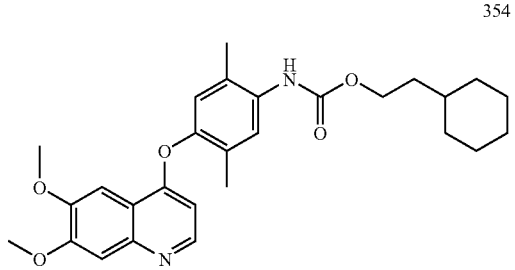
355 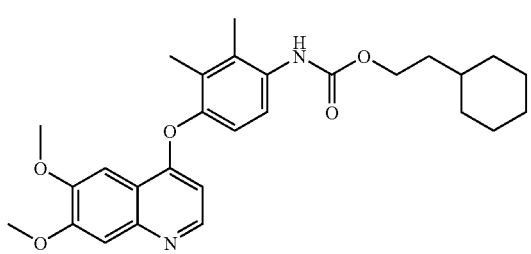
356 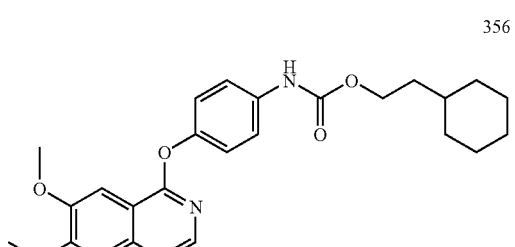
357 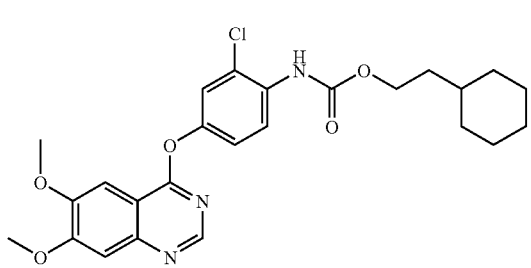
358 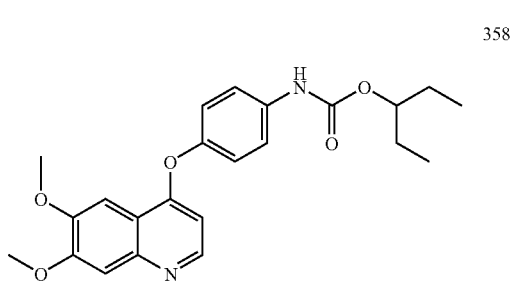

-continued
359
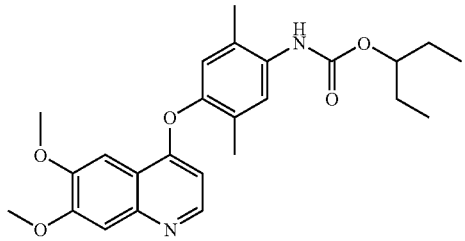
360
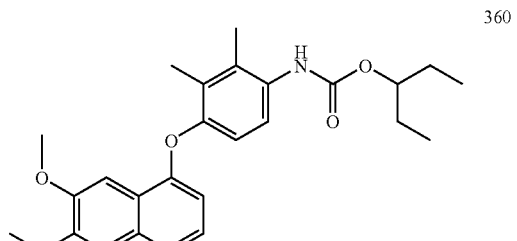
361
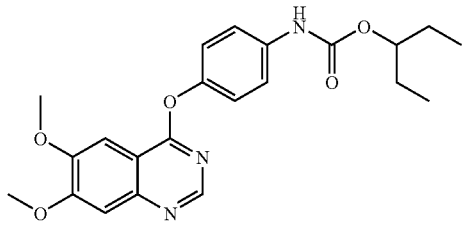
362
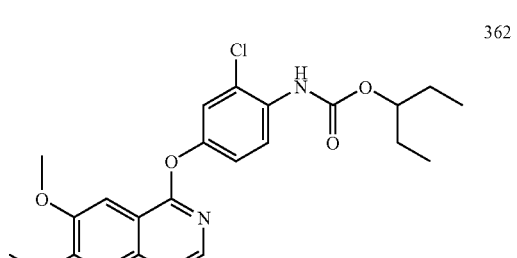
363
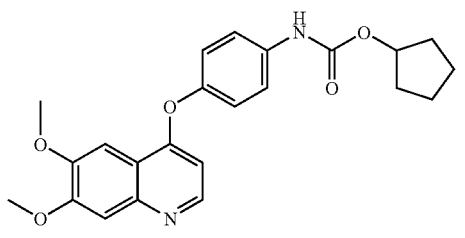
364
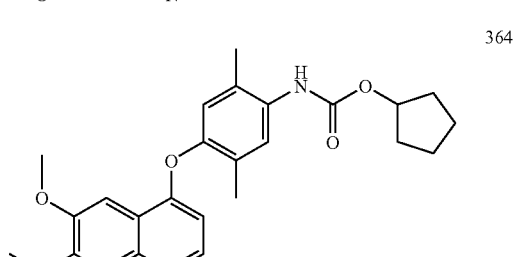
365
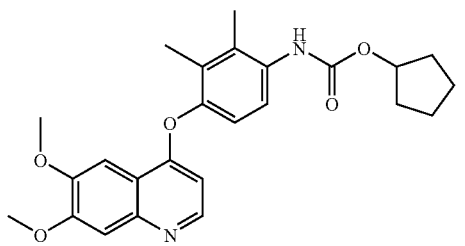
366
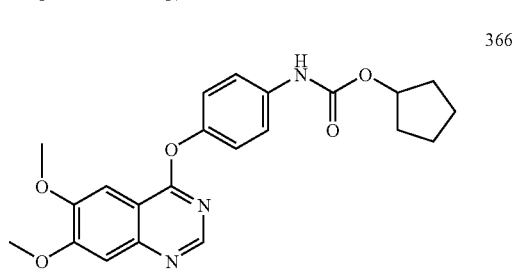
367
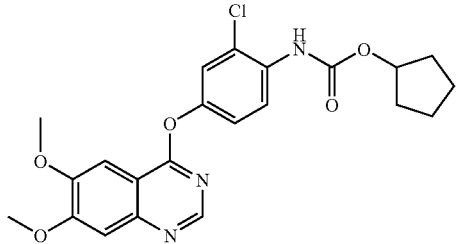
368
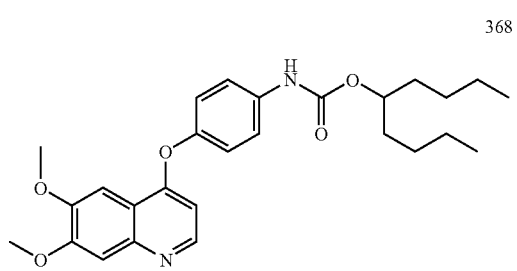
369
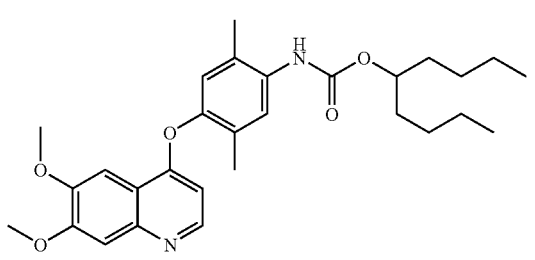
370
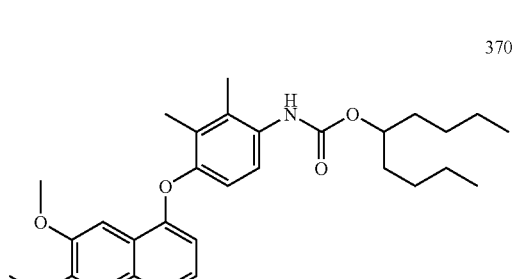

-continued
371
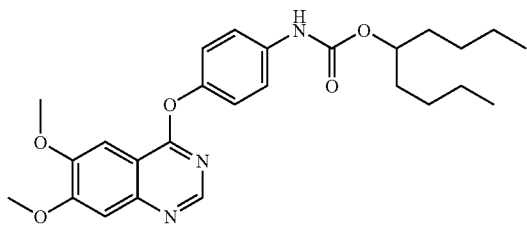
372
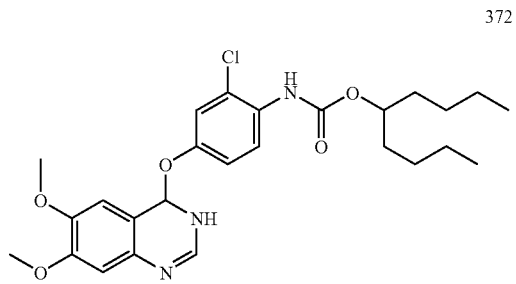
373
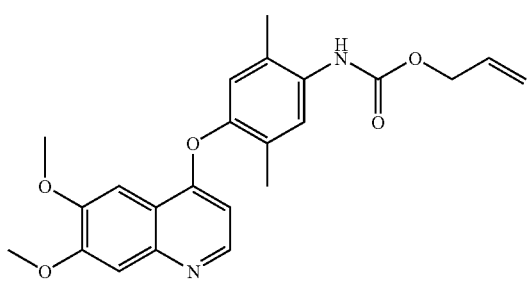
374
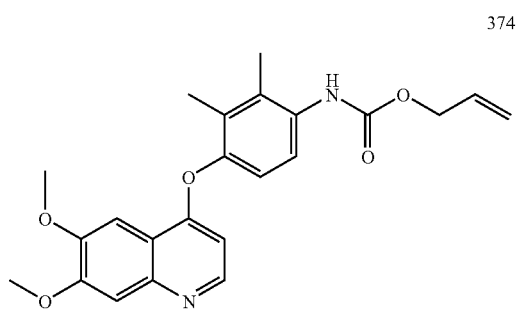
375
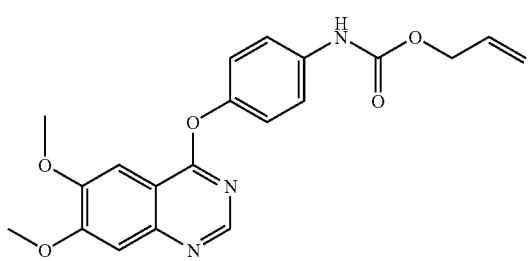
376
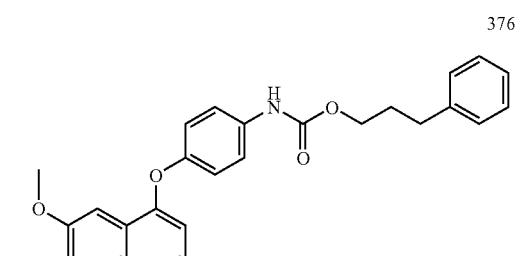
377
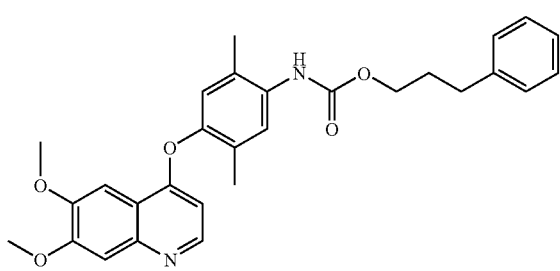
378
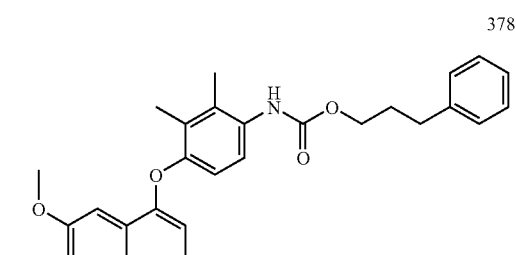
379
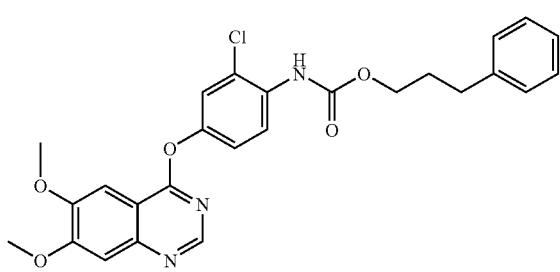
380
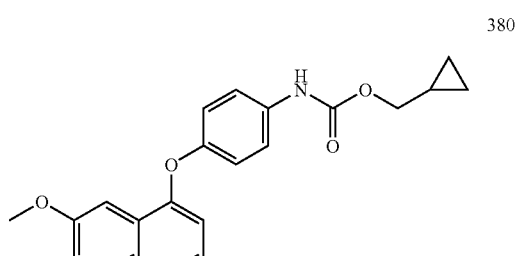

-continued
381
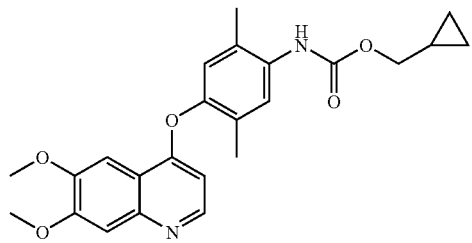
382
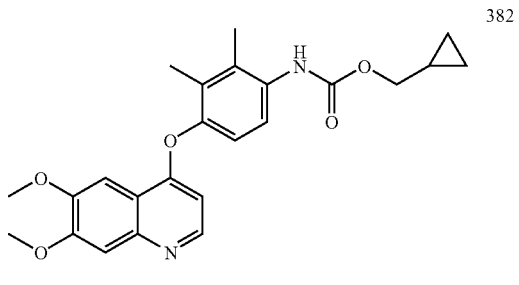
383
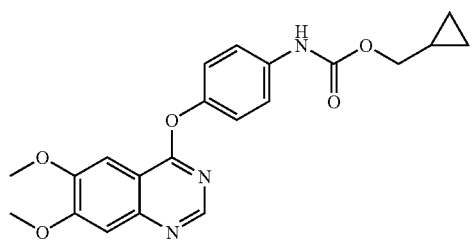
384
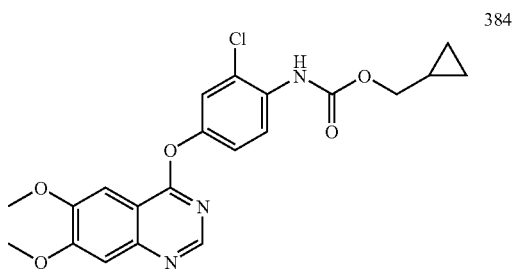
385
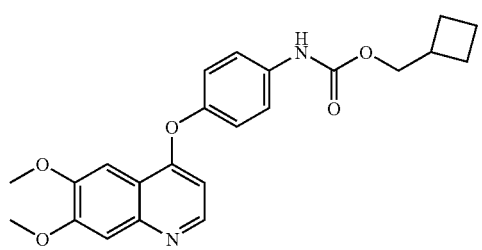
386
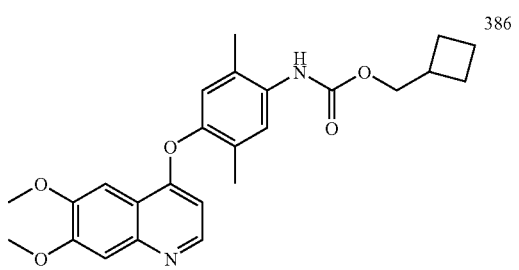
387
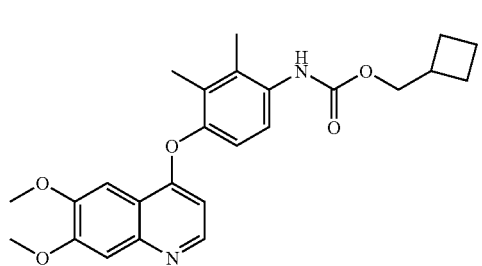
388
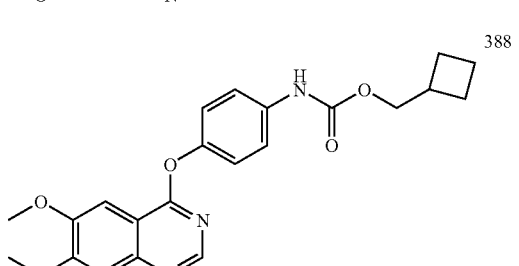
389
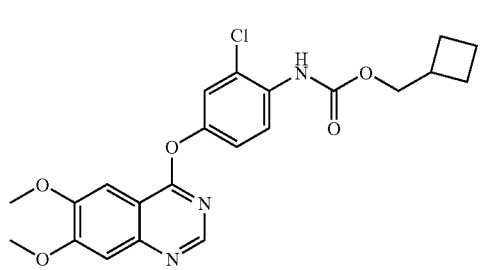
390
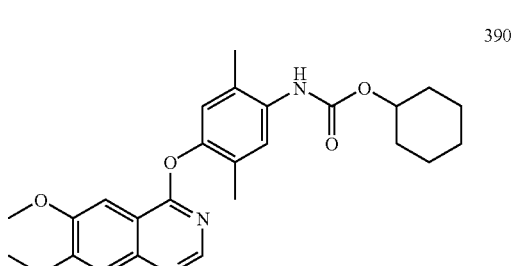
391
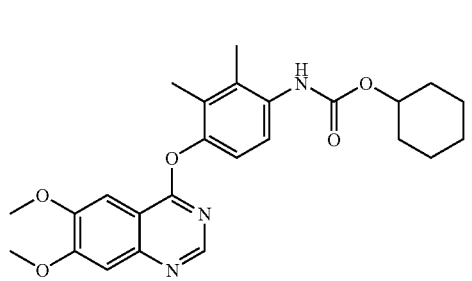
392
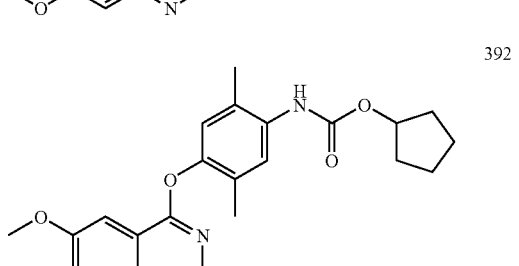

-continued
393
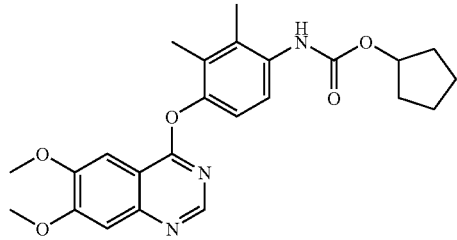
394
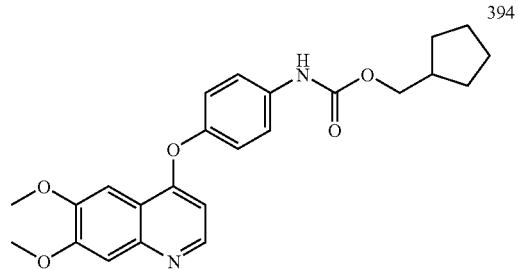
395
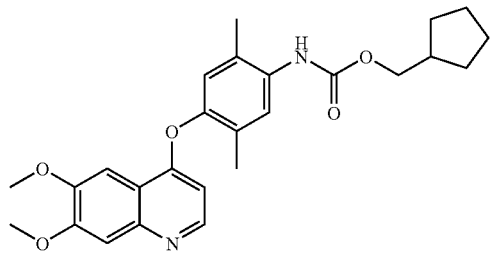
396
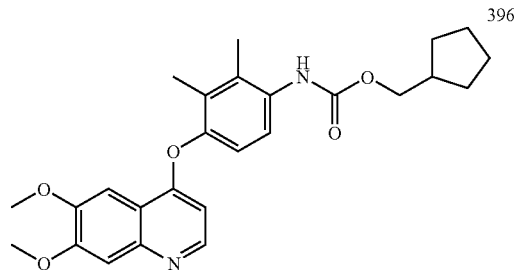
397
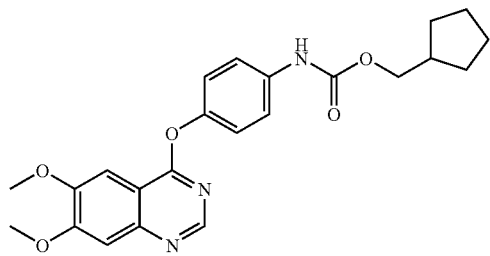
398
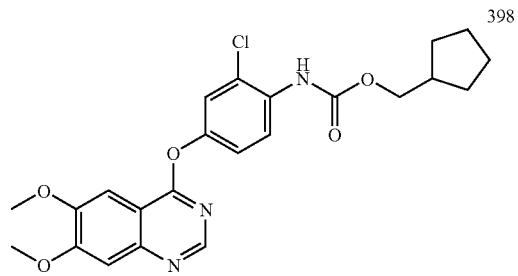
399
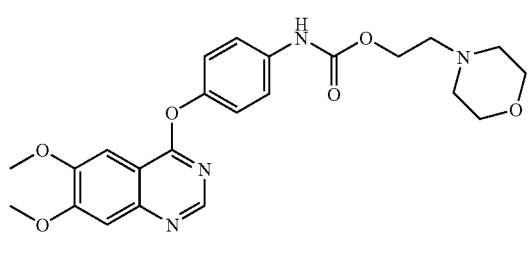
400
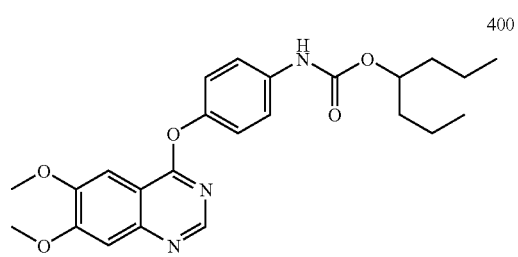
401
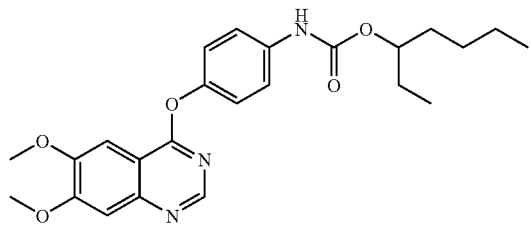
402
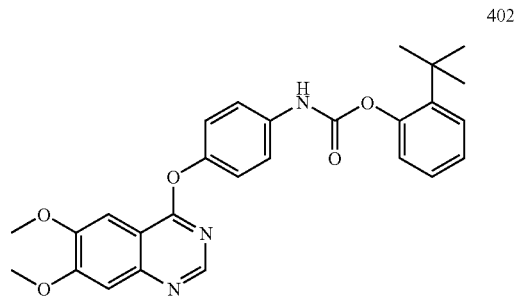

-continued
403
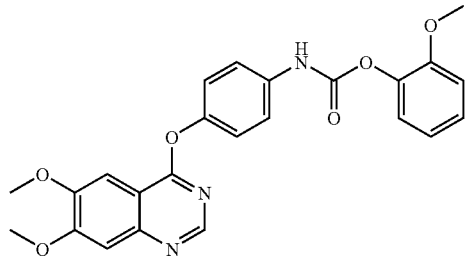
404
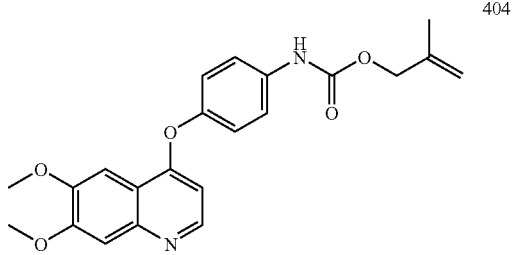
405
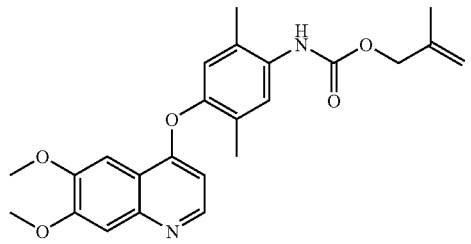
406
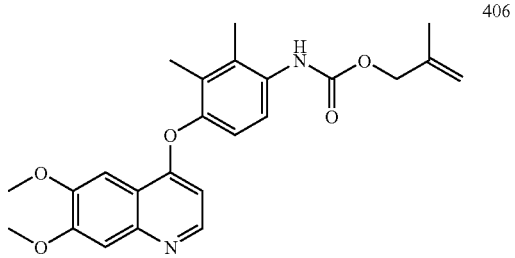
407
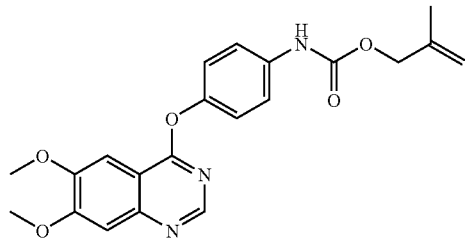
408
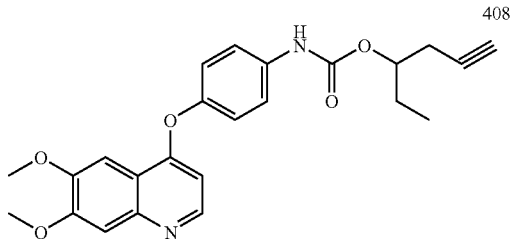
409
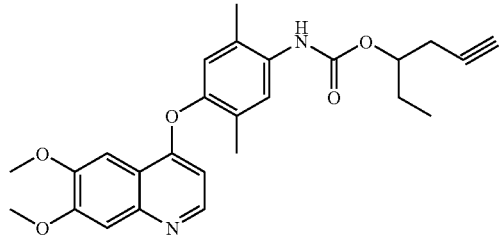
410
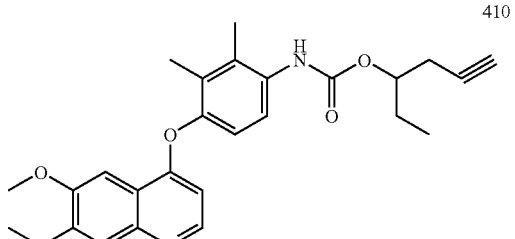
411
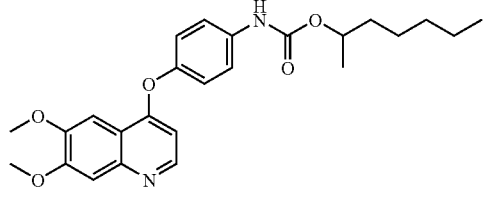
412
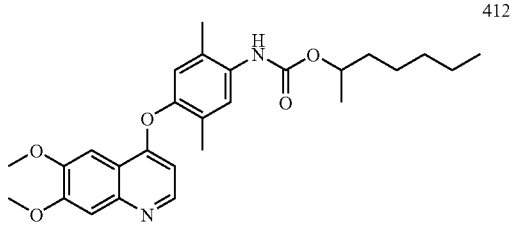
413
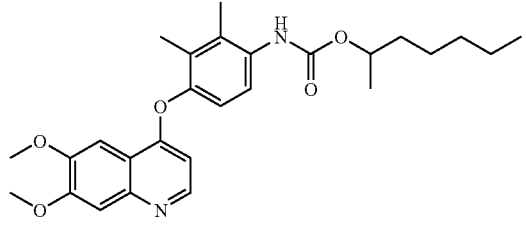
414
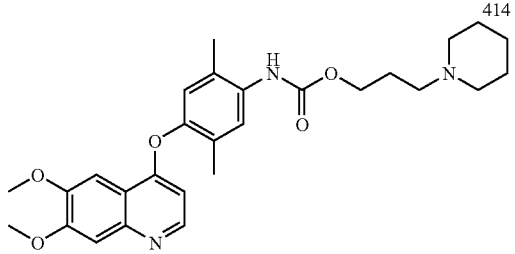

-continued
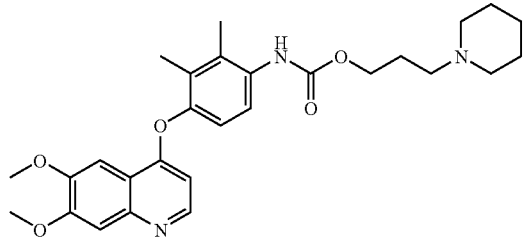
415
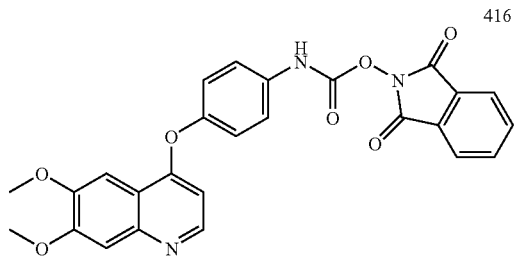
416
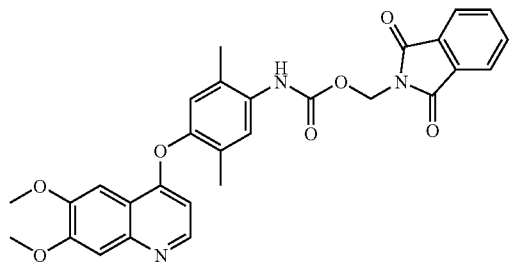
417
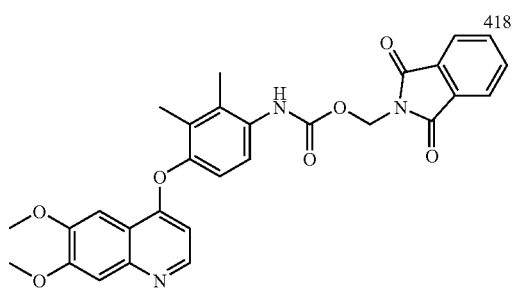
418
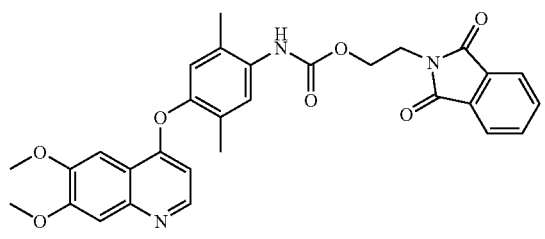
419
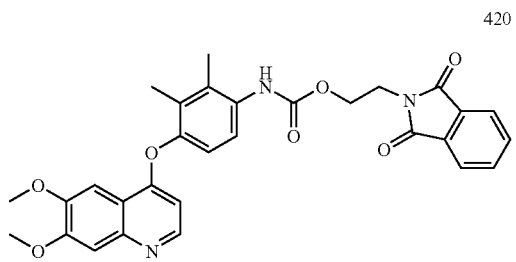
420
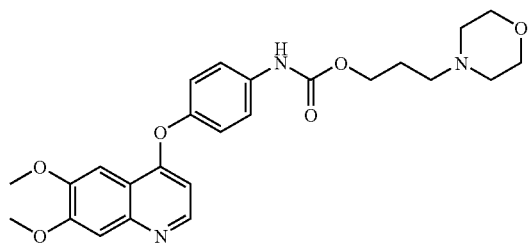
421
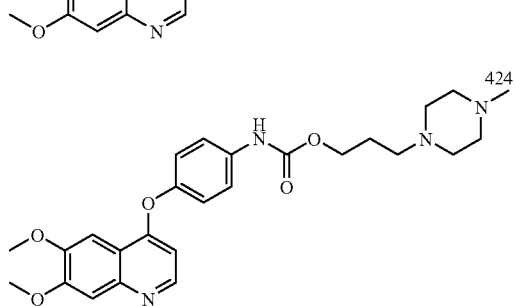
422
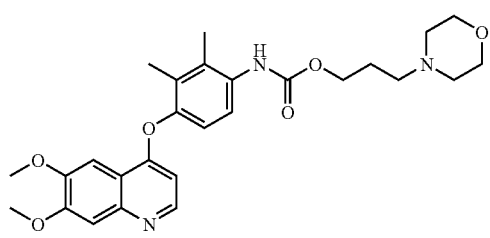
423
424

-continued
425
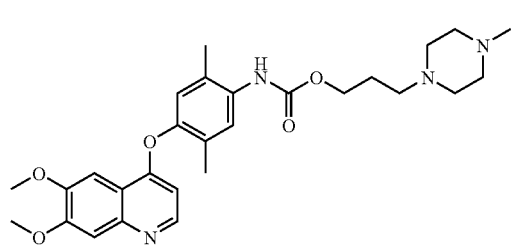
426
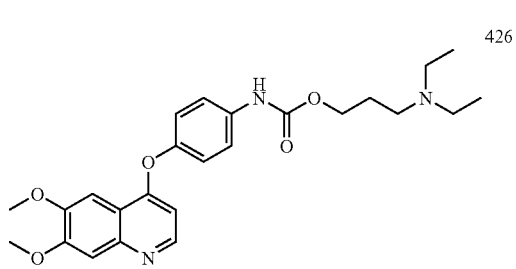
427
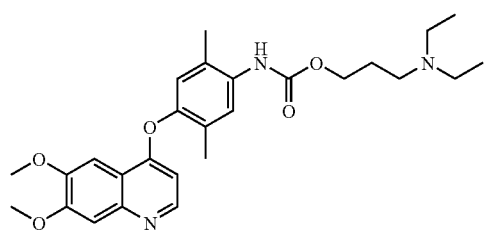
428
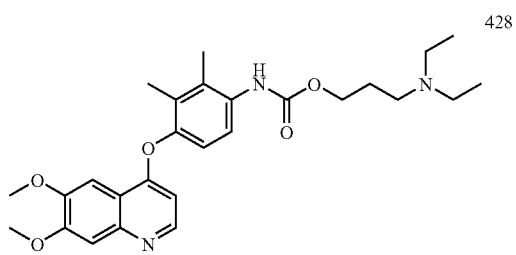
429
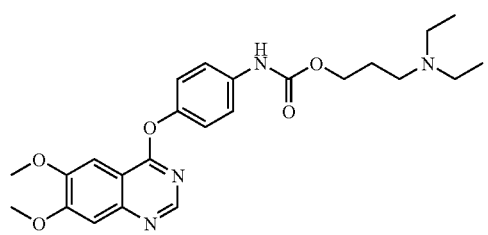
430
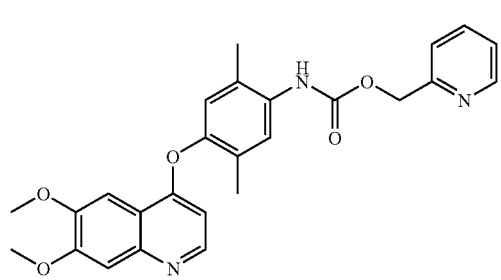
431
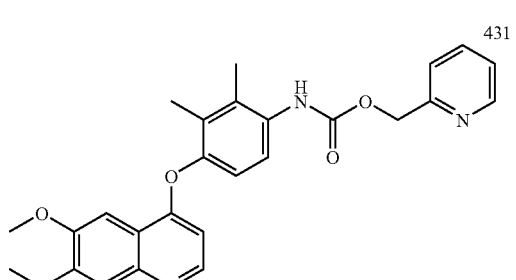
432
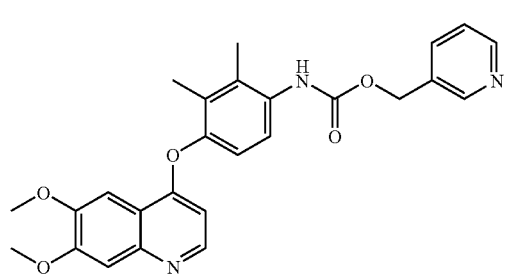
433
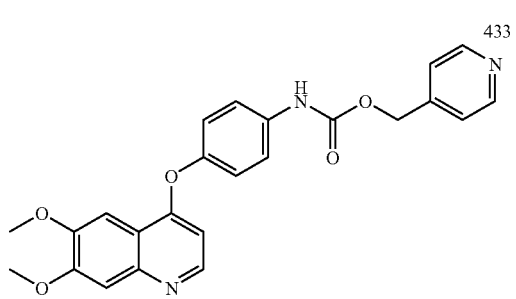

-continued
434
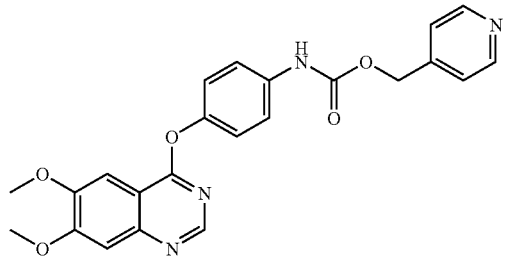
435
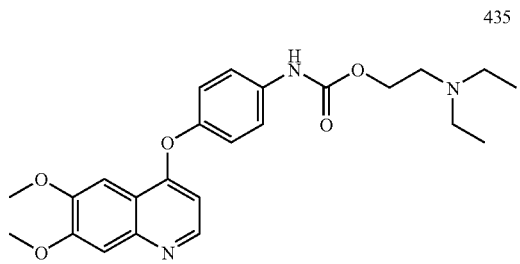
436
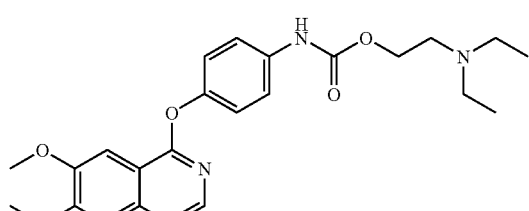
437
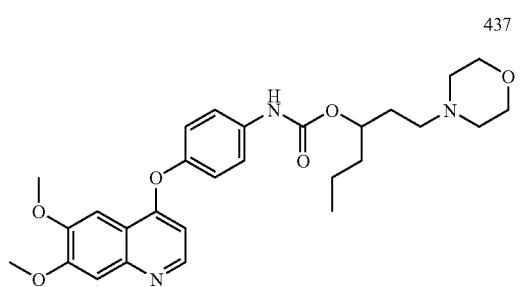
438
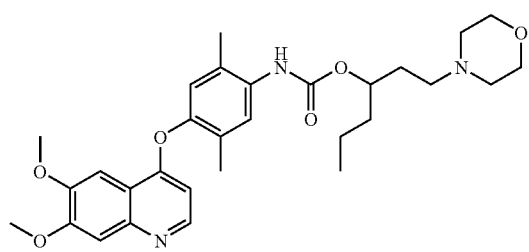
439
440
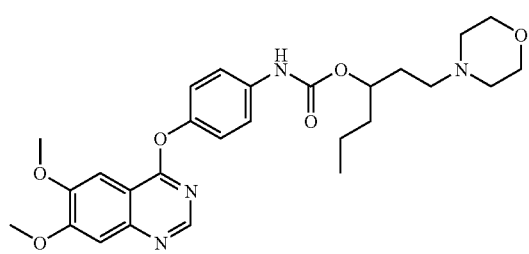
441
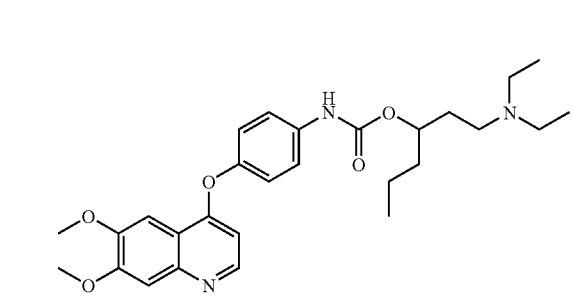
442
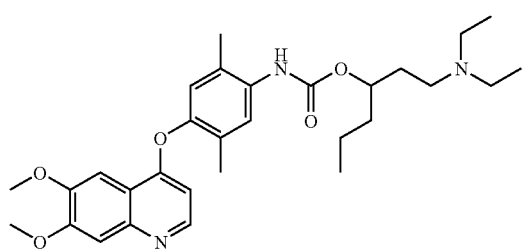
443
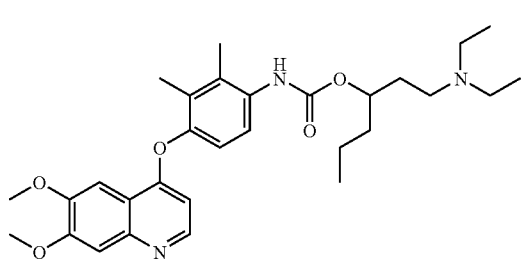

-continued
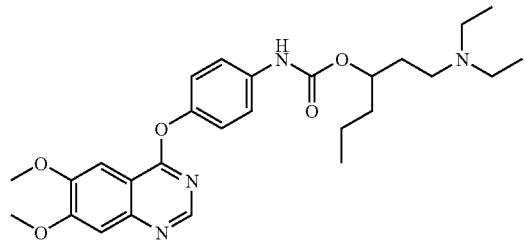
444
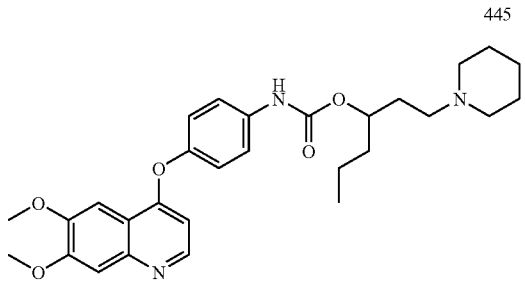
445
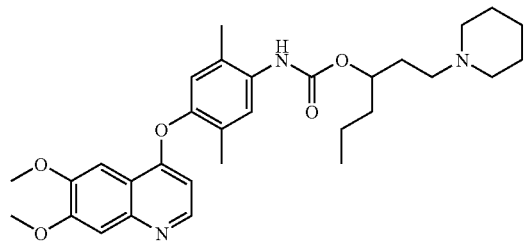
446
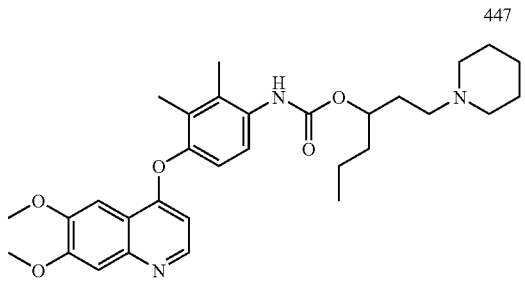
447
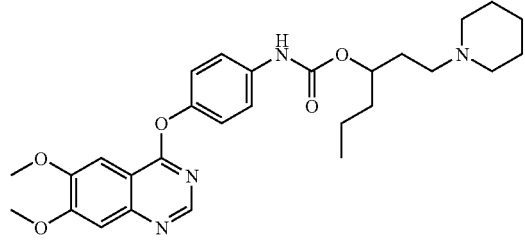
448
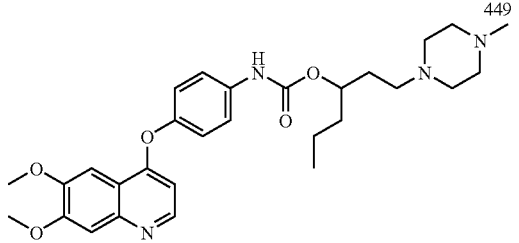
449
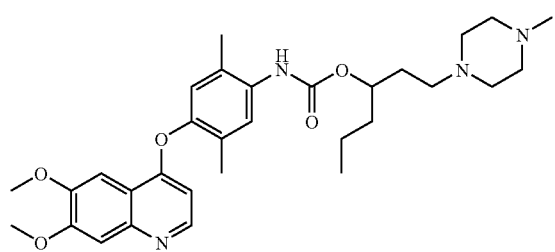
450
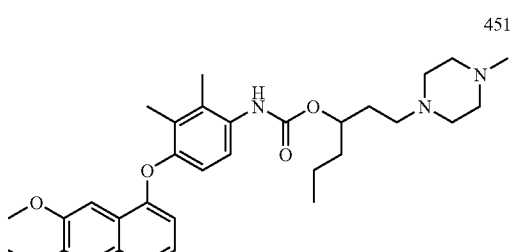
451
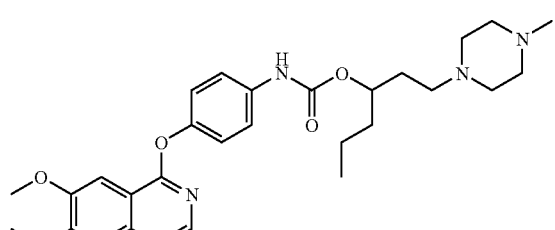
452
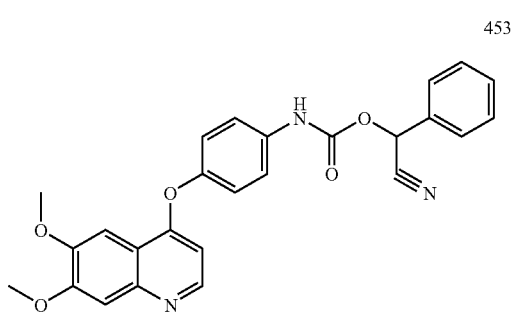
453

-continued
454
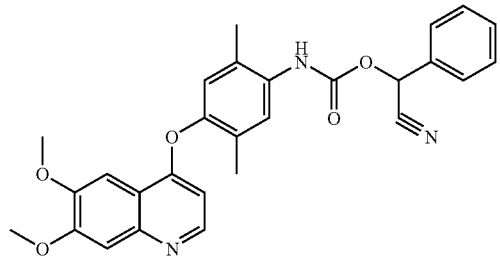
455
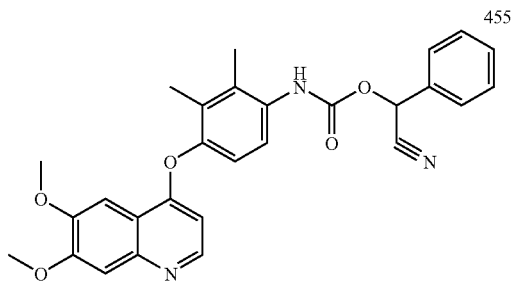
456
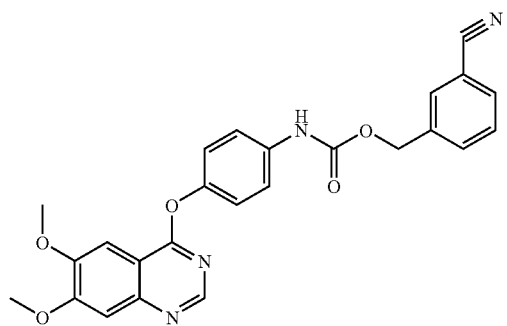
457
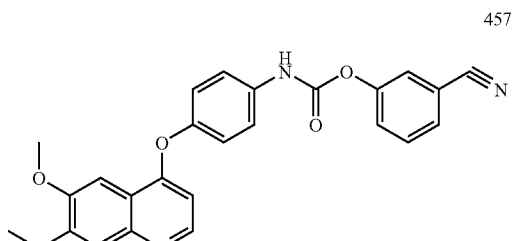
458
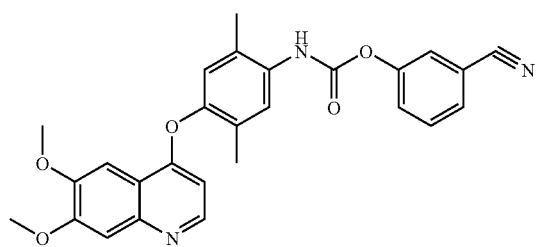
459
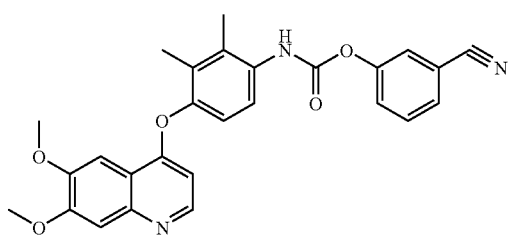
460
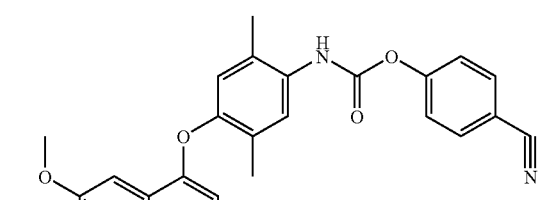
461
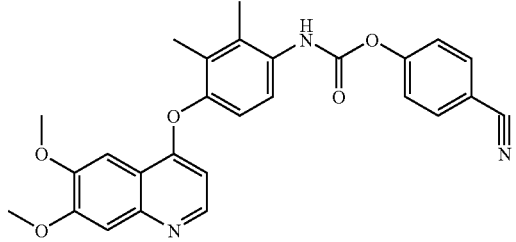
462
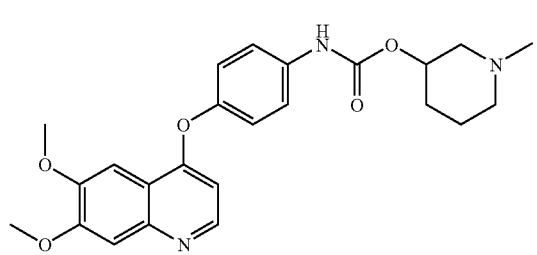
463
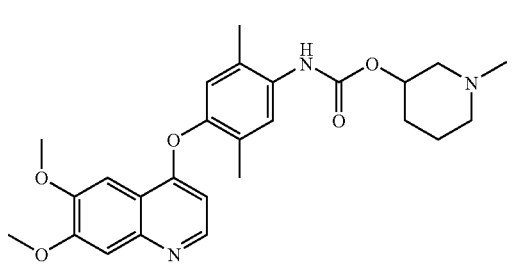

-continued
464
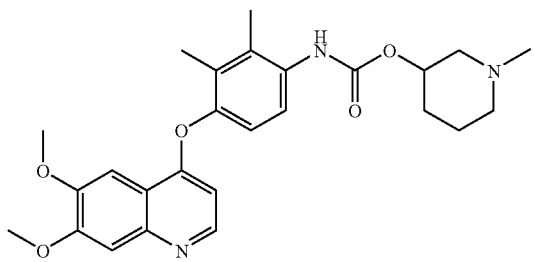
465
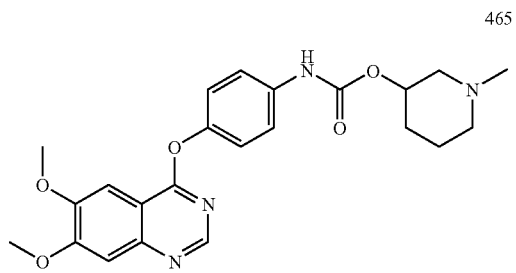
466
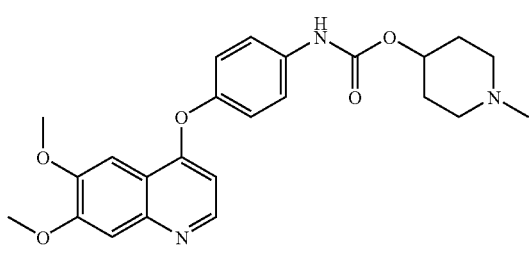
467
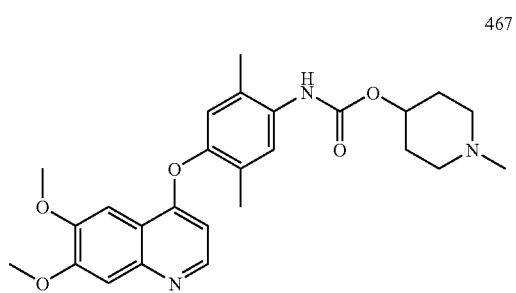
468
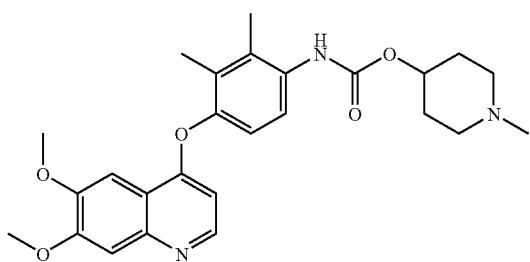
469
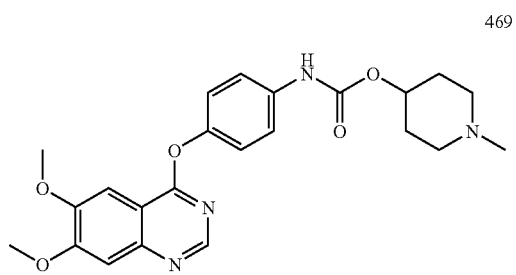
470
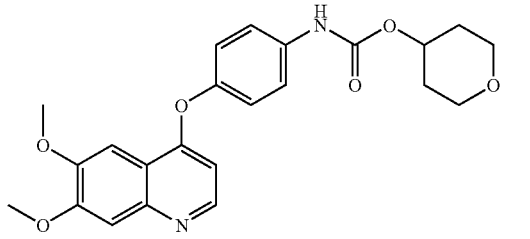
471
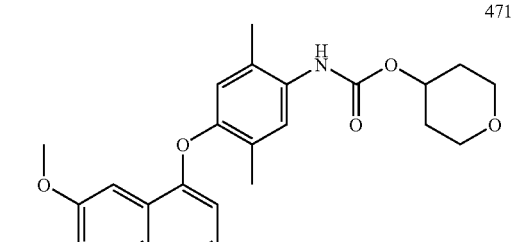
472
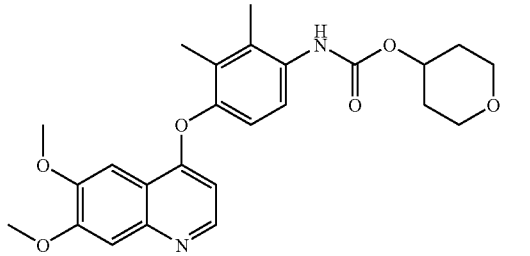
473
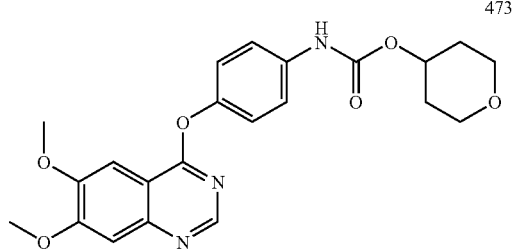

-continued
474
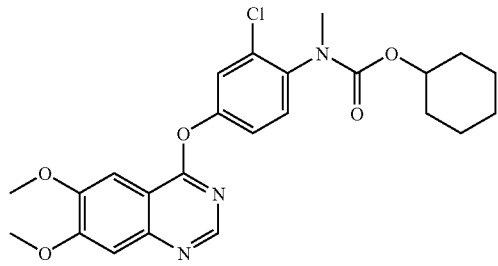
475
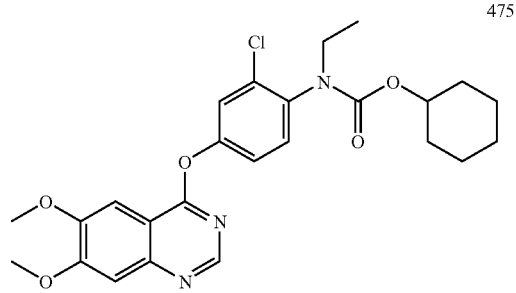
476
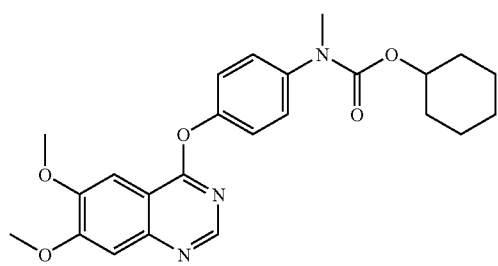
477
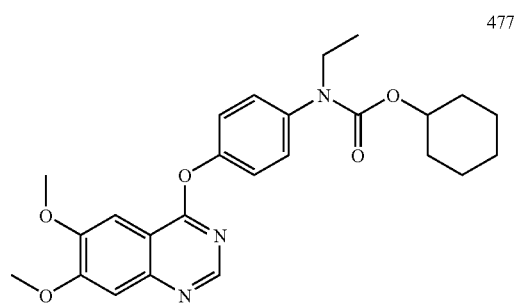
478
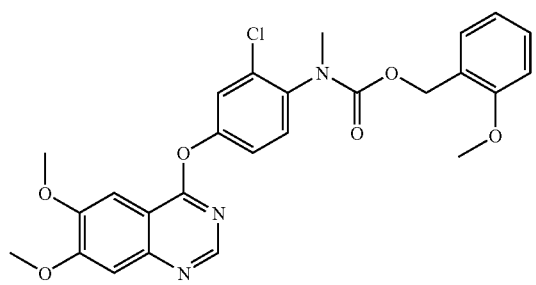
479
480
481
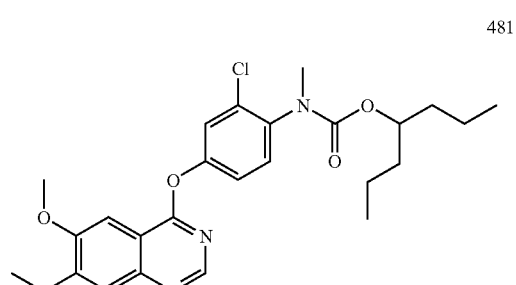
482
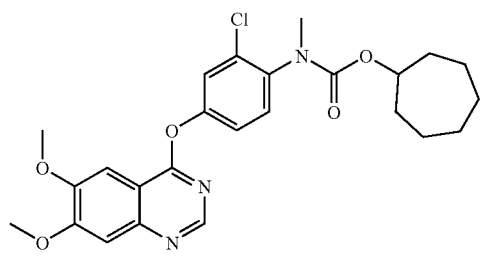
483
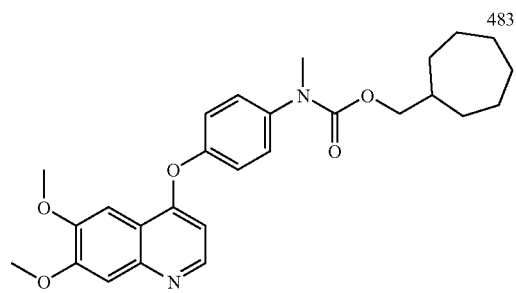

-continued
484
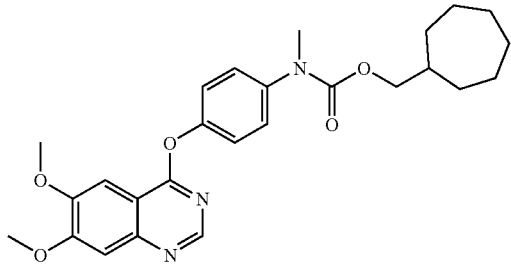
485
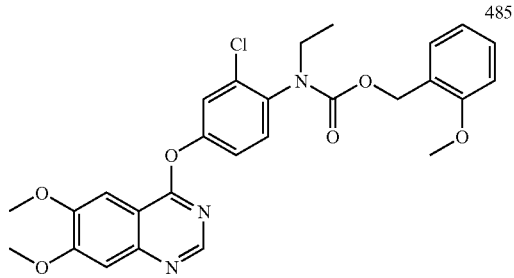
486
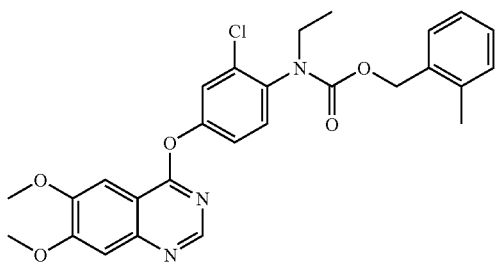
487
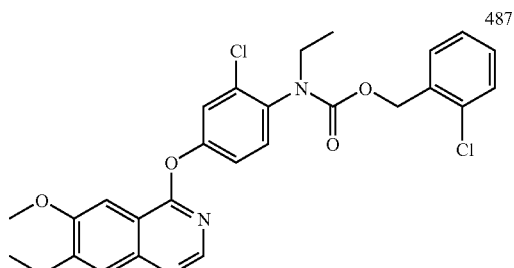
488
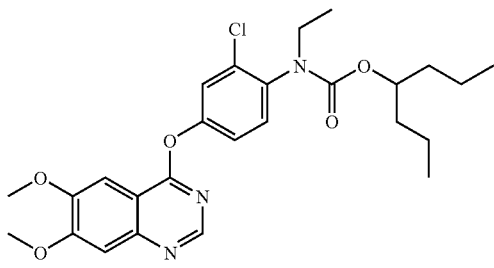
489
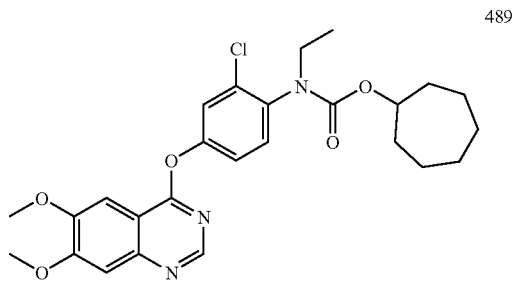
490
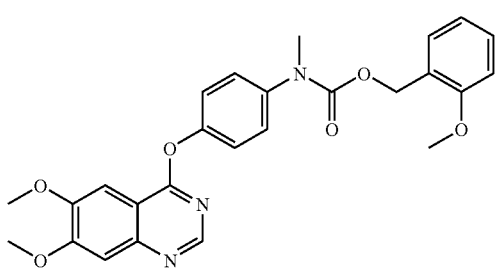
491
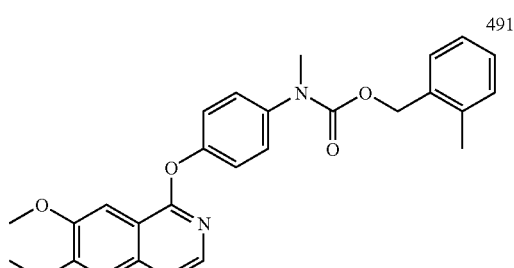
492
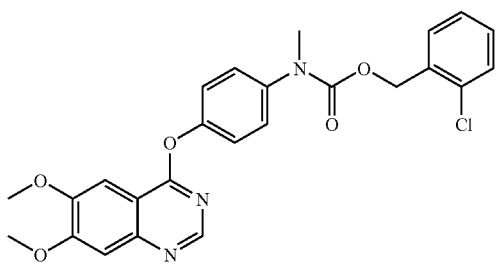
493
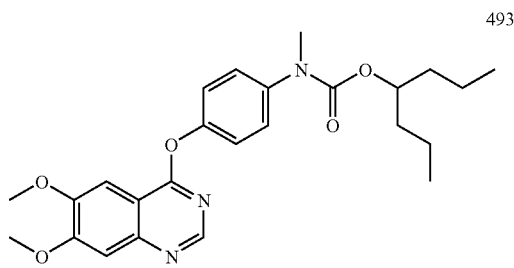

-continued
494
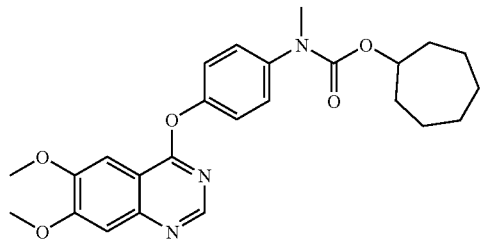
495
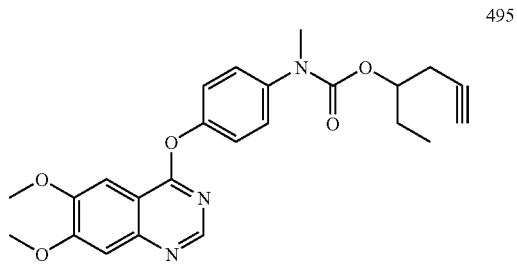
496
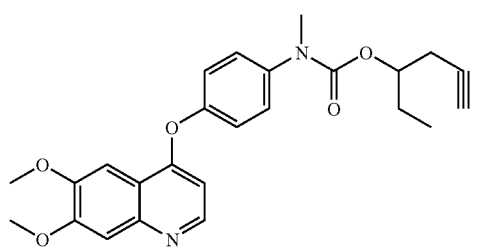
497
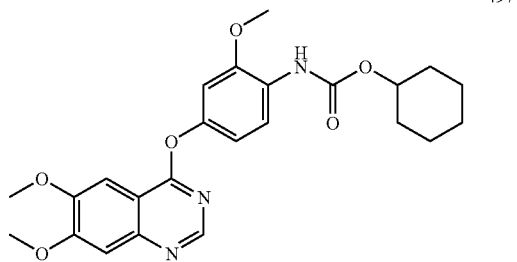
498
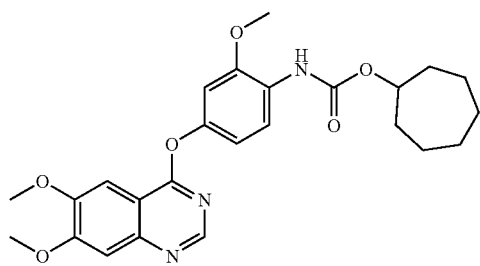
499
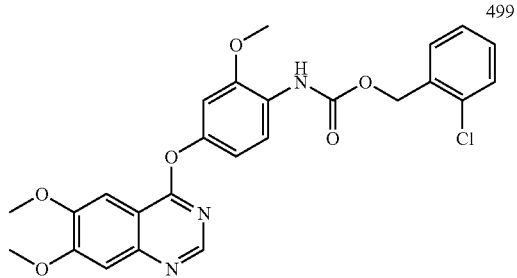
500
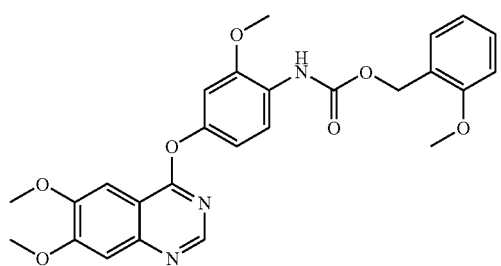
501
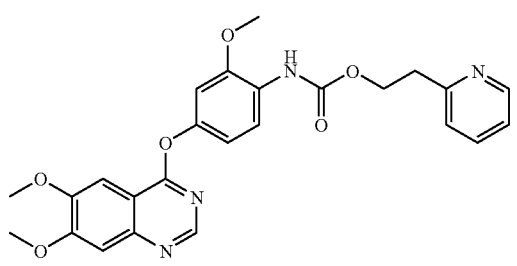
502
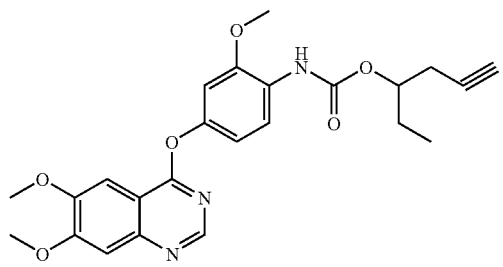
503
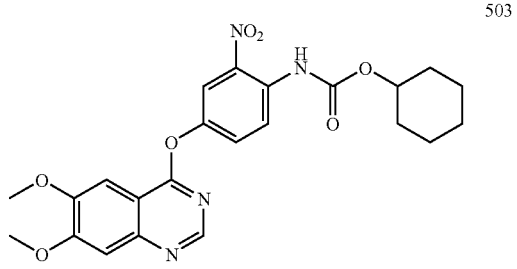

-continued
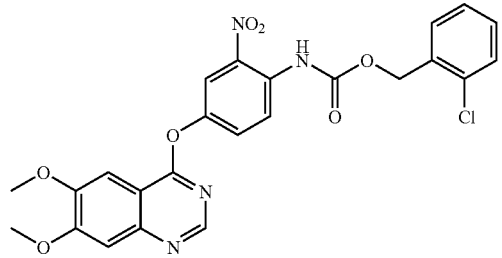
504
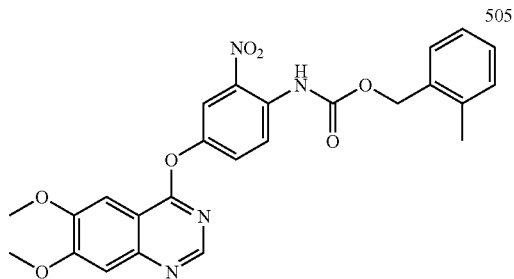
505
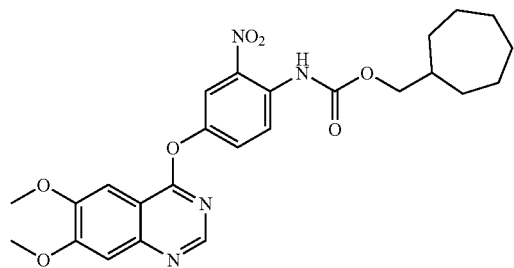
506
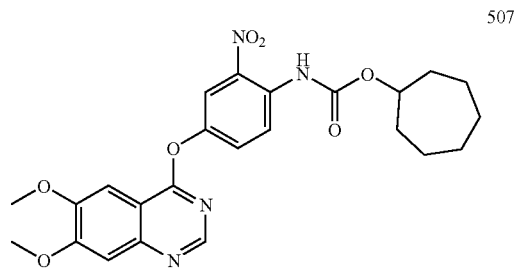
507
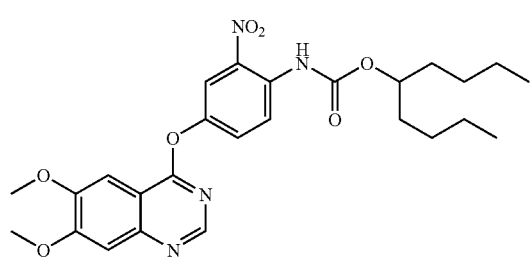
508
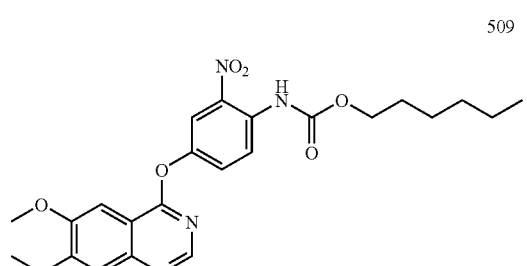
509
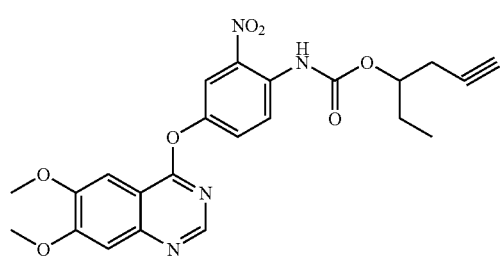
510
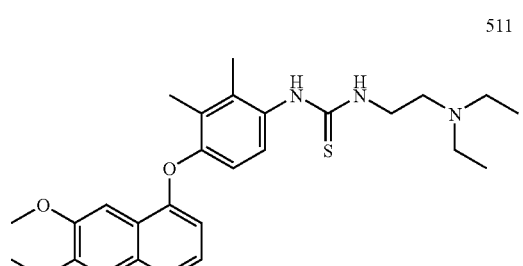
511
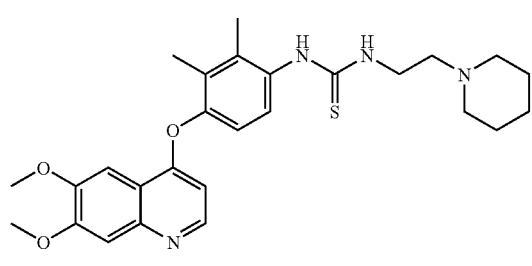
512
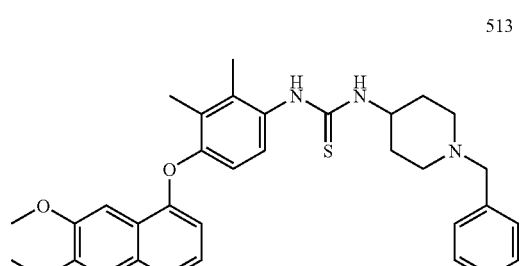
513

-continued
514
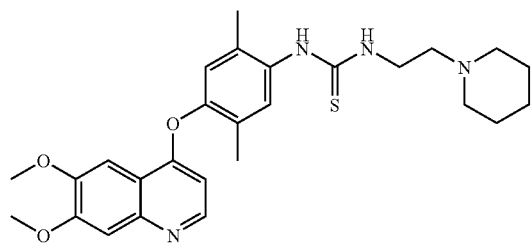
515
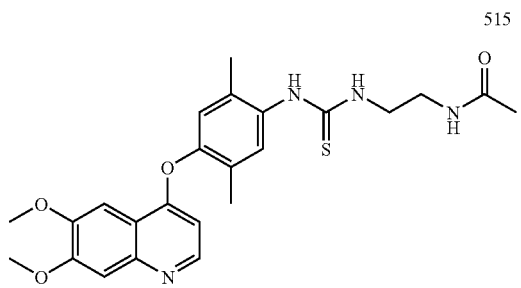
516
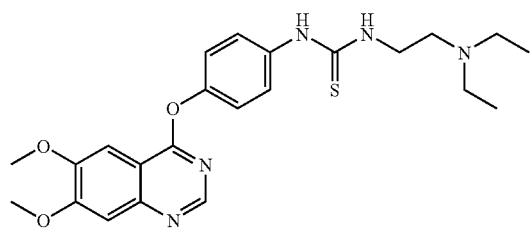
517
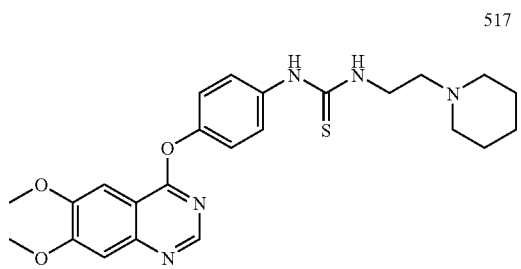
518
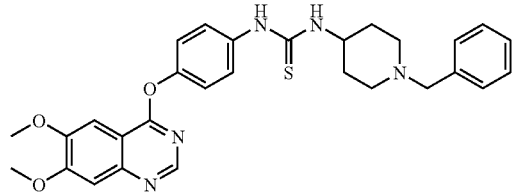
519
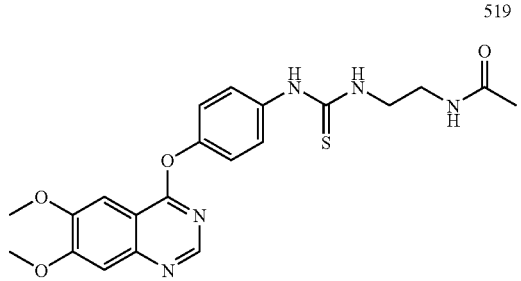
520
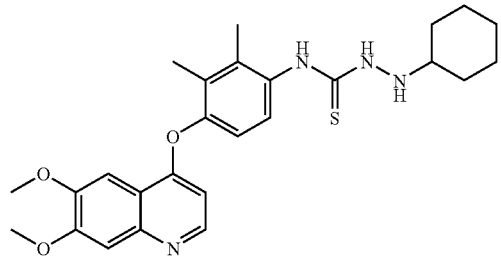
521
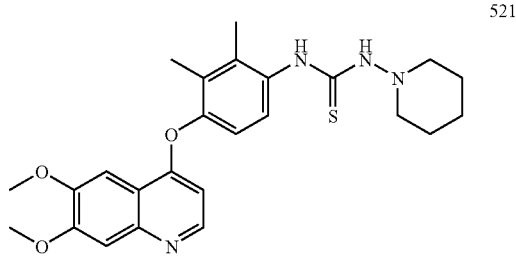
522
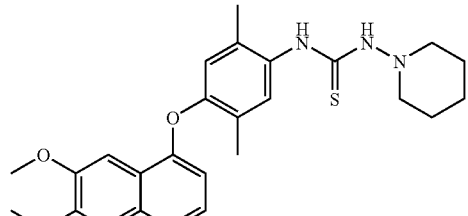
523
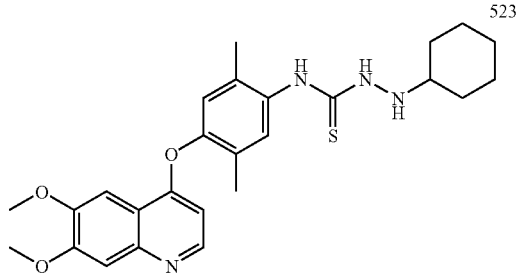

-continued
651  652
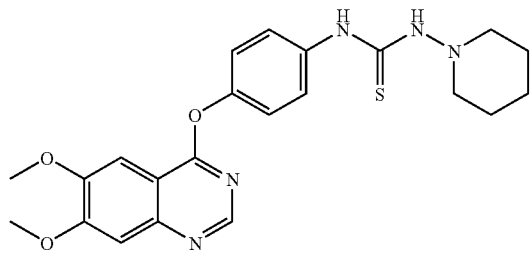
524
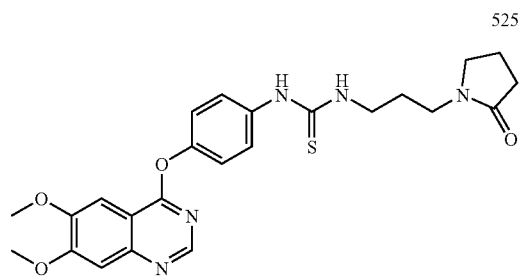
525
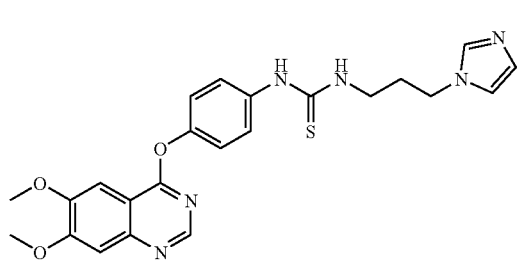
526
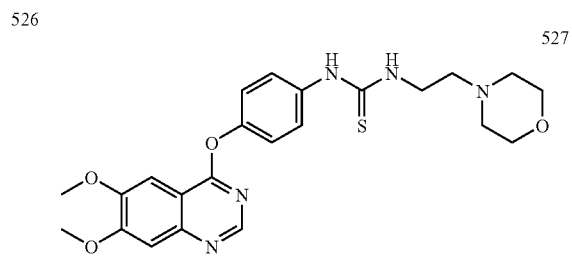
527
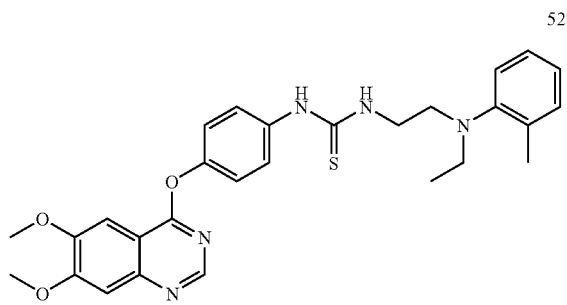
528
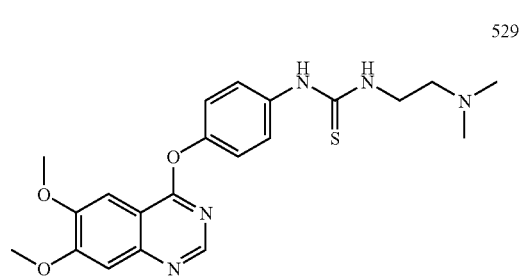
529
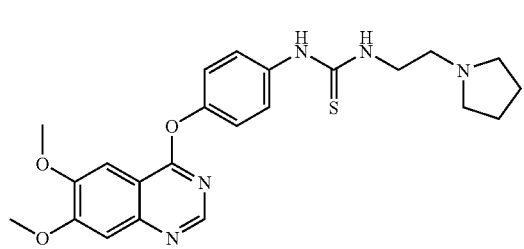
530
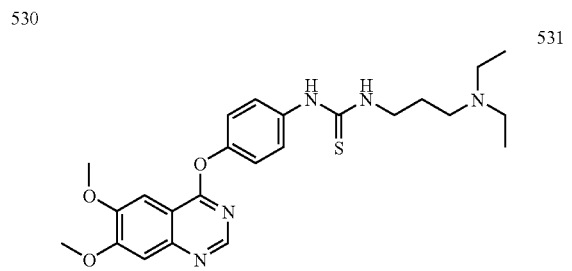
531
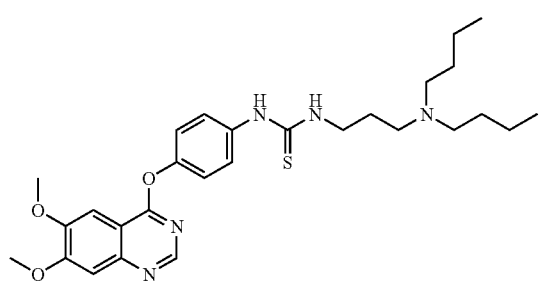
532
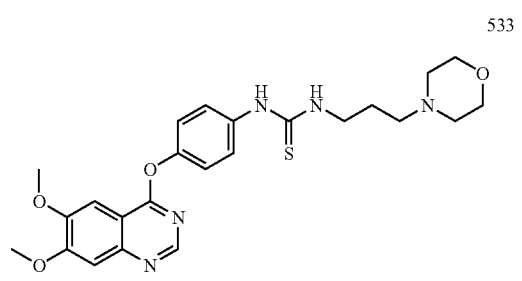
533

-continued
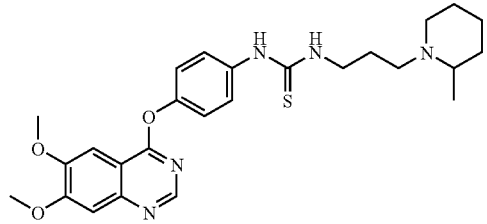
534
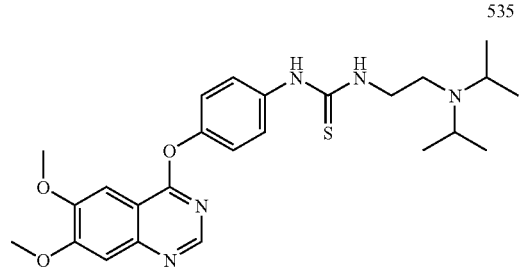
535
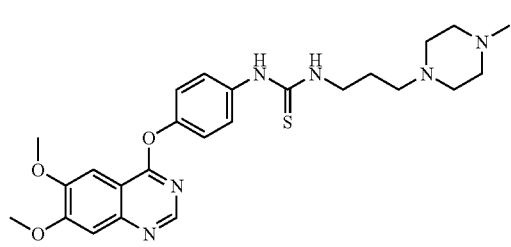
536
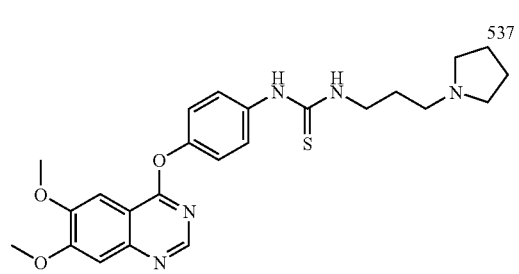
537
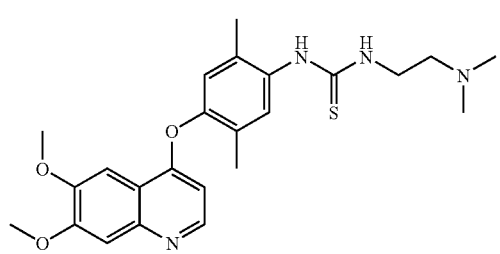
538
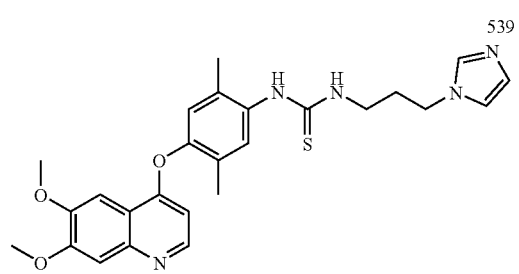
539
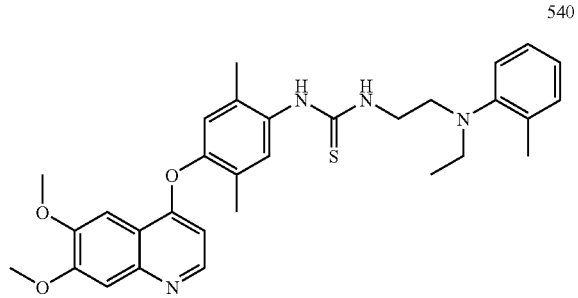
540
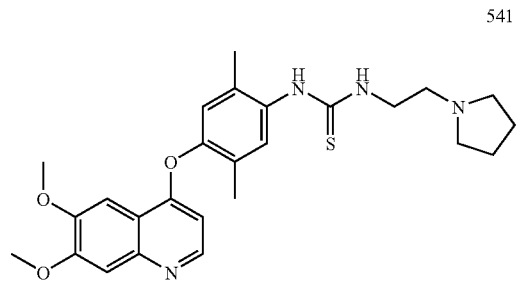
541
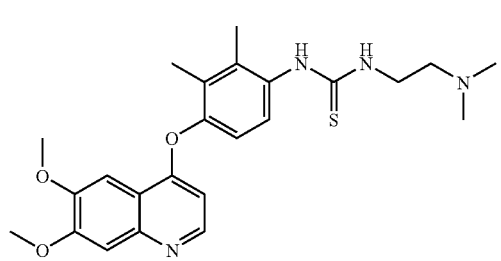
542
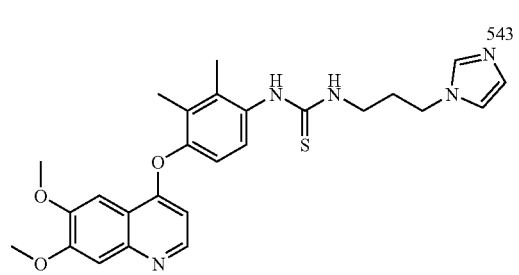
543

-continued
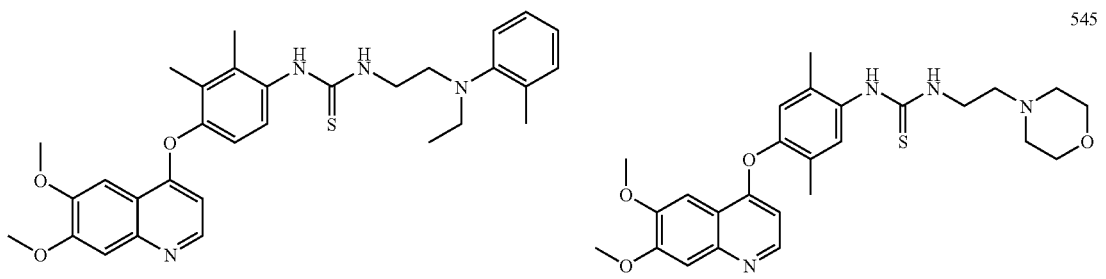
544
545
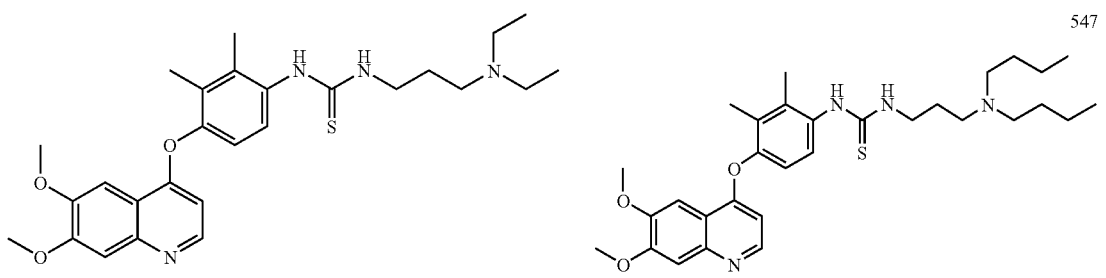
546
547
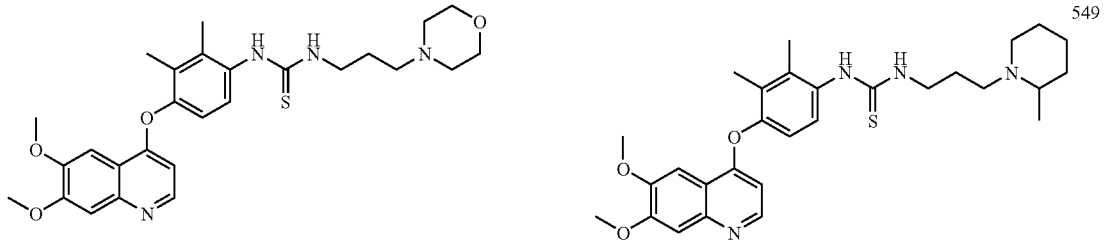
548
549
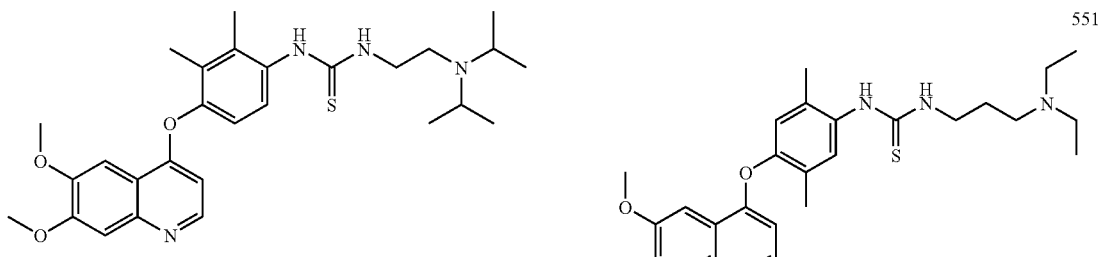
550
551
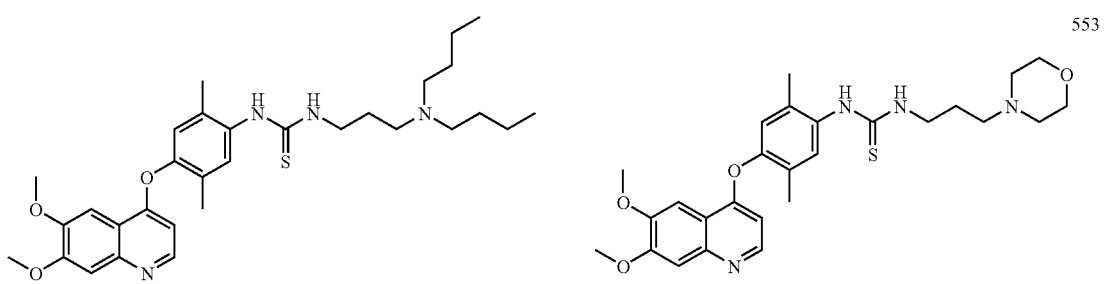
552
553

-continued
554
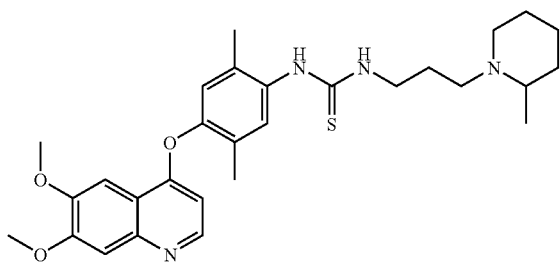
555
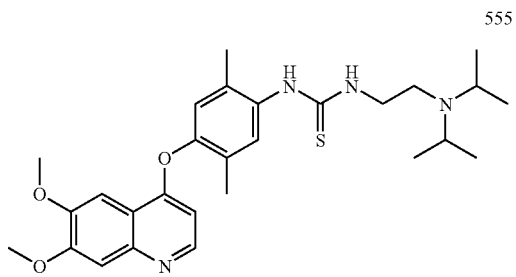
556
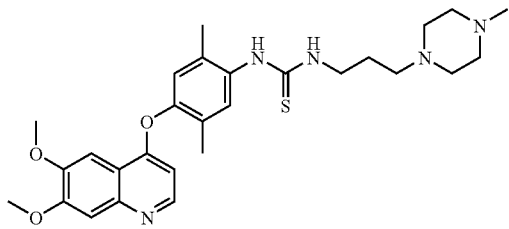
557
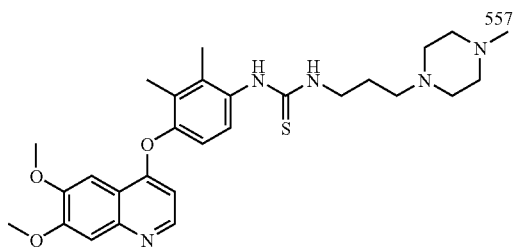
558
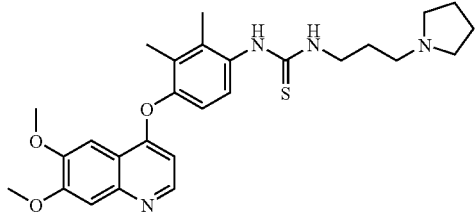
559
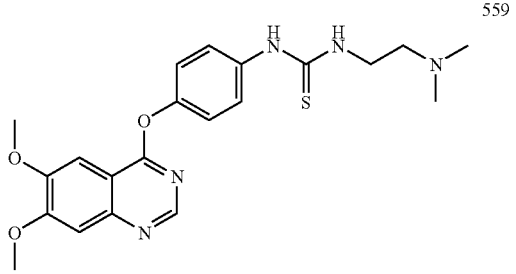
560
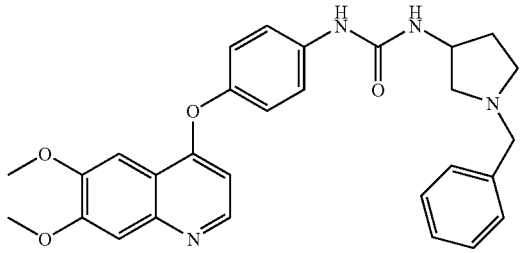
561
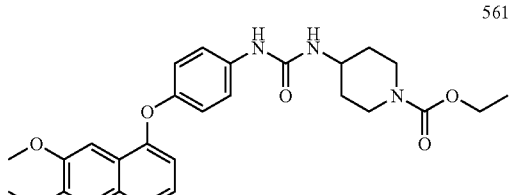
562
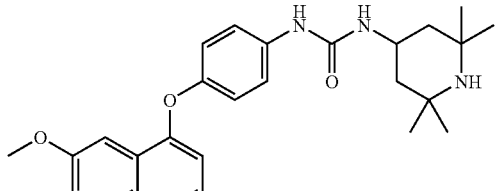
563
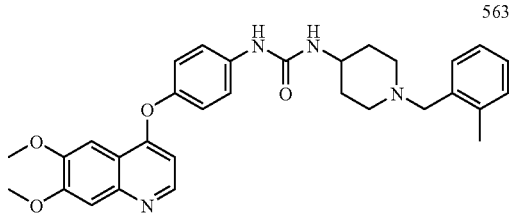
564
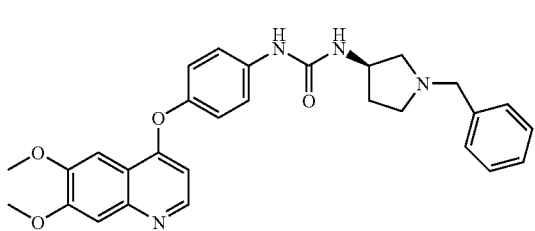
565
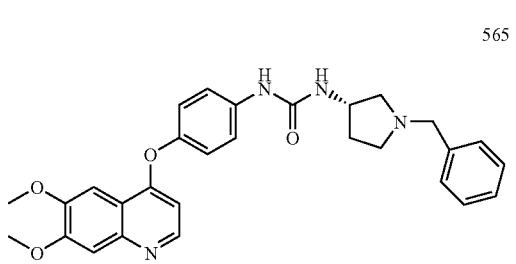

-continued
566
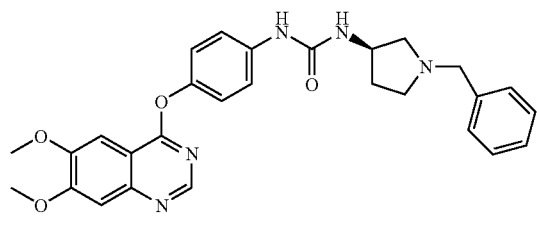
567
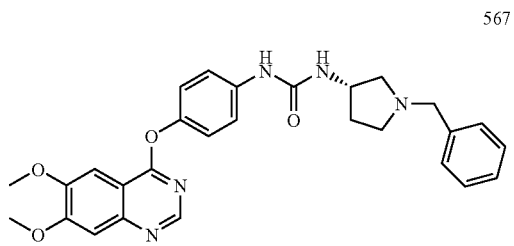
568
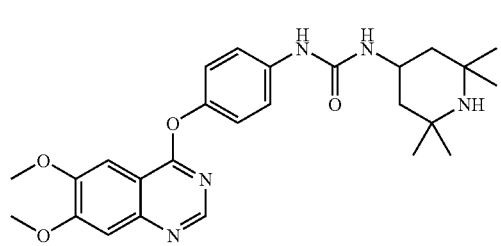
569
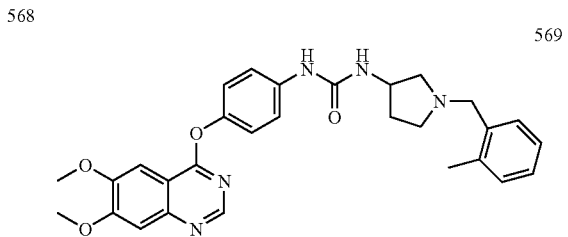
570
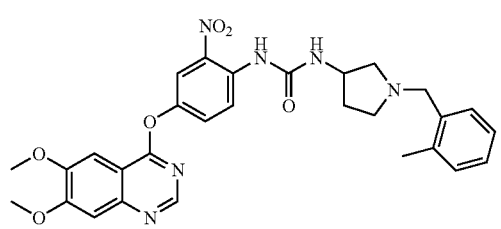
571
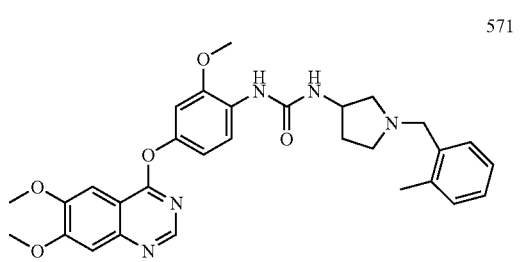
572
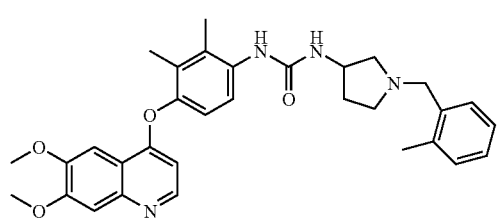
573
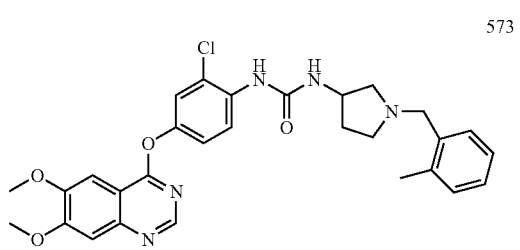
574
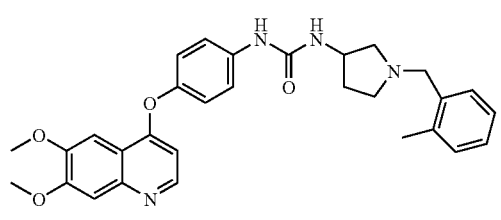
575
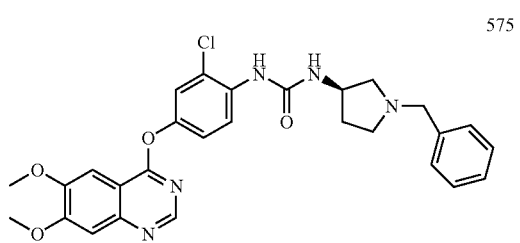
576
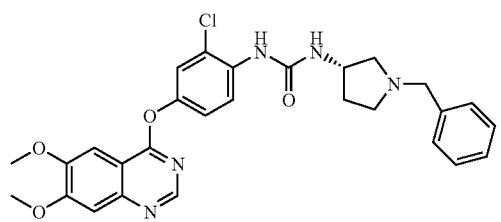
577
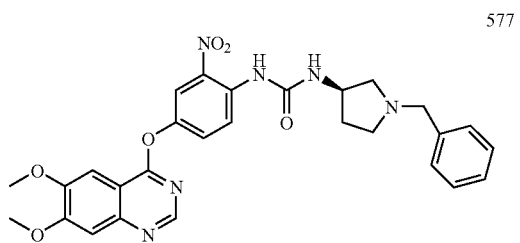

-continued
578
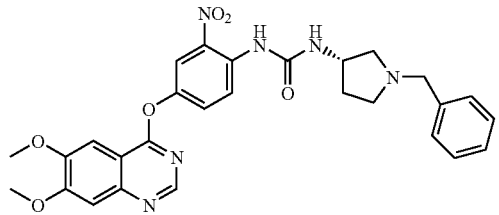
579
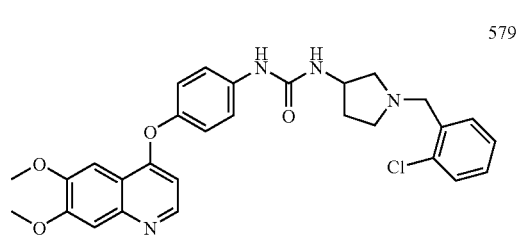
580
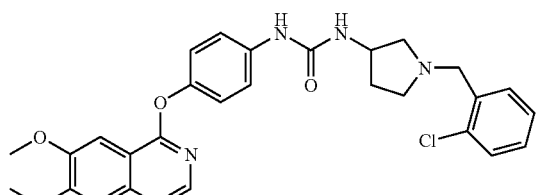
581
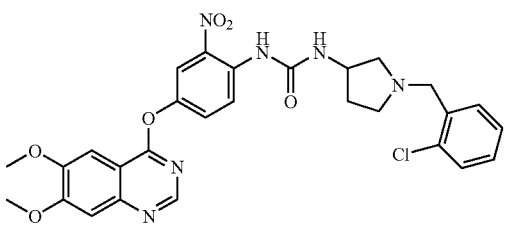
582
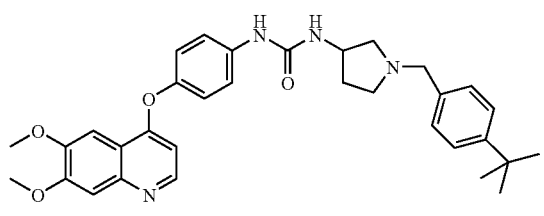
583
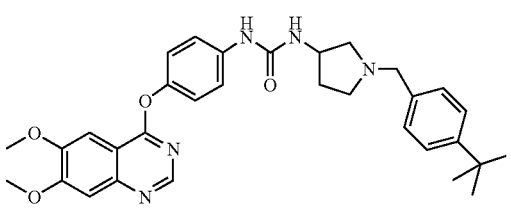
584
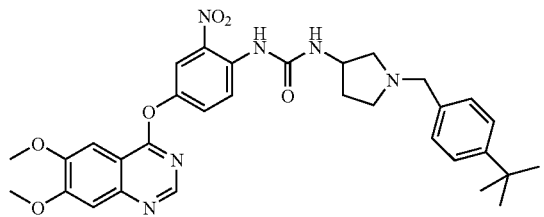
585
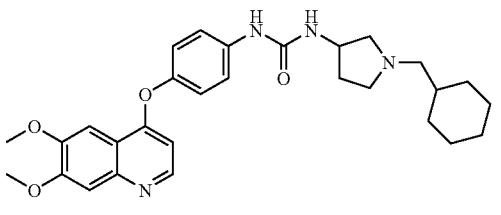
586
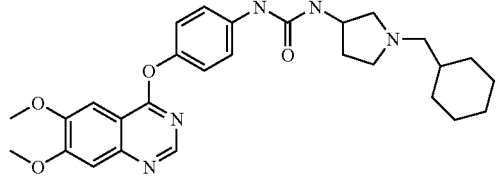
587
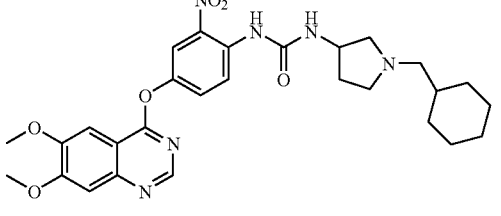
588
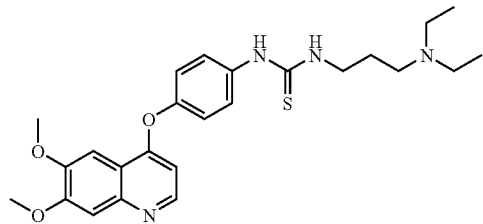
589
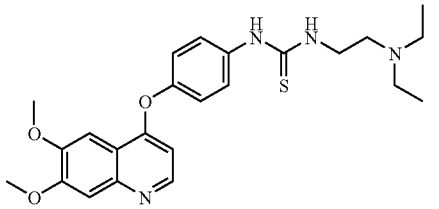

-continued
590
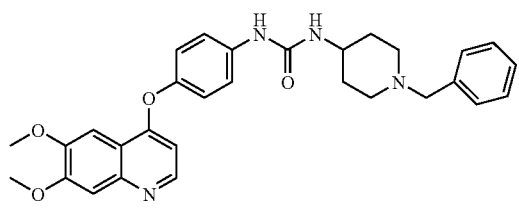
591
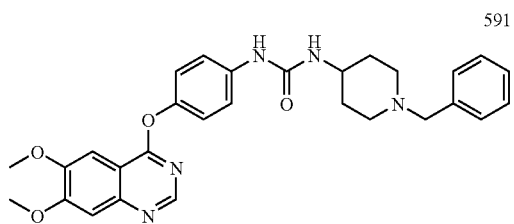
592
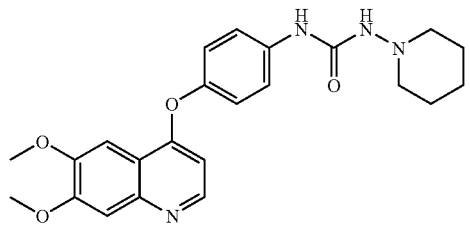
593
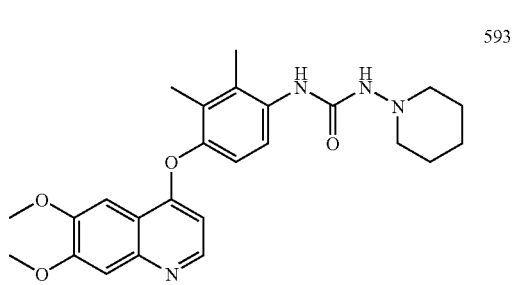
594
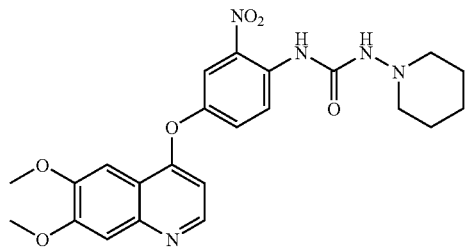
595
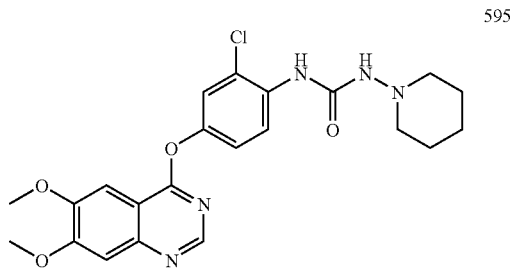
596
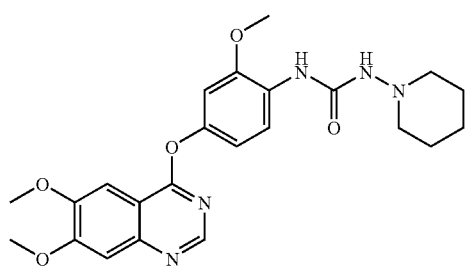
597
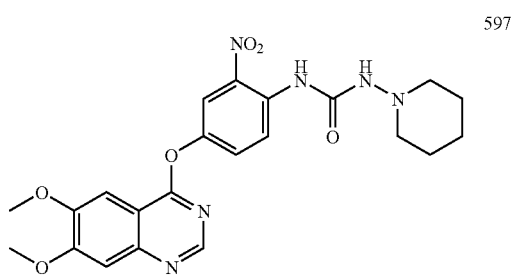
598
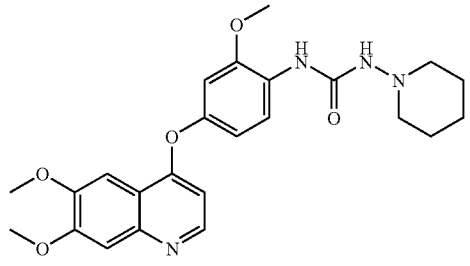
599
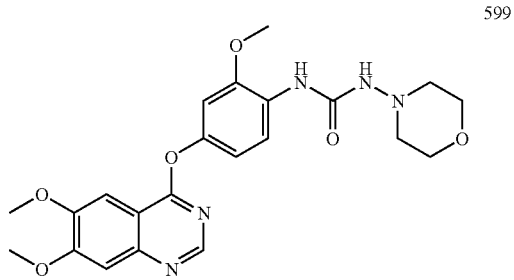

-continued
600
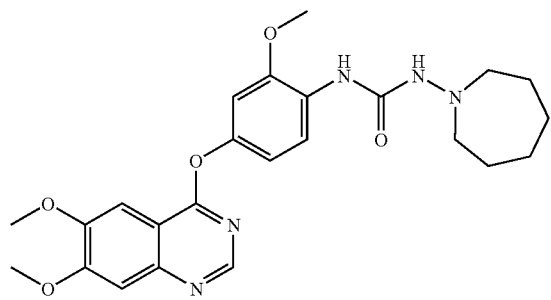
601
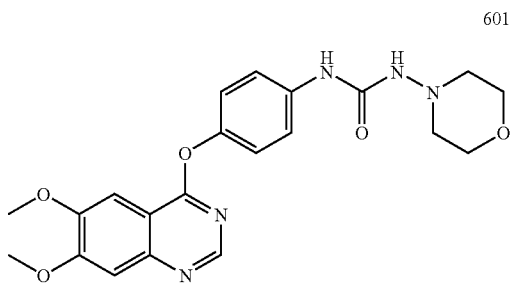
602
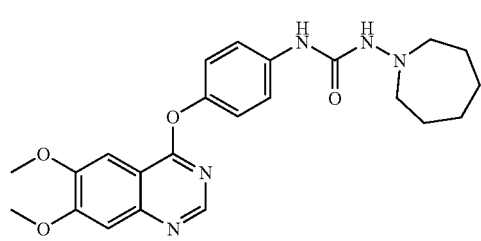
603
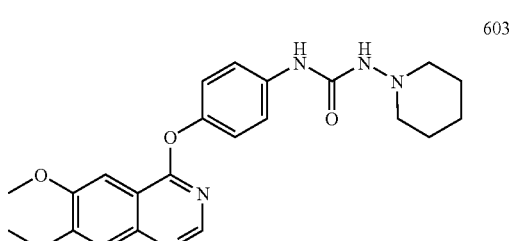
604
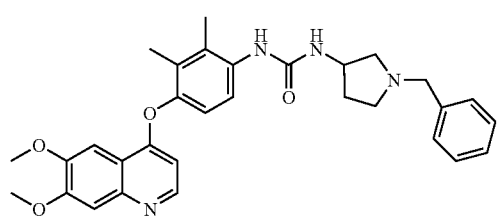
605
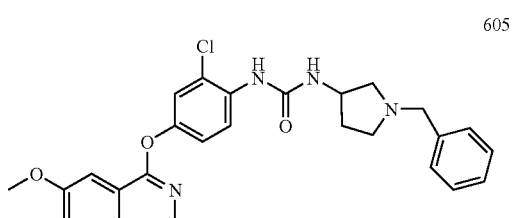
606
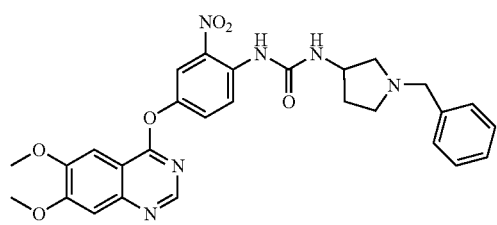
607
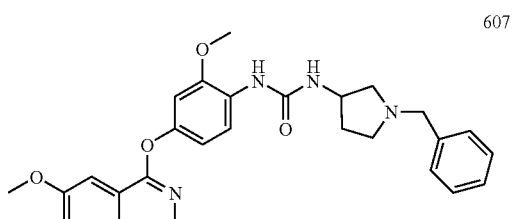
608
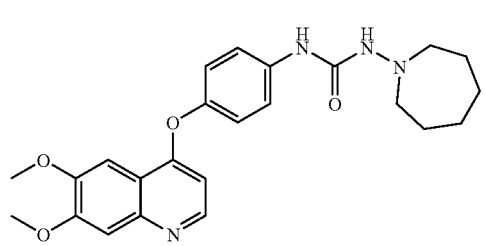
609
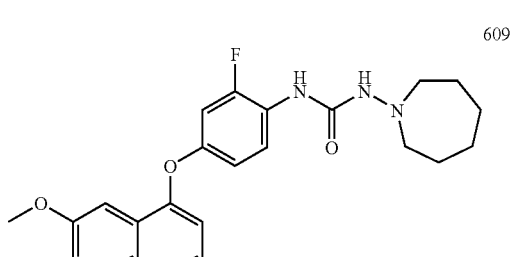
610
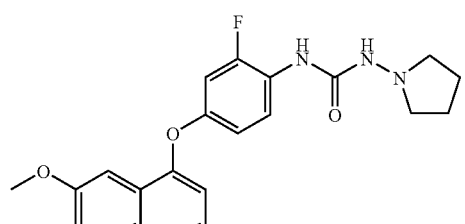
611
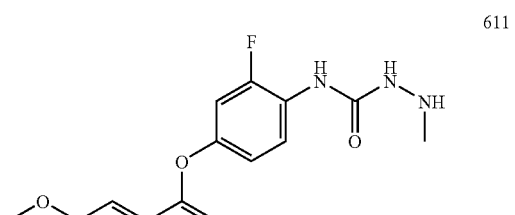

-continued
667
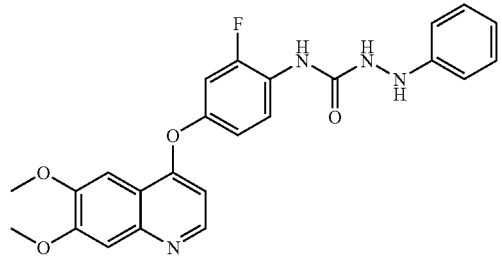
612
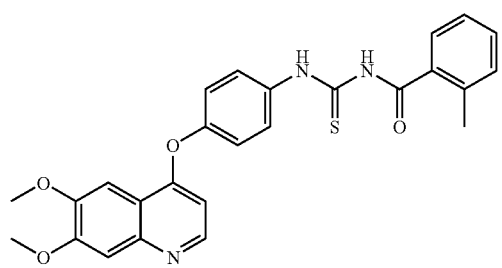
614
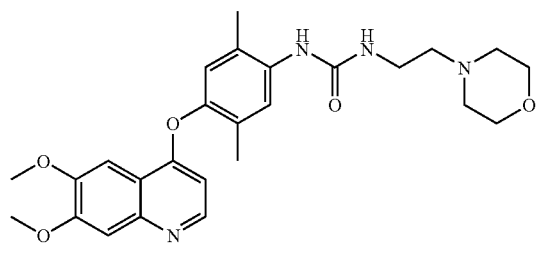
616
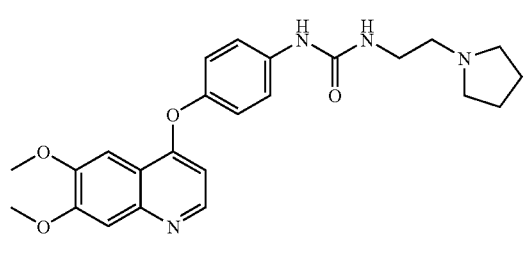
618
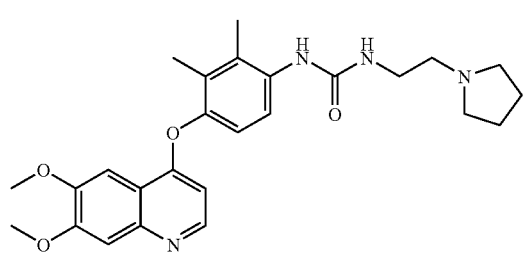
620
668
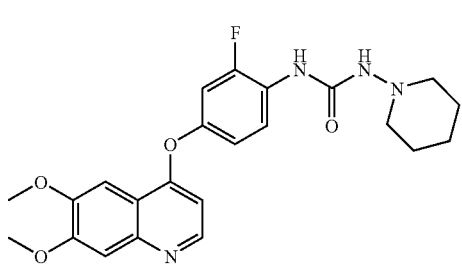
613
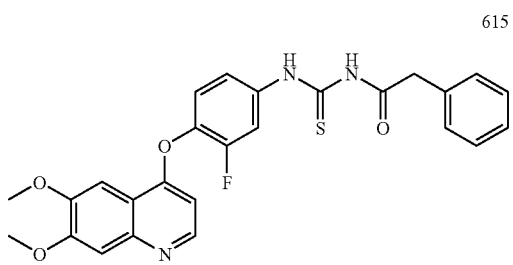
615
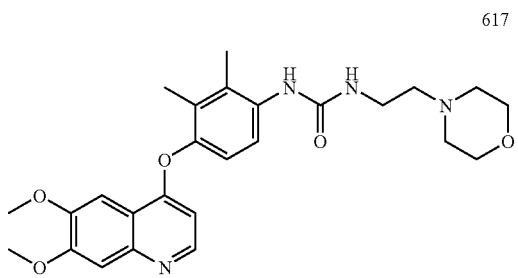
617
619
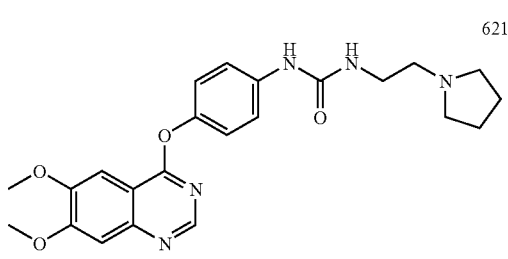
621

-continued
622
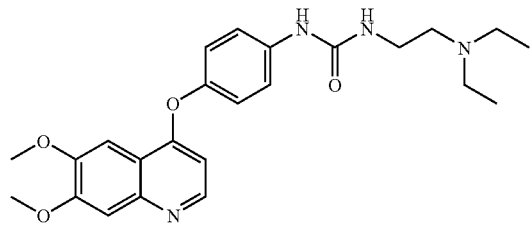
623
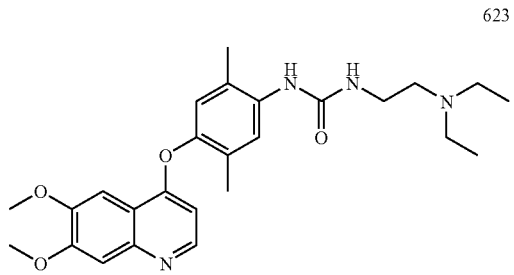
624
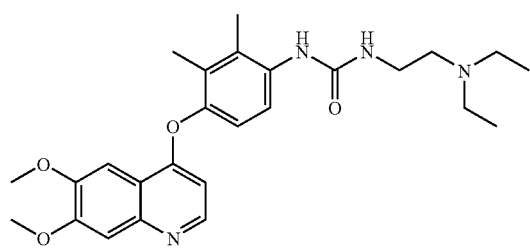
625
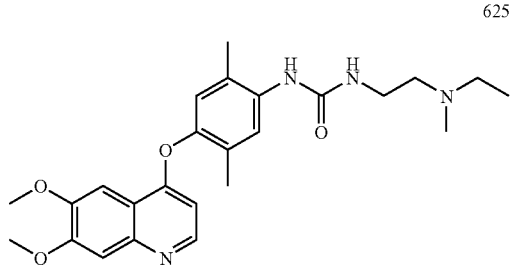
626
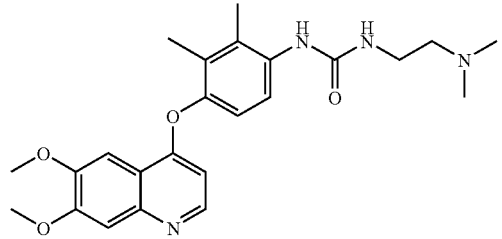
627
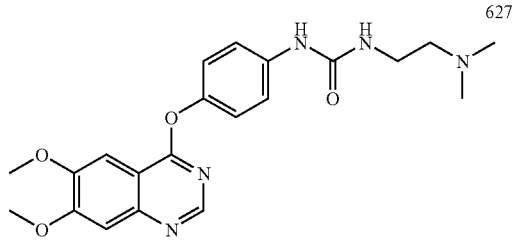
628
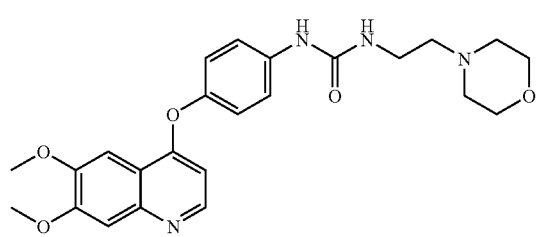
629
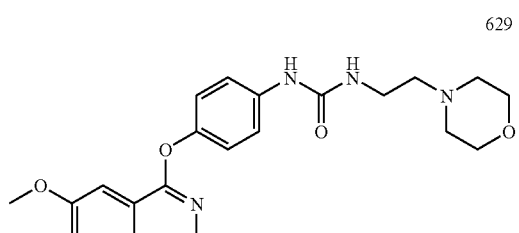
630
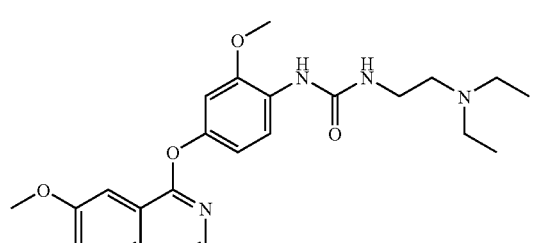
631
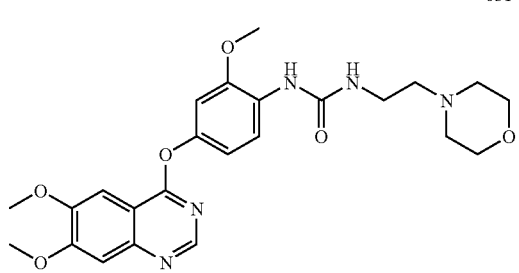

-continued
632
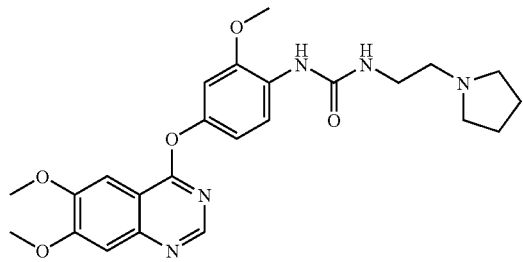
633
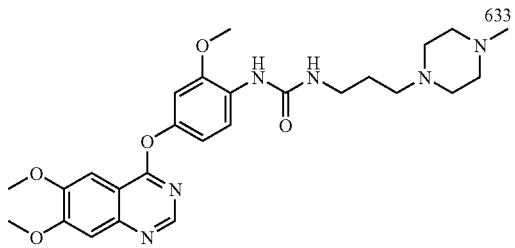
634
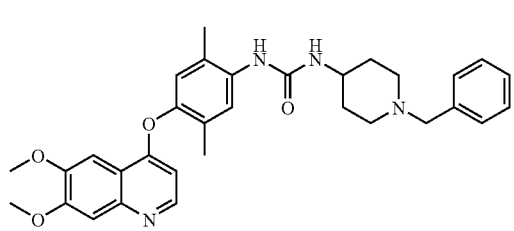
635
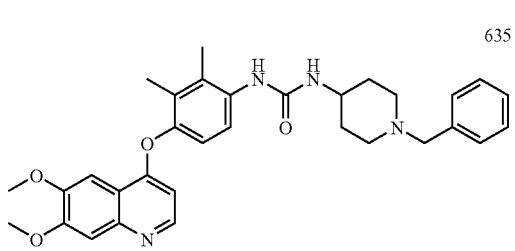
636
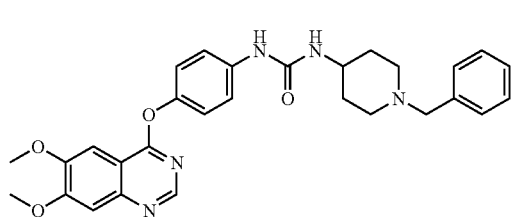
637
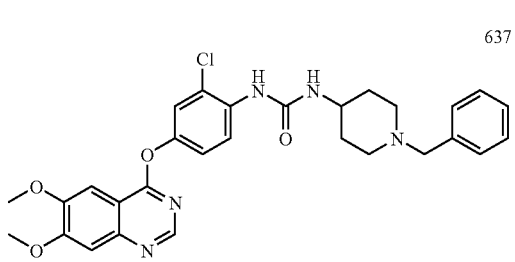
638
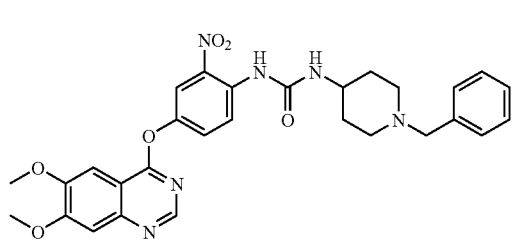
639
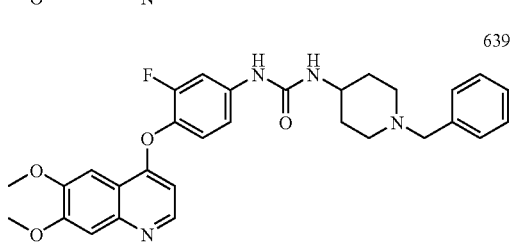
640
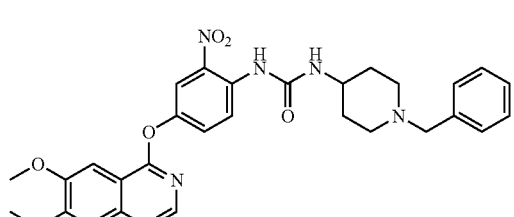
641
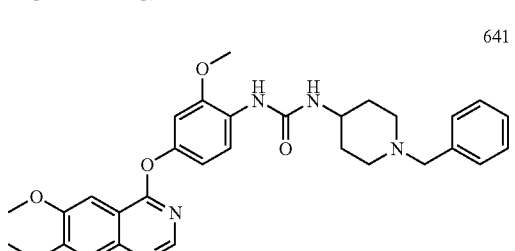
642
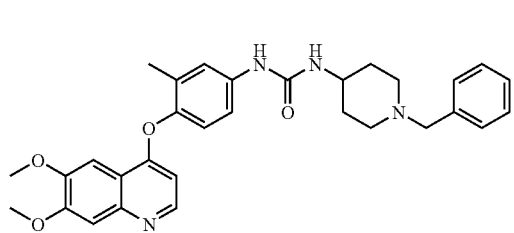
643
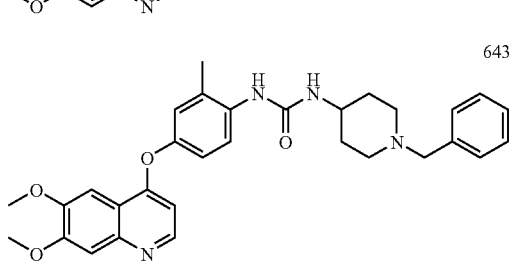

-continued
644
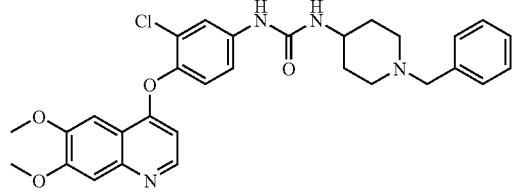
645
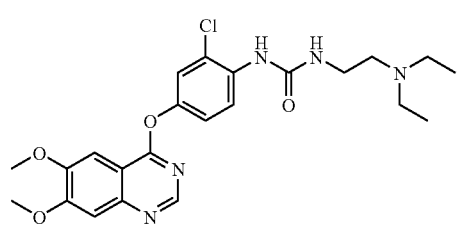
646
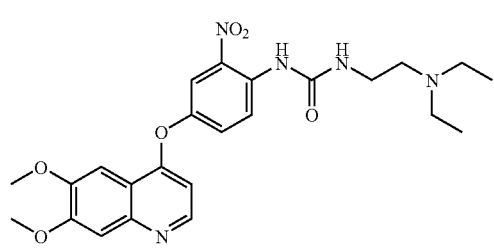
647
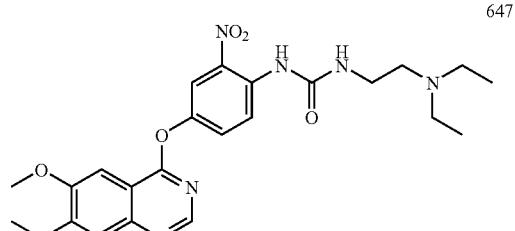
648
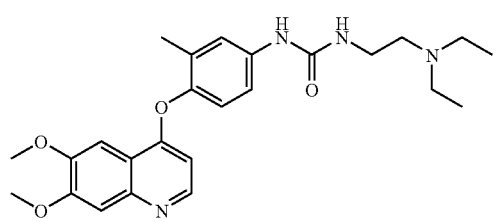
649
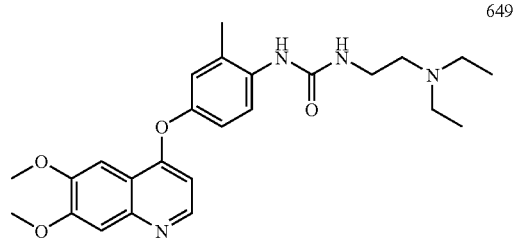
650
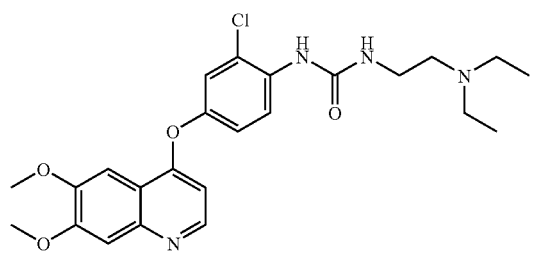
651
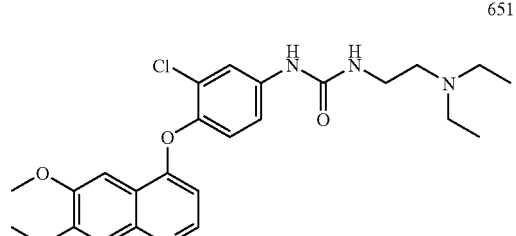
652
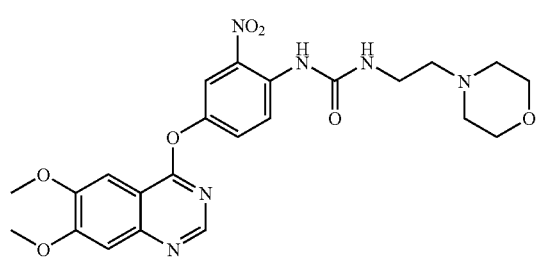
653
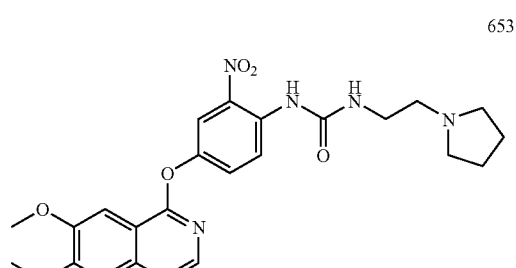

-continued
654
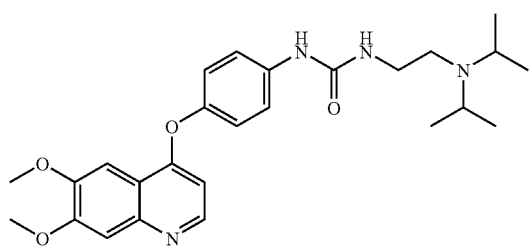
655
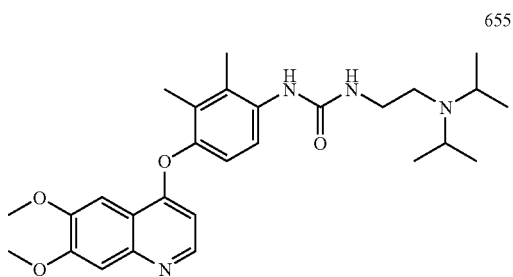
656
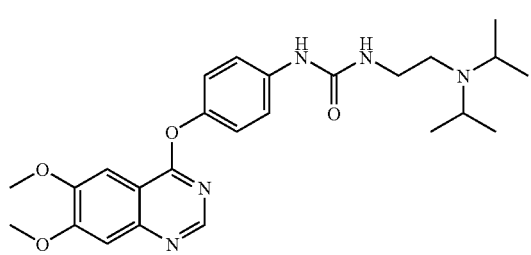
657
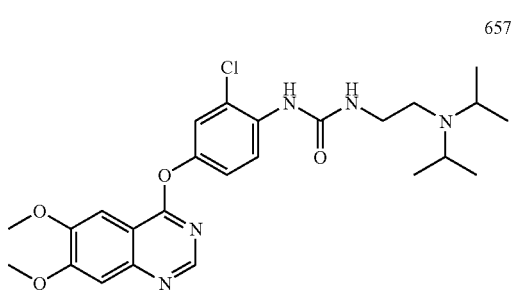
658
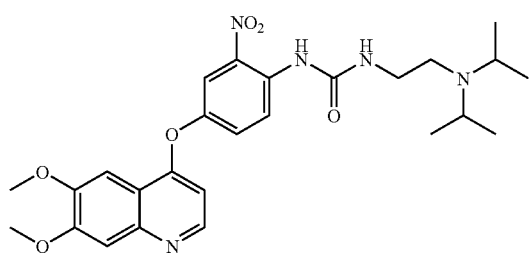
659
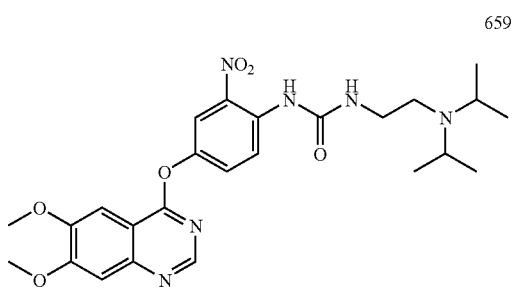
660
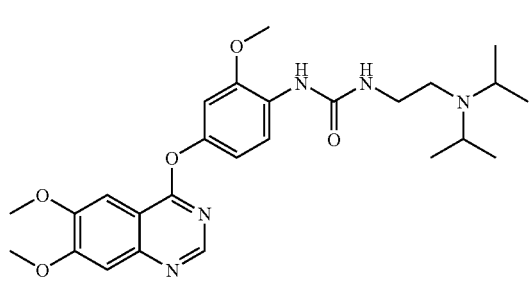
661
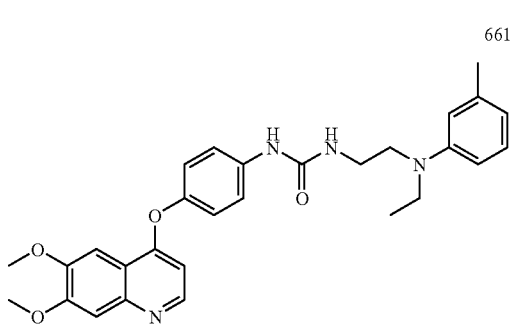
662
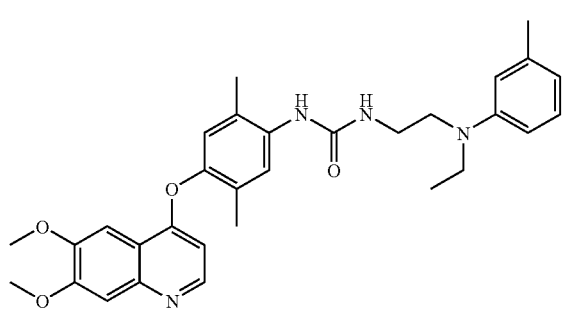
663
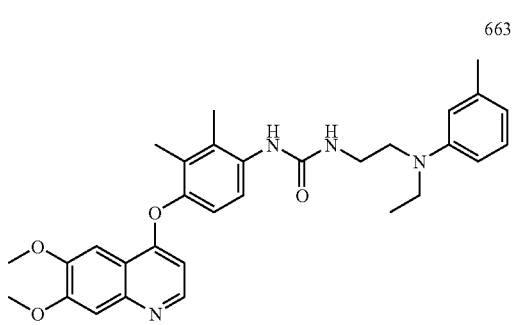

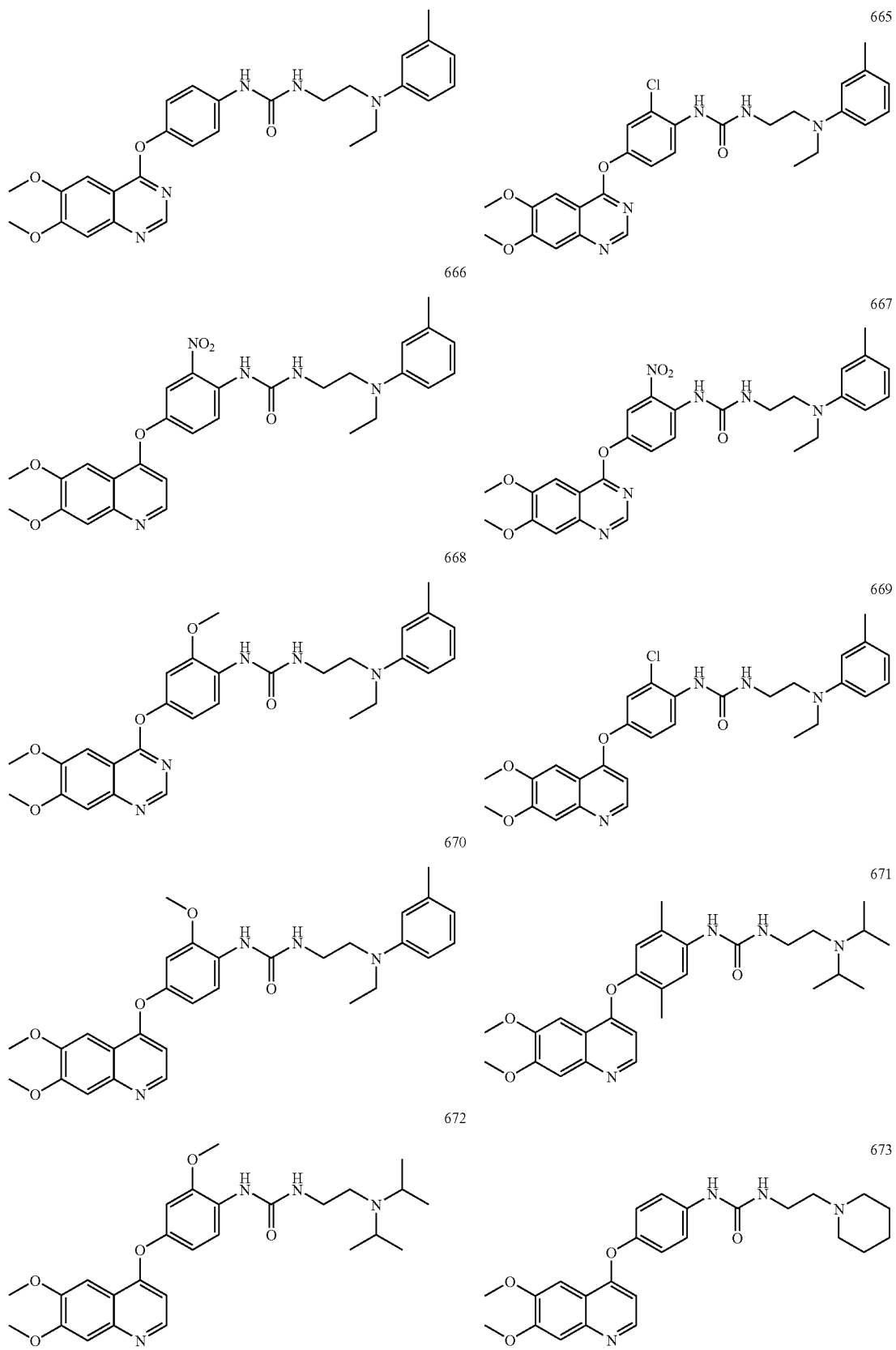

-continued
674
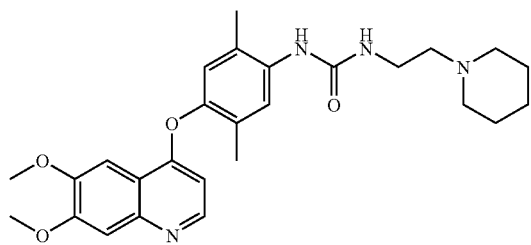
675
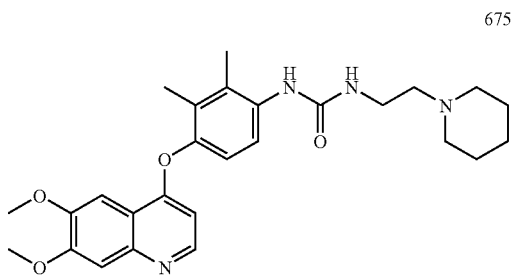
676
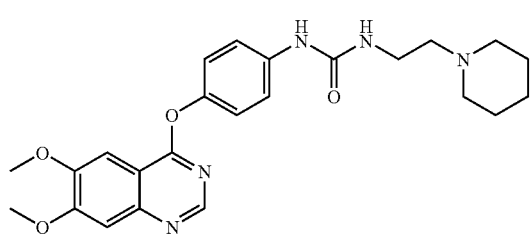
677
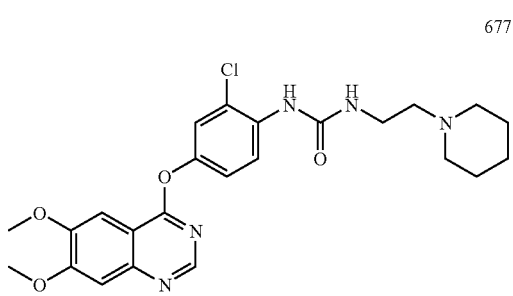
678
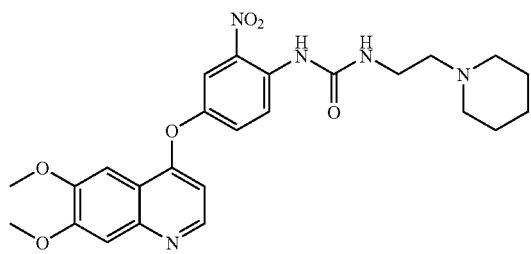
679
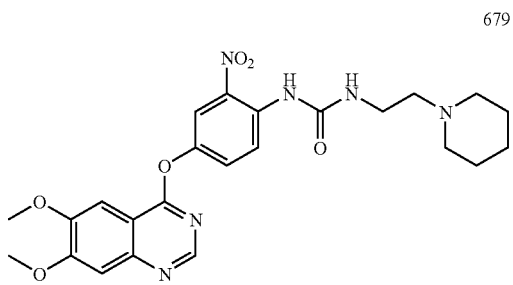
680
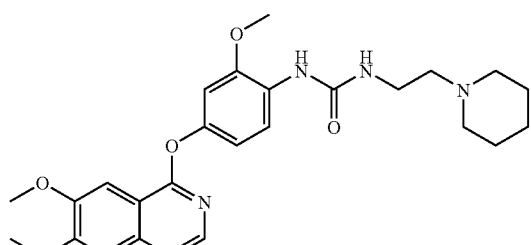
681
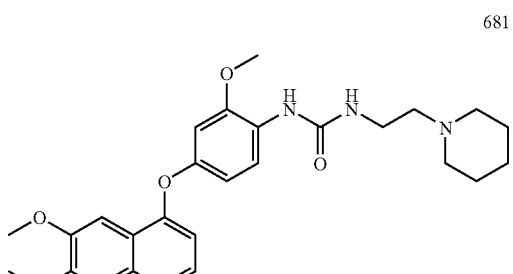
682
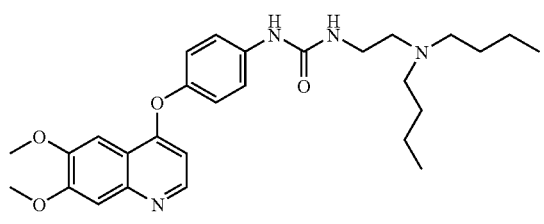
683
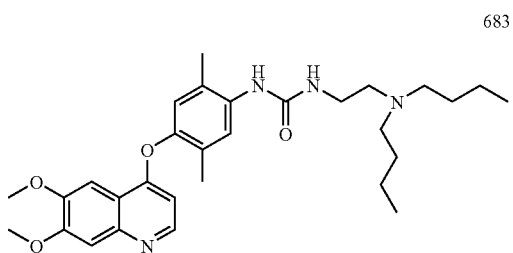

-continued
684
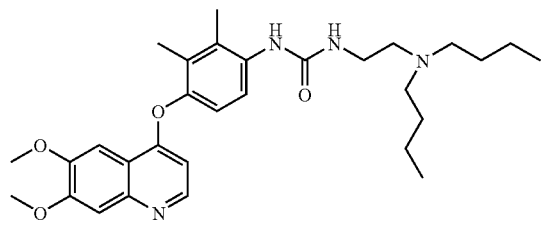
685
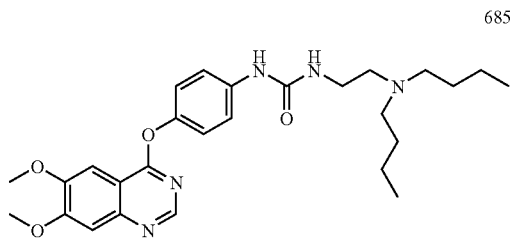
686
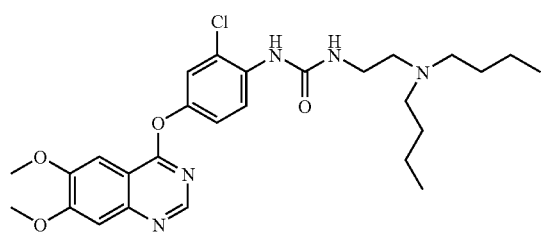
687
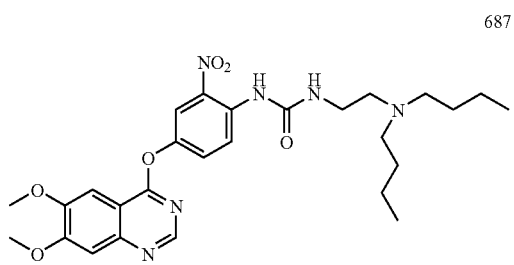
688
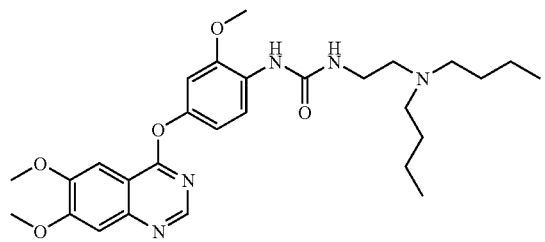
689
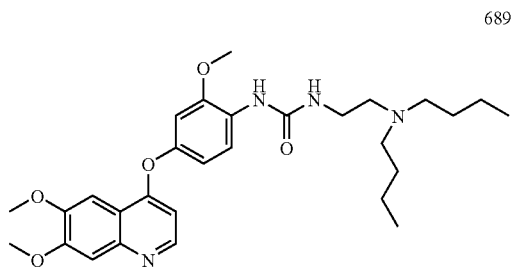
690
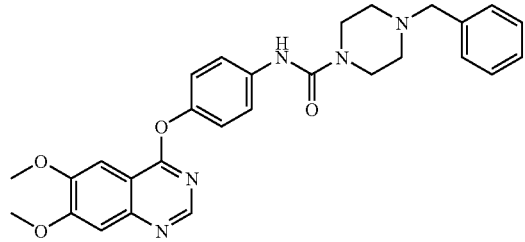
691
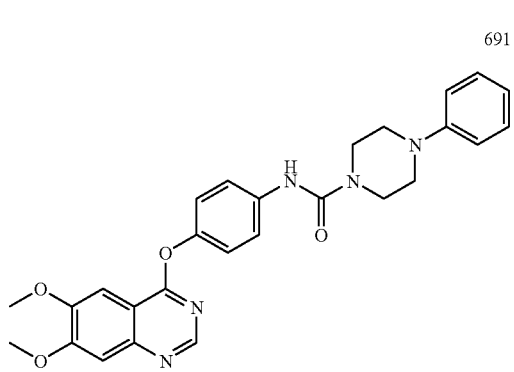
692
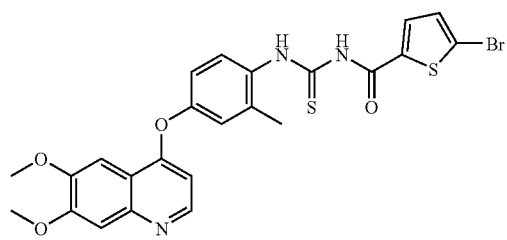
693
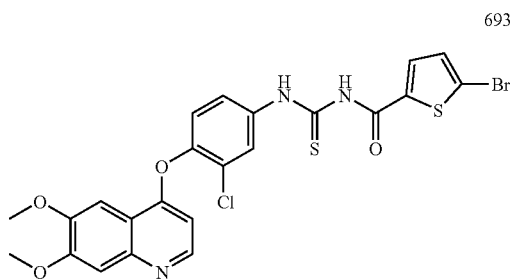

-continued
694
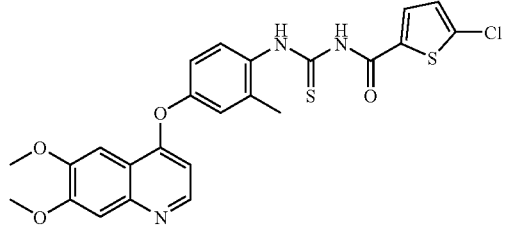
695
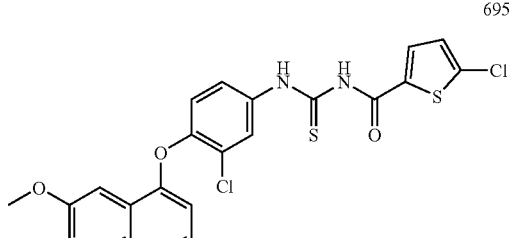
696
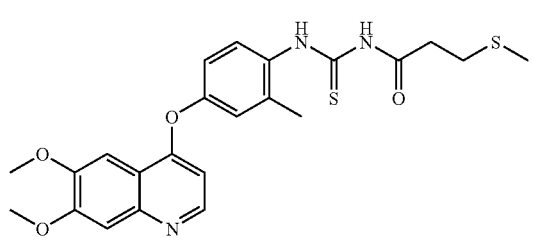
697
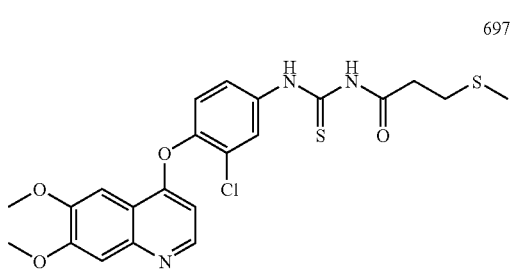
698
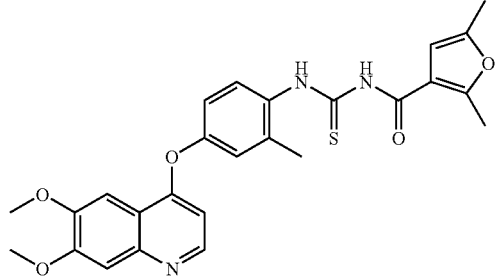
699
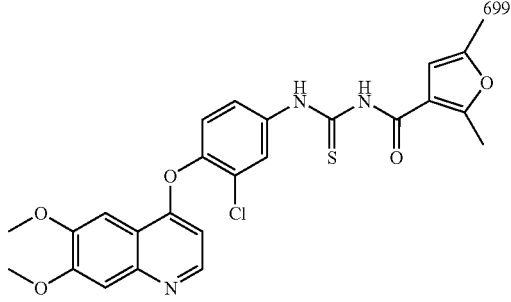
700
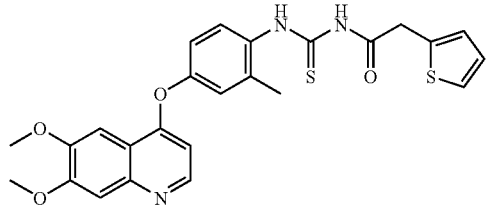
701
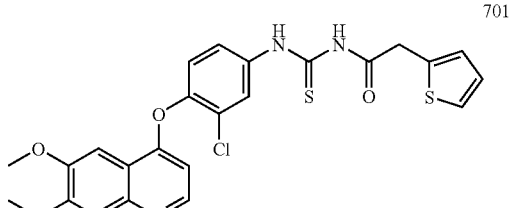
702
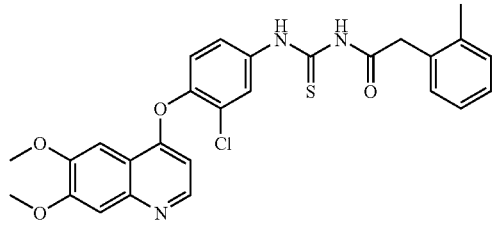
703
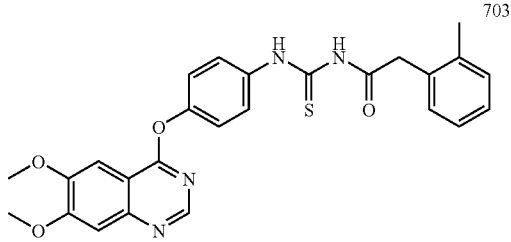
704
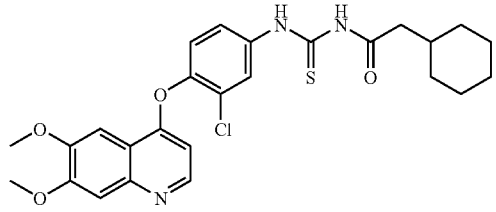
705
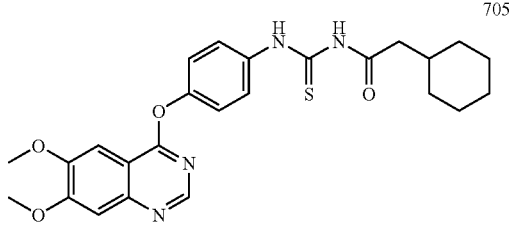

-continued
706 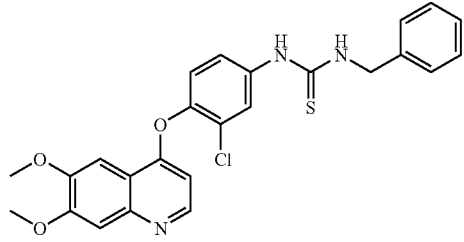
707 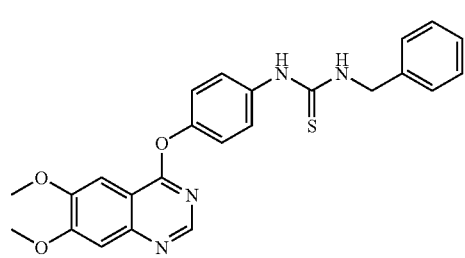
708 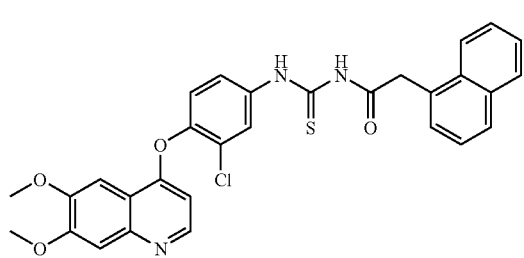
709 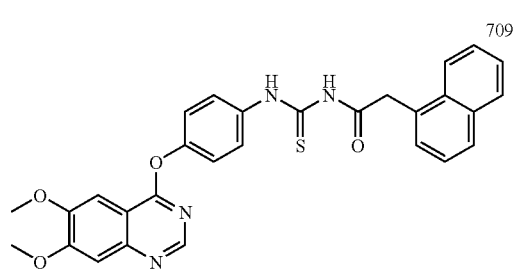
710 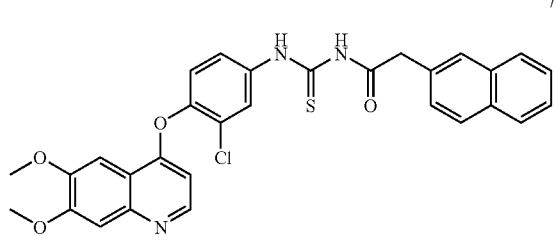
711 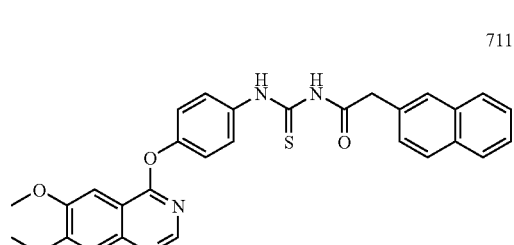
712 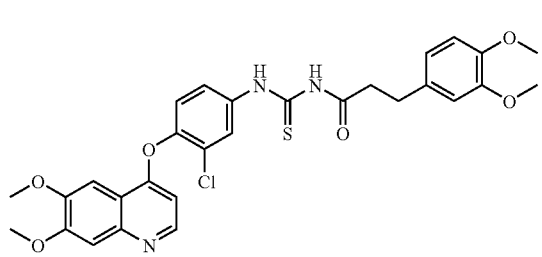
713 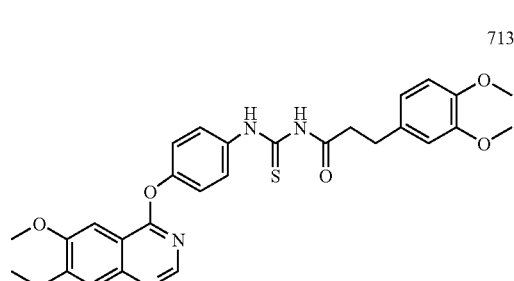
714 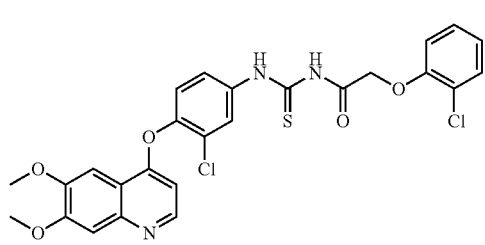
715 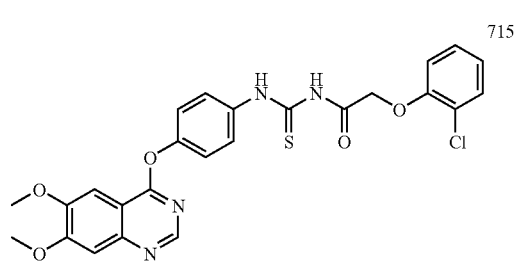

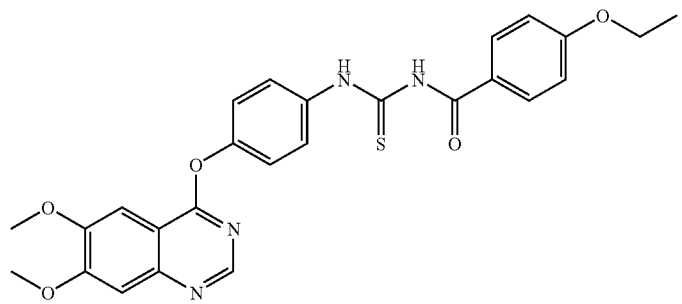
716
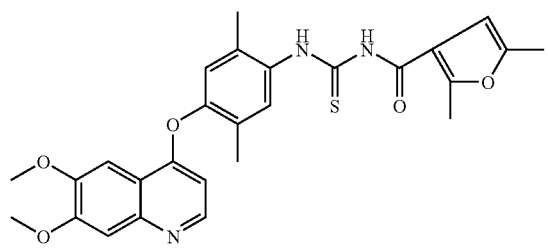
717
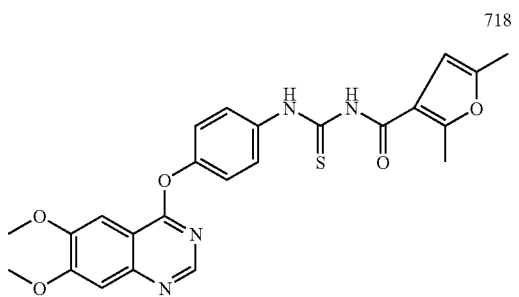
718
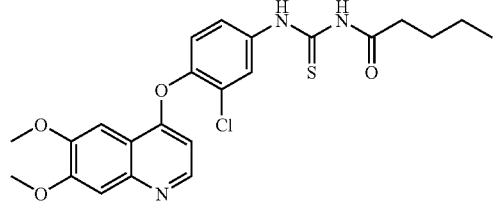
719
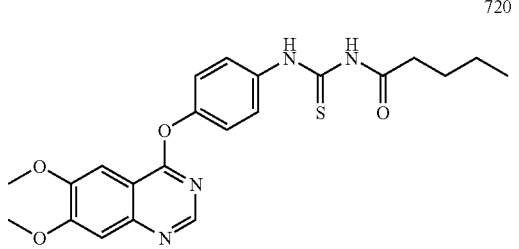
720
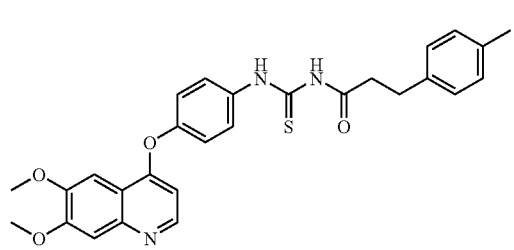
721
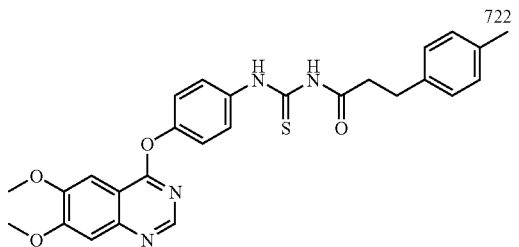
722
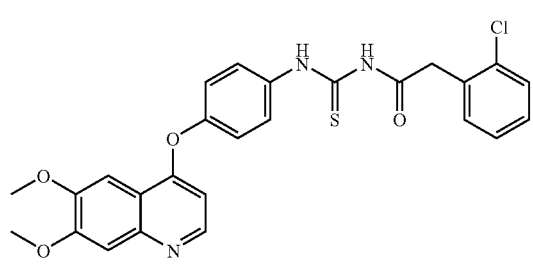
723
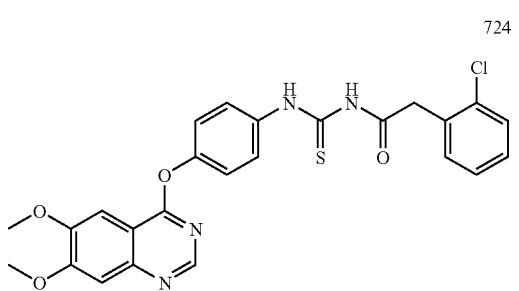
724

-continued
725
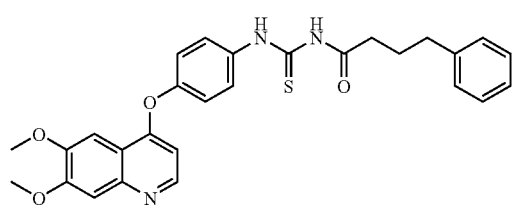
726
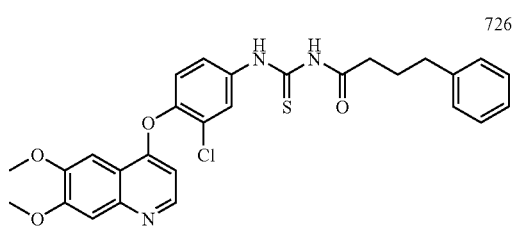
727
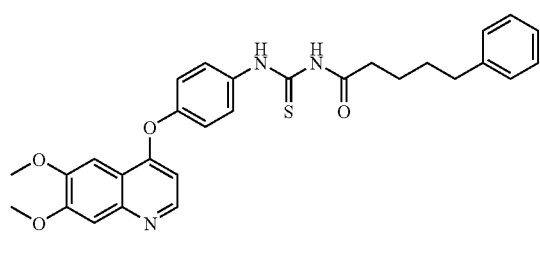
728
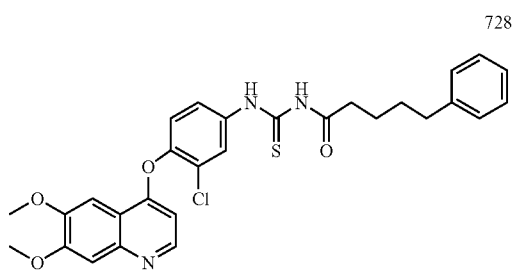
729
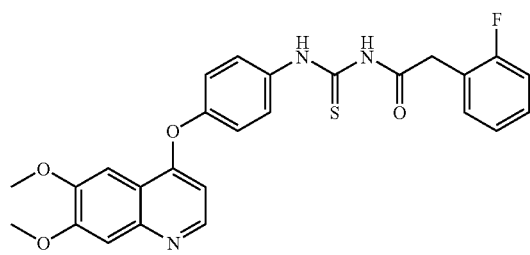
730
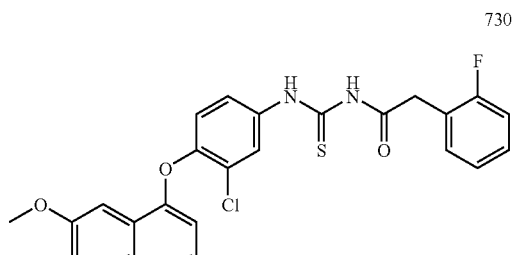
731
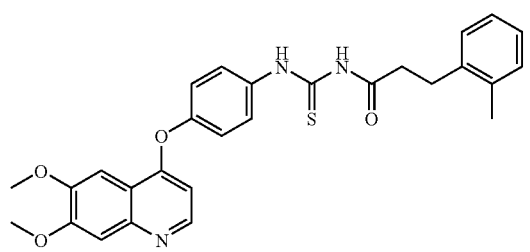
732
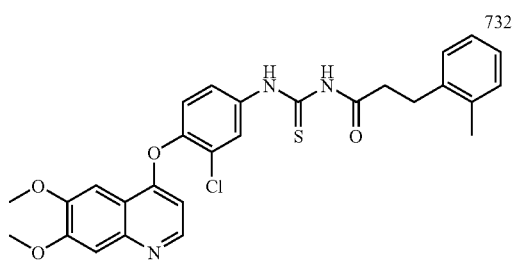
733
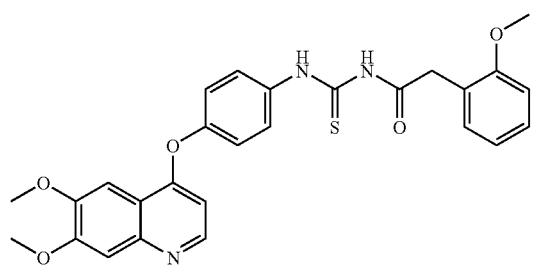
734
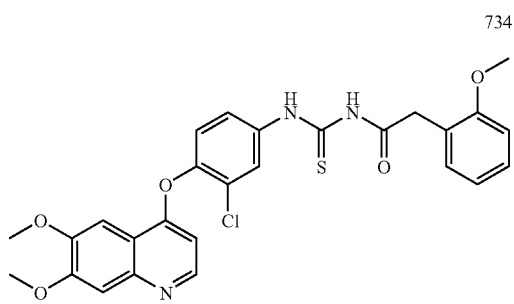

-continued
735
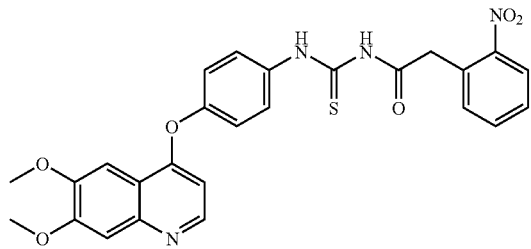
736
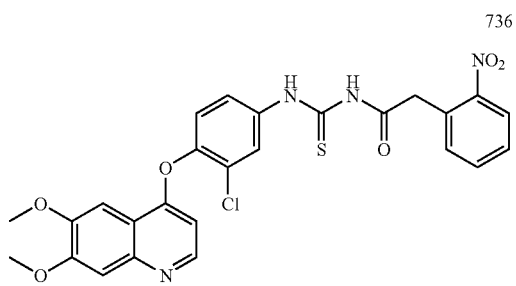
737
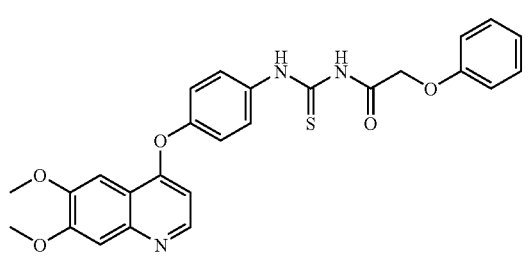
738
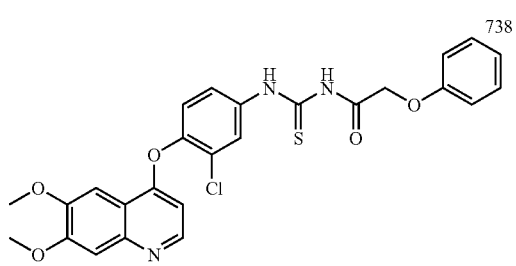
739
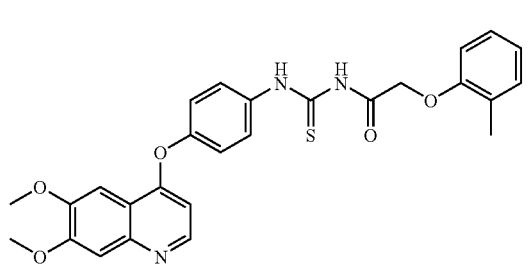
740
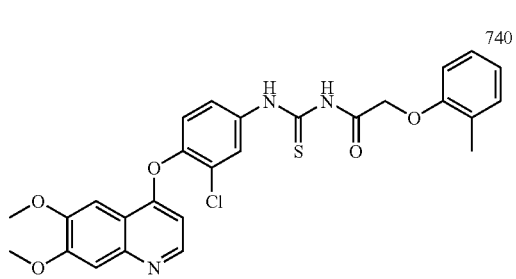
741
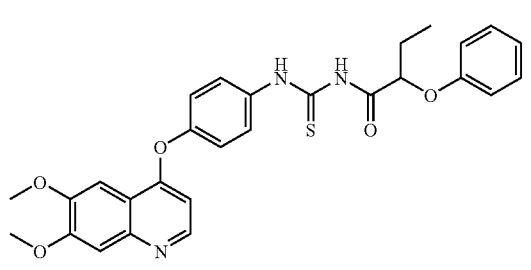
742
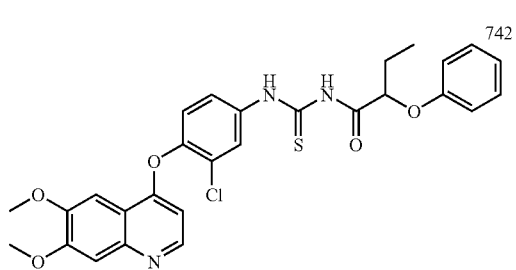
743
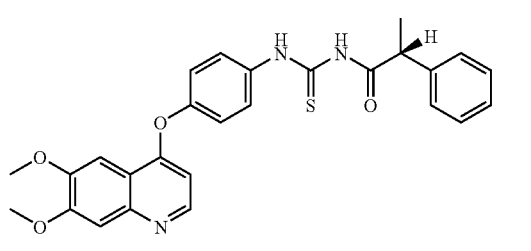
744
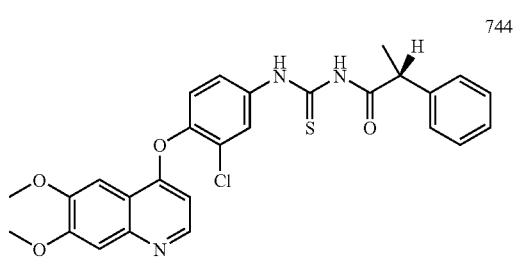
745
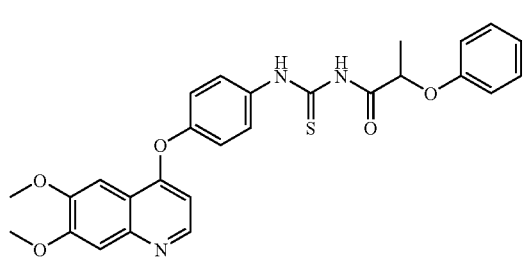
746
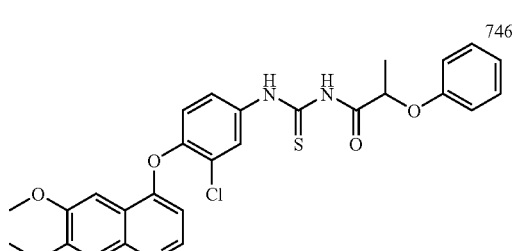

-continued
747
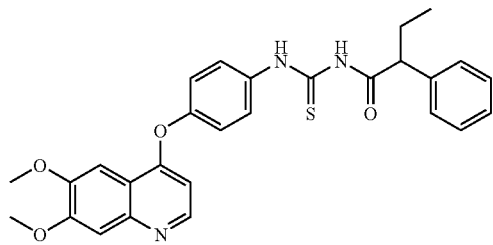
748
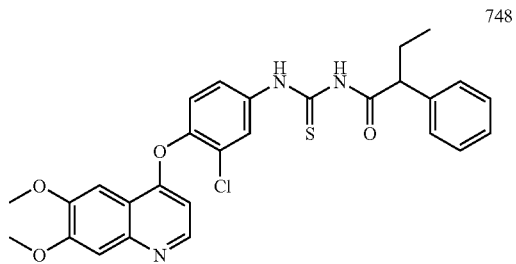
749
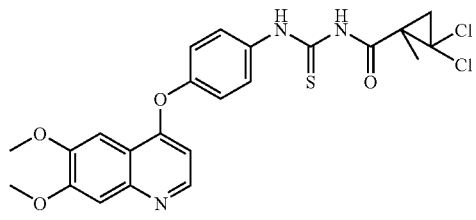
750
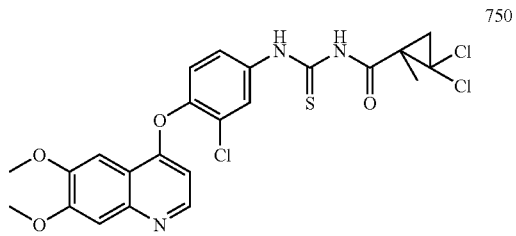
751
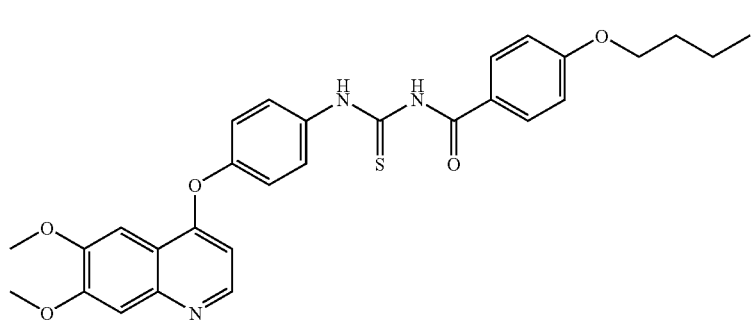
752
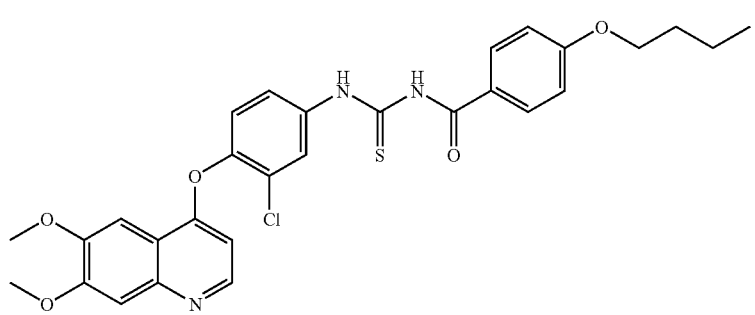
753
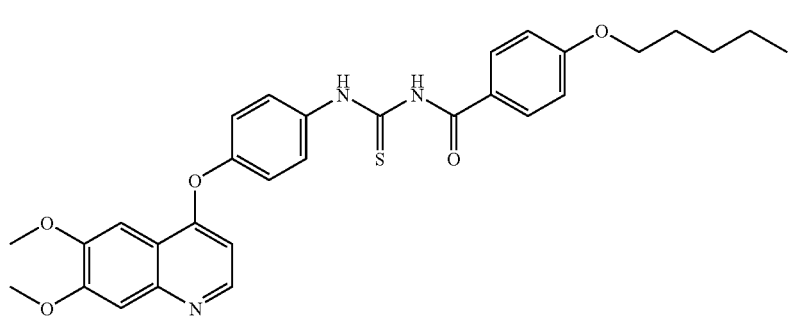

-continued
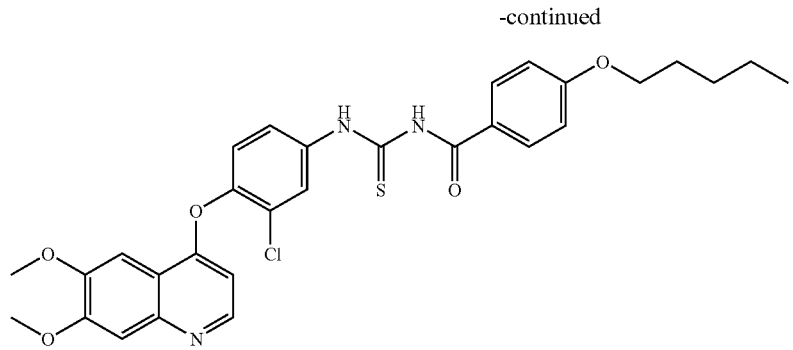
754
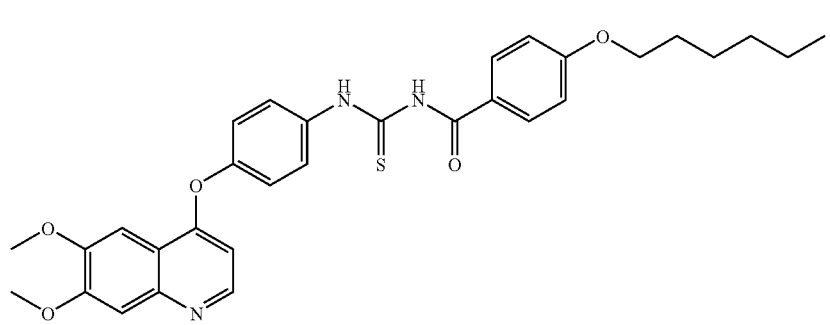
755
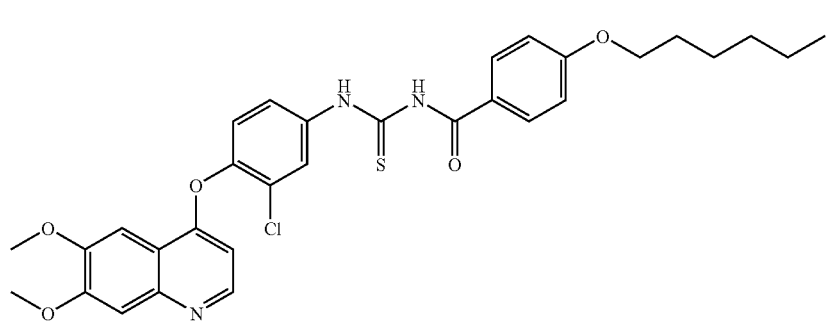
756
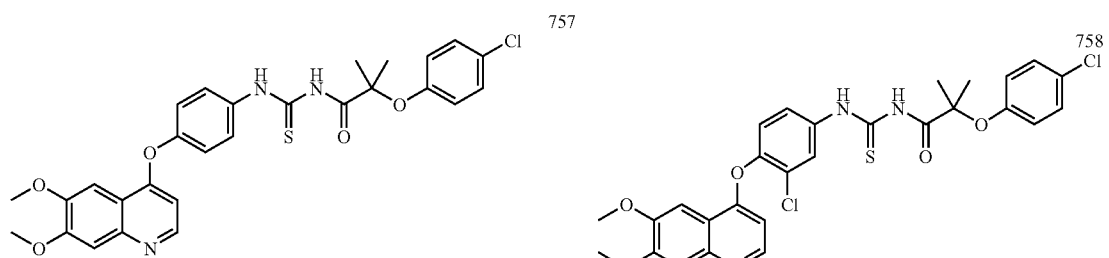
757 758
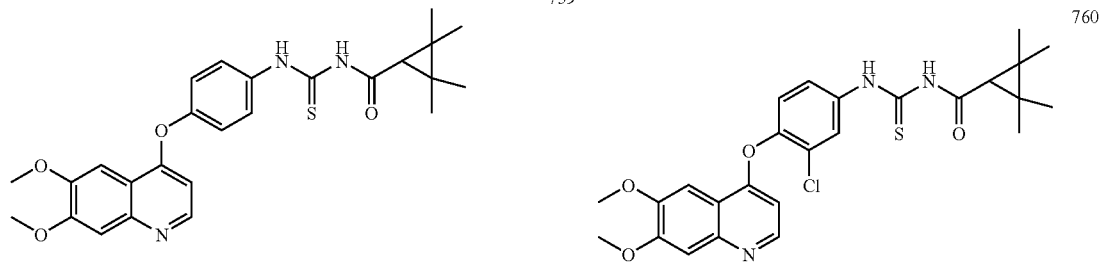
759 760

-continued
761
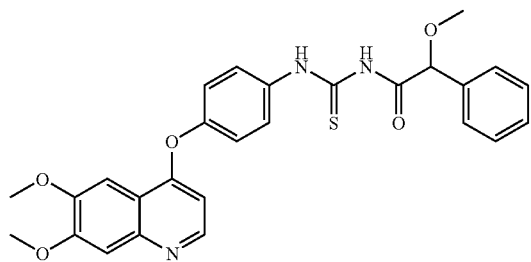
762
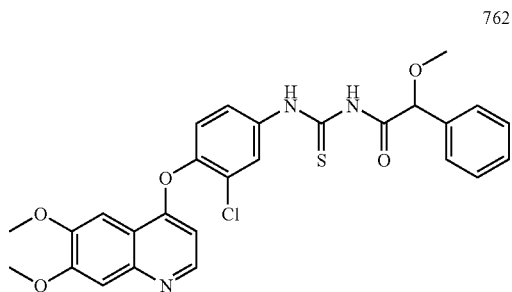
763
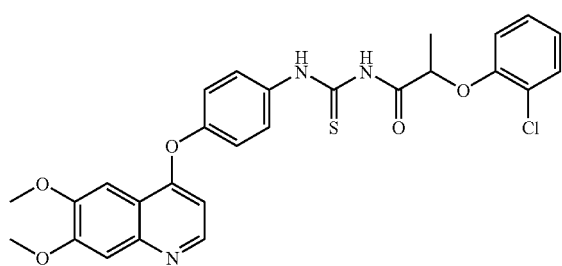
764
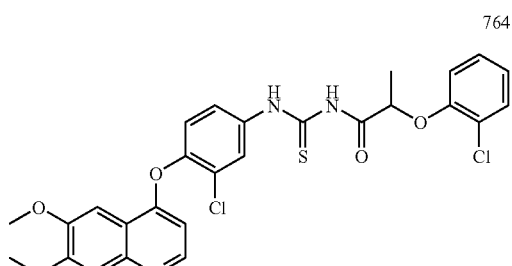
765
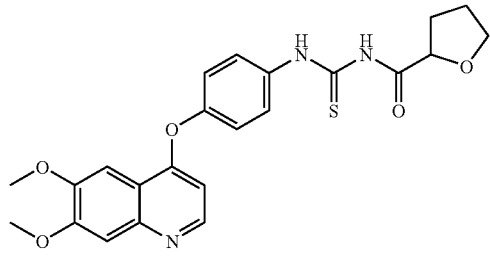
766
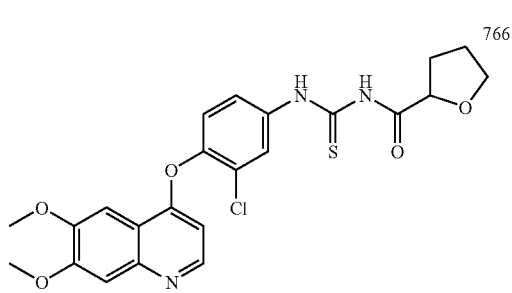
767
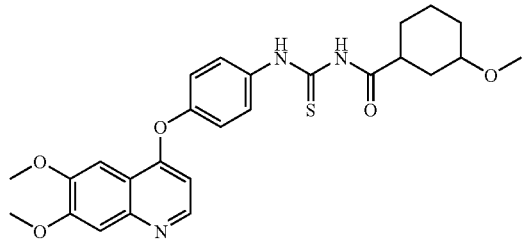
768
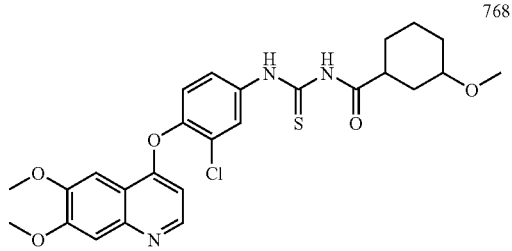
769
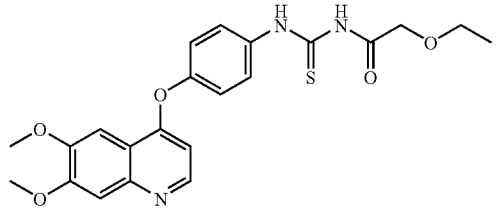
770
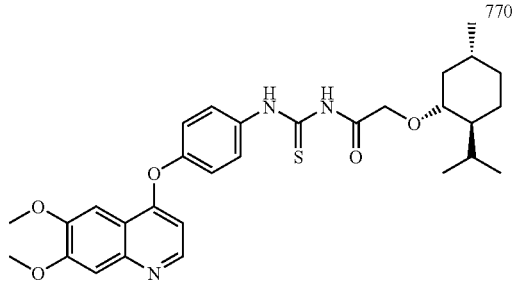

771 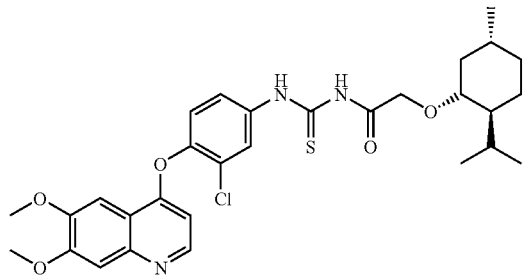
772 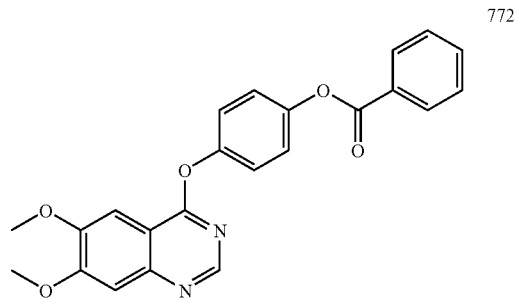
773 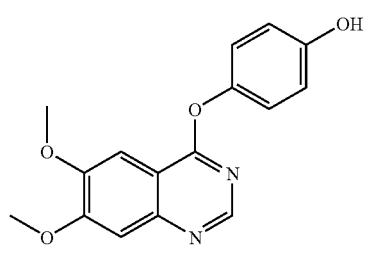
774 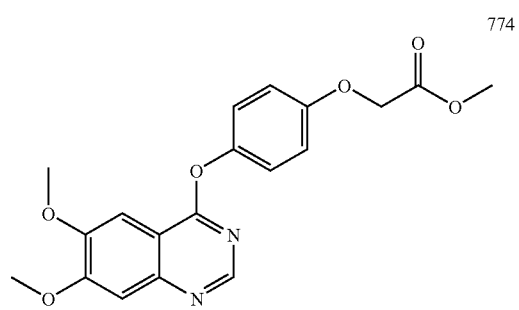
775 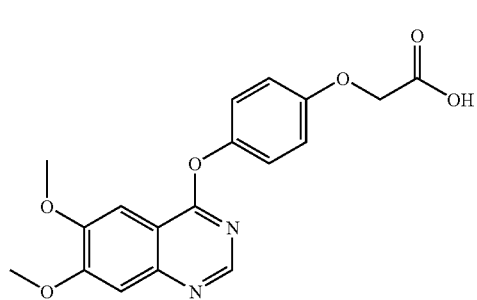
776 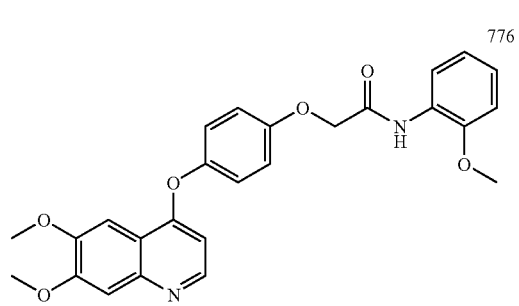
777 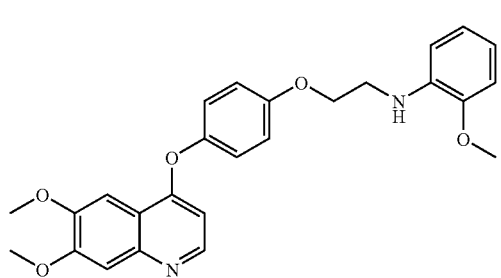
778 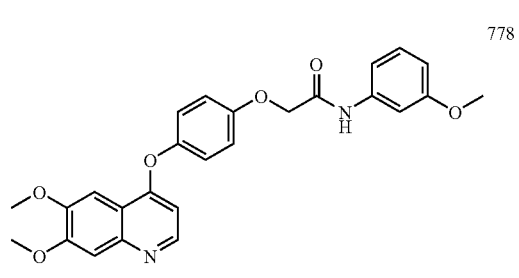
779 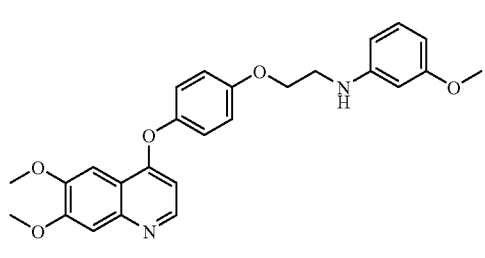
780 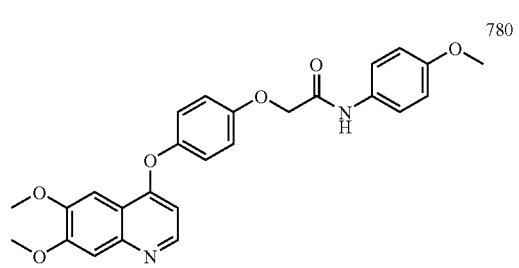

-continued
781
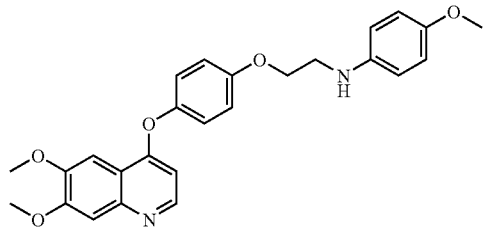
782
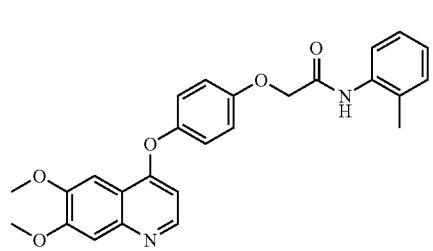
783
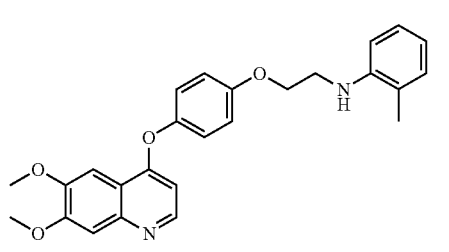
784
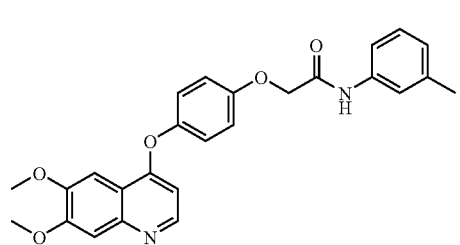
785
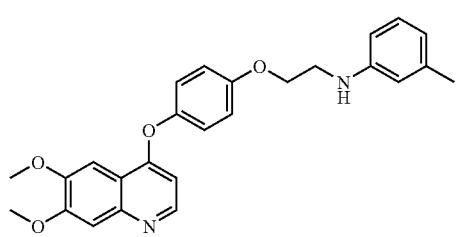
786
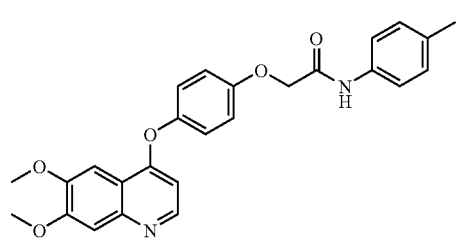
787
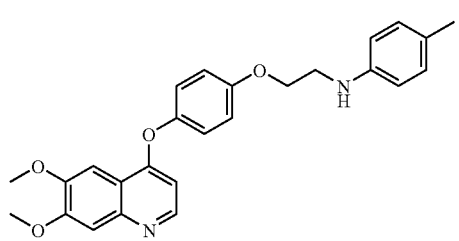
788
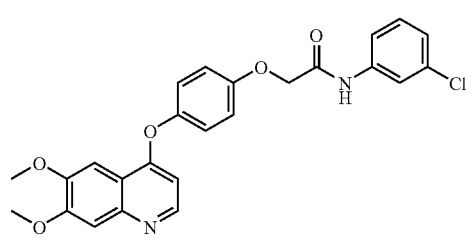
789
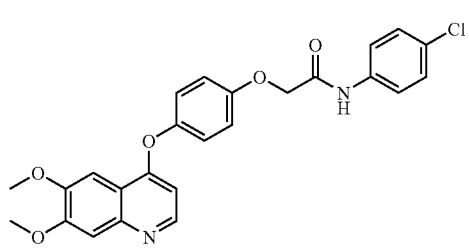
790
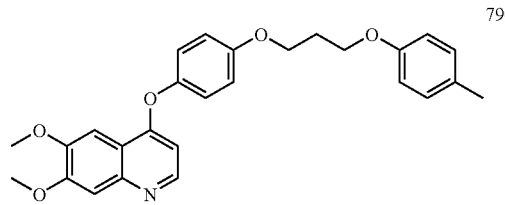
791
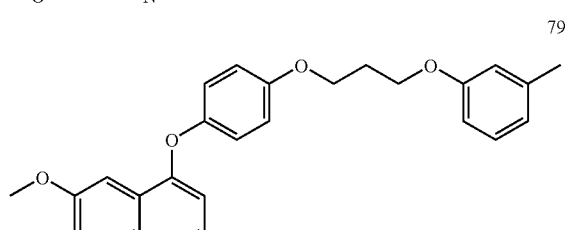
792
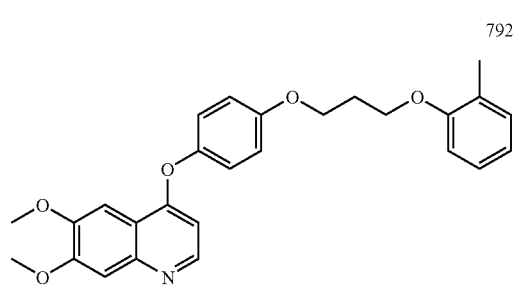

-continued
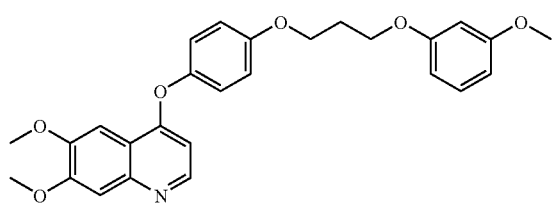
793
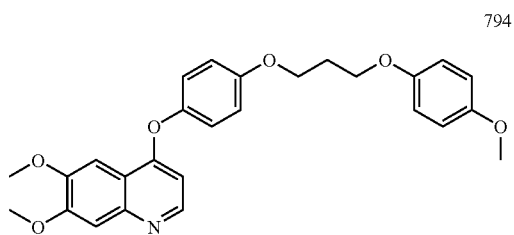
794
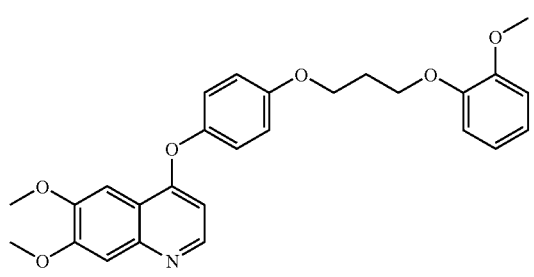
795
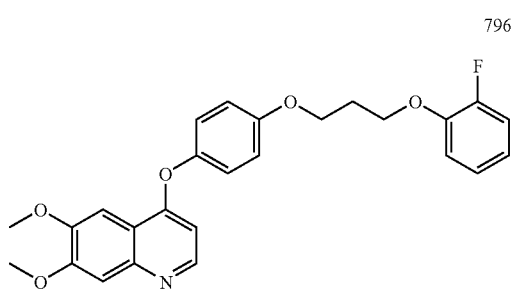
796
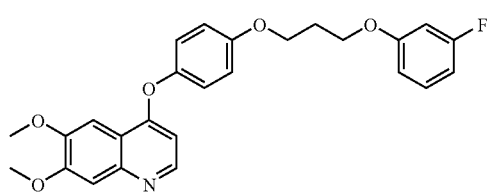
797
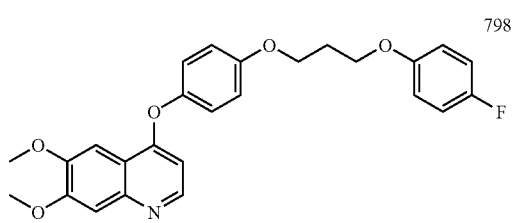
798
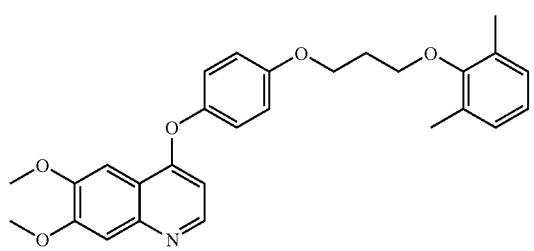
799
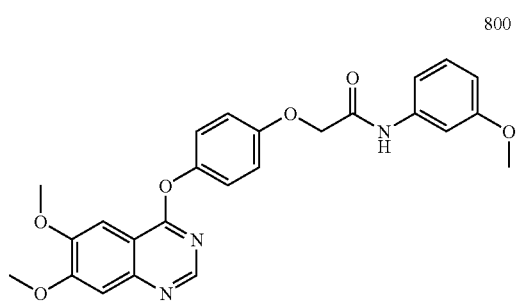
800
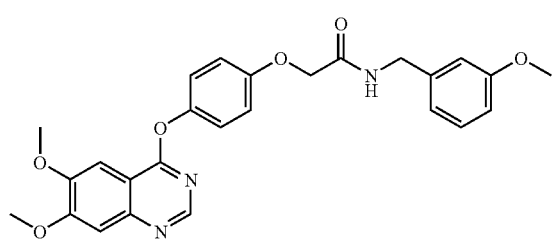
801
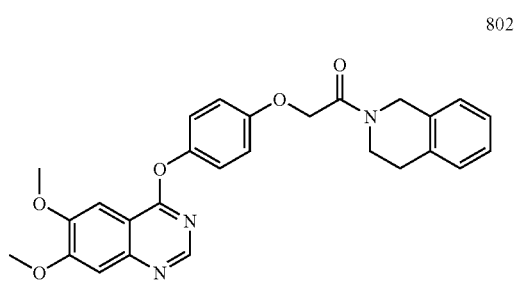
802

-continued
803
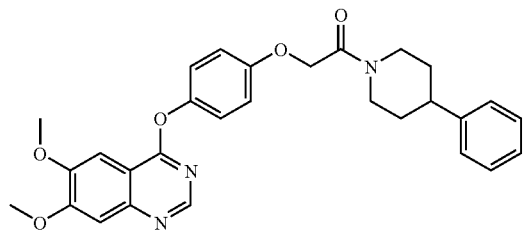
804
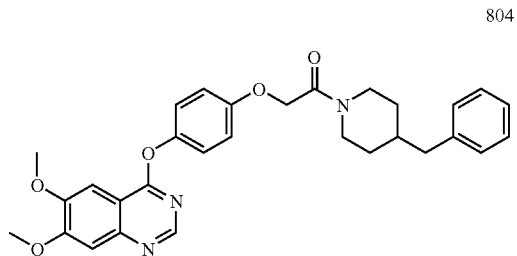
805
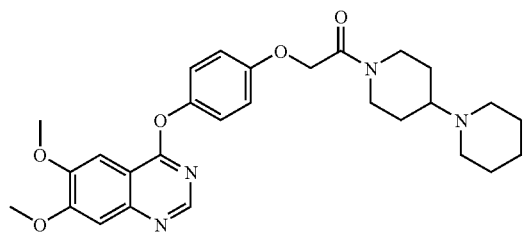
806
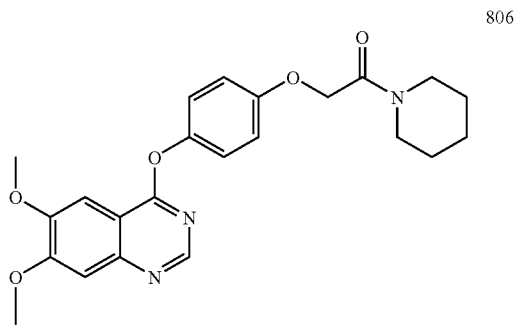
807
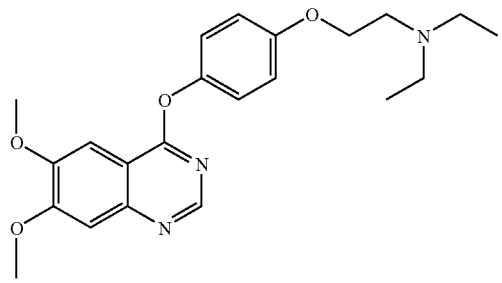
808
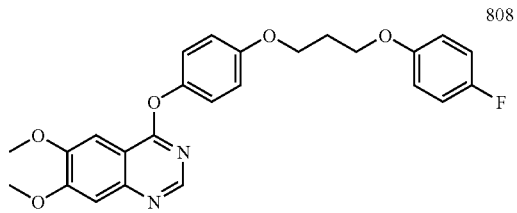
809
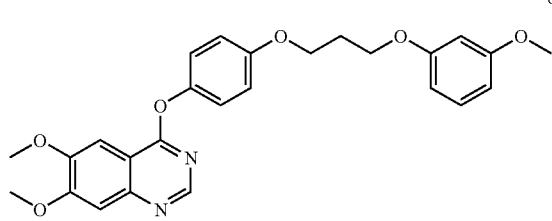
810
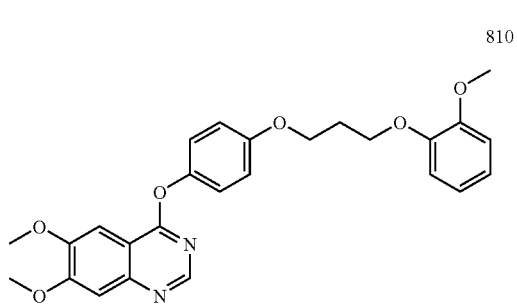
811
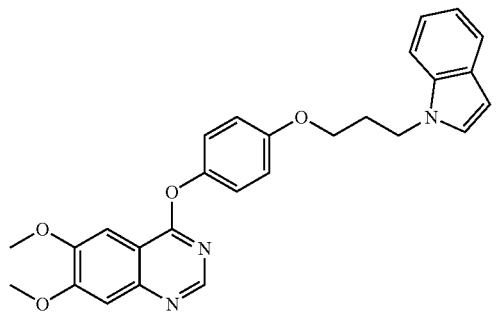
812
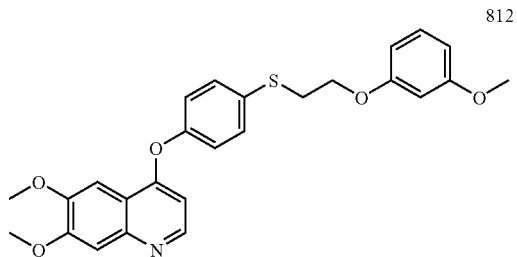

-continued
813
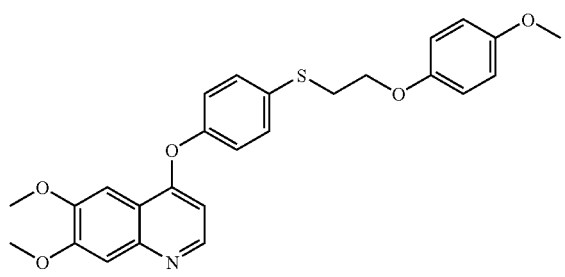
814
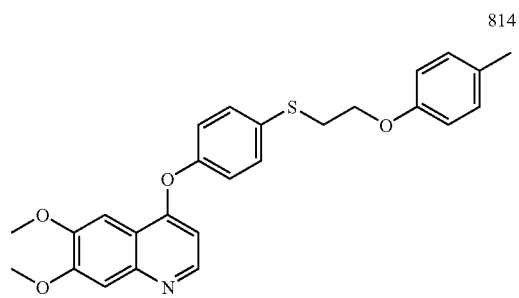
815
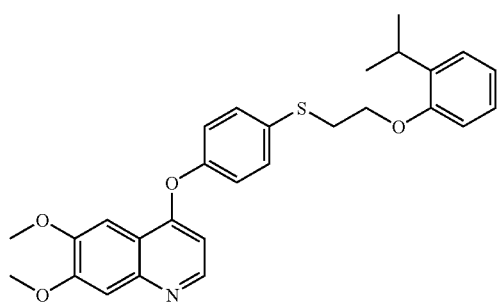
816
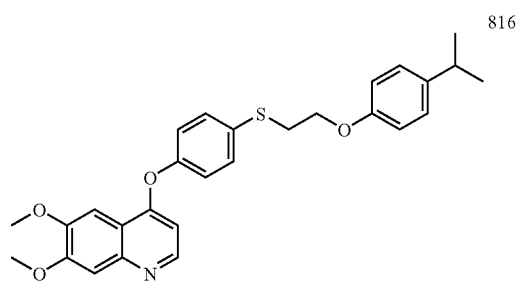
817
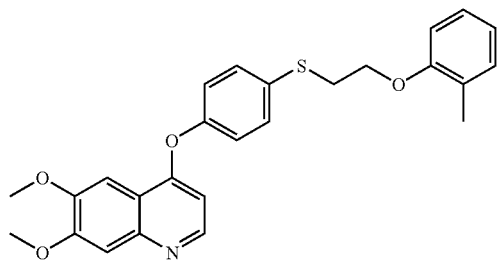
818
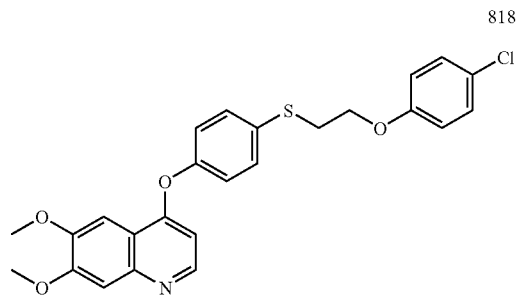
819
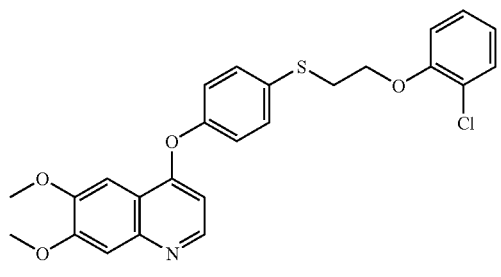
820
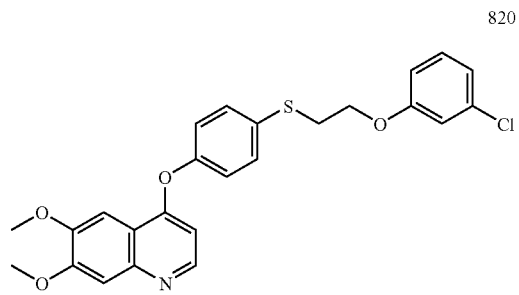
821
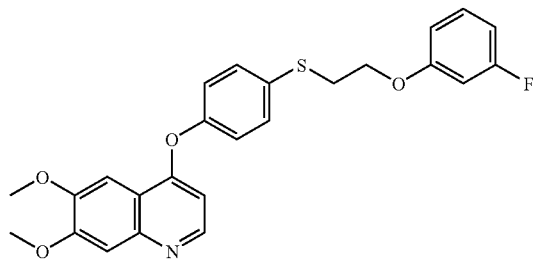
822
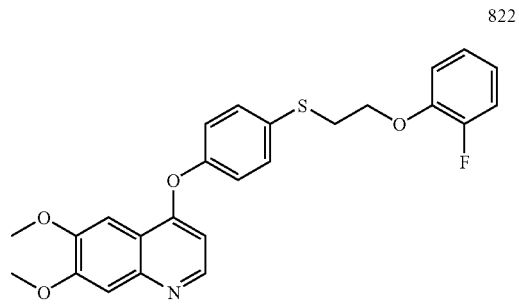

-continued
823
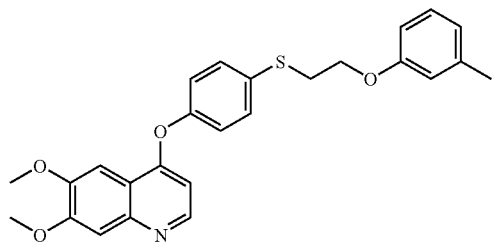
824
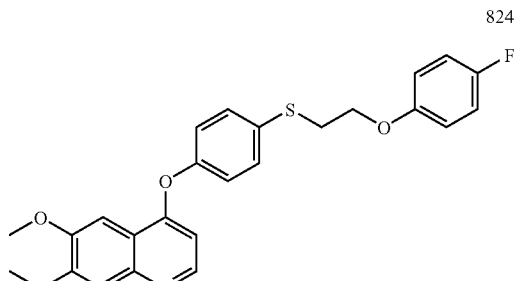
825
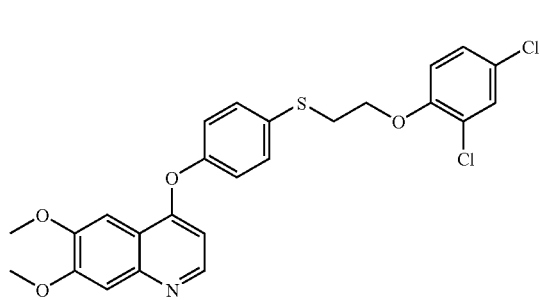
826
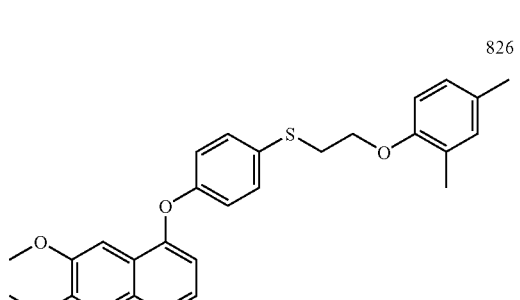
827
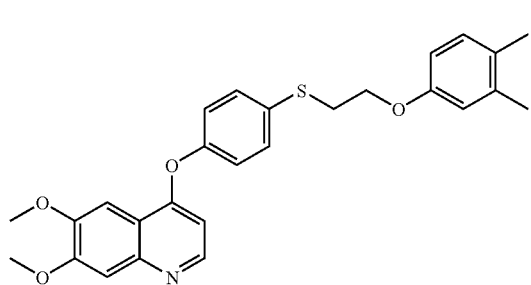
828
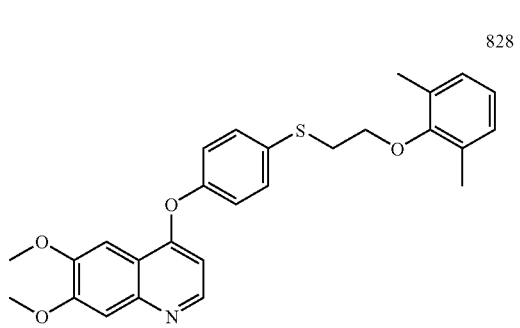
829
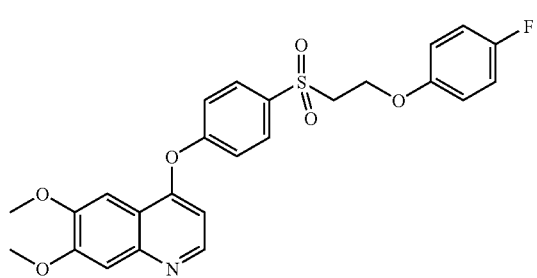
830
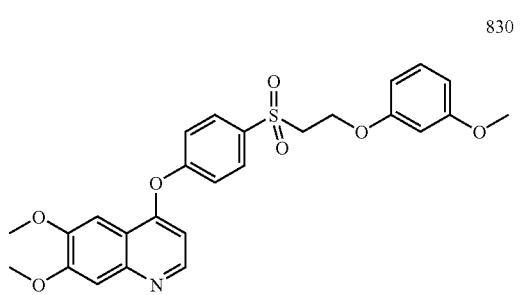
831
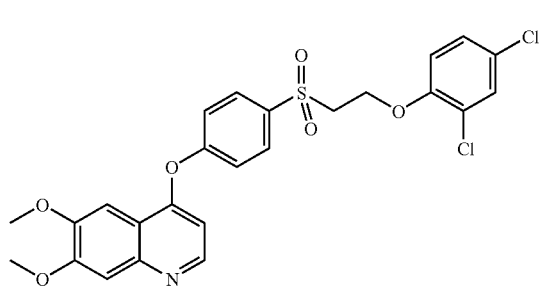
832
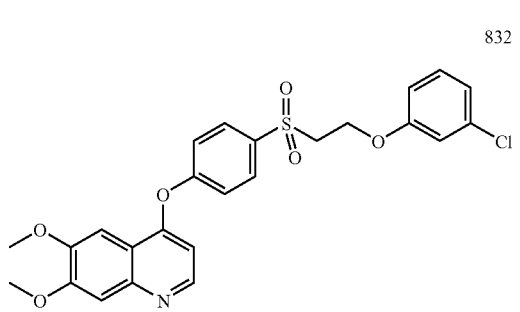

-continued
833
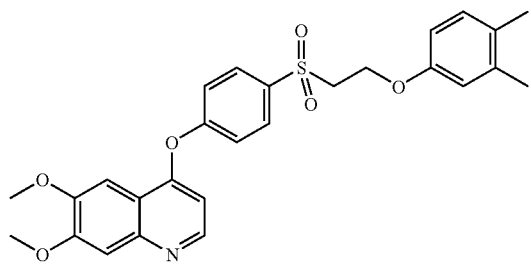
834
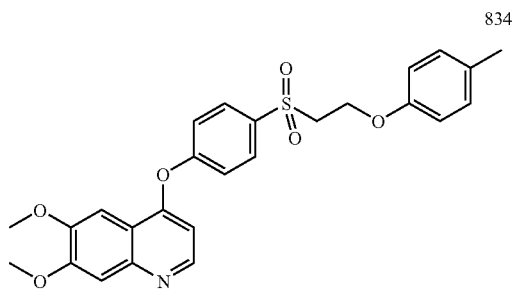
835
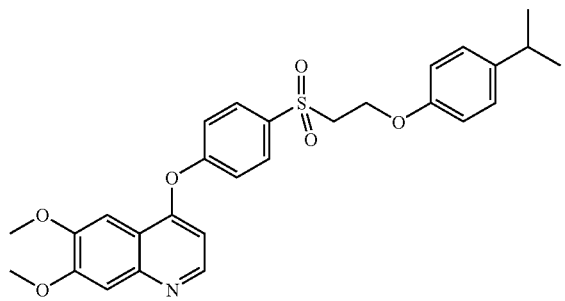
836
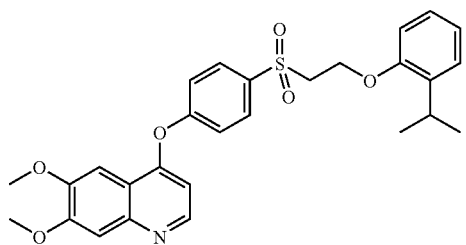
837
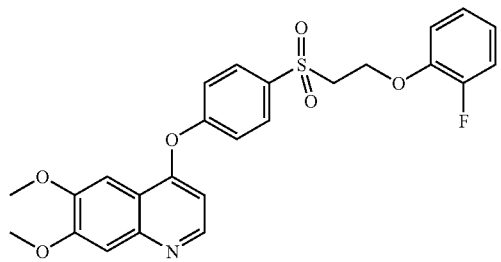
838
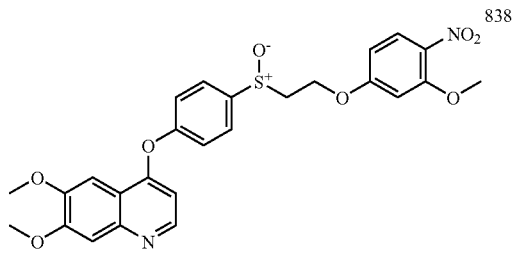
839
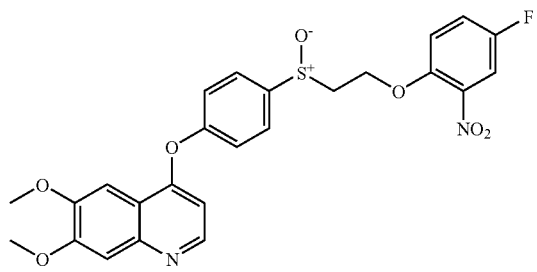
840
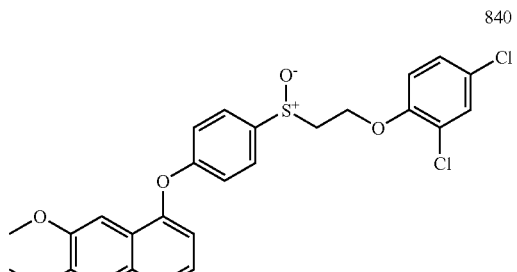
841
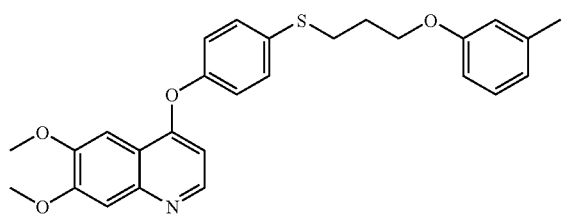
842
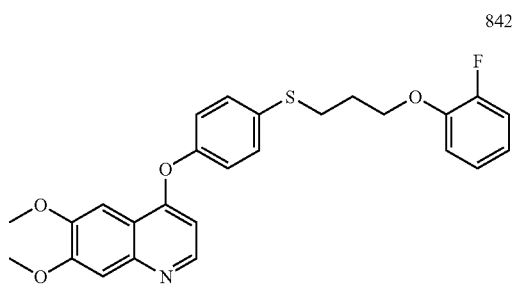

-continued
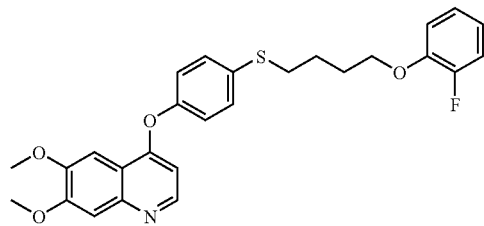
843
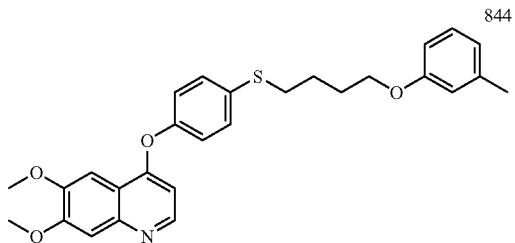
844
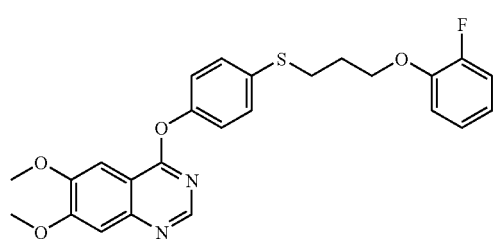
845
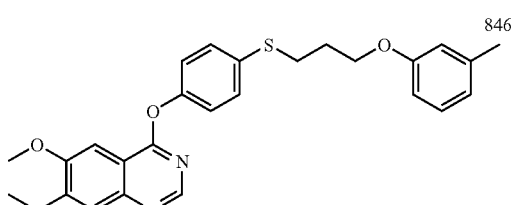
846
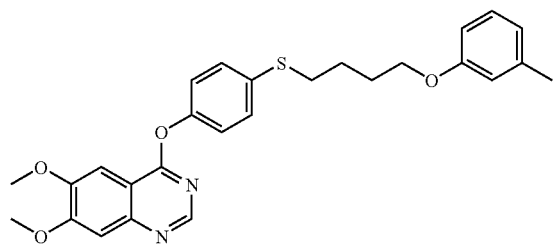
847
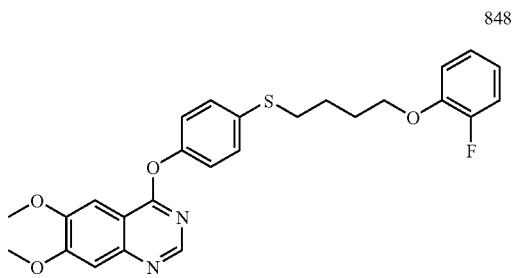
848
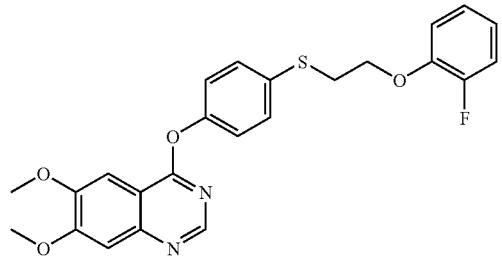
849
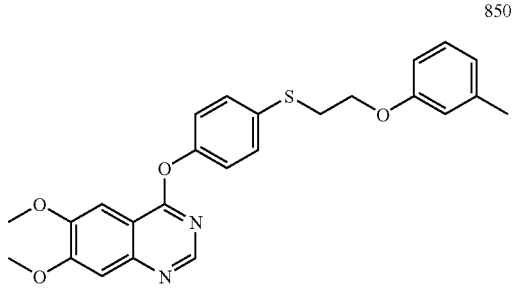
850
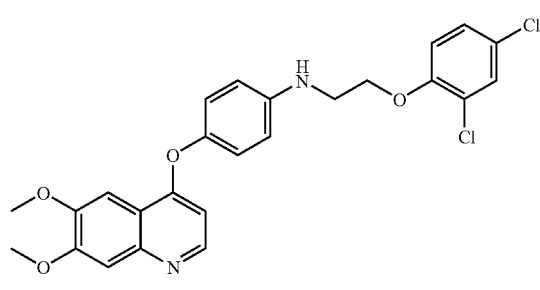
851
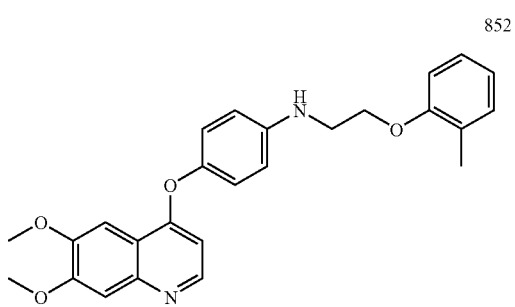
852

-continued
853 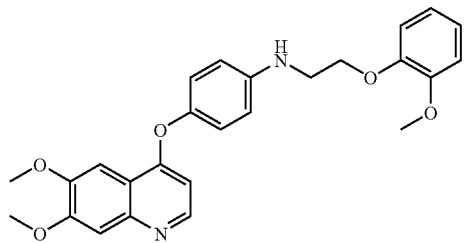
854 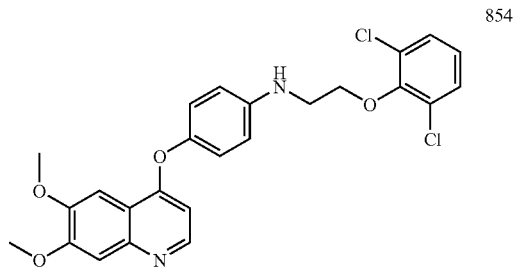
855 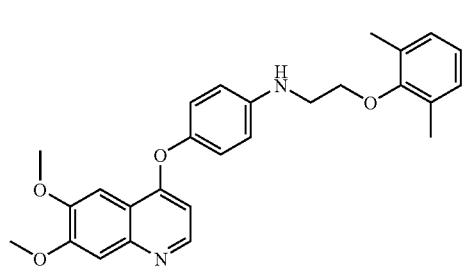
856 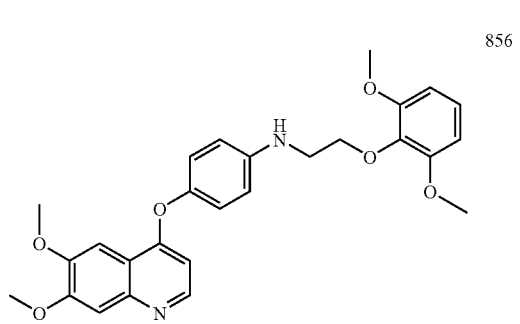
857 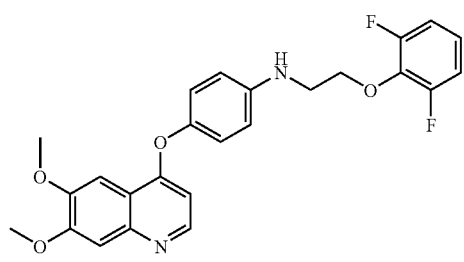
858 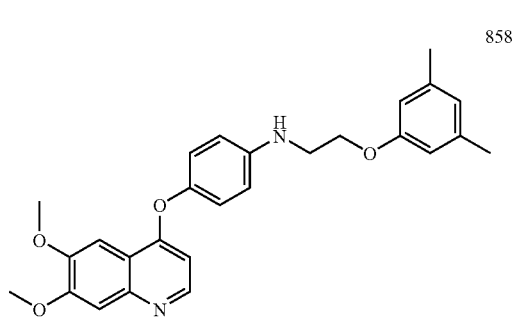
859 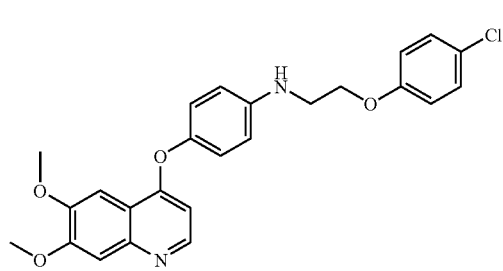
860 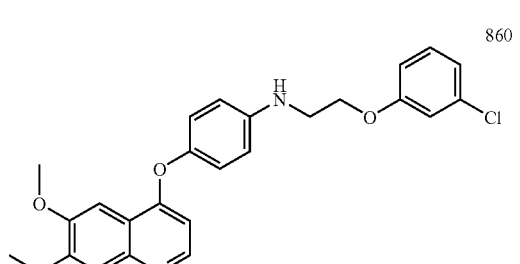
861 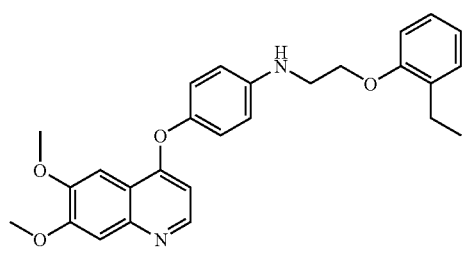
862 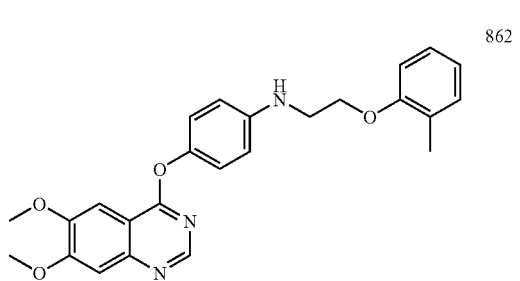

-continued
863
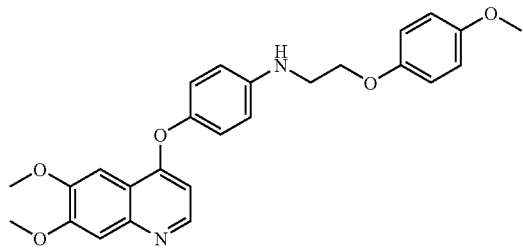
864
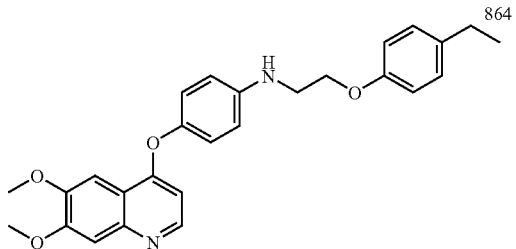
865
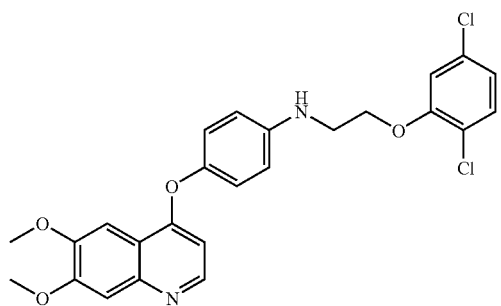
866
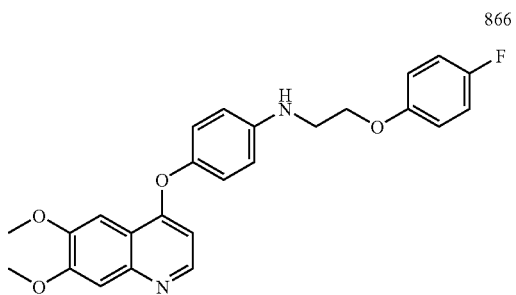
867
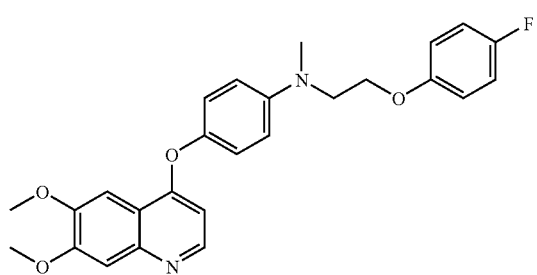
868
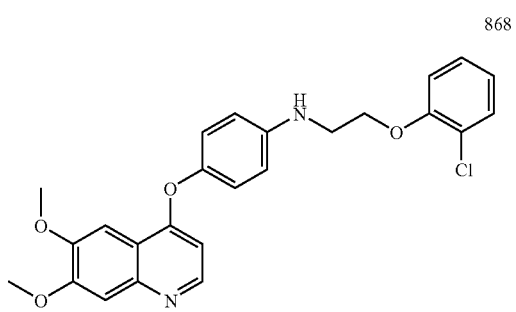
869
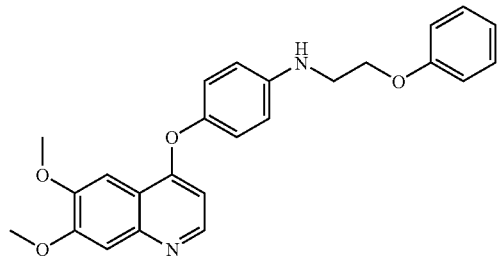
870
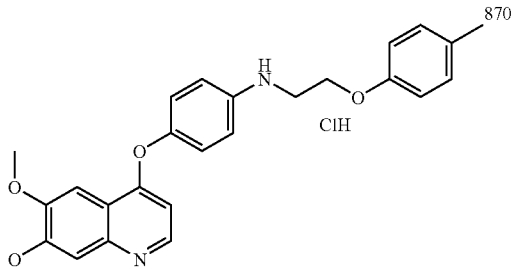
871
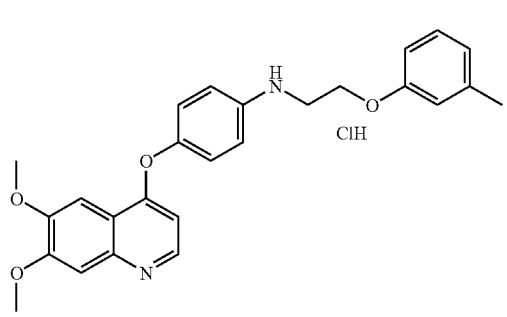
872
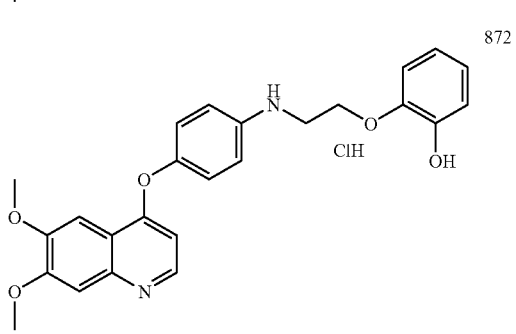

-continued
873
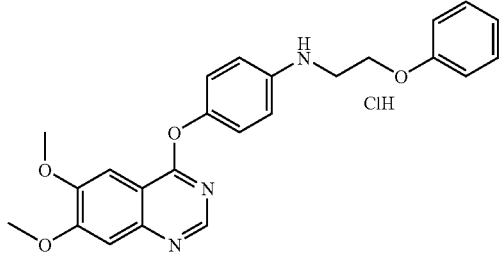
874
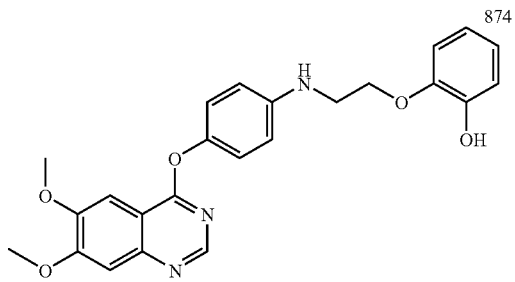
875
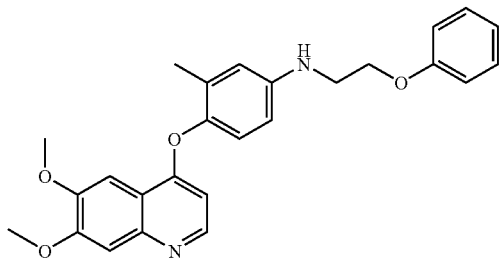
876
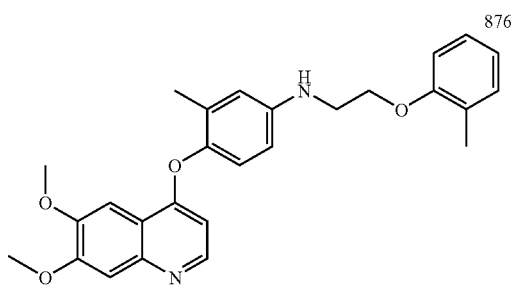
877
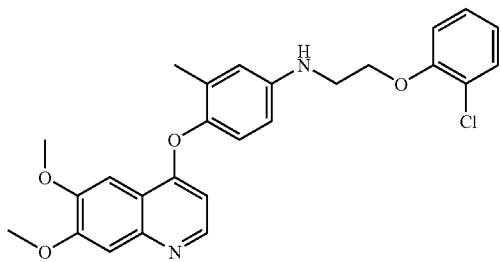
878
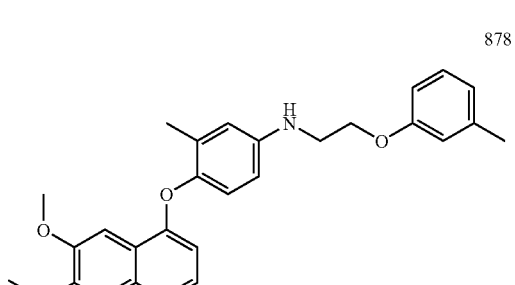
879
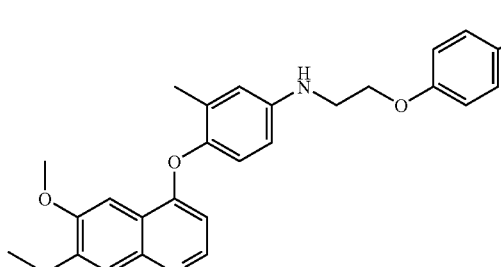
880
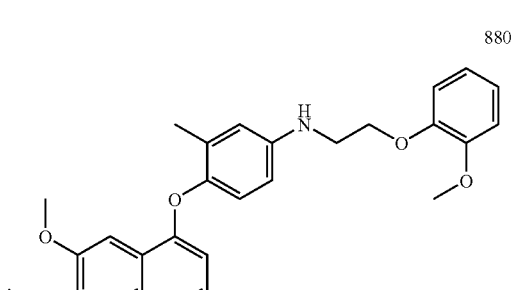
881
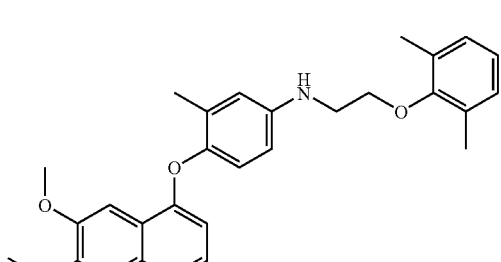
882
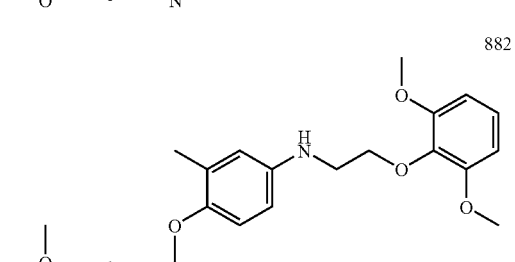

-continued
883
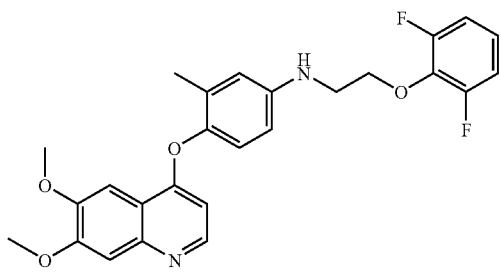
884
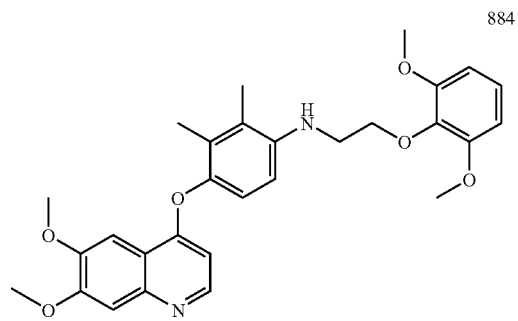
885
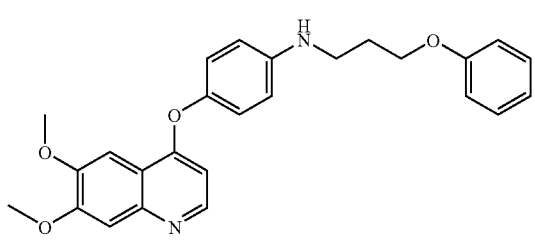
886
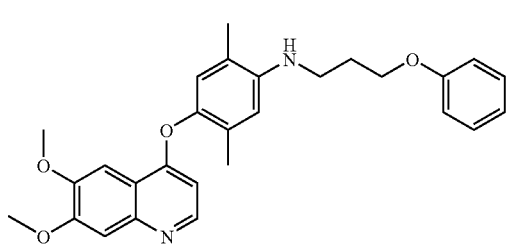
887
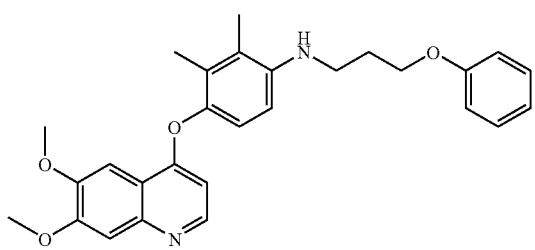
888
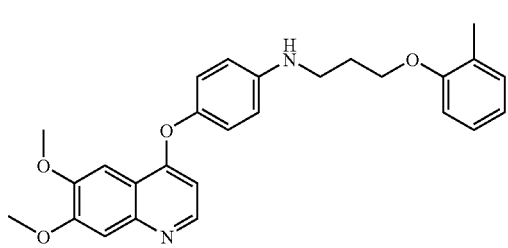
889
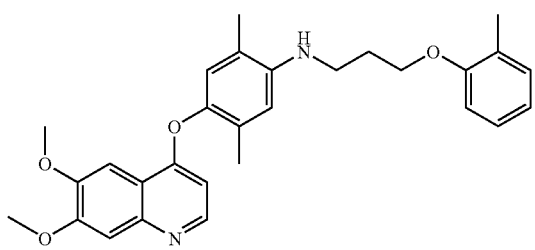
890
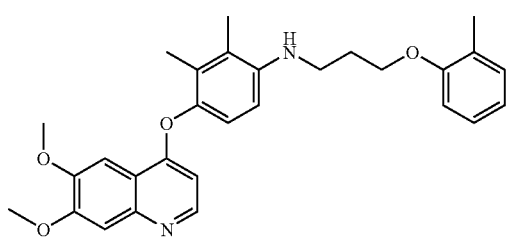
891
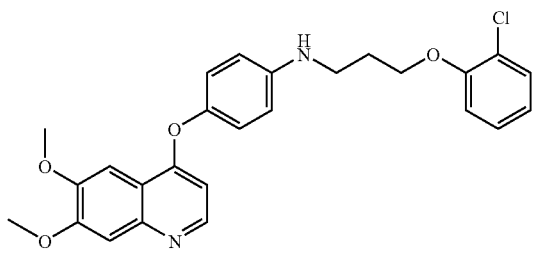
892
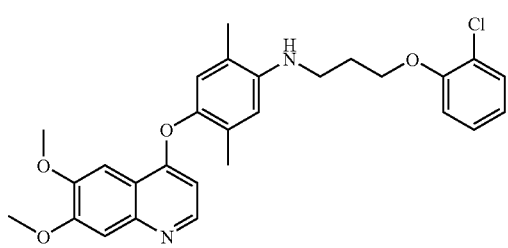

-continued
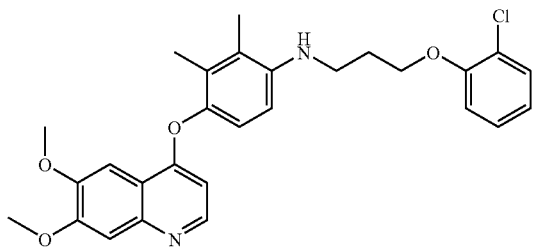
893
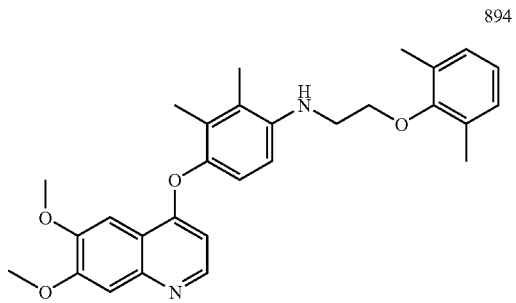
894
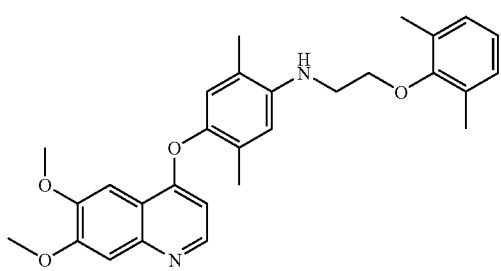
895
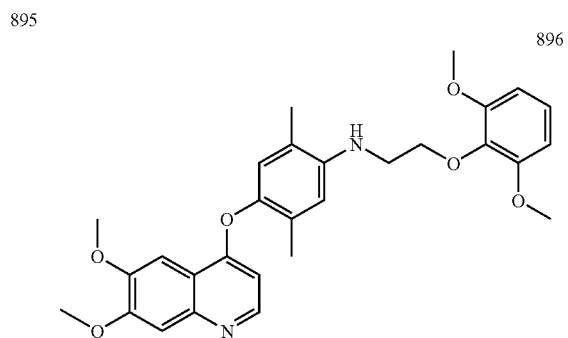
896
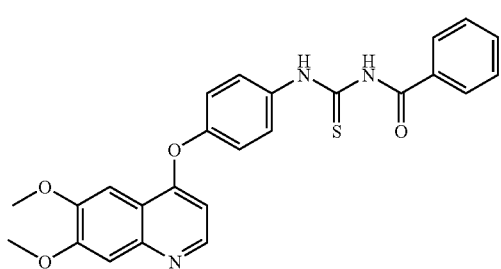
897
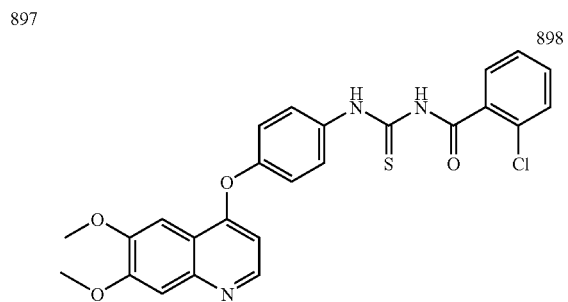
898
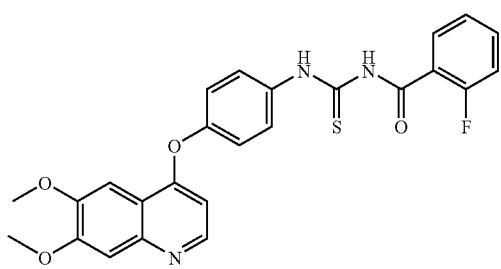
899
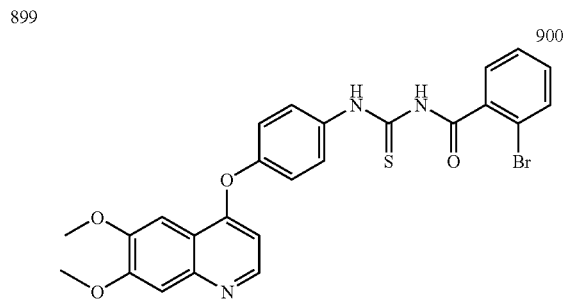
900
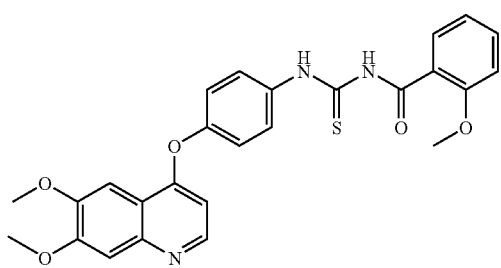
901
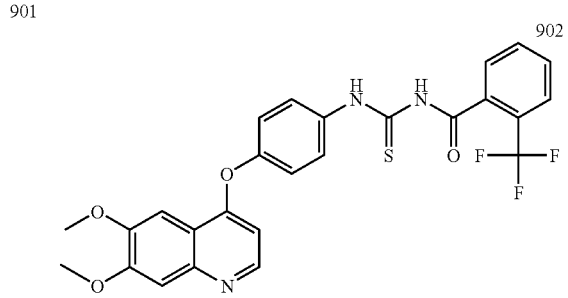
902

-continued
903
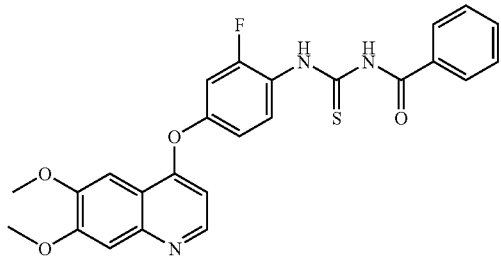
904
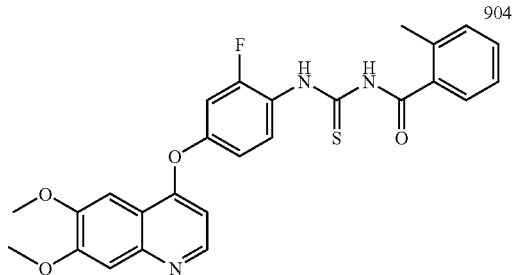
905
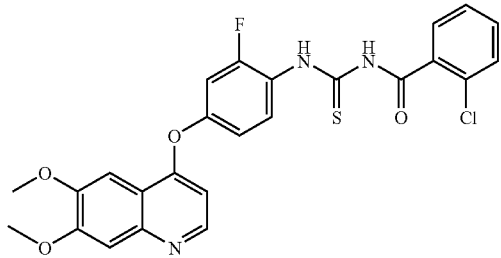
906
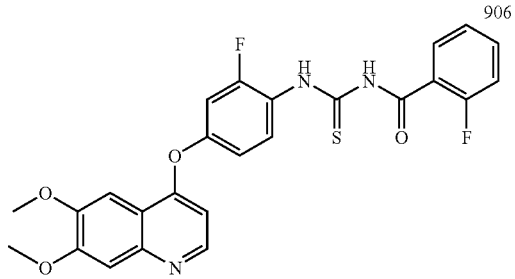
907
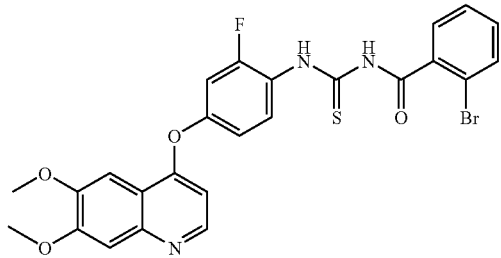
908
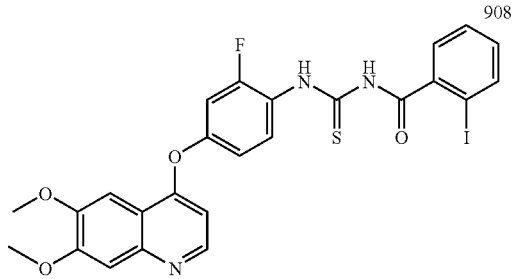
909
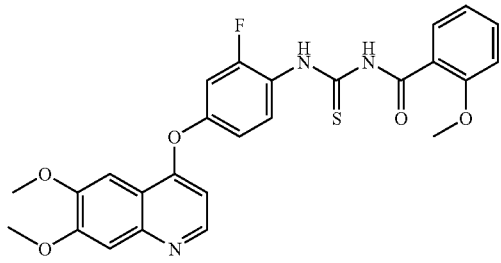
910
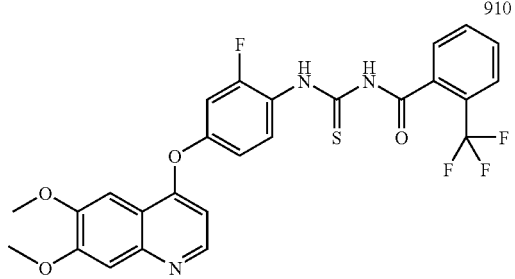
911
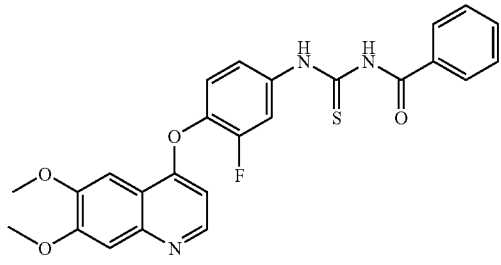
912
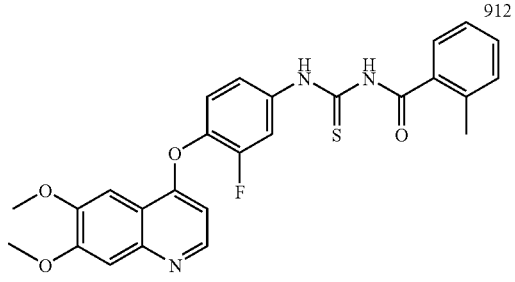

-continued
913
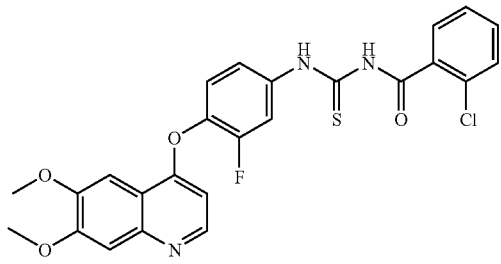
914
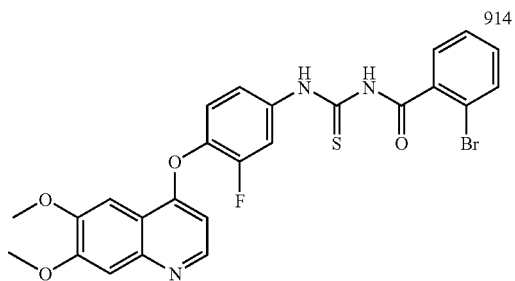
915
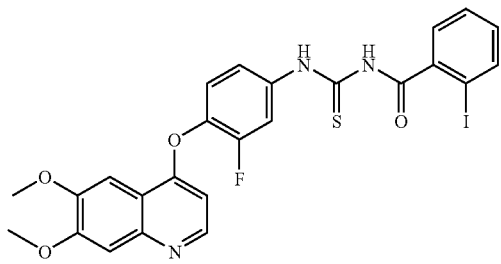
916
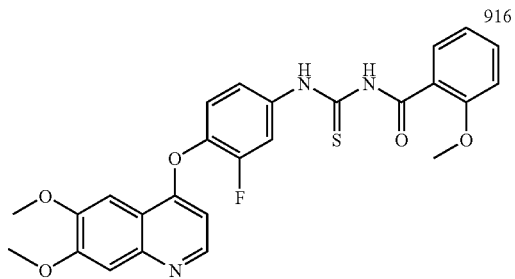
917
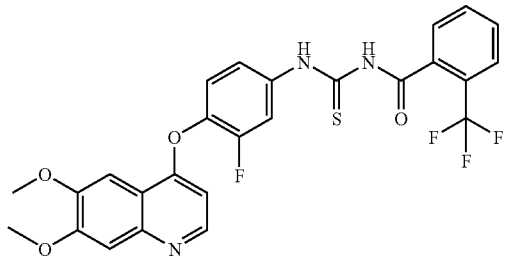
918
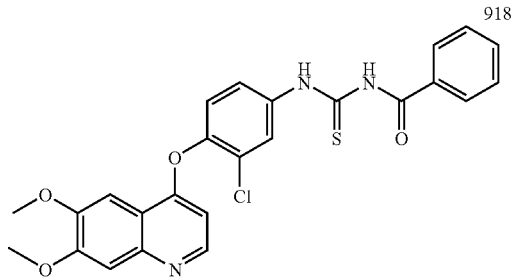
919
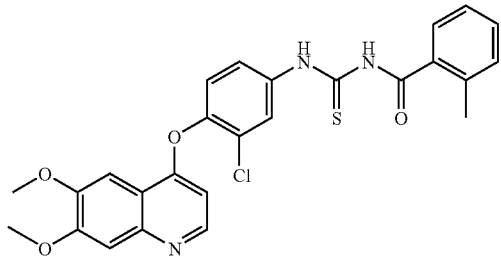
920
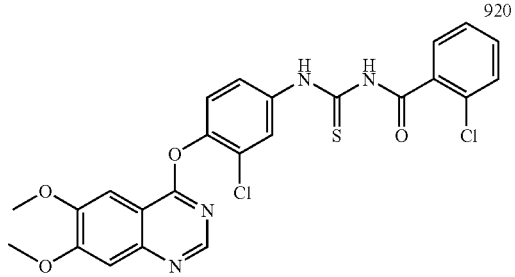
921
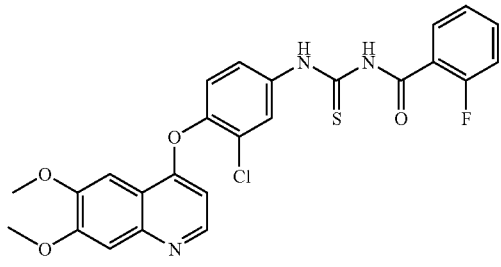
922
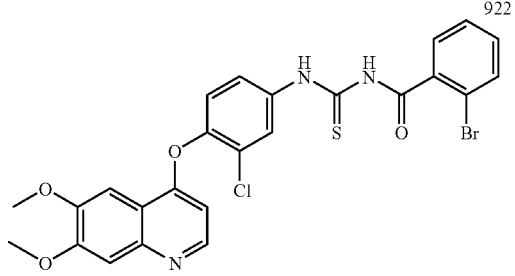

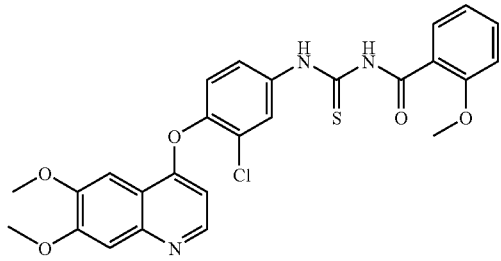
923
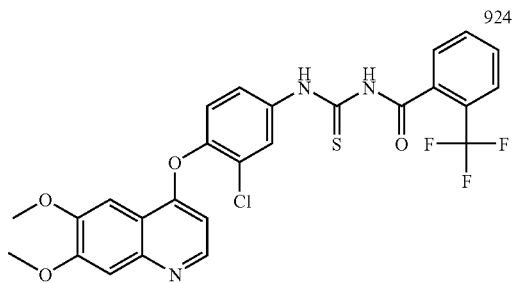
924
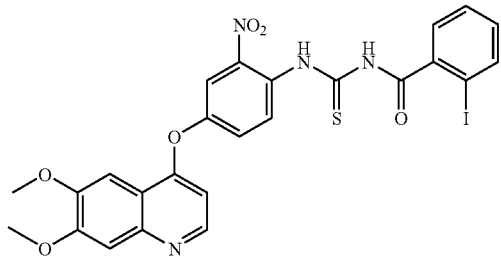
925
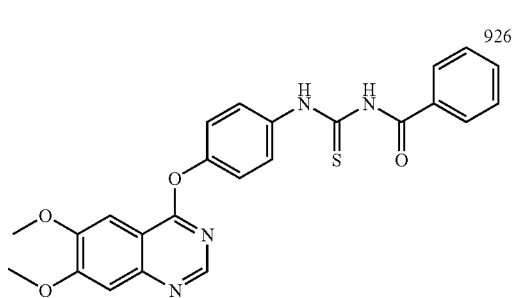
926
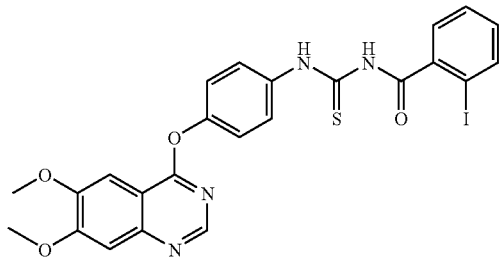
927
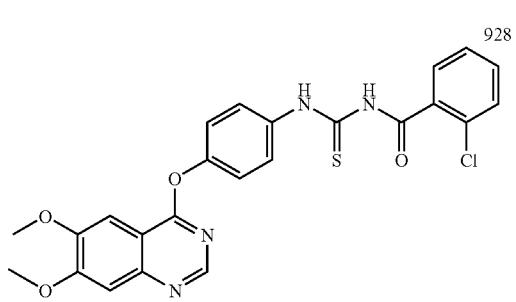
928
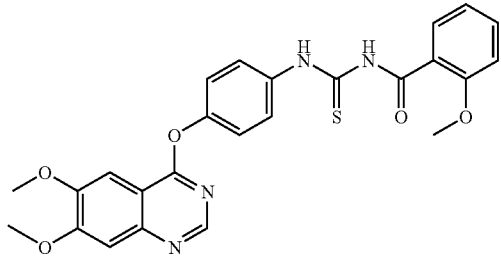
929
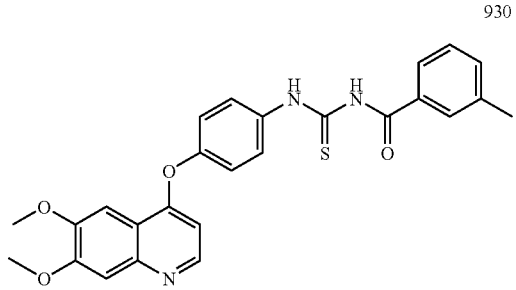
930
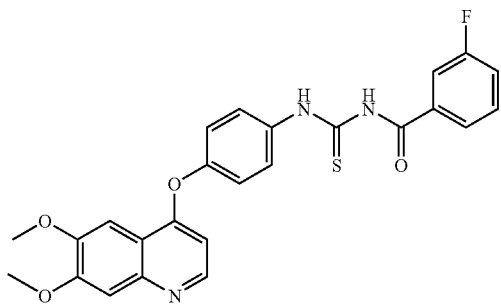
931
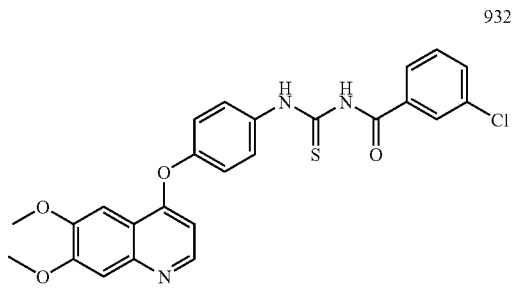
932

933 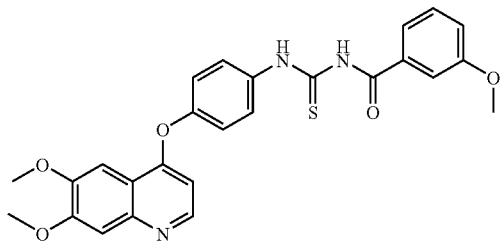
935 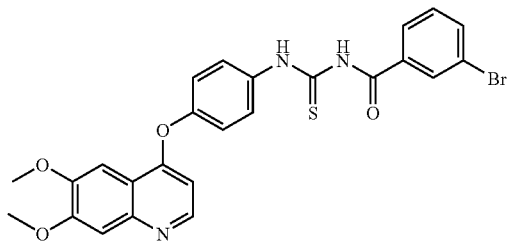
937 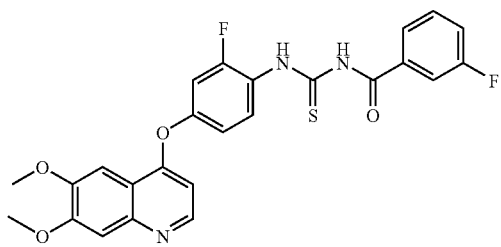
939 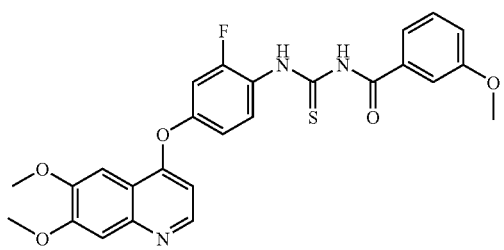
941 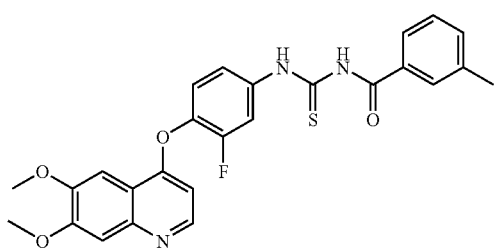
943 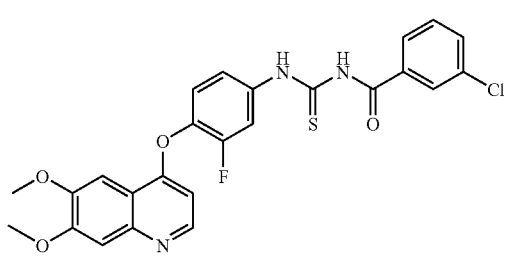
934 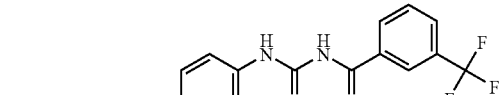
936 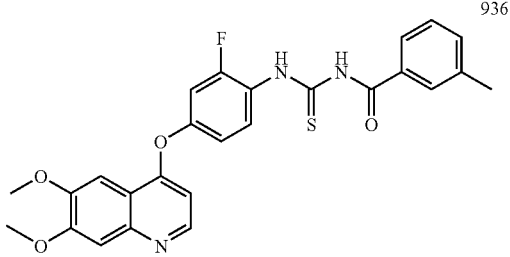
938 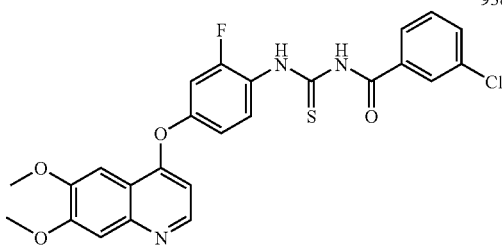
940 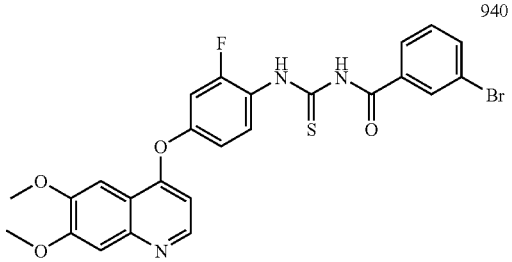
942 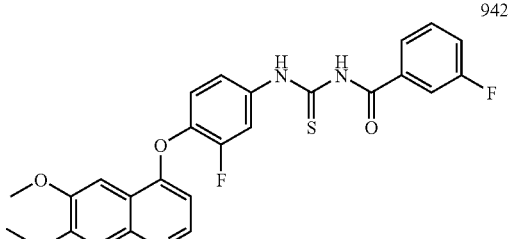
944 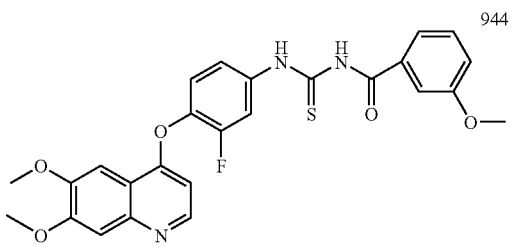

-continued
945
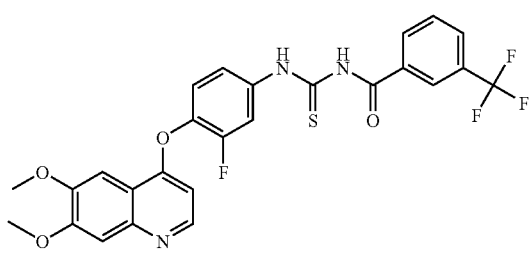
946
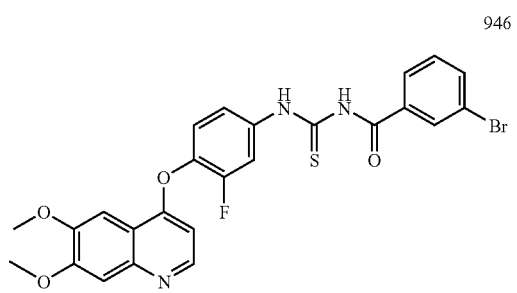
947
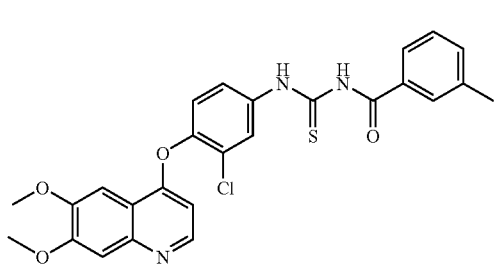
948
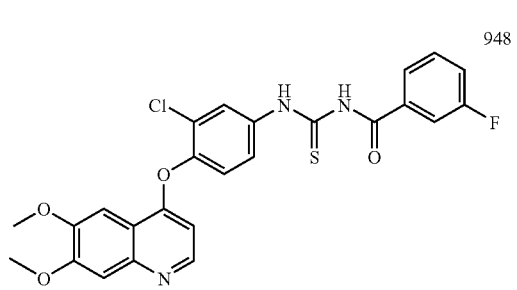
949
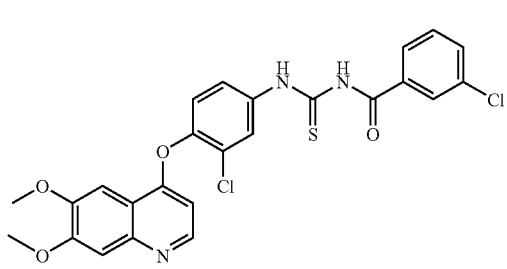
950
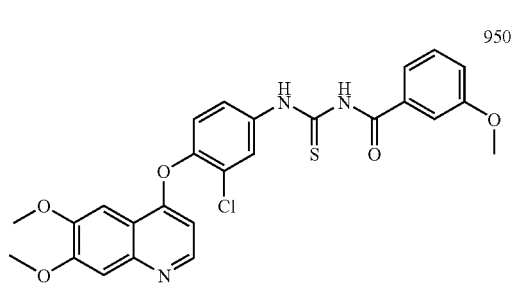
951
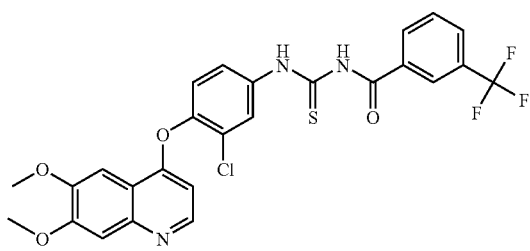
952
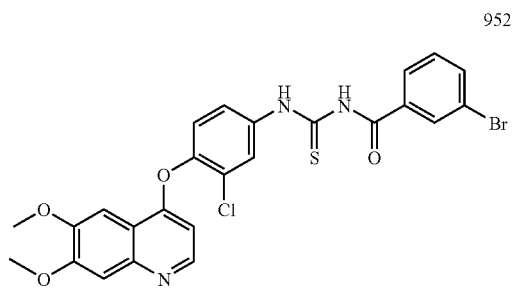
953
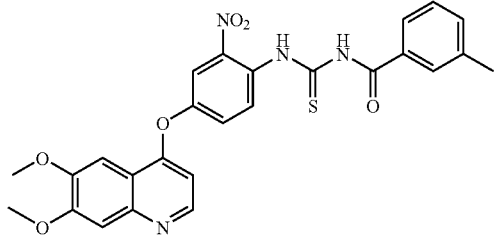
954
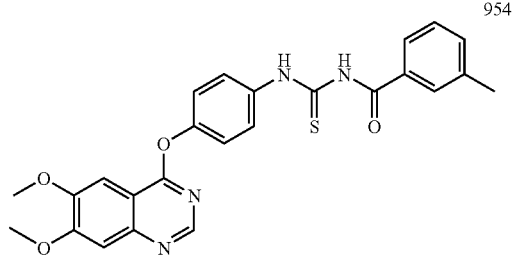

-continued
955
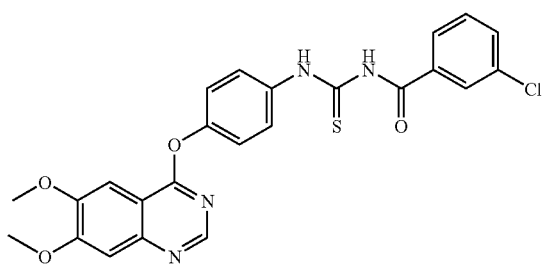
956
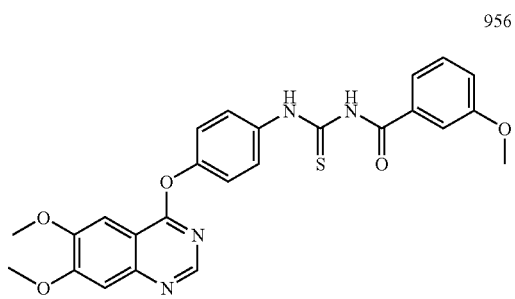
957
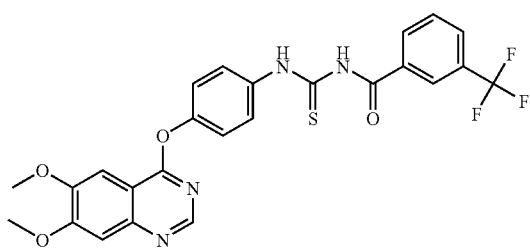
958
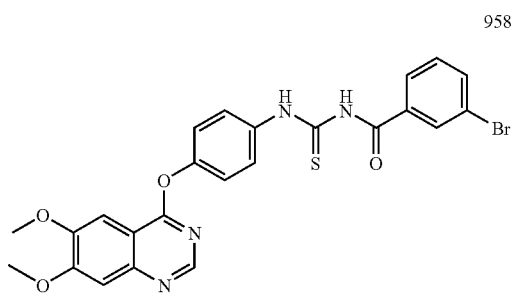
959
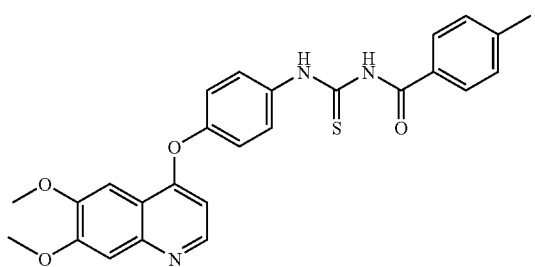
960
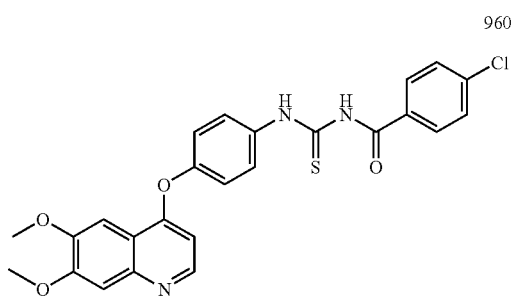
961
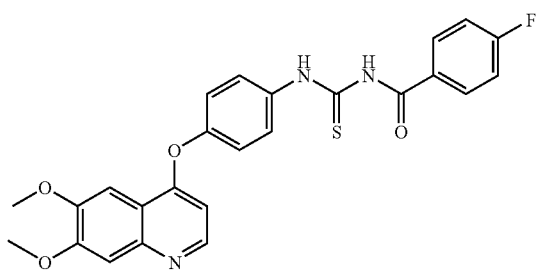
962
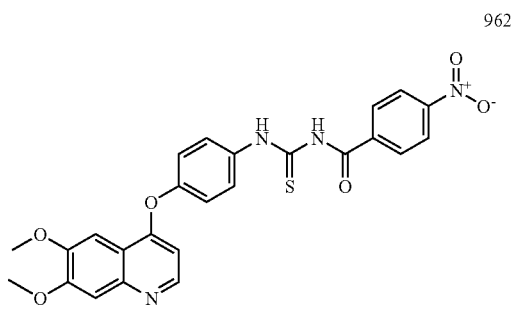
963
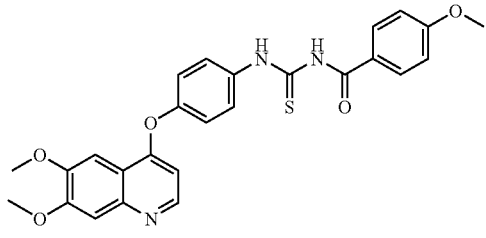
964
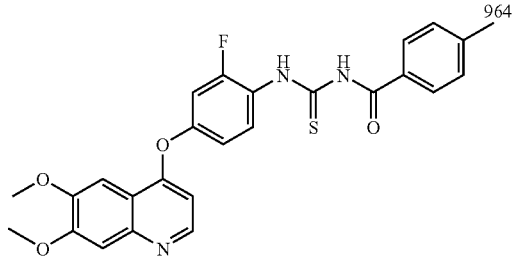

-continued
965
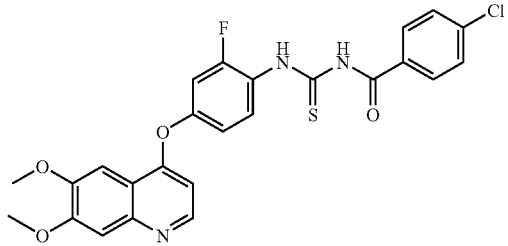
966
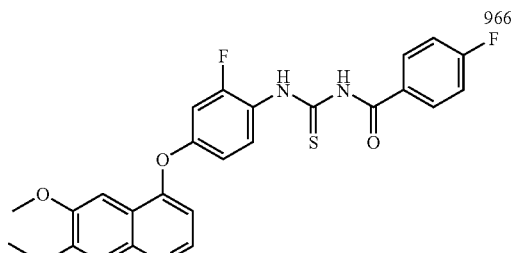
967
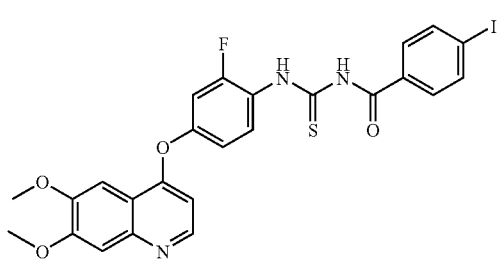
968
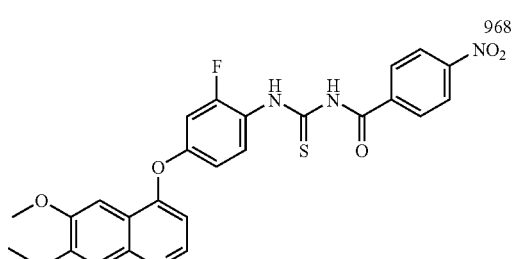
969
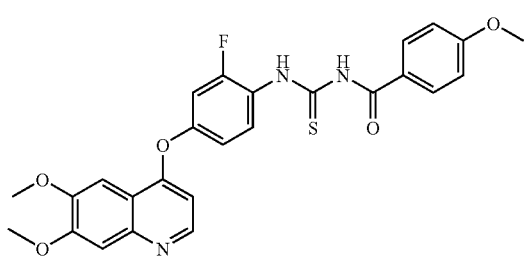
970
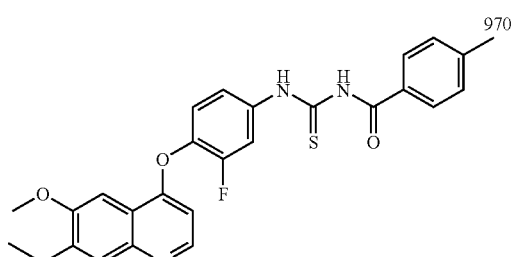
971
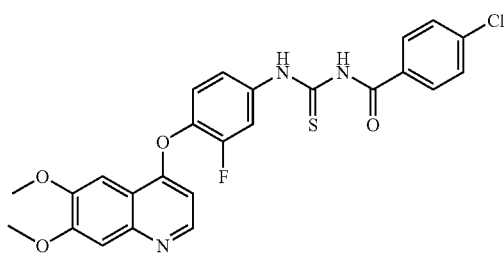
972
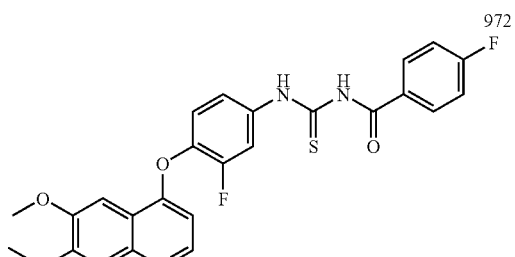
973
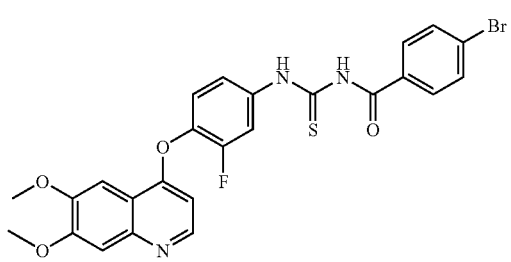
974
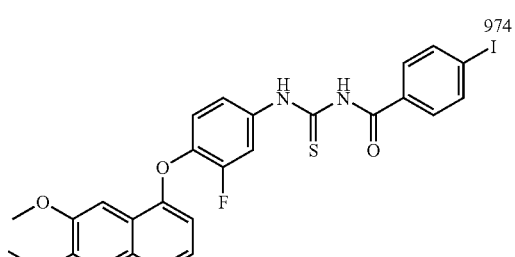
975
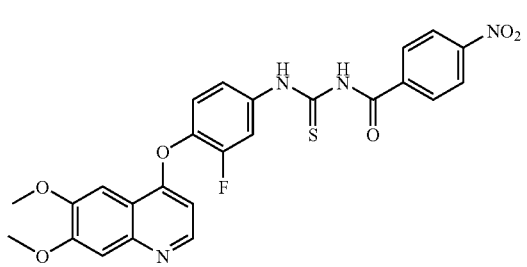
976
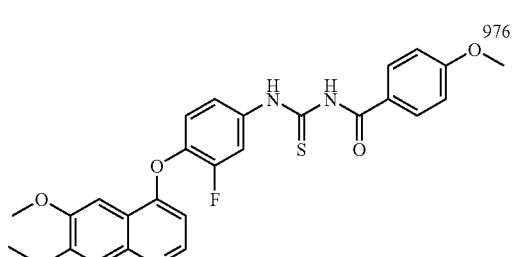

-continued
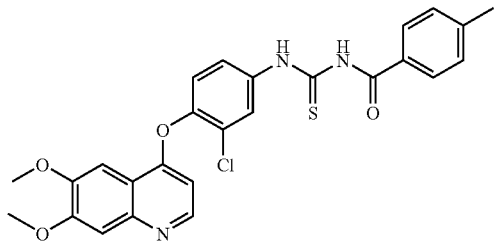
977
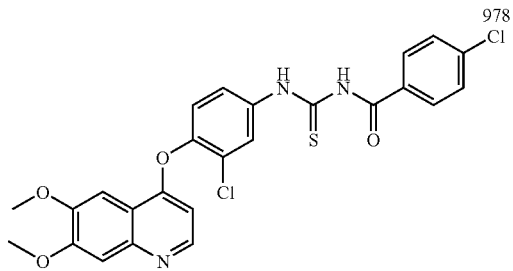
978
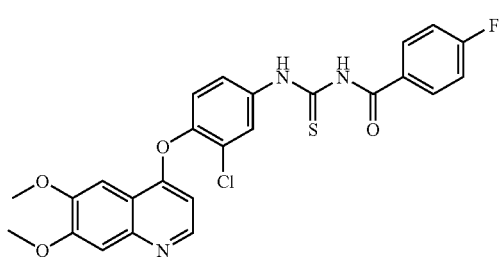
979
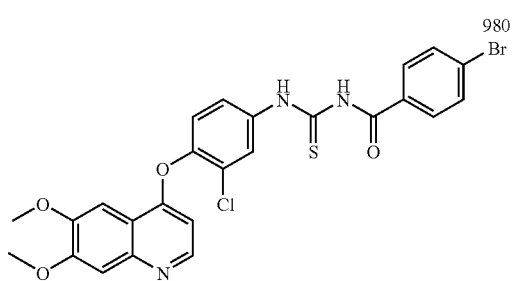
980
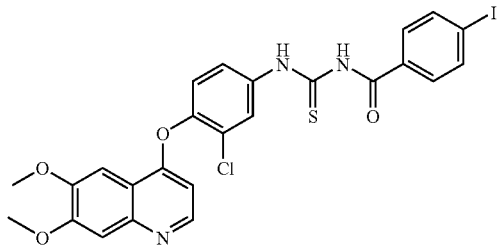
981
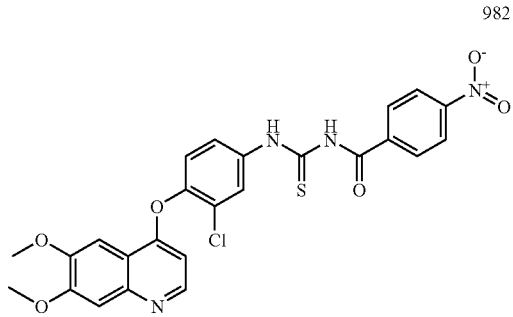
982
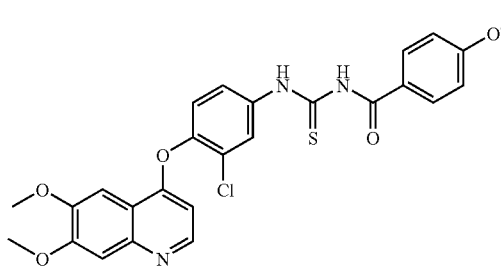
983
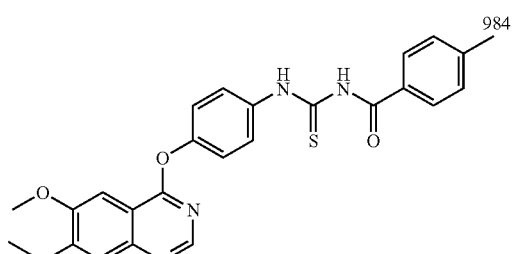
984
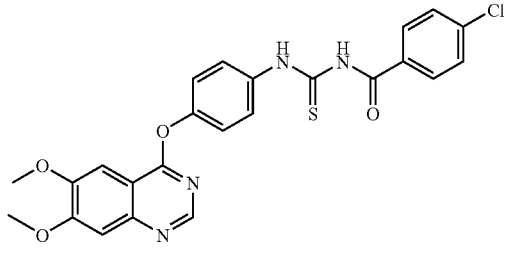
985
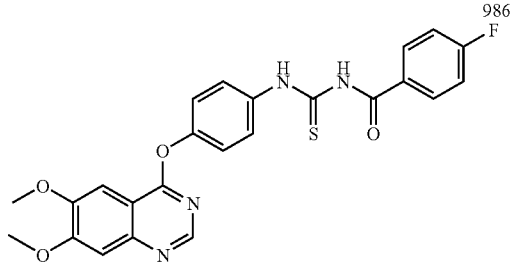
986

-continued
987
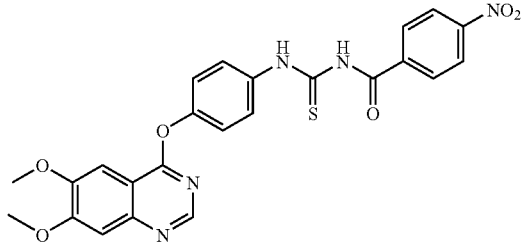
988
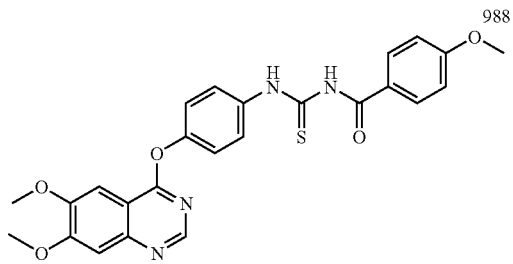
989
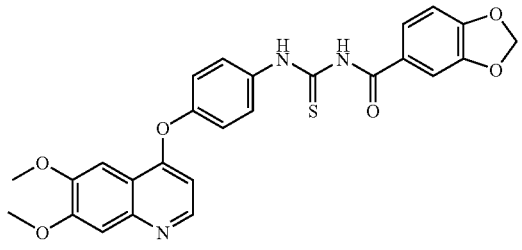
990
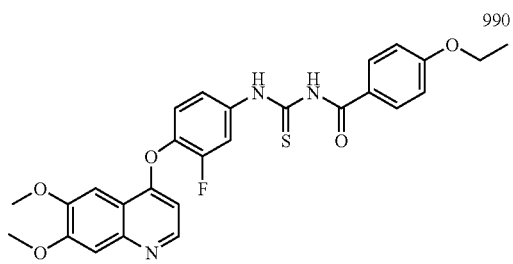
991
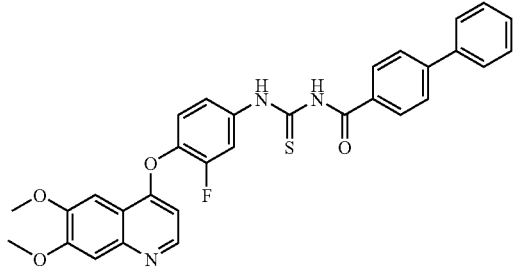
992
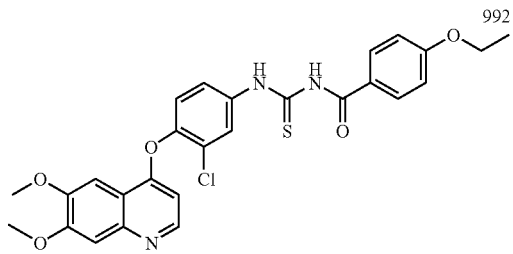
993
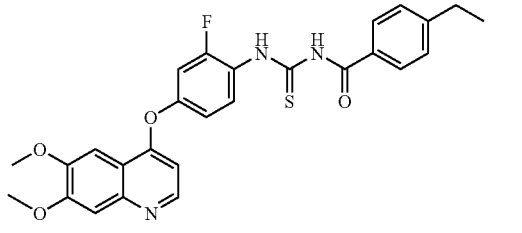
994
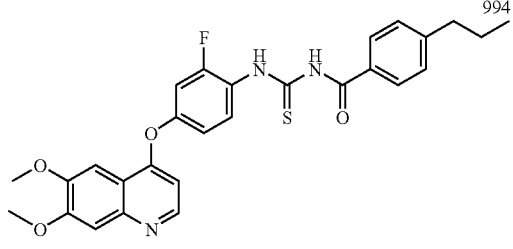
995
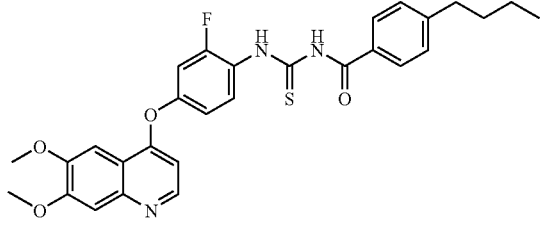
996
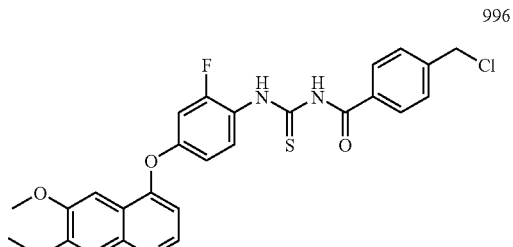
997
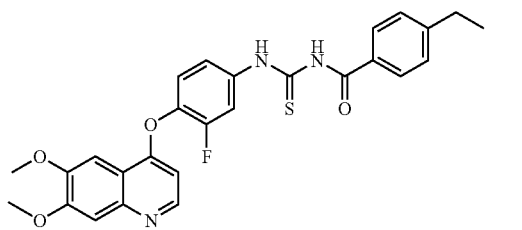
998
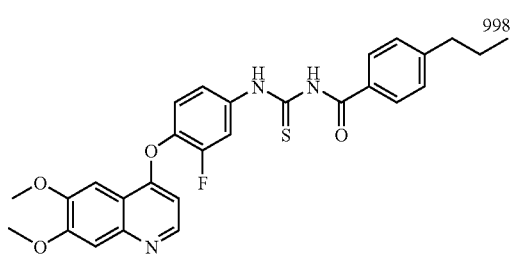

-continued
999
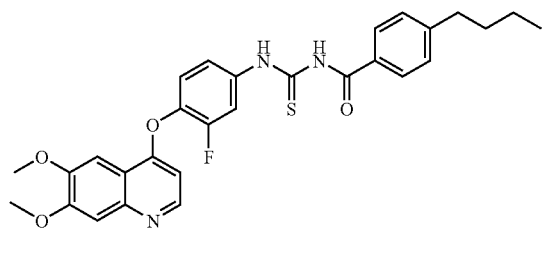
1000
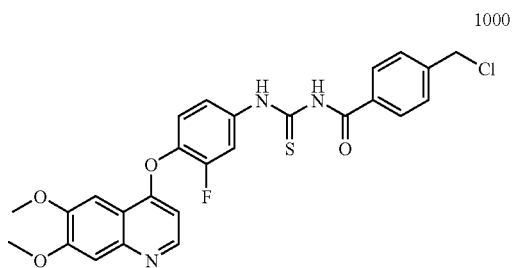
1001
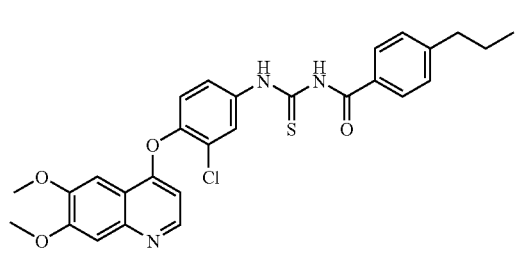
1002
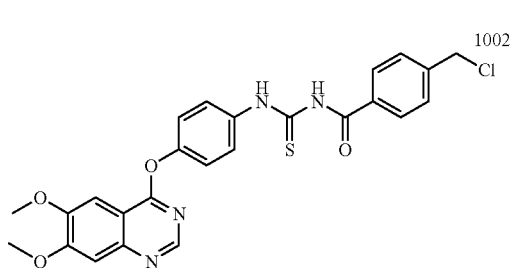
1003
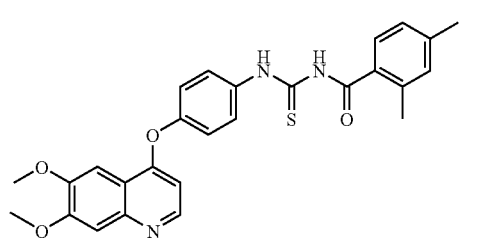
1004
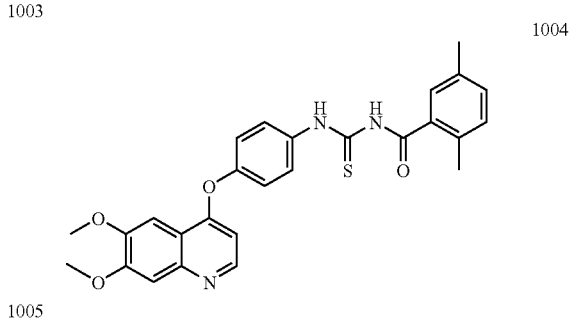
1005
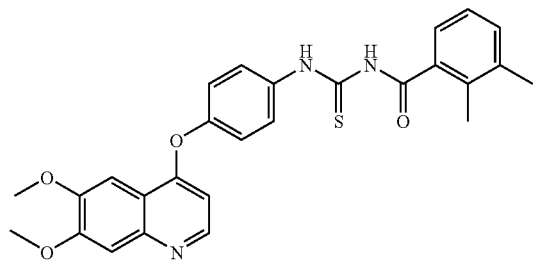
1006
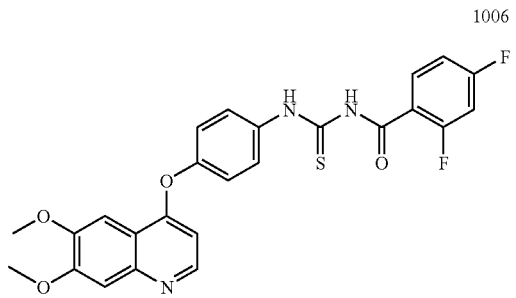
1007
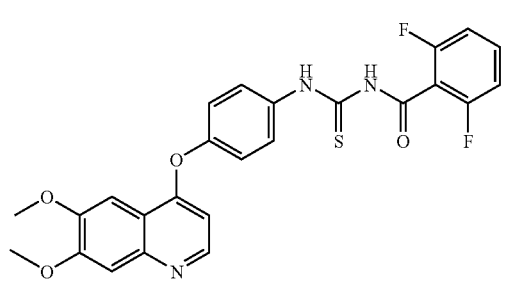
1008
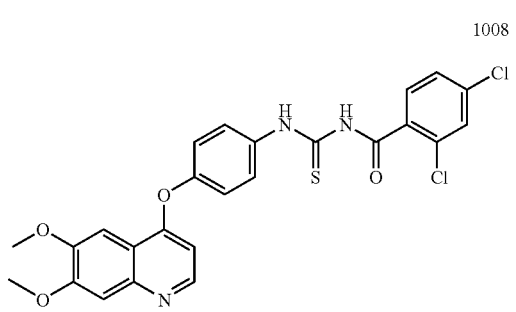

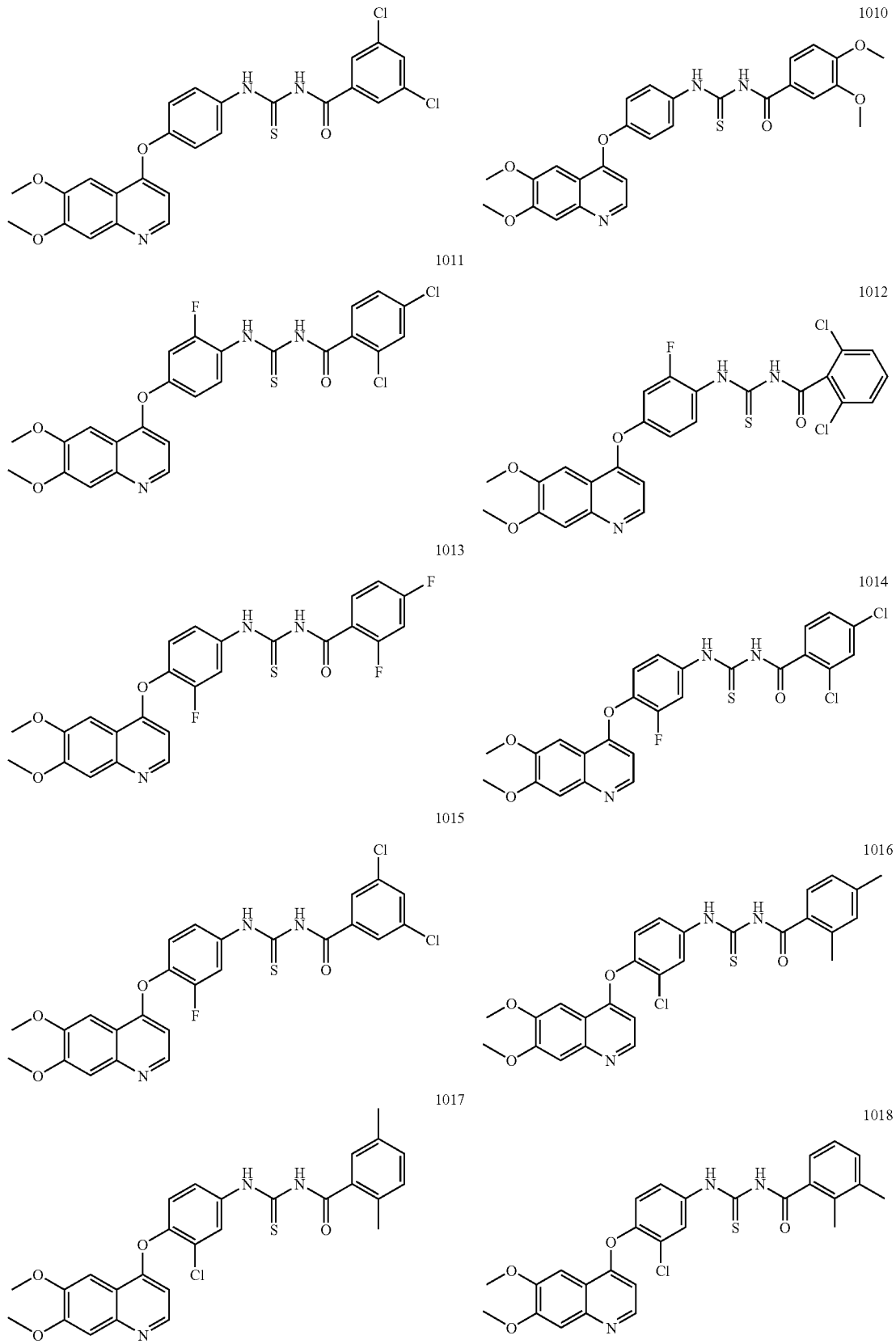

-continued
1019
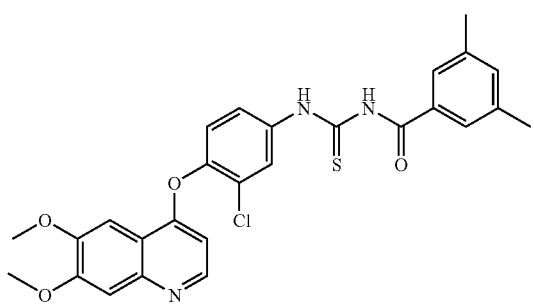
1020
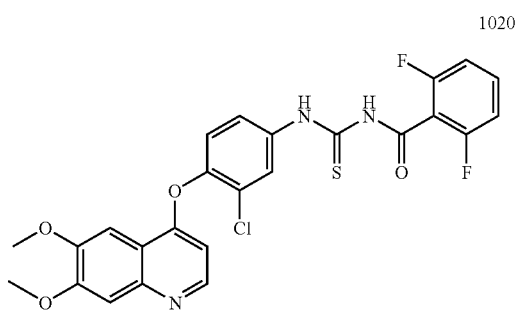
1021
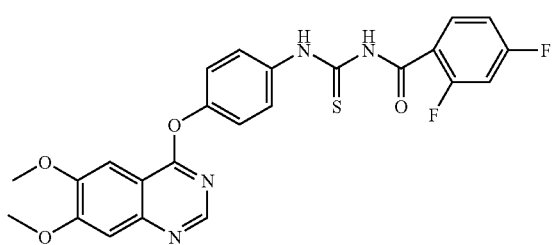
1022
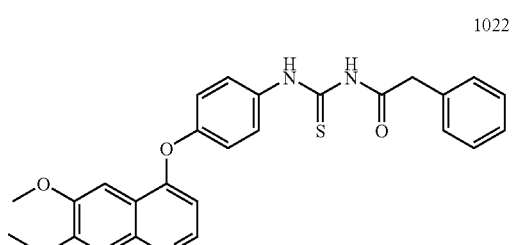
1023
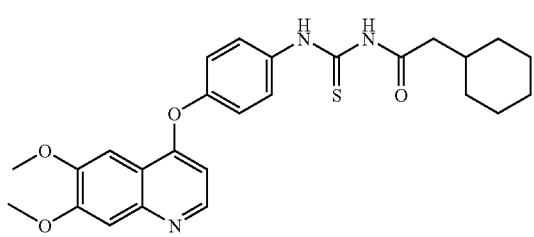
1024
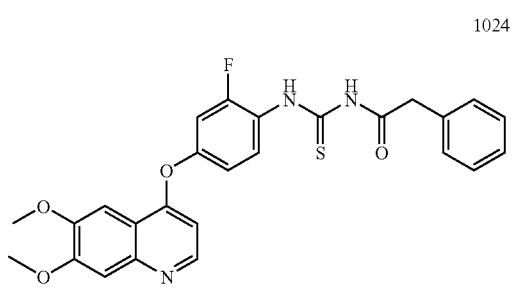
1025
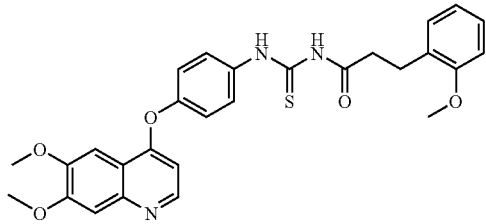
1026
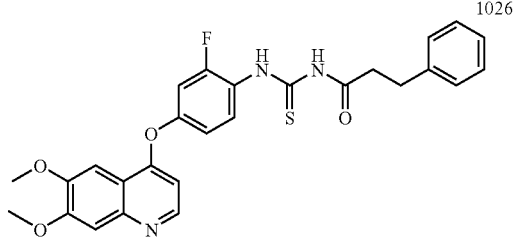
1027
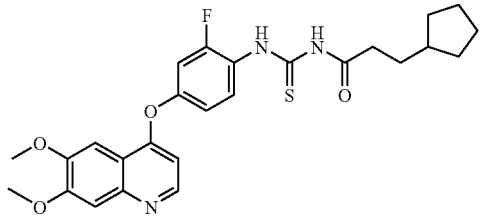
1028
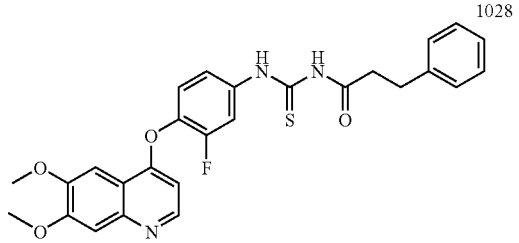

-continued
1029
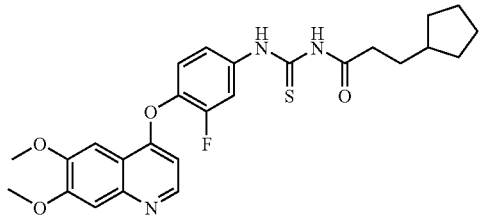
1030
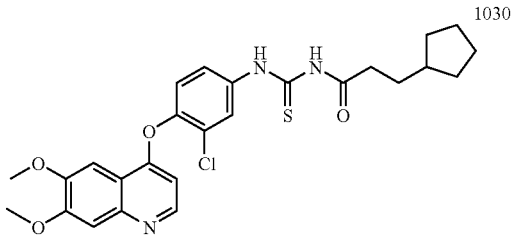
1031
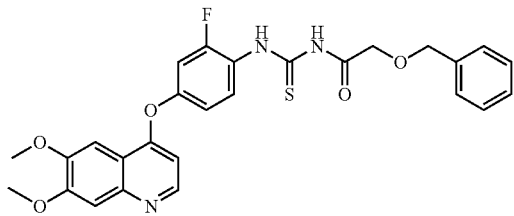
1032
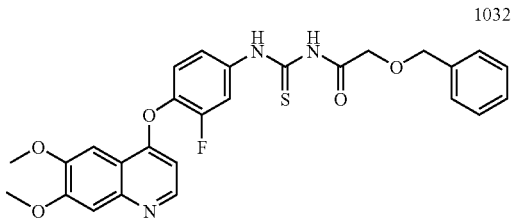
1033
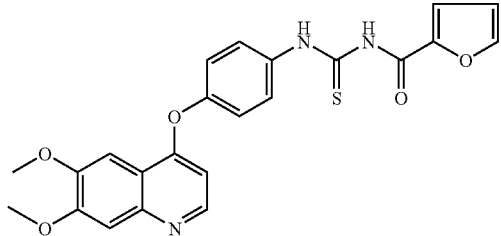
1034
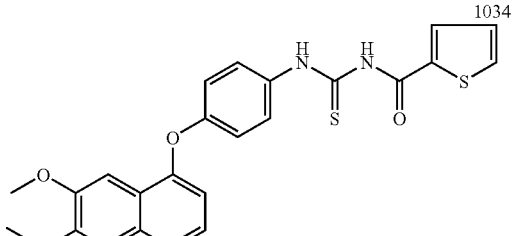
1035
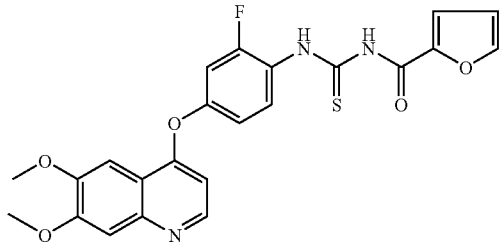
1036
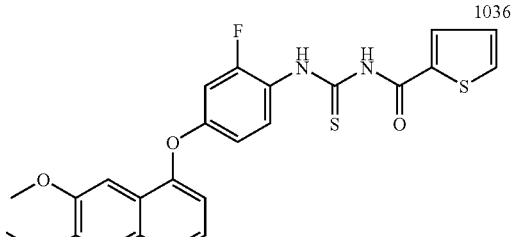
1037
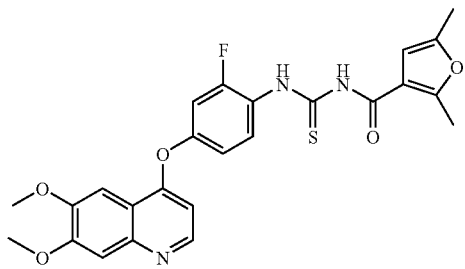
1038
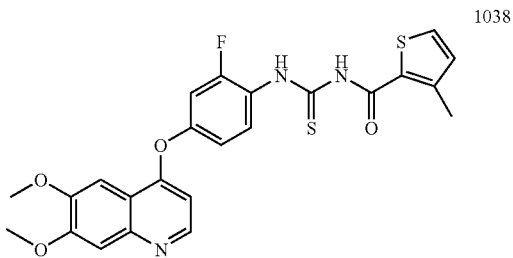
1039
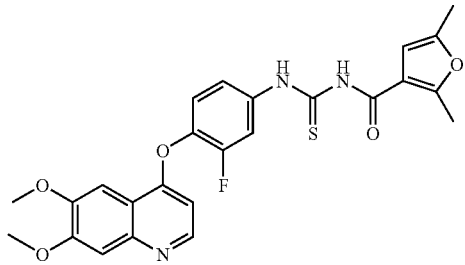
1040
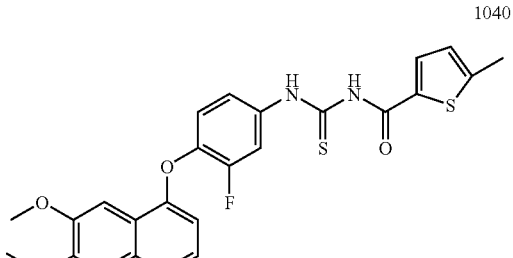

-continued
1041
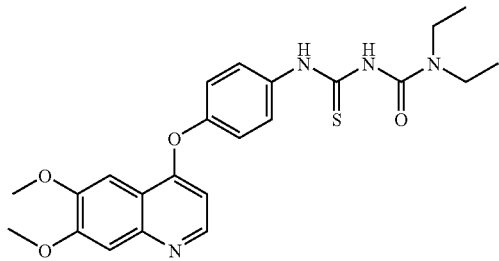
1042
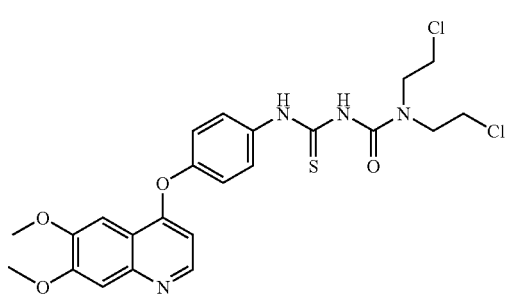
1043
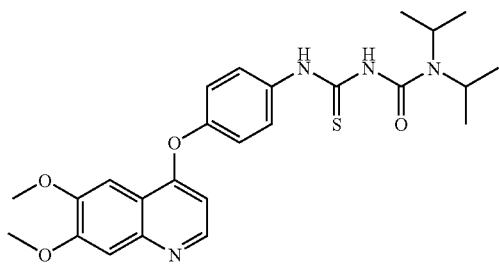
1044
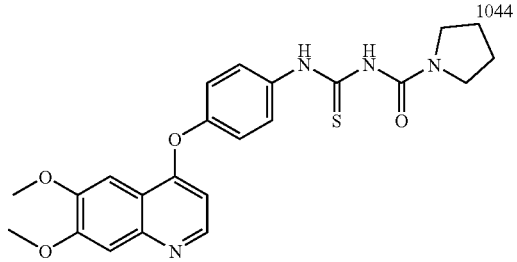
1045
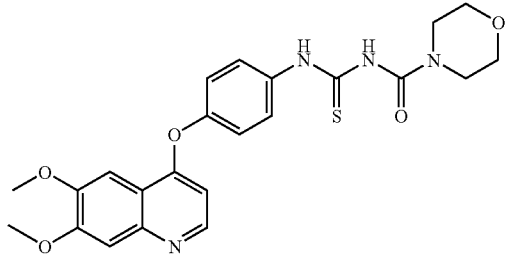
1046
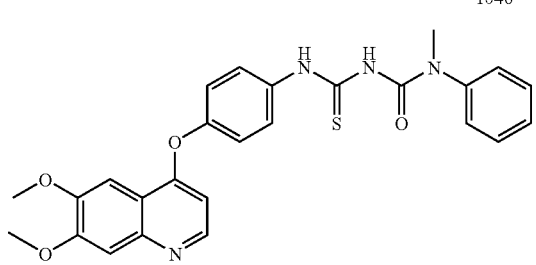
1047
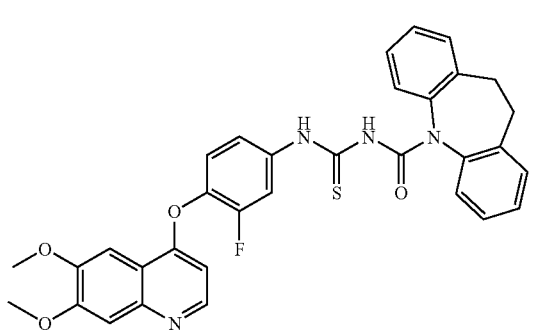
1048
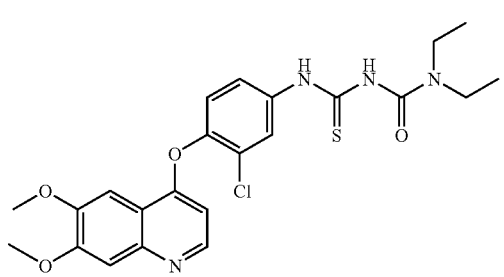
1049
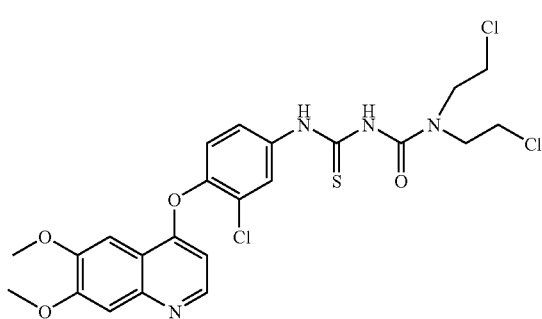
1050
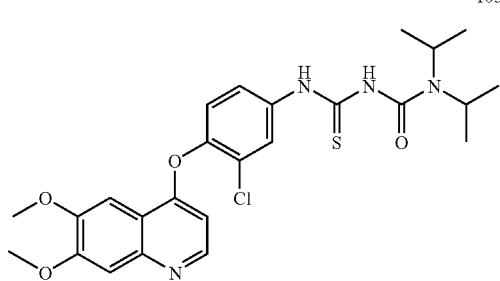

-continued
1051
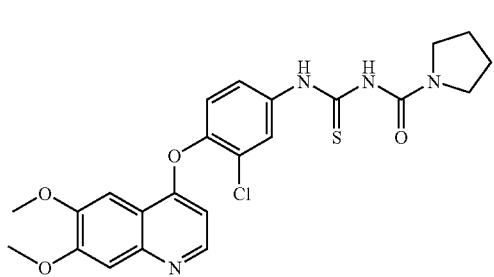
1052
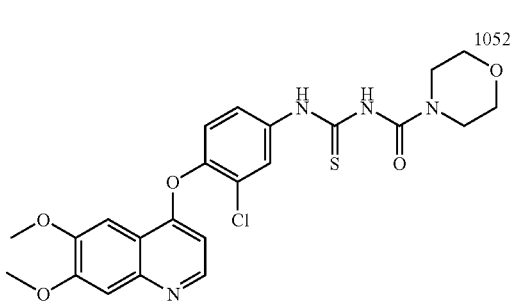
1053
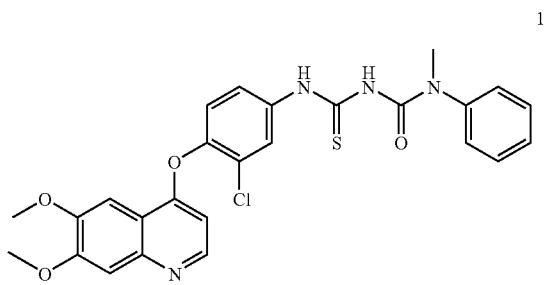
1054
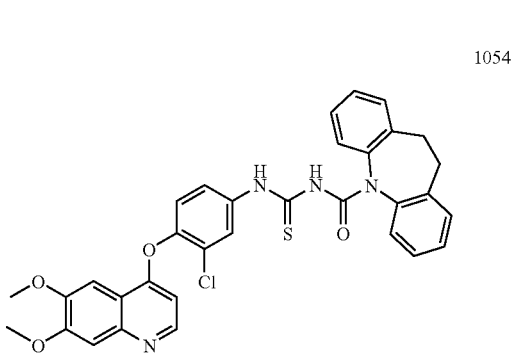
1055
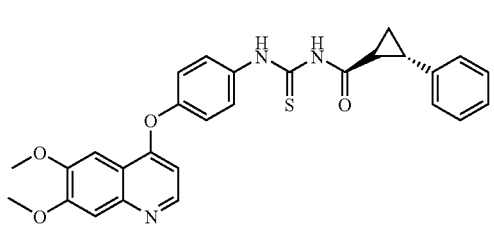
1056
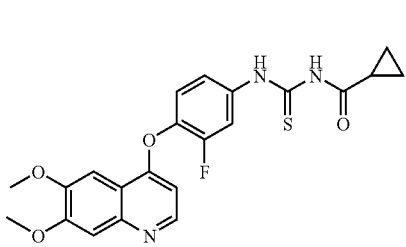
1057
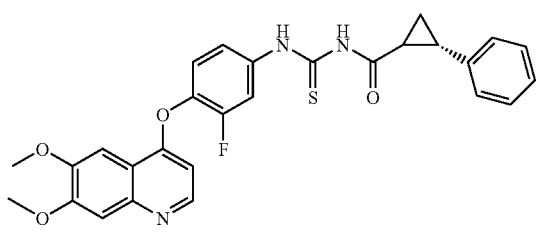
1058
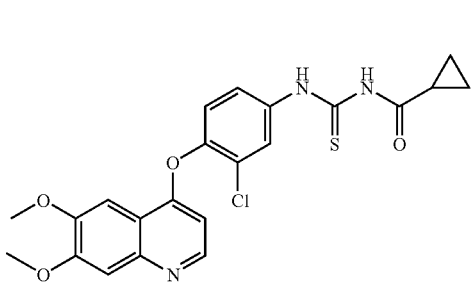
1059
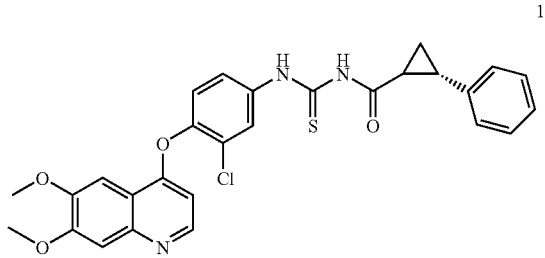
1060
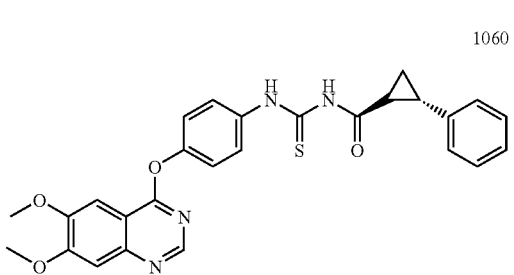

-continued
1061
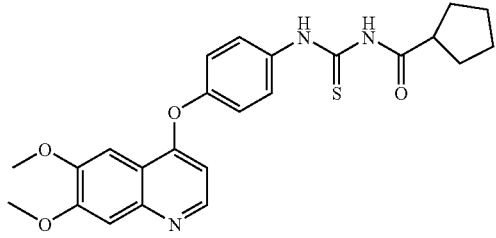
1062
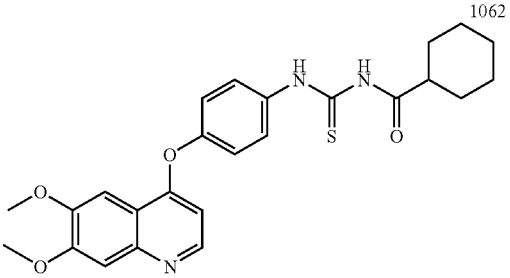
1063
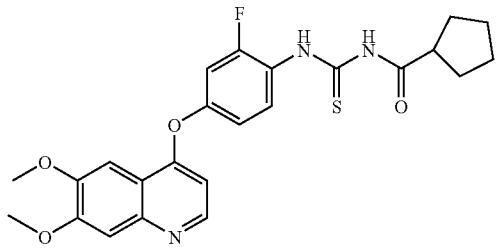
1064
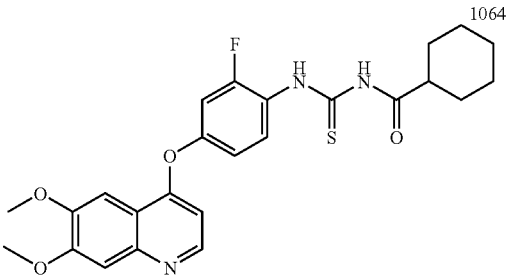
1065
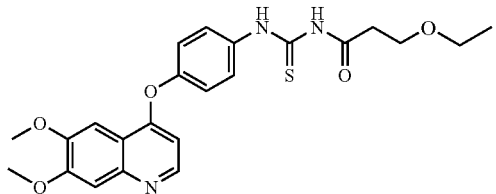
1066
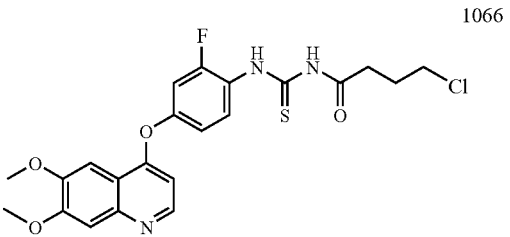
1067
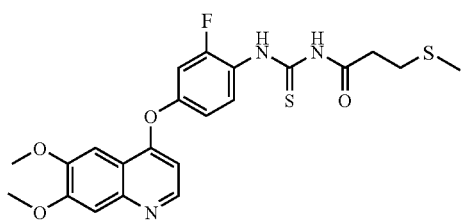
1068
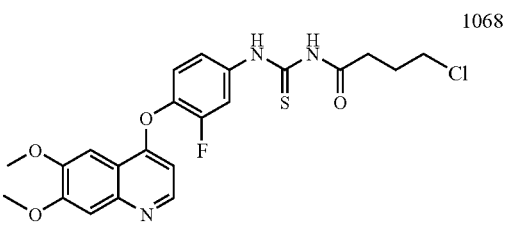
1069
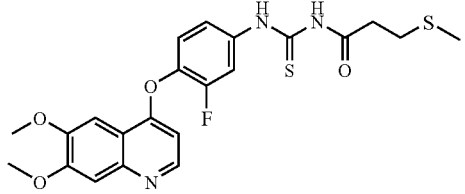
1070
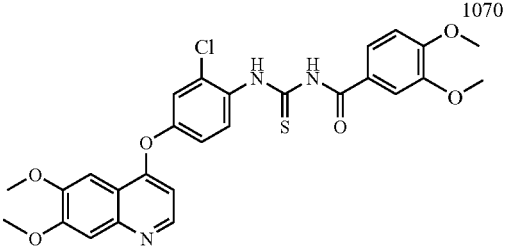
1071
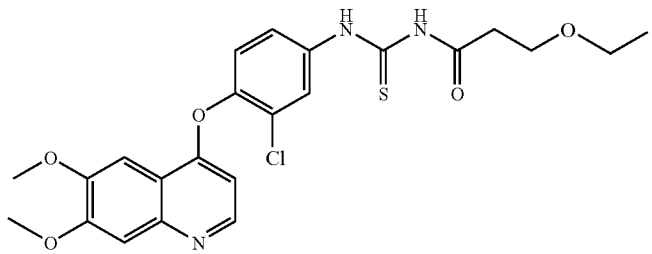

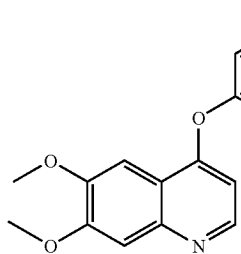
1072
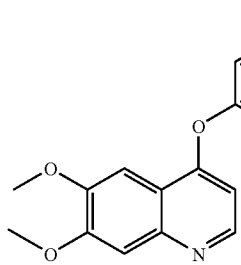
1073
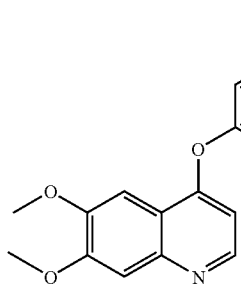
1074
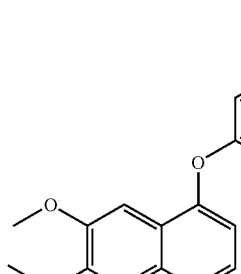
1075
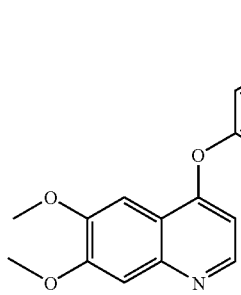
1076

-continued
1077
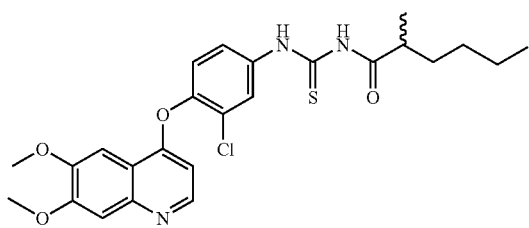
1078
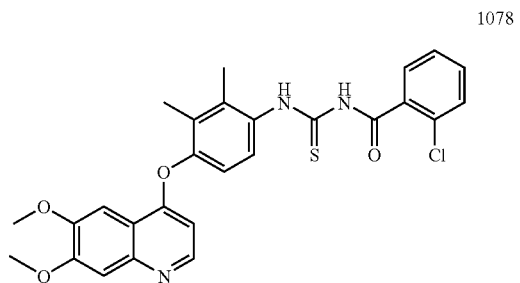
1079
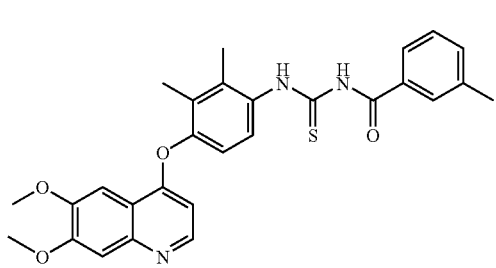
1080
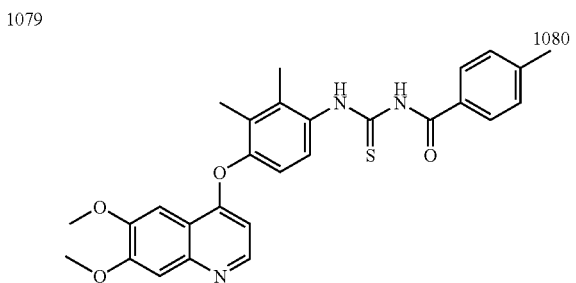
1081
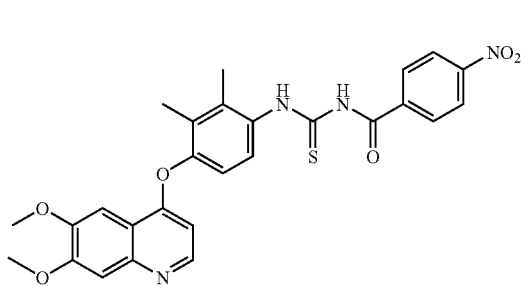
1082
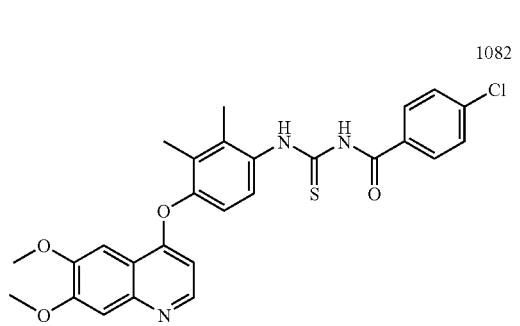
1083
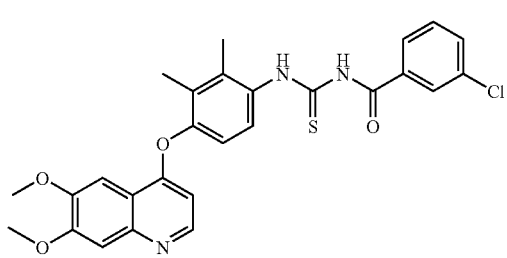
1084
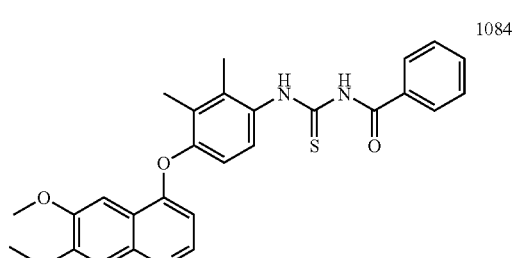
1085
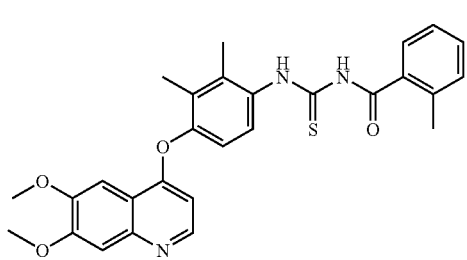
1086
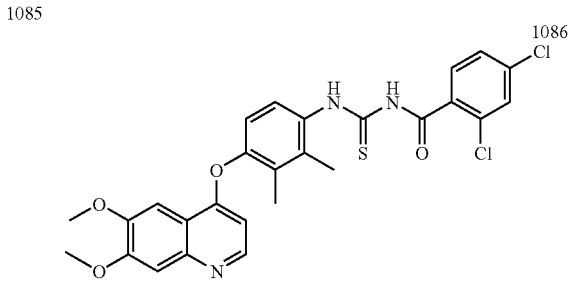

-continued
1087
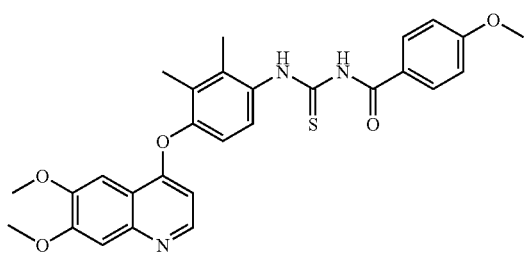
1088
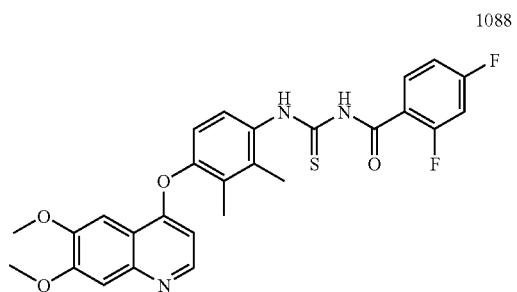
1089
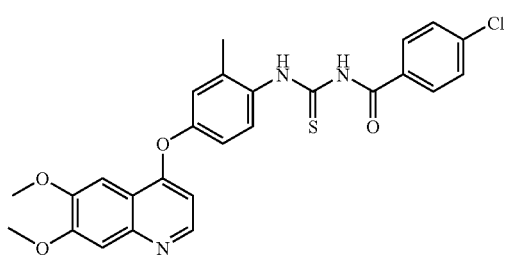
1090
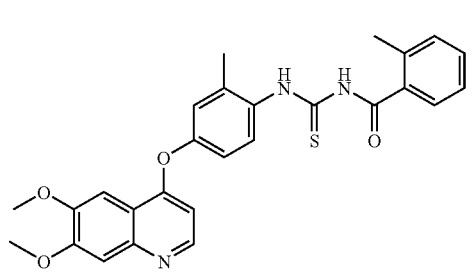
1091
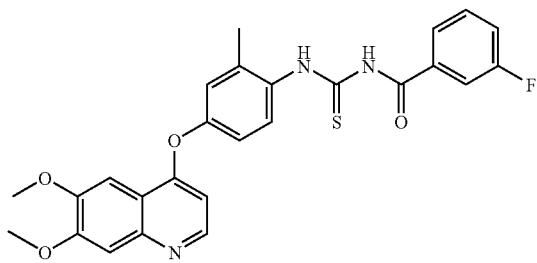
1092
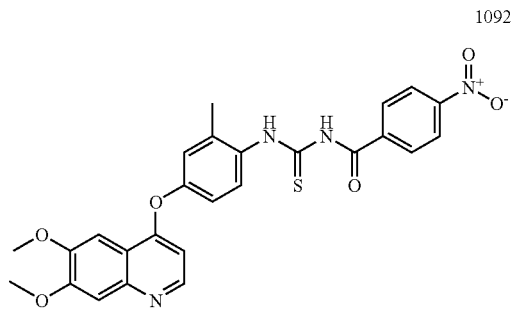
1093
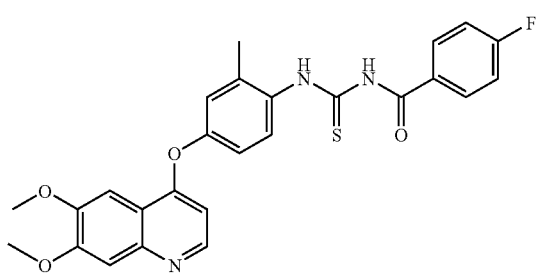
1094
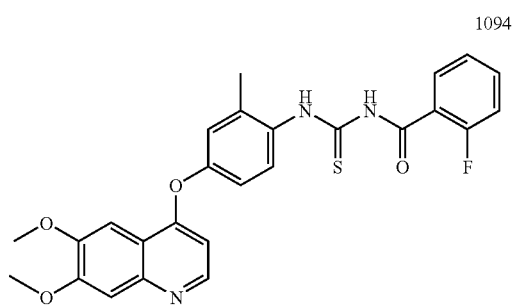
1095
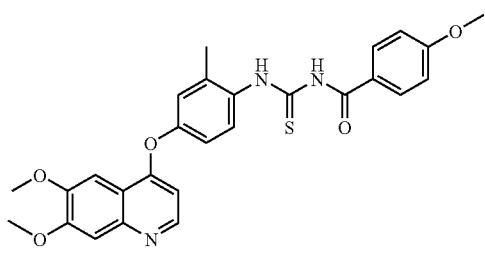
1096
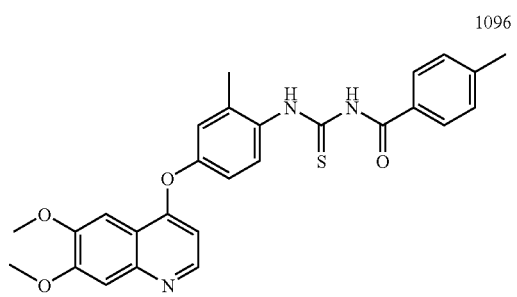

-continued
1097
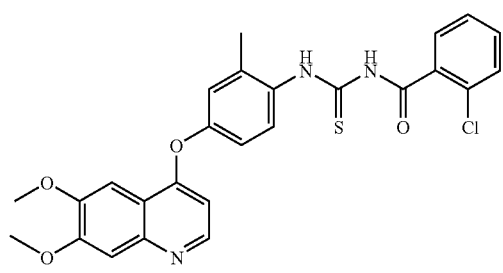
1098
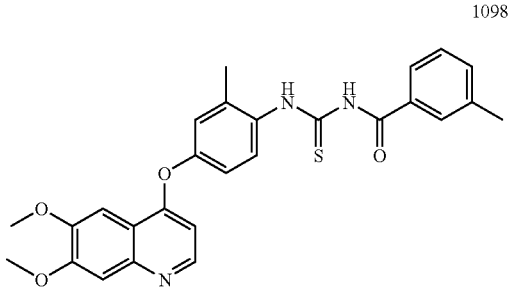
1099
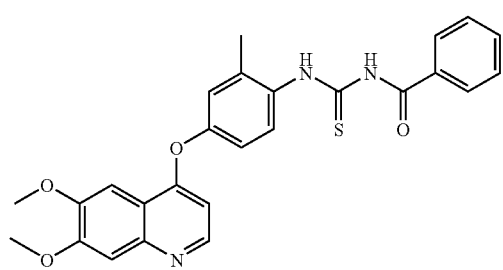
1100
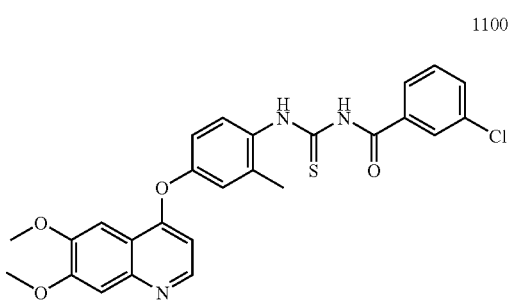
1101
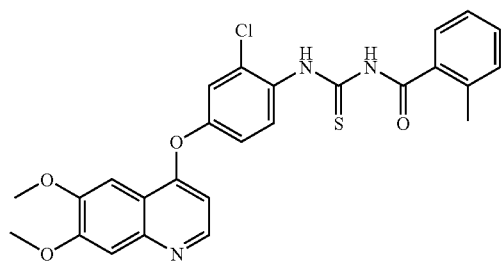
1102
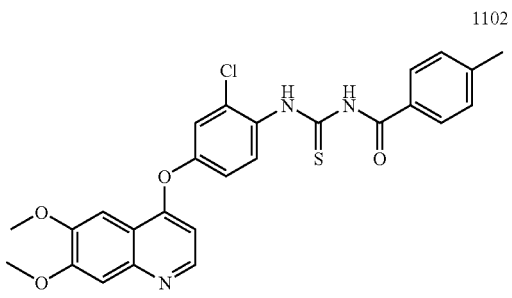
1103
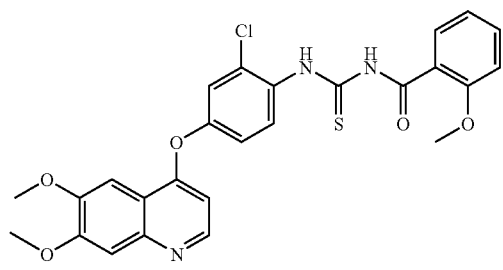
1104
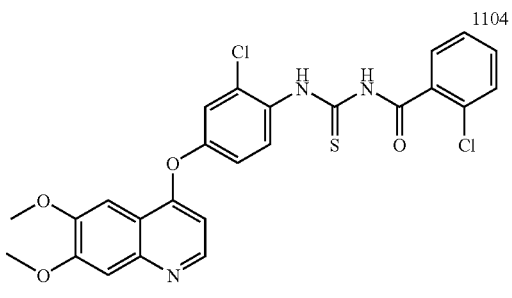
1105
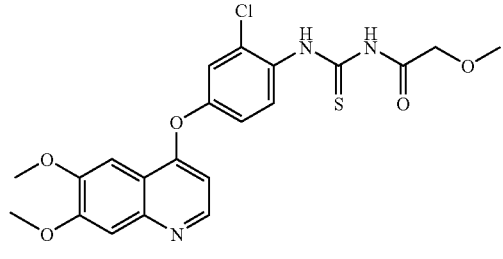
1106
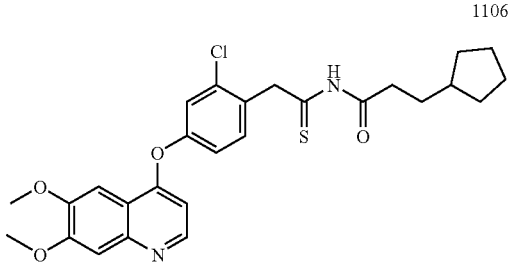

-continued
1107
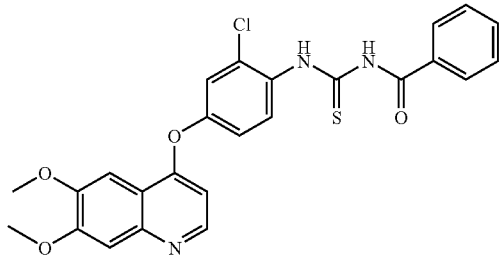
1108
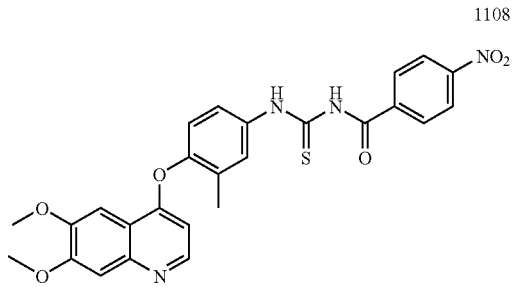
1109
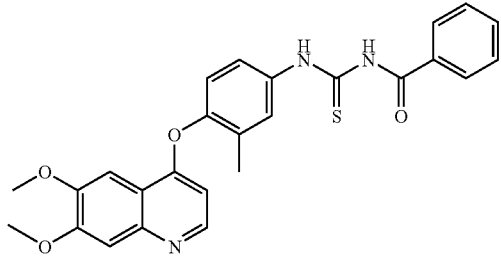
1110
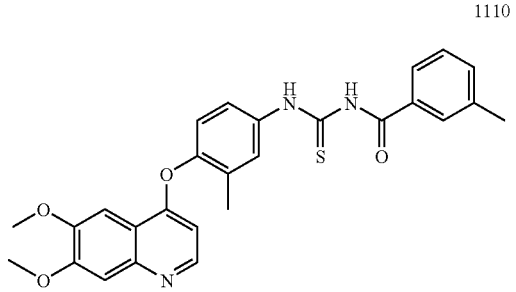
1111
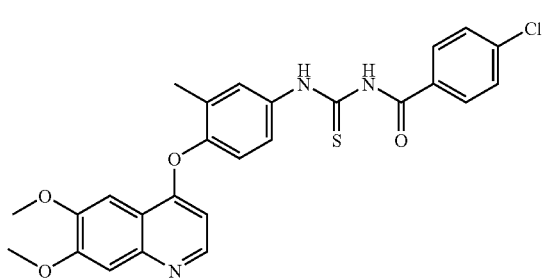
1112
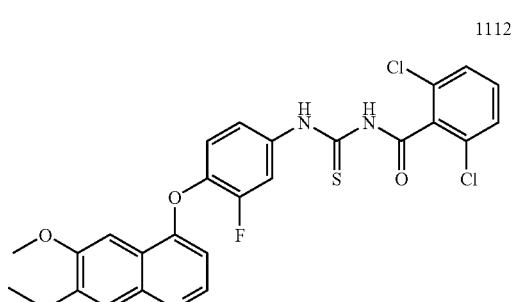
1113
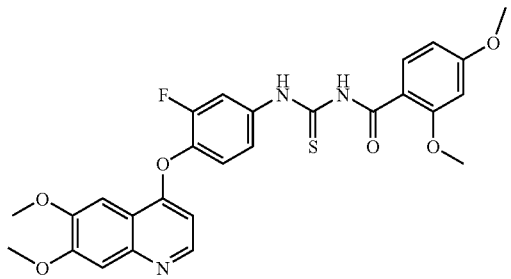
1114
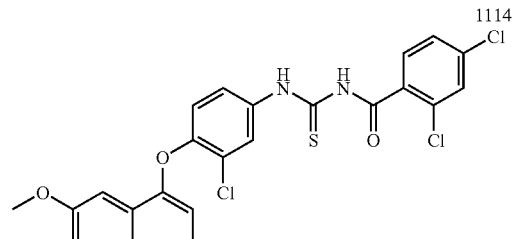
1115
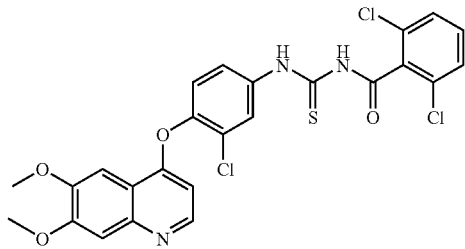
1116
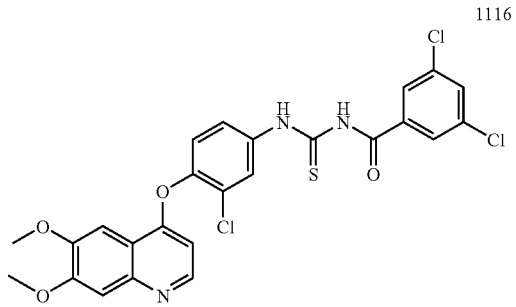

-continued
1117
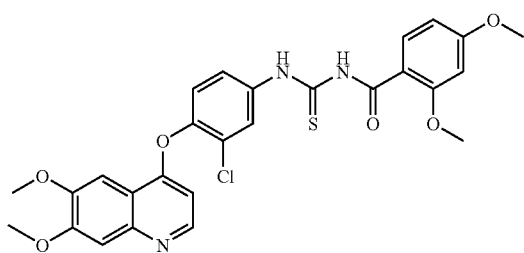
1118
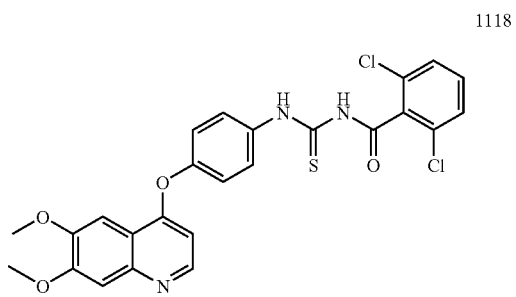
1119
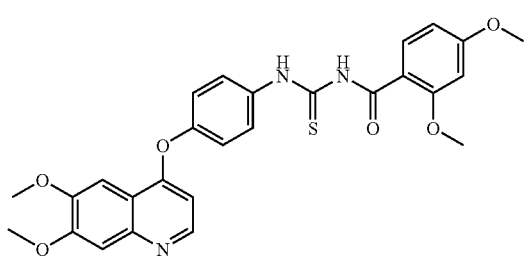
1120
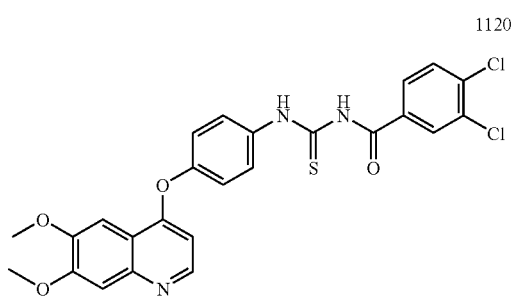
1121
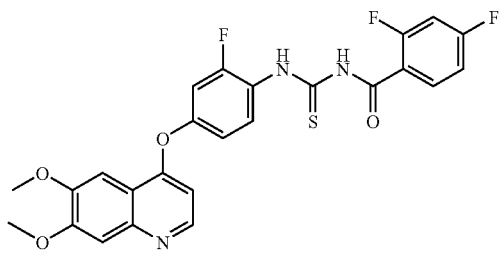
1122
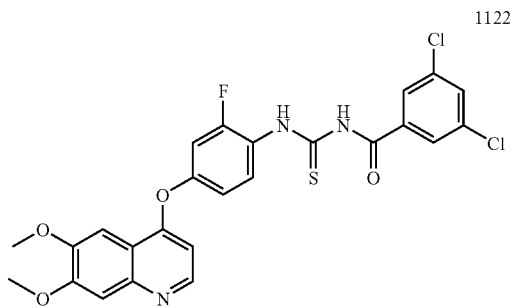
1123
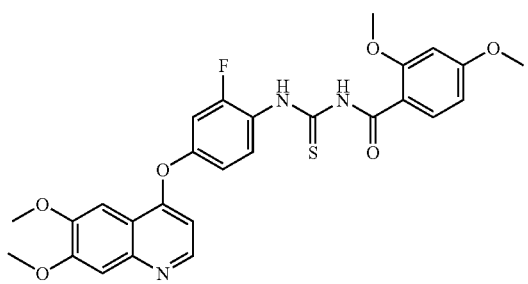
1124
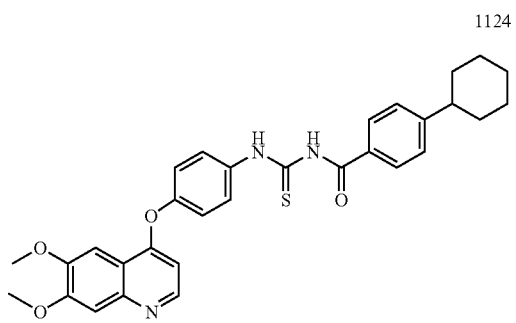
1125
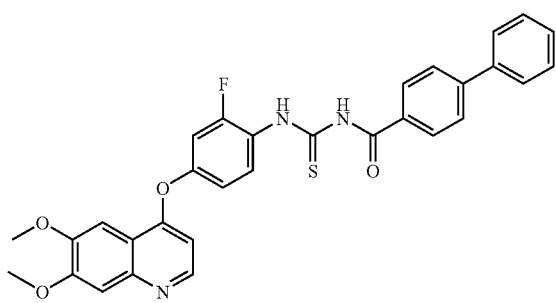
1126
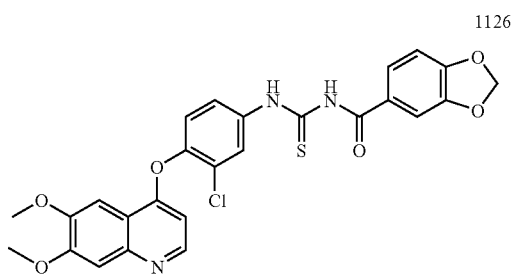

-continued
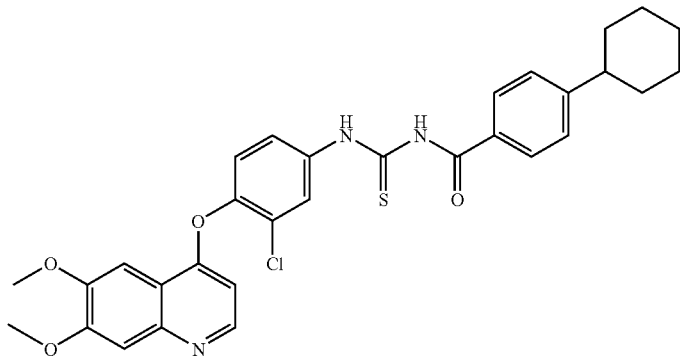
1127
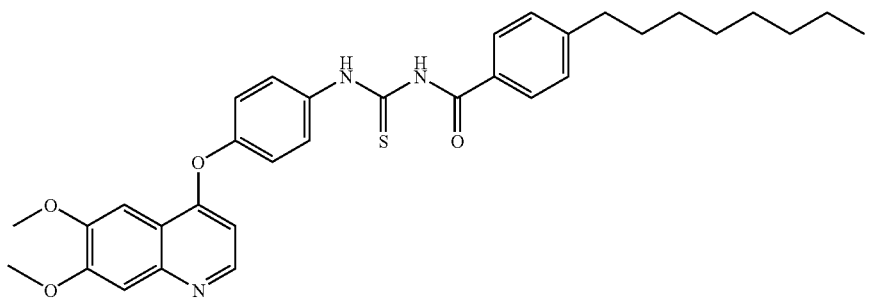
1128
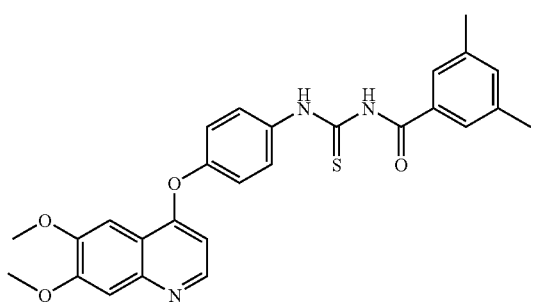
1129
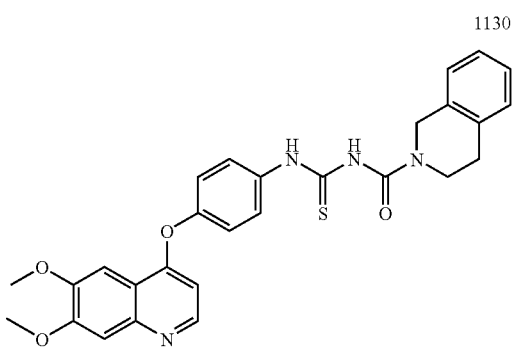
1130
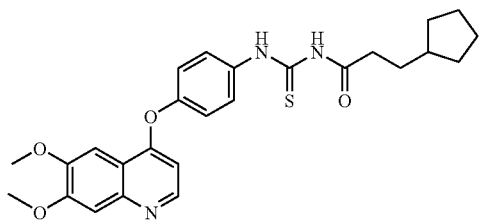
1131
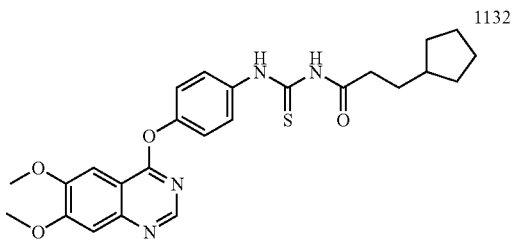
1132
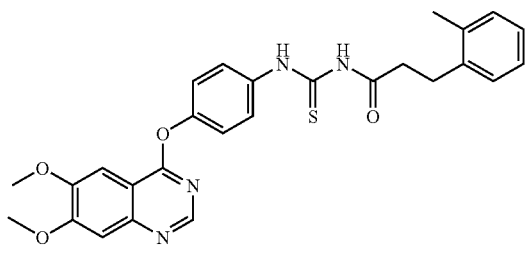
1133
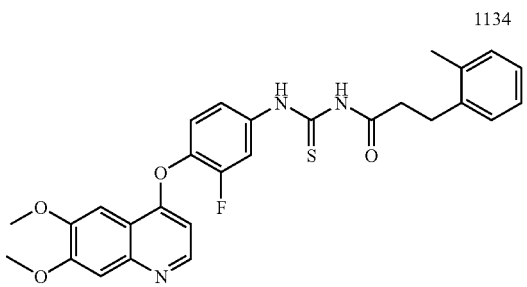
1134

-continued
1135
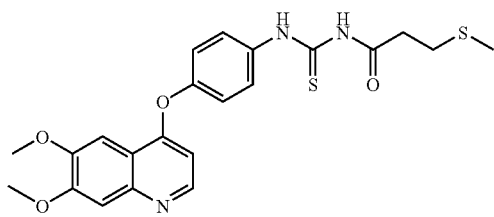
1136
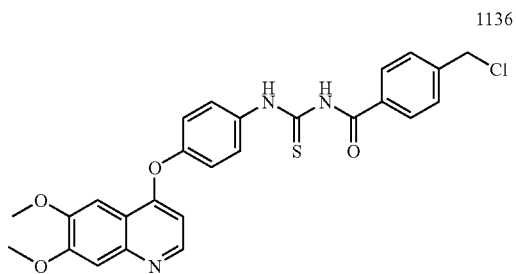
1137
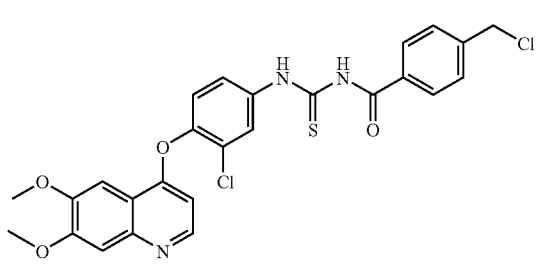
1138
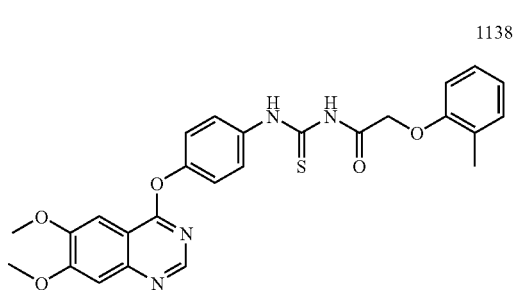
1139
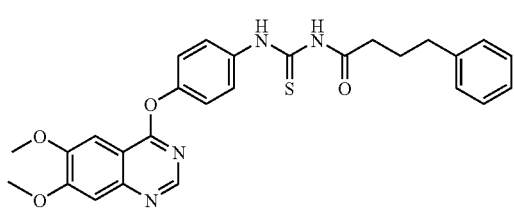
1140
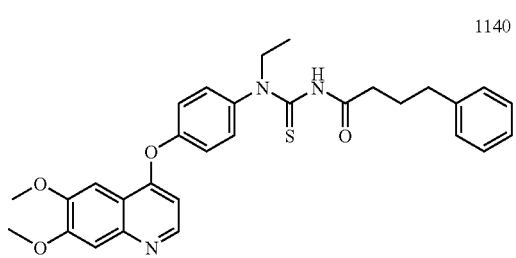
1141
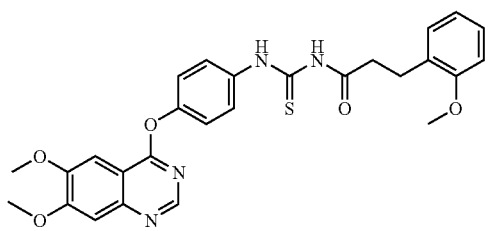
1142
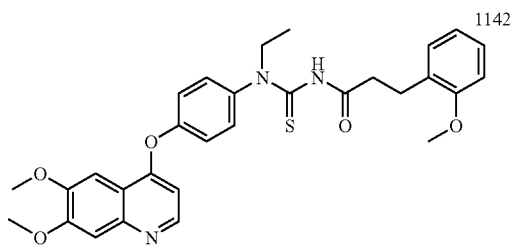
1143
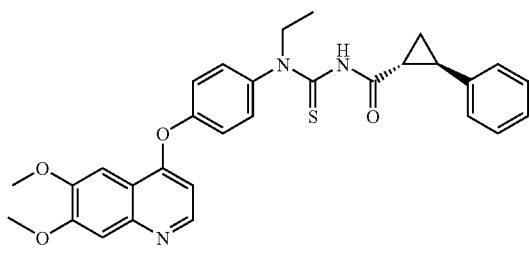
1144
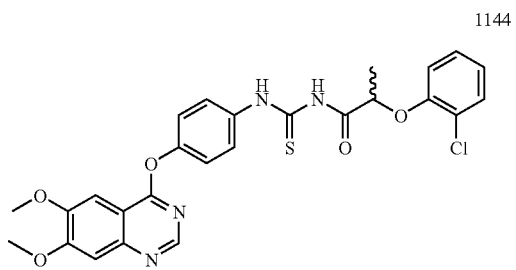

-continued
1145
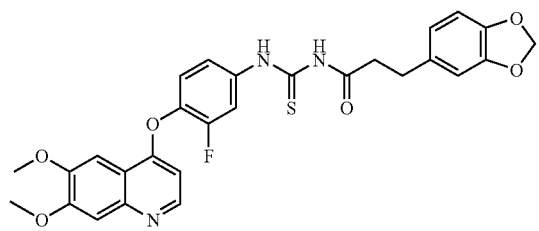
1146
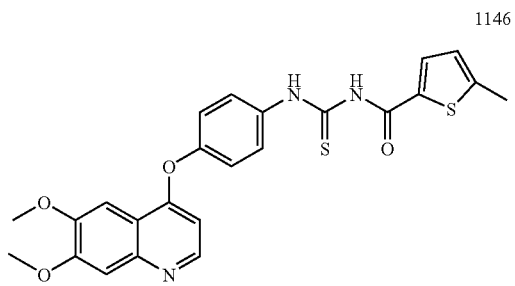
1147
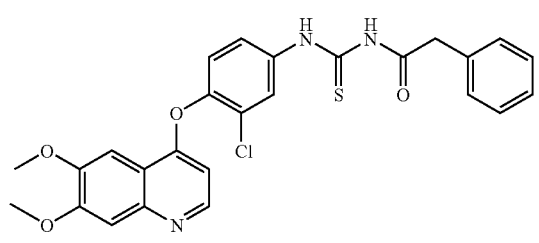
1148
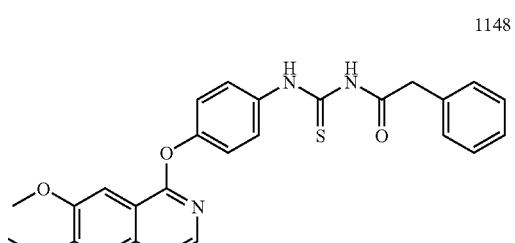
1149
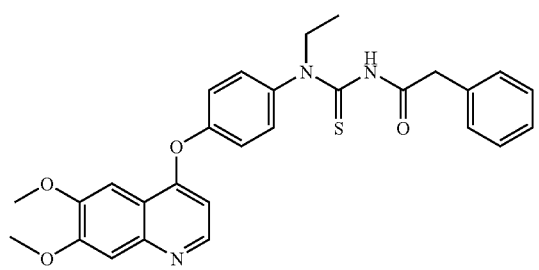
1150
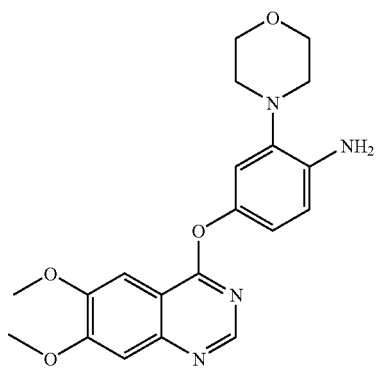
1151
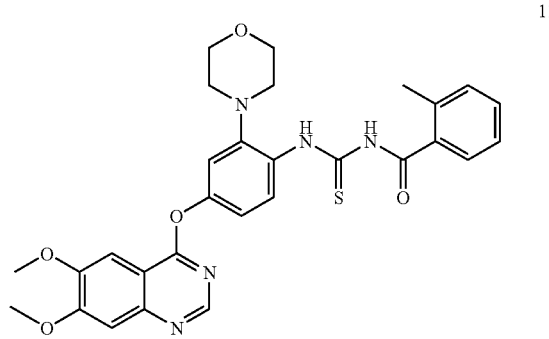
1152
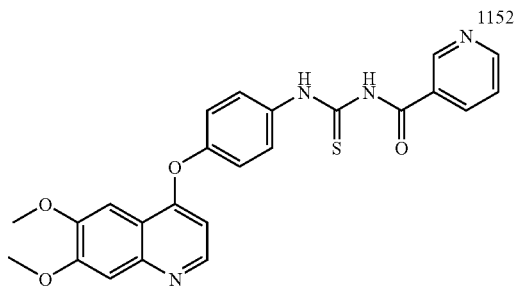
1153
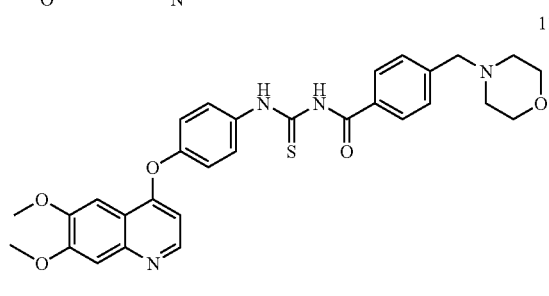
1154
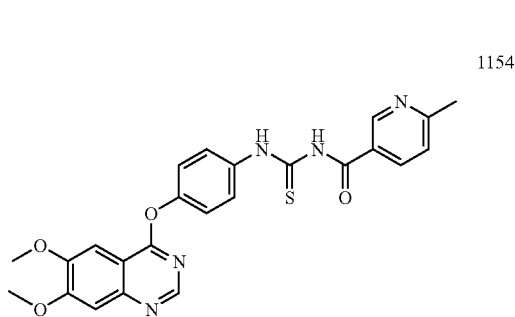

-continued
1155
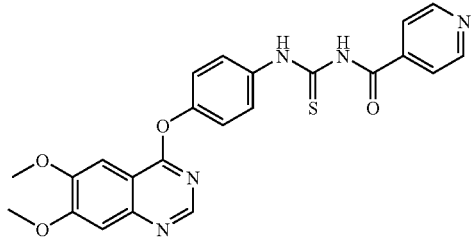
1156
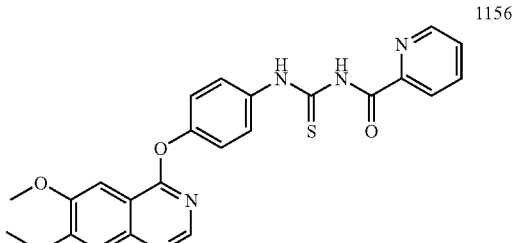
1157
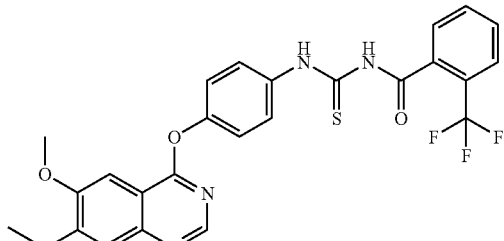
1158
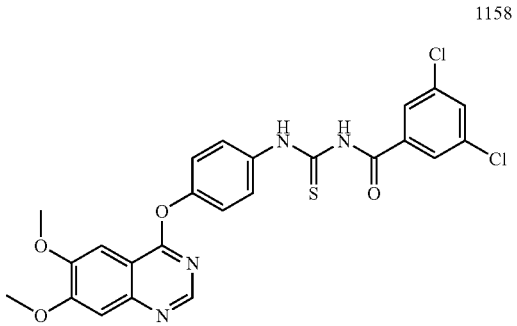
1159
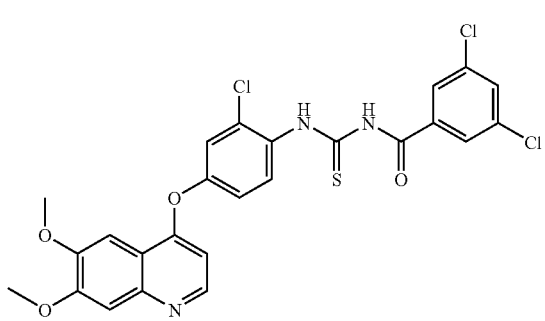
1160
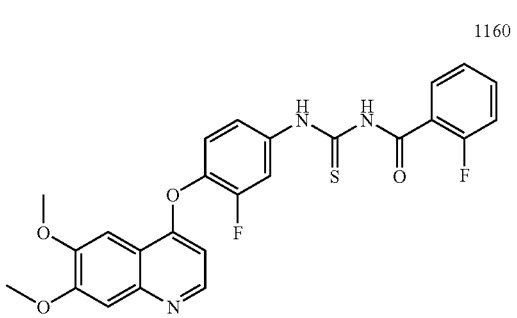
1161
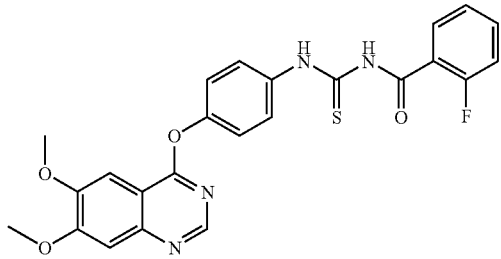
1162
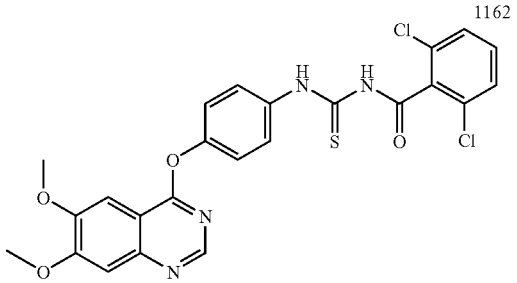
1163
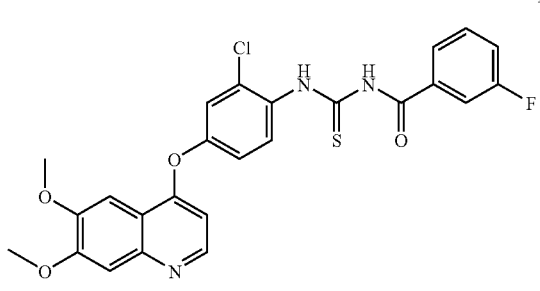
1164
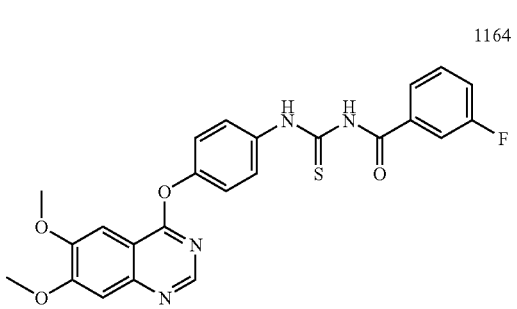

-continued
1165
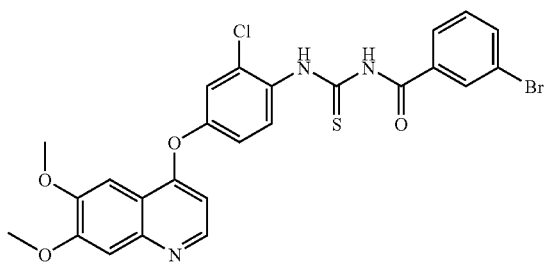
1166
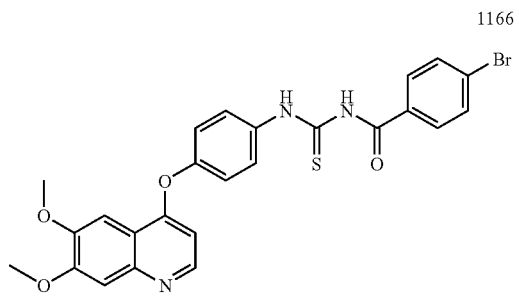
1167
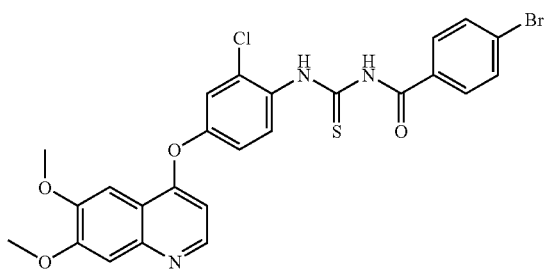
1168
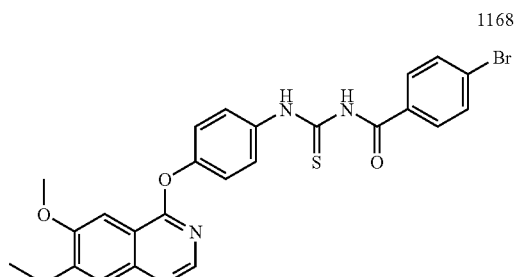
1169
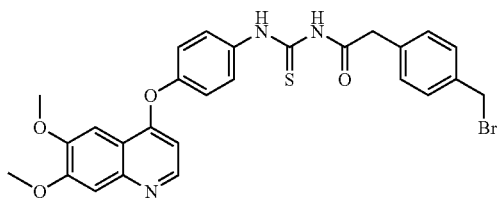
1170
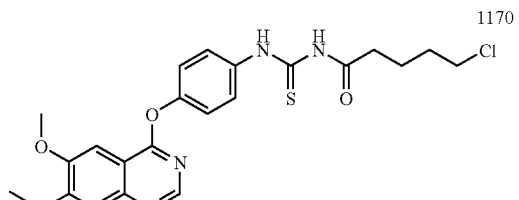
1171
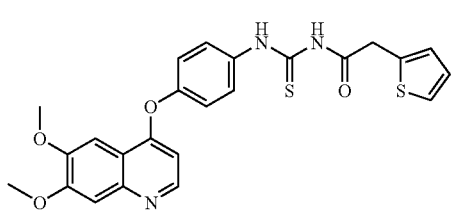
1172
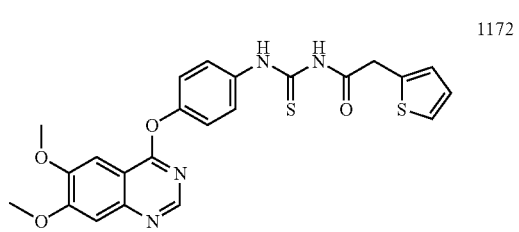
1173
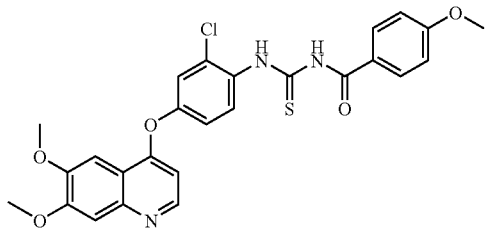
1174
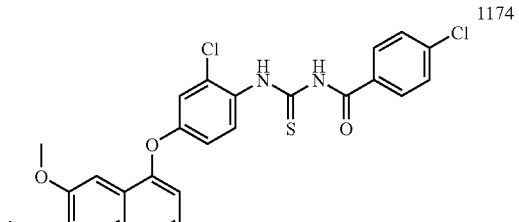
1175
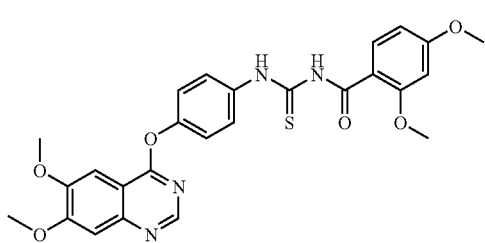
1176
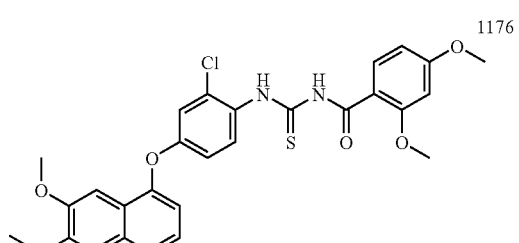

-continued
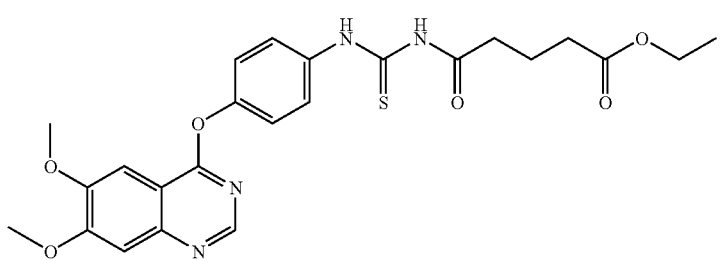
1177
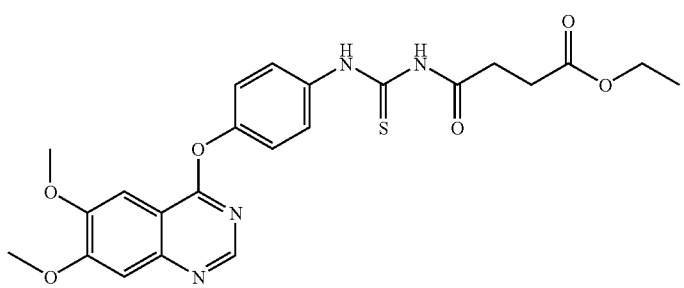
1178
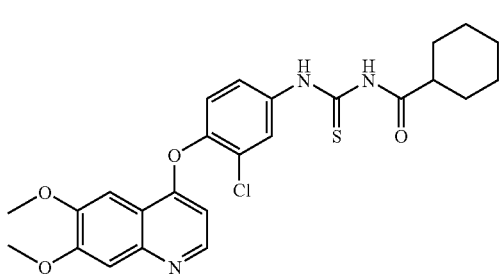
1179
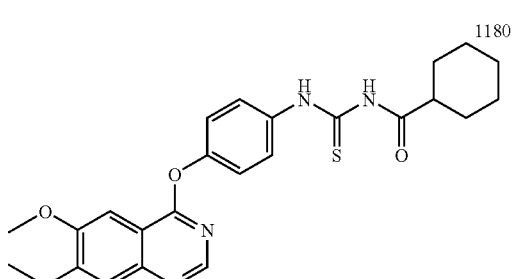
1180
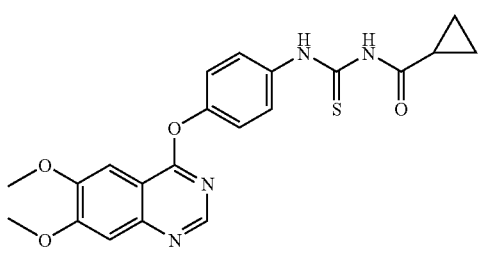
1181
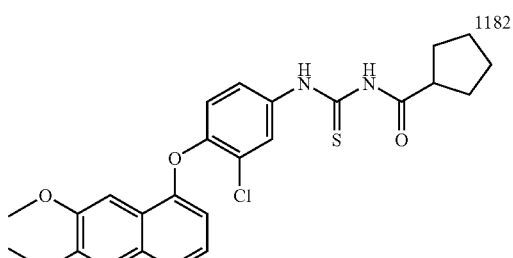
1182
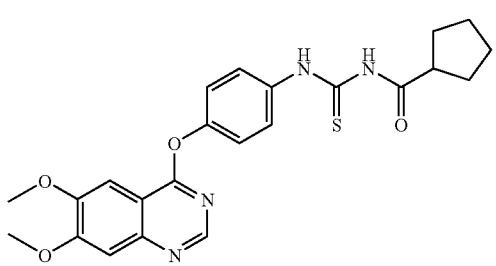
1183
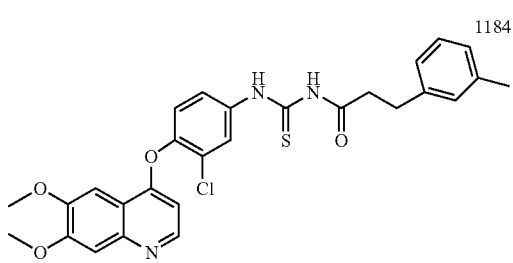
1184
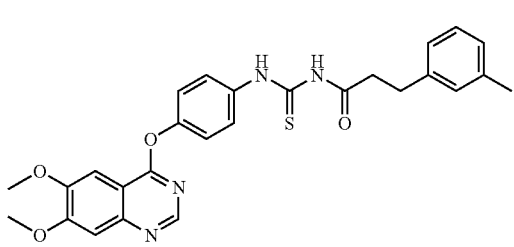
1185
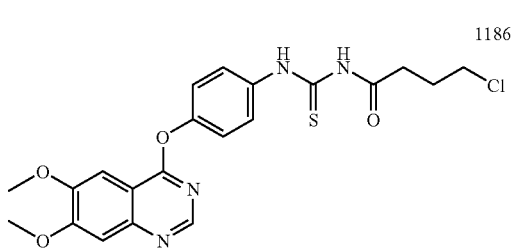
1186

-continued
1187
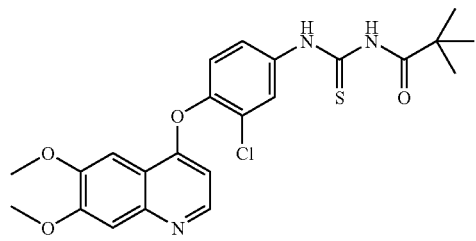
1188
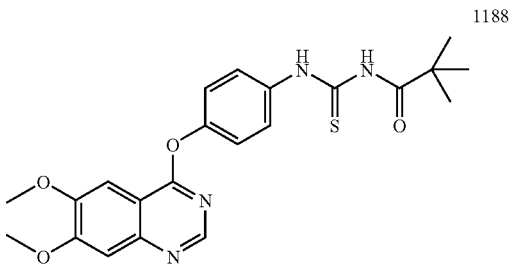
1189
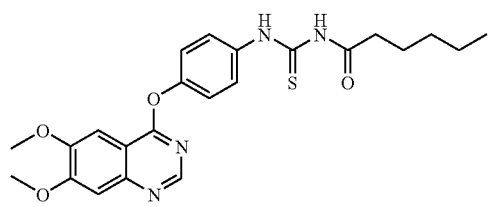
1190
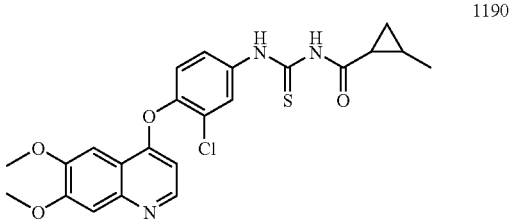
1191
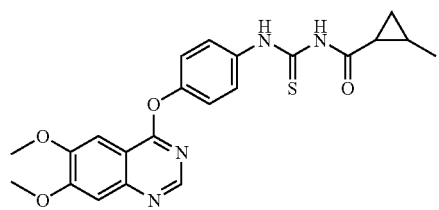
1192
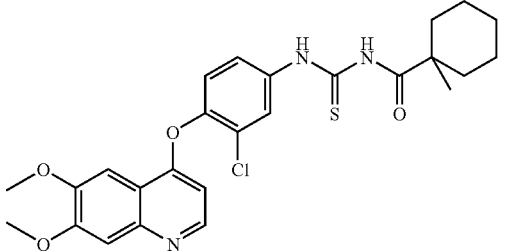
1193
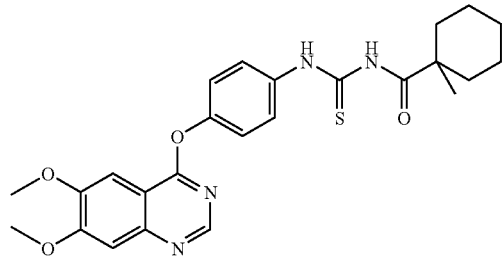
1194
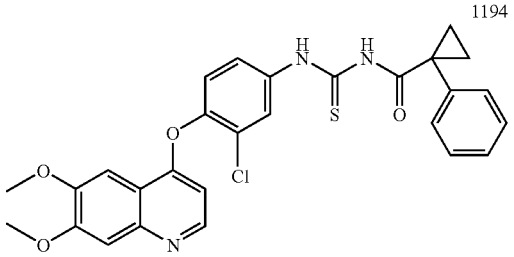
1195
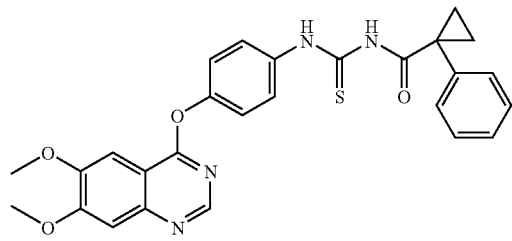
1196
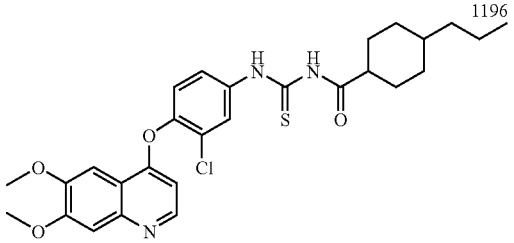
1197
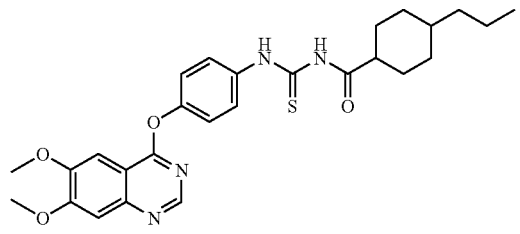
1198
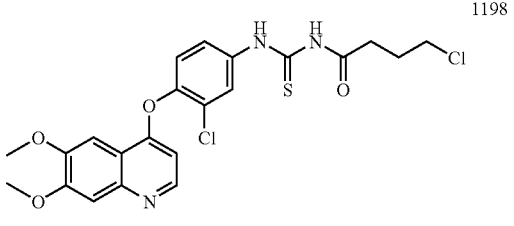

-continued
1199
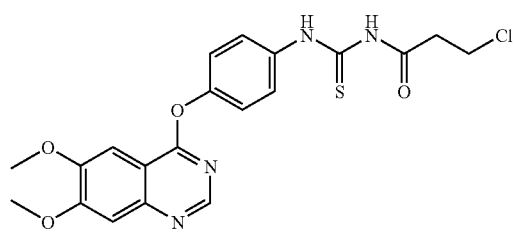
1200
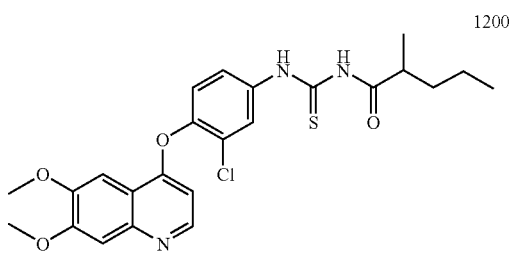
1201
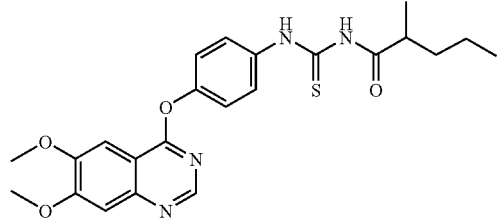
1202
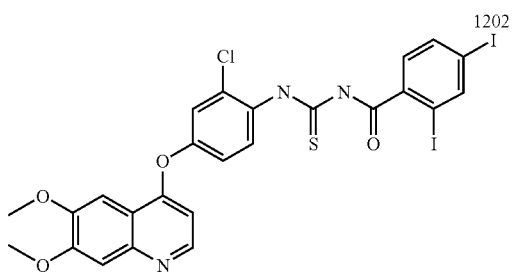
1203
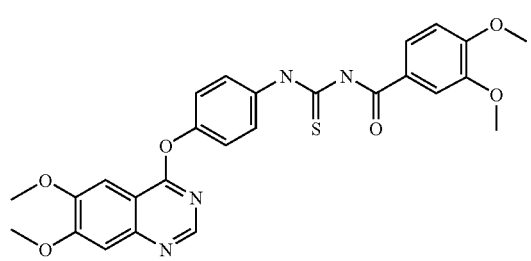
1204
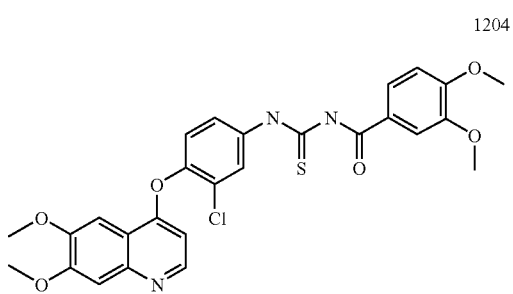
1205
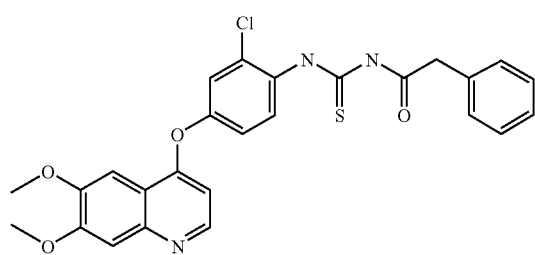
1206
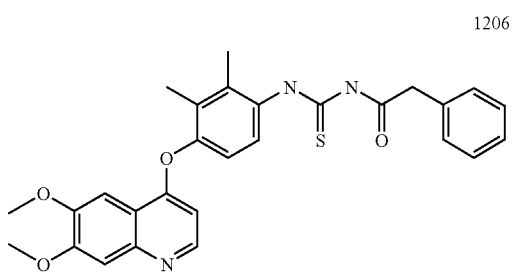
1207
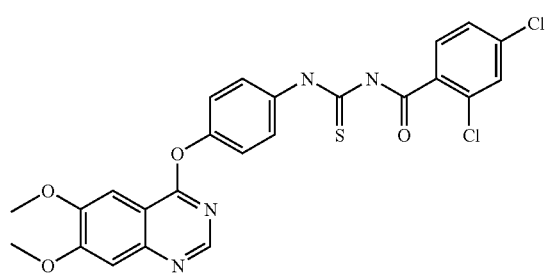
1208
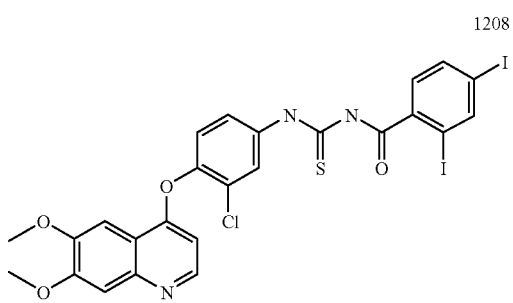

-continued
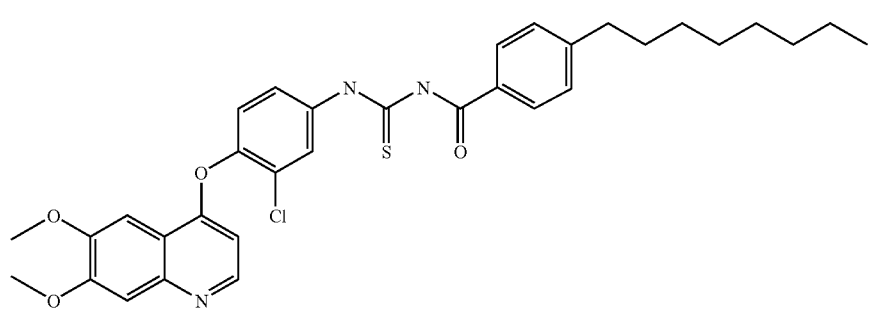
1209
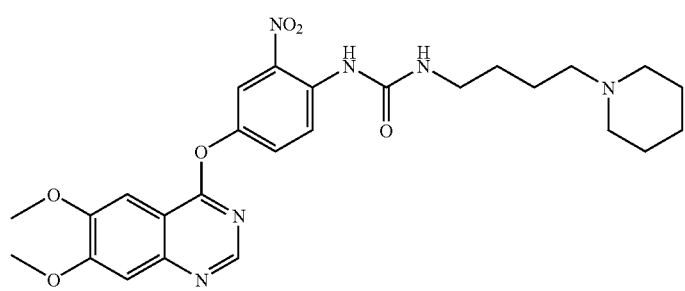
1210
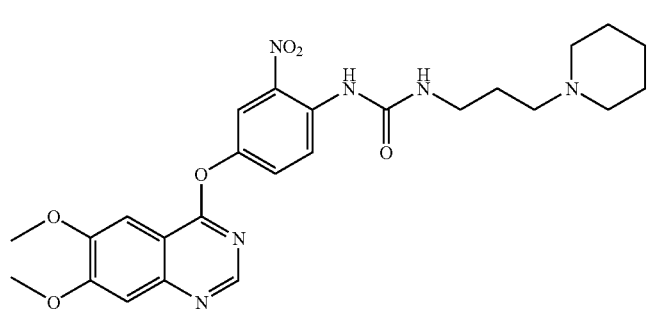
1211
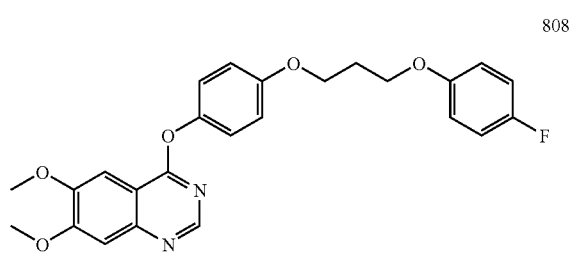
808
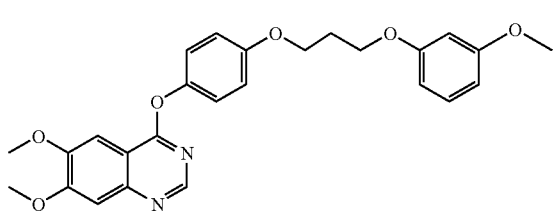
809

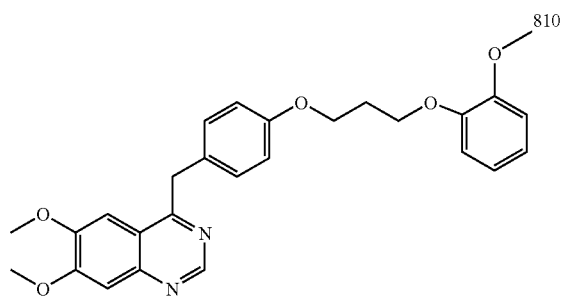
810
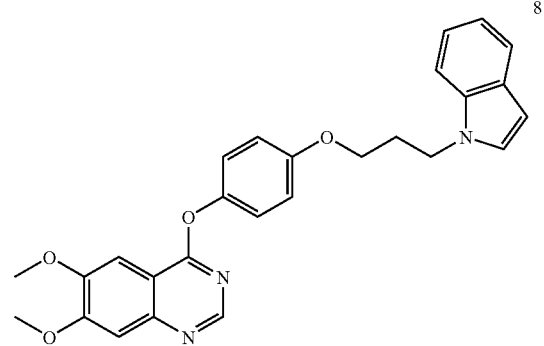
811
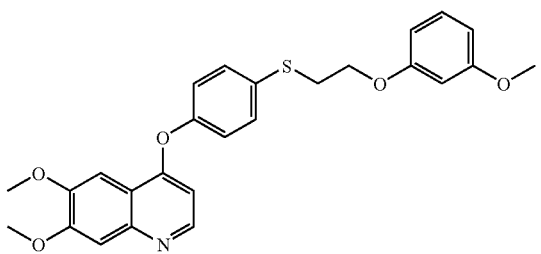
812
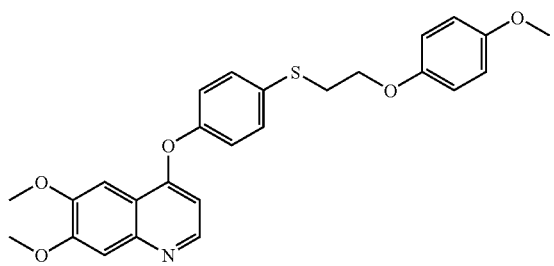
813
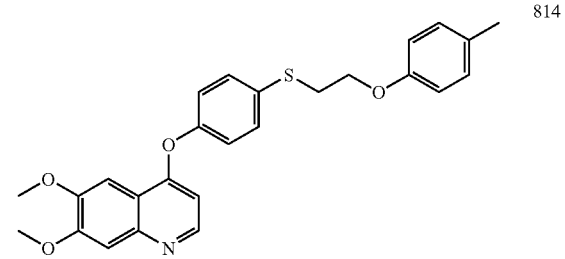
814

-continued
815
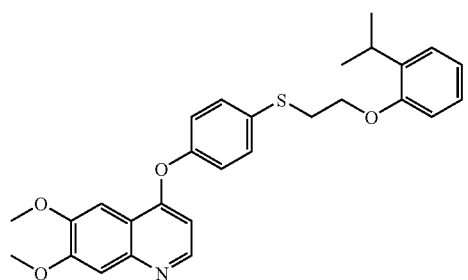
816
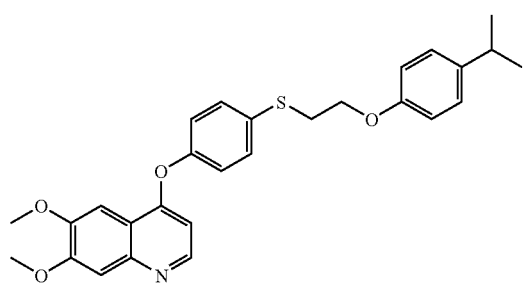
817
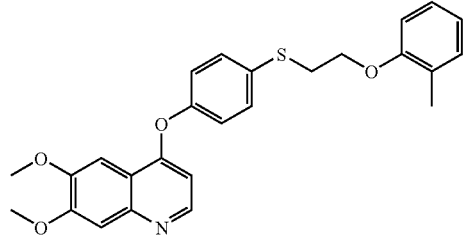
818
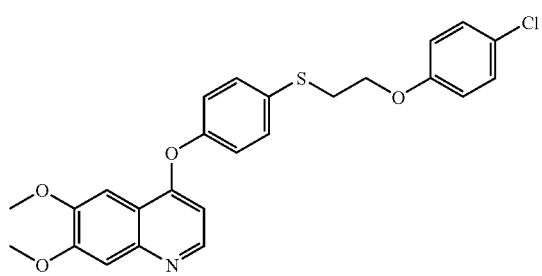
819
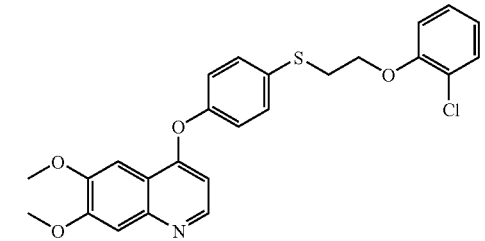
820

-continued
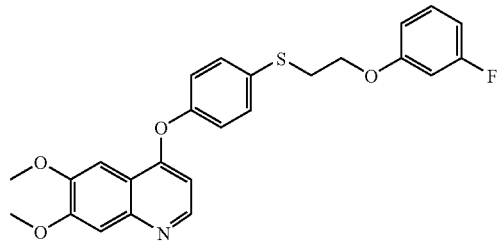
821
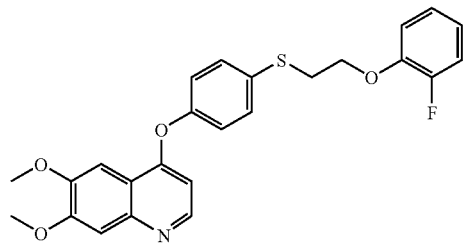
822
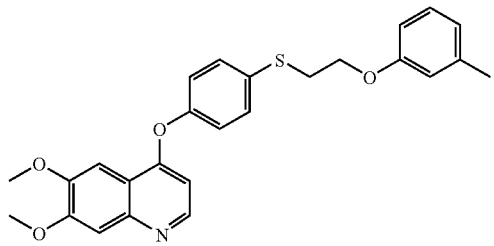
823
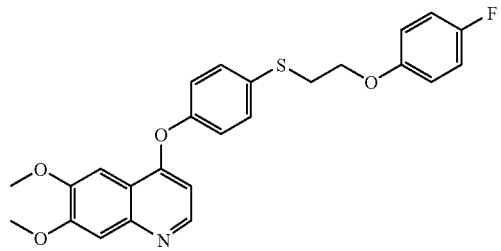
824
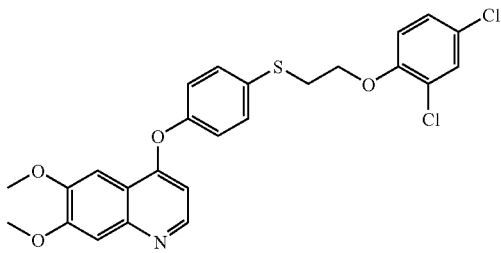
825
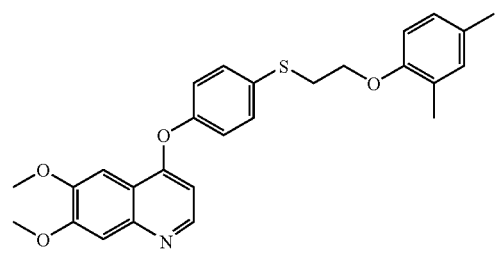
826

-continued
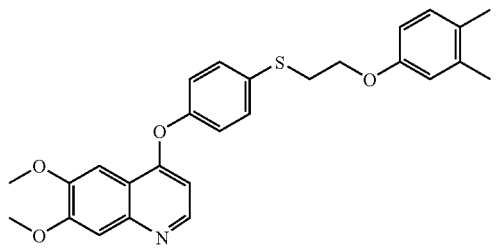
827
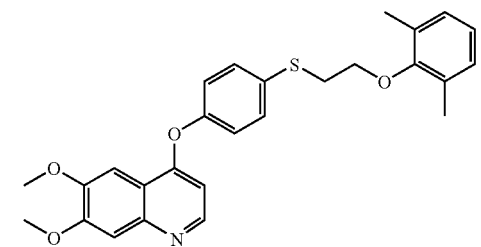
828
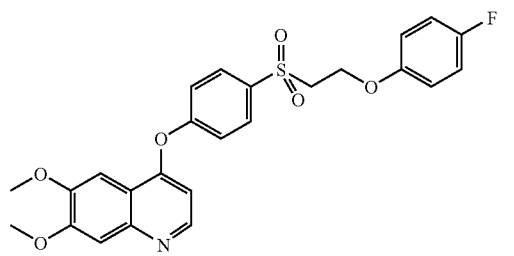
829
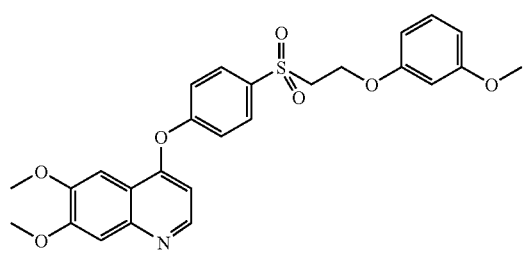
830
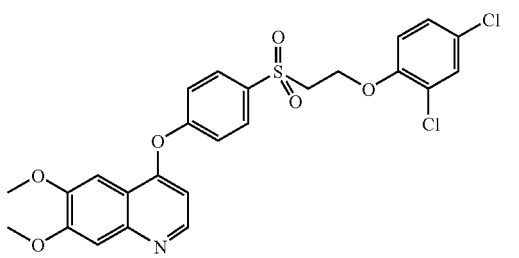
831
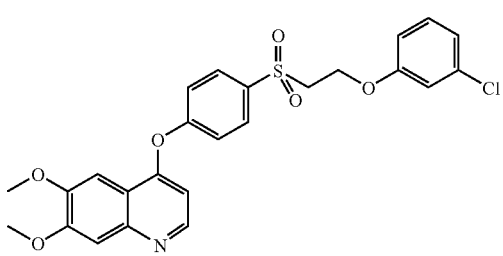
832

-continued
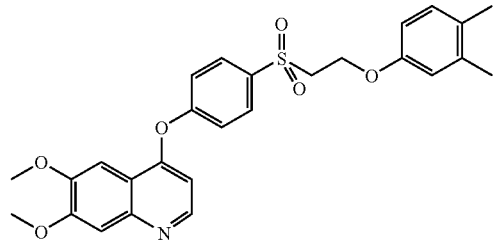
833
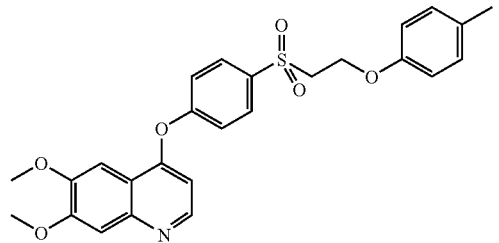
834
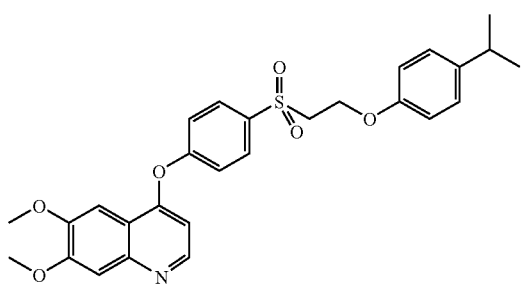
835
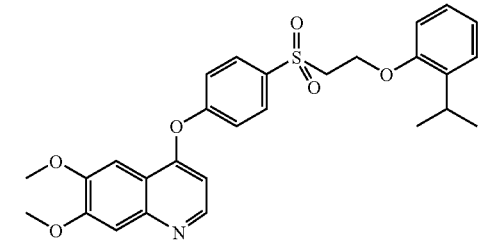
836
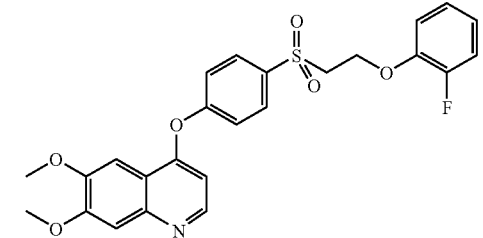
837
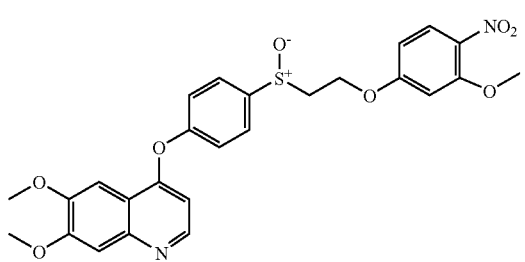
838

-continued
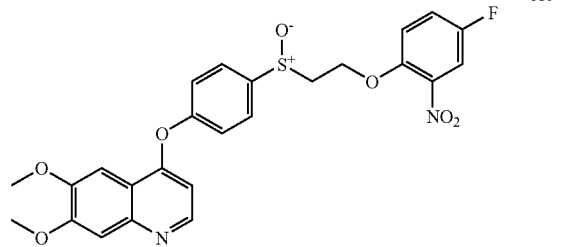
839
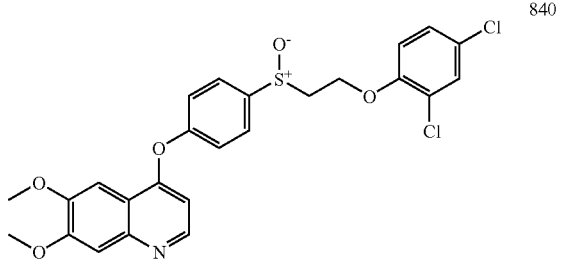
840
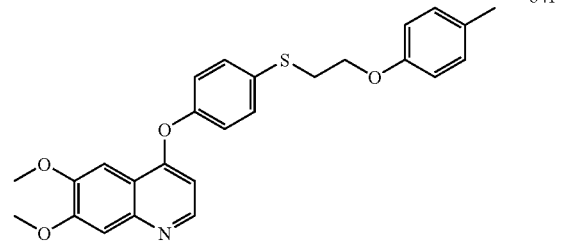
841
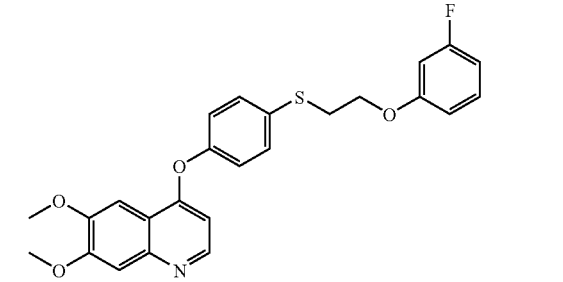
842
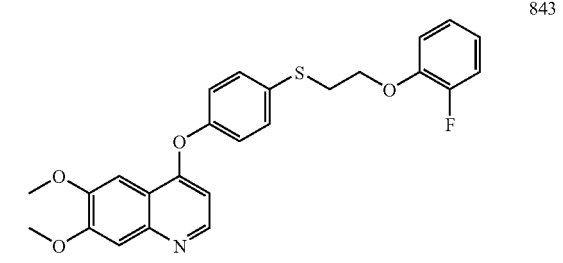
843
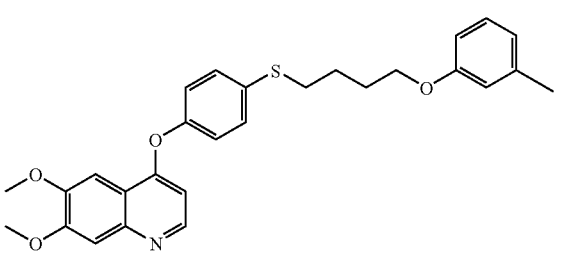
844

-continued
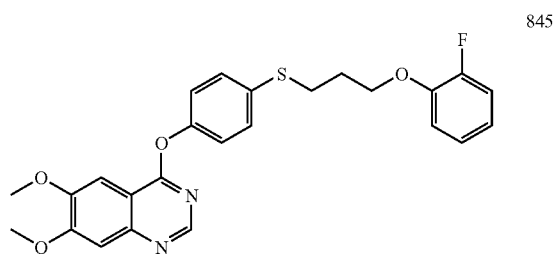
845
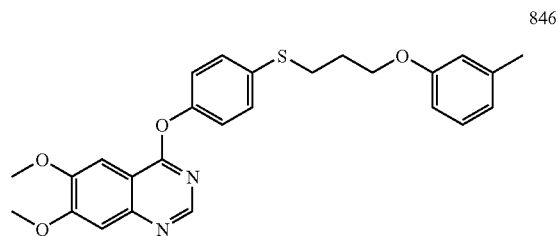
846
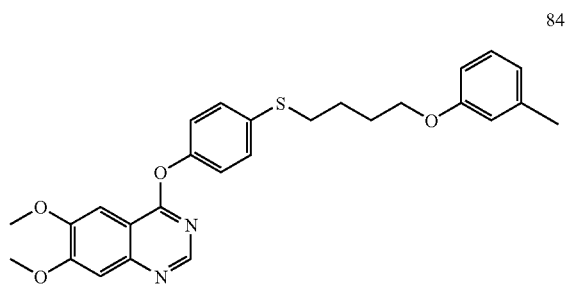
847
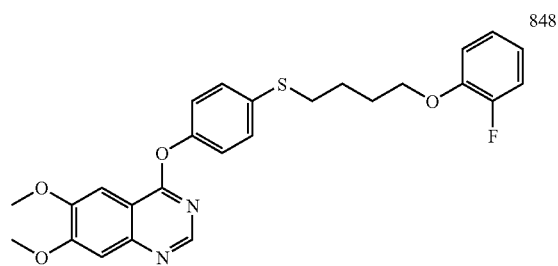
848
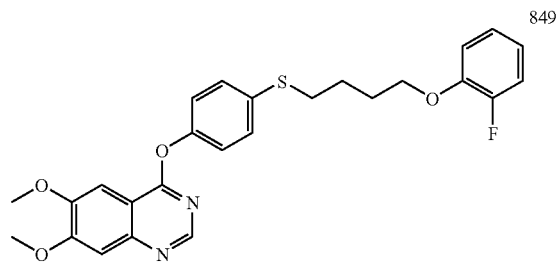
849
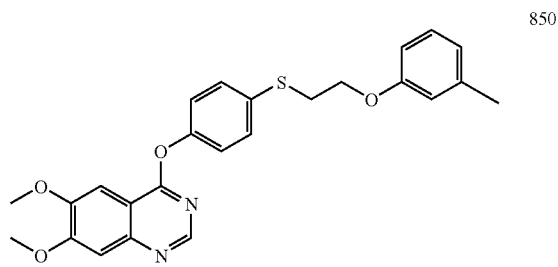
850

-continued
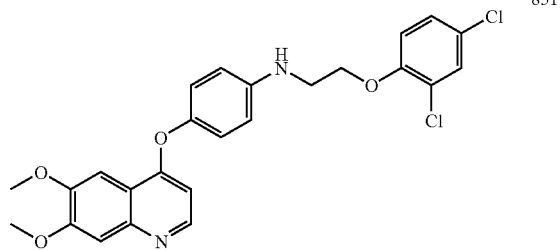
851
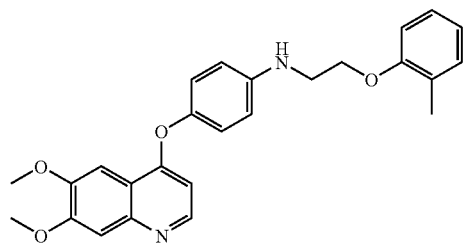
852
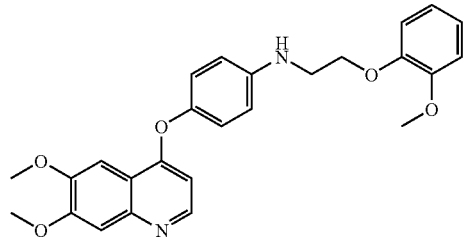
853
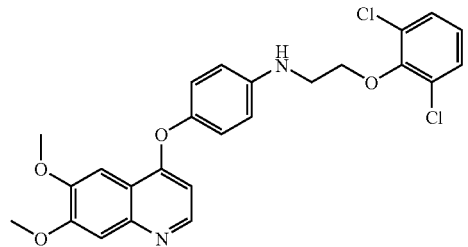
854
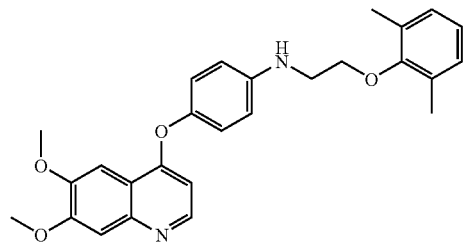
855
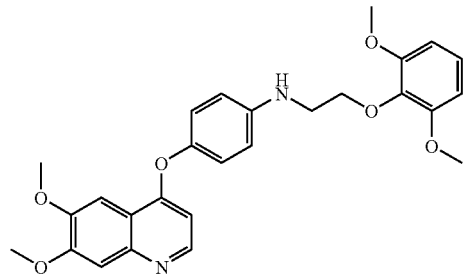
856

-continued
857
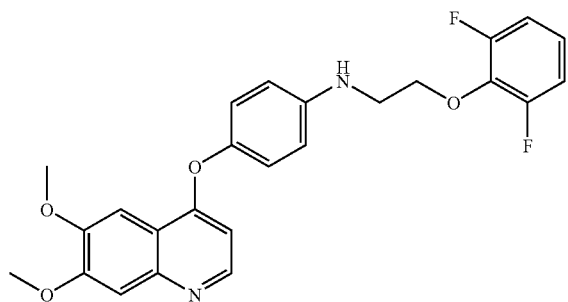
858
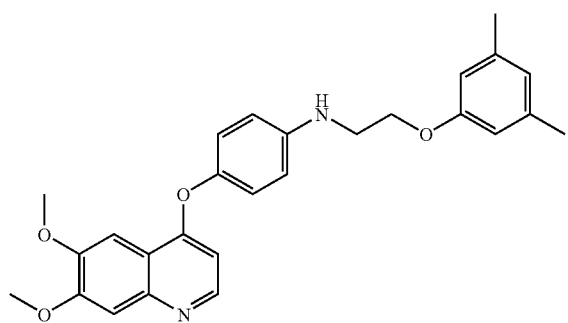
859
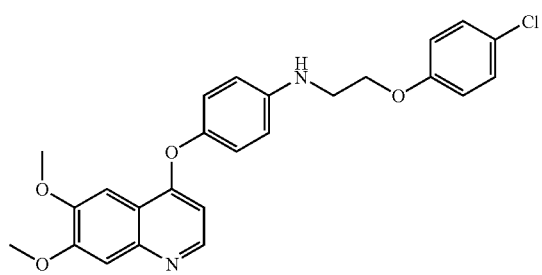
860
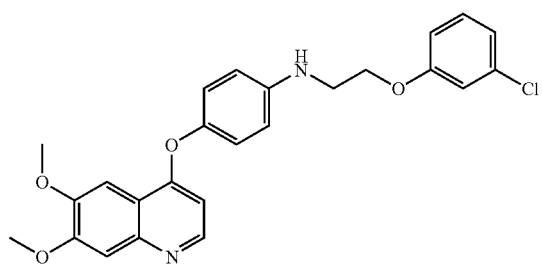
861
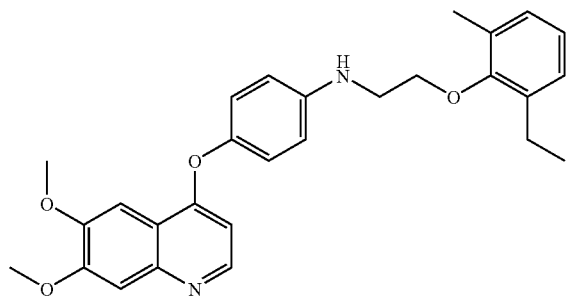

-continued
862
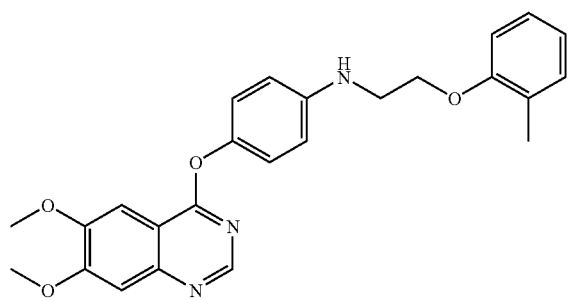
863
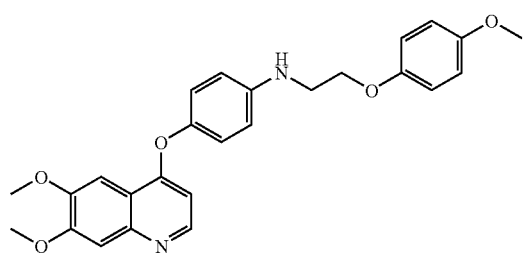
864
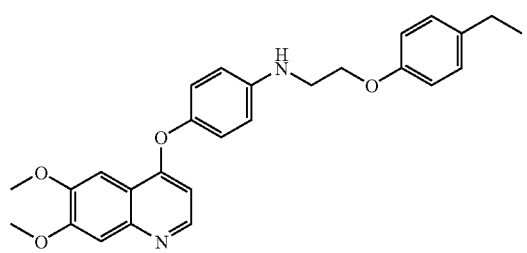
865
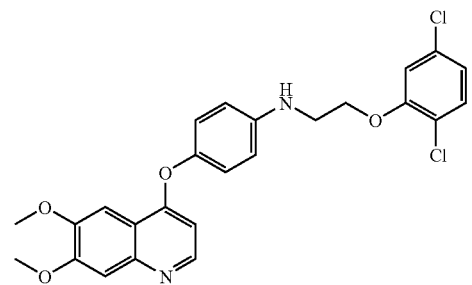
866
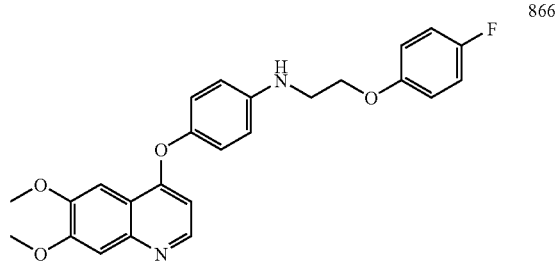

-continued
867
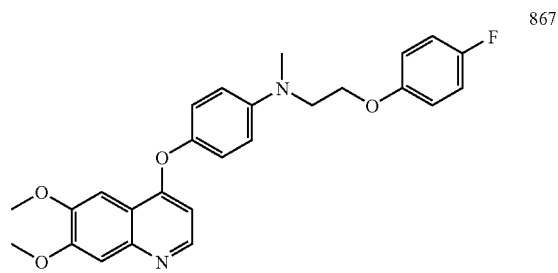
868
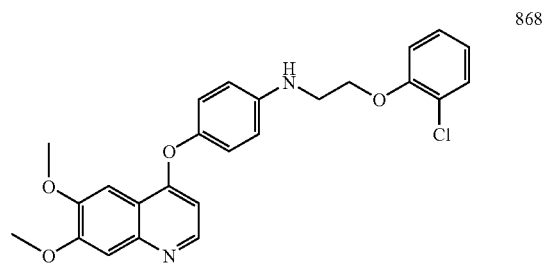
869
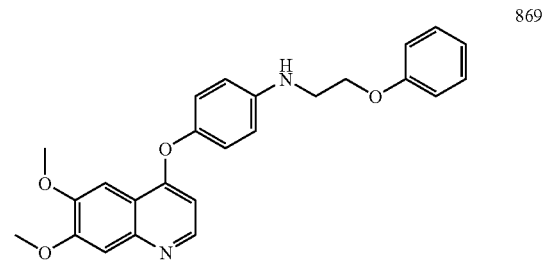
870
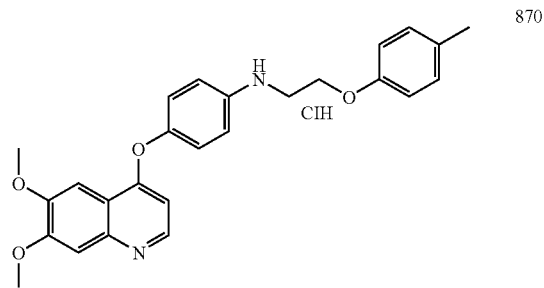
871
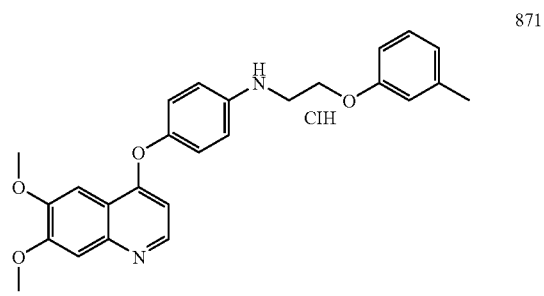
872
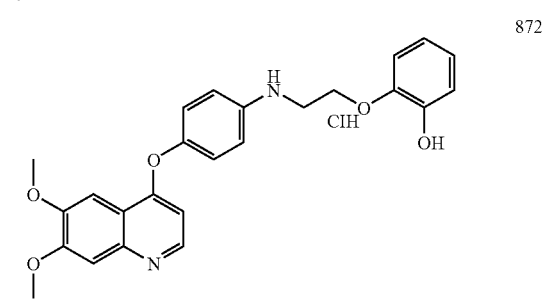

-continued
873
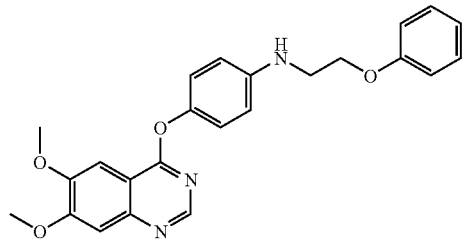
874
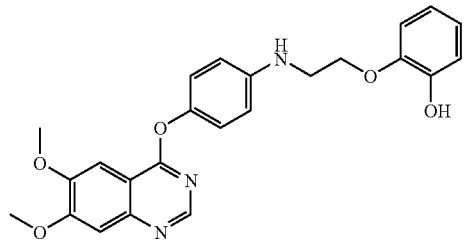
875
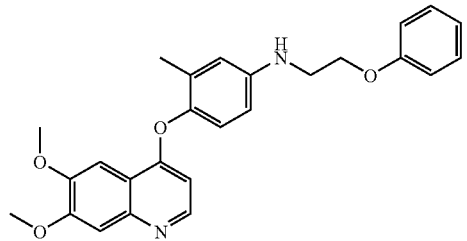
876
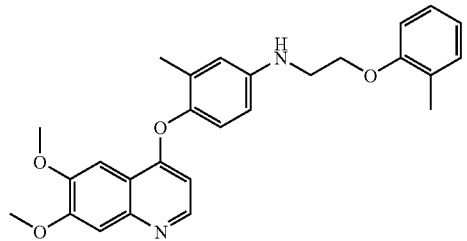
877
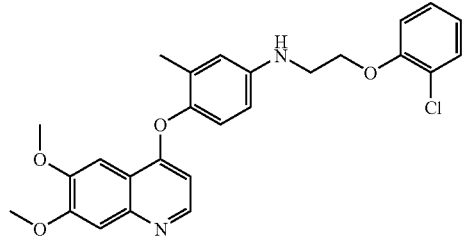
878
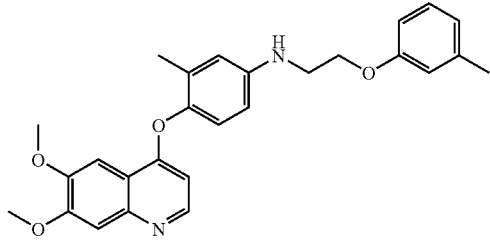

-continued
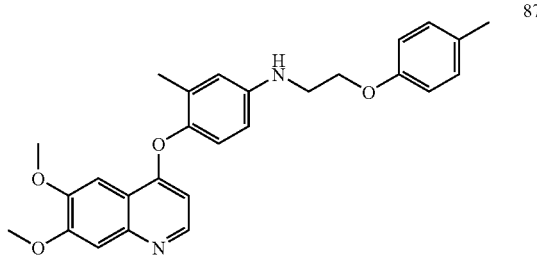
879
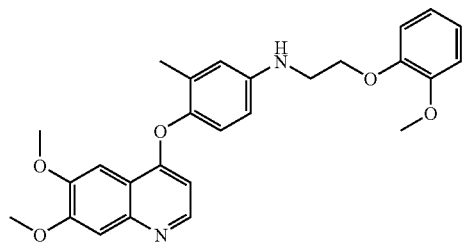
880
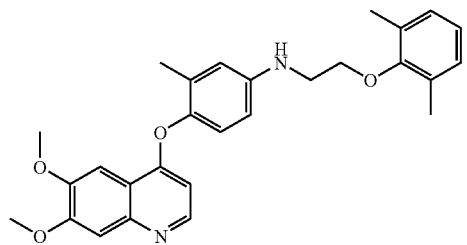
881
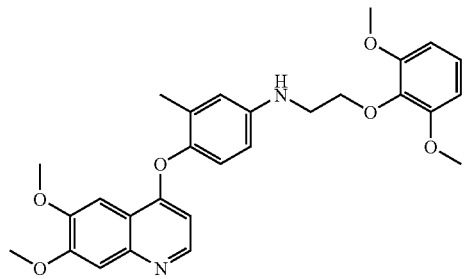
882
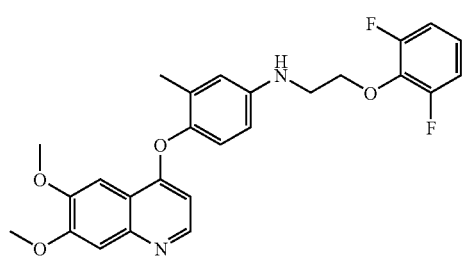
883
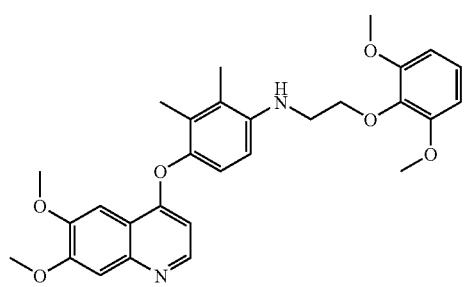
884

-continued
885
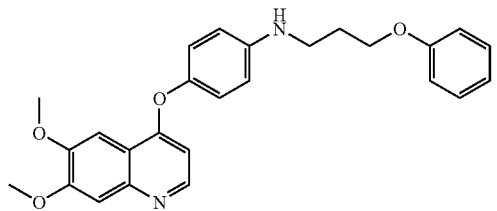
886
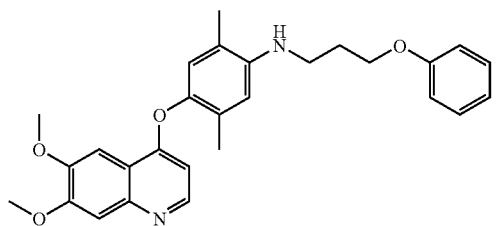
887
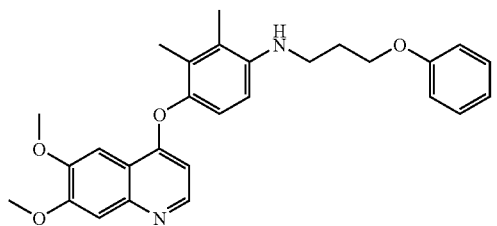
888
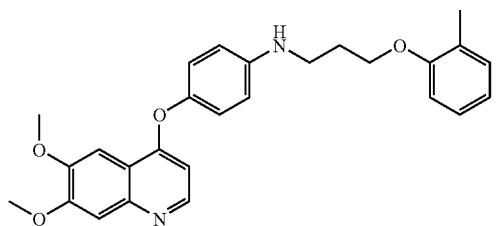
889
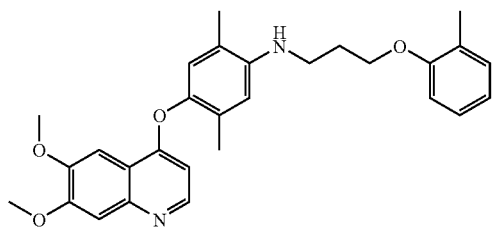
890
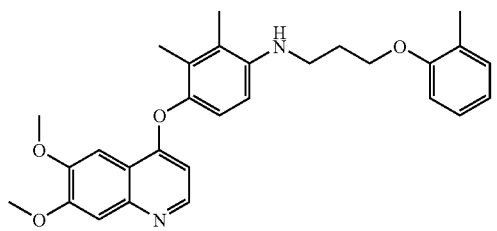
891
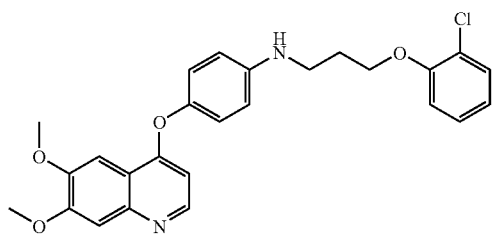

-continued
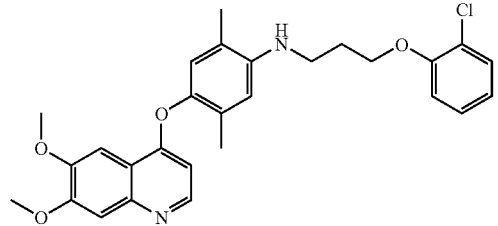
892
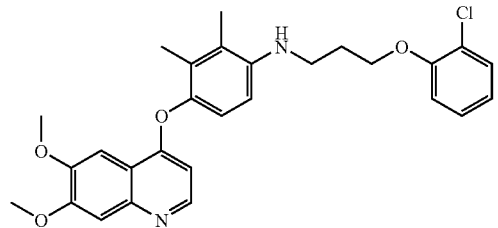
893
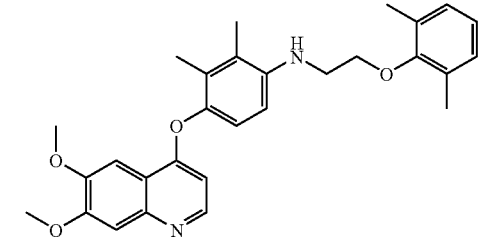
894
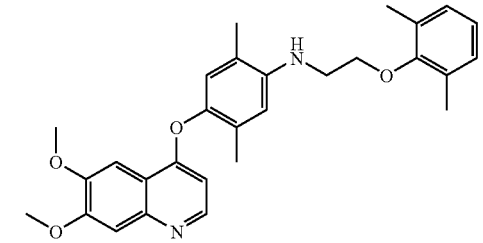
895
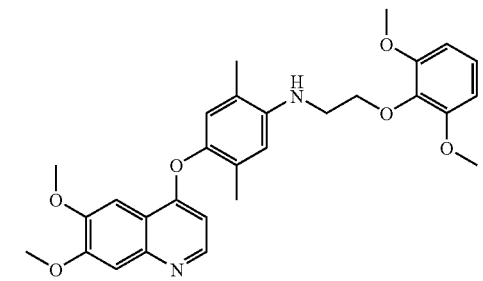
896
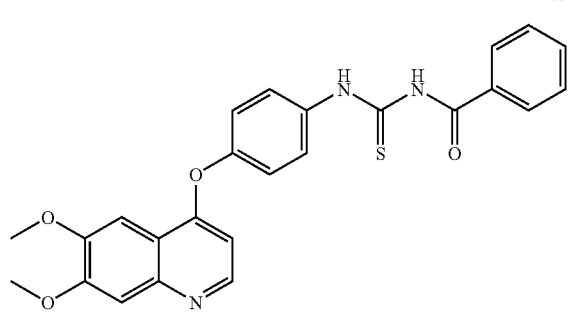
897

-continued
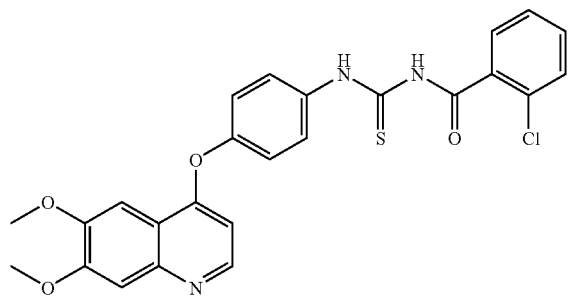
898
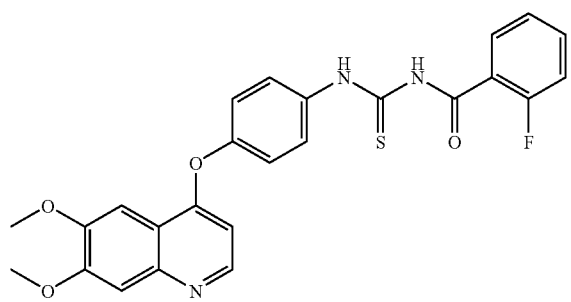
899
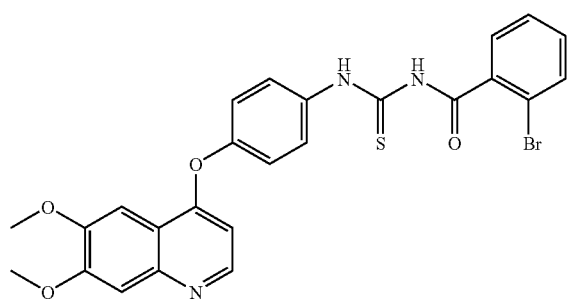
900
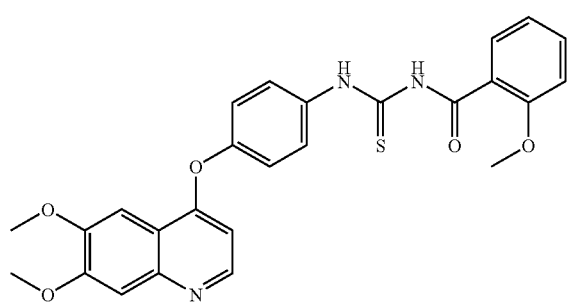
901
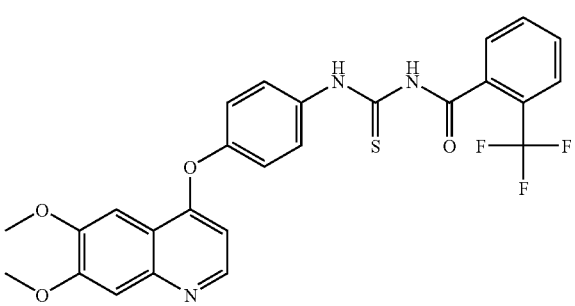
902

-continued
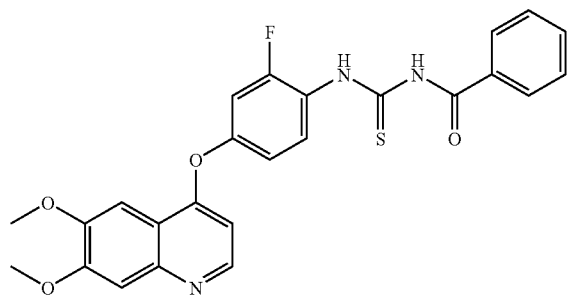
903
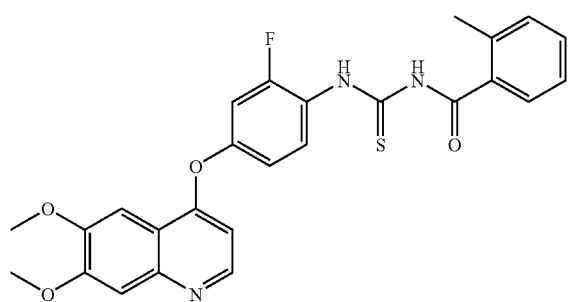
904
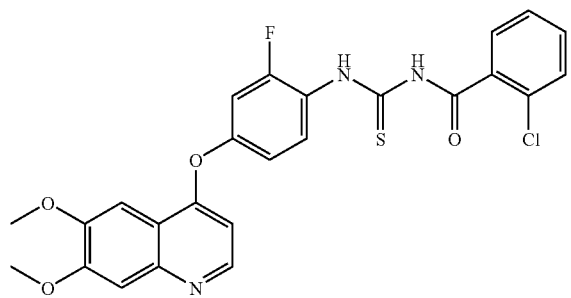
905
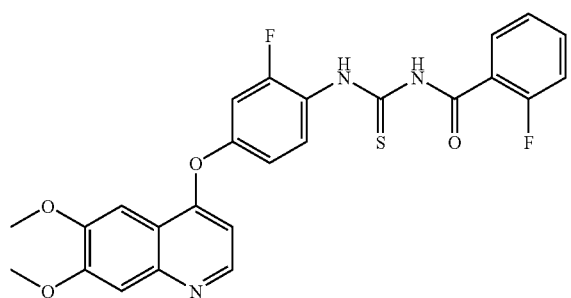
906
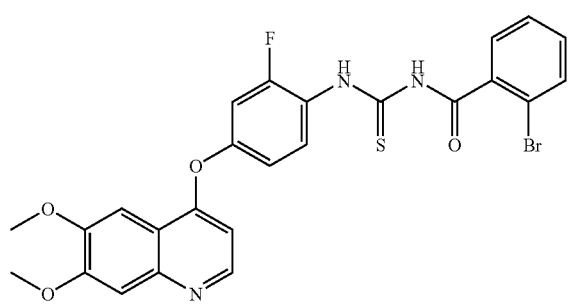
907

-continued
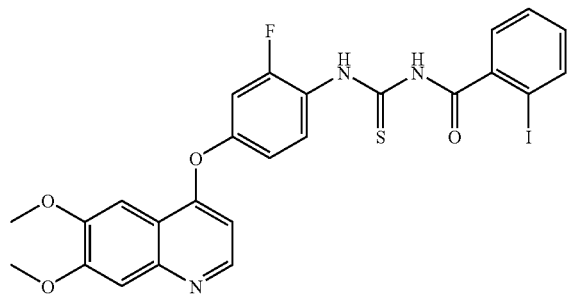
908
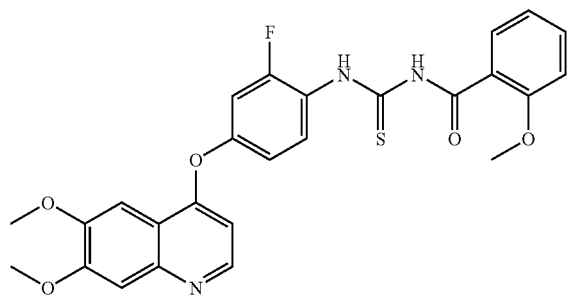
909
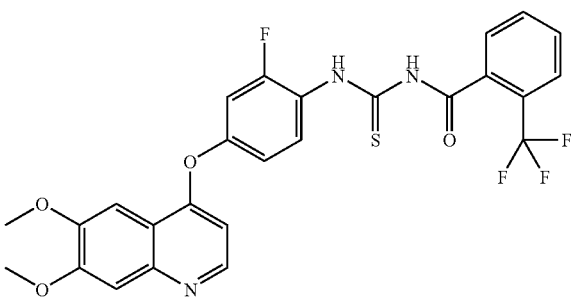
910
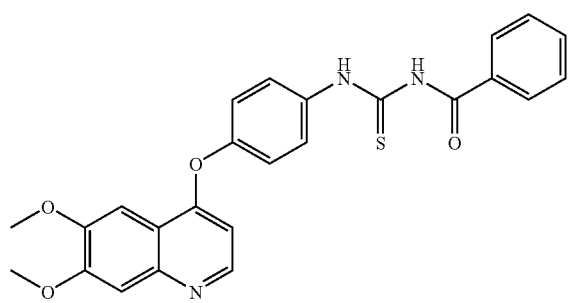
911
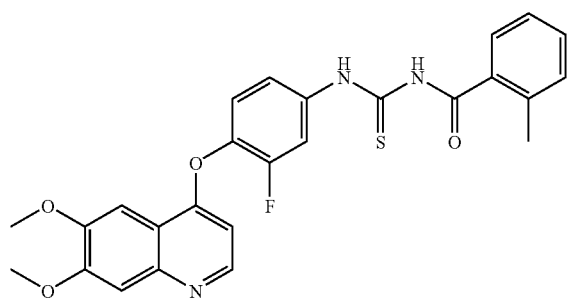
912

-continued
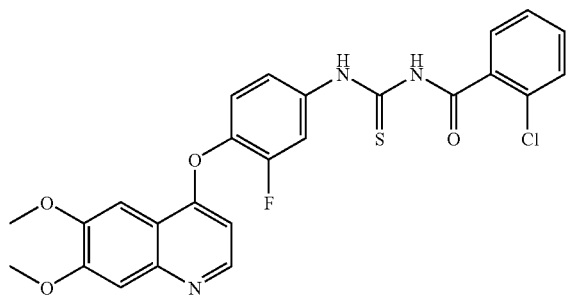
913
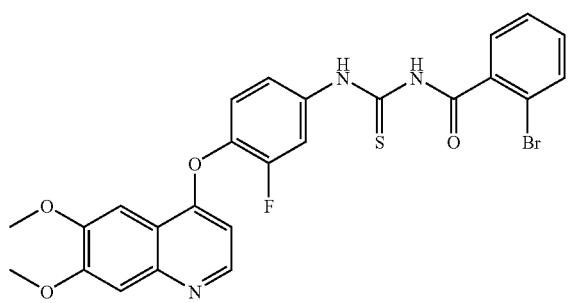
914
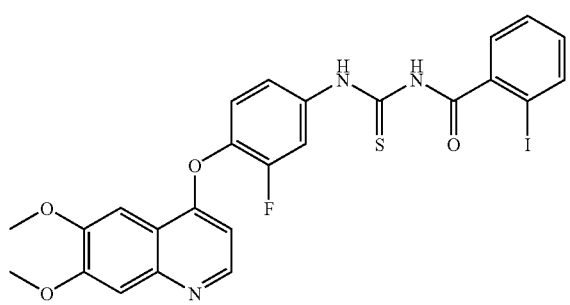
915
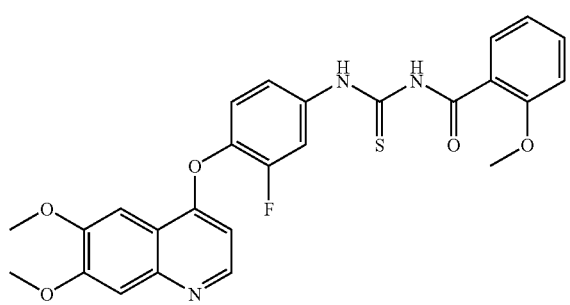
916
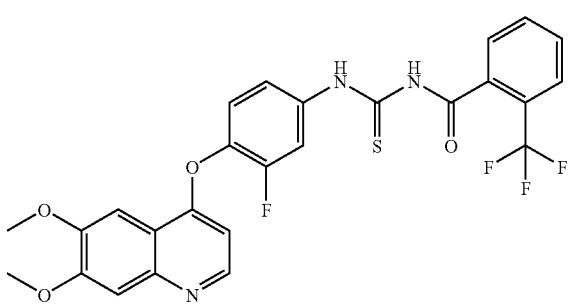
917

-continued
918
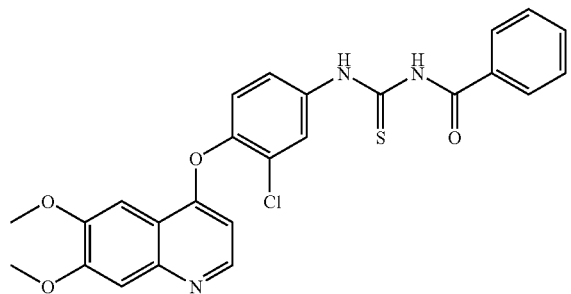
919
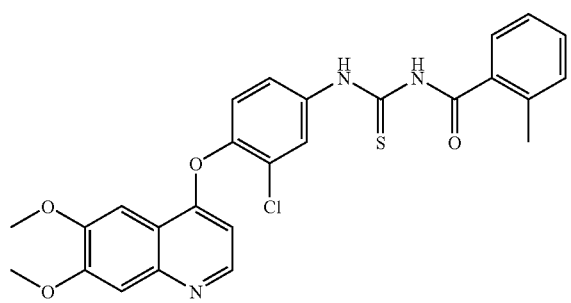
920
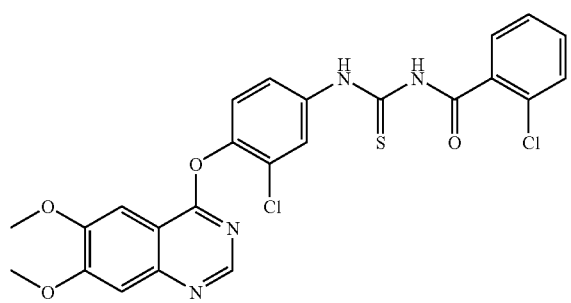
921
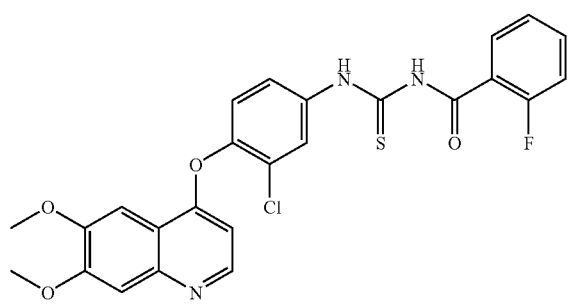
922
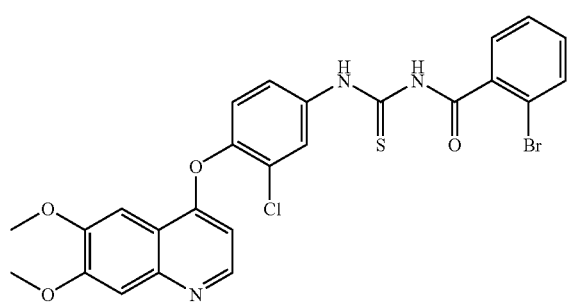

-continued
923
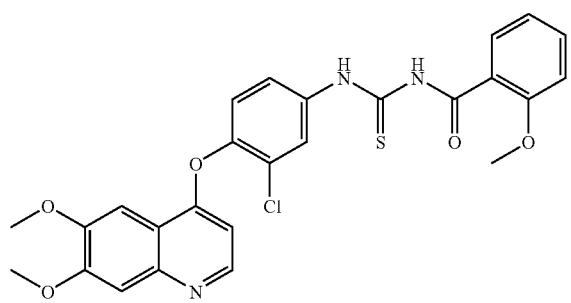
924
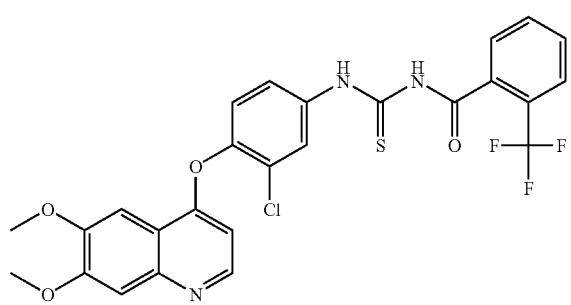
925
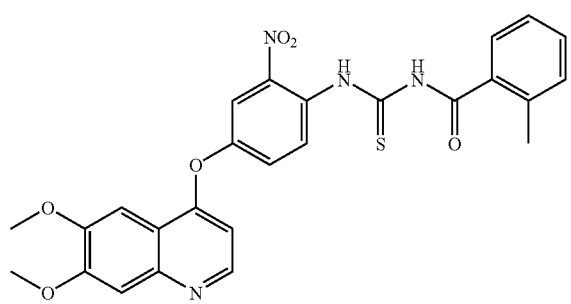
926
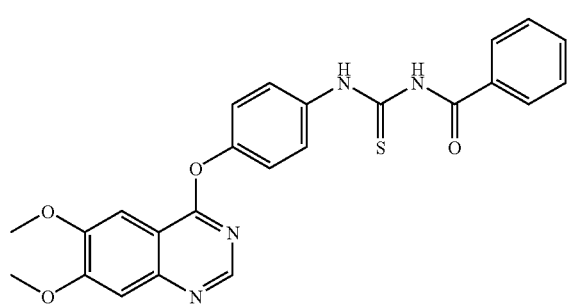
927
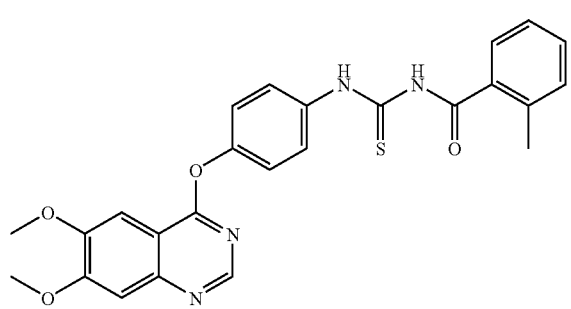

-continued
928
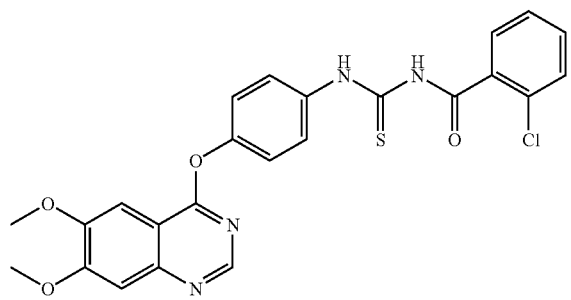
929
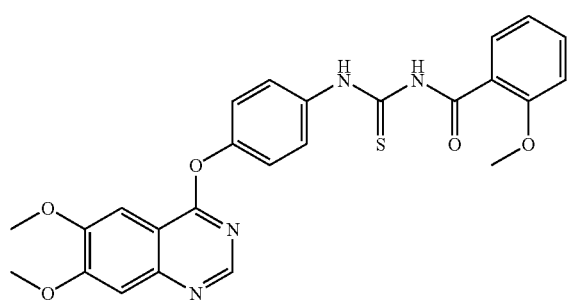
930
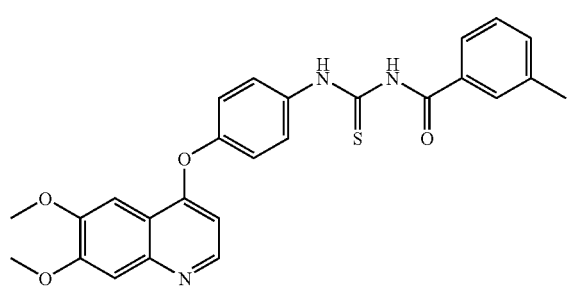
931
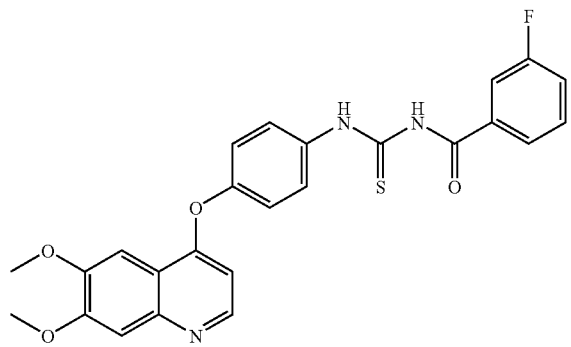
932
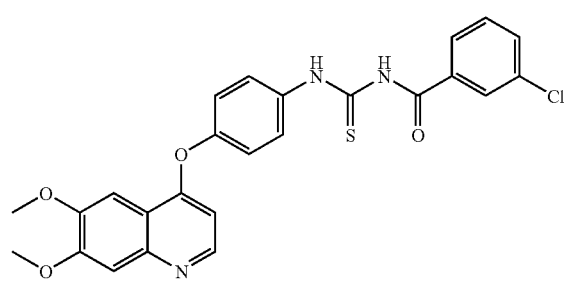

-continued
933
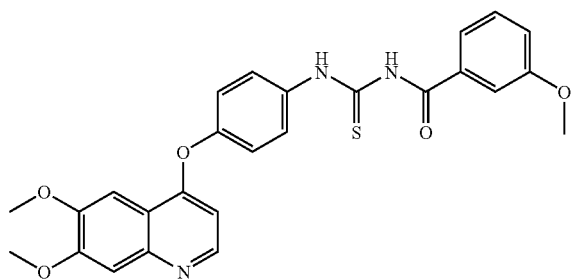
934
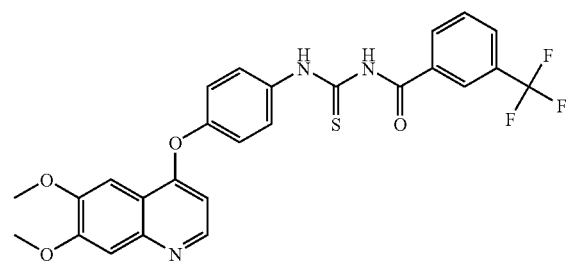
935
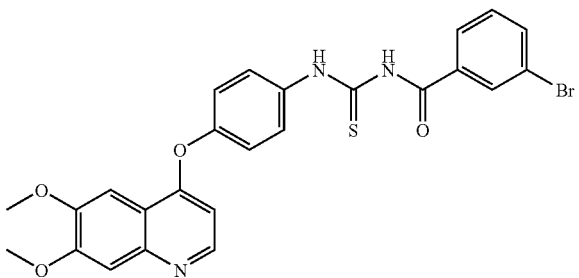
936
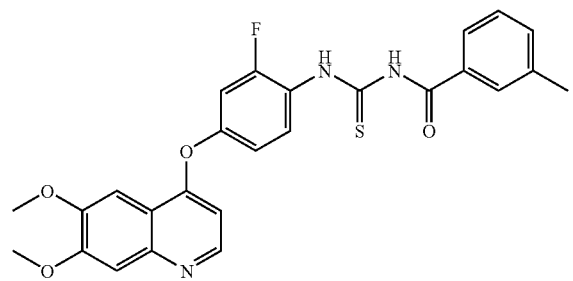
937
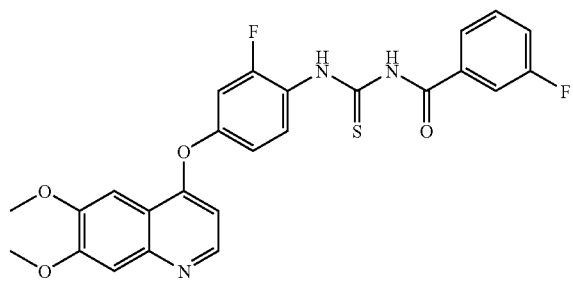

-continued
938
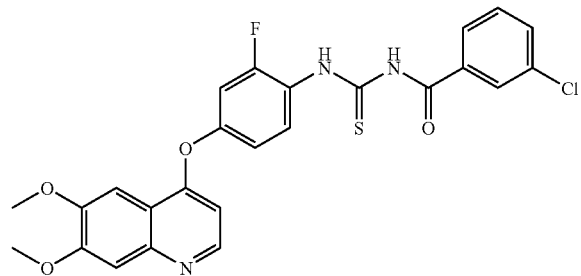
939
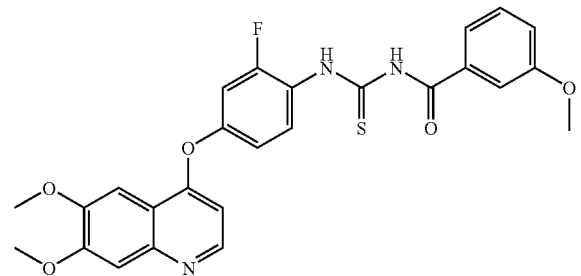
940
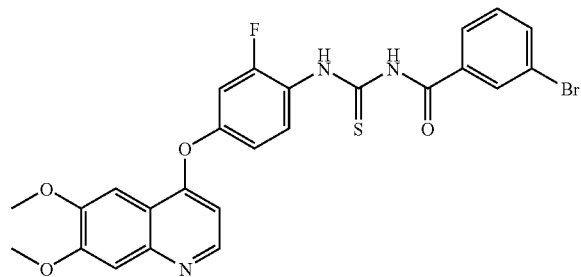
941
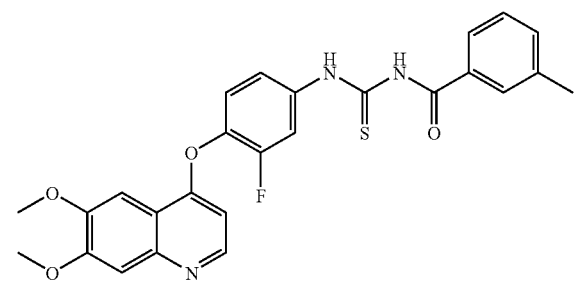
942
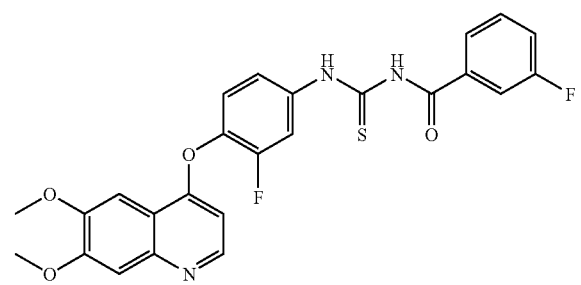

-continued
943
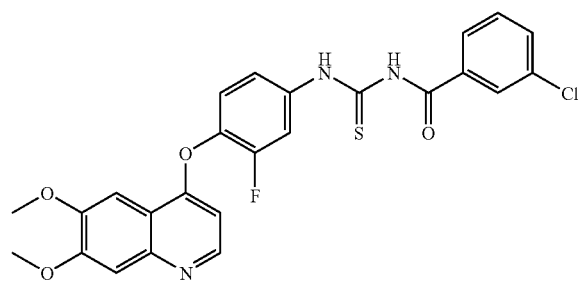
944
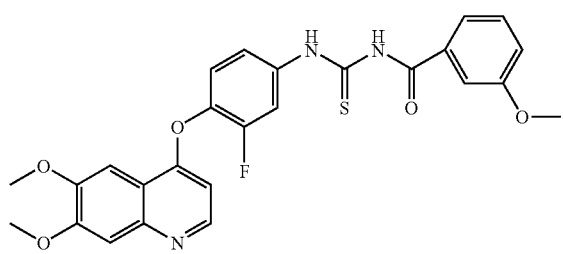
945
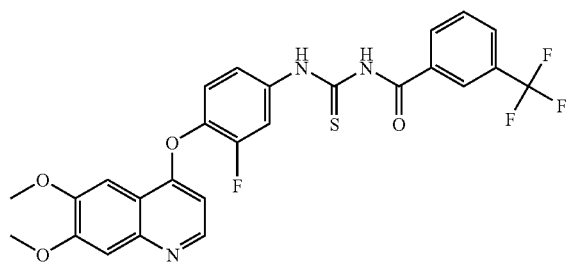
946
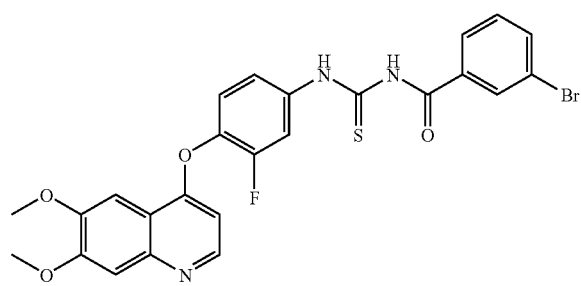
947
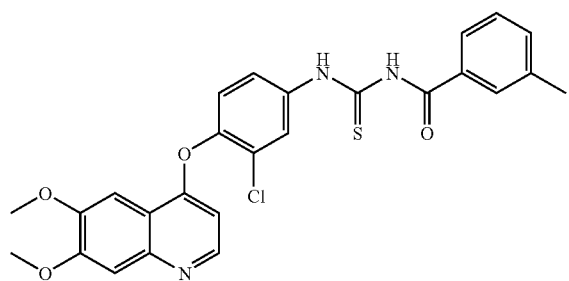

-continued
948
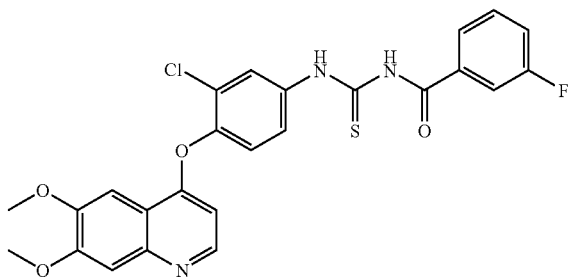
949
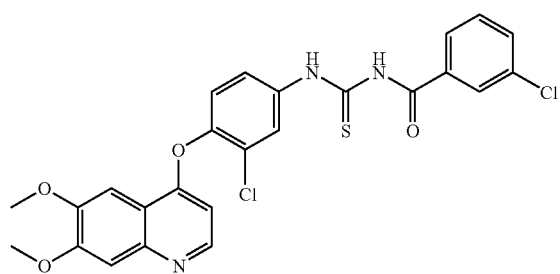
950
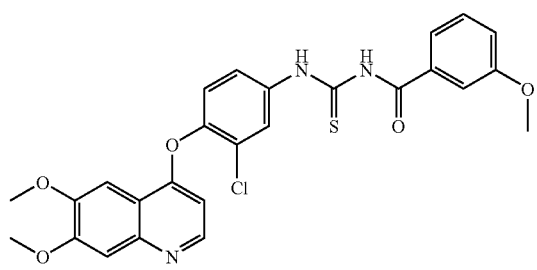
951
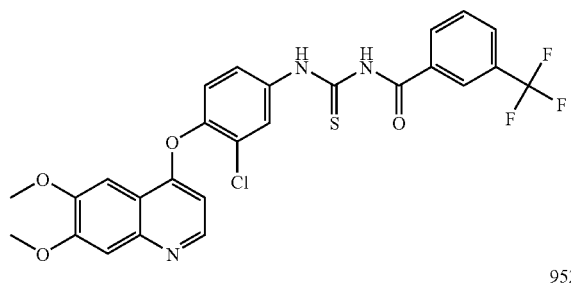
952
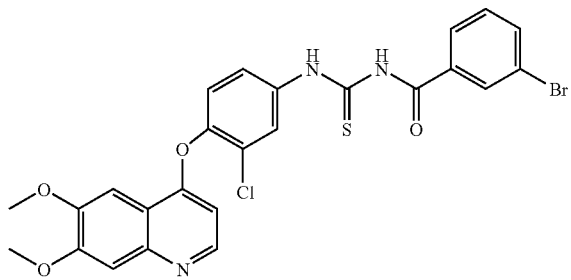

-continued
953
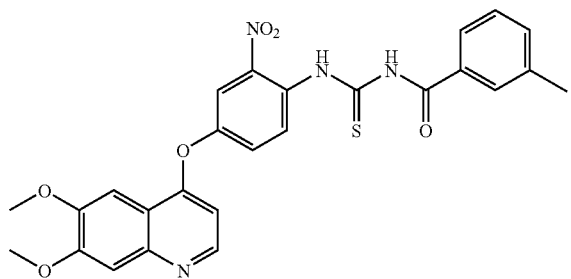
954
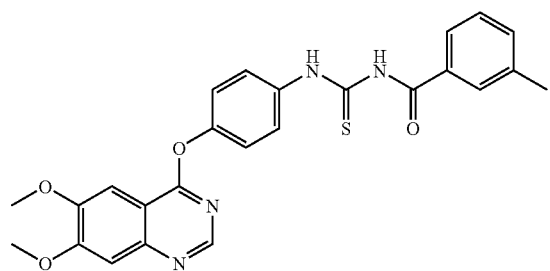
955
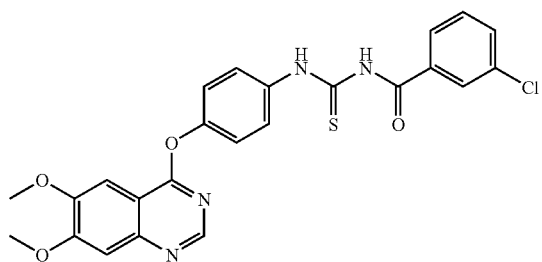
956
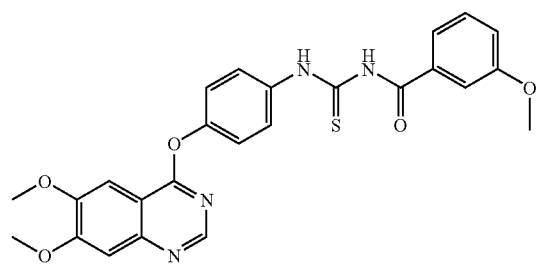
957
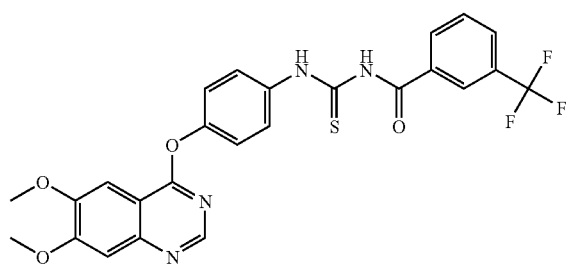

-continued
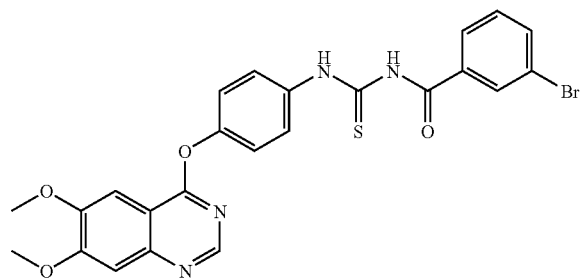
958
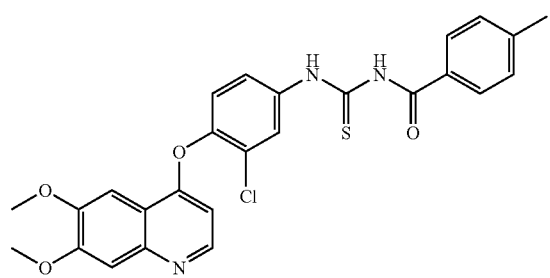
959
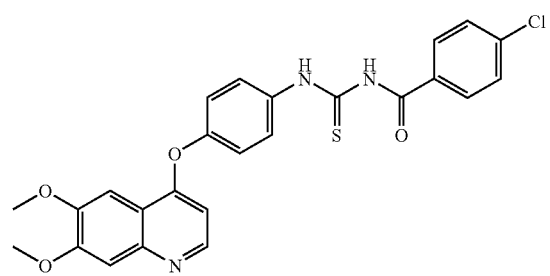
960
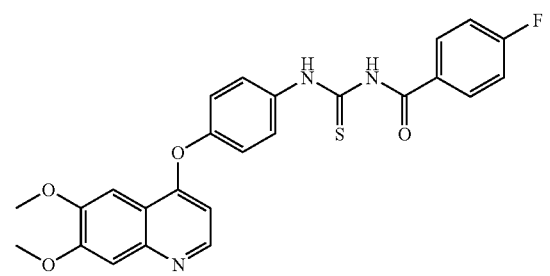
961
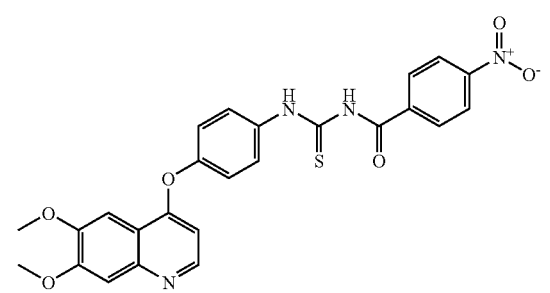
962

-continued
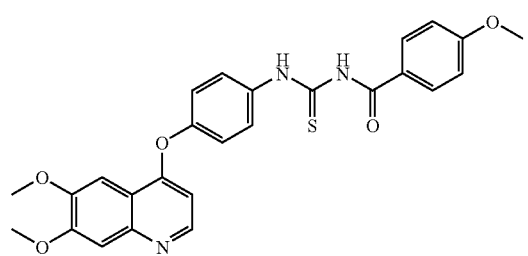
963
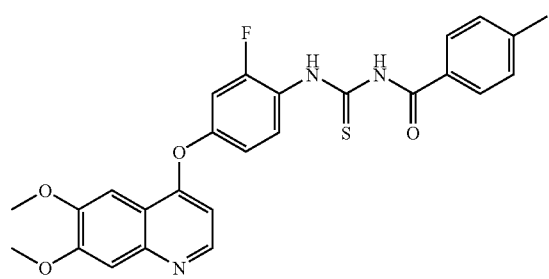
964
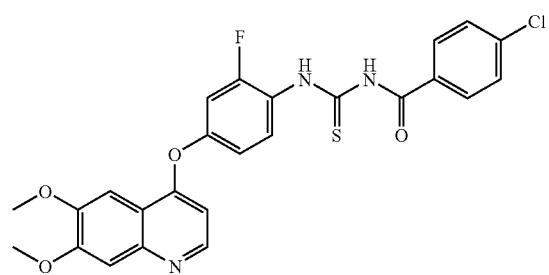
965
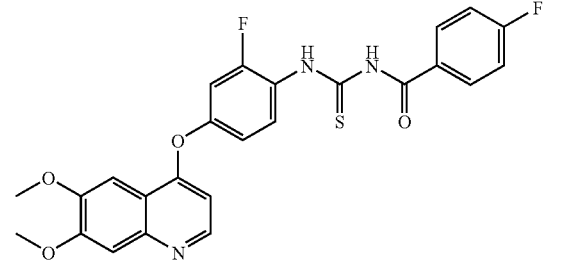
966
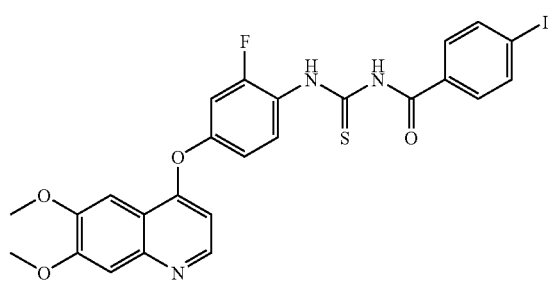
967

-continued
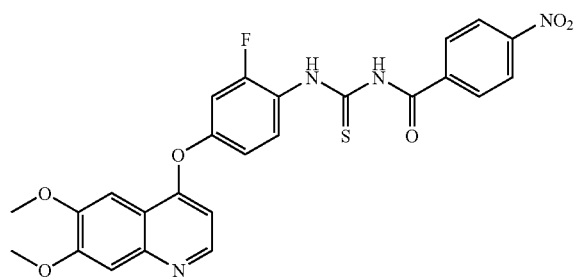
968
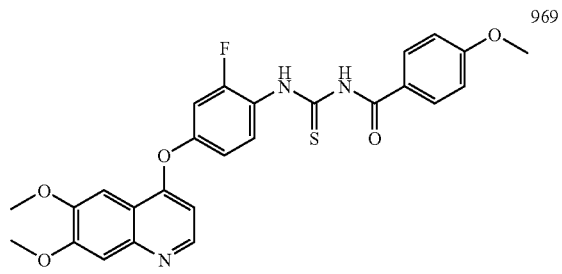
969
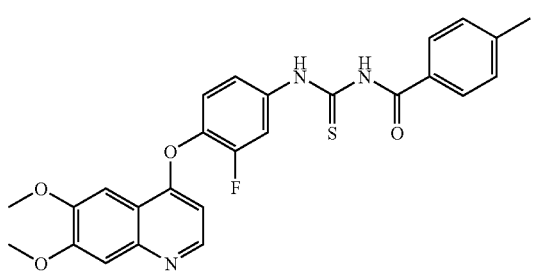
970
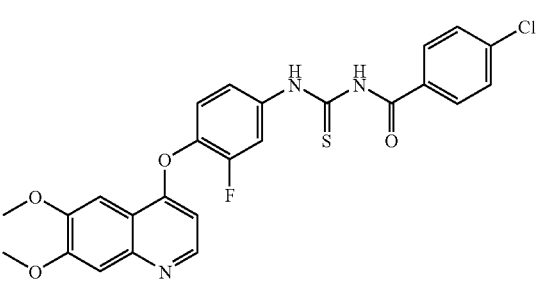
971
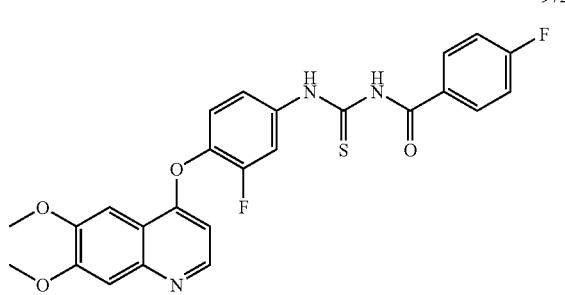
972

-continued
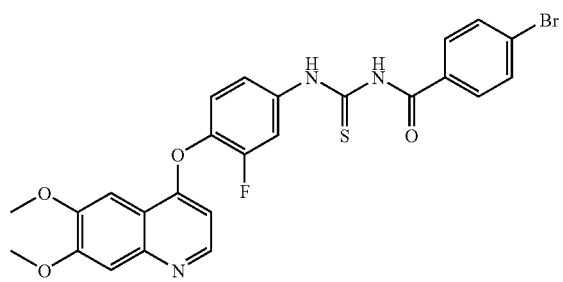
973
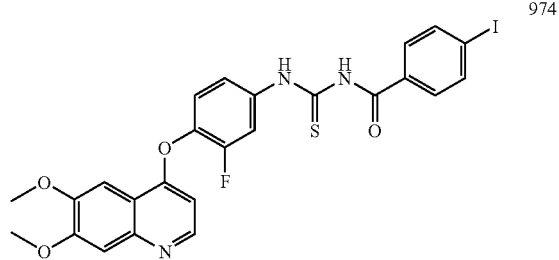
974
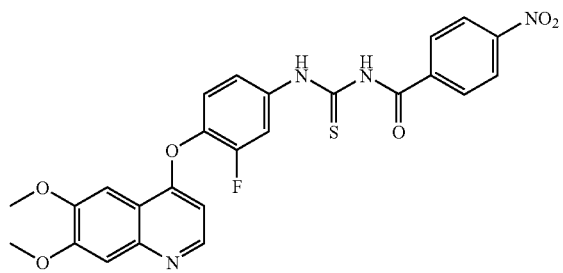
975
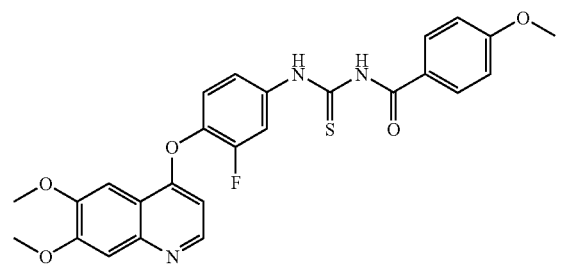
976
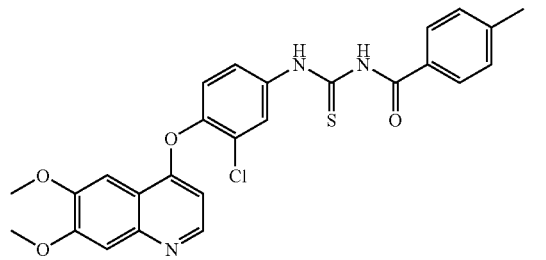
977

-continued
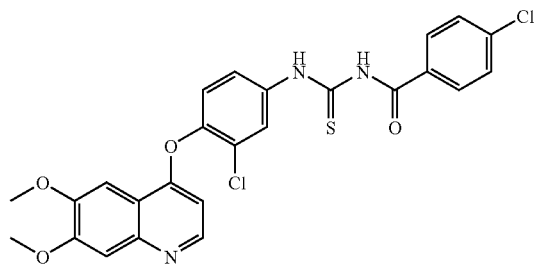
978
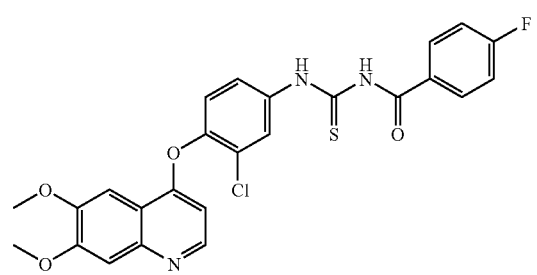
979
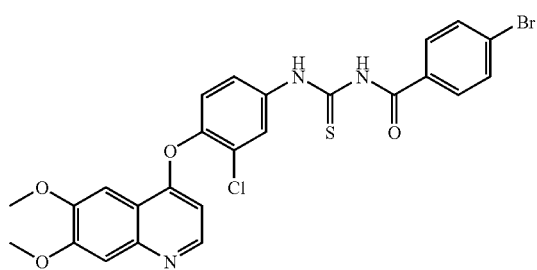
980
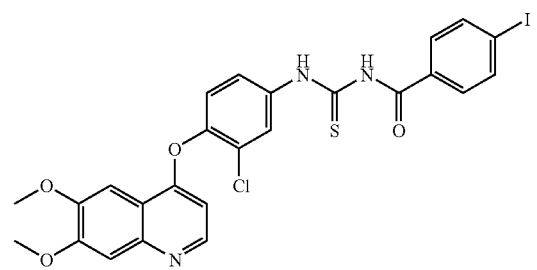
981
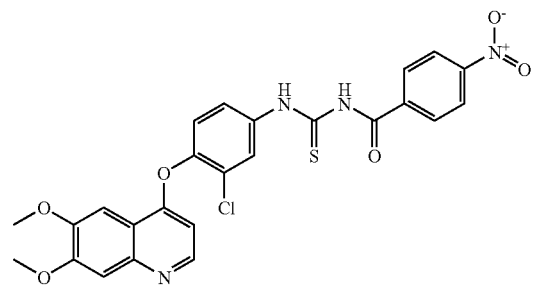
928

-continued
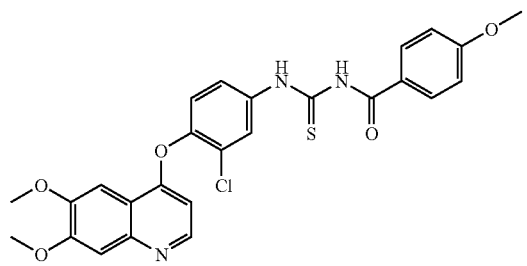
983
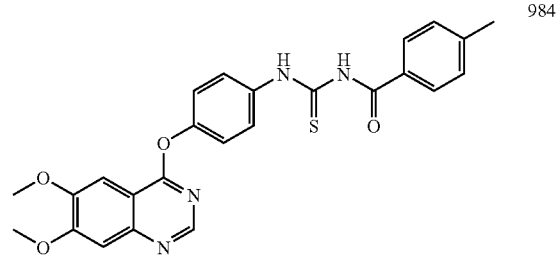
984
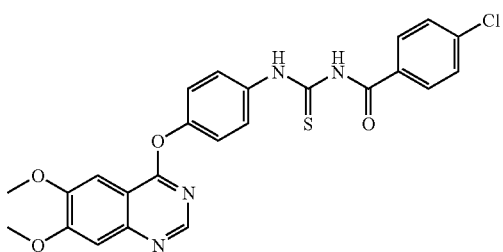
985
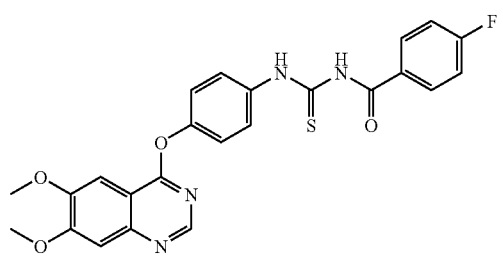
986
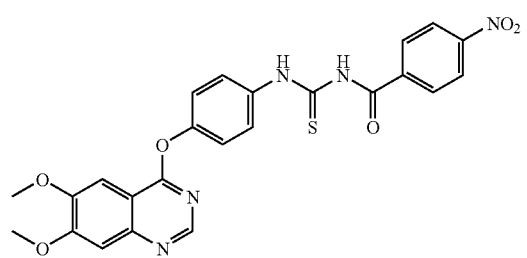
987
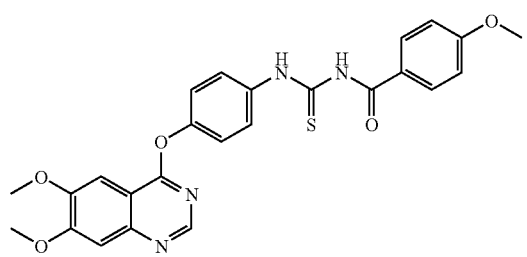
988

-continued
989
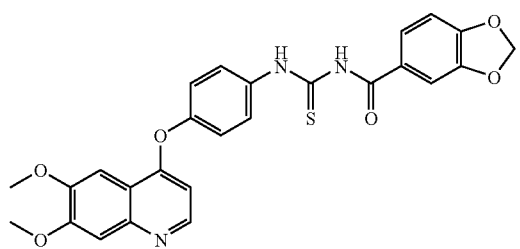
990
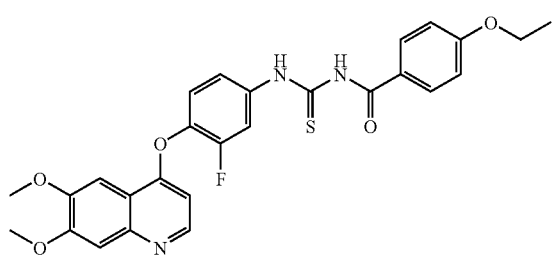
991
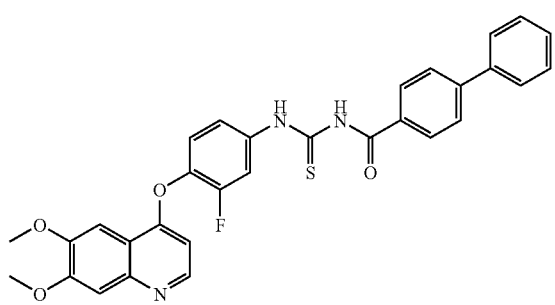
992
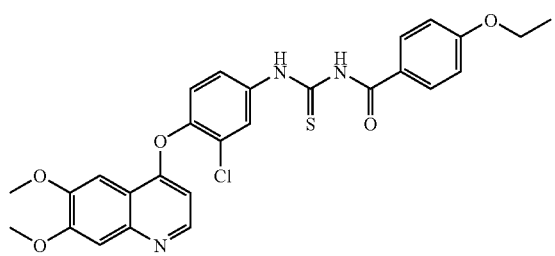
993
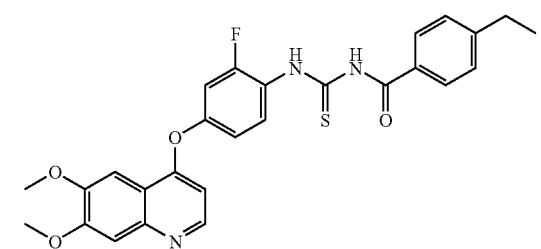

-continued
994
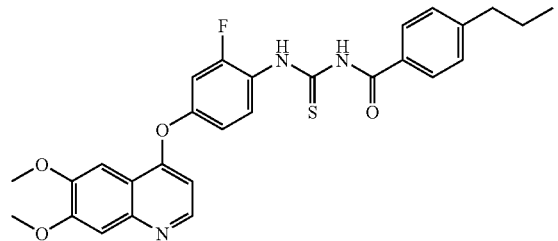
995
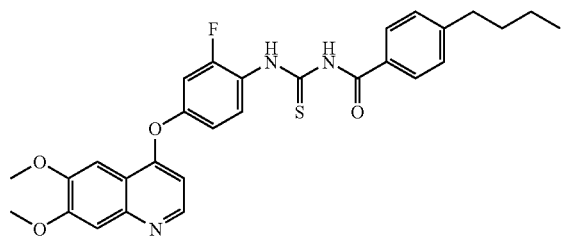
996
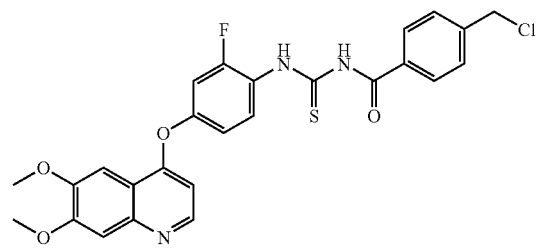
997
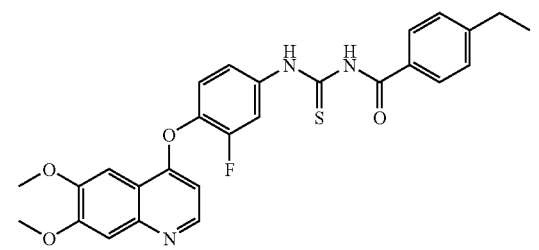
998
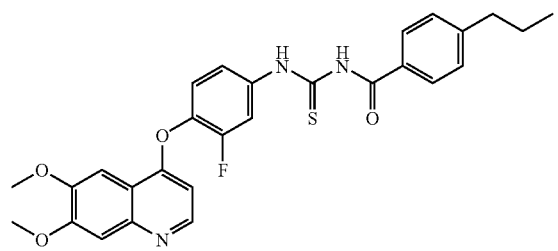
999
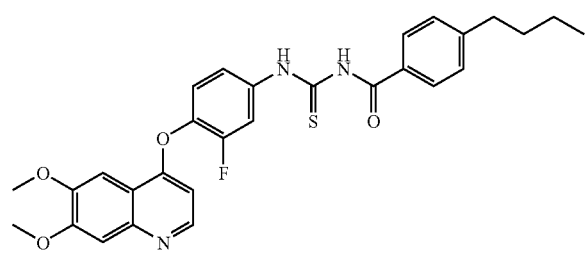

-continued
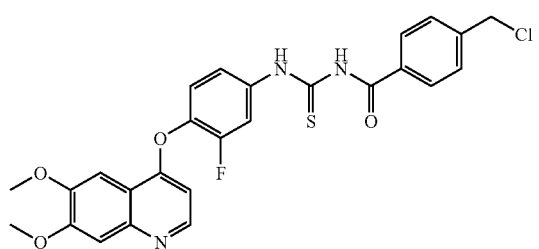
1000
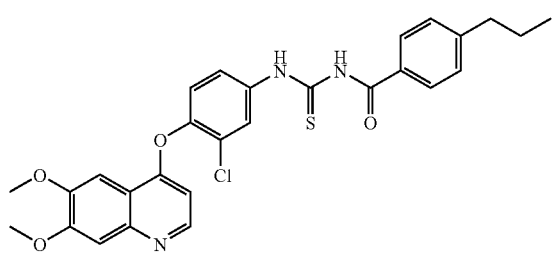
1001
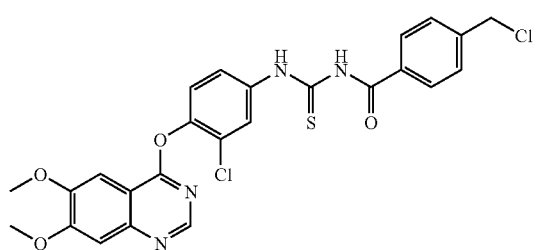
1002
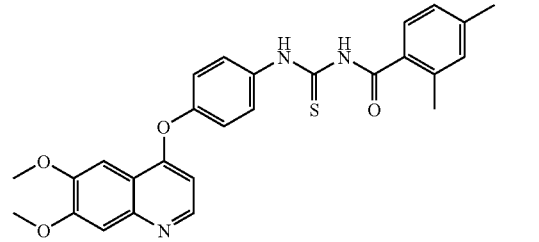
1003
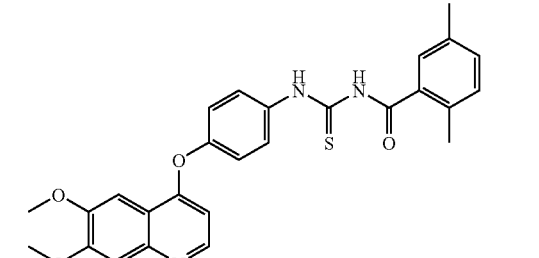
1004
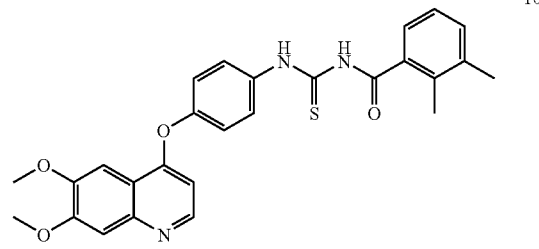
1005

-continued
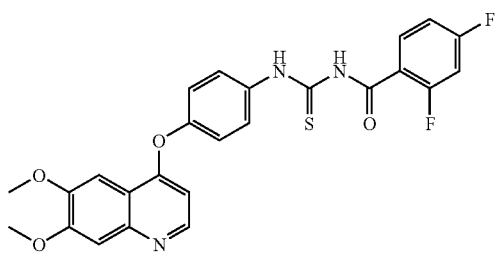
1006
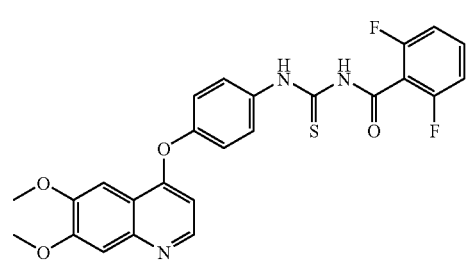
1007
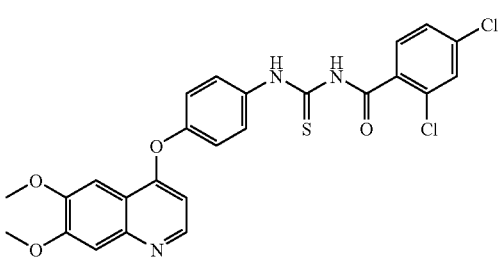
1008
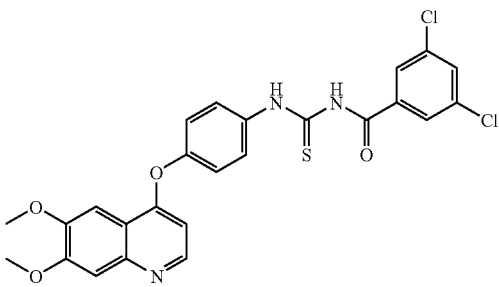
1009
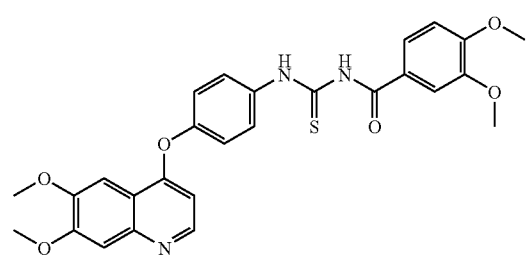
1010

-continued
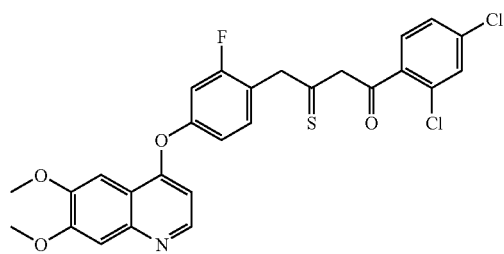
1011
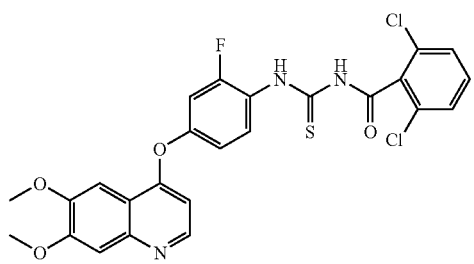
1012
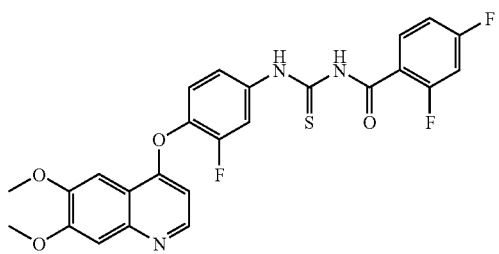
1013
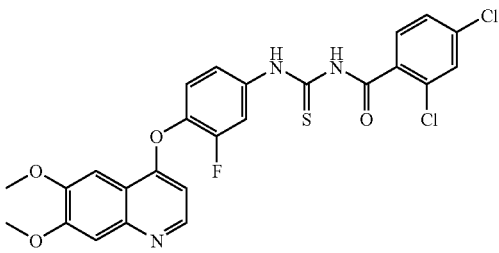
1014
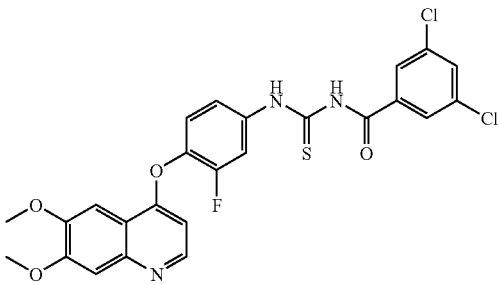
1015

-continued
1016
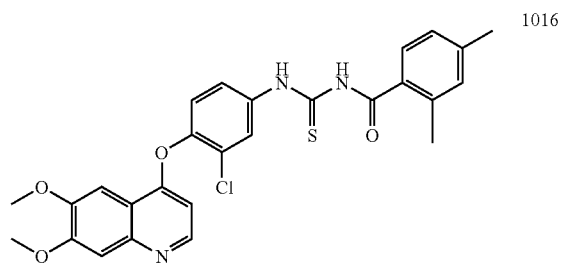
1017
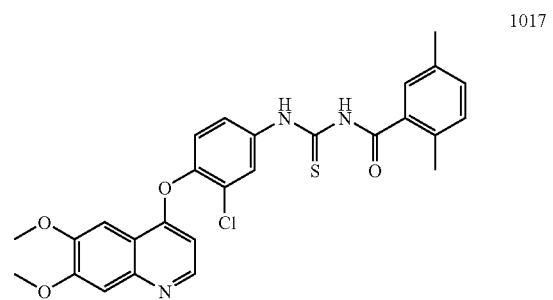
1018
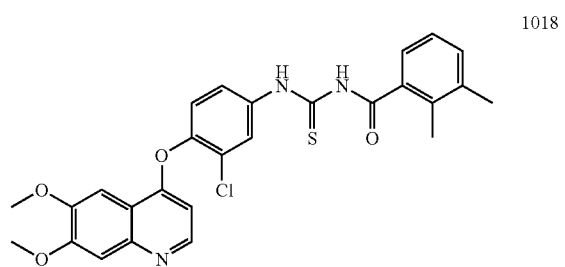
1019
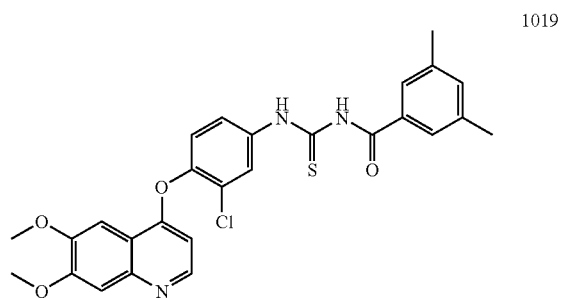
1020
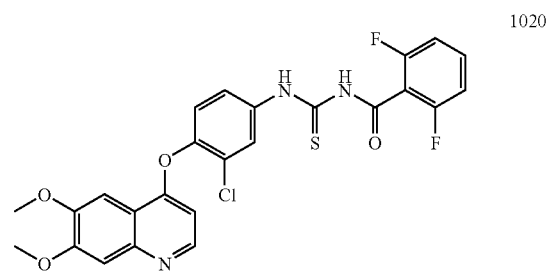
1021
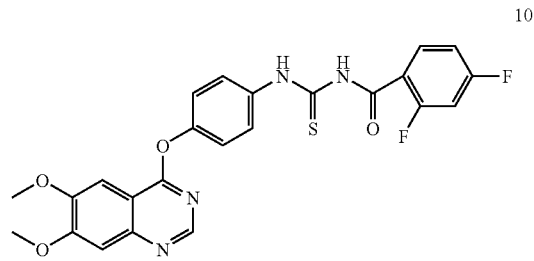

-continued
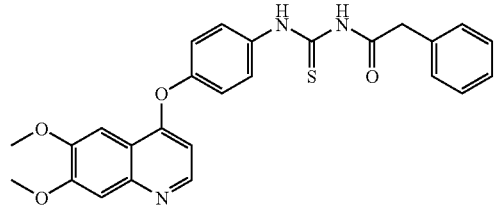
1022
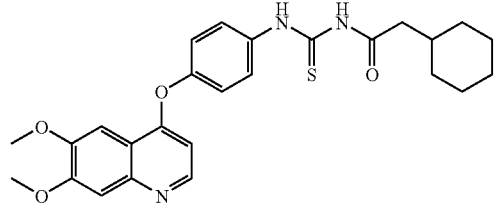
1023
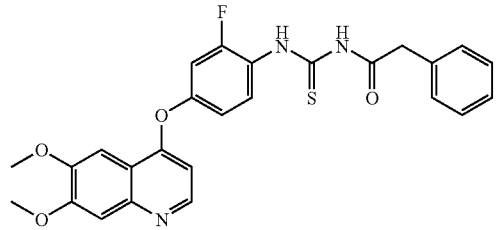
1024
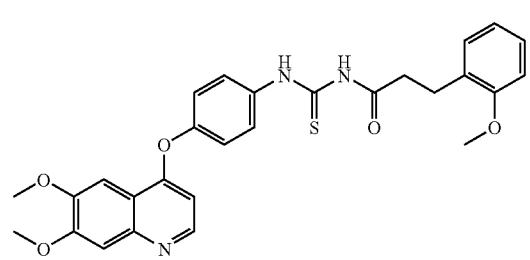
1025
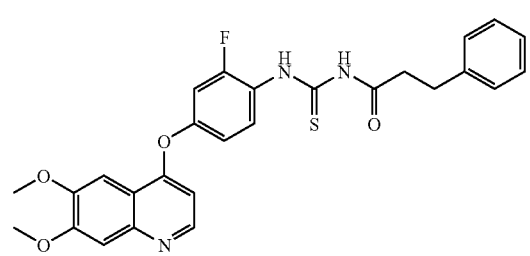
1026
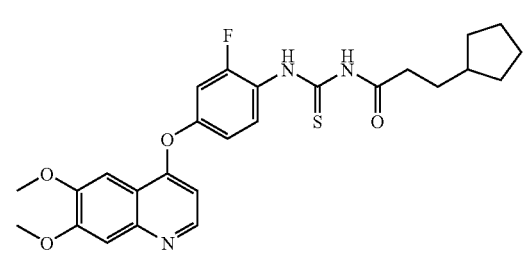
1027

-continued
1028
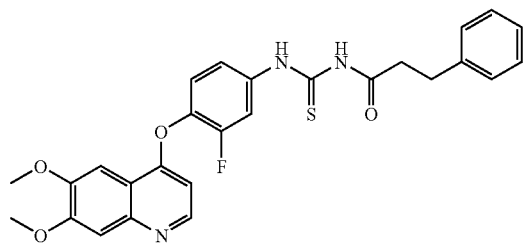
1029
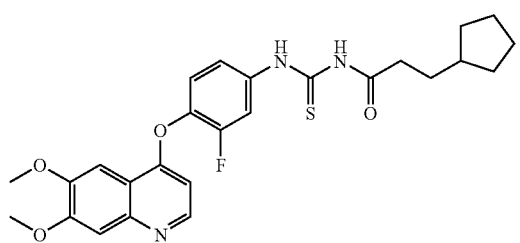
1030
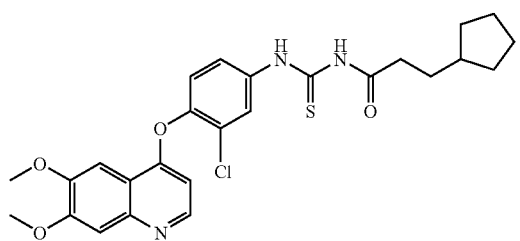
1031
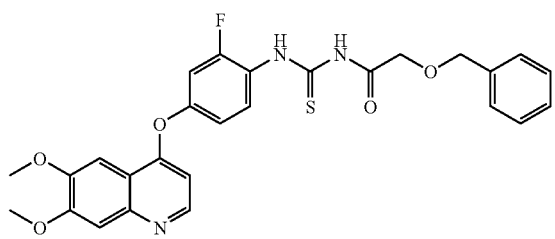
1032
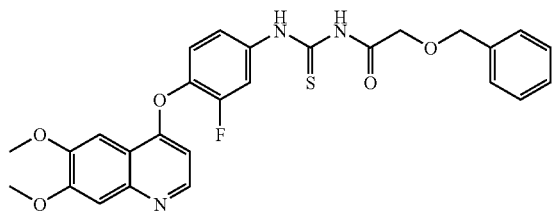
1033
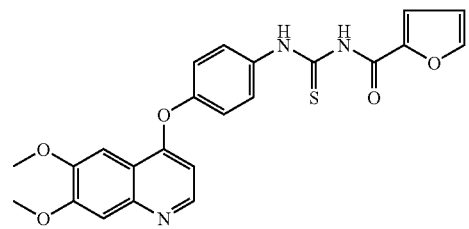

-continued
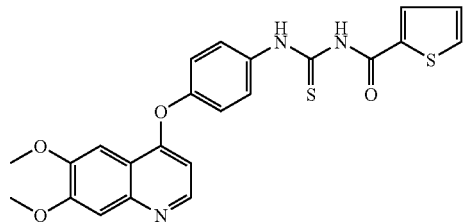
1034
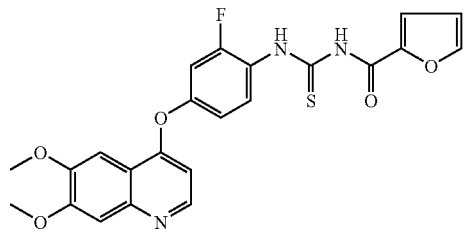
1035
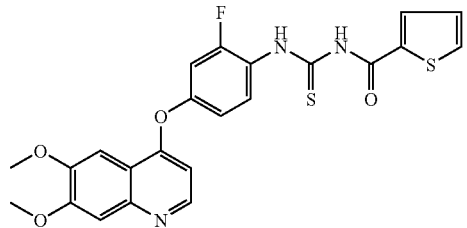
1036
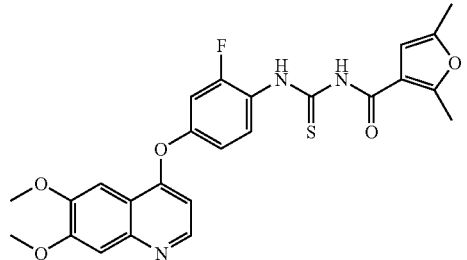
1037
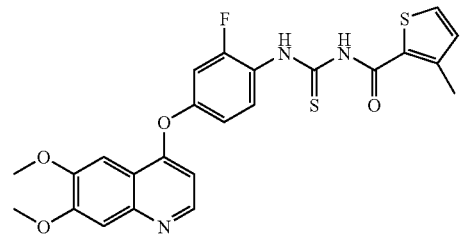
1038
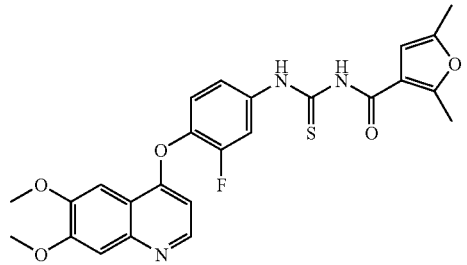
1039

-continued
1040
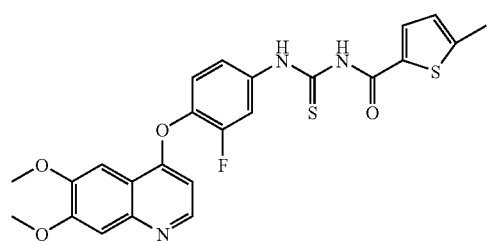
1041
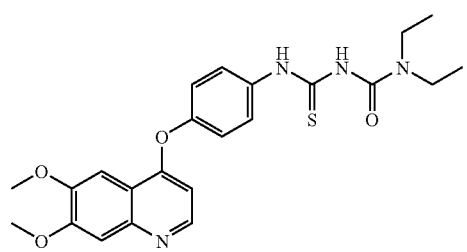
1042
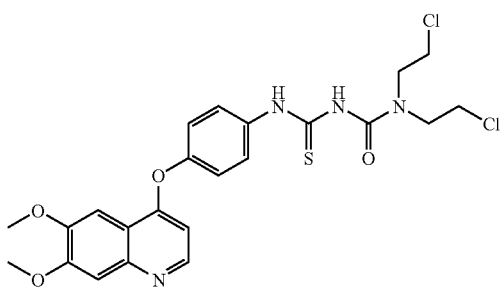
1043
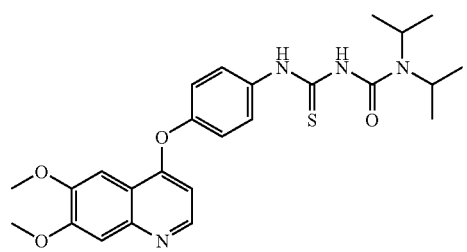
1044
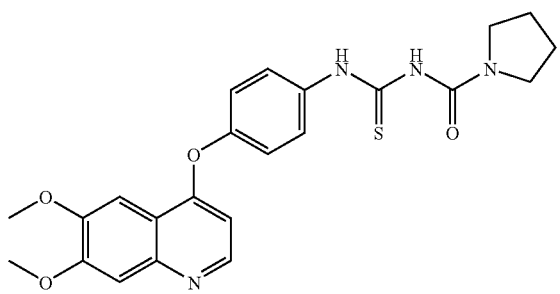

-continued
1045
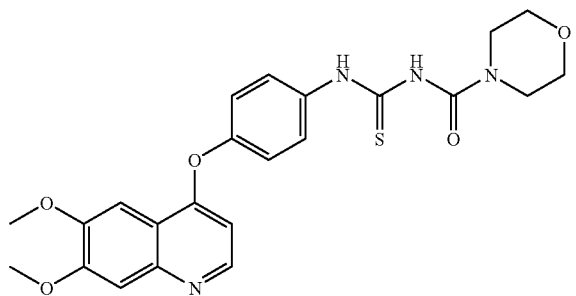
1046
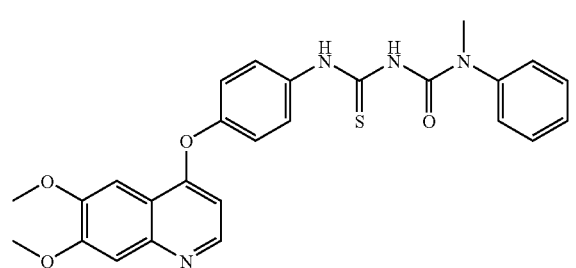
1047
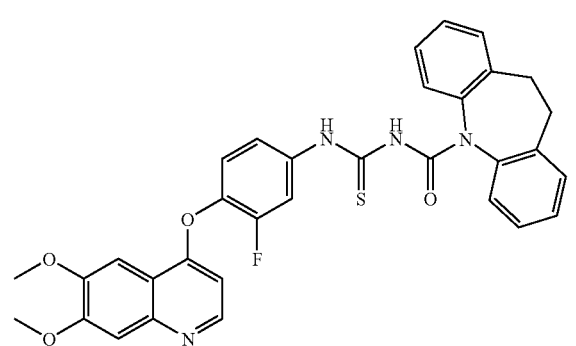
1048
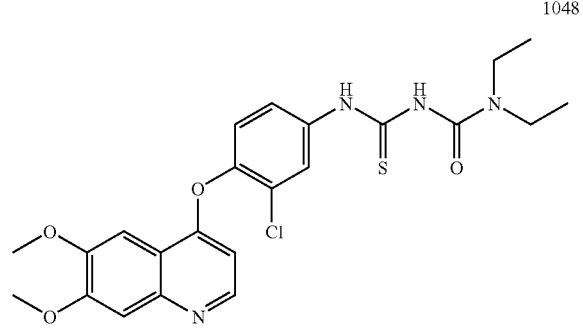
1049
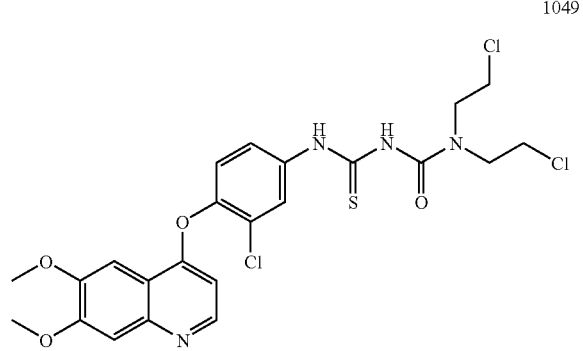

-continued
1050
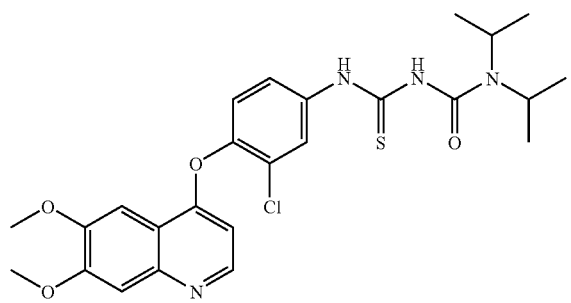
1051
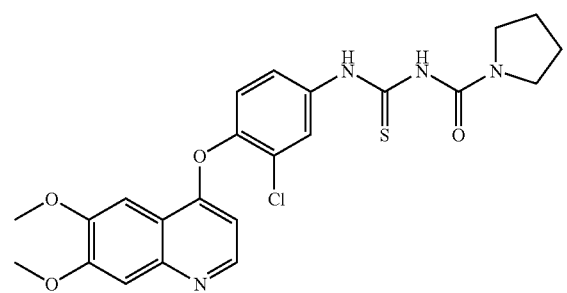
1052
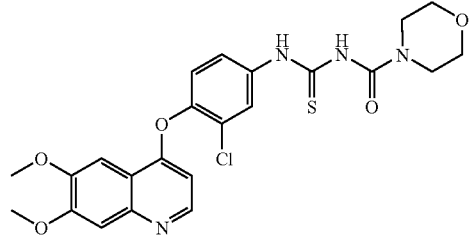
1053
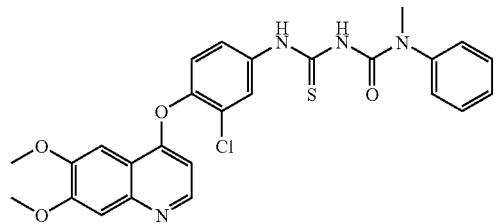
1054
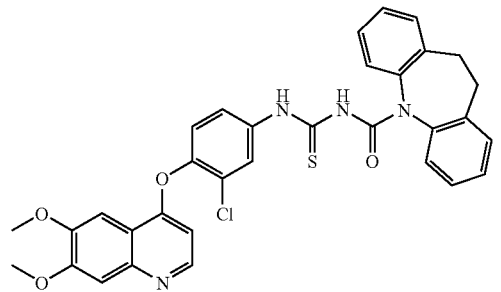

-continued
1055
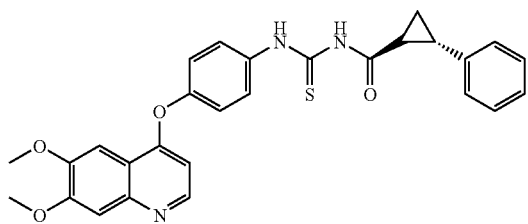
1056
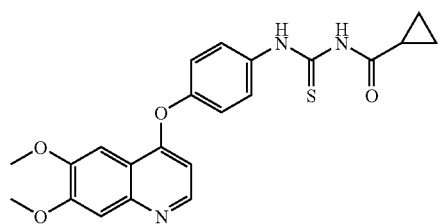
1057
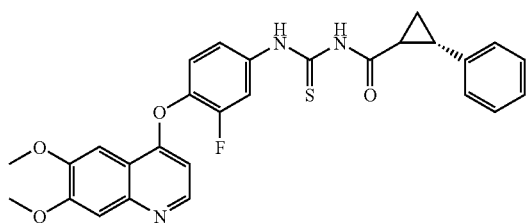
1058
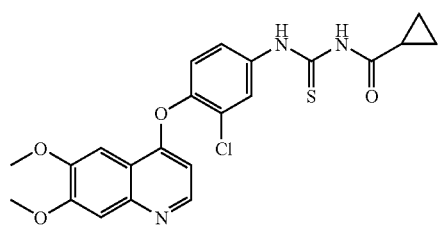
1059
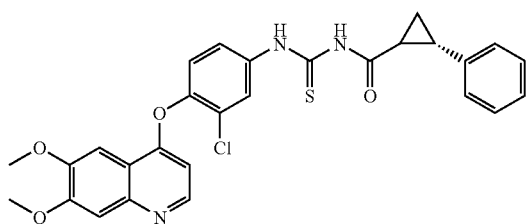
1060
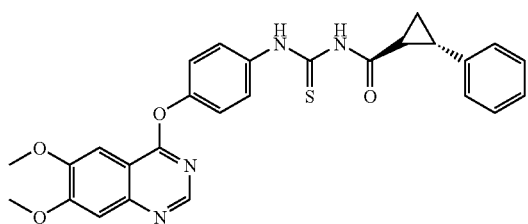

-continued
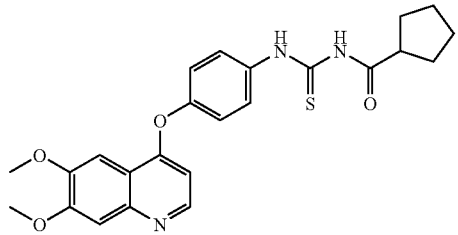
1061
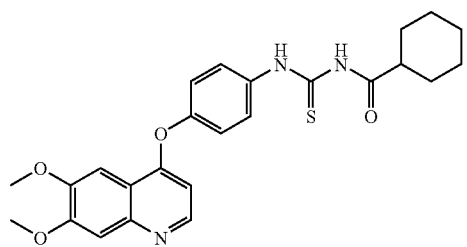
1062
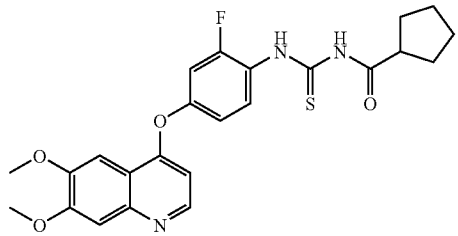
1063
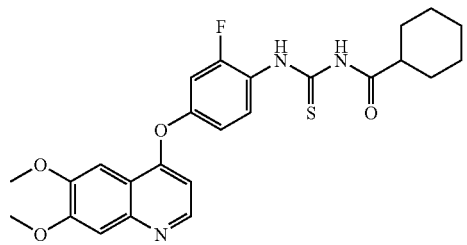
1064
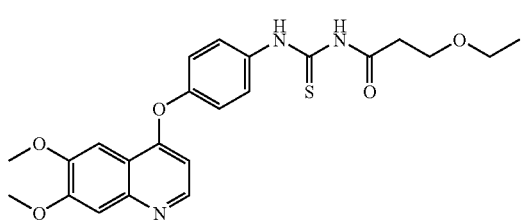
1065
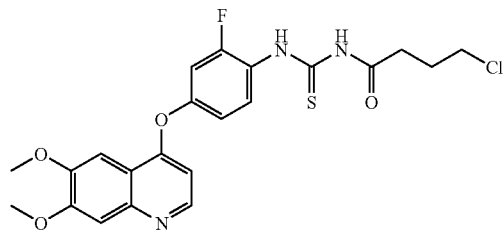
1066

1067
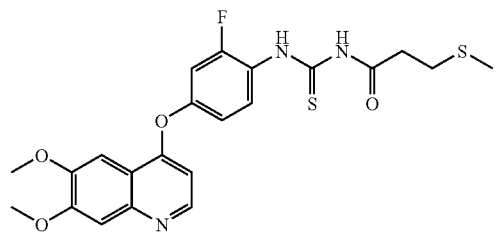
1068
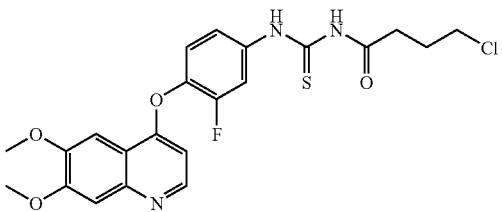
1069
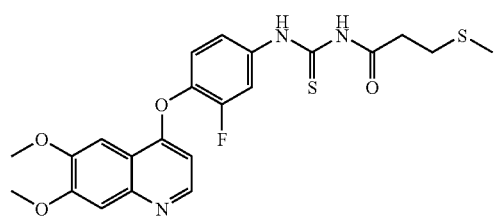
1070
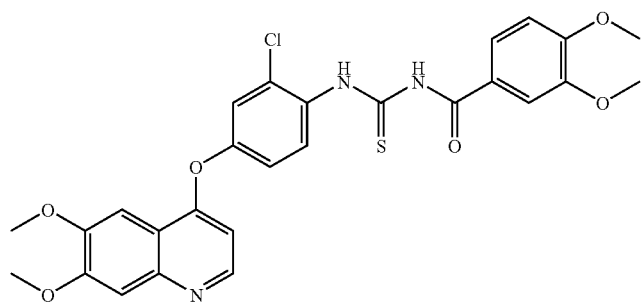
1071
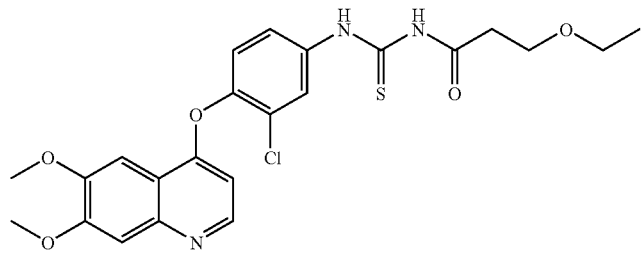
1072
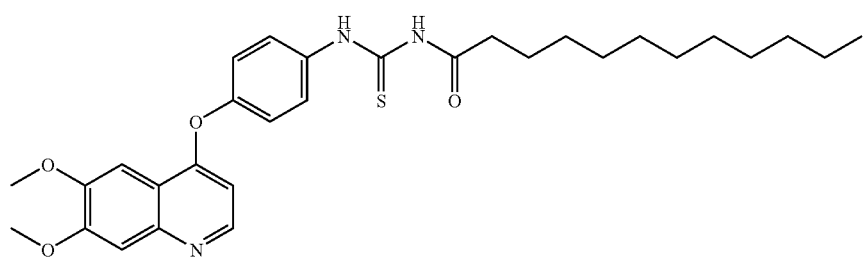

-continued
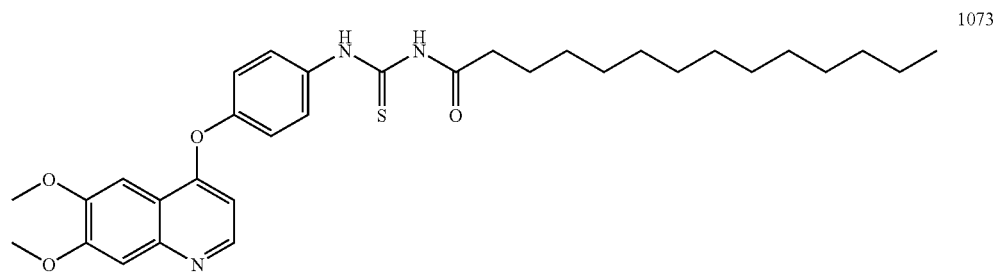
1073
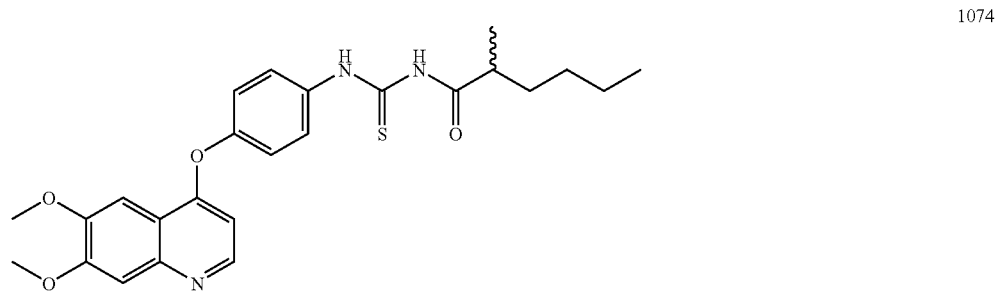
1074
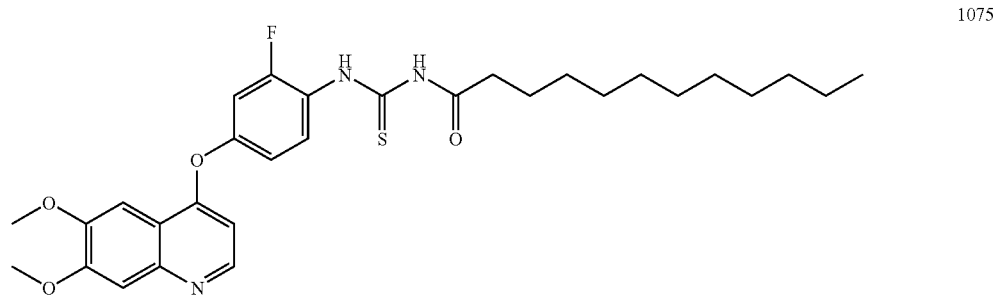
1075
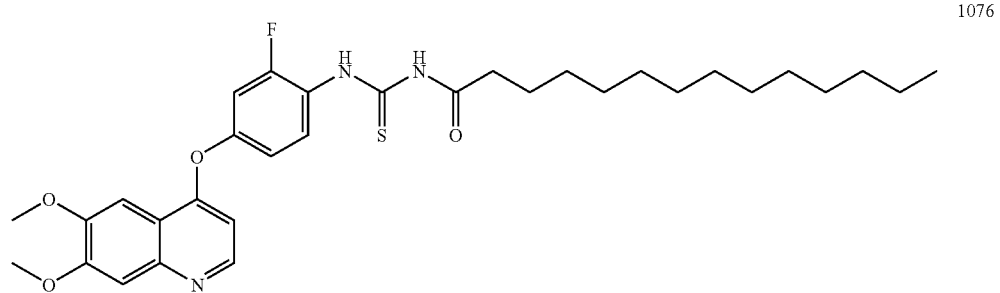
1076
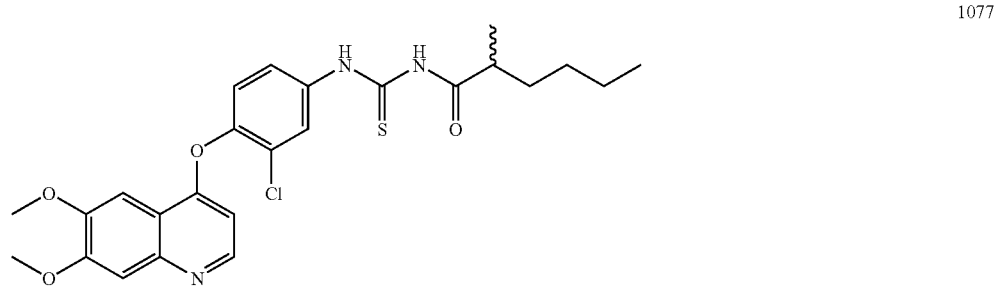
1077

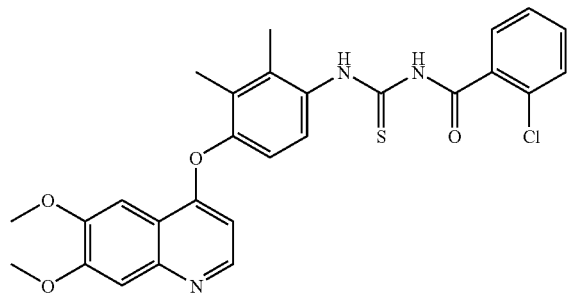
1078
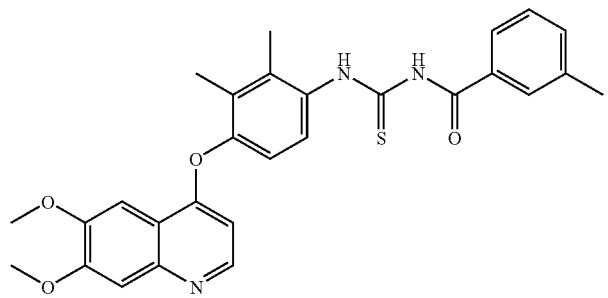
1079
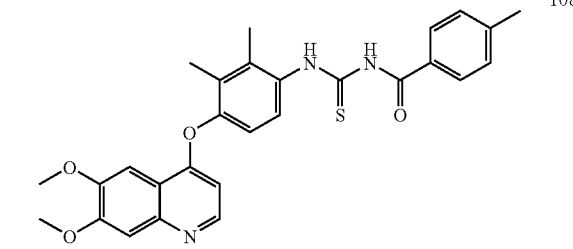
1080
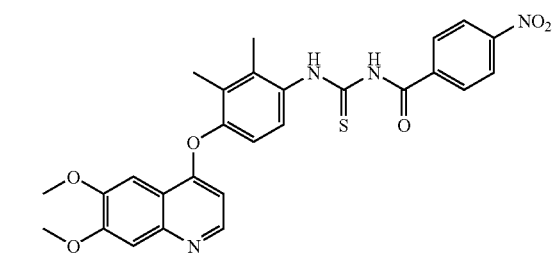
1081
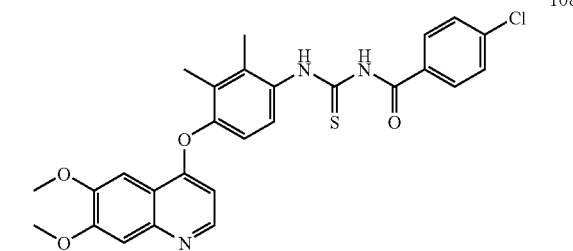
1082
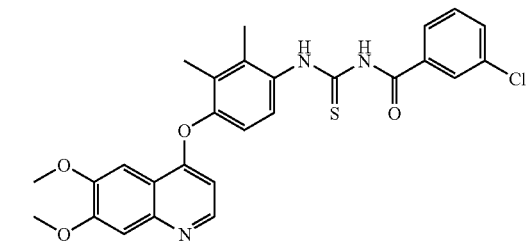
1083

-continued
1084
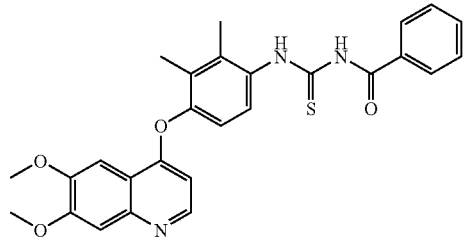
1085
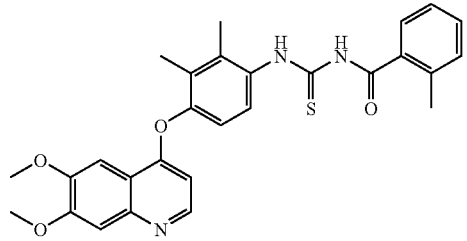
1086
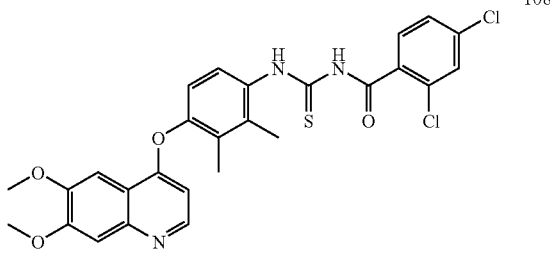
1087
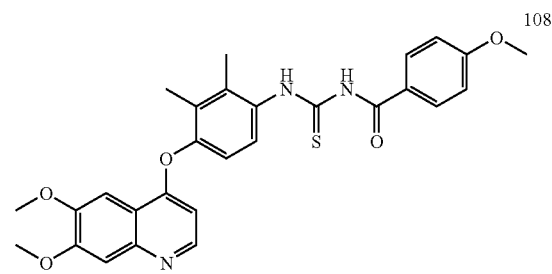
1088
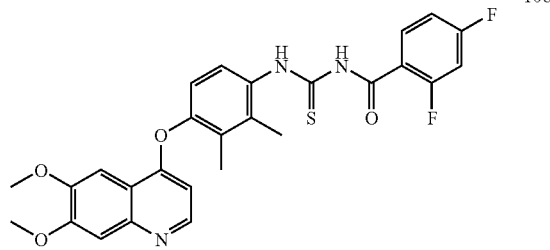
1089
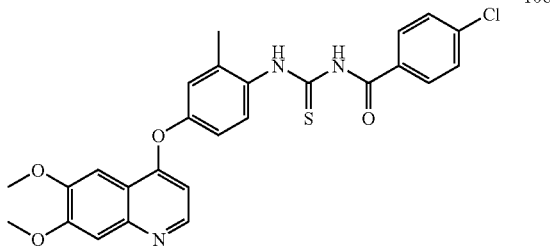

-continued
1090
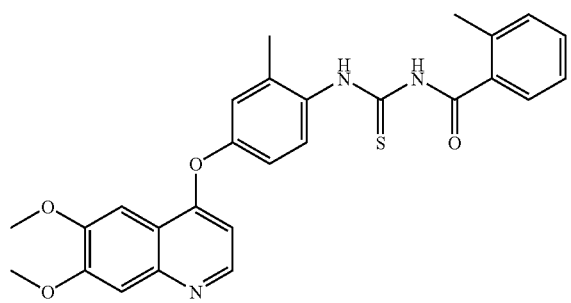
1091
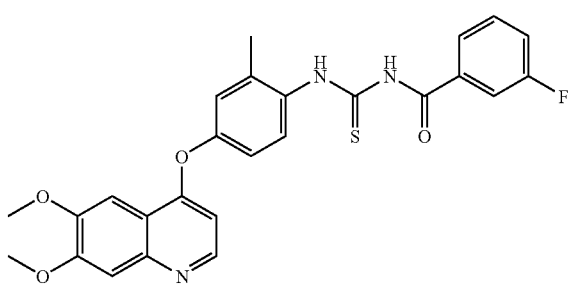
1092
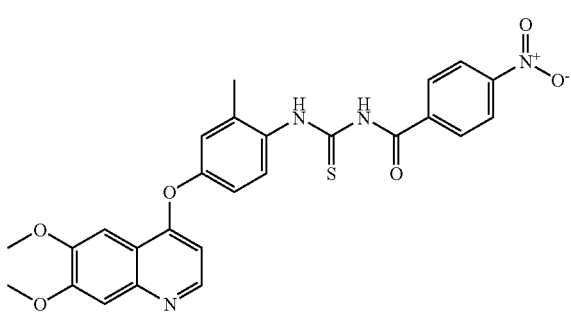
1093
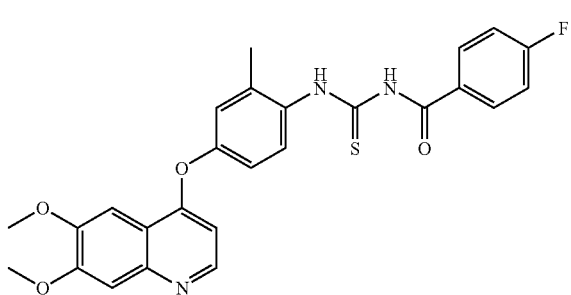
1094
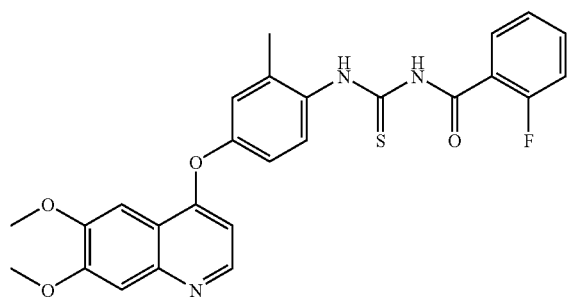

-continued
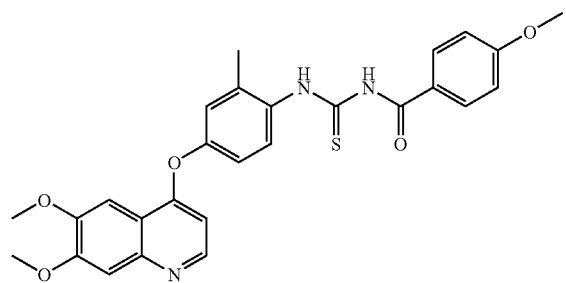
1095
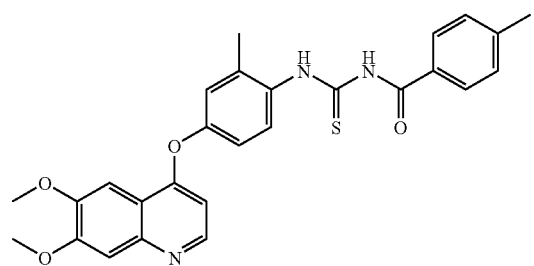
1096
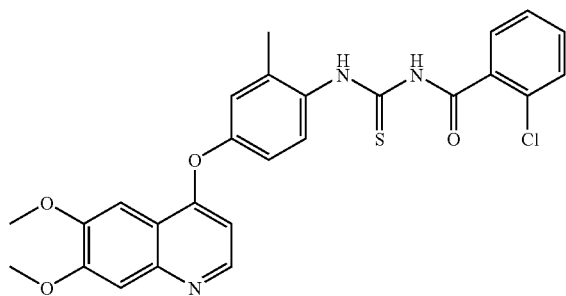
1097
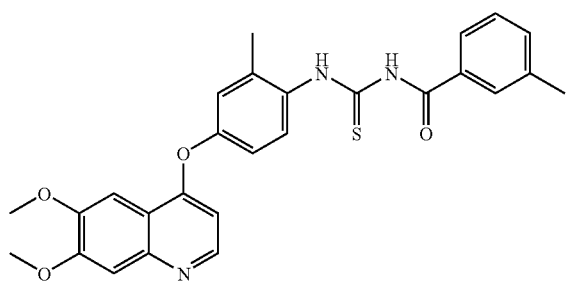
1098
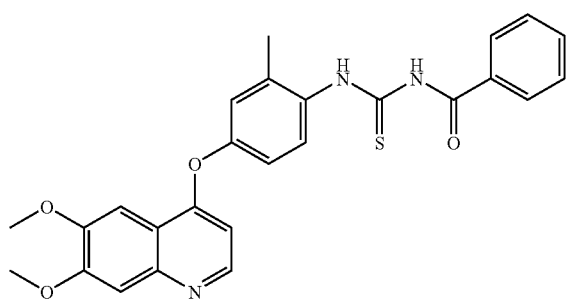
1099

-continued
1100
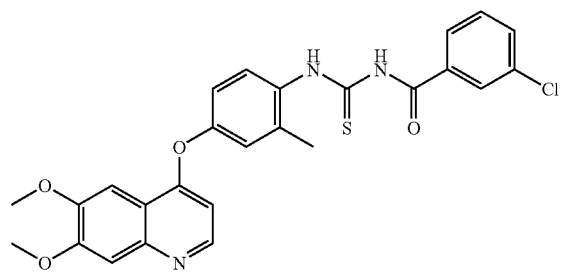
1101
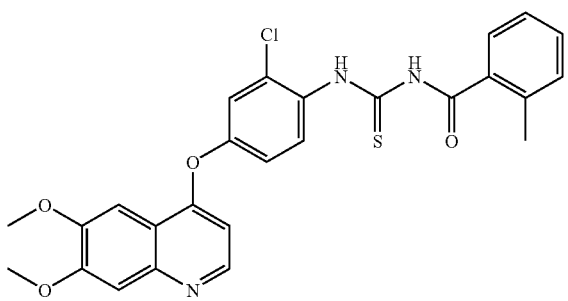
1102
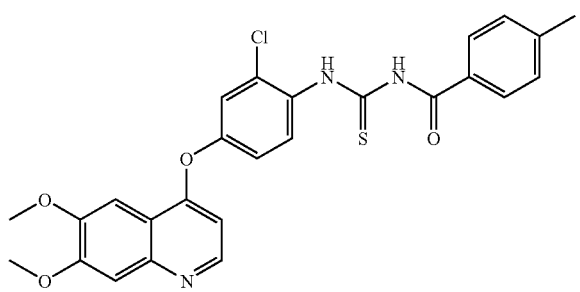
1103
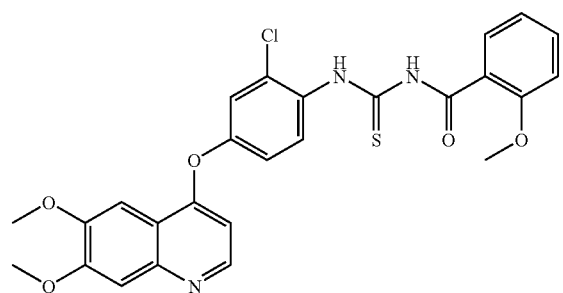
1104
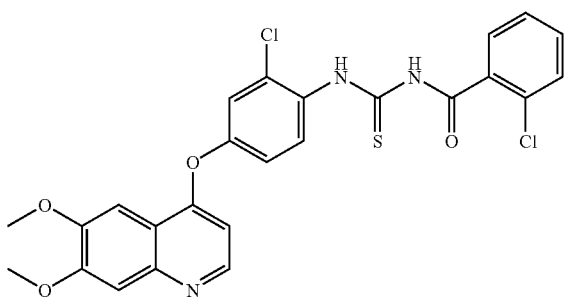

-continued
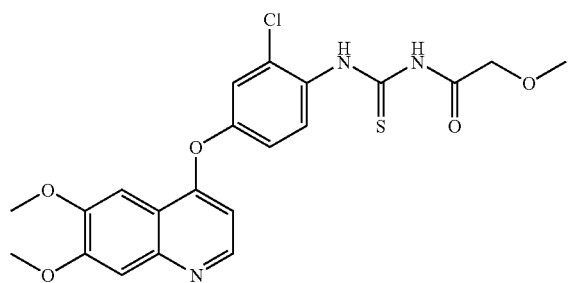
1105
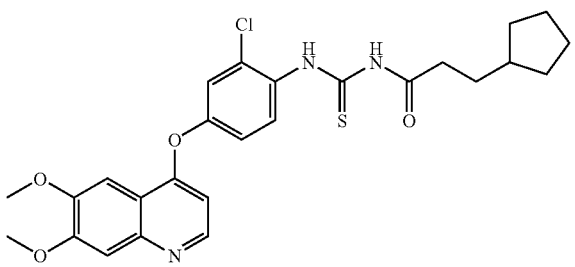
1106
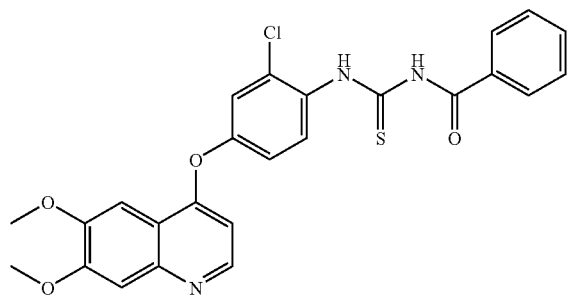
1107
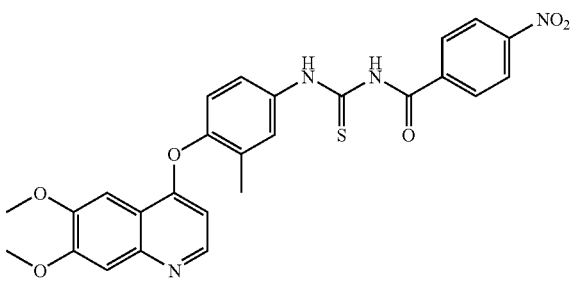
1108
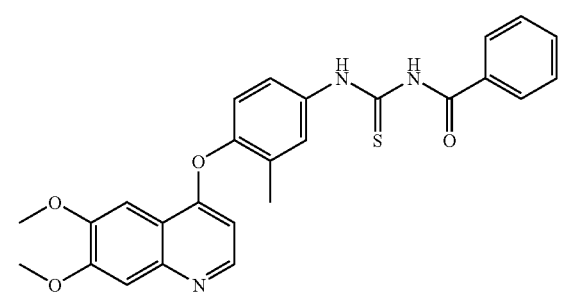
1109

-continued
1110
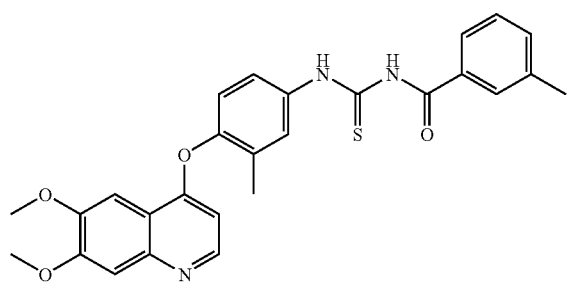
1111
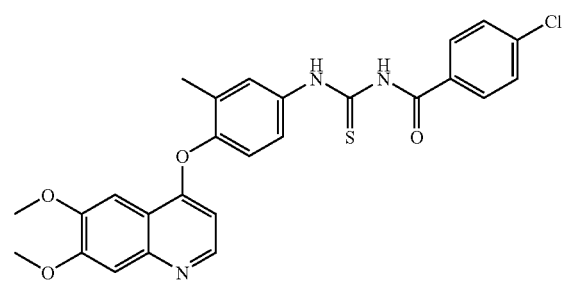
1112
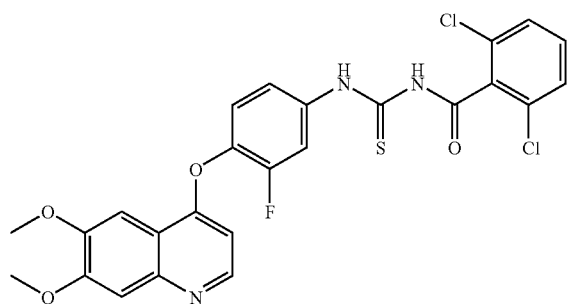
1113
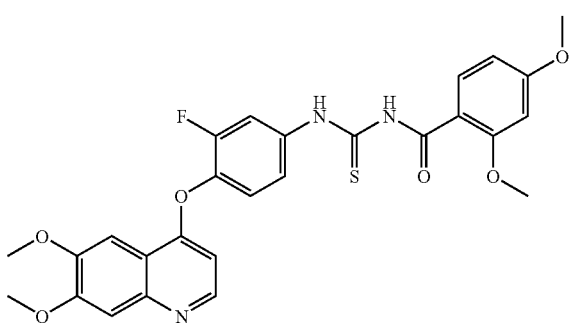
1114
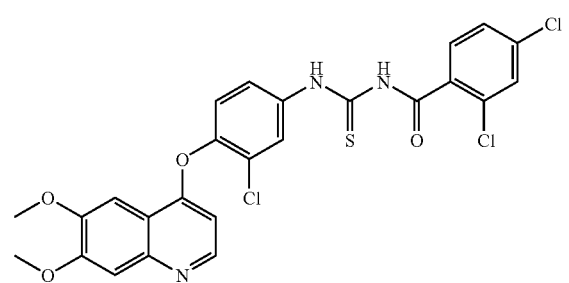

-continued
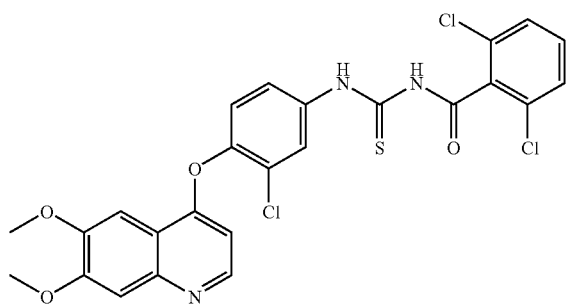
1115
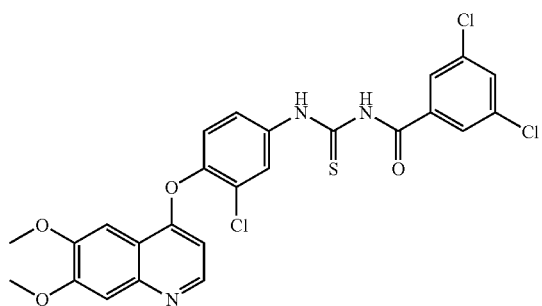
1116
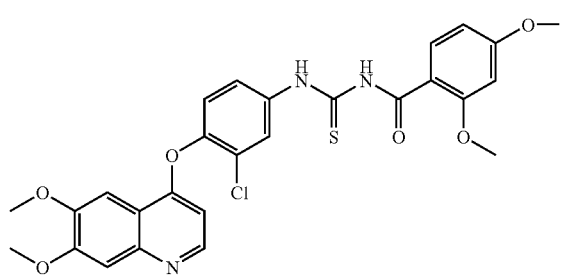
1117
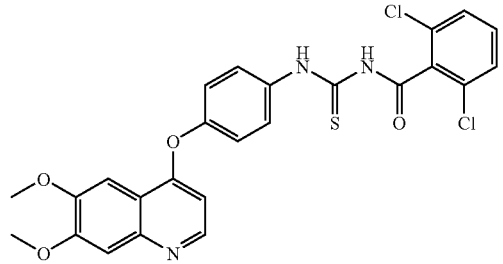
1118
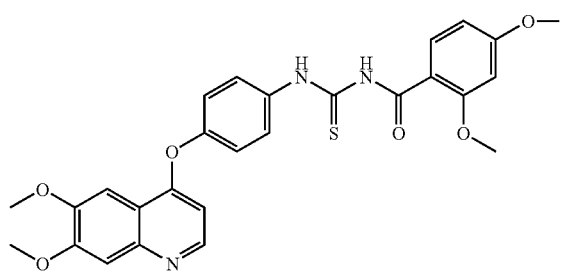
1119

-continued
1120
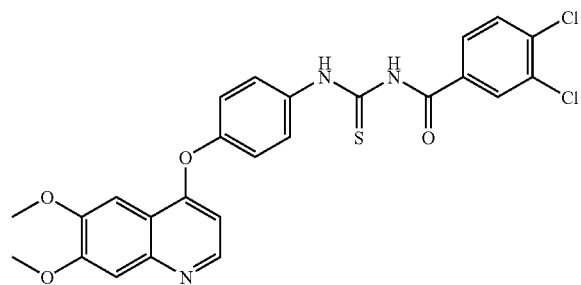
1121
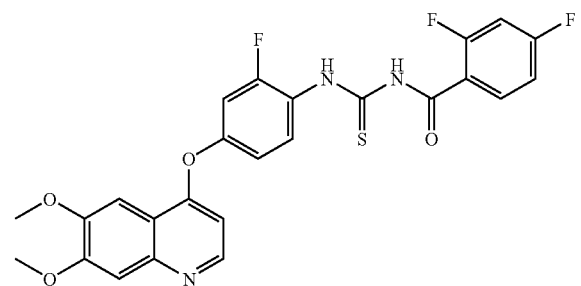
1122
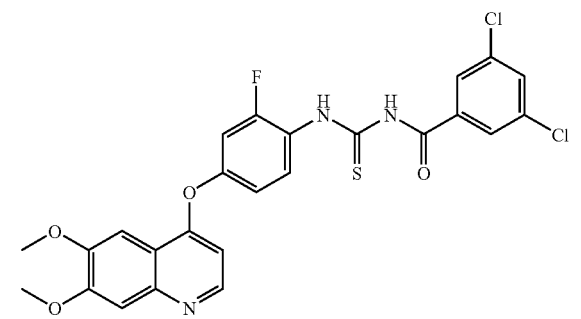
1123
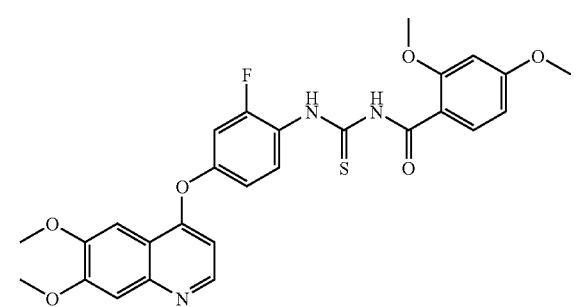
1124
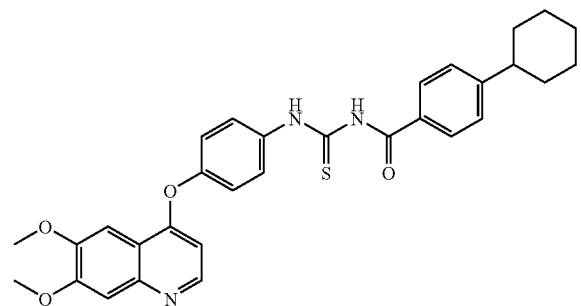

-continued
1125
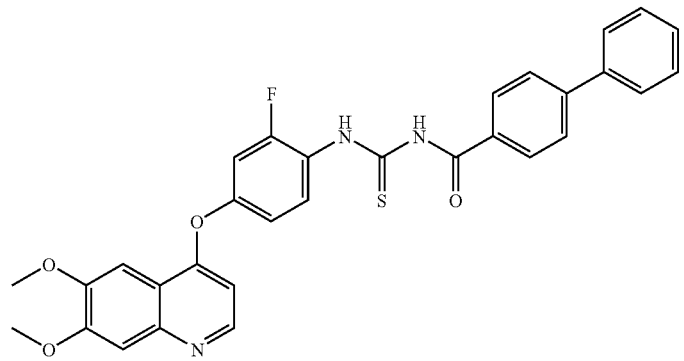
1126
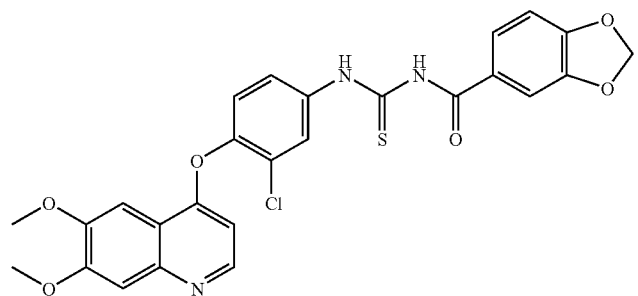
1127
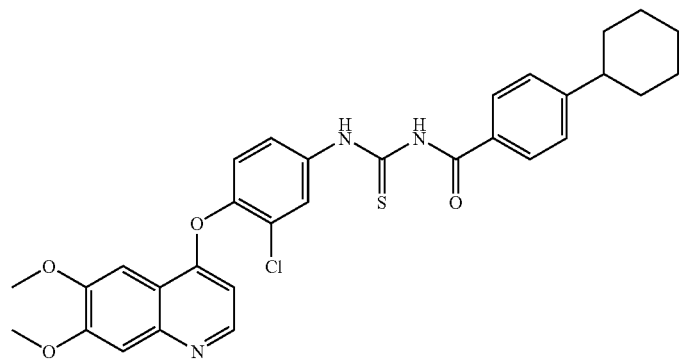
1128
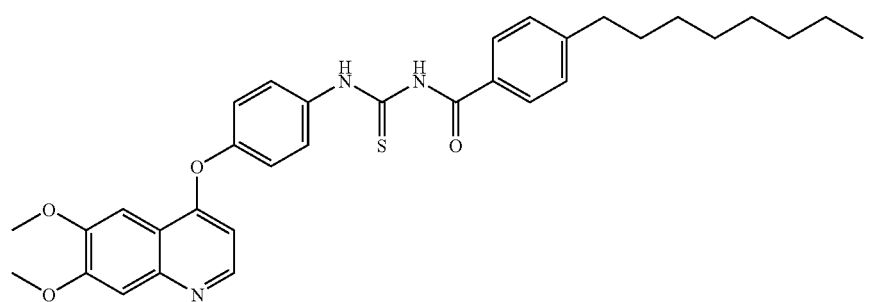

-continued
1129
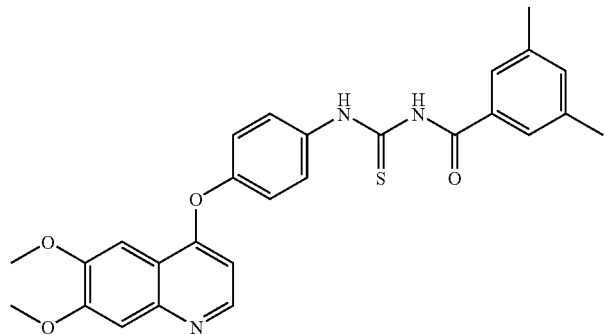
1130
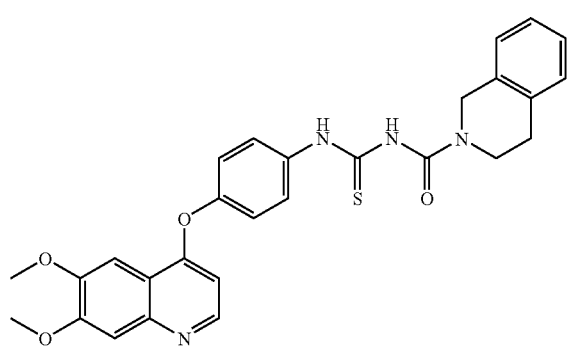
1131
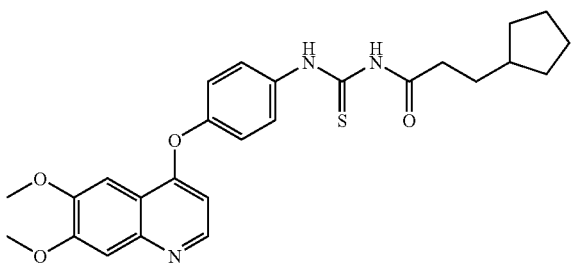
1132
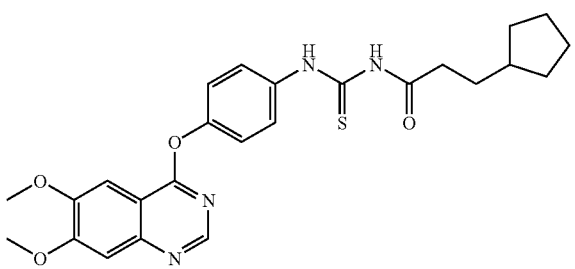
1133
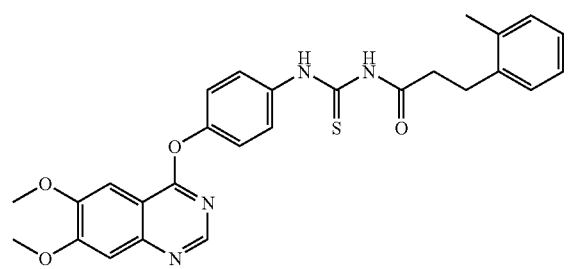

-continued
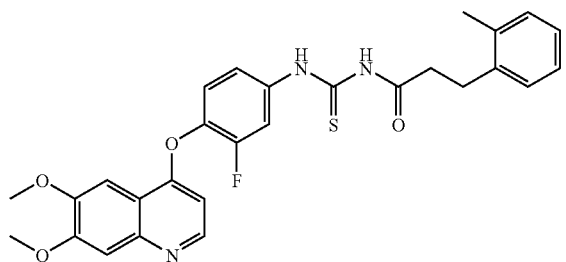
1134
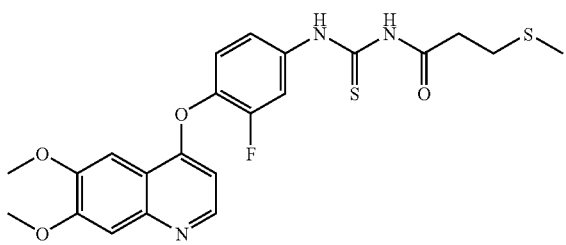
1135
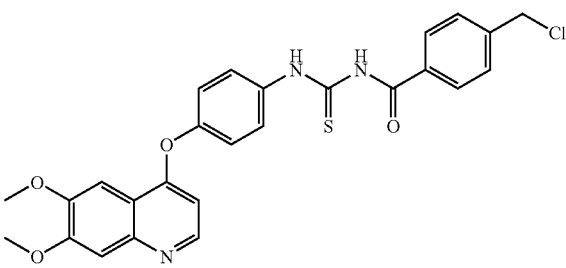
1136
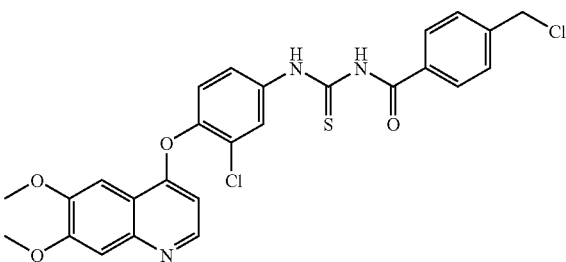
1137
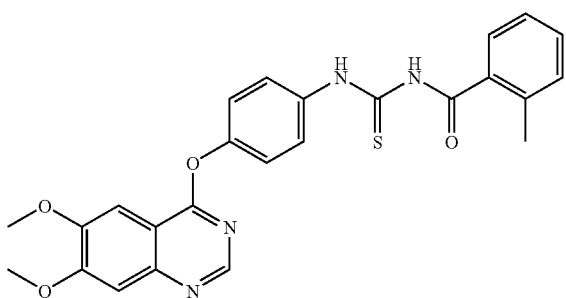
1138

-continued
1139
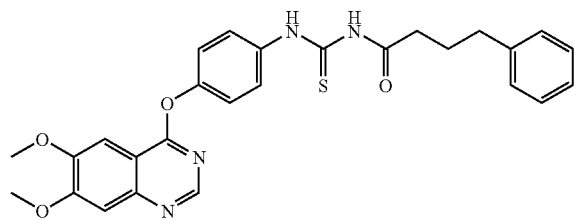
1140
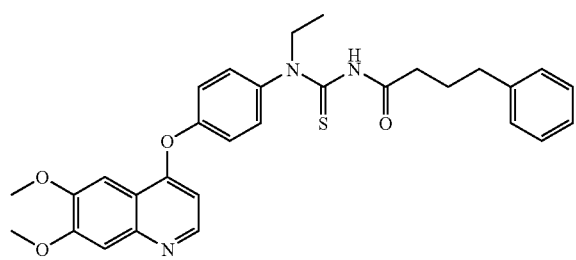
1141
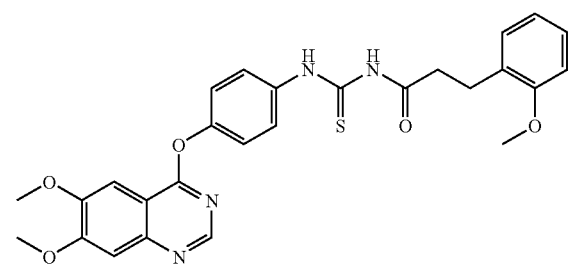
1142
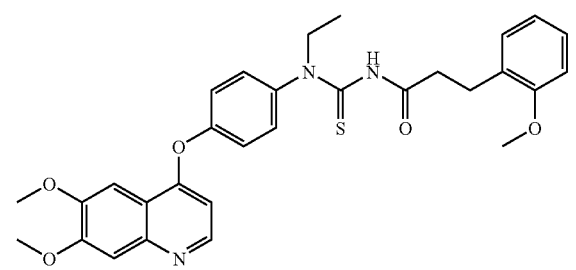
1143
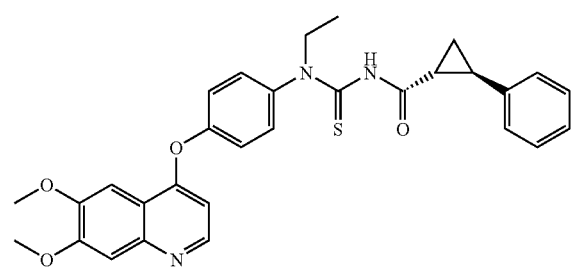

-continued
1144
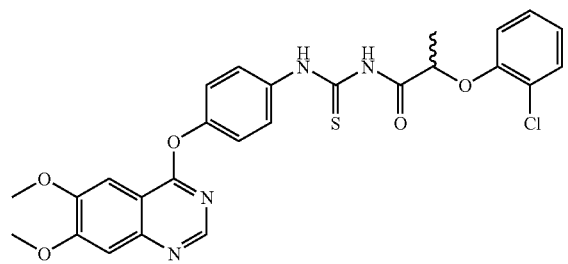
1145
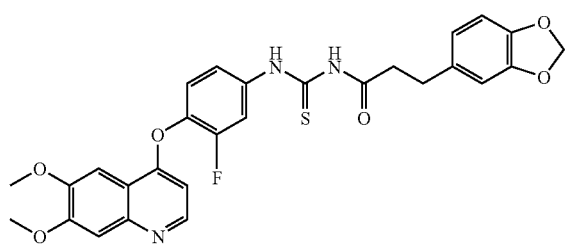
1146
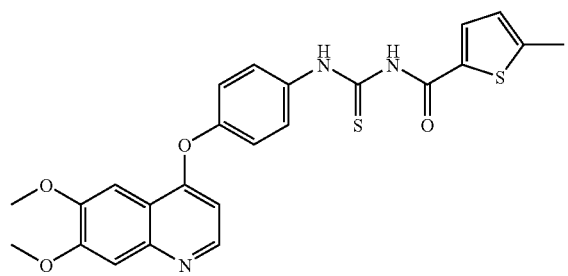
1147
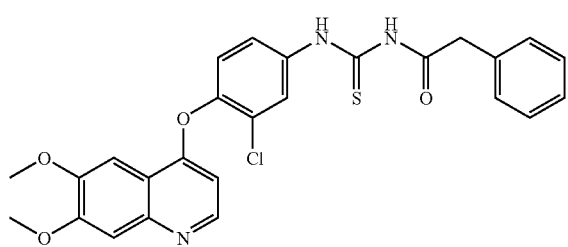
1148
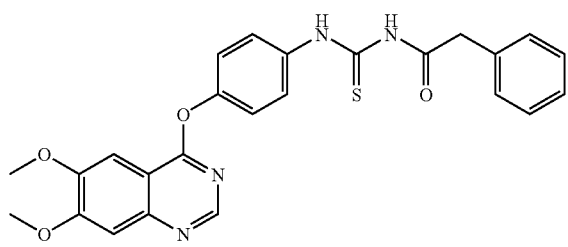

-continued
1149
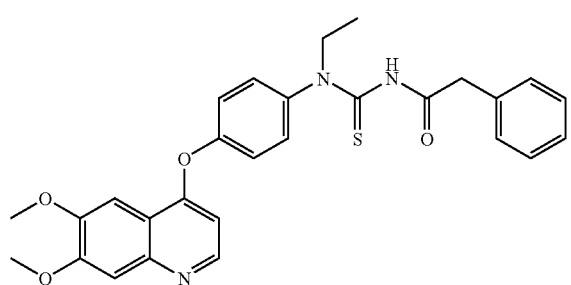
1150
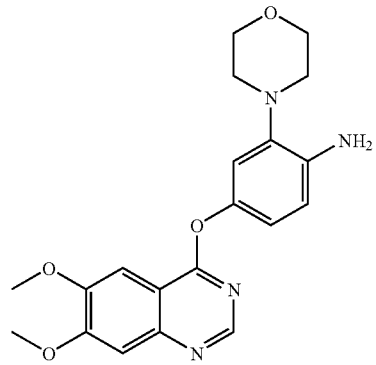
1151
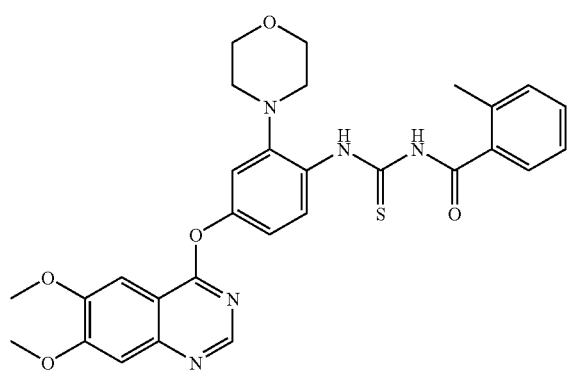
1152
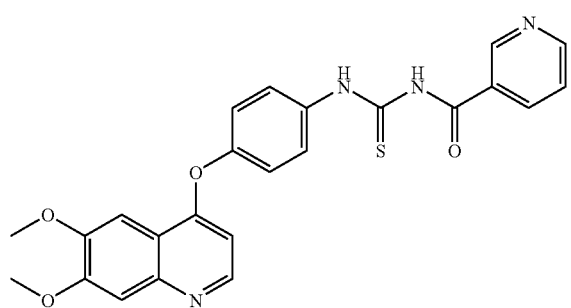

-continued
1153
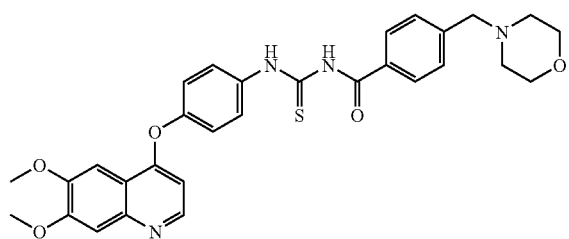
1154
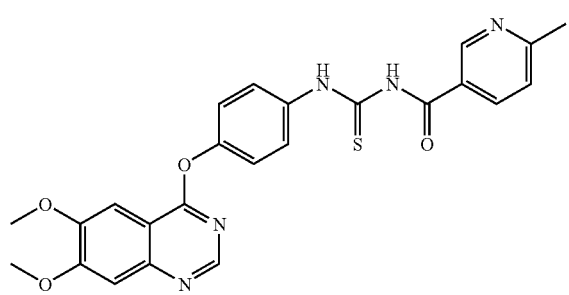
1155
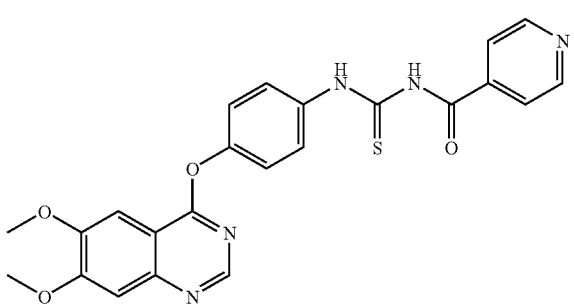
1156
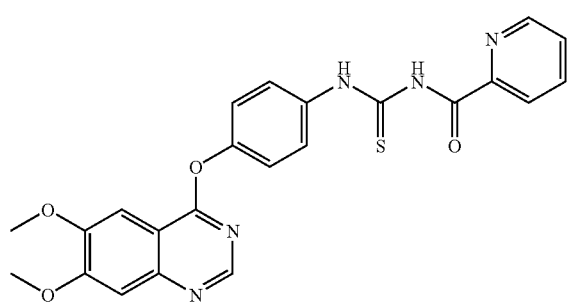
1157
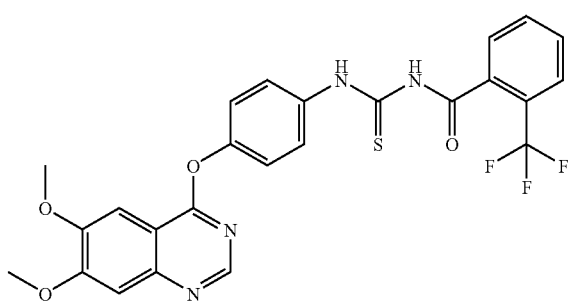

-continued
1158
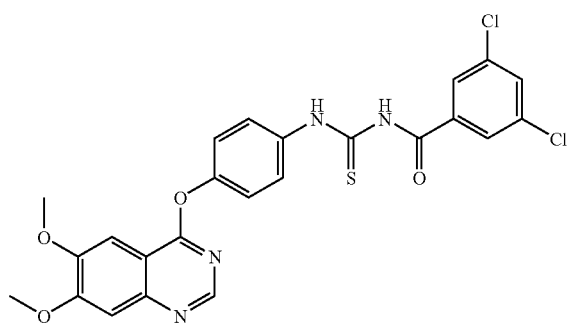
1159
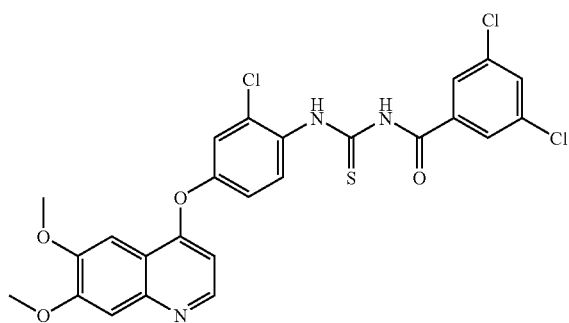
1160
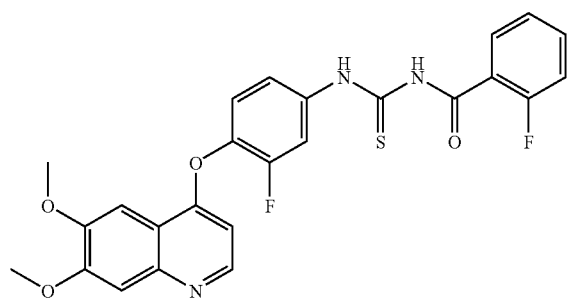
1161
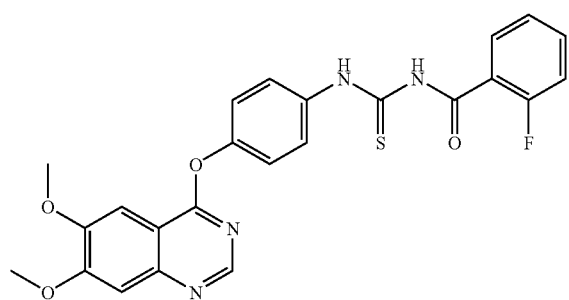

-continued
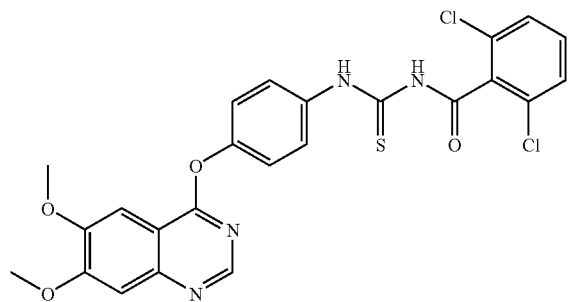
1162
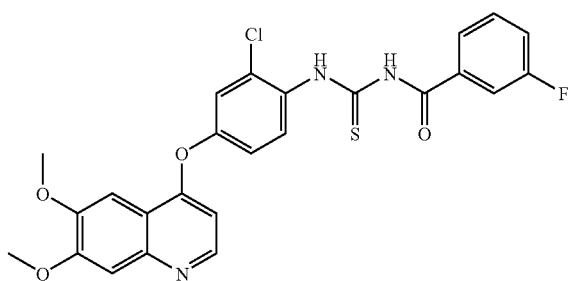
1163
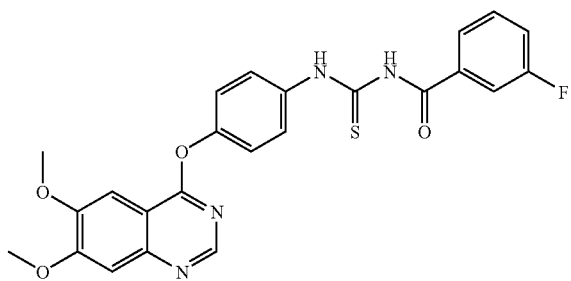
1164
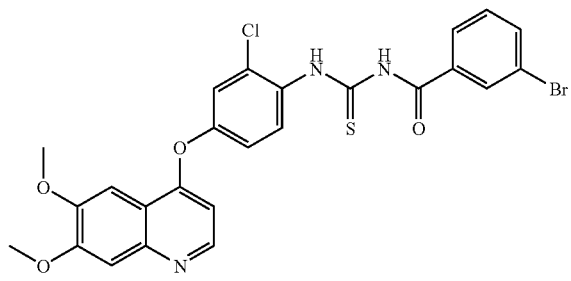
1165
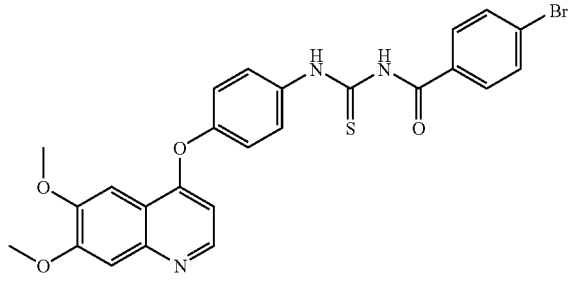
1166

-continued
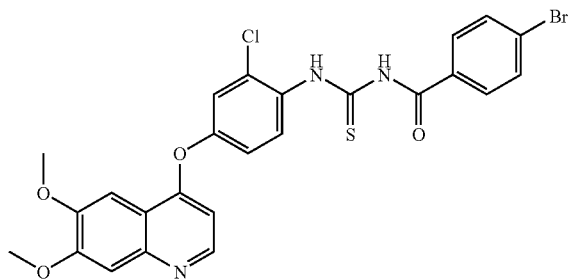
1167
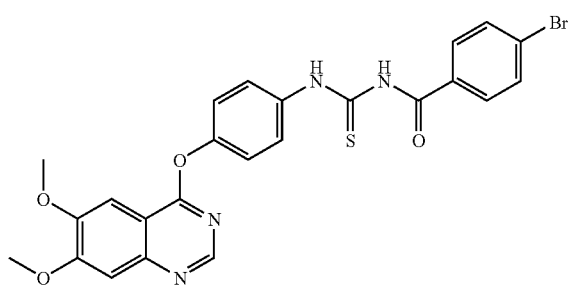
1168
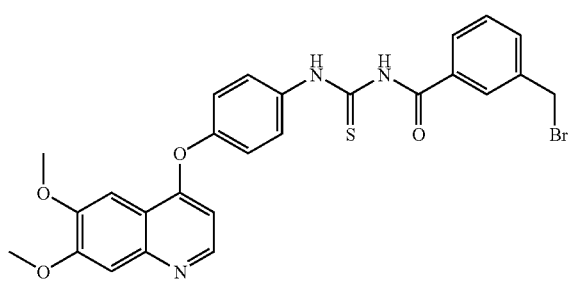
1169
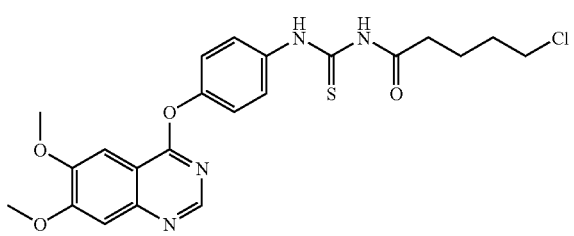
1170
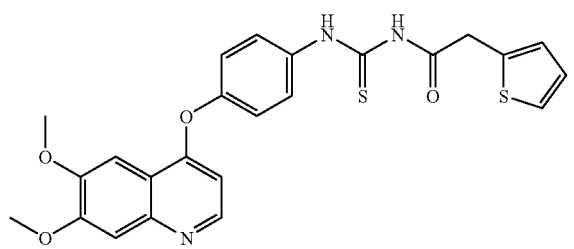
1171

-continued
1172
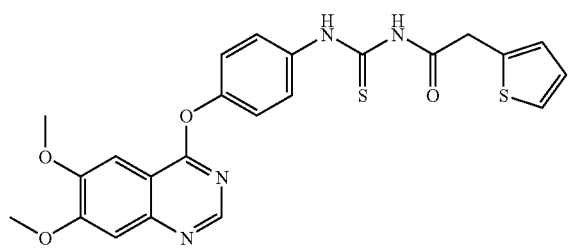
1173
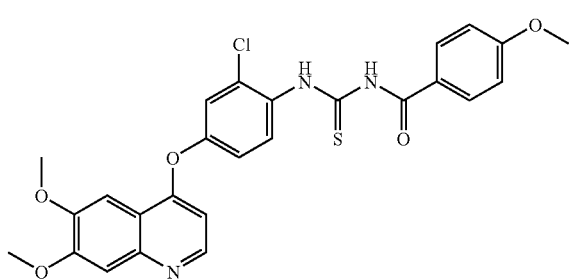
1174
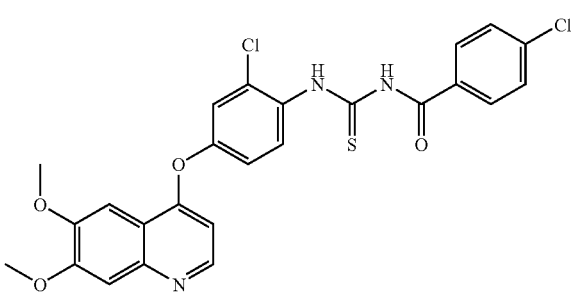
1175
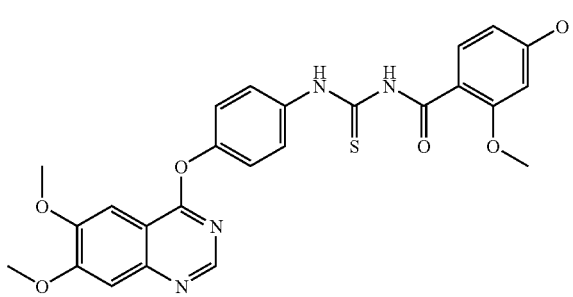
1176
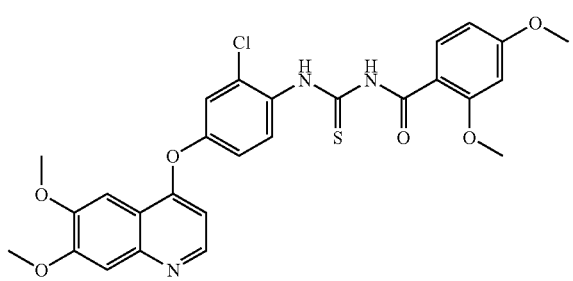

-continued
1177
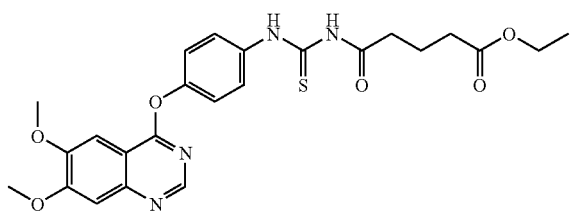
1178
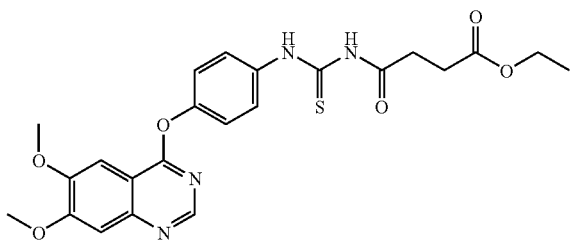
1179
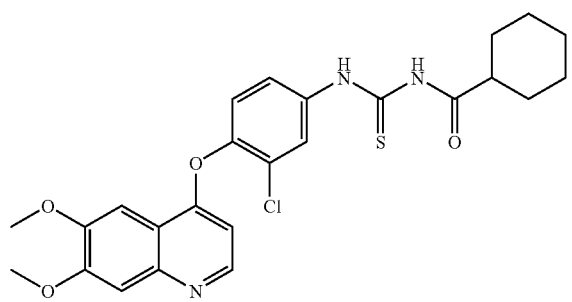
1180
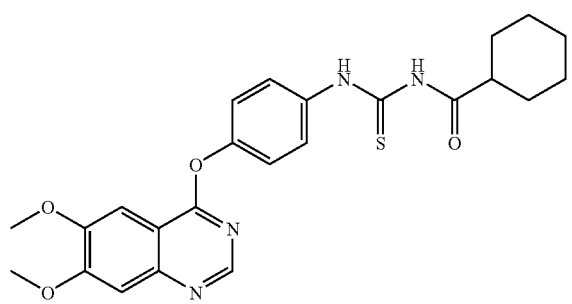
1181
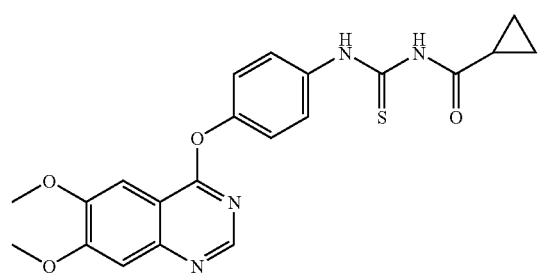

-continued
1182
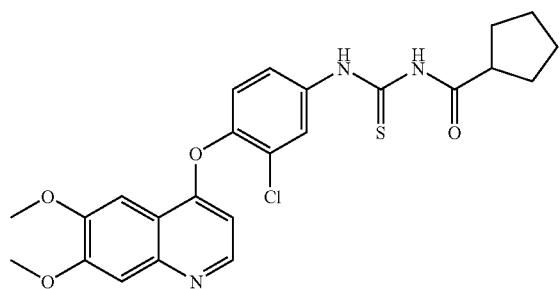
1183
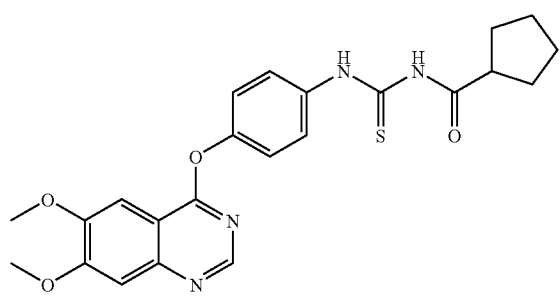
1184
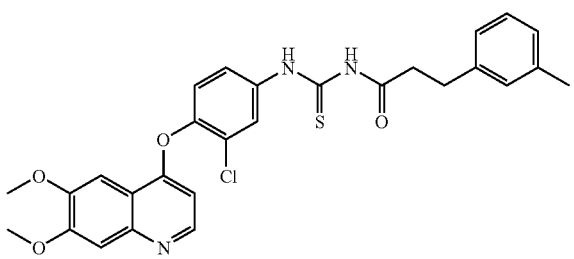
1185
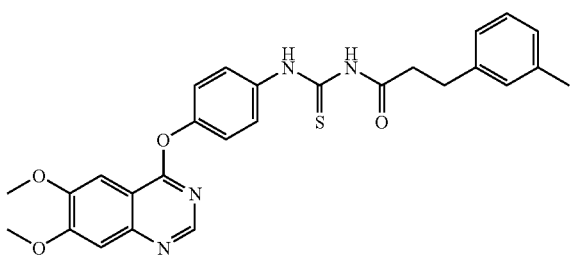
1186
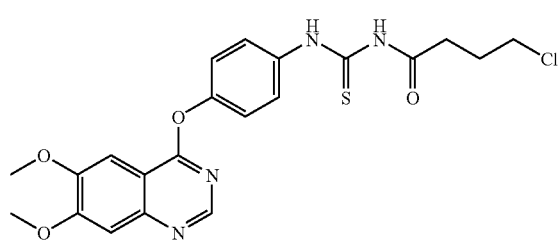

-continued
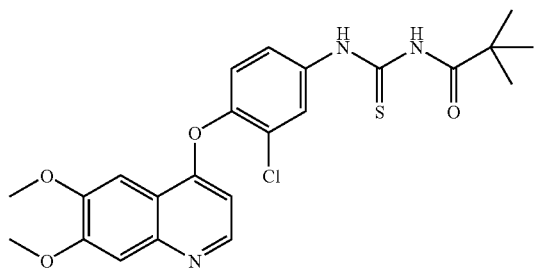
1187
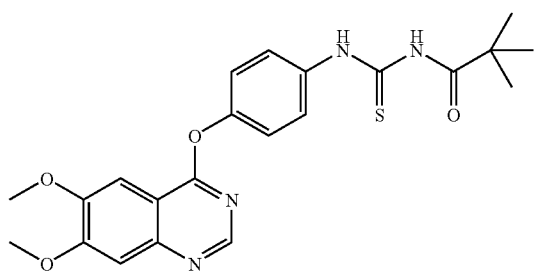
1188
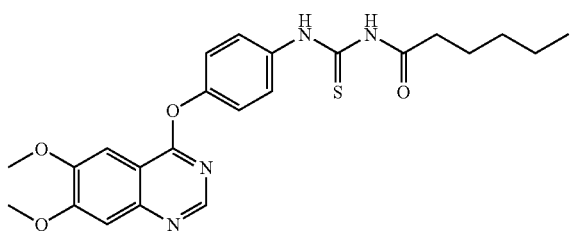
1189
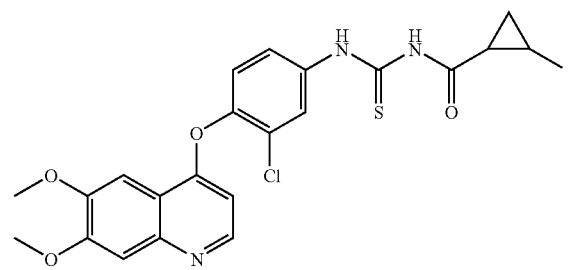
1190
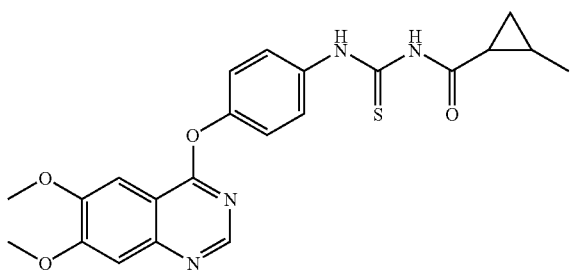
1191

-continued
1192
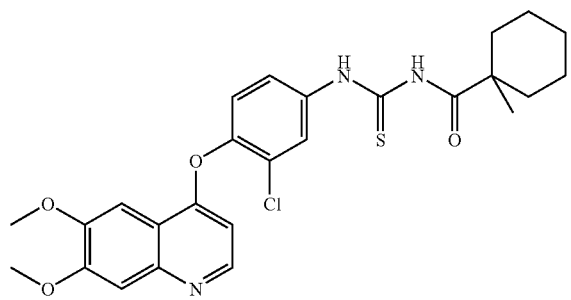
1193
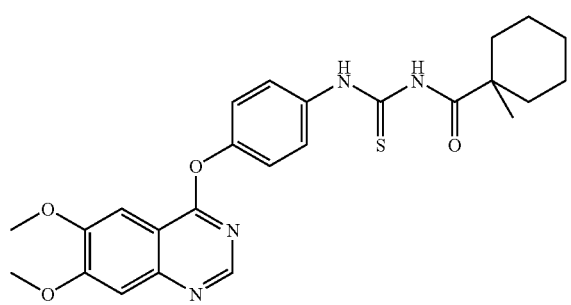
1194
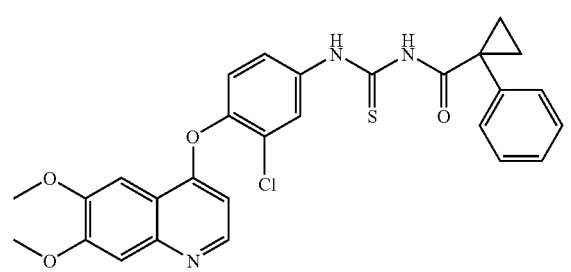
1195
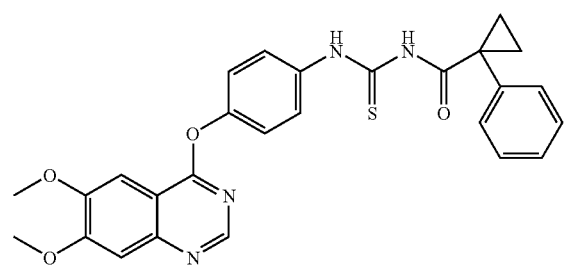
1196
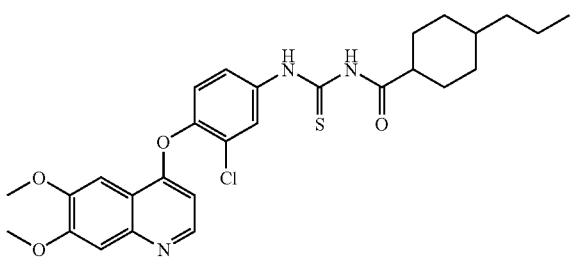

-continued
1197
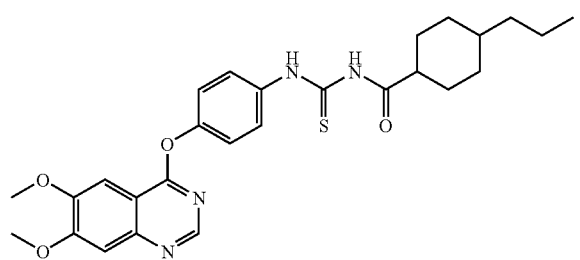
1198
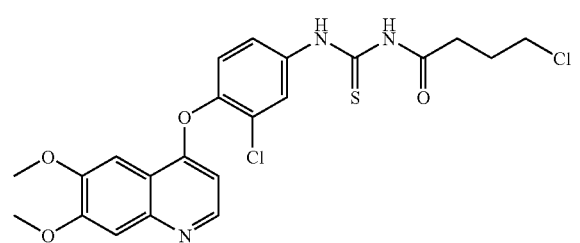
1199
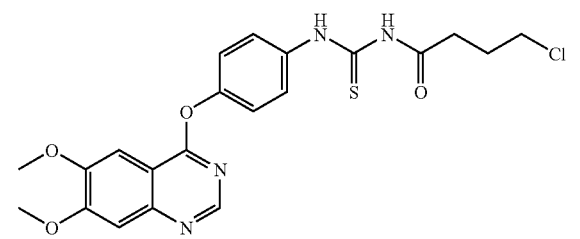
1200
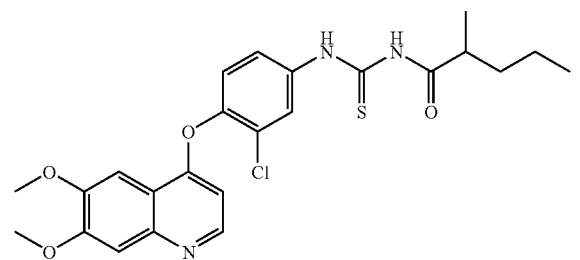
1201
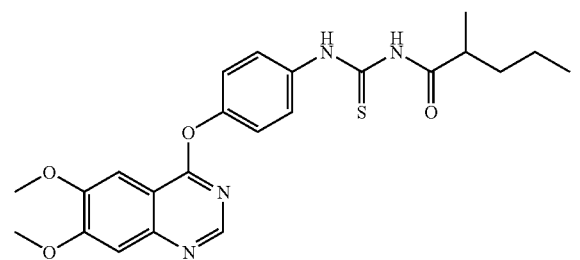

-continued
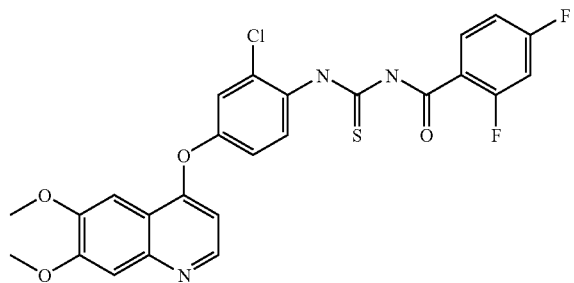
1202
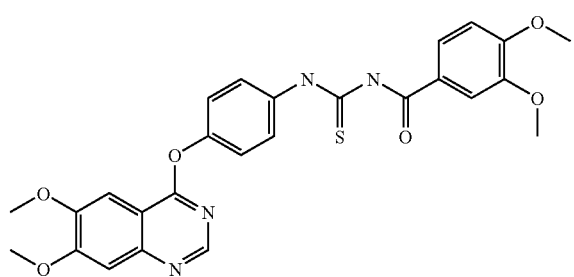
1203
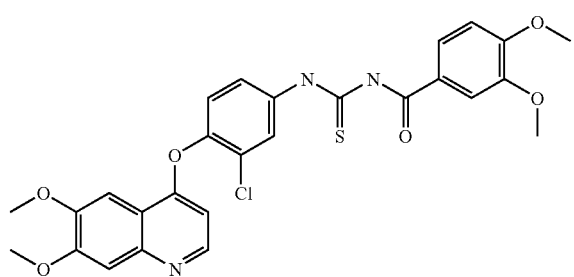
1204
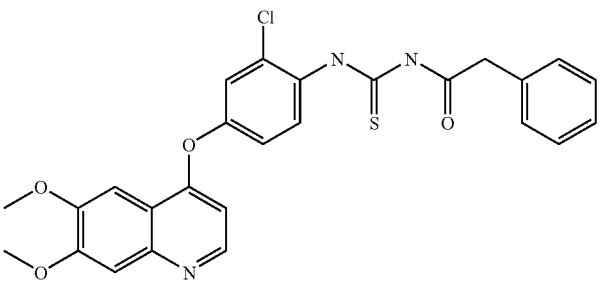
1205
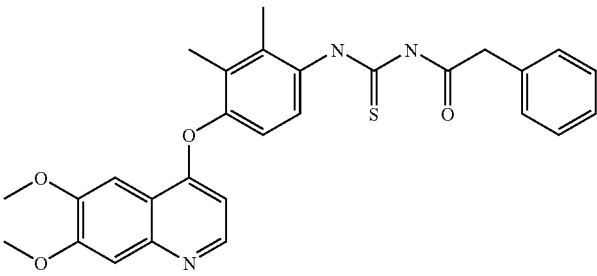
1206

1207
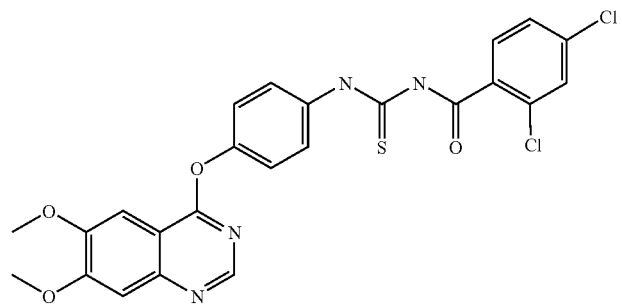
1208
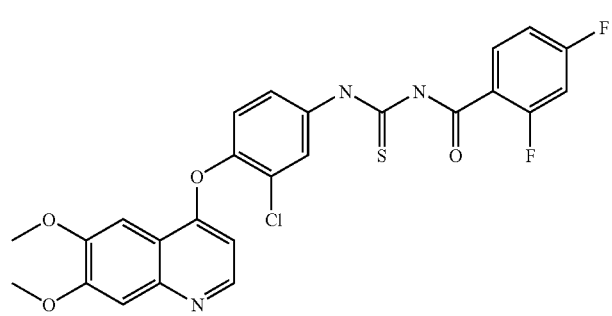
1209
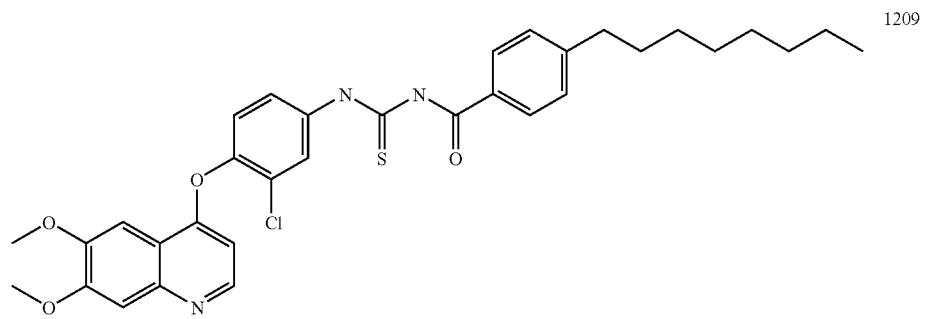
1210
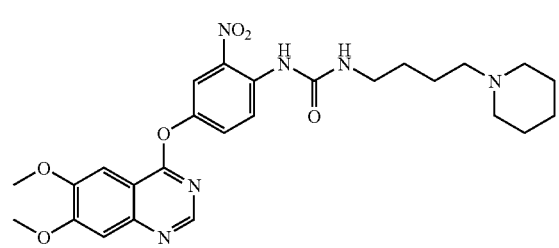
1211
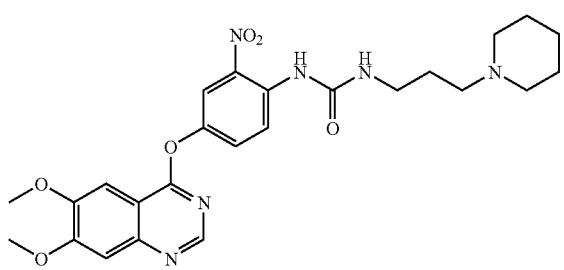

The invention claimed is:

1. A compound represented by formula (I) or a pharmacologically acceptable salt or solvate thereof:

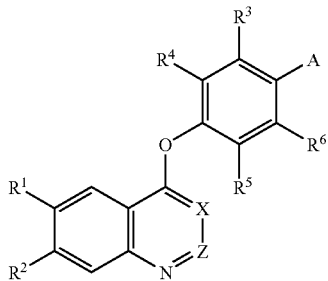
(I)

wherein

X and Z represent —CH

R¹ and R², which may be the same or different, represent a hydrogen atom or $C_{1-4}$ alkoxy optionally substituted by a halogen atom;

R³, R⁴, R⁵, and R⁶, which may be the same or different, represent a hydrogen atom; a halogen atom; $C_{1-4}$ alkyl optionally substituted by a halogen atom; $C_{1-4}$ alkoxy optionally substituted by a halogen atom; nitro; amino; or morpholyl;

A represents a group selected from the group consisting of formulae (i) to (vii), wherein R¹¹ and R¹², which may be the same or different, represent a hydrogen atom, $C_{1-4}$ alkyl optionally substituted by a halogen atom, or $C_{1-4}$ alkylcarbonyl optionally substituted by a halogen atom;

provided that compounds wherein R³, R⁴, R⁵ and R⁶ represent a hydrogen atom and A represents group (v) wherein u is 0 (zero) and R¹⁹ represents phenyl optionally substituted by a halogen atom, $C_{1-4}$ alkyl, or $C_{1-4}$ alkoxy are excluded:

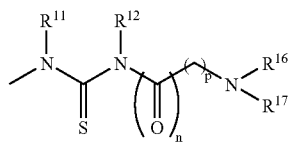
(i)

wherein i is an integer of 1 to 4,

R¹³ and R¹⁴, which may be the same or different, represent a hydrogen atom; $C_{1-6}$ alkyl optionally substituted by a halogen atom; or phenyl optionally substituted by a halogen atom or $C_{1-4}$ alkyl optionally substituted by a halogen atom, R¹³ and R¹⁴ may form a five- to seven-membered saturated or unsaturated heterocyclic ring optionally containing one or more additional hetero-atoms together with the nitrogen atom to which they are attached, and this heterocyclic ring is optionally substituted by a halogen atom or $C_{1-4}$ alkyl optionally substituted by a halogen atom, or, R¹³ or R¹⁴ may form $C_{1-4}$ alkylene optionally substituted by a halogen atom together with R¹²;

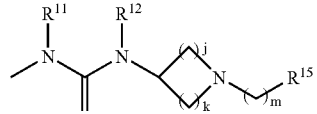
(ii)

wherein j is an integer of 0 to 3, k is an integer of 0 to 3, provided that both j and k are not 0 (zero), m is an integer of 0 to 2, carbon atoms in the following

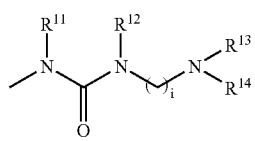

are optionally substituted by one or more $C_{1-4}$ alkyl groups, which may be the same or different, optionally substituted by a halogen atom, and R¹⁵ represents a hydrogen atom; cyclic $C_{3-7}$ alkyl optionally substituted by a halogen atom; phenyl optionally substituted by $C_{1-6}$ alkyl or a halogen atom; or $C_{1-4}$ alkoxycarbonyl;

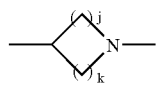
(iii)

wherein n is 0 (zero) or 1, p is an integer of 1 to 10, and

R¹⁶ and R¹⁷, which may be the same or different, represent a hydrogen atom; $C_{1-6}$ alkyl optionally substituted by a halogen atom; $C_{1-4}$ alkylcarbonyl optionally substituted by a halogen atom; cyclic $C_{3-7}$ alkyl optionally substituted by $C_{1-4}$ alkyl optionally substituted by a halogen atom; or phenyl optionally substituted by a halogen atom or $C_{1-4}$ alkyl optionally substituted by a halogen atom, or R¹⁶ and R¹⁷ may form a five- to seven-membered saturated or unsaturated heterocyclic ring optionally containing one or more additional hetero-atoms together with the nitrogen atom to which they are attached, this heterocyclic ring is optionally condensed with another one or two carbocyclic or heterocyclic ring to form a ten- to twelve-membered saturated or unsaturated bicyclic carbocyclic ring or heterocyclic ring or a ten- to fifteen-membered saturated or unsaturated tricyclic carbocyclic ring or heterocyclic ring, and these heterocyclic rings are optionally substituted by an oxygen atom or $C_{1-4}$ alkyl optionally substituted by a halogen atom;

(iv)

$$\underset{S}{\overset{R^{11}}{\underset{|}{N}}}-\underset{}{\overset{R^{12}}{\underset{|}{N}}}-\left(\underset{O_p}{\|}\right)_{q}\left(\right)_{s}^{r}N-\left(\right)_{t}R^{18}$$

wherein
q is 0 (zero) or 1,
r is an integer of 0 to 3,
s is an integer of 0 to 3, provided that both r and s are not 0 (zero),
t is an integer of 0 to 2,
carbon atoms in the following (structure showing azetidine-type ring with r and s substituents)

are optionally substituted by one or more $C_{1-4}$ alkyl groups, which may be the same or different, and $R^{18}$ represents a hydrogen atom; phenyl optionally substituted by a halogen atom or $C_{1-6}$ alkyl optionally substituted by a halogen atom; or $C_{1-4}$ alkoxycarbonyl optionally substituted by a halogen atom;

(v)

$$\underset{S}{\overset{R^{11}}{\underset{|}{N}}}-\underset{}{\overset{R^{12}}{\underset{|}{N}}}-\left(\underset{O}{\|}\right)_{u}R^{19}$$

wherein
u is 0 (zero) or 1,
$R^{19}$ represents
(1) phenyl which is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$, which may be the same or different, represent a hydrogen atom or $C_{1-4}$ alkyl optionally substituted by a halogen atom; phenyl optionally substituted by a halogen atom; a halogen atom; or cyano,
(2) phenoxy of which the phenyl portion is optionally substituted by $C_{1-10}$ alkyl optionally substituted by a halogen atom; $C_{1-10}$ alkoxy optionally substituted by a halogen atom; —$NR^{31}R^{32}$ wherein $R^{31}$ and $R^{32}$ are as defined above; phenyl optionally substituted by a halogen atom; a halogen atom; or cyano,
(3) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom; phenyl optionally substituted by a halogen atom; cyclic $C_{3-7}$ alkyl optionally substituted by a halogen atom; or a halogen atom,
(4) a five- to seven-membered saturated or unsaturated heterocyclic ring which is optionally condensed with another carbocyclic or heterocyclic ring to form a ten- to twelve-membered bicyclic saturated or unsaturated heterocyclic ring optionally substituted by $C_{1-4}$ alkyl optionally substituted by a halogen atom, or a halogen atom, (vi)

$$\underset{}{\overset{R^{11}}{\underset{|}{N}}}-\underset{O}{\overset{}{\underset{\|}{C}}}-O-R^{20}$$

wherein
$R^{20}$ represents:
(1) phenyl optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$, which may be the same or different, represent a hydrogen atom or $C_{1-4}$ alkyl optionally substituted by a halogen atom; phenyl optionally substituted by a halogen atom; a halogen atom; or cyano,
(2) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom,
(3) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom,
(4) $C_{1-20}$ alkyl,
(5) $C_{2-6}$ alkenyl, or
(6) $C_{2-6}$ alkynyl, and
wherein (4) $C_{1-20}$ alkyl, (5) $C_{2-6}$ alkenyl, and (6) $C_{2-6}$ alkynyl are optionally substituted by one or more of the following groups:
(a) phenyl optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$ are as defined above; phenyl optionally substituted by a halogen atom; a halogen atom; or cyano,
(b) phenoxy of which the phenyl portion is optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$ are as defined above; phenyl optionally substituted by a halogen atom; a halogen atom; or cyano,
(c) phenylthio of which the phenyl portion is optionally substituted by $C_{1-6}$ alkyl optionally substituted by a halogen atom; $C_{1-6}$ alkoxy optionally substituted by a halogen atom; —$NR^{35}R^{36}$ wherein $R^{35}$ and $R^{36}$ are as defined above; phenyl optionally substituted by a halogen atom; a halogen atom; or cyano,
(d) —$NR^{37}R^{38}$ wherein $R^{37}$ and $R^{38}$ are as defined in $R^{13}$ and $R^{14}$,
(e) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom,
(f) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom,
(g) naphthyl, or
(h) cyano;

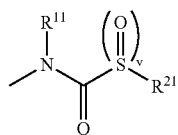

(vii)

wherein
v is an integer of 0 to 2,
$R^{21}$ represents
(1) phenyl optionally substituted by $C_{1-6}$ alkyl optionally substituted by a halogen atom; $C_{1-6}$ alkoxy optionally substituted by a halogen atom; —$NR^{39}R^{40}$ wherein $R^{39}$ and $R^{40}$, which may be the same or different, represent a hydrogen atom or $C_{1-4}$ alkyl optionally substituted by a halogen atom; phenyl optionally substituted by a halogen atom; a halogen atom; or cyano,
(2) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom,
(3) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom,
(4) $C_{1-20}$ alkyl,
(5) $C_{2-6}$ alkenyl, or
(6) $C_{2-6}$ alkynyl, and
wherein (4) $C_{1-20}$ alkyl, (5) $C_{2-6}$ alkenyl, and (6) $C_{2-6}$ alkynyl are optionally substituted by one or more of the following groups:
(a) phenyl optionally substituted by $C_{1-6}$ alkyl optionally substituted by a halogen atom; $C_{1-6}$ alkoxy optionally substituted by a halogen atom; —$NR^{39}R^{40}$ wherein $R^{39}$ and $R^{40}$ are as defined above; phenyl optionally substituted by a halogen atom; a halogen atom; or cyano,
(b) phenoxy of which the phenyl portion is optionally substituted by $C_{1-6}$ alkyl optionally substituted by a halogen atom; $C_{1-6}$ alkoxy optionally substituted by a halogen atom; —$NR^{39}R^{40}$ wherein $R^{39}$ and $R^{40}$ are as defined above; phenyl optionally substituted by a halogen atom; a halogen atom; or cyano,
(c) phenylthio of which the phenyl portion is optionally substituted by $C_{1-6}$ alkyl optionally substituted by a halogen atom; $C_{1-6}$ alkoxy optionally substituted by a halogen atom; —$NR^{39}R^{40}$ wherein $R^{39}$ and $R^{40}$ are as defined above; phenyl optionally substituted by a halogen atom; a halogen atom; or cyano,
(d) —$NR^{41}R^{42}$ wherein $R^{41}$ and $R^{42}$ are as defined in $R^{13}$ and $R^{14}$,
(e) cyclic $C_{3-7}$ alkyl which is optionally condensed with another carbocyclic ring or heterocyclic ring to form an eight- to twelve-membered bicyclic saturated or unsaturated carbocyclic ring or heterocyclic ring and the carbocyclic ring and the heterocyclic ring are optionally substituted by $C_{1-4}$ alkyl optionally substituted by a halogen atom, or a halogen atom,
f) a five- to seven-membered saturated or unsaturated heterocyclic ring which is optionally condensed with another carbocyclic ring or heterocyclic ring to form a ten- to twelve-membered bicyclic saturated or unsaturated heterocyclic ring optionally substituted by $C_{1-4}$ alkyl optionally substituted by a halogen atom, or a halogen atom,
(g) naphthyl, or
(h) cyano.

2. The compound according to claim 1, wherein $R^1$ and $R^2$ represent $C_{1-4}$ alkoxy and at least one of $R^3$, $R^4$, $R^5$, and $R^6$ represents a group other than a hydrogen atom.

3. The compound according to claim 1, wherein $R^1$ and $R^2$ represent $C^{1-4}$ alkoxy, $R^3$ represents a group other than a hydrogen atom, and $R^4$, $R^5$, and $R^6$ represent a hydrogen atom.

4. The compound according to claim 1, wherein $R^1$ and $R^2$ represent $C_{1-4}$ alkoxy and A represents group (i) wherein i is an integer of 1 to 3; and $R^{13}$ and $R^{14}$, which may be the same or different, represent $C_{1-4}$ alkyl, or may form a five- to seven-membered saturated heterocyclic ring optionally substituted by $C_{1-4}$ alkyl together with the nitrogen atom to which they are attached.

5. The compound according to claim 1, wherein $R^1$ and $R^2$ represent $C_{1-4}$ alkoxy, $R^3$, $R^4$, $R^5$, and $R^6$ represent a hydrogen atom, and A represents group (i) wherein i is an integer of 1 to 3 and $R^{13}$ and $R^{14}$, which may be the same or different, represent $C_{1-4}$ alkyl, or may form a five- to seven-membered saturated heterocyclic ring optionally substituted by $C_{1-4}$ alkyl together with the nitrogen atom to which they are attached.

6. The compound according to claim 1, wherein $R^1$ and $R^2$ represent $C_{1-4}$ alkoxy, $R^3$ represents a group other than a hydrogen atom, $R^4$, $R^5$, and $R^6$ represent a hydrogen atom, and A represents group (i) wherein i is an integer of 1 to 3 and $R^{13}$ and $R^{14}$, which may be the same or different, represent $C_{1-4}$ alkyl, or may form a five- to seven-membered saturated heterocyclic ring optionally substituted by $C_{1-4}$ alkyl together with the nitrogen atom to which they are attached.

7. The compound according to claim 1, wherein $R^1$ and $R^2$ represent $C_{1-4}$ alkoxy, $R^3$ represents nitro, $R^4$, $R^5$, and $R^6$ represent a hydrogen atom, and A represents group (i) wherein i is an integer of 1 to 3 and $R^{13}$ and $R^{14}$, which may be the same or different, represent $C_{1-4}$ alkyl, or may form a five- to seven-membered saturated heterocyclic ring optionally substituted by $C_{1-4}$ alkyl together with the nitrogen atom to which they are attached.

8. The compound according to claim 1, wherein $R^1$ and $R^2$ represent $C_{1-4}$ alkoxy and A represents group (ii) wherein j is 1 or 2, k is 1 or 2, m is 1 or 2, and $R^{15}$ represents optionally substituted phenyl.

9. The compound according to claim 1, wherein $R^1$ and $R^2$ represent $C_{1-4}$ alkoxy, $R^3$, $R^4$, $R^5$, and $R^6$ represent a hydrogen atom, and A represents group (ii) wherein j is 1 or 2, k is 1 or 2, m is 1 or 2, and $R^{15}$ represents optionally substituted phenyl.

10. The compound according to claim 1, wherein $R^1$ and $R^2$ represent $C_{1-4}$ alkoxy, $R^3$ represents a group other than a hydrogen atom, $R^4$, $R^5$, and $R^6$ represent a hydrogen atom, and A represents group (ii) wherein j is 1 or 2, k is 1 or 2, m is 1 or 2, and $R^{15}$ represents optionally substituted phenyl.

11. The compound according to claim 1, wherein $R^1$ and $R^2$ represent $C_{1-4}$ alkoxy and A represents group (iii) wherein n is 0 (zero); p is an integer of 1 to 3; and $R^{16}$ and $R^{17}$, which may be the same or different, represent $C_{1-4}$ alkyl, or may form a five- to seven-membered saturated heterocyclic ring optionally substituted by $C_{1-4}$ alkyl or an oxygen atom together with the nitrogen atom to which they are attached.

12. The compound according to claim 1, wherein $R^1$ and $R^2$ represent $C_{1-4}$ alkoxy, $R^3$, $R^4$, $R^5$ and $R^6$ represent a hydrogen atom, and A represents group (iii) wherein n is 0 (zero); p is an integer of 1 to 3; and $R^{16}$ and $R^{17}$, which may be the same or different, represent $C_{1-4}$ alkyl, or may form a five- to seven-membered saturated heterocyclic ring optionally substituted by $C_{1-4}$ alkyl or an oxygen atom together with the nitrogen atom to which they are attached.

13. The compound according to claim 1, wherein $R^1$ and $R^2$ represent $C_{1-4}$ alkoxy, $R^3$ represents a group other than a hydrogen atom, $R^4$, $R^5$ and $R^6$ represent a hydrogen atom, and A represents group (iii) wherein n is 0 (zero), p is an integer of 1 to 3, and $R^{16}$ and $R^{17}$, which may be the same or different, represent $C_{1-4}$ alkyl, or may form a five- to seven-membered saturated heterocyclic ring optionally substituted by $C_{1-4}$ alkyl or an oxygen atom together with the nitrogen atom to which they are attached.

14. The compound according to claim 1, wherein $R^1$ and $R^2$ represent $C_{1-4}$ alkoxy and A represents group (iv) wherein q is 0 (zero), r is 1 or 2, s is 1 or 2, t is 1 or 2, and $R^{18}$ represents optionally substituted phenyl.

15. The compound according to claim 1, wherein $R^1$ and $R^2$ represent $C_{1-4}$ alkoxy, $R^3$, $R^4$, $R^5$ and $R^6$ represent a hydrogen atom, and A represents group (iv) wherein q is 0 (zero), r is 1 or 2, s is 1 or 2, t is 1 or 2, and $R^{18}$ represents optionally substituted phenyl.

16. The compound according to claim 1, wherein $R^1$ and $R^2$ represent $C_{1-4}$ alkoxy, $R^3$ represents a group other than a hydrogen atom, $R^4$, $R^5$, and $R^6$ represent a hydrogen atom, and A represents group (iv) wherein q is 0 (zero), r is 1 or 2, s is 1 or 2, t is 1 or 2, and $R^{18}$ represents optionally substituted phenyl.

17. The compound according to claim 1, wherein $R^1$ and $R^2$ represent $C_{1-4}$ alkoxy and A represents group (v) wherein u is 1 and $R^{19}$ represents optionally substituted phenyl.

18. The compound according to claim 1, wherein $R^1$ and $R^2$ represent $C_{1-4}$ alkoxy, $R^3$, $R^4$, $R^5$, and $R^6$ represent a hydrogen atom, and A represents group (v) wherein u is 1 and $R^{19}$ represents optionally substituted phenyl.

19. The compound according to claim 1, wherein $R^1$ and $R^2$ represent $C_{1-4}$ alkoxy, $R^5$ represents a group other than a hydrogen atom, $R^3$, $R^4$, and $R^6$ represent a hydrogen atom, and A represents group (v) wherein u is 1 and $R^{19}$ represents optionally substituted phenyl.

20. The compound according to claim 1, wherein $R^1$ and $R^2$ represent $C_{1-4}$ alkoxy and A represents group (vi) wherein $R^{20}$ represents optionally substituted phenyl, or $C_{1-6}$ alkyl optionally substituted by optionally substituted phenyl.

21. The compound according to claim 1, wherein $R^1$ and $R^2$ represent $C_{1-4}$ alkoxy and A represents group (vii) wherein $R^{21}$ represents optionally substituted phenyl, or $C_{1-6}$ alkyl optionally substituted by optionally substituted phenyl.

22. The compound according to claim 1, wherein $R^1$ and $R^2$ represent $C_{1-4}$ alkoxy, $R^3$ represents morpholyl, $R^4$, $R^5$, and $R^6$ represent a hydrogen atom.

23. The compound of claim 1, selected from the group consisting of:

(4) 1-(3-Chlorophenyl)ethylN-{4-[(6,7-dimethoxy-4-quinolyl)oxy]-2,3-dimethylphenyl}carbamate;

(5) 1-(3-Chlorophenyl)ethylN-{4-[(6,7-dimethoxy-4-quinolyl)oxy]-2,5-dimethylphenyl}carbamate;

(8) 4-FluorobenzylN-{4-[(6,7-dimethoxy-4-quinolyl)oxy]phenyl}carbamate;

(9) 4-FluorobenzylN-{4-[(6,7-dimethoxy-4-quinolyl)oxy]-2,3-dimethylphenyl}carbamate;

(10) 4-FluorobenzylN-{4-[(6,7-dimethoxy-4-quinolyl)oxy]-2,5-dimethylphenyl}carbamate;

(13) 1-(2-Chlorophenyl)ethylN-{4-[(6,7-dimethoxy-4-quinolyl)oxy]phenyl}carbamate;

(14) 1-(2-Chlorophenyl)ethylN-{4-[(6,7-dimethoxy-4-quinolyl)oxy]-2,3-dimethylphenyl}carbamate;

(17) 3-(2-Chlorophenoxy)propylN-{4-[(6,7-dimethoxy-4-quinolyl)oxy]-2,3-dimethylphenyl}carbamate;

(18) 3-(2-Chlorophenoxy)propylN-{4-[(6,7-dimethoxy-4-quinolyl)oxy]-2,5-dimethylphenyl}carbamate;

(21) 4-(Trifluoromethyl)benzylN-{4-[(6,7-dimethoxy-4-quinolyl)oxy]phenyl}carbamate;

(22) 4-(Trifluoromethyl)benzylN-{4-[(6,7-dimethoxy-4-quinolyl)oxy]-2,3-dimethylphenyl}carbamate;

(23) 4-(Trifluoromethyl)benzylN-{4-[(6,7-dimethoxy-4-quinolyl)oxy]-2,5-dimethylphenyl}carbamate;

(26) 3-(2-Chlorophenoxy)propylN-{4-[(6,7-dimethoxy-4-quinolyl)oxy]phenyl}carbamate;

(27) 3-(4-Chlorophenoxy)propylN-{4-[(6,7-dimethoxy-4-quinolyl)oxy]phenyl}carbamate;

(28) 3-(4-Chlorophenoxy)propylN-{4-[(6,7-dimethoxy-4-quinolyl)oxy]-2,3-dimethylpheny}carbamate;

(29) 3-(4-Chlorophenoxy)propylN-{4-[(6,7-dimethoxy-4-quinolyl)oxy]-2,5-dimethylphenyl}carbamate;

(32) 1-(4-Methoxyphenyl)ethylN-{4-[(6,7-dimethoxy-4-quinolyl)oxy]phenyl}carbamate;

(33) 1-(4-Methoxyphenyl)ethylN-{4-[(6,7-dimethoxy-4-quinolyl)oxy]-2,3-dimethylphenyl}carbamate;

(34) 1-(4-Methoxyphenyl)ethylN-{4-[(6,7-dimethoxy-4-quinolyl)oxy]-2,5-dimethylphenyl}carbamate;

(37) 3-[(4-Methylphenyl)sulfanyl]propylN-{4-[(6,7-dimethoxy-4-quinolyl)oxy]phenyl}carbamate;

(38) 3-[(4-Methylphenyl)sulfanyl]propylN-{4-[(6,7-dimethoxy-4-quinolyl)oxy]-2,3-dimethylphenyl}-carbamate;

(39) 3-[(4-Methylphenyl)sulfanyl]propylN-{4-[(6,7-dimethoxy-4-quinolyl)oxy]-2,5-dimethylphenyl}-carbamate;

(42) 3-(4-Methoxyphenoxy)propylN-{4-[(6,7-dimethoxy-4-quinolyl)oxy]phenyl}carbamate;

(43) 3-(4-Methoxyphenoxy)propylN-{4-[(6,7-dimethoxy-4-quinolyl)oxy]-2,3-dimethylphenyl}carbamate;

(44) 3-(4-Methoxyphenoxy)propylN-{4-[(6,7-dimethoxy-4-quinolyl)oxy]-2,5-dimethylphenyl}carbamate;

(47) 3-(3-Methoxyphenoxy)propylN-{4-[(6,7-dimethoxy-4-quinolyl)oxy]phenyl}carbamate;

(48) 3-(3-Methoxyphenoxy)propylN-{4-[(6,7-dimethoxy-4-quinolyl)oxy]-2,3-dimethylphenyl}carbamate;

(49) 3-(3-Methoxyphenoxy)propylN-{4-[(6,7-dimethoxy-4-quinolyl)oxy]-2,5-dimethylphenyl}carbamate;
(52) 1-(3-Methoxyphenyl)ethylN-{4-[(6,7-dimethoxy-4-quinolyl)oxy]phenyl}carbamate;
(53) 1-(3-Methoxyphenyl)ethylN-{4-[(6,7-dimethoxy-4-quinolyl)oxy]-2,3-dimethylphenyl}carbamate;
(54) 1-(3-Methoxyphenyl)ethylN-{4-[(6,7-dimethoxy-4-quinolyl)oxy]-2,5-dimethylphenyl}carbamate;
(57) 4-(Tert-butyl)benzylN-{4-[(6,7-dimethoxy-4-quinolyl)oxy]phenyl}carbamate;
(58) 4-(Tert-butyl)benzylN-{4-[(6,7-dimethoxy-4-quinolyl)oxy]-2,3-dimethylphenyl}carbamate;
(59) 4-(Tert-butyl)benzylN-{4-[(6,7-dimethoxy-4-quinolyl)oxy]-2,5-dimethylphenyl}carbamate;
(62) 3,4-DimethoxybenzylN-{4-[(6,7-dimethoxy-4-quinolyl)oxy]phenyl}carbamate;
(63) 3,4-DimethoxybenzylN-{4-[(6,7-dimethoxy-4-quinolyl)oxy]-2,3-dimethylphenyl}carbamate;
(64) 3,4-DimethoxybenzylN-{4-[(6,7-dimethoxy-4-quinolyl)oxy]-2,5-dimethylphenyl}carbamate;
(67) 2,5-DimethoxybenzylN-{4-[(6,7-dimethoxy-4-quinolyl)oxy]phenyl}carbamate;
(68) 2,5-DimethoxybenzylN-{4-[(6,7-dimethoxy-4-quinolyl)oxy]-2,3-dimethylphenyl}carbamate;
(69) 2,5-DimethoxybenzylN-{4-[(6,7-dimethoxy-4-quinolyl)oxy]-2,5-dimethylphenyl}carbamate;
(72) 3-{[4-(Tert-butyl)phenyl]sulfanyl}-propylN-{4-[(6,7-dimethoxy-4-quinolyl)oxy]phenyl}carbamate;
(73) 3-{[4-(Tert-butyl)phenyl]sulfanyl}propylN-{4-[(6,7-dimethoxy-4-quinolyl)oxy]-2,3-dimethylphenyl}carbamate;
(74) 3-{[4-(Tert-butyl)phenyl]sulfanyl}propylN-{4-[(6,7-dimethoxy-4-quinolyl)oxy]-2,5-dimethylphenyl}carbamate;
(77) 3-[(4-Chloro-2-methylphenyl)sulfanyl]-propylN-{4-[(6,7-dimethoxy-4-quinolyl)oxy]phenyl}-carbamate;
(78) 3-[(4-Chloro-2-methylphenyl)sulfanyl]-propylN-{4-[(6,7-dimethoxy-4-quinolyl)oxy]-2,3-dimethylphenyl}carbamate;
(79) 3-[(4-Chloro-2-methylphenyl)sulfanyl]-propylN-{4-[(6,7-dimethoxy-4-quinolyl)oxy]-2,5-dimethylphenyl}carbamate;
(82) 3-(Trifluoromethyl)phenethylN-{4-[(6,7-dimethoxy-4-quinolyl)oxy]phenyl}carbamate;
(83) 3-(Trifluoromethyl)phenethylN-{4-[(6,7-dimethoxy-4-quinolyl)oxy]-2,3-dimethylphenyl}-carbamate;
(84) 3-(Trifluoromethyl)phenethylN-{4-[(6,7-dimethoxy-4-quinolyl)oxy]-2,5-dimethylphenyl}-carbamate;
(87) 1-[3-(Trifluoromethyl)phenyl]ethylN-{4-[(6,7-dimethoxy-4-quinolyl)oxy]phenyl}carbamate;
(88) 1-[3-(Trifluoromethyl)phenyl]ethylN-{4-[(6,7-dimethoxy-4-quinolyl)oxy]-2,3-dimethylphenyl}-carbamate;
(89) 1-[3-(Trifluoromethyl)phenyl]ethylN-{4-[(6,7-dimethoxy-4-quinolyl)oxy]-2,5-dimethylphenyl}-carbamate;
(92) 1-(2,4,5-Trifluorophenyl)ethylN-{4-[(6,7-dimethoxy-4-quinolyl)oxy]phenyl}carbamate;
(93) 1-(2,4,5-Trifluorophenyl)ethylN-{4-[(6,7-dimethoxy-4-quinolyl)oxy]-2,3-dimethylphenyl}-carbamate;
(94) 1-(2,4,5-Trifluorophenyl)ethylN-{4-[(6,7-dimethoxy-4-quinolyl)oxy]-2,5-dimethylphenyl}-carbamate;
(97) 1-(3-Fluorophenyl)ethylN-{4-[(6,7-dimethoxy-4-quinolyl)oxy]phenyl}carbamate;
(98) 1-(3-Fluorophenyl)ethylN-{4-[(6,7-dimethoxy-4-quinolyl)oxy]-2,3-dimethylphenyl}carbamate;
(99) 1-(3-Fluorophenyl)ethylN-{4-[(6,7-dimethoxy-4-quinolyl)oxy]-2,5-dimethylphenyl}carbamate;
(102) 1-(4-Fluorophenyl)ethylN-{4-[(6,7-dimethoxy-4-quinolyl)oxy]phenyl}carbamate;
(103) 1-(4-Fluorophenyl)ethylN-{4-[(6,7-dimethoxy-4-quinolyl)oxy]-2,3-dimethylphenyl}carbamate;
(104) 1-(4-Fluorophenyl)ethylN-{4-[(6,7-dimethoxy-4-quinolyl)oxy]-2,5-dimethylphenyl}carbamate;
(107) 4-Methylbenzyl{4-[(6,7-dimethoxy-4-quinolyl)oxy]anilino}methanethioate;
(108) 4-Methylbenzyl{4-[(6,7-dimethoxy-4-quinolyl)oxy]-2,3-dimethylanilino}methanethioate;
(109) 4-Methylbenzyl{4-[(6,7-dimethoxy-4-quinolyl)oxy]-2,5-dimethylanilino}methanethioate;
(112) 1-(2-Bromophenyl)ethylN-{4-[(6,7-dimethoxy-4-quinolyl)oxy]phenyl}carbamate;
(113) 1-(2-Bromophenyl)ethylN-{4-[(6,7-dimethoxy-4-quinolyl)oxy]-2,3-dimethylphenyl}carbamate;
(114) 1-(2-Bromophenyl)ethylN-{4-[(6,7-dimethoxy-4-quinolyl)oxy]-2,5-dimethylphenyl}carbamate;
(117) 1-(3-Bromophenyl)ethylN-{4-[(6,7-dimethoxy-4-quinolyl)oxy]phenyl}carbamate;
(118) 1-(3-Bromophenyl)ethylN-{4-[(6,7-dimethoxy-4-quinolyl)oxy]-2,3-dimethylphenyl}carbama;
(119) 1-(3-Bromophenyl)ethylN-{4-[(6,7-dimethoxy-4-quinolyl)oxy]-2,5-dimethylphenyl}carbamate;
(122) 1-(2-Fluorophenyl)ethylN-{4-[(6,7-dimethoxy-4-quinolyl)oxy]phenyl}carbamate;
(123) 1-(2-Fluorophenyl)ethylN-{4-[(6,7-dimethoxy-4-quinolyl)oxy]-2,3-dimethylphenyl}carbamate;
(124) 1-(2-Fluorophenyl)ethylN-{4-[(6,7-dimethoxy-4-quinolyl)oxy]-2,5-dimethylphenyl}carbamate;
(127) 1-(2-Ethoxyphenyl)ethylN-{4-[(6,7-dimethoxy-4-quinolyl)oxy]phenyl}carbamate;
(128) 1-(2-Ethoxyphenyl)ethylN-{4-[(6,7-dimethoxy-4-quinolyl)oxy]-2,3-dimethylphenyl}carbamate;
(129) 1-(2-Ethoxyphenyl)ethylN-{4-[(6,7-dimethoxy-4-quinolyl)oxy]-2,5-dimethylphenyl}carbamate;
(132) 1-(4-Methylphenyl)ethylN-{4-[(6,7-dimethoxy-4-quinolyl)oxy]phenyl}carbamate;
(133) 1-(4-Methylphenyl)ethylN-{4-[(6,7-dimethoxy-4-quinolyl)oxy]-2,3-dimethylphenyl}carbamate;
(134) 1-(4-Methylphenyl)ethylN-{4-[(6,7-dimethoxy-4-quinolyl)oxy]-2,5-dimethylphenyl}carbamate;
(137) 3-[(4-Methylphenyl)sulfanyl]ethylN-{4-[(dimethoxy-4-quinolyl)oxy]-phenyl}carbamate;
(138) 3-[(4-Methylphenyl)sulfanyl]ethylN-{4-[(6,7-dimethoxy-4-quinolyl)oxy]-2,3-dimethylphenyl}carbamate;
(139) 3-[(4-Methylphenyl)sulfanyl]ethylN-{4-[(6,7-dimethoxy-4-quinolyl)oxy]-2,5-dimethylphenyl}carbamate;
(142) 3-(2-Fluorophenoxy)propylN-{4-[(6,7-dimethoxy-4-quinolyl)oxy]phenyl}carbamate;
(143) 3-(2-Fluorophenoxy)propylN-{4-[(6,7-dimethoxy-4-quinolyl)oxy]-2,3-dimethylphenyl}carbamate;
(144) 3-(2-Fluorophenoxy)propylN-{4-[(6,7-dimethoxy-4-quinolyl)oxy]-2,5-dimethylphenyl}carbamate;
(147) 3-(3-Fluorophenoxy)propylN-{4-[(6,7-dimethoxy-4-quinolyl)oxy]phenyl}carbamate;
(148) 3-(3-Fluorophenoxy)propylN-{4-[(6,7-dimethoxy-4-quinolyl)oxy]-2,3-dimethylphenyl}carbamate;
(149) 3-(3-Fluorophenoxy)propylN-{4-[(6,7-dimethoxy-4-quinolyl)oxy]-2,5-dimethylphenyl}carbamate;

(152) 3-(4-Fluorophenoxy)propylN-{4-[(6,7-dimethoxy-4-quinolyl)oxy]phenyl}carbamate;
(153) 3-(4-Fluorophenoxy)propylN-{4-[(6,7-dimethoxy-4-quinolyl)oxy]-2,3-dimethylphenyl}carbamate;
(154) 3-(4-Fluorophenoxy)propylN-{4-[(6,7-dimethoxy-4-quinolyl)oxy]-2,5-dimethylphenyl}carbamate;
(157) 3-(2-Methoxyphenoxy)propylN-{4-[(6,7-dimethoxy-4-quinolyl)oxy]phenyl}carbamate;
(158) 3-(2-Methoxyphenoxy)propylN-{4-[(6,7-dimethoxy-4-quinolyl)oxy]-2,3-dimethylphenyl}carbamate;
(159) 3-(2-Methoxyphenoxy)propylN-{4-[(6,7-dimethoxy-4-quinolyl)oxy]-2,5-dimethylphenyl}carbamate;
(161) 3-(3-Methoxyphenoxy)propylN-{4-[(6,7-dimethoxy-4-quinolyl)oxy]phenyl}carbamate;
(162) 3-(3-Methoxyphenoxy)propylN-{4-[(6,7-dimethoxy-4-quinolyl)oxy]-2,3-dimethylphenyl}carbamate;
(163) 3-(3-Methoxyphenoxy)propylN-{4-[(6,7-dimethoxy-4-quinolyl)oxy]-2,5-dimethylphenyl}carbamate;
(165) 2-[(2,5-dimethylphenyl)sulfanyl]ethylN-{4-[(6,7-dimethoxy-4-quinolyl)oxy]phenyl}carbamate;
(166) 2-[(2,5-Dimethylphenyl)sulfanyl]ethylN-{4-[(6,7-dimethoxy-4-quinolyl)oxy]-2,3-dimethyl-phenyl}carbamate;
(167) 2-[(2,5-Dimethylphenyl)sulfanyl]ethylN-{4-[(6,7-Dimethoxy-4-quinolyl)oxy]-2,5-dimethyl-phenyl}carbamate;
(169) 3-[(2,5-Dimethylphenyl)sulfanyl)propylN-{4-[(6,7-dimethoxy-4-quinolyl)oxy]phenyl}carbamate;
(170) 3-[(2,5-Dimethylphenyl)sulfanyl]propylN-{4-[(6,7-dimethoxy-4-quinolyl)oxy]-2,3-dimethyl-phenyl carbamate;
(171) 3-[(2,5-Dimethylphenyl)sulfanyl]propylN-{4-[(6,7-dimethoxy-4-quinolyl)oxy]-2,5-dimethyl-phenyl}carbamate;
(173) 3-(2-Pyridylsulfanyl)propylN-{4-[(6,7-dimethoxy-4-quinolyl)oxy]-2,3-dimethylphenyl}-carbamate;
(174) 3-(2-Pyridylsulfanyl)propylN-{4-[(6,7-dimethoxy-4-quinolyl)oxy]-2,5-dimethylphenyl}-carbamate;
(176) 4-Chloro-2-methylphenyl{4-[(6,7-dimethoxy-4-quinolyl)oxy]anilino}methanethioate;
(177) 4-Chloro-2-methylphenyl{4-[(6,7-dimethoxy-4-quinolyl)oxy]-2,3-dimethylanilino}methane-thioate;
(178) 4-Chloro-2-methylphenyl{4-[(6,7-dimethoxy-4-quinolyl)oxy]-2,5-dimethylanilino}methane-thioate;
(180) 1-[3-(Trifluoromethoxy)phenyl]ethylN-{4-[(6,7-dimethoxy-4-quinolyl)oxy]phenyl}carbamate;
(181) 1-[3-(Trifluoromethoxy)phenyl]ethylN-{4-[(6,7-dimethoxy-4-quinolyl)oxy]-2,3-dimethylphenyl}-carbamate;
(182) 1-[3-(Tnfluoromethoxy)phenyl]ethylN-{4-[(6,7-dimethoxy-4-quinolyl)oxy]-2,5-dimethylphenyl}carbamate;
(184) 1-PhenylbutylN-{4-[(6,7-dimethoxy-4-quinolyl)oxy]phenyl}carbamate;
(185) 1-PhenylbutylN-{4-[(6,7-dimethoxy-4-quinolyl)oxy]-2,3-dimethylphenyl}carbamate;
(186) 1-PhenylbutylN-{4-[(6,7-dimethoxy-4-quinolyl)oxy]-2,5-dimethylphenyl}carbamate;
(188) 2-(Dimethylamino)ethylN-{4-[(6,7-dimethoxy-4-quinolyl)oxy]phenyl}carbamate;
(189) 2-(Dimethylamino)ethylN-{4-[(6,7-dimethoxy-4-quinolyl)oxy]-2,3-dimethylphenyl}carbamate;
(190) 2-(Dimethylamino)ethylN-{4-[(6,7-dimethoxy-4-quinolyl)oxy]-2,5-dimethylphenyl}carbamate;
(192) 4-(Dimethylamino)butylN-{4-[(6,7-dimethoxy-4-quinolyl)oxy]phenyl}carbamate;
(193) 4-(Dimethylamino)butylN-{4-[(6,7-dimethoxy-4-quinolyl)oxy]-2,3-dimethylphenyl}carbamate;
(195) 2-Methyl-1-phenylpropylN-{4-[(6,7-dimethoxy-4-quinolyl)oxy]phenyl}carbamate;
(196) 2-Methyl-1-phenylpropylN-{4-[(6,7-dimethoxy-4-quinolyl)oxy]-2,3-dimethylphenyl}carbamate;
(197) 2-Methyl-1-phenylpropylN-{4-[(6,7-dimethoxy-4-quinolyl)oxy]-2,5-dimethylphenyl}carbamate;
(199) 1-[3-(Dimethylamino)phenyl]ethylN-{4-[(6,7-dimethoxy-4-quinolyl)oxy]phenyl}carbamate;
(200) 1-[3-(Dimethylamino)phenyl]ethylN-{4-[(6,7-dimethoxy-4-quinolyl)oxy]-2,3-dimethylphenyl}-carbamate;
(201) 1-[3-(Dimethylamino)phenyl]ethylN-{4-[(6,7-dimethoxy-4-quinolyl)oxy]-2,5-dimethylphenyl}carbamate;
(203) 2-(2-Fluorophenoxy)ethylN-{4-[(6,7-dimethoxy-4-quinolyl)oxy]phenyl}carbamate;
(204) 2-(2-Fluorophenoxy)ethylN-{4-[(6,7-dimethoxy-4-quinolyl)oxy]-2,3-dimethylphenyl}carbamate;
(205) 2-(2-Fluorophenoxy)ethylN-{4-[(6,7-dimethoxy-4-quinolyl)oxy]-2,5-dimethylphenyl}carbamate;
(207) 2-(3-Fluorophenoxy)ethylN-{4-[(6,7-dimethoxy-4-quinolyl)oxy]phenyl}carbamate;
(208) 2-(3-Fluorophenoxy)ethylN-{4-[(6,7-dimethoxy-4-quinolyl)oxy]-2,3-dimethylphenyl}carbamate;
(209) 2-(3-Fluorophenoxy)ethylN-{4-[(6,7-dimethoxy-4-quinolyl)oxy]-2,5-dimethylphenyl}carbamate;
(214) 3-MethoxyphenylN-{4-[(6,7-dimethoxy-4-quinolyl)oxy]phenyl}carbamate;
(215) PropylN-{4-[(6,7-Dimethoxy-4-quinolin)oxy]-2,3-dimethylphenyl}carbamate;
(216) PhenylN-{4-[(6,7-dimethoxy-4-quinolyl)oxy]phenyl}carbamate;
(217) PhenylN-{4-[(6,7-dimethoxy-4-quinolyl)oxy]-2,3-dimethylphenyl}carbamate;
(218) BenzylN-{4-[(6,7-dimethoxy-4-quinolyl)oxy]-2,5-dimethylphenyl}carbamate;
(219) BenzylN-{4-[(6,7-dimethoxy-4-quinolyl)oxy]-2,3-dimethylphenyl}carbamate;
(221) CyclohexylN-{4-[(6,7-dimethoxy-4-quinolyl)oxy]-2,5-dimethylphenyl}carbamate;
(222) CyclohexylN-{4-[(6,7-dimethoxy-4-quinolyl)oxy]-2,3-dimethylphenyl}carbamate;
(223) 2-MethylphenylN-{4-[(6,7-dimethoxy-4-quinolyl)oxy]phenyl}carbamate;
(224) PhenylN-{4-[(6,7-dimethoxy-4-quinolyl)oxy]-2,5-dimethylphenyl}carbamate;
(226) 3-MethoxybenzylN-{4-[(6,7-dimethoxy-4-quinolyl)oxy]phenyl}carbamate;
(227) 2-ChlorobenzylN-{4-[(6,7-dimethoxy-4-quinolyl)oxy]phenyl}carbamate;
(228) 3-ChlorobenzylN-{4-[(6,7-dimethoxy-4-quinolyl)oxy]phenyl}carbamate;
(229) 4-ChlorobenzylN-{4-[(6,7-dimethoxy-4-quinolyl)oxy]phenyl}carbamate;
(230) CyclohexylN-{4-[(6,7-dimethoxy-4-quinolyl)oxy]phenyl}carbamate;
(231) BenzylN-{4-[(6,7-dimethoxy-4-quinolyl)oxy]phenyl}carbamate;
(232) 2-MethylbenzylN-{4-[(6,7-dimethoxy-4-quinolyl)oxy]-2,3-dimethylphenyl}carbamate;

(233) 3-MethylbenzylN-{4-[(6,7-dimethoxy-4-quinolyl)oxy]-2,3-dimethylphenyl}carbamate;
(234) 4-MethylbenzylN-{4-[(6,7-dimethoxy-4-quinolyl)oxy]-2,3-dimethylphenyl}carbamate;
(235) 2-ChlorobenzylN-{4-[(6,7-dimethoxy-4-quinolyl)oxy]-2,3-dimethylphenyl}carbamate;
(236) 3-ChlorobenzylN-{4-[(6,7-dimethoxy-4-quinolyl)oxy]-2,3-dimethylphenyl}carbamate;
(237) 4-ChlorobenzylN-{4-[(6,7-dimethoxy-4-quinolyl)oxy]-2,3-dimethylphenyl}carbamate;
(238) 3-MethoxybenzylN-{4-[(6,7-dimethoxy-4-quinolyl)oxy]-2,3-dimethylphenyl}carbamate;
(239) 2-MethoxybenzylN-{4-[(6,7-dimethoxy-4-quinolyl)oxy]-2,5-dimethylphenyl}carbamate;
(240) 3-MethoxybenzylN-{4-[(6,7-dimethoxy-4-quinolyl)oxy]-2,5-dimethylphenyl}carbamate;
(241) 2-ChlorobenzylN-{4-[(6,7-dimethoxy-4-quinolyl)oxy]-2,5-dimethylphenyl}carbamate;
(242) 3-ChlorobenzylN-{4-[(6,7-dimethoxy-4-quinolyl)oxy]-2,5-dimethylphenyl}carbamate;
(243) 4-ChlorobenzylN-{4-[(6,7-dimethoxy-4-quinolyl)oxy]-2,5-dimethylphenyl}carbamate;
(244) PropylN-{4-[(6,7-dimethoxy-4-quinolyl)oxy]-2,5-dimethylphenyl}carbamate;
(245) 2-MethylbenzylN-{4-[(6,7-dimethoxy-4-quinolyl)oxy]-2,5-dimethylphenyl}carbamate;
(246) 2-NaphthylmethylN-{4-[(6,7-dimethoxy-4-quinolyl)oxy]-2,5-dimethylphenyl}carbamate;
(247) PropylN-{4-[(6,7-dimethoxy-4-quinolyl)oxy]phenyl}carbamate;
(248) 2-MethoxybenzylN-{4-[(6,7-dimethoxy-4-quinolyl)oxy]phenyl}carbamate;
(249) 4-MethoxybenzylN-{4-[(6,7-dimethoxy-4-quinolyl)oxy]phenyl}carbamate;
(250) 2-MethylbenzylN-{4-[(6,7-dimethoxy-4-quinolyl)oxy]phenyl}carbamate;
(251) 3-MethylbenzylN-{4-[(6,7-dimethoxy-4-quinolyl)oxy]phenyl}carbamate;
(252) 4-MethylbenzylN-{4-[(6,7-dimethoxy-4-quinolyl)oxy]phenyl}carbamate;
(253) 2-MethylbenzylN-{4-[(6,7-dimethoxy-4-quinolyl)oxy]-2,5-dimethylphenyl}carbamate;
(254) 3-MethylbenzylN-{4-[(6,7-dimethoxy-4-quinolyl)oxy]-2,5-dimethylphenyl}carbamate;
(255) 4-MethylbenzylN-{4-[(6,7-dimethoxy-4-quinolyl)oxy]-2,5-dimethylphenyl}carbamate;
(256) HexylN-{4-[(6,7-dimethoxy-4-quinolyl)oxy]phenyl}carbamate;
(257) 4-ButylphenylN-{4-[(6,7-dimethoxy-4-quinolyl)oxy]phenyl}carbamate;
(258) 1-EthylbutylN-{4-[(6,7-dimethoxy-4-quinolyl)oxy]phenyl}carbamate;
(259) 4-(Tert-butyl)phenylN-{4-[(6,7-dimethoxy-4-quinolyl)oxy]phenyl}carbamate;
(260) 2-MethoxyphenylN-{4-[(6,7-dimethoxy-4-quinolyl)oxy]phenyl}carbamate;
(261) HexylN-{4-[(6,7-Dimethoxy-4-quinolyl)oxy]-2,3-dimethylphenyl}carbamate;
(262) HexylN-{4-[(6,7-dimethoxy-4-quinolyl)oxy]-2,5-dimethylphenyl}carbamate;
(263) 1-PhenylpropylN-{4-[(6,7-dimethoxy-4-quinolyl)oxy]phenyl}carbamate;
(264) 1-PhenylpropylN-{4-[(6,7-dimethoxy-4-quinolyl)oxy]-2,5-dimethylphenyl}carbamate;
(265) 1-PhenylpropylN-{4-[(6,7-dimethoxy-4-quinolyl)oxy]-2,3-dimethylphenyl}carbamate;
(266) 4-PentenylN-{4-[(6,7-dimethoxy-4-quinolyl)oxy]phenyl}carbamate;
(267) 4-PentenylN-{4-[(6,7-dimethoxy-4-quinolyl)oxy]-2,5-dimethylphenyl}carbamate;
(268) 4-PentenylN-{4-[(6,7-dimethoxy-4-quinolyl)oxy]-2,3-dimethylphenyl}carbamate;
(269) 2,6-DimethylphenylN-{4-[(6,7-dimethoxy-4-quinolyl)oxy]phenyl}carbamate;
(270) 2,6-DimethylphenylN-{4-[(6,7-dimethoxy-4-quinolyl)oxy]-2,5-dimethylphenyl}carbamate;
(271) 2,6-DimethylphenylN-{4-[(6,7-dimethoxy-4-quinolyl)oxy]-2,3-dimethylphenyl}carbamate;
(272) 4-ButylphenylN-{4-[(6,7-dimethoxy-4-quinolyl)oxy]-2,5-dimethylphenyl}carbamate;
(273) 4-ButylphenylN-{4-[(6,7-dimethoxy-4-quinolyl)oxy]-2,3-dimethylphenyl}carbamate;
(274) 4-(Tert-butyl)phenylN-{4-[(6,7-dimethoxy-4-quinolyl)oxy]-2,5-dimethylphenyl}carbamate;
(275) 4-(Tert-butyl)phenylN-{4-[(6,7-dimethoxy-4-quinolyl)oxy]-2,3-dimethylphenyl}carbamate;
(276) 1-EthylbutylN-{4-[(6,7-dimethoxy-4-quinolyl)oxy]-2,5-dimethylphenyl}carbamate;
(277) 1-EthylbutylN-{4-[(6,7-dimethoxy-4-quinolyl)oxy]-2,3-dimethylphenyl}carbamate;
(278) 2-MethoxyphenylN-{4-[(6,7-dimethoxy-4-quinolyl)oxy]-2,5-dimethylphenyl}carbamate;
(279) 2-MethoxyphenylN-{4-[(6,7-dimethoxy-4-quinolyl)oxy]-2,3-dimethylphenyl}carbamate;
(280) 2,6-DimethoxyphenylN-{4-[(6,7-dimethoxy-4-quinolyl)oxy]phenyl}carbamate;
(281) 2,6-DimethoxyphenylN-{4-[(6,7-dimethoxy-4-quinolyl)oxy]-2,5-dimethylphenyl}carbamate;
(282) 2,6-DimethoxyphenylN-{4-[(6,7-dimethoxy-4-quinolyl)oxy]-2,3-dimethylphenyl}carbamate;
(283) CyclohexylmethylN-{4-[(6,7-dimethoxy-4-quinolyl)oxy]phenyl}carbamate;
(284) CyclohexylmethylN-{4-[(6,7-dimethoxy-4-quinolyl)oxy]-2,5-dimethylphenyl}carbamate;
(285) CyclohexylmethylN-{4-[(6,7-dimethoxy-4-quinolyl)oxy]-2,3-dimethylphenyl}carbamate;
(286) CycloheptylN-{4-[(6,7-dimethoxy-4-quinolyl)oxy]phenyl}carbamate;
(287) CycloheptylN-{4-[(6,7-dimethoxy-4-quinolyl)oxy]-2,5-dimethylphenyl}carbamate;
(288) CycloheptylN-{4-[(6,7-dimethoxy-4-quinolyl)oxy]-2,3-dimethylphenyl}carbamate;
(289) 2-MethylphenylN-{4-[(6,7-dimethoxy-4-quinolyl)oxy]-2,5-dimethylphenyl}carbamate;
(290) 3-MethoxyphenylN-{4-[(6,7-dimethoxy-4-quinolyl)oxy]-2,5-dimethylphenyl}carbamate;
(291) 3-MethoxyphenylN-{4-[(6,7-dimethoxy-4-quinolyl)oxy]-2,3-dimethylphenyl}carbamate;
(292) 1,2,3,4-Tetrahydro-2-naphthalenylN-{4-[(6,7-dimethoxy-4-quinolyl)oxy]-2,5-dimethylphenyl}carbamate;
(293) 1,2,3,4-Tetrahydro-2-naphthalenylN-{4-[(6,7-dimethoxy-4-quinolyl)oxy]-2,3-dimethylphenyl}carbamate;
(294) 4-PhenylphenylN-{4-[(6,7-dimethoxy-4-quinolyl)oxy]phenyl}carbamate;
(295) 4-PhenylphenylN-{4-[(6,7-dimethoxy-4-quinolyl)oxy]-2,5-dimethylphenyl}carbamate;
(296) 4-PhenylphenylN-{4-[(6,7-dimethoxy-4-quinolyl)oxy]-2,3-dimethylphenyl}carbamate;
(297) PhenethylN-{4-[(6,7-dimethoxy-4-quinolyl)oxy]phenyl}carbamate;

(298) PhenethylN-{4-[(6,7-dimethoxy-4-quinolyl)oxy]-2,5-dimethylphenyl}carbamate;
(299) PhenethylN-{4-[(6,7-dimethoxy-4-quinolyl)oxy]-2,3-dimethylphenyl}carbamate;
(300) 2-(Tert-butyl)phenylN-{4-[(6,7-dimethoxy-4-quinolyl)oxy]phenyl}carbamate;
(301) 2-(Tert-butyl)phenylN-{4-[(6,7-dimethoxy-4-quinolyl)oxy]-2,5-dimethylphenyl}carbamate;
(302) 2-(Tert-butyl)phenylN-{4-[(6,7-dimethoxy-4-quinolyl)oxy]-2,3-dimethylphenyl}carbamate;
(303) 2-PiperidinoethylN-{4-[(6,7-dimethoxy-4-quinolyl)oxy]phenyl}carbamate;
(304) 2-PiperidinoethylN-{4-[(6,7-dimethoxy-4-quinolyl)oxy]-2,5-dimethylphenyl}carbamate;
(305) 2-PiperidinoethylN-{4-[(6,7-dimethoxy-4-quinolyl)oxy]-2,3-dimethylphenyl}carbamate;
(306) 2-MorpholinoethylN-{4-[(6,7-dimethoxy-4-quinolyl)oxy]phenyl}carbamate;
(307) 2-MorpholinoethylN-{4-[(6,7-dimethoxy-4-quinolyl)oxy]-2,5-dimethylphenyl}carbamate;
(308) 2-MorpholinoethylN-{4-[(6,7-dimethoxy-4-quinolyl)oxy]-2,3-dimethylphenyl}carbamate;
(309) 6-(Dimethylamino)hexylN-{4-[(6,7-dimethoxy-4-quinolyl)oxy]phenyl}carbamate;
(310) 6-(Dimethylamino)hexylN-{4-[(6,7-dimethoxy-4-quinolyl)oxy]-2,5-dimethylphenyl}carbamate;
(311) 6-(Dimethylamino)hexylN-{4-[(6,7-dimethoxy-4-quinolyl)oxy]-2,3-dimethylphenyl}carbamate;
(321) ButylN-{4-[(6,7-dimethoxy-4-quinolyl)oxy]phenyl}carbamate;
(322) ButylN-{4-[(6,7-dimethoxy-4-quinolyl)oxy]-2,5-dimethylphenyl}carbamate;
(323) ButylN-{4-[(6,7-dimethoxy-4-quinolyl)oxy]-2,3-dimethylphenyl}carbamate;
(324) IsopropylN-{4-[(6,7-dimethoxy-4-quinolyl)oxy]phenyl}carbamate;
(325) IsopropylN-{4-[(6,7-dimethoxy-4-quinolyl)oxy]-2,3-dimethylphenyl}carbamate;
(326) OctadecylN-{4-[(6,7-dimethoxy-4-quinolyl)oxy]phenyl}carbamate;
(327) OctadecylN-{4-[(6,7-dimethoxy-4-quinolyl)oxy]-2,5-dimethylphenyl}carbamate;
(328) OctadecylN-{4-[(6,7-dimethoxy-4-quinolyl)oxy]-2,3-dimethylphenyl}carbamate;
(329) 1-EthylpentylN-{4-[(6,7-dimethoxy-4-quinolyl)oxy]phenyl}carbamate;
(330) 1-EthylpentylN-{4-[(6,7-dimethoxy-4-quinolyl)oxy]-2,5-dimethylphenyl}carbamate;
(331) 1-EthylpentylN-{4-[(6,7-dimethoxy-4-quinolyl)oxy]-2,3-dimethylphenyl}carbamate;
(332) 1-PropylbutylN-{4-[(6,7-dimethoxy-4-quinolyl)oxy]phenyl}carbamate;
(333) 1-PropylbutylN-{4-[(6,7-dimethoxy-4-quinolyl)oxy]-2,5-dimethylphenyl}carbamate;
(334) 1-PropylbutylN-{4-[(6,7-dimethoxy-4-quinolyl)oxy]-2,3-dimethylphenyl}carbamate;
(347) IsopropylN-{4-[(6,7-dimethoxy-4-quinolyl)oxy]-2,5-dimethylphenyl}carbamate;
(348) CycloheptylmethylN-{4-[(6,7-dimethoxy-4-quinolyl)oxy]phenyl}carbamate;
(349) CycloheptylmethylN-{4-[(6,7-dimethoxy-4-quinolyl)oxy]-2,5-dimethylphenyl}carbamate;
(350) CycloheptylmethylN-{4-[(6,7-dimethoxy-4-quinolyl)oxy]-2,3-dimethylphenyl}carbamate;
(353) 2-CyclohexylethylN-{4-[(6,7-dimethoxy-4-quinolyl)oxy]phenyl}carbamate;
(354) 2-CyclohexylethylN-{4-[(6,7-dimethoxy-4-quinolyl)oxy]-2,5-dimethylphenyl}carbamate;
(355) 2-CyclohexylethylN-{4-[(6,7-dimethoxy-4-quinolyl)oxy]-2,3-dimethylphenyl}carbamate;
(358) 1-EthylpropylN-{4-[(6,7-dimethoxy-4-quinolyl)oxy]phenyl}carbamate;
(359) 1-EthylpropylN-{4-[(6,7-dimethoxy-4-quinolyl)oxy]-2,5-dimethylphenyl}carbamate;
(360) 1-EthylpropylN-{4-[(6,7-dimethoxy-4-quinolyl)oxy]-2,3-dimethylphenyl}carbamate;
(363) CyclopentylN-{4-[(6,7-dimethoxy-4-quinolyl)oxy]phenyl}carbamate;
(364) CyclopentylN-{4-[(6,7-dimethoxy-4-quinolyl)oxy]-2,5-dimethylphenyl}carbamate;
(365) CyclopentylN-{4-[(6,7-dimethoxy-4-quinolyl)oxy]-2,3-dimethylphenyl}carbamate;
(368) 1-ButylpentylN-{4-[(6,7-dimethoxy-4-quinolyl)oxy]phenyl}carbamate;
(369) 1-ButylpentylN-{4-[(6,7-dimethoxy-4-quinolyl)oxy]-2,5-dimethylphenyl}carbamate;
(370) 1-ButylpentylN-{4-[(6,7-dimethoxy-4-quinolyl)oxy]-2,3-dimethylphenyl}carbamate;
(373) AllylN-{4-[(6,7-dimethoxy-4-quinolyl)oxy]-2,5-dimethylphenyl}carbamate;
(374) AllylN-{4-[(6,7-dimethoxy-4-quinolyl)oxy]-2,3-dimethylphenyl}carbamate;
(376) 3-PhenylpropylN-{4-[(6,7-dimethoxy-4-quinolyl)oxy]phenyl}carbamate;
(377) 3-PhenylpropylN-{4-[(6,7-dimethoxy-4-quinolyl)oxy]-2,5-dimethylphenyl}carbamate;
(378) 3-PhenylpropylN-{4-[(6,7-dimethoxy-4-quinolyl)oxy]-2,3-dimethylphenyl}carbamate;
(380) CyclopropylmethylN-{4-[(6,7-dimethoxy-4-quinolyl)oxy]phenyl}carbamate;
(381) CyclopropylmethylN-{4-[(6,7-dimethoxy-4-quinolyl)oxy]-2,5-dimethylphenyl}carbamate;
(382) CyclopropylmethylN-{4-[(6,7-dimethoxy-4-quinolyl)oxy]-2,3-dimethylphenyl}carbamate;
(385) CyclobutylmethylN-{4-[(6,7-dimethoxy-4-quinolyl)oxy]phenyl}carbamate;
(386) CyclobutylmethylN-{4-[(6,7-dimethoxy-4-quinolyl)oxy]-2,5-dimethylphenyl}carbamate;
(387) CyclobutylmethylN-{4-[(6,7-dimethoxy-4-quinolyl)oxy]-2,3-dimethylphenyl}carbamate;
(394) CyclopentylmethylN-{4-[(6,7-dimethoxy-4-quinolyl)oxy]phenyl}carbamate;
(395) CyclopentylmethylN-{4-[(6,7-dimethoxy-4-quinolyl)oxy]-2,5-dimethylphenyl}carbamate;
(396) CyclopentylmethylN-{4-[(6,7-dimethoxy-4-quinolyl)oxy]-2,3-dimethylphenyl}carbamate;
(404) 2-MethylallylN-{4-[(6,7-dimethoxy-4-quinolyl)oxy]phenyl}carbamate;
(405) 2-MethylallylN-{4-[(6,7-dimethoxy-4-quinolyl)oxy]-2,5-dimethylphenyl}carbamate;
(406) 2-MethylallylN-{4-[(6,7-dimethoxy-4-quinolyl)oxy]-2,3-dimethylphenyl}carbamate;
(408) 1-Ethyl-3-butynylN-{4-[(6,7-dimethoxy-4-quinolyl)oxy]phenyl}carbamate;
(409) 1-Ethyl-3-butynylN-{4-[(6,7-dimethoxy-4-quinolyl)oxy]-2,5-dimethylphenyl}carbamate;
(410) 1-Ethyl-3-butynylN-{4-[(6,7-dimethoxy-4-quinolyl)oxy]-2,3-dimethylphenyl}carbamate;
(411) 1-MethylhexylN-{4-[(6,7-dimethoxy-4-quinolyl)oxy]phenyl}carbamate;
(412) 1-MethylhexylN-{4-[(6,7-dimethoxy-4-quinolyl)oxy]-2,5-dimethylphenyl}carbamate;

(413) 1-MethylhexylN-{4-[(6,7-dimethoxy-4-quinolyl)oxy]-2,3-dimethylphenyl}carbamate;
(414) 3-PiperidinopropylN-{4-[(6,7-dimethoxy-4-quinolyl)oxy]-2,5-dimethylphenyl}carbamate;
(415) 3-PiperidinopropylN-{4-[(6,7-dimethoxy-4-quinolyl)oxy]-2,3-dimethylphenyl}carbamate;
(416) 1,3-Dioxo-2,3-dihydro-1H-2-isoindolylN-{4-[(6,7-dimethoxy-4-quinolyl)oxy]phenyl}carbamate;
(417) (1,3-Dioxo-2,3-dihydro-1H-2-isoindolyl)methylN-{4-[(6,7-dimethoxy-4-quinolyl)oxy-2,5-dimethylphenyl}carbamate;
(418) (1,3-Dioxo-2,3-dihydro-1H-2-isoindolyl)methylN-{4-[(6,7-dimethoxy-4-quinolyl)oxy]-2,3-dimethylphenyl}carbamate;
(419) 2-(1,3-Dioxo-2,3-dihydro-1H-2-isoindolyl)ethylN-{4-[(6,7-dimethoxy-4-quinolyl)oxy-2,5-dimethylphenyl}carbamate;
(420) 2-(1,3-Dioxo-2,3-dihydro-1H-2-isoindolyl)ethylN-{4-[(6,7-dimethoxy-4-quinolyl)oxy-2,3-dimethylphenyl}carbamate;
(421) 3-MorpholinopropylN-{4-[(6,7-dimethoxy-4-quinolyl)oxy]phenyl}carbamate;
(422) 3-MorpholinopropylN-{4-[(6,7-dimethoxy-4-quinolyl)oxy]-2,5-dimethylphenyl}carbamate;
(423) 3-MorpholinopropylN-{4-[(6,7-dimethoxy-4-quinolyl)oxy]-2,5-dimethylphenyl}carbamate;
(424) 3-(4-Methylpiperazino)propylN-{4-[(6,7-dimethoxy-4-quinolyl)oxy]phenyl}carbamate;
(425) 3-(4-Methylpiperazino)propylN-{4-[(6,7-dimethoxy-4-quinolyl)oxy]-2,5-dimethylphenyl}carbamate
(426) 3-(Diethylamino)propylN-{4-[(6,7-dimethoxy-4-quinolyl)oxy]phenyl}carbamate;
(427) 3-(Diethylamino)propylN-{4-[(6,7-dimethoxy-4-quinolyl)oxy]-2,5-dimethylphenyl}carbamate;
(428) 3-(Diethylamino)propylN-{4-[(6,7-dimethoxy-4-quinolyl)oxy]-2,3-dimethylphenyl}carbamate;
(430) 2-PyridylmethylN-{4-[(6,7-dimethoxy-4-quinolyl)oxy]-2,5-dimethylphenyl}carbamate;
(431) 2-PyridylmethylN-{4-[(6,7-dimethoxy-4-quinolyl)oxy]-2,3-dimethylphenyl}carbamate;
(432) 3-PyridylmethylN-{4-[(6,7-dimethoxy-4-quinolyl)oxy]-2,3-dimethylphenyl}carbamate;
(433) 4-PyridylmethylN-{4-[(6,7-dimethoxy-4-quinolyl)oxy]phenyl}carbamate;
(435) 2-(Diethylamino)ethylN-{4-[(6,7-dimethoxy-4-quinolyl)oxy]phenyl}carbamate;
(437) 1-(2-Morpholinoethyl)butylN-{4-[(6,7-dimethoxy-4-quinolyl)oxy]phenyl}carbamate;
(438) 1-(2-Morpholinoethyl)butylN-{4-[(6,7-dimethoxy-4-quinolyl)oxy]-2,5-dimethylphey}carbamate;
(439) 1-(2-Morpholinoethyl)butylN-{4-[(6,7-dimethoxy-4-quinolyl)oxy]-2,3-dimethylphey}carbamate;
(441) 1-[2-(Diethylamino)ethyl]butylN-{4-[(6,7-dimethoxy-4-quinolyl)oxy]phenyl}carbamate;
(442) 1-[2-(Diethylamino)ethyl]butylN-{4-[(6,7-dimethoxy-4-quinolyl)oxy]-2,5-dimethylphenyl}carbamate;
(443) 1-[2-(Diethylamino)ethyl]butylN-{4-[(6,7-dimethoxy-4-quinolyl)oxy]-2,3-dimethylphenyl}carbamate;
(445) 1-(2-Piperidinoethyl)butylN-{4-[(6,7-dimethoxy-4-quinolyl)oxy]phenyl}carbamate;
(446) 1-(2-Piperidinoethyl)butylN-{4-[(6,7-dimethoxy-4-quinolyl)oxy]-2,5-dimethylphenyl}carbamate;
(447) 1-(2-Piperidinoethyl)butylN-{4-[(6,7-dimethoxy-4-quinolyl)oxy]-2,3-dimethylphenyl}carbamate;
(449) 1-[2-(4-Methylpiperazino)ethyl]butylN-{4-[(6,7-dimethoxy-4-quinolyl)oxy]phenyl}carbamate;
(450) 1-[2-(4-Methylpiperazino)ethyl]butylN-{4-[(6,7-dimethoxy-4-quinolyl)oxy]-2,5-dimethylphenyl}carbamate;
(451) 1-[2-(4-Methylpiperazino)ethyl]butylN-{4-[(6,7-dimethoxy-4-quinolyl)oxy]-2,3-dimethylphenyl}carbamate;
(453) Cyano(phenyl)methylN-{4-[(6,7-dimethoxy-4-quinolyl)oxy]phenyl}carbamate;
(454) Cyano(phenyl)methylN-{4-[(6,7-dimethoxy-4-quinolyl)oxy]-2,5-dimethylphenyl}carbamate;
(455) Cyano(phenyl)methylN-{4-[(6,7-dimethoxy-4-quinolyl)oxy]-2,3-dimethylphenyl}carbamate;
(457) 3-CyanophenylN-{4-[(6,7-dimethoxy-4-quinolyl)oxy]phenyl}carbamate;
(458) 3-CyanophenylN-{4-[(6,7-dimethoxy-4-quinolyl)oxy]-2,5-dimethylphenyl}carbamate;
(459) 3-CyanophenylN-{4-[(6,7-dimethoxy-4-quinolyl)oxy]-2,3-dimethylphenyl}carbamate;
(460) 4-CyanophenylN-{4-[(6,7-dimethoxy-4-quinolyl)oxy]-2,5-dimethylphenyl}carbamate;
(461) 4-CyanophenylN-{4-[(6,7-dimethoxy-4-quinolyl)oxy]-2,3-dimethylphenyl}carbamate;
(462) 1-Methyl-3-piperidylN-{4-[(6,7-dimethoxy-4-quinolyl)oxy]phenyl}carbamate;
(463) 1-Methyl-3-piperidylN-{4-[(6,7-dimethoxy-4-quinolyl)oxy]-2,5-dimethylphenyl}carbamate;
(464) 1-Methyl-3-piperidylN-{4-[(6,7-dimethoxy-4-quinolyl)oxy]-2,3-dimethylphenyl}carbamate;
(466) 1-Methyl-4-piperidylN-{4-[(6,7-dimethoxy-4-quinolyl)oxy]phenyl}carbamate;
(467) 1-Methyl-4-piperidylN-{4-[(6,7-dimethoxy-4-quinolyl)oxy]-2,5-dimethylphenyl}carbamate;
(468) 1-Methyl-4-piperidylN-{4-[(6,7-dimethoxy-4-quinolyl)oxy]-2,3-dimethylphenyl}carbamate;
(470) Tetrahydro-2H-4-pyranylN-{4-[(6,7-dimethoxy-4-quinolyl)oxy]phenyl}carbamate;
(471) Tetrahydro-2H-4-pyranylN-{4-[(6,7-dimethoxy-4-quinolyl)oxy]-2,5-dimethylphenyl}carbamate;
(472) Tetrahydro-2H-4-pyranylN-{4-[(6,7-dimethoxy-4-quinolyl)oxy]-2,3-dimethylphenyl}carbamate;
(483) CycloheptylmethylN-{4-[(6,7-dimethoxy-4-quinolyl)oxy]phenyl}N-methylcarbamate;
(496) 1-Ethyl-3-butynylN-{4-[(6,7-dimethoxy-4-quinolyl)oxy]phenyl}N-methylcarbamate;
(511) N-{4-[(6,7-Dimethoxy-4-quinolyl)oxy]-2,3-dimethylphenyl}-N'-(2-diethylaminoethyl)thiourea;
(512) N-{4-[(6,7-Dimethoxy-4-quinolyl)oxy]-2,3-dimethylphenyl}-N'-(2-piperidinylethyl)thiourea;
(513) N-{4-[(6,7-Dimethoxy-4-quinolyl)oxy]-2,3-dimethylphenyl}-N'-[4-(N-benzyl)piperidinyl]thiourea;
(514) N-{4-[(6,7-Dimethoxy-4-quinolyl)oxy]-2,5-dimethylphenyl}-N'-(2-piperidinylethyl)thiourea;
(515) N-{4-[(6,7-Dimethoxy-4-quinolyl)oxy]-2,5-dimethylphenyl}-N'-(2-acetamidoethyl)thiourea;
(520) N-{4-[(6,7-Dimethoxy-4-quinolyl)oxy]-2,3-dimethylphenyl}-N'-(N-cyclohexylamino)thiourea;
(521) N-{4-[(6,7-Dimethoxy-4-quinolyl)oxy]-2,3-dimethylphenyl}-N'-(1-piperidinyl)thiourea;
(522) N-{4-[(6,7-Dimethoxy-4-quinolyl)oxy]-2,5-dimethylphenyl}-N'-(1-piperidinyl)thiourea;
(523) N-{4-[(6,7-Dimethoxy-4-quinolyl)oxy]-2,5-dimethylphenyl}-N'-(N-cyclohexylamino)thiourea;
(538) N-{4-[(6,7-Dimethoxy-4-quinolyl)oxy]-2,5-dimethylphenyl}-N'-(2-dimethylaminoethyl)thiourea;

(539) N-{4-[(6,7-Dimethoxy-4-quinolyl)oxy]-2,5-dimethylphenyl}-N'-[3-(1-imidazoyl)propyl]thiourea;
(540) N-{4-[(6,7-Dimethoxy-4-quinolyl)oxy]-2,5-dimethylphenyl}-N'-{2-[N-ethyl-N-(o-tolyl)amino]ethyl}thiourea;
(541) N-{4-[(6,7-Dimethoxy-4-quinolyl)oxy]-2,5-dimethylphenyl}-N'-[2-(1-pyrrolidinyl)ethyl]thiourea;
(542) N-{4-[(6,7-Dimethoxy-4-quinolyl)oxy]-2,3-dimethylphenyl}-N'-(2-dimethylaminoethyl)thiourea;
(543) N-{4-[(6,7-Dimethoxy-4-quinolyl)oxy]-2,3-dimethylphenyl}-N'-[3-(1-imidazoyl)propyl]thiourea;
(544) N-{4-[(6,7-Dimethoxy-4-quinolyl)oxy]-2,3-dimethylphenyl}-N'-{2-[N-ethyl-N-(o-tolyl)amino]ethyl}thiourea;
(545) N-{4-[(6,7-Dimethoxy-4-quinolyl)oxy]-2,5-dimethylphenyl}-N'-[2-(1-morpholino)ethyl]thiourea;
(546) N-{4-[(6,7-Dimethoxy-4-quinolyl)oxy]-2,3-dimethylphenyl}-N'-(3-diethylaminopropyl)thiourea;
(547) N-{4-[(6,7-Dimethoxy-4-quinolyl)oxy]-2,3-dimethylphenyl}-N'-(3-dibutylaminopropyl)thiourea;
(548) N-{4-[(6,7-Dimethoxy-4-quinolyl)oxy]-2,3-dimethylphenyl}-N'-[3-(1-morpholino)propyl]thiourea;
(549) N-{4-[(6,7-Dimethoxy-4-quinolyl)oxy]-2,3-dimethylphenyl}-N'-[3-(2-methylpiperidinyl)propyl]-thiourea;
(550) N-{4-[(6,7-Dimethoxy-4-quinolyl)oxy]-2,3-dimethylphenyl}-N'-(2-diisopropylaminoethyl)thiourea;
(551) N-{4-[(6,7-Dimethoxy-4-quinolyl)oxy]-2,5-dimethylphenyl}-N'-(3-diethylaminopropyl)thiourea;
(552) N-{4-[(6,7-Dimethoxy-4-quinolyl)oxy]-2,5-dimethylphenyl}-N'-(3-dibutylaminopropyl)thiourea;
(553) N-{4-[(6,7-Dimethoxy-4-quinolyl)oxy]-2,5-dimethylphenyl}-N'-[3-(1-morpholino)propyl]thiourea;
(554) N-{4-[(6,7-Dimethoxy-4-quinolyl)oxy]-2,5-dimethylphenyl}-N'-[3-(2-methylpiperidinyl)propyl]-thiourea;
(555) N-{4-[(6,7-Dimethoxy-4-quinolyl)oxy]-2,5-dimethylphenyl}-N'-(2-diisopropylaminoethyl)thiourea;
(556) N-{4-[(6,7-Dimethoxy-4-quinolyl)oxy]-2,5-dimethylphenyl}-N'-[3-(4-methylpiperazinyl)propyl]-thiourea;
(557) N-{4-[(6,7-Dimethoxy-4-quinolyl)oxy]-2,3-dimethylphenyl}-N'-[3-(4-methylpiperazinyl)propyl]-thiourea;
(558) -{4-[(6,7-Dimethoxy-4-quinolyl)oxy]-2,3-dimethylphenyl}-N'-[3-(1-piperidinyl)propyl]thiourea;
(560) N-(1-Benzyltetrahydro-1H-3-pyrrolyl)-N'-{4-[(6,7-dimethoxy-4-quinolyl)oxy]phenyl}urea;
(561) Ethyl4-[({4-[(6,7-dimethoxy-4-quinolyl)oxy]anilino}carbonyl)amino]-1-piperidine-carboxylate;
(562) N-{4-[(6,7-Dimethoxy-4-quinolyl)oxy]-phenyl}-N'-(2,2,6,6-tetramethyl-4-piperidyl)urea;
(564) N-[(3R)-1-Benzyltetrahydro-1H-3-pyrrolyl]-N'-{4-[(6,7-dimethoxy-4-quinolyl)oxy]phenyl}urea;
(565) N-[(3S)-1-Benzyltetrahydro-1H-3-pyrrolyl]-N'-{4-[(6,7-dimethoxy-4-quinolyl)oxy]phenyl}-urea;
(568) N-{4-[(6,7-Dimethoxy-4-quinolyl)-oxy]phenyl}-N'-[1-(2-methylbenzyl)-4-piperidyl]urea;
(572) N-{4-[(6,7-Dimethoxy-4-puinolyl)oxy]-2,3-dimethylphenyl}-N'-[1-(2-methylbenzyl)tetrahydro-1H-3-pyrrolyl]urea;
(574) N-{4-[(6,7-Dimethoxy-4-quinolyl)oxy]-phenyl}-N'-[1-(2-methylbenzyl)tetrahydro-1H-3-pyrrolyl]-urea;
(579) N-[1-(2-Chlorobenzyl)tetrahydro-1H-3-pyrrolyl]-N'-{4-[(6,7-dimethoxy-4-quinolyl)oxy]phenyl}-urea;
(582) N-{1-[4-(Tert-butyl)benzyl]tetrahydro-1H-3-pyrrolyl}-N'-{4-[(6,7-dimethoxy-4-quinolyl)oxy]-phenyl}urea;
(585) N-[1-(Cyclohexylmethyl)tetrahydro-1H-3-pyrrolyl]-N'-{4-[(6,7-dimethoxy-4-quinolyl)oxy]-phenyl}urea;
(588) N-{4-[(6,7-Dimethoxy-4-quinolyl)oxy]-phenyl}-N'-(2-diethylaminopropyl)thiourea;
(589) N-{4-[(6,7-Dimethoxy-4-quinolyl)oxy]-phenyl}-N'-(2-diethylaminoethyl)thiourea;
(590) N-{4-[(6,7-Dimethoxy-4-quinolyl)-oxy]phenyl}-N'-[4-(N-benzyl)piperidinyl]urea;
(604) N-{4-[(6,7-Dimethoxy-4-quinolyl)oxy]-2,3-dimethylphenyl}-N'-[4-(N-benzyl)piperidinyl]urea;
(605) N-{4-[(6,7-Dimethoxy-4-quinolyl)oxy]-2-chlorophenyl}-N'-[4-(N-benzyl)piperidinyl]urea;
(607) N-{4-[(6,7-Dimethoxy-4-quinolyl)oxy]-2-methoxyphenyl}-N'-[4-(N-benzyl)piperidinyl]urea;
(614) N-{4-[(6,7-Dimethoxy-4-quinolyl)oxy]-phenyl}-N'-(2-methylbenzoyl)thiourea;
(616) N-{4-[(6,7-Dimethoxy-4-quinolyl)oxy]-2,5-dimethylphenyl}-N'-(2-morpholinoethyl)urea;
(617) N-{4-[(6,7-Dimethoxy-4-quinolyl)oxy]-2,3-dimethylphenyl}-N'-(2-morpholinoethyl)urea;
(618) N-{4-[(6,7-Dimethoxy-4-quinolyl)oxy]-phenyl}-N'-(2-tetrahydro-1H-1-pyrrolylethyl)urea;
(619) N-{4-[(6,7-Dimethoxy-4-quinolyl)oxy]-2,5-dimethylphenyl}-N'-(2-tetrahydro-1H-1-pyrrolyl-ethyl)urea;
(620) N-{4-[(6,7-Dimethoxy-4-quinolyl)oxy]-2,3-dimethylphenyl}-N'-(2-tetrahydro-1H-1-pyrrolyl-ethyl)urea;
(622) N-[2-(Diethylamino)ethyl]-N'-{4-[(6,7-dimethoxy-4-quinolyl)oxy]phenyl}urea;
(623) N-[2-(Diethylamino)ethyl]-N'-{4-[(6,7-dimethoxy-4-quinolyl)oxy]-2,5-dimethylphenyl}urea;
(624) N-[2-(Diethylamino)ethyl]-N'-{4-[(6,7-dimethoxy-4-quinolyl)oxy]-2,3-dimethylphenyl}urea;
(625) N-{4-[(6,7-Dimethoxy-4-quinolyl)oxy]-2,5-dimethylphenyl}-N'-[2-(dimethylamino)ethyl]urea;
(626) N-{4-[(6,7-Dimethoxy-4-quinolyl)oxy]-2,3-dimethylphenyl}-N'-[2-(dimethylamino)ethyl]urea;
(634) N-(1-Benzyl-4-piperidyl)-N'-{4-[(6,7-dimethoxy-4-quinolyl)oxy]-2,5-dimethylphenyl}urea;
(635) N-(1-Benzyl-4-piperidyl)-N'-{4-[(6,7-dimethoxy-4-quinolyl)oxy]-2,3-dimethylphenyl}urea;
(638) N-(1-Benzyl-4-piperidyl)-N'-{4-[(6,7-dimethoxy-4-quinolyl)oxy]-2-nitrophenyl}urea;
(639) N-(1-Benzyl-4-piperidyl)-N'-{4-[(6,7-dimethoxy-4-quinolyl)oxy]-3-fluorophenyl}urea;
(642) N-(1-Benzyl-4-piperidyl)-N'-{4-[(6,7-dimethoxy-4-quinolyl)oxy]-3-methylphenyl}urea;
(643) N-(1-Benzyl-4-piperidyl)-N'-{4-[(6,7-dimethoxy-4-quinolyl)oxy]-2-methylphenyl}urea;
(644) N-(1-Benzyl-4-piperidyl)-N'-{3-chloro-4-[(6,7-dimethoxy-4-quinolyl)oxy]phenyl}urea;
(646) N-[2-(Diethylamino)ethyl]-N'-{4-[(6,7-dimethoxy-4-quinolyl)oxy]-2-nitrophenyl}urea;
(648) N-[2-(Diethylamino)ethyl]-N'-{4-[(6,7-dimethoxy-4-quinolyl)oxy]-3-methylphenyl}urea;
(649) N-[2-(Diethylamino)ethyl]-N'-{4-[(6,7-dimethoxy-4-quinolyl)oxy]-2-methylphenyl}urea;
(650) N-{2-Chloro-4-[(6,7-dimethoxy-4-quinolyl)oxy]phenyl}-N'-[2-(diethylamino)ethyl]urea;
(651) N-{3-Chloro-4-[(6,7-dimethoxy-4-quinolyl)oxy]phenyl}-N'-[2-(diethylamino)ethyl]urea;

(654) N-[2-(Diisopropylamino)ethyl]-N'-{4-[(6,7-dimethoxy-4-quinolyl)oxy]phenyl}urea;
(655) N-[2-(Diisopropylamino)ethyl]-N'-{4-[(6,7-dimethoxy-4-quinolyl)oxy]-2,3-dimethylphenyl}urea;
(658) N-[2-(Diisopropylamino)ethyl]-N'-{4-[(6,7-dimethoxy-4-quinolyl)oxy]-2-nitrophenyl}urea;
(661) N-{4-[(6,7-Dimethoxy-4-quinolyl)oxy]phenyl}-N'-[2-(ethyl-3-methylanilino)-ethyl]urea;
(662) N-{4-[(6,7-Dimethoxy-4-quinolyl)oxy]-2,5-dimethylphenyl}-N'-[2-(ethyl-3-methylanilino)ethyl]-urea;
(663) N-{4-[(6,7-Dimethoxy-4-quinolyl)oxy]-2,3-dimethylphenyl}-N'-[2-(ethyl-3-methylanilino)ethyl]-urea;
(666) N-{4-[(6,7-Dimethoxy-4-quinolyl)oxy]-2-nitrophenyl}-N'-[2-(ethyl-3-methylanilino)ethyl]urea;
(669) N-{2-Chloro-4-[(6,7-dimethoxy-4-quinolyl)oxy]phenyl}-N'-[2-(ethyl-3-methylanilino)-ethyl]urea;
(670) N-{4-[(6,7-Dimethoxy-4-quinolyl)oxy]-2-methoxyphenyl}-N'-[2-(ethyl-3-methylanilino)ethyl]urea;
(671) N-[2-(Diisopropylamino)ethyl]-N'-{4-[(6,7-dimethoxy-4-quinolyl)oxy]-2,5-dimethylphenyl}urea;
(672) N-[2-(Diisopropylamino)ethyl]-N'-{4-[(6,7-dimethoxy-4-quinolyl)oxy]-2-methoxyphenyl}urea;
(673) N-{4-[(6,7-Dimethoxy-4-quinolyl)oxy]-phenyl}-N'-(2-piperidinoethyl)urea;
(674) N-{4-[(6,7-Dimethoxy-4-quinolyl)oxy]-2,5-dimethylphenyl}-N'-(2-piperidinoethyl)urea;
(675) N-{4-[(6,7-Dimethoxy-4-quinolyl)oxy]-2,3-dimethylphenyl}-N'-(2-piperidinoethyl)urea;
(678) N-{4-[(6,7-Dimethoxy-4-quinolyl)oxy]-2-nitrophenyl}-N'-(2-piperidinoethyl)urea;
(681) N-{4-[(6,7-Dimethoxy-4-quinolyl)oxy]-2-methoxyphenyl}-N'-(2-piperidinoethyl)urea;
(682) N-[2-(Dibutylamino)ethyl]-N'-{4-[(6,7-dimethoxy-4-quinolyl)oxy]phenyl}urea;
(683) N-[2-(Dibutylamino)ethyl]-N'-{4-[(6,7-dimethoxy-4-quinolyl)oxy]-2,5-dimethylphenyl}urea;
(684) N-[2-(Dibutylamino)ethyl]-N'-{4-[(6,7-dimethoxy-4-quinolyl)oxy]-2,3-dimethylphenyl}urea;
(689) N-[2-(Dibutylamino)ethyl]-N'-{4-[(6,7-dimethoxy-4-quinolyl)oxy]-2-methoxyphenyl}urea; and
(692) N-[(5-Bromo-2-thienyl)carbonyl]-N'-{4-[(6,7-dimethoxy-4-quinolyl)oxy]-2-methylphenyl}thiourea;
(693) N-[(5-Bromo-2-thienyl)carbonyl]-N'-{3-chloro-4-[(6,7-dimethoxy-4-quinolyl)oxy]phenyl}thiourea;
(694) N-[(5-Chloro-2-thienyl)carbonyl]-N'-{4[(6,7-dimethoxy-4-quinolyl)oxy]-2-methylphenyl}thio-urea;
(695) N-{3-Chloro-4-[(6,7-dimethoxy-4-quinolyl)oxy]phenyl}-N'-[(5-chloro-2-thienyl)carbonyl]-thiourea;
(698) N-{4-[(6,7-Dimethoxy-4-quinolyl)-oxy]-2-methylphenyl}-N'-[(2,5-dimethyl-3-furyl)-carbonyl]thiourea;
(699) N-{3-Chloro-4-[(6,7-dimethoxy-4-quinolyl)oxy]phenyl}-N'-[(2,5-dimethyl-3-furyl)-carbonyl]thiourea;
(706) N-Benzyl-N'-{3-chloro-4-[(6,7-dimethoxy-4-quinolyl)oxy]phenyl}thiourea
(717) N-{4-[(6,7-Dimethoxy-4-quinolyl)oxy]-2,5-dimethylphenyl}-N'-[(2,5-dimethyl-3-furyl)carbonyl]-thiourea;
(749) N-[(2,2-Dichloro-1-methylcyclopropyl)-carbonyl]-N'-{4-[(6,7-dimethoxy-4-quinolyl)oxy]phenyl}thiourea;
(750) N-{3-Chloro-4-[(6,7-dimethoxy-4-quinolyl)oxy]phenyl}-N'-[(2,2-dichloro-1-methylcyclo-propyl)carbonyl]thiourea;
(751) N-(4-Butoxybenzoyl)-N'-{4-[(6,7-dimethoxy-4-quinolyl)oxy]phenyl}thiourea;
(752) N-(4-Butoxybenzoyl)-N'-{3-chloro-4-[(6,7-dimethoxy-4-quinolyl)oxy]phenyl}thiourea;
(753) N-{4-[(6,7-Dimethoxy-4-quinolyl)oxy-phenyl}-N'-[4-(pentyloxy)benzoyl]thiourea;
(754) N-{3-Chloro-4-[(6,7-dimethoxy-4-quinolyl)oxy]phenyl}-N'-[4-(pentyloxy)benzoyl]thiourea;
(755) N-{4-[(6,7-Dimethoxy-4-quinolyl)oxy]-phenyl}-N'-[4-(hexyloxy)benzoyl]thiourea;
(756) N-{3-Chloro-4-[(6,7-dimethoxy-4-quinolyl)oxy]phenyl}-N'-[4-(hexyloxy)benzoyl]thiourea;
(759) N-{4-[(6,7-Dimethoxy-4-quinolyl)oxy]-phenyl}-N'-(2,2,3,3-tetramethylcyclopropyl)carbonyl ]-thiourea;
(760) N-{3-Chloro-4-[(6,7-dimethoxy-4-quinolyl)oxy]phenyl}-N'-[(2,2,3,3-tetramethylcyclo-propyl)carbonyl]thiourea;
(765) N-{4-[(6,7-Dimethoxy-4-quinolyl)oxy]-phenyl}-N'-tetrahydro-2-furanylcarbonylthiourea;
(766) N-{3-Chloro-4-[(6,7-dimethoxy-4-quinolyl)oxy]phenyl}-N'-tetrahydro-2-furanylcarbonyl-thiourea;
(767) N-{4-[(6,7-Dimethoxy-4-quinolyl)oxy]-phenyl}-N'-[(3-methoxycyclohexyl)carbonyl]thiourea;
(768) N-{3-Chloro-4-[(6,7-dimethoxy-4-quinolyl)oxy]phenyl}-N'-[(3-methoxycyclohexyl)carbonyl]-thiourea;
(897) N-Benzoyl-N'-{4-[(6,7-dimethoxy-4-quinolyl)oxy]phenyl}thiourea;
(898) N-(2-Chlorobenzoyl)-N'-{4-[(6,7-dimethoxy-4-quinolyl)oxy]phenyl}thiourea;
(899) N-{4-[(6,7-Dimethoxy-4-quinolyl)oxy]-phenyl}-N'-(2-fluorobenzoyl)thiourea;
(900) N-(2-Bromobenzoyl)-N'-{4-[(6,7-dimethoxy-4-quinolyl)oxy]phenyl}thiourea;
(901) N-{4-[(6,7-Dimethoxy-4-quinolyl)oxy]-phenyl}-N'-(2-methoxybenzoyl)thiourea;
(902) N-{4-[(6,7-Dimethoxy-4-quinolyl)oxy]-phenyl}-N'-[2-(trifluoromethyl)benzoyl]thiourea;
(903) N-Benzoyl-N'-{4-[(6,7-dimethoxy-4-quinolyl)oxy]-2-fluorophenyl}thiourea;
(904) N-{4-[(6,7-Dimethoxy-4-quinolyl)oxy]-2-fluorophenyl}-N'-(2-methylbenzoyl)thiourea;
(905) N-(2-Chlorobenzoyl)-N'-{4-[(6,7-dimethoxy-4-quinolyl)oxy]-2-fluorophenyl}thiourea;
(906) N-{4-[(6,7-Dimethoxy-4-quinolyl)oxy]-2-fluorophenyl}-N'-(2-fluorobenzoyl)thiourea;
(907) N-(2-Bromobenzoyl)-N'-{4-[(6,7-dimethoxy-4-quinolyl)oxy]-2-fluorophenyl}thiourea;
(908) N-{4-[(6,7-Dimethoxy-4-quinolyl)oxy]-2-fluorophenyl}-N'-(2-iodobenzoyl)thiourea;
(909) N-{4-[(6,7-Dimethoxy-4-quinolyl)oxy]-2-fluorophenyl}-N'-(2-methoxybenzoyl)thiourea;
(910) N-{4-[(6,7-Dimethoxy-4-quinolyl)oxy]-2-fluorophenyl}-N'-[2-(trifluoromethyl)benzoyl]thiourea;
(911) N-Benzoyl-N'-{4-[(6,7-dimethoxy-4-quinolyl)oxy]-3-fluorophenyl}thiourea;
(912) N-{4-[(6,7-Dimethoxy-4-quinolyl)oxy]-3-fluorophenyl}-N'-(2-methylbenzoyl)thiourea;
(913) N-(2-Chlorobenzoyl)-N'-{4-[(6,7-dimethoxy-4-quinolyl)oxy]-3-fluorophenyl}thiourea;
(914) N-(2-Bromobenzoyl)-N'-{4-[(6,7-dimethoxy-4-quinolyl)oxy]-3-fluorophenyl}thiourea;
(915) N-{4-[(6,7-Dimethoxy-4-quinolyl)oxy]-3-fluorophenyl}-N'-(2-iodobenzoyl)thiourea;
(916) N-{4-[(6,7-Dimethoxy-4-quinolyl)oxy]-3-fluorophenyl}-N'-(2-methoxybenzoyl)thiourea;
(917) N-{4-[(6,7-Dimethoxy-4-quinolyl)oxy]-3-fluorophenyl}-N'-[2-(trifluoromethyl) benzoyl]thiourea;

(918) N-Benzoyl-N'-{3-chloro-4-[(6,7-dimethoxy-4-quinolyl)oxy]phenyl}thiourea;
(919) N-{3-Chloro-4-[(6,7-dimethoxy-4-quinolyl)oxy]phenyl}-N'-(2-methylbenzoyl)thiourea;
(921) N-{3-Chloro-4-[(6,7-dimethoxy-4-quinolyl)oxy]phenyl}-N'-(2-fluorobenzoyl)thiourea;
(922) N-(2-Bromobenzoyl)-N'-{3-chloro-4-[(6,7-dimethoxy-4-quinolyl)oxy]phenyl}thiourea;
(923) N-{3-Chloro-4-[(6,7-dimethoxy-4-quinolyl)oxy]phenyl}-N'-(2-methoxybenzoyl)thiourea;
(924) N-{3-Chloro-4-[(6,7-dimethoxy-4-quinolyl)oxy]phenyl}-N'-[2-(trifluoromethyl)benzoyl]thiourea;
(925) N-{4-[(6,7-Dimethoxy-4-quinolyl)oxy]-2-nitrophenyl}-N'-(2-methylbenzoyl)thiourea;
(930) N-{4-[(6,7-Dimethoxy-4-quinolyl)oxy]-phenyl}-N'-(3-methylbenzoyl)thiourea;
(931) N-{4-[(6,7-Dimethoxy-4-quinolyl)oxy]-phenyl}-N'-(3-fluorobenzoyl)thiourea;
(932) N-(3-Chlorobenzoyl)-N'-{4-[(6,7-dimethoxy-4-quinolyl)oxy]phenyl}thiourea;
(933) N-{4-[(6,7-Dimethoxy-4-quinolyl)oxy]-phenyl}-N'-(3-methoxybenzoyl)thiourea;
(934) N-{4-[(6,7-Dimethoxy-4-quinolyl)oxy]-phenyl}-N'-[3-(trifluoromethyl)benzoyl]thiourea;
(935) N-(3-Bromobenzoyl)-N'-{4-[(6,7-dimethoxy-4-quinolyl)oxy]phenyl}thiourea;
(936) N-{4-[(6,7-Dimethoxy-4-quinolyl)oxy]-2-fluorophenyl}-N'-(3-methylbenzoyl)thiourea;
(937) N-{4-[(6,7-Dimethoxy-4-quinolyl)oxy]-2-fluorophenyl}-N'-(3-fluorobenzoyl)thiourea;
(938) N-(3-Chlorobenzoyl)-N'-{4-[(6,7-dimethoxy-4-quinolyl)oxy]-2-fluorophenyl}thiourea;
(939) N-{4-[(6,7-Dimethoxy-4-quinolyl)oxy]-2-fluorophenyl}-N'-(3-methoxybenzoyl)thiourea;
(940) N-(3-Bromobenzoyl)-N'-{4-[(6,7-dimethoxy-4-quinolyl)oxy]-2-fluorophenyl}thiourea;
(941) N-{4-[(6,7-Dimethoxy-4-quinolyl)oxy]-3-fluorophenyl}-N'-(3-methylbenzoyl)thiourea;
(942) N-{4-[(6,7-Dimethoxy-4-quinolyl)oxy]-3-fluorophenyl}-N'-(3-fluorobenzoyl)thiourea;
(943) N-(3-Chlorobenzoyl)-N'-{4-[(6,7-dimethoxy-4-quinolyl)oxy]-3-fluorophenyl}thiourea;
(944) N-{4-[(6,7-Dimethoxy-4-quinolyl)oxy]-3-fluorophenyl}-N'-(3-methoxybenzoyl)thiourea;
(945) N-{4-[(6,7-Dimethoxy-4-quinolyl)oxy]-3-fluorophenyl}-N'-[3-(trifluoromethyl)benzoyl]thiourea;
(946) N-(3-Bromobenzoyl)-N'-{4-[(6,7-dimethoxy-4-quinolyl)oxy]-3-fluorophenyl}thiourea;
(947) N-{3-Chloro-4-[(6,7-dimethoxy-4-quinolyl)oxy]phenyl}-N'-(3-methylbenzoyl)thiourea;
(948) N-{3-Chloro-4-[(6,7-dimethoxy-4-quinolyl)oxy]phenyl}-N'-(3-fluorobenzoyl)thiourea;
(949) N-(3-Chlorobenzoyl)-N'-[3-chloro-4-(6,7-dimethoxy-4-quinolyl)oxy]phenyl}thiourea;
(950) N-{3-Chloro-4-[(6,7-dimethoxy-4-quinolyl)oxy]phenyl}-N'-(3-methoxybenzoyl)thiourea;
(951) N-{3-Chloro-4-[(6,7-dimethoxy-4-quinolyl)oxy]phenyl}-N'-[3-(trifluoromethyl)benzoyl]-thiourea;
(952) N-(3-Bromobenzoyl)-N'-{3-chloro-4-[(6,7-dimethoxy-4-quinolyl)oxy]phenyl}thiourea;
(953) N-{4-[(6,7-Dimethoxy-4-quinolyl)oxy]-2-nitrophenyl}-N'-(3-methylbenzoyl)thiourea;
(959) N-{4-[(6,7-Dimethoxy-4-quinolyl)-oxy]phenyl}-N'-(4-methylbenzoyl)thiourea;
(960) N-(4-Chlorobenzoyl)-N'-{4-[(6,7-dimethoxy-4-quinolyl)oxy]phenyl}thiourea;
(961) N-{4-[(6,7-Dimethoxy-4-quinolyl)oxy]-phenyl}-N'-(4-fluorobenzoyl)thiourea;
(962) N-{4-[(6,7-Dimethoxy-4-quinolyl)oxy]-phenyl}-N'-(4-nitrobenzoyl)thiourea;
(963) N-{4-[(6,7-Dimethoxy-4-quinolyl)oxy]-phenyl}-N'-(4-methoxybenzoyl)thiourea;
(964) N-{4-[(6,7-Dimethoxy-4-quinolyl)oxy]-2-fluorophenyl}-N'-(4-methylbenzoyl)thiourea;
(965) N-(4-Chlorobenzoyl)-N'-{4-[(6,7-dimethoxy-4-quinolyl)oxy]-2-fluorophenyl}thiourea;
(966) N-{4-[(6,7-Dimethoxy-4-quinolyl)oxy]-2-fluorophenyl}-N'-(4-fluorobenzoyl)thiourea;
(967) N-{4-[(6,7-Dimethoxy-4-quinolyl)oxy]-2-fluorophenyl}-N'-(4-iodobenzoyl)thiourea;
(968) N-{4-[(6,7-Dimethoxy-4-quinolyl)oxy]-2-fluorophenyl}-N'-(4-nitrobenzoyl)thiourea;
(969) N-{4-[(6,7-Dimethoxy-4-quinolyl)oxy]-2-fluorophenyl}-N'-(4-methoxybenzoyl)thiourea;
(970) N-{4-[(6,7-Dimethoxy-4-quinolyl)oxy]-3-fluorophenyl}-N'-(4-methylbenzoyl)thiourea;
(971) N-(4-Chlorobenzoyl)-N'-{4-[(6,7-dimethoxy-4-quinolyl)oxy]-3-fluorophenyl}thiourea;
(972) N-{4-[(6,7-Dimethoxy-4-quinolyl)oxy]-3-fluorophenyl}-N'-(4-fluorobenzoyl)thiourea;
(973) N-(4-Bromobenzoyl)-N'-{4-[(6,7-dimethoxy-4-quinolyl)oxy]-3-fluorophenyl}thiourea;
(974) N-{4-[(6,7-Dimethoxy-4-quinolyl)oxy]-3-fluorophenyl}-N'-(4-iodobenzoyl)thiourea;
(975) N-{4-[(6,7-Dimethoxy-4-quinolyl)oxy]-3-fluorophenyl}-N'-(4-nitrobenzoyl)thiourea;
(976) N-{4-[(6,7-Dimethoxy-4-quinolyl)oxy]-3-fluorophenyl}-N'-(4-methoxybenzoyl)thiourea;
(977) N-{3-Chloro-4-[(6,7-dimethoxy-4-quinolyl)oxy]phenyl}-N'-(4-methylbenzoyl)thiourea;
(978) N-(4-Chlorobenzoyl)-N'-[3-chloro-4-(6,7-dimethoxy-4-quinolyl)oxy]phenyl}thiourea;
(979) N-{3-Chloro-4-[(6,7-dimethoxy-4-quinolyl)oxy]phenyl}-N'-(4-fluorobenzoyl)thiourea;
(980) N-(4-Bromobenzoyl)-N'-{3-chloro-4-[(6,7-dimethoxy-4-quinolyl)oxy]phenyl}thiourea;
(981) N-{3-Chloro-4-[(6,7-dimethoxy-4-quinolyl)oxy]phenyl}-N'-(4-iodobenzoyl)thiourea;
(982) N-{3-Chloro-4-[(6,7-dimethoxy-4-quinolyl)oxy]phenyl}-N'-(4-nitrobenzoyl)thiourea;
(983) N-{3-Chloro-4-[(6,7-dimethoxy-4-quinolyl)oxy]phenyl}-N'-(4-methoxybenzoyl)thiourea;
(989) N-(1,3-Benzodioxol-5-ylcarbonyl)-N'-{4-[(6,7-dimethoxy-4-quinolyl)oxy]phenyl}thiourea;
(990) N-{4-[(6,7-Dimethoxy-4-quinolyl)oxy]-3-fluorophenyl}-N'-(4-ethoxybenzoyl)thiourea;
(991) N-{4-[(6,7-Dimethoxy-4-quinolyl)oxy]-3-fluorophenyl}-N'-(4-phenylbenzoyl)thiourea;
(992) N-{3-Chloro-4-[(6,7-dimethoxy-4-quinolyl)oxy]phenyl}-N'-(4-ethoxybenzoyl)thiourea;
(993) N-{4-[(6,7-Dimethoxy-4-quinolyl)oxy]-2-fluoropheny}-N'-(4-ethylbenzoyl)thiourea;
(994) N-{4-[(6,7-Dimethoxy-4-quinolyl)oxy]-2-fluorophenyl}-N'-(4-propylbenzoyl)thiourea;
(995) N-(4-Butylbenzoyl)-N'-{4-[(6,7-dimethoxy-4-quinolyl)oxy]-2-fluorophenyl}thiourea;
(996) N-[4-(Chloromethyl)benzoyl]-N'-{4-[(6,7-dimethoxy-4-quinolyl)oxy]-2-fluorophenyl}thiourea;
(997) N-{4-[(6,7-Dimethoxy-4-quinolyl)oxy]-3-fluorophenyl}-N'-(4-ethylbenzoyl)thiourea;
(998) N-{4-[(6,7-Dimethoxy-4-quinolyl)oxy]-3-fluorophenyl}-N'-(4-propylbenzoyl)thiourea;

(999) N-(4-Butylbenzoyl)-N'-{4-[(6,7-dimethoxy-4-quinolyl)oxy]-3-fluorophenyl}thiourea;
(1000) N-[4-(Chloromethyl)benzoyl]-N'-{4-[(6,7-dimethoxy-4-quinolyl)oxy]-3-fluorophenyl}thiourea;
(1001) N-{3-Chloro-4-[(6,7-dimethoxy-4-quinolyl)oxy]phenyl}-N'-(4-propylbenzoyl)thiourea;
(1003) N-{4-[(6,7-Dimethoxy-4-quinolyl)oxy]-phenyl}-N'-(2,4-dimethylbenzoyl)thiourea;
(1004) N-{4-[(6,7-Dimethoxy-4-quinolyl)oxy]-phenyl}-N'-(2,5-dimethylbenzoyl)thiourea;
(1005) N-{4-[(6,7-Dimethoxy-4-quinolyl)oxy]-phenyl}-N'-(2,3-dimethylbenzoyl)thiourea;
(1006) N-(2,4-Difluorobenzoyl)-N'-{4-[(6,7-dimethoxy-4-quinolyl)oxy]phenyl}thiourea;
(1007) N-(2,6-Difluorobenzoyl)-N'-{4-[(6,7-dimethoxy-4-quinolyl)oxy]phenyl}thiourea;
(1008) N-(2,4-Dichlorobenzoyl)-N'-{4-[(6,7-dimethoxy-4-quinolyl)oxy]phenyl}thiourea;
(1009) N-(3,5-Dichlorobenzoyl)-N'-{4-[(6,7-dimethoxy-4-quinolyl)oxy]phenyl}thiourea;
(1010) N-(3,4-Dimethoxybenzoyl)-N'-{4-[(6,-dimethoxy-4-quinolyl)oxy]phenyl}thiourea;
(1011) N-(2,4-Dichlorobenzoyl)-N'-{4-[(6,7-dimethoxy-4-quinolyl)oxy]-2-fluorophenyl}thiourea;
(1012) N-(2,6-Dichlorobenzoyl)-N'-{4-[(6,7-dimethoxy-4-quinolyl)oxy]-2-fluorophenyl}thiourea;
(1013) N-(2,4-Difluorobenzoyl)-N'-{4-[(6,7-dimethoxy-4-quinolyl)oxy]-3-fluorophenyl}thiourea;
(1014) N-(2,4-Dichlorobenzoyl)-N'-{4-[(6,7-dimethoxy-4-quinolyl)oxy]-3-fluorophenyl}thiourea;
(1015) N-(3,5-Dichlorobenzoyl)-N'-{4-[(6,7-Dimethoxy-4-quinolyl)oxy]-3-fluorophenyl}thiourea;
(1016) N-{3-Chloro-4-[(6,7-dimethoxy-4-quinolyl)oxy]phenyl}-N'-(2,4-dimethylbenzoyl)thiourea;
(1017) N-{3-Chloro-4-[(6,7-dimethoxy-4-quinolyl)oxy]phenyl}-N'-(2,5-dimethylbenzoyl)thiourea;
(1018) N-{3-Chloro-4-[(6,7-dimethoxy-4-quinolyl)oxy]phenyl}-N'-(2,3-dimethylbenzoyl)thiourea;
(1019) N-{3-Chloro-4-[(6,7-dimethoxy-4-quinolyl)oxy]phenyl}-N'-(3,5-dimethylbenzoyl)thiourea;
(1020) N-{3-Chloro-4-[(6,7-dimethoxy-4-quinolyl)oxy]phenyl}-N'-(2,6-difluorobenzoyl)thiourea;
(1033) N-{4-[(6,7-Dimethoxy-4-quinolyl)oxy]-phenyl}-N'-(2-furylcarbonyl)thiourea;
(1034) N-{4-[(6,7-Dimethoxy-4-quinolyl)oxy]-phenyl}-N'-(3-thienylcarbonyl)thiourea;
(1035) N-{4-[(6,7-Dimethoxy-4-quinolyl)oxy]-2-fluorophenyl}-N'-(2-furylcarbonyl)thiourea;
(1036) N-{4-[(6,7-Dimethoxy-4-quinolyl)oxy]-2-fluorophenyl}-N'-(3-thienylcarbonyl)thiourea;
(1037) N-{4-[(6,7-Dimethoxy-4-quinolyl)oxy]-2-fluorophenyl}-N'-[(2,5-dimethyl-3-furyl)carbonyl]-thiourea;
(1038) N-{4-[(6,7-Dimethoxy-4-quinolyl)oxy]-2-fluorophenyl}-N'-[(3-methyl-2-thienyl)carbonyl]thio-urea;
(1039) N-{4-[(6,7-Dimethoxy-4-quinolyl)oxy]-3-fluorophenyl}-N'-[(2,5-dimethyl-3-furyl)carbonyl]thio-urea;
(1040) N-{4-[(6,7-Dimethoxy-4-quinolyl)oxy]-3-fluorophenyl}-N'-[(5-methyl-2-thienyl)carbonyl]thio-urea;
(1044) N-{4-[(6,7-Dimethoxy-4-quinolyl)oxy]-phenyl}-N'-tetrahydro-1H-1-pyrrolylcarbonylthiourea;
(1045) N-{4-[(6,7-Dimethoxy-4-quinolyl)oxy]-phenyl}-N'-morpholinocarbonylthiourea;
(1051) N-{3-Chloro-4-[(6,7-dimethoxy-4-quinolyl)oxy]phenyl}-N'-tetrahydro-1H-1-pyrrolyl-carbonylthiourea;
(1052) N-{3-Chloro-4-[(6,7-dimethoxy-4-quinolyl)oxy]phenyl}-N'-morpholinocarbonylthiourea;
(1055) N-{4-[(6,7-Dimethoxy-4-quinolyl)oxy]-phenyl}-N'-[(2-phenylcyclopropyl)carbonyl]thiourea;
(1056) N-Cyclopropylcarbonyl-N'-{4-[(6,7-dimethoxy-4-quinolyl)oxy]-3-fluorophenyl}thiourea;
(1057) N-{4-[(6,7-Dimethoxy-4-quinolyl)oxy]-3-fluorophenyl}-N'-[(2-phenylcyclopropyl)carbonyl]thio-urea;
(1058) N-{3-Chloro-4-[(6,7-dimethoxy-4-quinolyl)oxy]phenyl}-N'-cyclopropylcarbonylthiourea;
(1059) N-{3-Chloro-4-[(6,7-dimethoxy-4-quinolyl)oxy]phenyl}-N'-[(2-phenylcyclopropyl)carbonyl]-thiourea;
(1061) N-Cyclopentylcarbonyl-N'-{4-[(6,7-dimethoxy-4-quinolyl)oxy]phenyl}thiourea;
(1062) N-Cyclohexylcarbonyl-N'-{4-[(6,7-dimethoxy-4-quinolyl)oxy]phenyl}thiourea;
(1063) N-Cyclopentylcarbonyl-N'-{4-[(6,7-dimethoxy-4-quinolyl)oxy]-2-fluorophenyl}thiourea;
(1064) N-Cyclohexylcarbonyl-N'-{4-[(6,7-dimethoxy-4-quinolyl)oxy]-2-fluorophenyl}thiourea;
(1070) N-(3,4-Dimethoxybenzoyl)-N'-{4-[(6,7-dimethoxy-4-quinolyl)oxy]-3-fluorophenyl}thiourea;
(1078) N-(2-Chlorobenzoyl)-N'-{4-[(6,7-dimethoxy-4-quinolyl)oxy]-2,3-dimethylphenyl}thiourea;
(1079) N-{4-[(6,7-Dimethoxy-4-quinolyl)oxy]-2,3-dimethylphenyl}-N'-(3-methylbenzoyl)thiourea;
(1080) N-{4-[(6,7-Dimethoxy-4-quinolyl)oxy]-2,3-dimethylphenyl}-N'-(4-methylbenzoyl)thiourea;
(1081) N-{4-[(6,7-Dimethoxy-4-quinolyl)oxy]-2,3-dimethylphenyl}-N'-(4-nitrobenzoyl)thiourea;
(1082) N-(4-Chlorobenzoyl)-N'-{4-[(6,7-dimethoxy-4-quinolyl)oxy]-2,3-dimethylphenyl}thiourea;
(1083) N-(3-Chlorobenzoyl)-N'-{4-[(6,7-dimethoxy-4-quinolyl)oxy]-2,3-dimethylphenyl}thiourea;
(1084) N-Benzoyl-N'-{4-[(6,7-dimethoxy-4-quinolyl)oxy]-2,3-dimethylphenyl}thiourea;
(1085) N-{4-[(6,7-Dimethoxy-4-quinolyl)oxy]-2,3-dimethylphenyl}-N'-(2-methylbenzoyl)thiourea;
(1086) N-(2,4-Dichlorobenzoyl)-N'-{4-[(6,7-dimethoxy-4-quinolyl)oxy]-22-dimethylphenyl}thiourea;
(1087) N-{4-[(6,7-Dimethoxy-4-quinolyl)oxy]-2,3-dimethylphenyl}-N'-(4-methoxybenzoyl)thiourea;
(1088) N-(2,4-Difluorobenzoyl)-N'-{4-[(6,7-dimethoxy-4-quinolyl)oxy]-2,3-dimethylphenyl}thiourea;
(1089) N-(4-Chlorobenzoyl)-N'-{4-[(6,7-dimethoxy-4-quinolyl)oxy]-2-methylphenyl}thiourea;
(1090) N-{4-[(6,7-Dimethoxy-4-quinolyl)oxy]-2-methylphenyl}-N'-(2-methylbenzoyl)thiourea;
(1091) N-{4-[(6,7-Dimethoxy-4-quinolyl)oxy]-2-methylphenyl}-N'-(3-fluorobenzoyl)thiourea;
(1092) N-{4-[(6,7-Dimethoxy-4-quinolyl)oxy]-2-methylphenyl}-N'-(4-nitrobenzoyl)thiourea;
(1093) N-{4-[(6,7-Dimethoxy-4-quinolyl)oxy]-2-methylphenyl}-N'-(4-fluorobenzoyl)thiourea;
(1094) N-{4-[(6,7-Dimethoxy-4-quinolyl)oxy]-2-methylphenyl}-N'-(2-fluorobenzoyl)thiourea;
(1095) N-{4-[(6,7-Dimethoxy-4-quinolyl)oxy]-2-methylphenyl}-N'-(4-methoxybenzoyl)thiourea;
(1096) N-{4-[(6,7-Dimethoxy-4-quinolyl)oxy]-2-methylphenyl}-N'-(4-methylbenzoyl)thiourea;
(1097) N-(2-Chlorobenzoyl)-N'-{4-[(6,7-dimethoxy-4-quinolyl)oxy]-2-methylphenyl}thiourea;
(1098) N-{4-[(6,7-Dimethoxy-4-quinolyl)oxy]-2-methylphenyl}-N'-(3-methylbenzoyl)thiourea;
(1099) N-Benzoyl-N'-{4-[(6,7-dimethoxy-4-quinolyl)oxy]-2-methylphenyl}thiourea;

(1100) N-(3-Chlorobenzoyl)-N'-{4-[(6,7-dimethoxy-4-quinolyl)oxy]-2-methylphenyl}thiourea;
(1101) N-{2-Chloro-4-[(6,7-dimethoxy-4-quinolyl)oxy]phenyl}-N'-(2-methylbenzoyl)thiourea;
(1102) N-{2-Chloro-4-[(6,7-dimethoxy-4-quinolyl)oxy]phenyl}-N'-(4-methylbenzoyl)thiourea;
(1103) N-{2-Chloro-4-[(6,7-dimethoxy-4-quinolyl)oxy]phenyl}-N'-(2-methoxybenzoyl)thiourea;
(1104) N-(2-Chlorobenzoyl)-N'-{2-chloro-4-[(6,7-dimethoxy-4-quinolyl)oxy]phenyl}thiourea;
(1107) N-Benzoyl-N'-{2-chloro-4-[(6,7-dimethoxy-4-quinolyl)oxy]phenyl}thiourea;
(1108) N-{4-[(6,7-Dimethoxy-4-quinolyl)oxy]-3-methylphenyl}-N'-(4-nitrobenzoyl)thiourea;
(1109) N-Benzoyl-N'-{4-[(6,7-dimethoxy-4-quinolyl)oxy]-3-methylphenyl}thiourea;
(1110) N-{4-[(6,7-Dimethoxy-4-quinolyl)oxy]-3-methylphenyl}-N'-(3-methylbenzoyl)thiourea;
(1111) N-(4-Chlorobenzoyl)-N'-{4-[(6,7-dimethoxy-4-quinolyl)oxy]-3-methylphenyl}thiourea;
(1112) N-(2,6-Dichlorobenzoyl)-N'-{4-[(6,7-dimethoxy-4-quinolyl)oxy]-3-fluorophenyl}thiourea;
(1113) N-(2,4-Dimethoxybenzoyl)-N'-{4-[(6,7-dimethoxy-4-quinolyl)oxy]-3-fluorophenyl}thiourea;
(1114) N-{3-Chloro-4-[(6,7-dimethoxy-4-quinolyl)oxy]phenyl}-N'-(2,4-dichlorobenzoyl)thiourea;
(1115) N-{3-Chloro-4-[(6,7-dimethoxy-4-quinolyl)oxy]phenyl}-N'-(2,6-dichlorobenzoyl)thiourea;
(1116) N-{3-Chloro-4-[(6,7-dimethoxy-4-quinolyl)oxy]phenyl}-N'-(3,5-dichlorobenzoyl)thiourea;
(1117) N-{3-Chloro-4-[(6,7-dimethoxy-4-quinolyl)oxy]phenyl}-N'-(2,4-dimethoxybenzoyl)thiourea;
(1118) N-(2,6-Dichlorobenzoyl)-N'-{4-[(6,7-dimethoxy-4-quinolyl)oxy]phenyl}thiourea;
(1119) N-(2,4-Dimethoxybenzoyl)-N'-{4-[(6,7-dimethoxy-4-quinolyl)oxy]phenyl}thiourea;
(1120) N-(3,4-Dichlorobenzoyl)-N'-{4-[(6,7-dimethoxy-4-quinolyl)oxy]phenyl}thiourea;
(1121) N-(2,4-Difluorobenzoyl)-N'-{4-[(6,7-dimethoxy-4-quinolyl)oxy]-2-fluorophenyl}thiourea;
(1122) N-(3,5-Dichlorobenzoyl)-N'-{4-[(6,7-dimethoxy-4-quinolyl)oxy]-2-fluorophenyl}thiourea;
(1123) N-(2,4-Dimethoxybenzoyl)-N'-{4-[(6,7-dimethoxy-4-quinolyl)oxy]-2-fluorophenyl}thiourea;
(1124) N-(4-Cyclohexylbenzoyl)-N'-{4-[(6,7-dimethoxy-4-quinolyl)oxy]phenyl}thiourea;
(1125) N-(4-Phenylbenzoyl)-N'-{4-[(6,7-dimethoxy-4-quinolyl)oxy]-2-fluorophenyl}thiourea;
(1126) N-(1,3-Benzodioxol-5-ylcarbonyl)-N'-{3-chloro-4-[(6,7-dimethoxy-4-quinolyl)oxy]phenyl}thio-urea;
(1127) N-{3-Chloro-4-[(6,7-dimethoxy-4-quinolyl)oxy]phenyl}-N'-(4-cyclohexylbenzoyl)thiourea;
(1128) N-{4-[(6,7-Dimethoxy-4-quinolyl)oxy]-phenyl}-N'-(4-octylbenzoyl)thiourea;
(1129) N-{4-[(6,7-Dimethoxy-4-quinolyl)oxy]-phenyl}-N'-(3,5-dimethylbenzoyl)thiourea;
(1130) N-{4-[(6,7-Dimethoxy-4-quinolyl)oxy]-phenyl}-N'-(1,2,3,4-tetrahydro-2-isoquinolylcarbonyl)-thiourea;
(1136) N-[4-(Chloromethyl)benzoyl]-N'-{4-[(6,7-dimethoxy-4-quinolyl)oxy]phenyl}thiourea;
(1137) N-{3-Chloro-4-[(6,7-dimethoxy-4-quinolyl)oxy]phenyl}-N'-[4-(chloromethyl)benzoyl]thio-urea;
(1143) N-{4-[(6,7-Dimethoxy-4-quinolyl)oxy]-phenyl}N-ethyl-N'-[(2-phenylcyclopropyl)carbonyl]thio-urea;
(1146) N-{4-[(6,7-Dimethoxy-4-quinolyl)oxy]-phenyl}-N'-[(5-methyl-2-thienyl)carbonyl]thiourea;
(1152) N-{4-[(6,7-Dimethoxy-4-quinolyl)oxy]-phenyl}-N'-(3-pyridylcarbonyl)thiourea;
(1153) N-{4-[(6,7-Dimethoxy-4-quinolyl)oxy]-phenyl}-N'-[4-(morpholinomethyl)benzoyl]thiourea; (1159) N-{2-Chloro-4-[(6,7-dimethoxy-4-quinolyl)oxy]phenyl}-N'-(3,5-dichlorobenzoyl)thiourea;
(1160) N-{4-[(6,7-Dimethoxy-4-quinolyl)oxy]-3-fluorophenyl}-N'-(2-fluorobenzoyl)thiourea;
(1163) N-{2-Chloro-4-[(6,7-dimethoxy-4-quinolyl)oxy]phenyl}-N'-(3-fluorobenzoyl)thiourea;
(1165) N-(3-Bromobenzoyl)-N'-{2-chloro-4-[(6,7-dimethoxy-4-quinolyl)oxy]phenyl}thiourea;
(1166) N-(4-Bromobenzoyl)-N'-{4-[(6,7-dimethoxy-4-quinolyl)oxy]phenyl}thiourea;
(1167) N-(4-Bromobenzoyl)-N'-{2-chloro-4-[(6,7-dimethoxy-4-quinolyl)oxy]phenyl}thiourea;
(1173) N-{2-Chloro-4-[(6,7-dimethoxy-4-quinolyl)oxy]phenyl}-N'-(4-methoxybenzoyl)thiourea;
(1174) N-(4-Chlorobenzoyl)-N'-{2-chloro-4-[(6,7-dimethoxy-4-quinolyl)oxy]phenyl}thiourea;
(1176) N-{2-Chloro-4-[(6,7-dimethoxy-4-quinolyl)oxy]phenyl}-N'-(2,4dimethoxybenzoyl)thiourea;
(1179) N-{3-Chloro-4-[(6,7-dimethoxy-4-quinolyl)oxy]phenyl}-N'-cyclohexylcarbonylthiourea;
(1182) N-{3-Chloro-4-[(6,7-dimethoxy-4-quinolyl)oxy]phenyl}-N'-cyclopentylcarbonylthiourea;
(1190) N-{3-Chloro-4-[(6,7-dimethoxy-4-quinolyl)oxy]phenyl}-N'-[(2-methylcyclopropyl)carbonyl]thiourea;
(1192) N-{3-Chloro-4-[(6,7-dimethoxy-4-quinolyl)oxy]phenyl}-N'-[(1-methylcyclohexyl)carbonyl]-thiourea;
(1194) N-{3-Chloro-4-[(6,7-dimethoxy-4-quinolyl)oxy]phenyl}-N'-[(1-phenylcyclopropyl)carbonyl]-thiourea;
(1196) N-{3-Chloro-4-[(6,7-dimethoxy-4-quinolyl)oxy]phenyl}-N'-[(4-propylcyclohexyl)carbonyl]-thiourea;
(1202) N-{2-Chloro-4-[(6,7-dimethoxy-4-quinolyl)oxy]phenyl}-N'-(2,4-difluorobenzoyl)thiourea;
(1204) N-{3-Chloro-4-[(6,7-dimethoxy-4-quinolyl)oxy]phenyl}-N'-(3,4-dimethoxybenzoyl)thiourea;
(1208) N-{3-Chloro-4-[(6,7-dimethoxy-4-quinolyl)oxy]phenyl}-N'-(2,4-difluorobenzoyl)thiourea; and
(1209) N-{3-Chloro-4-[(6,7-dimethoxy-4-quinolyl)oxy]phenyl}-N'-(4-octylbenzoyl)thiourea.

24. A compound represented by formula (I) or a pharmacologically acceptable salt or solvate thereof:

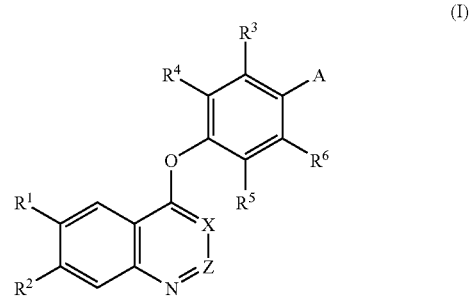

(I)

wherein
X and Z represent —CH;
$R^1$ and $R^2$ represent $C_{1-4}$ alkoxy;
$R^3$, $R^4$, $R^5$, and $R^6$, which may be the same or different, represent a hydrogen atom; a halogen atom; $C_{1-4}$ alkyl optionally substituted by a halogen atom; $C_{1-4}$ alkoxy optionally substituted by a halogen atom; nitro; amino; or morpholyl; and A represents group (viii):

(viii)

wherein
w is an integer of 1 to 4,
L represents —O—, —S(=O)$_y$—, wherein y is an integer of 0 to 2, or —N(—R$^{11}$)—,
M represents —O—, —C(=O)—O—, —S(=O)$_z$—, wherein z is an integer of 0 to 2, —N(—R$^{12}$)—, —C(=O)—N(—R$^{12}$)—, or —C(=O)—,
R$^{11}$ and R$^{12}$, which may be the same or different, represent a hydrogen atom, $C_{1-4}$ alkyl optionally substituted by a halogen atom, or $C_{1-4}$ alkylcarbonyl optionally substituted by a halogen atom;
R$^{22}$ represents a hydrogen atom; $C_{1-4}$ alkyl optionally substituted by a halogen atom; or phenyl optionally substituted by $C_{1-4}$ alkyl optionally substituted by a halogen atom, $C_{1-4}$ alkoxy optionally substituted by a halogen atom, nitro, amino, or a halogen atom,
when M represents —N(—R )— or —C(=O)—N(—R$^{12}$)—, R$^{22}$ and R$^{12}$ may form a five- to seven-membered saturated or unsaturated heterocyclic ring optionally containing one or more additional hetero-atoms together with the nitrogen atom to which they are attached, this heterocyclic ring is optionally condensed with another carbocyclic ring or heterocyclic ring to form a ten- to twelve-membered bicyclic saturated or unsaturated heterocyclic ring, and these heterocyclic rings are optionally substituted by $C_{1-4}$ alkyl optionally substituted by a halogen atom; phenyl; benzyl; or piperidine;
wherein, when L represents —O—, then M represents —O—, —C(=O)—O—, —N(—R$^{12}$)—, —C(=O)—N(R$^{12}$)—, or —C(=O)—; when L represents —S(=O)—, M represents —O—; and, when L represents —N(—R$^{11}$)—, then M represents —O—.

25. The compound of claim 25, which is selected from the group consisting of:
(776) N1-(2-Methoxyphenyl)-2-{4-[(6,7-dimethoxy-4-quinolyl)oxy]phenoxy}acetamide;
(777) N-(2-{4-[(6,7-Dimethoxy-4-quinolyl)-oxy]phenoxy}ethyl)-N-(2-methoxyphenyl)amine;
(778) N1-(3-Methoxyphenyl)-2-{4-[(6,7-dimethoxy-4-quinolyl)oxy]phenoxy}acetamide;
(779) N-(2-{4-[(6,7-Dimethoxy-4-quinolyl)-oxy]phenoxy}ethyl)-N-(3-methoxyphenyl)amine;
(780) N1-(4-Methoxyphenyl)-2-{4-[(6,7-dimethoxy-4-quinolyl)oxy]phenoxy}acetamide;
(781) N-(2-{4-[(6,7-Dimethoxy-4-quinolyl)-oxy]phenoxy}ethyl)-N-(4-methoxyphenyl)amine;
(782) N1-(2-Methylphenyl)-2-{4-[(6,7-dimethoxy-4-quinolyl)oxy]phenoxy}acetamide;
(783) N-(2-{4-[(6,7-Dimethoxy-4-quinolyl)-oxy]phenoxy}ethyl)-N-(2-methylphenyl)amine;
(784) N1-(3-Methylphenyl)-2-{4-[(6,7-dimethoxy-4-quinolyl)oxy]phenoxy}acetamide;
(785) N-(2-{4-[(6,7-Dimethoxy-4-quinolyl)-oxy]phenoxy}ethyl)-N-(3-methylphenyl)amine;
(786) N1-(4-Methylphenyl)-2-{4-[(6,7-dimethoxy-4-quinolyl)oxy]phenoxy}acetamide;
(787) N-(2-{4-[(6,7-Dimethoxy-4-quinolyl)-oxy]phenoxy}ethyl)-N-(4-methylphenyl)amine;
(788) N1-(3-Chlorophenyl)-2-{4-[(6,7-dimethoxy-4-quinolyl)oxy]phenoxy}acetamide;
(789) N1-(4-Chlorophenyl)-2-{4-[(6,7-dimethoxy-4-quinolyl)oxy]phenoxy}acetamide;
(790) 6,7-Dimethoxy-4-{4-[3-(4-methyl-phenoxy)propoxy]phenoxy}quinoline;
(791) 6,7-Dimethoxy-4-{4-[3-(3-methyl-phenoxy)propoxy]phenoxy}quinoline;
(792) 6,7-Dimethoxy-4-{4-[3-(2-methyl-phenoxy)propoxy]phenoxy}quinoline;
(793) 6,7-Dimethoxy-4-{4-[3-(3-methoxy-phenoxy)propoxy]phenoxy}quinoline;
(794) 6,7-Dimethoxy-4-{4-[3-(4-methoxy-phenoxy)propoxy]phenoxy}quinoline;
(795) 6,7-Dimethoxy-4-{4-[3-(2-methoxy-phenoxy)propoxy]phenoxy}quinoline;
(796) 4-{4-[3-(2-Fluorophenoxy)propoxy]-phenoxy}-6,7-dimethoxyquinoline;
(797) 4-{4-[3-(3-Fluorophenoxy)propoxy]-phenoxy}-6,7-dimethoxyquinoline;
(798) 4-{4-[3-(4-Fluorophenoxy)propoxy]-phenoxy}-6,7-dimethoxyquinoline;
(799) 4-{4-[3-(2,6-Dimethylphenoxy)propoxy]-phenoxy}-6,7-dimethoxyquinoline;
(812) 6,7-Dimethoxy-4-(4-{[2-(3-methoxy-phenoxy)ethyl]sulfanyl}phenoxy)quinoline;
(813) 6,7-Dimethoxy-4-(4-{[2-(4-methoxy-phenoxy)ethyl]sulfanyl}phenoxy)quinoline;
(814) 6,7-Dimethoxy-4-(4-{[2-(4-methyl-phenoxy)ethyl]sulfanyl}phenoxy)quinoline;
(815) 4-(4-{[2-(2-Isopropylphenoxy)ethyl]-sulfanyl}phenoxy)-6,7-dimethoxyquinoline;
(816) 4-(4-{[2-(4-Isopropylphenoxy)ethyl]-sulfanyl}phenoxy)-6,7-dimethoxyquinoline;
(817) 6,7-Dimethoxy-4-(4-{[2-(2-methyl-phenoxy)ethyl]sulfanyl}phenoxy)quinoline;
(818) 4-(4-{[2-(4-Chlorophenoxy)ethyl]-sulfanyl}phenoxy)-6,7-dimethoxyquinoline;
(819) 4-(4-{[2-(2-Chlorophenoxy)ethyl]-sulfanyl}phenoxy)-6,7-dimethoxyquinoline;
(820) 4-(4-{[2-(3-Chlorophenoxy)ethyl]-sulfanyl}phenoxy)-6,7-dimethoxyquinoline;
(821) 4-(4-{[2-(3-Fluorophenoxy)ethyl]-sulfanyl}phenoxy)-6,7-dimethoxyquinoline;
(822) 4-(4-{[2-(2-Fluorophenoxy)ethyl]-sulfanyl}phenoxy)-6,7-dimethoxyquinoline;
(823) 6,7-Dimethoxy-4-(4-{[2-(3-methyl-phenoxy)ethyl]sulfanyl}phenoxy)quinoline;
(824) 4-(4-{[2-(4-Fluorophenoxy)ethyl]-sulfanyl}phenoxy)-6,7-dimethoxyquinoline;
(825) 4-(4-{[2-(2,4-Dichlorophenoxy)ethyl]-sulfanyl}phenoxy)-6,7-dimethoxyquinoline;
(826) 4-(4-{[2-(2,4-Dimethylphenoxy)ethyl]-sulfanyl}phenoxy)-6,7-dimethoxyquinoline;
(827) 4-(4-{[2-(3    ,4-Dimethylphenoxy)ethyl]-sulfanyl}phenoxy)-6,7-dimethoxyquinoline;
(828) 4-(4-{[2-(2,6-Dimethylphenoxy)ethyl]-sulfanyl}phenoxy)-6,7-dimethoxyquinoline;
(829) 4-[(6,7-Dimethoxy-4-quinolyl)oxy]-phenyl[2-(4-fluorophenoxy)ethyl]sulfone;
(830) 4-[(6,7-Dimethoxy-4-quinolyl)oxy]-phenyl[2-(3-methoxyphenoxy)ethyl]sulfone;
(831) 2-(2,4-Dichlorophenoxy)ethyl{4-[(6,7-dimethoxy-4-quinolyl)oxy]phenyl}sulfone;

(832) 2-(3-Chlorophenoxy)ethyl{4-[(6,7-dimethoxy-4-quinolyl)oxy]phenyl}sulfone;
(833) 4-[(6,7-Dimethoxy-4-quinolyl)oxy]-phenyl[[2-(3,4-dimethylphenoxy)ethyl]sulfone;
(834) -[(6,7-Dimethoxy-4-quinolyl)oxy]-phenyl[2-(4-methylphenoxy)ethyl]sulfone;
(835) 4-[(6,7-Dimethoxy-4-quinolyl)oxy]-phenyl[2-(4-isopropylphenoxy)ethyl]sulfone;
(836) 4-[(6,7-Dimethoxy-4-quinolyl)oxy]-phenyl[2-(2-isopropylphenoxy)ethyl]sulfone;
(837) 4-[(6,7-Dimethoxy-4-quinolyl)oxy]-phenyl[2-(2-fluorophenoxy)ethyl]sulfone;
(838) {4-[(6,7-Dimethoxy-4-quinolyl)oxy]-phenyl}[2-(3-methoxy-4-nitrophenoxy) ethyl]sulfoxide;
(839) {4-[(6,7-Dimethoxy-4-quinolyl)oxy]-phenyl}[2-(4-fluoro-2-nitrophenoxy) ethyl]sulfoxide;
(840) [2-(2,4-Dichlorophenoxy)ethyl]{4-[(6,7-dimethoxy-4-quinolyl)oxy]phenyl}sulfoxide;
(841) 6,7-Dimethoxy-4-(4-{[3-(3-methyl-phenoxy)propyl]sulfanyl}phenoxy)quinoline;
(842) 4-(4-{[3-(2-Fluorophenoxy)propyl]sulfanyl}phenoxy)-6,7-dimethoxyquinoline;
(843) 4-(4-{[4-(2-Fluorophenoxy)butyl]sulfanyl}phenoxy)-6,7-dimethoxyquinoline;
(844) 6,7-Dimethoxy-4-(4-{[4-(3-methyl-phenoxy)butyl]sulfanyl}phenoxy)quinoline;
(851) N-[2-(2,4-Dichlorophenoxy)ethyl]-N-{4-[(6,7-dimethoxy-4-quinolyl)oxy]phenyl}amine;
(852) N-{4-[(6,7-Dimethoxy-4-quinolyl)oxy]-phenyl}-N-[2-(2-methylphenoxy)ethyl]amine;
(853) N-{4-[(6,7-Dimethoxy-4-quinolyl)oxy]-phenyl}-N-[2-(2-methoxyphenoxy) ethyl]amine;
(854) N-[2-(2,6-Dichlorophenoxy)ethyl]-N-{4-[(6,7-dimethoxy-4-quinolyl)oxy]phenyl}amine;
(855) N-{4-[(6,7-Dimethoxy-4-quinolyl)oxy]-phenyl}-N-[2-(2,6-dimethylphenoxy) ethyl]amine;
(856) N-[2-(2,6-Dimethoxyphenoxy)ethyl]-N-{4-[(6,7-dimethoxy-4-quinolyl)oxy]phenyl}amine;
(857) N-[2-(2,6-Difluorophenoxy)ethyl]-N-{4-[(6,7-dimethoxy-4-quinolyl)oxy]phenyl}amine;
(858) N-{4-[(6,7-Dimethoxy-4-quinolyl)oxy]-phenyl}-N-[2-(3,5-dimethylphenoxy) ethyl]amine;
(859) N-[2-(4-Chlorophenoxy)ethyl]-N-{4-[(6,7-dimethoxy-4-quinolyl)oxy]phenyl}amine;
(860) N-[2-(3-Chlorophenoxy)ethyl]-N-{4-[(6,7-dimethoxy-4-quinolyl)oxy]phenyl}amine;
(861) N-{4-[(6,7-Dimethoxy-4-quinolyl)oxy]-phenyl}-N-[2-(2-ethylphenoxy)ethyl]amine;
(863) N-{4-[(6,7-Dimethoxy-4-quinolyl)oxy]-phenyl}-N-[2-(4-methoxyphenoxy) ethyl]amine;
(864) N-{4-[(6,7-Dimethoxy-4-quinolyl)oxy]-phenyl}-N-[2-(4-ethylphenoxy)ethyl]amine;
(865) N-[2-(2,5-Dichlorophenoxy)ethyl]-N-{4-[(6,7-dimethoxy-4-quinolyl)oxy]phenyl}amine;
(866) N-{4-[(6,7-Dimethoxy-4-quinolyl)oxy]-phenyl}-N-[2-(4-fluorophenoxy)ethyl]amine;
(867) N-{4-[(6,7-Dimethoxy-4-quinolyl)oxy]-phenyl}-N-[2-(4-fluorophenoxy)ethyl]-N-methylamine;
(868) N-[2-(2-Chlorophenoxy)ethyl]-N-{4-[(6,7-dimethoxy-4-quinolyl)oxy]phenyl}amine;
(869) N-{4-[(6,7-Dimethoxy-4-quinolyl)oxy]-phenyl}-N-(2-phenoxyethyl)amine;
(870) N-{4-[(6,7-Dimethoxy-4-quinolyl)oxy]-phenyl}-N-[2-(4-methylphenoxy)ethyl]amine;
(871) N-{4-[(6,7-Dimethoxy-4-quinolyl)oxy]-phenyl}-N-[2-(3-methylphenoxy)ethyl]amine;
(872) 2-(2-{4-[(6,7-Dimethoxy-4-quinolyl)-oxy]anilino}ethoxy)phenol;
(875) N-{4-[(6,7-Dimethoxy-4-quinolyl)oxy]-3-methylphenyl}-N-(2-phenoxyethyl)amine;
(876) N-{4-[(6,7-Dimethoxy-4-quinolyl)oxy]-3-methylphenyl}-N-[2-(2-methylphenoxy) ethyl]amine;
(877) N-[2-(2-Chlorophenoxy)ethyl]-N-{4-[(6,7-dimethoxy-4-quinolyl)oxy]-3-methylphenyl}amine;
(878) N-{4-[(6,7-Dimethoxy-4-quinolyl)oxy]-3-methylphenyl}-N-[2-(3-methylphenoxy) ethyl]amine;
(879) N-{4-[(6,7-Dimethoxy-4-quinolyl)oxy]-3-methylphenyl}-N-[2-(4-methylphenoxy) ethyl]amine;
(880) N-{4-[(6,7-Dimethoxy-4-quinolyl)oxy]-3-methylphenyl}-N-[2-(2-methoxyphenoxy) ethyl]amine;
(881) N-{4-[(6,7-Dimethoxy-4-quinolyl)oxy]-3-methylphenyl}-N-[2-(2,6-dimethylphenoxy) ethyl]amine;
(882) N-[2-(2,6-Dimethoxyphenoxy)ethyl]-N-{4-[(6,7-dimethoxy-4-quinolyl)oxy]-3-methylphenyl}amine;
(883) N-[2-(2,6-Difluorophenoxy)ethyl]-N-{4-[(6,7-dimethoxy-4-quinolyl)oxy]-3-methylphenyl}amine;
(884) N-[2-(2,6-Dimethoxyphenoxy)ethyl]-N-{4-[(6,7-dimethoxy-4-quinolyl)oxy]-2,3-dimethylphenyl}-amine;
(885) N-{4-[(6,7-Dimethoxy-4-quinolyl)oxy]-phenyl}-N-(3-phenoxypropyl)amine;
(886) N-{4-[(6,7-Dimethoxy-4-quinolyl)oxy]-2,5-dimethylphenyl}-N-(3-phenoxypropyl)amine;
(887) N-{4-[(6,7-Dimethoxy-4-quinolyl)oxy]-2,3-dimethylphenyl}-N-(3-phenoxypropyl)amine;
(888) N-{4-[(6,7-Dimethoxy-4-quinolyl)oxy]-phenyl}-N-[3-(2-methylphenoxy)propyl]amine;
(889) N-{4-[(6,7-Dimethoxy-4-quinolyl)oxy]-2,5-dimethylphenyl}-N-[3-(2-methylphenoxy) propyl]amine;
(890) N-{4-[(6,7-Dimethoxy-4-quinolyl)oxy]-2,3-dimethylphenyl}-N-[3-(2-methylphenoxy)propyl]amine;
(891) N-[3-(2-Chlorophenoxy)propyl]-N-{4-[(6,7-dimethoxy-4-quinolyl)oxy]phenyl}amine;
(892) N-[3-(2-Chlorophenoxy)propyl]-N-{4-[(6,7-dimethoxy-4-quinolyl)oxy]-2,5-dimethylphenyl}amine;
(893) N-[3-(2-Chlorophenoxy)propyl]-N-{4-[(6,7-dimethoxy-4-quinolyl)oxy]-2,3-dimethylphenyl}amine;
(894) N-{4-[(6,7-Dimethoxy-4-quinolyl)oxy]-2,3-dimethylphenyl}-N-[2-(2,6-dimethylphenoxy)ethyl]amine;
(895) N-{4-[(6,7-Dimethoxy-4-quinolyl)oxy]-2,5-dimethylphenyl}-N-[2-(2,6-dimethylphenoxy) ethyl]amine; and
(896) N-[2-(2,6-Dimethoxyphenoxy)ethyl]-N-{4-[(6,7-dimethoxy-4-quinolyl)oxy]-2,5-dimethylphenyl}amine.

26. A compound represented by formula (I) or a pharmacologically acceptable salt or solvate thereof:

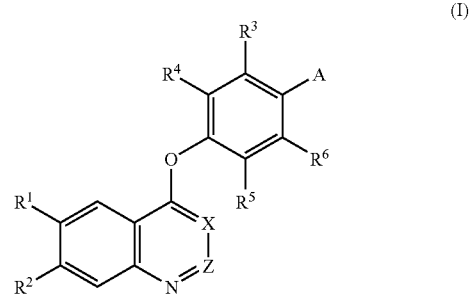

(I)

wherein
X and Z represent —CH;
R$^1$ and R$^2$ represent C$_{1-4}$ alkoxy;
R$^3$, R$^4$, R$^5$, and R$^6$, which may be the same or different, represent a hydrogen atom; a halogen atom; C$_{1-4}$ alkyl optionally substituted by a halogen atom; C$_{1-4}$ alkoxy optionally substituted by a halogen atom; nitro; amino; or morpholyl;
wherein
at least one of R$^3$, R$^4$, R$^5$, and R$^6$ represents a group other than a hydrogen atom, and
A represents group (viii):

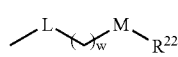 (viii)

wherein
w is an integer of 1 to 4,
L represents —O—, —S(=O)$_y$—, wherein y is an integer of 0 to 2, or —N(—R$^{11}$)—,
M represents —O—, —C(=O)—O—, —S(=O)$_z$—, wherein z is an integer of 0 to 2, —N(—R$^{12}$)—, —C(=O)—N(—R$^{12}$)—, or —C(=O)—,
R$^{11}$ and R$^{12}$, which may be the same or different, represent a hydrogen atom, C$_{1-4}$ alkyl optionally substituted by a halogen atom, or C$_{1-4}$ alkylcarbonyl optionally substituted by a halogen atom;
R$^{22}$ represents a hydrogen atom; C$_{1-4}$ alkyl optionally substituted by a halogen atom; or phenyl optionally substituted by C$_{1-4}$ alkyl optionally substituted by a halogen atom, C$_{1-4}$ alkoxy optionally substituted by a halogen atom, nitro, amino, or a halogen atom, when M represents —N(—R$^{12}$)— or —C(=O)—N(—R$^{12}$)—, R$^{22}$ and R$^{12}$ may form a five- to seven-membered saturated or unsaturated heterocyclic ring optionally containing one or more additional hetero-atoms together with the nitrogen atom to which they are attached, this heterocyclic ring is optionally condensed with another carbocyclic ring or heterocyclic ring to form a ten- to twelve-membered bicyclic saturated or unsaturated heterocyclic ring, and these heterocyclic rings are optionally substituted by C$_{1-4}$ alkyl optionally substituted by a halogen atom; phenyl; benzyl; or piperidine.

27. A composition comprising:
the compound of claim 1 or a pharmacologically acceptable salt thereof or a solvate thereof.

28. A method for treating a disease mediated by the autophosphorylation of a PDGF receptor comprising:
administering to a subject in need thereof an effective amount of the compound of claim 1, wherein said disease is selected from the group consisting of angiostenosis, chronic rheumatism, and organ fibrosis.

29. A method for treating a disease mediated by the autophosphorylation of a PDGF receptor comprising administering to a subject in need thereof an effective amount of the compound of claim 1, wherein said disease is myeloid leukemia.

30. A method for inhibiting angiostenosis comprising administering an amount of the compound of claim 1 effective to inhibit angiostenosis.

* * * * *